US012448353B2

(12) United States Patent
Seda et al.

(10) Patent No.: US 12,448,353 B2
(45) Date of Patent: Oct. 21, 2025

(54) COMPOUND, MATERIAL FOR ORGANIC ELECTROLUMINESCENT ELEMENT, ORGANIC ELECTROLUMINESCENT ELEMENT, AND ELECTRONIC DEVICE

(71) Applicant: IDEMITSU KOSAN CO., LTD., Tokyo (JP)

(72) Inventors: Keita Seda, Tokyo (JP); Ryota Takahashi, Tokyo (JP); Yuki Nakano, Tokyo (JP); Yuichiro Kawamura, Tokyo (JP); Fabrice Eckes, Basel (CH)

(73) Assignee: IDEMITSU KOSAN CO., LTD., Tokyo (JP)

( * ) Notice: Subject to any disclaimer, the term of this patent is extended or adjusted under 35 U.S.C. 154(b) by 888 days.

(21) Appl. No.: 17/762,037

(22) PCT Filed: Sep. 24, 2020

(86) PCT No.: PCT/JP2020/036064
§ 371 (c)(1),
(2) Date: Mar. 18, 2022

(87) PCT Pub. No.: WO2021/060384
PCT Pub. Date: Apr. 1, 2021

(65) Prior Publication Data

US 2022/0363638 A1 Nov. 17, 2022

(30) Foreign Application Priority Data

Sep. 25, 2019 (JP) ................................ 2019-174433

(51) Int. Cl.

| | |
|---|---|
| ***C07D 209/86*** | (2006.01) |
| ***H10K 50/15*** | (2023.01) |
| ***H10K 85/60*** | (2023.01) |

(52) U.S. Cl.
CPC .......... *C07D 209/86* (2013.01); *H10K 50/15* (2023.02); *H10K 85/654* (2023.02); *H10K 85/6574* (2023.02)

(58) Field of Classification Search
CPC ... H10K 85/623; H10K 85/633; C07C 211/61
See application file for complete search history.

(56) References Cited

U.S. PATENT DOCUMENTS

2002/0022151 A1 2/2002 Ishikawa et al.
2009/0023957 A1* 1/2009 Watanabe .............. C07F 7/081 585/27

(Continued)

FOREIGN PATENT DOCUMENTS

JP 2002-043057 A 2/2002
JP 2004-256497 A 9/2004

(Continued)

OTHER PUBLICATIONS

International Searching Authority, "International Search Report," issued in connection with International Patent Application No. PCT/JP2020/036064, dated Nov. 17, 2020.
International Searching Authority, "Written Opinion," issued in connection with International Patent Application No. PCT/JP2020/036064, dated Nov. 17, 2020.

(Continued)

*Primary Examiner* — Sean M DeGuire
(74) *Attorney, Agent, or Firm* — Foley & Lardner LLP

(57) ABSTRACT

A compound is represented by a formula (2) below and has at least one group represented by a formula (20) below. In (Continued)

the formula (2): m is 0, 1, 2, or 3, n is 0, 1, 2 or 3, and m+n is an integer of 1 or more.

(2)

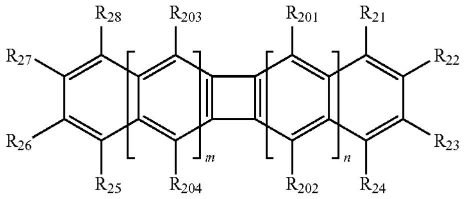

(20)

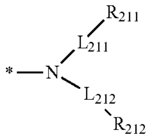

25 Claims, 1 Drawing Sheet

(56) References Cited

U.S. PATENT DOCUMENTS

| | | | |
|---|---|---|---|
| 2019/0288222 | A1 | 9/2019 | Moon et al. |
| 2020/0321536 | A1 | 10/2020 | Takahashi |

FOREIGN PATENT DOCUMENTS

| | | | |
|---|---|---|---|
| JP | 2006-156980 | A | 6/2006 |
| JP | 2006-328006 | A | 12/2006 |
| JP | 2007-165378 | A | 6/2007 |
| JP | 2007-208032 | A | 8/2007 |
| JP | 2007-224011 | A | 9/2007 |
| JP | 2009-227652 | A | 10/2009 |
| JP | 2017-109980 | A | 6/2017 |
| WO | WO-2018/105888 | A1 | 6/2018 |
| WO | WO-2018/181462 | A1 | 10/2018 |
| WO | WO-2019/070083 | A1 | 4/2019 |

OTHER PUBLICATIONS

Translation of International Searching Authority, "Written Opinion," issued in connection with International Patent Application No. PCT/JP2020/036064, dated Nov. 17, 2020.

* cited by examiner

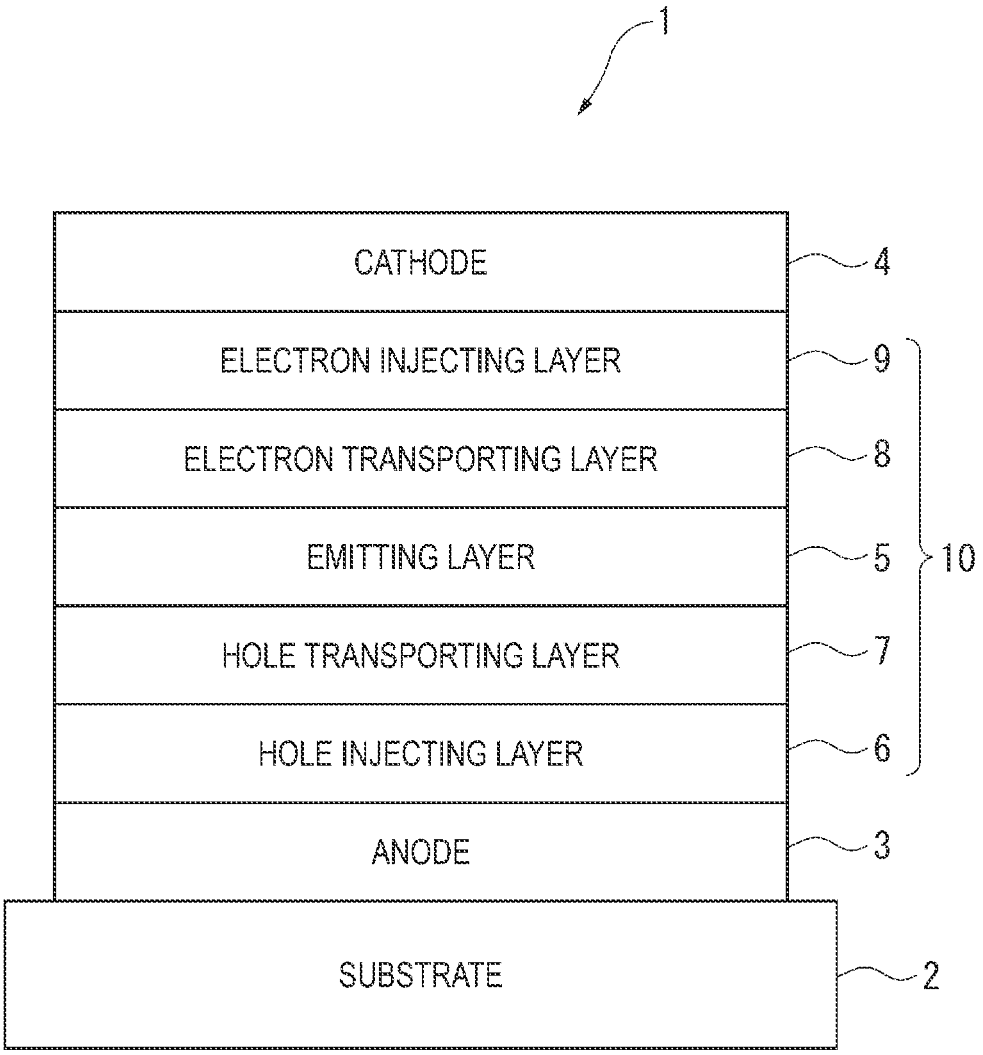
1
CATHODE
4
ELECTRON INJECTING LAYER
9
ELECTRON TRANSPORTING LAYER
8
EMITTING LAYER
5
10
HOLE TRANSPORTING LAYER
7
HOLE INJECTING LAYER
6
ANODE
3
SUBSTRATE
2

COMPOUND, MATERIAL FOR ORGANIC ELECTROLUMINESCENT ELEMENT, ORGANIC ELECTROLUMINESCENT ELEMENT, AND ELECTRONIC DEVICE

CROSS-REFERENCE TO RELATED APPLICATIONS

The present application claims priority under 37 U.S.C. § 371 to International Patent Application No. PCT/JP2020/036064, filed Sep. 24, 2020, which claims priority to and the benefit of Japanese Patent Application No. 2019-174433, filed on Sep. 25, 2019. The contents of these applications are hereby incorporated by reference in their entireties.

TECHNICAL FIELD

The present invention relates to a compound, an organic-electroluminescence-device material, an organic electroluminescence device, and an electronic device.

BACKGROUND ART

When a voltage is applied to an organic electroluminescence device (hereinafter, occasionally referred to as an organic EL device), holes are injected from an anode and electrons are injected from a cathode into an emitting layer. The injected electrons and holes are recombined in the emitting layer to form excitons. Specifically, according to the electron spin statistics theory, singlet excitons and triplet excitons are generated at a ratio of 25%:75%.

The organic EL device has been applied to a full-color display for mobile phones, televisions and the like. Various studies have been made for compounds to be used for the organic EL device in order to enhance the performance of the organic EL device (e.g., see Patent Literatures 1 to 9).

CITATION LIST

Patent Literature(s)

Patent Literature 1: JP 2002-43057 A
Patent Literature 2: JP 2004-256497 A
Patent Literature 3: JP 2006-156980 A
Patent Literature 4: JP 2006-328006 A
Patent Literature 5: JP 2007-208032 A
Patent Literature 6: JP 2007-224011 A
Patent Literature 7: JP 2009-227652 A
Patent Literature 8: JP 2017-109980 A
Patent Literature 9: International Publication No. WO2018/181462

SUMMARY OF THE INVENTION

Problems to be Solved by the Invention

The performance of the organic EL device is evaluable in terms of luminous efficiency. An element for improving the luminous efficiency is to use a compound having a high photoluminescence quantum yield (PLQY).

An object of the invention is to provide a compound having a high photoluminescence quantum yield and exhibiting a fluorescence spectrum having a high blue color purity.

Also, an object of the invention is also to provide an organic-electroluminescence-device material and an organic electroluminescence device which contain a compound having a high PLQY, and an electronic device including the organic electroluminescence device.

Further, an object of the invention is also to provide a compound capable of improving luminous efficiency, an organic-electroluminescence-device material containing the compound, an organic electroluminescence device having an improved luminous efficiency, and an electronic device including the organic electroluminescence device.

Means for Solving the Problem(s)

According to an aspect of the invention, a compound represented by a formula (2) below and having at least one group represented by a formula (20) below is provided.

[Formula 1]

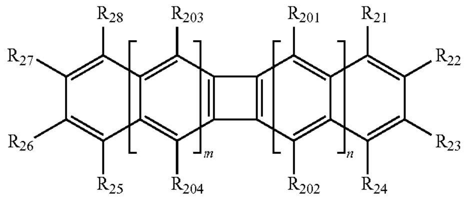

(2)

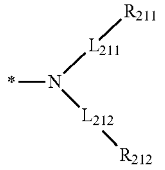

(20)

In the formula (2):

m is 0, 1, 2 or 3;

n is 0, 1, 2 or 3;

m+n is an integer of 1 or more;

at least one combination of adjacent two or more of $R_{21}$ to $R_{28}$ and $R_{201}$ to $R_{204}$ are mutually bonded to form a substituted or unsubstituted monocyclic ring, mutually bonded to form a substituted or unsubstituted fused ring, or not mutually bonded;

$R_{21}$ to $R_{28}$ and $R_{201}$ to $R_{204}$ not forming the monocyclic ring and not forming the fused ring are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, a substituted or unsubstituted heterocyclic group having 5 to 50 ring atoms, or the group represented by the formula (20);

when n is 2 or 3, at least two $R_{201}$ are the same or different, and at least two $R_{202}$ are the same or different;

when m is 2 or 3, at least two $R_{203}$ are the same or different, and at least two $R_{204}$ are the same or different;

at least one of $R_{21}$ to $R_{28}$ or $R_{201}$ to $R_{204}$ is the group represented by the formula (20);

in the group represented by the formula (20), a combination of $R_{211}$ and $R_{212}$ are mutually bonded to form a substituted or unsubstituted monocyclic ring, mutually bonded to form a substituted or unsubstituted fused ring, or not mutually bonded;

$R_{211}$ and $R_{212}$ not forming the monocyclic ring and not forming the fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{211}$ and $L_{212}$ are each independently a single bond, a substituted or unsubstituted arylene group having 6 to 50 ring carbon atoms, or a substituted or unsubstituted divalent heterocyclic group having 5 to 50 ring atoms; and

* in the formula (20) represents a bonding position to a structure of the compound represented by the formula (2).

In the compound represented by the formula (2):

$R_{901}$ to $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when two or more $R_{901}$ are present, the two or more $R_{901}$ are mutually the same or different;

when two or more $R_{902}$ are present, the two or more $R_{902}$ are mutually the same or different;

when two or more $R_{903}$ are present, the two or more $R_{903}$ are mutually the same or different;

when two or more $R_{904}$ are present, the two or more $R_{904}$ are mutually the same or different;

when two or more $R_{905}$ are present, the two or more $R_{905}$ are mutually the same or different;

when two or more $R_{906}$ are present, the two or more $R_{906}$ are mutually the same or different; and when two or more $R_{907}$ are present, the two or more $R_{907}$ are mutually the same or different.

According to another aspect of the invention, an organic-electroluminescence-device material containing the compound according to the above aspect of the invention is provided.

According to still another aspect of the invention, there is provided an organic electroluminescence device including a cathode, an anode, and one or more organic layers between the cathode and the anode, in which at least one layer of the one or more organic layers contains the compound according to the above aspect of the invention.

According to a further aspect of the invention, there is provided an organic electroluminescence device including a cathode, an anode, and one or more organic layers between the cathode and the anode, in which at least one layer of the one or more organic layers contains the compound according to the above aspect of the invention and a compound represented by a formula (10).

[Formula 2]

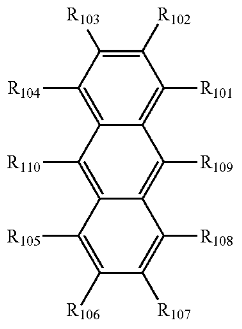

(10)

In the formula (10):

at least one combination of adjacent two or more of $R_{101}$ to $R_{110}$ are mutually bonded to form a substituted or unsubstituted monocyclic ring, mutually bonded to form a substituted or unsubstituted fused ring, or not mutually bonded; and $R_{101}$ to $R_{110}$ not forming the monocyclic ring and not forming the fused ring are each independently a hydrogen atom, a substituent R, or a group represented by a formula (11) below.

$$-L_{101}-Ar_{101} \quad (11)$$

In the formula (11):

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

the substituent R is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms;

when two or more substituents R are present, the two or more substituents R are mutually the same or different;

$R_{901}$ to $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when two or more $R_{901}$ are present, the two or more $R_{901}$ are mutually the same or different;

when two or more $R_{902}$ are present, the two or more $R_{902}$ are mutually the same or different;

when two or more $R_{903}$ are present, the two or more $R_{903}$ are mutually the same or different;

when two or more $R_{904}$ are present, the two or more $R_{904}$ are mutually the same or different;

when two or more $R_{905}$ are present, the two or more $R_{905}$ are mutually the same or different;

when two or more $R_{906}$ are present, the two or more $R_{906}$ are mutually the same or different;

when two or more $R_{907}$ are present, the two or more $R_{907}$ are mutually the same or different;

at least one of $R_{101}$ to $R_{110}$ not forming the monocyclic ring and not forming the fused ring is the group represented by the formula (11);

when two or more groups represented by the formula (11) are present, the two or more groups represented by the formula (11) are mutually the same or different;

when two or more $L_{101}$ are present, two or more $L_{101}$ are mutually the same or different; and when two or more $Ar_{101}$ are present, the two or more $Ar_{101}$ are mutually the same or different.

According to a further aspect of the invention, an electronic device including the organic electroluminescence device according to the above aspect of the invention is provided.

According to a further of the invention, a compound having a high photoluminescence quantum yield and exhibiting a fluorescence spectrum having a high blue color purity can be provided. According to a further of the invention, an organic-electroluminescence-device material and an organic electroluminescence device which contain a compound having a high PLQY, and an electronic device including the organic electroluminescence device can be provided. According to a further of the invention, a compound capable of improving luminous efficiency, an organic-electroluminescence-device material containing the compound, an organic electroluminescence device having an improved luminous efficiency, and an electronic device including the organic electroluminescence device can be provided.

BRIEF EXPLANATION OF DRAWINGS

The FIGURE schematically shows an exemplary arrangement of an organic electroluminescence device according to an exemplary embodiment of the invention.

DESCRIPTION OF EMBODIMENT(S)

Definitions

Herein, a hydrogen atom includes isotope having different numbers of neutrons, specifically, protium, deuterium and tritium.

In chemical formulae herein, it is assumed that a hydrogen atom (i.e. protium, deuterium and tritium) is bonded to each of bondable positions that are not annexed with signs "R" or the like or "D" representing a deuterium.

Herein, the ring carbon atoms refer to the number of carbon atoms among atoms forming a ring of a compound (e.g., a monocyclic compound, fused-ring compound, crosslinking compound, carbon ring compound, and heterocyclic compound) in which the atoms are bonded with each other to form the ring. When the ring is substituted by a substituent (s), carbon atom(s) contained in the substituent(s) is not counted in the ring carbon atoms. Unless otherwise specified, the same applies to the "ring carbon atoms" described later. For instance, a benzene ring has 6 ring carbon atoms, a naphthalene ring has 10 ring carbon atoms, a pyridine ring has 5 ring carbon atoms, and a furan ring has 4 ring carbon atoms. Further, for instance, 9,9-diphenylfluorenyl group has 13 ring carbon atoms and 9,9'-spirobifluorenyl group has 25 ring carbon atoms.

When a benzene ring is substituted by a substituent in a form of, for instance, an alkyl group, the number of carbon atoms of the alkyl group is not counted in the number of the ring carbon atoms of the benzene ring. Accordingly, the benzene ring substituted by an alkyl group has 6 ring carbon atoms. When a naphthalene ring is substituted by a substituent in a form of, for instance, an alkyl group, the number of carbon atoms of the alkyl group is not counted in the number of the ring carbon atoms of the naphthalene ring. Accordingly, the naphthalene ring substituted by an alkyl group has 10 ring carbon atoms.

Herein, the ring atoms refer to the number of atoms forming a ring of a compound (e.g., a monocyclic compound, fused-ring compound, crosslinking compound, carbon ring compound, and heterocyclic compound) in which the atoms are bonded to each other to form the ring (e.g., monocyclic ring, fused ring, and ring assembly). Atom(s) not forming the ring (e.g., hydrogen atom(s) for saturating the valence of the atom which forms the ring) and atom(s) in a substituent by which the ring is substituted are not counted as the ring atoms. Unless otherwise specified, the same applies to the "ring atoms" described later. For instance, a pyridine ring has 6 ring atoms, a quinazoline ring has 10 ring atoms, and a furan ring has 5 ring atoms. For instance, the number of hydrogen atom(s) bonded to a pyridine ring or the number of atoms forming a substituent are not counted as the pyridine ring atoms. Accordingly, a pyridine ring bonded with a hydrogen atom(s) or a substituent(s) has 6 ring atoms. For instance, the hydrogen atom(s) bonded to carbon atom(s) of a quinazoline ring or the atoms forming a substituent are not counted as the quinazoline ring atoms. Accordingly, a quinazoline ring bonded with hydrogen atom(s) or a substituent(s) has 10 ring atoms.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. Herein, "YY" is larger than "XX," "XX" representing an integer of 1 or more and "YY" representing an integer of 2 or more.

Herein, "XX to YY atoms" in the description of "substituted or unsubstituted ZZ group having XX to YY atoms" represent atoms of an unsubstituted ZZ group and does not include atoms of a substituent(s) of the substituted ZZ group. Herein, "YY" is larger than "XX," "XX" representing an integer of 1 or more and "YY" representing an integer of 2 or more.

Herein, an unsubstituted ZZ group refers to an "unsubstituted ZZ group" in a "substituted or unsubstituted ZZ group," and a substituted ZZ group refers to a "substituted ZZ group" in a "substituted or unsubstituted ZZ group."

Herein, the term "unsubstituted" used in a "substituted or unsubstituted ZZ group" means that a hydrogen atom(s) in the ZZ group is not substituted with a substituent(s). The hydrogen atom(s) in the "unsubstituted ZZ group" is protium, deuterium, or tritium.

Herein, the term "substituted" used in a "substituted or unsubstituted ZZ group" means that at least one hydrogen atom in the ZZ group is substituted with a substituent. Similarly, the term "substituted" used in a "BB group substituted by AA group" means that at least one hydrogen atom in the BB group is substituted with the AA group.

Substituents Mentioned Herein

Substituents mentioned herein will be described below.

An "unsubstituted aryl group" mentioned herein has, unless otherwise specified herein, 6 to 50, preferably 6 to 30, more preferably 6 to 18 ring carbon atoms.

An "unsubstituted heterocyclic group" mentioned herein has, unless otherwise specified herein, 5 to 50, preferably 5 to 30, more preferably 5 to 18 ring atoms.

An "unsubstituted alkyl group" mentioned herein has, unless otherwise specified herein, 1 to 50, preferably 1 to 20, more preferably 1 to 6 carbon atoms.

An "unsubstituted alkenyl group" mentioned herein has, unless otherwise specified herein, 2 to 50, preferably 2 to 20, more preferably 2 to 6 carbon atoms.

An "unsubstituted alkynyl group" mentioned herein has, unless otherwise specified herein, 2 to 50, preferably 2 to 20, more preferably 2 to 6 carbon atoms.

An "unsubstituted cycloalkyl group" mentioned herein has, unless otherwise specified herein, 3 to 50, preferably 3 to 20, more preferably 3 to 6 ring carbon atoms.

An "unsubstituted arylene group" mentioned herein has, unless otherwise specified herein, 6 to 50, preferably 6 to 30, more preferably 6 to 18 ring carbon atoms.

An "unsubstituted divalent heterocyclic group" mentioned herein has, unless otherwise specified herein, 5 to 50, preferably 5 to 30, more preferably 5 to 18 ring atoms.

An "unsubstituted alkylene group" mentioned herein has, unless otherwise specified herein, 1 to 50, preferably 1 to 20, more preferably 1 to 6 carbon atoms.

Substituted or Unsubstituted Aryl Group

Specific examples (specific example group G1) of the "substituted or unsubstituted aryl group" mentioned herein include unsubstituted aryl groups (specific example group G1A) below and substituted aryl groups (specific example group G1B). (Herein, an unsubstituted aryl group refers to an "unsubstituted aryl group" in a "substituted or unsubstituted aryl group," and a substituted aryl group refers to a "substituted aryl group" in a "substituted or unsubstituted aryl group." A simply termed "aryl group" herein includes both of an "unsubstituted aryl group" and a "substituted aryl group."

The "substituted aryl group" refers to a group derived by substituting at least one hydrogen atom in an "unsubstituted aryl group" with a substituent. Examples of the "substituted aryl group" include a group derived by substituting at least one hydrogen atom in the "unsubstituted aryl group" in the specific example group G1A below with a substituent, and examples of the substituted aryl group in the specific example group G1B below. It should be noted that the examples of the "unsubstituted aryl group" and the "substituted aryl group" mentioned herein are merely exemplary, and the "substituted aryl group" mentioned herein includes a group derived by further substituting a hydrogen atom bonded to a carbon atom of a skeleton of a "substituted aryl group" in the specific example group G1B below, and a group derived by further substituting a hydrogen atom of a substituent of the "substituted aryl group" in the specific example group G1B below.

Unsubstituted Aryl Group (Specific Example Group G1A):

a phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, benzanthryl group, phenanthryl group, benzophenanthryl group, phenalenyl group, pyrenyl group, chrysenyl group, benzochrysenyl group, triphenylenyl group, benzotriphenylenyl group, tetracenyl group, pentacenyl group, fluorenyl group, 9,9'-spirobifluorenyl group, benzofluorenyl group, dibenzofluorenyl group, fluoranthenyl group, benzofluoranthenyl group, a perylenyl group, and a monovalent aryl group derived by removing one hydrogen atom from cyclic structures represented by formulae (TEMP-1) to (TEMP-15) below.

[Formula 3]

(TEMP-1)

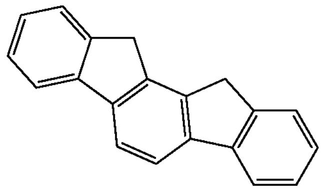

(TEMP-2)

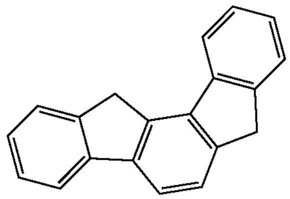

(TEMP-3)

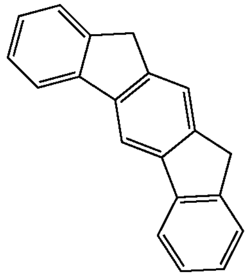

(TEMP-4)

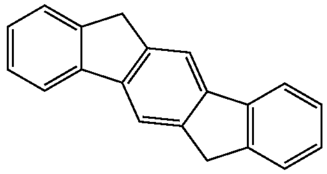

(TEMP-5)

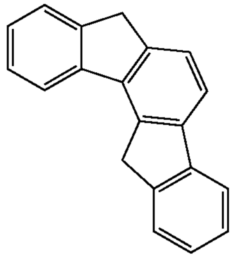

(TEMP-6)

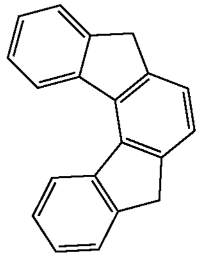

-continued (TEMP-7)

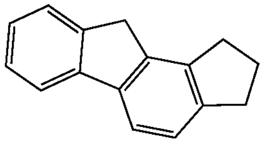

(TEMP-8)

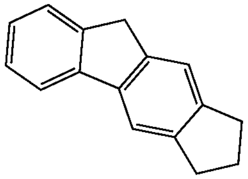

(TEMP-9)

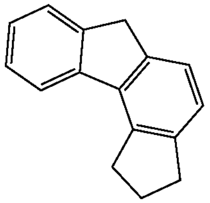

[Formula 4]

(TEMP-10)

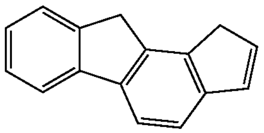

(TEMP-11)

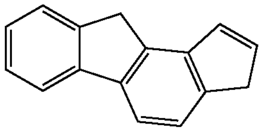

(TEMP-12)

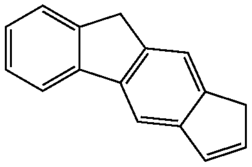

(TEMP-13)

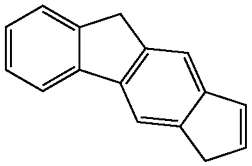

(TEMP-14)

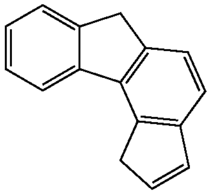

-continued (TEMP-15)

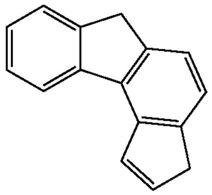

Substituted Aryl Group (Specific Example Group G1B):

o-tolyl group, m-tolyl group, p-tolyl group, para-xylyl group, meta-xylyl group, ortho-xylyl group, para-isopropylphenyl group, meta-isopropylphenyl group, ortho-isopropylphenyl group, para-t-butylphenyl group, meta-t-butylphenyl group, ortho-t-butylphenyl group, 3,4,5-trimethylphenyl group, 9,9-dimethylfluorenyl group, 9,9-diphenylfluorenyl group, 9,9-bis(4-methylphenyl)fluorenyl group, 9,9-bis(4-isopropylphenyl)fluorenyl group, 9,9-bis(4-t-butylphenyl)fluorenyl group, cyanophenyl group, triphenylsilylphenyl group, trimethylsilylphenyl group, phenylnaphthyl group, naphthylphenyl group, and a group derived by substituting at least one hydrogen atom of a monovalent group derived from the cyclic structures represented by the formulae (TEMP-1) to (TEMP-15) with a substituent.

Substituted or Unsubstituted Heterocyclic Group

The “heterocyclic group” mentioned herein refers to a cyclic group having at least one hetero atom in the ring atoms. Specific examples of the hetero atom include a nitrogen atom, oxygen atom, sulfur atom, silicon atom, phosphorus atom, and boron atom.

The “heterocyclic group” mentioned herein is a monocyclic group or a fused-ring group.

The “heterocyclic group” mentioned herein is an aromatic heterocyclic group or a non-aromatic heterocyclic group.

Specific examples (specific example group G2) of the “substituted or unsubstituted heterocyclic group” mentioned herein include unsubstituted heterocyclic groups (specific example group G2A) and substituted heterocyclic groups (specific example group G2B). (Herein, an unsubstituted heterocyclic group refers to an “unsubstituted heterocyclic group” in a “substituted or unsubstituted heterocyclic group,” and a substituted heterocyclic group refers to a “substituted heterocyclic group” in a “substituted or unsubstituted heterocyclic group.”) A simply termed “heterocyclic group” herein includes both of “unsubstituted heterocyclic group” and “substituted heterocyclic group.”

The “substituted heterocyclic group” refers to a group derived by substituting at least one hydrogen atom in an “unsubstituted heterocyclic group” with a substituent. Specific examples of the “substituted heterocyclic group” include a group derived by substituting at least one hydrogen atom in the “unsubstituted heterocyclic group” in the specific example group G2A below with a substituent, and examples of the substituted heterocyclic group in the specific example group G2B below. It should be noted that the examples of the “unsubstituted heterocyclic group” and the “substituted heterocyclic group” mentioned herein are merely exemplary, and the “substituted heterocyclic group” mentioned herein includes a group derived by further substituting a hydrogen atom bonded to a ring atom of a skeleton of a “substituted heterocyclic group” in the specific example group G2B below, and a group derived by further substituting a hydrogen atom of a substituent of the "substituted heterocyclic group" in the specific example group G2B below.

The specific example group G2A includes, for instance, unsubstituted heterocyclic groups including a nitrogen atom (specific example group G2A1) below, unsubstituted heterocyclic groups including an oxygen atom (specific example group G2A2) below, unsubstituted heterocyclic groups including a sulfur atom (specific example group G2A3) below, and monovalent heterocyclic groups (specific example group G2A4) derived by removing a hydrogen atom from cyclic structures represented by formulae (TEMP-16) to (TEMP-33) below.

The specific example group G2B includes, for instance, substituted heterocyclic groups including a nitrogen atom (specific example group G2B1) below, substituted heterocyclic groups including an oxygen atom (specific example group G2B2) below, substituted heterocyclic groups including a sulfur atom (specific example group G2B3) below, and groups derived by substituting at least one hydrogen atom of the monovalent heterocyclic groups (specific example group G2B4) derived from the cyclic structures represented by formulae (TEMP-16) to (TEMP-33) below.

Unsubstituted Heterocyclic Groups Including Nitrogen Atom (Specific Example Group G2A1):

pyrrolyl group, imidazolyl group, pyrazolyl group, triazolyl group, tetrazolyl group, oxazolyl group, isoxazolyl group, oxadiazolyl group, thiazolyl group, isothiazolyl group, thiadiazolyl group, a pyridyl group, pyridazynyl group, a pyrimidinyl group, pyrazinyl group, a triazinyl group, indolyl group, isoindolyl group, indolizinyl group, quinolizinyl group, quinolyl group, isoquinolyl group, cinnolyl group, phthalazinyl group, quinazolinyl group, quinoxalinyl group, benzimidazolyl group, indazolyl group, phenanthrolinyl group, phenanthridinyl group, acridinyl group, phenazinyl group, carbazolyl group, benzocarbazolyl group, morpholino group, phenoxazinyl group, phenothiazinyl group, azacarbazolyl group, and diazacarbazolyl group.

Unsubstituted Heterocyclic Groups Including Oxygen Atom (Specific Example Group G2A2):

furyl group, oxazolyl group, isoxazolyl group, oxadiazolyl group, xanthenyl group, benzofuranyl group, isobenzofuranyl group, a dibenzofuranyl group, naphthobenzofuranyl group, benzoxazolyl group, benzisoxazolyl group, phenoxazinyl group, morpholino group, dinaphthofuranyl group, azadibenzofuranyl group, diazadibenzofuranyl group, azanaphthobenzofuranyl group, and diazanaphthobenzofuranyl group.

Unsubstituted Heterocyclic Groups Including Sulfur Atom (Specific Example Group G2A3):

thienyl group, thiazolyl group, isothiazolyl group, thiadiazolyl group, benzothiophenyl group (benzothienyl group), isobenzothiophenyl group (isobenzothienyl group), dibenzothiophenyl group (dibenzothienyl group), naphthobenzothiophenyl group (nahthobenzothienyl group), benzothiazolyl group, benzisothiazolyl group, phenothiazinyl group, dinaphthothiophenyl group (dinaphthothienyl group), azadibenzothiophenyl group (azadibenzothienyl group), diazadibenzothiophenyl group (diazadibenzothienyl group), azanaphthobenzothiophenyl group (azanaphthobenzothienyl group), and diazanaphthobenzothiophenyl group (diazanaphthobenzothienyl group).

Monovalent Heterocyclic Groups Derived by Removing One Hydrogen Atom from Cyclic Structures Represented by Formulae (TEMP-16) to (TEMP-33) (Specific Example Group G2A4):

[Formula 5]

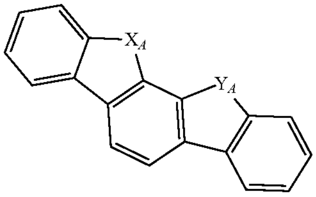
(TEMP-16)

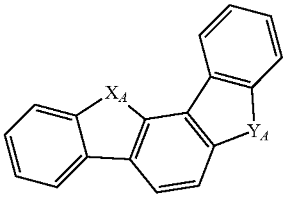
(TEMP-17)

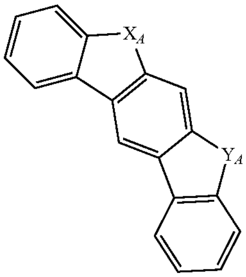
(TEMP-18)

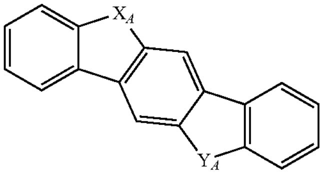
(TEMP-19)

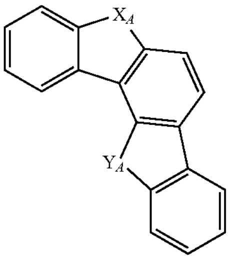
(TEMP-20)

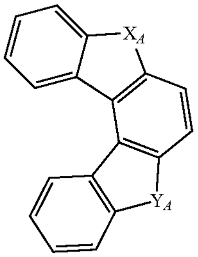
(TEMP-21)

-continued (TEMP-22)

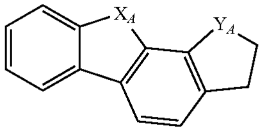

(TEMP-23)

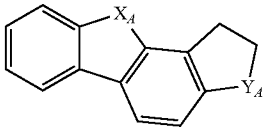

(TEMP-24)

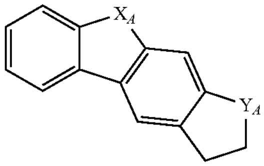

[Formula 6]

(TEMP-25)

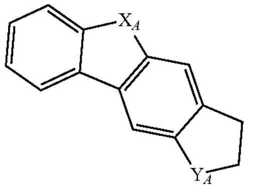

(TEMP-26)

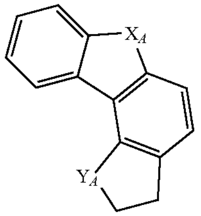

(TEMP-27)

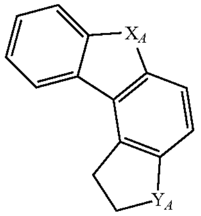

(TEMP-28)

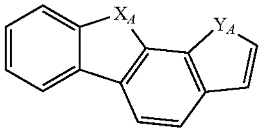

(TEMP-29)

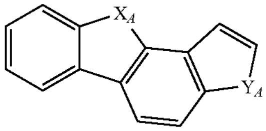

(TEMP-30)

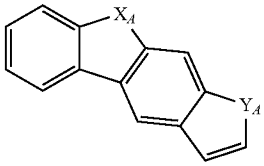

-continued (TEMP-31)

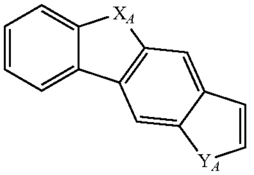

(TEMP-32)

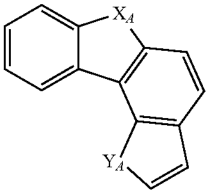

(TEMP-33)

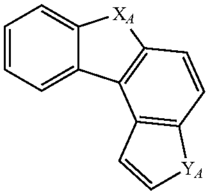

In the formulae (TEMP-16) to (TEMP-33), $X_A$ and $Y_A$ are each independently an oxygen atom, a sulfur atom, NH, or $CH_2$. However, at least one of $X_A$ or $Y_A$ is an oxygen atom, a sulfur atom, or NH.

When at least one of $X_A$ or $Y_A$ in the formulae (TEMP-16) to (TEMP-33) is NH or $CH_2$, the monovalent heterocyclic groups derived from the cyclic structures represented by the formulae (TEMP-16) to (TEMP-33) include a monovalent group derived by removing one hydrogen atom from NH, or $CH_2$.

Substituted Heterocyclic Groups Including Nitrogen Atom (Specific Example Group G2B1):

(9-phenyl)carbazolyl group, (9-biphenylyl)carbazolyl group, (9-phenyl)phenylcarbazolyl group, (9-naphthyl) carbazolyl group, diphenylcarbazole-9-yl group, phenylcarbazole-9-yl group, methylbenzimidazolyl group, ethylbenzimidazolyl group, phenyltriazinyl group, biphenylyltriazinyl group, diphenyltriazinyl group, phenylquinazolinyl group, and biphenylquinazolinyl group.

Substituted Heterocyclic Groups Including Oxygen Atom (Specific Example Group G2B2):

phenyldibenzofuranyl group, methyldibenzofuranyl group, t-butyldibenzofuranyl group, and monovalent residue of spiro[9H-xanthene-9,9'-[9H]fluorene].

Substituted Heterocyclic Groups Including Sulfur Atom (Specific Example Group G2B3):

phenyldibenzothiophenyl group, methyldibenzothiophenyl group, t-butyldibenzothiophenyl group, and monovalent residue of spiro[9H-thioxanthene-9,9'-[9H] fluorene].

Groups Obtained by Substituting at Least One Hydrogen Atom of Monovalent Heterocyclic Group Derived from Cyclic Structures Represented by Formulae (TEMP-16) to (TEMP-33) with Substituent (Specific Example Group G2B4):

The "at least one hydrogen atom of a monovalent heterocyclic group" means at least one hydrogen atom selected from a hydrogen atom bonded to a ring carbon atom of the monovalent heterocyclic group, a hydrogen atom bonded to a nitrogen atom of at least one of XA or YA in a form of NH, and a hydrogen atom of one of XA and YA in a form of a methylene group (CH2).

Substituted or Unsubstituted Alkyl Group

Specific examples (specific example group G3) of the "substituted or unsubstituted alkyl group" mentioned herein include unsubstituted alkyl groups (specific example group G3A) and substituted alkyl groups (specific example group G3B below). (Herein, an unsubstituted alkyl group refers to an "unsubstituted alkyl group" in a "substituted or unsubstituted alkyl group," and a substituted alkyl group refers to a "substituted alkyl group" in a "substituted or unsubstituted alkyl group.") A simply termed "alkyl roup" herein includes both of "unsubstituted alkyl group" and "substituted alkyl group."

The "substituted alkyl group" refers to a group derived by substituting at least one hydrogen atom in an "unsubstituted alkyl group" with a substituent. Specific examples of the "substituted alkyl group" include a group derived by substituting at least one hydrogen atom of an "unsubstituted alkyl group" (specific example group G3A) below with a substituent, and examples of the substituted alkyl group (specific example group G3B) below. Herein, the alkyl group for the "unsubstituted alkyl group" refers to a chain alkyl group. Accordingly, the "unsubstituted alkyl group" include linear "unsubstituted alkyl group" and branched "unsubstituted alkyl group." It should be noted that the examples of the "unsubstituted alkyl group" and the "substituted alkyl group" mentioned herein are merely exemplary, and the "substituted alkyl group" mentioned herein includes a group derived by further substituting a hydrogen atom bonded to a carbon atom of a skeleton of the "substituted alkyl group" in the specific example group G3B, and a group derived by further substituting a hydrogen atom of a substituent of the "substituted alkyl group" in the specific example group G3B.

Unsubstituted Alkyl Group (Specific Example Group G3A):

methyl group, ethyl group, n-propyl group, isopropyl group, n-butyl group, isobutyl group, s-butyl group, and t-butyl group.

Substituted Alkyl Group (Specific Example Group G3B):

heptafluoropropyl group (including isomer thereof), pentafluoroethyl group, 2,2,2-trifluoroethyl group, and trifluoromethyl group.

Substituted or Unsubstituted Alkenyl Group

Specific examples (specific example group G4) of the "substituted or unsubstituted alkenyl group" mentioned herein include unsubstituted alkenyl groups (specific example group G4A) and substituted alkenyl groups (specific example group G4B). (Herein, an unsubstituted alkenyl group refers to an "unsubstituted alkenyl group" in a "substituted or unsubstituted alkenyl group," and a substituted alkenyl group refers to a "substituted alkenyl group" in a "substituted or unsubstituted alkenyl group.") A simply termed "alkenyl roup" herein includes both of "unsubstituted alkenyl group" and "substituted alkenyl group."

The "substituted alkenyl group" refers to a group derived by substituting at least one hydrogen atom in an "unsubstituted alkenyl group" with a substituent. Specific examples of the "substituted alkenyl group" include an "unsubstituted alkenyl group" (specific example group G4A) substituted by a substituent, and examples of the substituted alkenyl group (specific example group G4B) below. It should be noted that the examples of the "unsubstituted alkenyl group" and the "substituted alkenyl group" mentioned herein are merely exemplary, and the "substituted alkenyl group" mentioned herein includes a group derived by further substituting a hydrogen atom of a skeleton of the "substituted alkenyl group" in the specific example group G4B with a substituent, and a group derived by further substituting a hydrogen atom of a substituent of the "substituted alkenyl group" in the specific example group G4B with a substituent.

Unsubstituted Alkenyl Group (Specific Example Group G4A):

vinyl group, allyl group, 1-butenyl group, 2-butenyl group, and 3-butenyl group.

Substituted Alkenyl Group (Specific Example Group G4B):

1,3-butanedienyl group, 1-methylvinyl group, 1-methylallyl group, 1,1-dimethylallyl group, 2-methylallyl group, and 1,2-dimethylallyl group.

Substituted or Unsubstituted Alkynyl Group

Specific examples (specific example group G5) of the "substituted or unsubstituted alkynyl group" mentioned herein include unsubstituted alkynyl groups (specific example group G5A) below. (Herein, an unsubstituted alkynyl group refers to an "unsubstituted alkynyl group" in a "substituted or unsubstituted alkynyl group," and a substituted alkynyl group refers to a "substituted alkynyl group" in a "substituted or unsubstituted alkynyl group.") A simply termed "alkynyl roup" herein includes both of "unsubstituted alkynyl group" and "substituted alkynyl group."

The "substituted alkynyl group" refers to a group derived by substituting at least one hydrogen atom in an "unsubstituted alkynyl group" with a substituent. Specific examples of the "substituted alkynyl group" include a group derived by substituting at least one hydrogen atom of the "unsubstituted alkynyl group" (specific example group G5A) below with a substituent.

Unsubstituted Alkynyl Group (Specific Example Group G5A): Ethynyl Group

Substituted or Unsubstituted Cycloalkyl Group

Specific examples (specific example group G6) of the "substituted or unsubstituted cycloalkyl group" mentioned herein include unsubstituted cycloalkyl groups (specific example group G6A) and substituted cycloalkyl groups (specific example group G6B). (Herein, an unsubstituted cycloalkyl group refers to an "unsubstituted cycloalkyl group" in a "substituted or unsubstituted cycloalkyl group," and a substituted cycloalkyl group refers to a "substituted cycloalkyl group" in a "substituted or unsubstituted cycloalkyl group.") A simply termed "cycloalkyl roup" herein includes both of "unsubstituted cycloalkyl group" and "substituted cycloalkyl group."

The "substituted cycloalkyl group" refers to a group derived by substituting at least one hydrogen atom of an "unsubstituted cycloalkyl group" with a substituent. Specific examples of the "substituted cycloalkyl group" include a group derived by substituting at least one hydrogen atom of the "unsubstituted cycloalkyl group" (specific example group G6A) below with a substituent, and examples of the substituted cycloalkyl group (specific example group G6B) below. It should be noted that the examples of the "unsubstituted cycloalkyl group" and the "substituted cycloalkyl group" mentioned herein are merely exemplary, and the "substituted cycloalkyl group" mentioned herein includes a group derived by substituting at least one hydrogen atom bonded to a carbon atom of a skeleton of the "substituted cycloalkyl group" in the specific example group G6B with a substituent, and a group derived by further substituting a hydrogen atom of a substituent of the "substituted cycloalkyl group" in the specific example group G6B with a substituent.

Unsubstituted Cycloalkyl Group (Specific Example Group G6A): cyclopropyl group, cyclobutyl group, cyclopentyl group, cyclohexyl group, 1-adamantyl group, 2-adamantyl group, 1-norbornyl group, and 2-norbornyl group.

Substituted Cycloalkyl Group (Specific Example Group G6B):

4-methylcyclohexyl group

Group represented by —Si($R_{901}$)($R_{902}$)($R_{903}$)

Specific examples (specific example group G7) of the group represented herein by —Si($R_{901}$)($R_{902}$)($R_{903}$) include: —Si(G1)(G1)(G1); —Si(G1)(G2)(G2); —Si(G1)(G1)(G2); —Si(G2)(G2)(G2); —Si(G3)(G3)(G3); and —Si(G6)(G6)(G6)

Herein: G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3; and G6 represents a "substituted or unsubstituted cycloalkyl group" in the specific example group G6.

A plurality of G1 in —Si(G1)(G1)(G1) are mutually the same or different.

A plurality of G2 in —Si(G1)(G2)(G2) are mutually the same or different.

A plurality of G1 in —Si(G1)(G1)(G2) are mutually the same or different.

A plurality of G2 in —Si(G2)(G2)(G2) are mutually the same or different.

The plurality of G3 in —Si(G3)(G3)(G3) are mutually the same or different.

A plurality of G6 in —Si(G6)(G6)(G6) are mutually the same or different.

Group Represented by —O—($R_{904}$)

Specific examples (specific example group G8) of a group represented by —O—($R_{904}$) herein include —O(G1); —O(G2); —O(G3); and —O(G6).

Herein: G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3; and G6 represents a "substituted or unsubstituted cycloalkyl group" in the specific example group G6.

Group Represented by —S—($R_{905}$)

Specific examples (specific example group G9) of a group represented herein by —S—($R_{905}$) include: —S(G1); —S(G2); —S(G3); and —S(G6).

Herein: G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3; and G6 represents a "substituted or unsubstituted cycloalkyl group" in the specific example group G6.

Group Represented by —N($R_{906}$)($R_{907}$)

Specific examples (specific example group G10) of a group represented herein by —N($R_{906}$)($R_{907}$) include: —N(G1)(G1); —N(G2)(G2); —N(G1)(G2); —N(G3)(G3); and —N(G6)(G6).

Herein: G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3; and G6 represents a "substituted or unsubstituted cycloalkyl group" in the specific example group G6.

A plurality of G1 in —N(G1)(G1) are mutually the same or different.

A plurality of G2 in —N(G2)(G2) are mutually the same or different.

A plurality of G3 in —N(G3)(G3) are mutually the same or different.

A plurality of G6 in —N(G6)(G6)) are mutually the same or different.

Halogen Atom

Specific examples (specific example group G11) of "halogen atom" mentioned herein include a fluorine atom, chlorine atom, bromine atom, and iodine atom.

Substituted or Unsubstituted Fluoroalkyl Group

The "substituted or unsubstituted fluoroalkyl group" mentioned herein refers to a group derived by substituting at least one hydrogen atom bonded to at least one of carbon atoms forming an alkyl group in the "substituted or unsubstituted alkyl group" with a fluorine atom, and also includes a group (perfluoro group) derived by substituting all of hydrogen atoms bonded to carbon atoms forming the alkyl group in the "substituted or unsubstituted alkyl group" with fluorine atoms. An "unsubstituted fluoroalkyl group" has, unless otherwise specified herein, 1 to 50, preferably 1 to 30, more preferably 1 to 18 carbon atoms. The "substituted fluoroalkyl group" refers to a group derived by substituting at least one hydrogen atom in a "fluoroalkyl group" with a substituent. It should be noted that the examples of the "substituted fluoroalkyl group" mentioned herein include a group derived by further substituting at least one hydrogen atom bonded to a carbon atom of an alkyl chain of a "substituted fluoroalkyl group" with a substituent, and a group derived by further substituting at least one hydrogen atom of a substituent of the "substituted fluoroalkyl group" with a substituent. Specific examples of the "substituted fluoroalkyl group" include a group derived by substituting at least one hydrogen atom of the "alkyl group" (specific example group G3) with a fluorine atom.

Substituted or Unsubstituted Haloalkyl Group

The "substituted or unsubstituted haloalkyl group" mentioned herein refers to a group derived by substituting at least one hydrogen atom bonded to carbon atoms forming the alkyl group in the "substituted or unsubstituted alkyl group" with a halogen atom, and also includes a group derived by substituting all hydrogen atoms bonded to carbon atoms forming the alkyl group in the "substituted or unsubstituted alkyl group" with halogen atoms. An "unsubstituted haloalkyl group" has, unless otherwise specified herein, 1 to 50, preferably 1 to 30, more preferably 1 to 18 carbon atoms. The "substituted haloalkyl group" refers to a group derived by substituting at least one hydrogen atom in a "haloalkyl group" with a substituent. It should be noted that the examples of the "substituted haloalkyl group" mentioned herein include a group derived by further substituting at least one hydrogen atom bonded to a carbon atom of an alkyl chain of a "substituted haloalkyl group" with a substituent, and a group derived by further substituting at least one hydrogen atom of a substituent of the "substituted haloalkyl group" with a substituent. Specific examples of the "substituted haloalkyl group" include a group derived by substituting at least one hydrogen atom of the "alkyl group" (specific example group G3) with a halogen atom. The haloalkyl group is sometimes referred to as a halogenated alkyl group.

Substituted or Unsubstituted Alkoxy Group

Specific examples of a "substituted or unsubstituted alkoxy group" mentioned herein include a group represented by —O(G3), G3 being the "substituted or unsubstituted alkyl group" in the specific example group G3. An "unsubstituted alkoxy group" has, unless otherwise specified herein, 1 to 50, preferably 1 to 30, more preferably 1 to 18 carbon atoms.

Substituted or Unsubstituted Alkylthio Group

Specific examples of a "substituted or unsubstituted alkylthio group" mentioned herein include a group represented by —S(G3), G3 being the "substituted or unsubstituted alkyl group" in the specific example group G3. An "unsubstituted alkylthio group" has, unless otherwise specified herein, 1 to 50, preferably 1 to 30, more preferably 1 to 18 carbon atoms.

Substituted or Unsubstituted Aryloxy Group

Specific examples of a "substituted or unsubstituted aryloxy group" mentioned herein include a group represented by —O(G1), G1 being the "substituted or unsubstituted aryl group" in the specific example group G1. An "unsubstituted aryloxy group" has, unless otherwise specified herein, 6 to 50, preferably 6 to 30, more preferably 6 to 18 ring carbon atoms.

Substituted or Unsubstituted Arylthio Group

Specific examples of a "substituted or unsubstituted arylthio group" mentioned herein include a group represented by —S(G1), G1 being the "substituted or unsubstituted aryl group" in the specific example group G1. An "unsubstituted arylthio group" has, unless otherwise specified herein, 6 to 50, preferably 6 to 30, more preferably 6 to 18 ring carbon atoms.

Substituted or Unsubstituted Trialkylsilyl Group

Specific examples of a "trialkylsilyl group" mentioned herein include a group represented by —Si(G3)(G3)(G3), G3 being the "substituted or unsubstituted alkyl group" in the specific example group G3. The plurality of G3 in —Si(G3)(G3)(G3) are mutually the same or different. Each of the alkyl groups in the "trialkylsilyl group" has, unless otherwise specified herein, 1 to 50, preferably 1 to 20, more preferably 1 to 6 carbon atoms.

Substituted or Unsubstituted Aralkyl Group

Specific examples of a "substituted or unsubstituted aralkyl group" mentioned herein include a group represented by (G3)-(G1), G3 being the "substituted or unsubstituted alkyl group" in the specific example group G3, G1 being the "substituted or unsubstituted aryl group" in the specific example group G1. Accordingly, the "aralkyl group" is a group derived by substituting a hydrogen atom of the "alkyl group" with a substituent in a form of the "aryl group," which is an example of the "substituted alkyl group." An "unsubstituted aralkyl group," which is an "unsubstituted alkyl group" substituted by an "unsubstituted aryl group," has, unless otherwise specified herein, 7 to 50 carbon atoms, preferably 7 to 30 carbon atoms, more preferably 7 to 18 carbon atoms.

Specific examples of the "substituted or unsubstituted aralkyl group" include a benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

Preferable examples of the substituted or unsubstituted aryl group mentioned herein include, unless otherwise specified herein, a phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, phenanthryl group, pyrenyl group, chrysenyl group, triphenylenyl group, fluorenyl group, 9,9'-spirobifluorenyl group, 9,9-dimethylfluorenyl group, and 9,9-diphenylfluorenyl group.

Preferable examples of the substituted or unsubstituted heterocyclic group mentioned herein include, unless otherwise specified herein, a pyridyl group, pyrimidinyl group, triazinyl group, quinolyl group, isoquinolyl group, quinazolinyl group, benzimidazolyl group, phenanthrolinyl group, carbazolyl group (1-carbazolyl group, 2-carbazolyl group, 3-carbazolyl group, 4-carbazolyl group, or 9-carbazolyl group), benzocarbazolyl group, azacarbazolyl group, diazacarbazolyl group, dibenzofuranyl group, naphthobenzofuranyl group, azadibenzofuranyl group, diazadibenzofuranyl group, dibenzothiophenyl group, naphthobenzothiophenyl group, azadibenzothiophenyl group, diazadibenzothiophenyl group, (9-phenyl)carbazolyl group ((9-phenyl)carbazole-1-yl group, (9-phenyl)carbazole-2-yl group, (9-phenyl)carbazole-3-yl group, or (9-phenyl)carbazole-4-yl group), (9-biphenylyl)carbazolyl group, (9-phenyl)phenylcarbazolyl group, diphenylcarbazole-9-yl group, phenylcarbazole-9-yl group, phenyltriazinyl group, biphenylyltriazinyl group, diphenyltriazinyl group, phenyldibenzofuranyl group, and phenyldibenzothiophenyl group.

The carbazolyl group mentioned herein is, unless otherwise specified herein, specifically a group represented by one of formulae below.

[Formula 7]

(TEMP-Cz1)

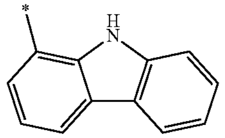

(TEMP-Cz2)

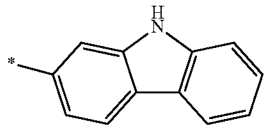

(TEMP-Cz3)

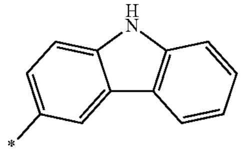

(TEMP-Cz4)

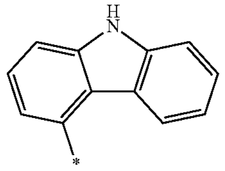

-continued (TEMP-Cz5)

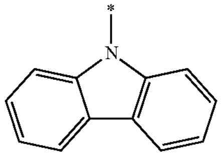

The (9-phenyl)carbazolyl group mentioned herein is, unless otherwise specified herein, specifically a group represented by one of formulae below.

[Formula 8]

(TEMP-Cz6)

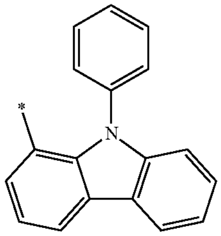

(TEMP-Cz7)

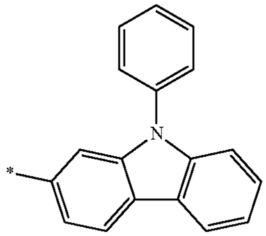

(TEMP-Cz8)

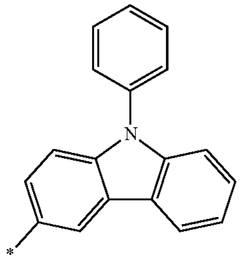

(TEMP-Cz9)

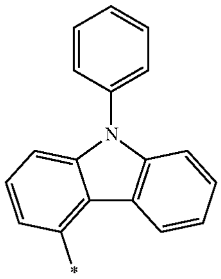

In the formulae (TEMP-Cz1) to (TEMP-Cz9), * represents a bonding position.

The dibenzofuranyl group and dibenzothiophenyl group mentioned herein are, unless otherwise specified herein, each specifically represented by one of formulae below.

[Formula 9]

(TEMP-34)

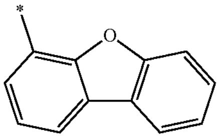

(TEMP-35)

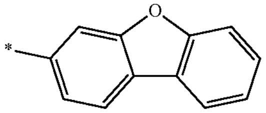

(TEMP-36)

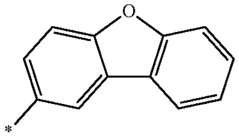

(TEMP-37)

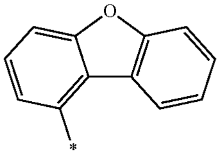

(TEMP-38)

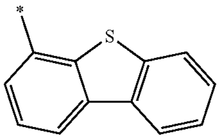

(TEMP-39)

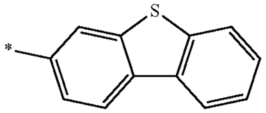

(TEMP-40)

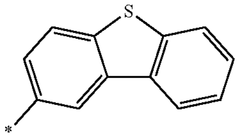

(TEMP-41)

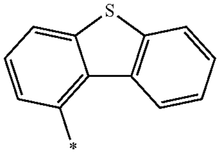

In the formulae (TEMP-34) to (TEMP-41), * represents a bonding position.

Preferable examples of the substituted or unsubstituted alkyl group mentioned herein include, unless otherwise specified herein, a methyl group, ethyl group, propyl group, isopropyl group, n-butyl group, isobutyl group, and t-butyl group.

Substituted or Unsubstituted Arylene Group

The "substituted or unsubstituted arylene group" mentioned herein is, unless otherwise specified herein, a divalent group derived by removing one hydrogen atom on an aryl ring of the "substituted or unsubstituted aryl group." Specific examples of the "substituted or unsubstituted arylene group" (specific example group G12) include a divalent group derived by removing one hydrogen atom on an aryl ring of the "substituted or unsubstituted aryl group" in the specific example group G1.

Substituted or Unsubstituted Divalent Heterocyclic Group

The "substituted or unsubstituted divalent heterocyclic group" mentioned herein is, unless otherwise specified herein, a divalent group derived by removing one hydrogen atom on a heterocyclic ring of the "substituted or unsubstituted heterocyclic group." Specific examples of the "substituted or unsubstituted heterocyclic group" (specific example group G13) include a divalent group derived by removing one hydrogen atom on a heterocyclic ring of the "substituted or unsubstituted heterocyclic group" in the specific example group G2.

Substituted or Unsubstituted Alkylene Group

The "substituted or unsubstituted alkylene group" mentioned herein is, unless otherwise specified herein, a divalent group derived by removing one hydrogen atom on an alkyl ring of the "substituted or unsubstituted alkyl group." Specific examples of the "substituted or unsubstituted alkylene group" (specific example group G14) include a divalent group derived by removing one hydrogen atom on an alkyl ring of the "substituted or unsubstituted alkyl group" in the specific example group G3.

The substituted or unsubstituted arylene group mentioned herein is, unless otherwise specified herein, preferably any one of groups represented by formulae (TEMP-42) to (TEMP-68) below.

[Formula 10]

(TEMP-42)

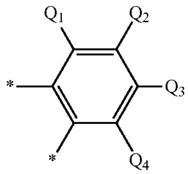

(TEMP-43)

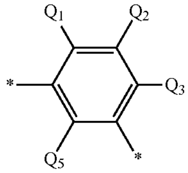

(TEMP-44)

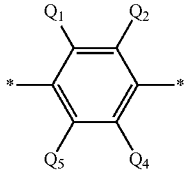

(TEMP-45)

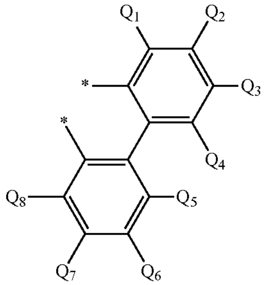

-continued (TEMP-46)

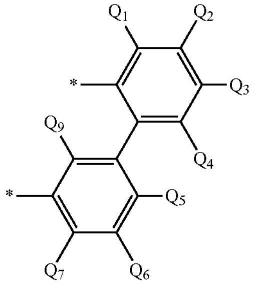

(TEMP-47)

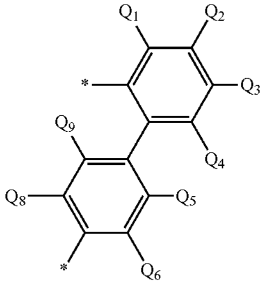

[Formula 11]

(TEMP-48)

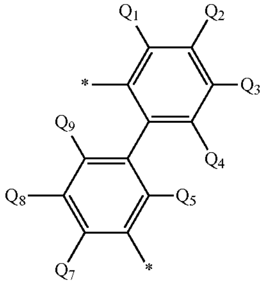

(TEMP-49)

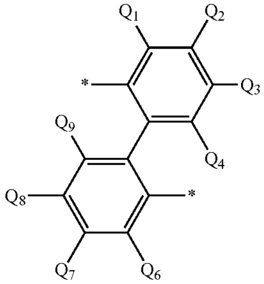

(TEMP-50)

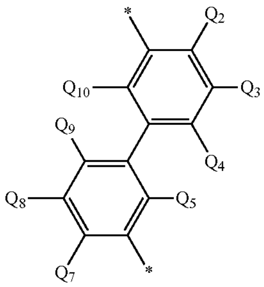

-continued (TEMP-51)

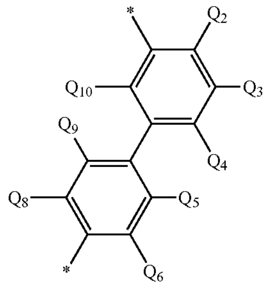

(TEMP-52)

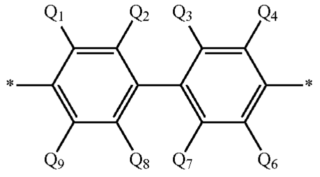

In the formulae (TEMP-42) to (TEMP-52), $Q_1$ to $Q_{10}$ each independently are a hydrogen atom or a substituent.

In the formulae (TEMP-42) to (TEMP-52), * represents a bonding position.

[Formula 12]

(TEMP-53)

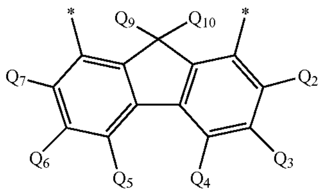

(TEMP-54)

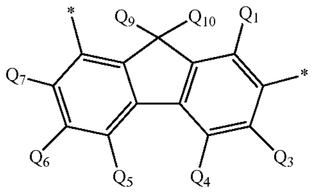

(TEMP-55)

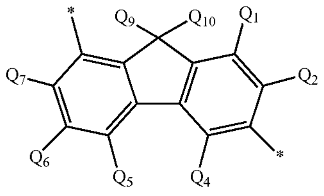

(TEMP-56)

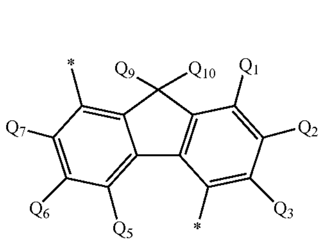

-continued (TEMP-57)

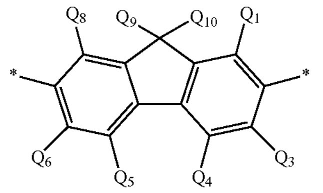

(TEMP-58)

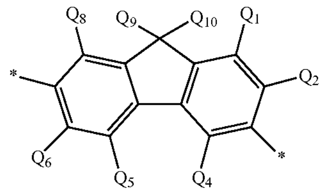

(TEMP-59)

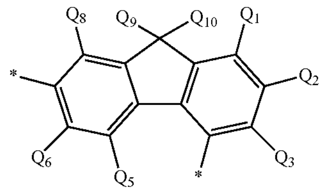

(TEMP-60)

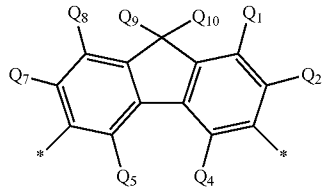

(TEMP-61)

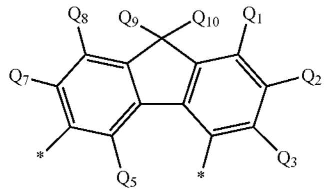

(TEMP-62)

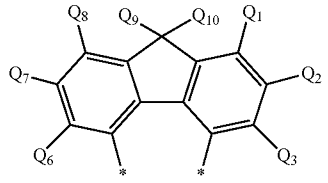

In the formulae (TEMP-53) to (TEMP-62), $Q_1$ to $Q_{10}$ each independently are a hydrogen atom or a substituent.

In the formulae, $Q_9$ and $Q_{10}$ may be mutually bonded through a single bond to form a ring.

In the formulae (TEMP-53) to (TEMP-62), * represents a bonding position.

[Formula 13]

(TEMP-63)

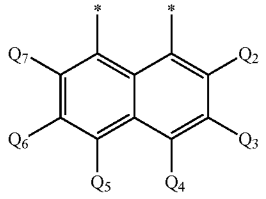

(TEMP-64)

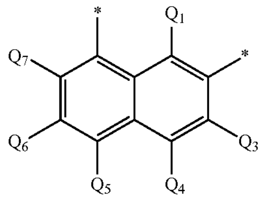

(TEMP-65)

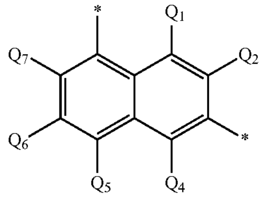

(TEMP-66)

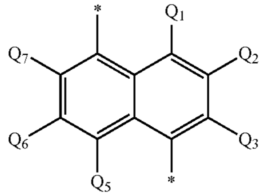

(TEMP-67)

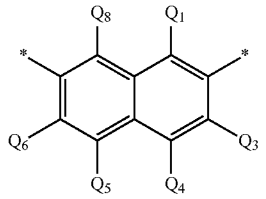

(TEMP-68)

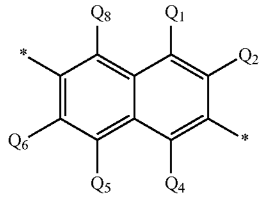

In the formulae (TEMP-63) to (TEMP-68), $Q_1$ to $Q_8$ each independently are a hydrogen atom or a substituent.

In the formulae (TEMP-63) to (TEMP-68), * represents a bonding position.

The substituted or unsubstituted divalent heterocyclic group mentioned herein is, unless otherwise specified herein, preferably a group represented by any one of formulae (TEMP-69) to (TEMP-102) below.

[Formula 14]

(TEMP-69)

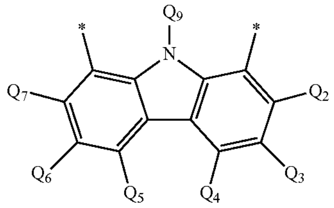

(TEMP-70)

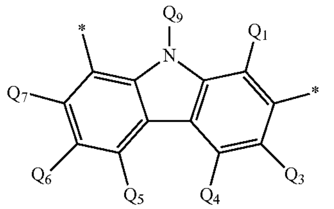

(TEMP-71)

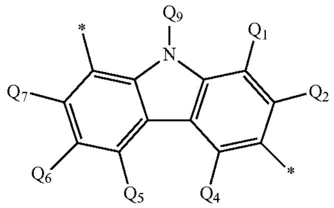

(TEMP-72)

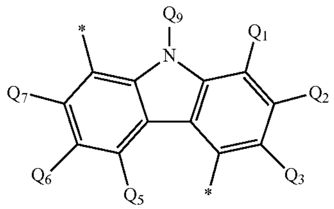

(TEMP-73)

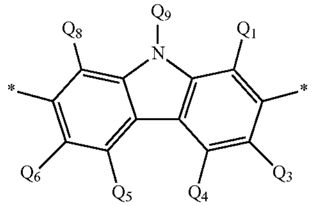

(TEMP-74)

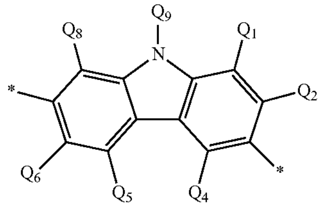

[Formula 15]

(TEMP-75)

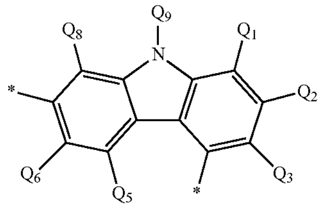

-continued
(TEMP-76)
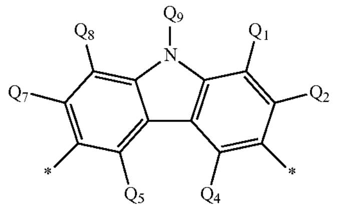
(TEMP-77)
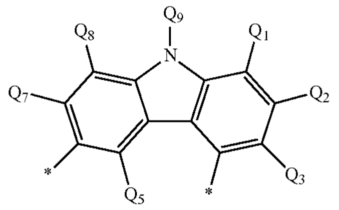
(TEMP-78)
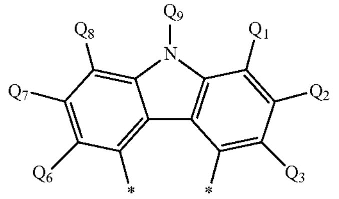
(TEMP-79)
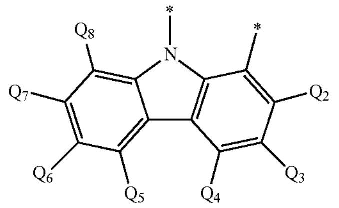
(TEMP-80)
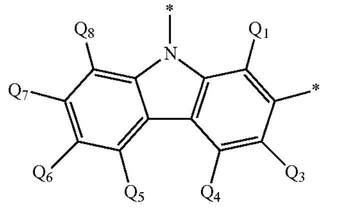
[Formula 16]
(TEMP-81)
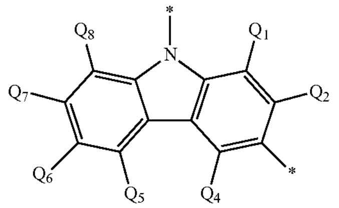
(TEMP-82)
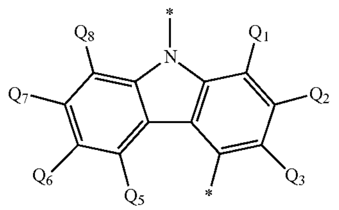
In the formulae (TEMP-69) to (TEMP-82), $Q_1$ to $Q_9$ each independently are a hydrogen atom or a substituent.
[Formula 17]
(TEMP-83)
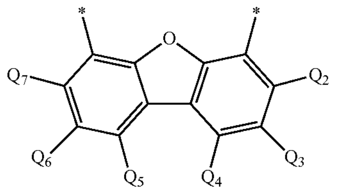
(TEMP-84)
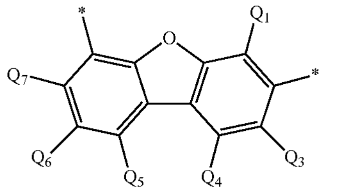
(TEMP-85)
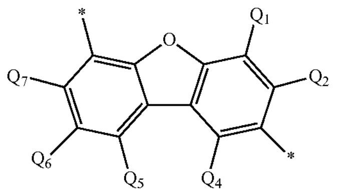
(TEMP-86)
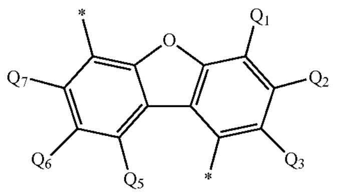
(TEMP-87)
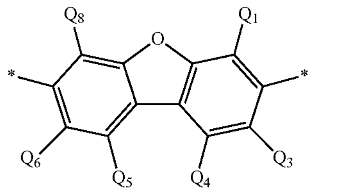
(TEMP-88)
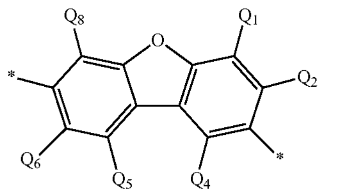
[Formula 18]
(TEMP-89)
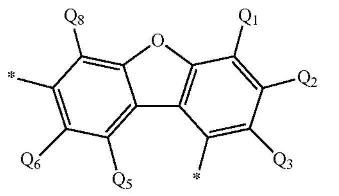

-continued (TEMP-90)

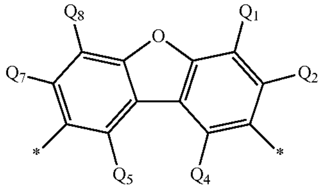

(TEMP-91)

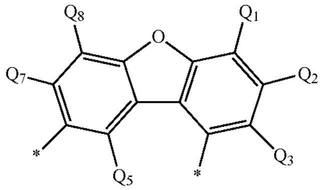

(TEMP-92)

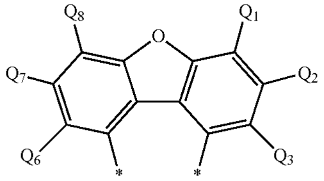

[Formula 19]

(TEMP-93)

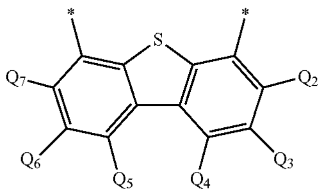

(TEMP-94)

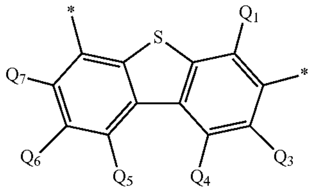

(TEMP-95)

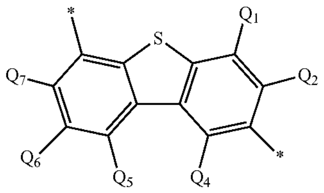

(TEMP-96)

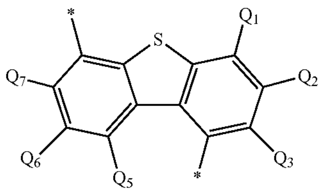

(TEMP-97)

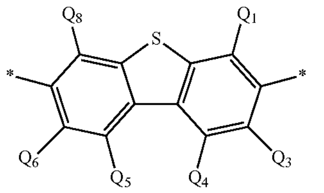

-continued (TEMP-98)

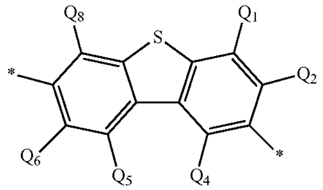

[Formula 20]

(TEMP-99)

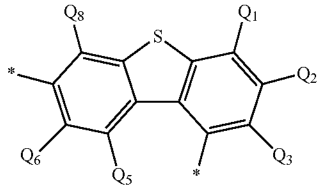

(TEMP-100)

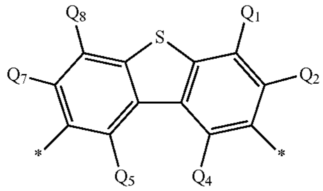

(TEMP-101)

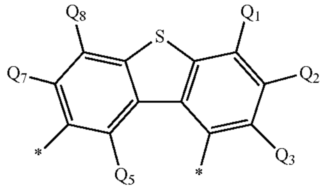

(TEMP-102)

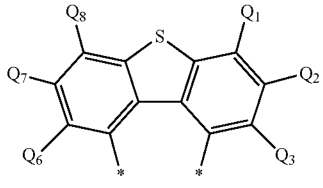

In the formulae (TEMP-83) to (TEMP-102), $Q_1$ to $Q_8$ each independently are a hydrogen atom or a substituent.

The substituent mentioned herein has been described above.

Instance of "Bonded to Form Ring"

Instances where "at least one combination of adjacent two or more (of . . . ) are mutually bonded to form a substituted or unsubstituted monocyclic ring, mutually bonded to form a substituted or unsubstituted fused ring, or not mutually bonded" mentioned herein refer to instances where "at least one combination of adjacent two or more (of . . . ) are mutually bonded to form a substituted or unsubstituted monocyclic ring, "at least one combination of adjacent two or more (of . . . ) are mutually bonded to form a substituted or unsubstituted fused ring," and "at least one combination of adjacent two or more (of . . . ) are not mutually bonded."

Instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (these instances will be sometimes collectively referred to as an instance of "bonded to form a ring"

hereinafter) will be described below. An anthracene compound having a basic skeleton in a form of an anthracene ring and represented by a formula (TEMP-103) below will be used as an example for the description.

[Formula 21]

(TEMP-103)

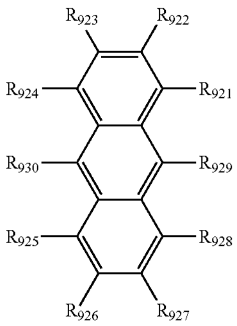

For instance, when "at least one combination of adjacent two or more of" $R_{921}$ to $R_{930}$ "are mutually bonded to form a ring," the pair of adjacent ones of $R_{921}$ to $R_{930}$ (i.e. the combination at issue) is a pair of $R_{921}$ and a pair of $R_{922}$, $R_{922}$ and $R_{923}$, a pair of $R_{923}$ and $R_{924}$, a pair of $R_{924}$ and $R_{930}$, a pair of $R_{930}$ and $R_{925}$, a pair of $R_{925}$ and $R_{926}$, a pair of $R_{926}$ and $R_{927}$, a pair of $R_{927}$ and $R_{928}$, a pair of $R_{928}$ and $R_{929}$, or a pair of $R_{929}$ and $R_{921}$.

The term "at least one combination" means that two or more of the above combinations of adjacent two or more of R921 to R930 may simultaneously form rings. For instance, when $R_{921}$ and $R_{922}$ are mutually bonded to form a ring $Q_A$ and $R_{925}$ and $R_{926}$ are simultaneously mutually bonded to form a ring $Q_B$, the anthracene compound represented by the formula (TEMP-103) is represented by a formula (TEMP-104) below.

[Formula 22]

(TEMP-104)

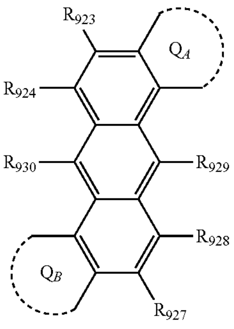

The instance where the "combination of adjacent two or more" form a ring means not only an instance where the "two" adjacent components are bonded but also an instance where adjacent "three or more" are bonded. For instance, $R_{921}$ and $R_{922}$ are mutually bonded to form a ring $Q_A$ and $R_{922}$, $R_{923}$ are mutually bonded to form a ring $Q_C$, and mutually adjacent three components ($R_{921}$, $R_{922}$ and $R_{923}$) are mutually bonded to form a ring fused to the anthracene basic skeleton. In this case, the anthracene compound represented by the formula (TEMP-103) is represented by a formula (TEMP-105) below. In the formula (TEMP-105) below, the ring $Q_A$ and the ring $Q_C$ share $R_{922}$.

[Formula 23]

(TEMP-105)

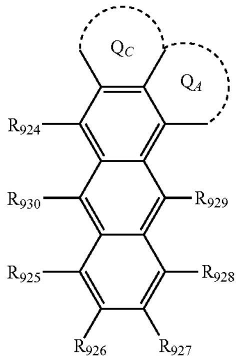

The formed "monocyclic ring" or "fused ring" may be, in terms of the formed ring in itself, a saturated ring or an unsaturated ring. When the "combination of adjacent two" form a "monocyclic ring" or a "fused ring," the "monocyclic ring" or "fused ring" may be a saturated ring or an unsaturated ring. For instance, the ring $Q_A$ and the ring $Q_B$ formed in the formula (TEMP-104) are each independently a "monocyclic ring" or a "fused ring." Further, the ring $Q_A$ and the ring $Q_C$ formed in the formula (TEMP-105) are each a "fused ring." The ring $Q_A$ and the ring $Q_C$ in the formula (TEMP-105) are fused to form a fused ring. When the ring $Q_A$ in the formula (TMEP-104) is a benzene ring, the ring $Q_A$ is a monocyclic ring. When the ring $Q_A$ in the formula (TMEP-104) is a naphthalene ring, the ring $Q_A$ is a fused ring.

The "unsaturated ring" represents an aromatic hydrocarbon ring or an aromatic heterocycle. The "saturated ring" represents an aliphatic hydrocarbon ring or a non-aromatic heterocycle.

Specific examples of the aromatic hydrocarbon ring include a ring formed by terminating a bond of a group in the specific example of the specific example group G1 with a hydrogen atom.

Specific examples of the aromatic heterocyclic ring include a ring formed by terminating a bond of an aromatic heterocyclic group in the specific example of the specific example group G2 with a hydrogen atom.

Specific examples of the aliphatic hydrocarbon ring include a ring formed by terminating a bond of a group in the specific example of the specific example group G6 with a hydrogen atom.

The phrase "to form a ring" herein means that a ring is formed only by a plurality of atoms of a basic skeleton, or by a combination of a plurality of atoms of the basic skeleton and one or more optional atoms. For instance, the ring $Q_A$ formed by mutually bonding $R_{921}$ and $R_{922}$ shown in the formula (TEMP-104) is a ring formed by a carbon atom of the anthracene skeleton bonded with $R_{921}$, a carbon atom of the anthracene skeleton bonded with $R_{922}$, and one or more optional atoms. Specifically, when the ring $Q_A$ is a monocyclic unsaturated ring formed by $R_{921}$ and $R_{922}$, the ring formed by a carbon atom of the anthracene skeleton bonded with $R_{921}$, a carbon atom of the anthracene skeleton bonded with $R_{922}$, and four carbon atoms is a benzene ring.

The "optional atom" is, unless otherwise specified herein, preferably at least one atom selected from the group consisting of a carbon atom, nitrogen atom, oxygen atom, and sulfur atom. A bond of the optional atom (e.g. a carbon atom and a nitrogen atom) not forming a ring may be terminated by a hydrogen atom or the like or may be substituted by an "optional substituent" described later. When the ring includes an optional element other than carbon atom, the resultant ring is a heterocycle.

The number of "one or more optional atoms" forming the monocyclic ring or fused ring is, unless otherwise specified herein, preferably in a range from 2 to 15, more preferably in a range from 3 to 12, further preferably in a range from 3 to 5.

Unless otherwise specified herein, the ring, which may be a "monocyclic ring" or "fused ring," is preferably a "monocyclic ring."

Unless otherwise specified herein, the ring, which may be a "saturated ring" or "unsaturated ring," is preferably an "unsaturated ring."

Unless otherwise specified herein, the "monocyclic ring" is preferably a benzene ring.

Unless otherwise specified herein, the "unsaturated ring" is preferably a benzene ring.

When "at least one combination of adjacent two or more" (of . . . ) are "mutually bonded to form a substituted or unsubstituted monocyclic ring" or "mutually bonded to form a substituted or unsubstituted fused ring," unless otherwise specified herein, at least one combination of adjacent two or more of components are preferably mutually bonded to form a substituted or unsubstituted "unsaturated ring" formed of a plurality of atoms of the basic skeleton, and 1 to 15 atoms of at least one element selected from the group consisting of carbon, nitrogen, oxygen and sulfur.

When the "monocyclic ring" or the "fused ring" has a substituent, the substituent is the substituent described in later-described "optional substituent." When the "monocyclic ring" or the "fused ring" has a substituent, specific examples of the substituent are the substituents described in the above under the subtitle "Substituents Mentioned Herein."

When the "saturated ring" or the "unsaturated ring" has a substituent, the substituent is, for instance, the substituent described in later-described "optional substituent." When the "monocyclic ring" or the "fused ring" has a substituent, specific examples of the substituent are the substituents described in the above under the subtitle "Substituents Mentioned Herein."

The above is the description for the instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (sometimes referred to as an instance "bonded to form a ring".

Substituent for Substituted or Unsubstituted Group

In an exemplary embodiment herein, a substituent for the substituted or unsubstituted group (sometimes referred to as an "optional substituent" hereinafter) is, for instance, a group selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, an unsubstituted aryl group having 6 to 50 ring carbon atoms, and an unsubstituted heterocyclic group having 5 to 50 ring atoms.

Herein, $R_{901}$ to $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when two or more $R_{901}$ are present, the two or more $R_{901}$ are mutually the same or different;

when two or more $R_{902}$ are present, the two or more $R_{902}$ are mutually the same or different;

when two or more $R_{903}$ are present, the two or more $R_{903}$ are mutually the same or different;

when two or more $R_{904}$ are present, the two or more $R_{904}$ are mutually the same or different;

when two or more $R_{905}$ are present, the two or more $R_{905}$ are mutually the same or different;

when two or more $R_{906}$ are present, the two or more $R_{906}$ are mutually the same or different; and when two or more $R_{907}$ are present, the two or more $R_{907}$ are mutually the same or different.

In an exemplary embodiment, a substituent for the substituted or unsubstituted group is selected from the group consisting of an alkyl group having 1 to 50 carbon atoms, an aryl group having 6 to 50 ring carbon atoms, and a heterocyclic group having 5 to 50 ring atoms.

In an exemplary embodiment, a substituent for the substituted or unsubstituted group is selected from the group consisting of an alkyl group having 1 to 18 carbon atoms, an aryl group having 6 to 18 ring carbon atoms, and a heterocyclic group having 5 to 18 ring atoms.

Specific examples of the above optional substituent are the same as the specific examples of the substituent described in the above under the subtitle "Substituent Mentioned Herein."

Unless otherwise specified herein, adjacent ones of the optional substituents may form a "saturated ring" or an "unsaturated ring," preferably a substituted or unsubstituted saturated five-membered ring, a substituted or unsubstituted saturated six-membered ring, a substituted or unsubstituted saturated five-membered ring, or a substituted or unsubstituted unsaturated six-membered ring, more preferably a benzene ring.

Unless otherwise specified herein, the optional substituent may further include a substituent. Examples of the substituent for the optional substituent are the same as the examples of the optional substituent.

Herein, numerical ranges represented by "AA to BB" represents a range whose lower limit is the value (AA) recited before "to" and whose upper limit is the value (BB) recited after "to."

First Exemplary Embodiment

Compound

A compound according to a first exemplary embodiment is a compound represented by a formula (2) below and having at least one group represented by a formula (20) below.

[Formula 24]

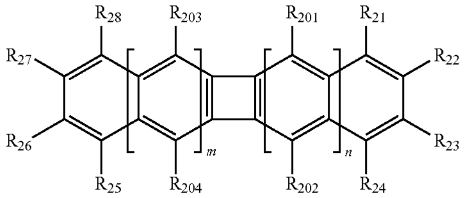

(2)

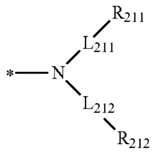

(20)

In the formula (2):

m is 0, 1, 2 or 3;

n is 0, 1, 2 or 3;

m+n is an integer of 1 or more;

at least one combination of adjacent two or more of $R_{21}$ to $R_{28}$ and $R_{201}$ to $R_{204}$ are mutually bonded to form a substituted or unsubstituted monocyclic ring, mutually bonded to form a substituted or unsubstituted fused ring, or not mutually bonded;

$R_{21}$ to $R_{28}$ and $R_{201}$ to $R_{204}$ not forming the monocyclic ring and not forming the fused ring are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, a substituted or unsubstituted heterocyclic group having 5 to 50 ring atoms, or the group represented by the formula (20);

when n is 2 or 3, at least two $R_{201}$ are the same or different, and at least two $R_{202}$ are the same or different;

when m is 2 or 3, at least two $R_{203}$ are the same or different, and at least two $R_{204}$ are the same or different;

at least one of $R_{21}$ to $R_{28}$ or $R_{201}$ to $R_{204}$ is the group represented by the formula (20);

in the group represented by the formula (20), a combination of $R_{211}$ and $R_{212}$ are mutually bonded to form a substituted or unsubstituted monocyclic ring, mutually bonded to form a substituted or unsubstituted fused ring, or not mutually bonded;

$R_{211}$ and $R_{212}$ not forming the monocyclic ring and not forming the fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{211}$ and $L_{212}$ are each independently a single bond, a substituted or unsubstituted arylene group having 6 to 50 ring carbon atoms, or a substituted or unsubstituted divalent heterocyclic group having 5 to 50 ring atoms; and

* in the formula (20) represents a bonding position to a structure of the compound represented by the formula (2).

In the compound represented by the formula (2):

$R_{901}$ to $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when two or more $R_{901}$ are present, the two or more $R_{901}$ are mutually the same or different;

when two or more $R_{902}$ are present, the two or more $R_{902}$ are mutually the same or different;

when two or more $R_{903}$ are present, the two or more $R_{903}$ are mutually the same or different;

when two or more $R_{904}$ are present, the two or more $R_{904}$ are mutually the same or different;

when two or more $R_{905}$ are present, the two or more $R_{905}$ are mutually the same or different;

when two or more $R_{906}$ are present, the two or more $R_{906}$ are mutually the same or different; and when two or more $R_{907}$ are present, the two or more $R_{907}$ are mutually the same or different.

Herein, examples of an aryl group having 6 to 50 ring carbon atoms include a tetraphenylenyl group, hexahydropyrenyl group, and indacenyl group in addition to the groups described in the section of "Definitions" herein.

Herein, examples of a heterocyclic group having 5 to 50 ring atoms include a benzodioxolyl group and a benzodioxynil group in addition to the groups described in the section of "Definitions" herein.

In the compound according to the exemplary embodiment, it is preferable that m is 1 and n is 1.

When m is 1 and n is 1, the compound represented by the formula (2) is a compound represented by a formula (22) below.

In the exemplary embodiment, the compound represented by the formula (2) is also preferably the compound represented by the formula (22) below.

[Formula 25]

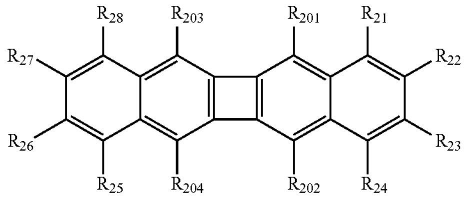

(22)

In the formula (22):

$R_{21}$ to $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, a substituted or unsubstituted heterocyclic group having 5 to 50 ring atoms, or the group represented by the formula (20);

at least one of $R_{21}$ to $R_{28}$ or $R_{201}$ to $R_{204}$ is the group represented by the formula (20); and in the compound represented by the formula (22), $R_{901}$ to $R_{907}$ are each independently the same as defined in the formula (2).

When m is 0 and n is 1, the compound represented by the formula (2) is a compound represented by a formula (22A) below.

[Formula 26]

(22A)

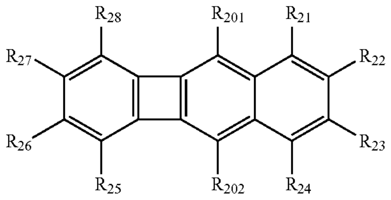

When m is 1 and n is 0, the compound represented by the formula (2) is a compound represented by a formula (22B) below.

[Formula 27]

(22B)

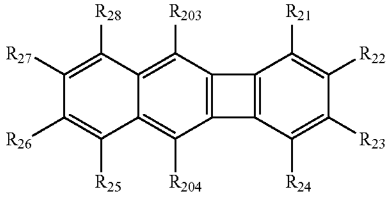

When m is 0 and n is 2, the compound represented by the formula (2) is a compound represented by a formula (22C) below.

[Formula 28]

(22C)

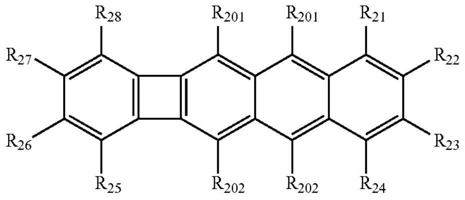

When m is 2 and n is 0, the compound represented by the formula (2) is a compound represented by a formula (22D) below.

[Formula 29]

(22D)

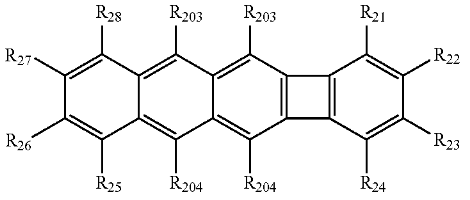

When m is 1 and n is 2, the compound represented by the formula (2) is a compound represented by a formula (22E) below.

[Formula 30]

(22E)

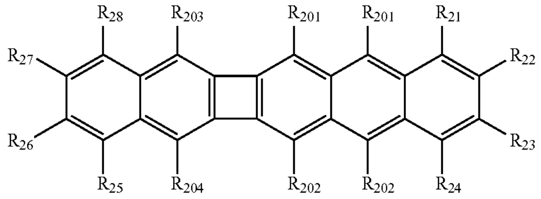

When m is 2 and n is 1, the compound represented by the formula (2) is a compound represented by a formula (22F) below.

[Formula 31]

(22F)

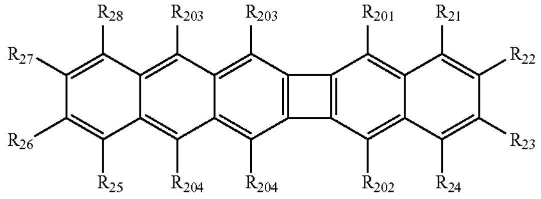

In the formulae (22A) to (22F):

$R_{21}$ to $R_{28}$ and $R_{201}$ to $R_{204}$ each represent the same as $R_{21}$ to $R_{28}$ and $R_{201}$ to $R_{204}$ in the formula (2);

when a plurality of $R_{201}$ are present, the plurality of $R_{201}$ are mutually the same or different;

when a plurality of $R_{202}$ are present, the plurality of $R_{202}$ are mutually the same or different;

when a plurality of $R_{203}$ are present, the plurality of $R_{203}$ are mutually the same or different;

when a plurality of $R_{204}$ are present, the plurality of $R_{204}$ are mutually the same or different; and at least one of $R_{21}$ to $R_{28}$ or $R_{201}$ to $R_{204}$ is the group represented by the formula (20).

The compound according to the exemplary embodiment preferably has at least one group selected from the group consisting of a group represented by a formula (20a) below and a group represented by a formula (20b) below.

[Formula 32]

(20a)

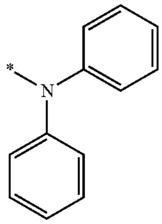

(20b)

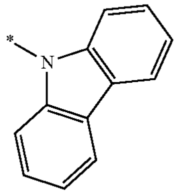

In the formulae (20a) and (20b), * each independently represents a bonding position to a structure of the compound represented by the formula (2).

The group represented by the formula (20b) is an example of the group represented by the formula (20) in which a combination of $R_{211}$ and $R_{212}$ are bonded to each other to form a substituted or unsubstituted fused ring.

Other examples of the group represented by the formula (20) in which a combination of $R_{211}$ and $R_{212}$ are bonded to each other to form a substituted or unsubstituted fused ring include a group represented by a formula (20c) and a group represented by a formula (20d).

[Formula 33]

(20c)

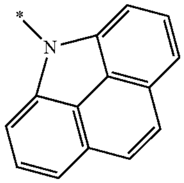

(20d)

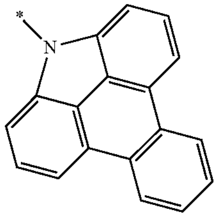

In the compound according to the exemplary embodiment, $L_{211}$ and $L_{212}$ are also preferably a single bond.

The compound represented by the formula (2) is also preferably a compound represented by a formula (23) below.

[Formula 34]

(23)

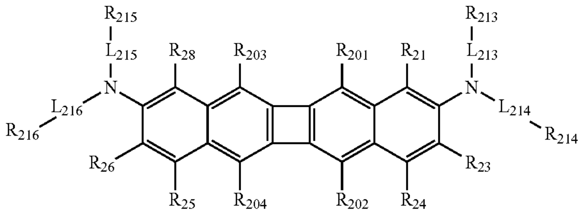

In the formula (23):

$R_{21}$, $R_{23}$, $R_{24}$ to $R_{26}$, $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, a substituted or unsubstituted heterocyclic group having 5 to 50 ring atoms, or the group represented by the formula (20);

a combination of $R_{213}$ and $R_{214}$ are mutually bonded to form a substituted or unsubstituted monocyclic ring, mutually bonded to form a substituted or unsubstituted fused ring, or not mutually bonded;

a combination of $R_{215}$ and $R_{216}$ are mutually bonded to form a substituted or unsubstituted monocyclic ring, mutually bonded to form a substituted or unsubstituted fused ring, or not mutually bonded;

$R_{213}$ to $R_{216}$ not forming the monocyclic ring and not forming the fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{213}$ to $L_{216}$ are each independently a single bond, a substituted or unsubstituted arylene group having 6 to 50 ring carbon atoms, or a substituted or unsubstituted divalent heterocyclic group having 5 to 50 ring atoms; and in the compound represented by the formula (23), $R_{901}$ to $R_{907}$ are each independently the same as defined in the formula (2).

In the compound according to the exemplary embodiment, $L_{213}$ to $L_{216}$ are also preferably a single bond.

The compound represented by the formula (23) is also preferably a compound represented by a formula (231) below.

[Formula 35]

(231)

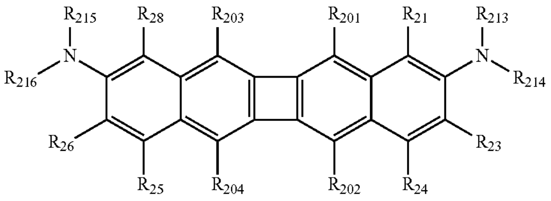

In the compounds represented by the formulae (23) and (231), it is also preferable that $R_{213}$ and $R_{214}$ are not bonded to each other, $R_{215}$ and $R_{216}$ are not bonded to each other, and $R_{213}$ to $R_{216}$ not forming the monocyclic ring and not forming the fused ring are each independently a substituted or unsubstituted aryl group having 6 to 50 ring carbon atoms.

In the compound according to the exemplary embodiment, $R_{213}$ to $R_{216}$ are preferably a substituted or unsubstituted phenyl group.

In the compounds represented by the formulae (23) and (231), when $R_{213}$ to $R_{216}$ are each a substituted or unsubstituted phenyl group, the compounds represented by the formulae (23) and (231) are represented by a formula (23A) and a formula (231A) below, respectively.

[Formula 36]

(23A)

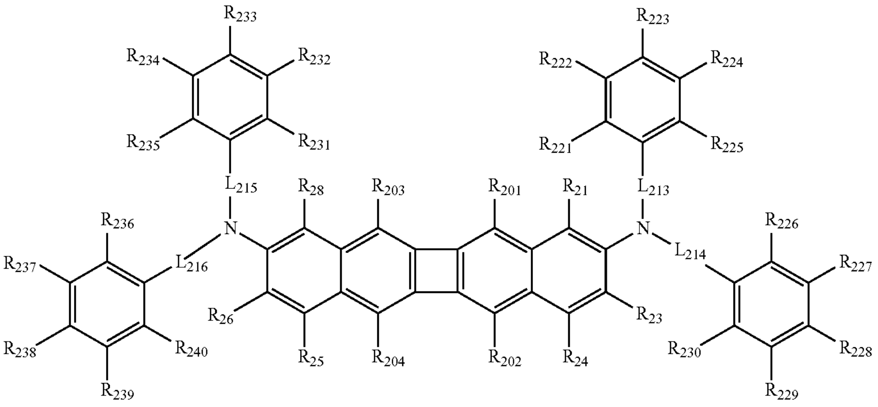

[Formula 37]

(231A)

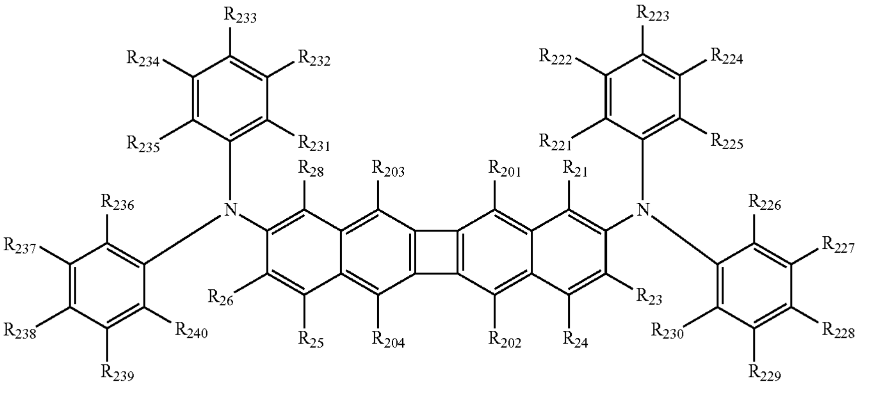

In the formula (231):

$R_{21}$, $R_{23}$, $R_{24}$ to $R_{26}$, $R_{28}$ and $R_{201}$ to $R_{204}$ each independently represent the same as $R_{21}$, $R_{23}$, $R_{24}$ to $R_{26}$, $R_{28}$ and $R_{201}$ to $R_{204}$ in the formula (23); and $R_{213}$ to $R_{216}$ each independently represent the same as $R_{213}$ to $R_{216}$ in the formula (23).

In the compounds represented by the formulae (23) and (231), $R_{213}$ and $R_{214}$ are preferably not bonded to each other.

In the compounds represented by the formulae (23) and (231), $R_{215}$ and $R_{216}$ are also preferably not bonded to each other.

In the formulae (23A) and (231A):

$R_{21}$, $R_{23}$, $R_{24}$ to $R_{26}$, $R_{28}$ and $R_{201}$ to $R_{204}$ each independently represent the same as $R_{21}$, $R_{23}$, $R_{24}$ to $R_{26}$, $R_{28}$ and $R_{201}$ to $R_{204}$ in the formula (23);

$L_{213}$ to $L_{216}$ each independently represent the same as $L_{213}$ to $L_{216}$ in the formula (23); and $R_{221}$ to $R_{240}$ are each independently a hydrogen atom, an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by $-Si(R_{901})(R_{902})(R_{903})$, a group represented by $-O-$ $(R_{904})$, a group represented by —S—$(R_{905})$, a group represented by —N$(R_{906})(R_{907})$, a halogen atom, a cyano group, a nitro group, an unsubstituted aryl group having 6 to 50 ring carbon atoms, or a substituted or unsubstituted heterocyclic group having 5 to 50 ring atoms.

The compound represented by the formula (2) is also preferably a compound represented by a formula (24) below.

[Formula 38]

(24)

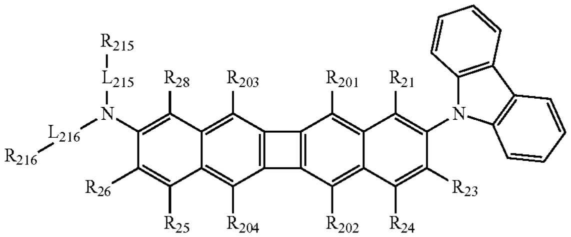

In the formula (24):

$R_{21}$, $R_{23}$, $R_{24}$ to $R_{26}$, $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si$(R_{901})(R_{902})(R_{903})$, a group represented by —O—$(R_{904})$, a group represented by —S—$(R_{905})$, a group represented by —N$(R_{906})(R_{907})$, a substituted or unsubstituted aryl group having 6 to 50 ring carbon atoms, a substituted or unsubstituted heterocyclic group having 5 to 50 ring atoms, or the group represented by the formula (20);

a combination of $R_{215}$ and $R_{216}$ are mutually bonded to form a substituted or unsubstituted monocyclic ring, mutually bonded to form a substituted or unsubstituted fused ring, or not mutually bonded;

$R_{215}$ and $R_{216}$ not forming the monocyclic ring and not forming the fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{215}$ and $L_{216}$ are each independently a single bond, a substituted or unsubstituted arylene group having 6 to 50 ring carbon atoms, or a substituted or unsubstituted divalent heterocyclic group having 5 to 50 ring atoms; and in the compound represented by the formula (24), $R_{901}$ to $R_{907}$ are each independently the same as defined in the formula (2).

The compound represented by the formula (24) is also preferably a compound represented by a formula (241) below.

[Formula 39]

(241)

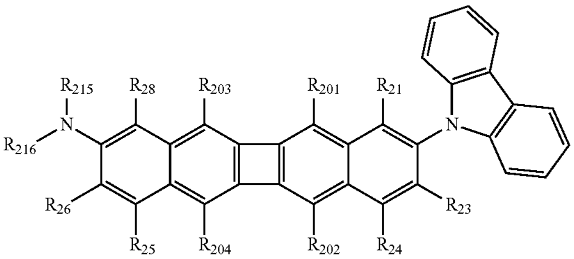

In the formula (241):

$R_{21}$, $R_{23}$, $R_{24}$ to $R_{26}$, $R_{28}$ and $R_{201}$ to $R_{204}$ each independently represent the same as $R_{21}$, $R_{23}$, $R_{24}$ to $R_{26}$, $R_{28}$ and $R_{201}$ to $R_{204}$ in the formula (24); and $R_{215}$ and $R_{216}$ each independently represent the same as $R_{215}$ and $R_{216}$ in the formula (24).

In the compounds represented by the formulae (24) and (241), $R_{215}$ and $R_{216}$ are also preferably not bonded to each other.

In the compounds represented by the formulae (24) and (241), it is also preferable that $R_{215}$ and $R_{216}$ are not bonded to each other, and $R_{215}$ and $R_{216}$ not forming the monocyclic ring and not forming the fused ring are each independently a substituted or unsubstituted aryl group having 6 to 50 ring carbon atoms.

In the compound according to the exemplary embodiment, $R_{215}$ and $R_{216}$ are preferably a substituted or unsubstituted phenyl group.

In the compounds represented by the formulae (24) and (241), when $R_{215}$ and $R_{216}$ are each a substituted or unsubstituted phenyl group, the compounds represented by the formulae (24) and (241) are represented by a formula (24A) and a formula (241A) below, respectively.

[Formula 40]

(24A)

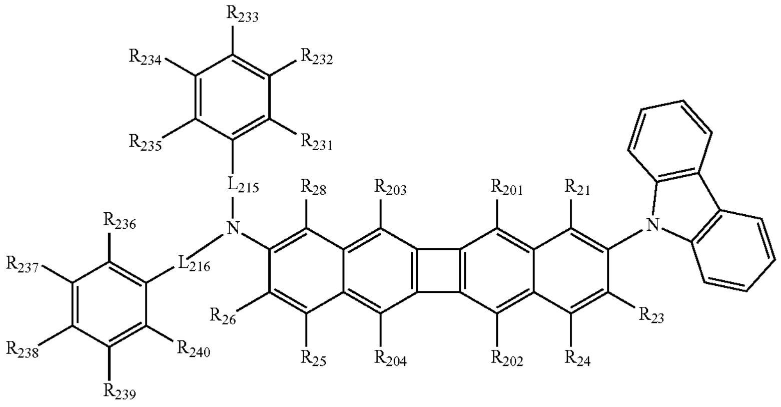

[Formula 41]

(241A)

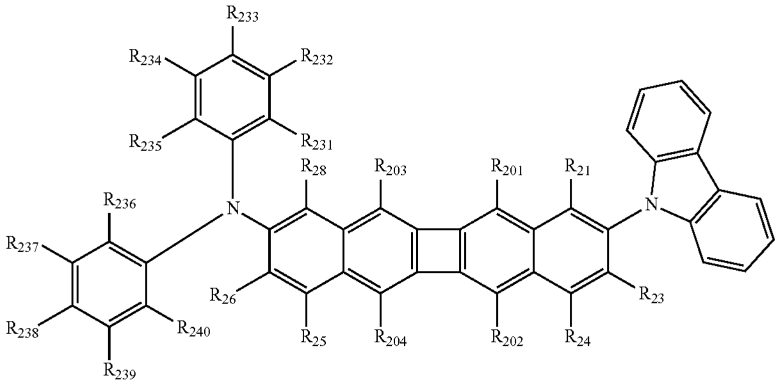

In the formulae (24A) and (241A):

$R_{21}$, $R_{23}$, $R_{24}$ to $R_{26}$, $R_{28}$ and $R_{201}$ to $R_{204}$ each independently represent the same as $R_{21}$, $R_{23}$, $R_{24}$ to $R_{26}$, $R_{28}$ and $R_{201}$ to $R_{204}$ in the formula (24); and $L_{215}$ and $L_{216}$ each independently represent the same as $L_{215}$ and $L_{216}$ in the formula (24);

$R_{231}$ to $R_{240}$ are each independently a hydrogen atom, an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, an unsubstituted aryl group having 6 to 50 ring carbon atoms, or a substituted or unsubstituted heterocyclic group having 5 to 50 ring atoms.

The compound represented by the formula (2) is also preferably a compound represented by a formula (25) below.

[Formula 42]

(25)

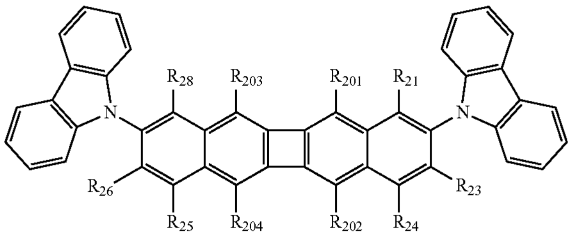

In the formula (25):

$R_{21}$, $R_{23}$, $R_{24}$ to $R_{26}$, $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, a substituted or unsubstituted heterocyclic group having 5 to 50 ring atoms, or the group represented by the formula (20); and in the compound represented by the formula (25), $R_{901}$ to $R_{907}$ are each independently the same as defined in the formula (2).

In the compound according to the exemplary embodiment, $R_{21}$, $R_{23}$, $R_{24}$ to $R_{26}$, $R_{28}$ and $R_{201}$ to $R_{204}$ are preferably each independently a hydrogen atom, a halogen atom, a substituted or unsubstituted alkyl group having 1 to 50 carbon atoms, a substituted or unsubstituted cycloalkyl group having 3 to 50 ring carbon atoms, or a group represented by —Si($R_{901}$)($R_{902}$)($R_{903}$).

The compound represented by the formula (2) is also preferably a compound represented by a formula (26) below.

[Formula 43]

(26)

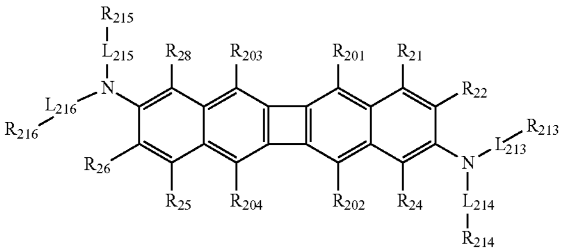

In the formula (26):

$R_{21}$, $R_{22}$, $R_{24}$ to $R_{26}$, $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, a substituted or unsubstituted heterocyclic group having 5 to 50 ring atoms, or the group represented by the formula (20);

a combination of $R_{213}$ and $R_{214}$ are mutually bonded to form a substituted or unsubstituted monocyclic ring, mutually bonded to form a substituted or unsubstituted fused ring, or not mutually bonded;

a combination of $R_{215}$ and $R_{216}$ are mutually bonded to form a substituted or unsubstituted monocyclic ring, mutually bonded to form a substituted or unsubstituted fused ring, or not mutually bonded;

$R_{213}$ to $R_{216}$ not forming the monocyclic ring and not forming the fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{213}$ to $L_{216}$ are each independently a single bond, a substituted or unsubstituted arylene group having 6 to 50 ring carbon atoms, or a substituted or unsubstituted divalent heterocyclic group having 5 to 50 ring atoms; and $R_{901}$ to $R_{907}$ in the compound represented by the formula (26) are each independently the same as defined in the formula (2).

The compound represented by the formula (26) is also preferably a compound represented by a formula (261) below.

[Formula 44]

(261)

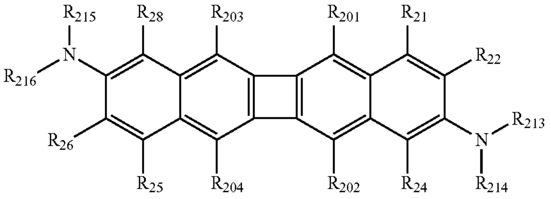

In the formula (261):

$R_{21}$, $R_{22}$, $R_{24}$ to $R_{26}$, $R_{28}$ and $R_{201}$ to $R_{204}$ each independently represent the same as $R_{21}$, $R_{22}$, $R_{24}$ to $R_{26}$, $R_{28}$ and $R_{201}$ to $R_{204}$ in the formula (26); and $R_{213}$ to $R_{216}$ each independently represent the same as $R_{213}$ to $R_{216}$ in the formula (26).

In the compounds represented by the formulae (26) and (261), it is also preferable that $R_{213}$ and $R_{214}$ are not bonded to each other.

In the compounds represented by the formulae (26) and (261), it is also preferable that $R_{215}$ and $R_{216}$ are not bonded to each other.

In the compounds represented by the formulae (26) and (261), it is also preferable that $R_{213}$ and $R_{214}$ are not bonded to each other, $R_{215}$ and $R_{216}$ are not bonded to each other, $R_{213}$ to $R_{216}$ not forming the monocyclic ring and not forming the fused ring are each independently a substituted or unsubstituted aryl group having 6 to 50 ring carbon atoms.

In the compound according to the exemplary embodiment, $R_{213}$ to $R_{216}$ are preferably a substituted or unsubstituted phenyl group.

In the compounds represented by the formulae (26) and (261), when $R_{213}$ to $R_{216}$ are a substituted or unsubstituted phenyl group, the compounds represented by the formulae (26) and (261) are represented by a formula (26A) and a formula (261A) below, respectively.

[Formula 45]

(26A)

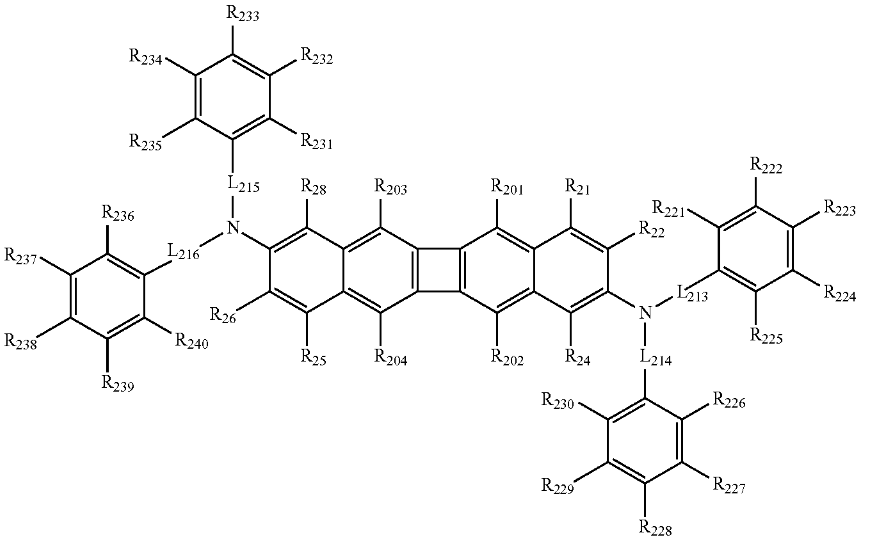

[Formula 46]

(261A)

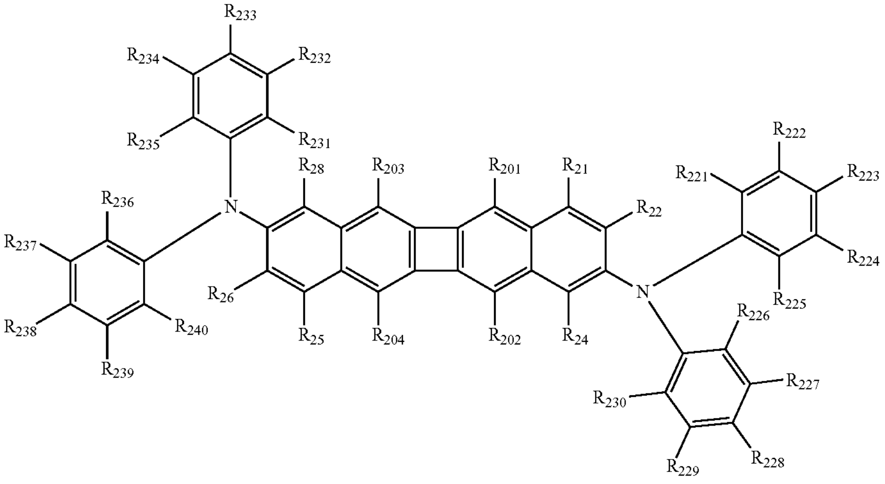

In the formulae (26A) and (261A):

$R_{21}$, $R_{22}$, $R_{24}$ to $R_{26}$, $R_{28}$ and $R_{201}$ to $R_{204}$ each independently represent the same as $R_{21}$, $R_{22}$, $R_{24}$ to $R_{26}$, $R_{28}$ and $R_{201}$ to $R_{204}$ in the formula (26);

$L_{213}$ to $L_{216}$ each independently represent the same as $L_{213}$ to $L_{216}$ in the formula (26);

$R_{221}$ to $R_{240}$ are each independently a hydrogen atom, an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, an unsubstituted aryl group having 6 to 50 ring carbon atoms, or an unsubstituted heterocyclic group having 5 to 50 ring atoms.

The compound represented by the formula (2) is also preferably a compound having two substituted or unsubstituted amino groups in a molecule (sometimes referred to as a diamine compound).

The compound represented by the formula (2) is also preferably a compound represented by a formula (27) below.

[Formula 47]

(27)

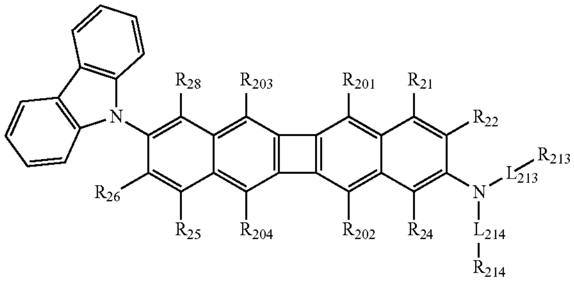

In the formula (27):

$R_{21}$, $R_{22}$, $R_{24}$ to $R_{26}$, $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, a substituted or unsubstituted heterocyclic group having 5 to 50 ring atoms, or the group represented by the formula (20);

a combination of $R_{213}$ and $R_{214}$ are mutually bonded to form a substituted or unsubstituted monocyclic ring, mutually bonded to form a substituted or unsubstituted fused ring, or not mutually bonded;

$R_{213}$ and $R_{214}$ not forming the monocyclic ring and not forming the fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{213}$ and $L_{214}$ are each independently a single bond, a substituted or unsubstituted arylene group having 6 to 50 ring carbon atoms, or a substituted or unsubstituted divalent heterocyclic group having 5 to 50 ring atoms; and $R_{901}$ to $R_{907}$ in the compound represented by the formula (27) are each independently the same as defined in the formula (2).

The compound represented by the formula (27) is also preferably a compound represented by a formula (271) below.

[Formula 48]

(271)

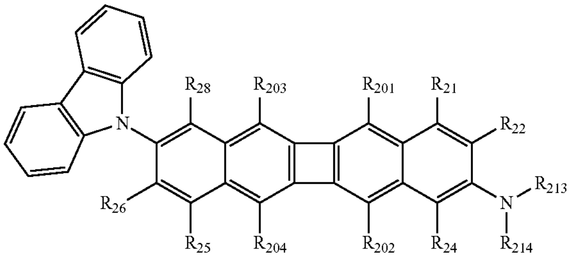

In the formula (271):

$R_{21}$, $R_{22}$, $R_{24}$ to $R_{26}$, $R_{28}$ and $R_{201}$ to $R_{204}$ each independently represent the same as $R_{21}$, $R_{22}$, $R_{24}$ to $R_{26}$, $R_{28}$ and $R_{201}$ to $R_{204}$ in the formula (27);

a combination of $R_{213}$ and $R_{214}$ are mutually bonded to form a substituted or unsubstituted monocyclic ring, mutually bonded to form a substituted or unsubstituted fused ring, or not mutually bonded; and $R_{213}$ and $R_{214}$ not forming the monocyclic ring and not forming the fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the compounds represented by the formulae (27) and (271), it is also preferable that $R_{213}$ and $R_{214}$ are not bonded to each other.

In the compounds represented by the formulae (27) and (271), it is also preferable that $R_{213}$ and $R_{214}$ are not bonded to each other, and $R_{213}$ and $R_{214}$ not forming the monocyclic ring and not forming the fused ring are each independently a substituted or unsubstituted aryl group having 6 to 50 ring carbon atoms.

In the compound according to the exemplary embodiment, $R_{213}$ and $R_{214}$ are preferably a substituted or unsubstituted phenyl group.

In the compounds represented by the formulae (27) and (271), when $R_{213}$ and $R_{214}$ are each a substituted or unsubstituted phenyl group, the compounds represented by the formulae (27) and (271) are represented by a formula (27A) and a formula (271A) below, respectively.

[Formula 49]

(27A)

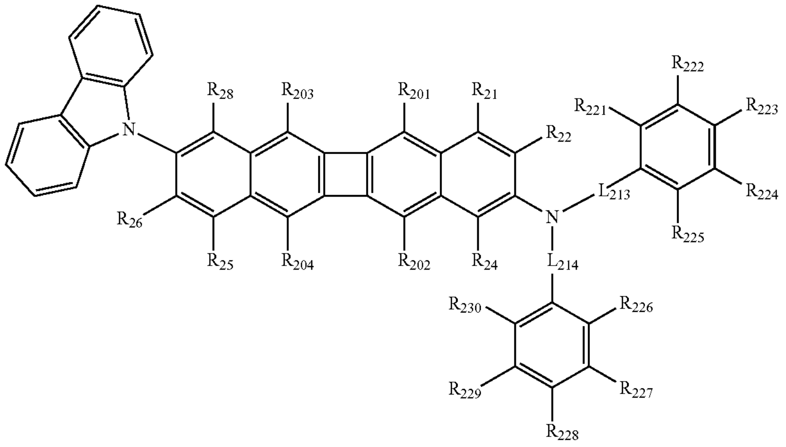

[Formula 50]

(271A)

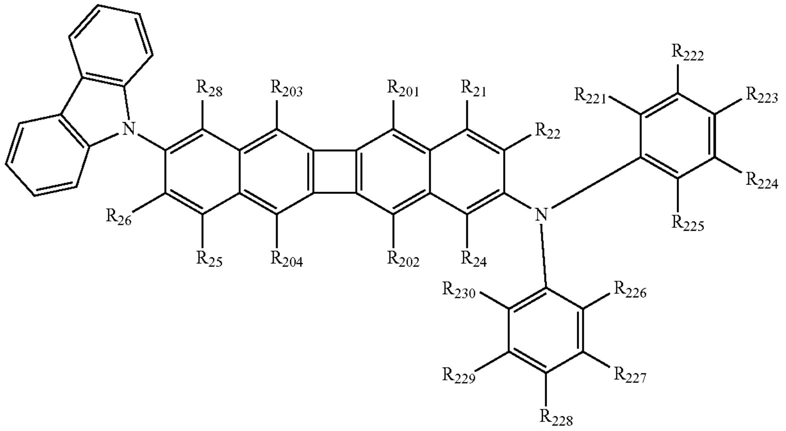

In the formulae (27A) and (271A):

$R_{21}$, $R_{22}$, $R_{24}$ to $R_{26}$, $R_{28}$ and $R_{201}$ to $R_{204}$ each independently represent the same as $R_{21}$, $R_{22}$, $R_{24}$ to $R_{26}$, $R_{28}$ and $R_{201}$ to $R_{204}$ in the formula (27);

$L_{213}$ and $L_{214}$ are each independently a single bond, a substituted or unsubstituted arylene group having 6 to 50 ring carbon atoms, or a substituted or unsubstituted divalent heterocyclic group having 5 to 50 ring atoms; and $R_{221}$ to $R_{230}$ are each independently a hydrogen atom, an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by —$Si(R_{901})(R_{902})(R_{903})$, a group represented by —O—($R_{904}$), a group represented by —S—($R_{905}$), a group represented by —$N(R_{906})(R_{907})$, a halogen atom, a cyano group, a nitro group, an unsubstituted aryl group having 6 to 50 ring carbon atoms, or an unsubstituted heterocyclic group having 5 to 50 ring atoms.

The compound represented by the formula (2) is also preferably a compound represented by a formula (28) below.

[Formula 51]

(28)

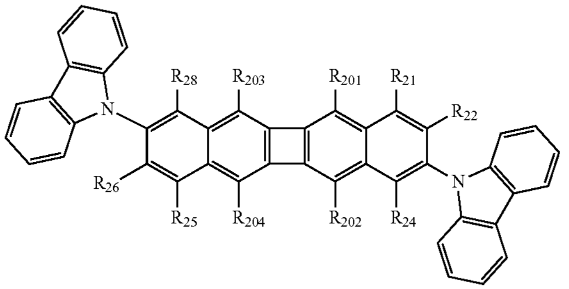

In the formula (28):

$R_{21}$, $R_{22}$, $R_{24}$ to $R_{26}$, $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, a substituted or unsubstituted heterocyclic group having 5 to 50 ring atoms, or the group represented by the formula (20); and $R_{901}$ to $R_{907}$ in the compound represented by the formula (28) are each independently the same as defined in the formula (2).

In the compound according to the exemplary embodiment, $R_{21}$, $R_{22}$, $R_{24}$ to $R_{26}$, $R_{28}$ and $R_{201}$ to $R_{204}$ are preferably each independently a hydrogen atom, a halogen atom, a substituted or unsubstituted alkyl group having 1 to 50 carbon atoms, a substituted or unsubstituted cycloalkyl group having 3 to 50 ring carbon atoms, or a group represented by —Si($R_{901}$)($R_{902}$)($R_{903}$).

The compound represented by the formula (2) is also preferably a compound represented by a formula (29) below.

[Formula 52]

(29)

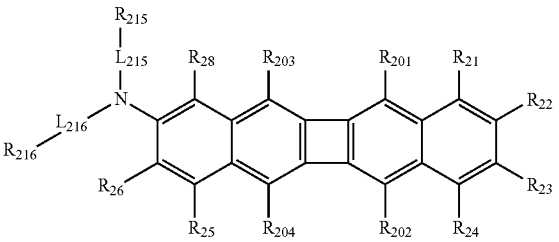

In the formula (29):

$R_{21}$ to $R_{26}$, $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aryl group having 6 to 50 ring carbon atoms, or a substituted or unsubstituted heterocyclic group having 5 to 50 ring atoms;

a combination of $R_{215}$ and $R_{216}$ are mutually bonded to form a substituted or unsubstituted monocyclic ring, mutually bonded to form a substituted or unsubstituted fused ring, or not mutually bonded;

$R_{215}$ and $R_{216}$ not forming the monocyclic ring and not forming the fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{215}$ and $L_{216}$ are each independently a single bond, a substituted or unsubstituted arylene group having 6 to 50 ring carbon atoms, or a substituted or unsubstituted divalent heterocyclic group having 5 to 50 ring atoms; and $R_{901}$ to $R_{905}$ in the compound represented by the formula (29) are each independently the same as defined in the formula (2).

In the compound represented by the formula (29), $R_{215}$ and $R_{216}$ are preferably a substituted or unsubstituted phenyl group.

In the compound represented by the formula (29), $R_{21}$ to $R_{26}$, $R_{28}$ and $R_{201}$ to $R_{204}$ are preferably each independently a hydrogen atom, a halogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a group represented by —Si($R_{901}$)($R_{902}$)($R_{903}$).

In the compound represented by the formula (29), it is also preferable that $R_{215}$ and $R_{216}$ are not bonded to each other.

In the compound represented by the formula (29), $L_{215}$ and $L_{216}$ are also preferably a single bond.

The compound represented by the formula (2) is also preferably a compound having only one substituted or unsubstituted amino group in a molecule (sometimes referred to as a monoamine compound).

The compound represented by the formula (2) is also preferably a compound represented by a formula (221) or a formula (222) below.

[Formula 53]

(221)

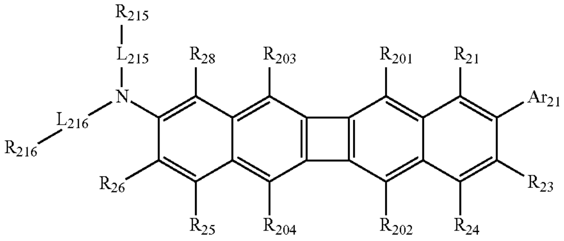

[Formula 54]

(222)

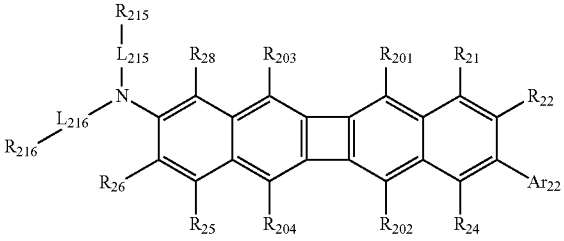

In the formulae (221) and (222):

$R_{21}$ to $R_{26}$, $R_{28}$ and $R_{201}$ to $R_{204}$ each represent the same as $R_{21}$ to $R_{26}$, $R_{28}$ and $R_{201}$ to $R_{204}$ in the formula (2);

$R_{215}$ and $R_{216}$ each independently represent the same as $R_{215}$ and $R_{216}$ in the formula (23);

$L_{215}$ and $L_{216}$ each independently represent the same as $L_{215}$ and $L_{216}$ in the formula (23); and $Ar_{21}$ and $Ar_{22}$ are each independently a substituted or unsubstituted aryl group having 6 to 50 ring carbon atoms.

The compounds represented by the formulae (221) and (222) are also preferably compounds represented by a formula (221A) and a formula (222A) below.

[Formula 55]

(221A)

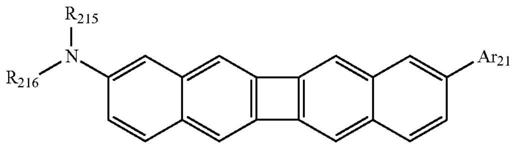

[Formula 56]

(222A)

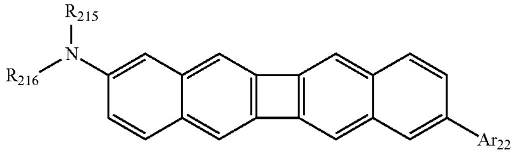

In the formulae (221A) and (222A):

$R_{215}$ and $R_{216}$ each independently represent the same as $R_{215}$ and $R_{216}$ in the formula (23); and $Ar_{21}$ and $Ar_{22}$ are each independently a substituted or unsubstituted aryl group having 6 to 50 ring carbon atoms.

The compound represented by the formula (2) is also preferably a compound represented by a formula (223) or a formula (224) below.

[Formula 57]

(223)

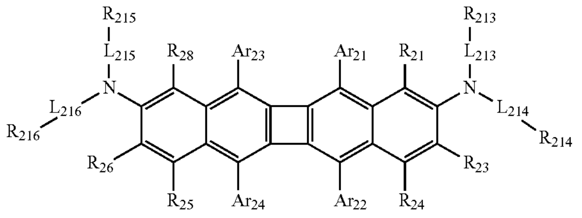

[Formula 58]

(224)

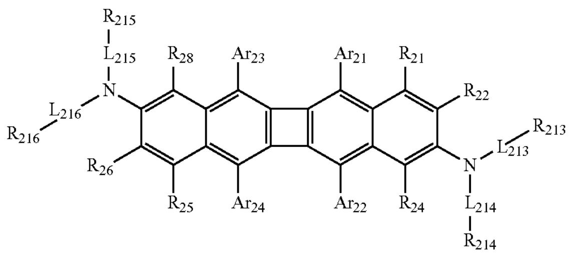

In the formulae (223) and (224):

$R_{21}$ to $R_{26}$ and $R_{28}$ each represent the same as $R_{21}$ to $R_{26}$ and $R_{28}$ in the formula (2);

$R_{213}$ to $R_{216}$ each independently represent the same as $R_{213}$ to $R_{216}$ in the formula (23);

$L_{213}$ to $L_{216}$ each independently represent the same as $L_{213}$ to $L_{216}$ in the formula (23); and $Ar_{21}$ to $Ar_{24}$ are each independently a substituted or unsubstituted aryl group having 6 to 50 ring carbon atoms.

The compounds represented by the formulae (223) and (224) are also preferably compounds represented by a formula (223A) and a formula (224A) below.

[Formula 59]

(223A)

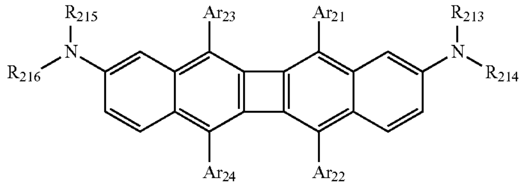

[Formula 60]

(224A)

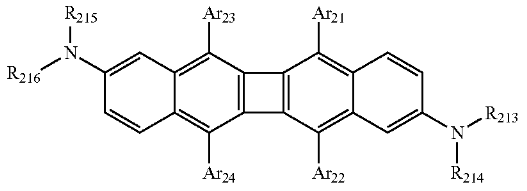

In the formulae (223A) and (224A):

$R_{213}$ to $R_{216}$ each independently represent the same as $R_{213}$ to $R_{216}$ in the formula (23); and $Ar_{21}$ to $Ar_{24}$ are each independently a substituted or unsubstituted aryl group having 6 to 50 ring carbon atoms.

The compound represented by the formula (2) is also preferably a compound represented by a formula (225) below.

[Formula 61]

(225)

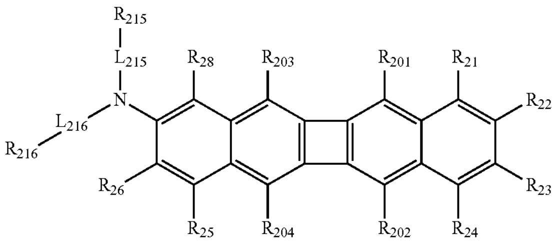

In the formula (225):

$R_{21}$ to $R_{26}$, $R_{28}$, $R_{203}$ and $R_{204}$ each represent the same as $R_{21}$ to $R_{26}$, $R_{28}$, $R_{203}$ and $R_{204}$ in the formula (2);

$R_{215}$ and $R_{216}$ each independently represent the same as $R_{215}$ and $R_{216}$ in the formula (23);

$L_{215}$ and $L_{216}$ each independently represent the same as $L_{215}$ and $L_{216}$ in the formula (23); and $Ar_{21}$ and $Ar_{22}$ are each independently a substituted or unsubstituted aryl group having 6 to 50 ring carbon atoms.

The compound represented by the formula (225) is also preferably a compound represented by a formula (225A) below.

[Formula 62]

(225A)

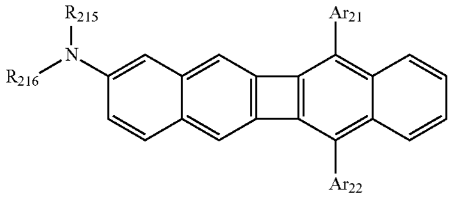

In the formula (225A):

$R_{215}$ and $R_{216}$ each independently represent the same as $R_{215}$ and $R_{216}$ in the formula (23); and $Ar_{21}$ and $Ar_{22}$ are each independently a substituted or unsubstituted aryl group having 6 to 50 ring carbon atoms.

The compound represented by the formula (2) is also preferably a compound represented by a formula (226) or a formula (227) below.

[Formula 63]

(226)

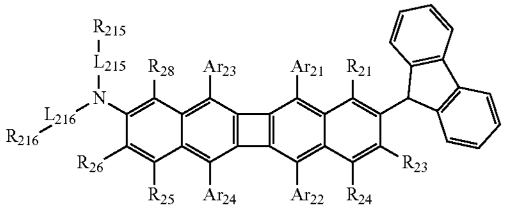

[Formula 64]

(227)

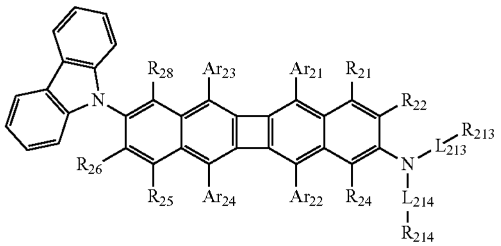

In the formulae (226) and (227):

$R_{21}$ to $R_{26}$ and $R_{28}$ each represent the same as $R_{21}$ to $R_{26}$ and $R_{28}$ in the formula (2);

$R_{213}$ to $R_{216}$ each independently represent the same as $R_{213}$ to $R_{216}$ in the formula (23);

$L_{213}$ to $L_{216}$ each independently represent the same as $L_{213}$ to $L_{216}$ in the formula (23); and $Ar_{21}$ to $Ar_{24}$ are each independently a substituted or unsubstituted aryl group having 6 to 50 ring carbon atoms.

The compound represented by the formula (226) or (227) is also preferably compound represented by a formula (226A) and a formula (227A) below.

[Formula 65]

(226A)

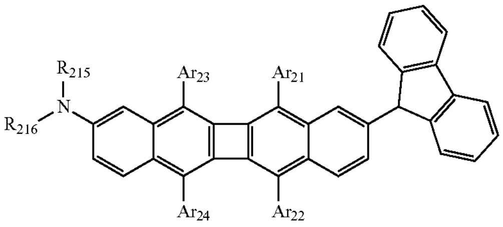

[Formula 66]

(227A)

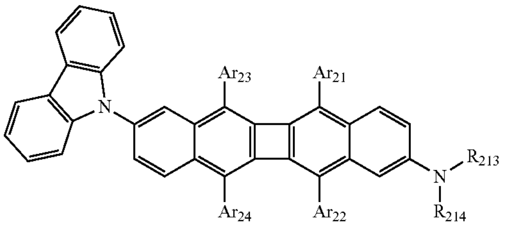

In the formulae (226A) and (227A):

$R_{213}$ to $R_{216}$ each independently represent the same as $R_{213}$ to $R_{216}$ in the formula (23); and $Ar_{21}$ to $Ar_{24}$ are each independently a substituted or unsubstituted aryl group having 6 to 50 ring carbon atoms.

In the exemplary embodiment, the group represented by the formula (20) is also preferably a compound represented by a formula (20X) below.

[Formula 67]

(20X)

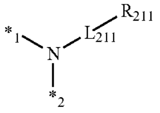

(200x)

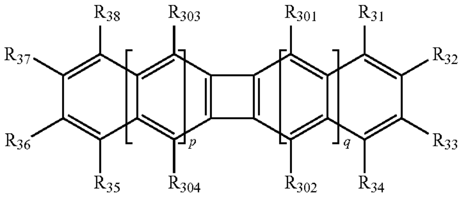

$R_{211}$ and $L_{211}$ in the formula (20X) represent the same as $R_{211}$ and $L_{211}$ in the formula (20).

*1 in the formula (20X) represents a bonding position to a structure represented by the formula (2).

*2 in the formula (20X) represents a bonding position to a structure represented by the formula (200X).

In the formula (200X):

p is 0, 1, 2 or 3;

q is 0, 1, 2 or 3;

p+q is an integer of 1 or more;

at least one combination of adjacent two or more of $R_{31}$ to $R_{38}$ and $R_{301}$ to $R_{304}$ are mutually bonded to form a substituted or unsubstituted monocyclic ring, mutually bonded to form a substituted or unsubstituted fused ring, or not mutually bonded;

$R_{31}$ to $R_{38}$ and $R_{301}$ to $R_{304}$ not forming the monocyclic ring and not forming the fused ring are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, a substituted or unsubstituted heterocyclic group having 5 to 50 ring atoms, or the group represented by the formula (20X);

at least one of $R_{31}$ to $R_{38}$ or $R_{301}$ to $R_{304}$ is the group represented by the formula (20X);

when q is 2 or 3, at least two $R_{301}$ are the same or different, and at least two $R_{302}$ are the same or different; and when p is 2 or 3, at least two $R_{303}$ are the same or different, and at least two $R_{304}$ are the same or different.

Details of each substituent in the compound according to the exemplary embodiment and details of a substituent for "substituted or unsubstituted" group are the same as defined in the section of "Definitions" herein.

Fluorescence Main Peak Wavelength

A fluorescence main peak wavelength of the compound according to the exemplary embodiment is preferably in a range from 380 nm to 500 nm, more preferably in a range from 400 nm to 480 nm, further preferably in a range from 425 nm to 470 nm, still further preferably in a range from 430 nm to 470 nm. A measurement method of the fluorescence main peak wavelength is the same as described in Examples herein.

PLQY

PLQY of the compound according to the exemplary embodiment is preferably 50% or more, more preferably 60% or more, further preferably 65% or more. A measurement method of PLQY is the same as described in Examples herein.

Manufacturing Method of Compound According to Exemplary Embodiment

The compound according to the exemplary embodiment can be manufactured by, for instance, a method described in the later-described Examples. The compound according to the exemplary embodiment can be manufactured by following reactions described in later-described Examples and using known alternative reactions or raw materials suitable for the desired substances.

Specific Examples of Compound According to Exemplary Embodiment

Specific examples of compound according to the exemplary embodiment includes the following compounds. However, the invention is by no means limited to the specific examples of the compound. In the specific examples, Me represents a methyl group, Et represents an ethyl group, Ph represents a phenyl group, and D represents a deutrium atom.

[Formula 68]

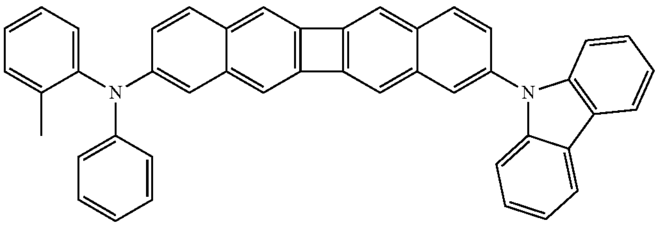

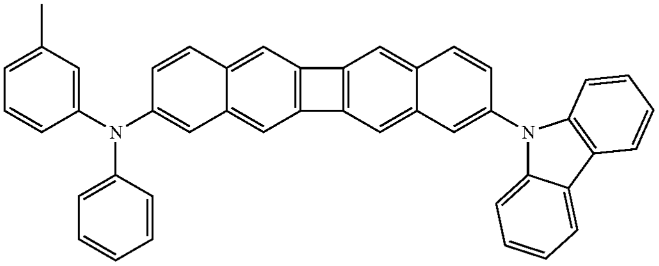

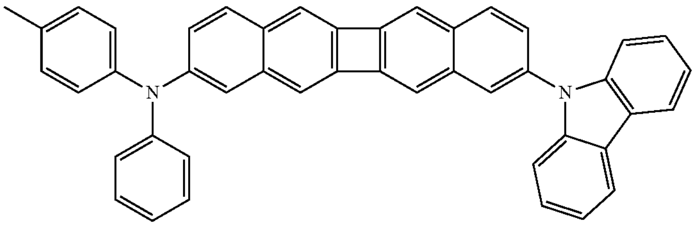

-continued
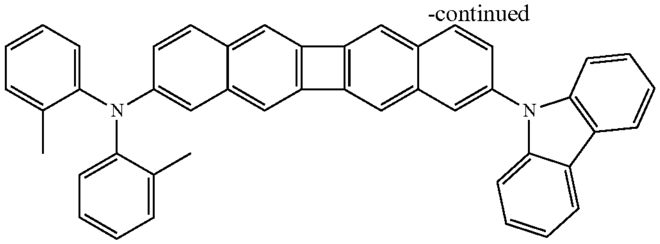
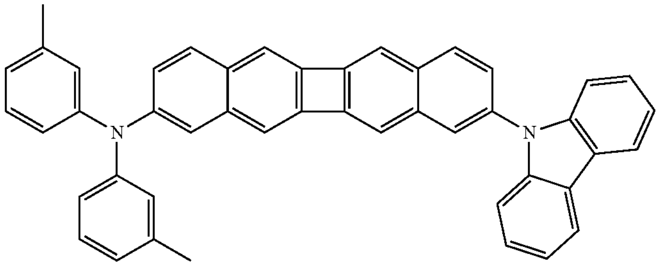
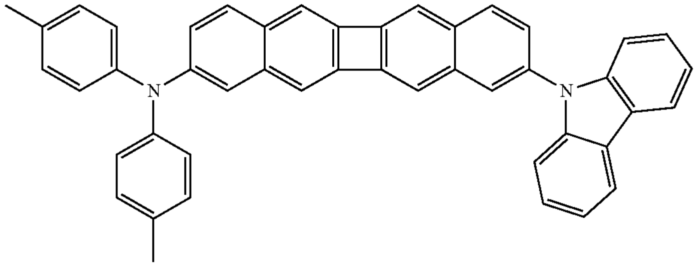
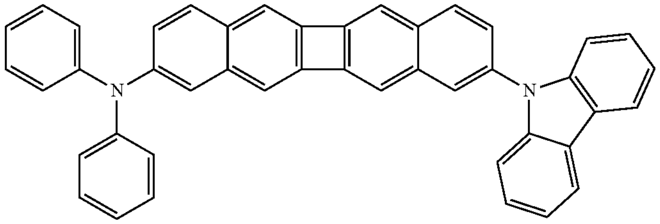
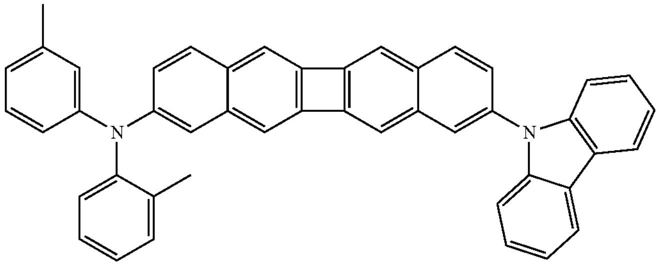
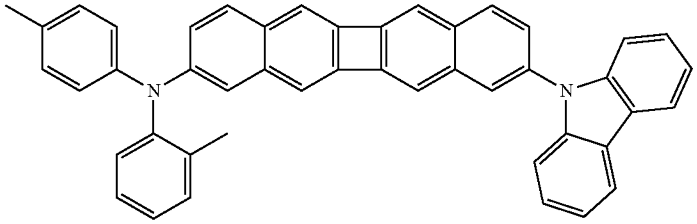
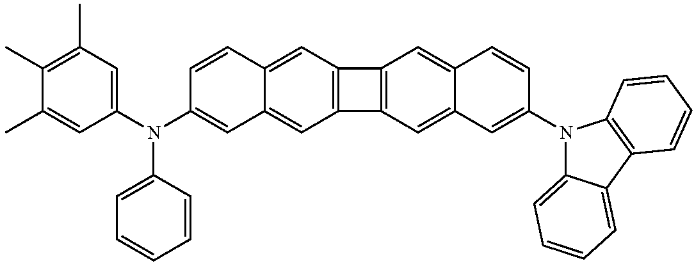

-continued
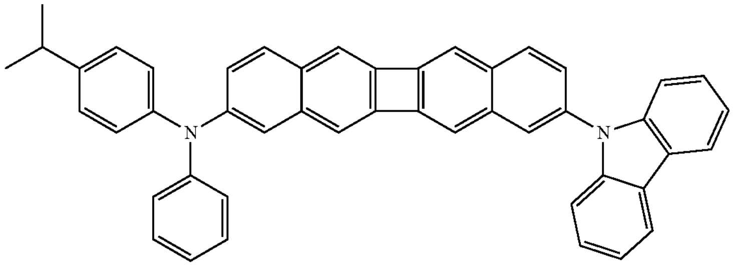
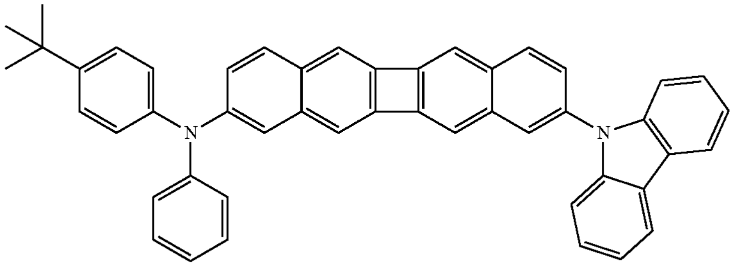
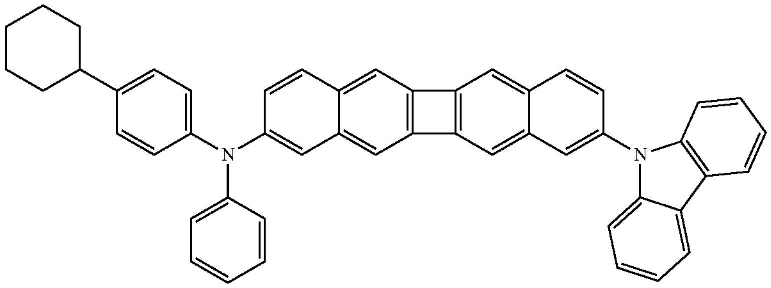
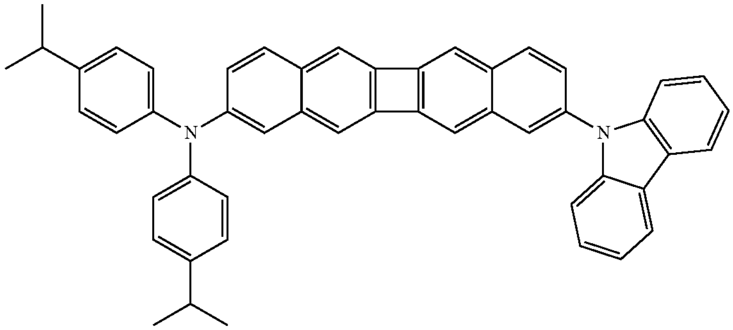
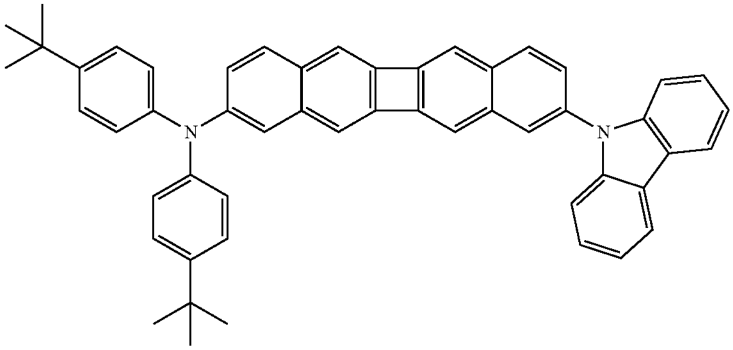

-continued
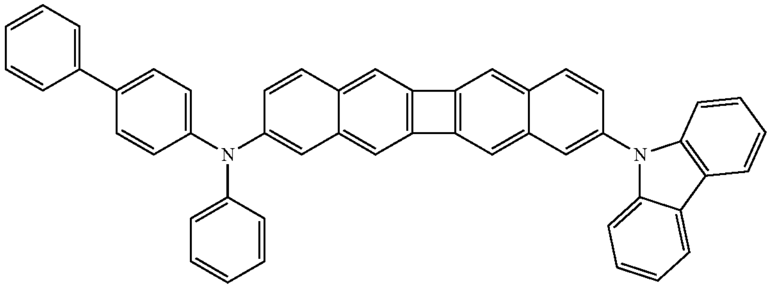
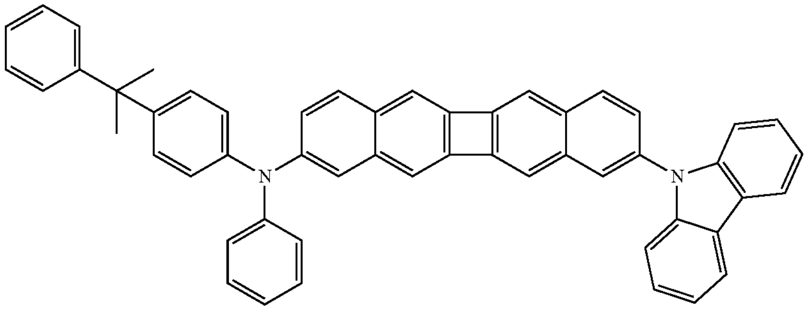
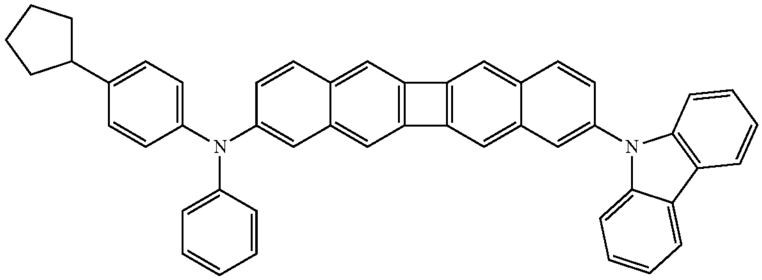
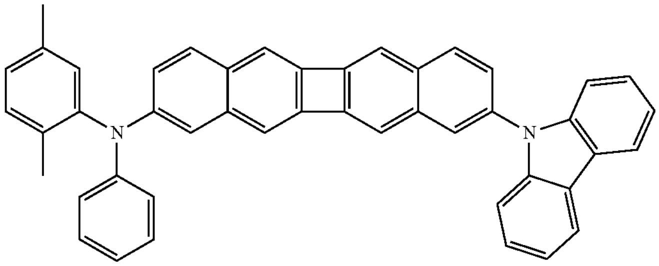
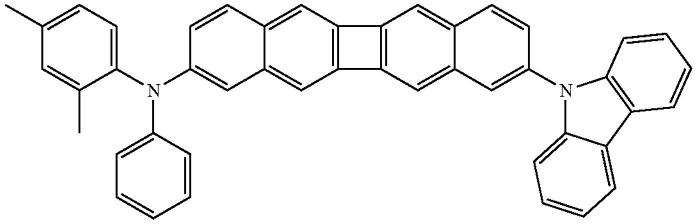
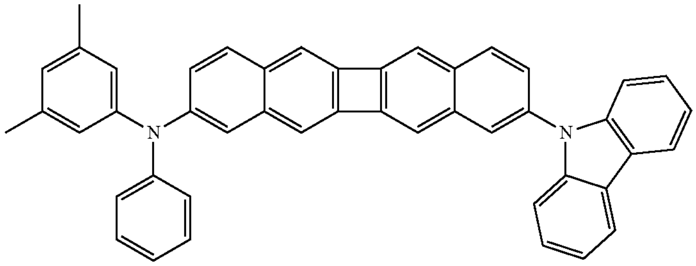

-continued
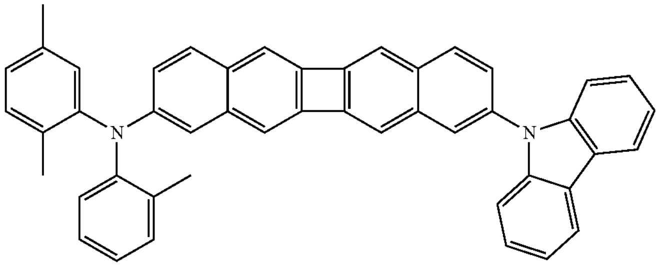
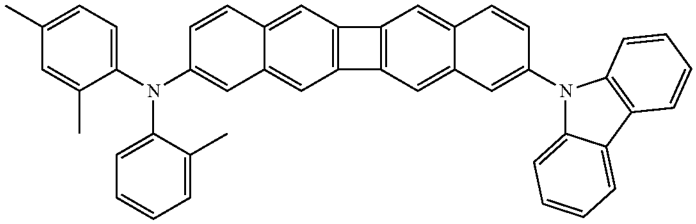
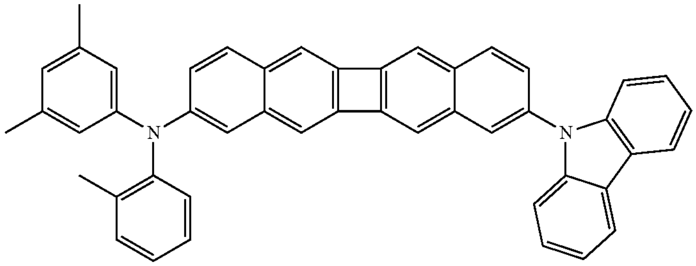
[Formula 69]
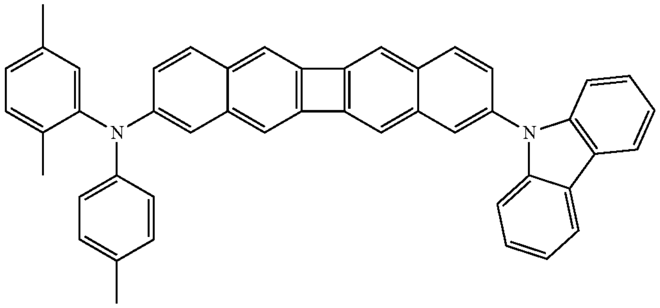
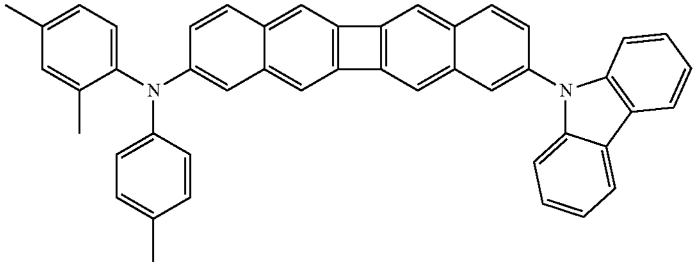
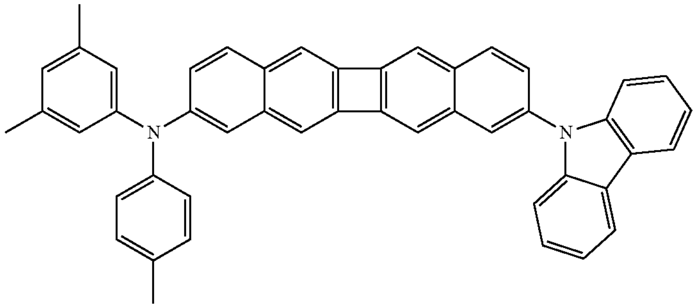

-continued
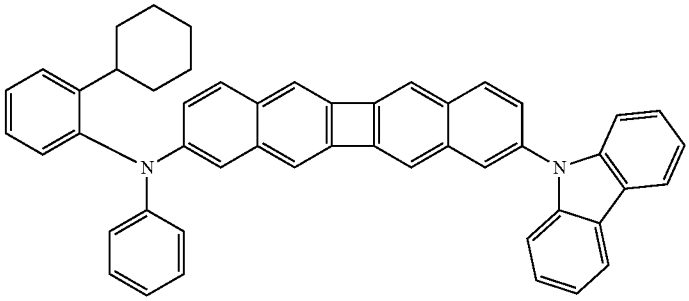
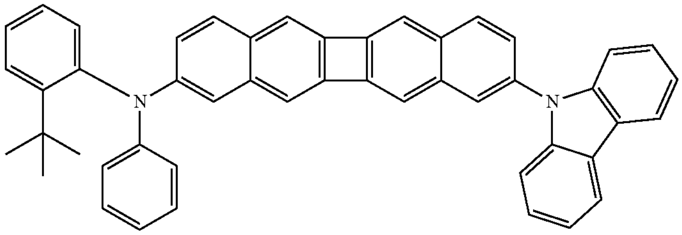
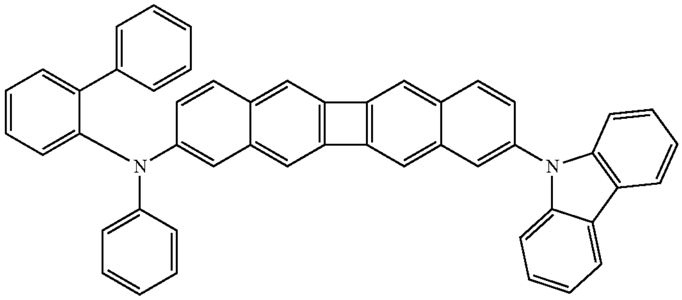
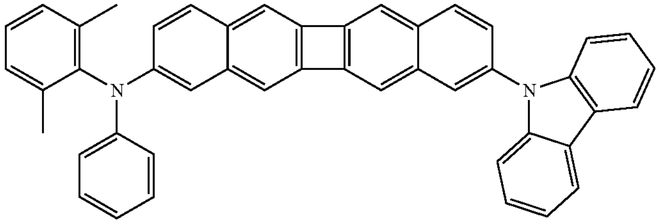
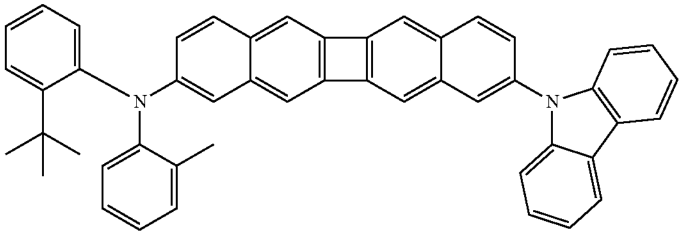
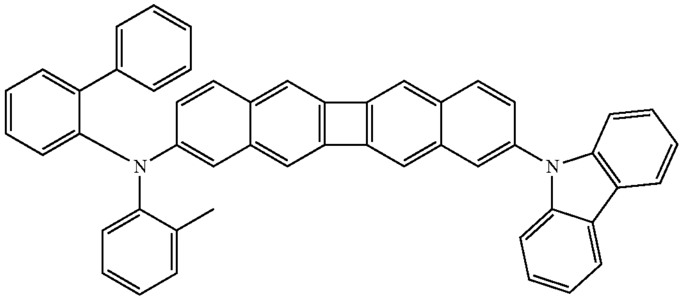

-continued
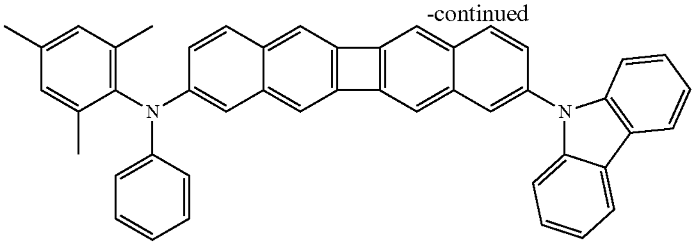
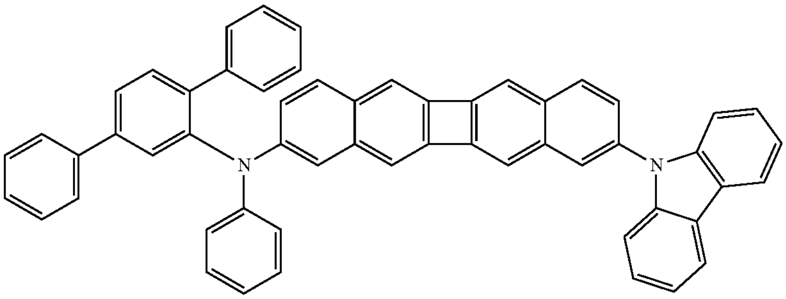
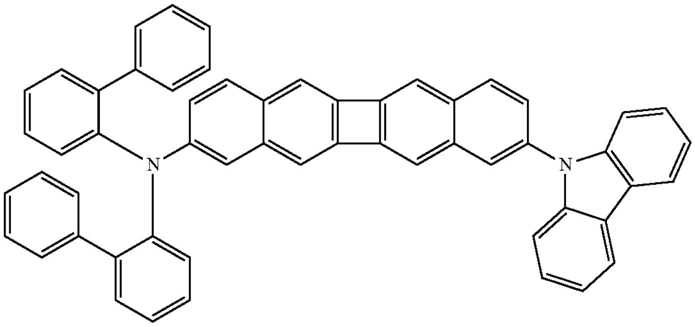
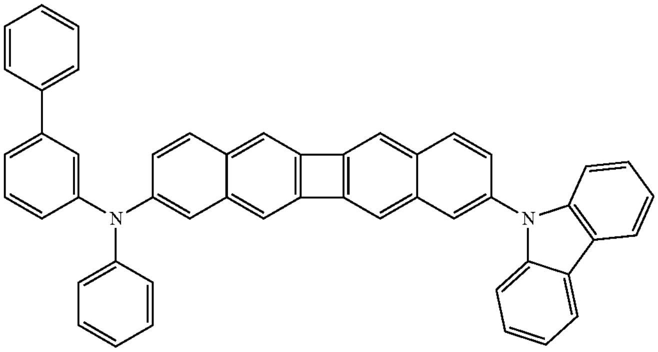
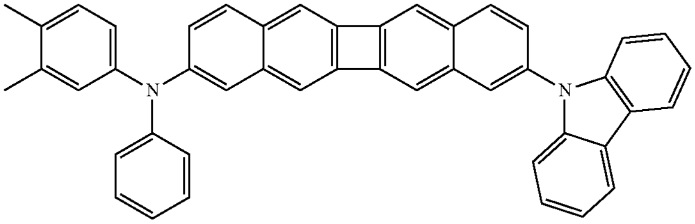
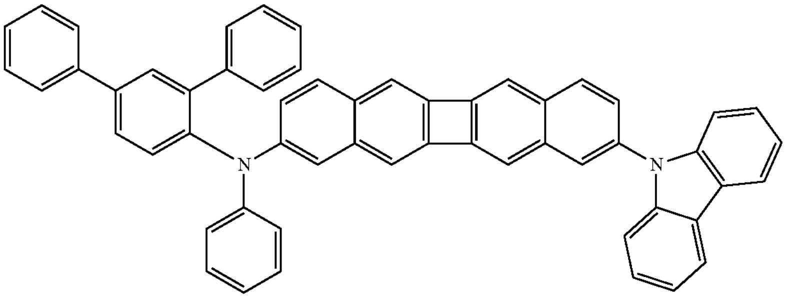

-continued
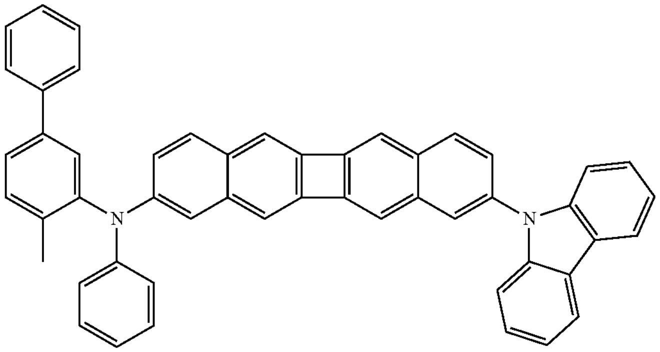
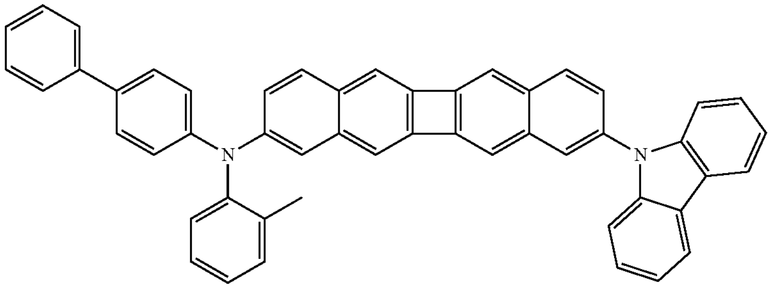
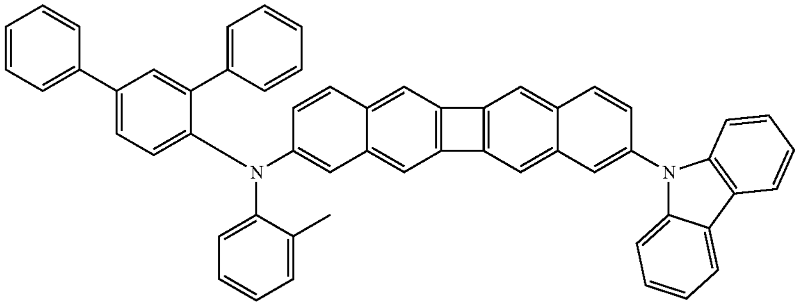
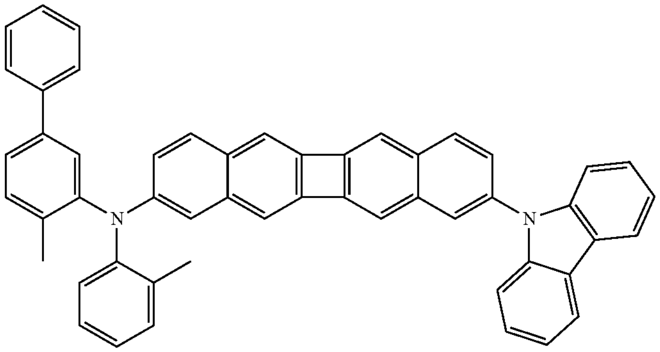
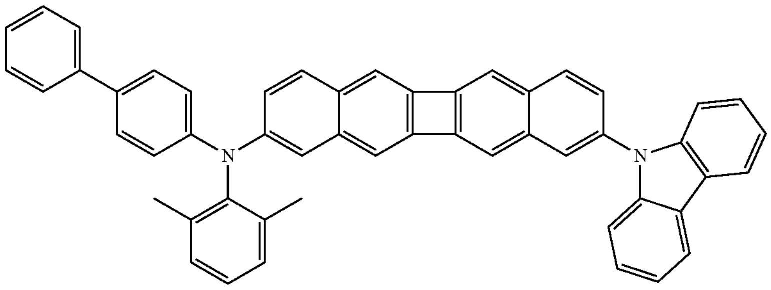

-continued
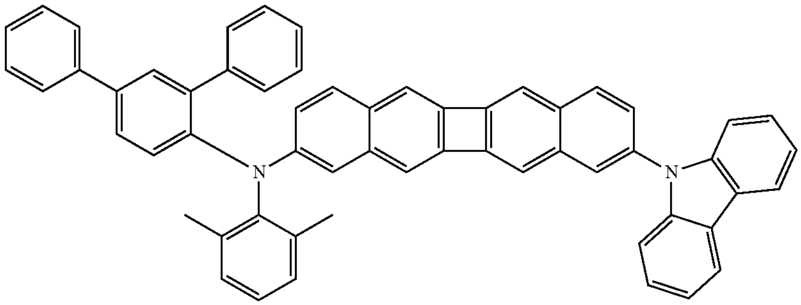
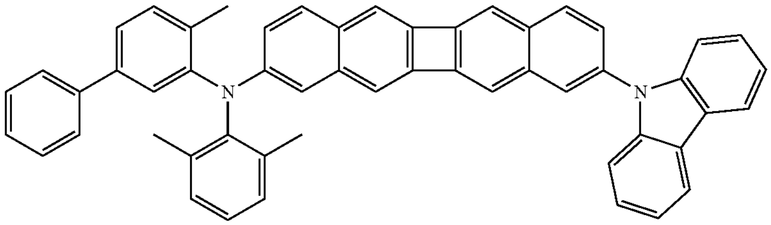
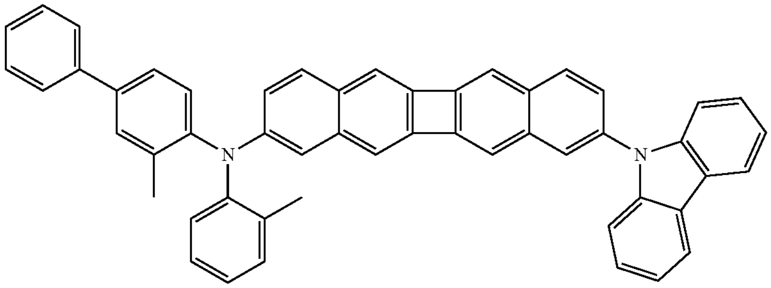
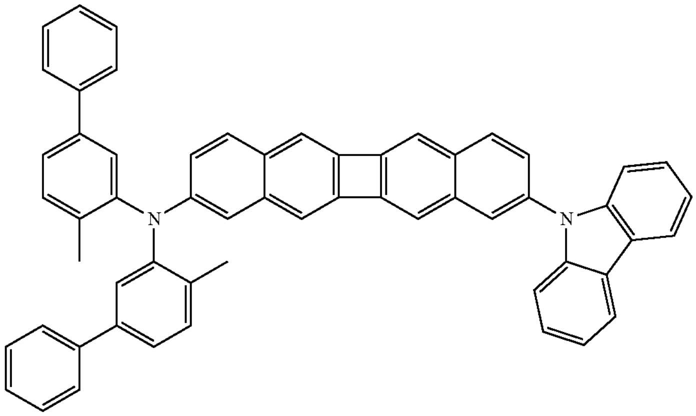
[Formula 70]
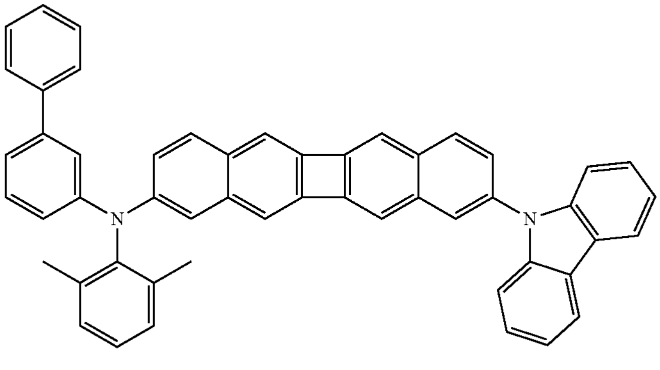

-continued
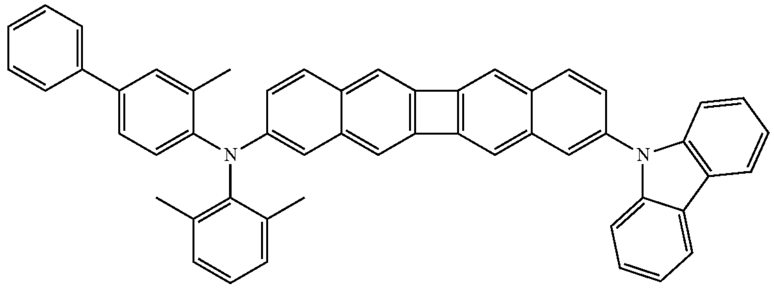
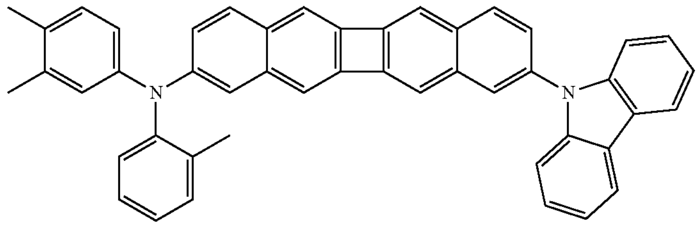
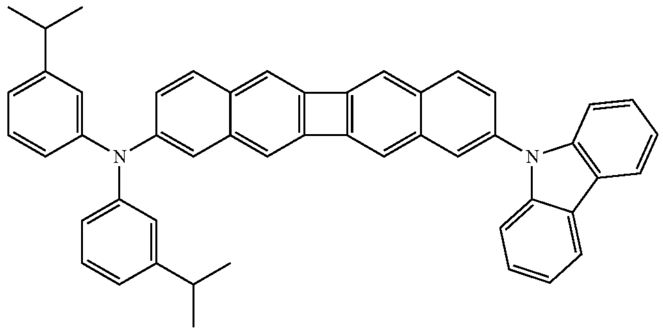
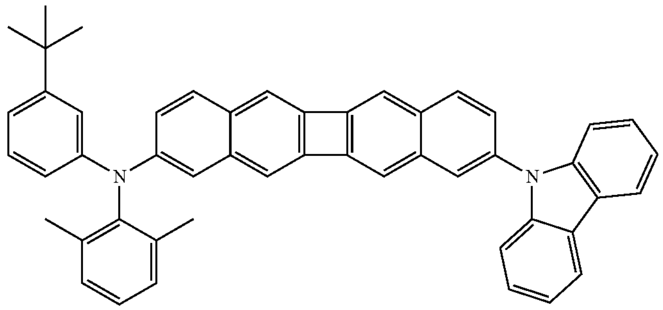
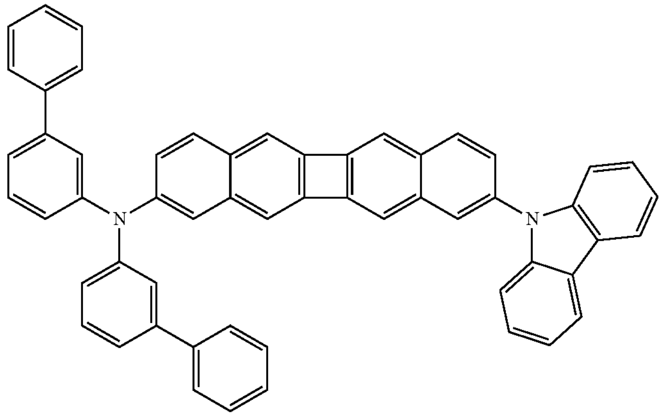

-continued
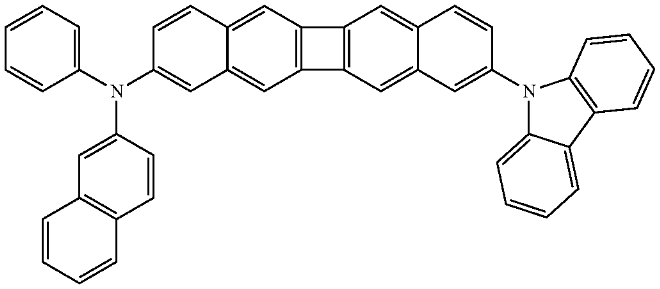
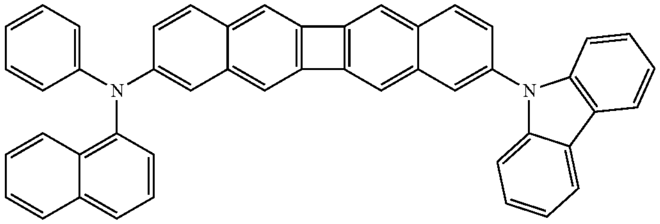
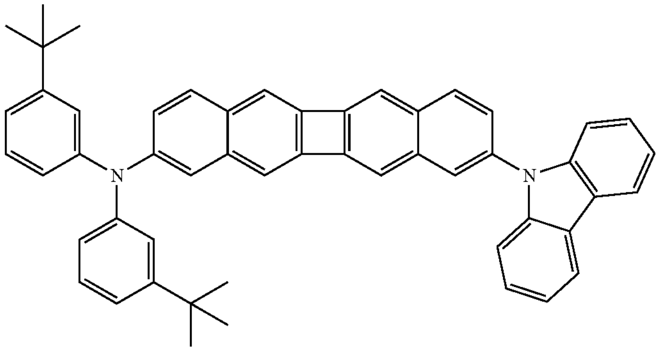
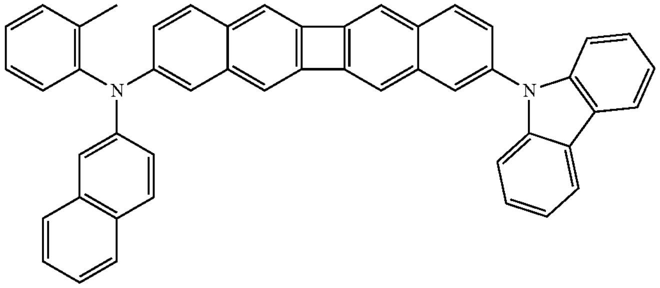
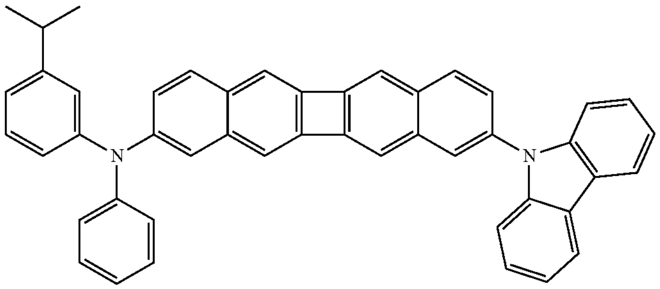

-continued
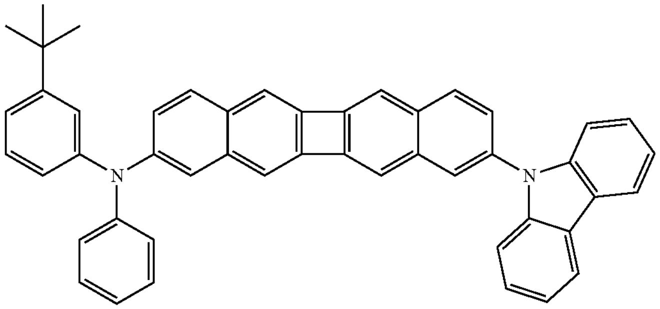
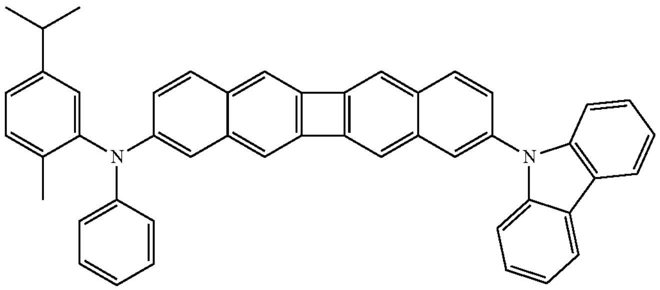
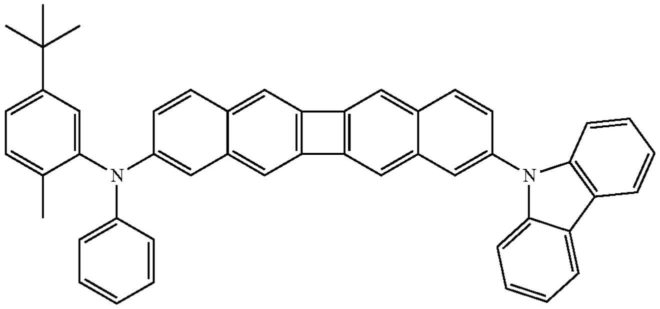
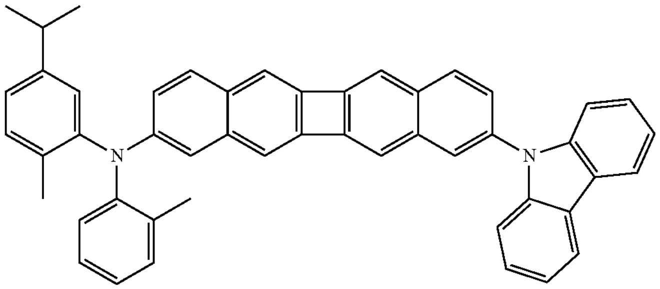
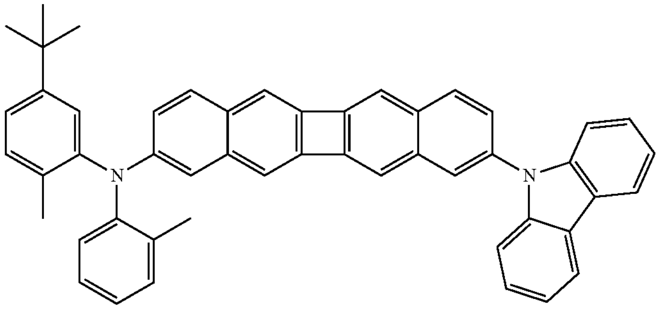

-continued
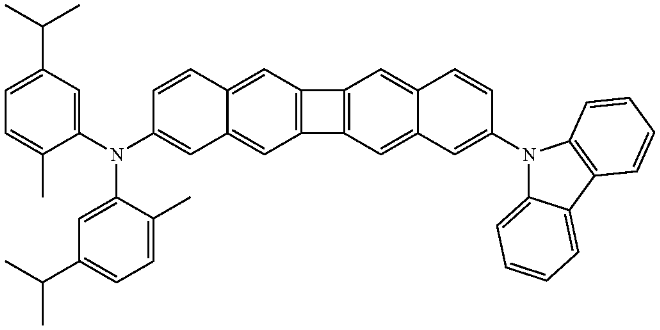
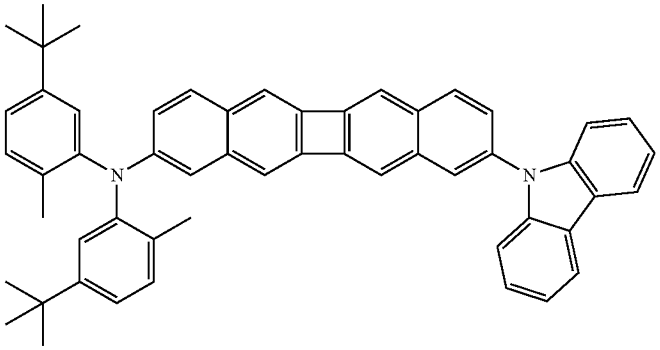 [SMILES: Cc1ccc(C(C)(C)C)cc1N(c1ccc2cc3c(cc2c1)-c1cc2cc(-n4c5ccccc5c5ccccc54)ccc2cc1-3)c1cc(C(C)(C)C)ccc1C]
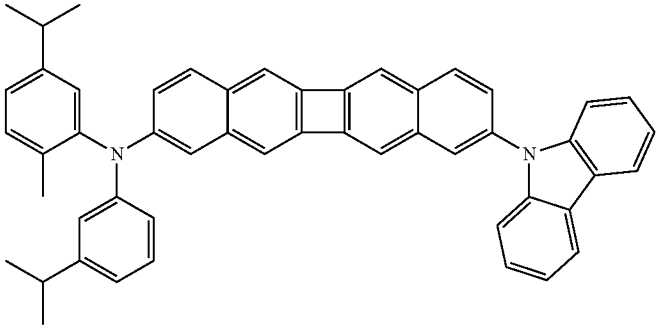
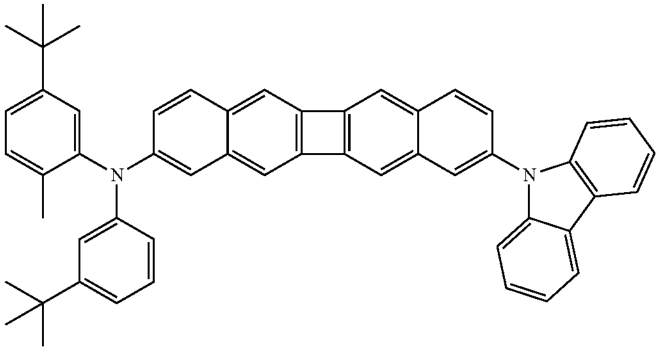
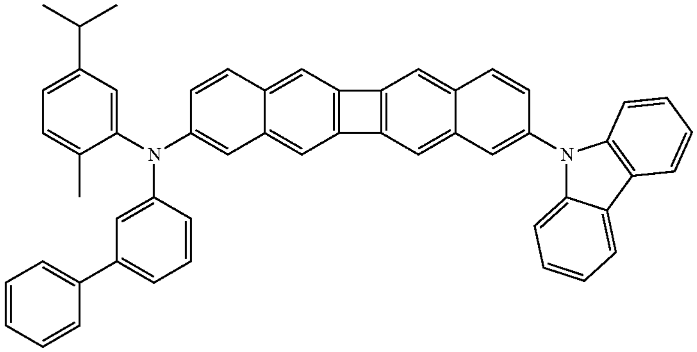

-continued
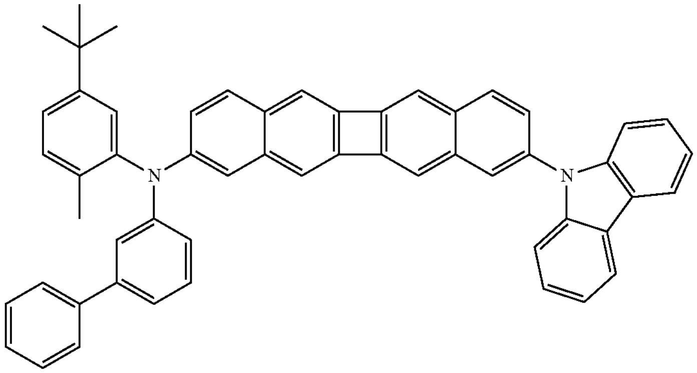
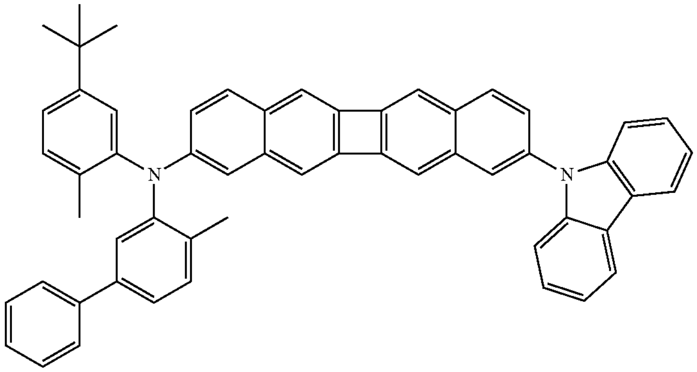
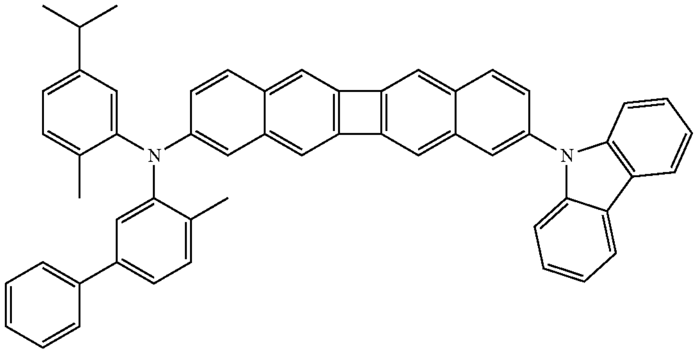
[Formula 71]
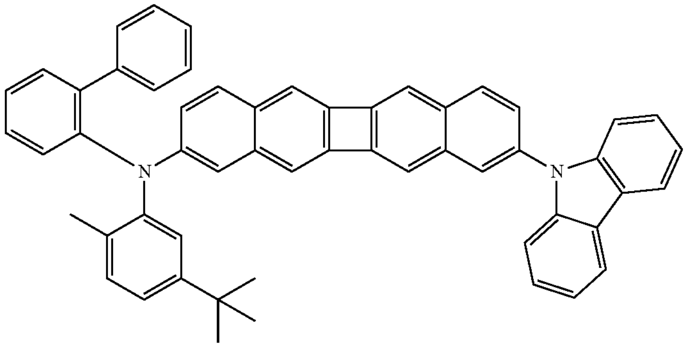

-continued
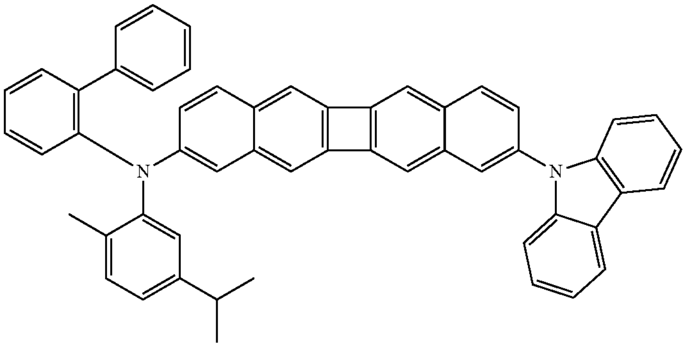
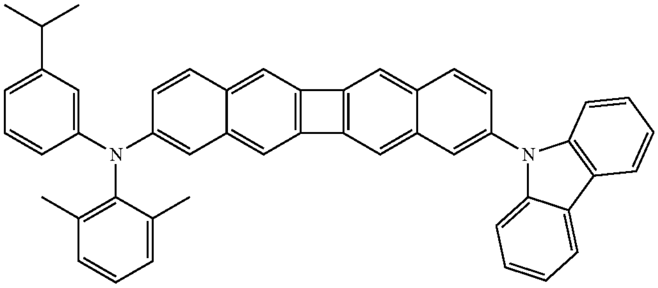
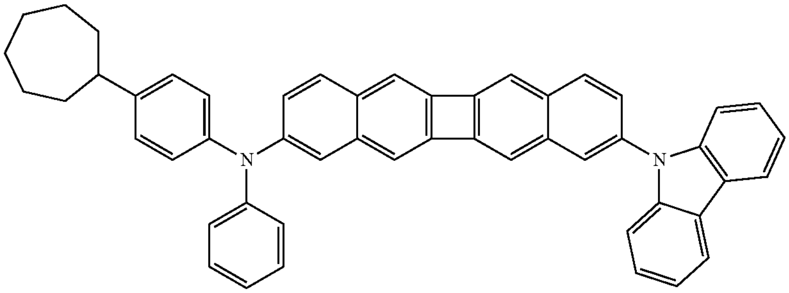
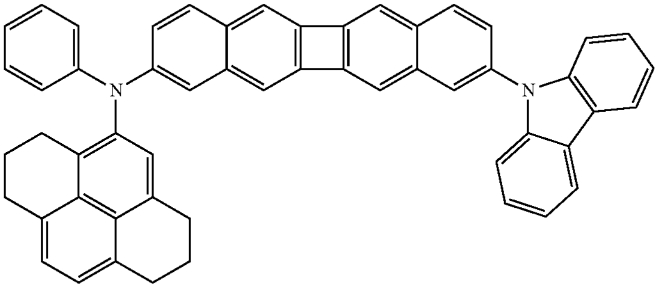
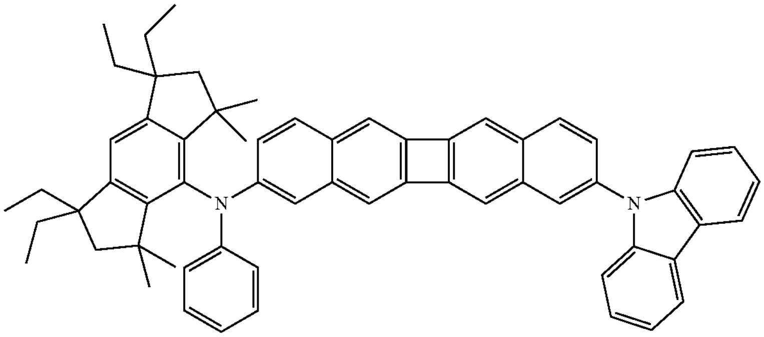

-continued
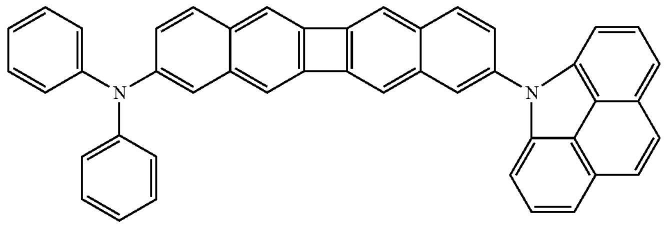
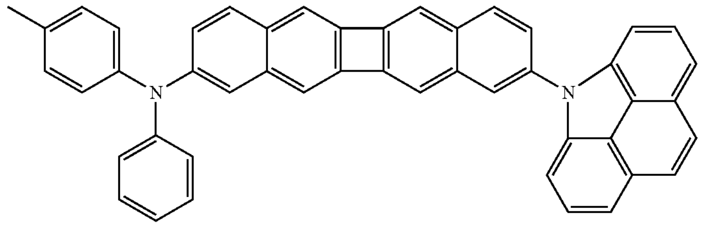
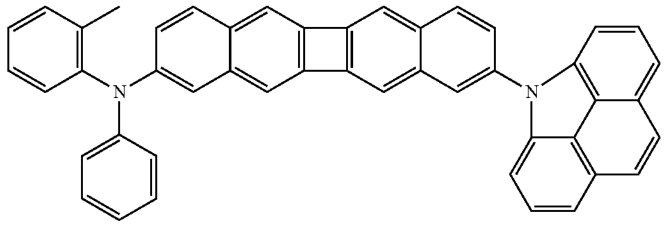
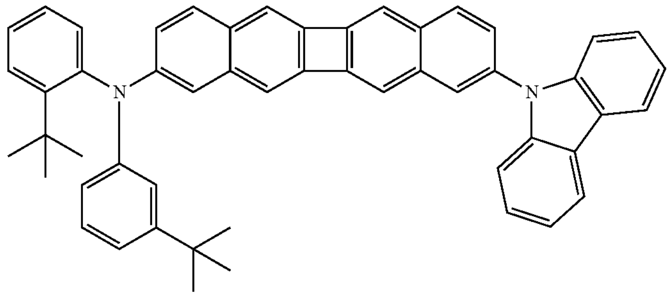
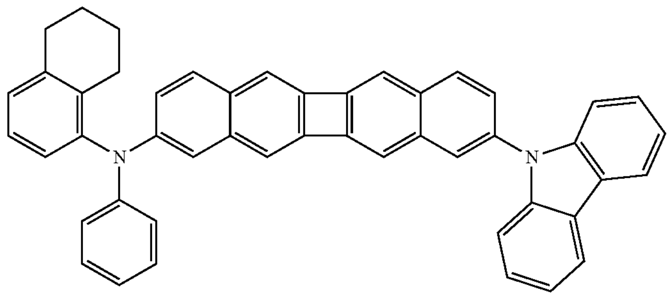
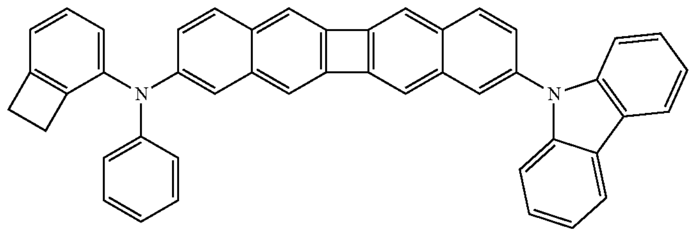

-continued
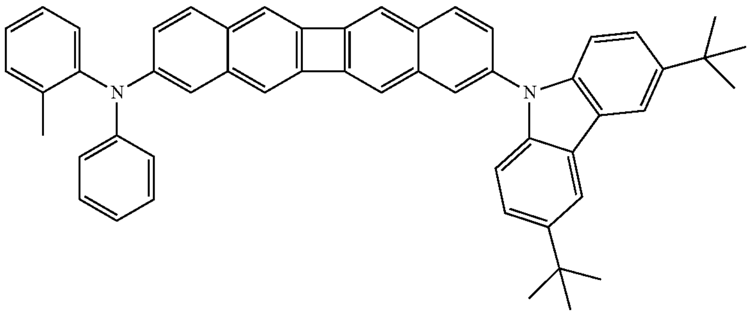
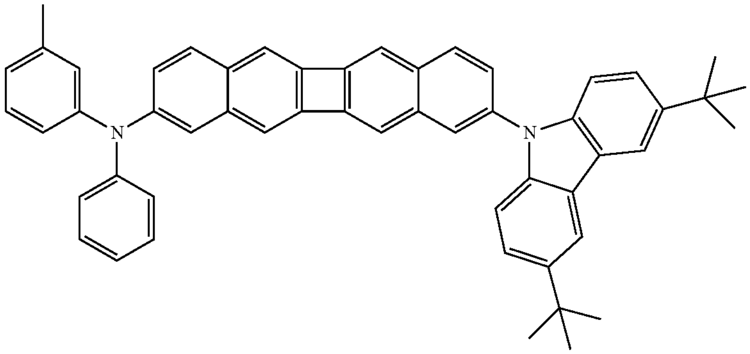
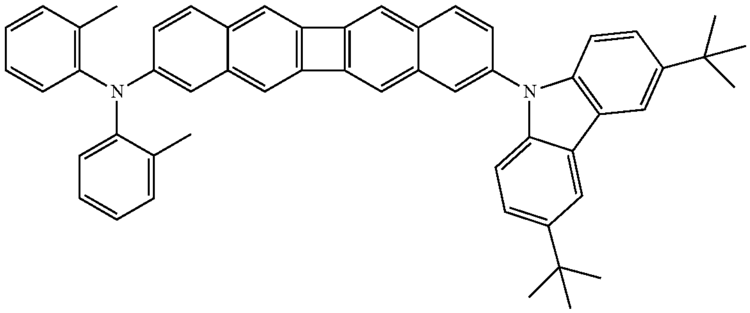
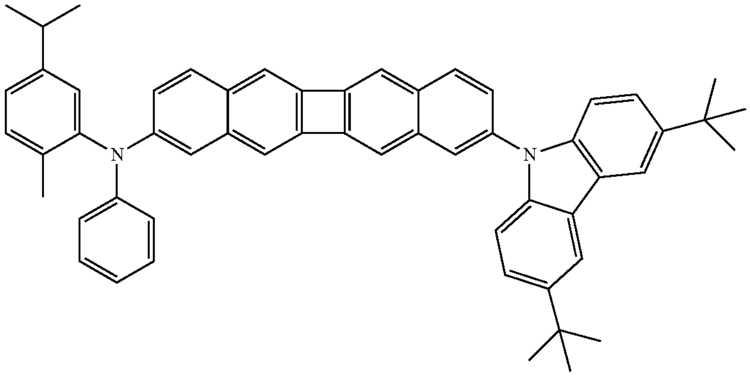

-continued
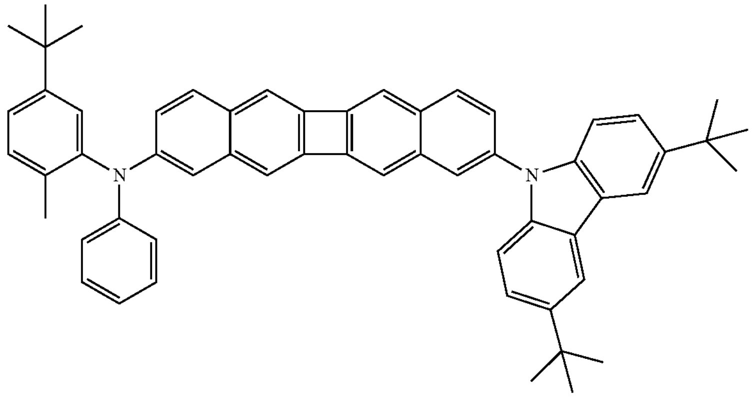
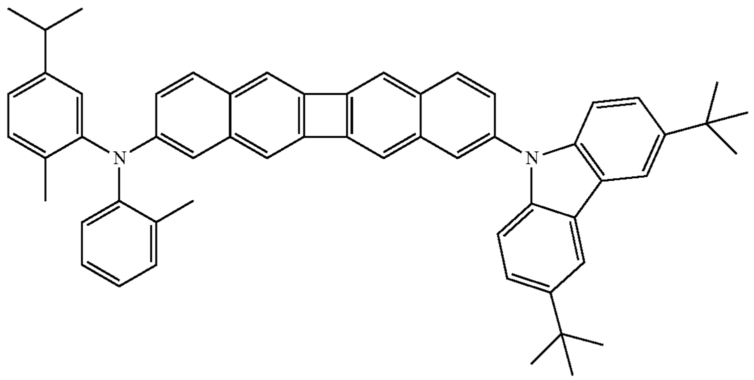
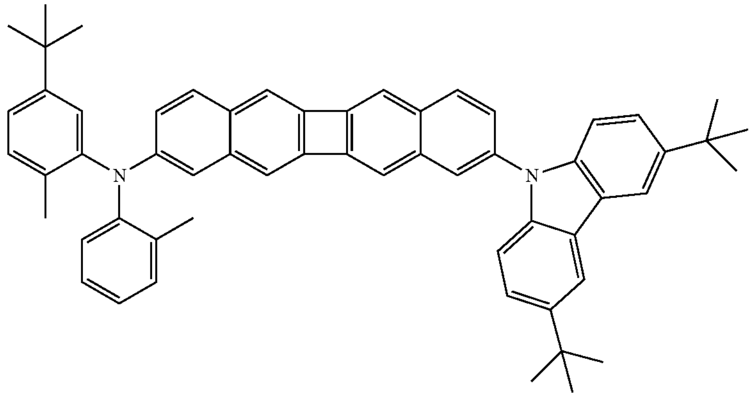
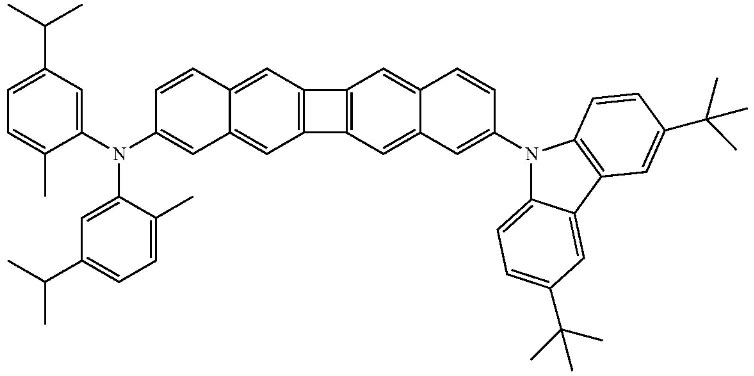

-continued
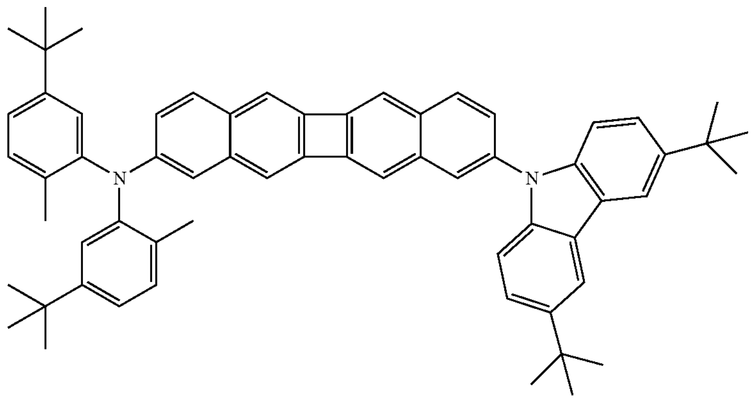
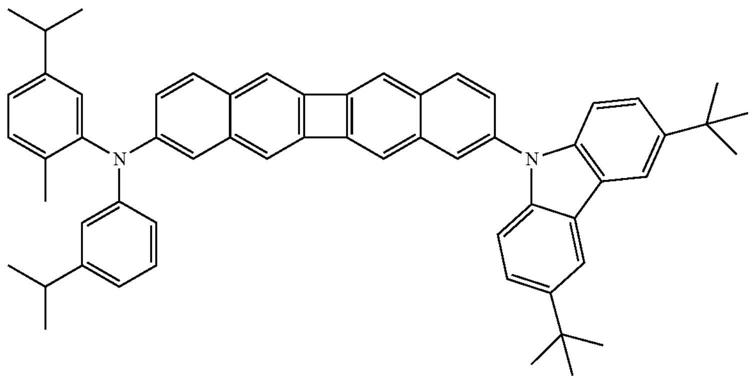
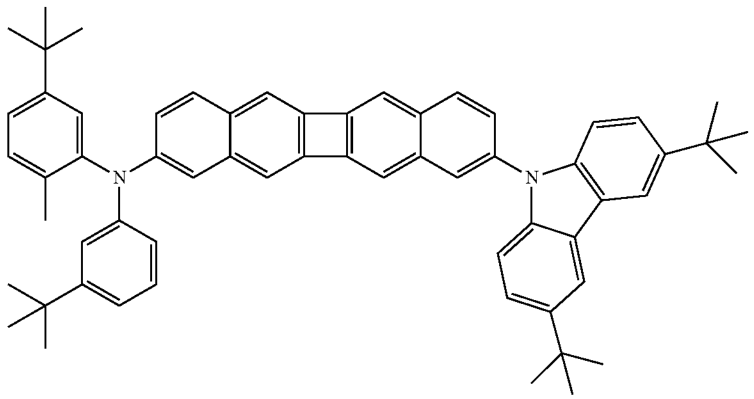
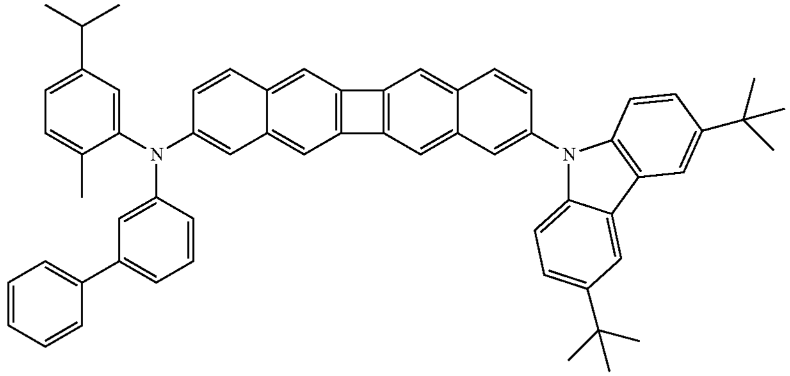

-continued
[Formula 72]
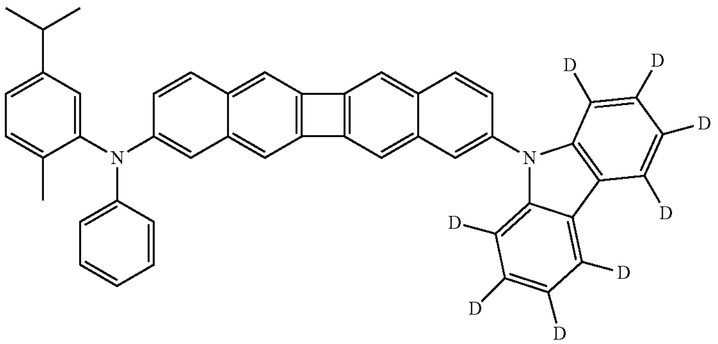
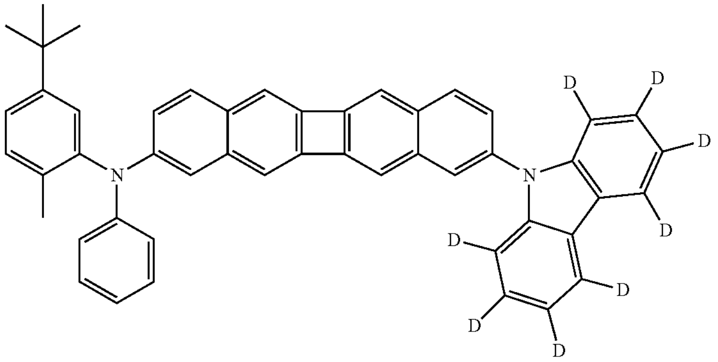
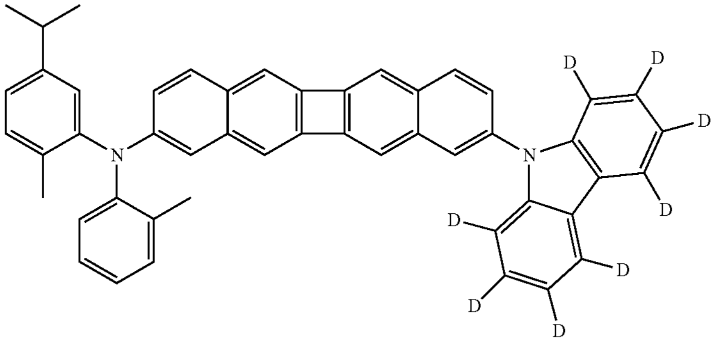
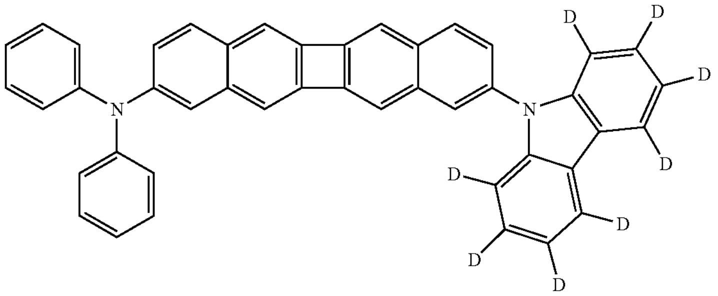
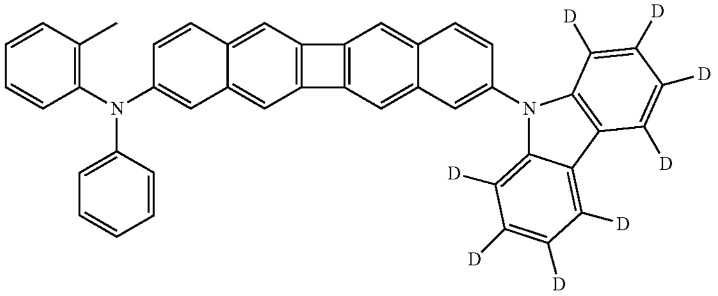

-continued
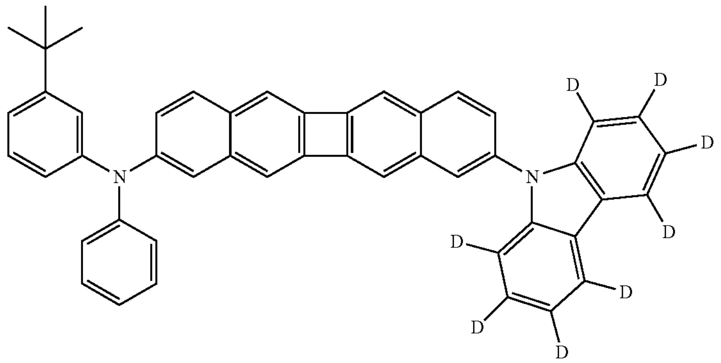
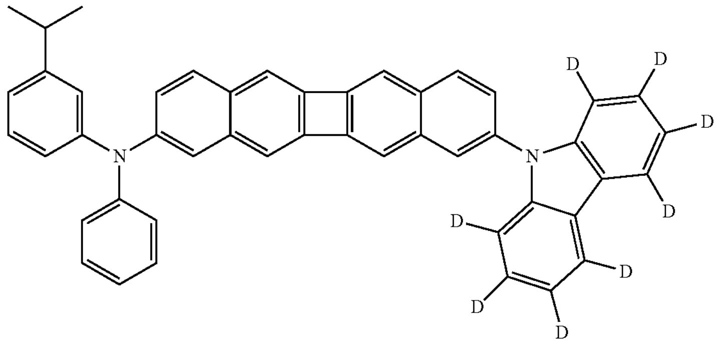
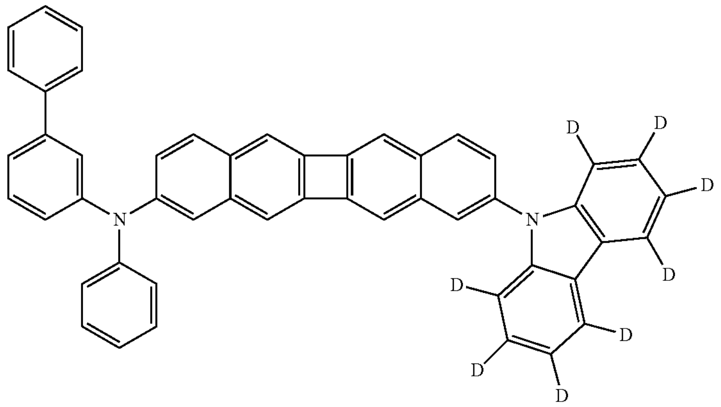
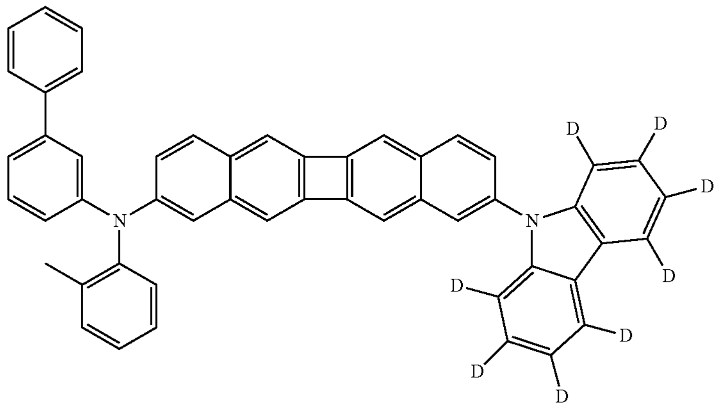

-continued
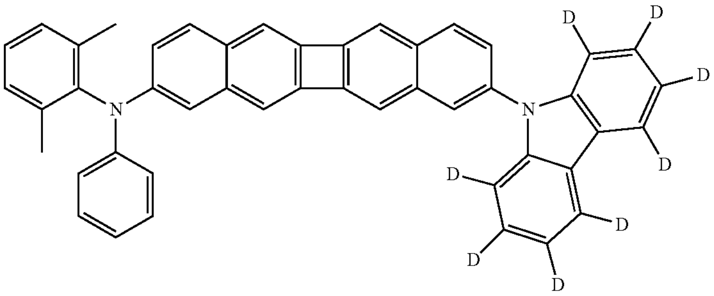
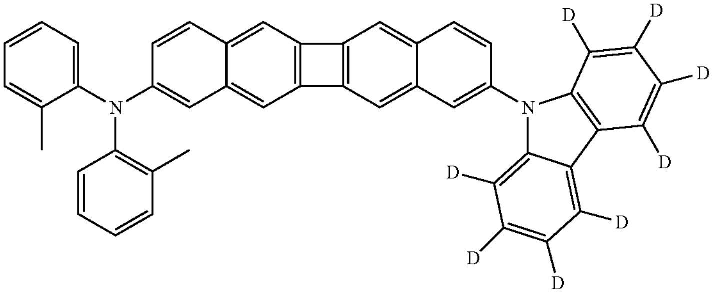
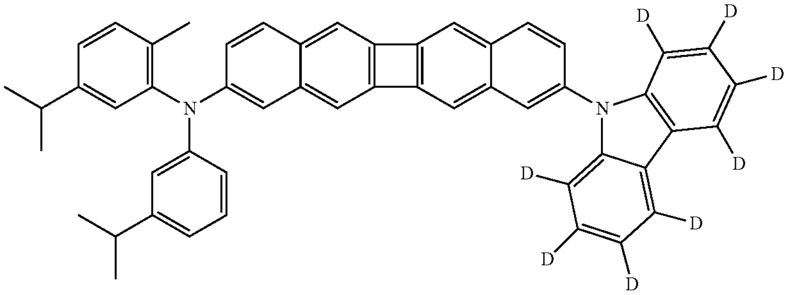
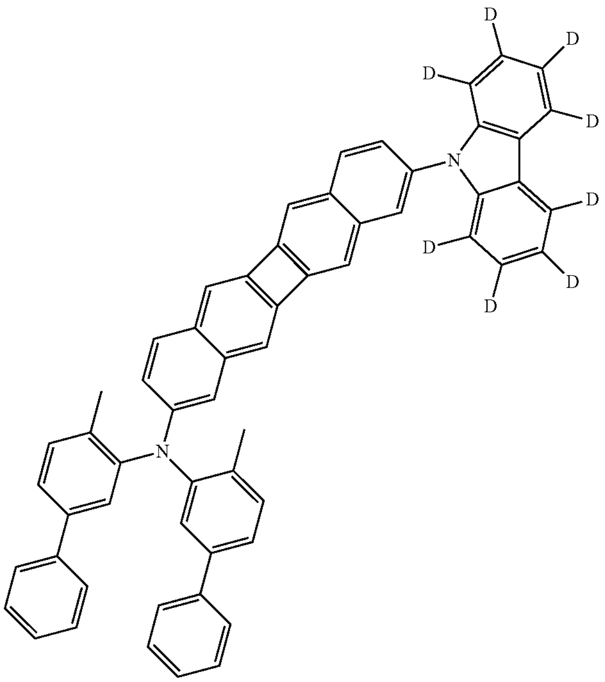

-continued
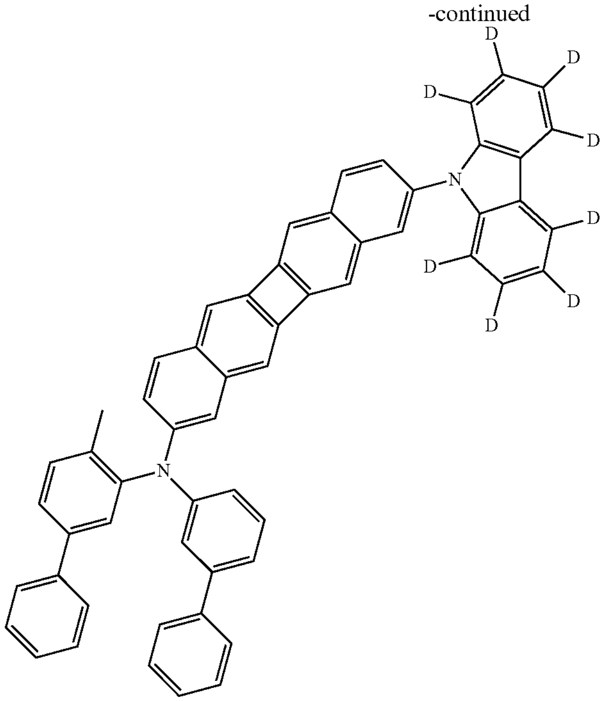
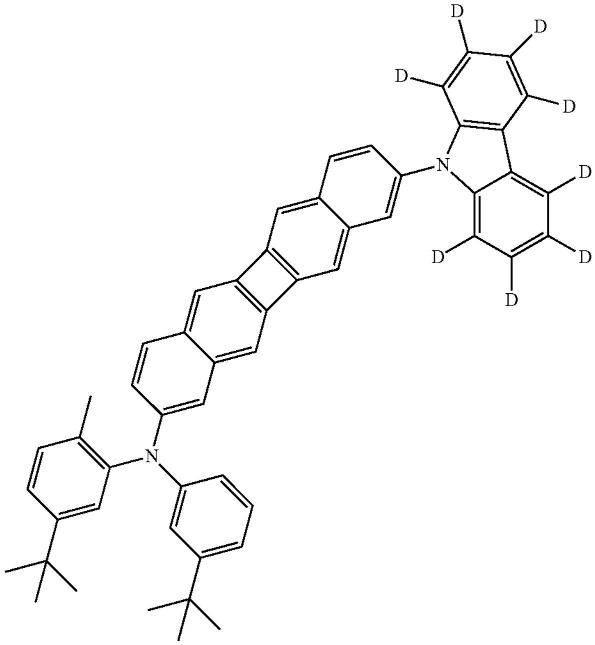

-continued
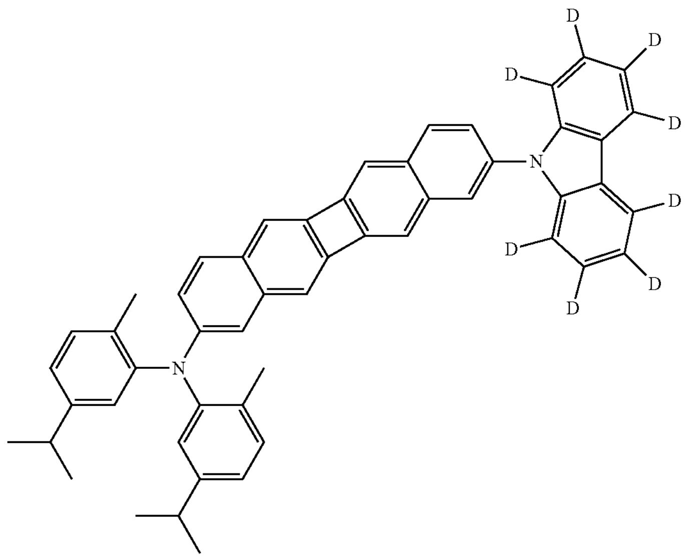
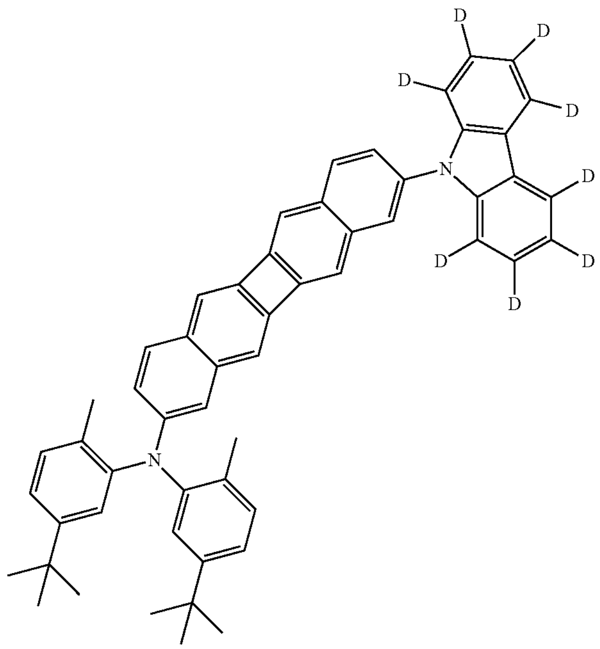

-continued
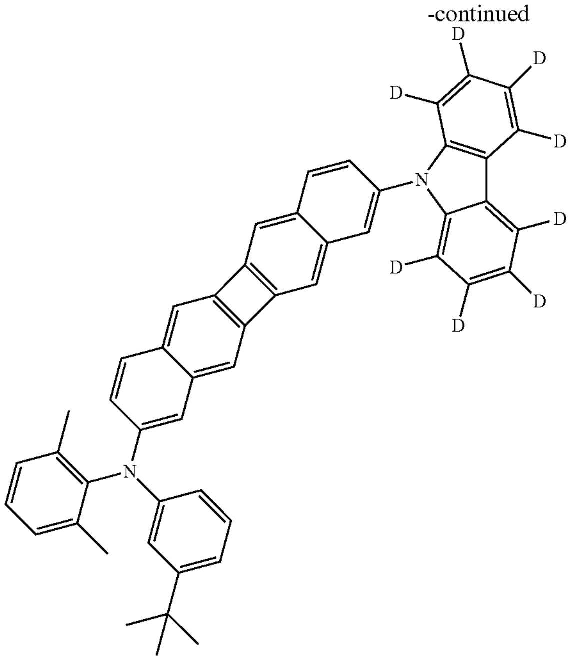
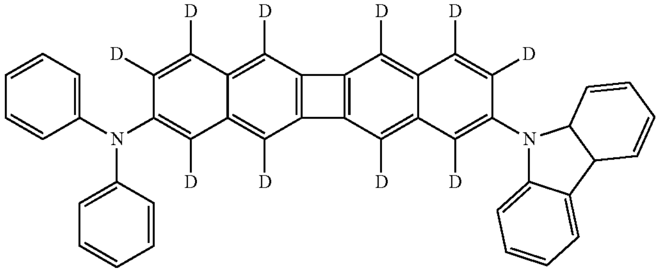
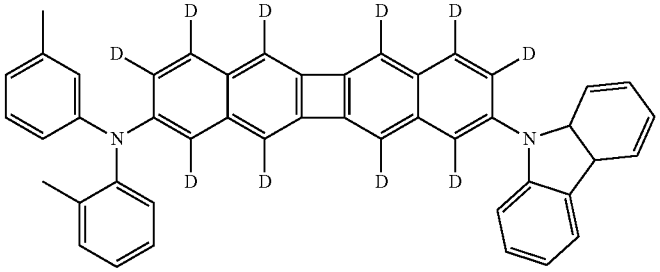
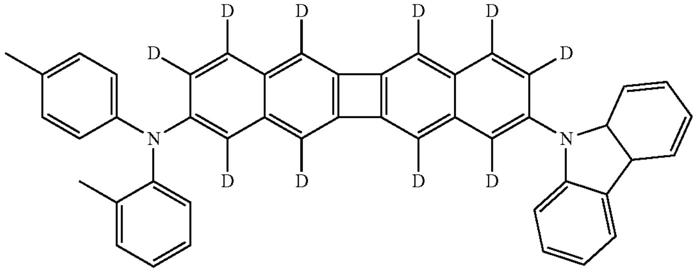
[Formula 73]
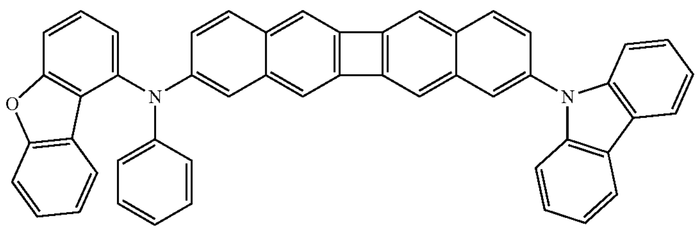

-continued
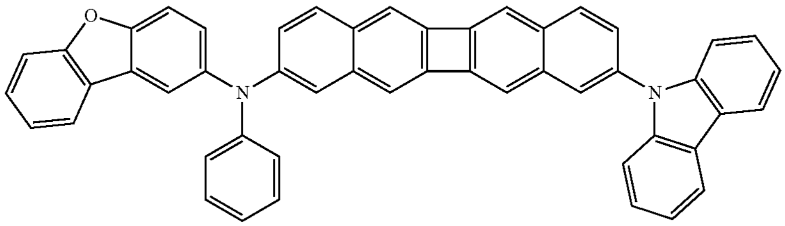
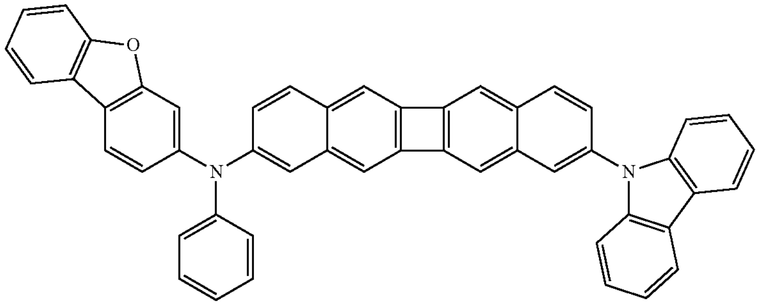
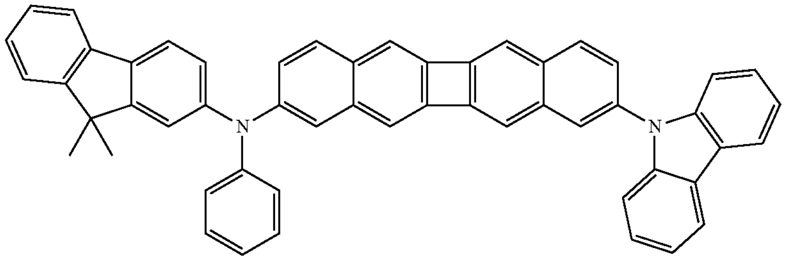
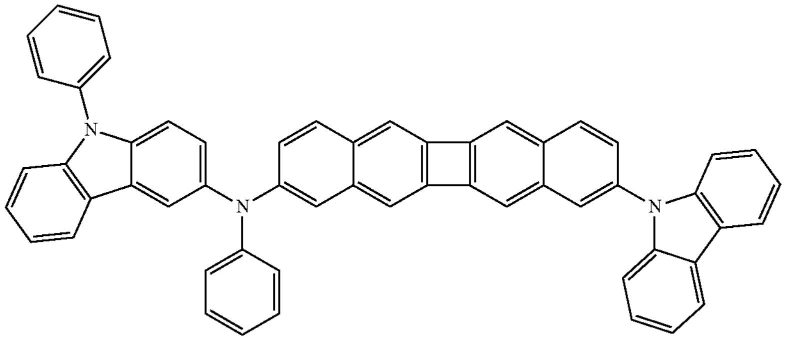
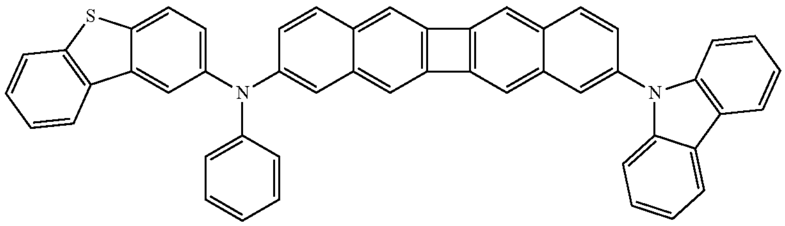
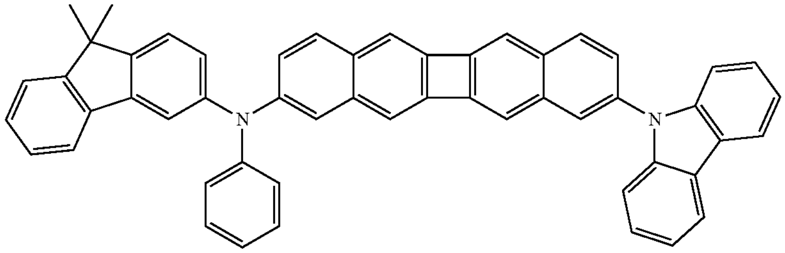

-continued
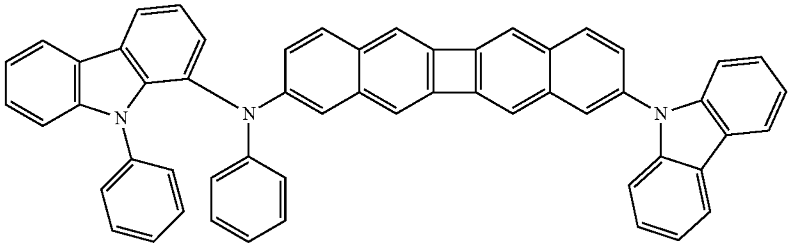
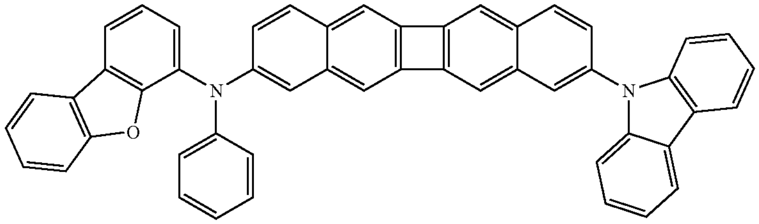
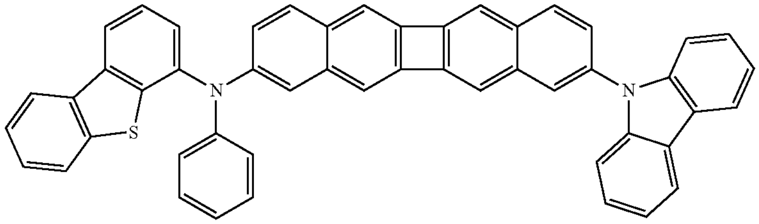
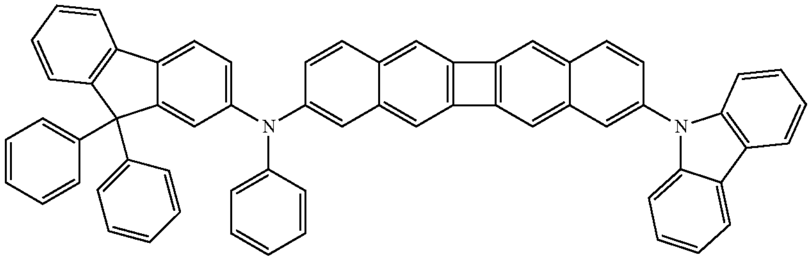
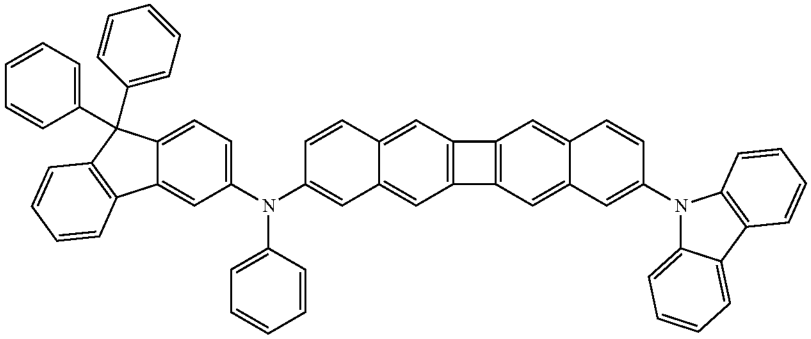
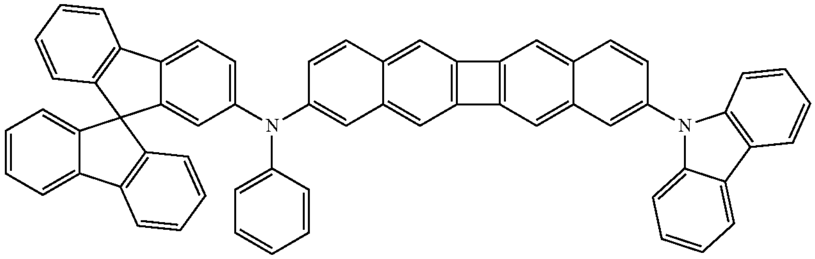

-continued
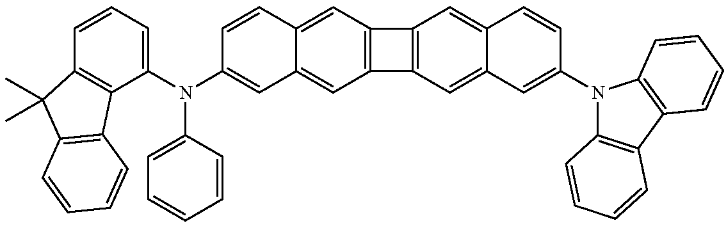
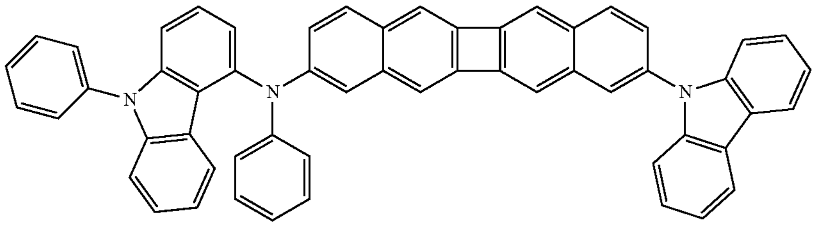
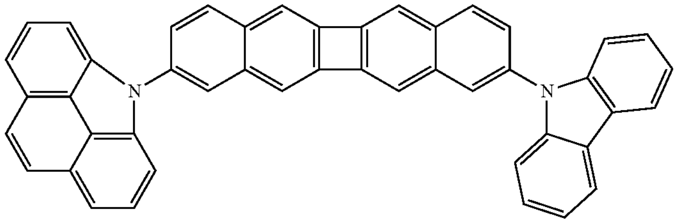
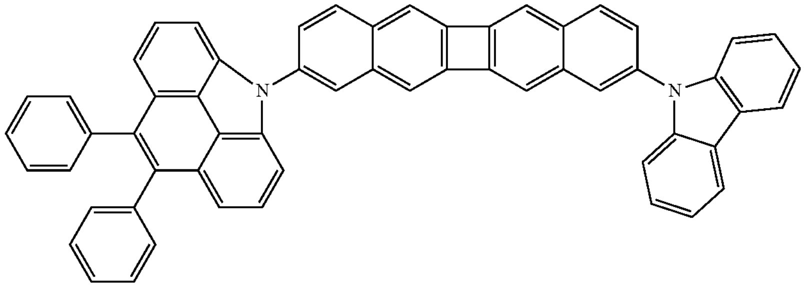
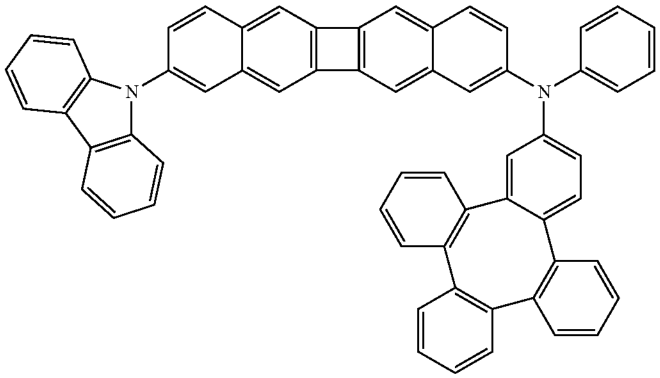
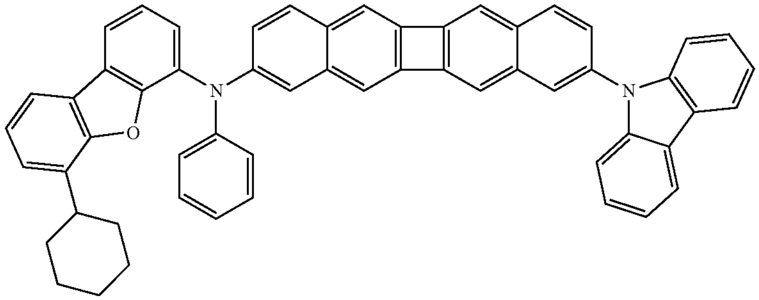

-continued
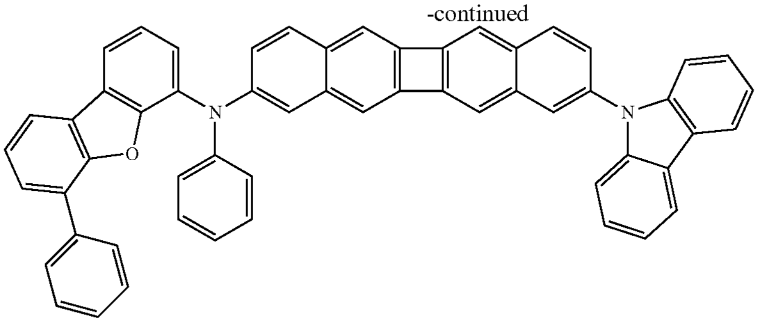
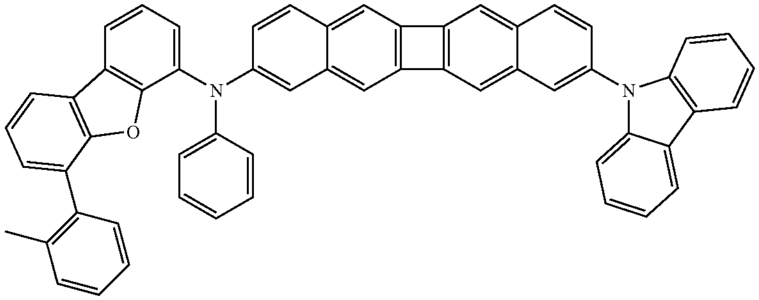
[Formula 74]
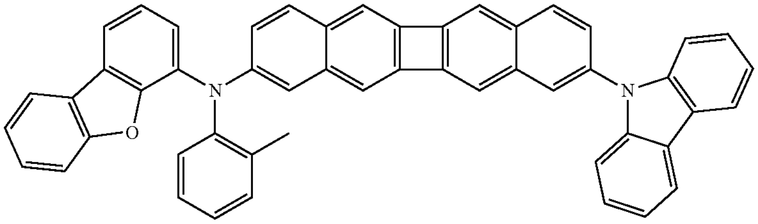
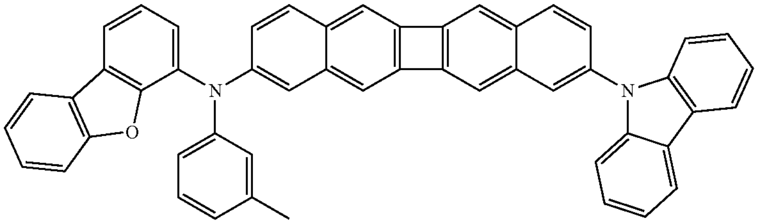
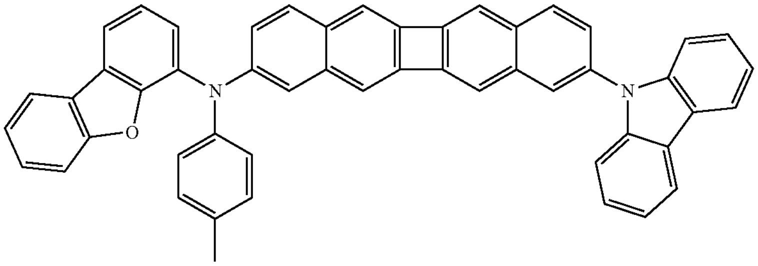
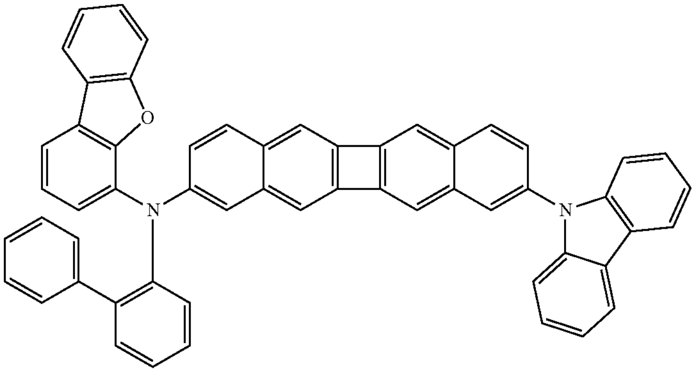

-continued
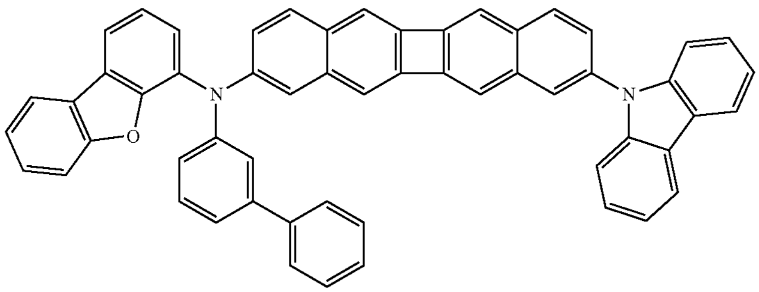
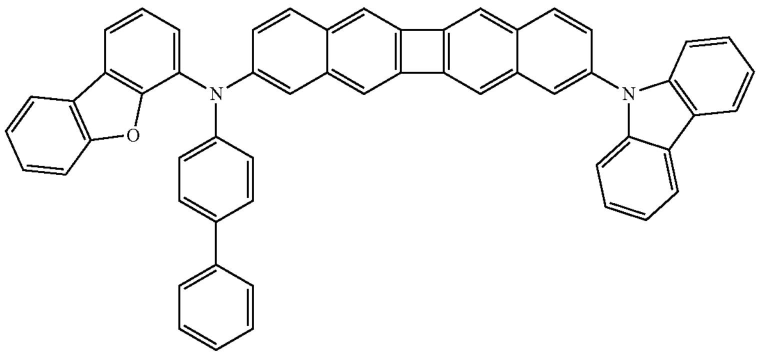
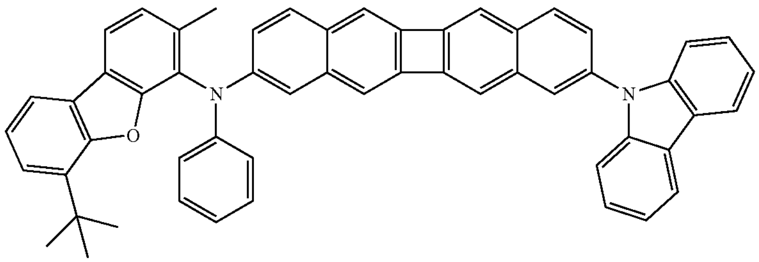
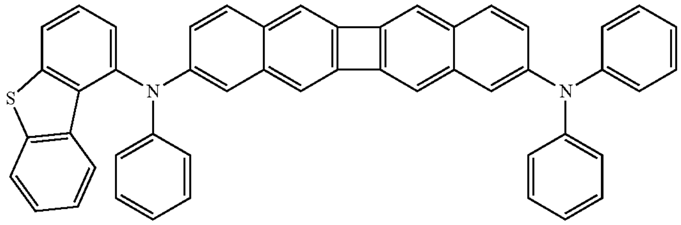
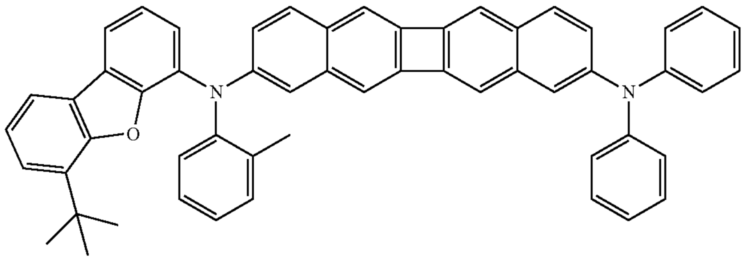
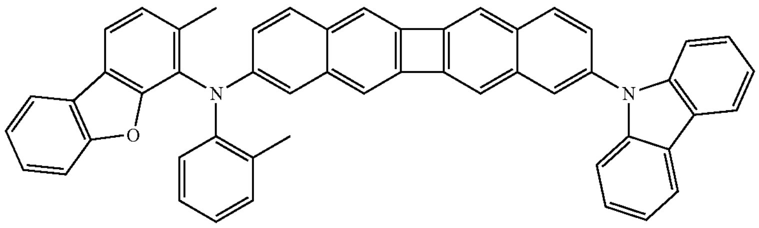

-continued
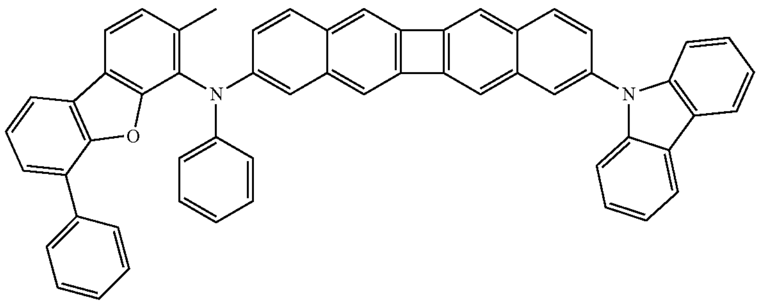
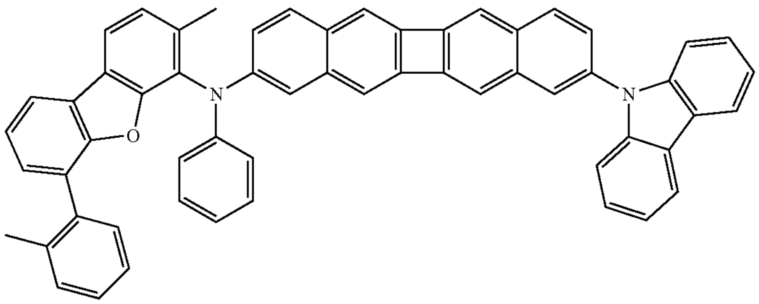
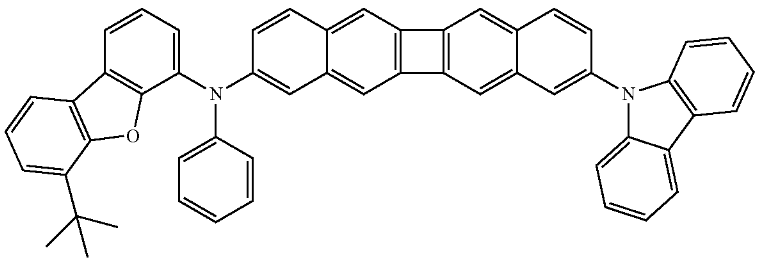
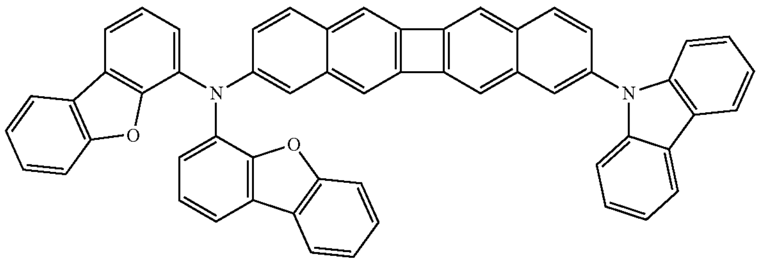
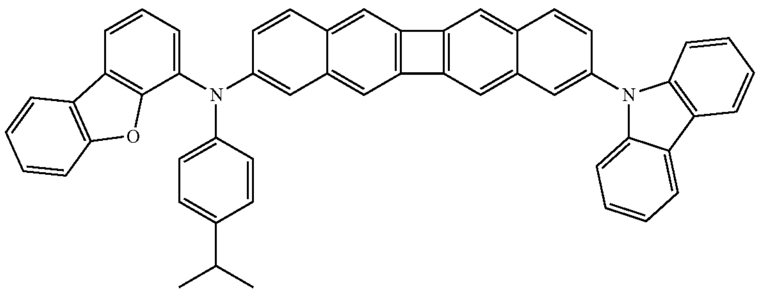
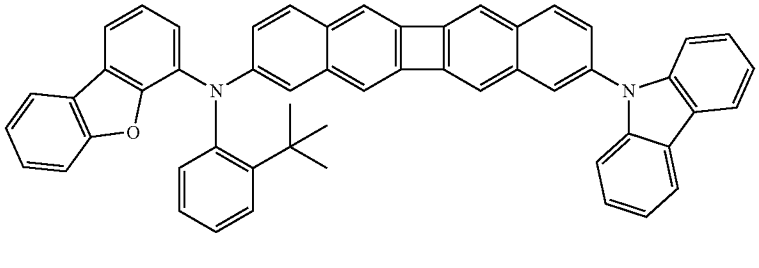

-continued
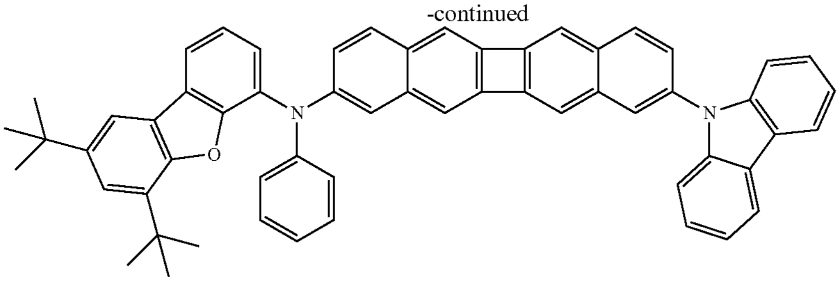
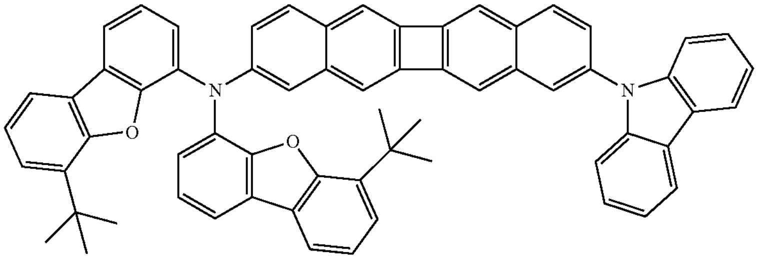
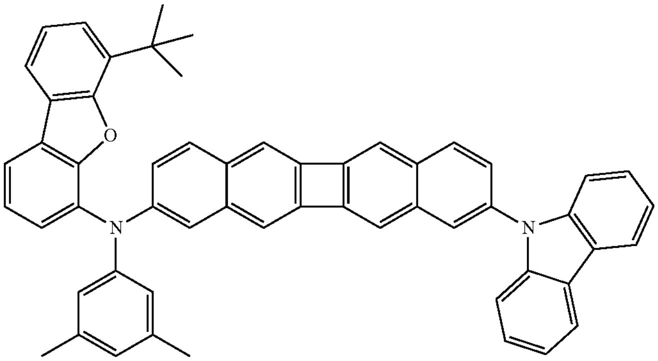
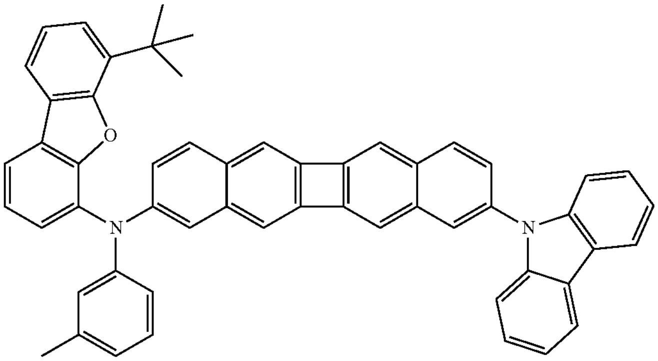
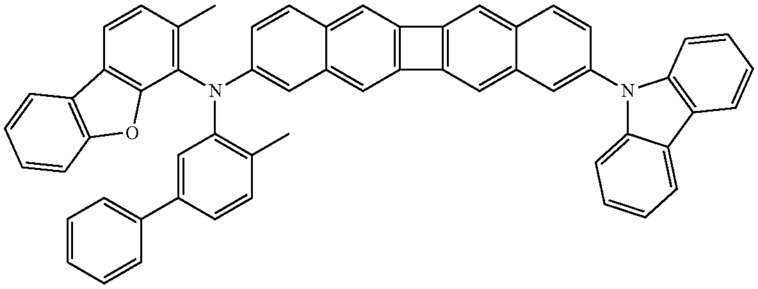

-continued
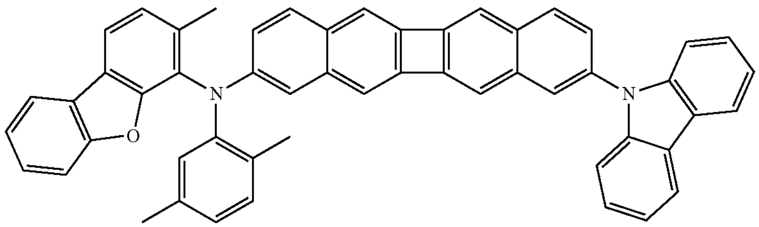
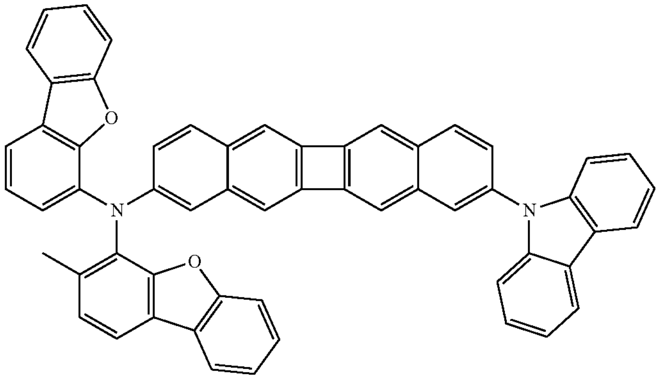
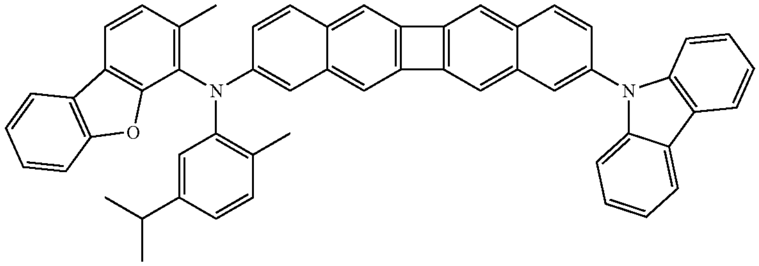
[Formula 75]
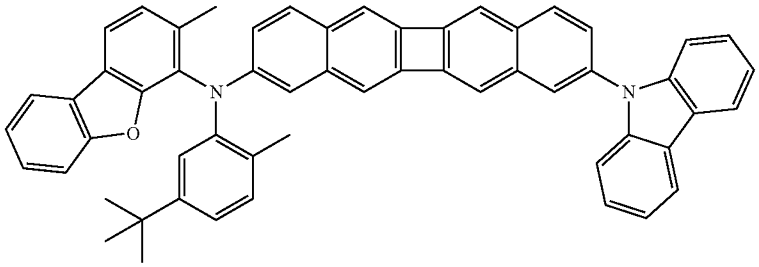
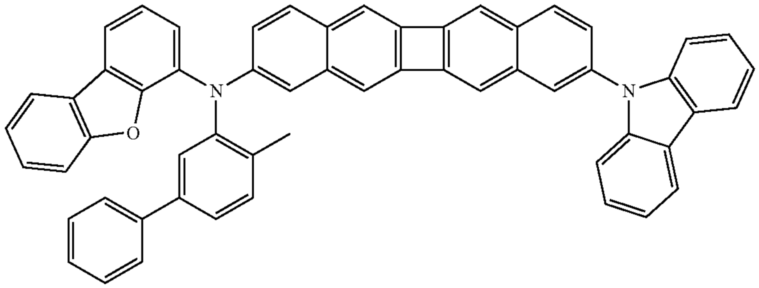

-continued
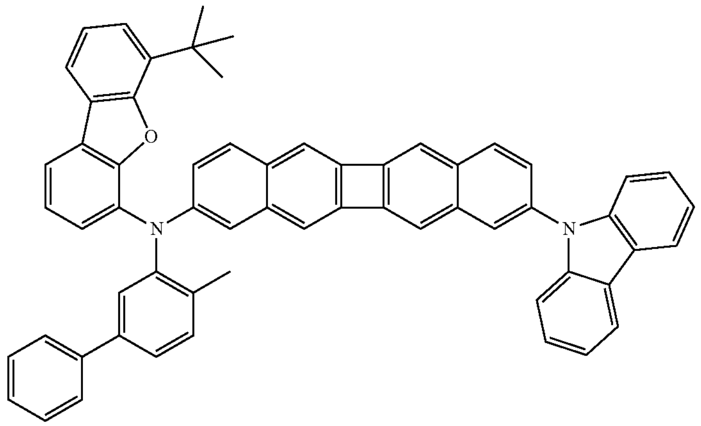
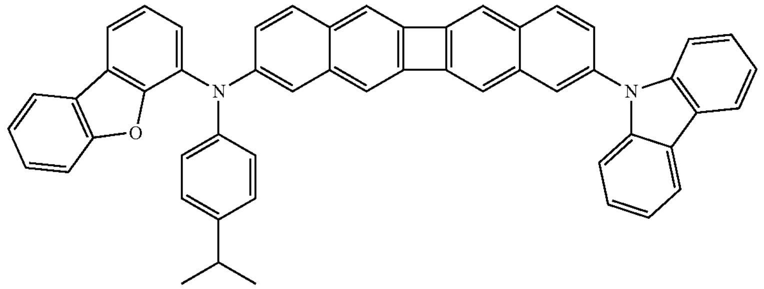
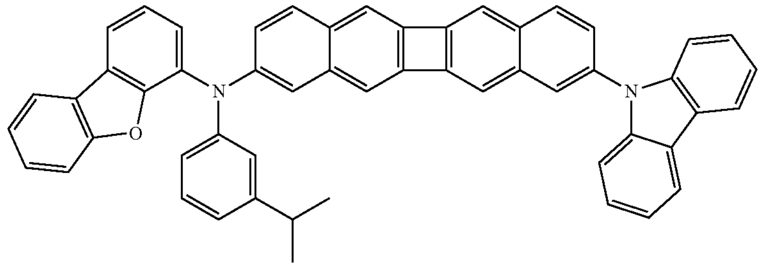
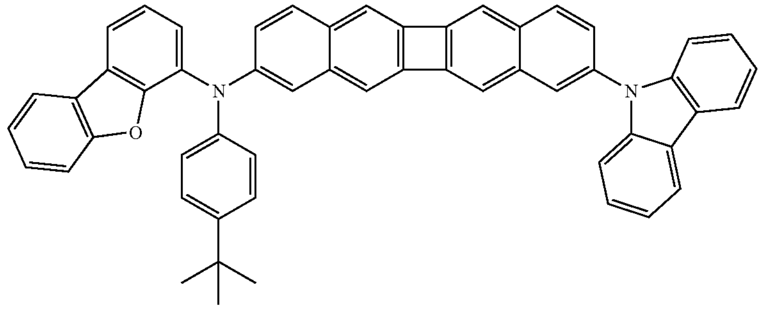
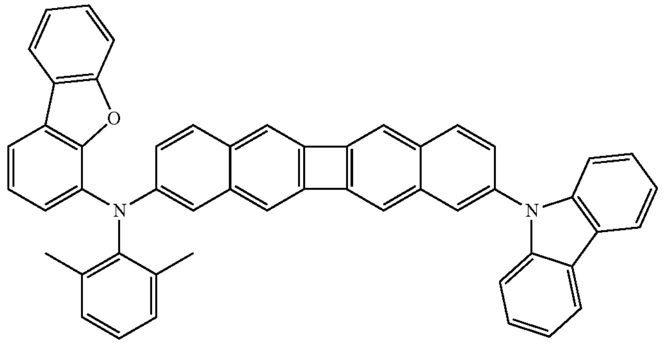

-continued
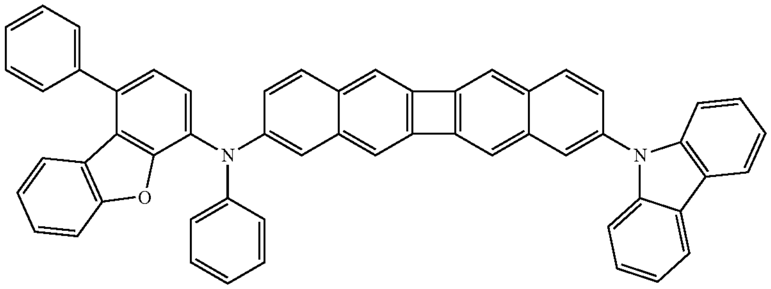
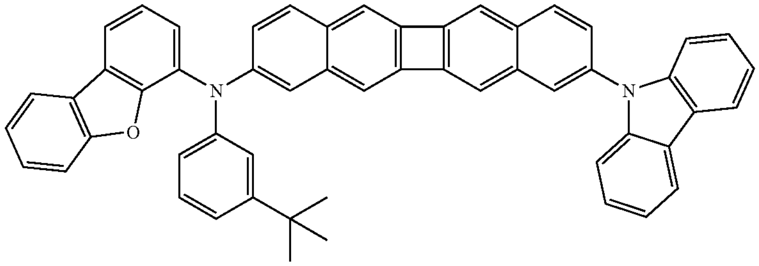
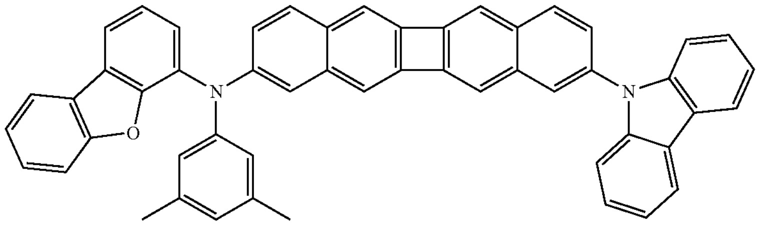
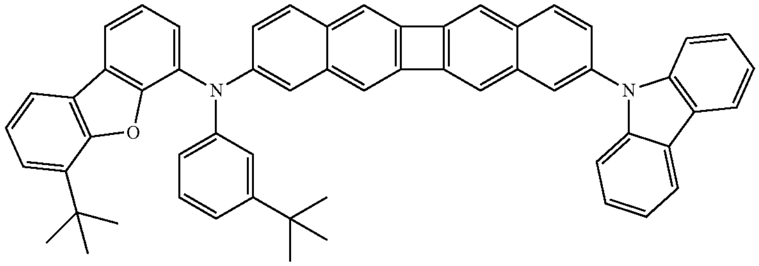
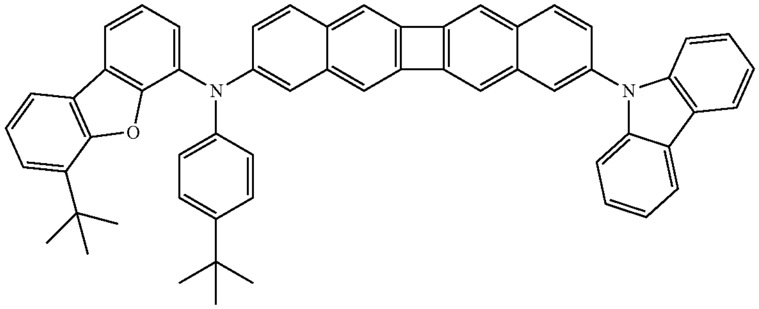
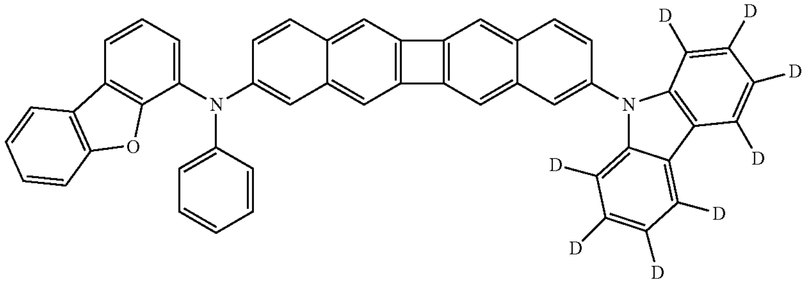

-continued
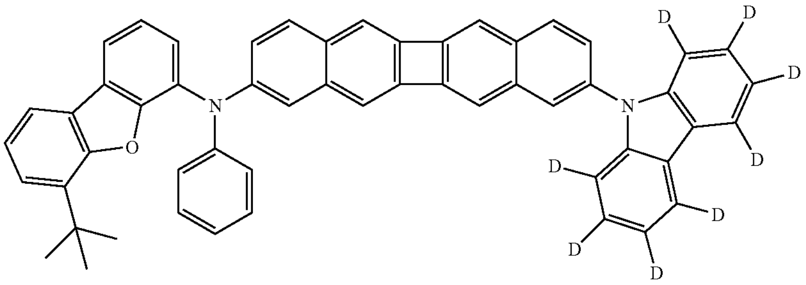
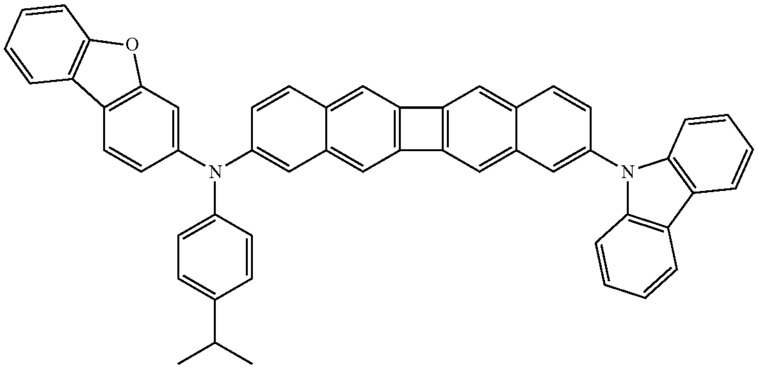
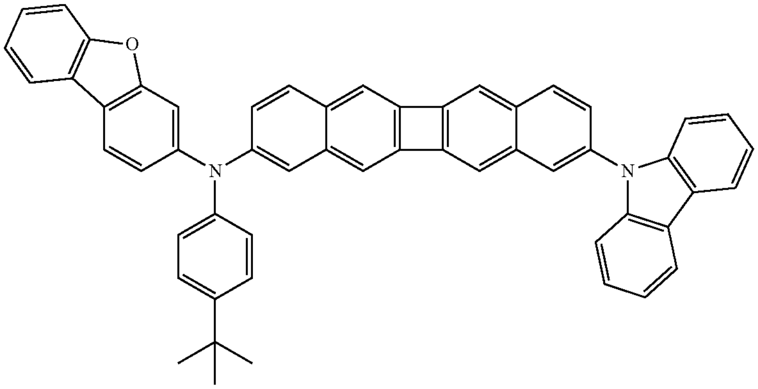
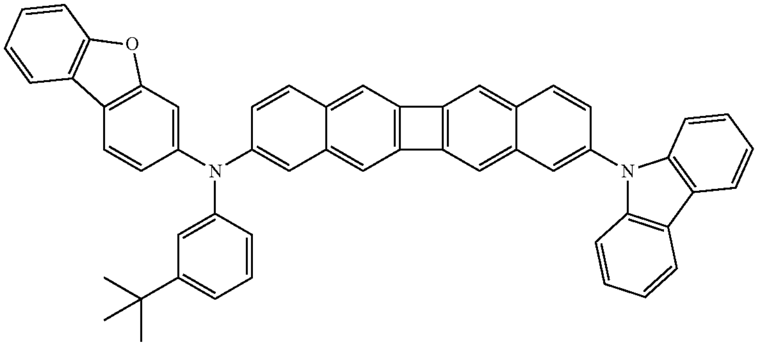
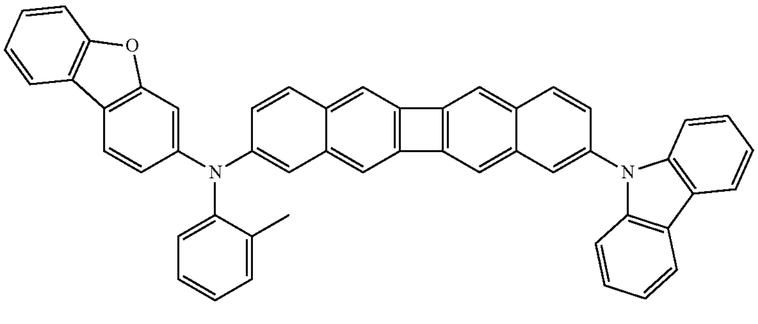

-continued
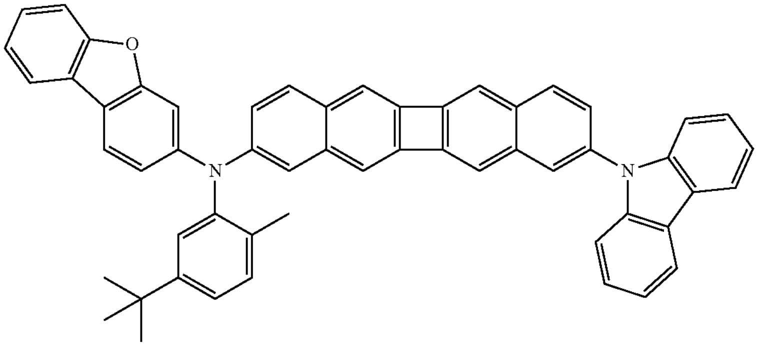
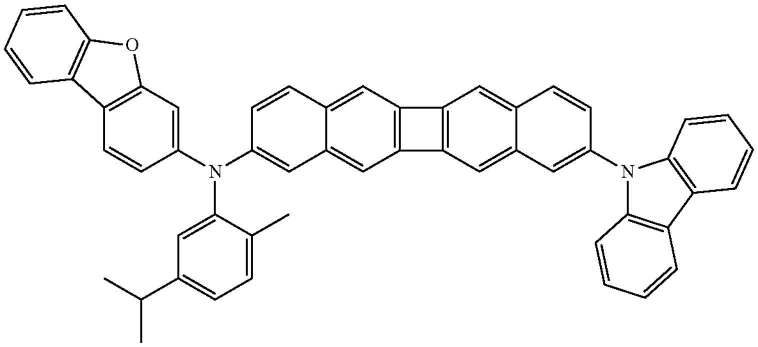
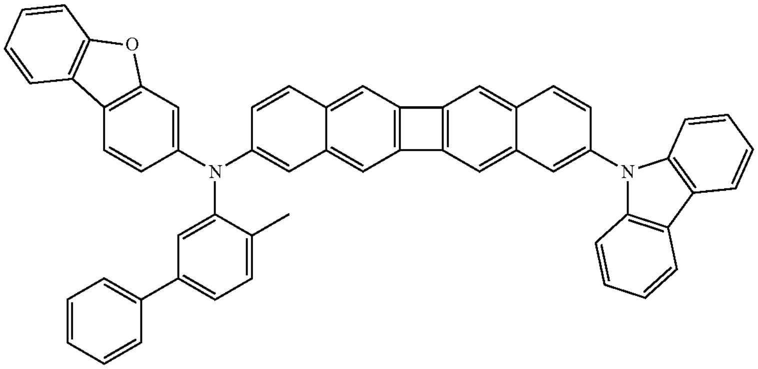
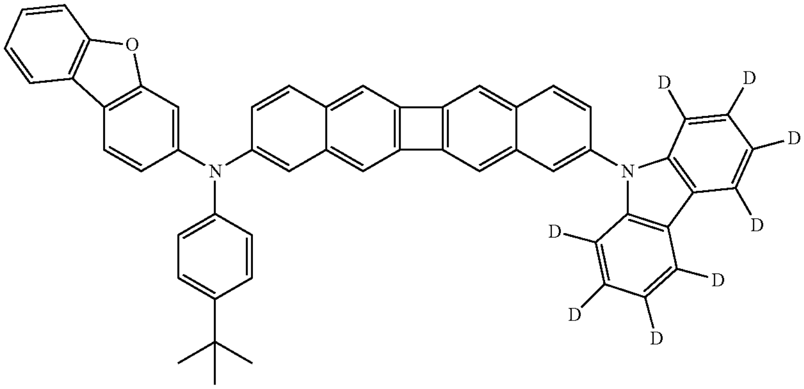

-continued
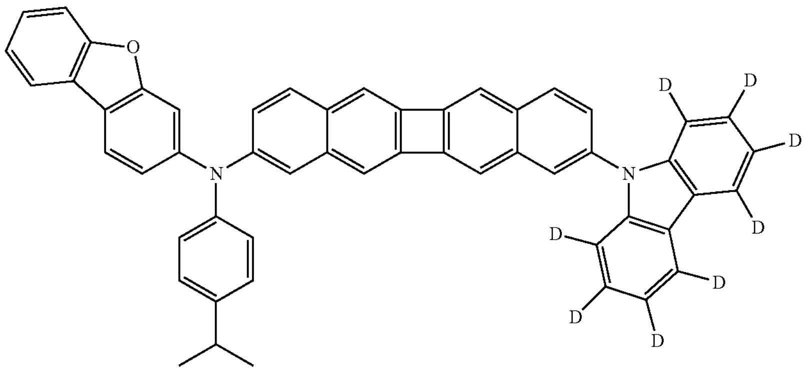
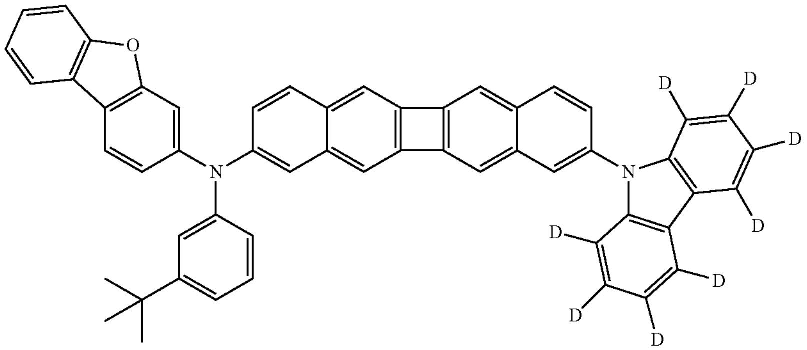
[Formula 76]
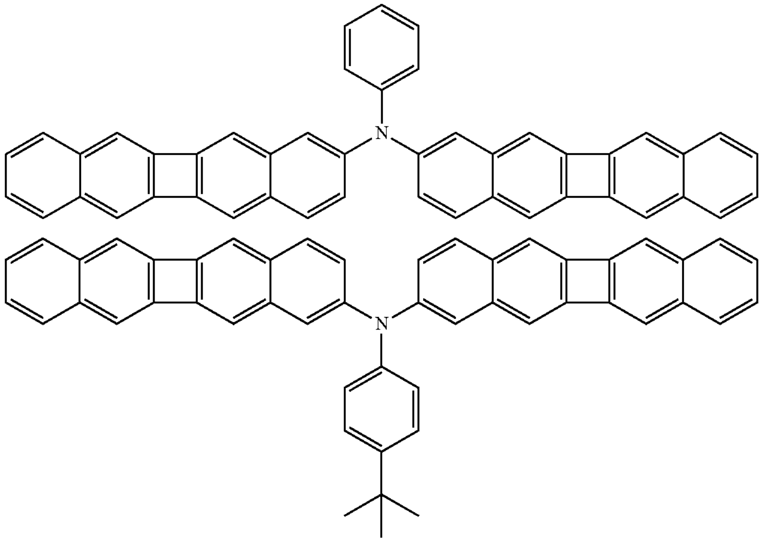

-continued
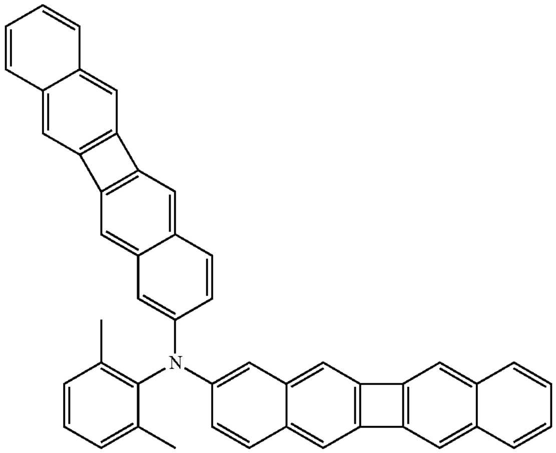
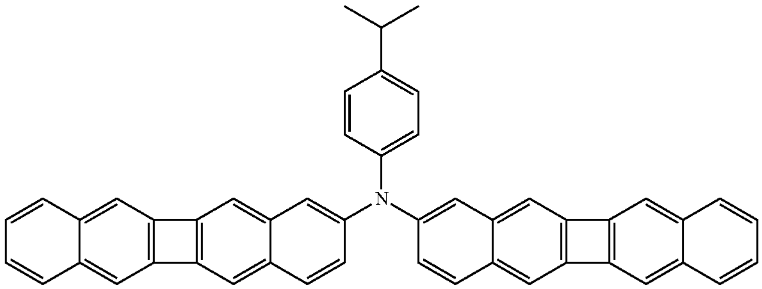
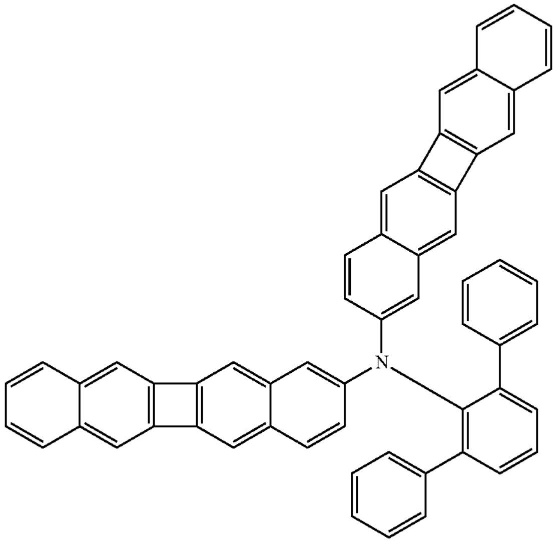
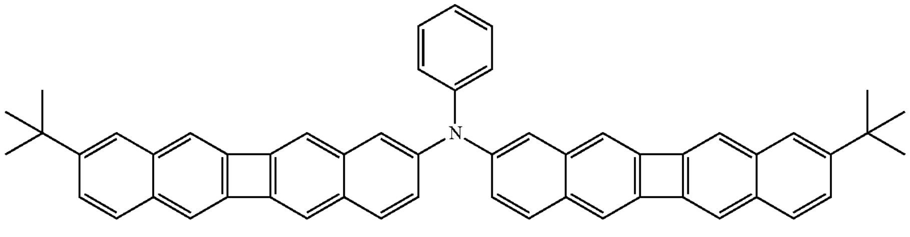

-continued
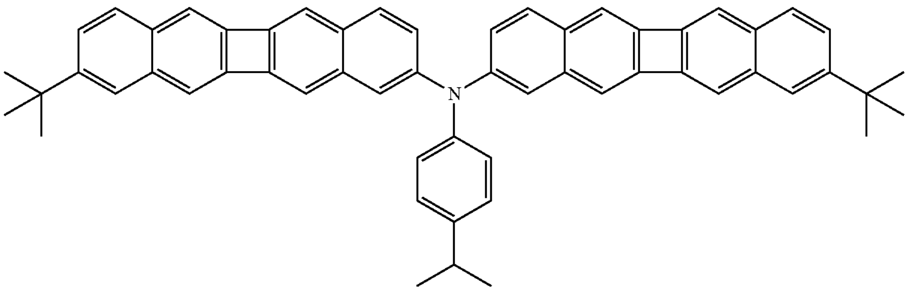
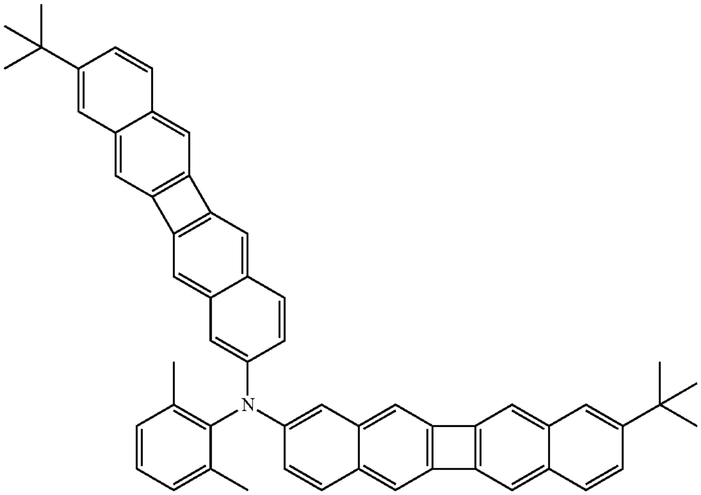
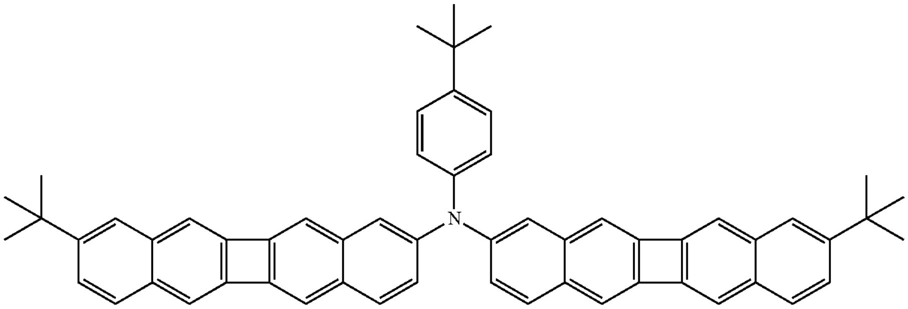
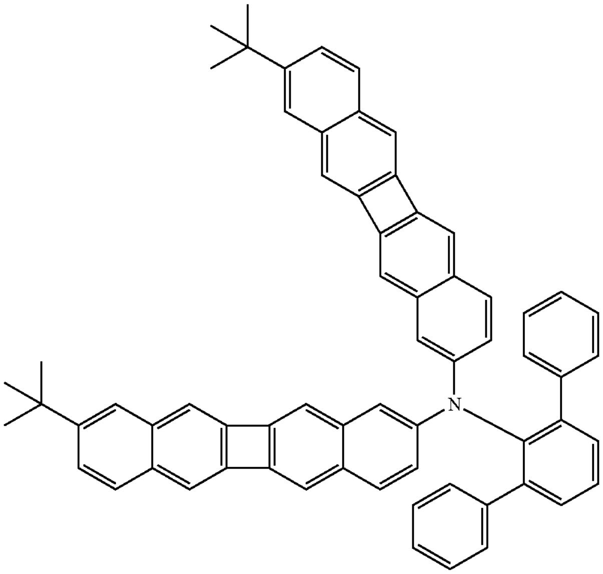

-continued
[Formula 77]
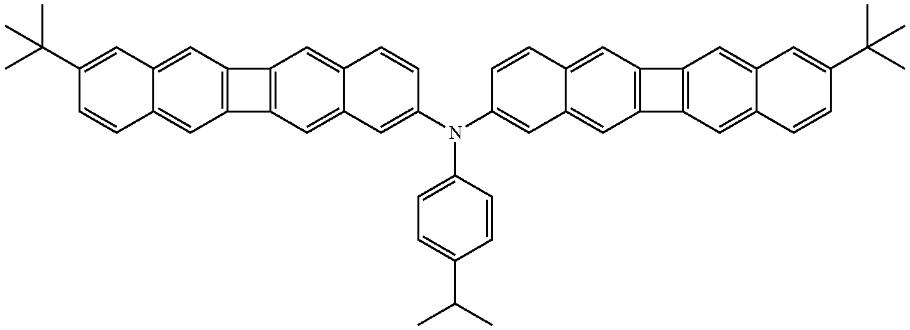
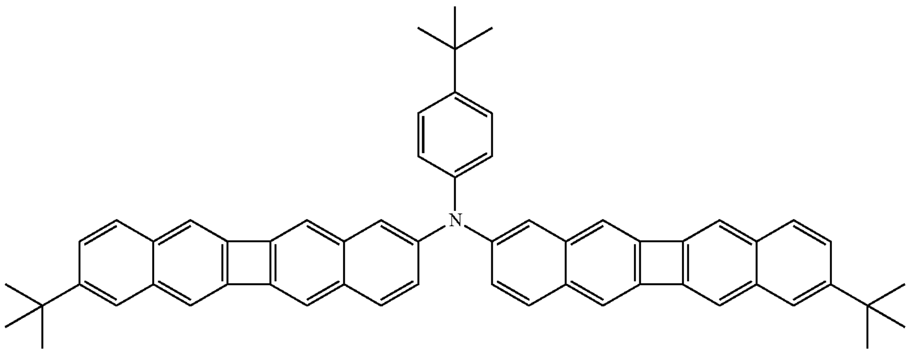
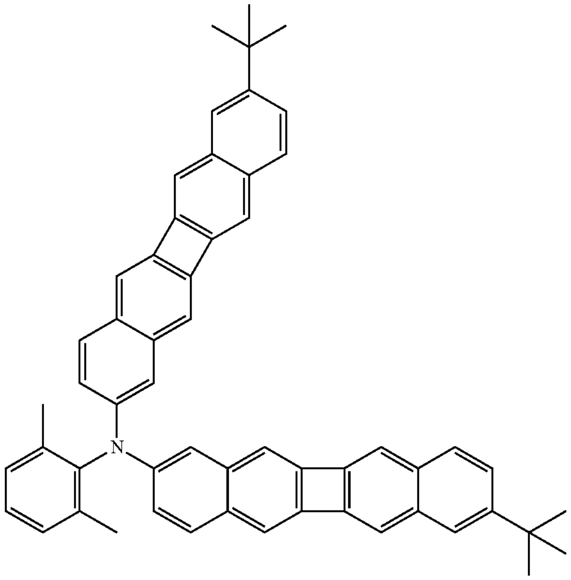
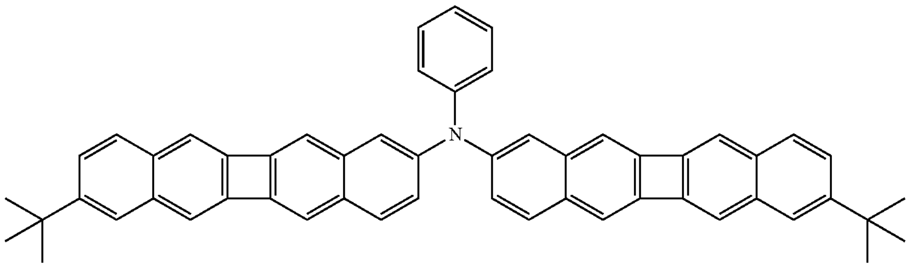

-continued
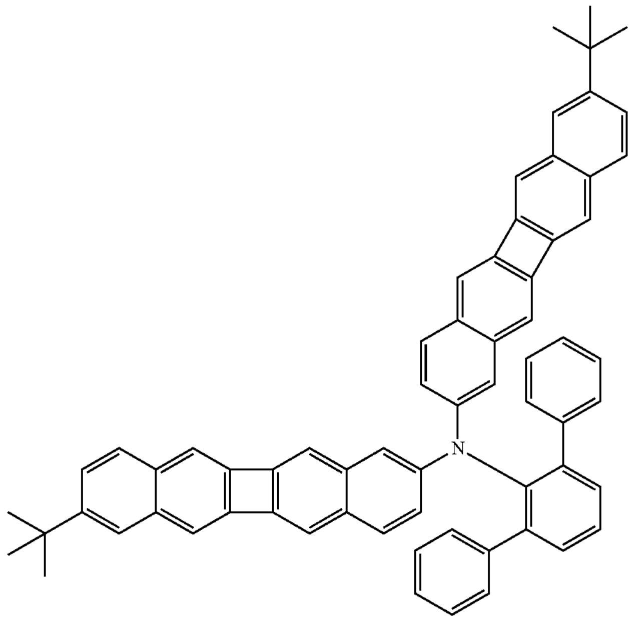
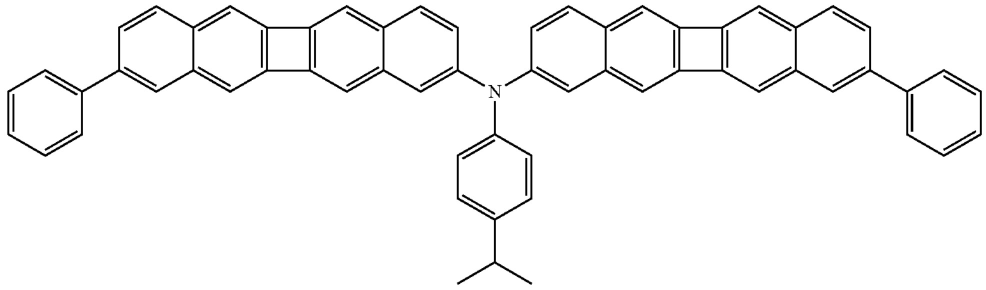
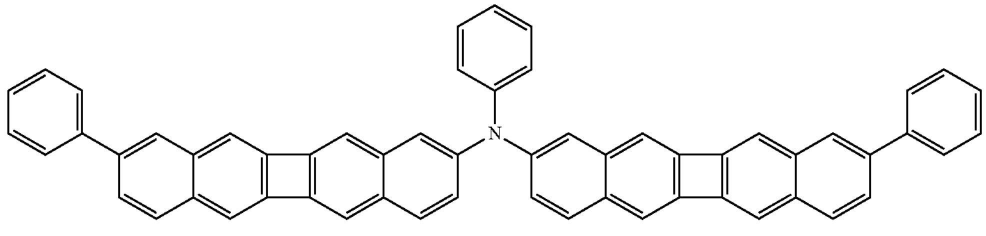

-continued
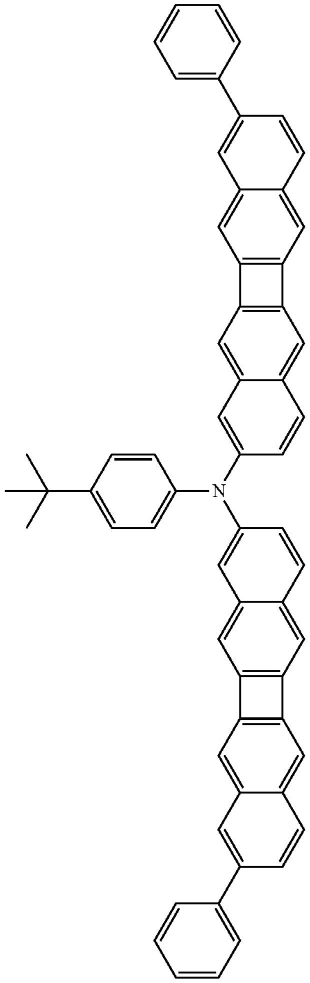
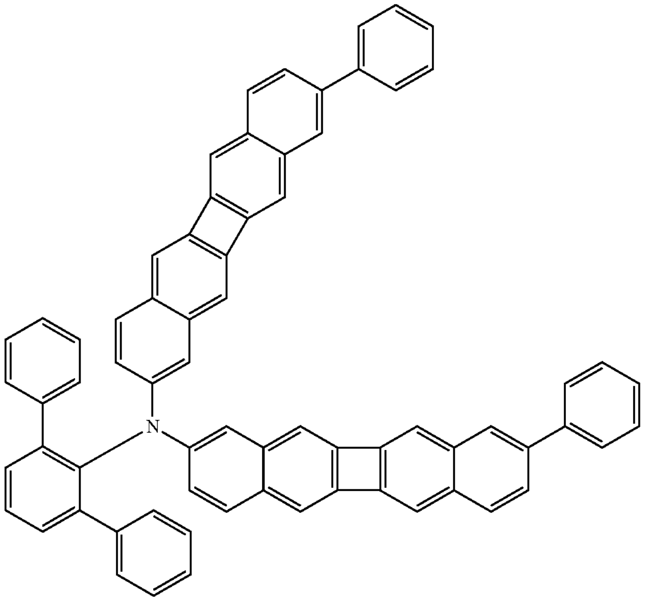
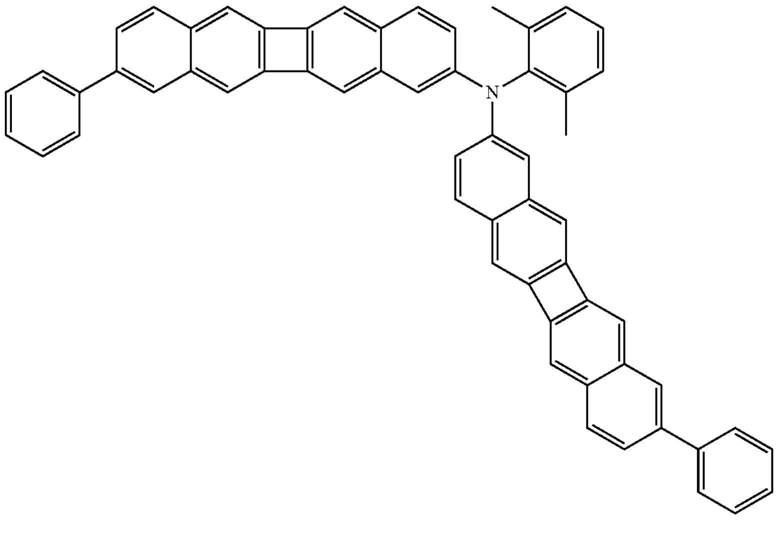

-continued
[Formula 78]
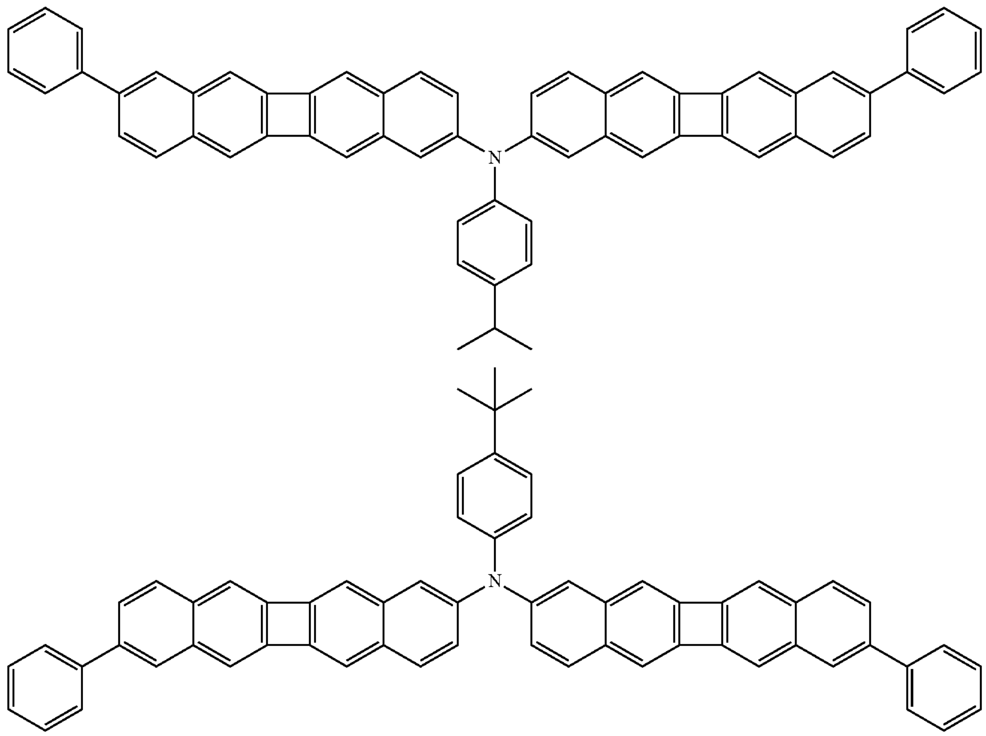

-continued
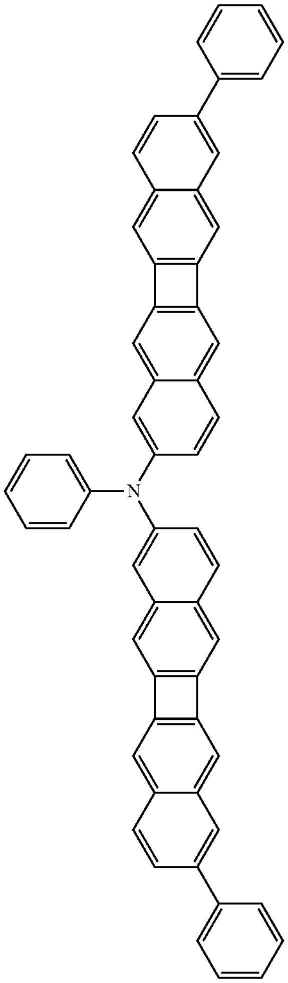
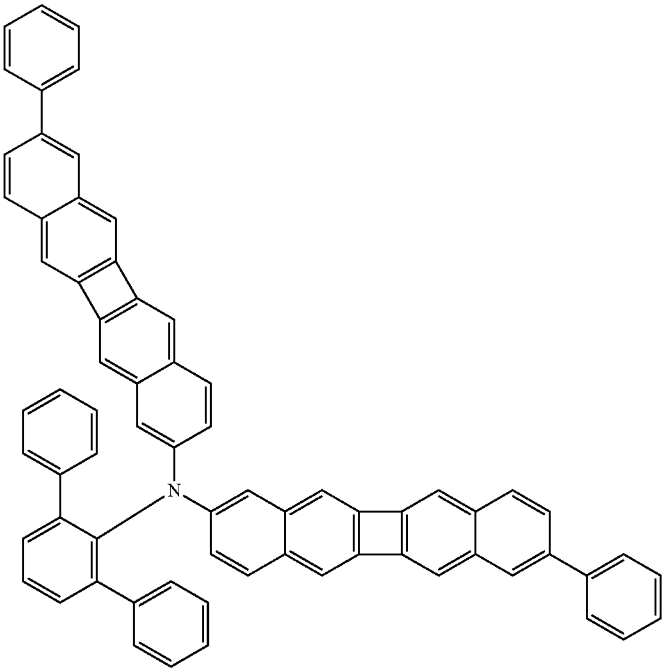
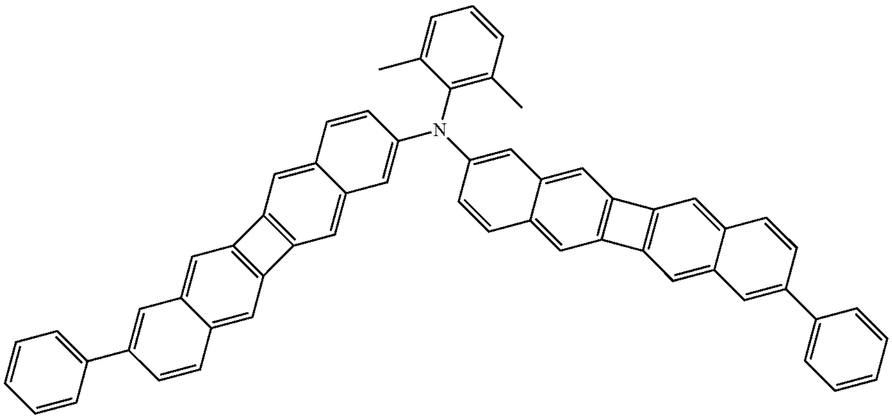

-continued
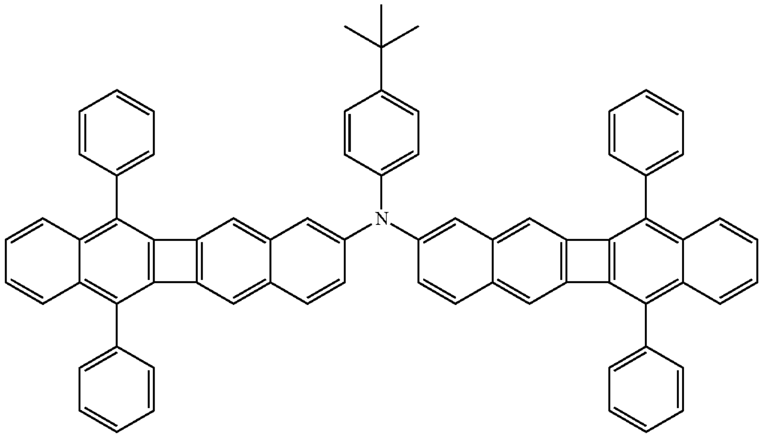
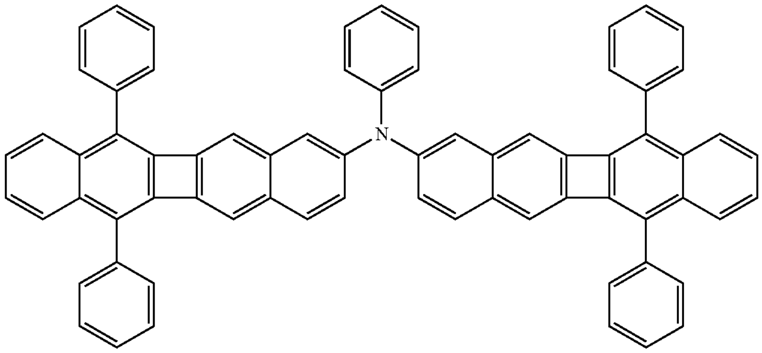
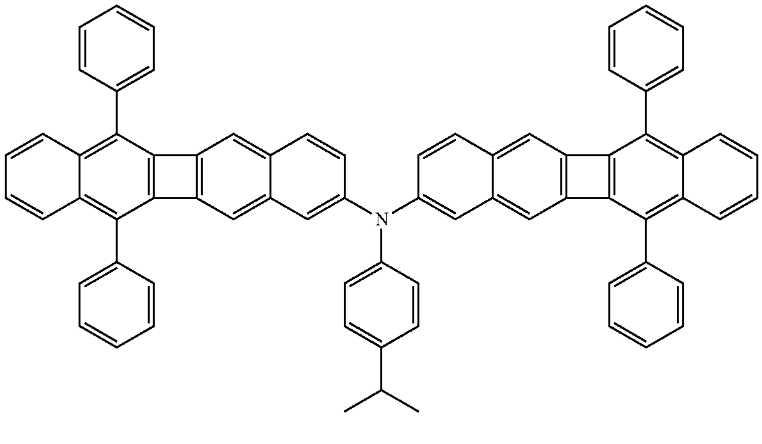

-continued
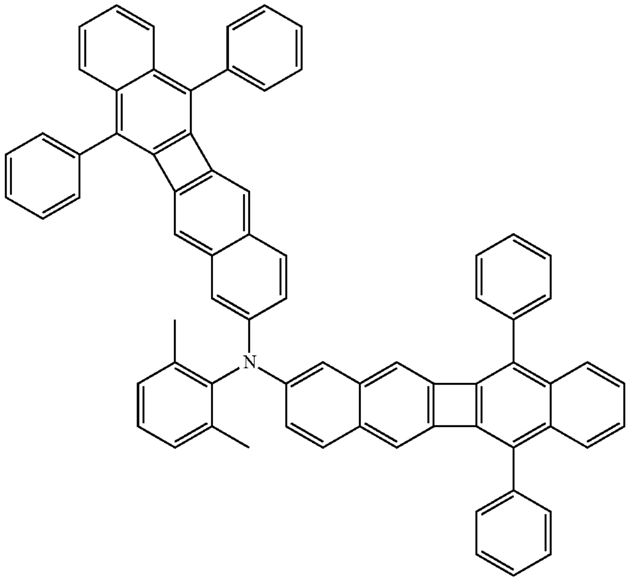
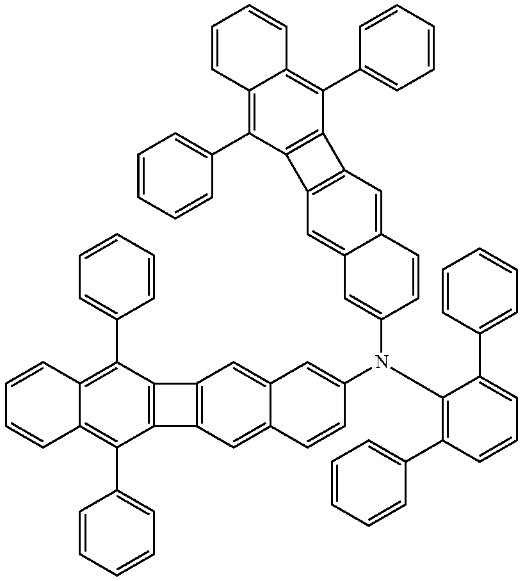
[Formula 79]
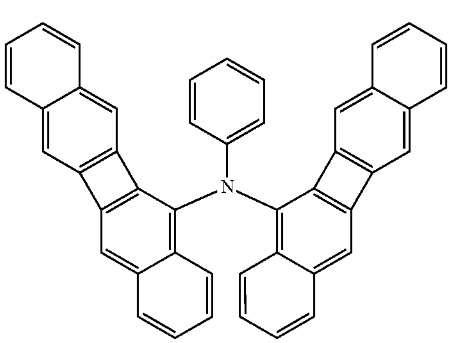
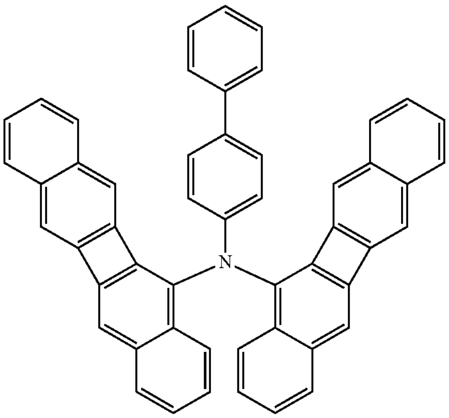

-continued
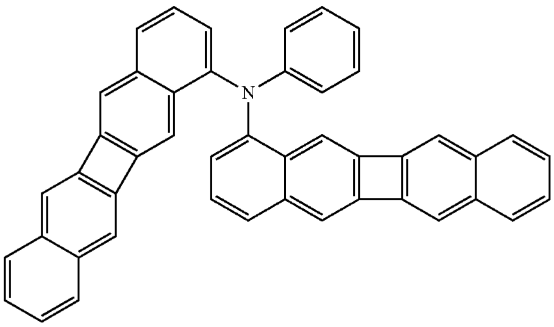
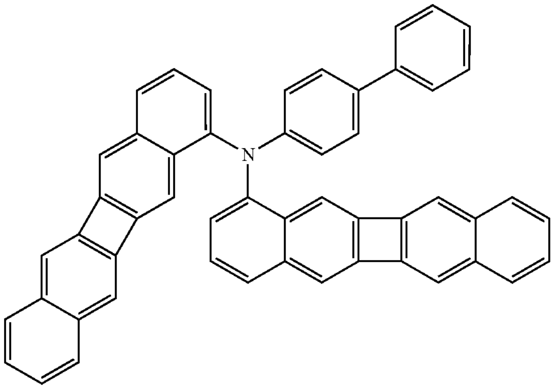
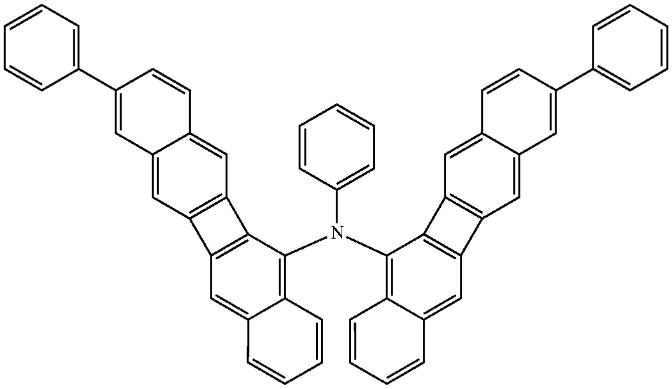
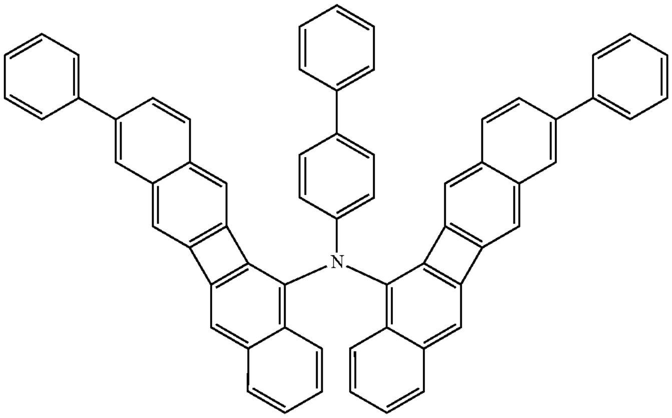
[Formula 80]
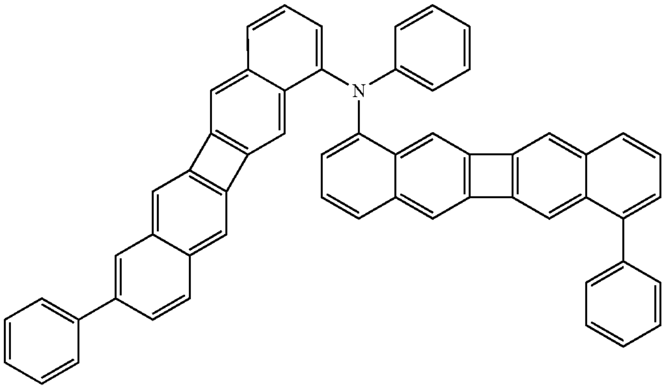

-continued
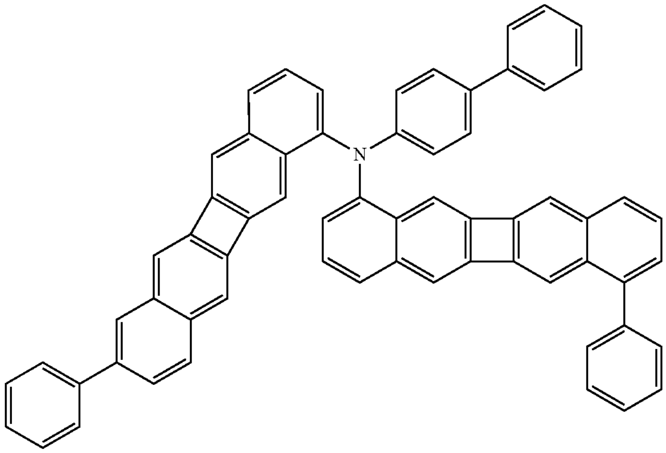
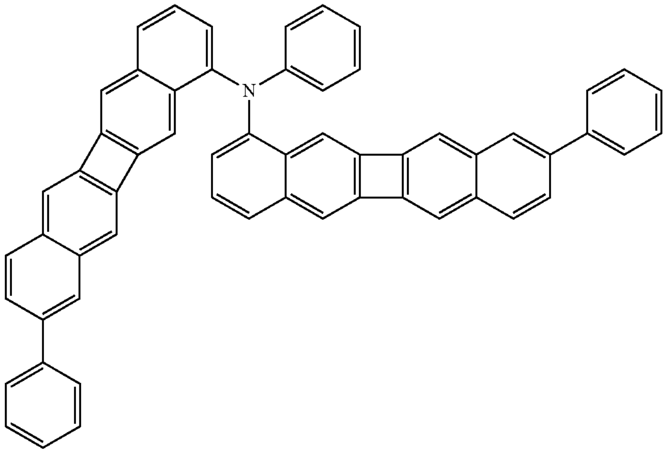
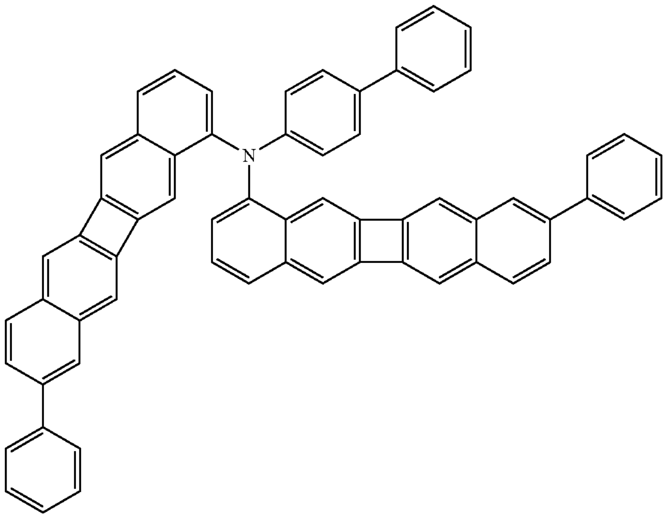

-continued
[Formula 81]
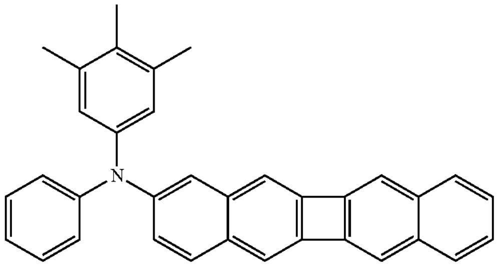
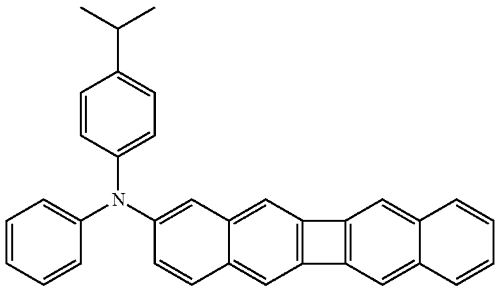
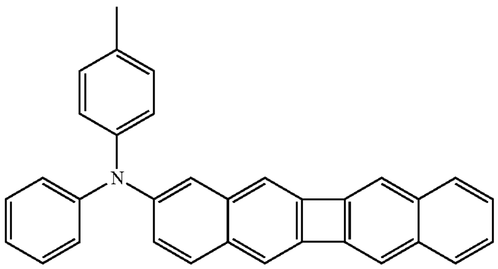
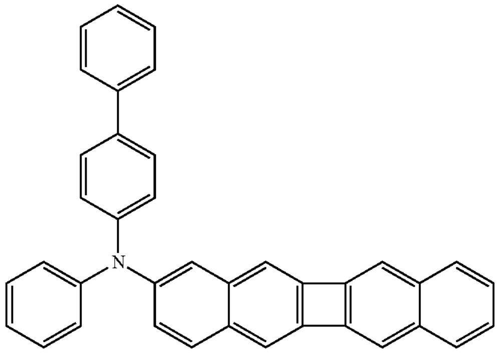
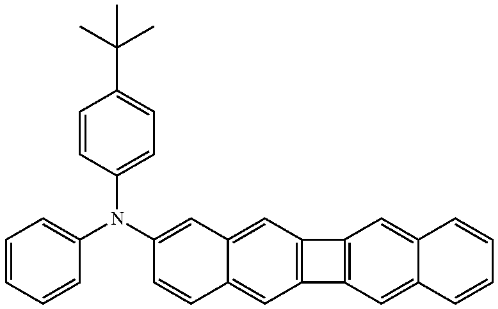
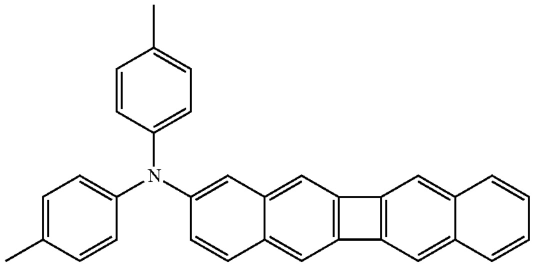
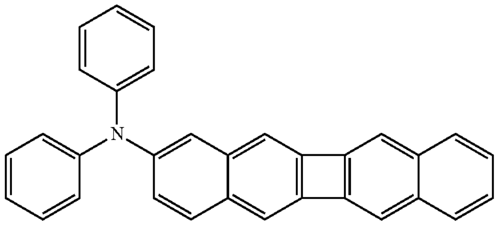
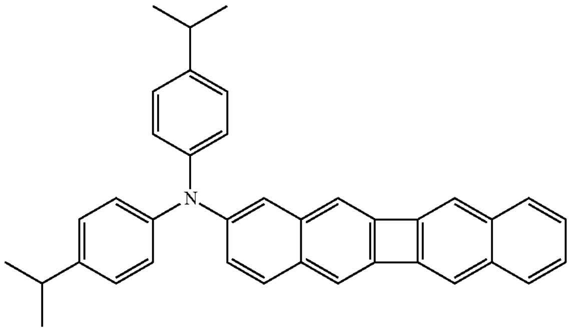
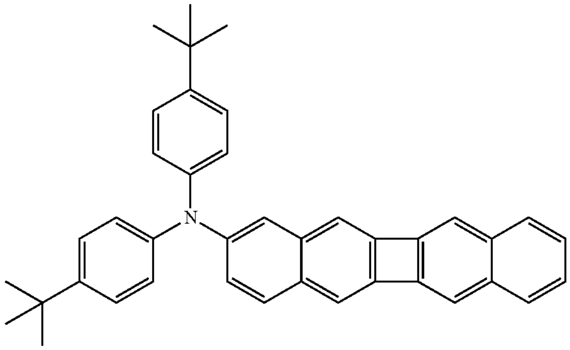
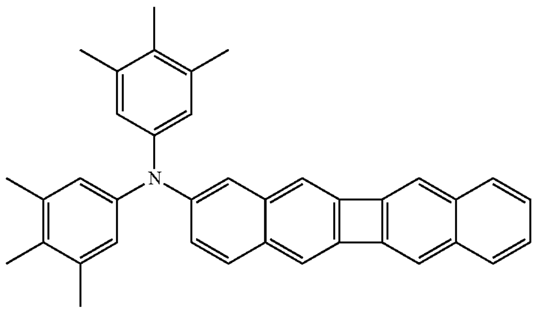

-continued
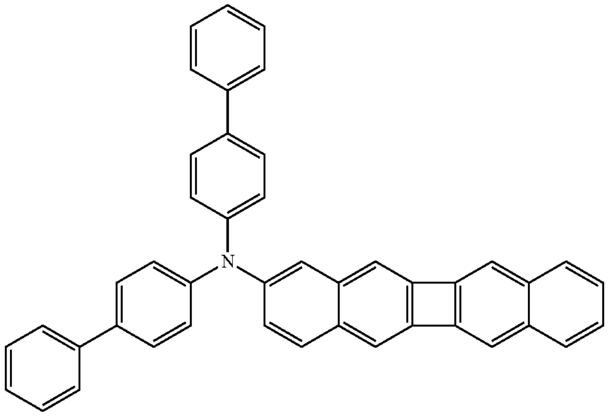
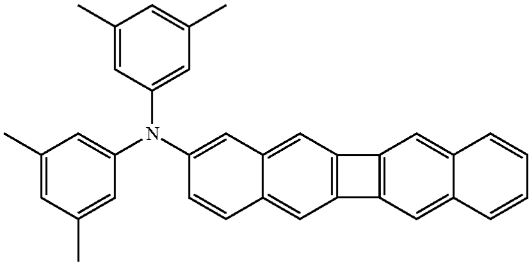
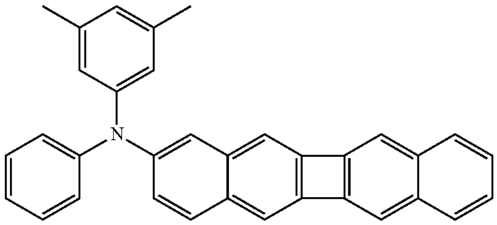
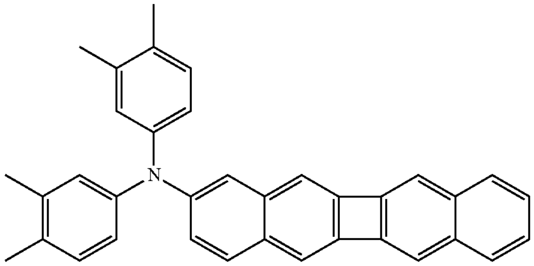
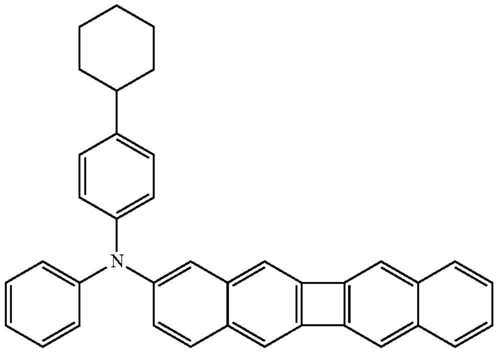
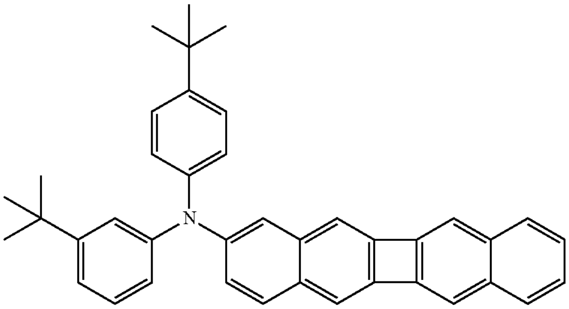
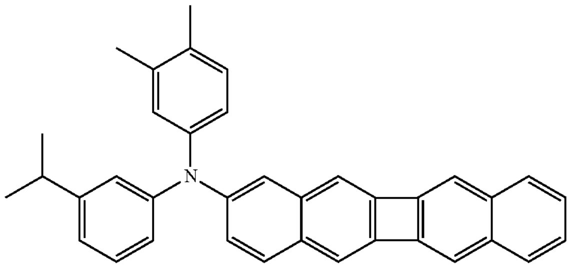
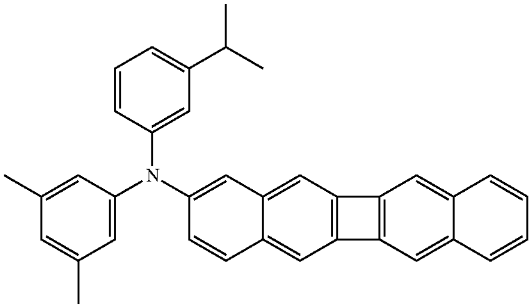
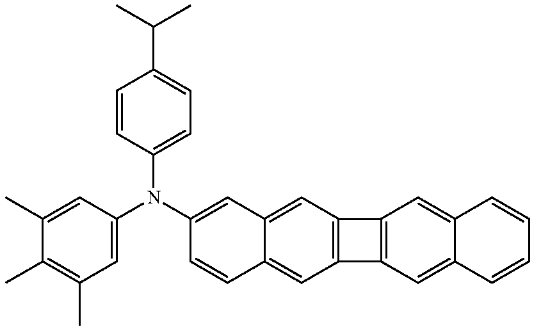
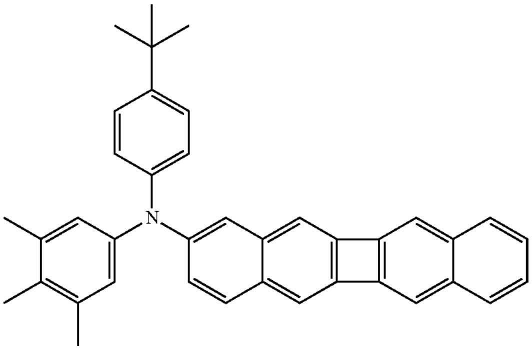

-continued
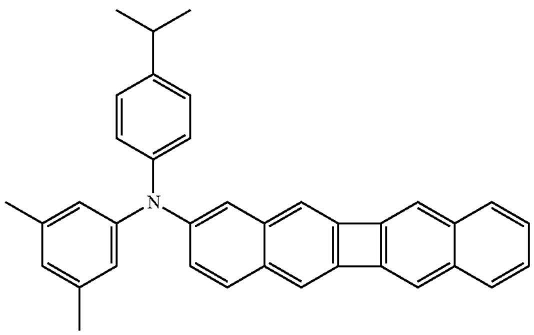
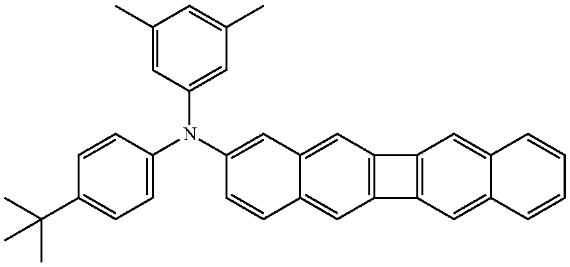
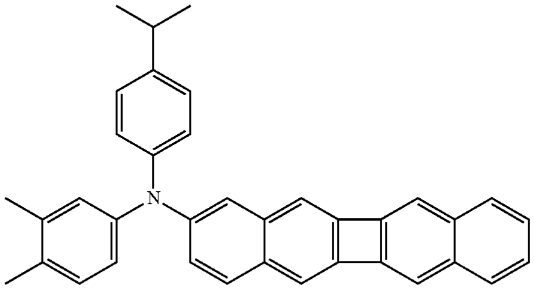
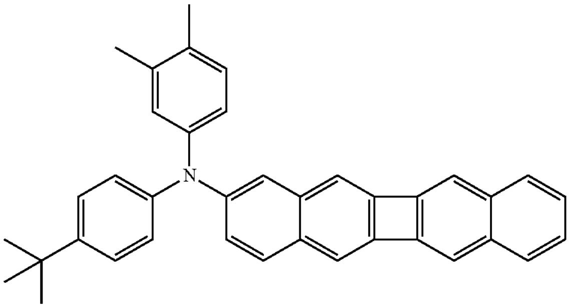
[Formula 82]
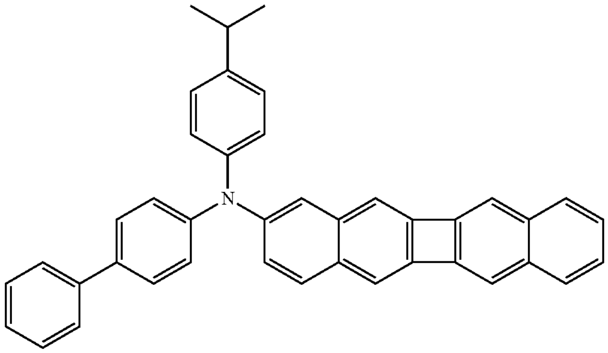
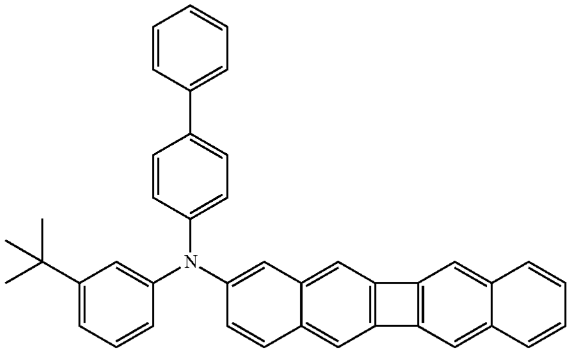
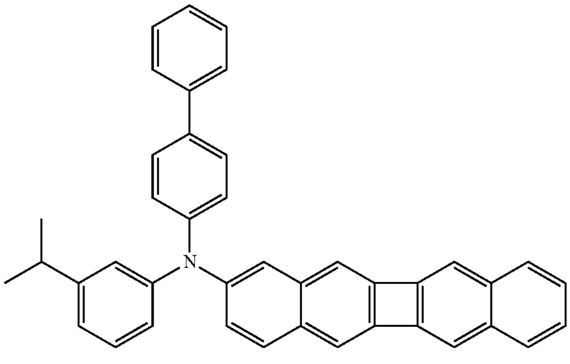

-continued
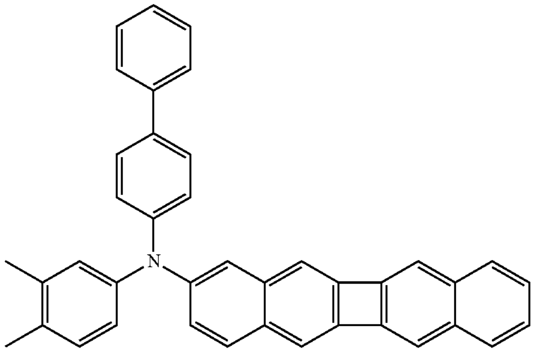
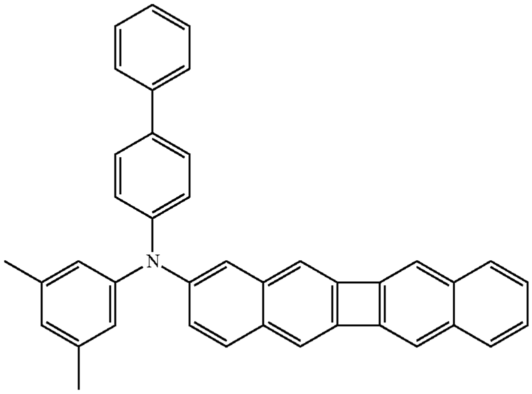
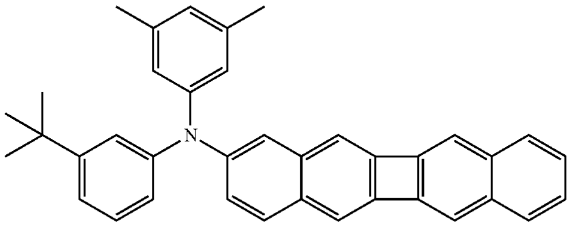
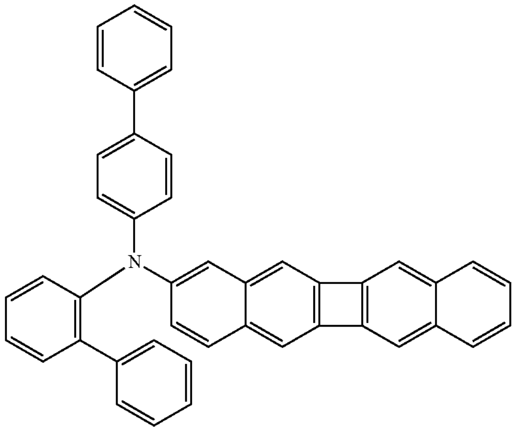
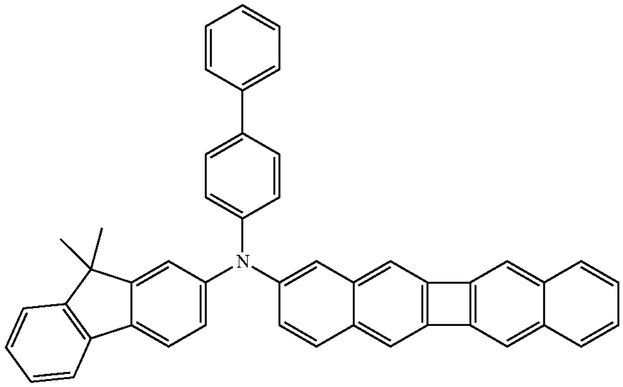
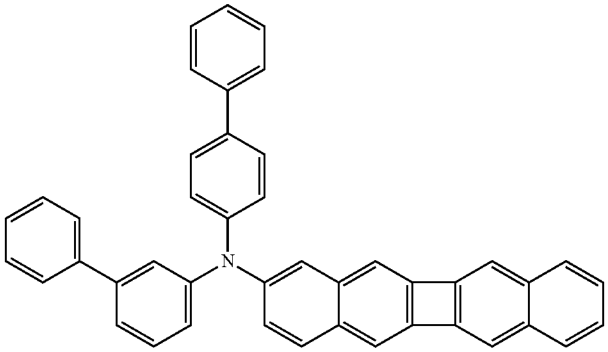

-continued
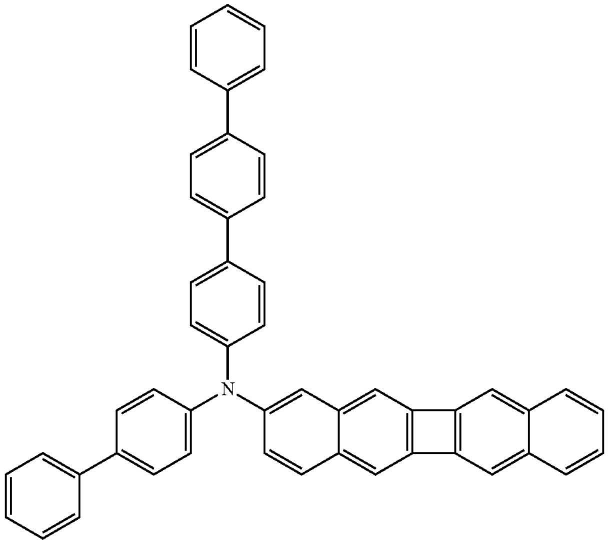
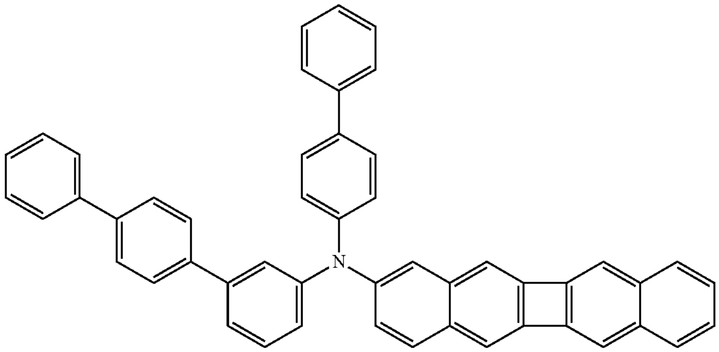
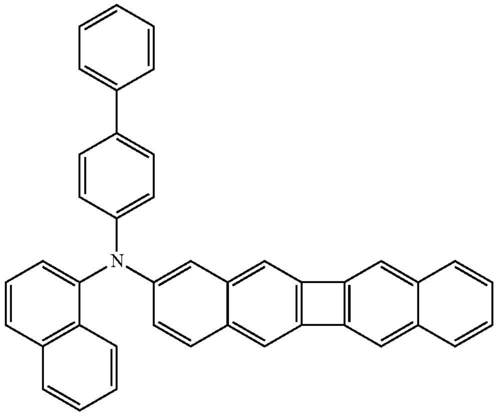
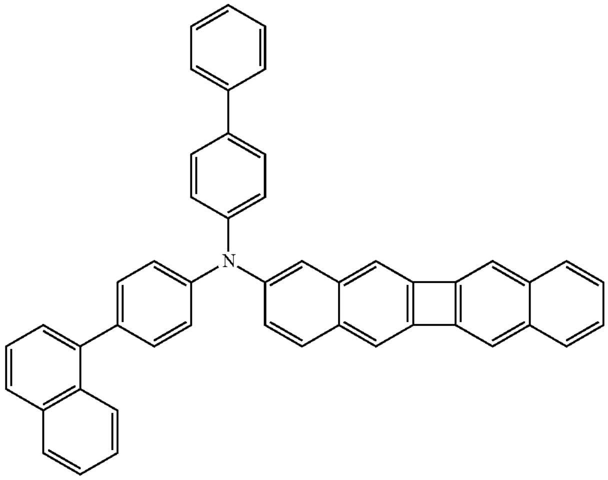

-continued
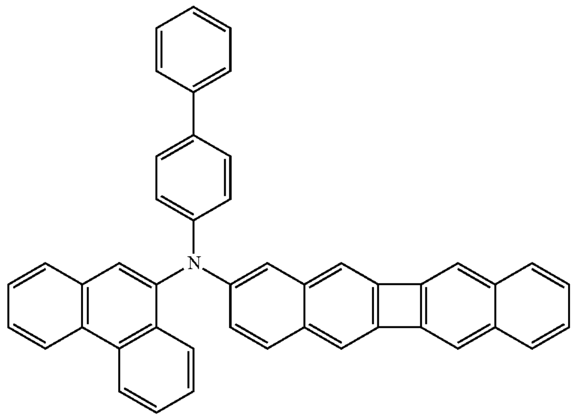
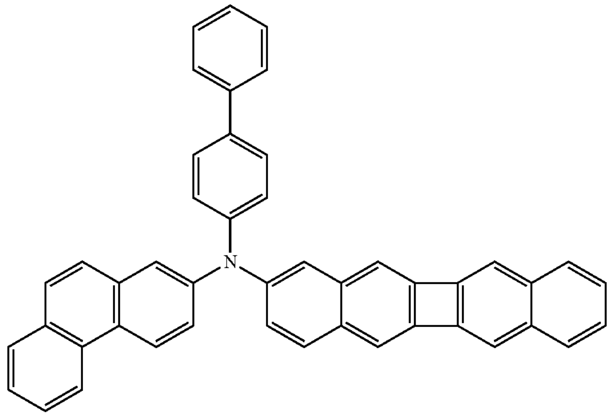
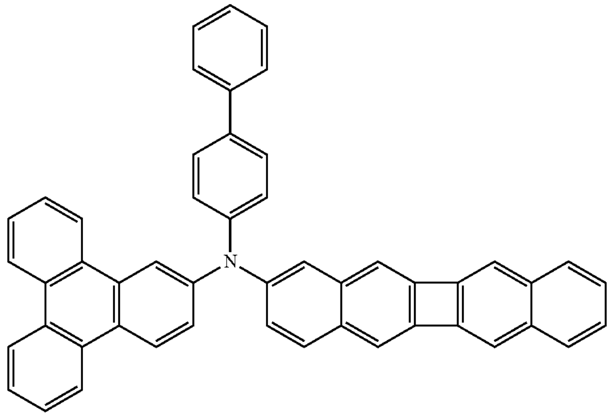

-continued
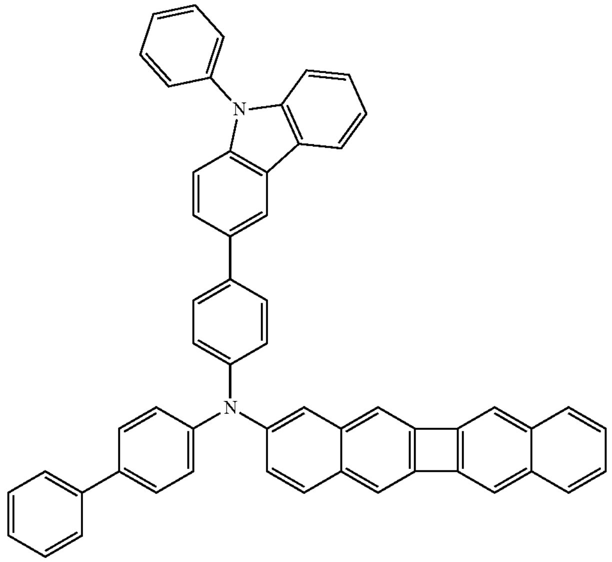
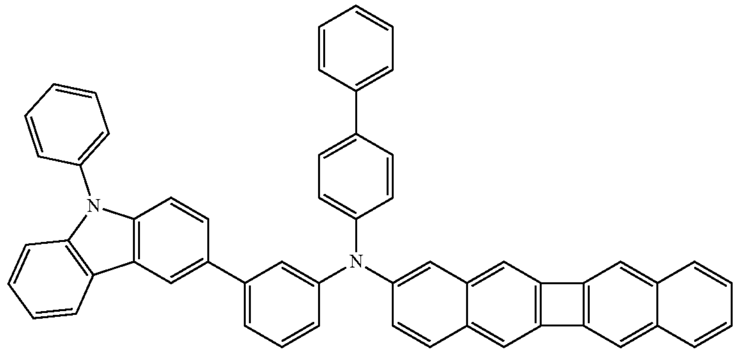
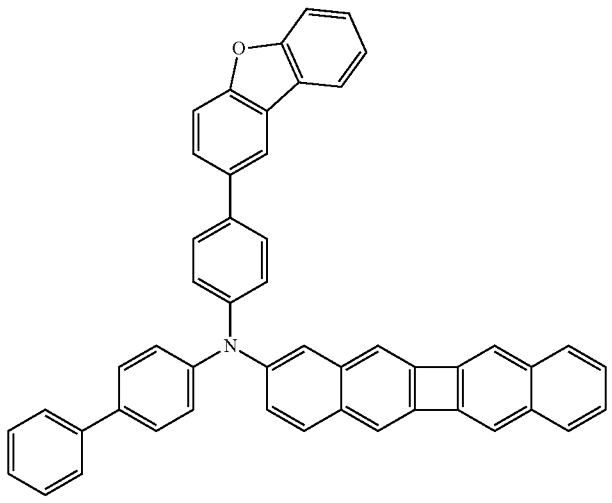

-continued
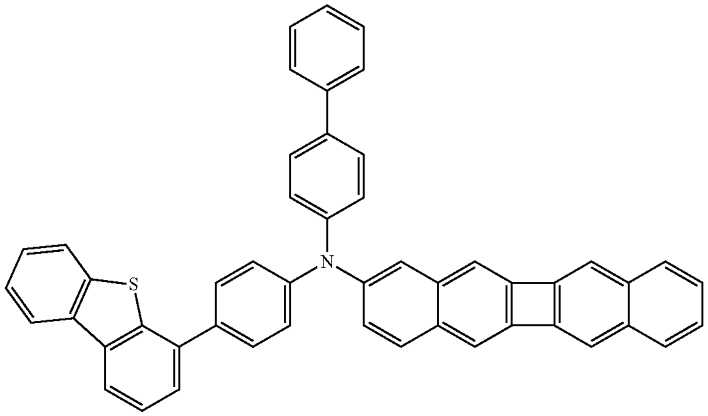
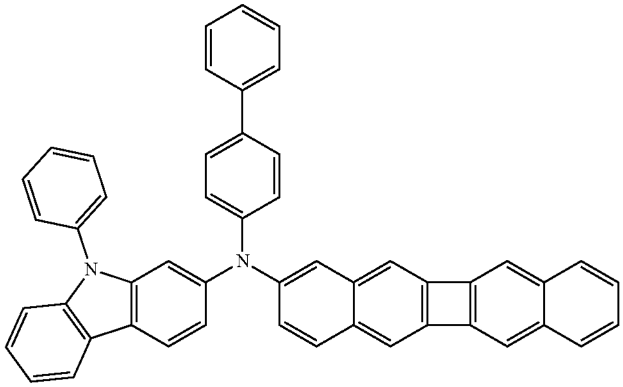
[Formula 83]
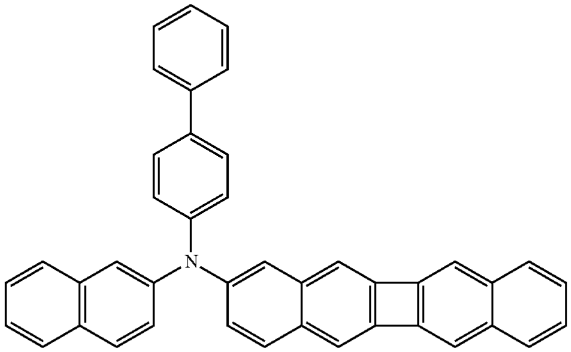
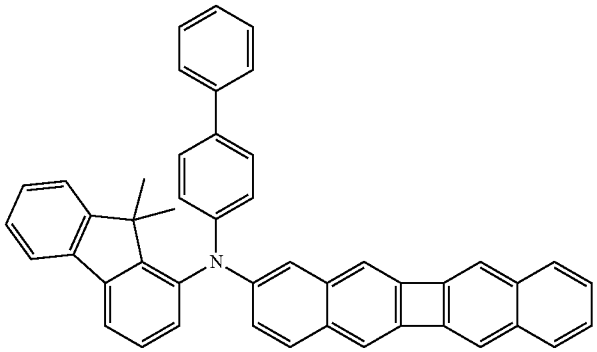

-continued
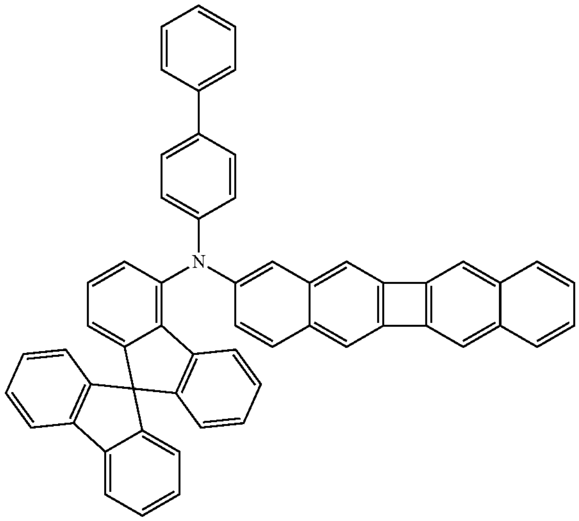
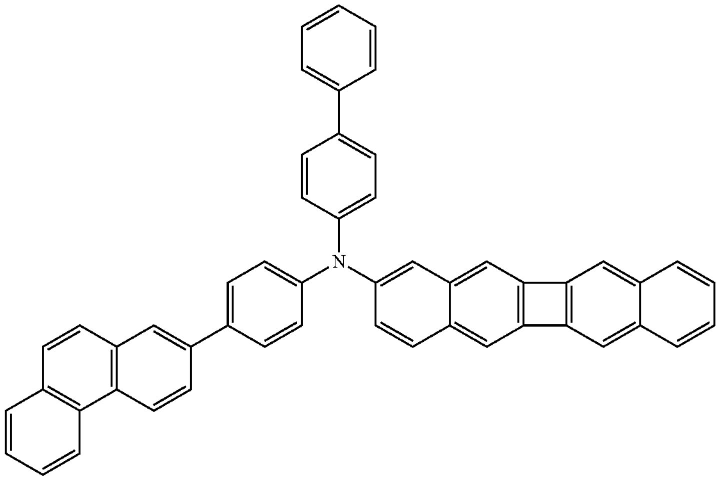
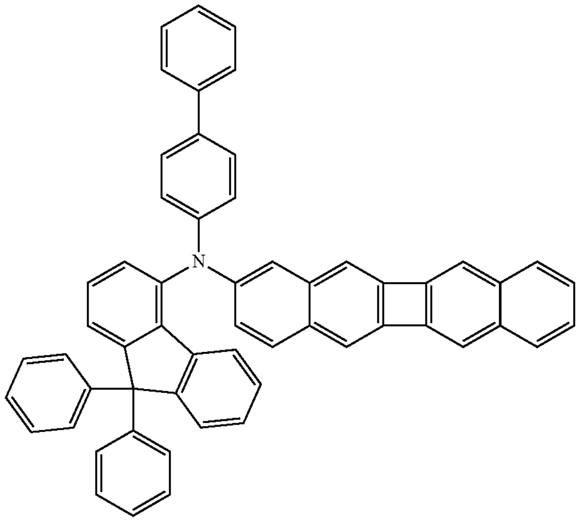

-continued
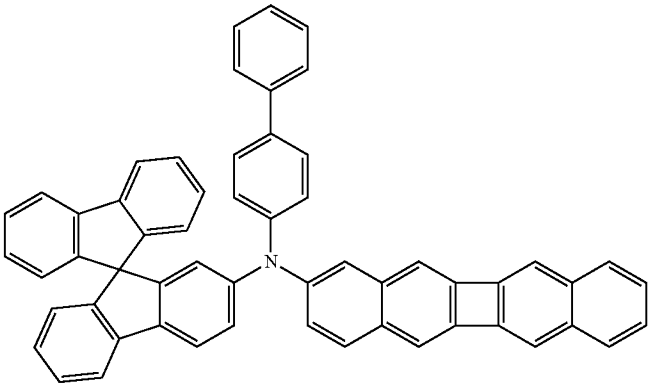
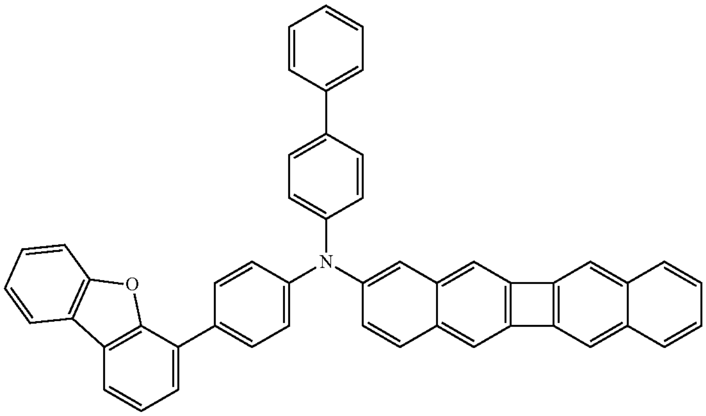
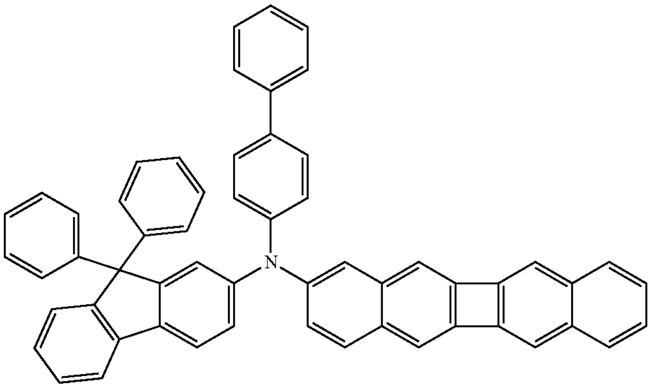
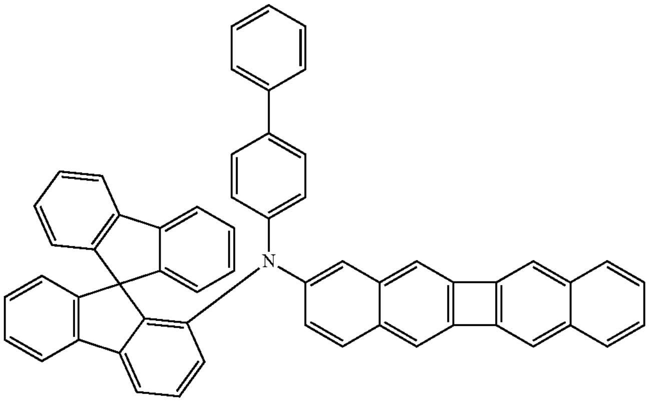

-continued
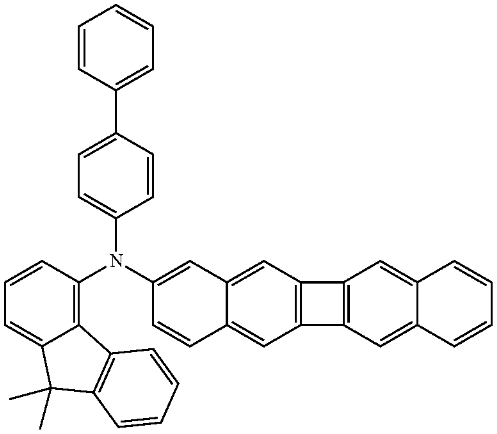
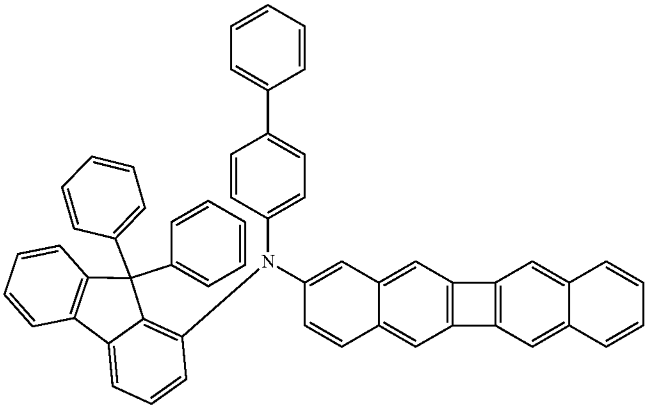
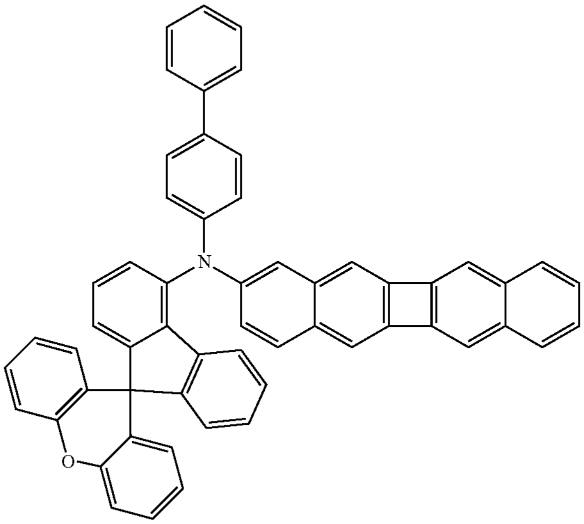
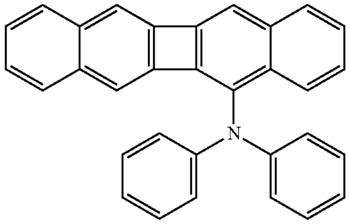
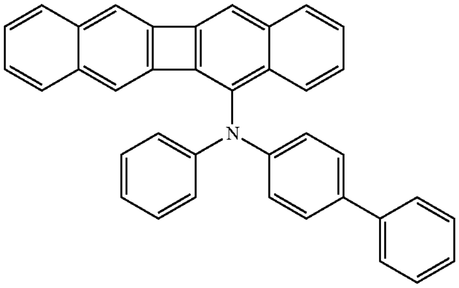
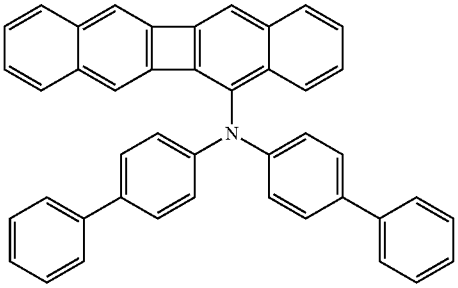
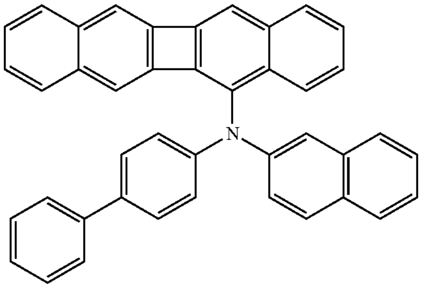
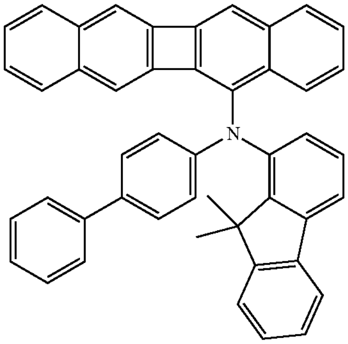

-continued
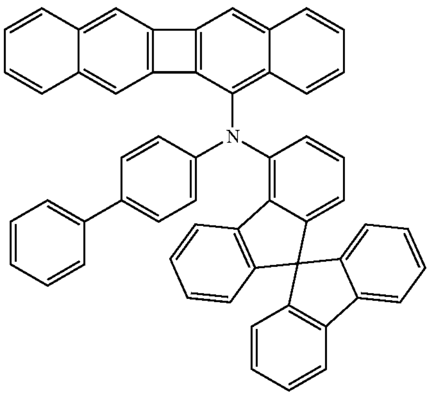
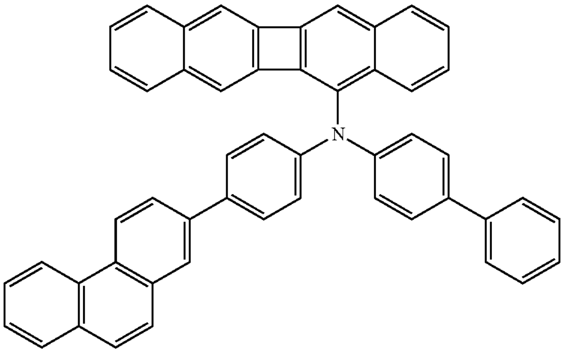
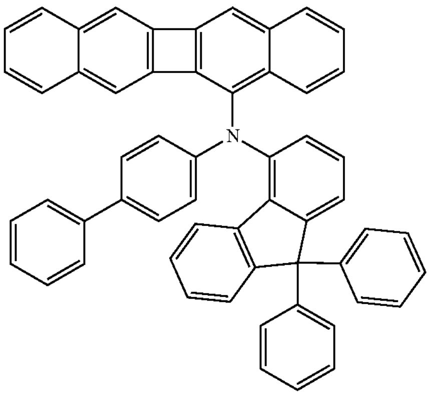
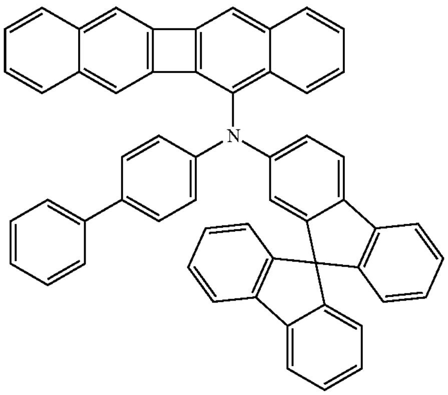
[Formula 84]
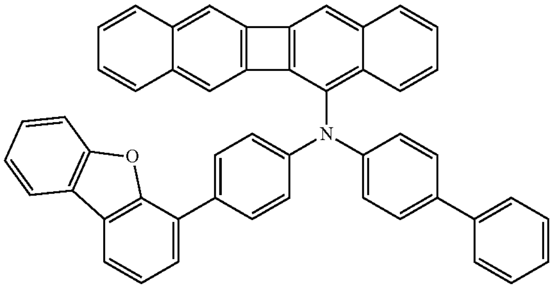
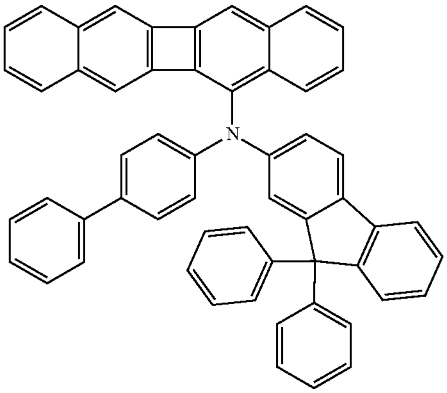
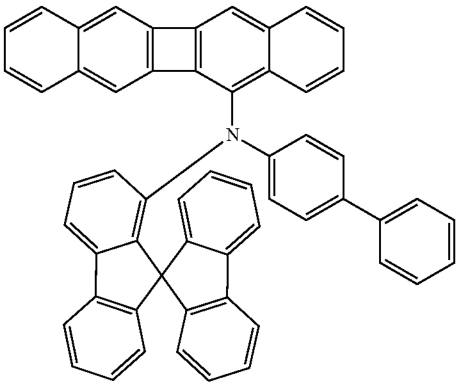
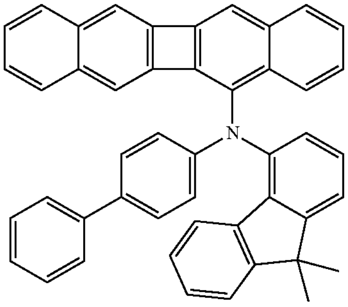

-continued
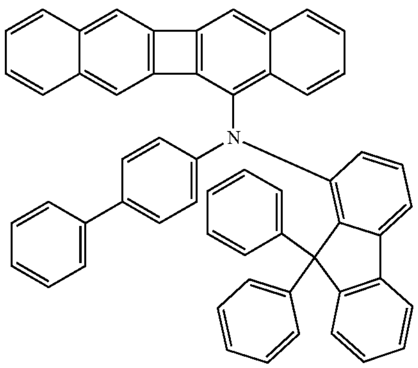
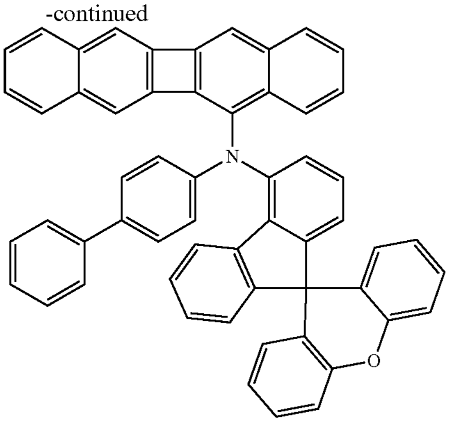
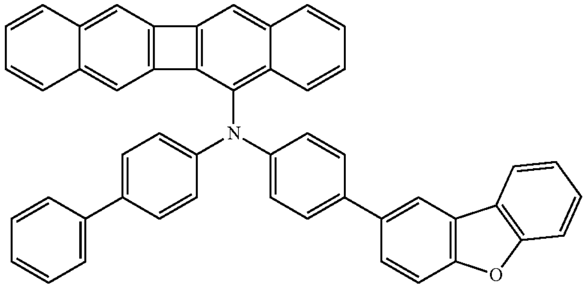
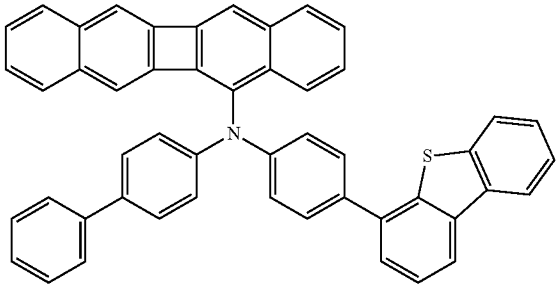
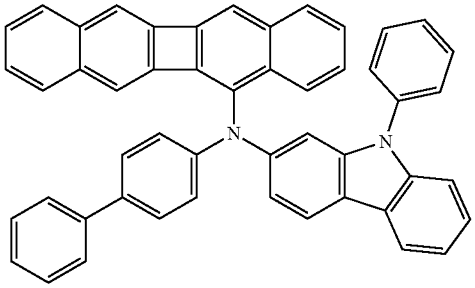
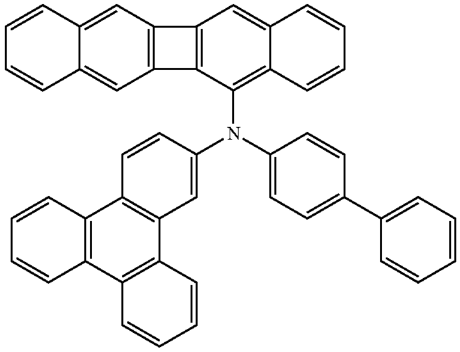
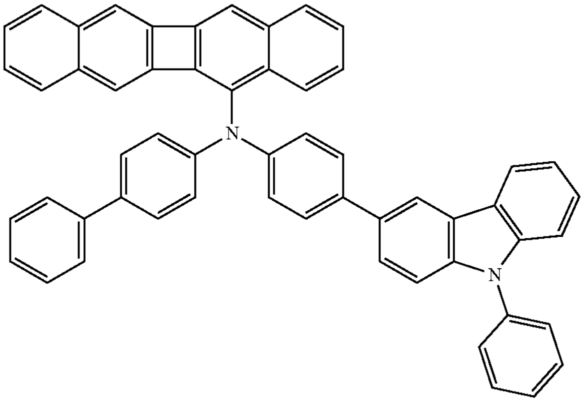
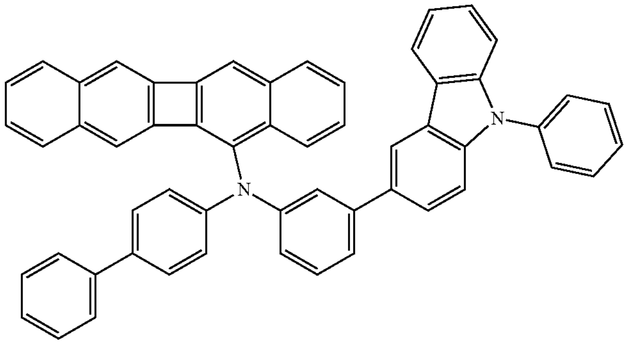
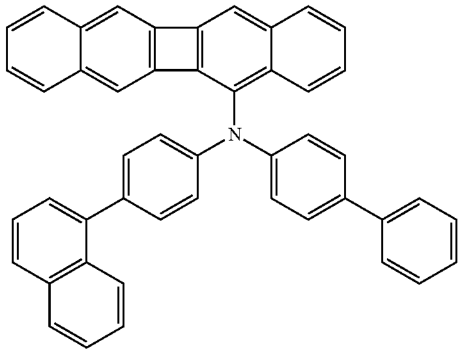

-continued
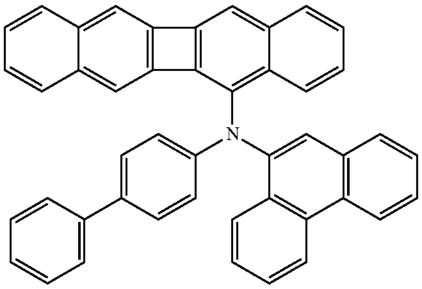
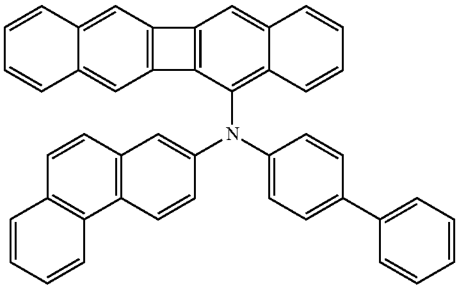
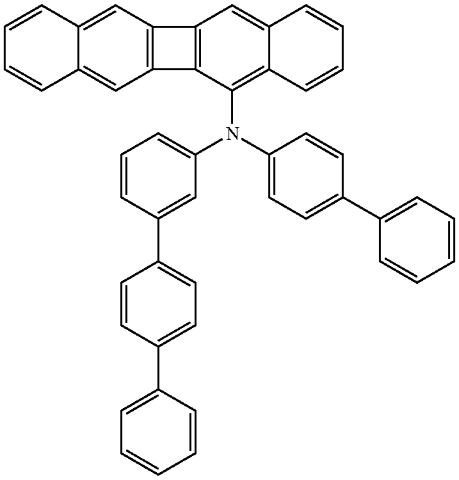
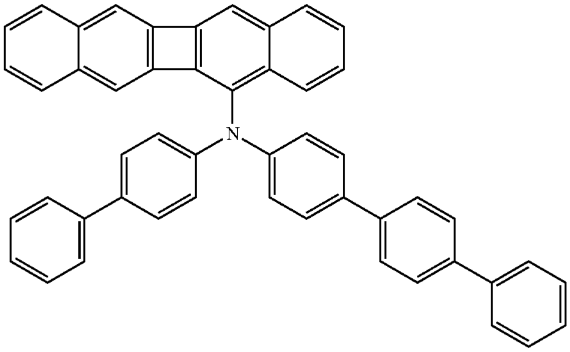
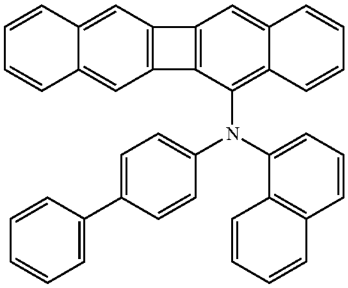
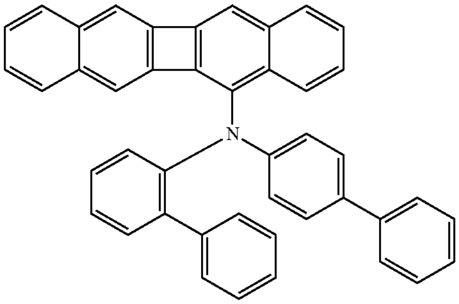
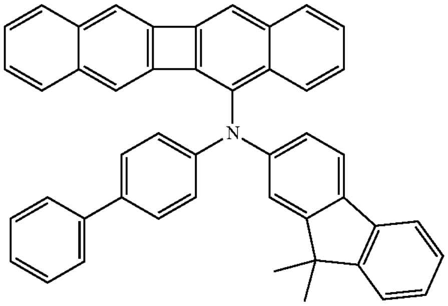
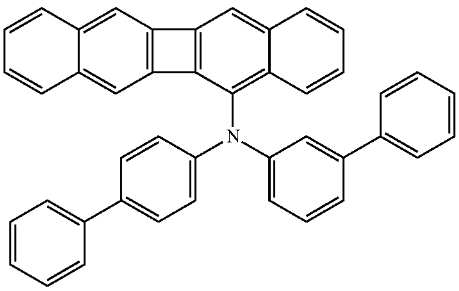
[Formula 85]
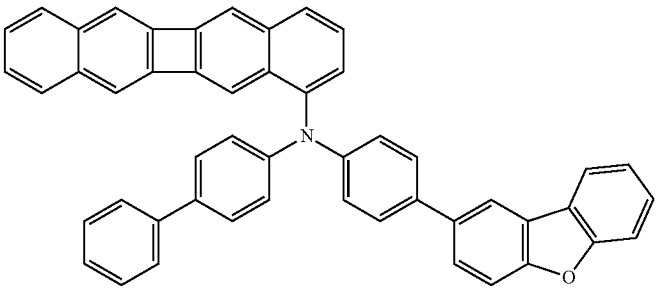

-continued
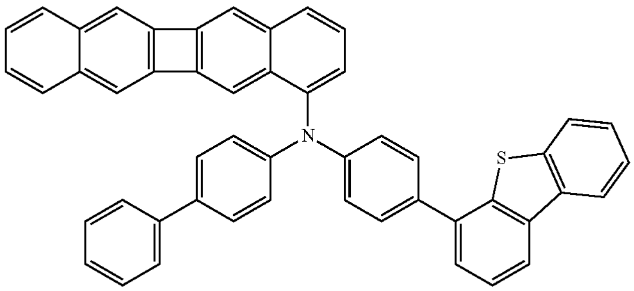
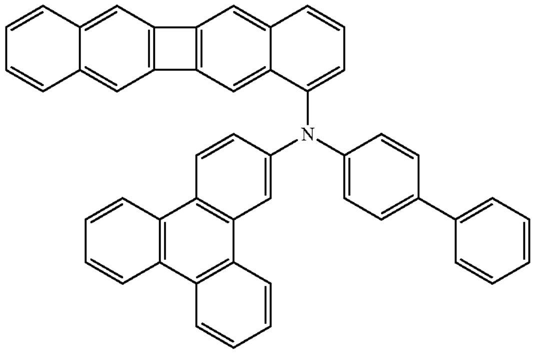
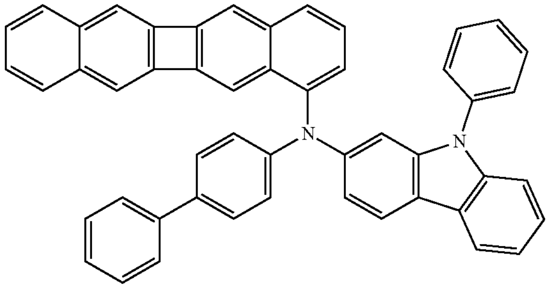
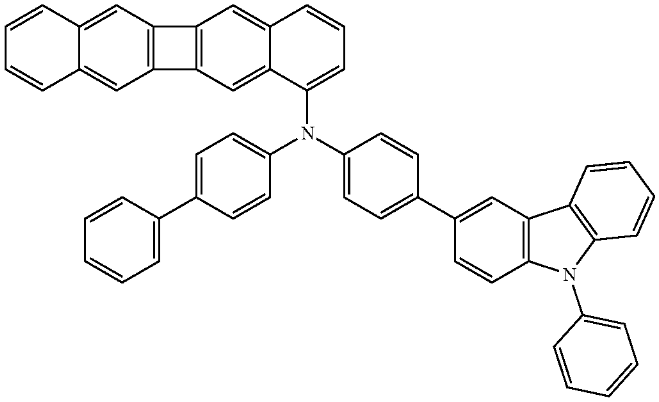
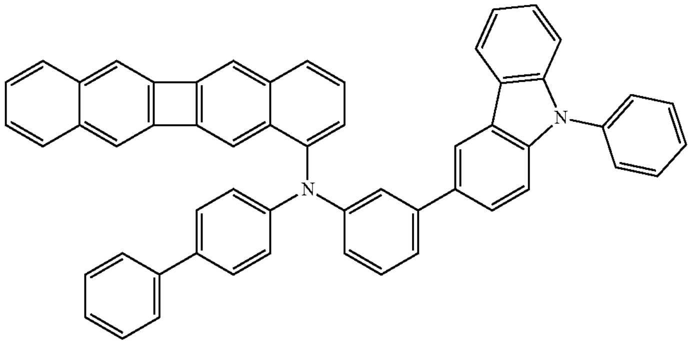
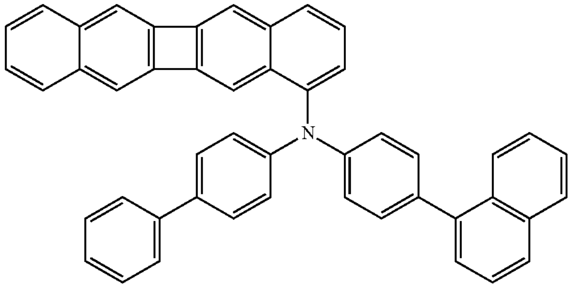

-continued
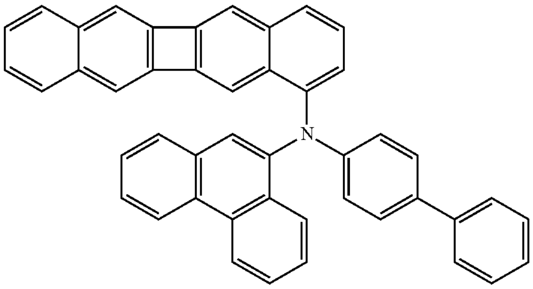
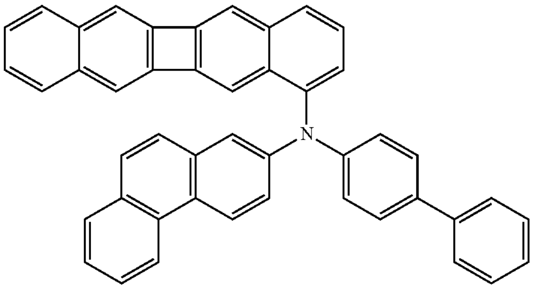
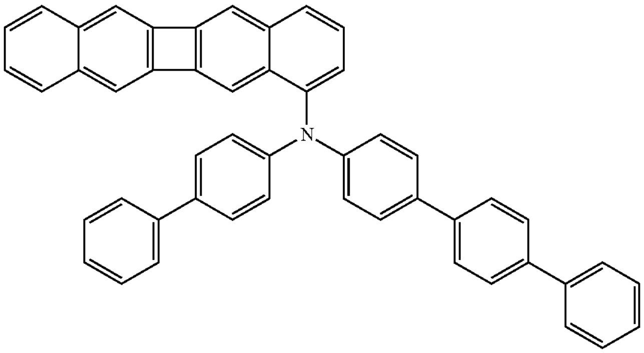
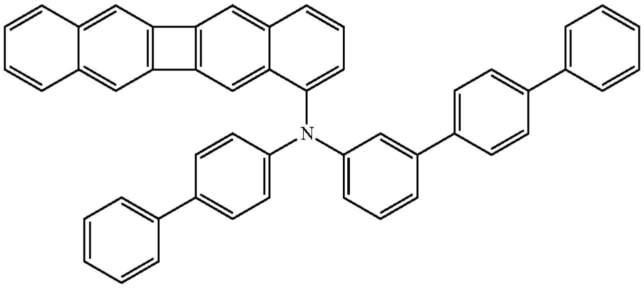
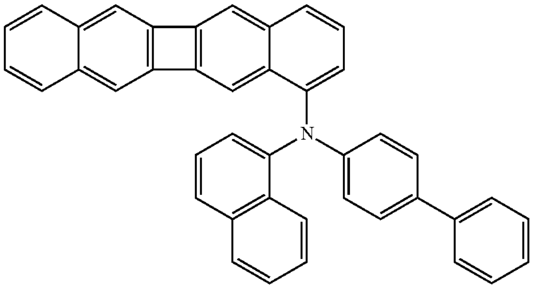
[Formula 86]
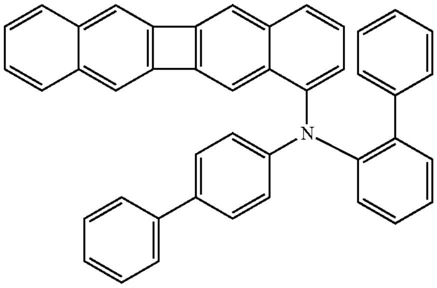
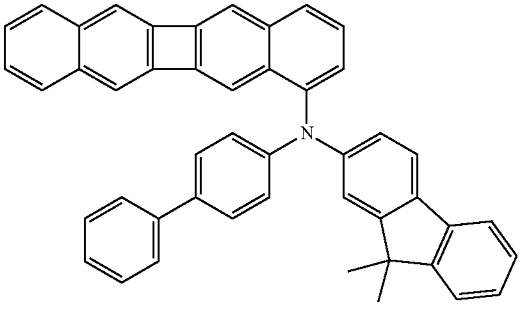

-continued
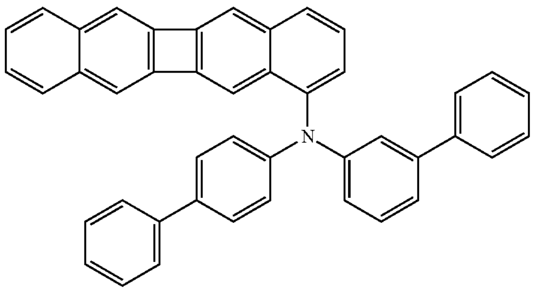
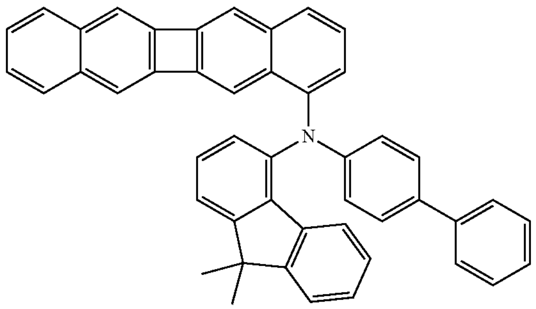
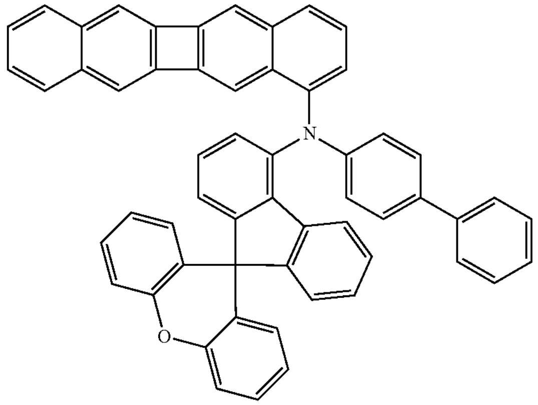
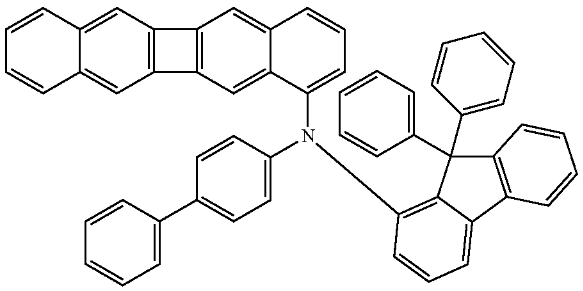
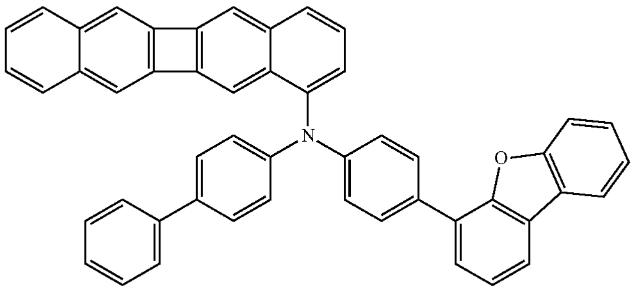
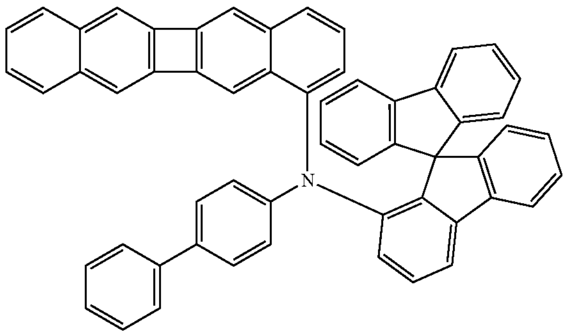
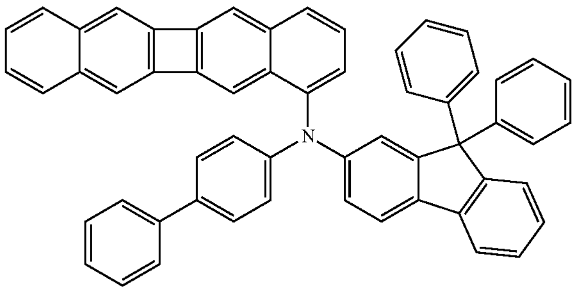
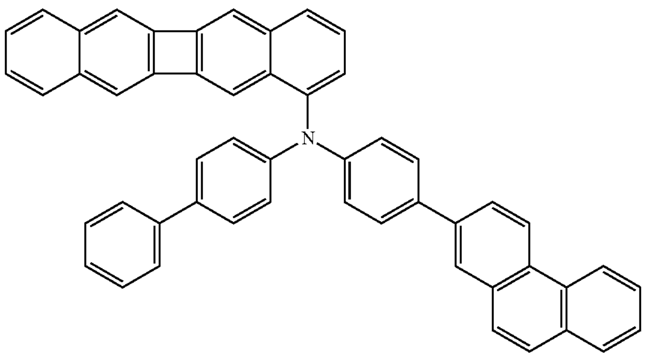

-continued
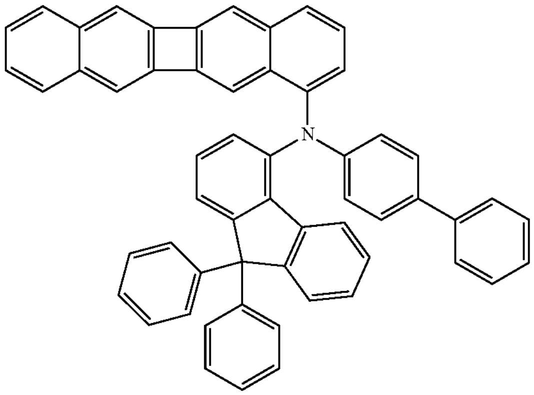
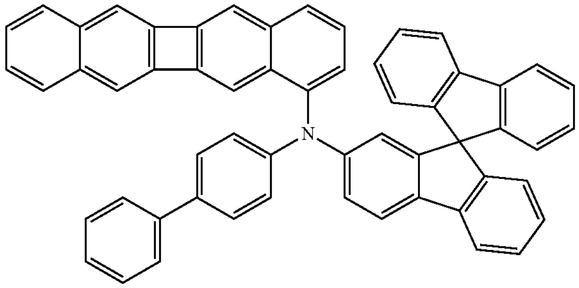
[Formula 87]
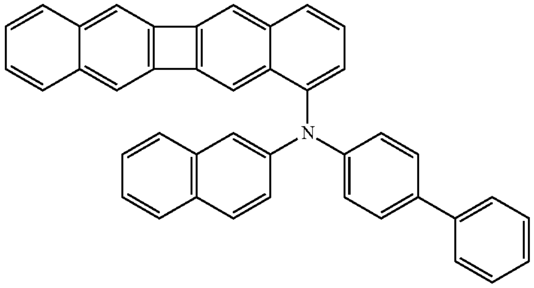
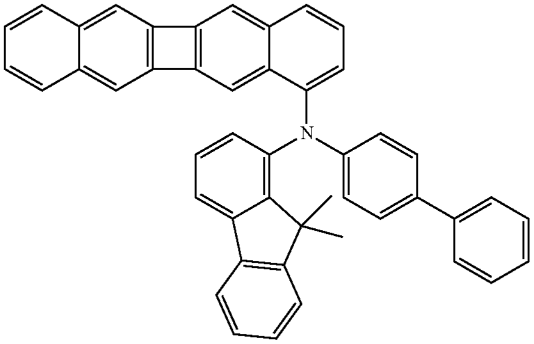
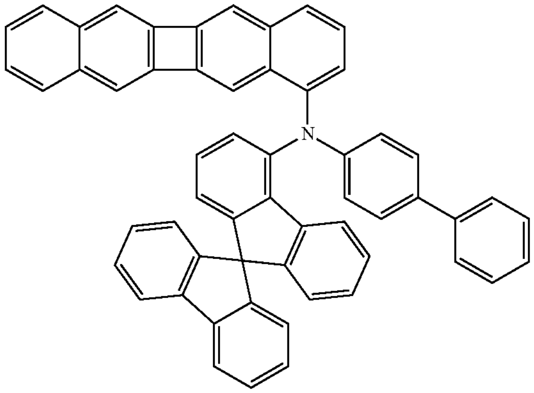
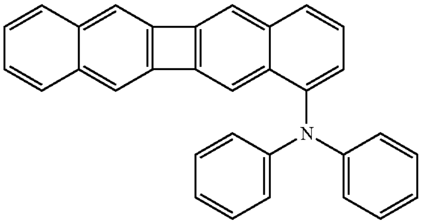
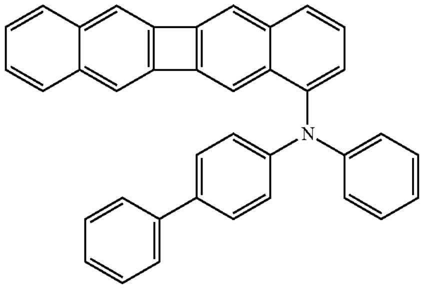
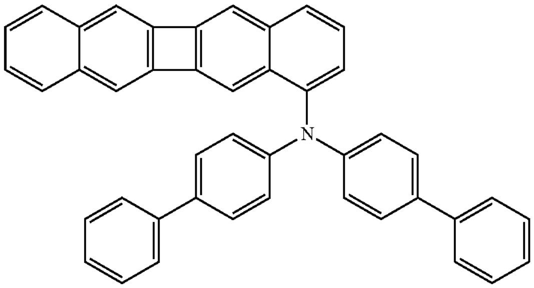

-continued
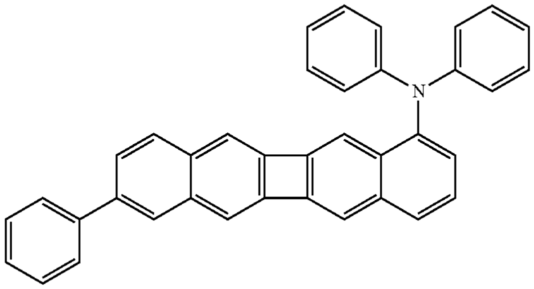
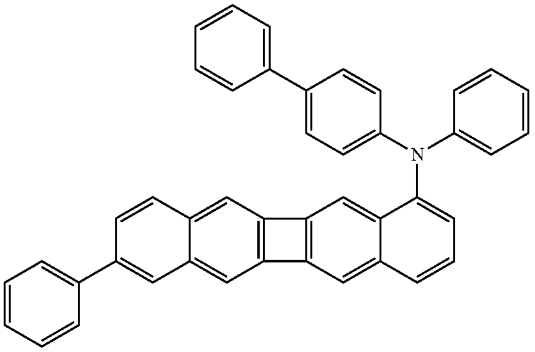
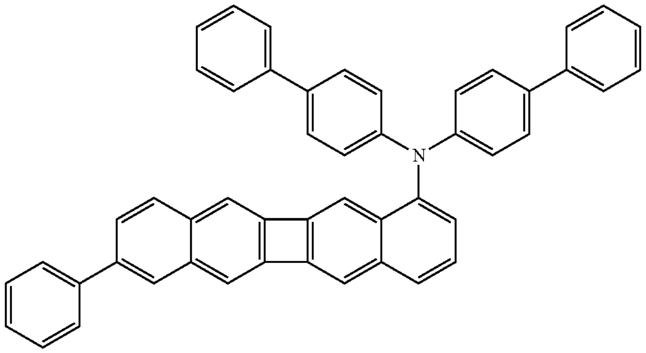
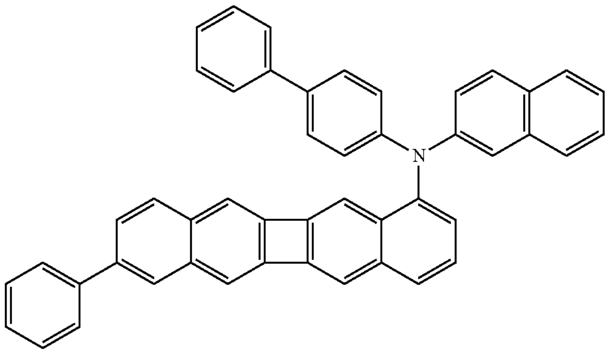
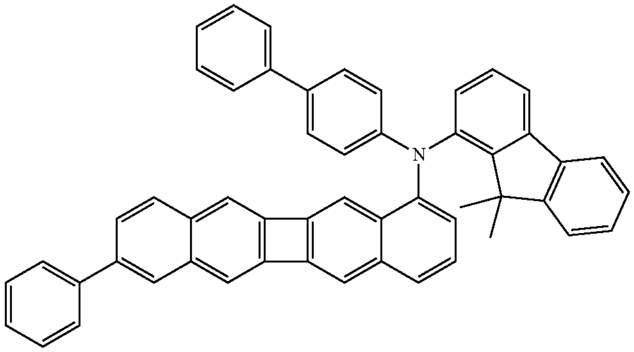

-continued
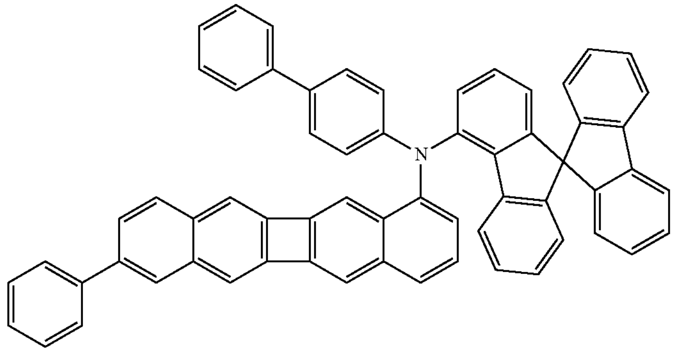
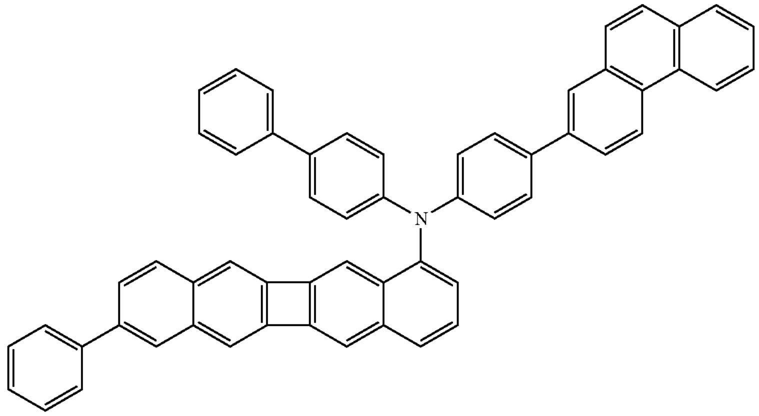
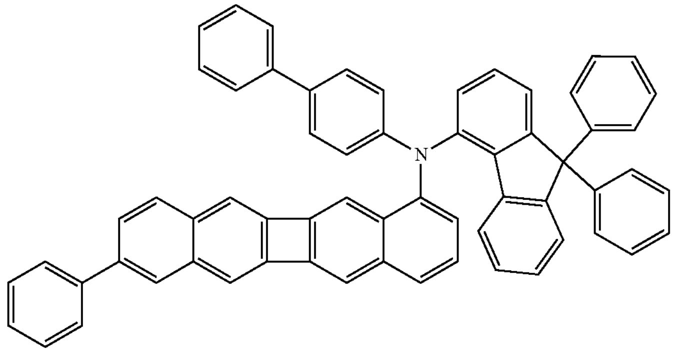
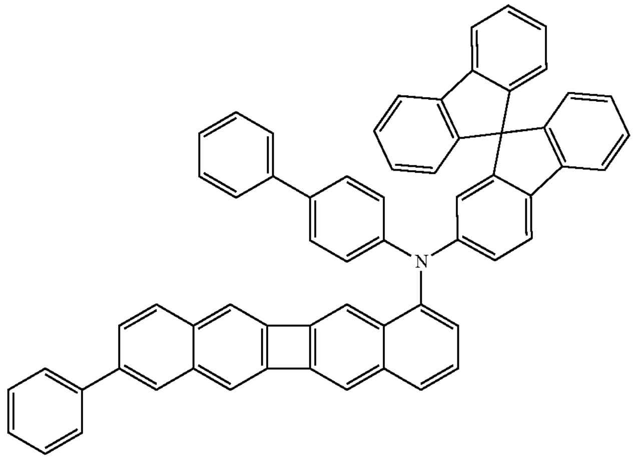

-continued
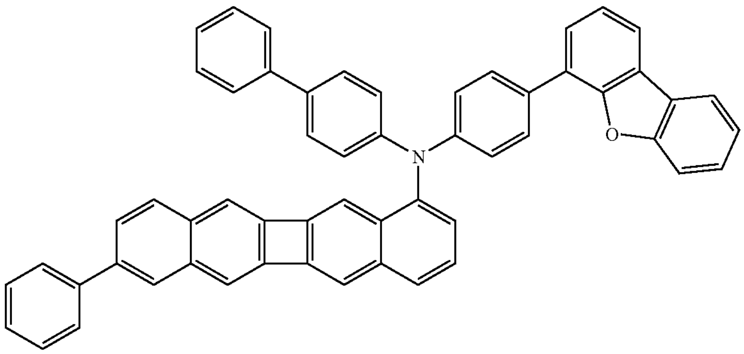
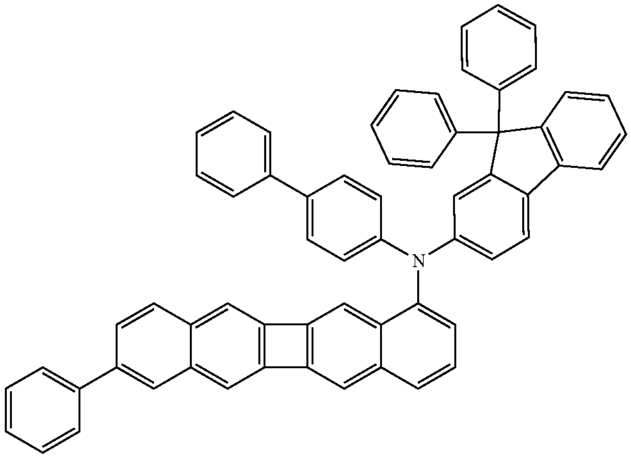
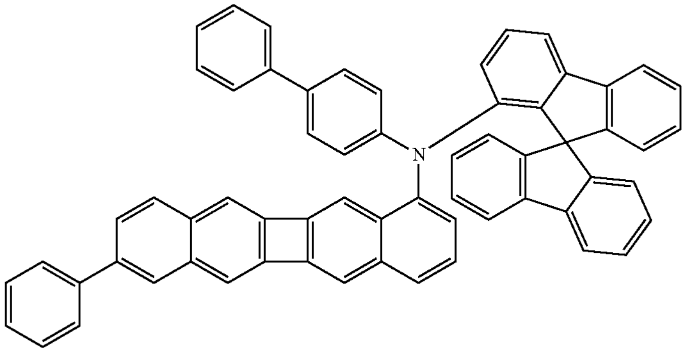
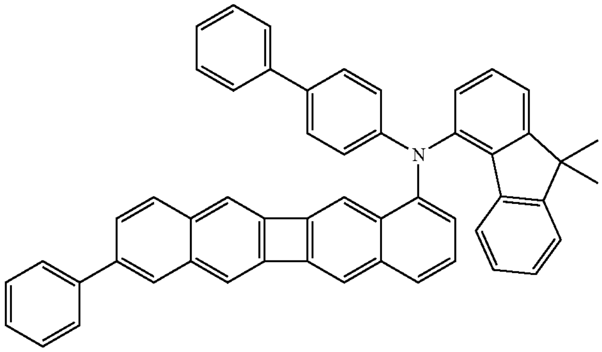

-continued
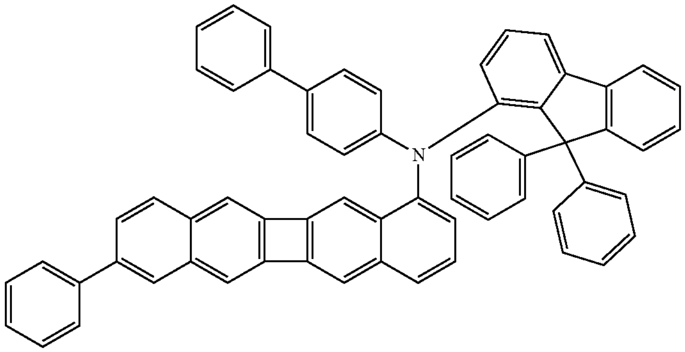
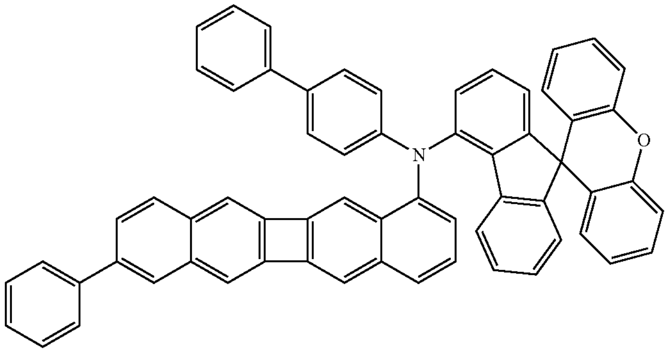
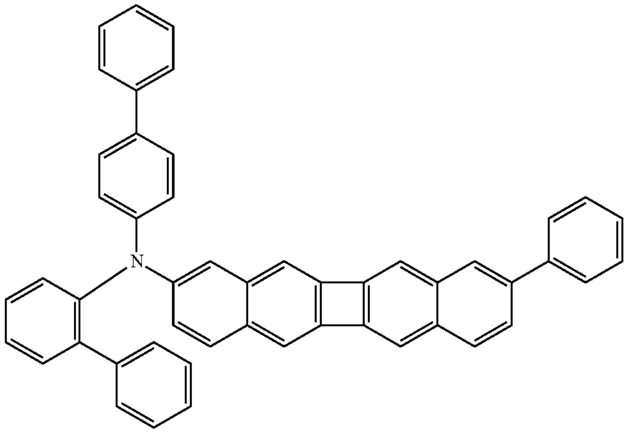
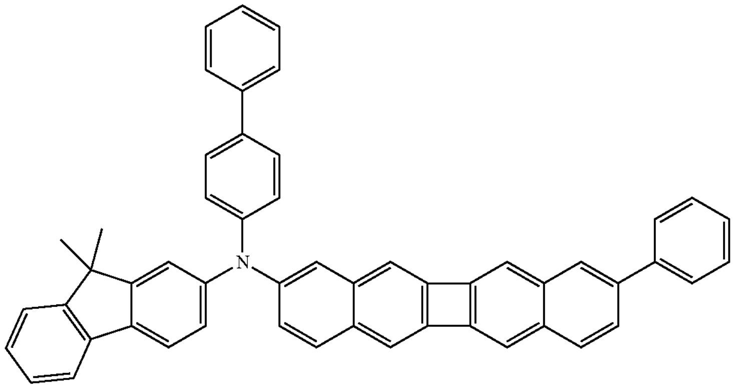

-continued
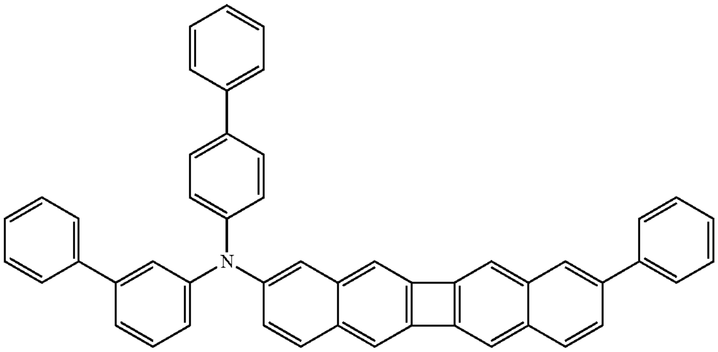
[Formula 88]
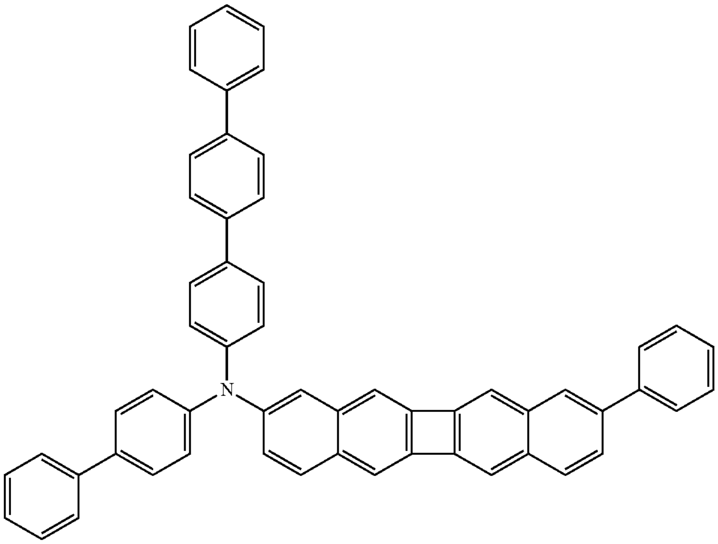
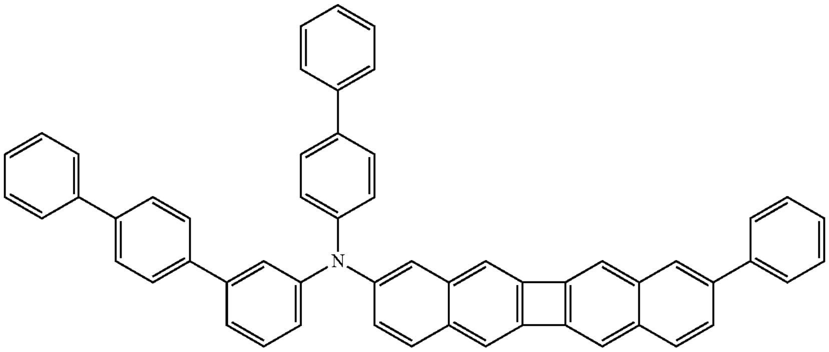
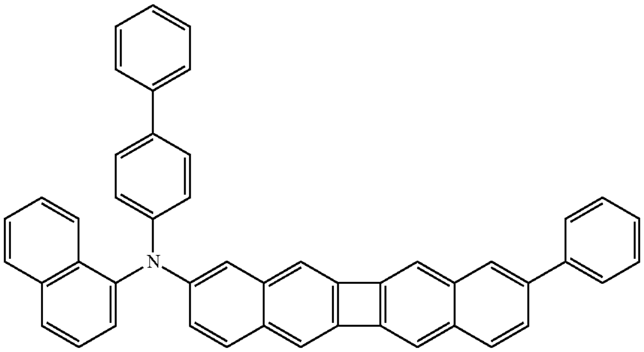

-continued
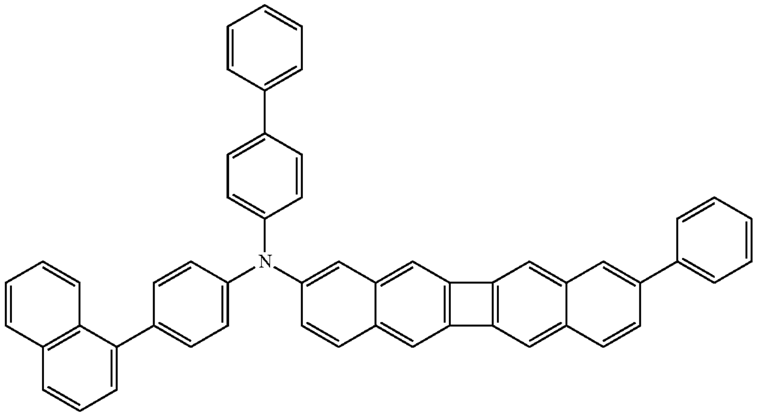
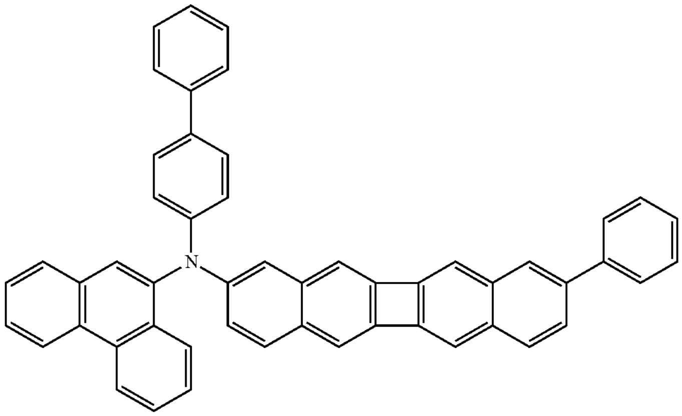
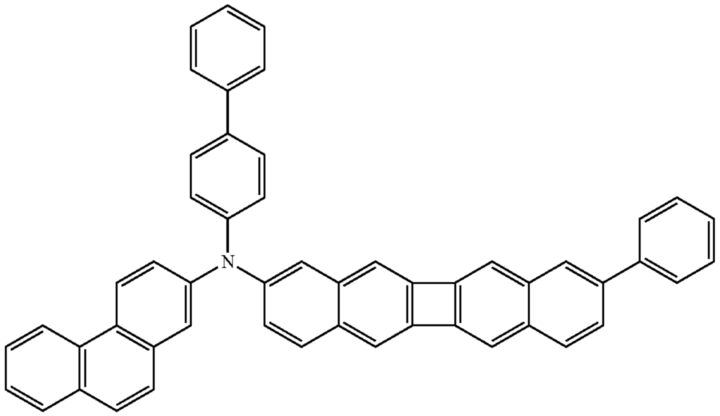
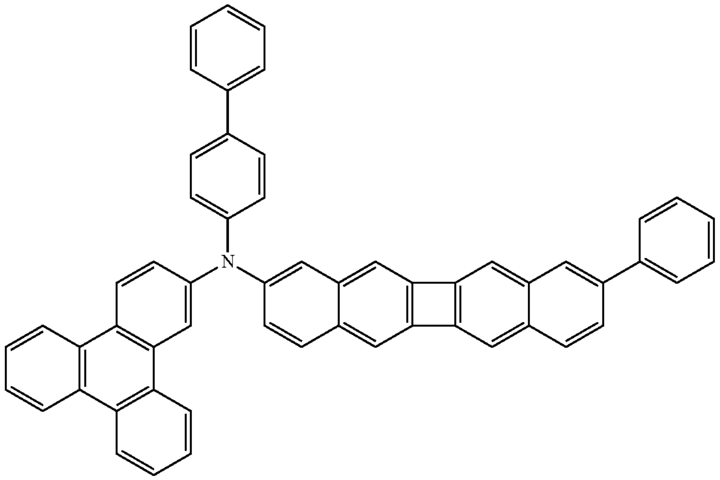

-continued
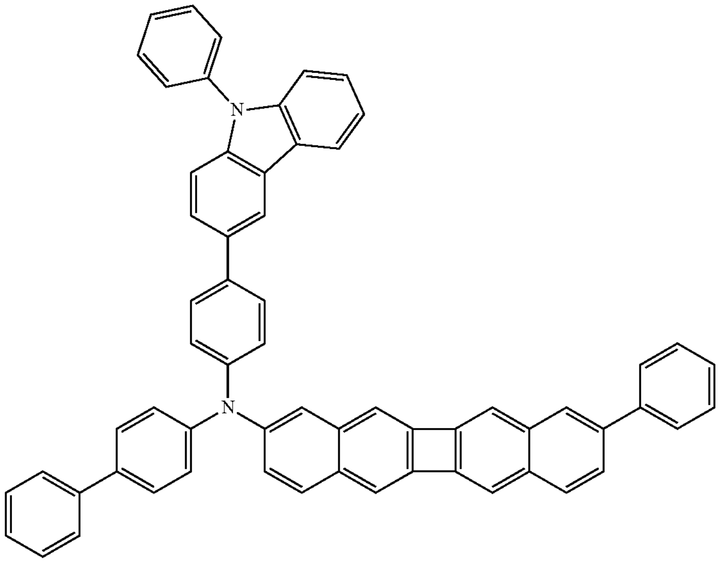
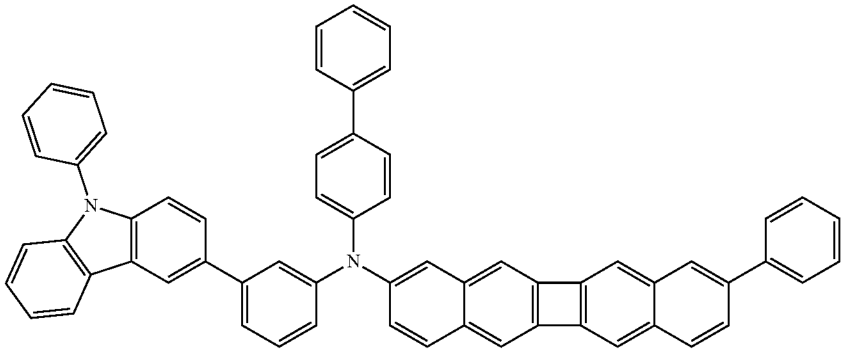
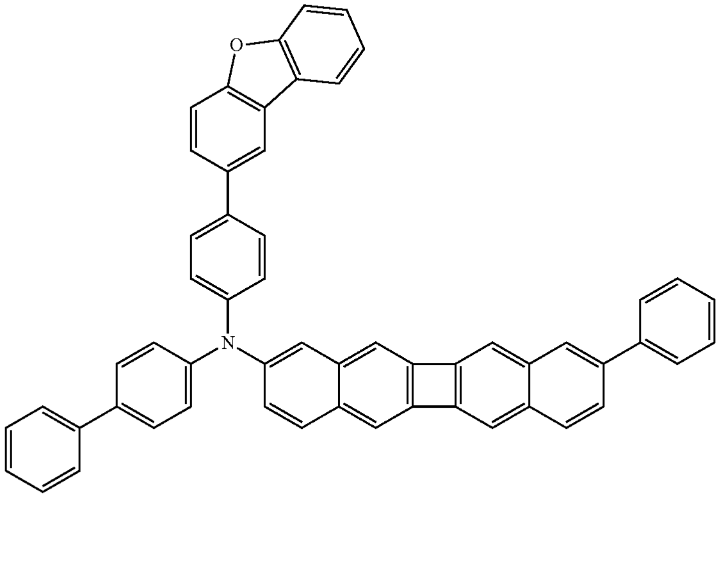

-continued
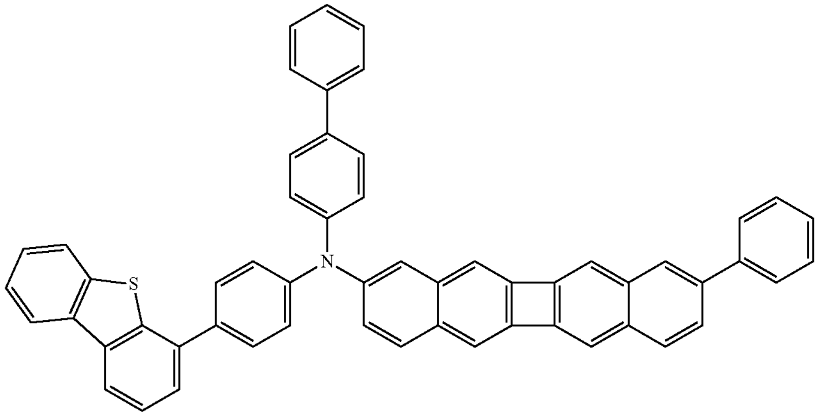
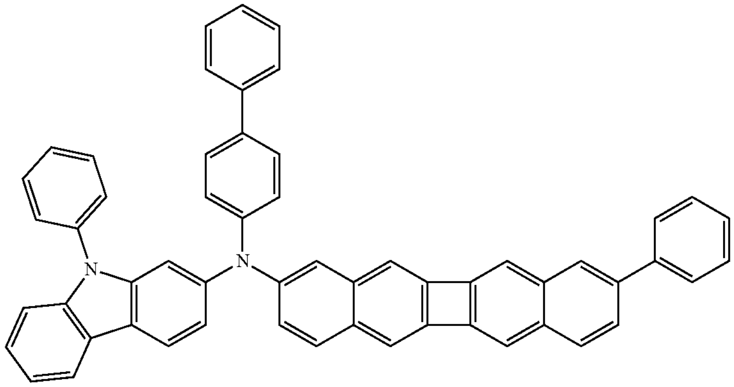
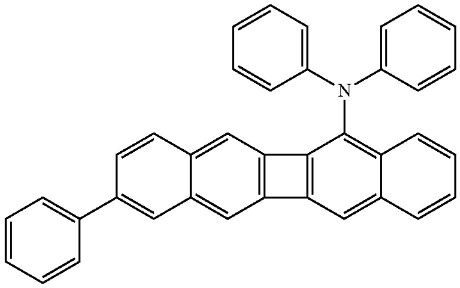
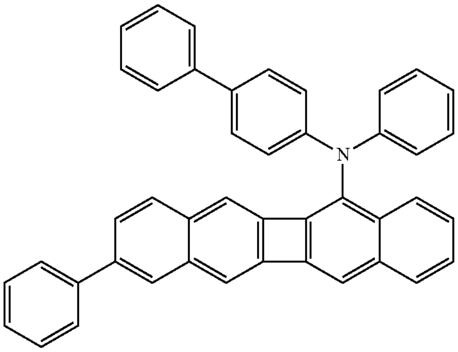
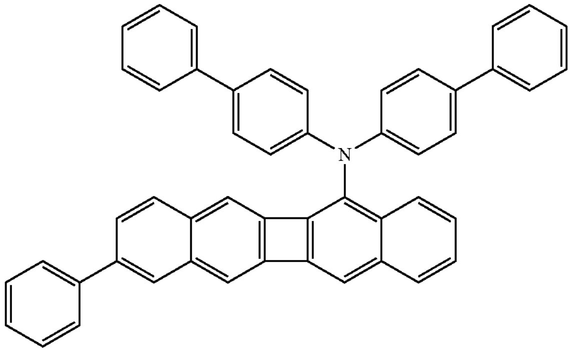
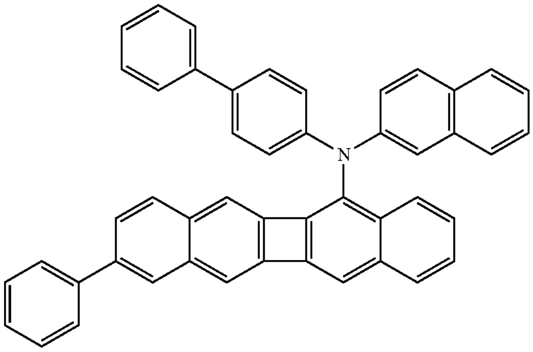

-continued
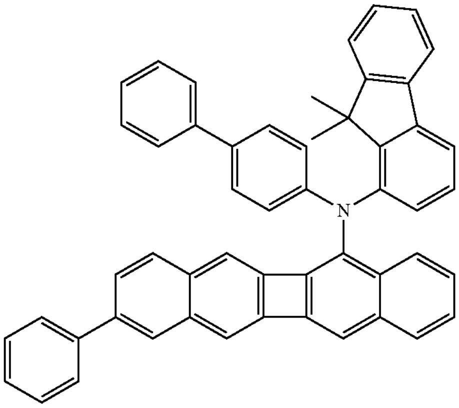
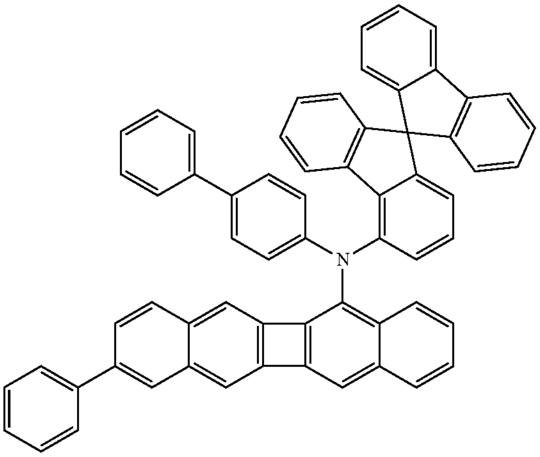
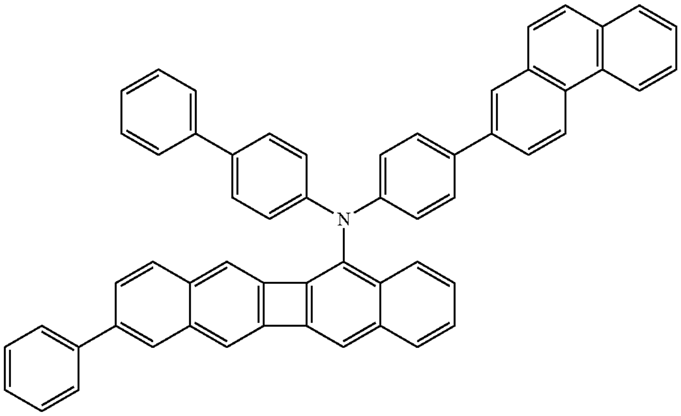
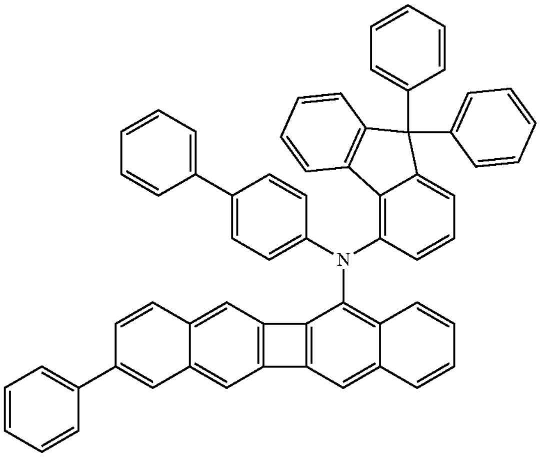
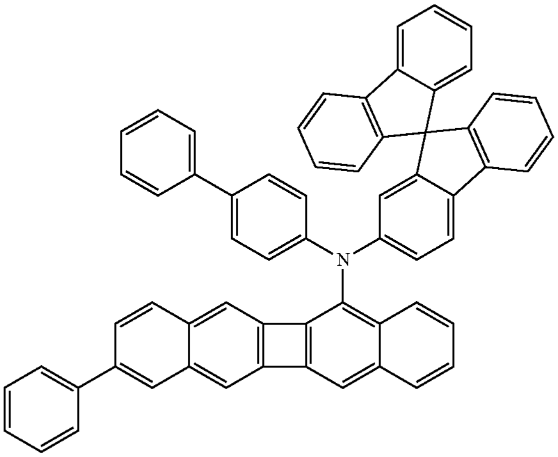
[Formula 89]
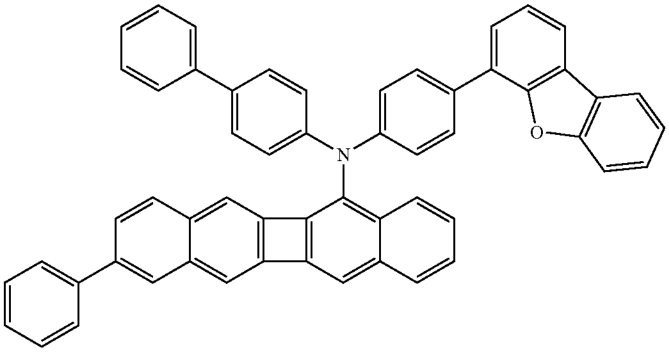

-continued
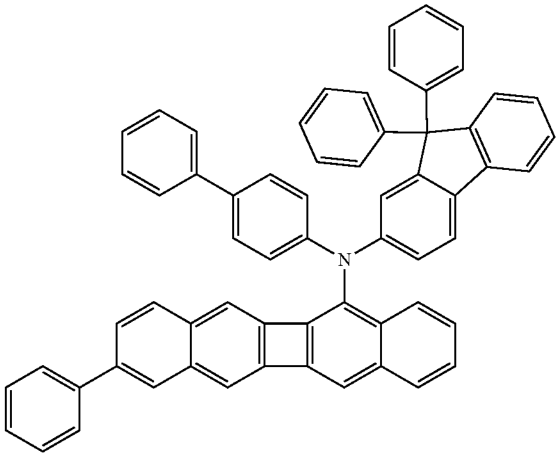
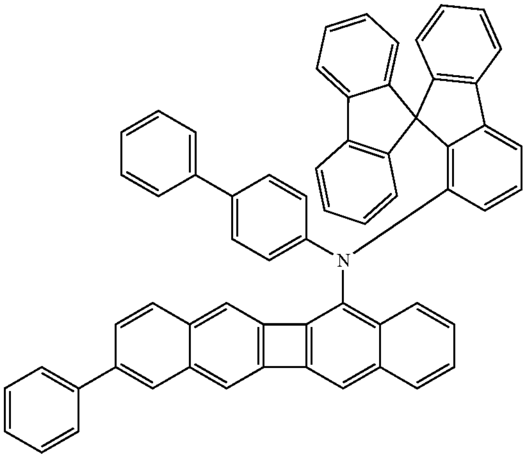
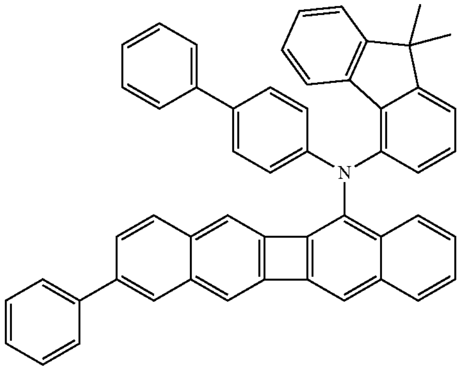
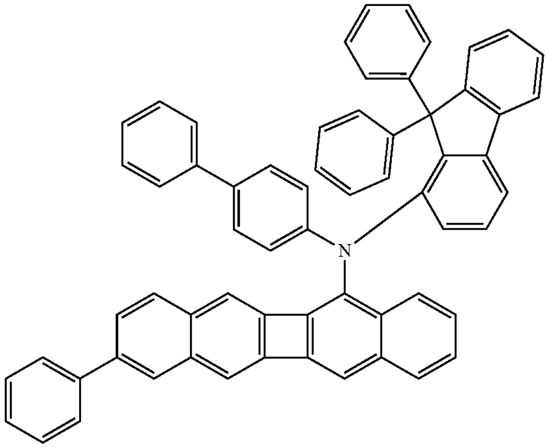
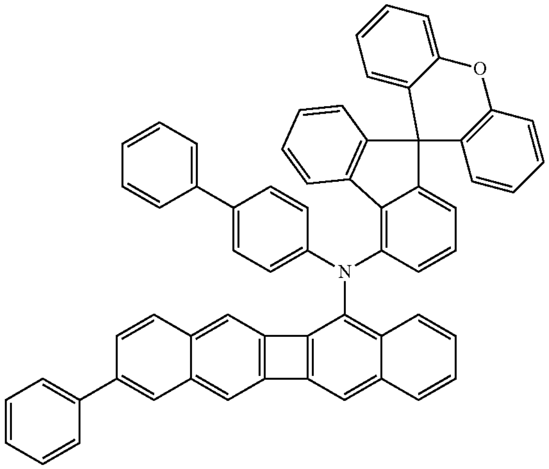
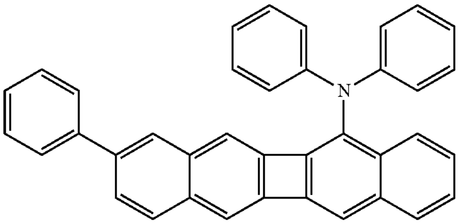
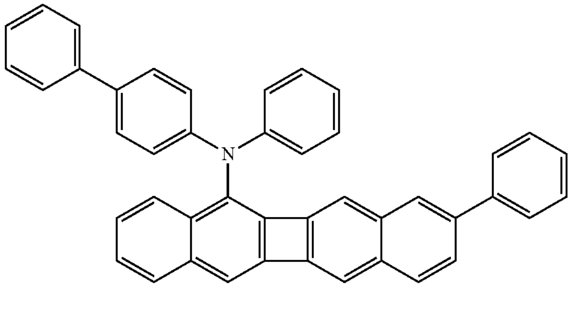

-continued
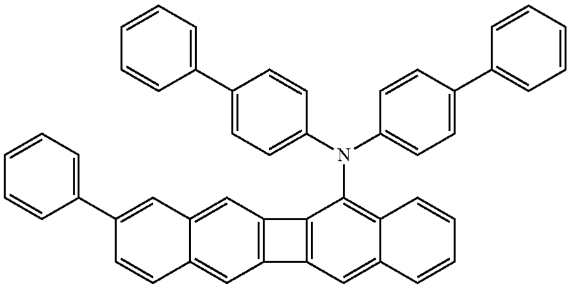
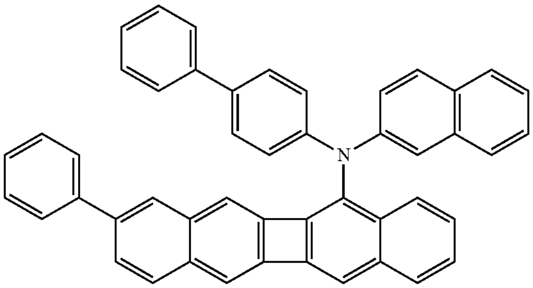
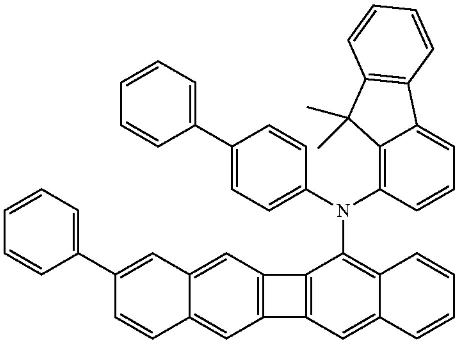
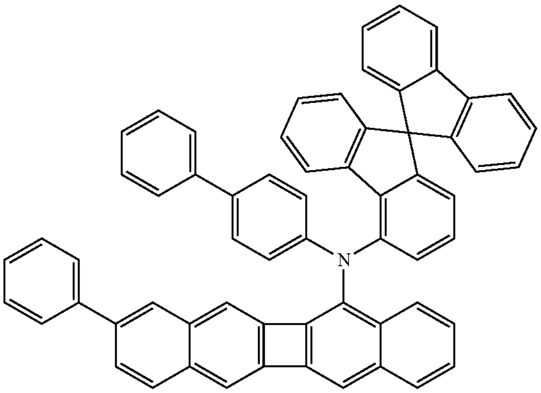
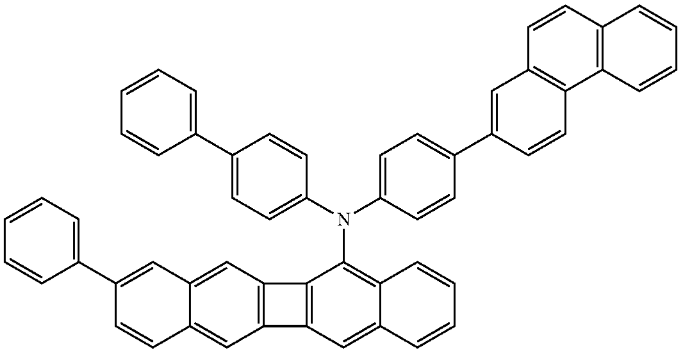
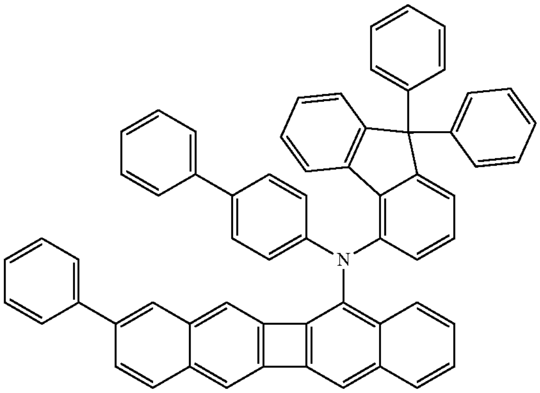
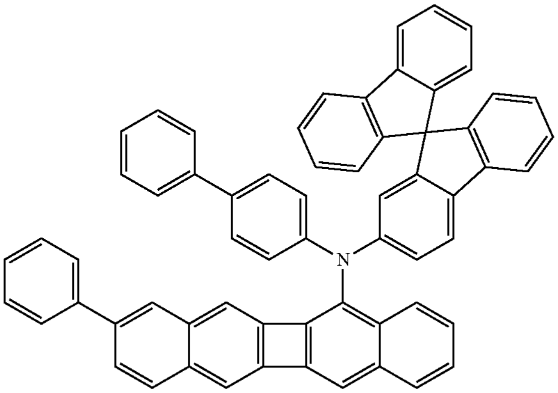

-continued
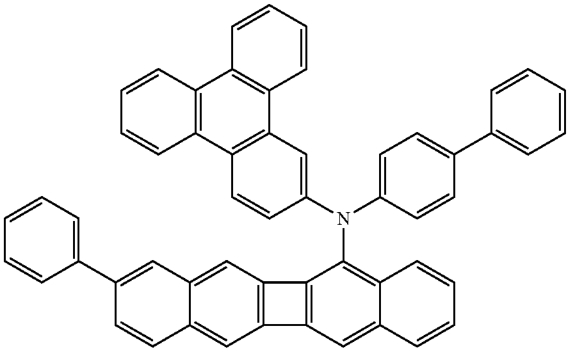
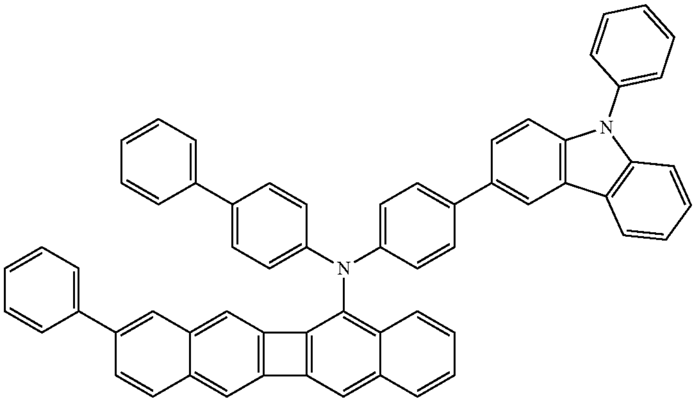
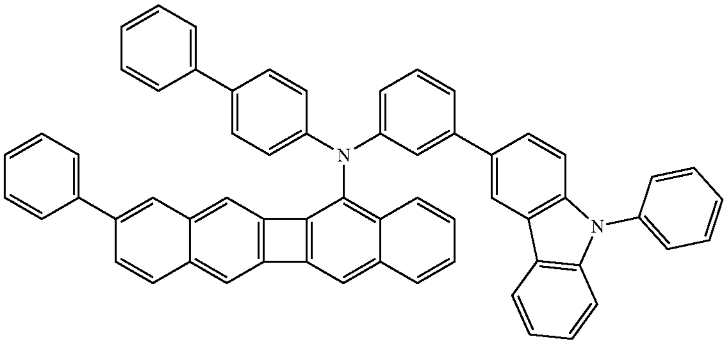
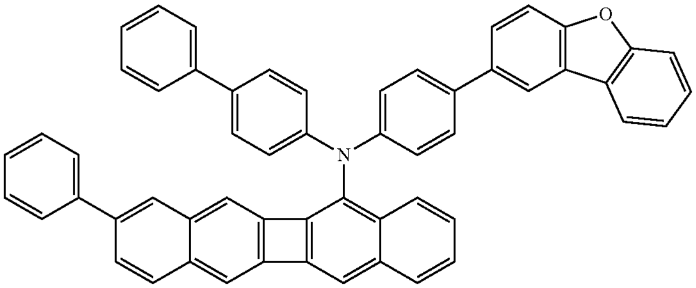
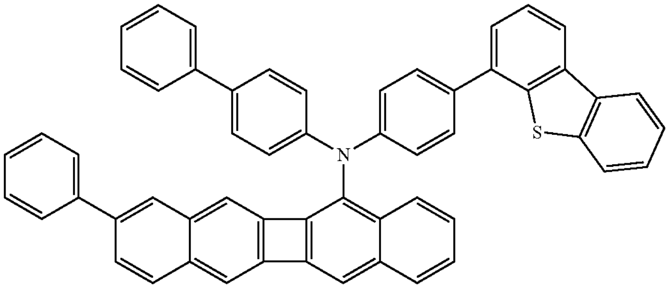

-continued
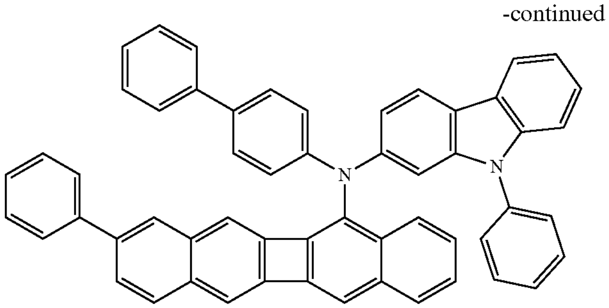
[Formula 90]
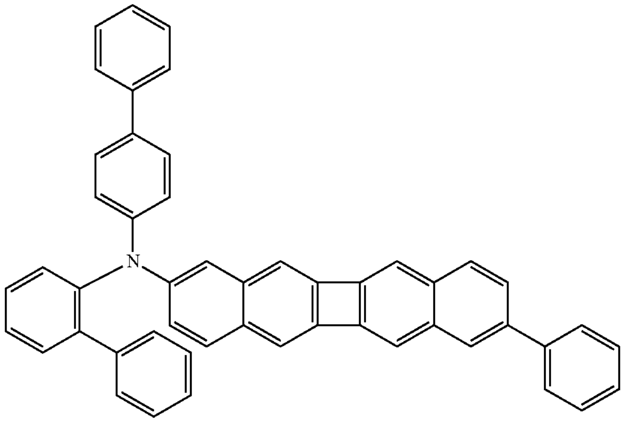
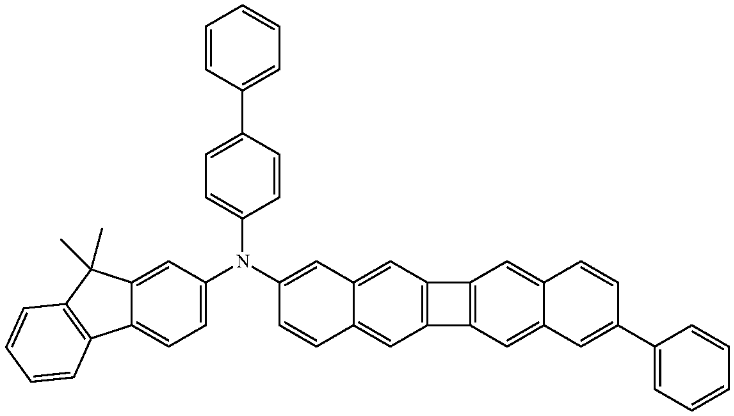
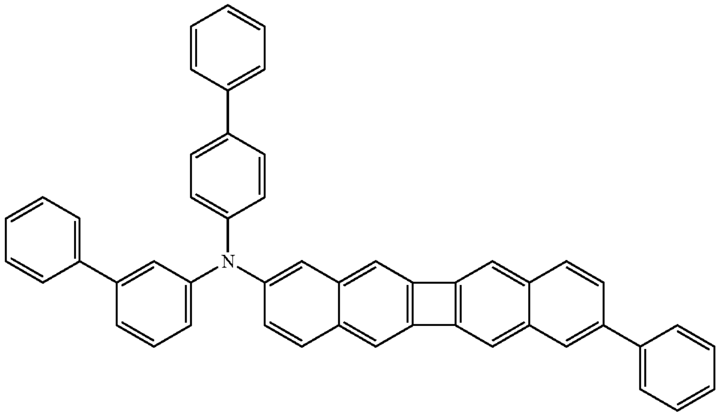

-continued
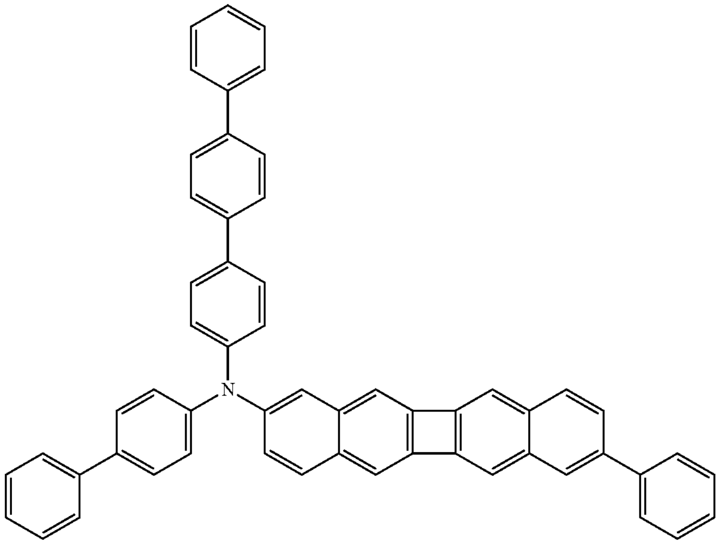
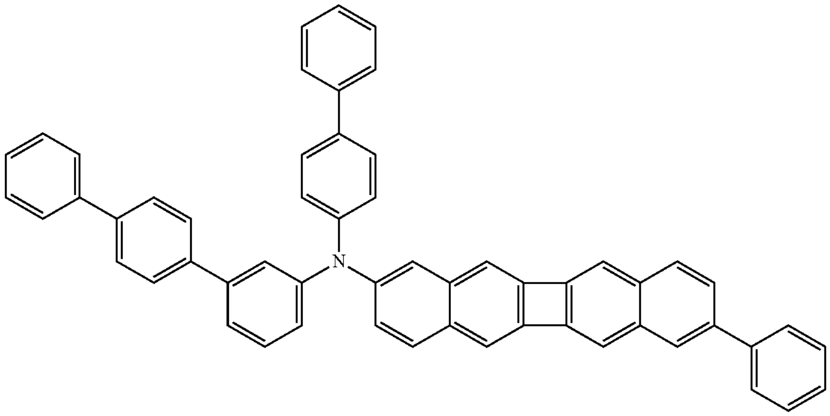
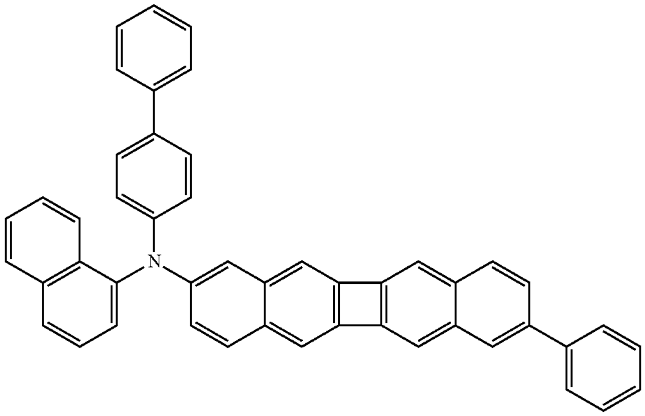

-continued
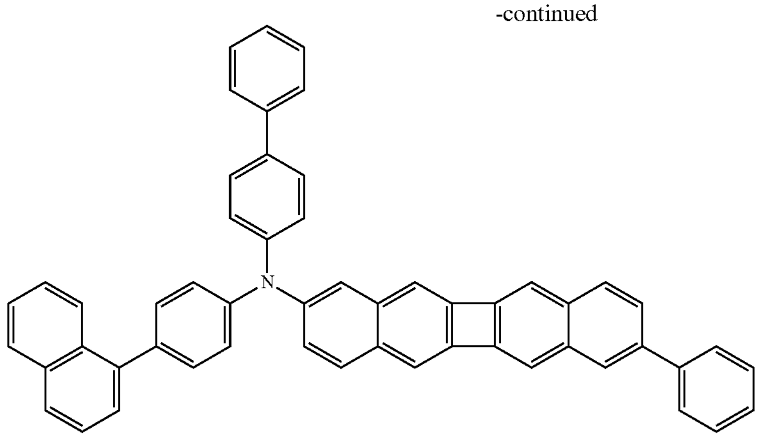
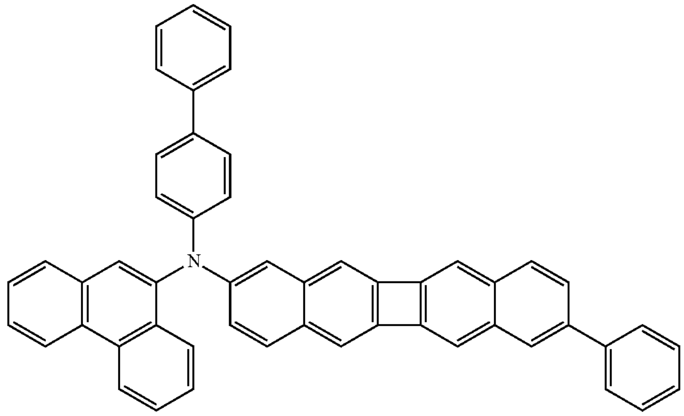
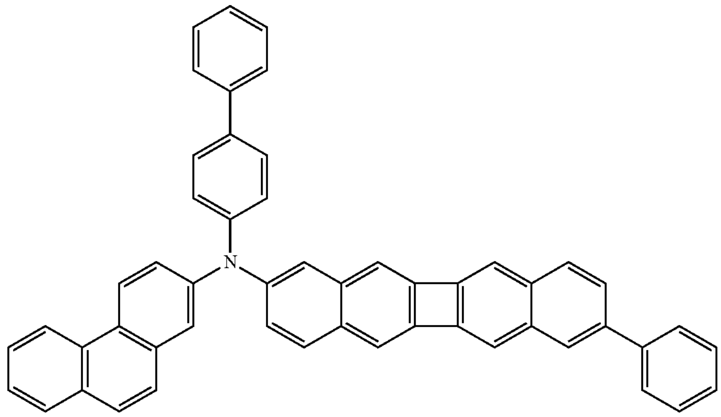
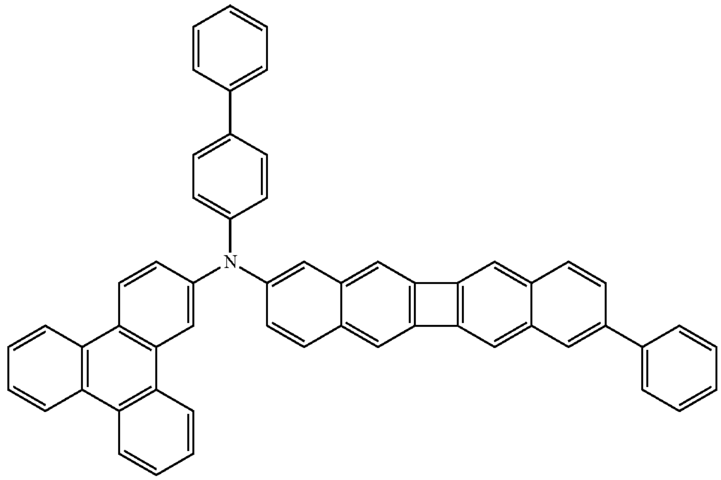

-continued
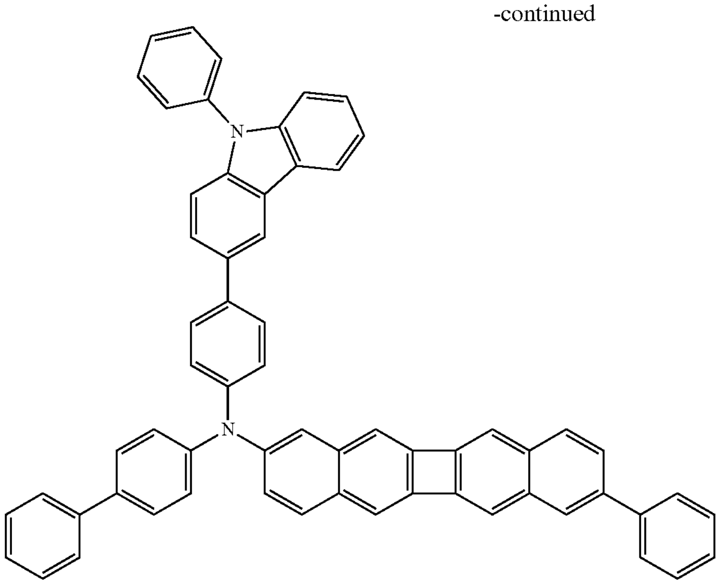
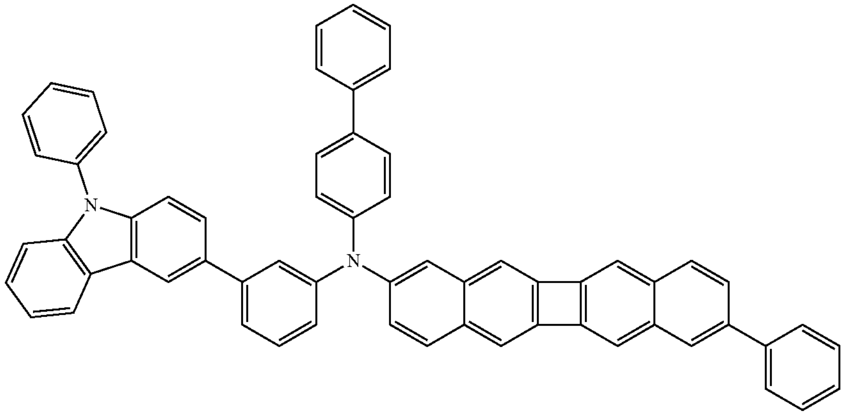
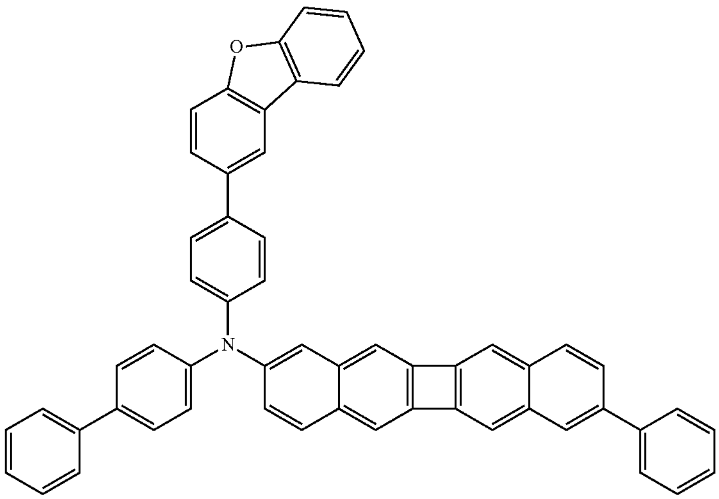

-continued
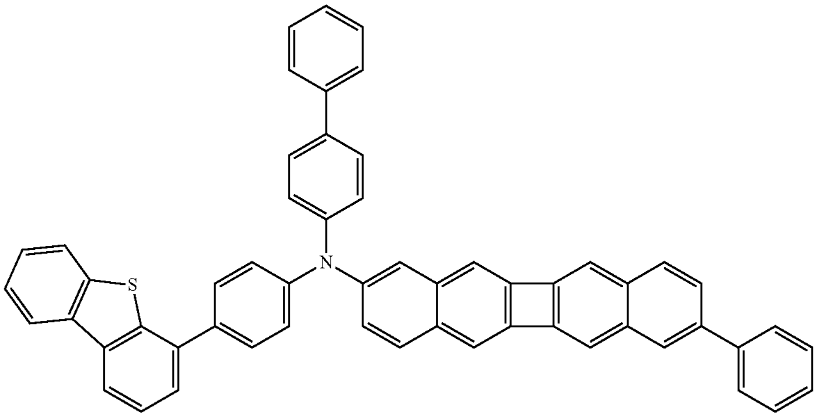
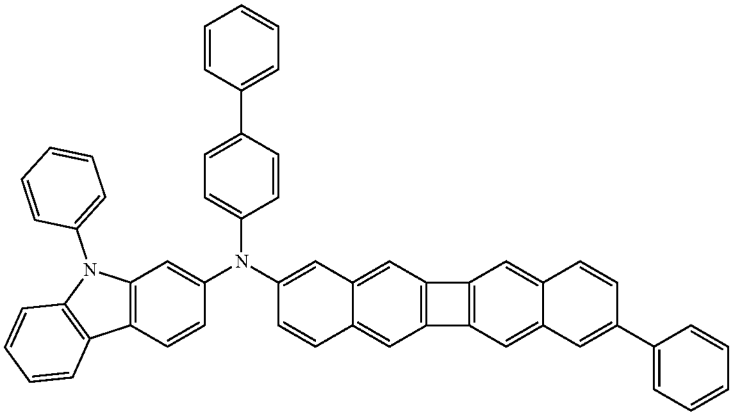
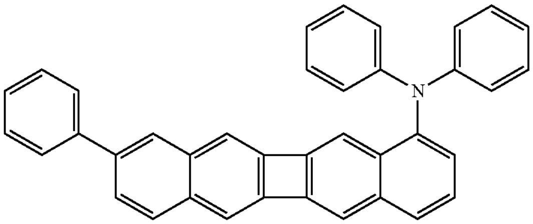
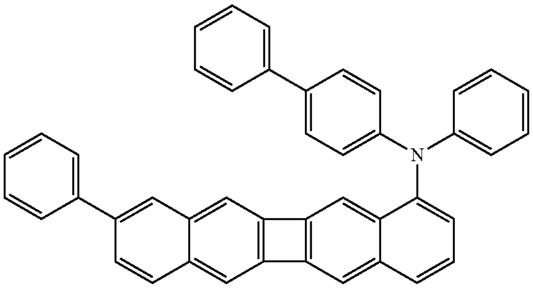
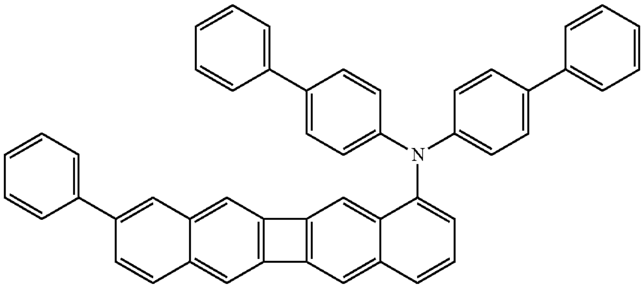
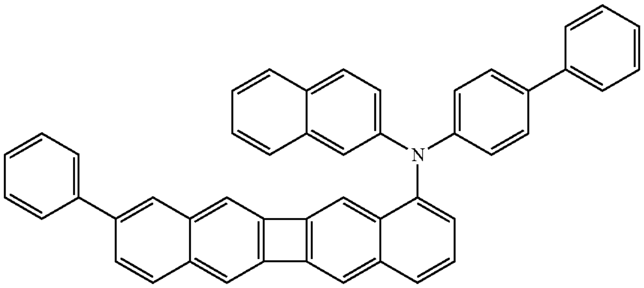

-continued
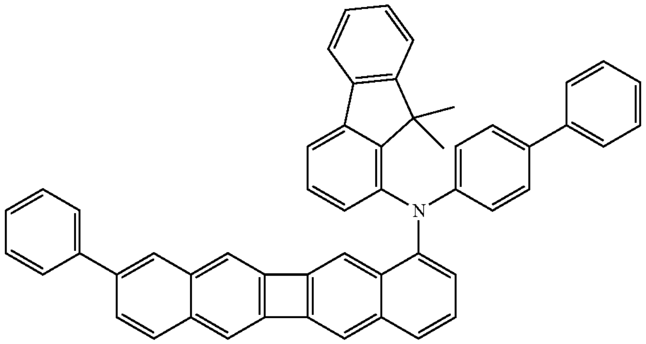
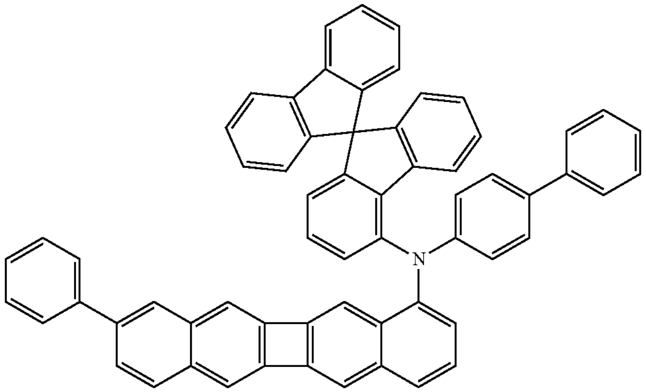
[Formula 91]
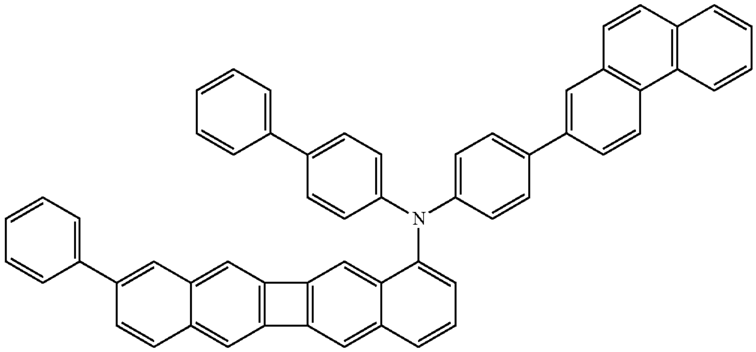
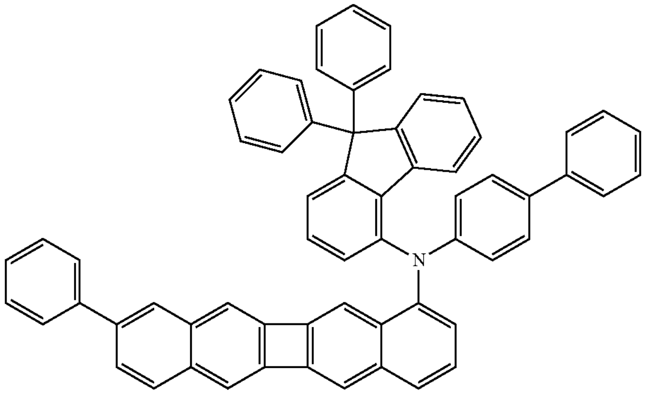

-continued
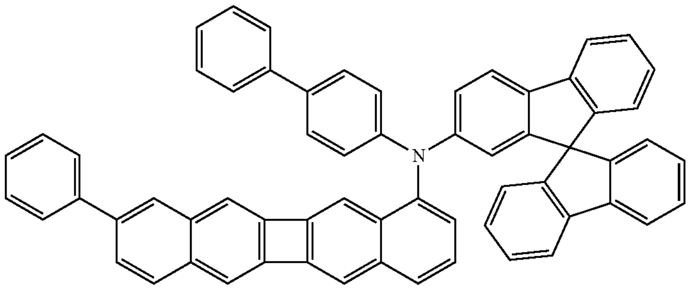
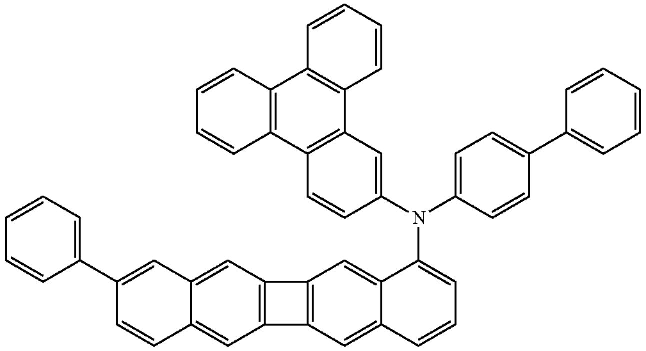
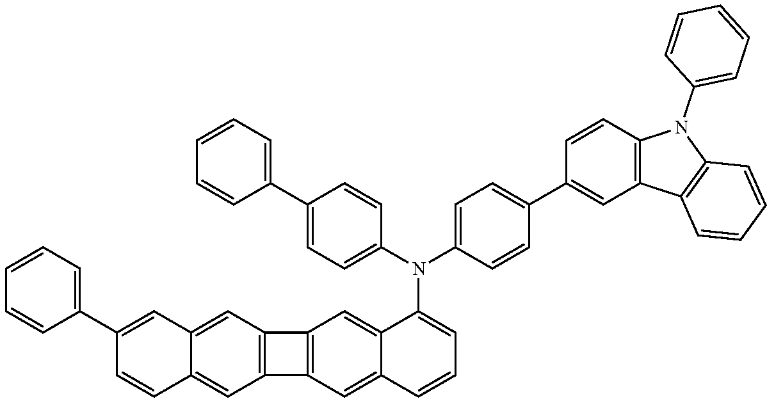
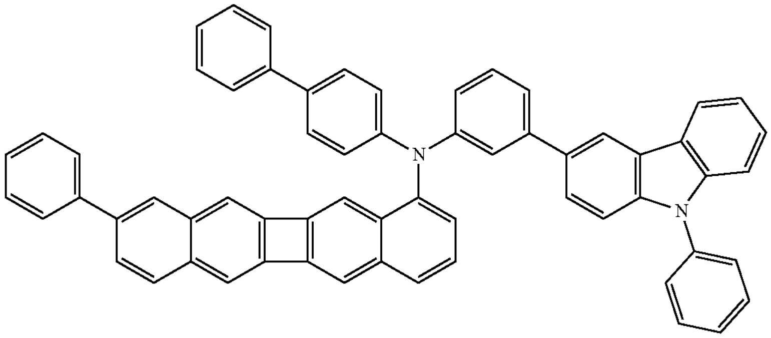
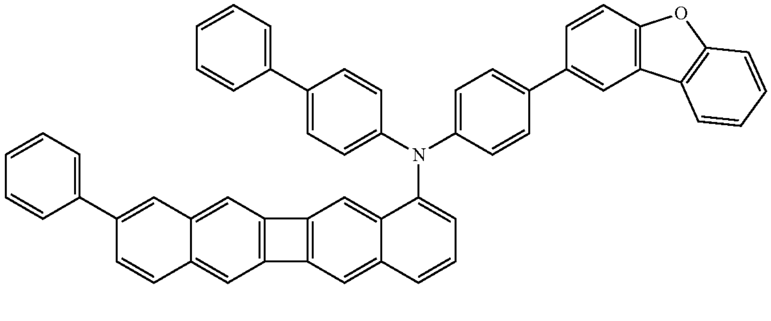

-continued
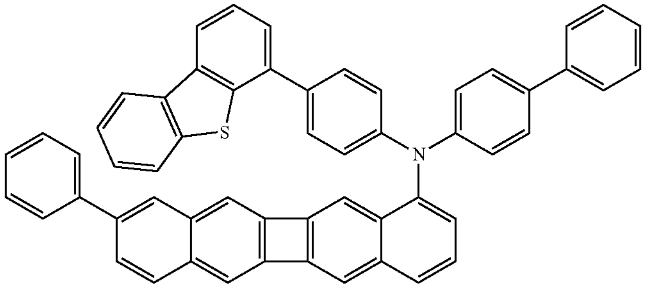
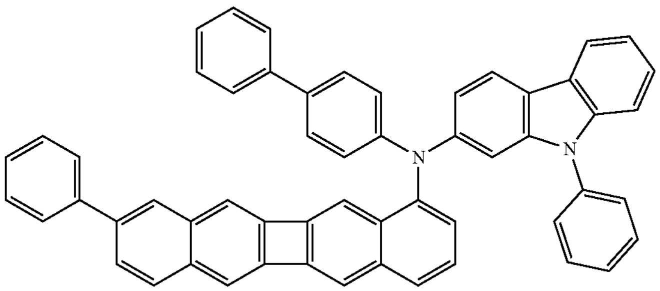
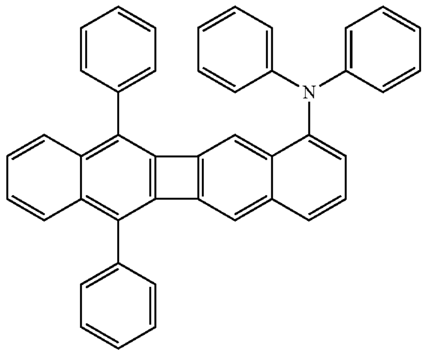
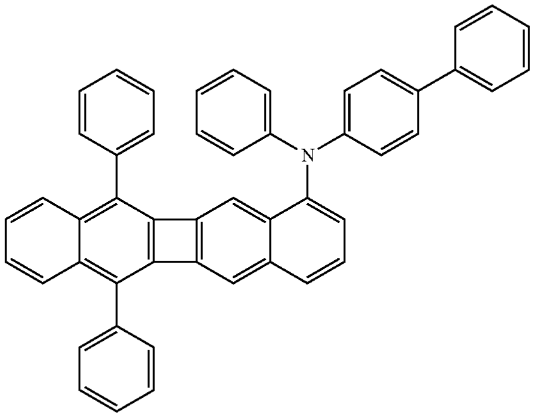
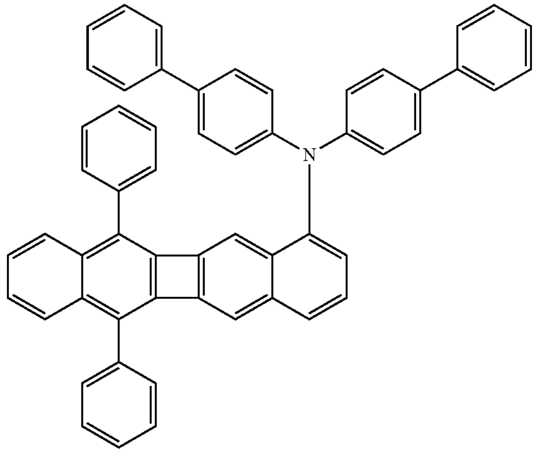
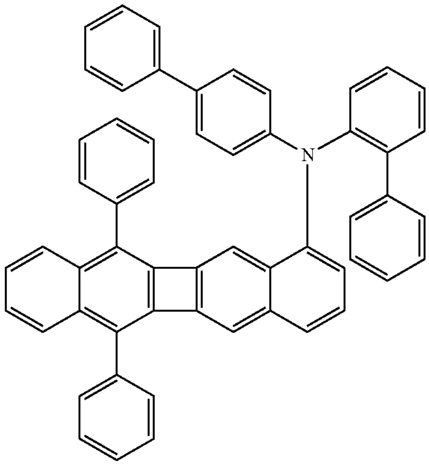
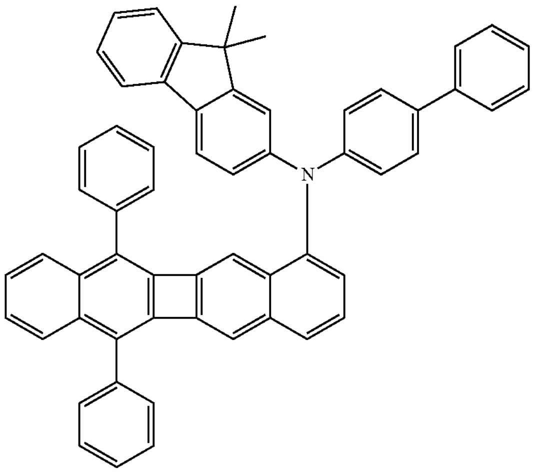

-continued
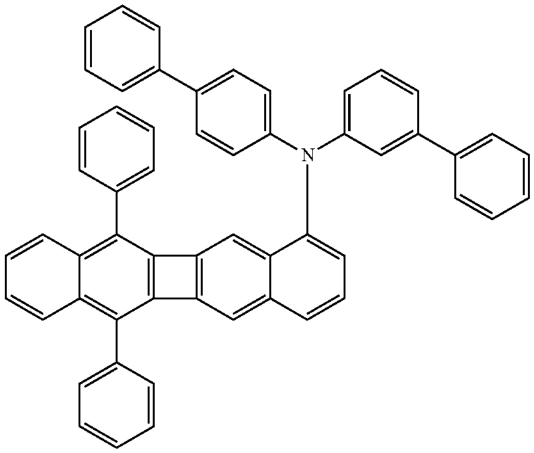
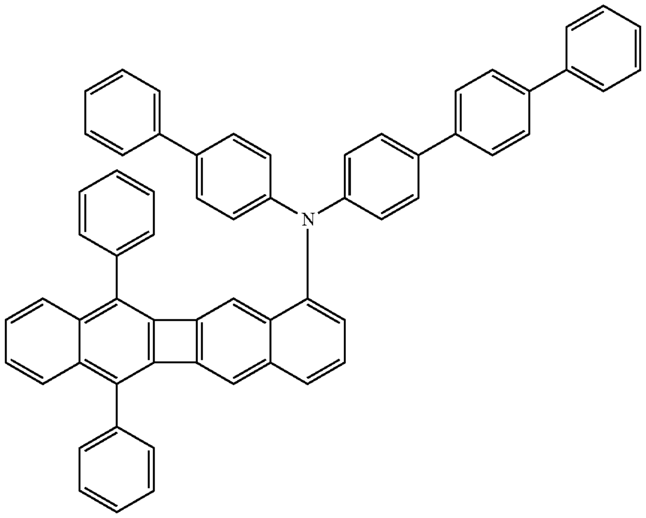
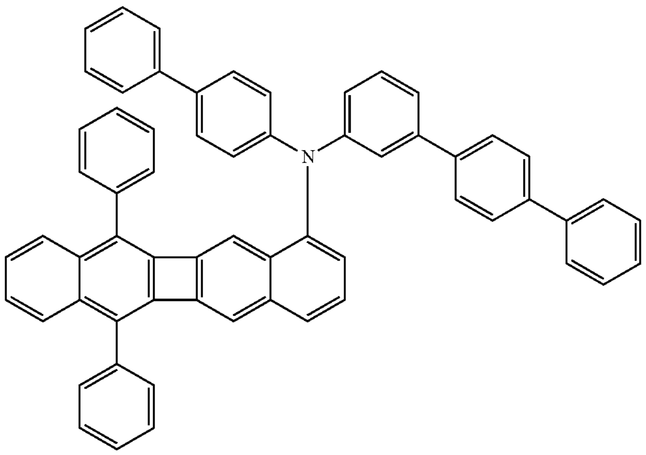

-continued
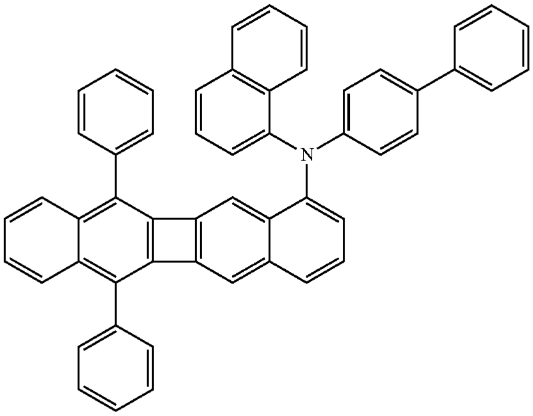
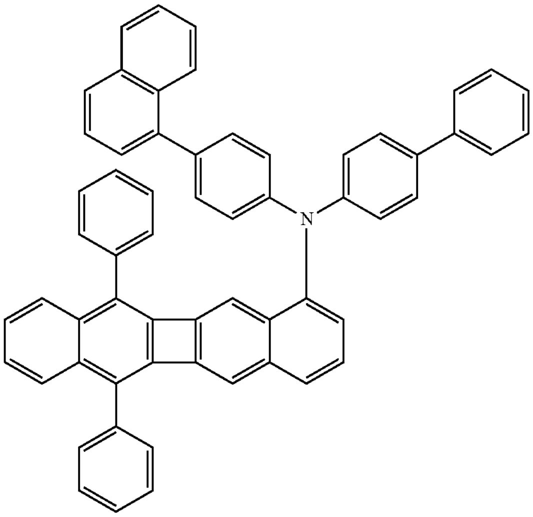
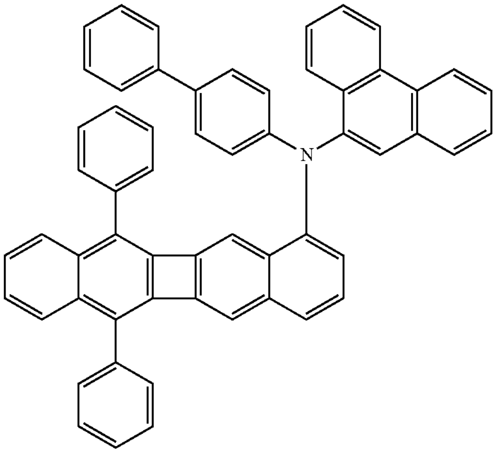
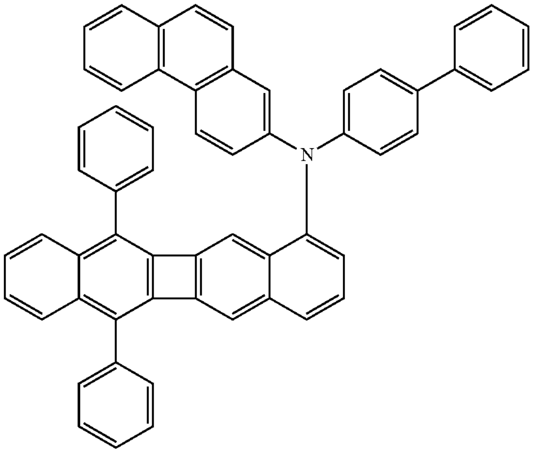
[Formula 92]
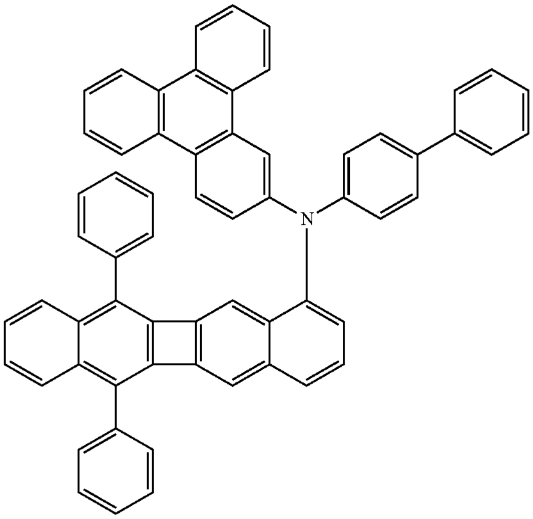

-continued
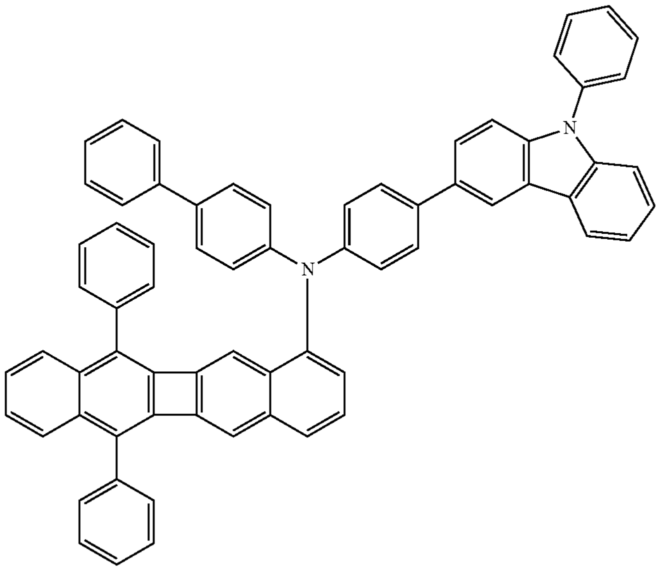
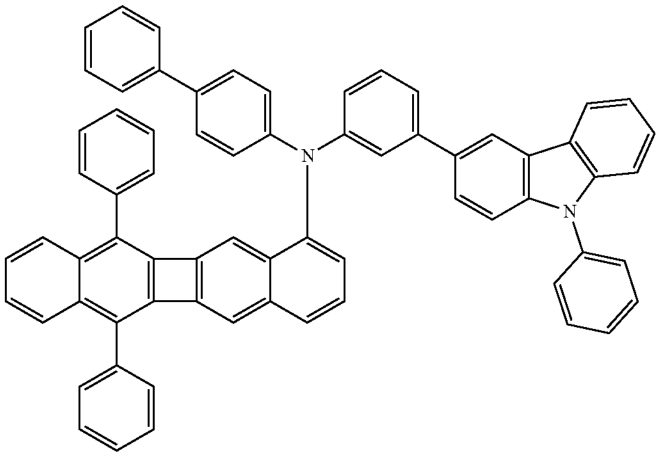
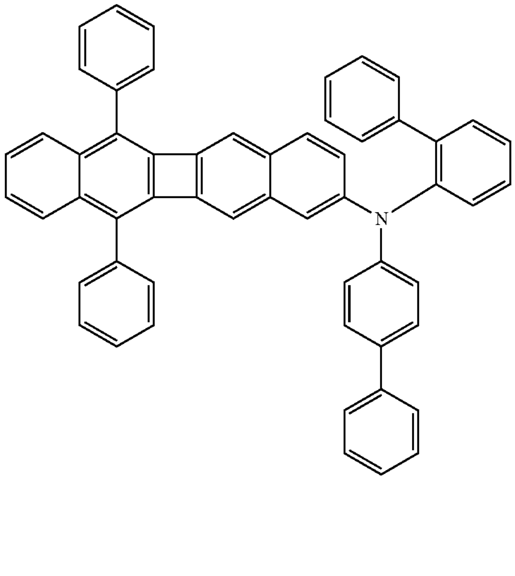

-continued
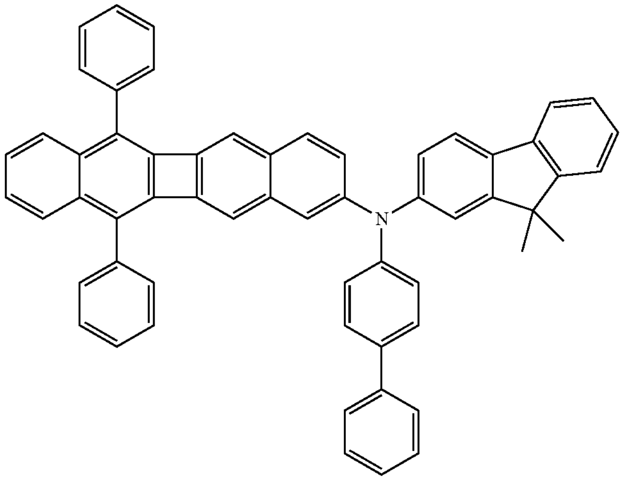
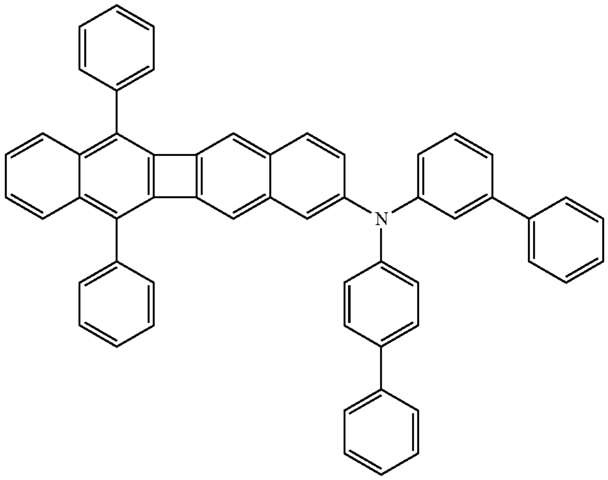
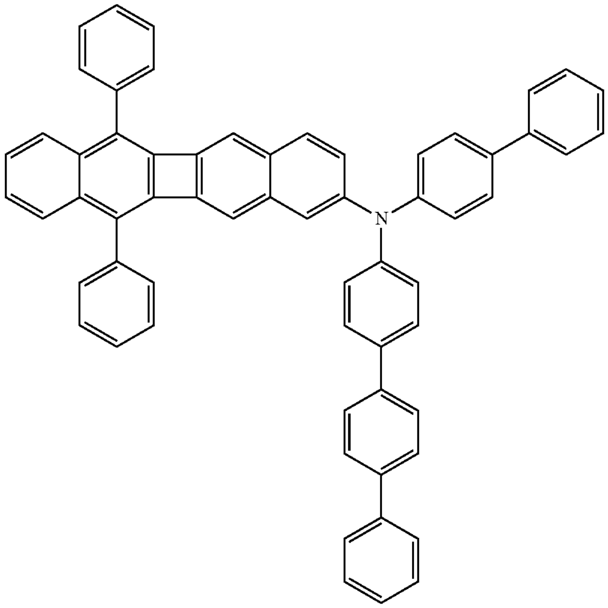

-continued
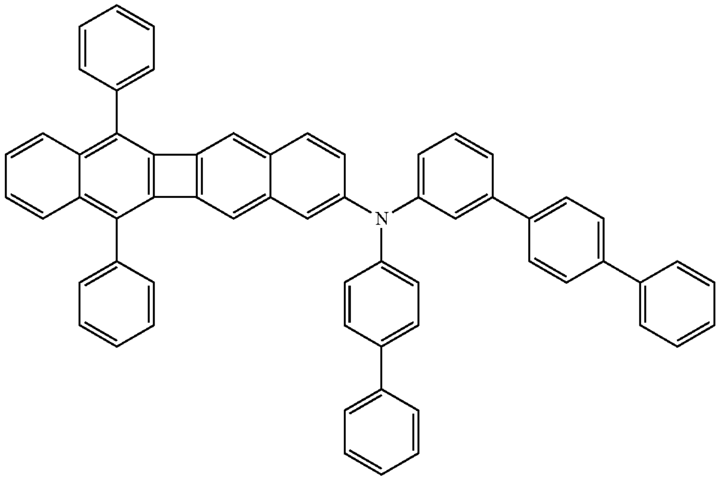
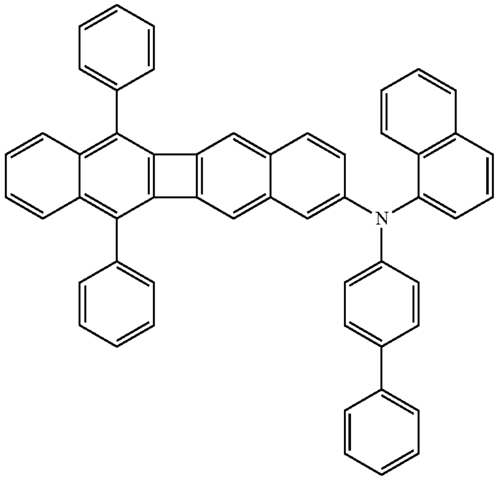
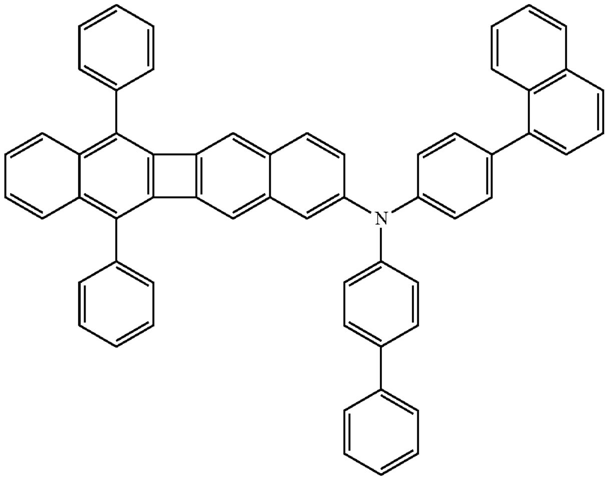
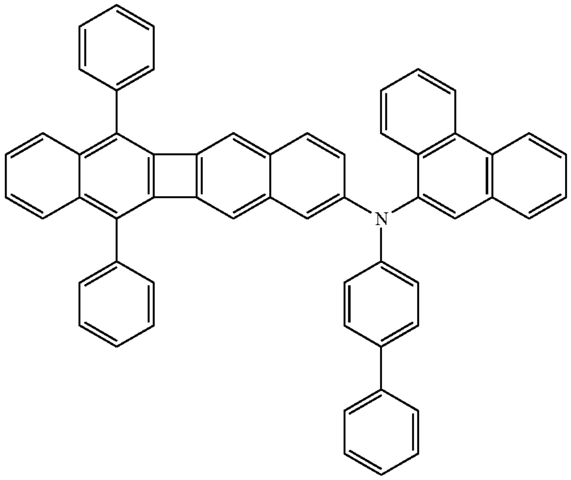

-continued
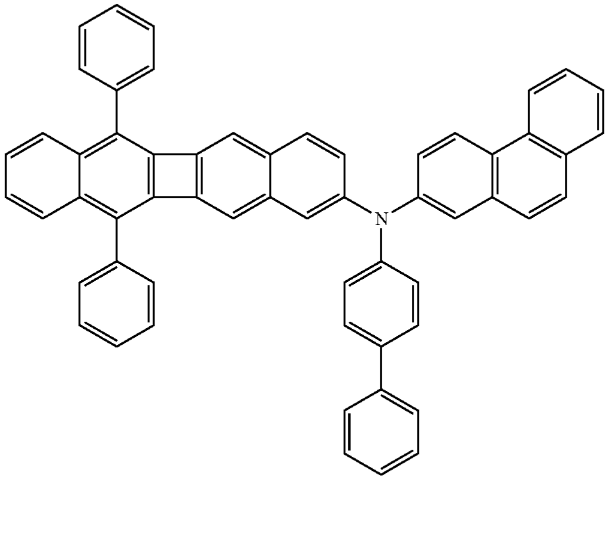
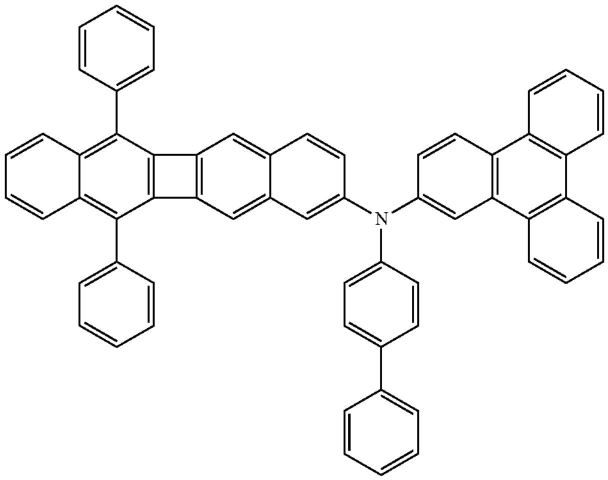
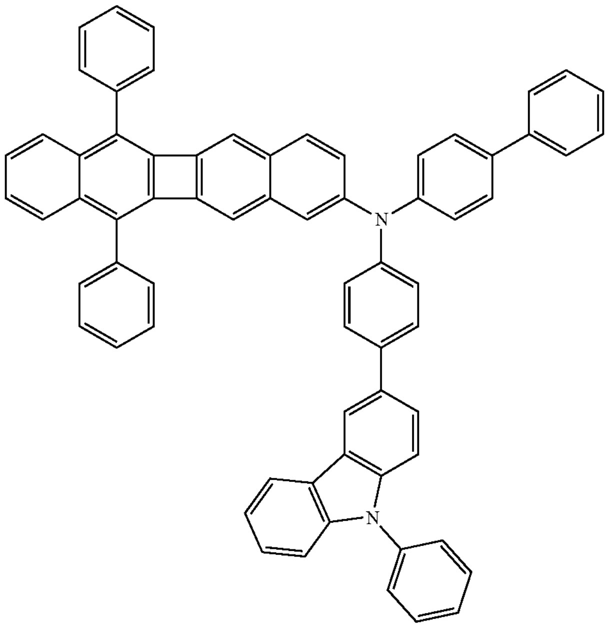

-continued
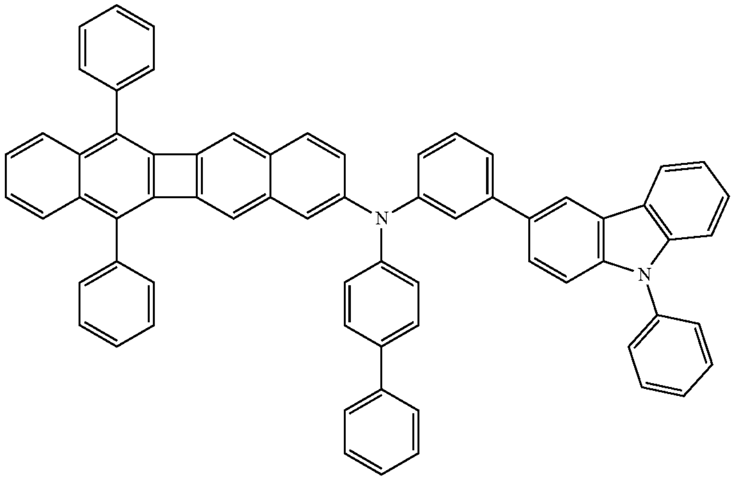
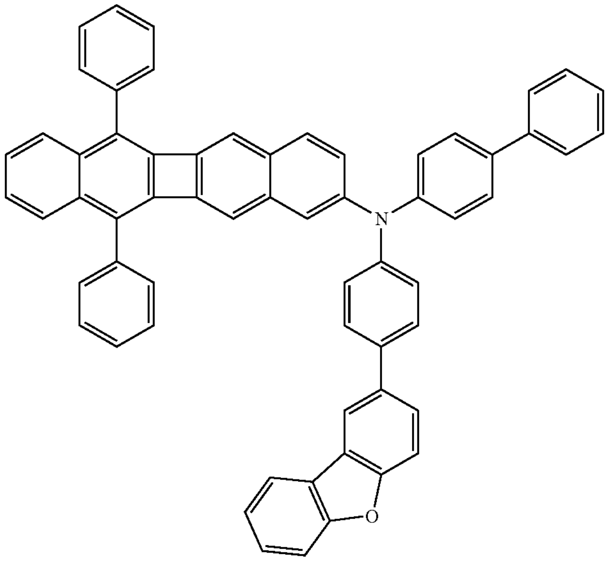
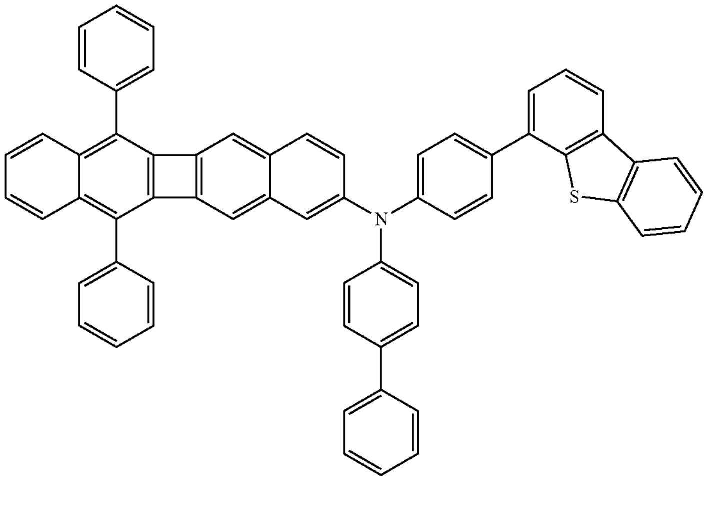

-continued
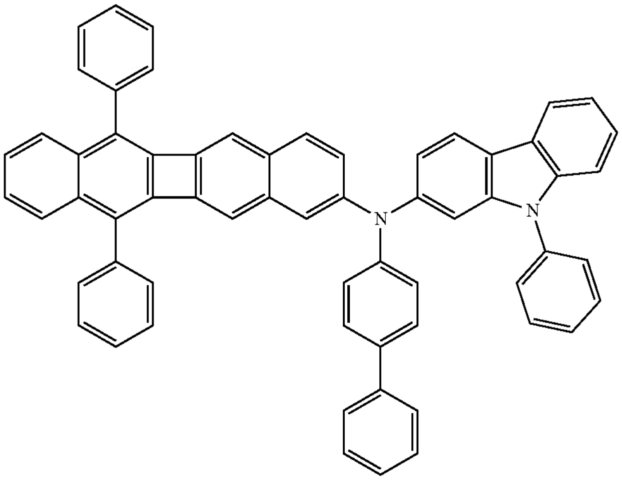
[Formula 93]
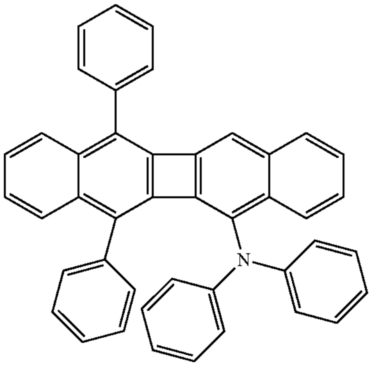
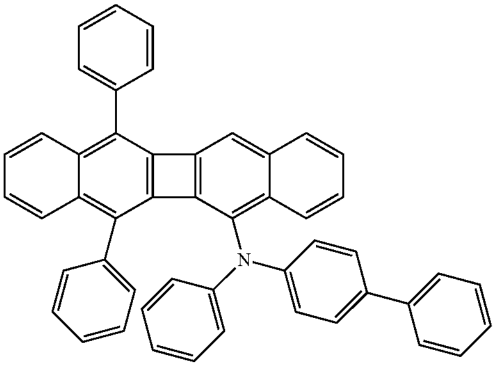
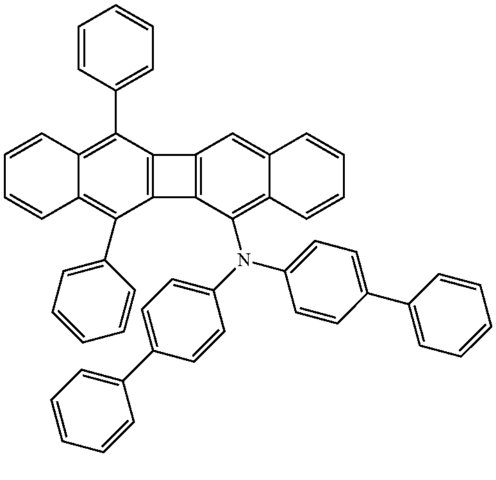
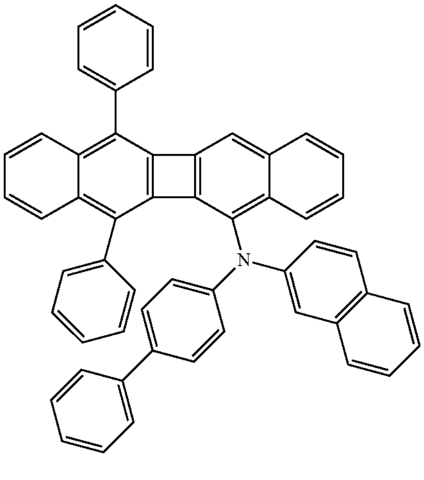

-continued
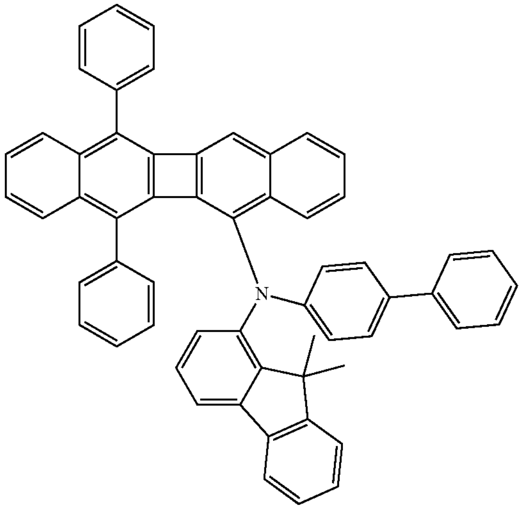
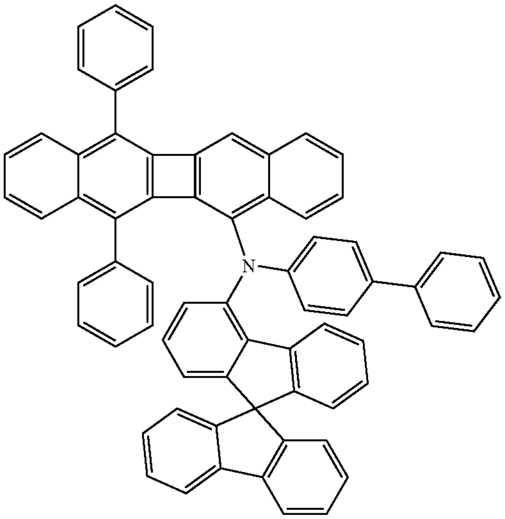
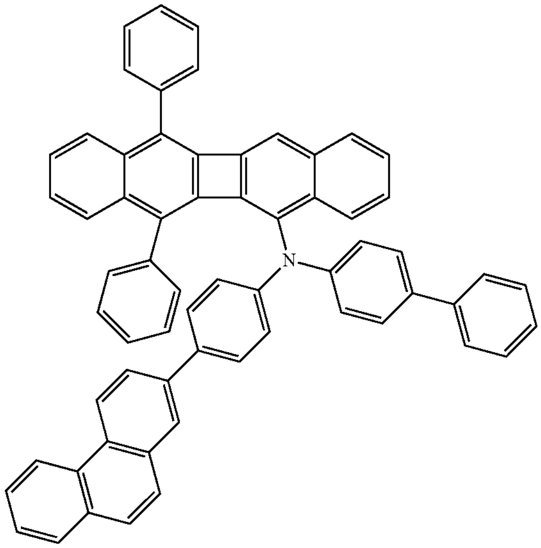
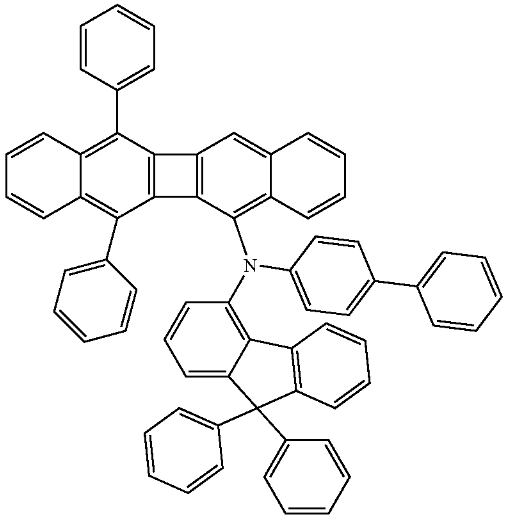
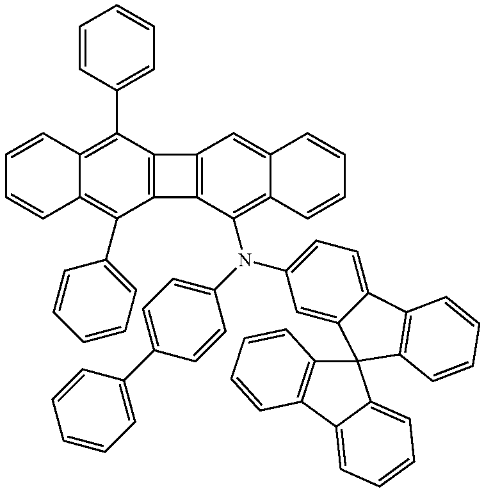

-continued
[Formula 94]
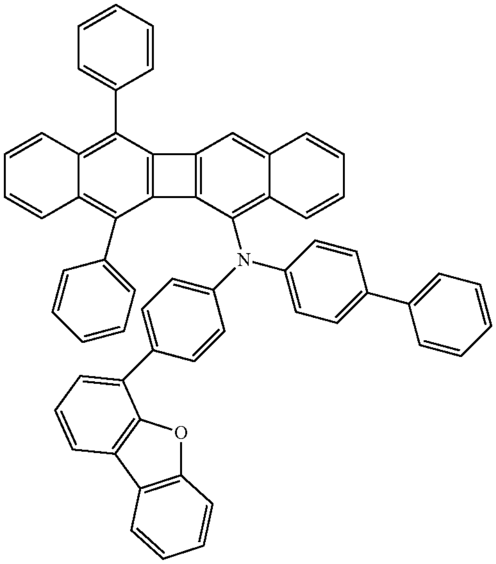
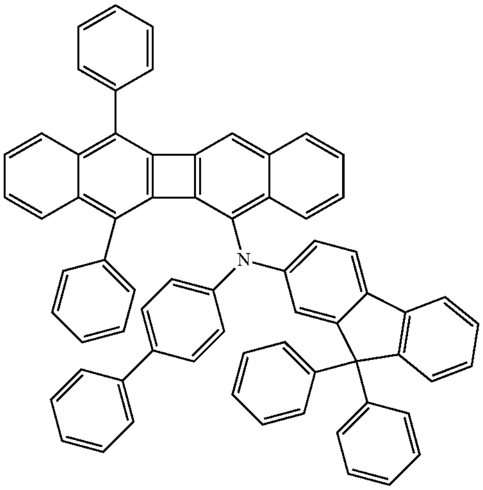
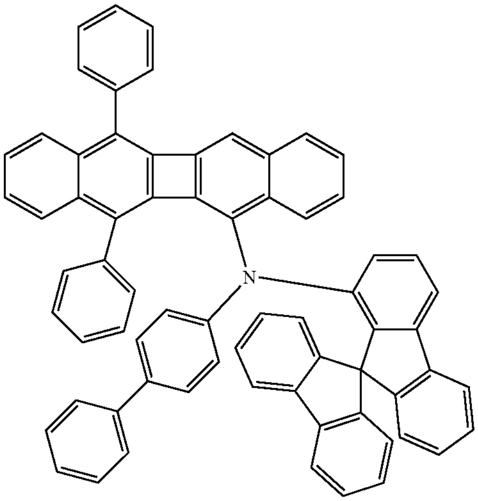
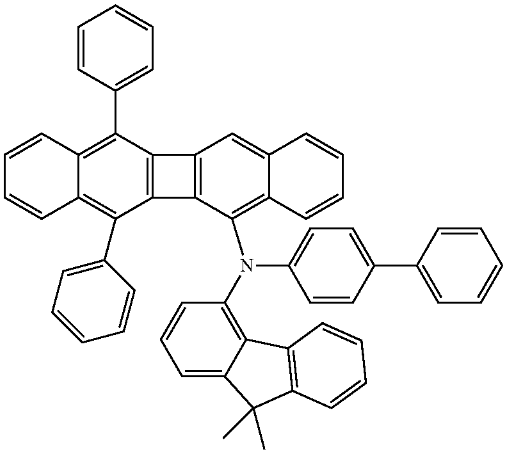
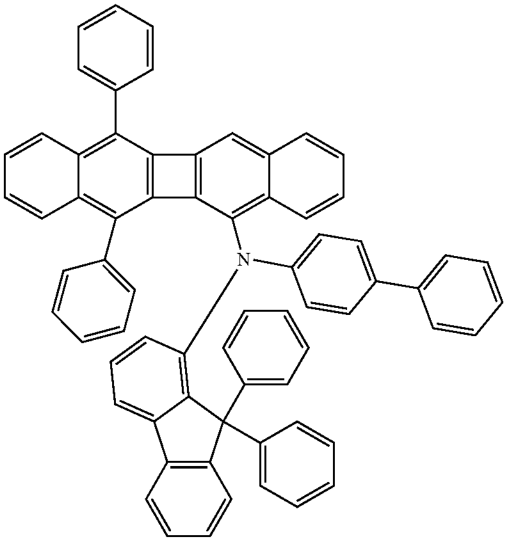
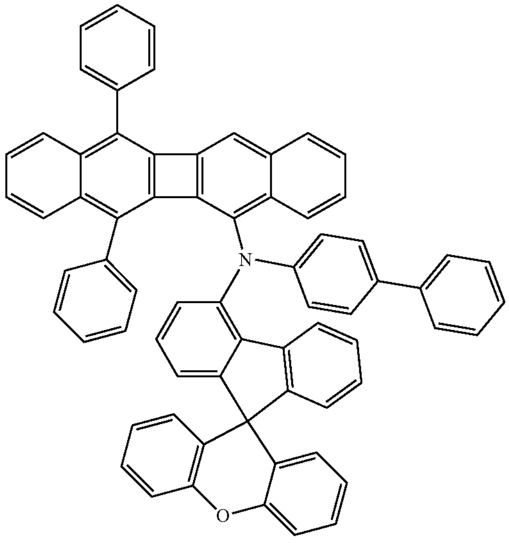

-continued
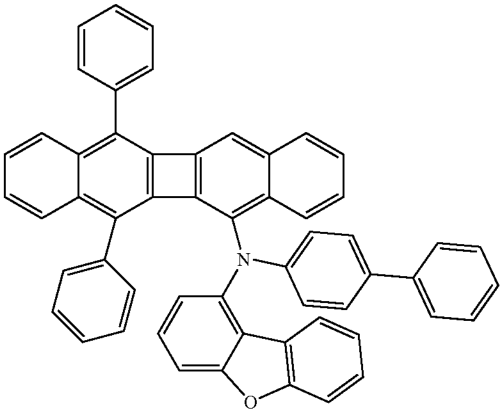
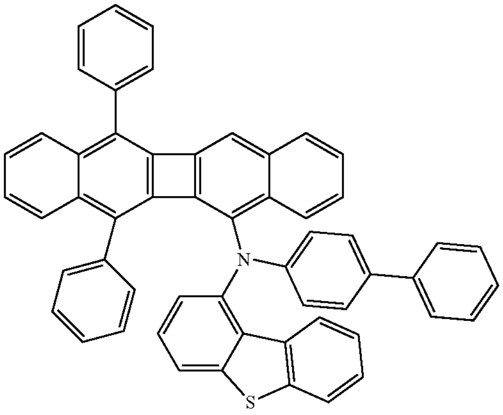
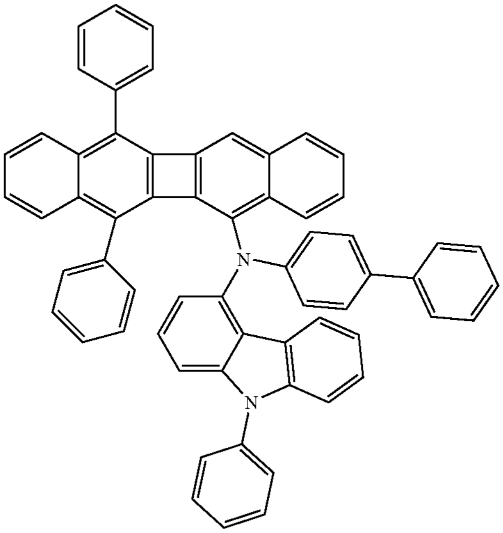
[Formula 95]
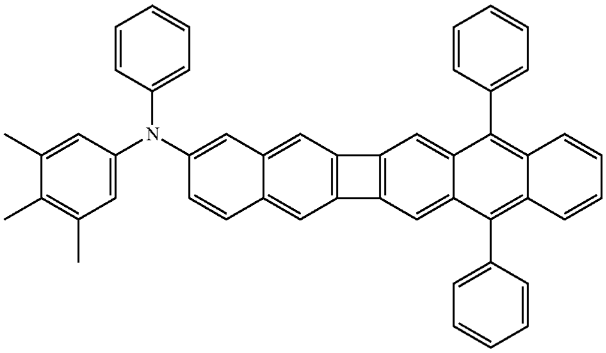
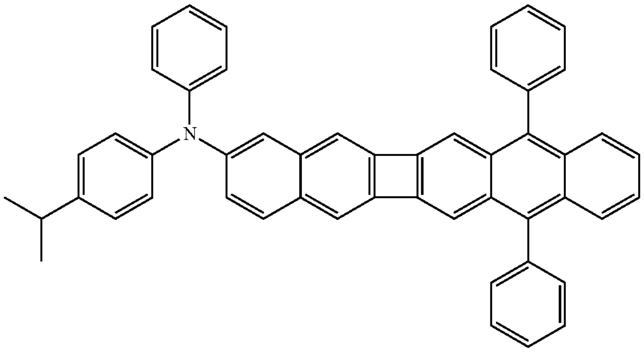

-continued
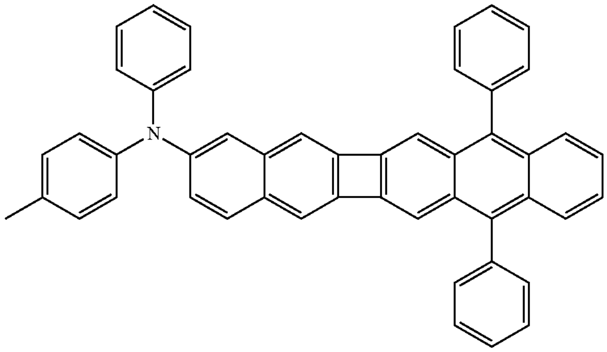
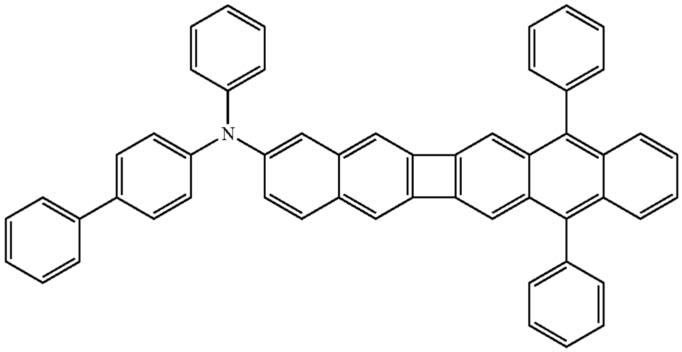
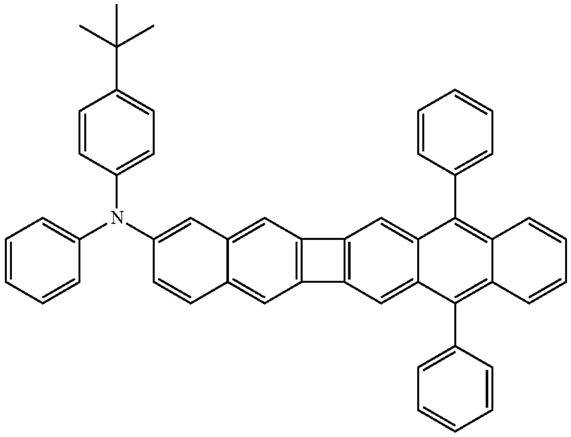
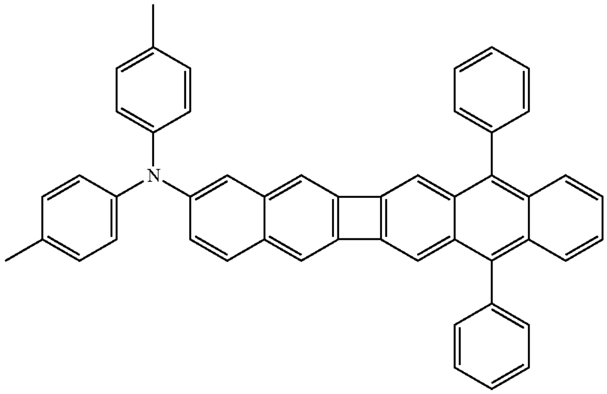

-continued
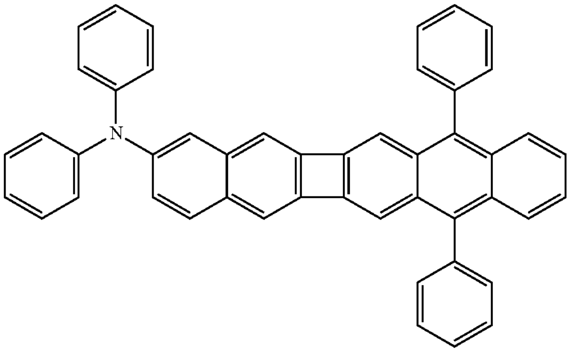
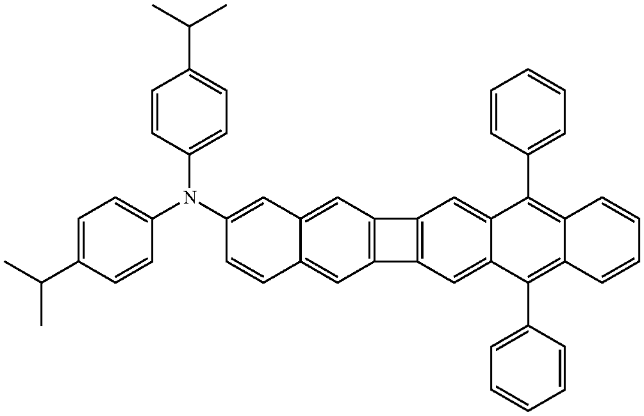
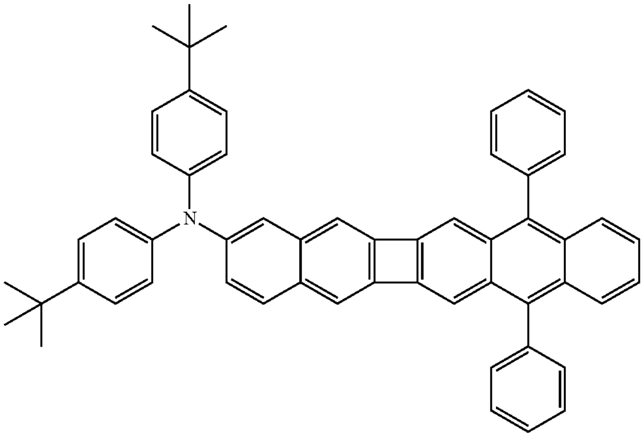
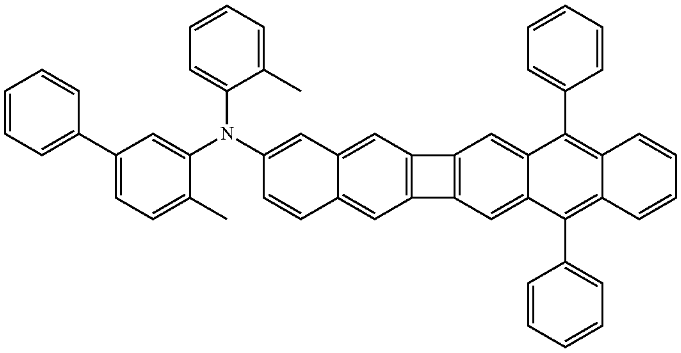

-continued
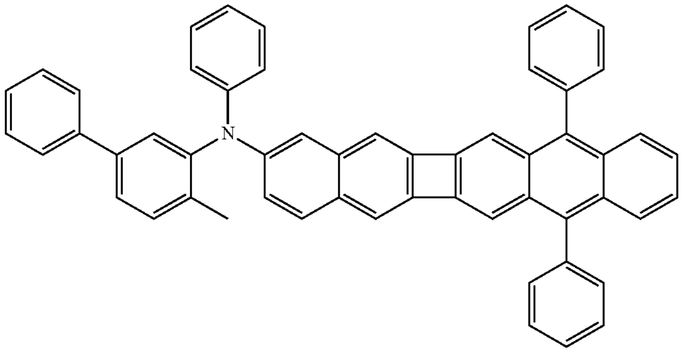
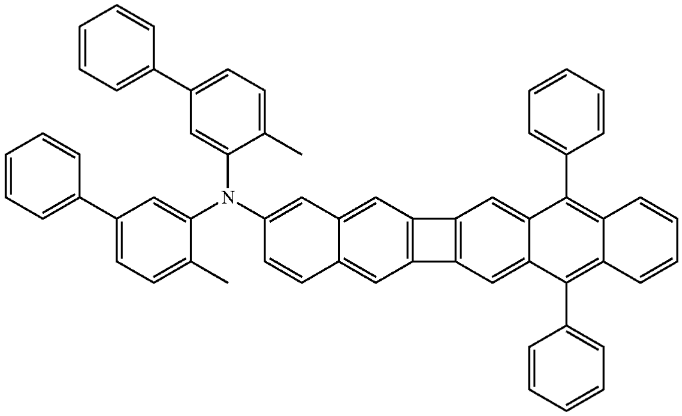
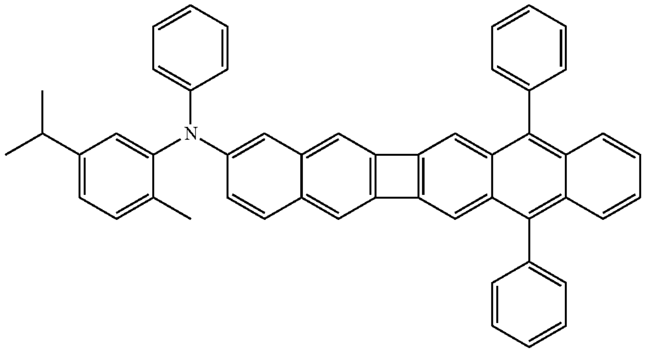
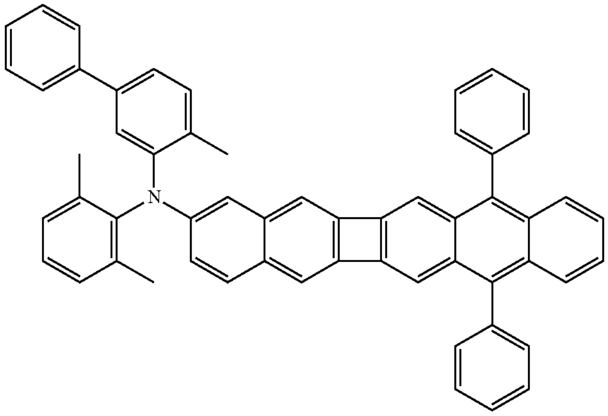

-continued
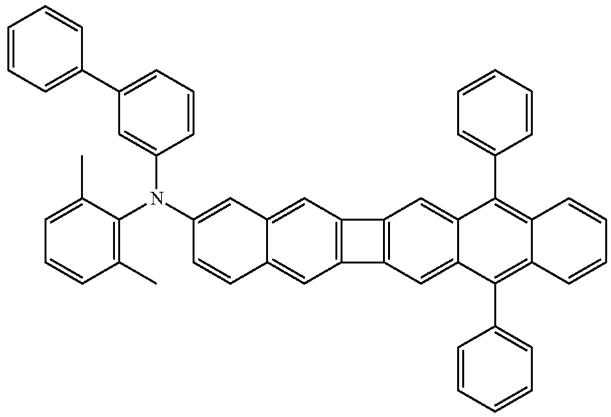
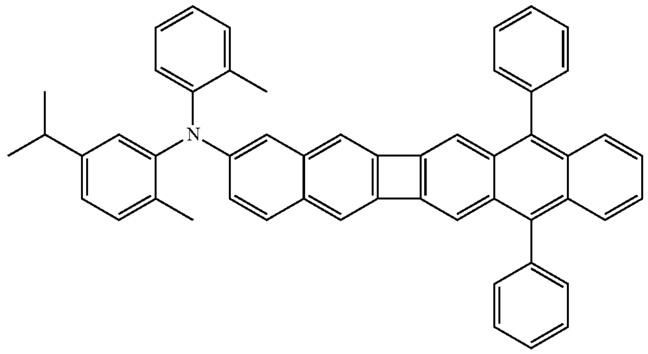
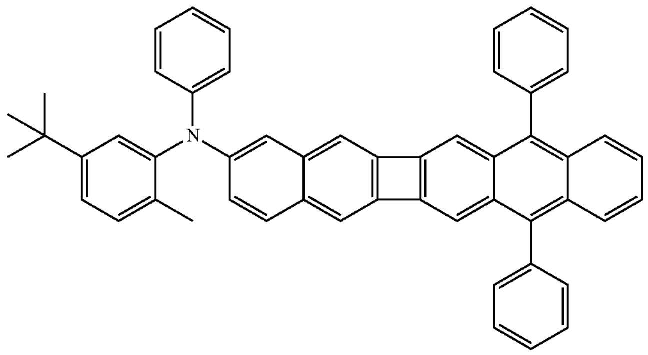
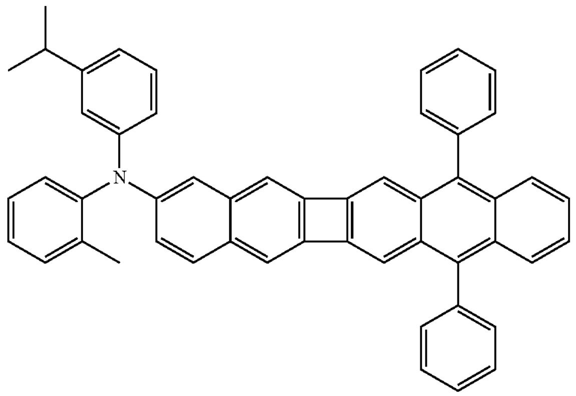

-continued
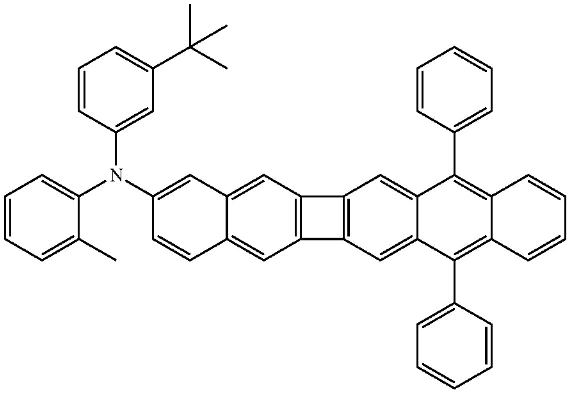
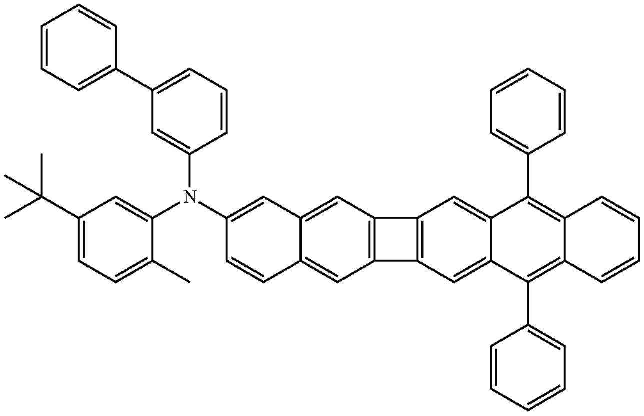
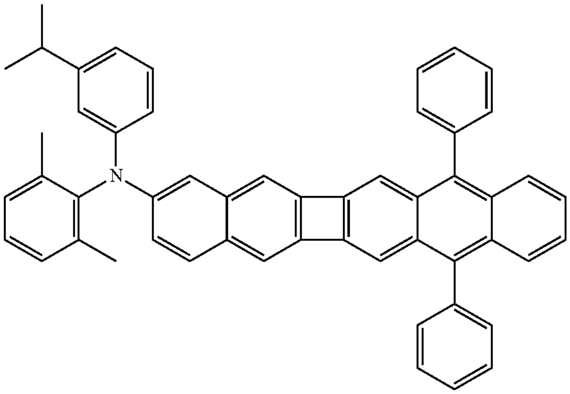
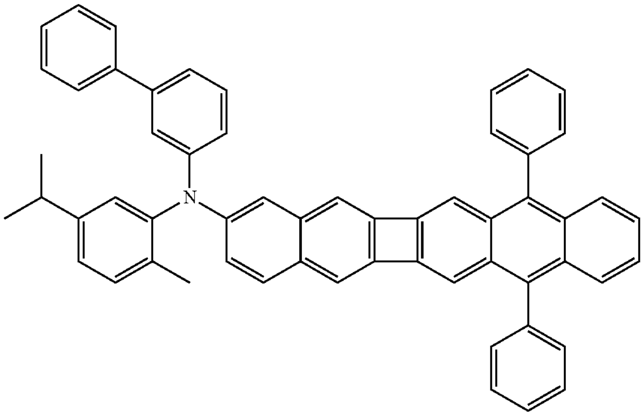

-continued
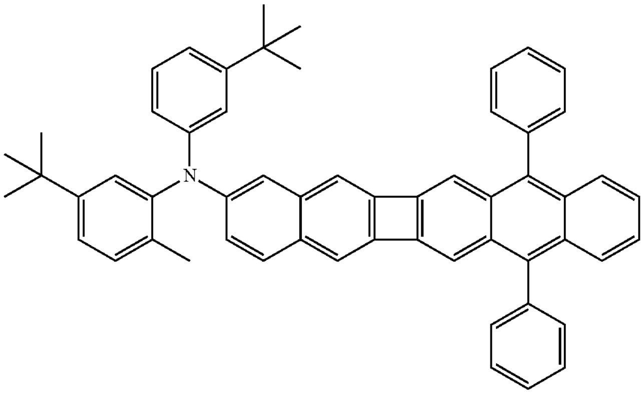
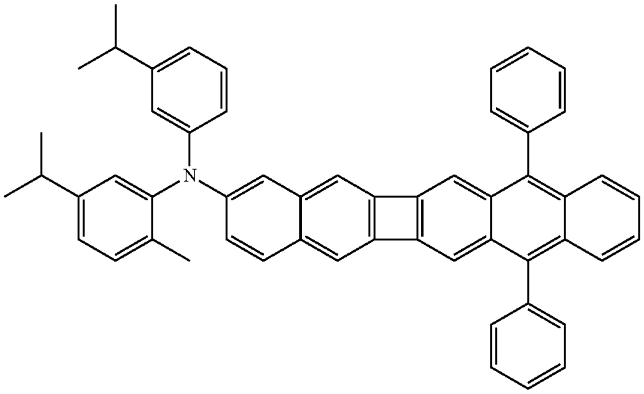
[Formula 96]
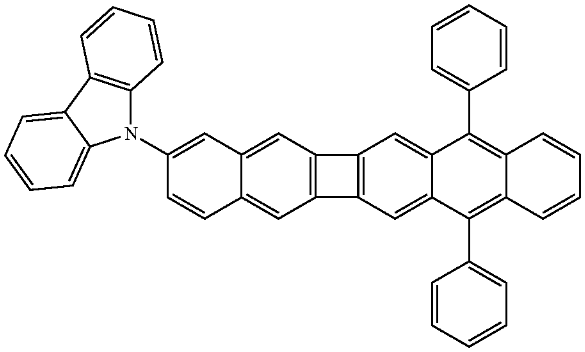
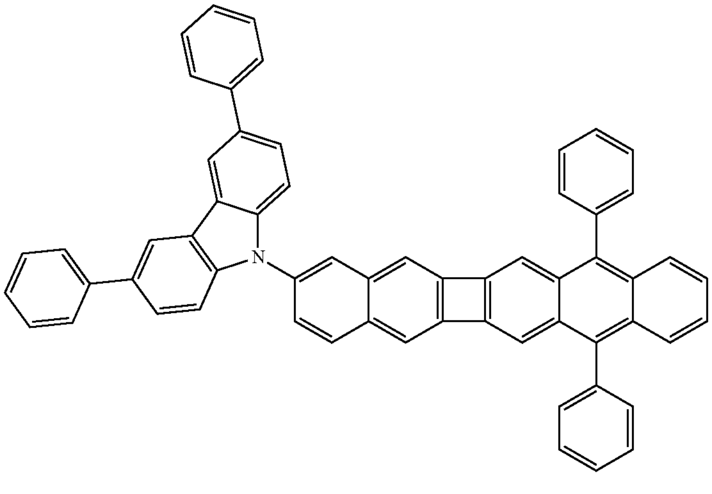

-continued
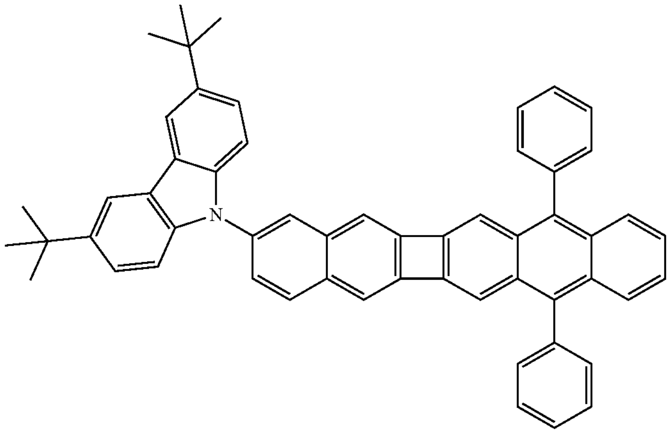
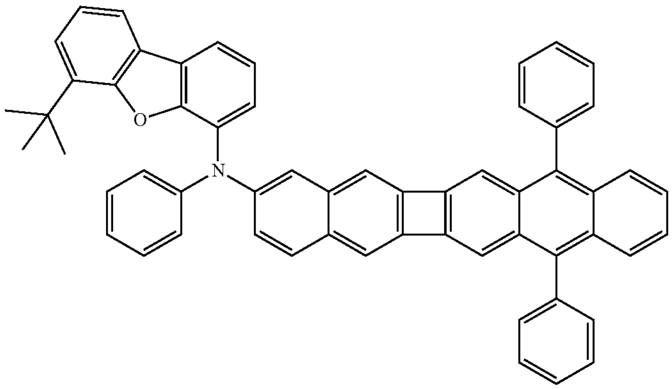
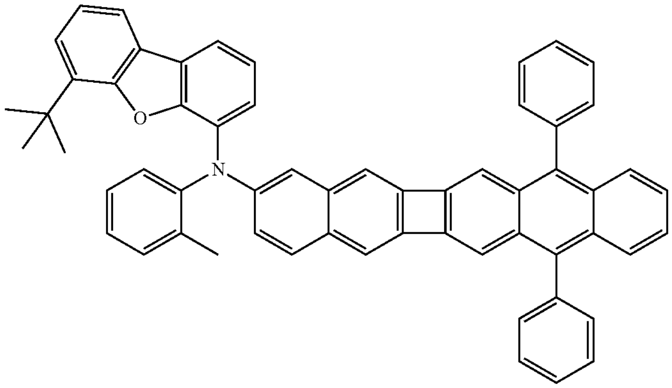
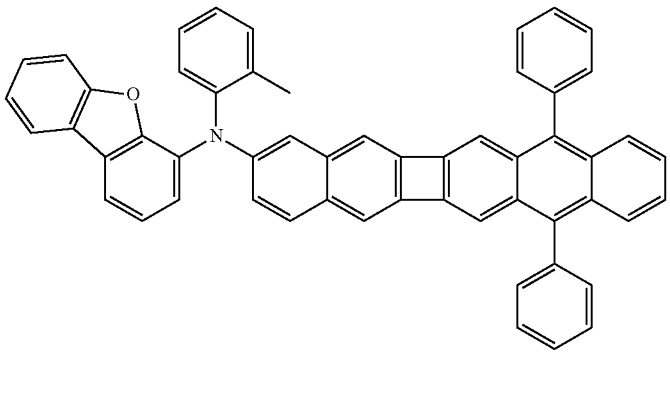

-continued
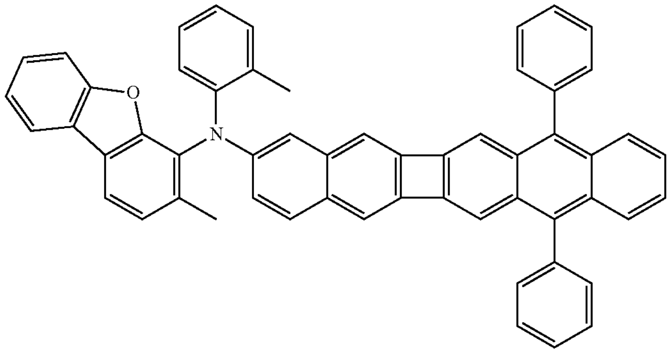
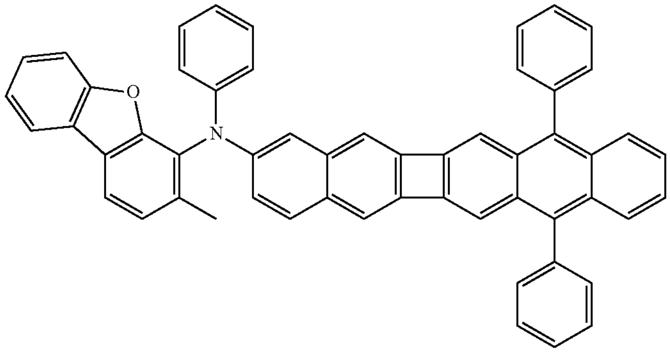
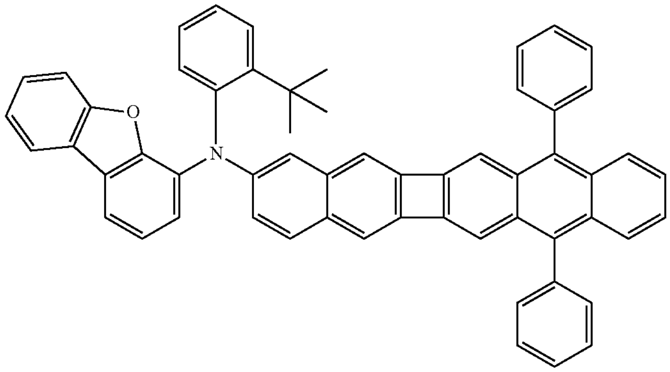
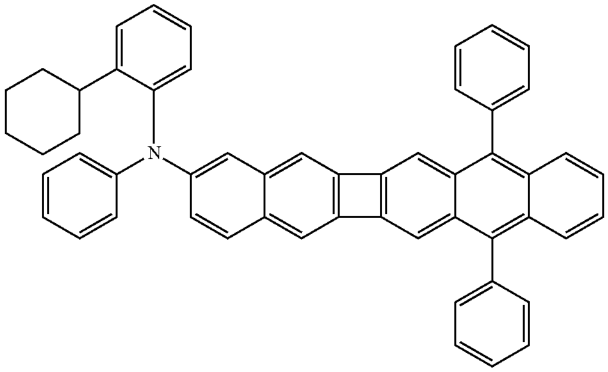

-continued
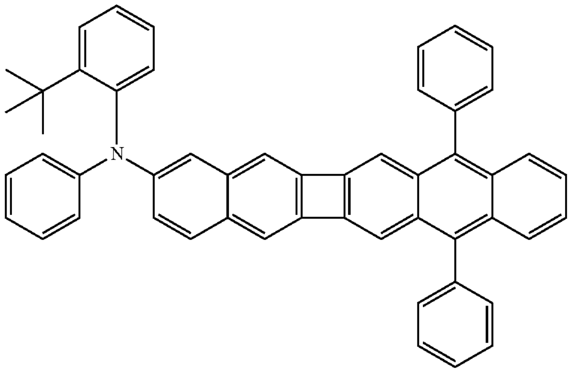
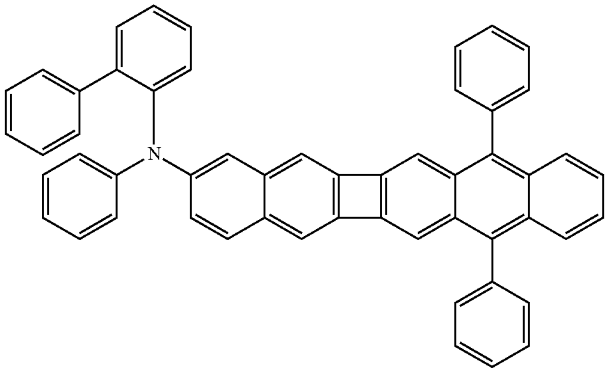
[Formula 97]
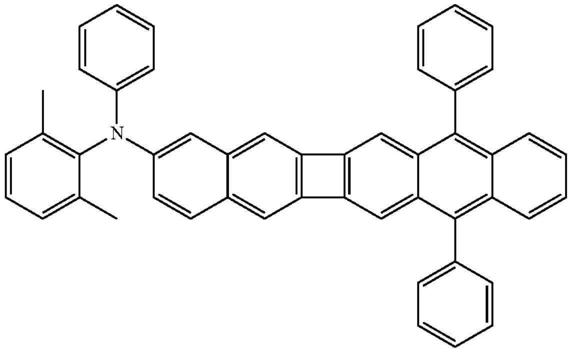
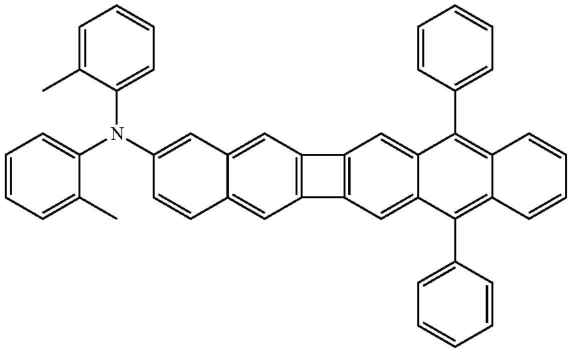

-continued
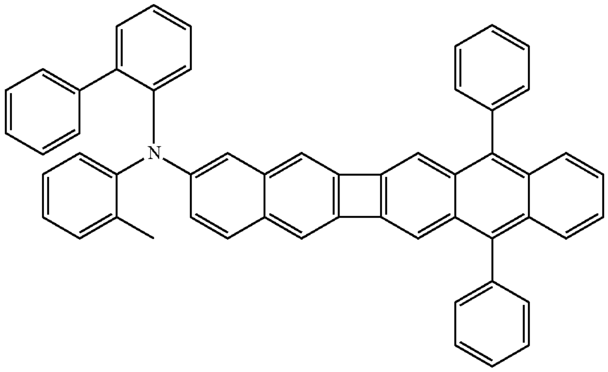
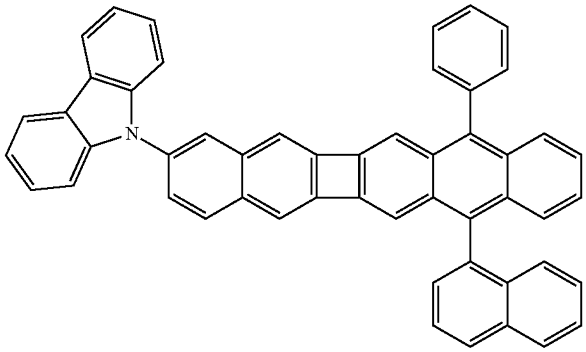
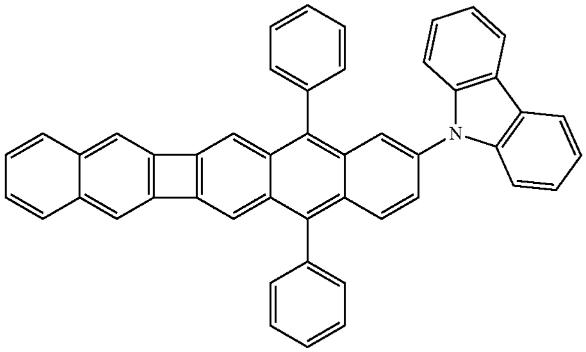
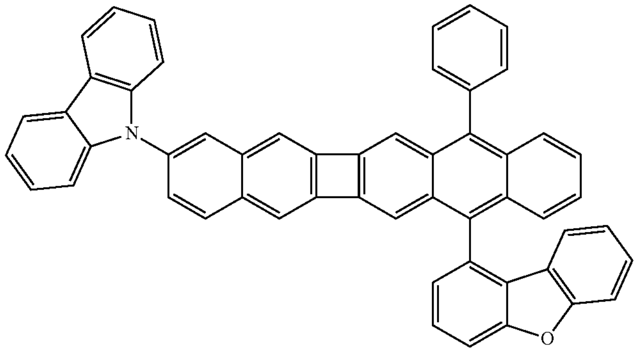
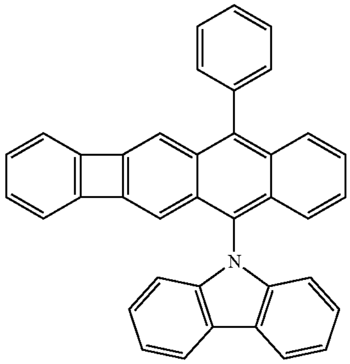

-continued
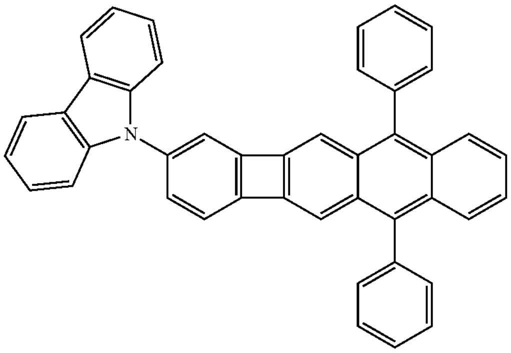
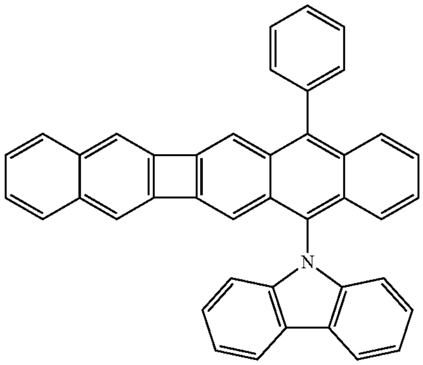
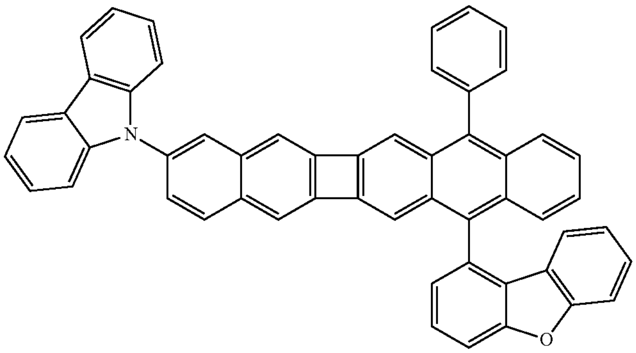
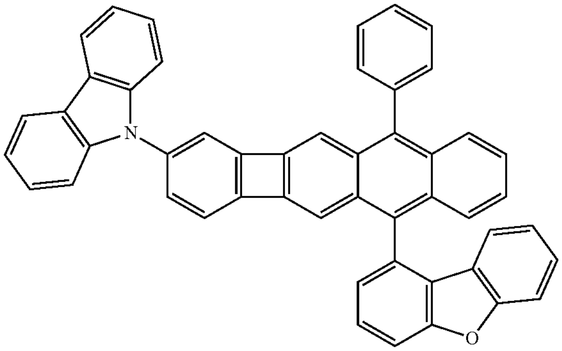
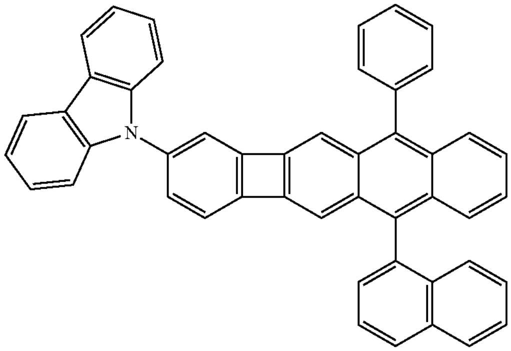
[Formula 98]
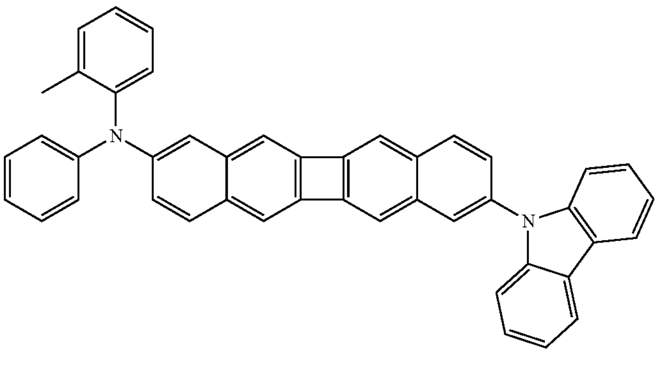

-continued
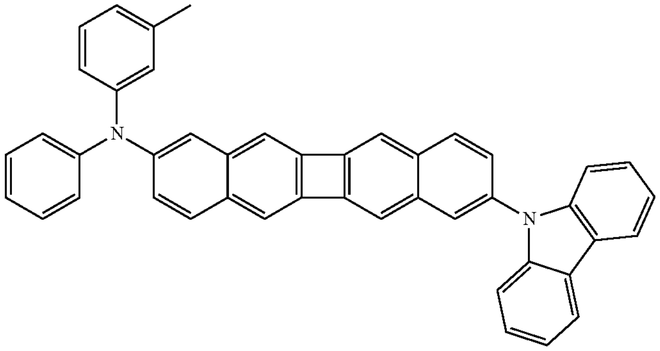
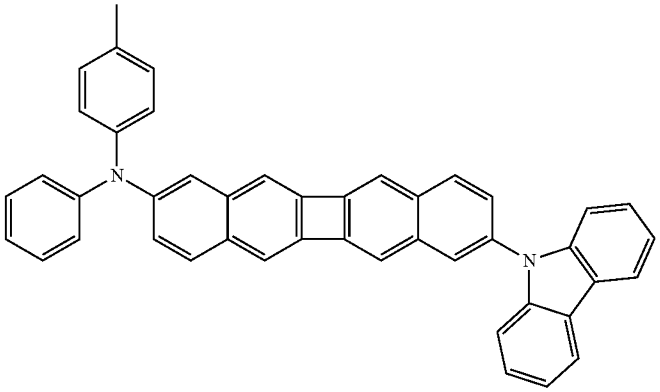
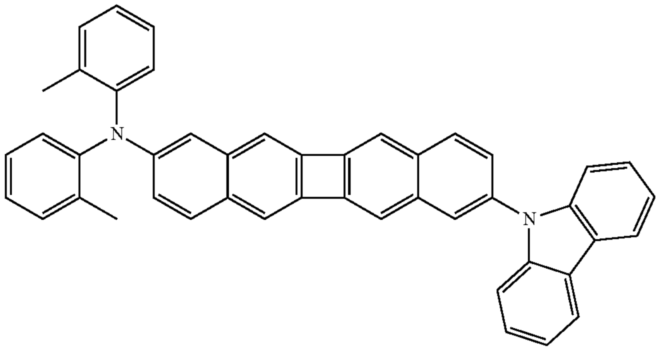
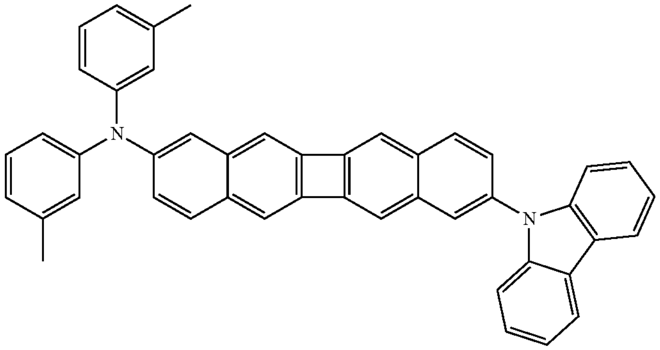

-continued
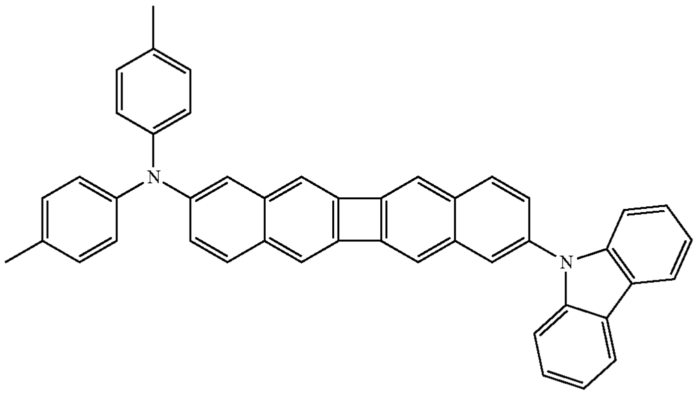
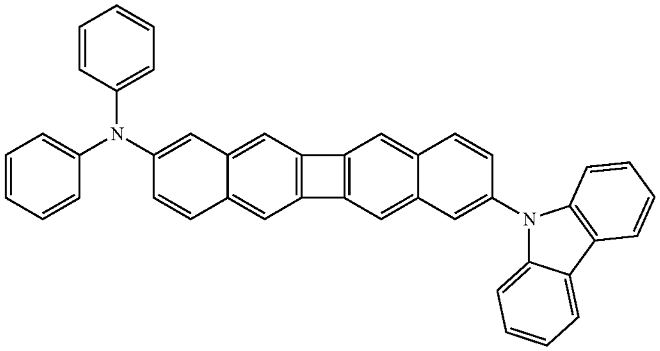
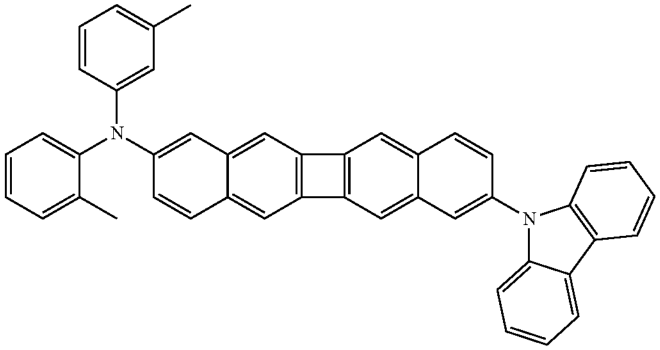
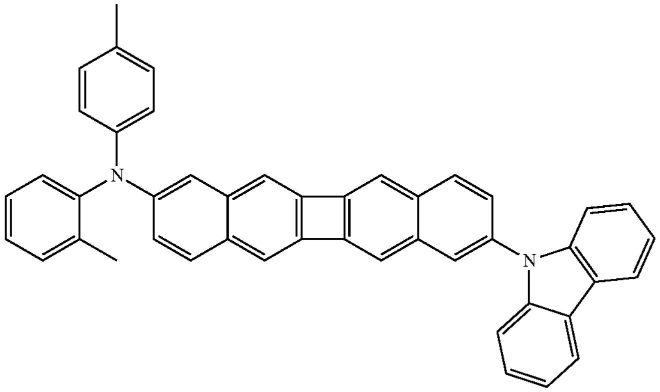

-continued
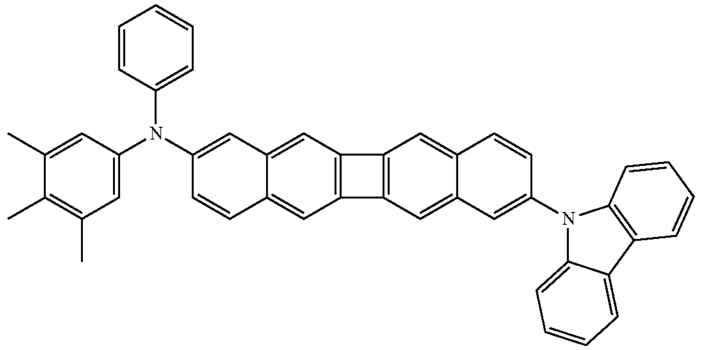
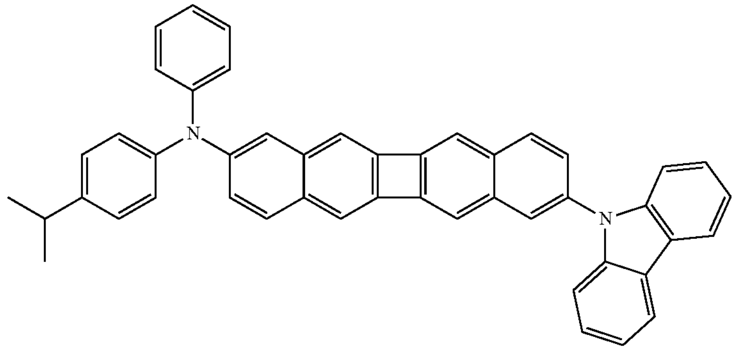
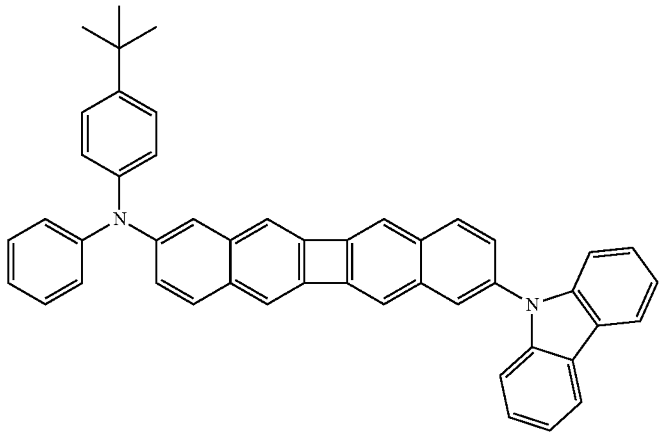
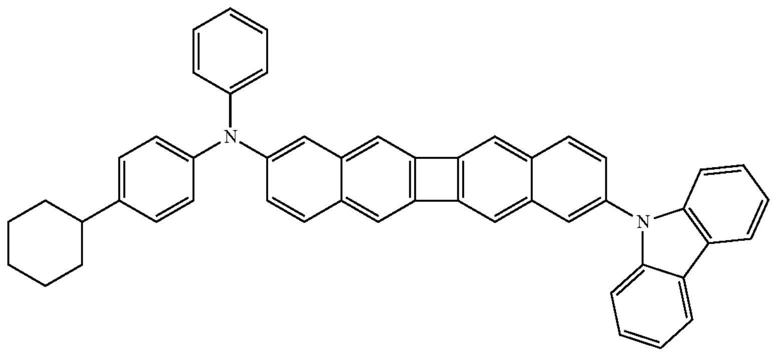

-continued
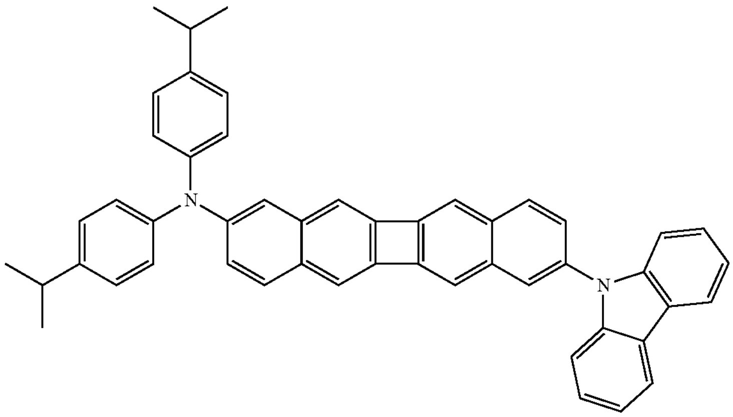
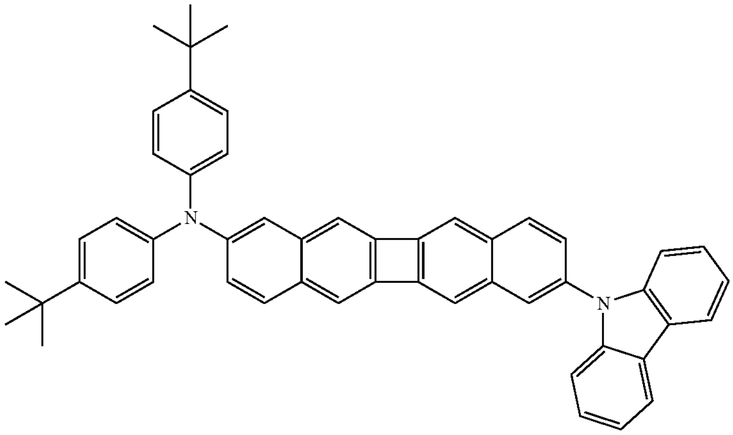
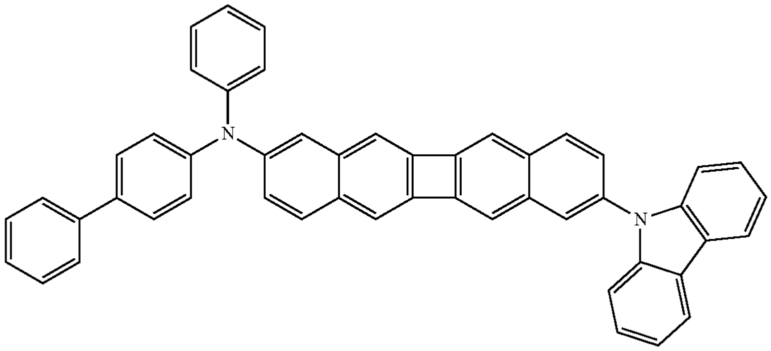
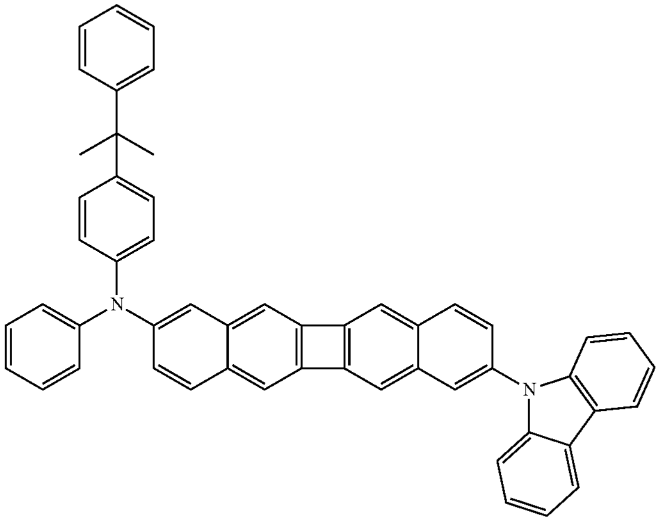

-continued
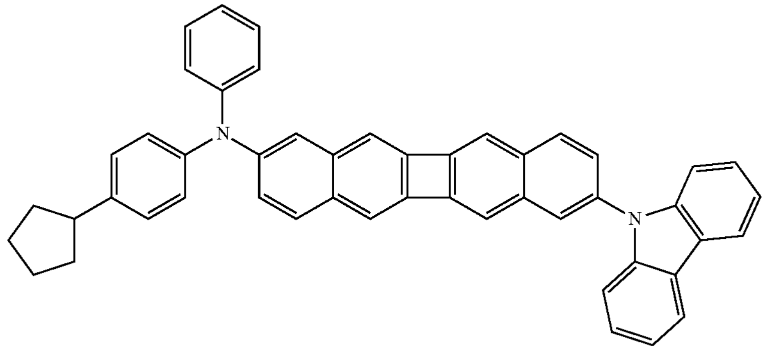
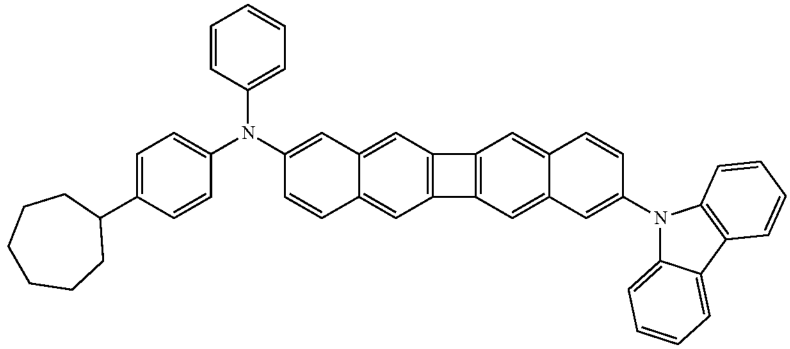
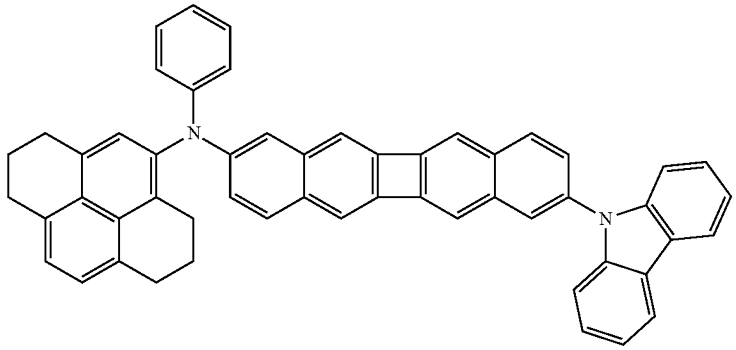
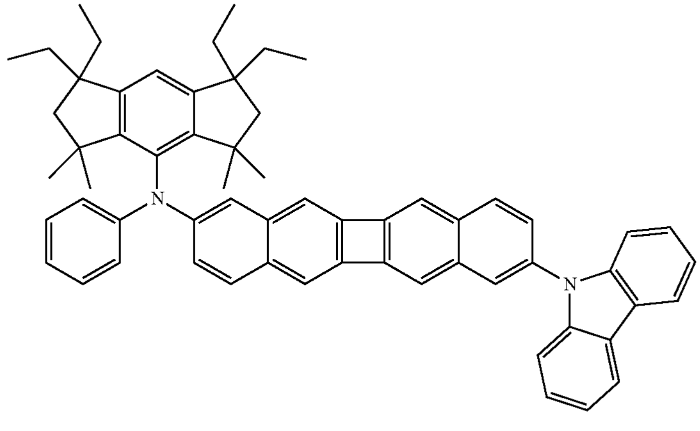

-continued
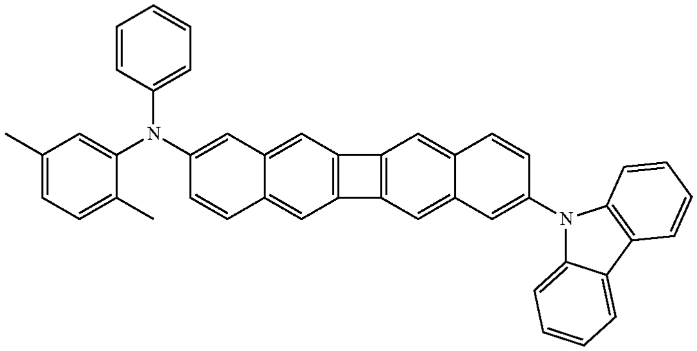
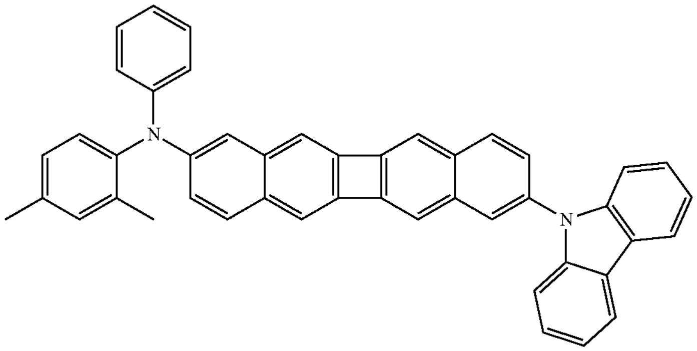
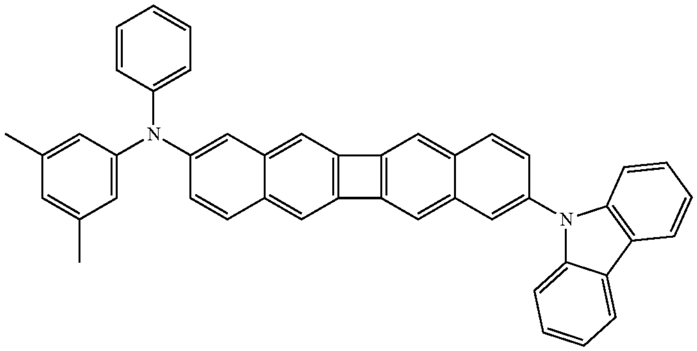
[Formula 99]
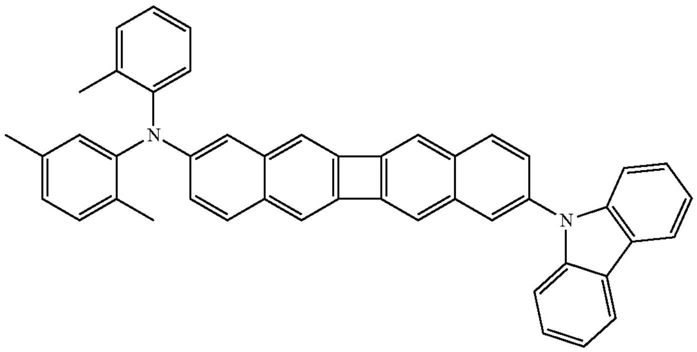

-continued
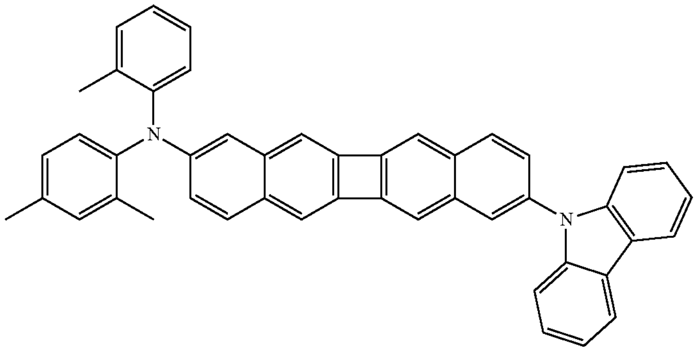
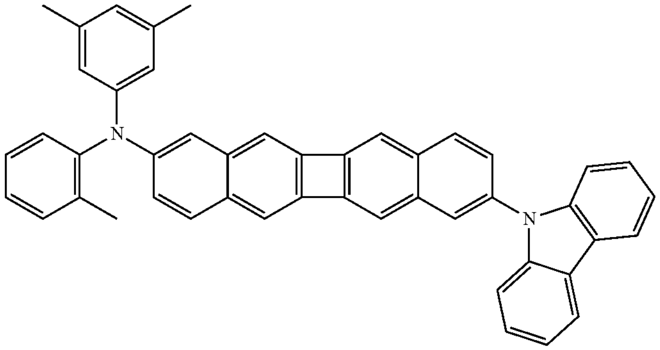
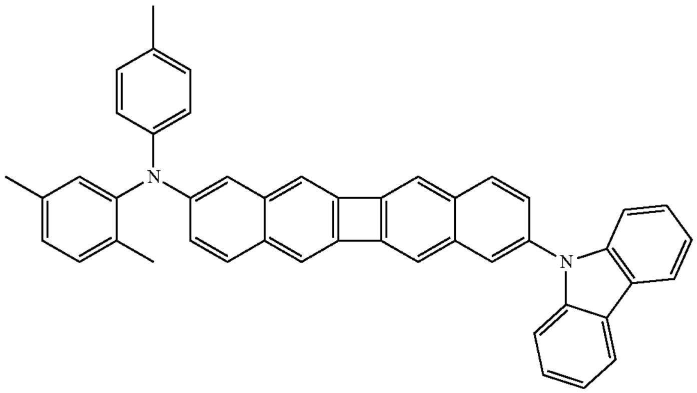
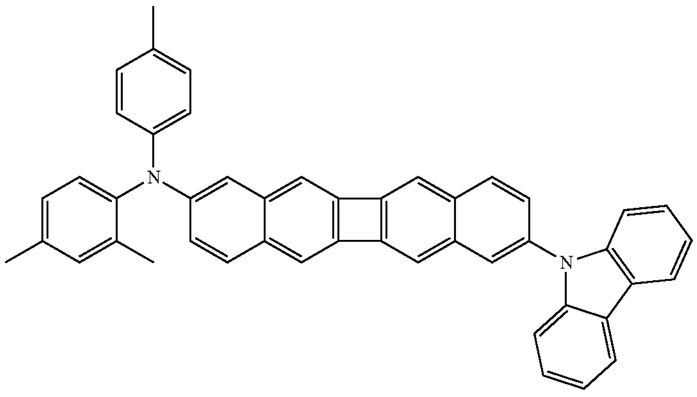

-continued
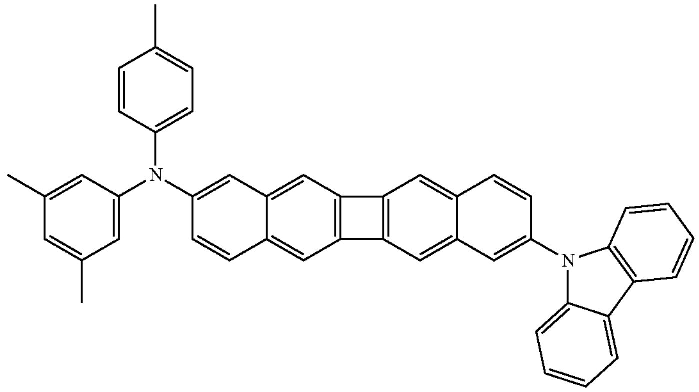
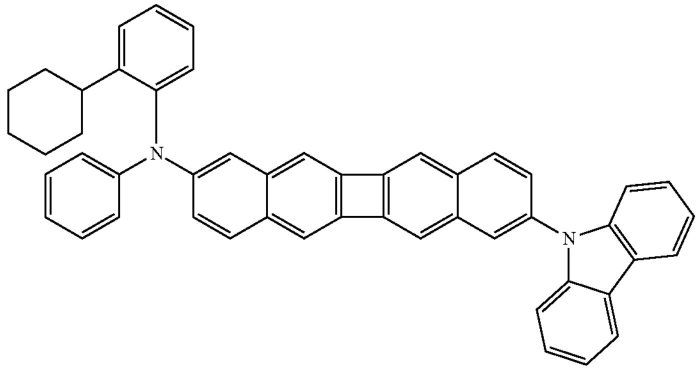
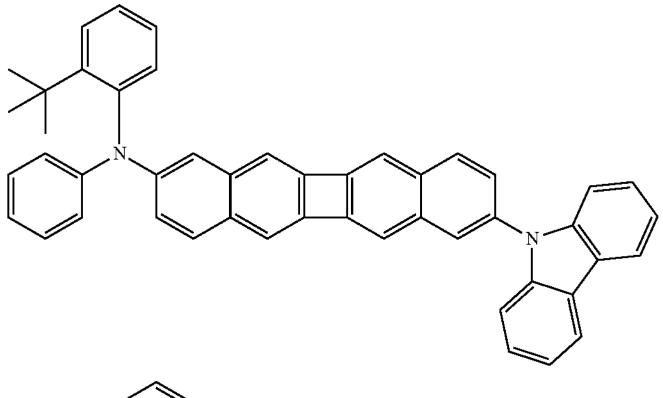
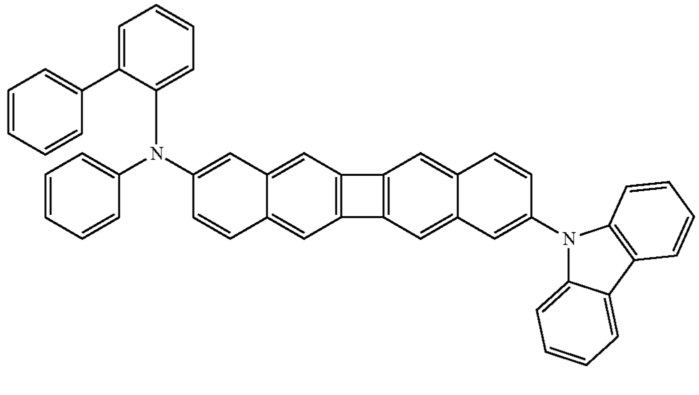

-continued
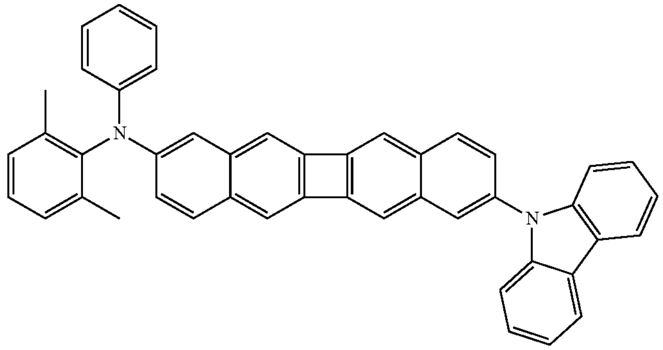
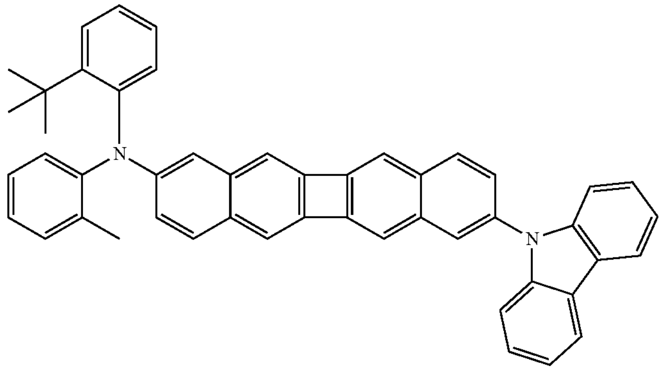
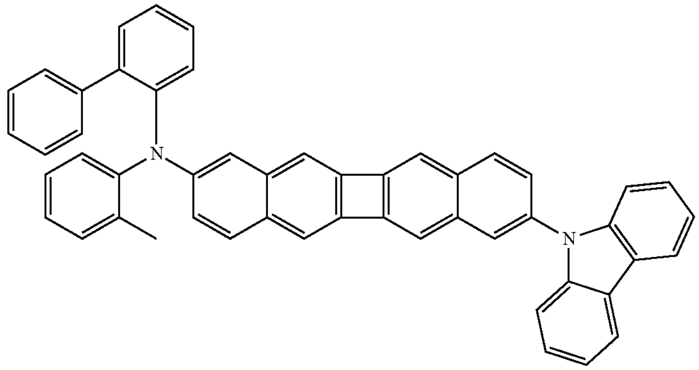
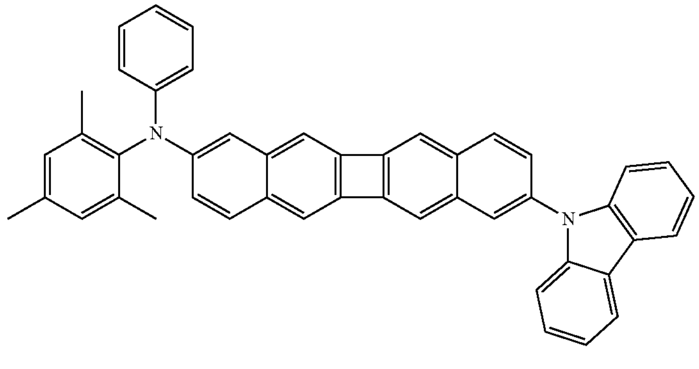

-continued
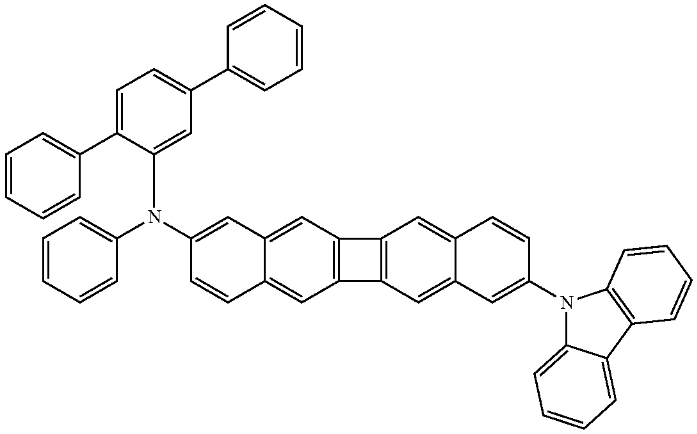
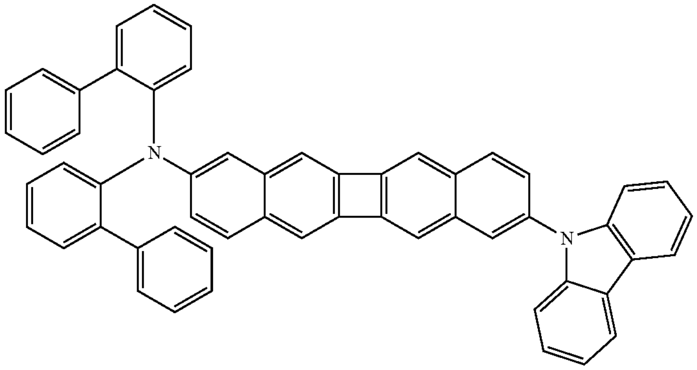
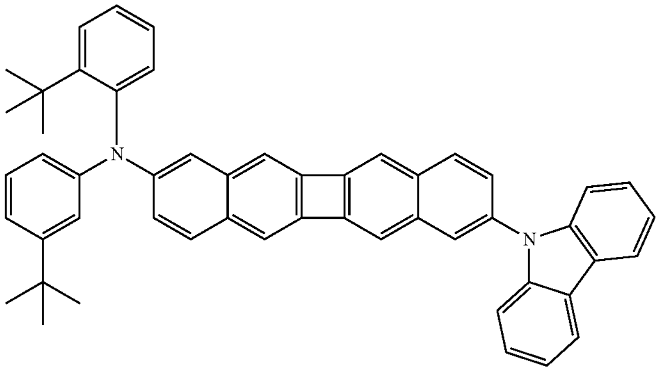
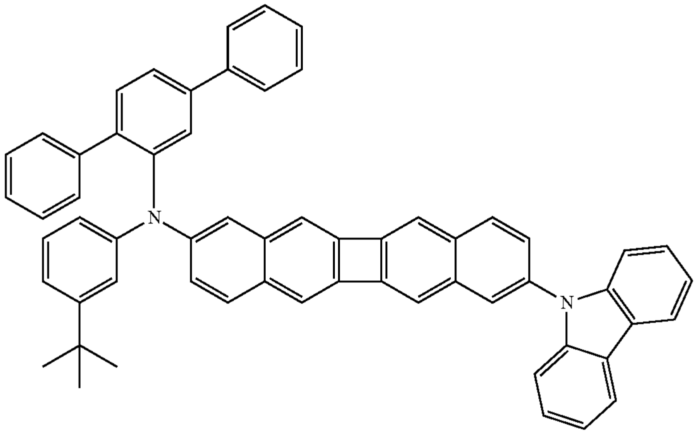

-continued
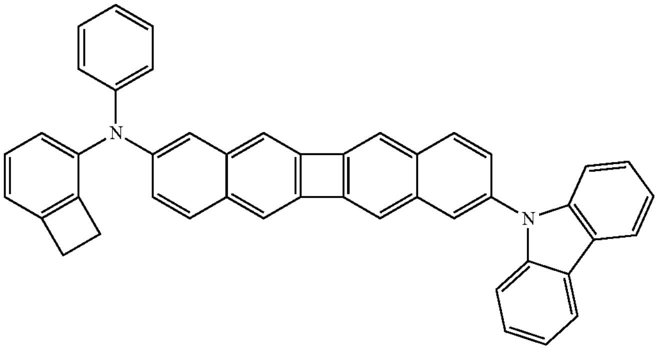
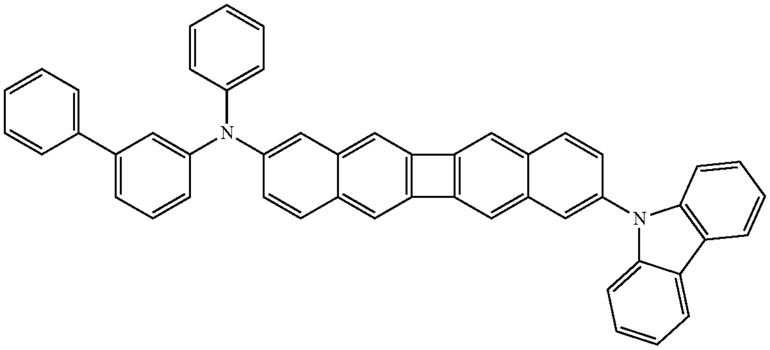
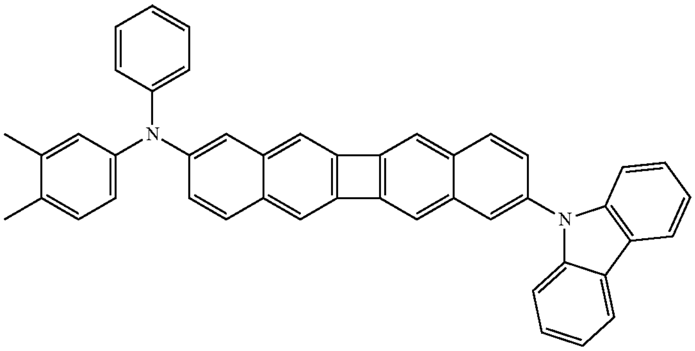
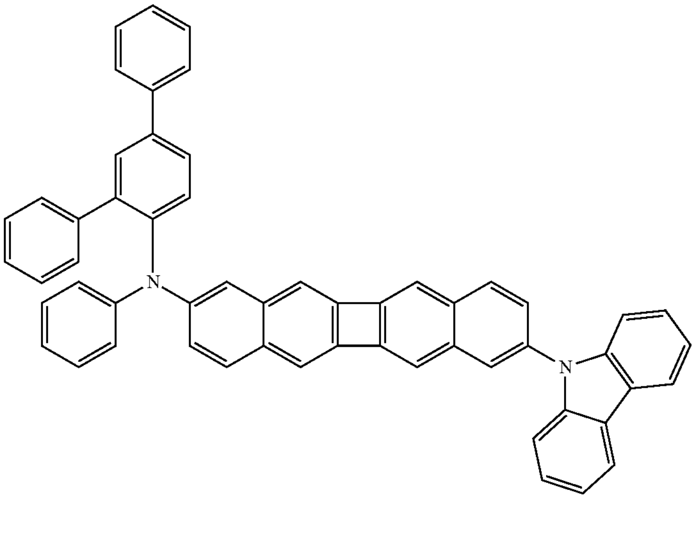

-continued
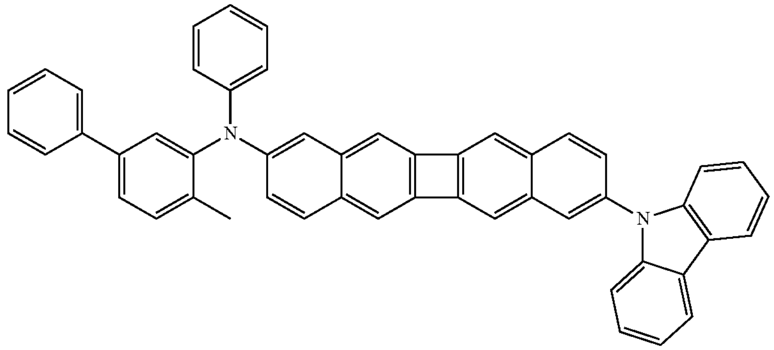
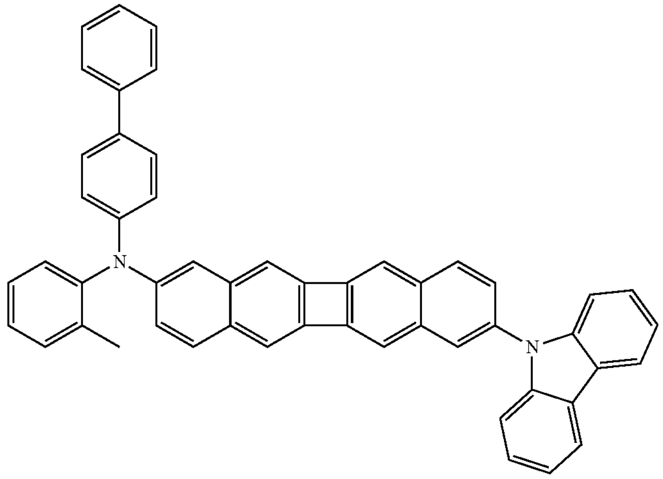
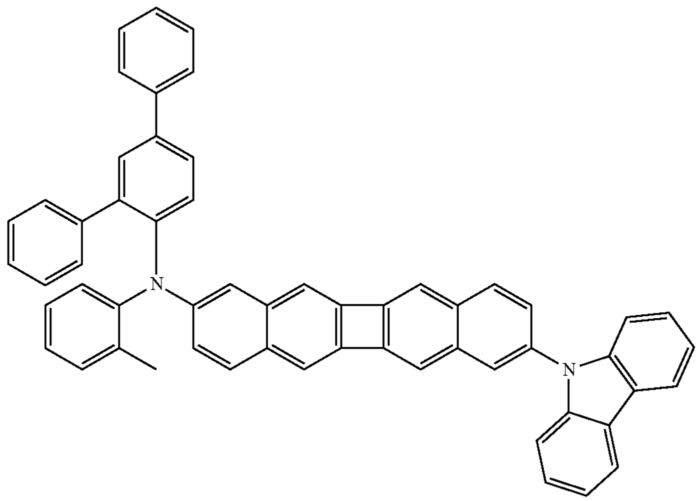
[Formula 100]
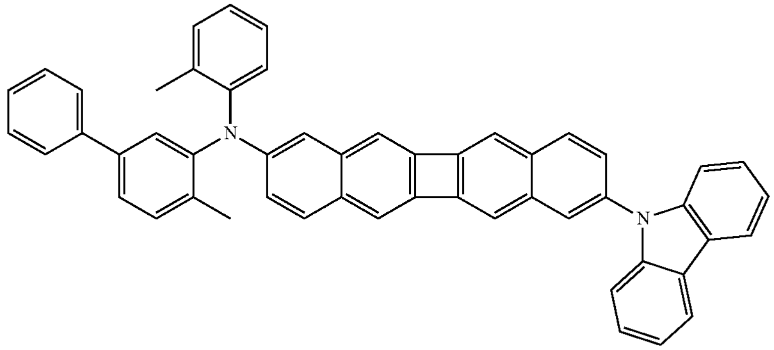

-continued
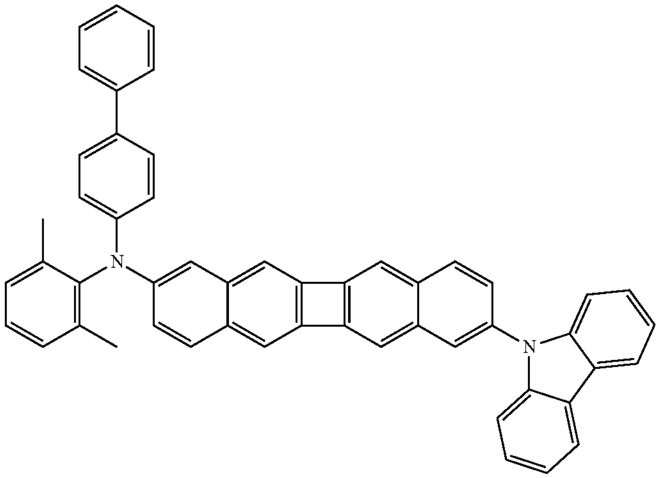
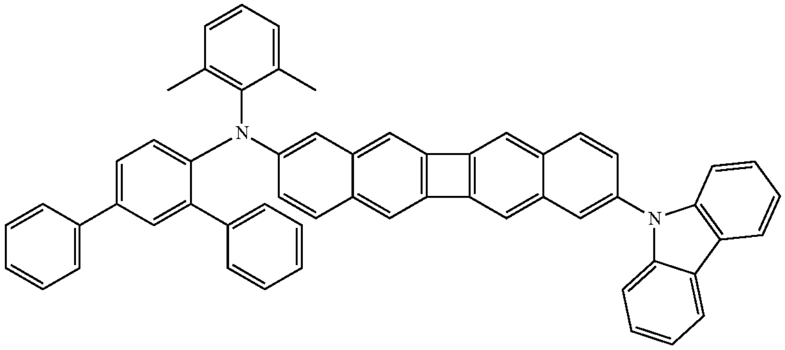
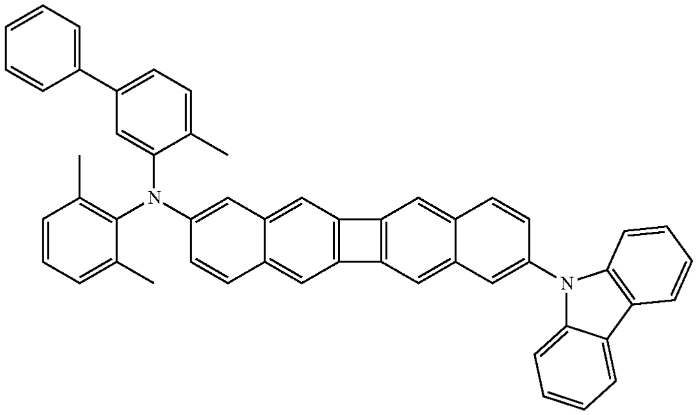
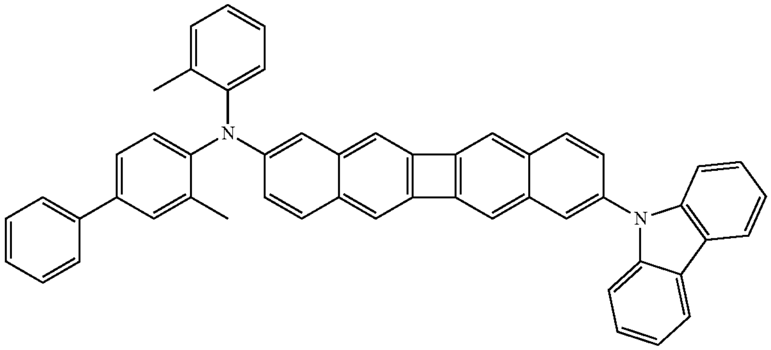

-continued
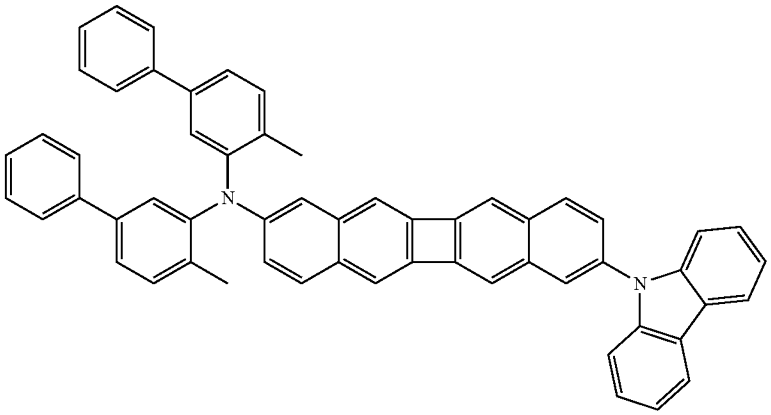
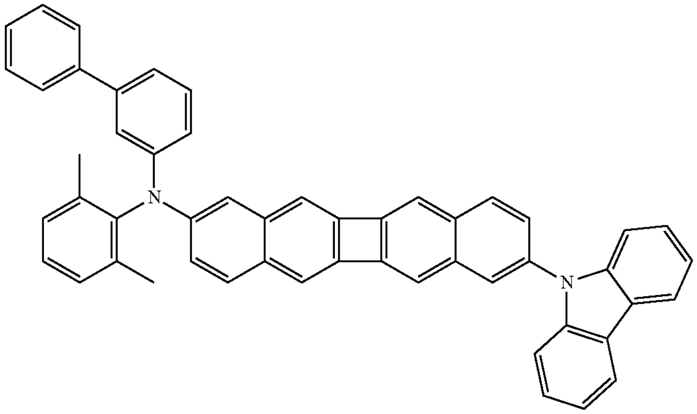
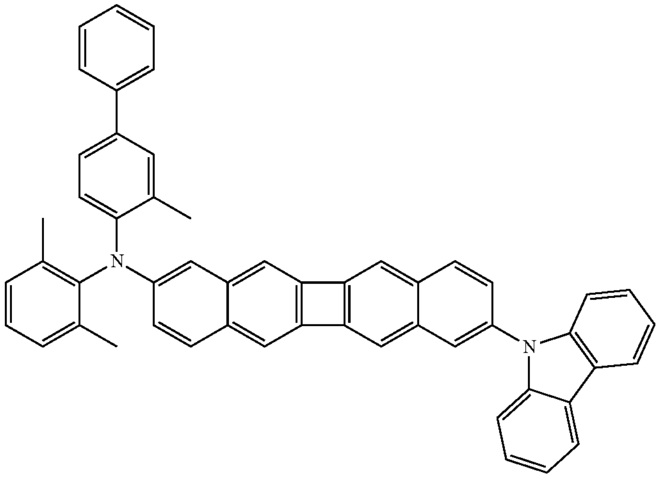
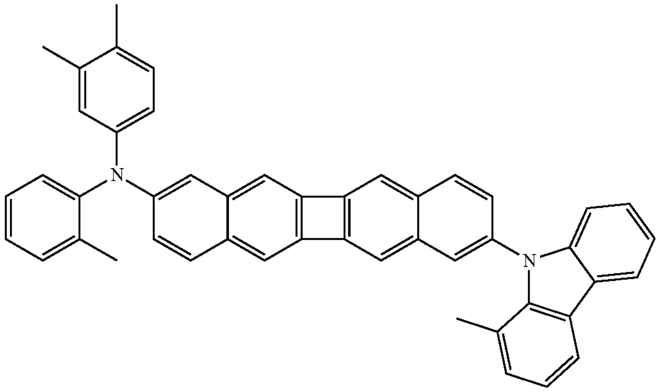

-continued
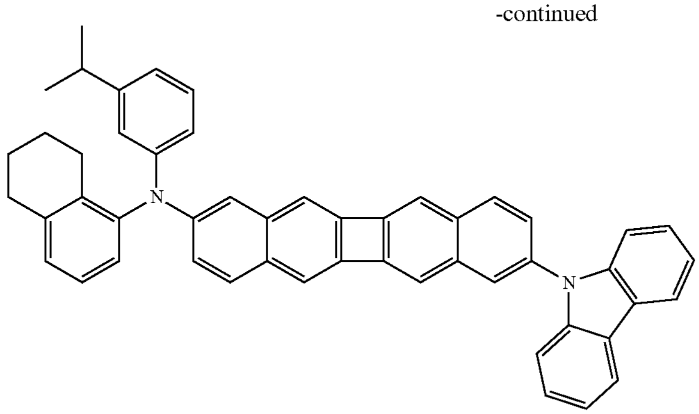
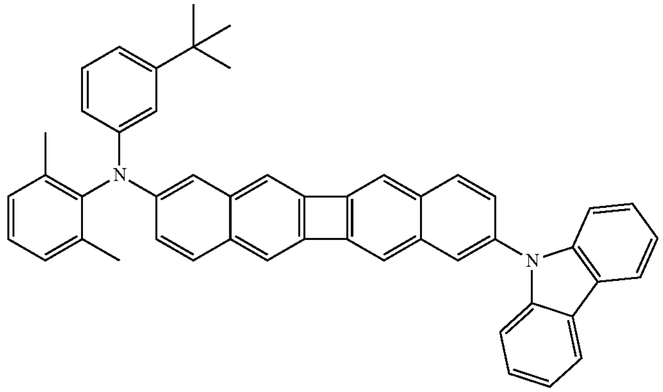
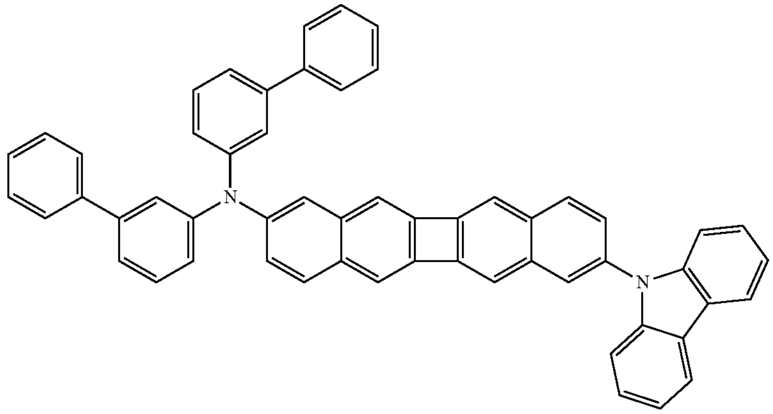
[Formula 101]
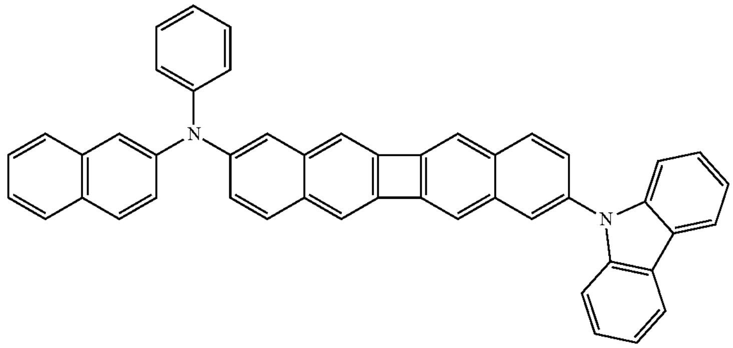

-continued
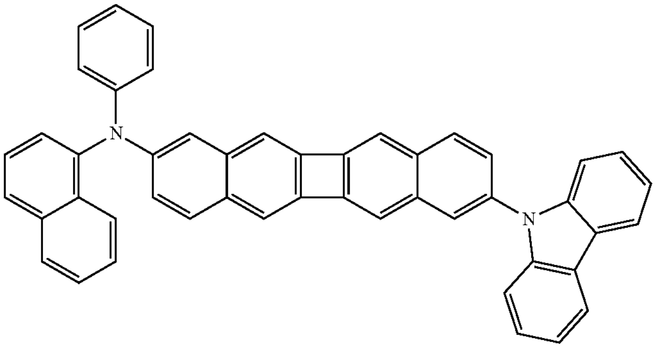
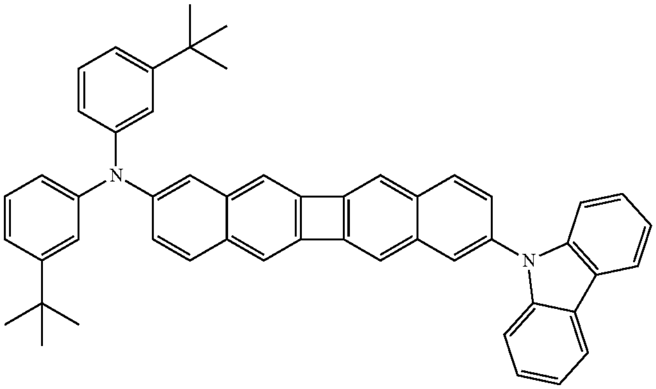
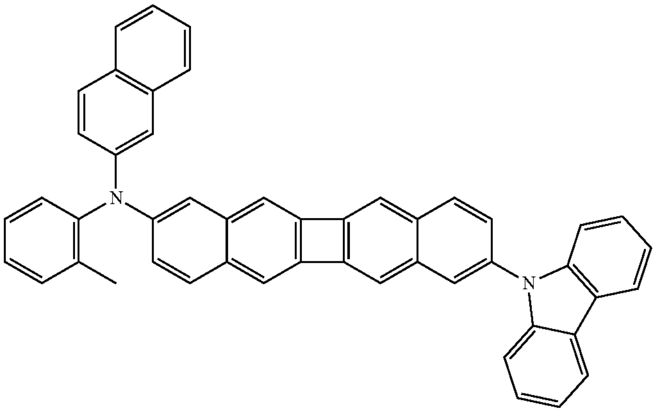
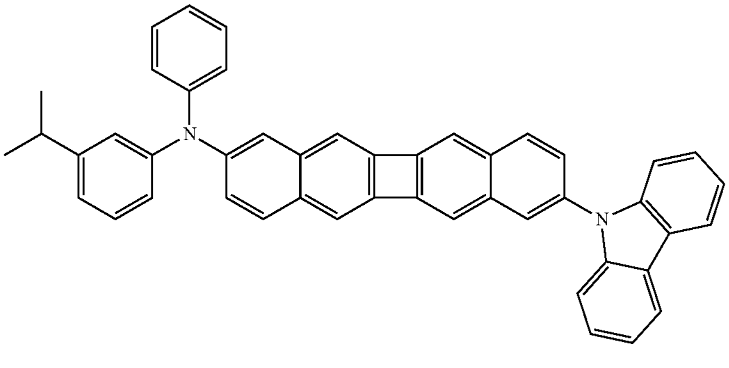

-continued
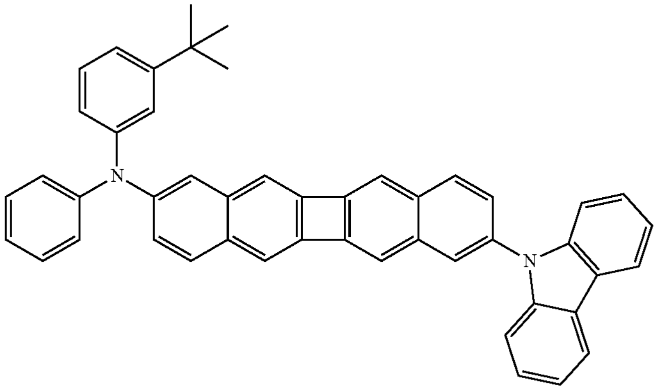
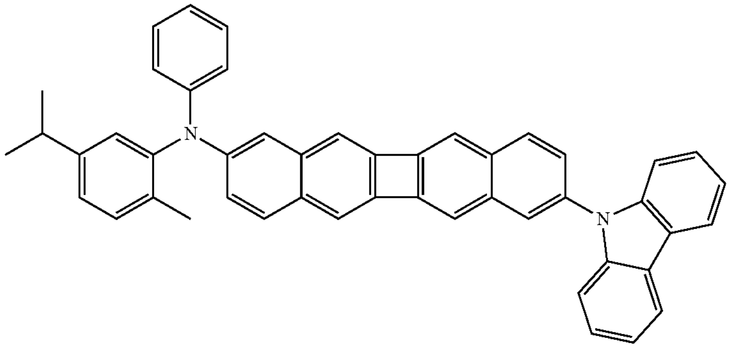
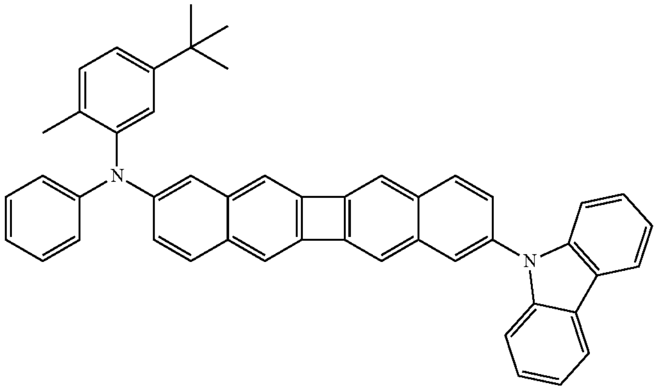
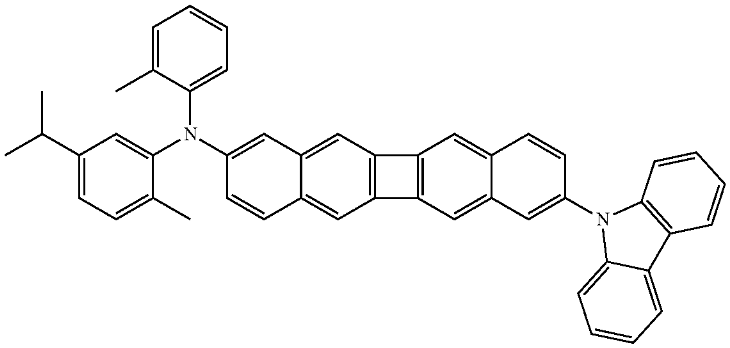

-continued
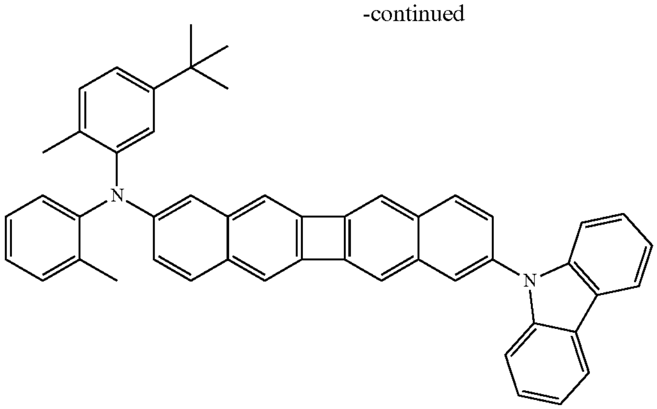
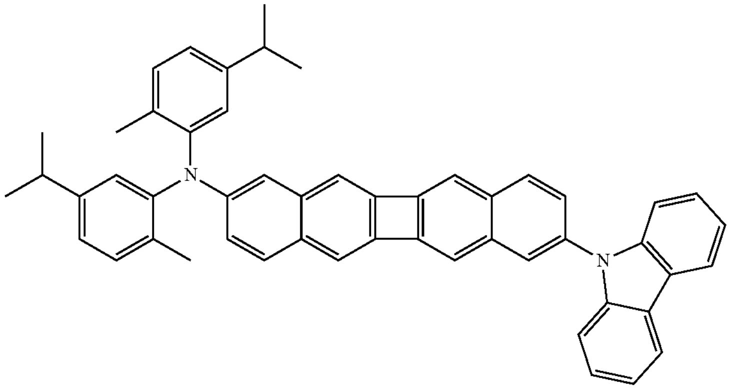
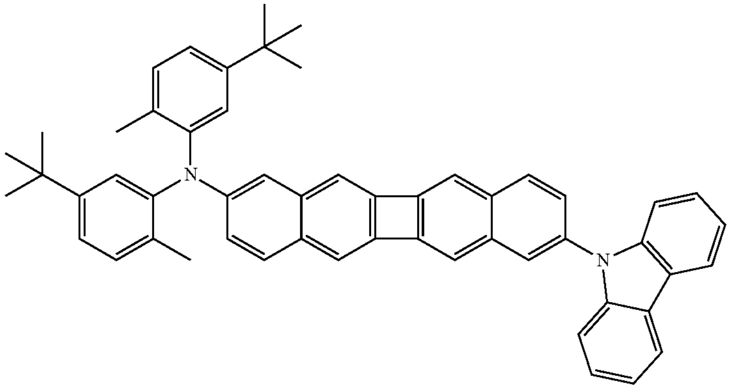
[Formula 102]
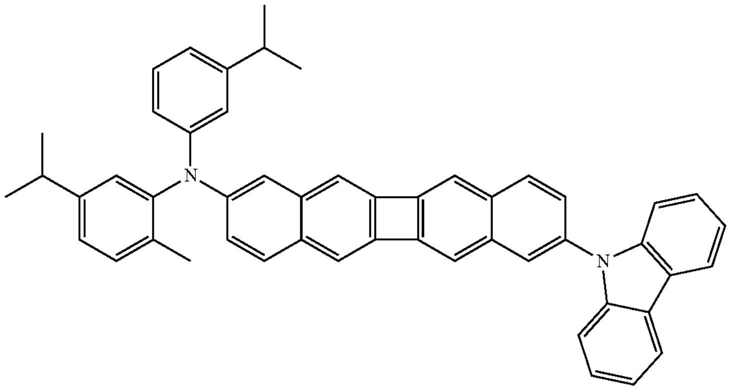

-continued
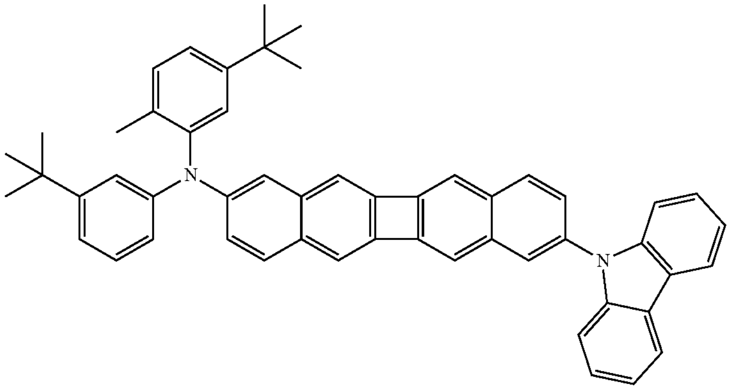
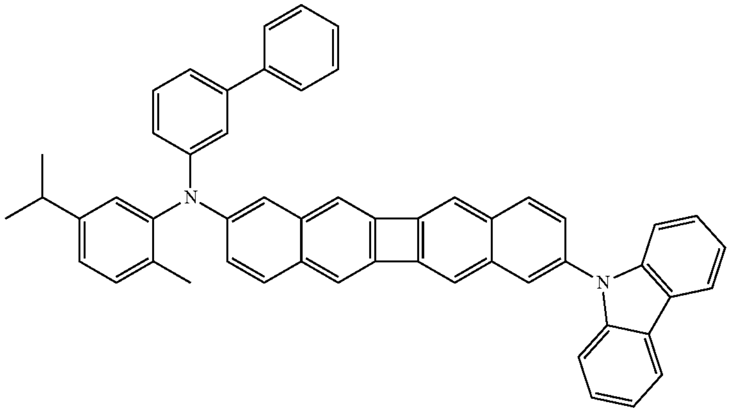
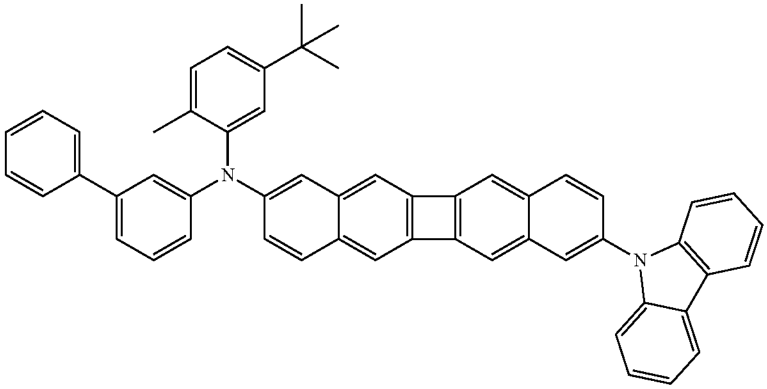
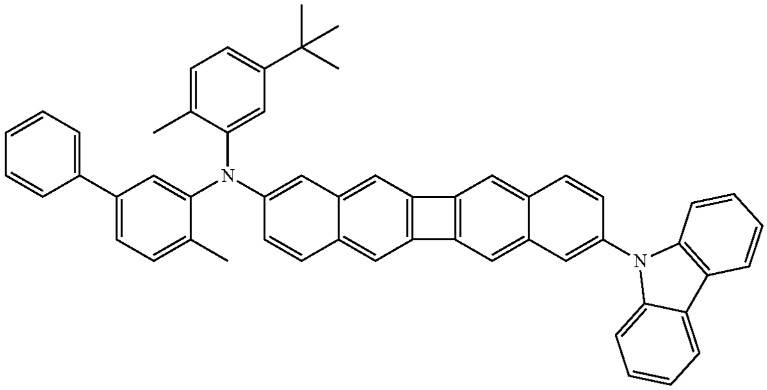

-continued
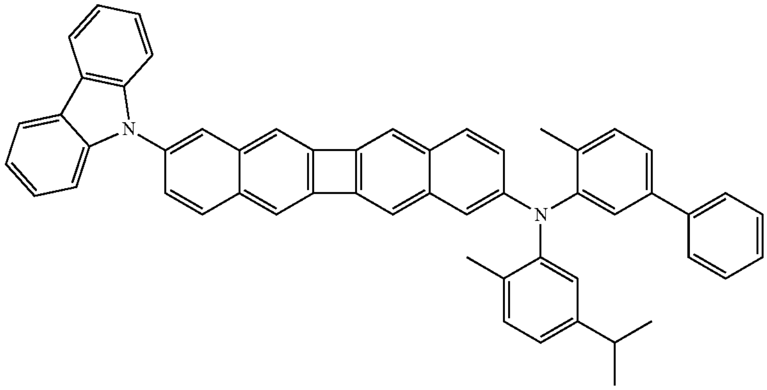
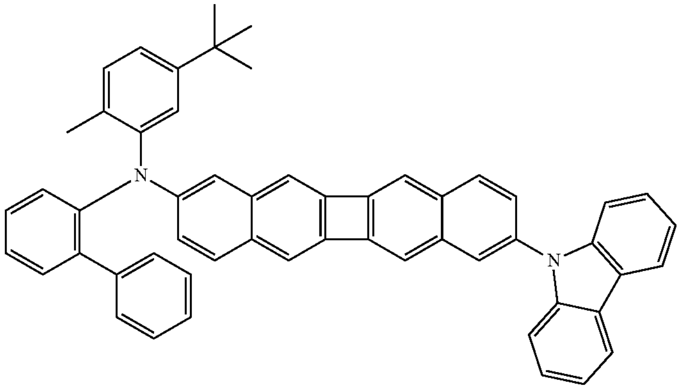
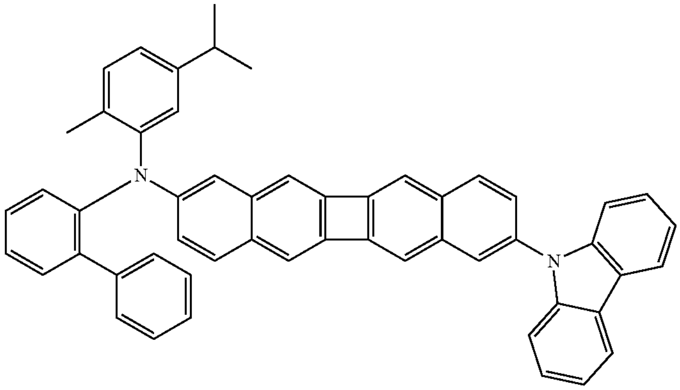
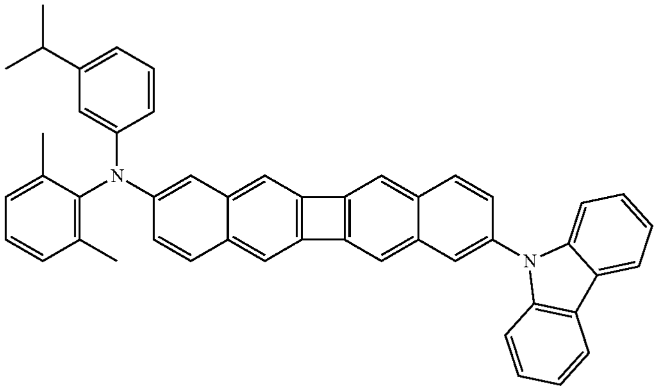

-continued
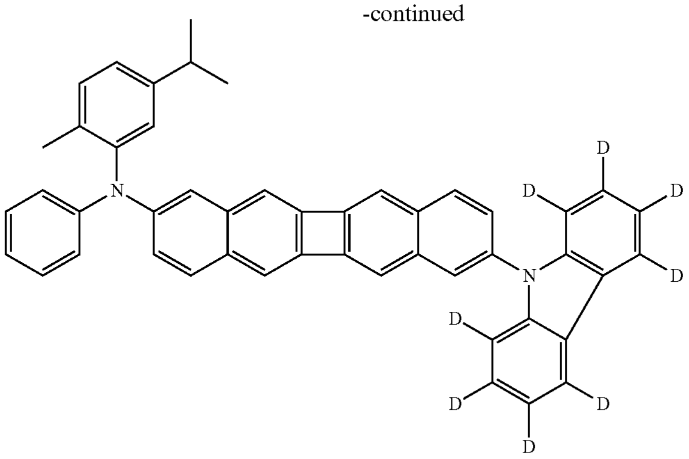
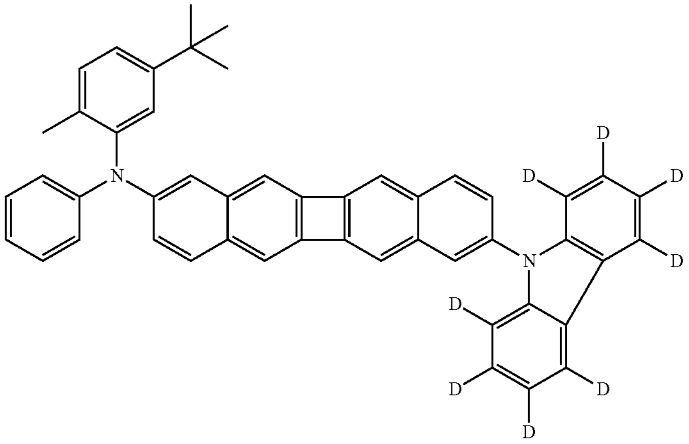
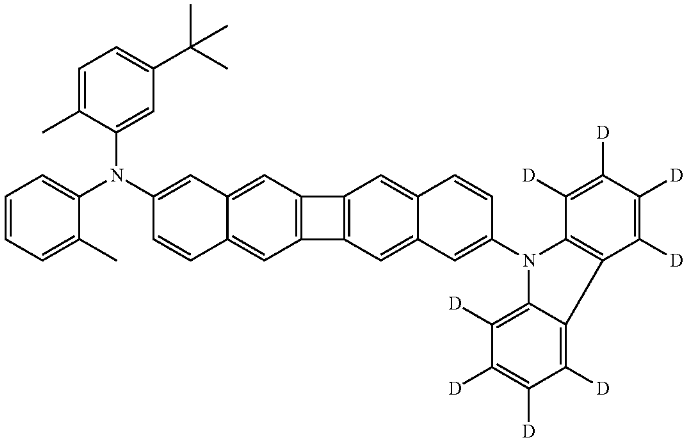
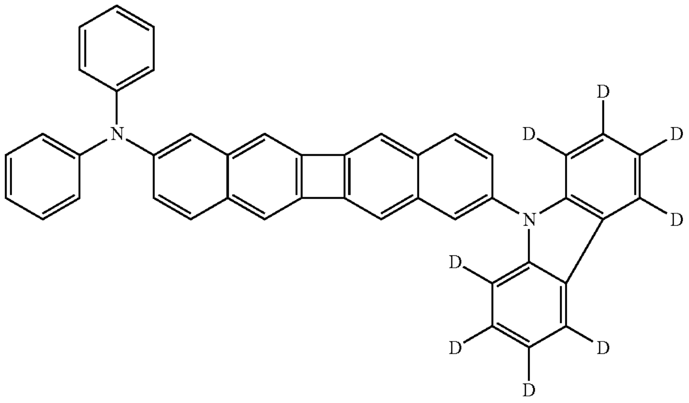

-continued
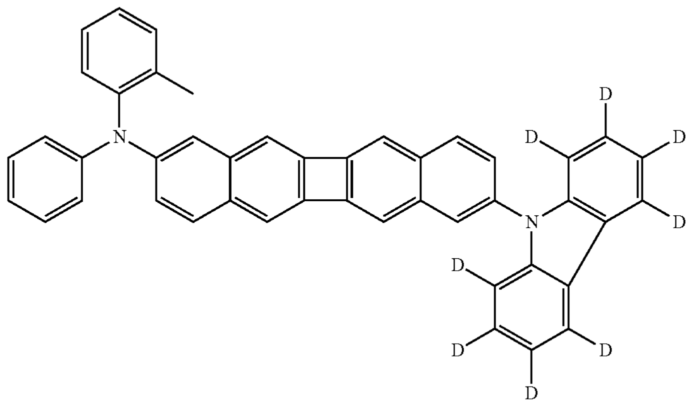
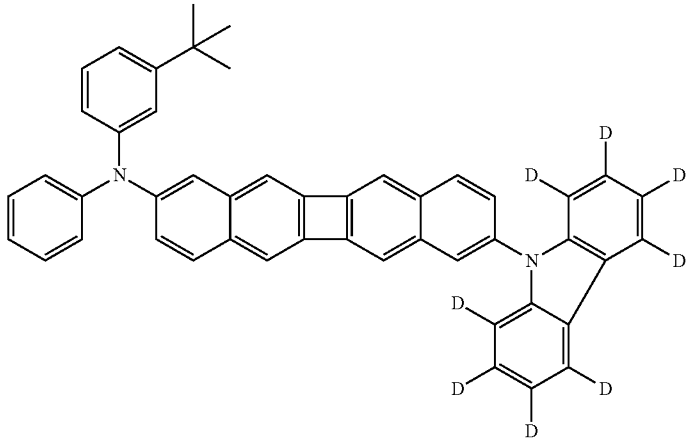
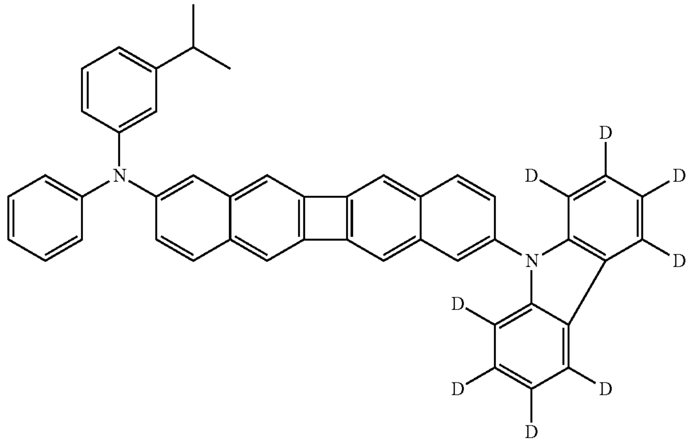

-continued
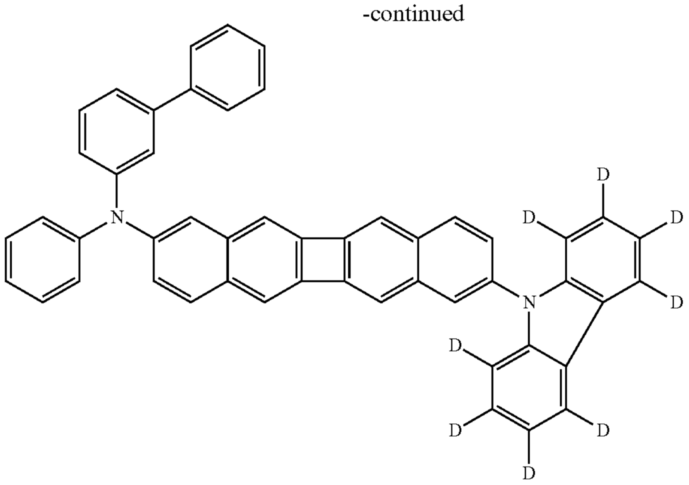
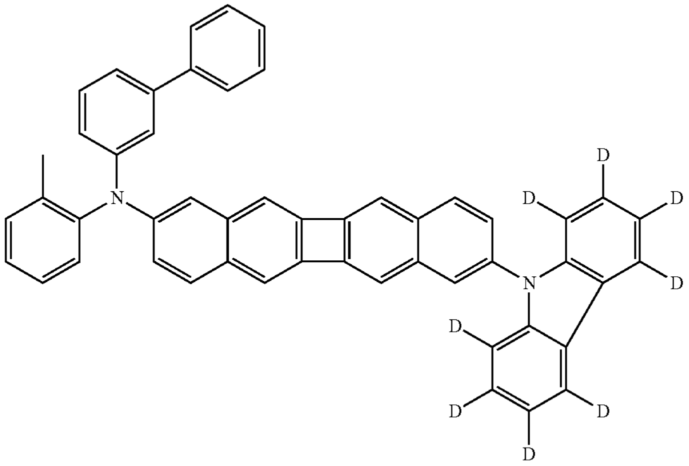
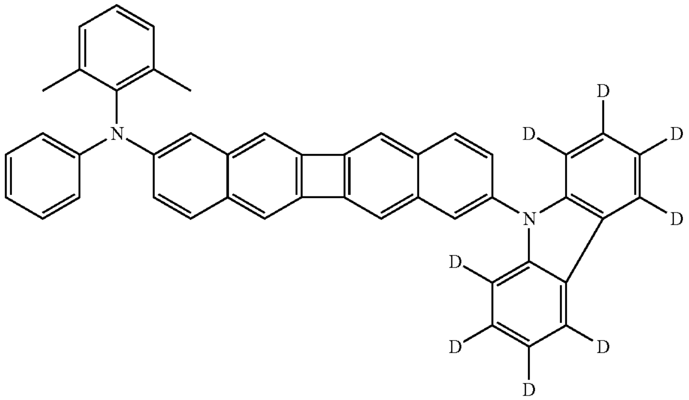
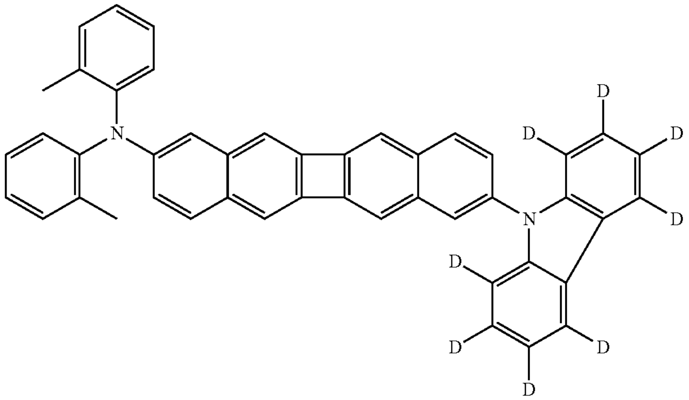

-continued
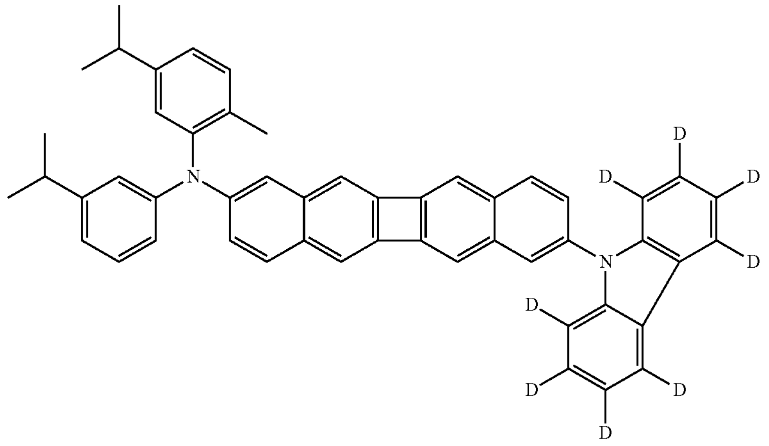
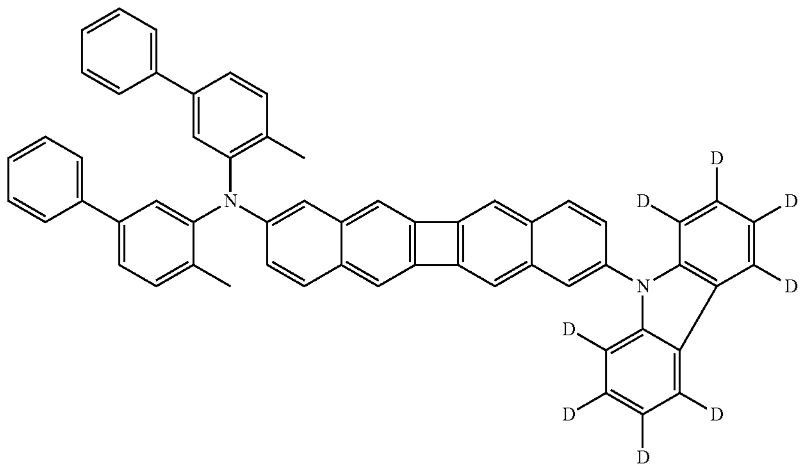
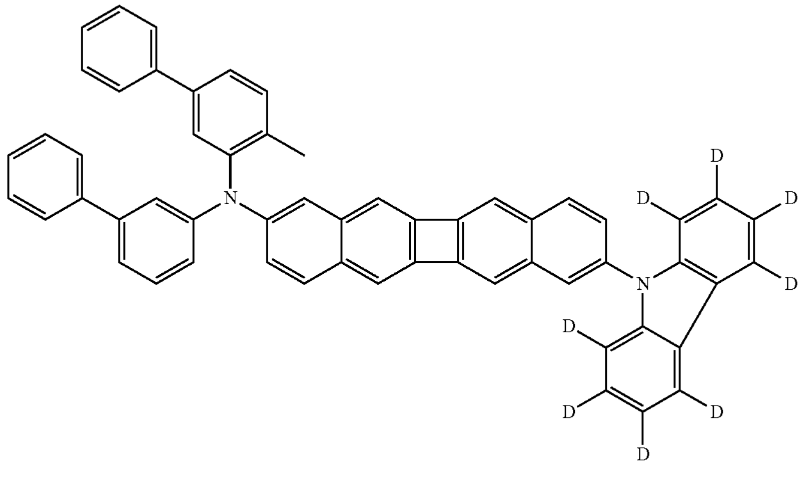

-continued
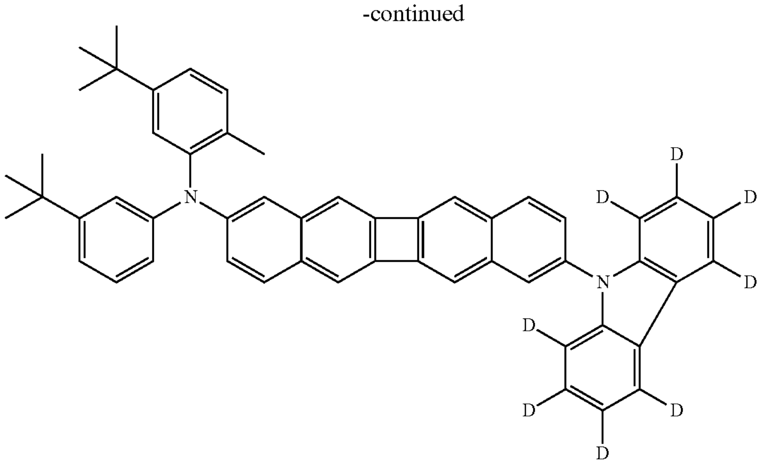
[Formula 103]
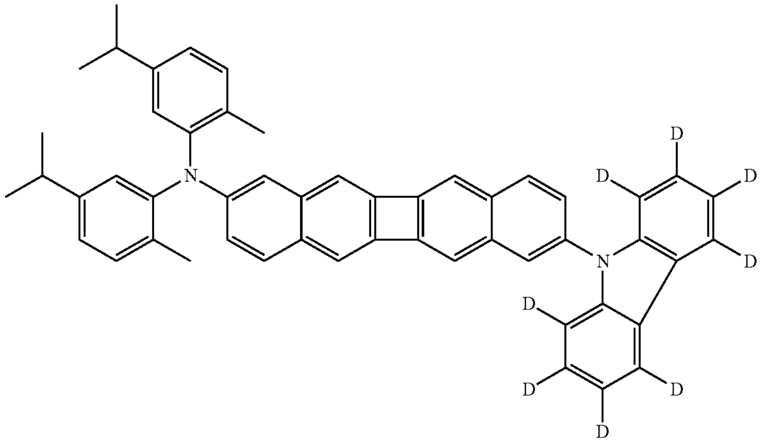
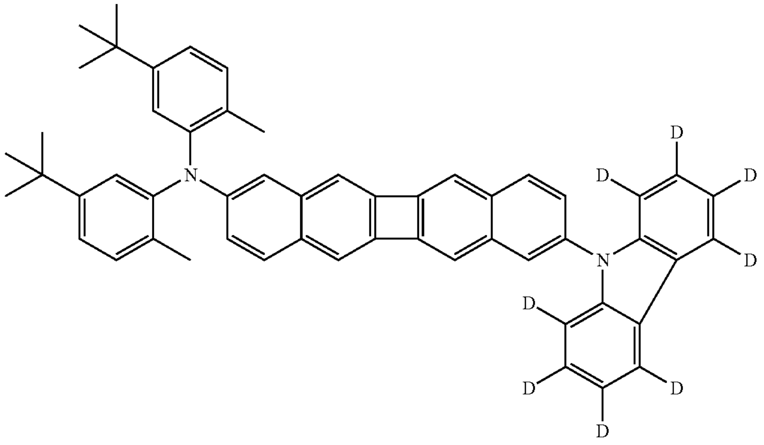

-continued
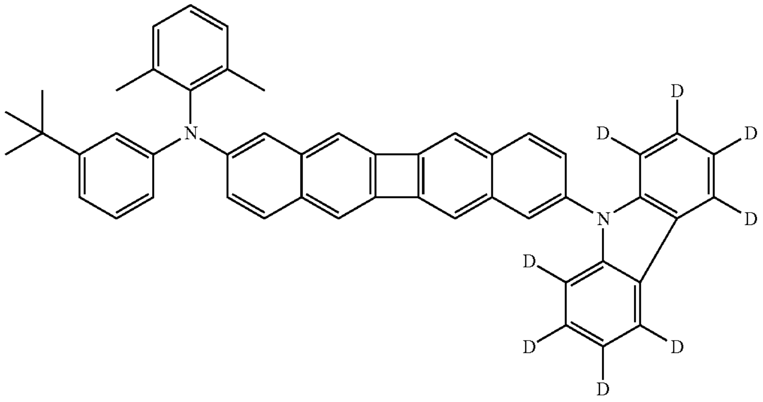
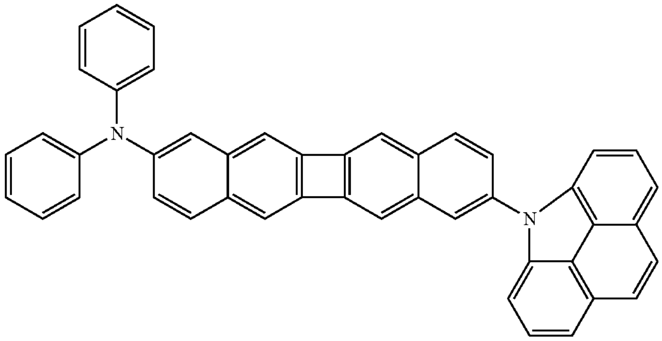
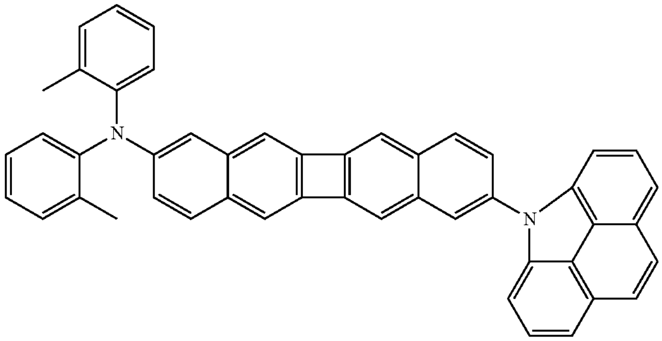
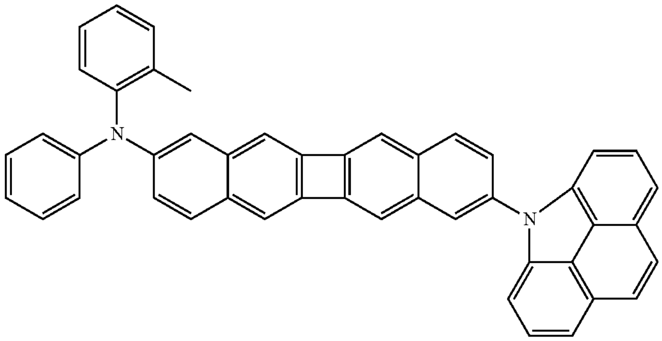

-continued
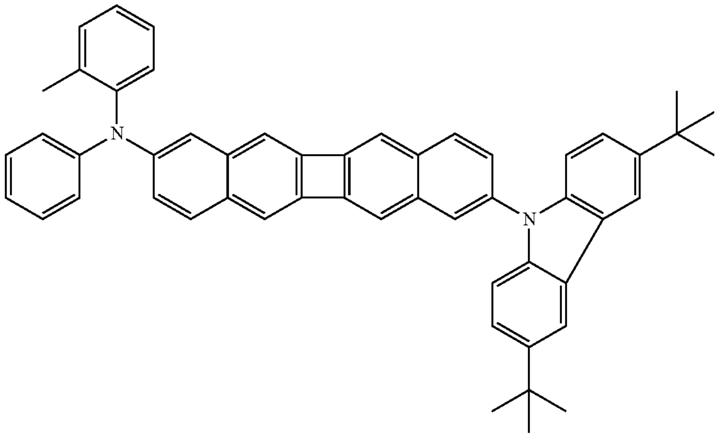
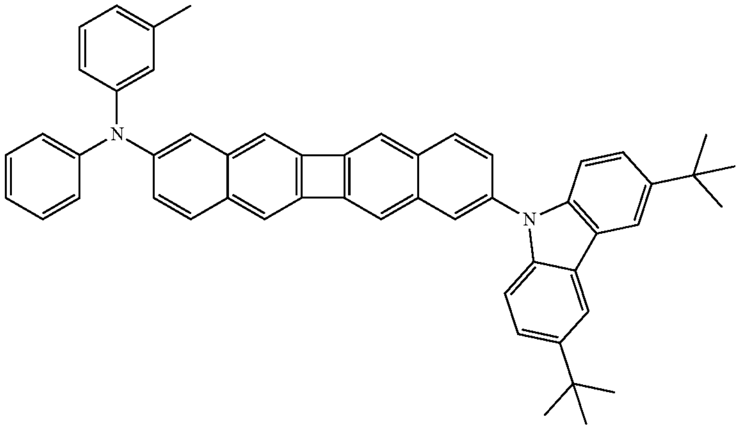
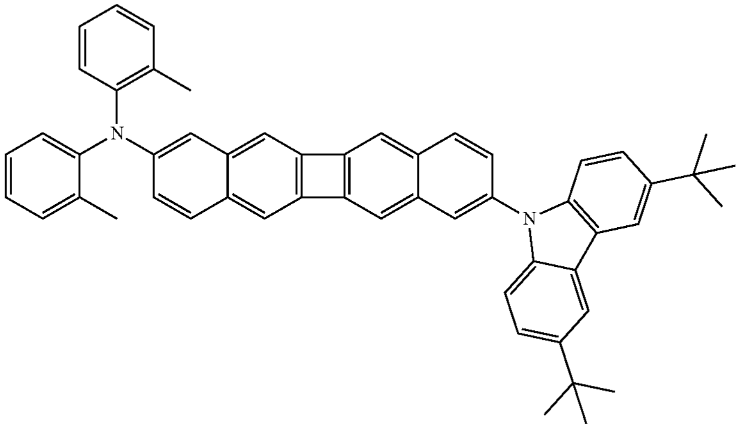

-continued
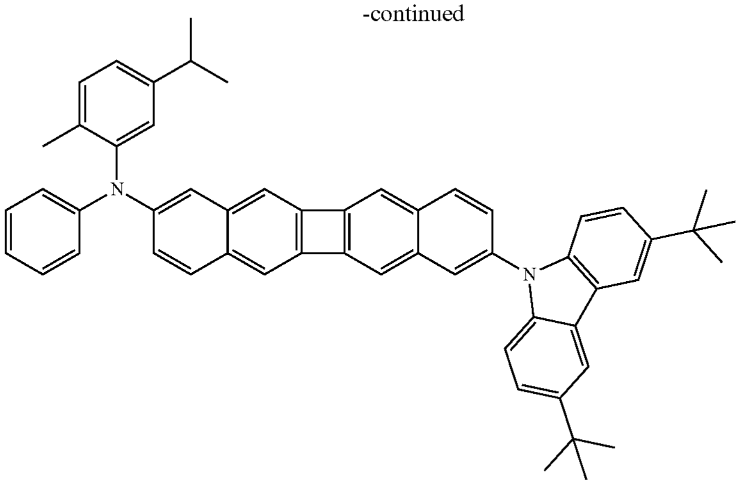
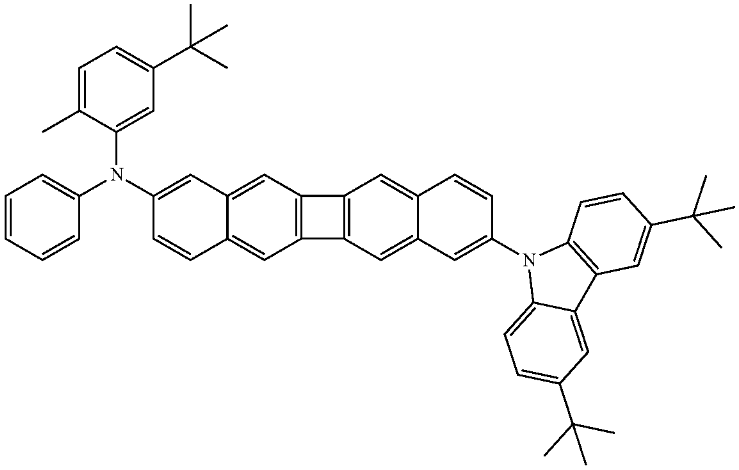
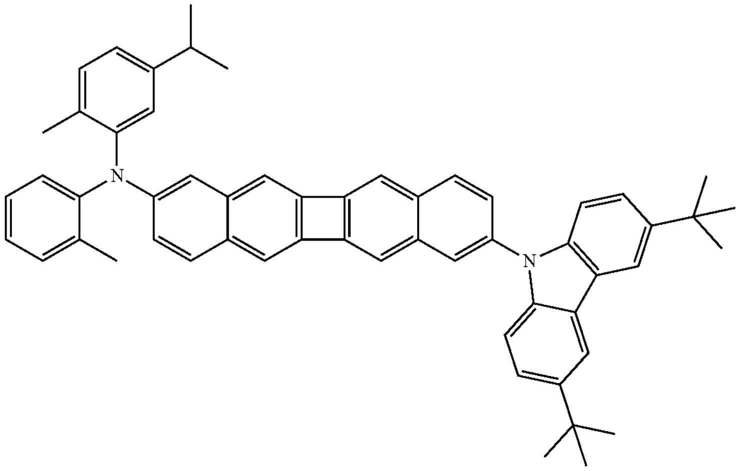

-continued
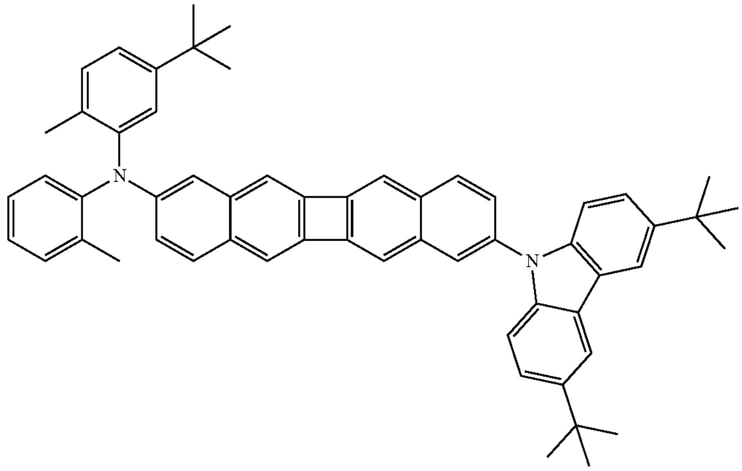
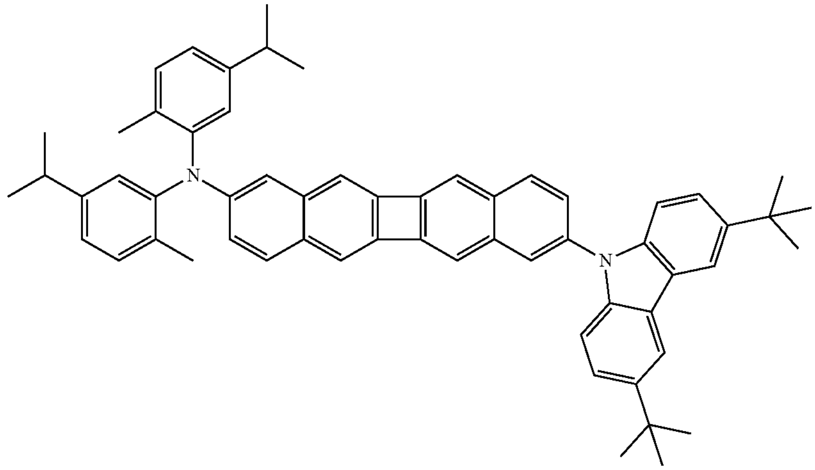
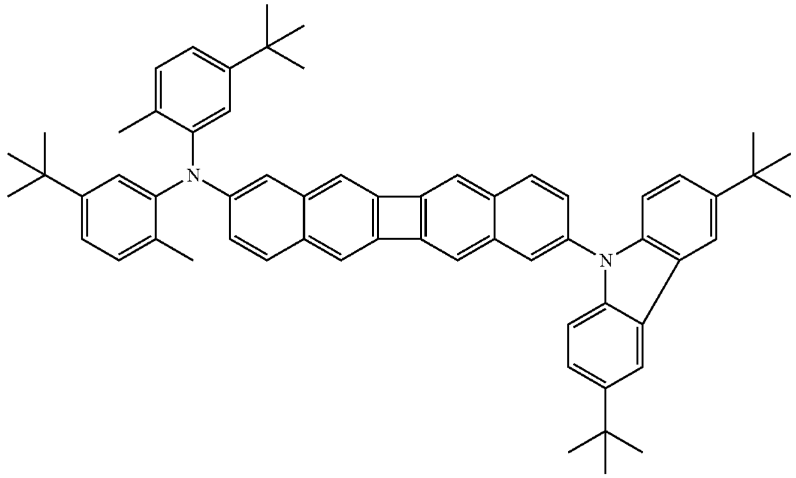

-continued
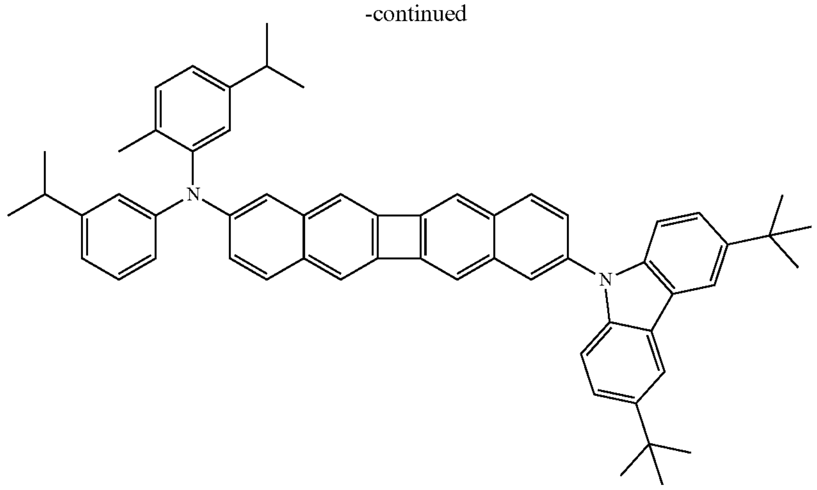
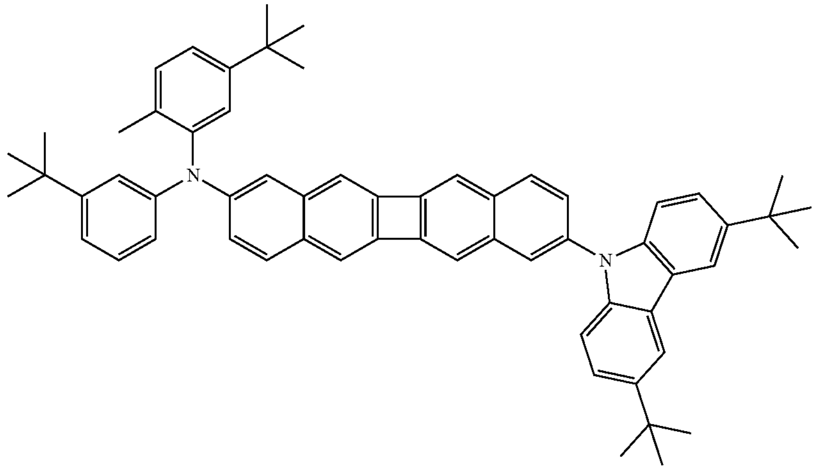
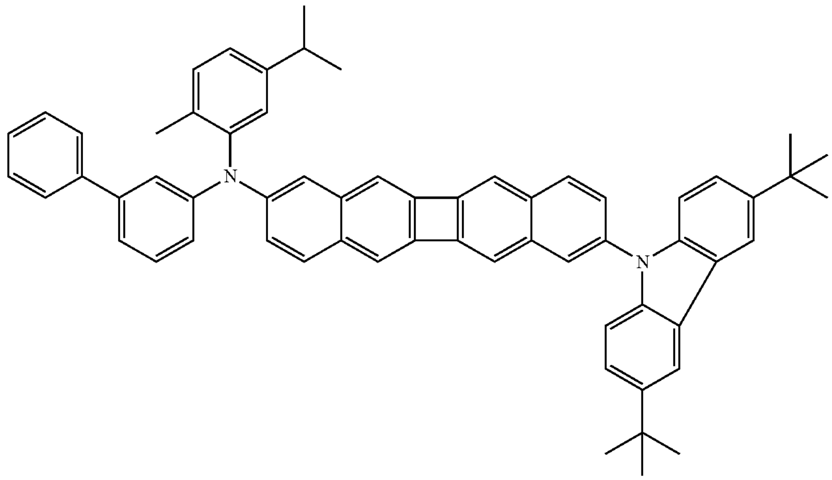

-continued
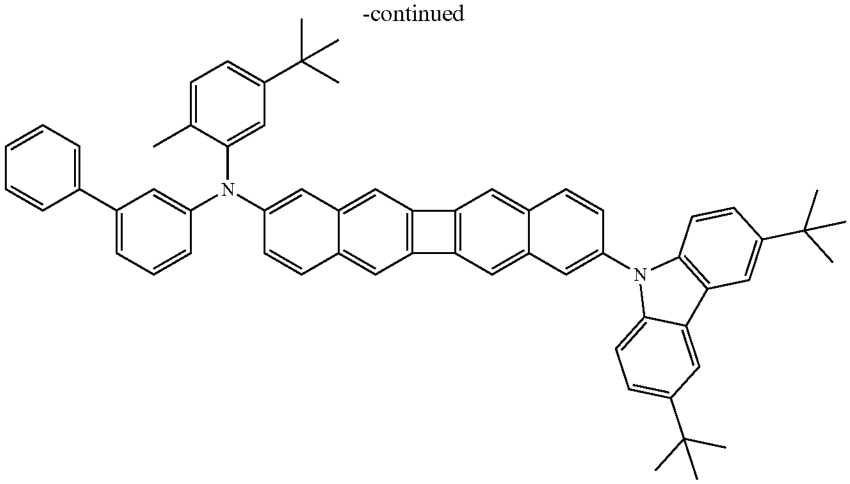
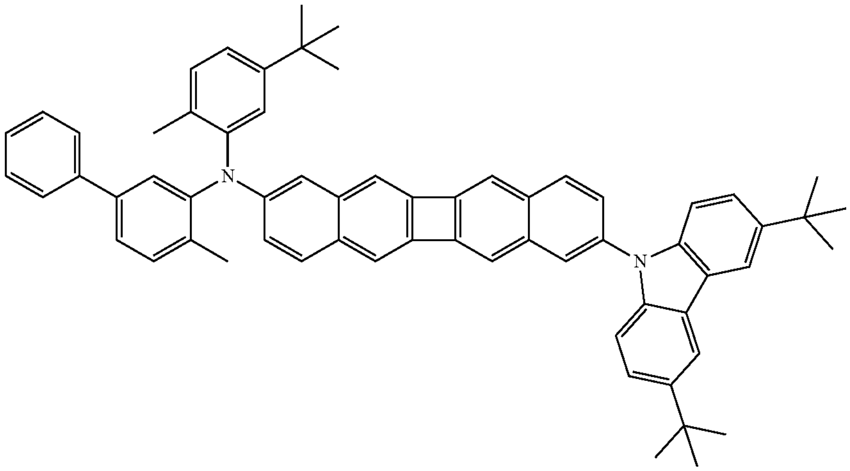
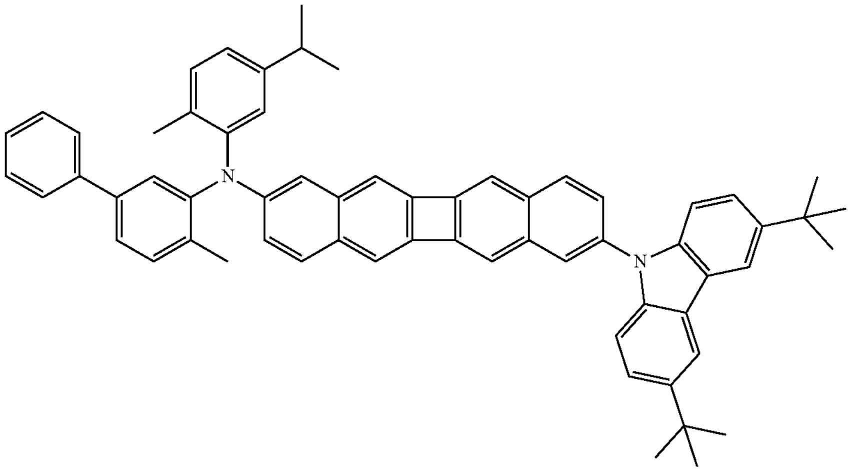

-continued
[Formula 104]
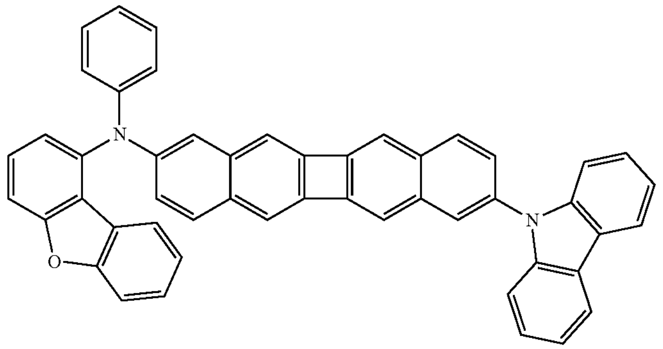
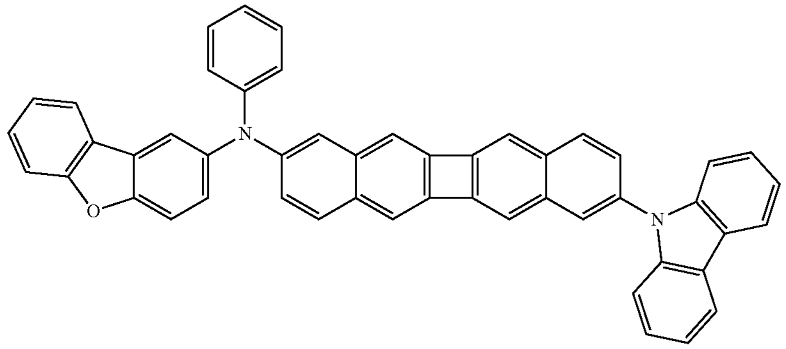
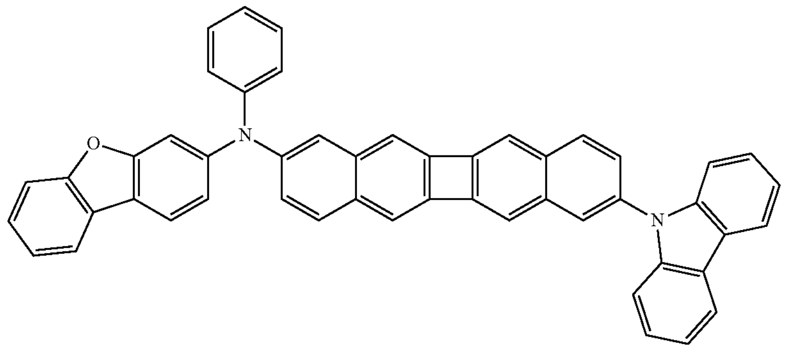
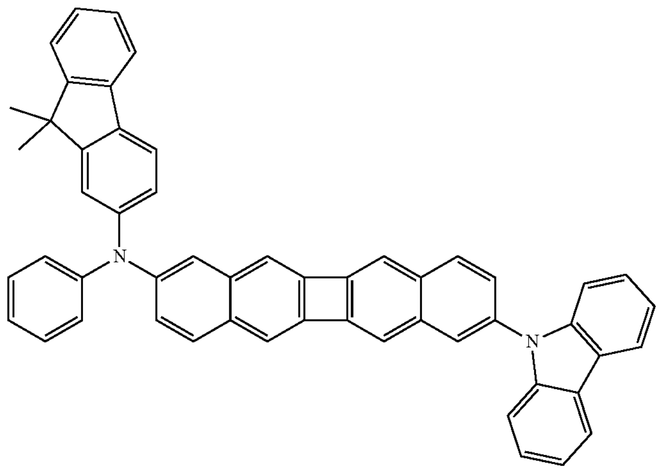

-continued
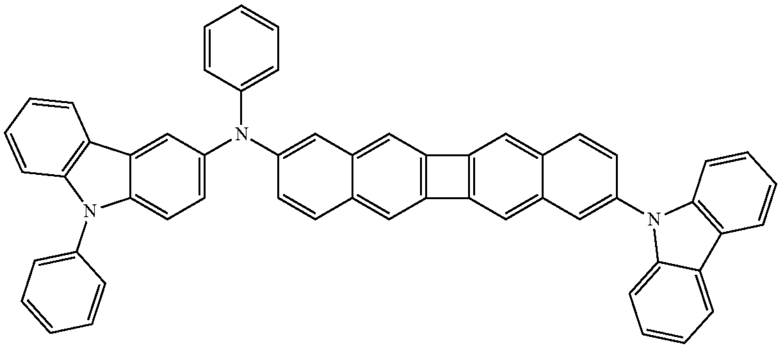
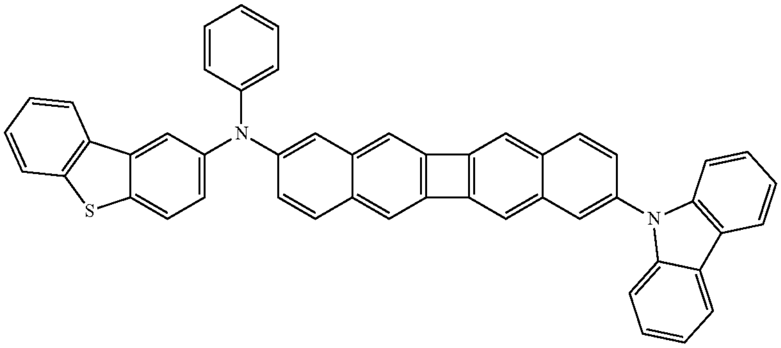
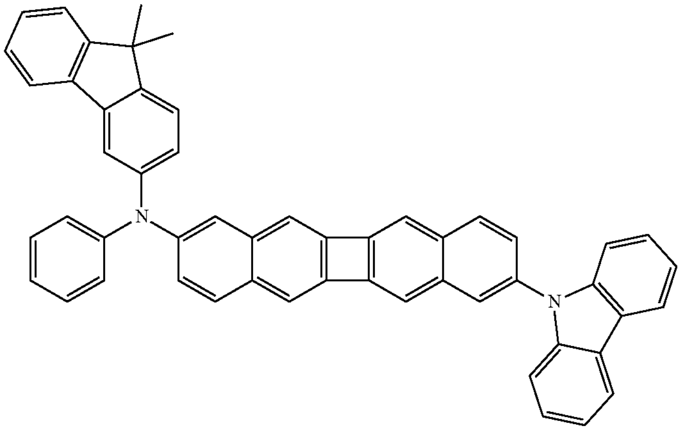
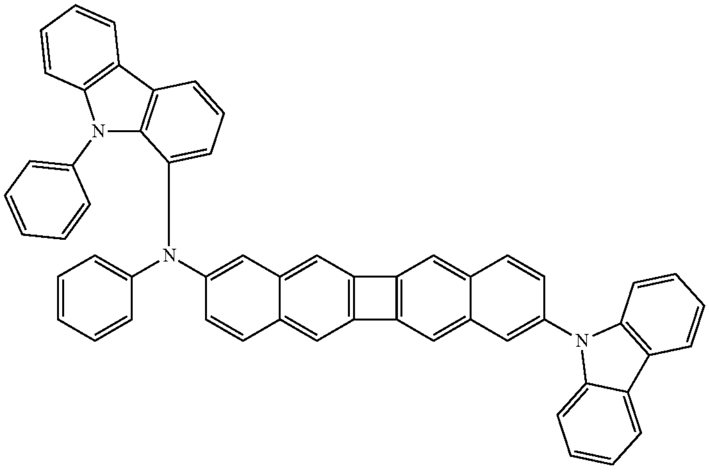

-continued
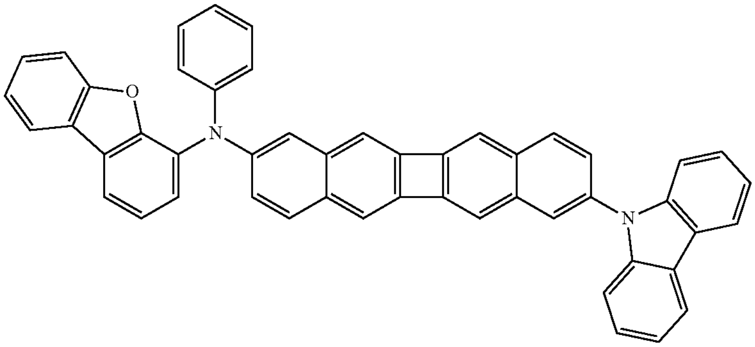
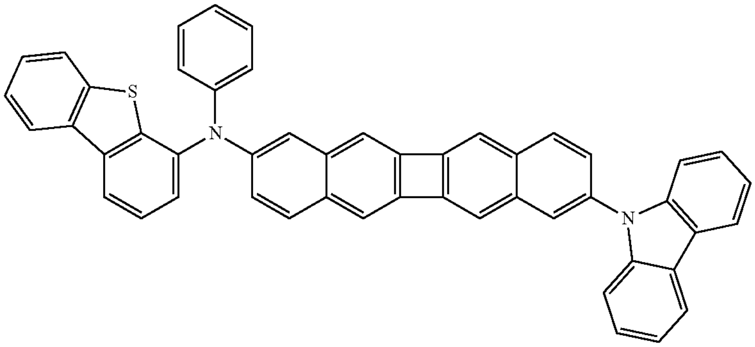
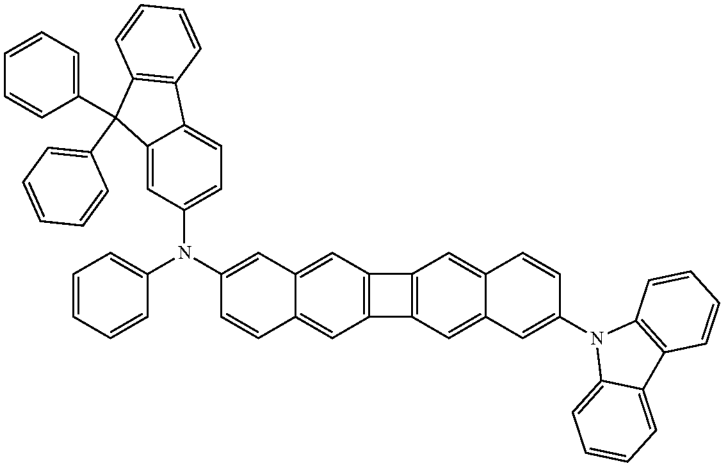
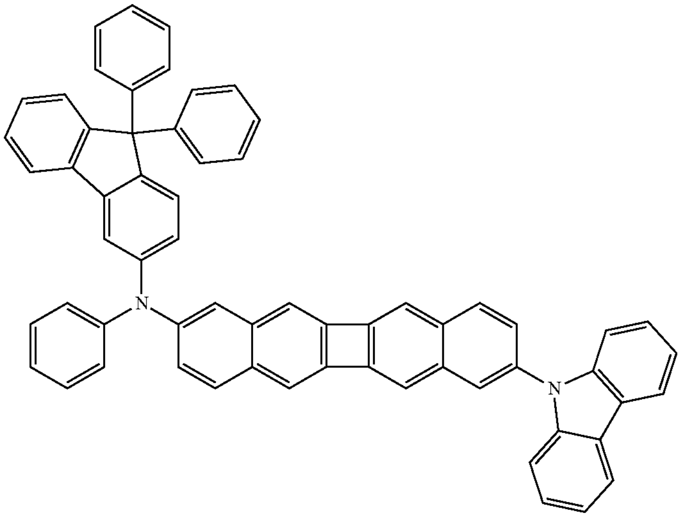

-continued
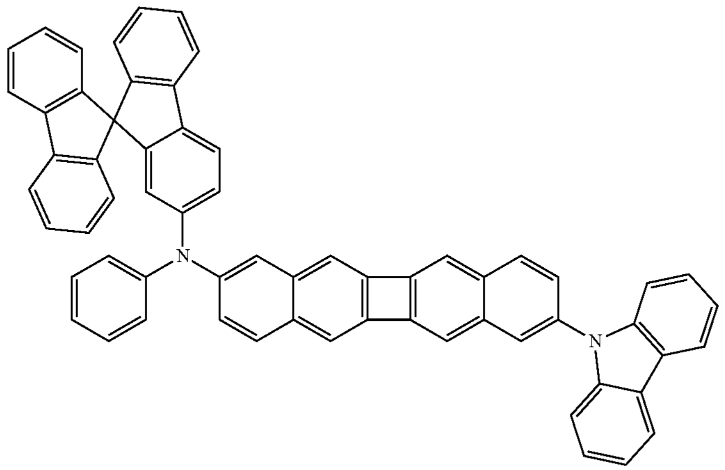
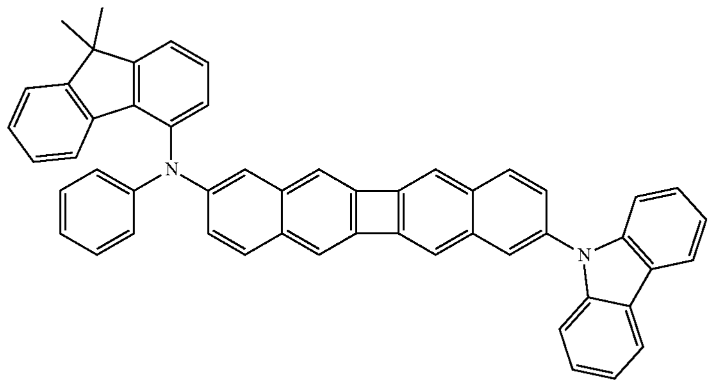
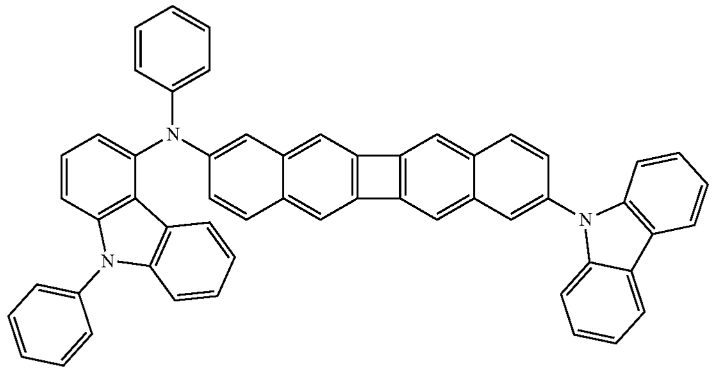
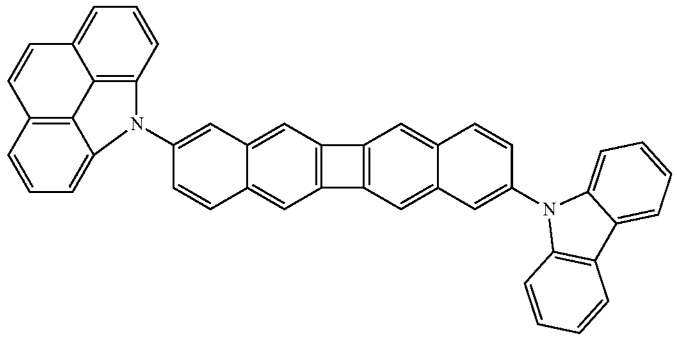

-continued
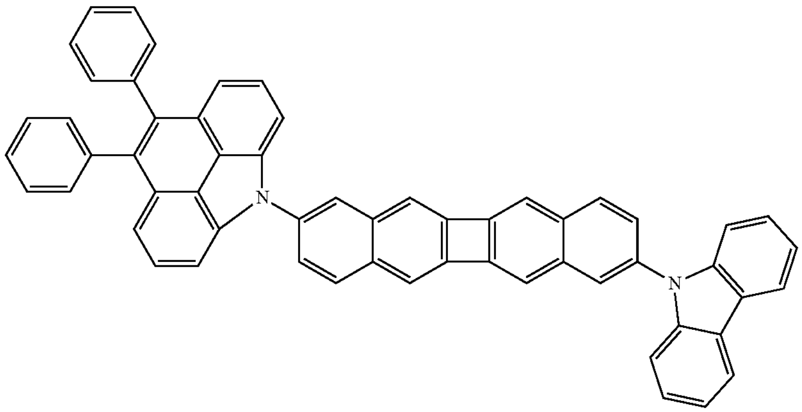
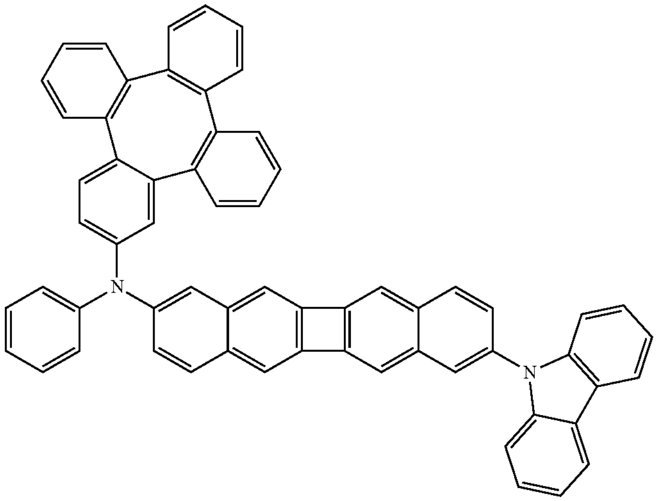
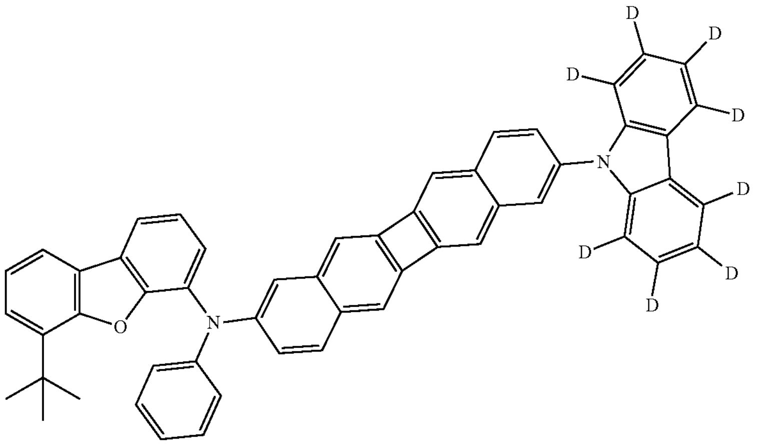

-continued
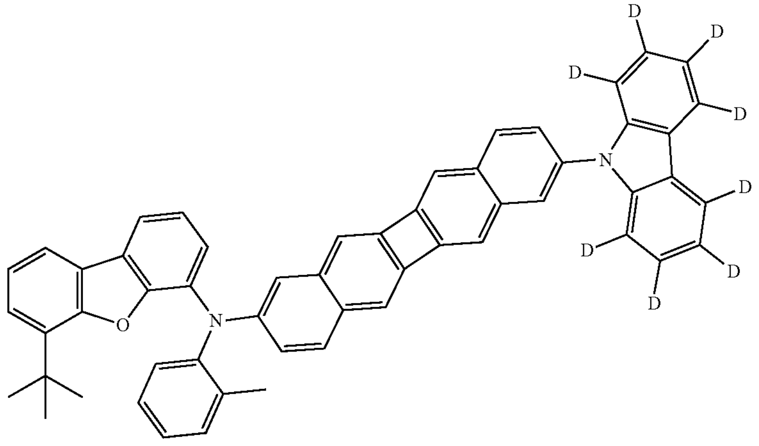
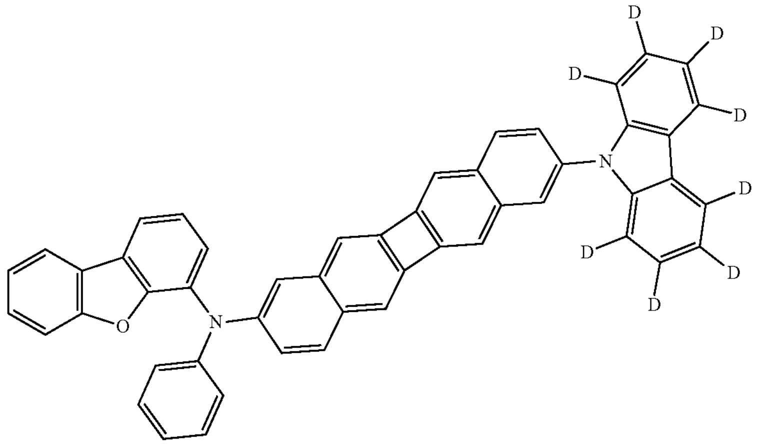
[Formula 105]
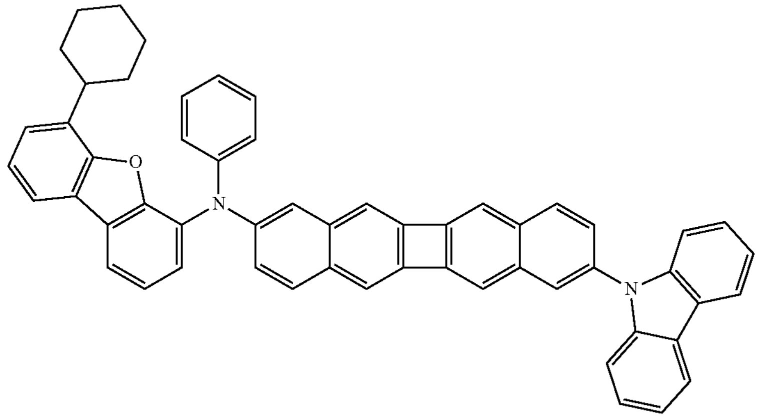

-continued
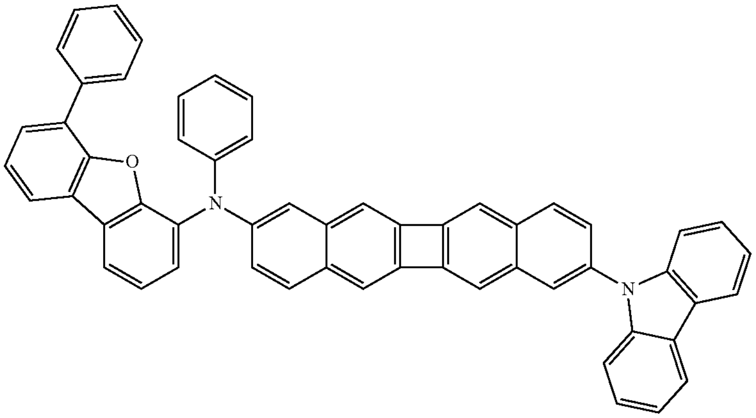
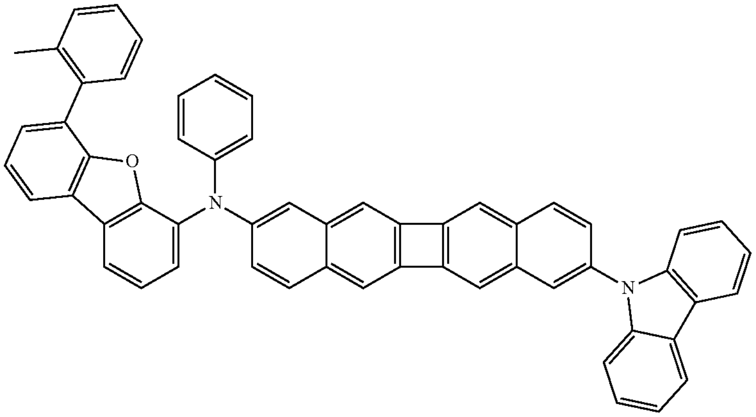
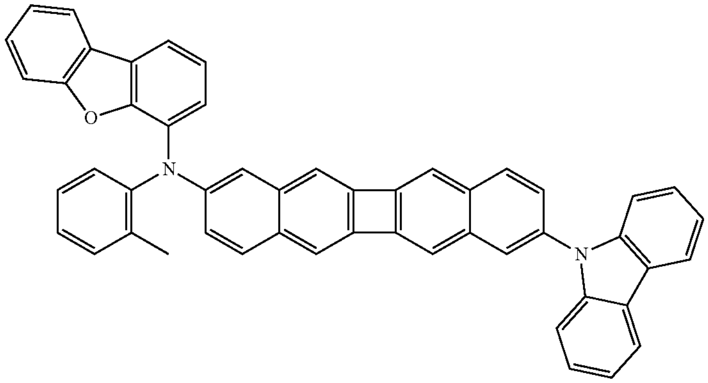
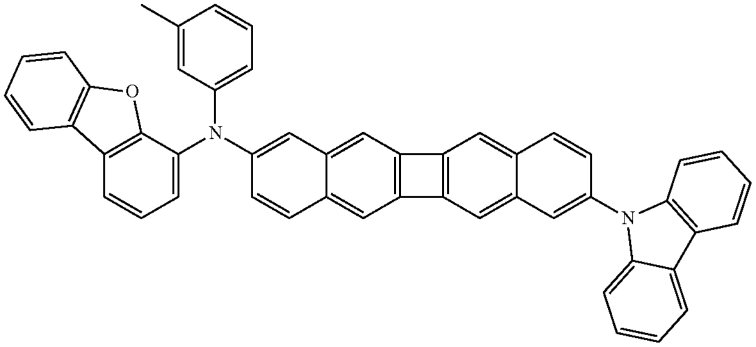

-continued
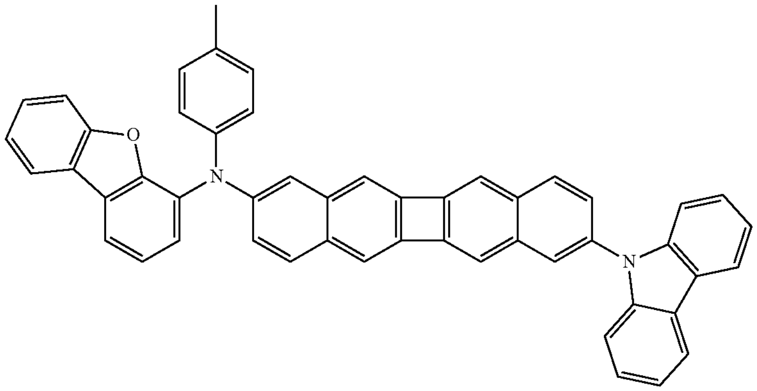
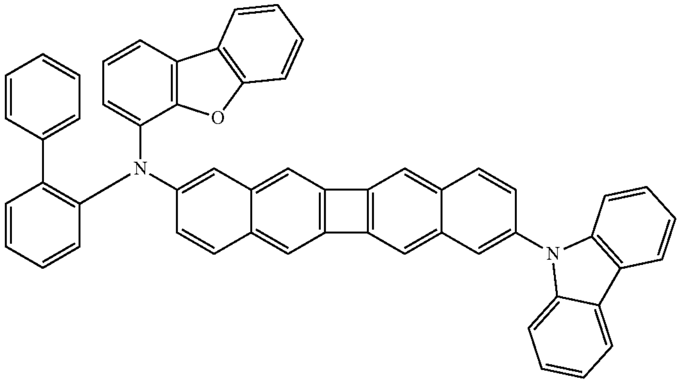
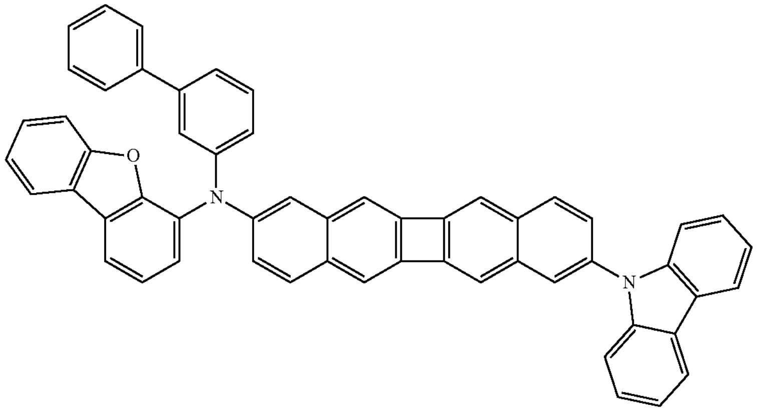
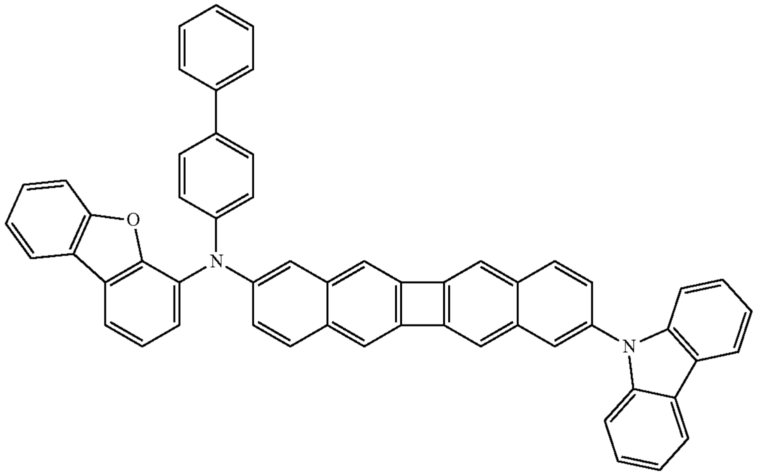

-continued
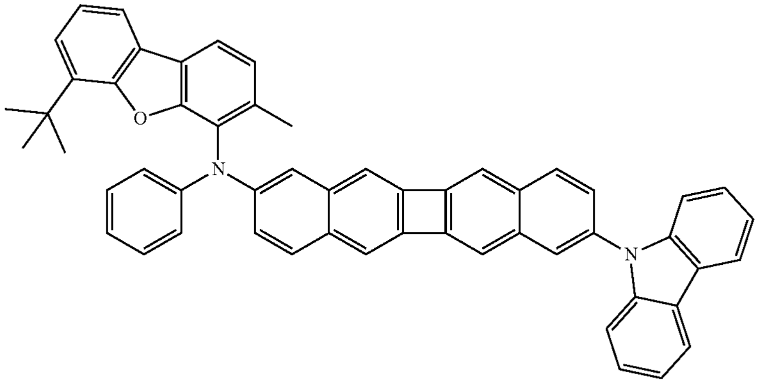
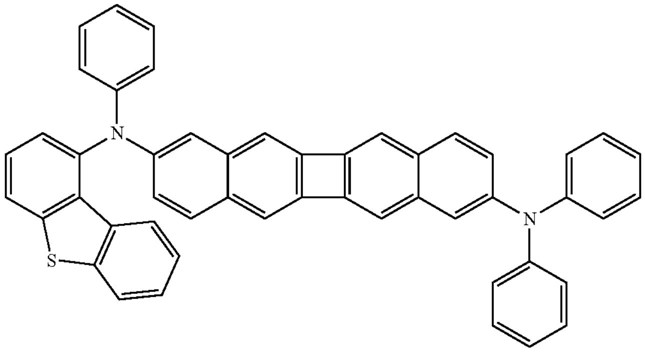
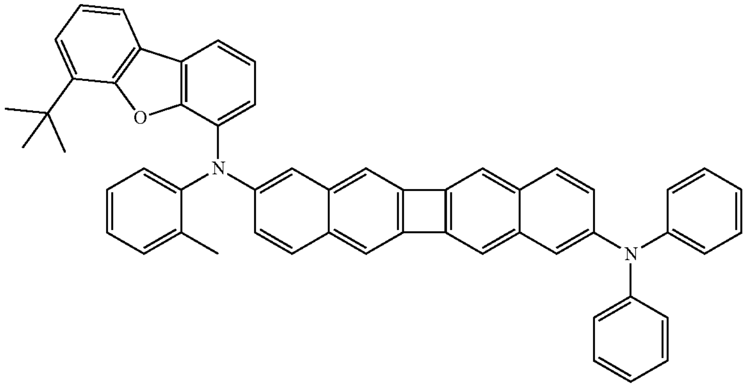
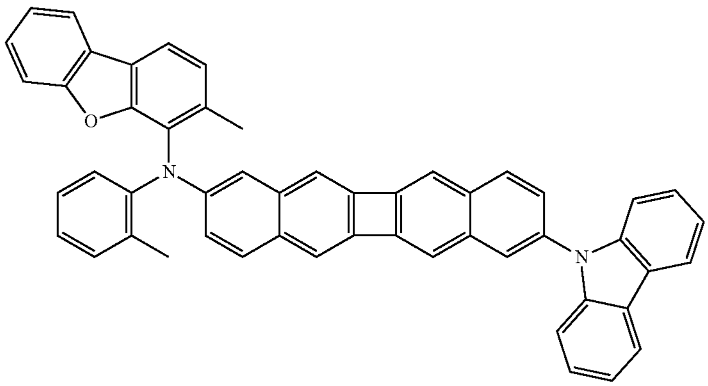

-continued
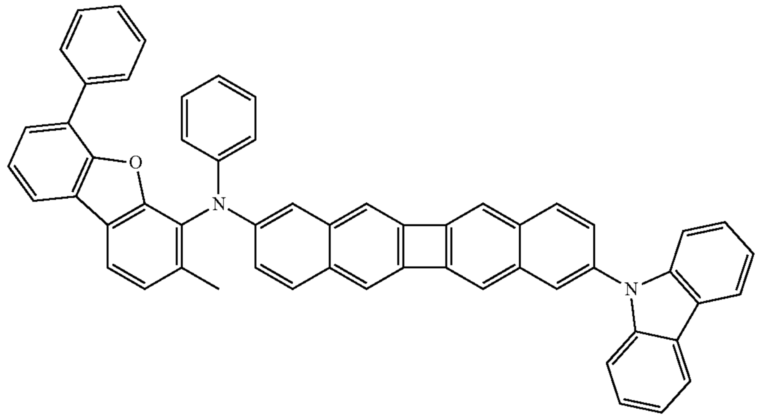
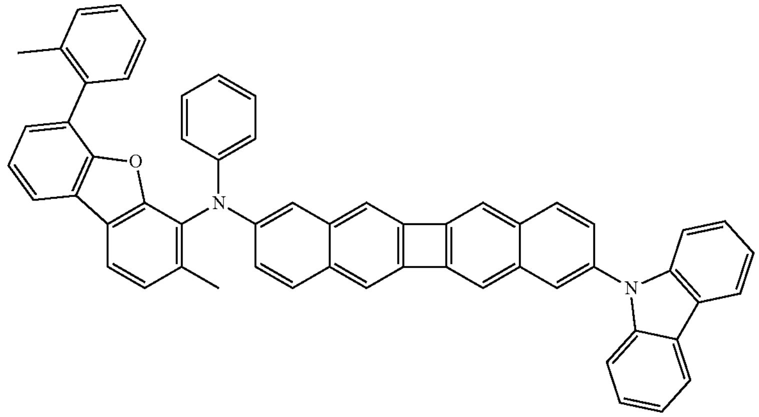
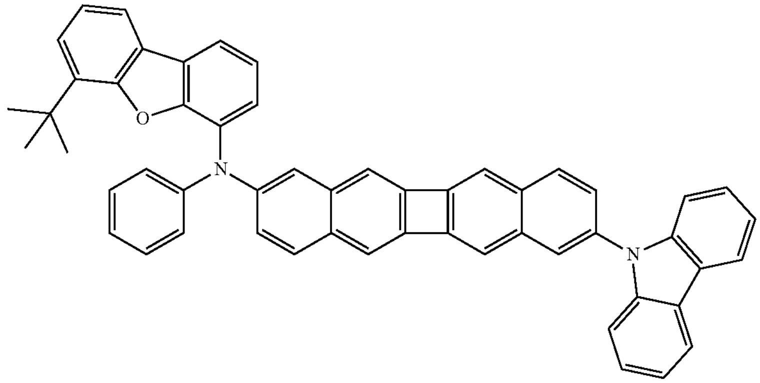
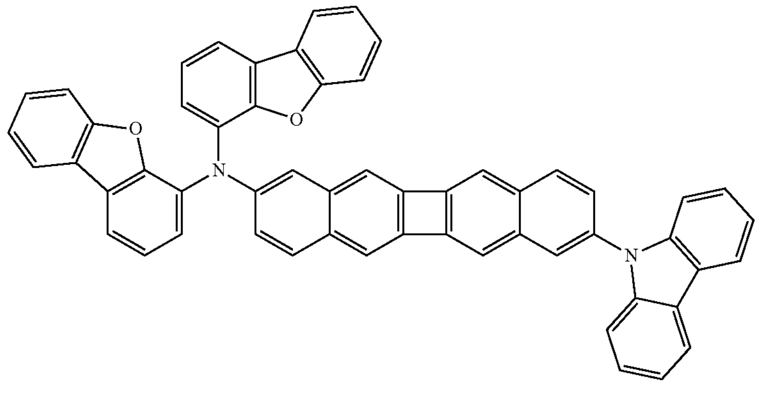

-continued
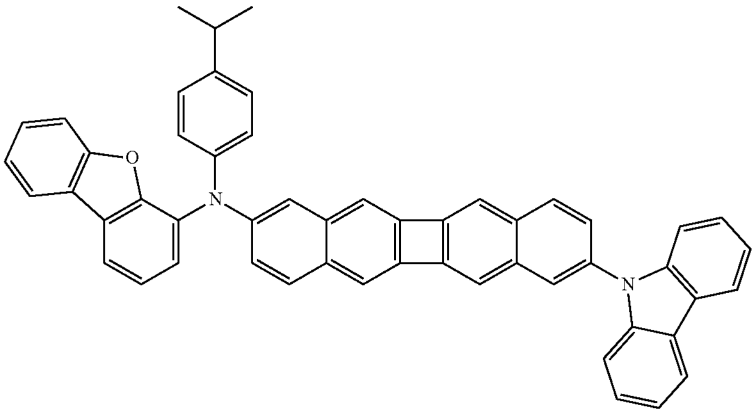
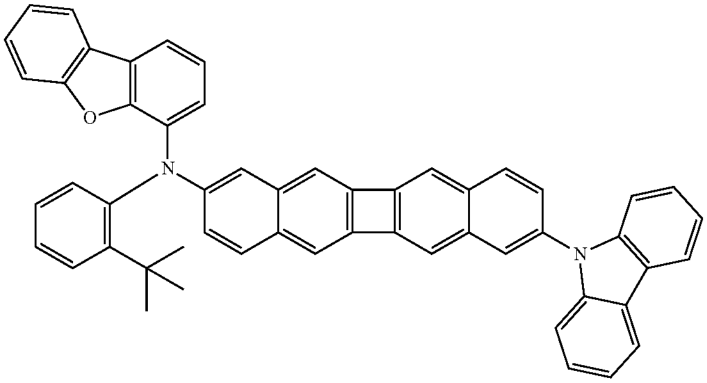
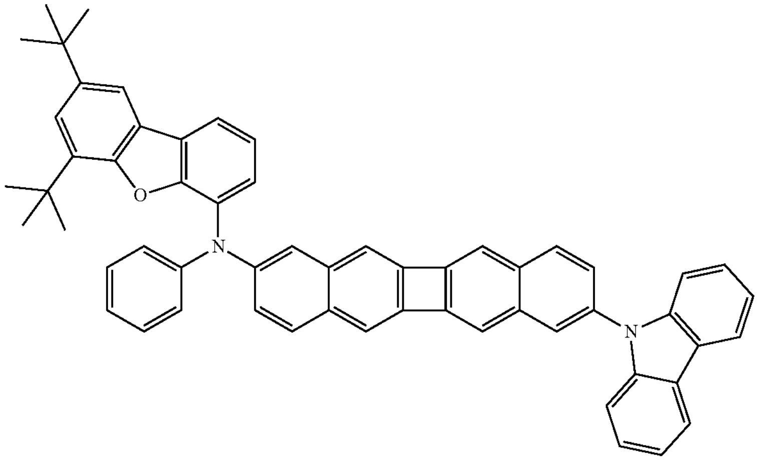
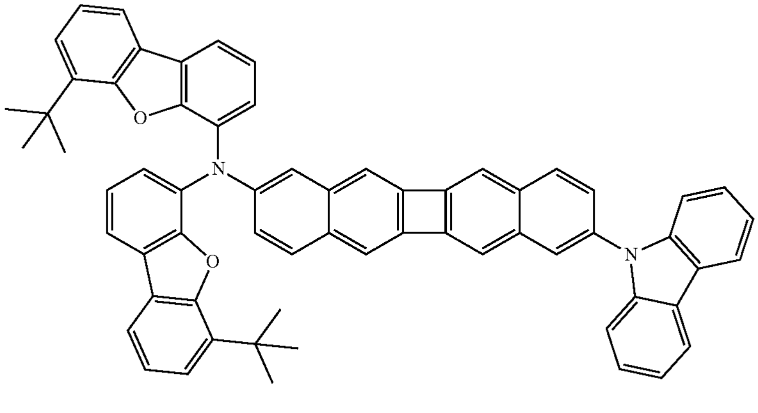

-continued
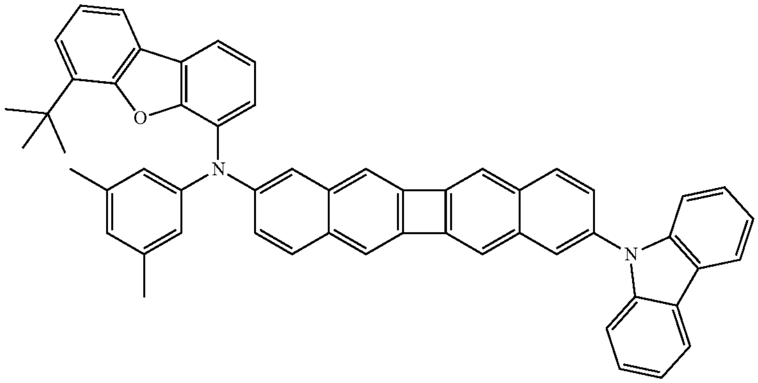
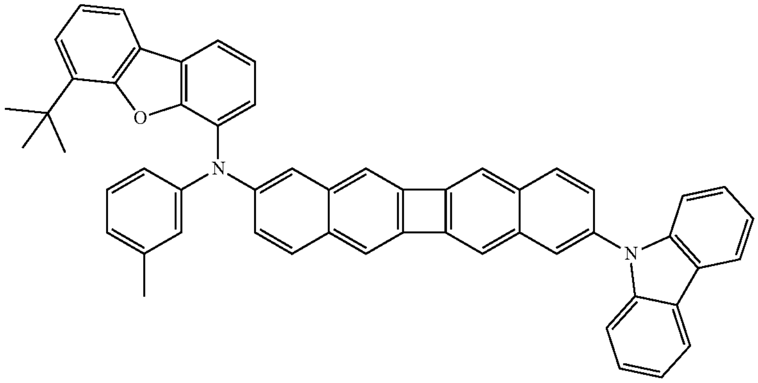
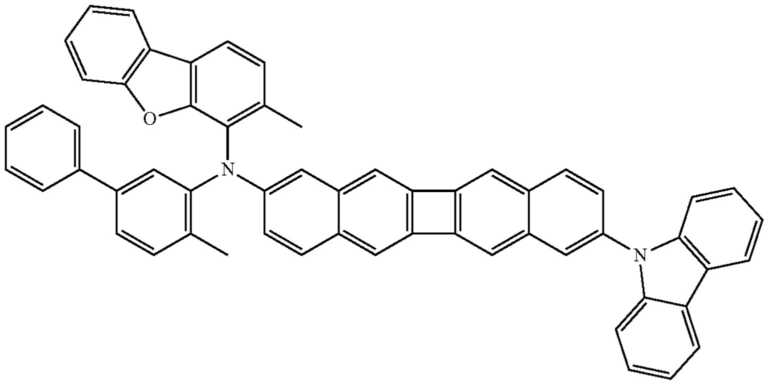
[Formula 106]
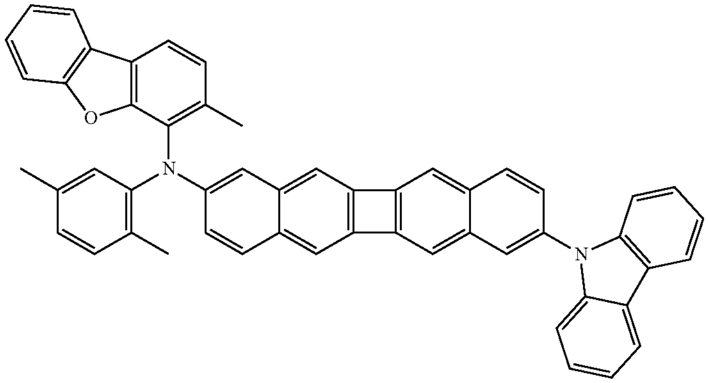

-continued
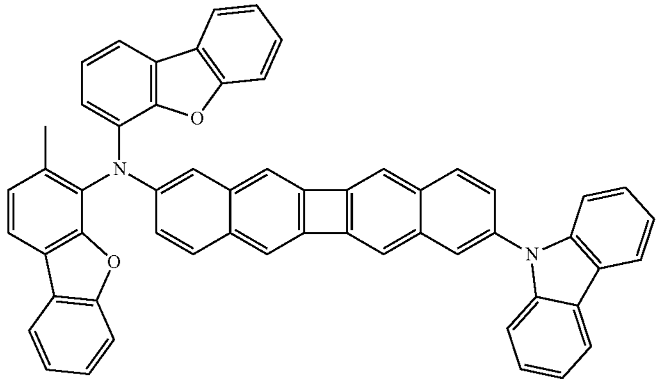
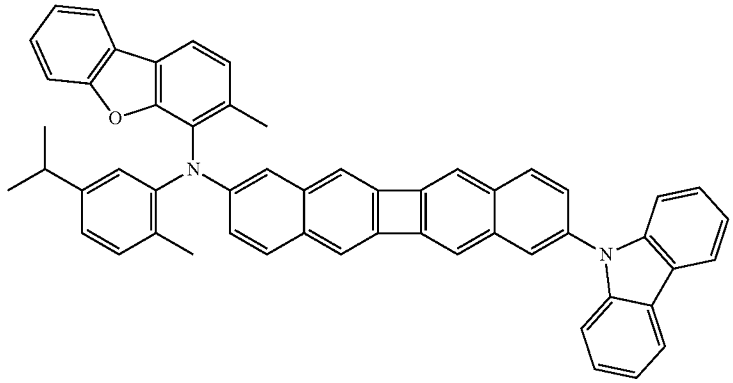
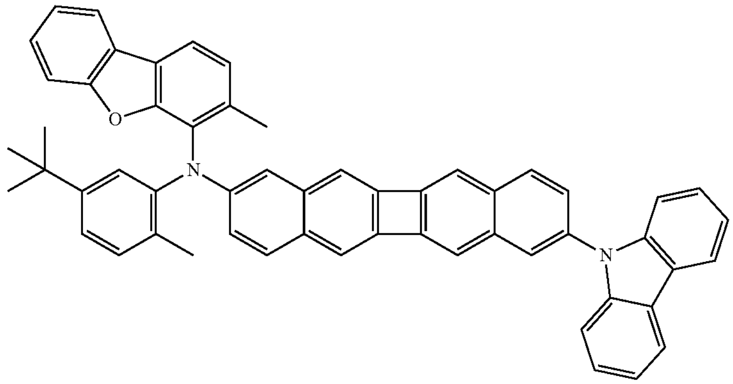
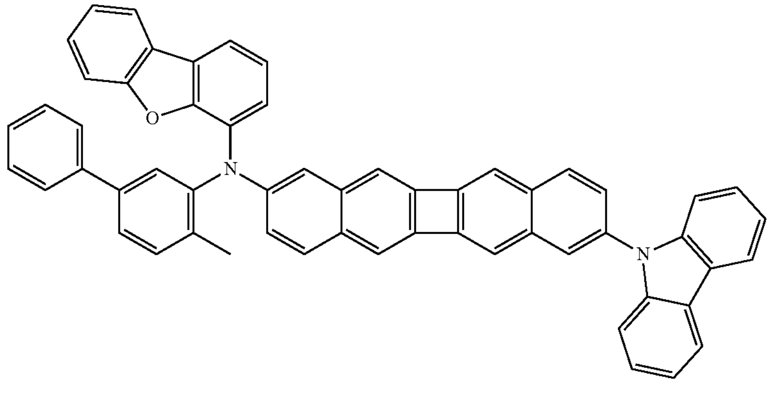

-continued
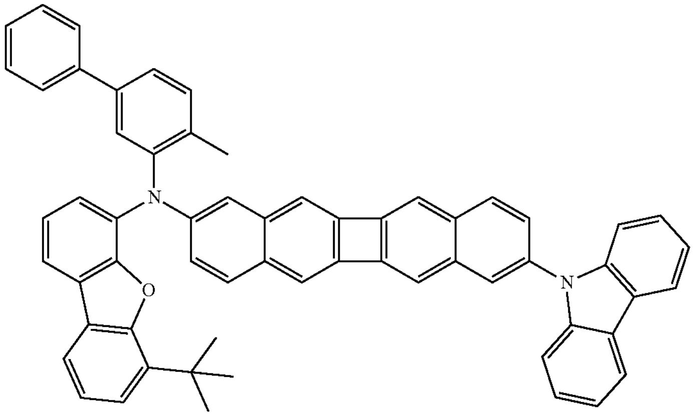
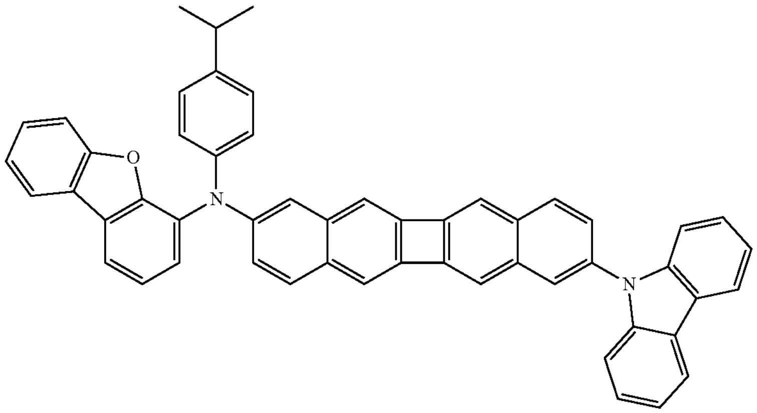
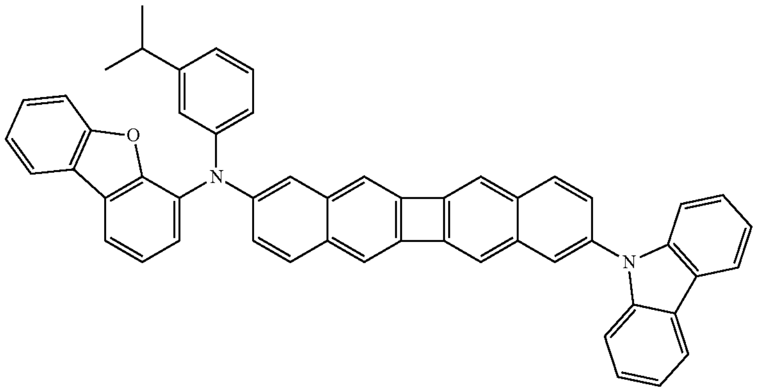
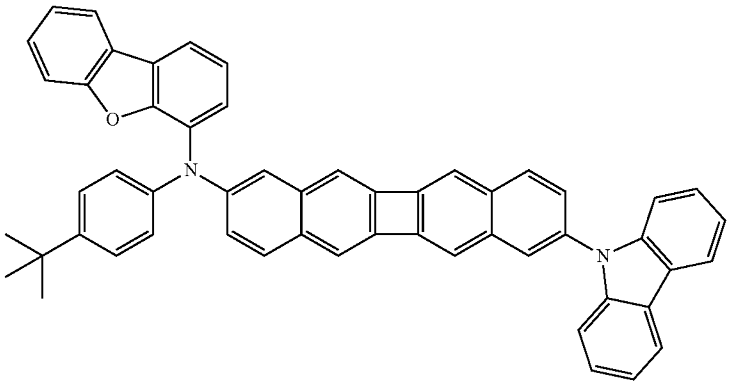

-continued
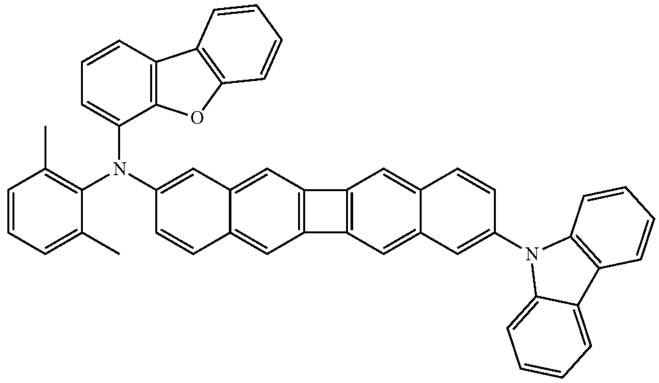
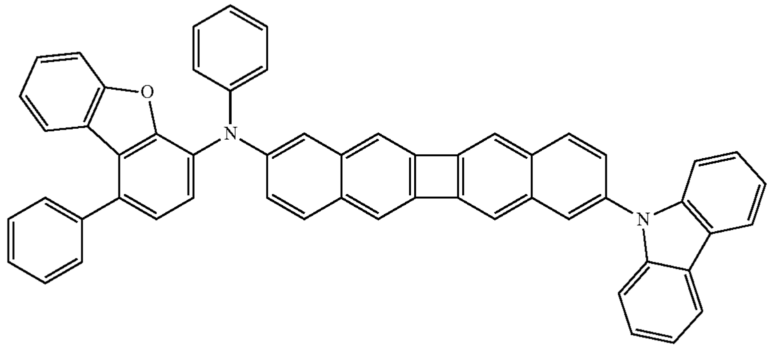
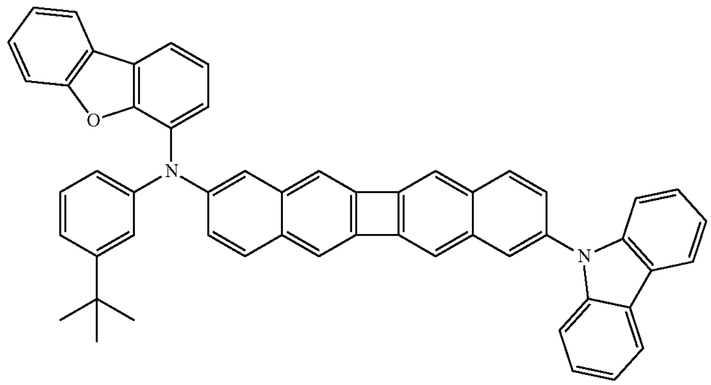
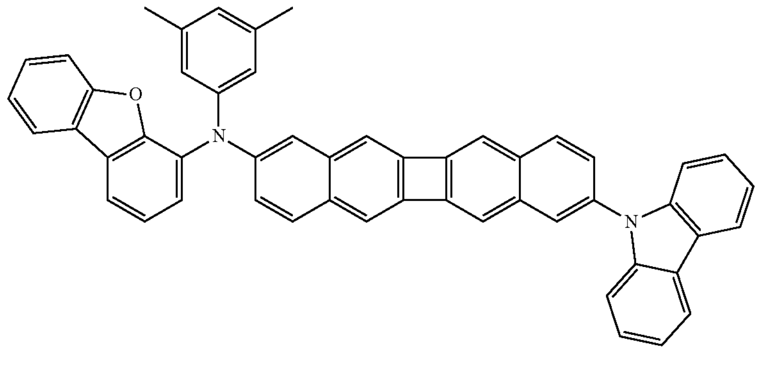

-continued
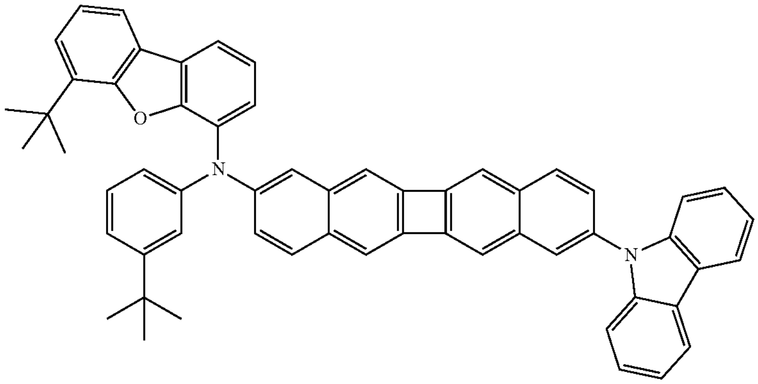
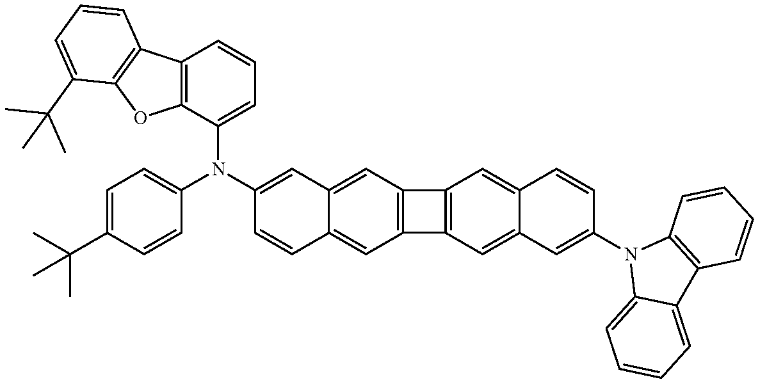
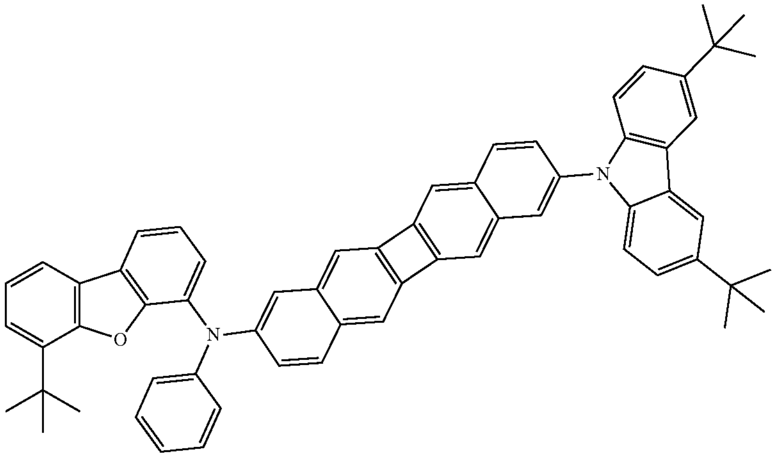
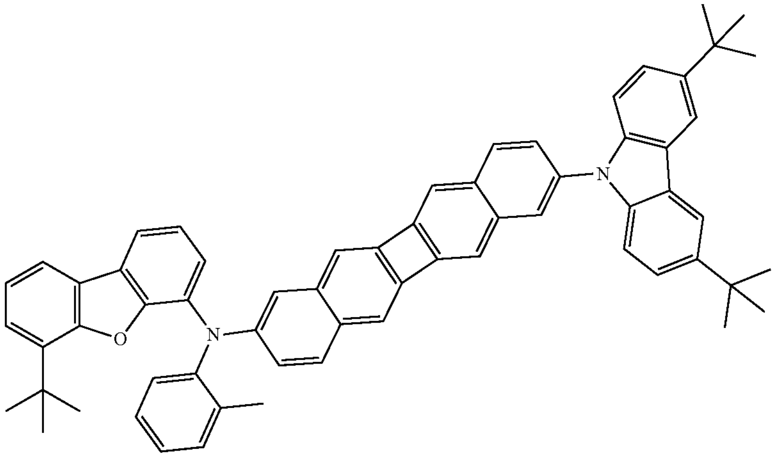

-continued
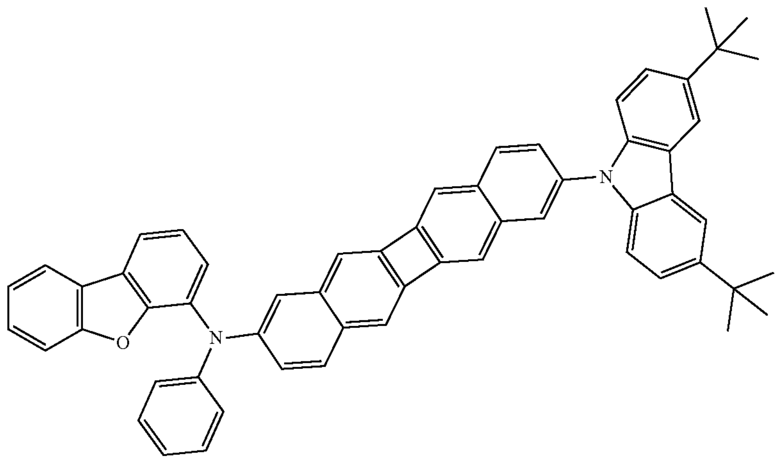
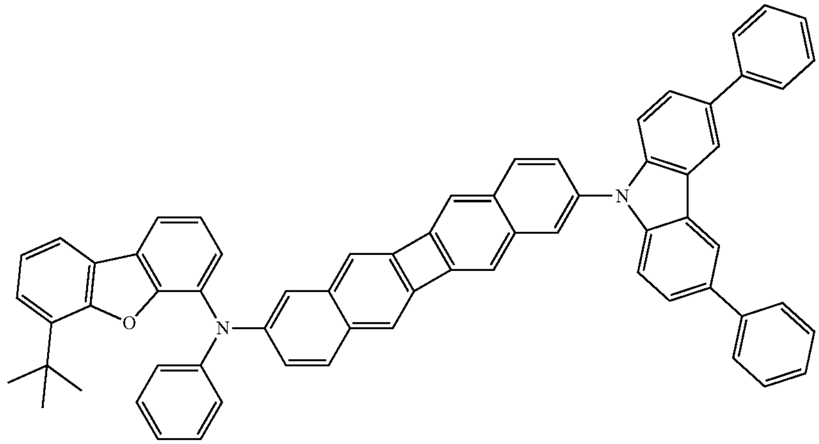
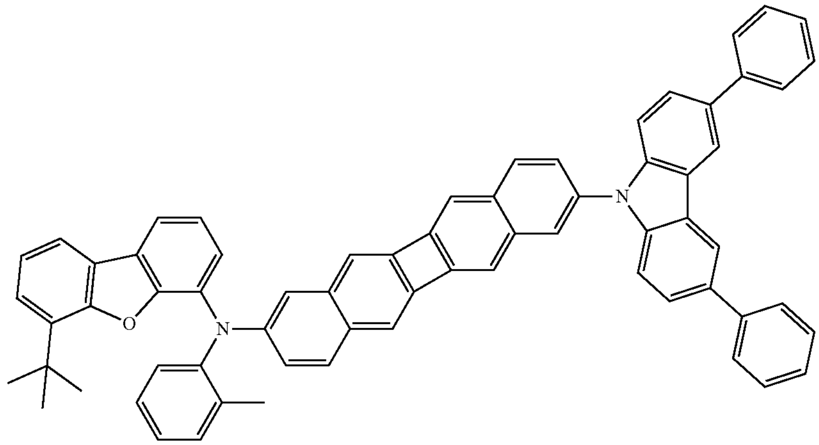

-continued
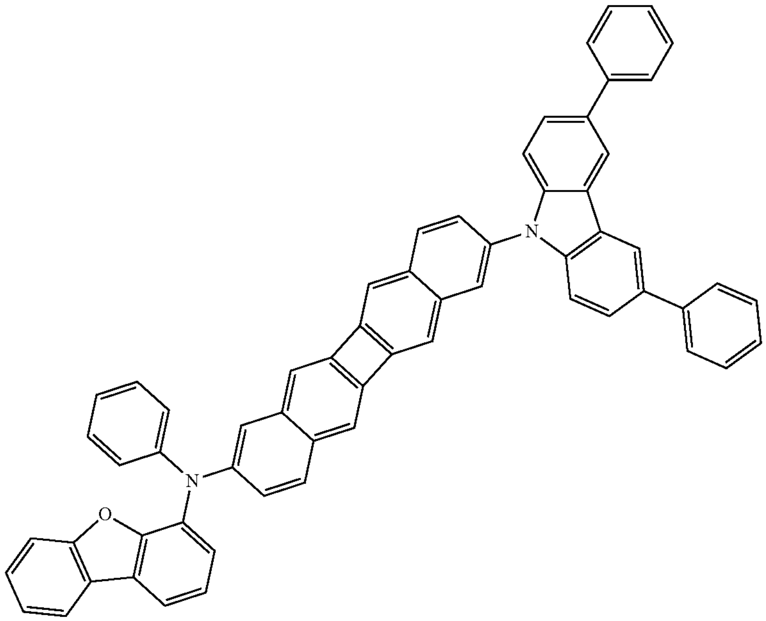
[Formula 107]
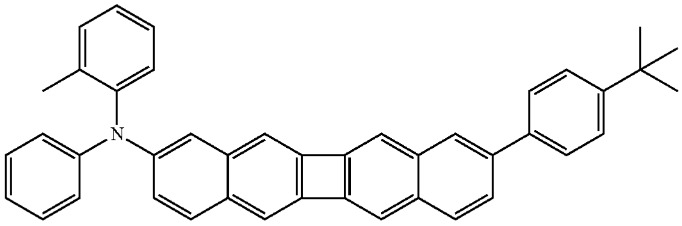
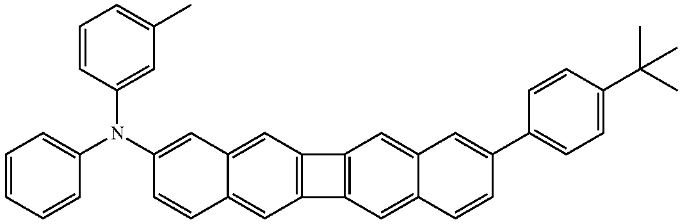
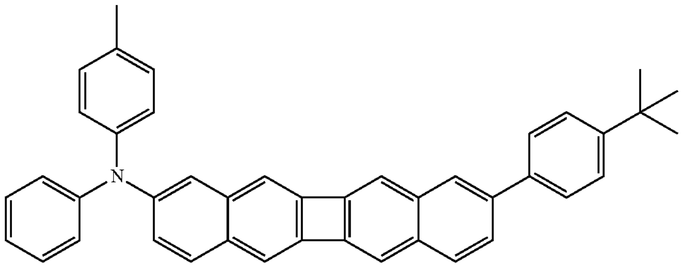
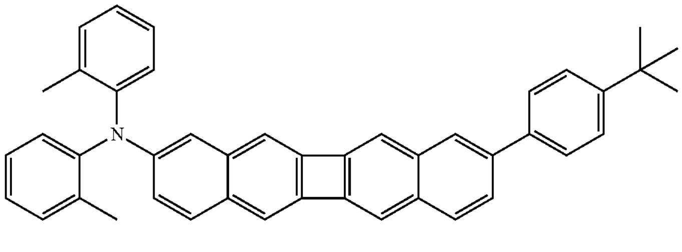

-continued
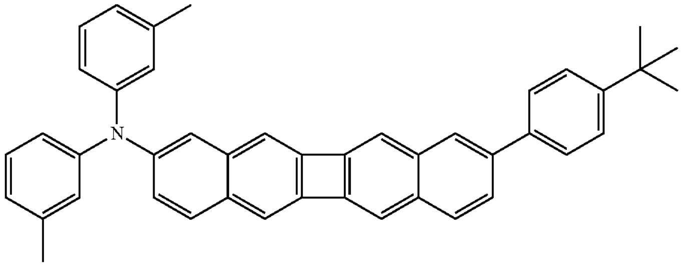
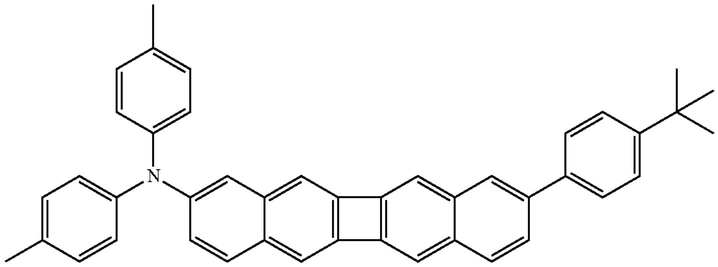
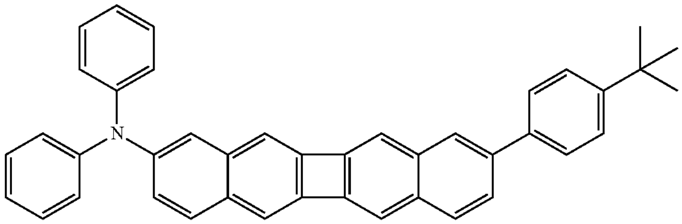
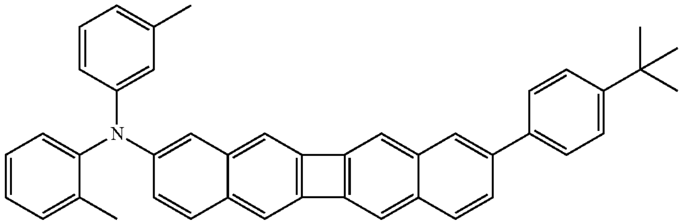
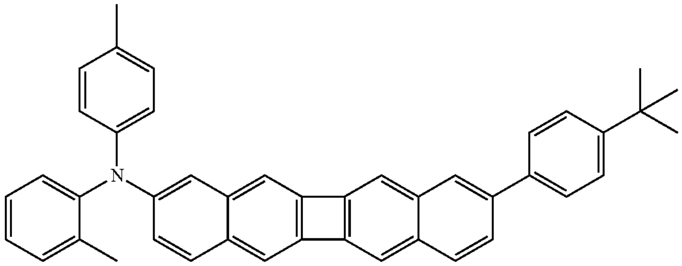
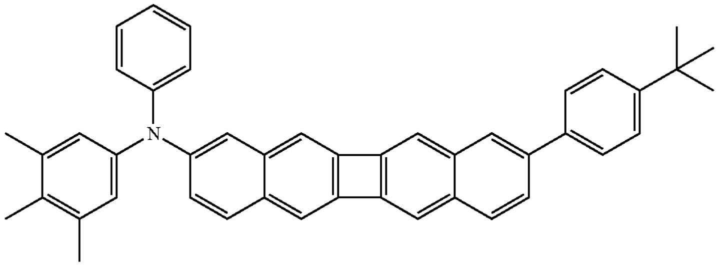

-continued
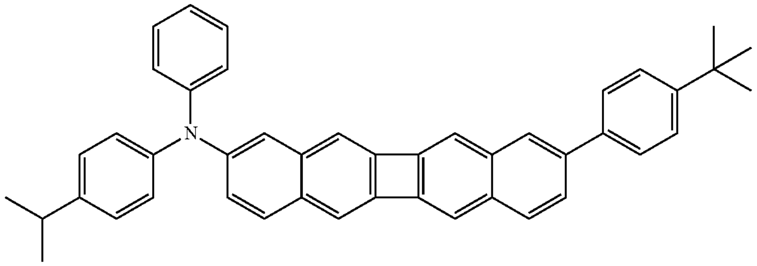
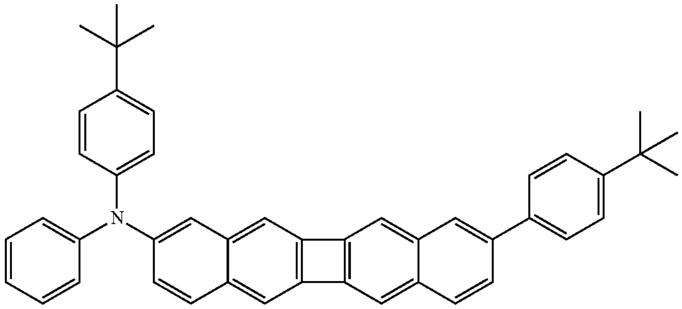
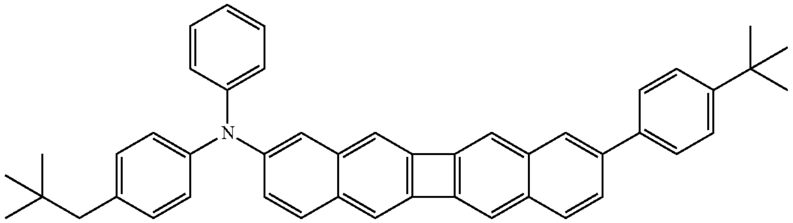
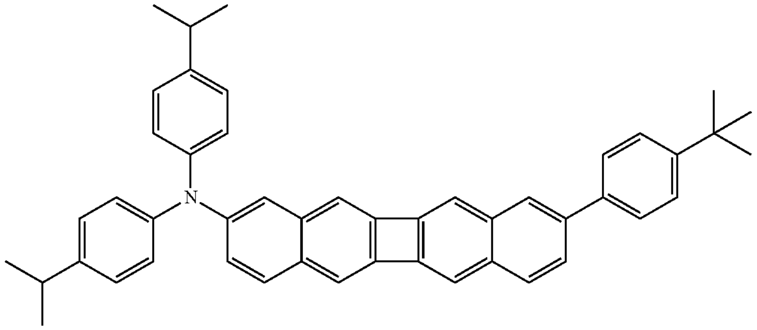
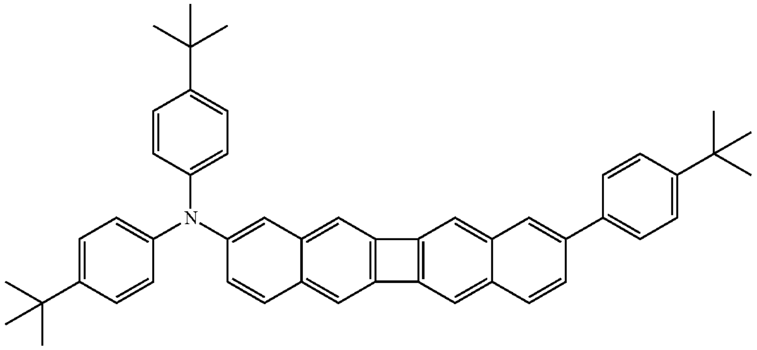

-continued
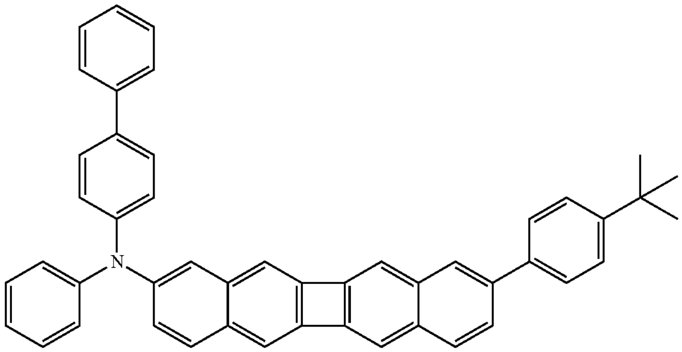
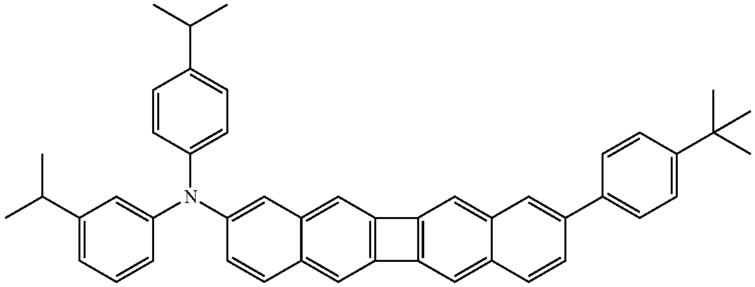
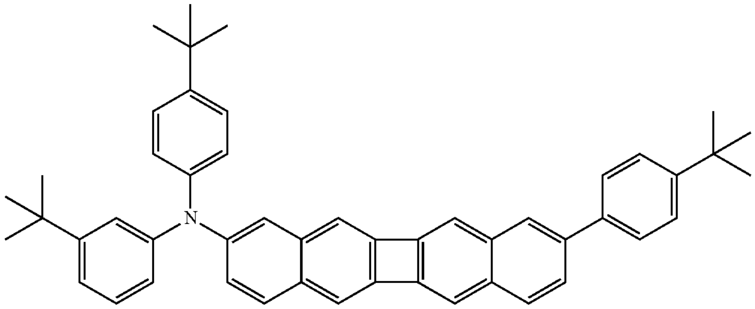
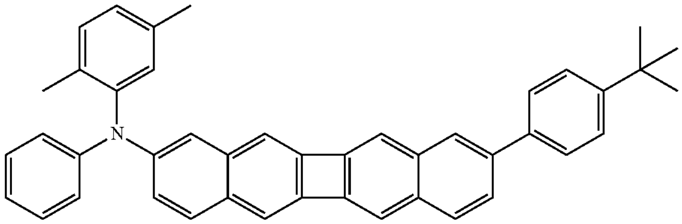
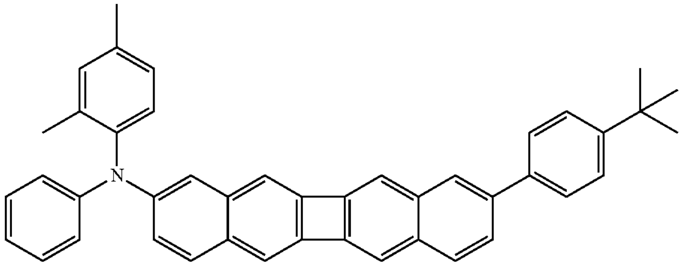
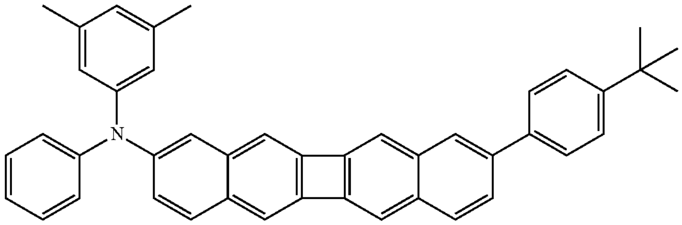

-continued
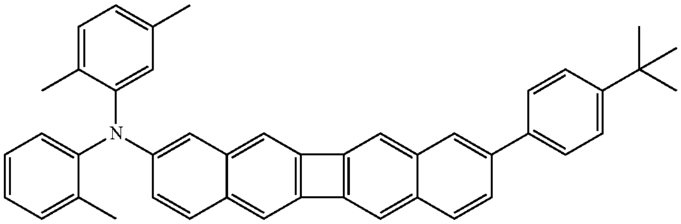
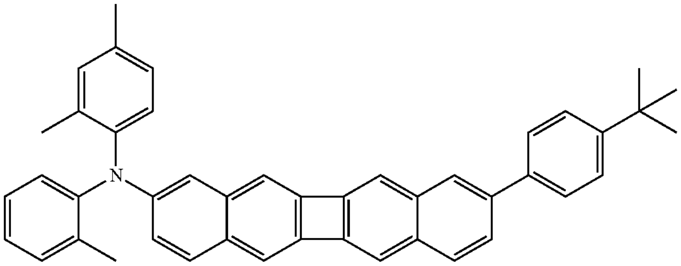
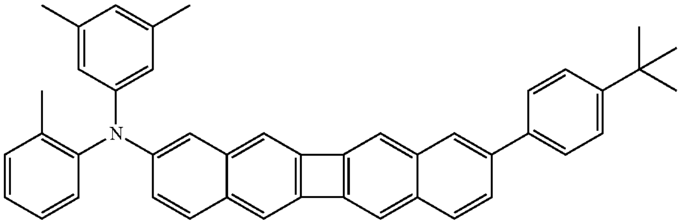
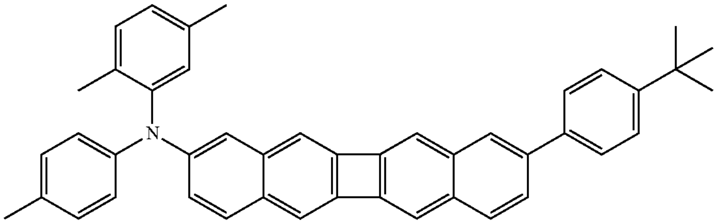
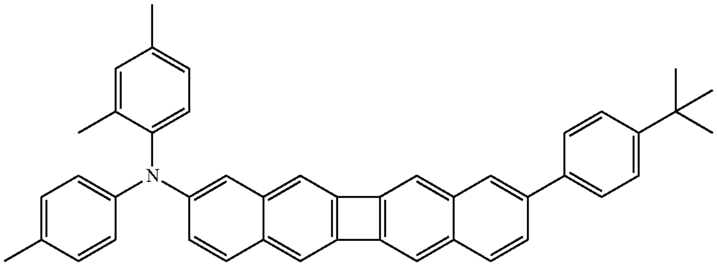
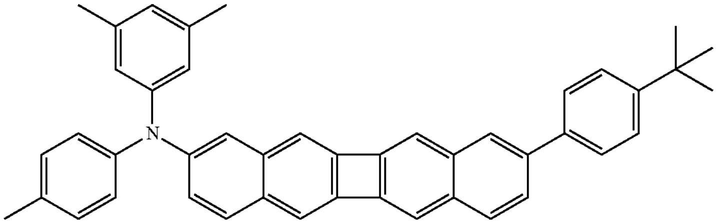
[Formula 108]
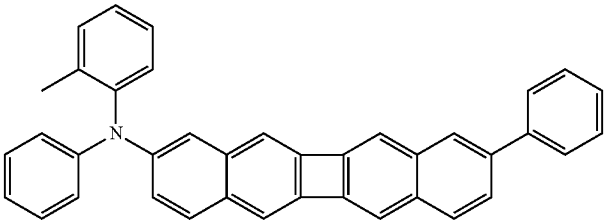

-continued
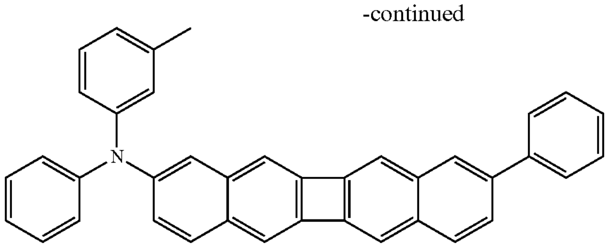
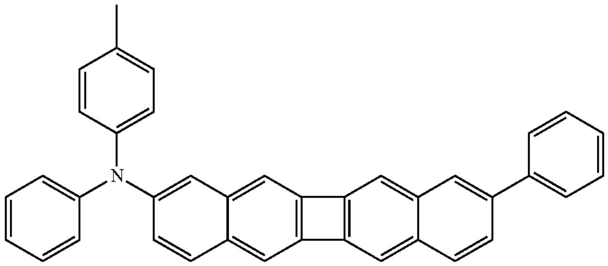
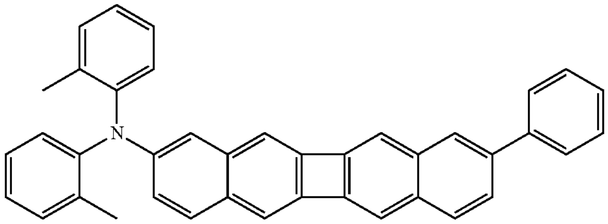
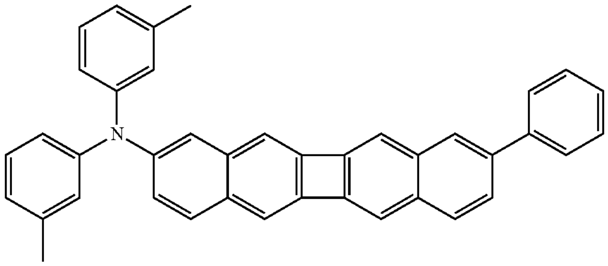
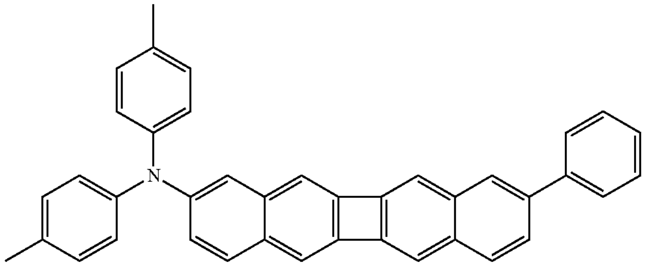
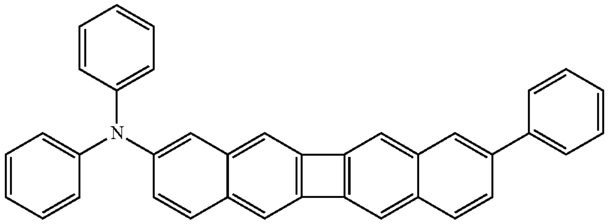
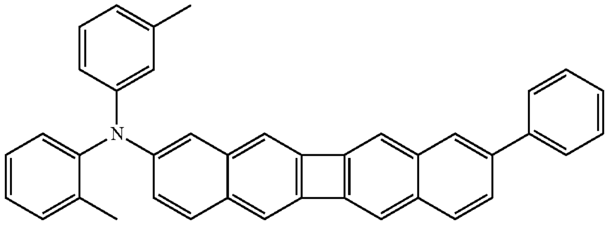

-continued
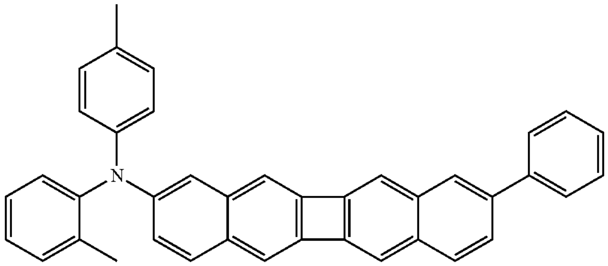
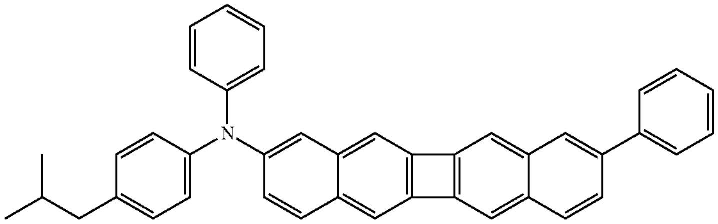
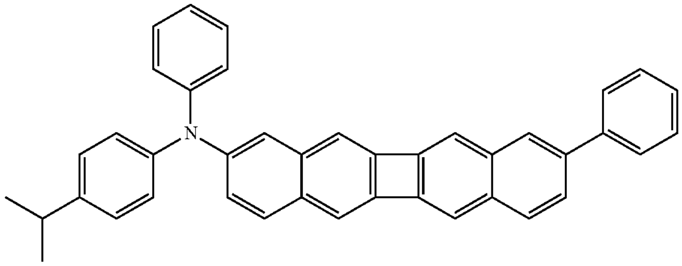
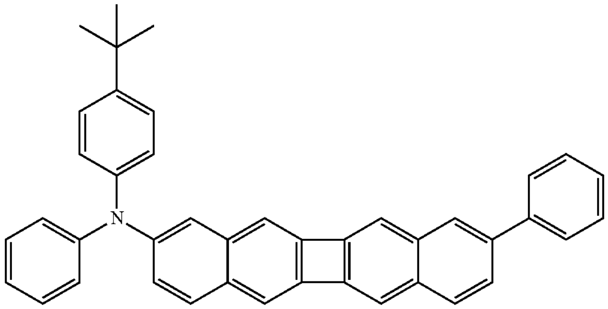
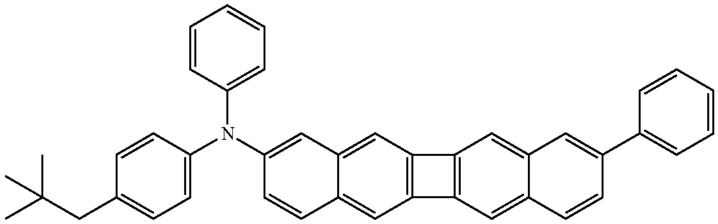
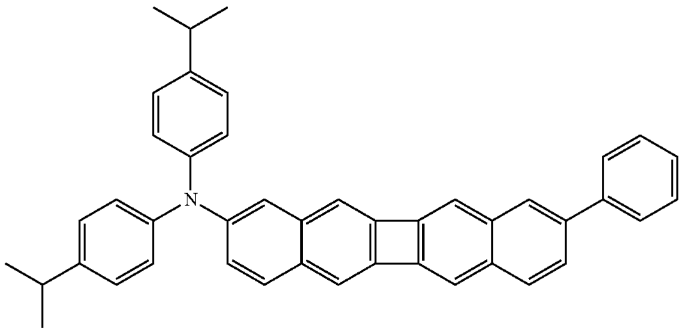

-continued
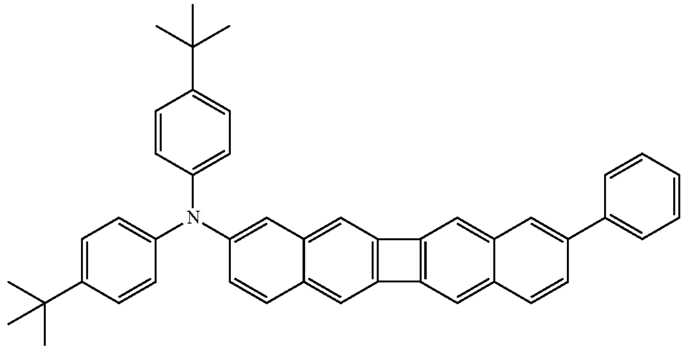
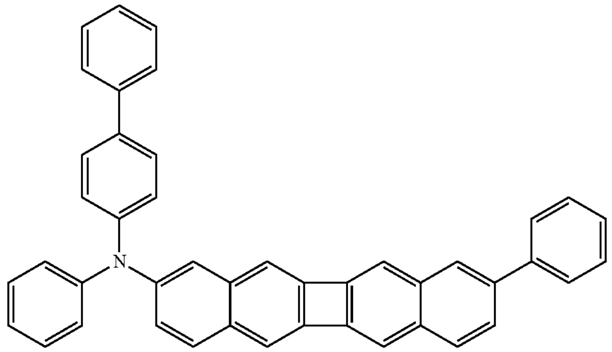
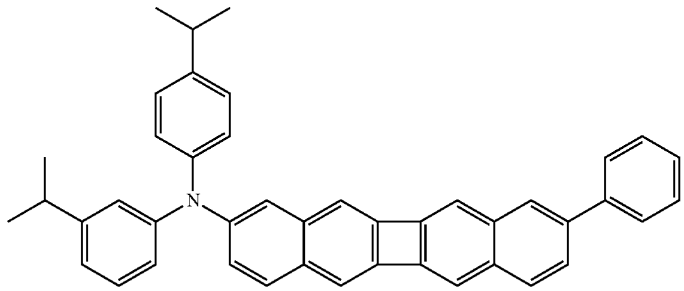
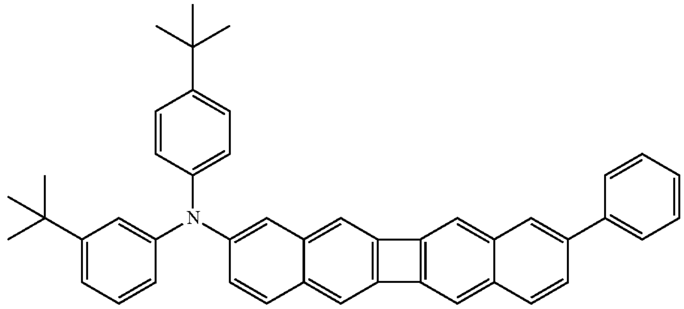
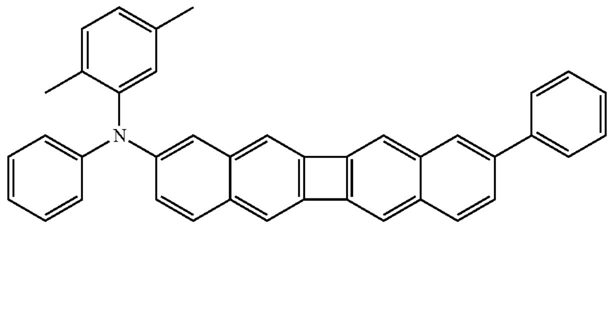

-continued
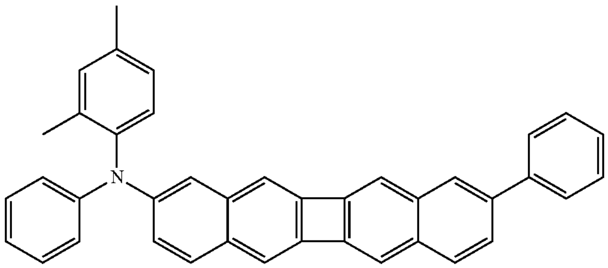
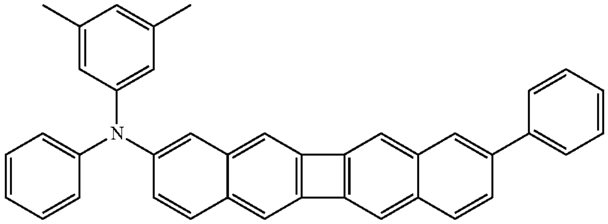
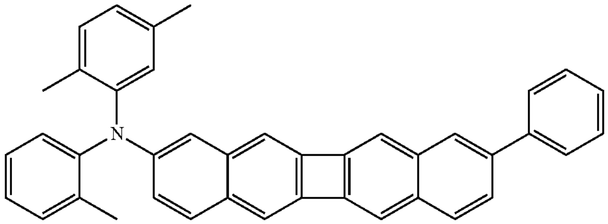
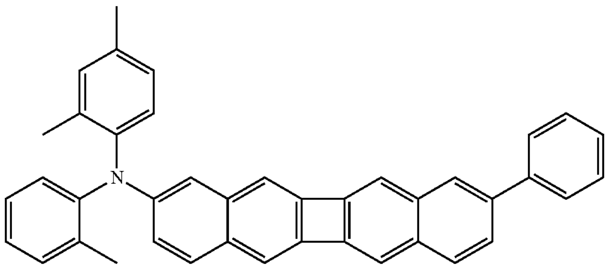
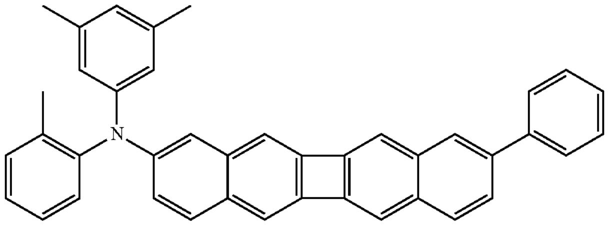
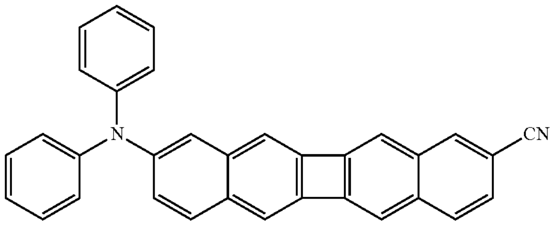
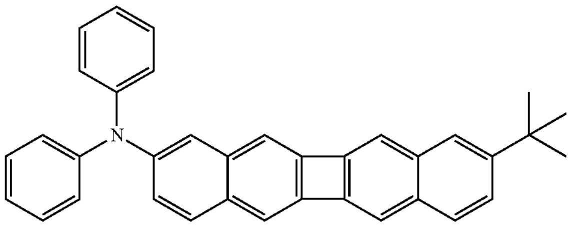

-continued
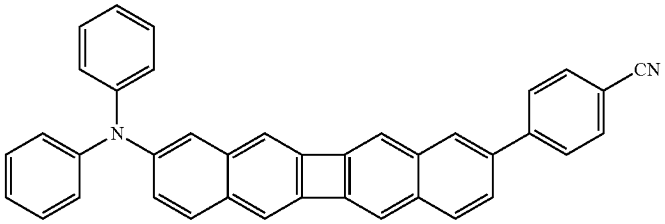
[Formula 109]
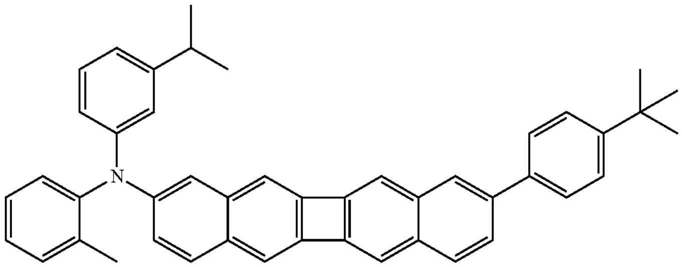
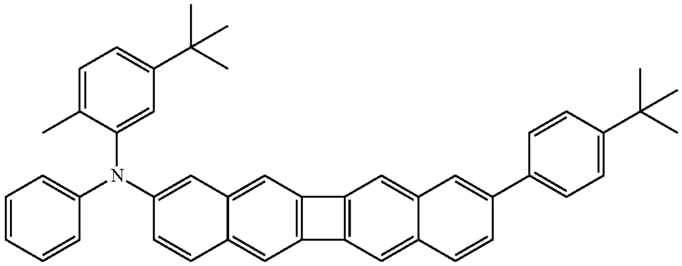
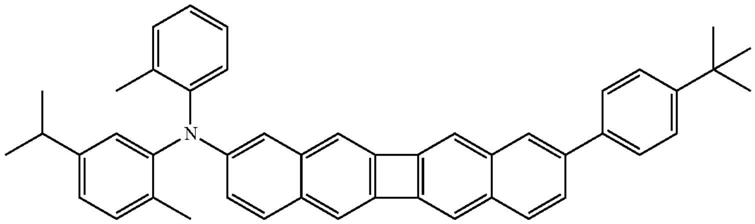
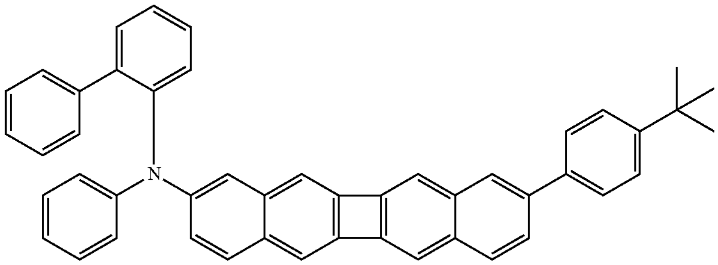
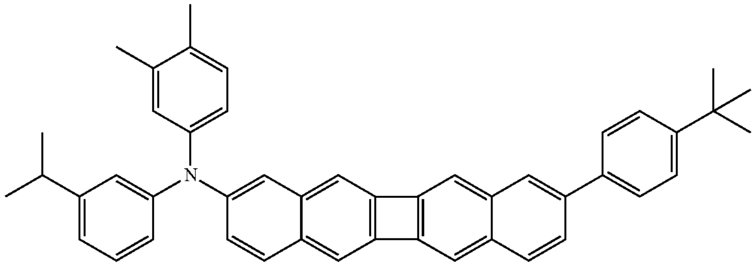

-continued
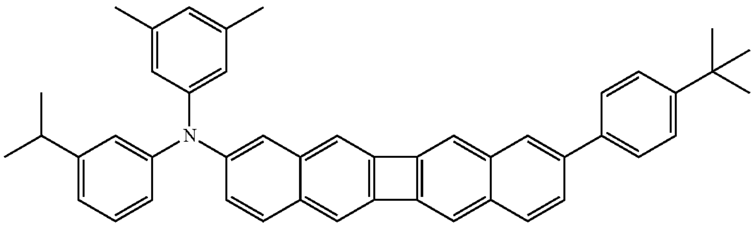
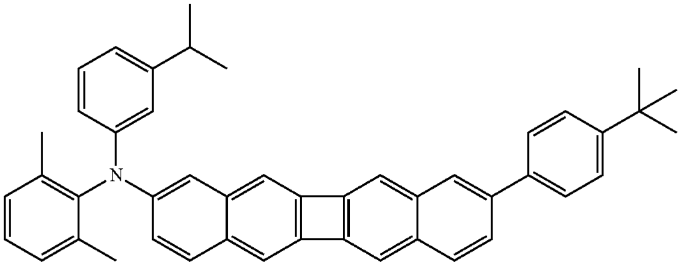
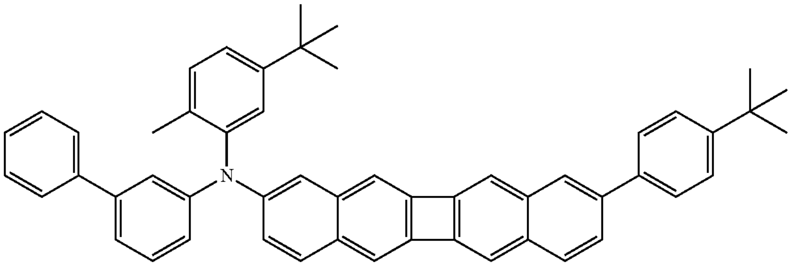
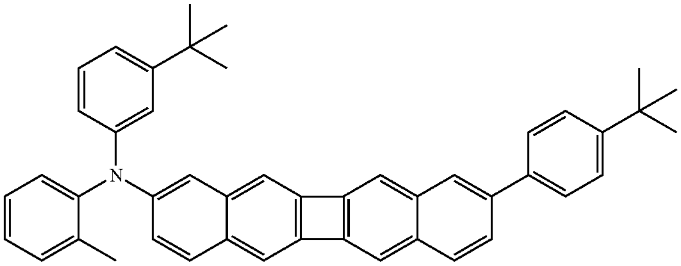
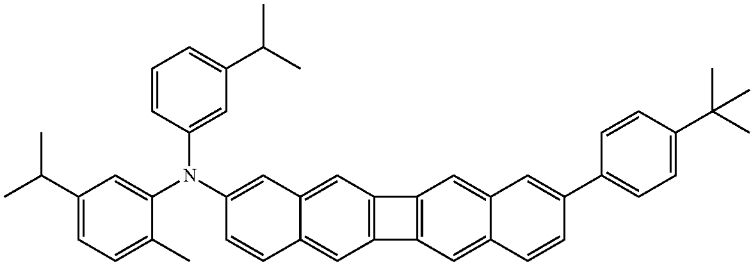
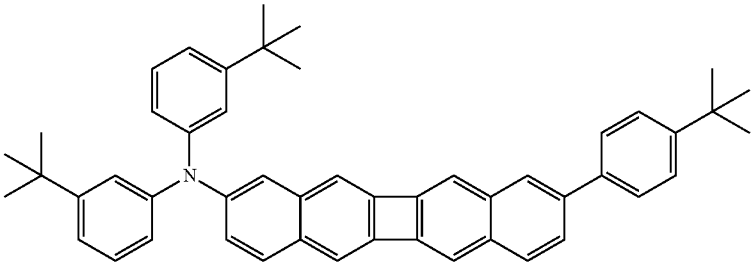

-continued
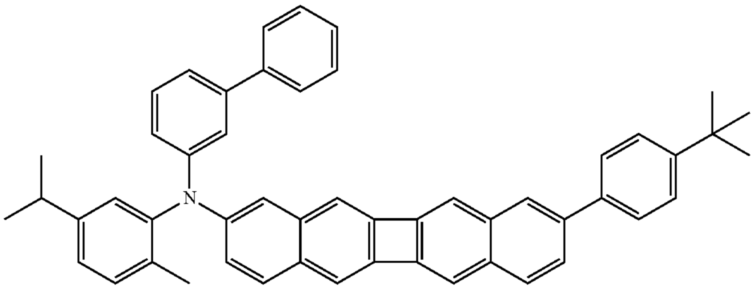
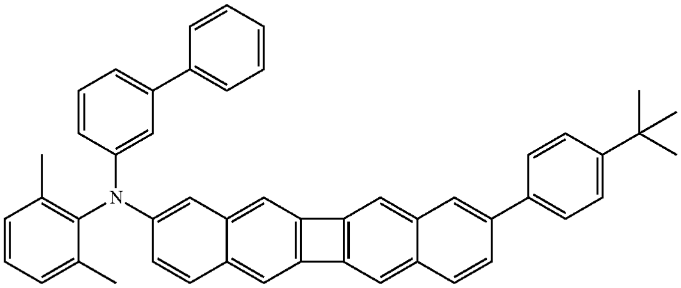
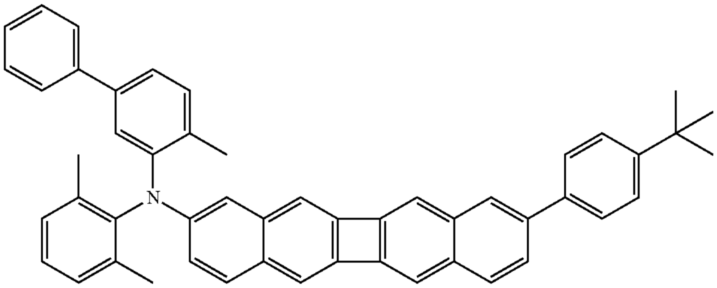
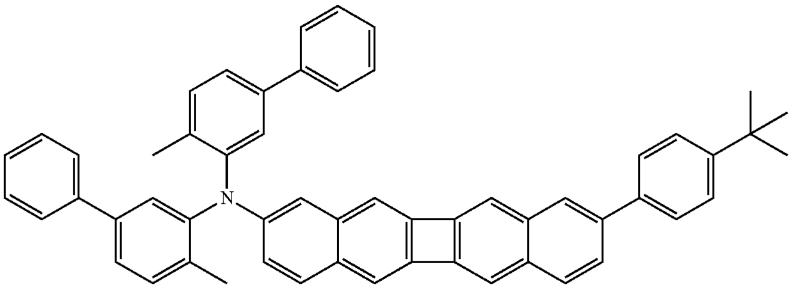
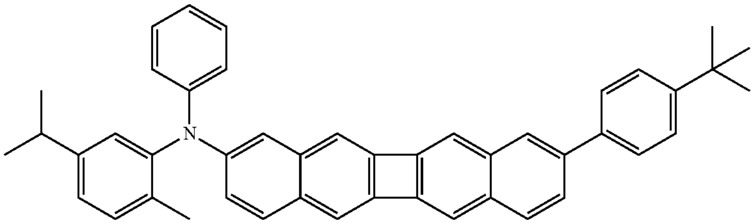
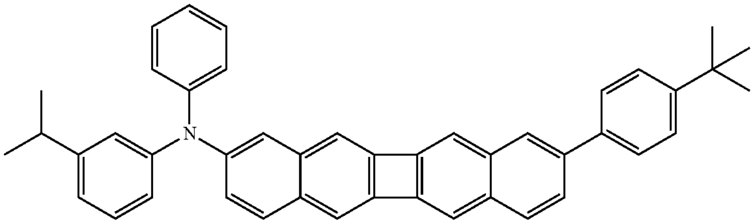

-continued
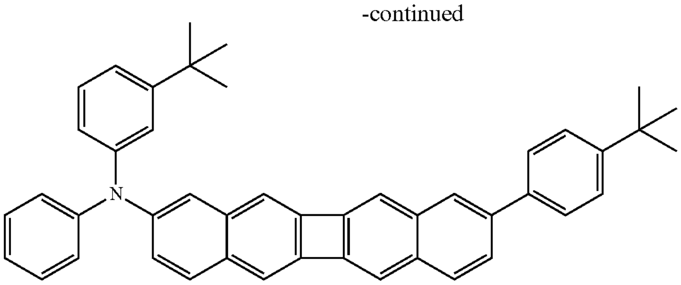
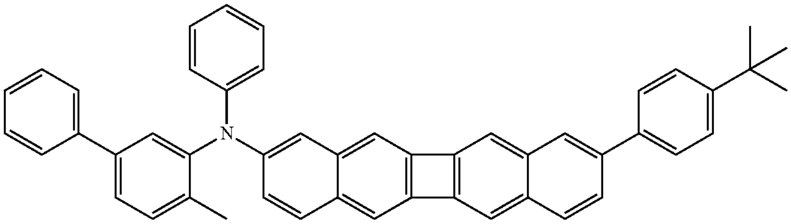
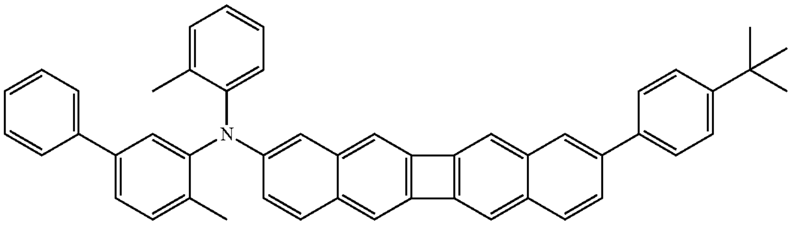
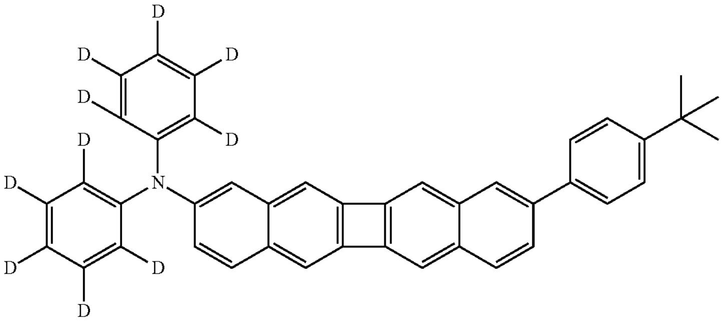
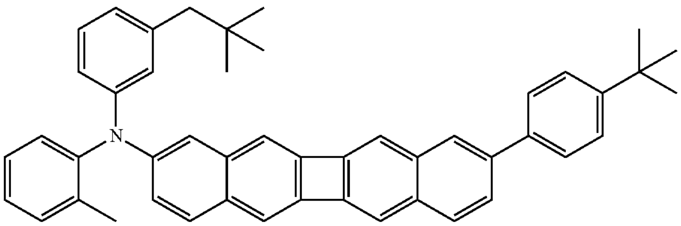
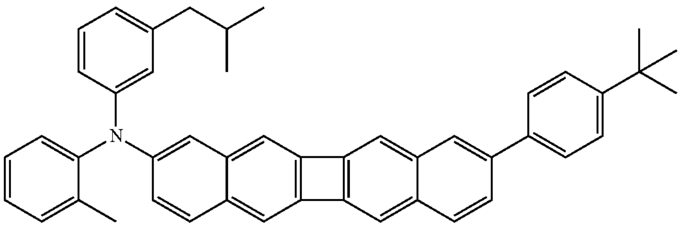
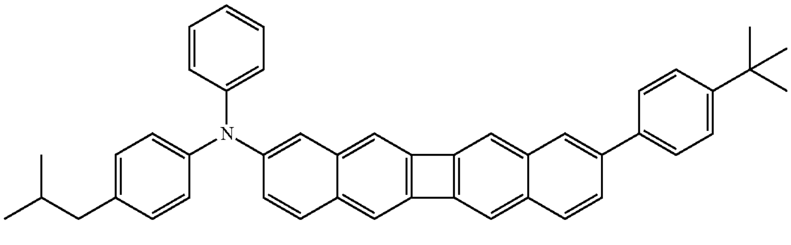

-continued
[Formula 110]
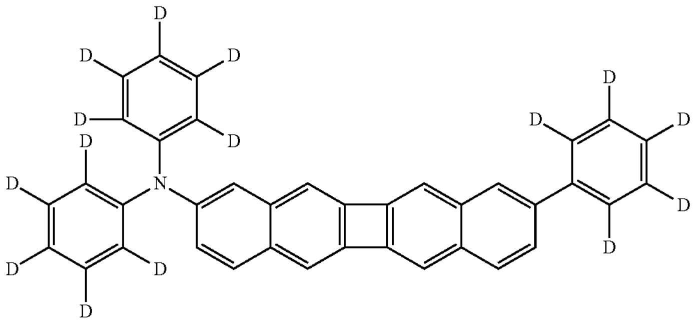
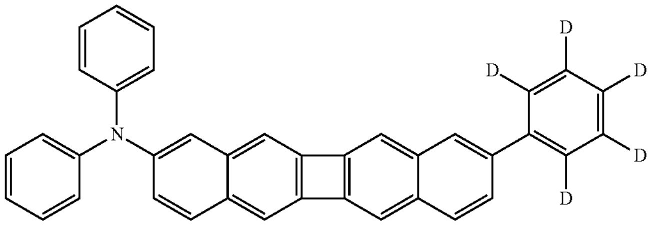
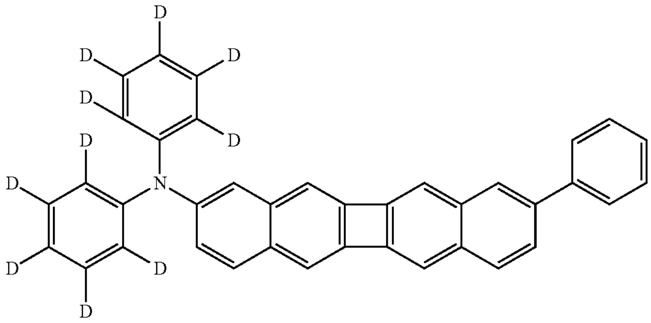
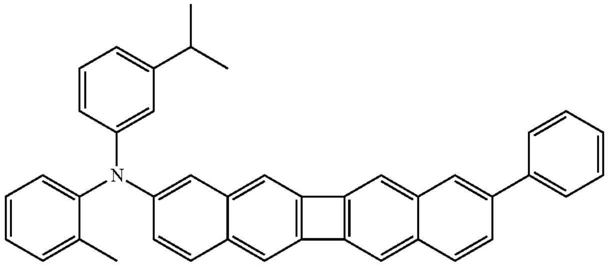
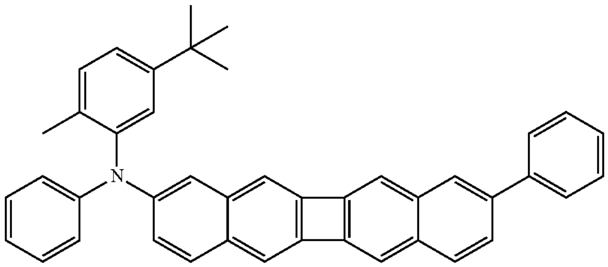
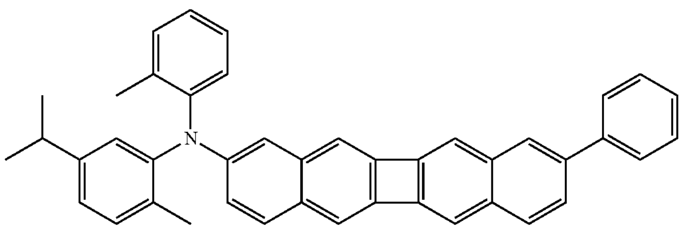

-continued
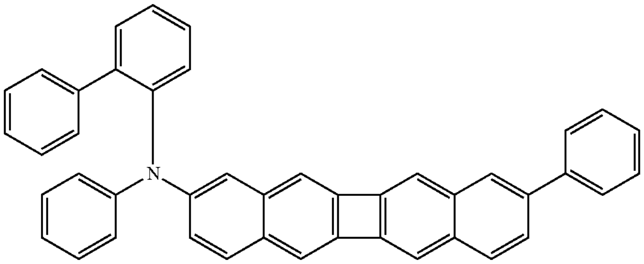
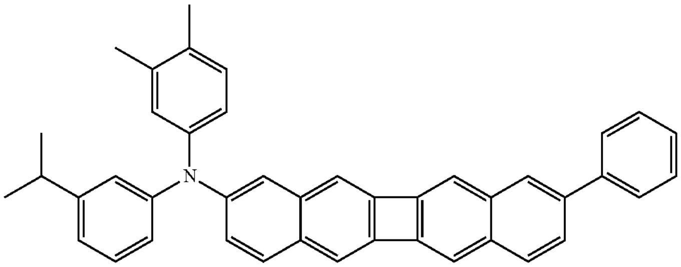
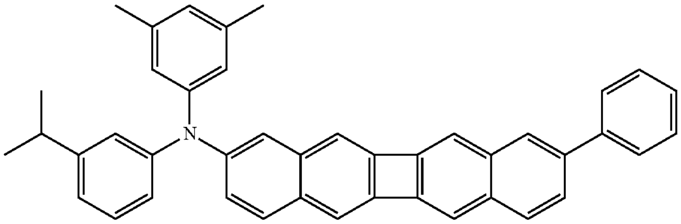
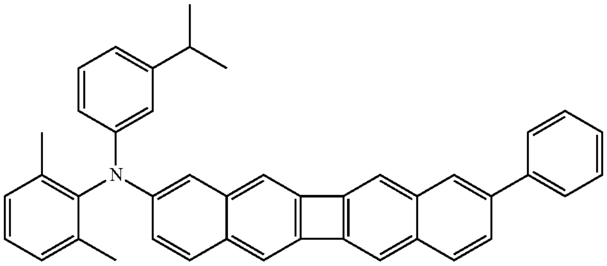
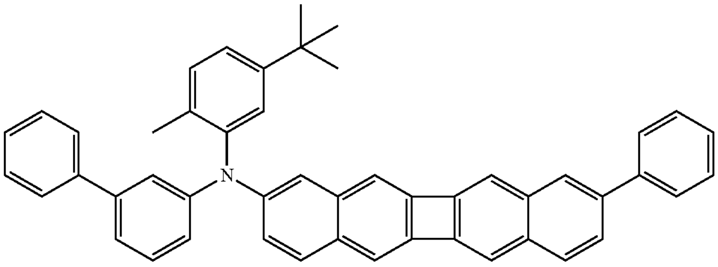
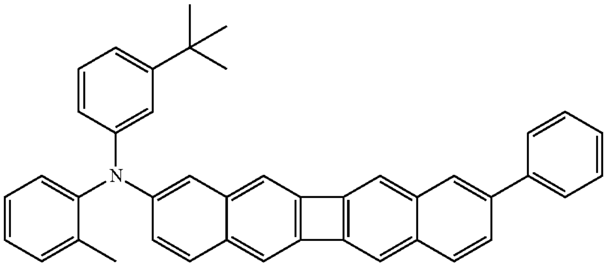

-continued
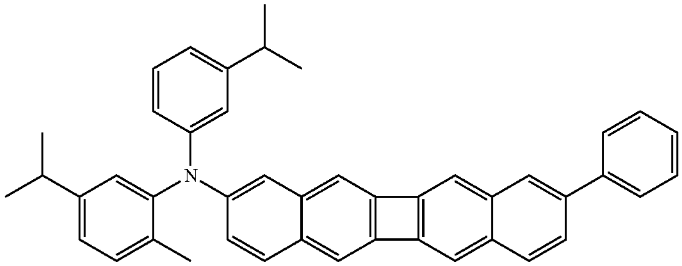
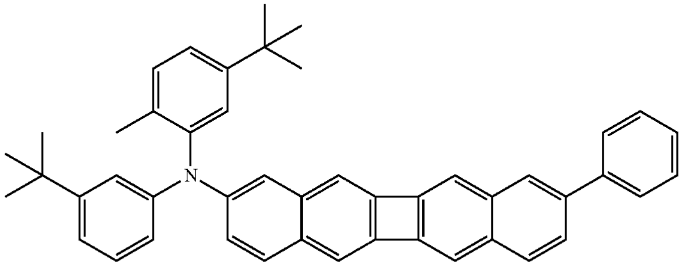
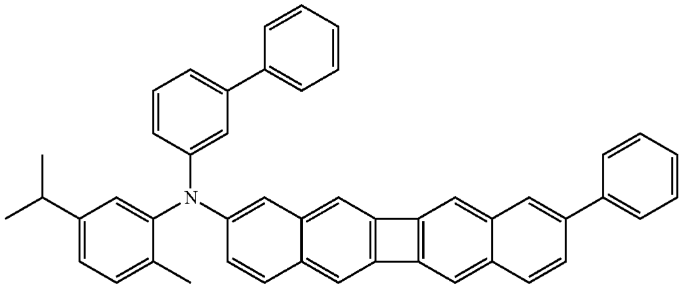
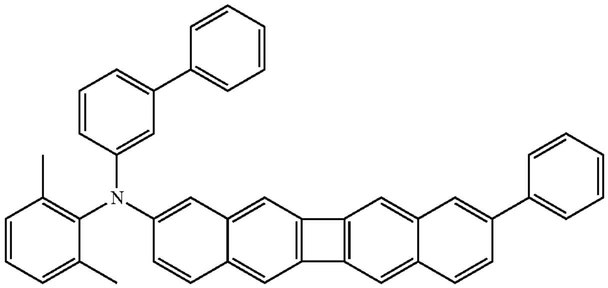
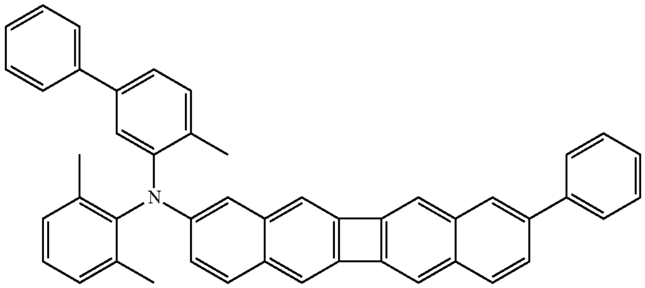
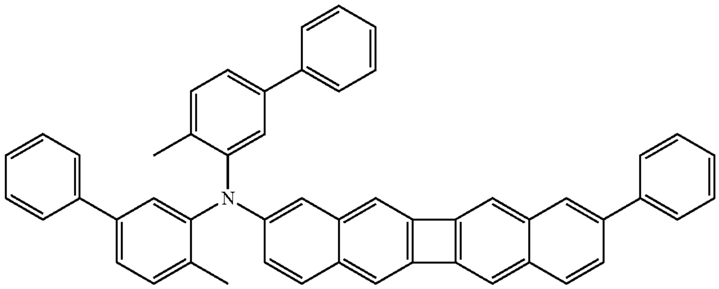

-continued
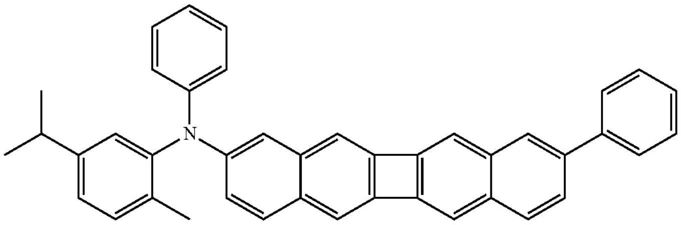
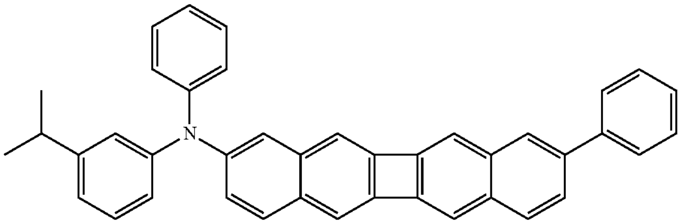
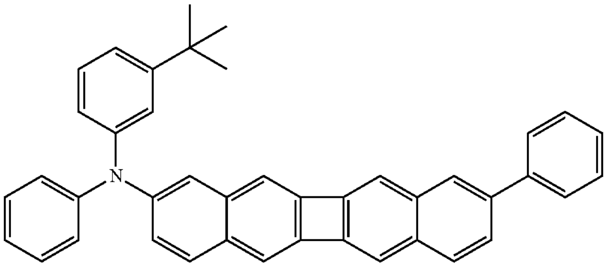
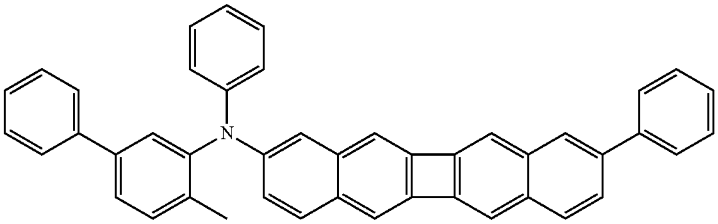
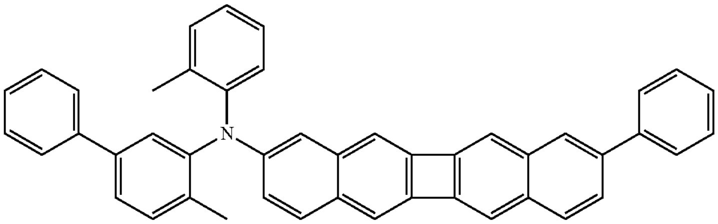
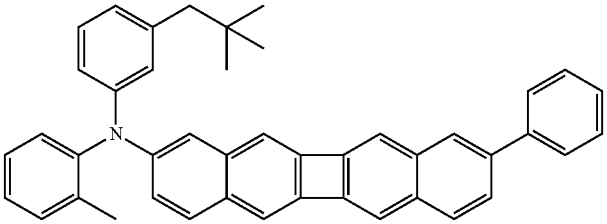
[Formula 111]
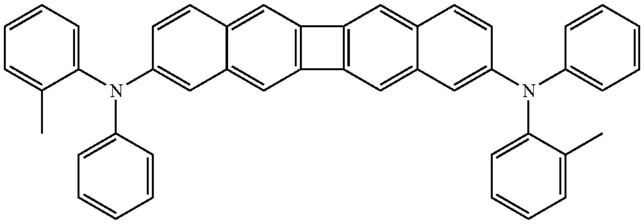

-continued
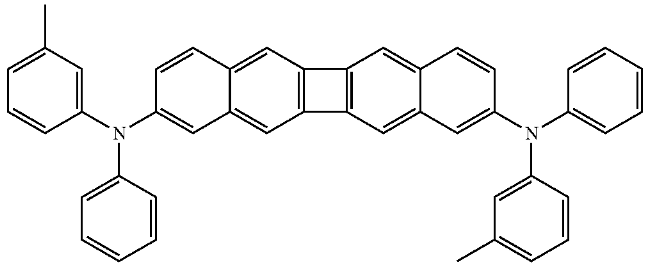
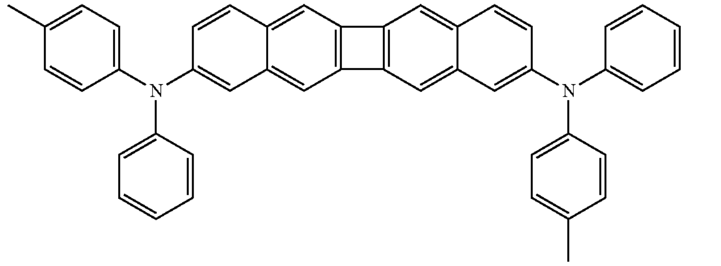
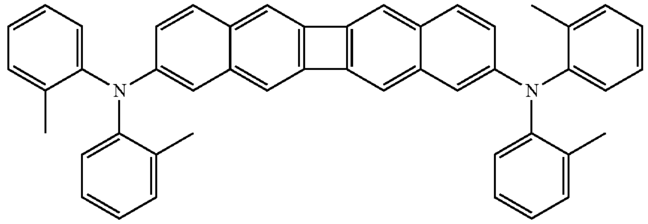
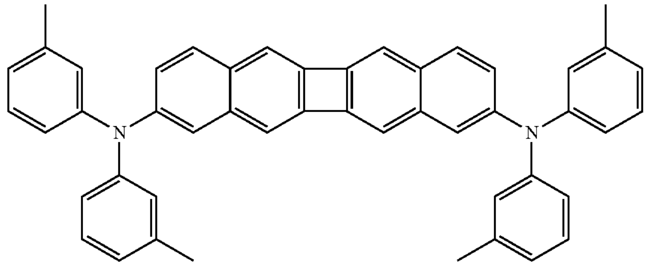
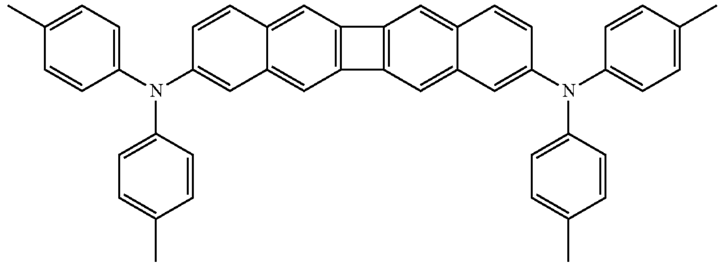
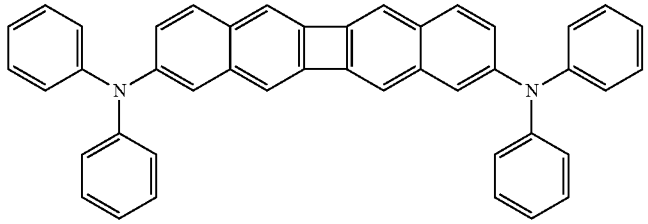

-continued
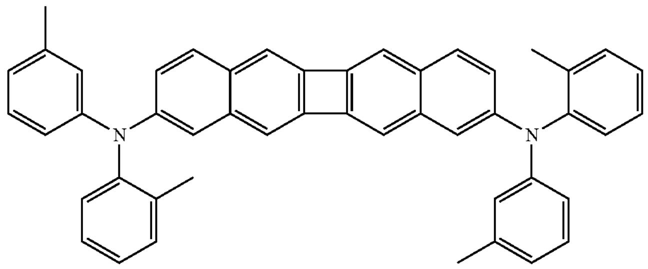
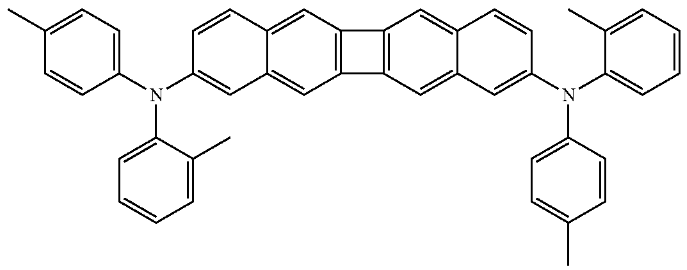
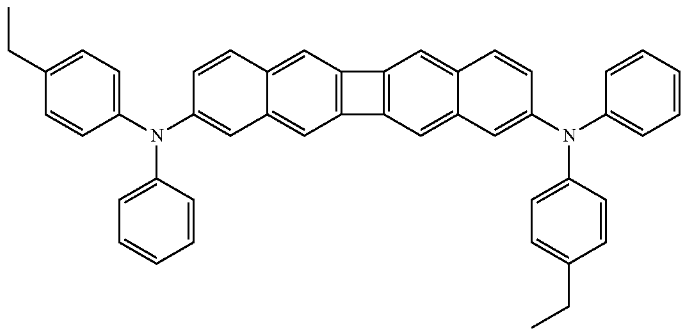
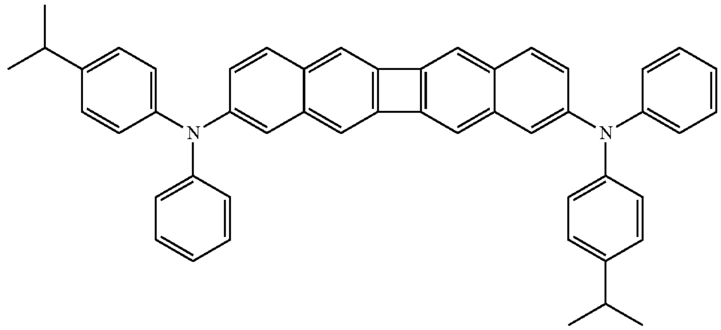
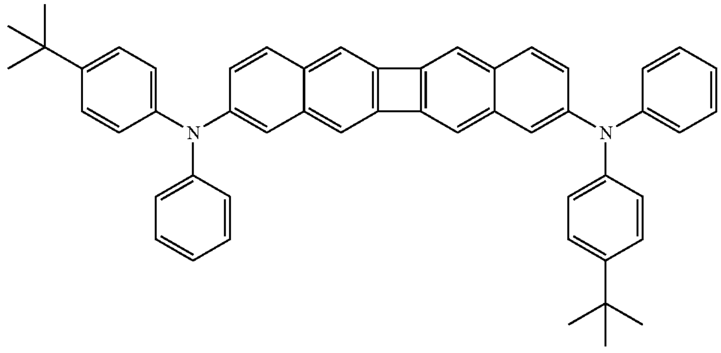

-continued
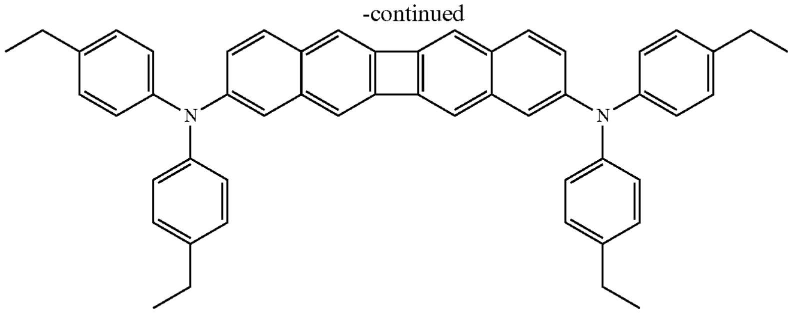
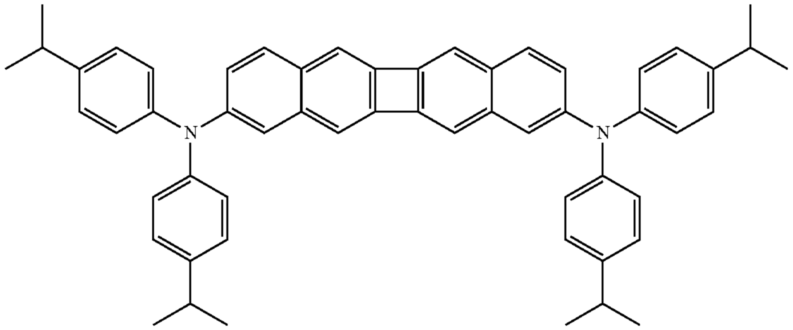
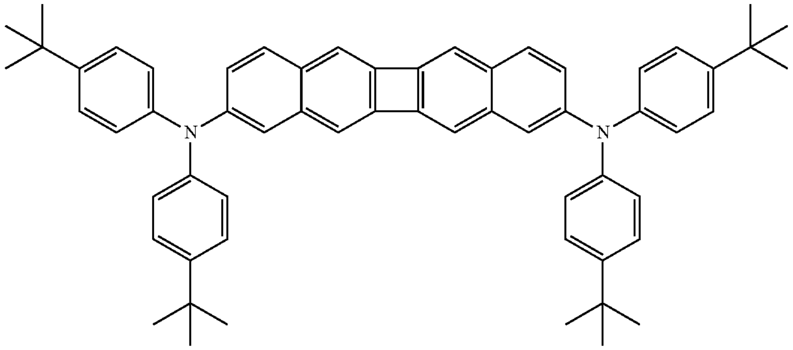
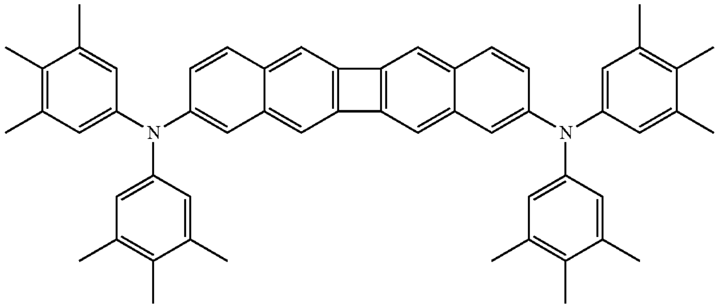
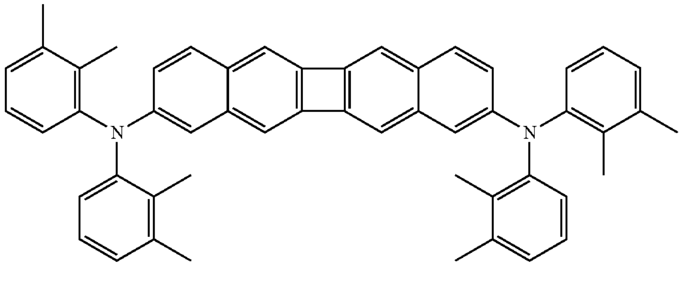

-continued
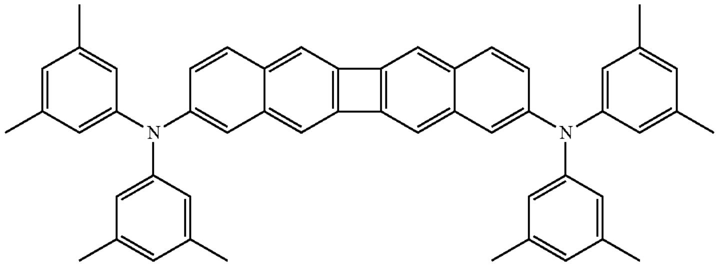
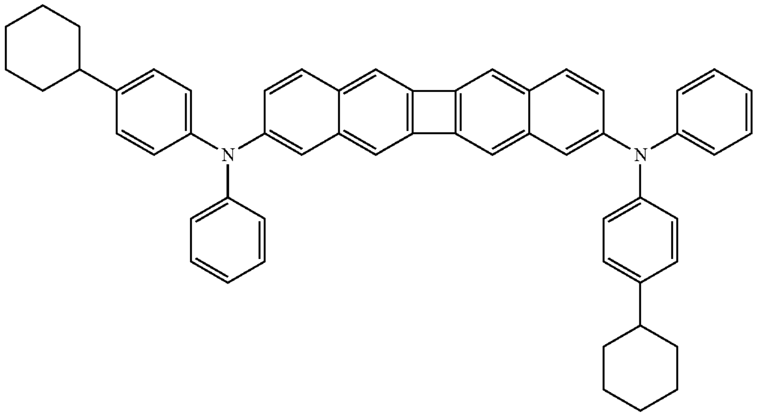
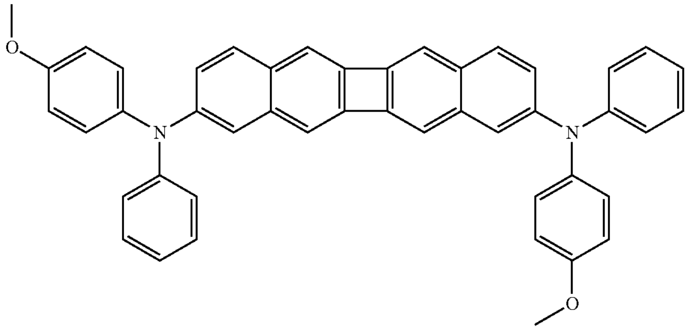
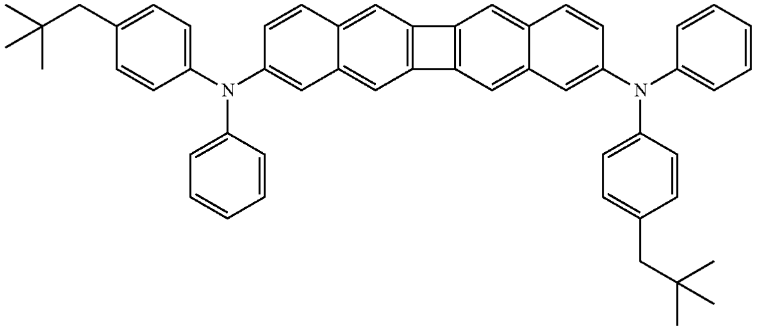

-continued
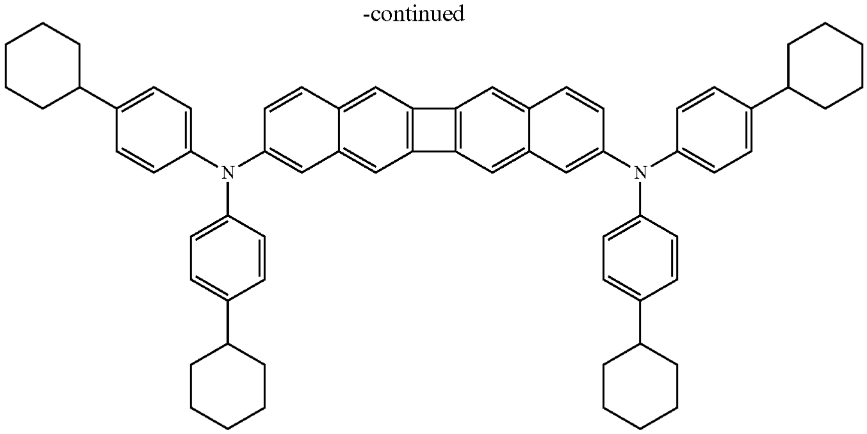
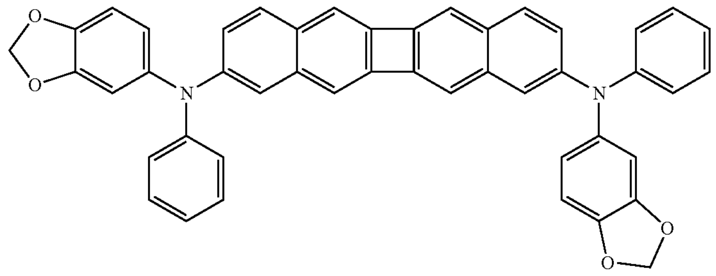
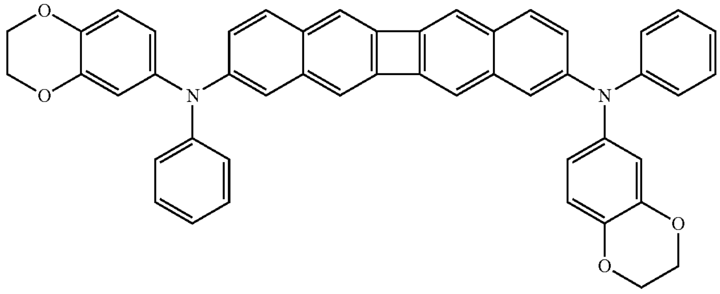
[Formula 112]
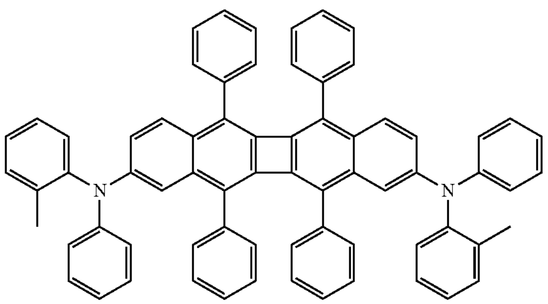
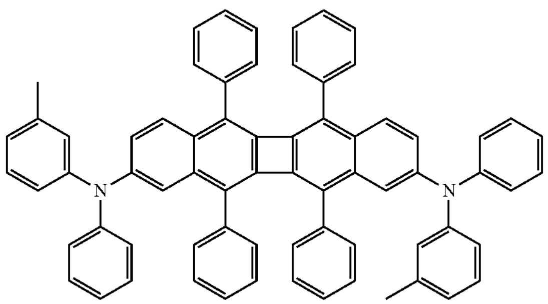

-continued
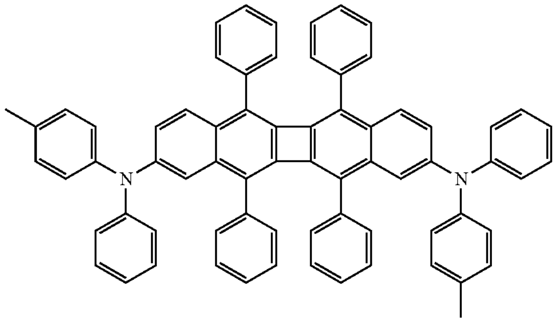
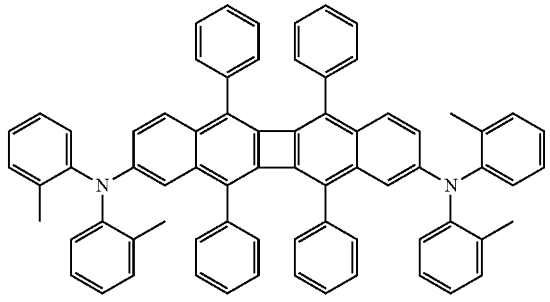
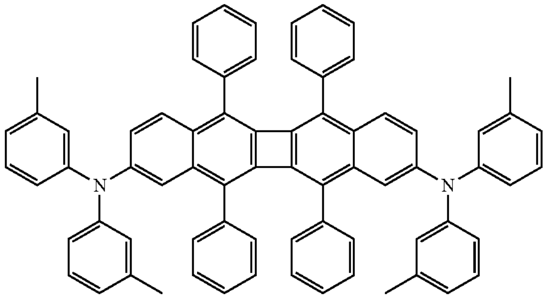
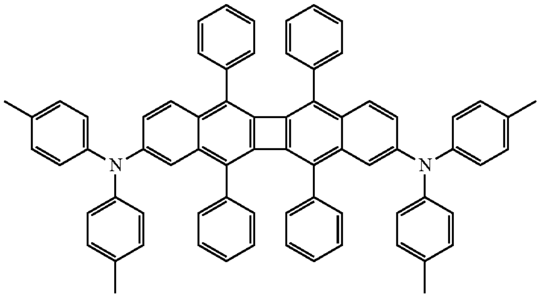
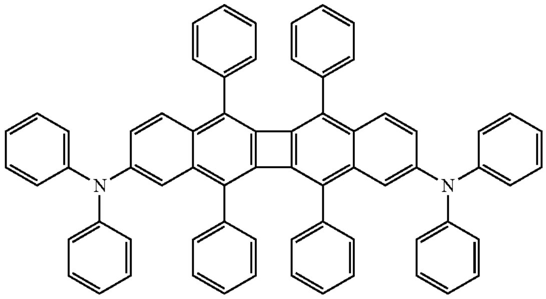
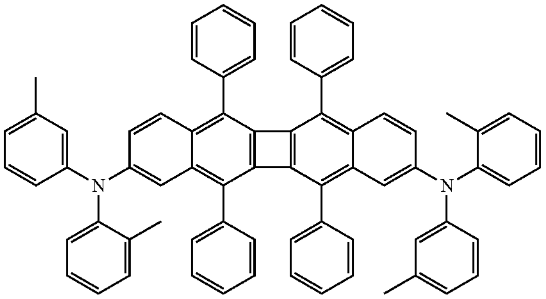
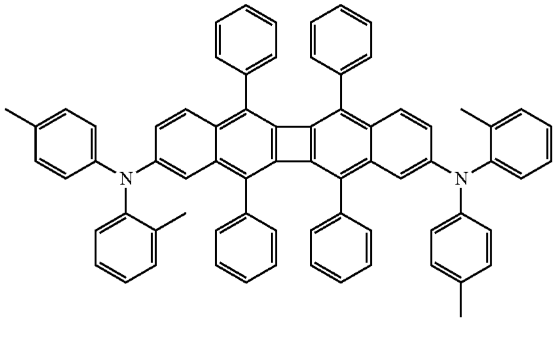
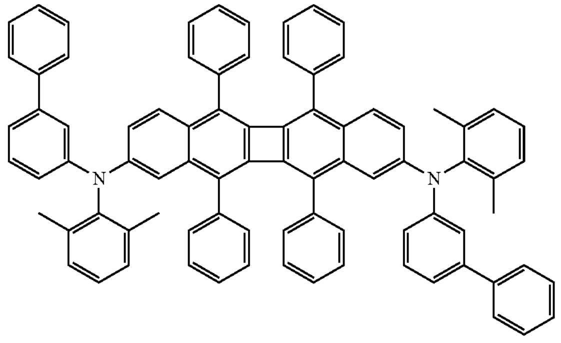
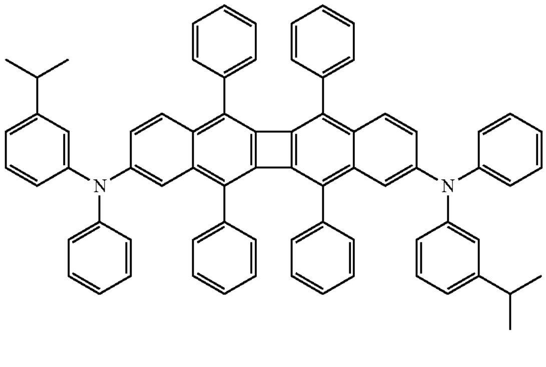
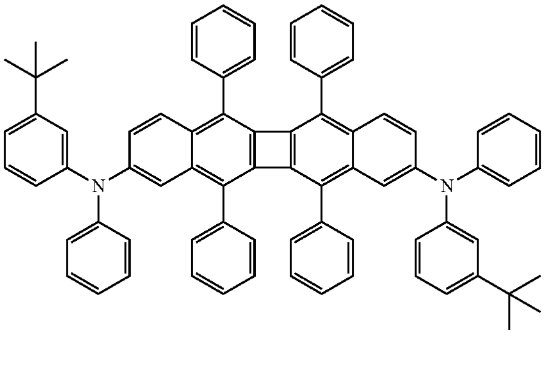

-continued
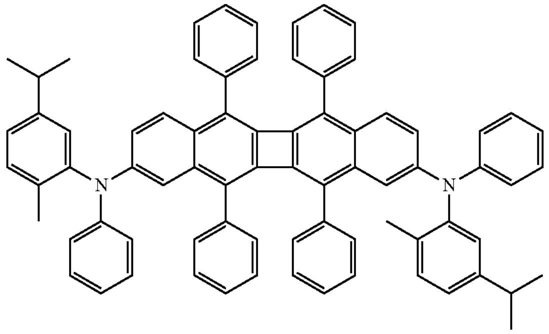
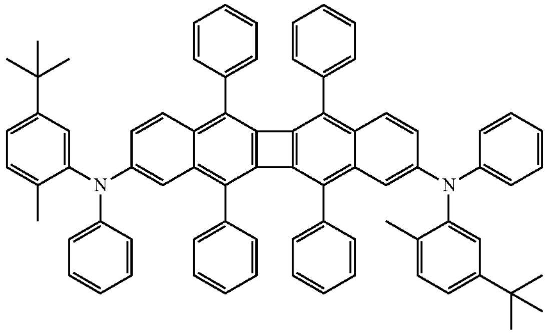
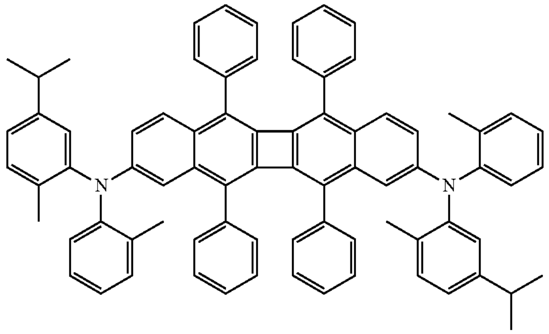
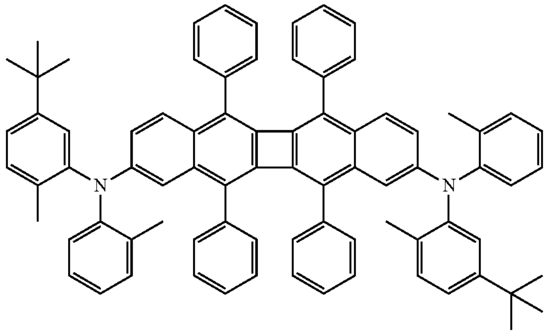
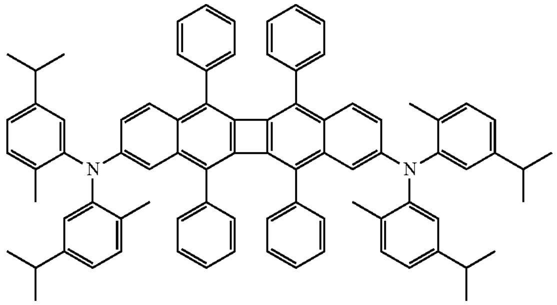
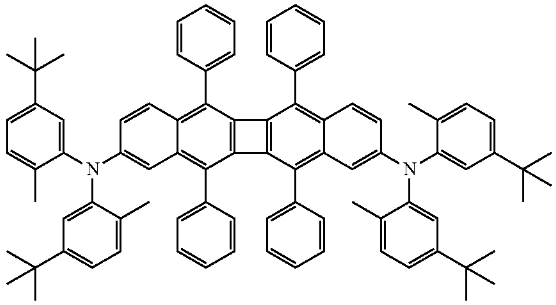
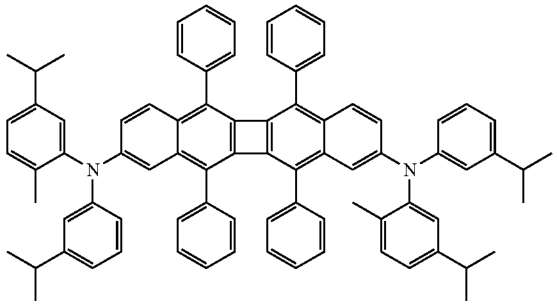
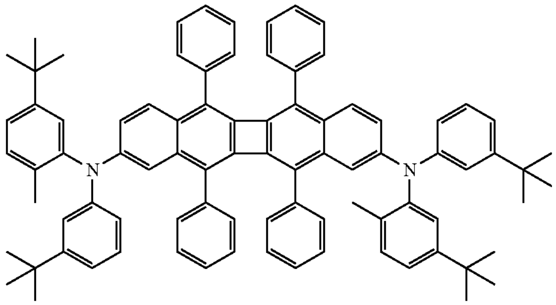
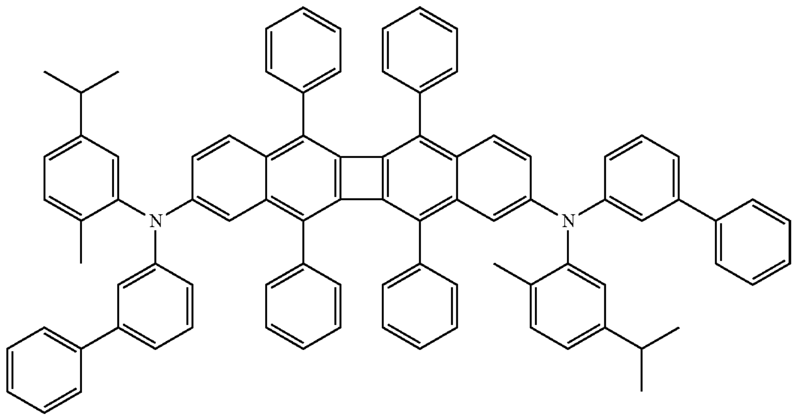

-continued
[Formula 113]
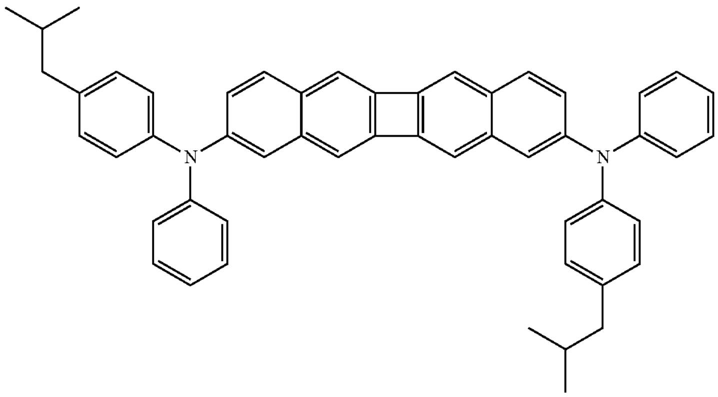
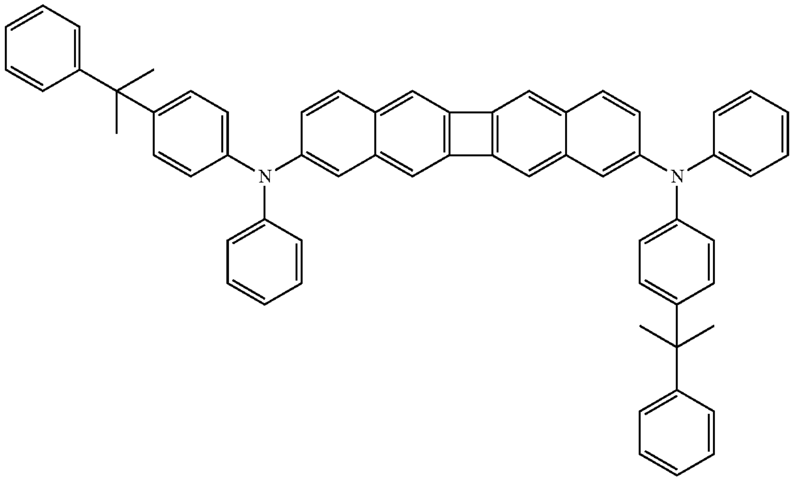
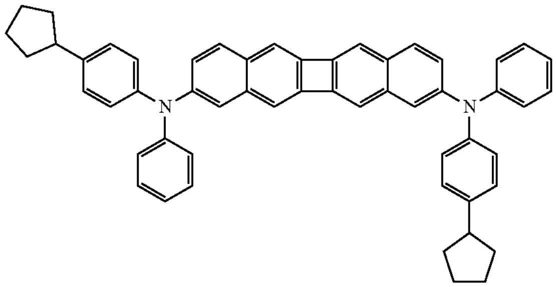
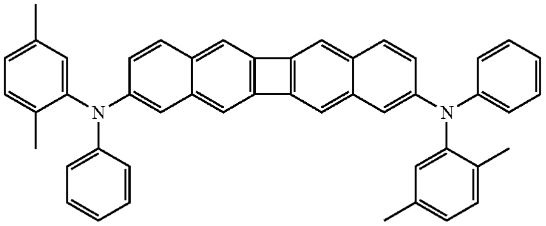
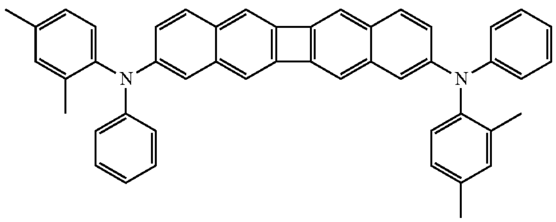
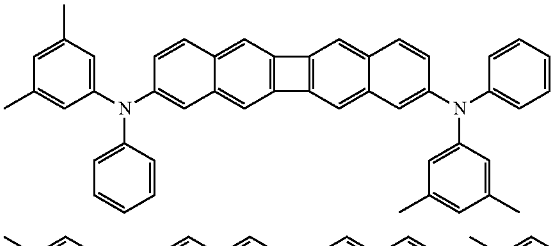
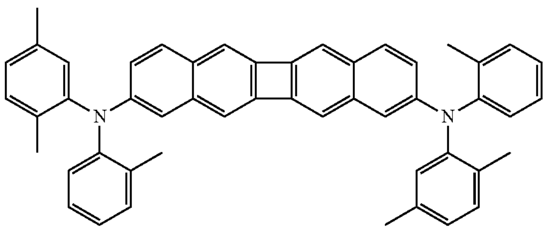
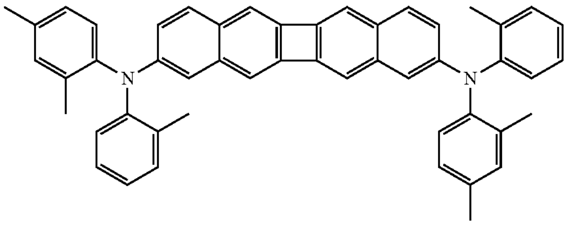

-continued
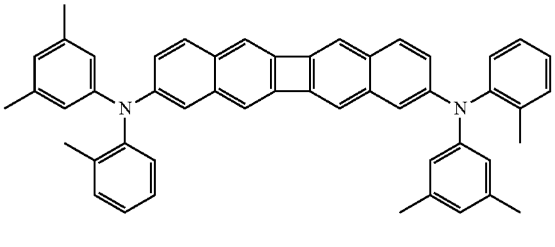
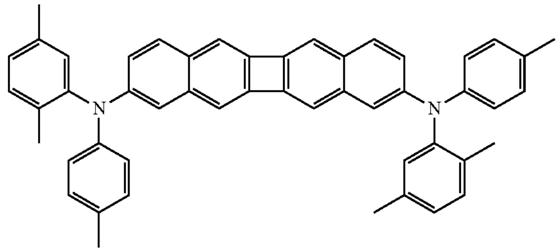
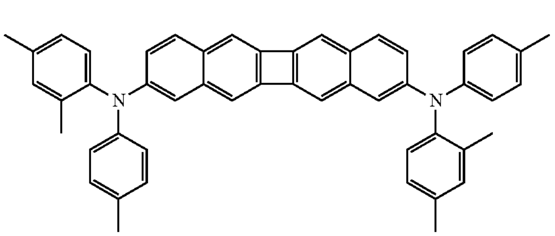
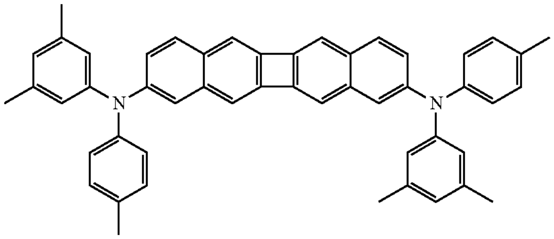
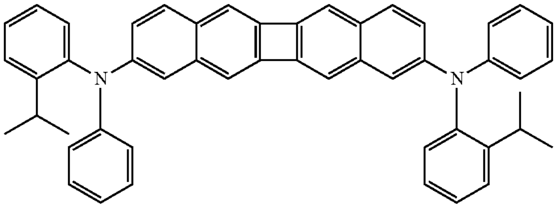
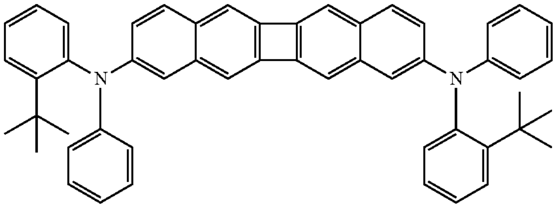
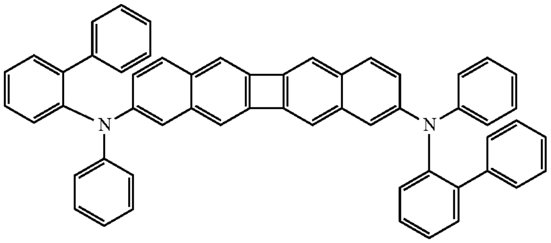
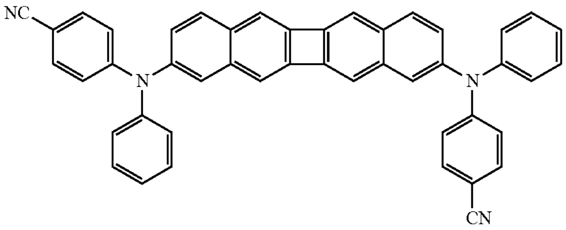
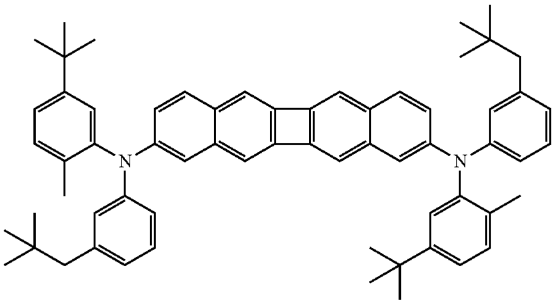
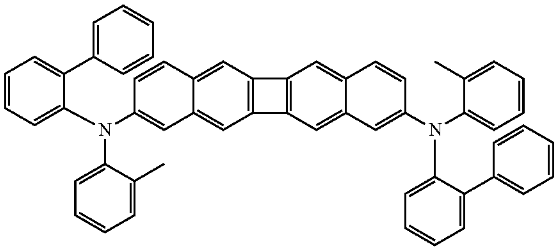
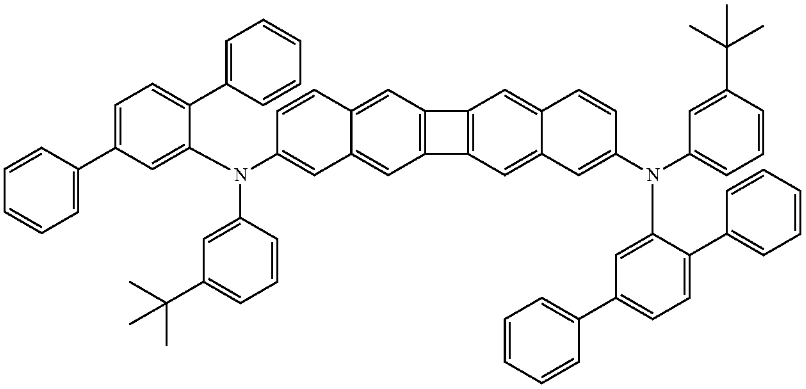

-continued
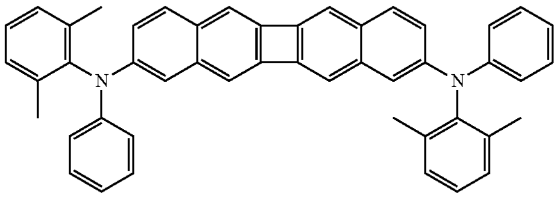
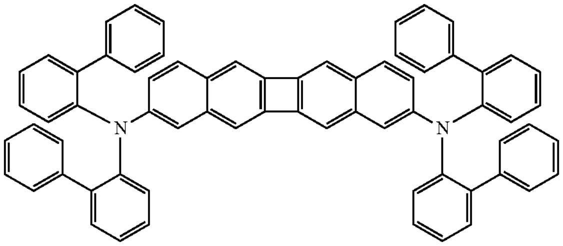
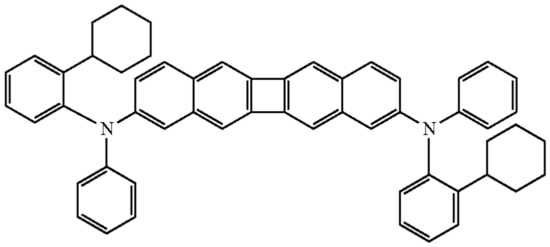
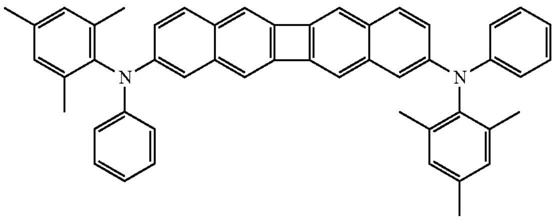
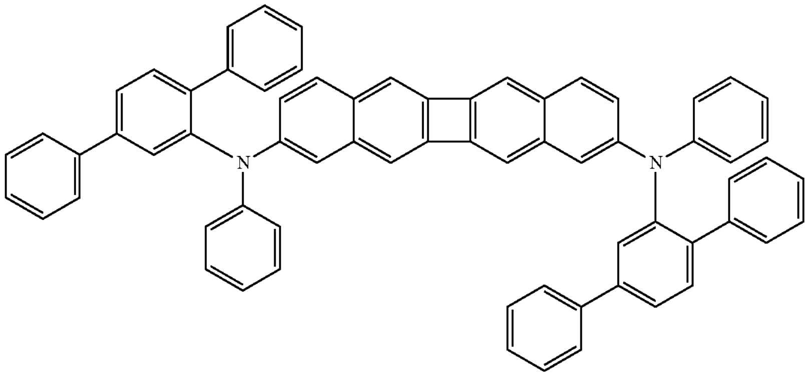
[Formula 114]
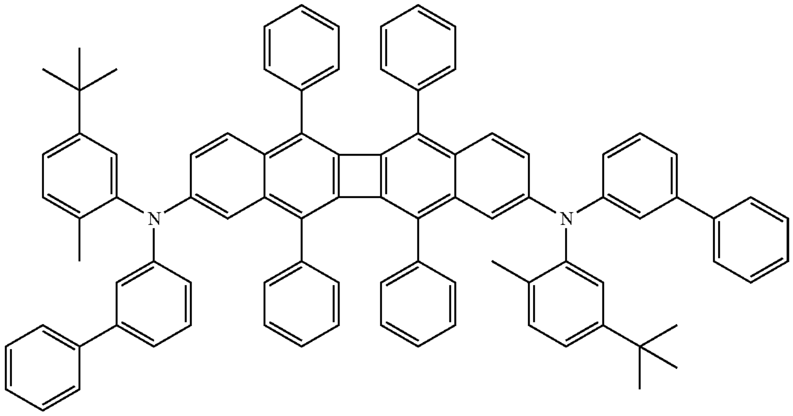

-continued
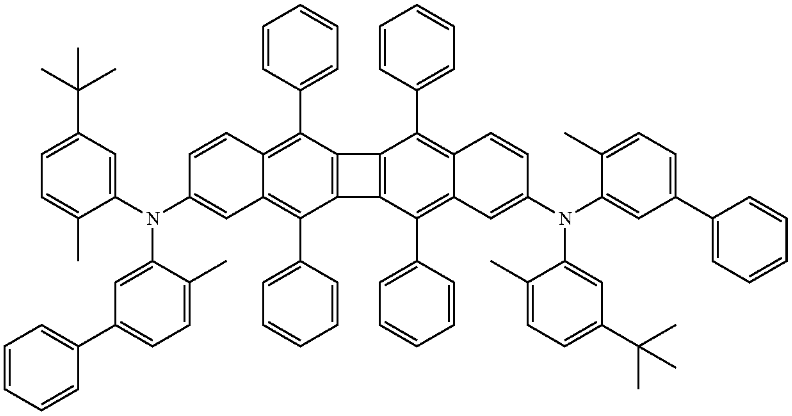
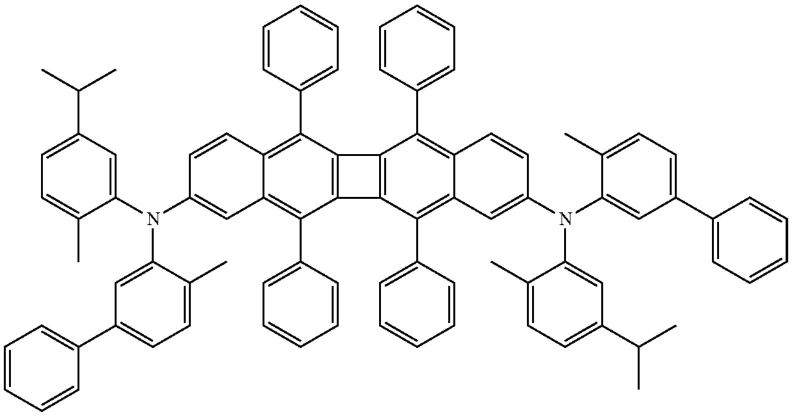
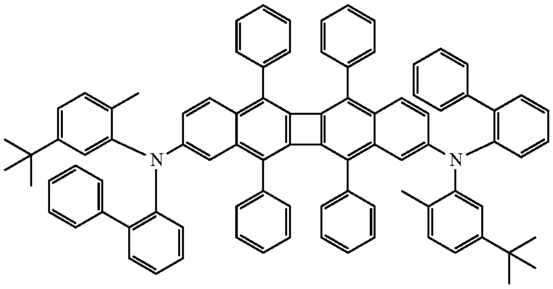
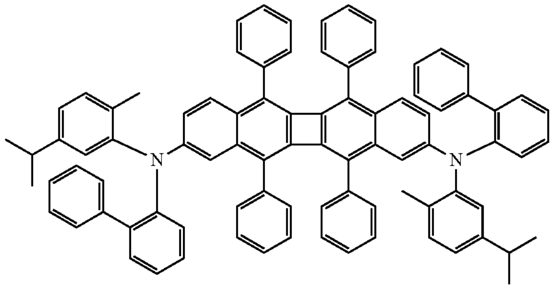
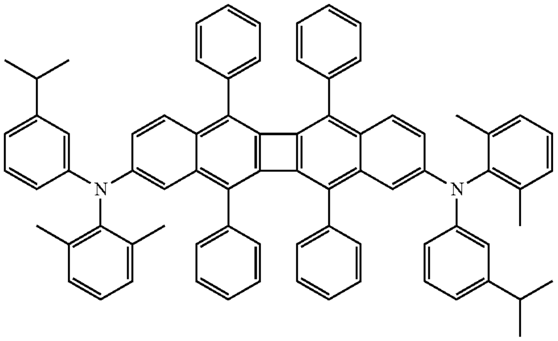
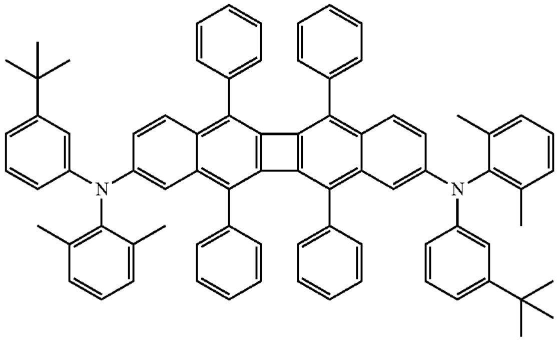

-continued
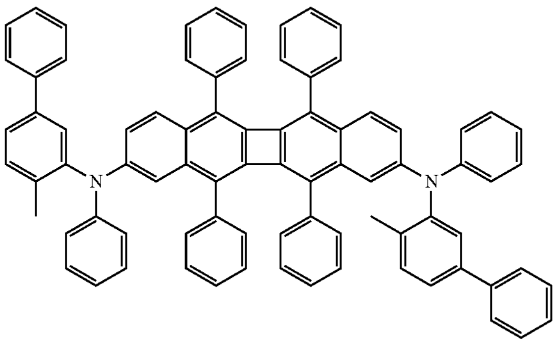
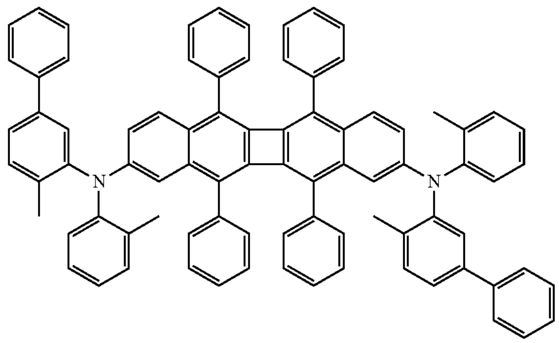
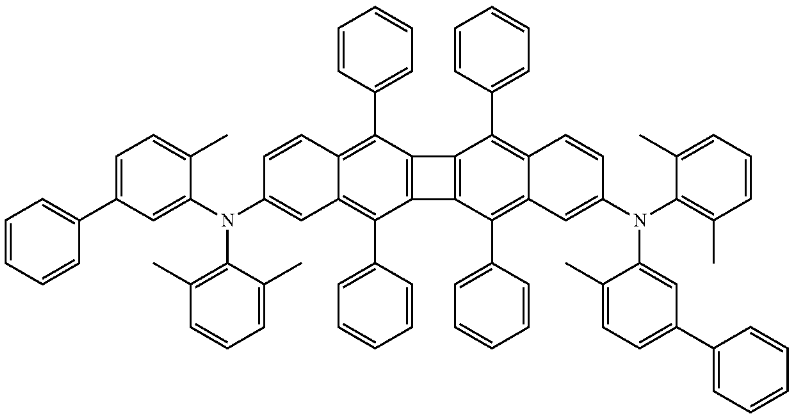
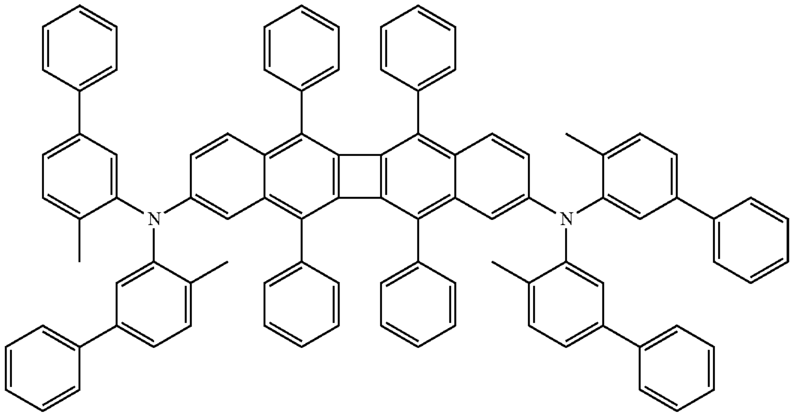
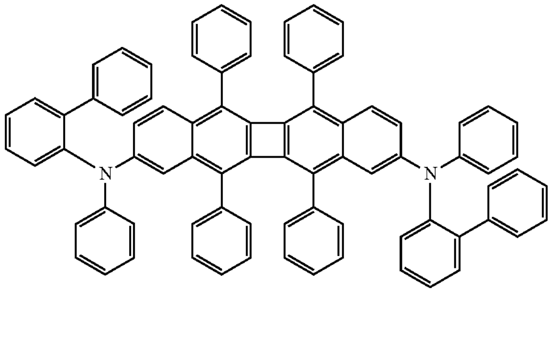
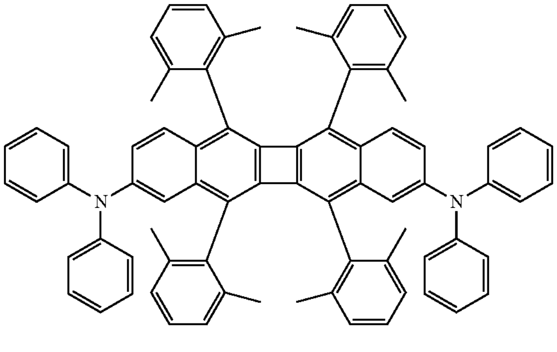

-continued
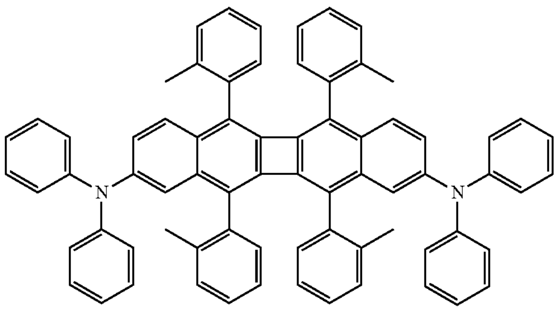
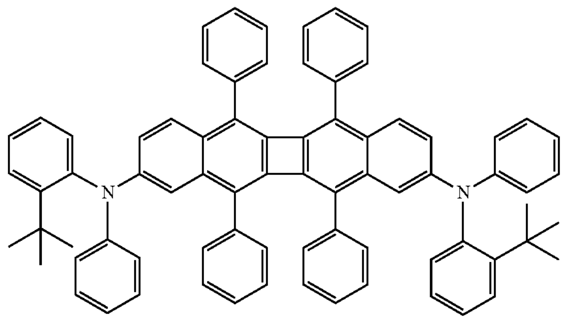
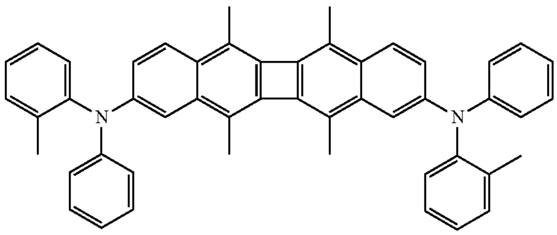
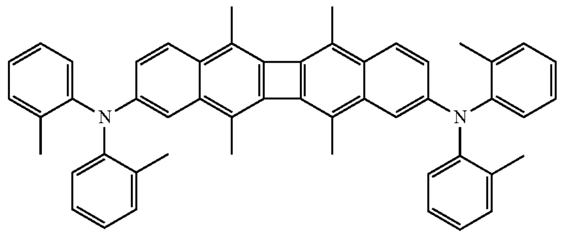
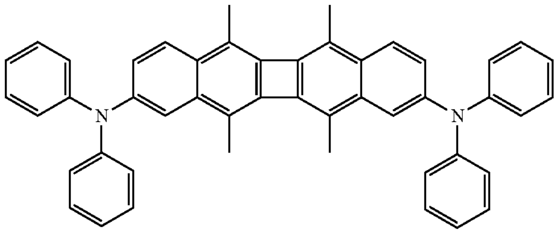
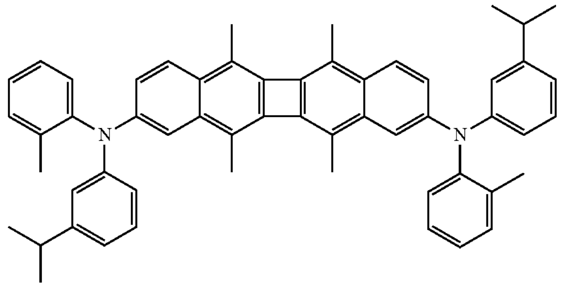
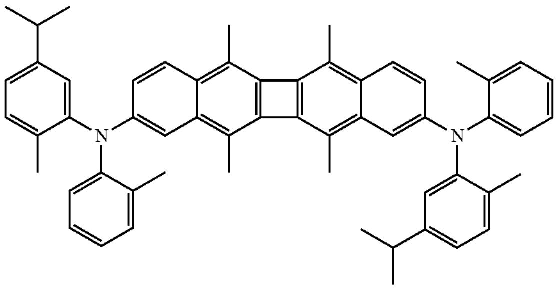
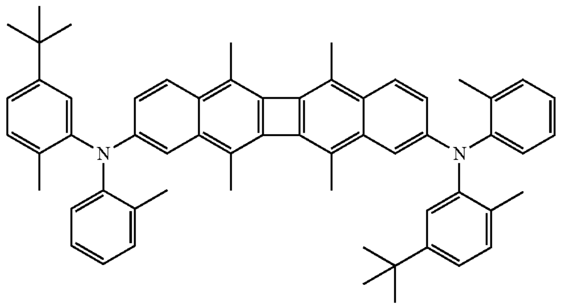
[Formula 115]
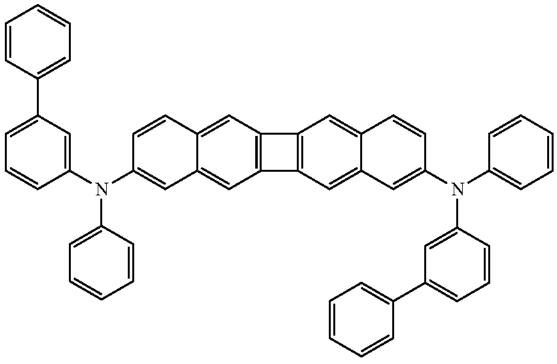
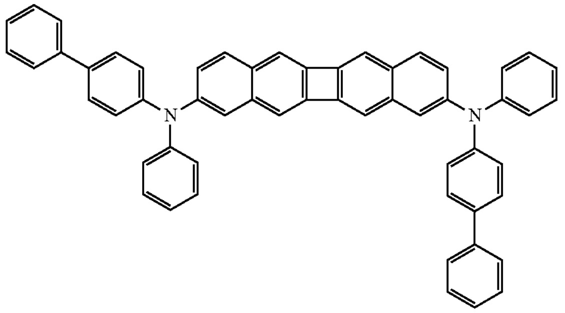

-continued
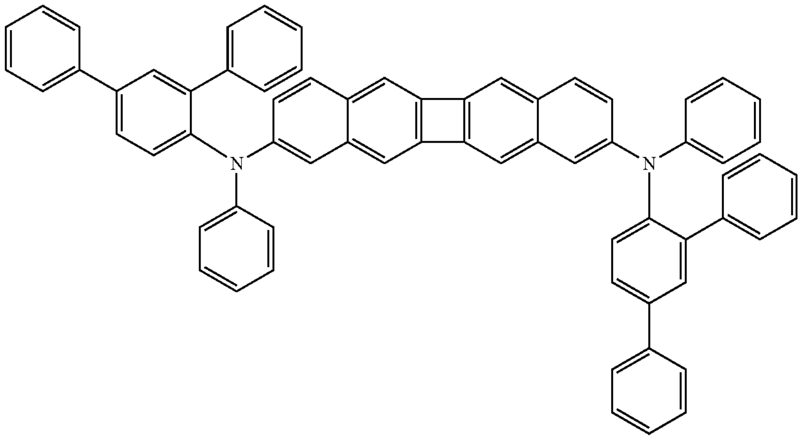
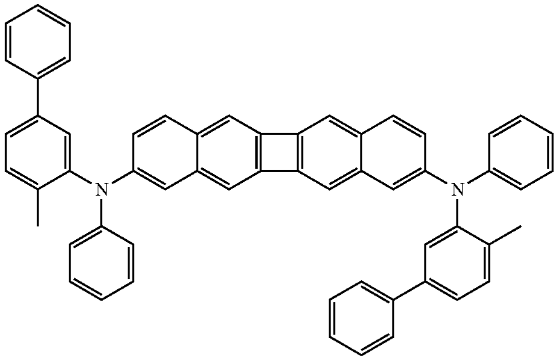
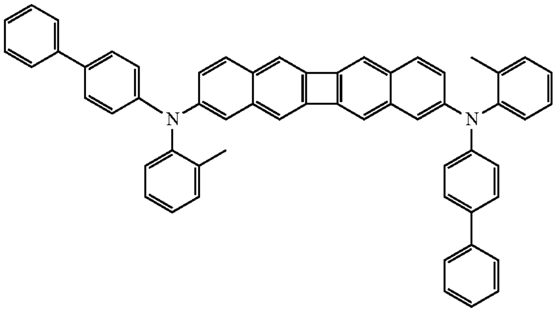
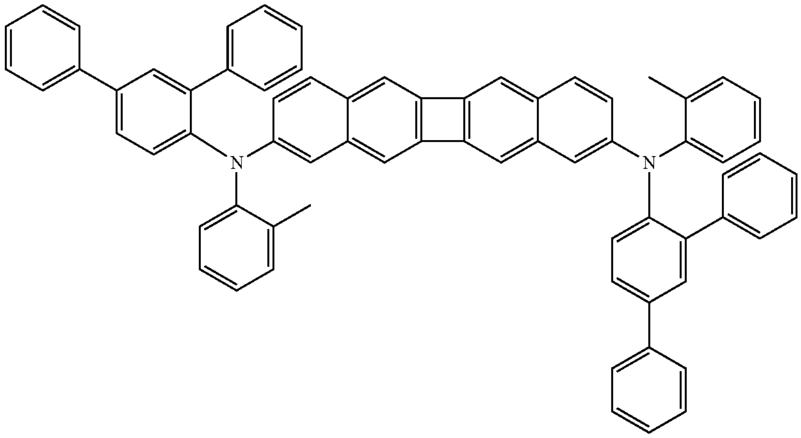
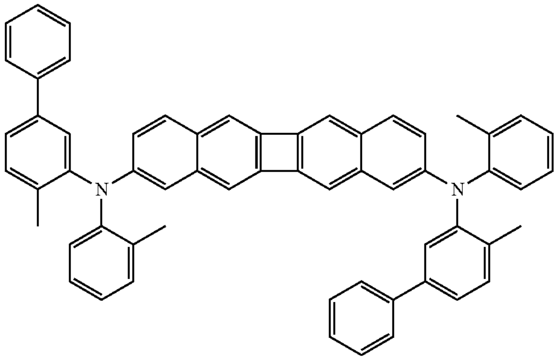
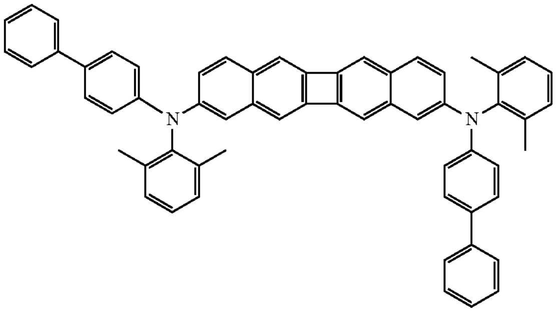

-continued
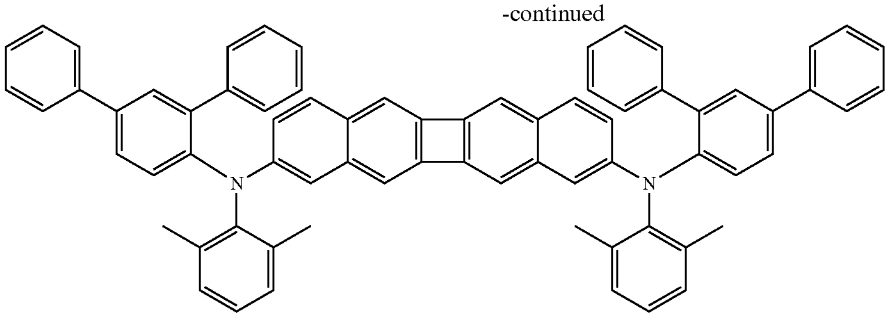
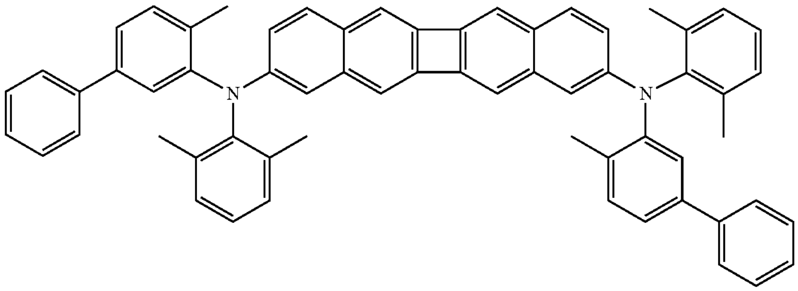
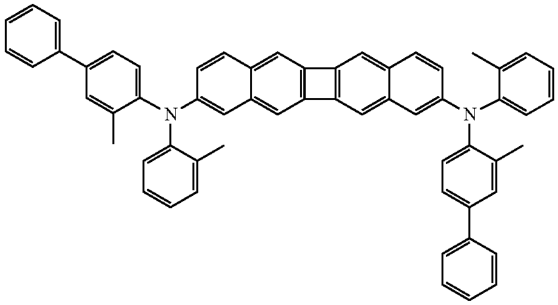
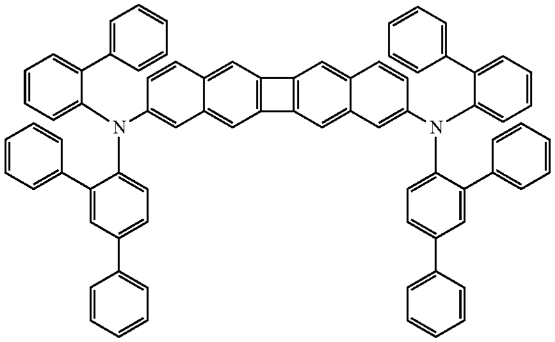
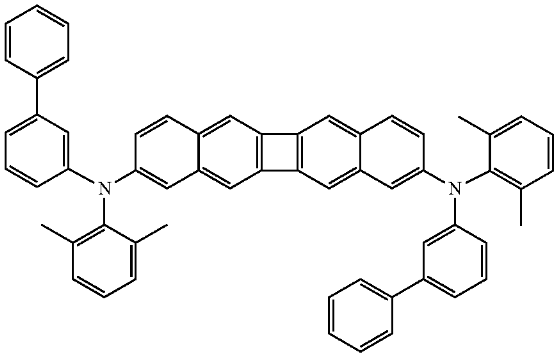
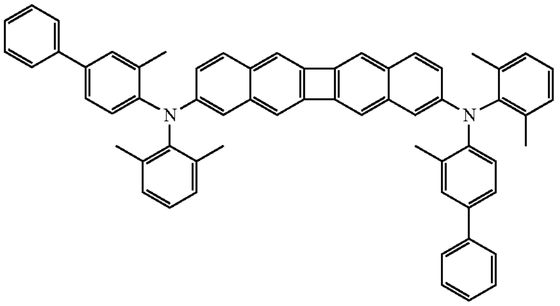
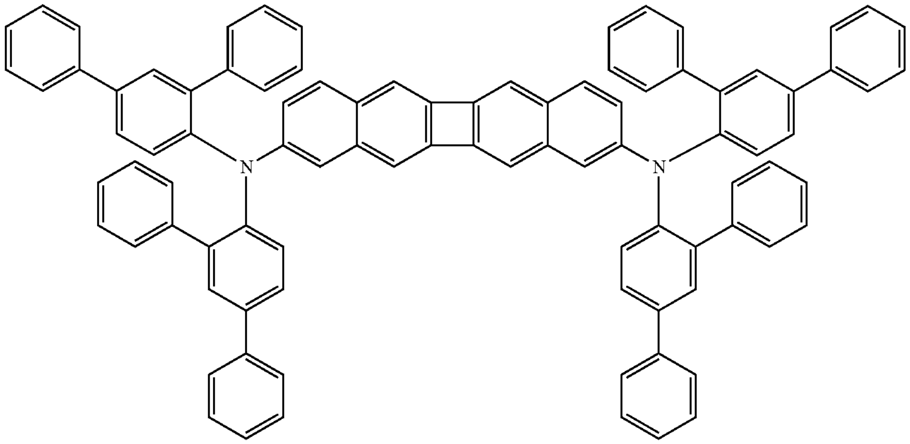

-continued
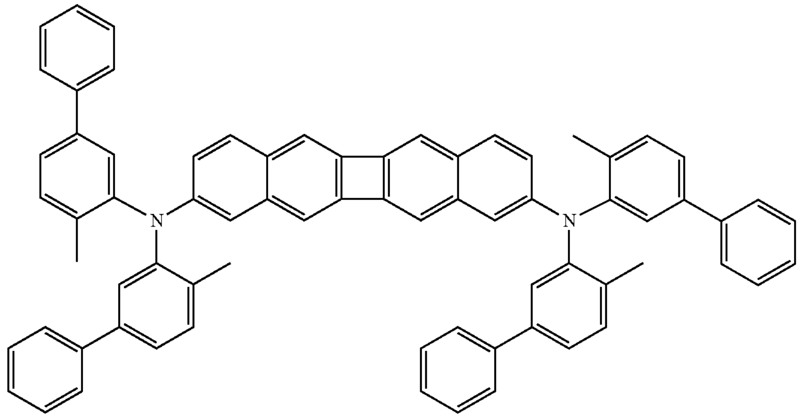
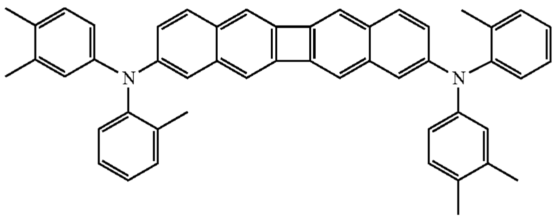
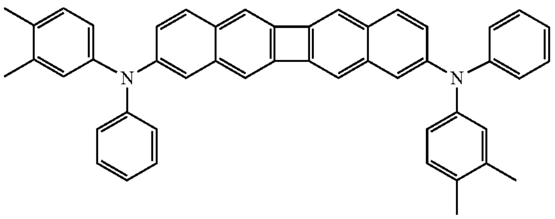
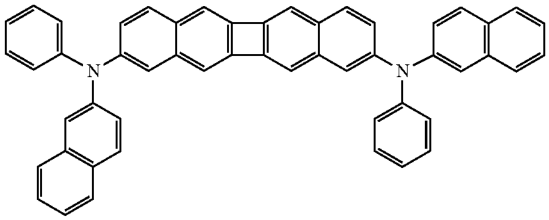
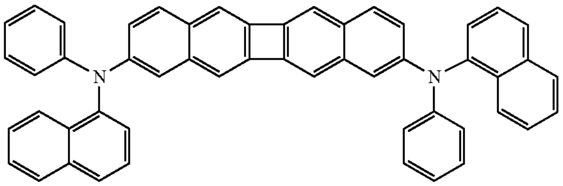
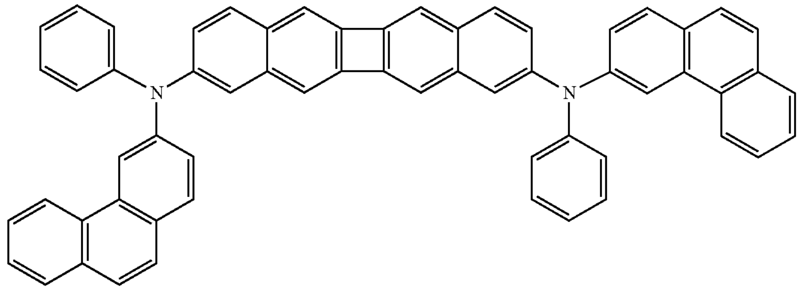
[Formula 116]
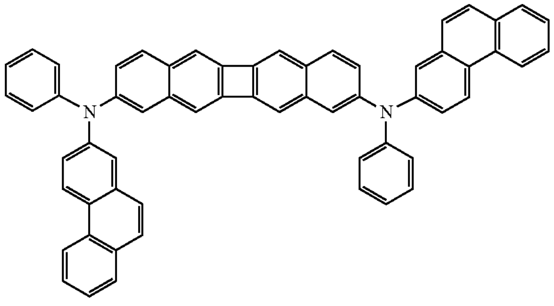
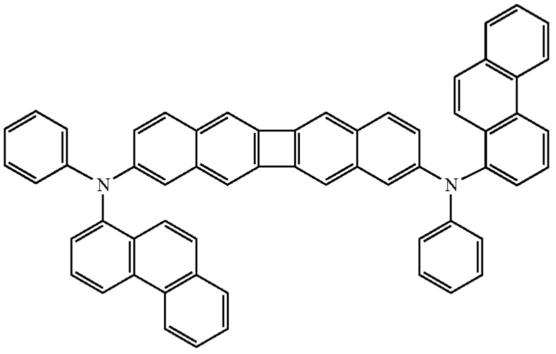

-continued
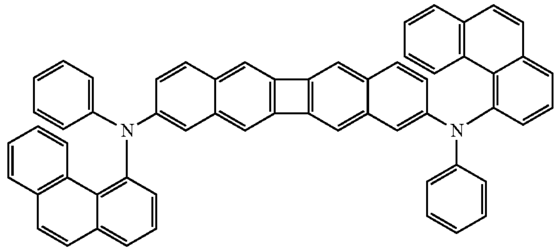
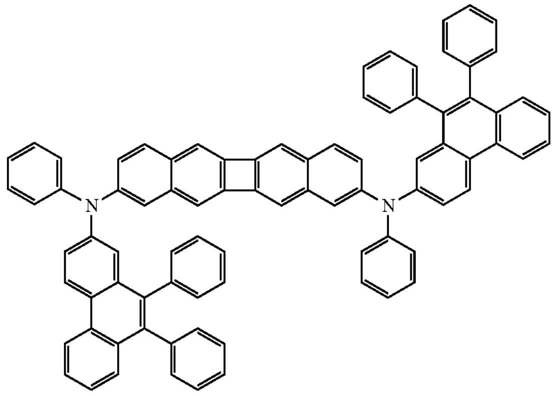
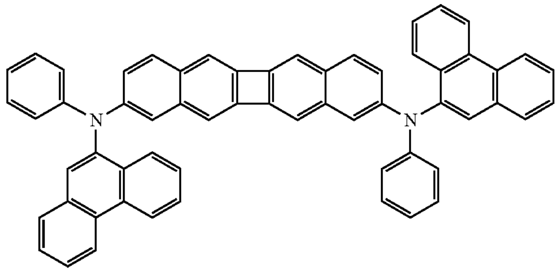
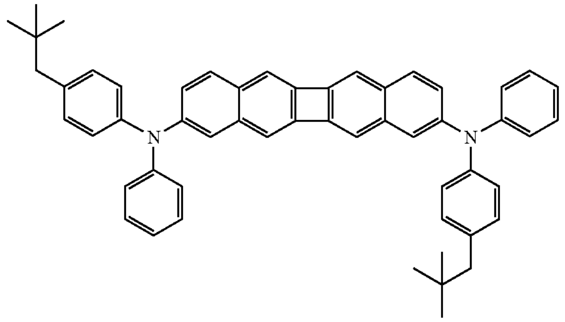
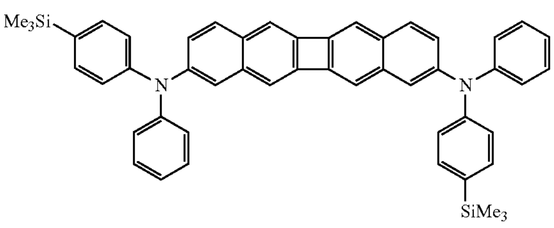
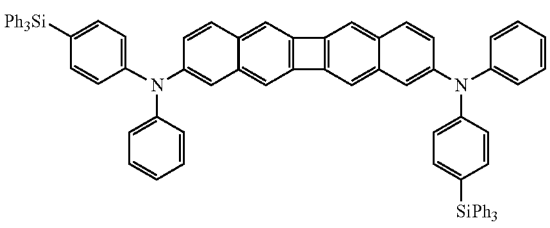
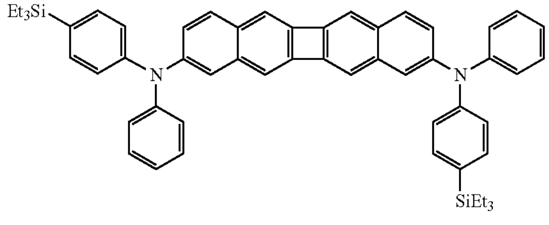
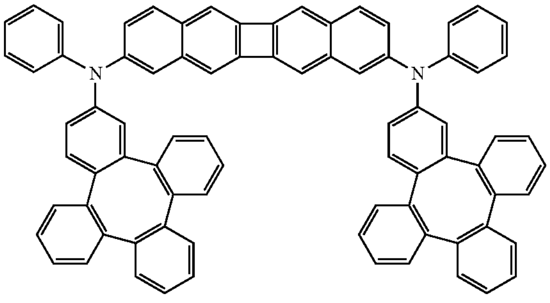
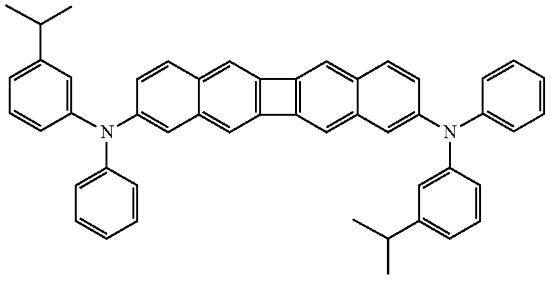
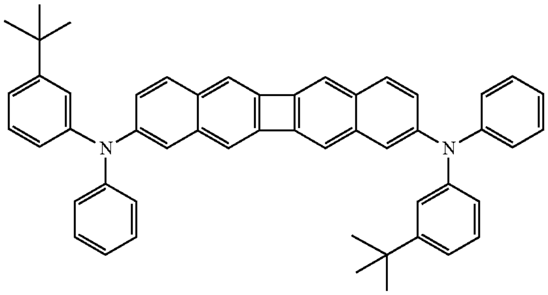

-continued
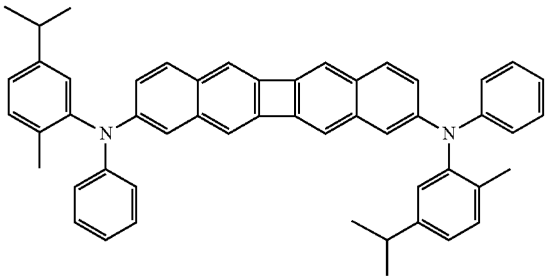
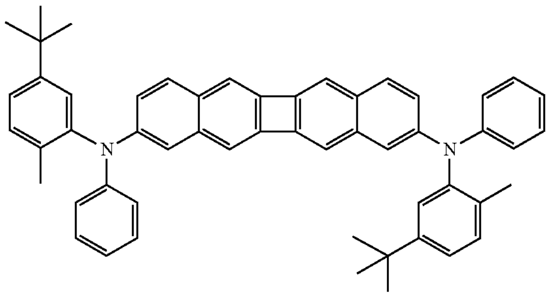
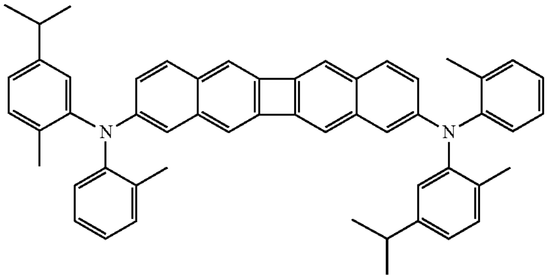
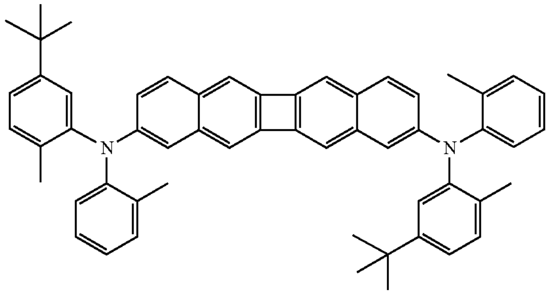
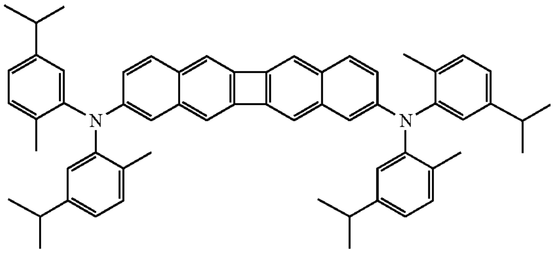
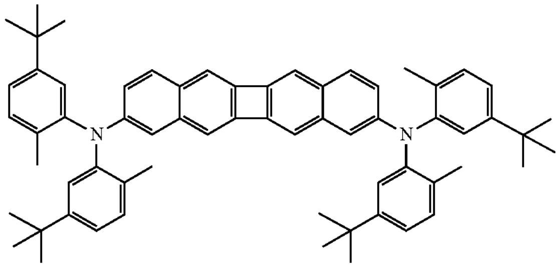
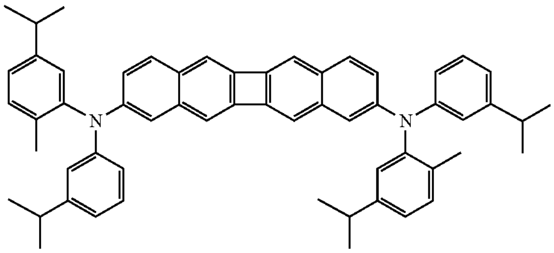
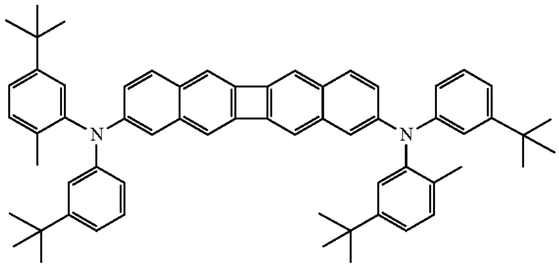
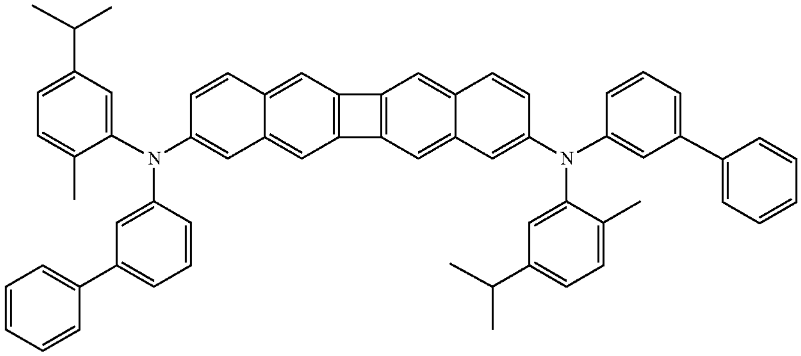

-continued
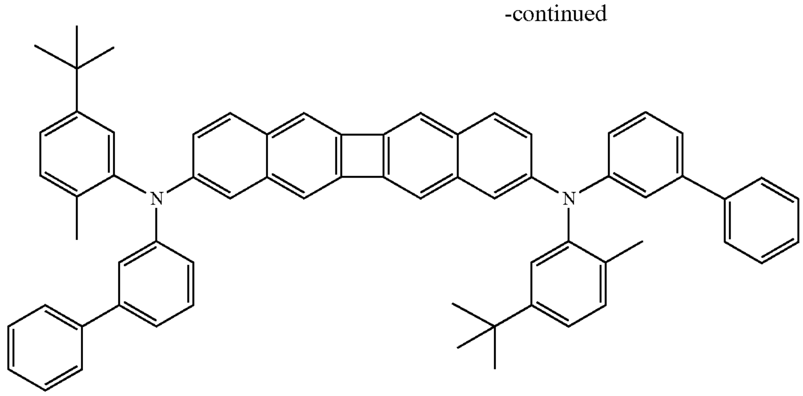
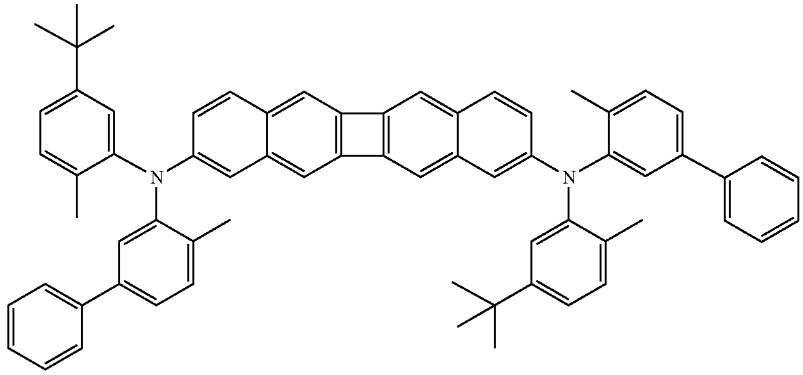
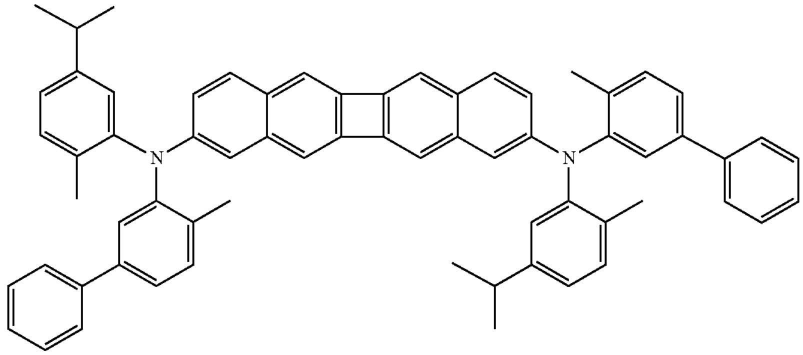
[Formula 117]
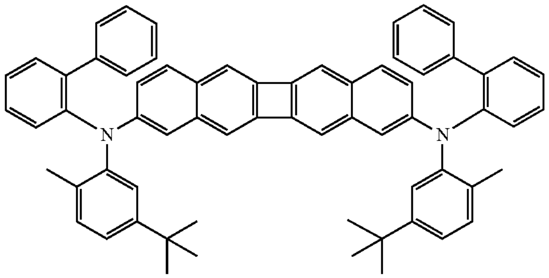
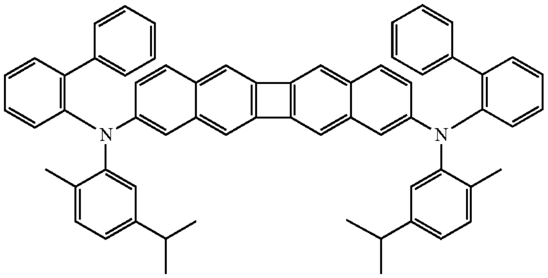
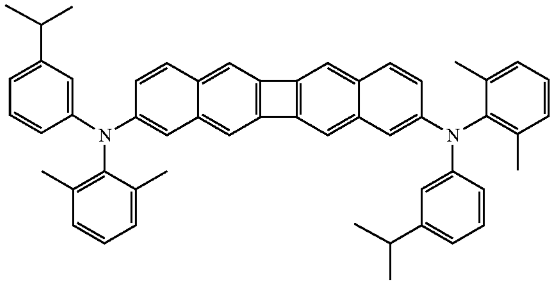
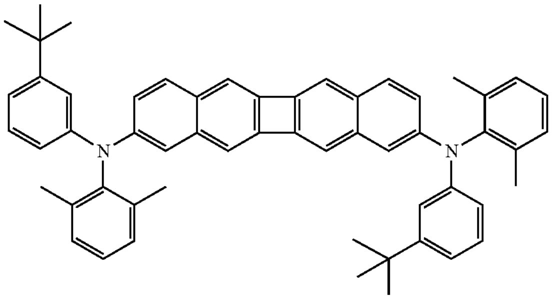

-continued
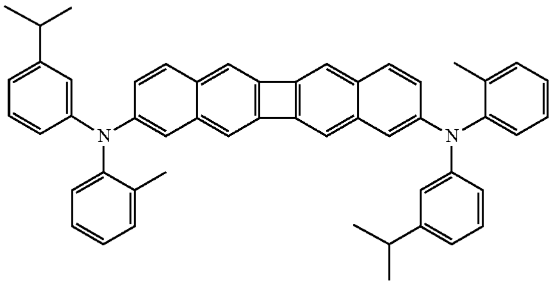
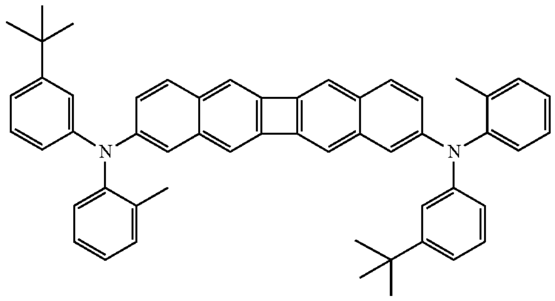
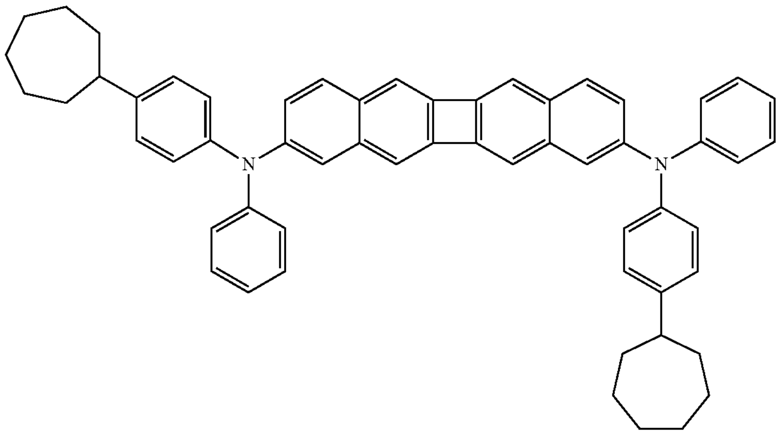
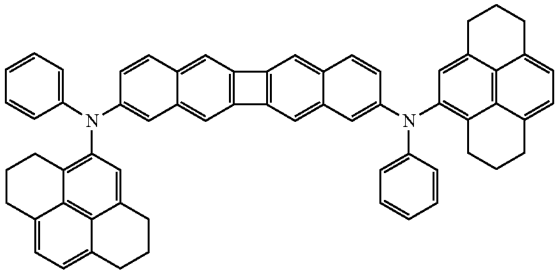
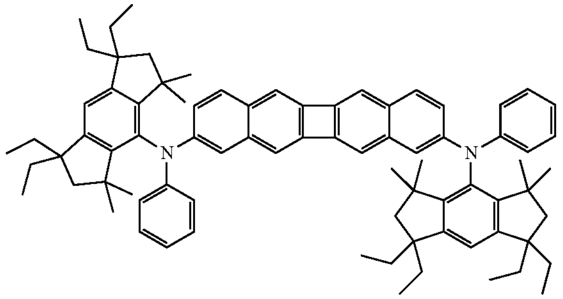
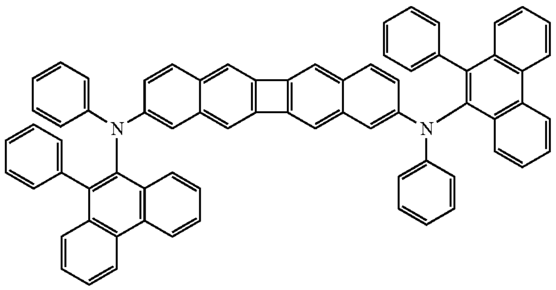
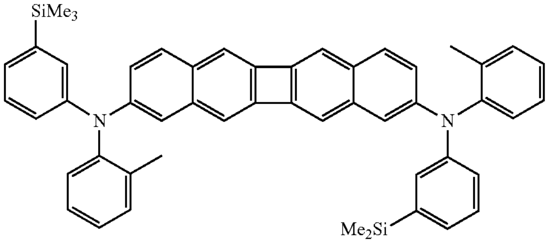
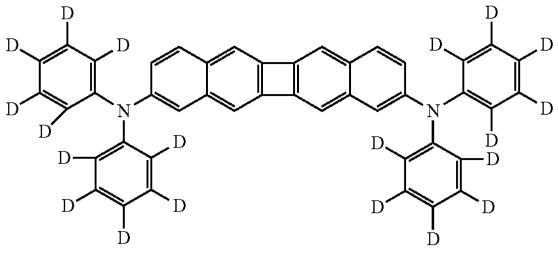
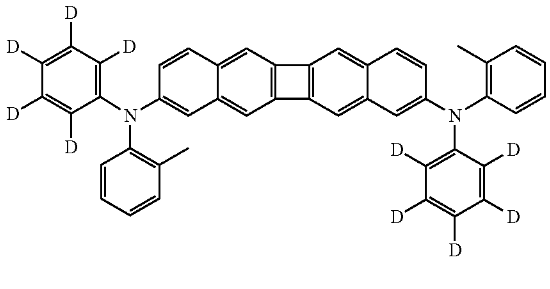

-continued
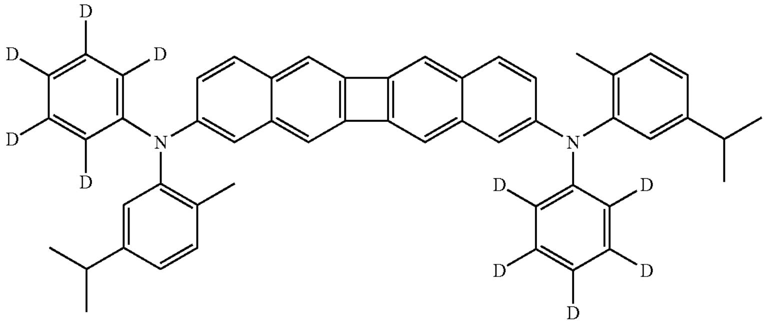
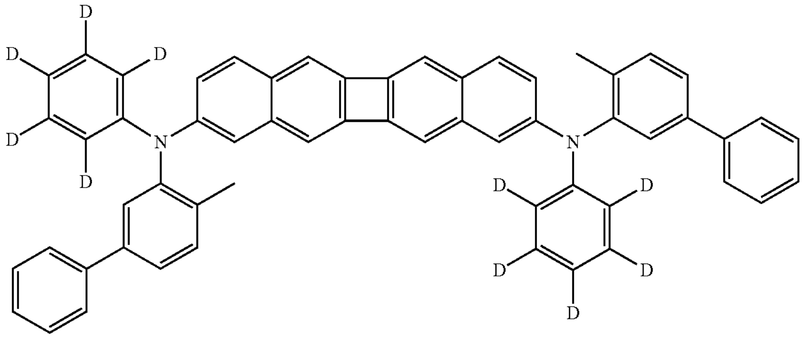
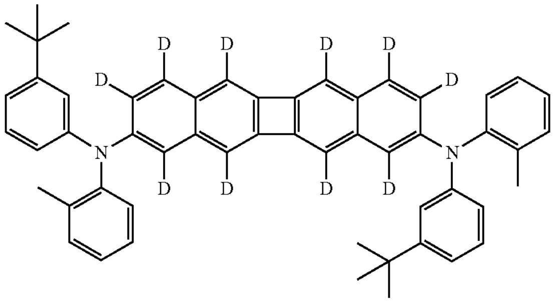
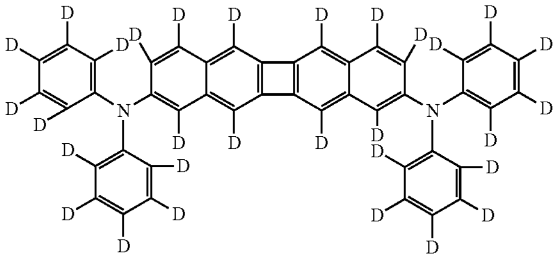
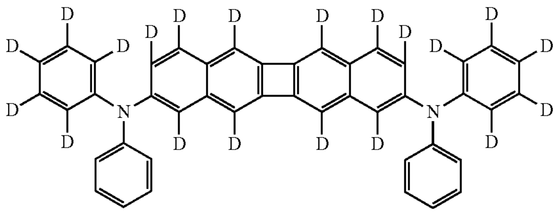
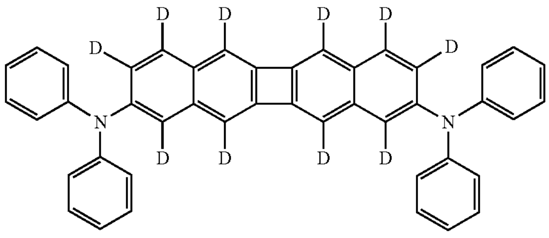
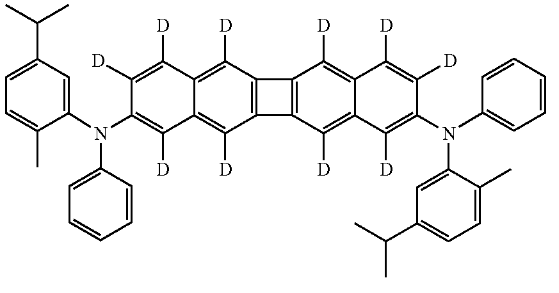
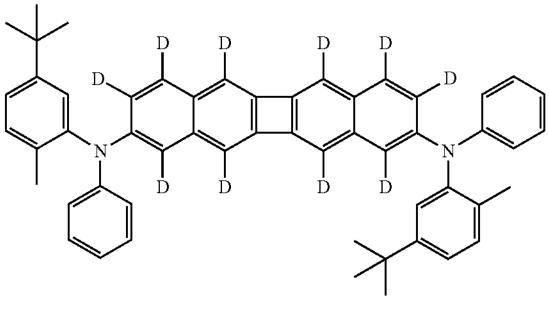

-continued
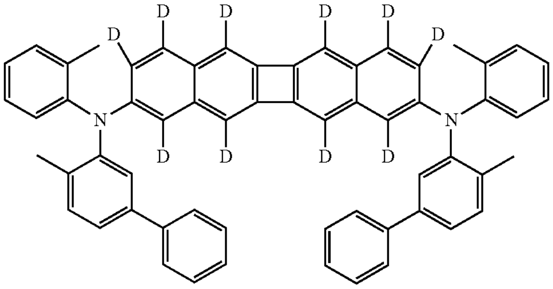
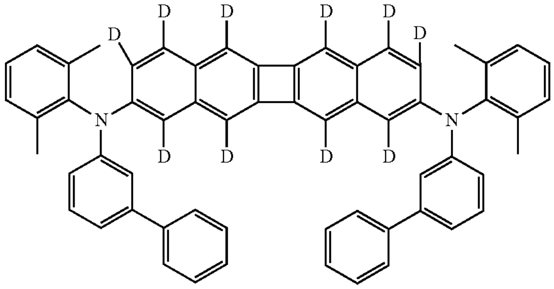
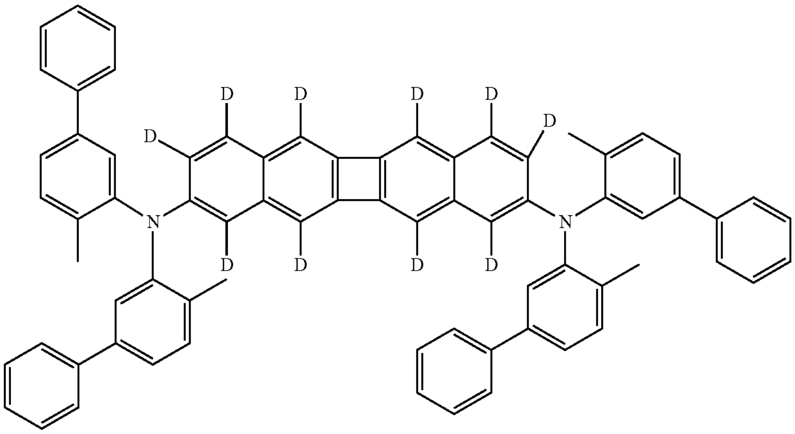
[Formula 118]
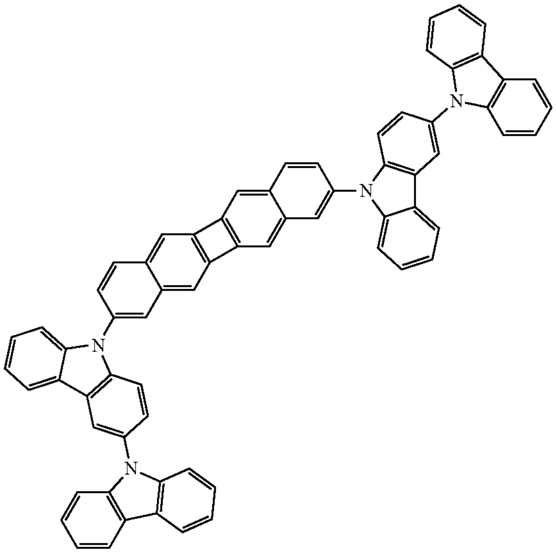
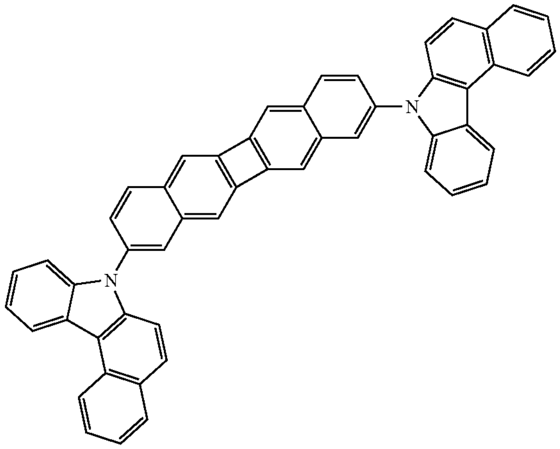

-continued
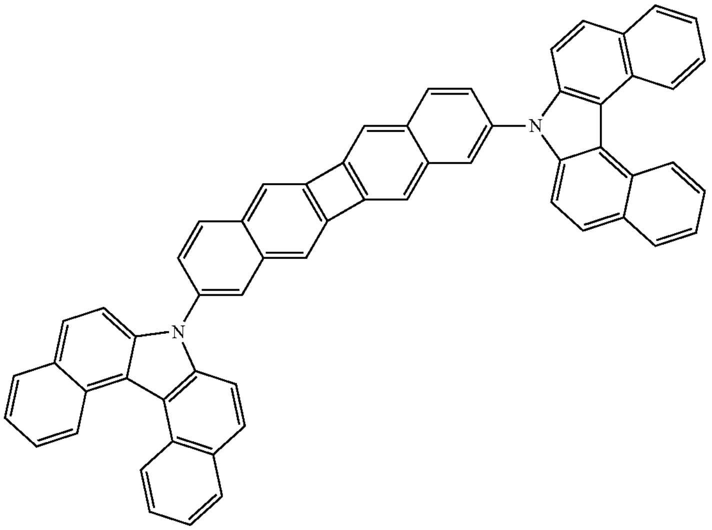
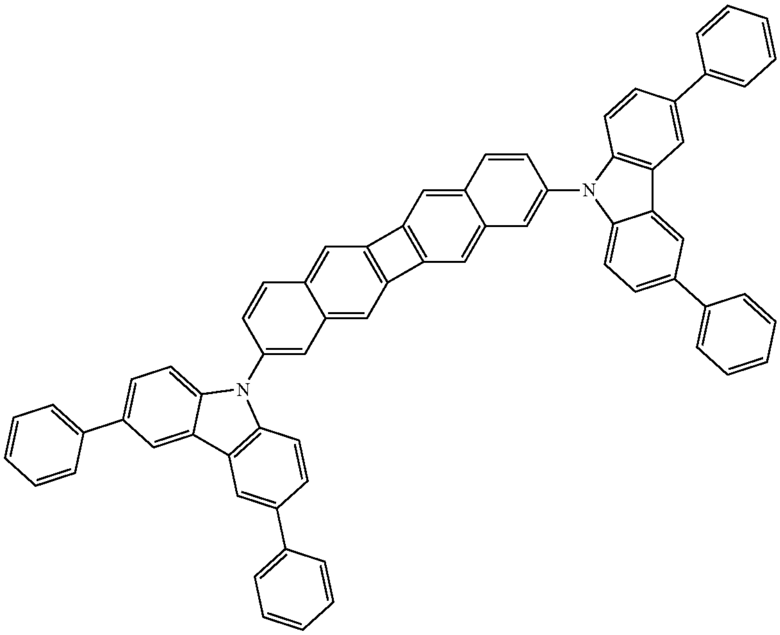
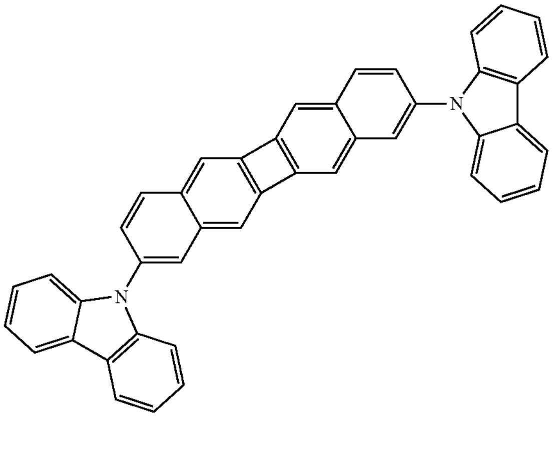
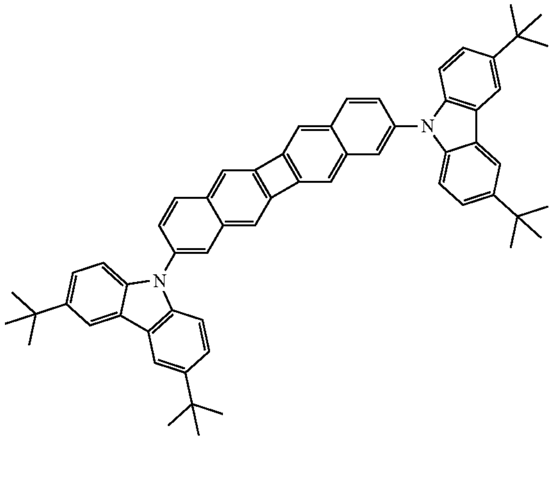

-continued
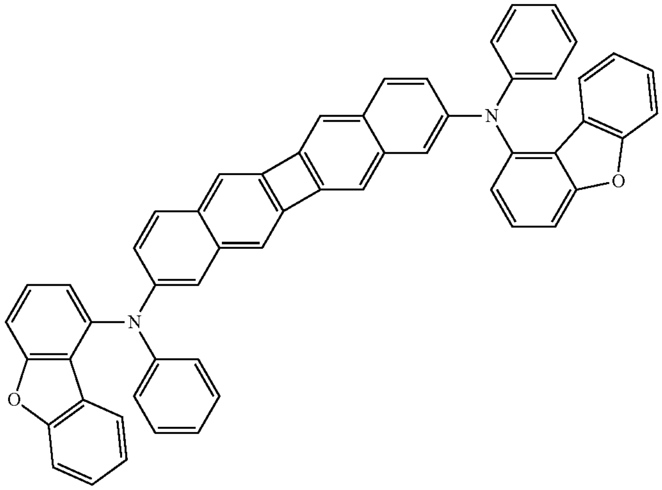
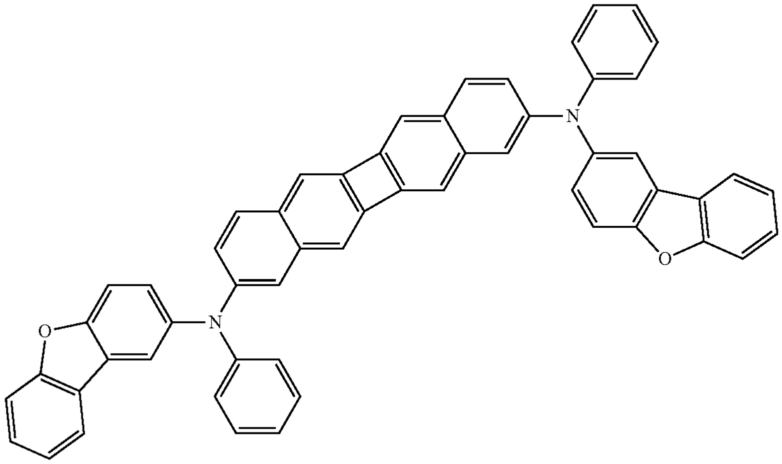
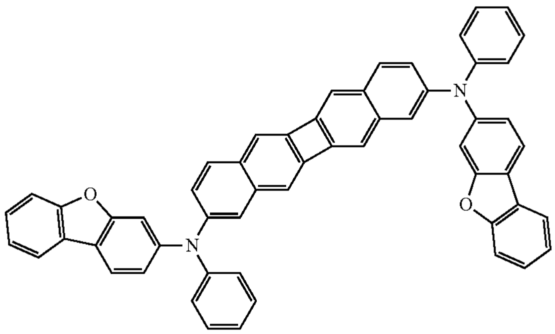
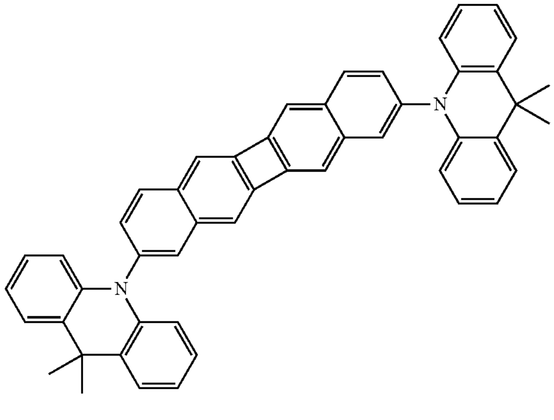

-continued
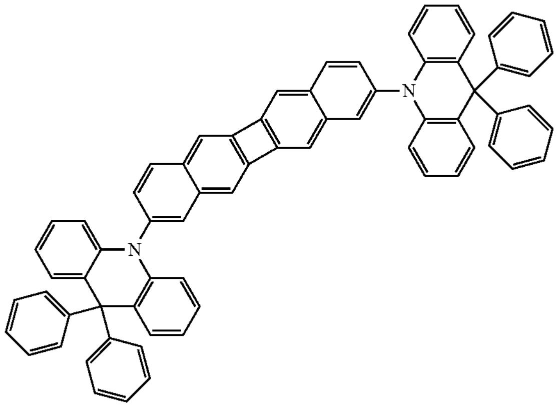
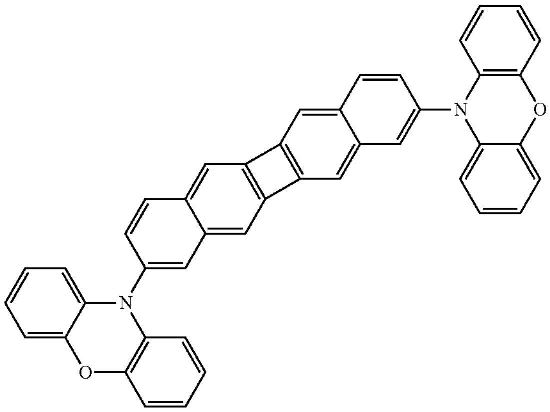
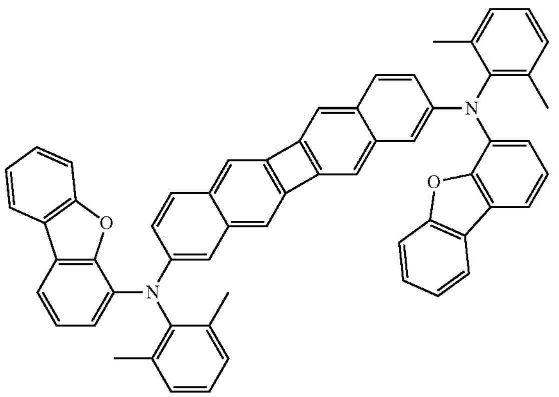
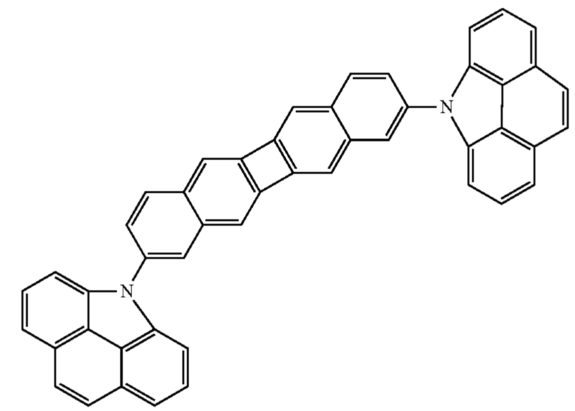
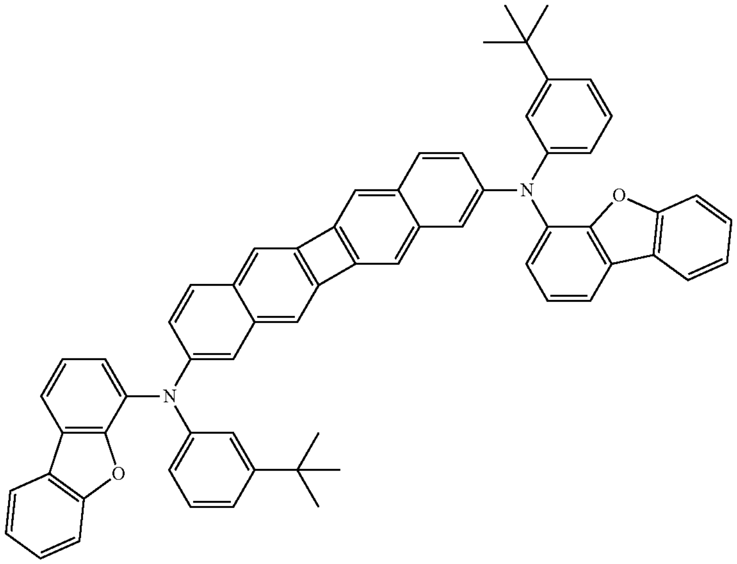

-continued
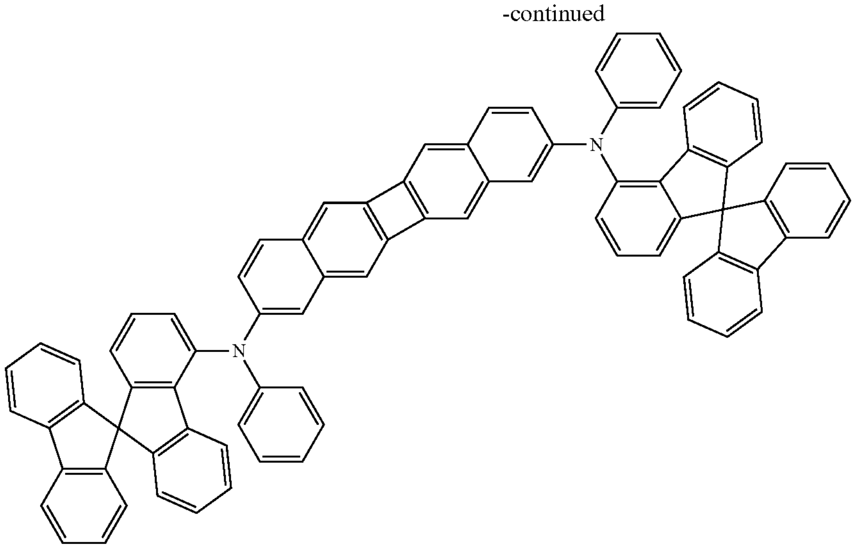
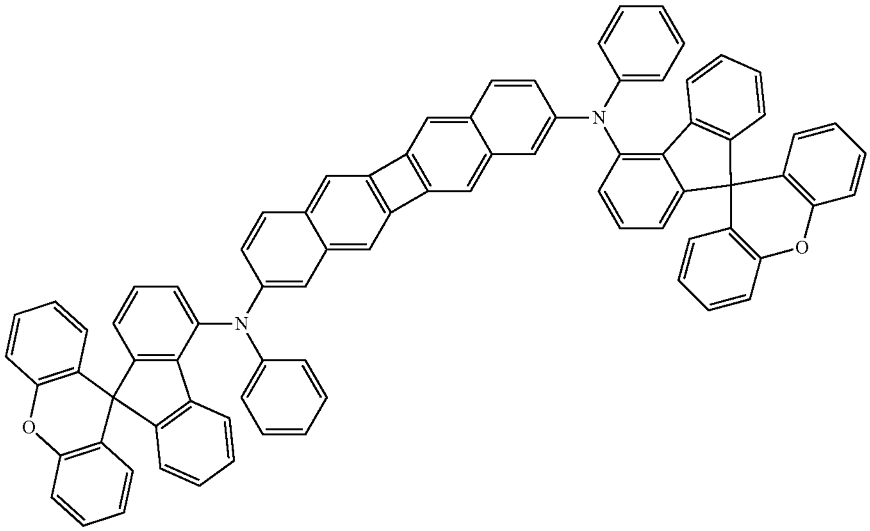
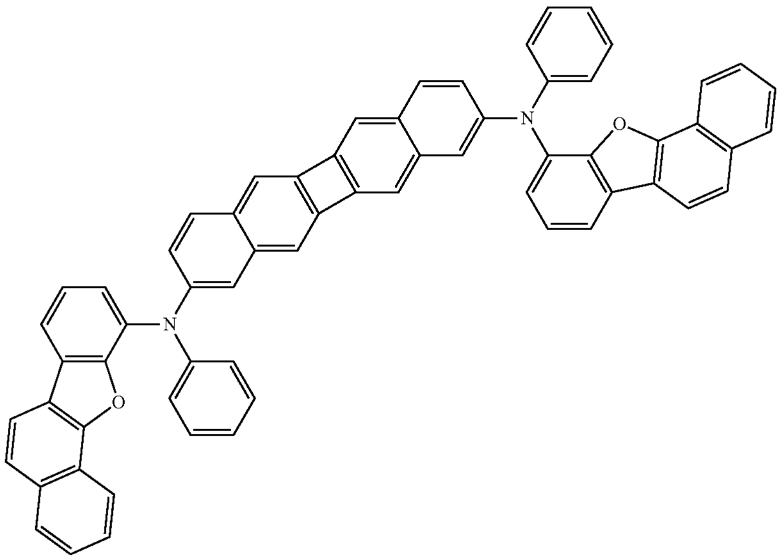

-continued
[Formula 119]
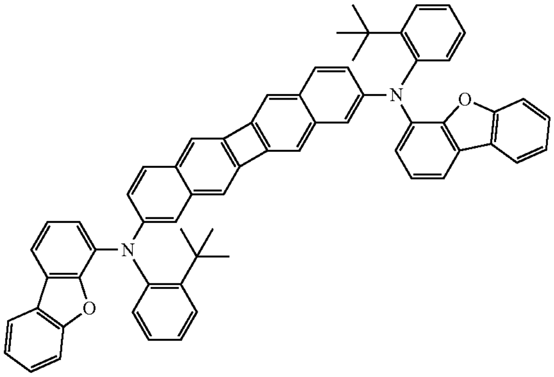
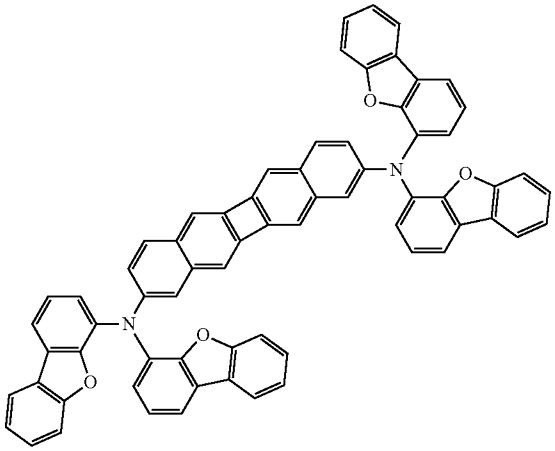
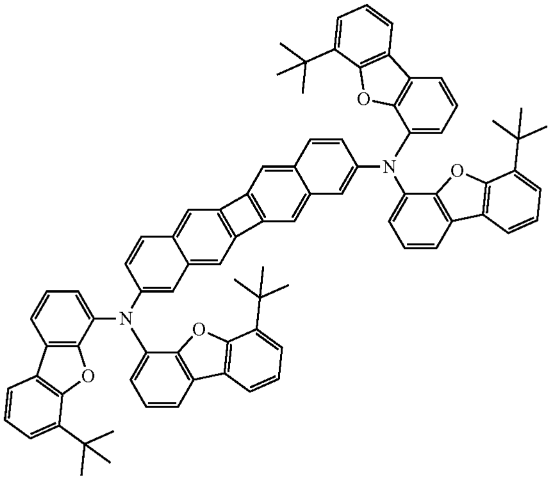
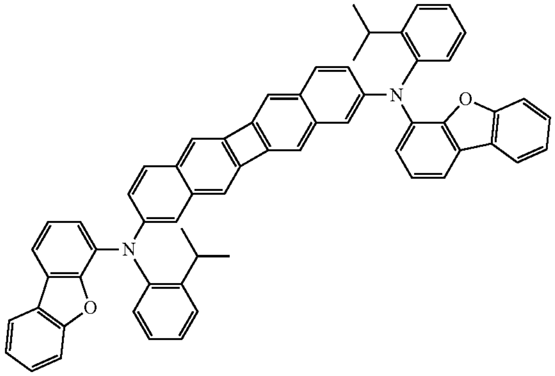
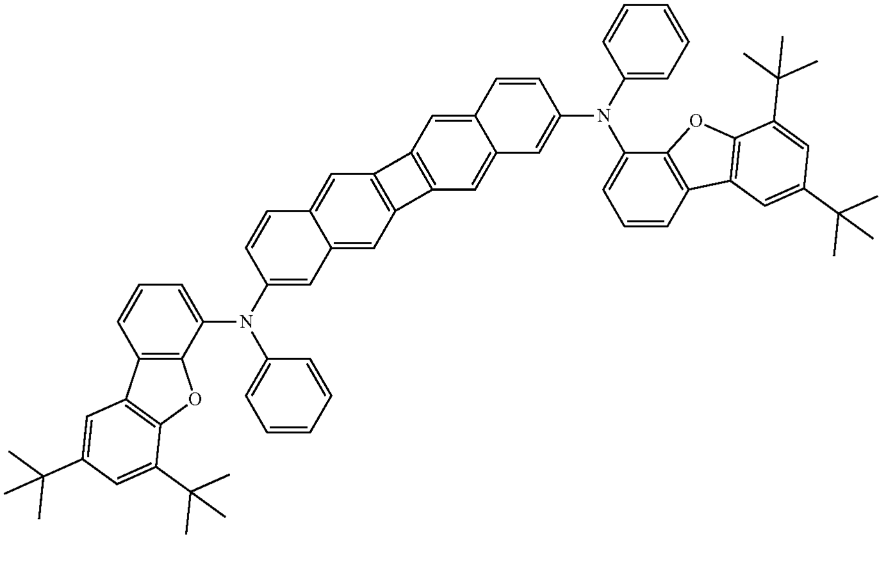

-continued
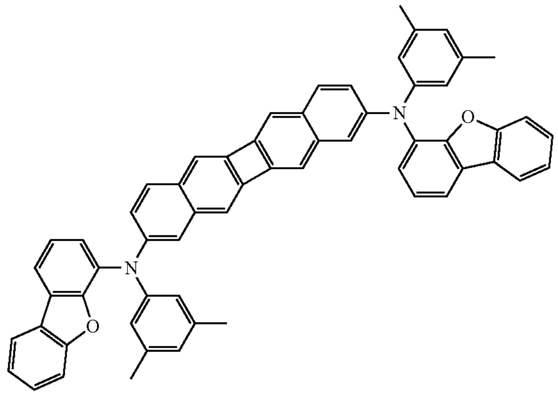
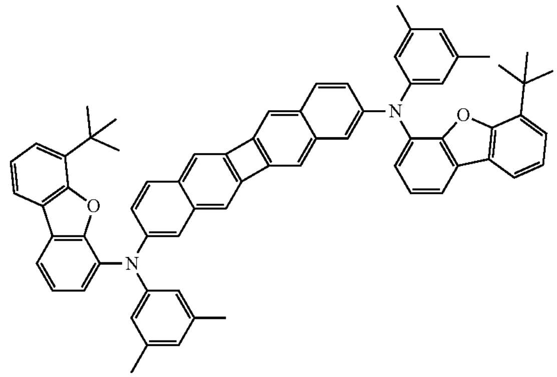
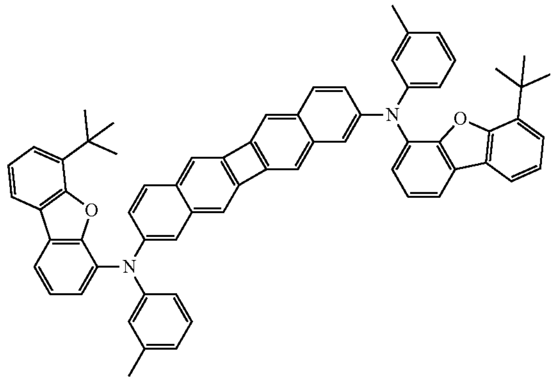
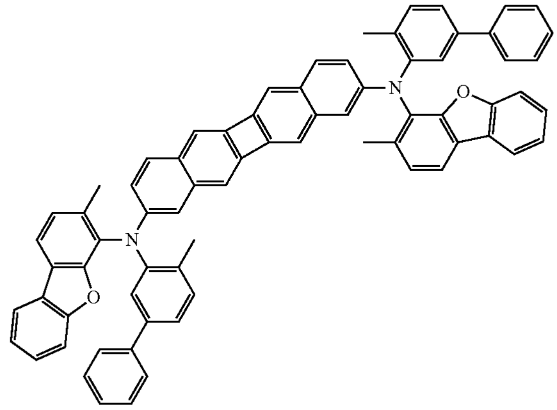
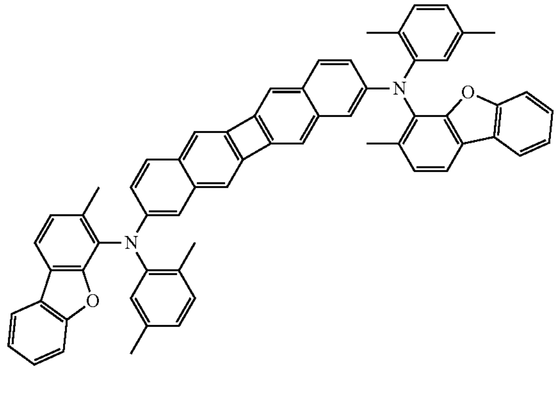
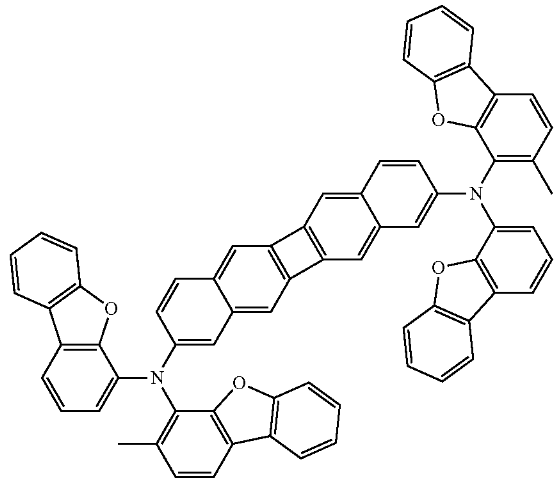
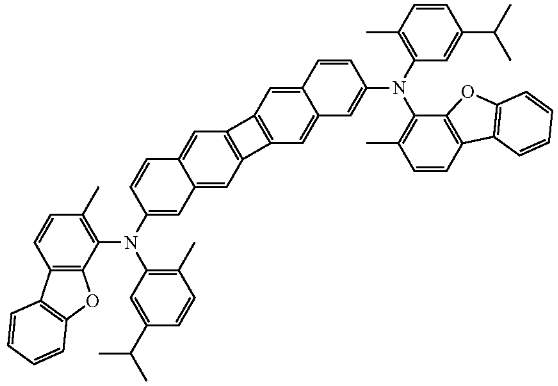
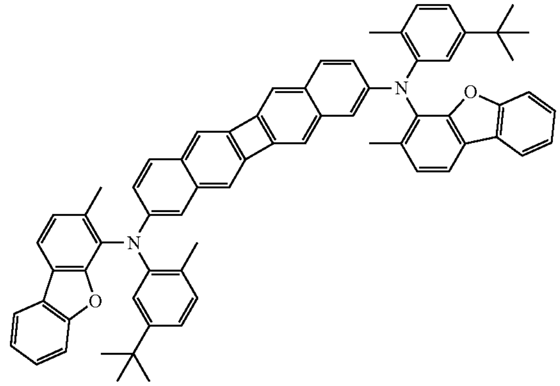

-continued
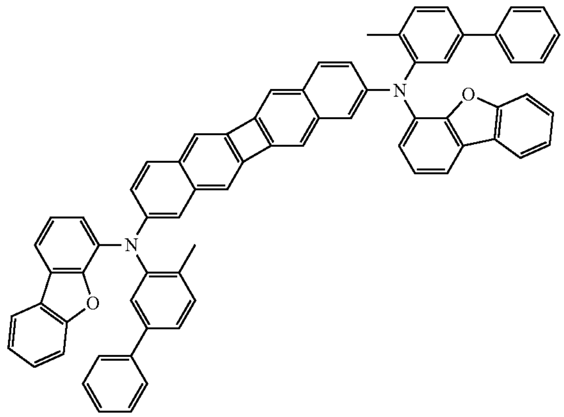
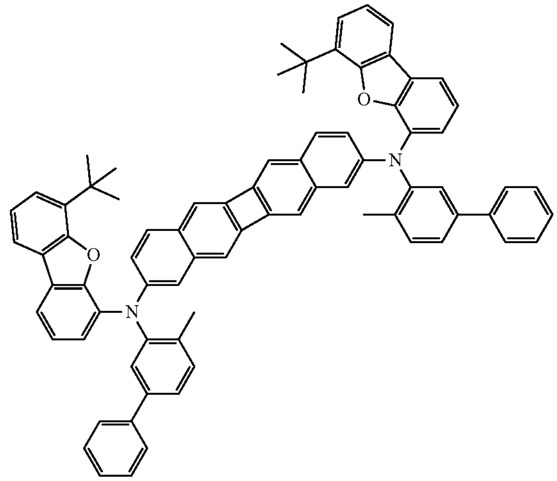
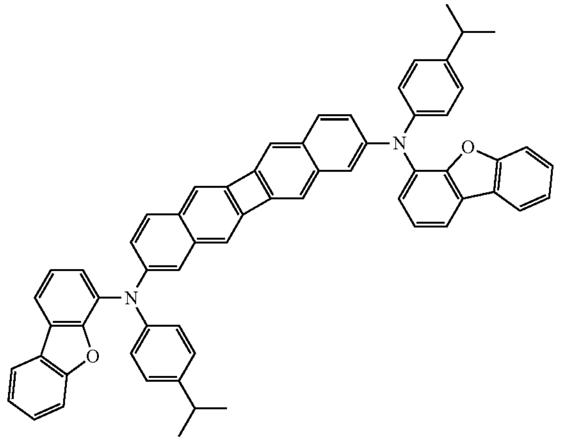
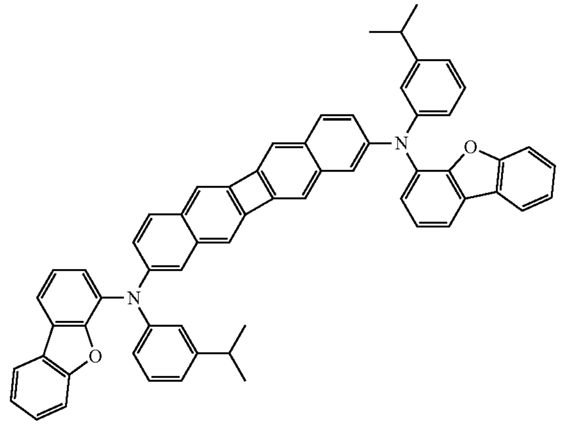
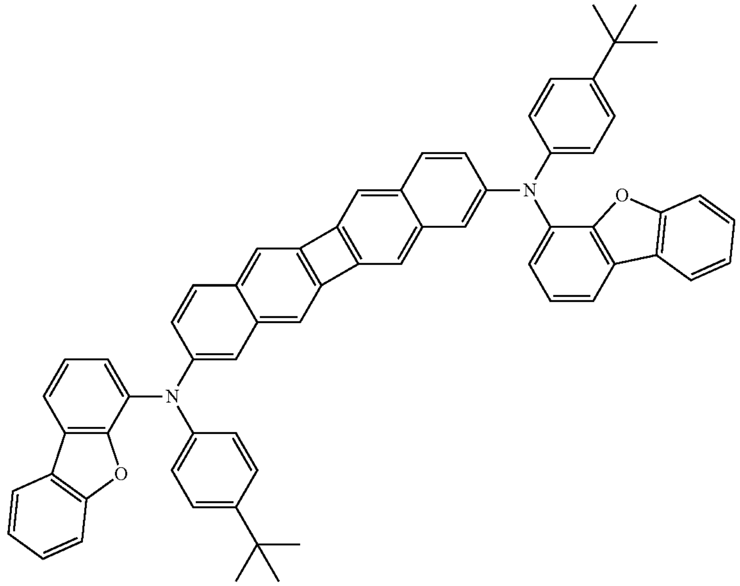

-continued
[Formula 120]
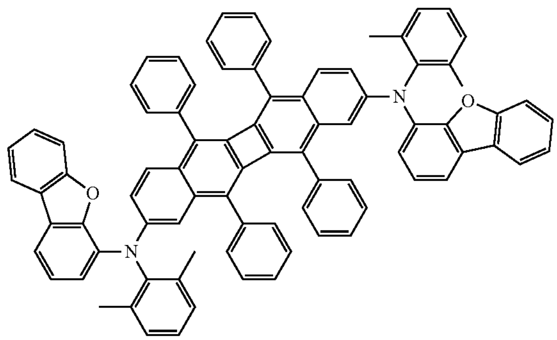
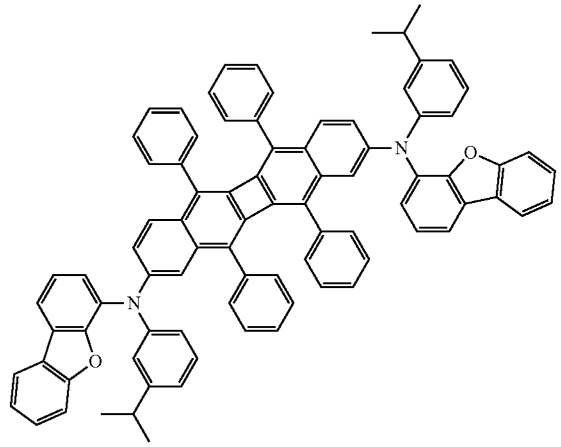
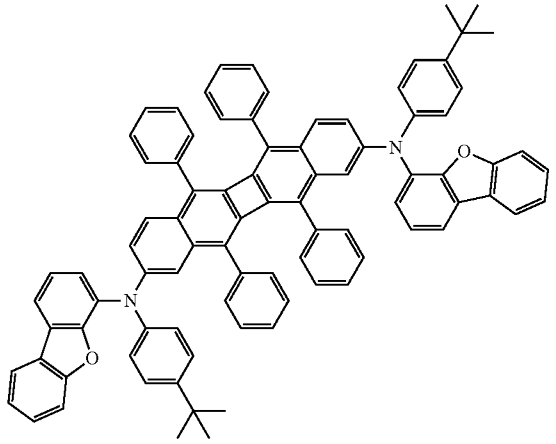
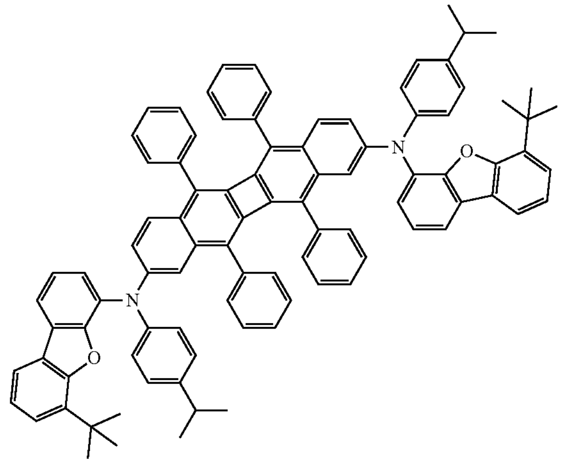
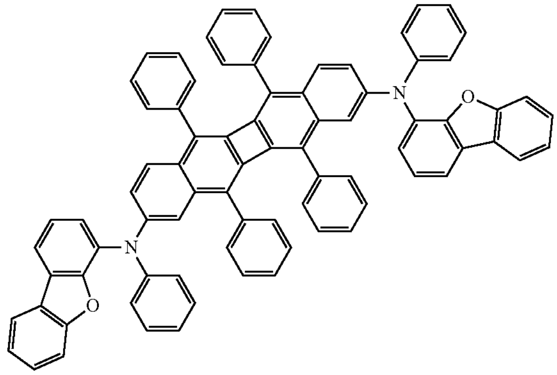
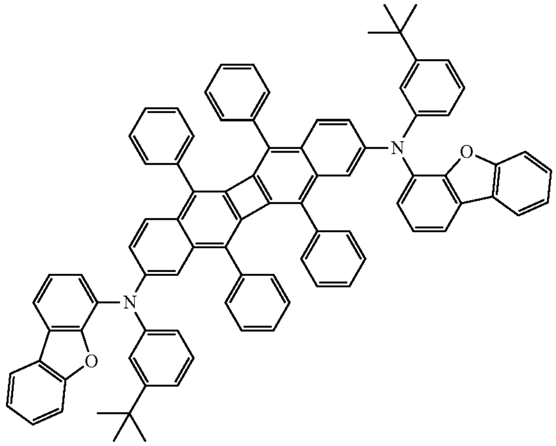

-continued
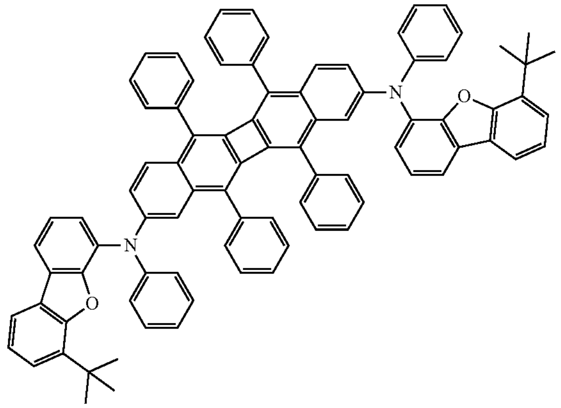
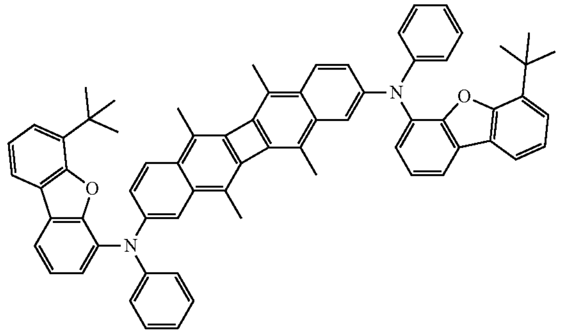
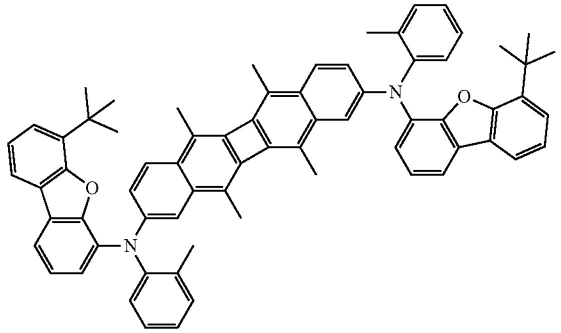
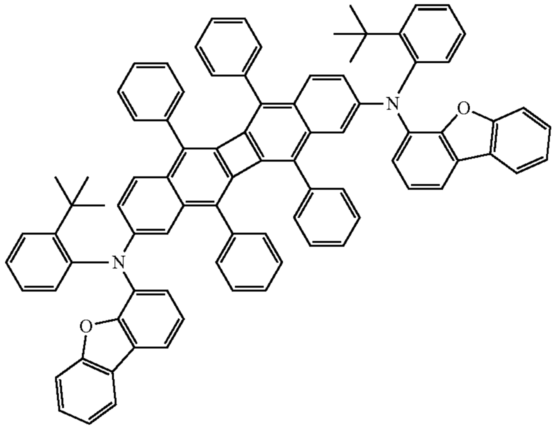
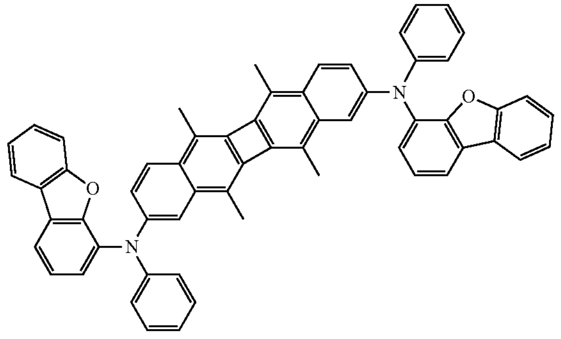
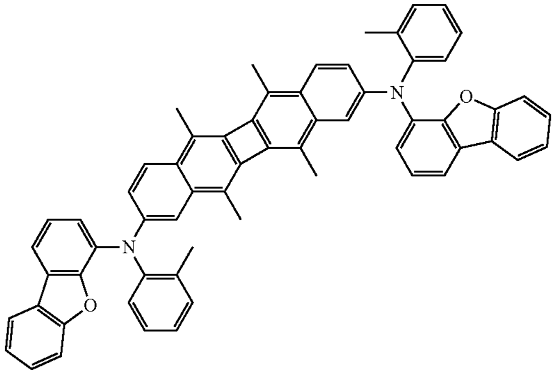
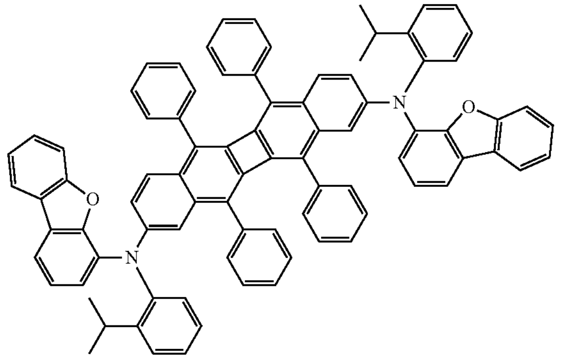
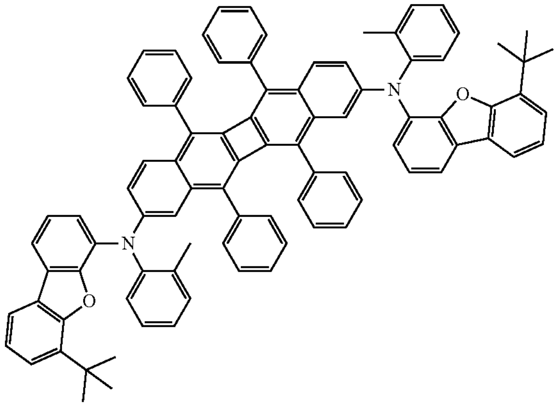

-continued
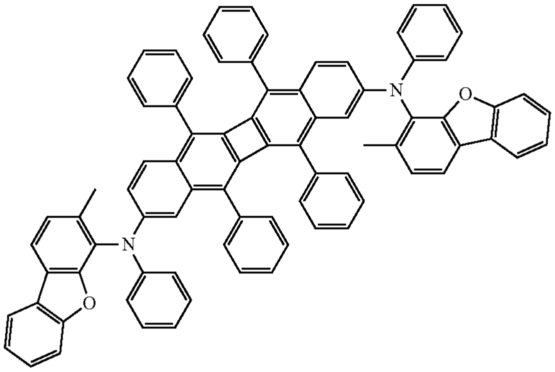
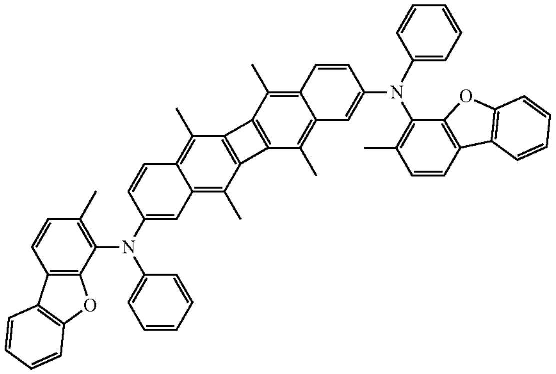
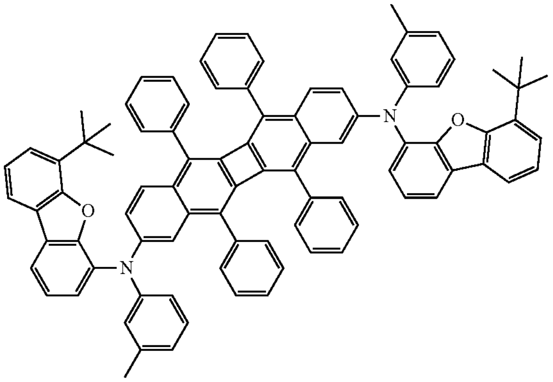
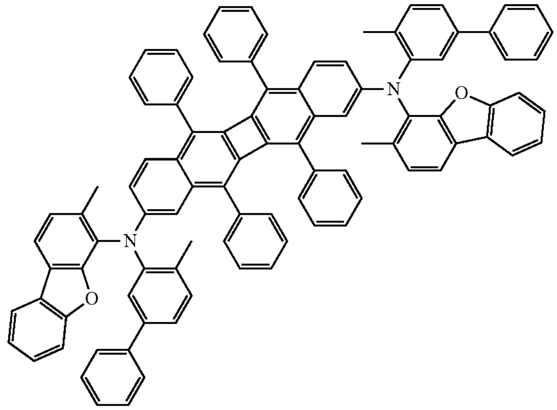
[Formula 121]
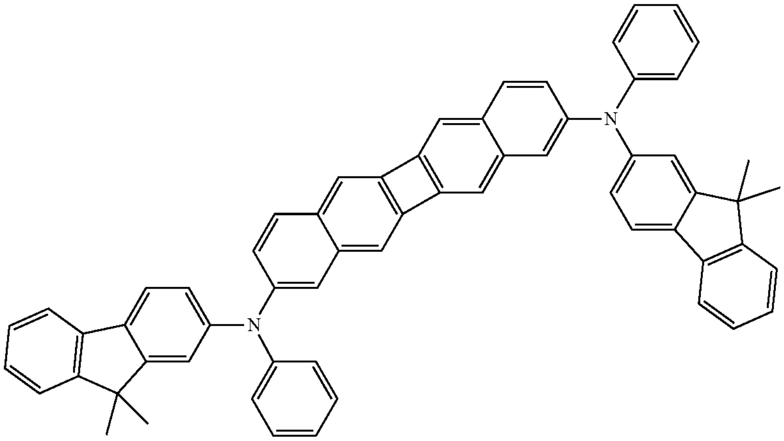
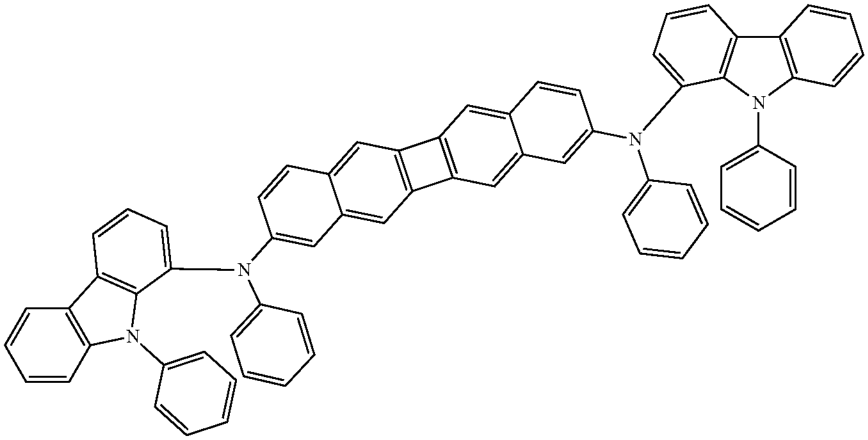

-continued
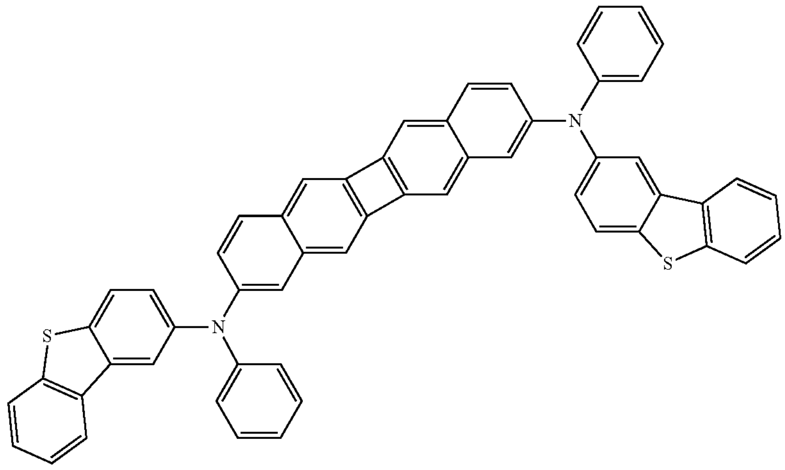
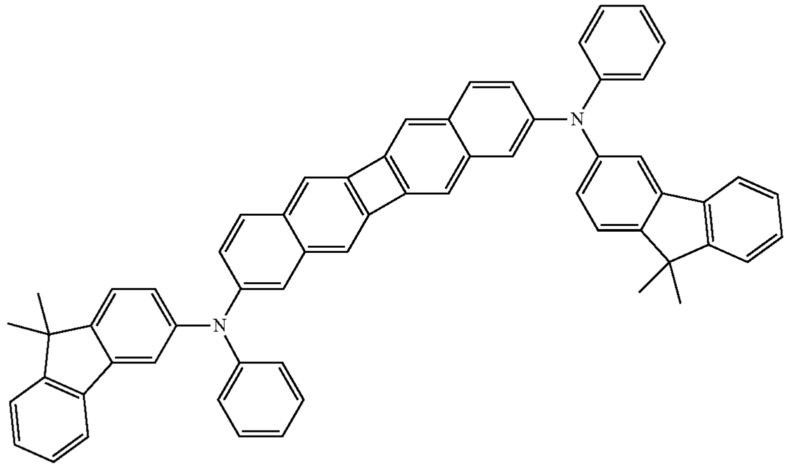
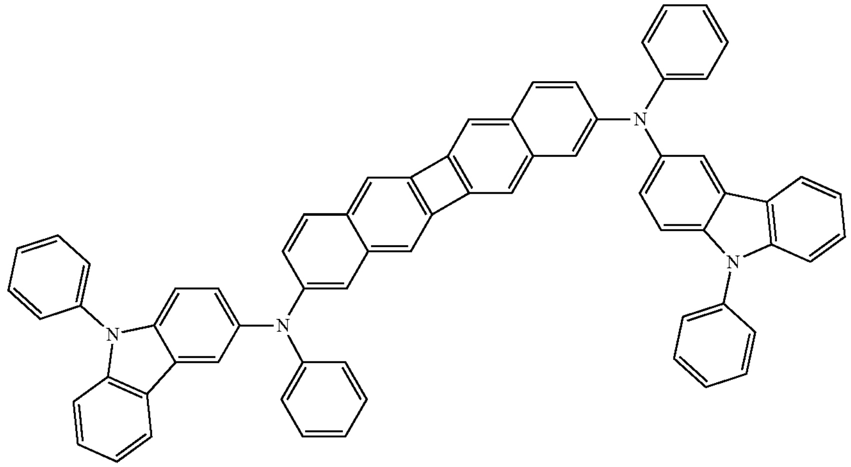

-continued
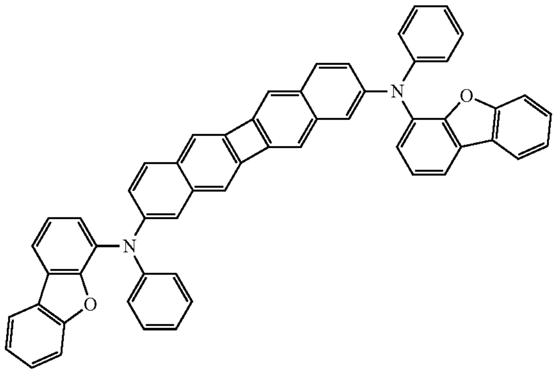
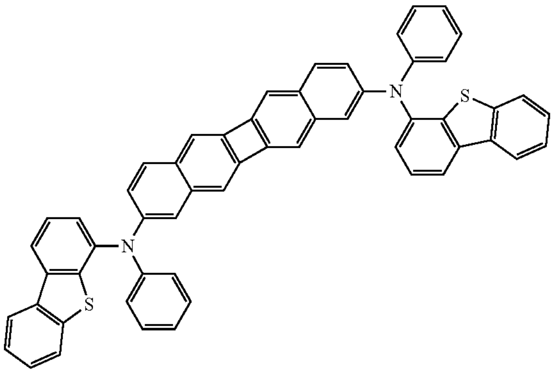
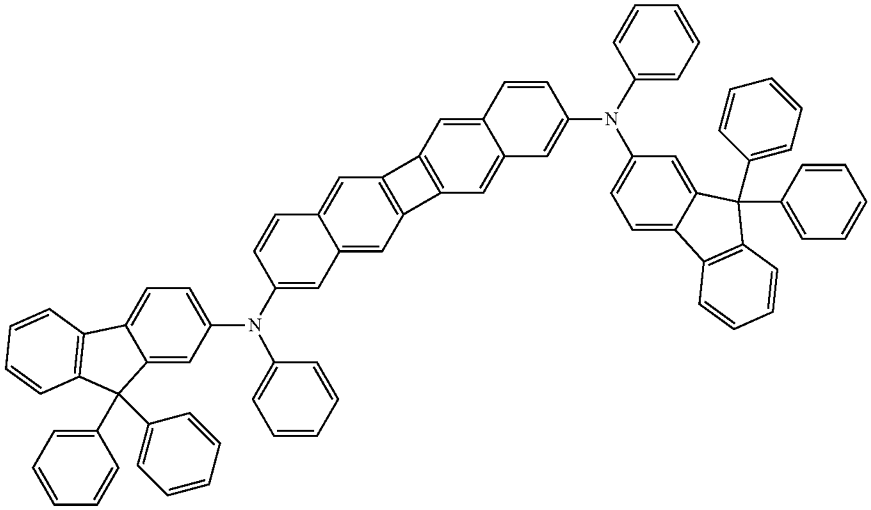
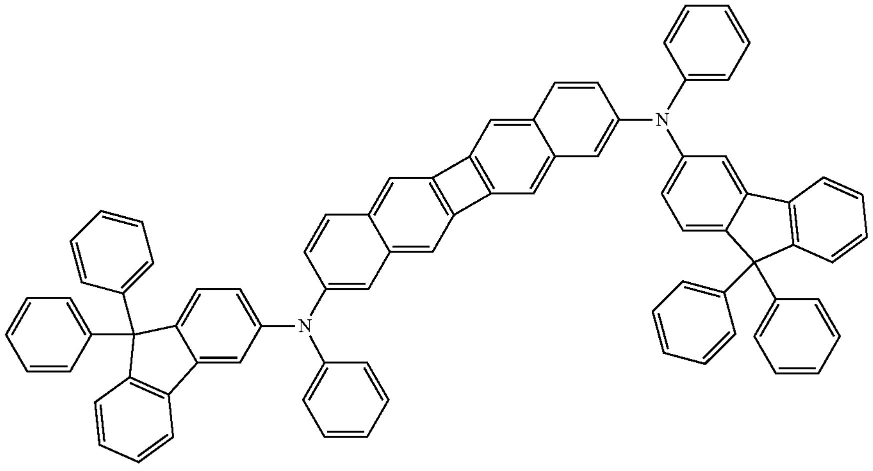

-continued
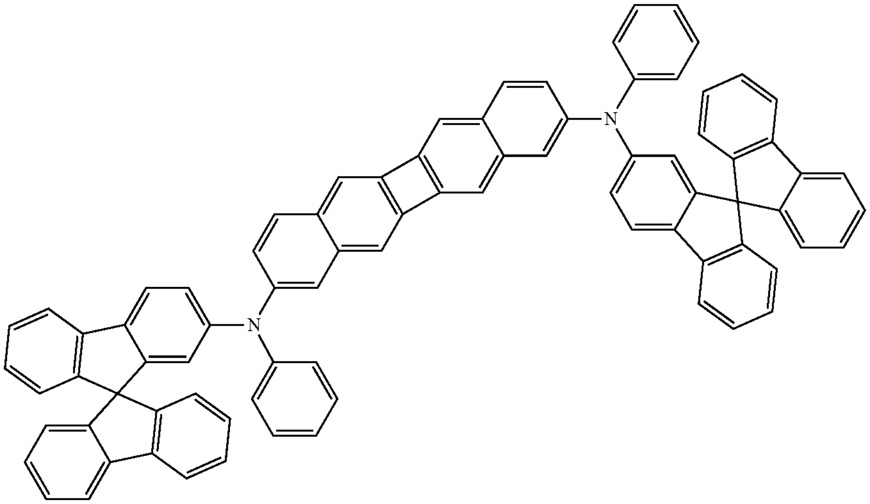
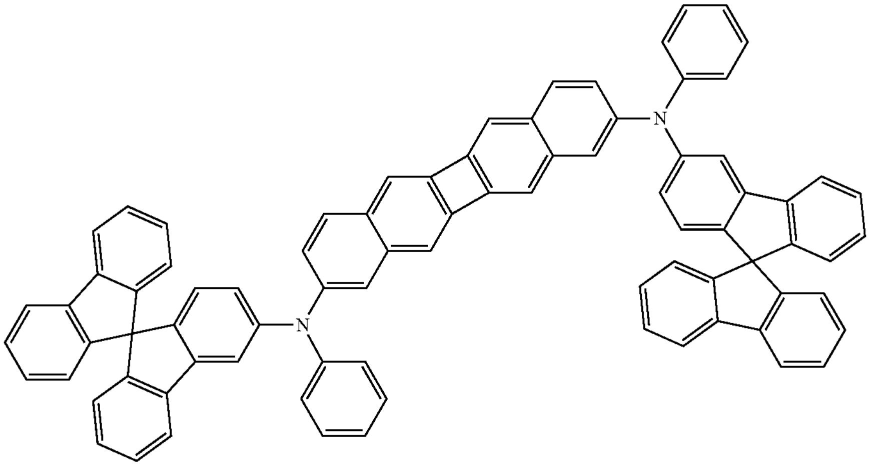
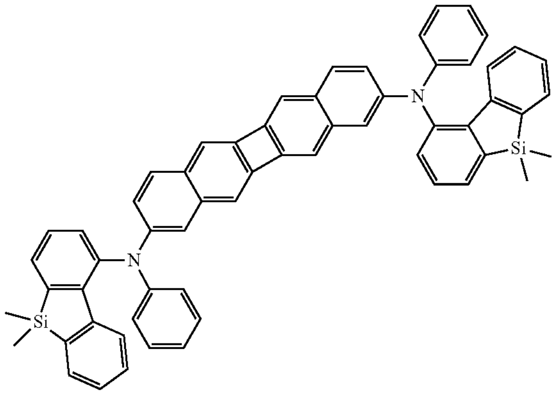
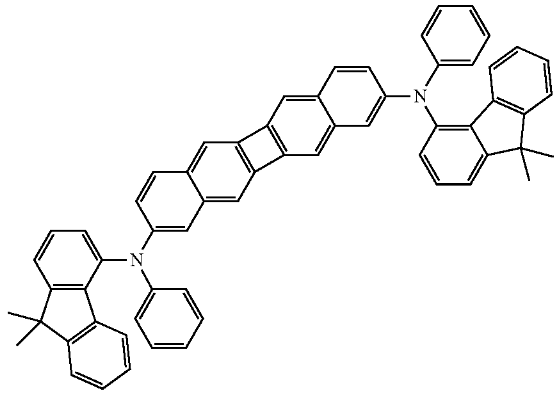

-continued
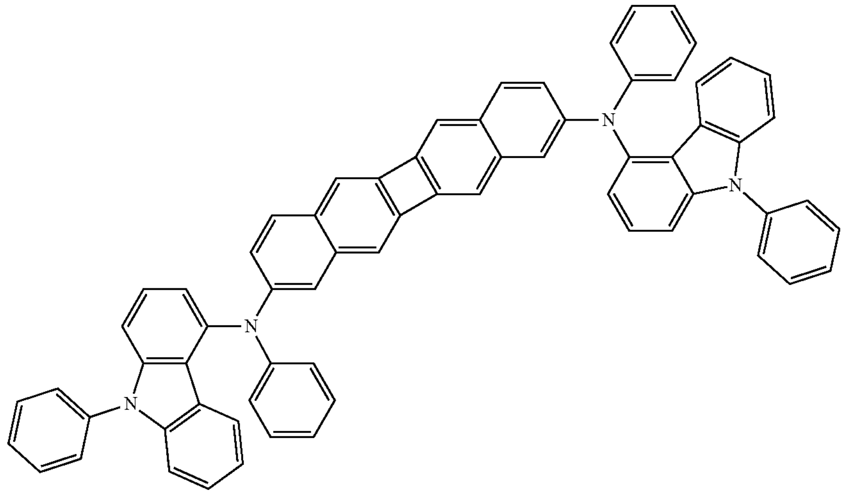
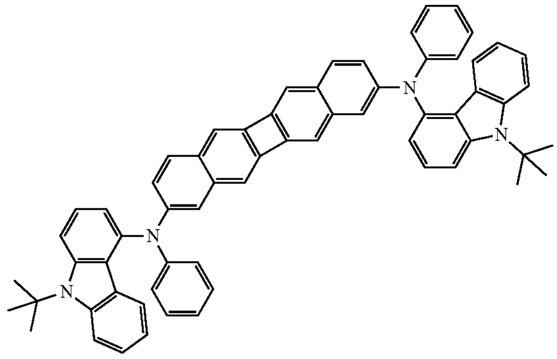
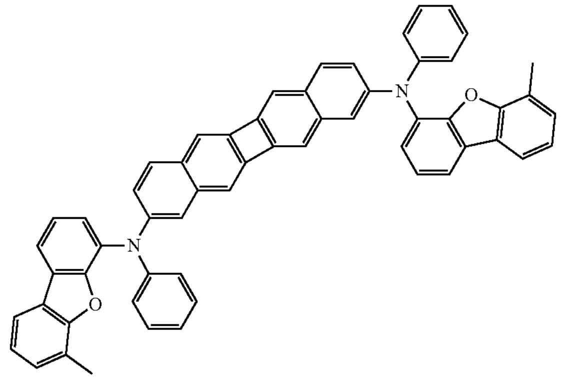
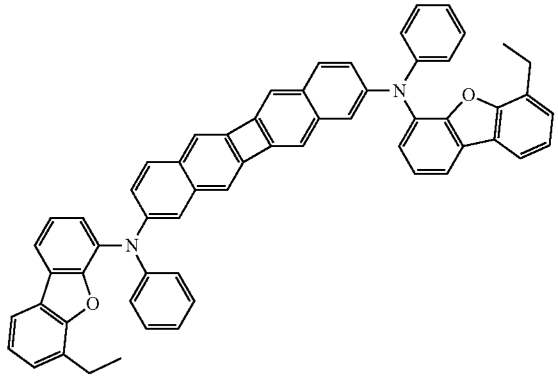
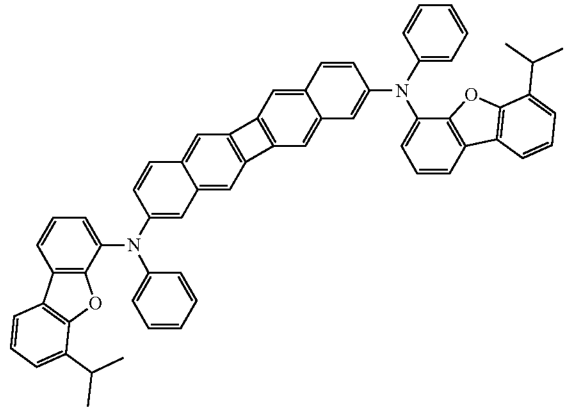
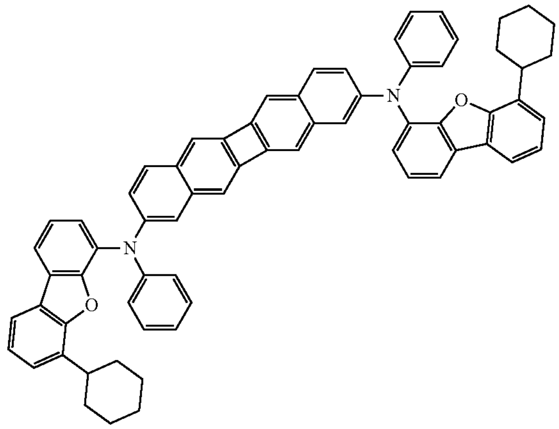
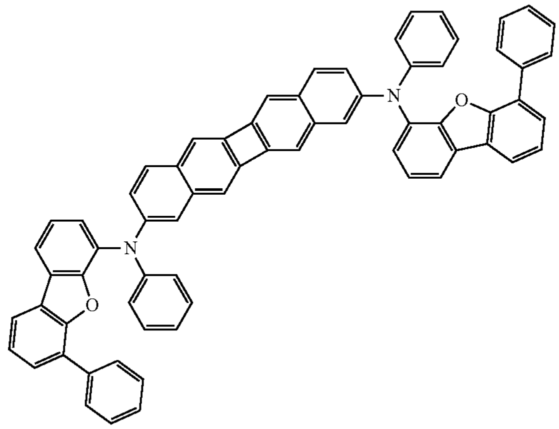

-continued
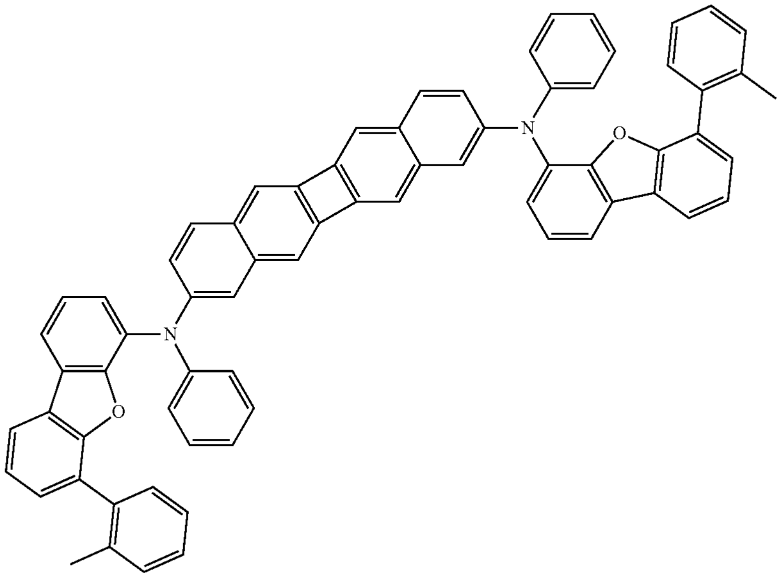
[Formula 122]
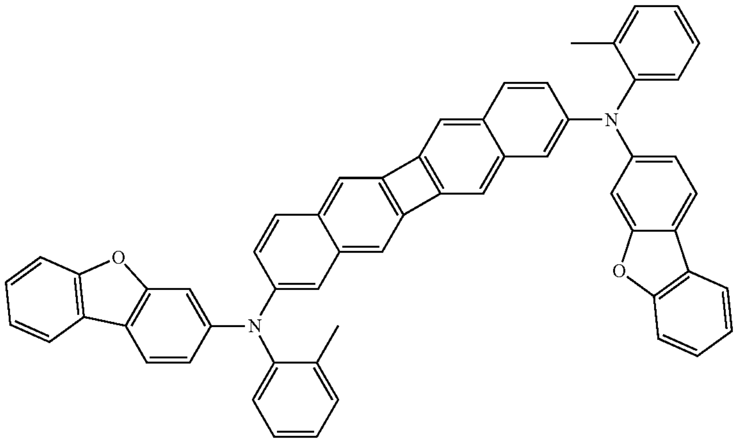
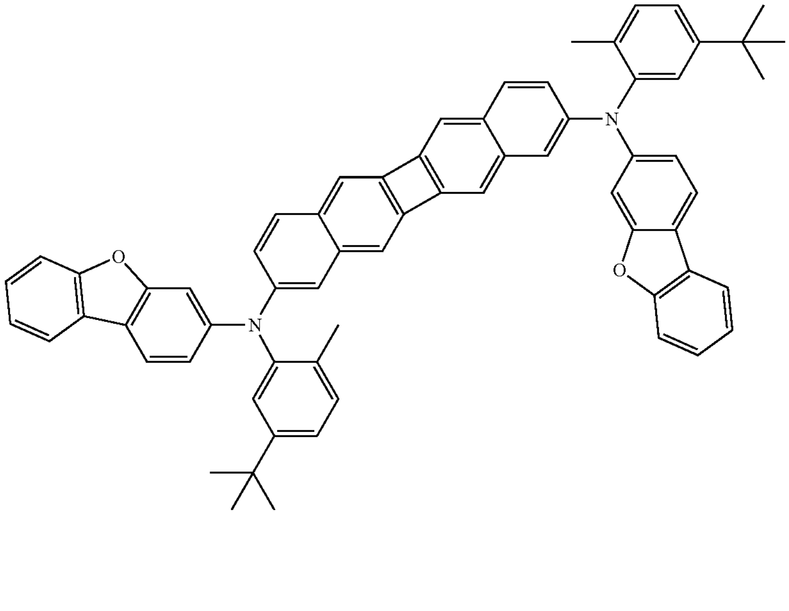

-continued
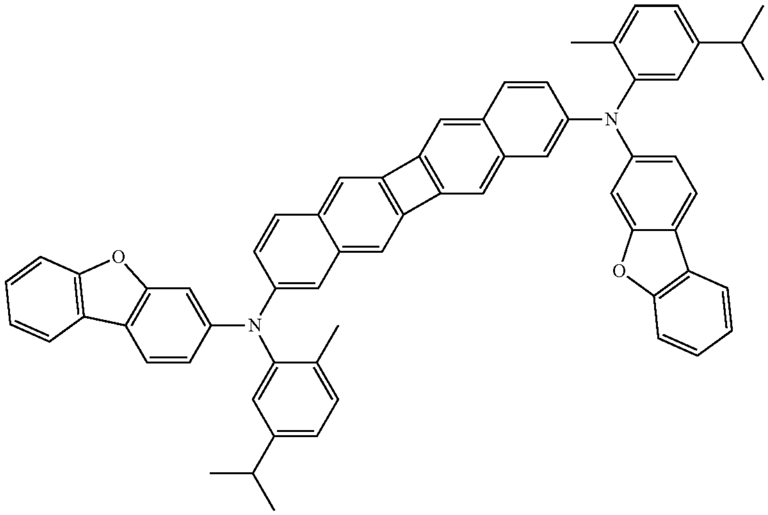
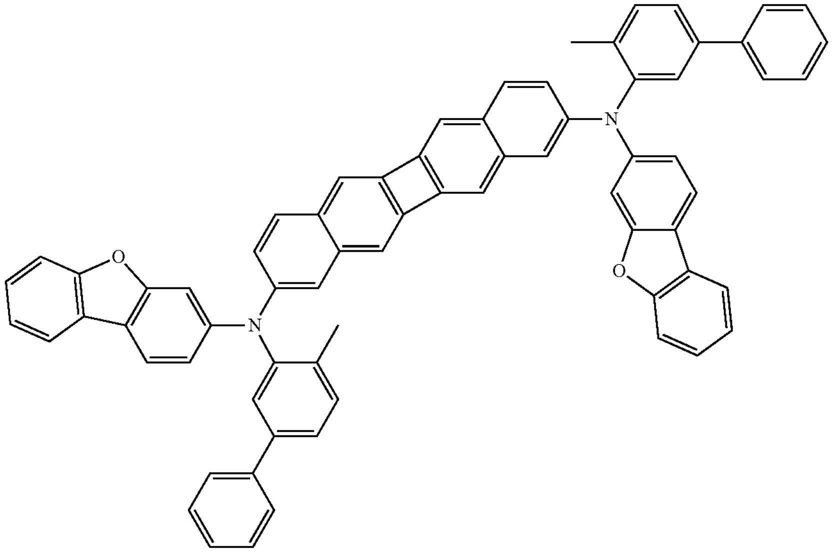
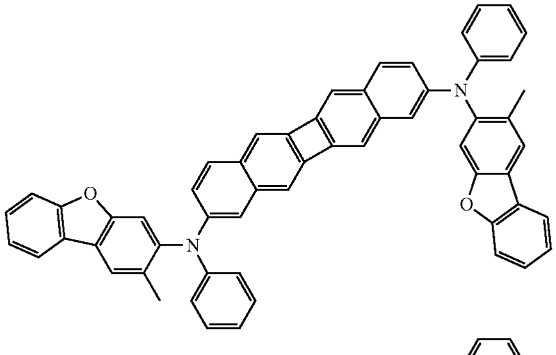
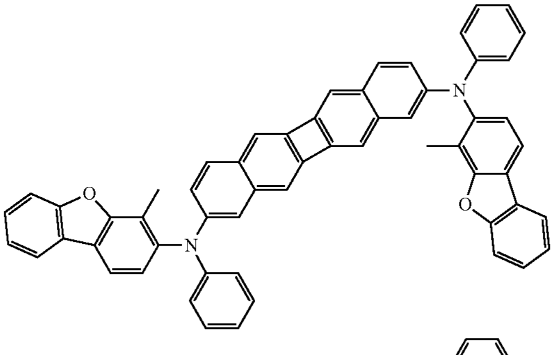
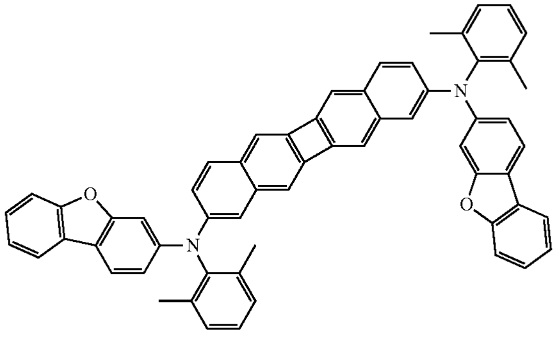
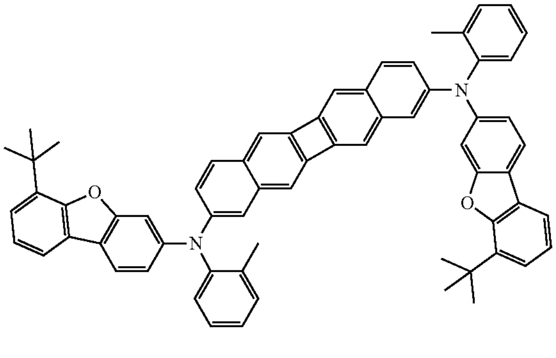

-continued
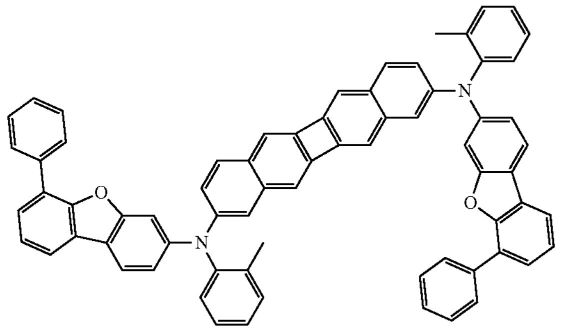
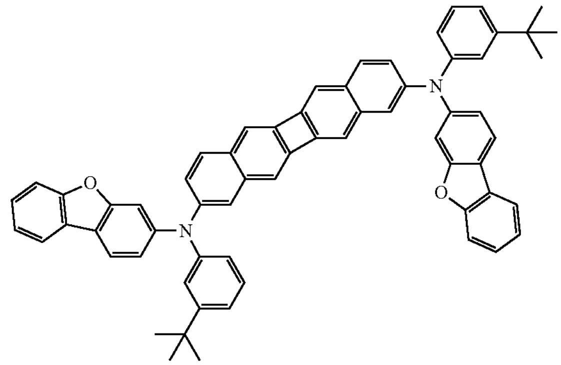
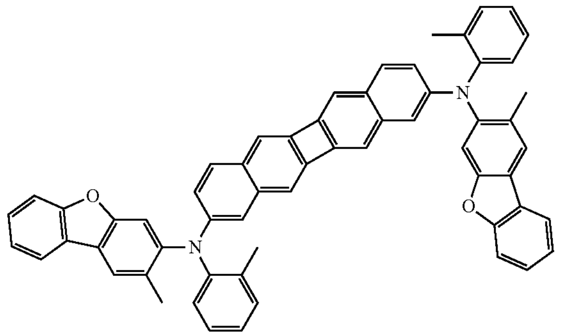
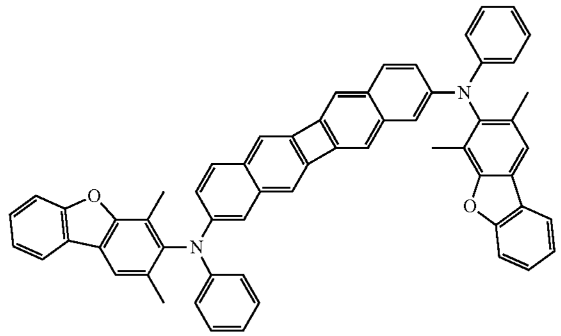
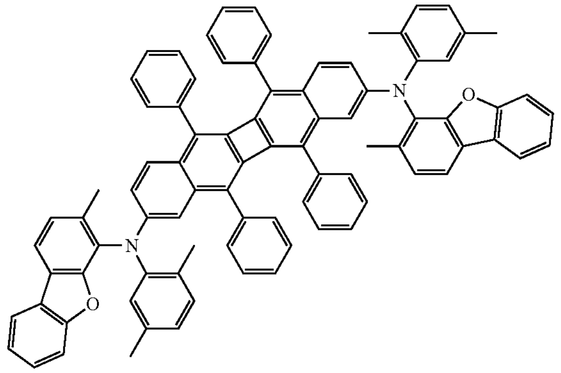
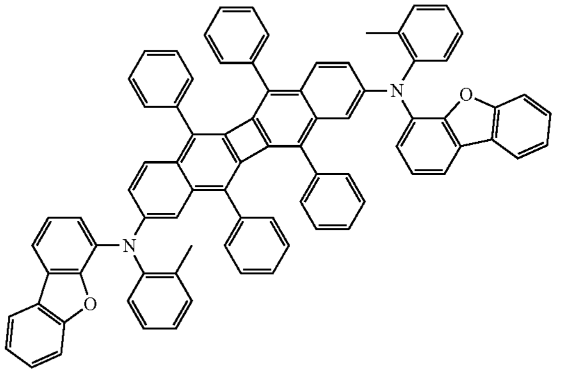
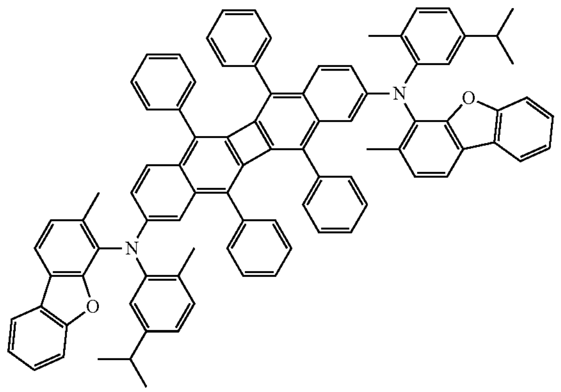
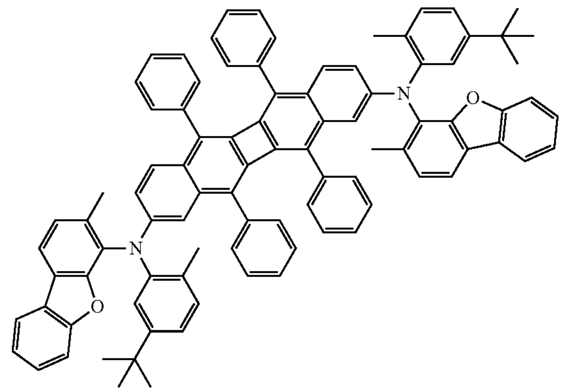

-continued
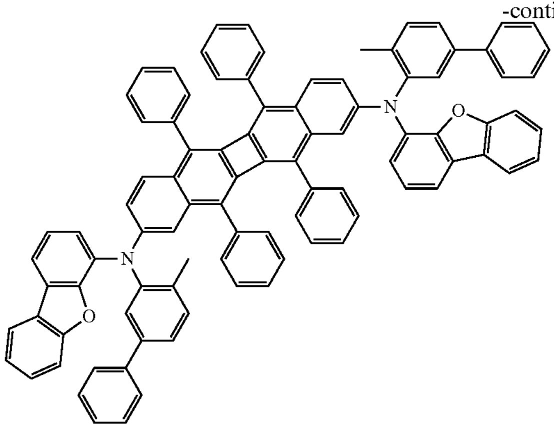
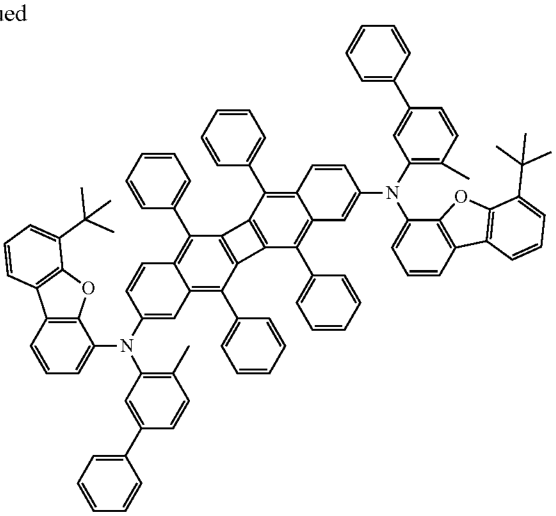
[Formula 123]
-continued
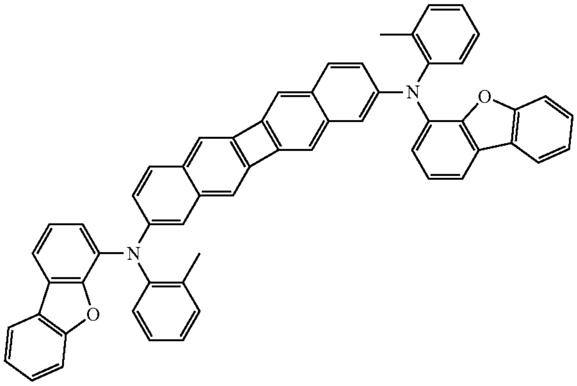
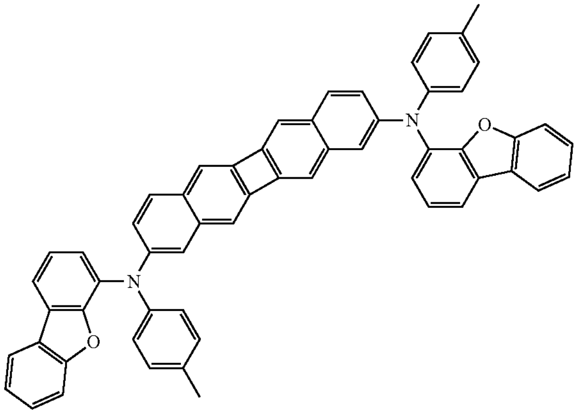
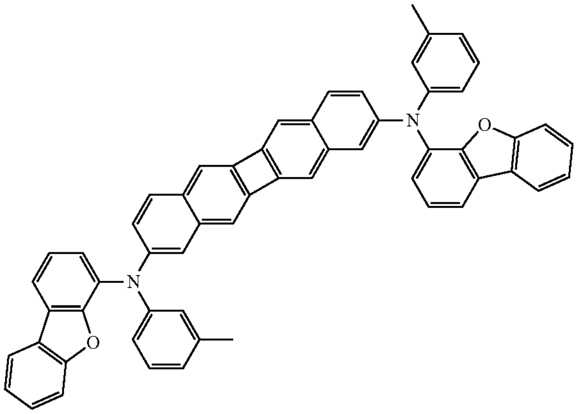
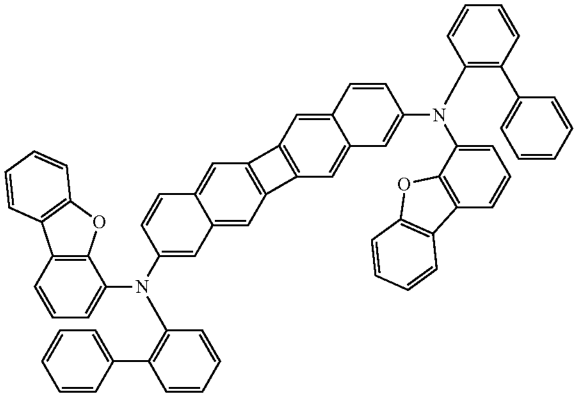

-continued
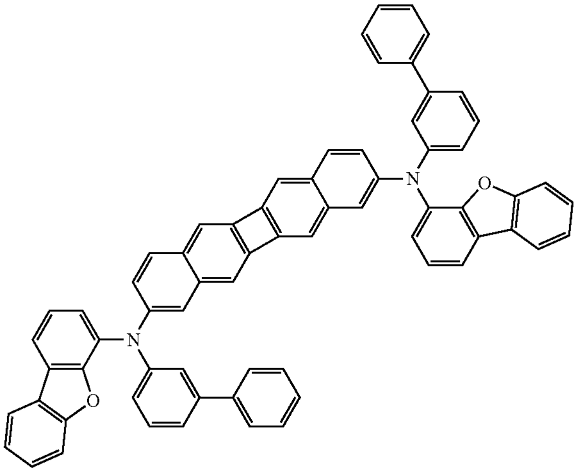
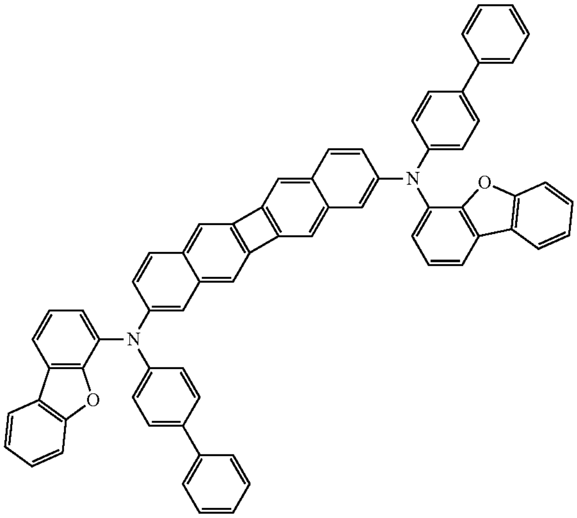
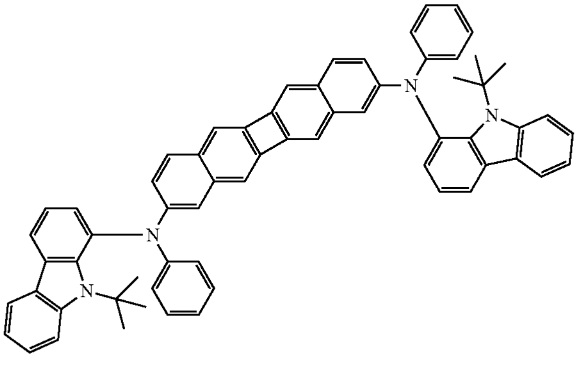
-continued
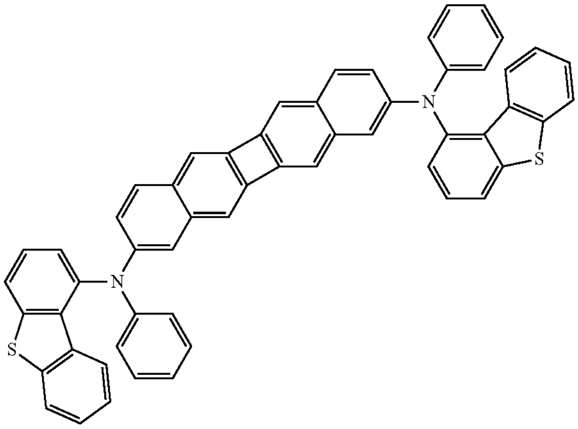
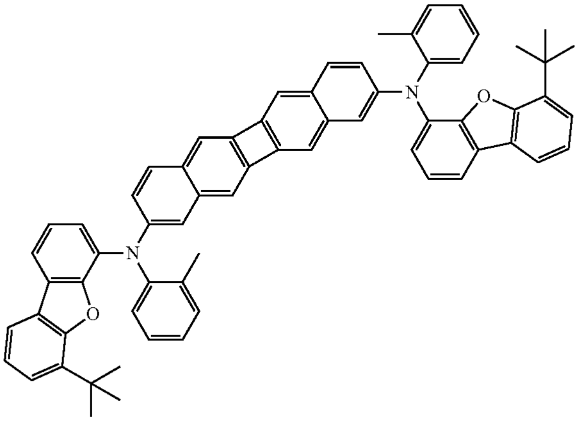
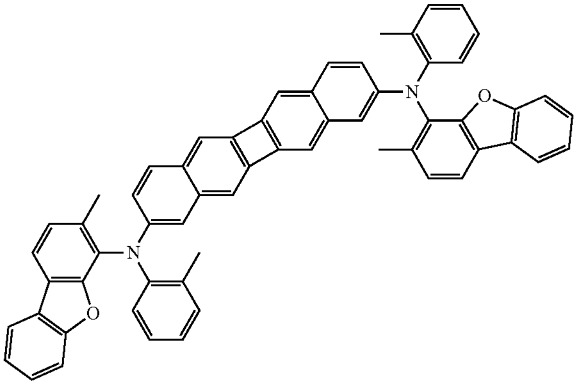
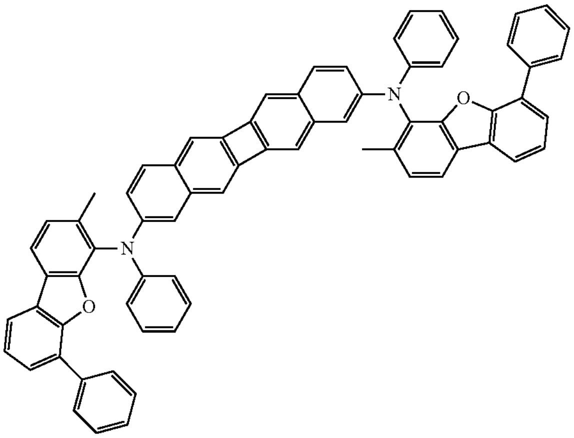

-continued
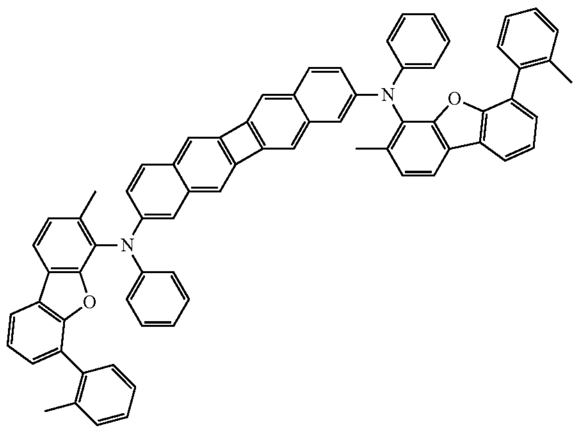
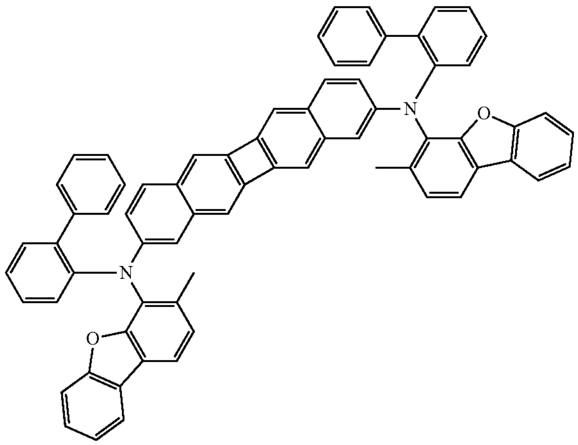
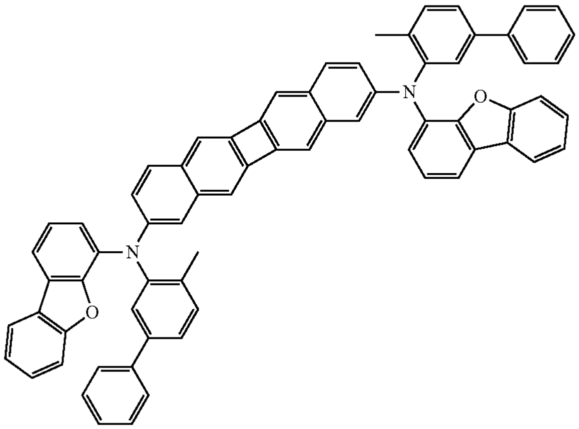
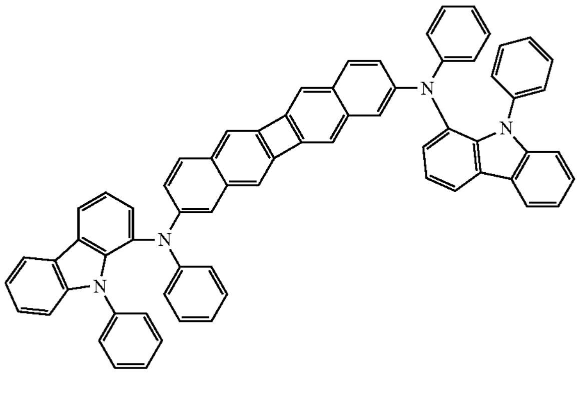
-continued
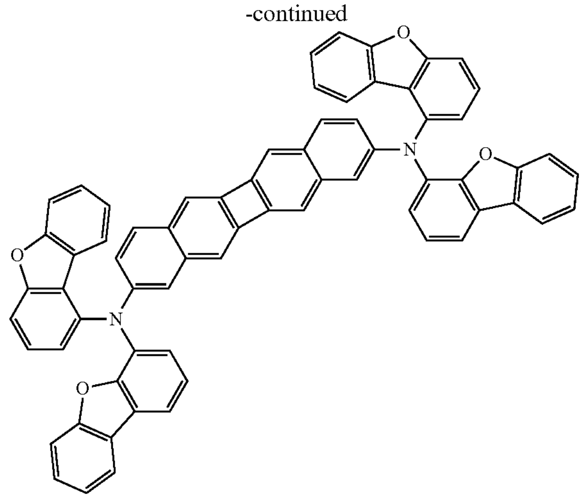
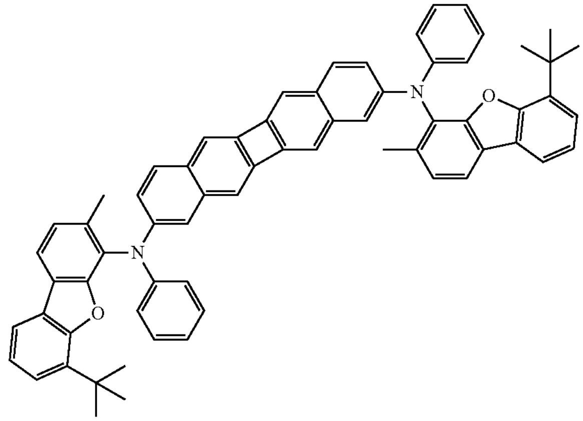
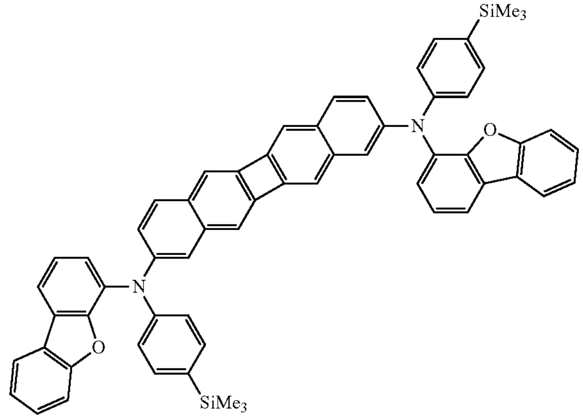
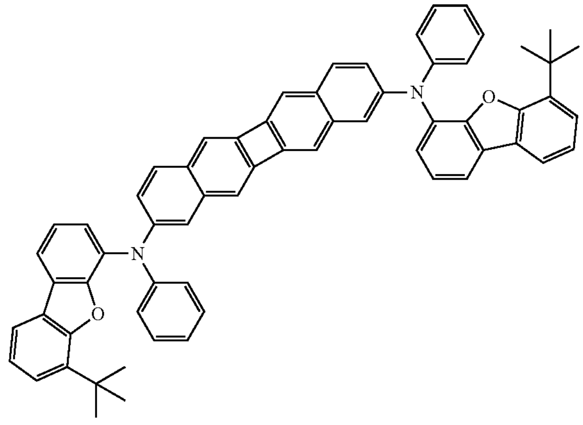

-continued
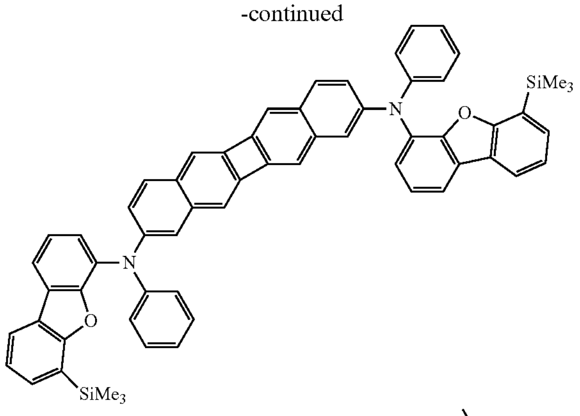
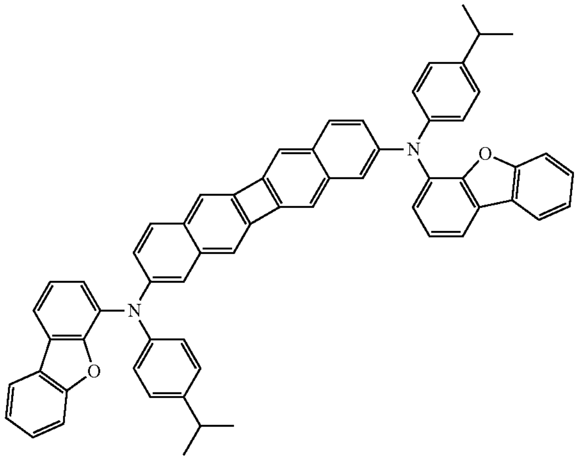
[Formula 124]
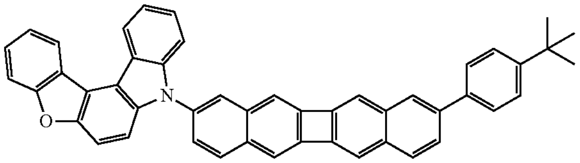
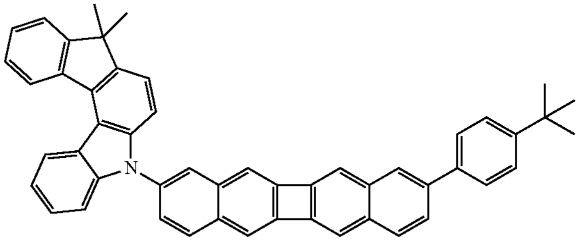
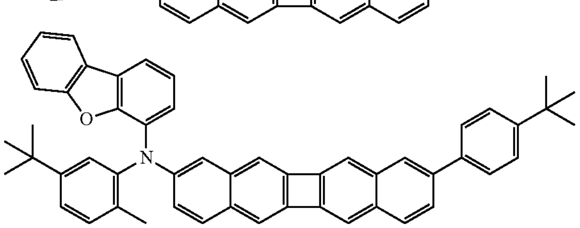
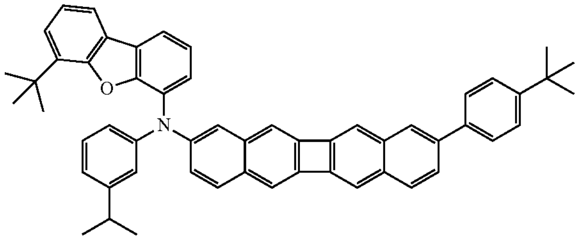
-continued
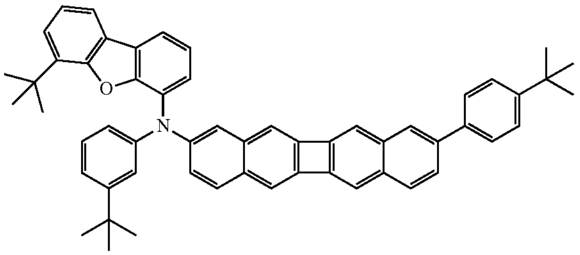
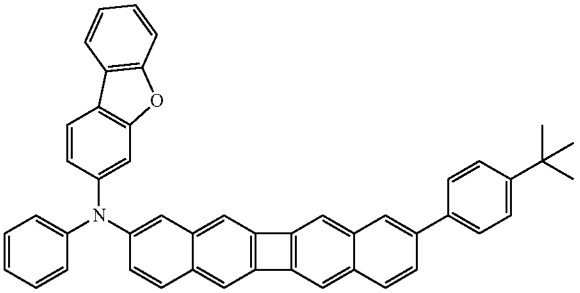
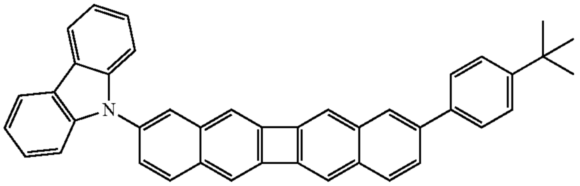
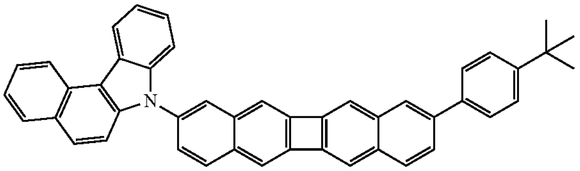
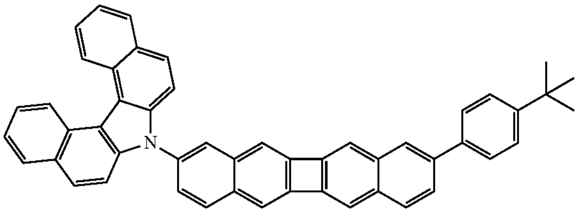
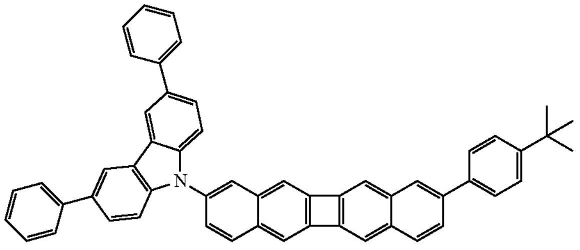
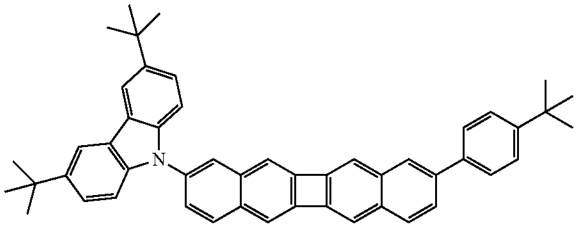

-continued
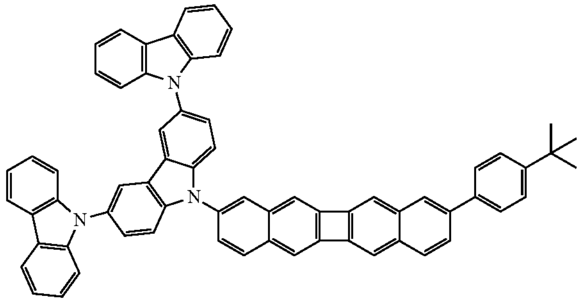
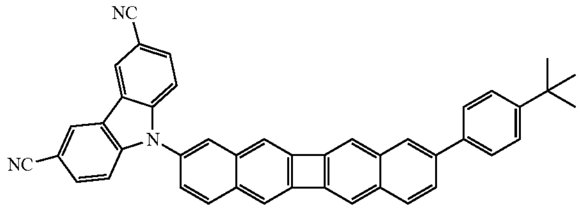
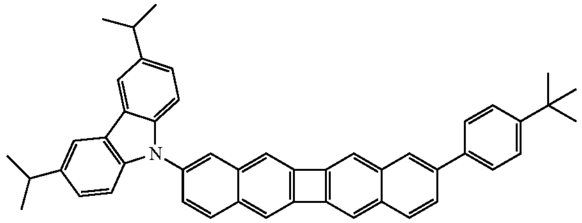
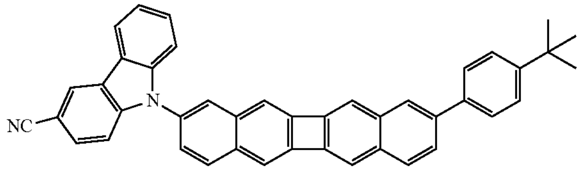
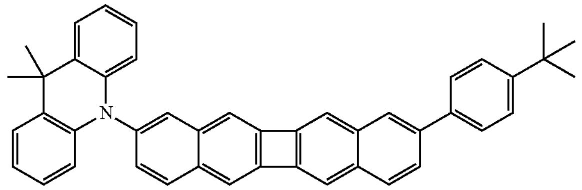
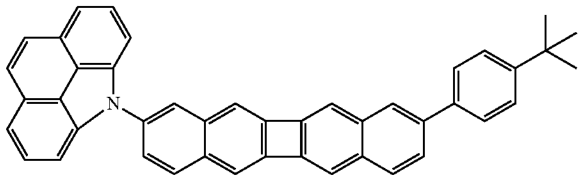
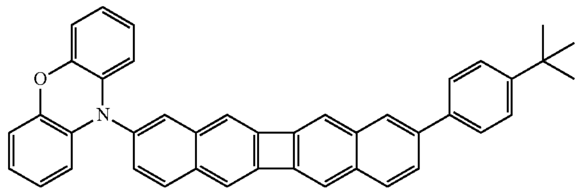
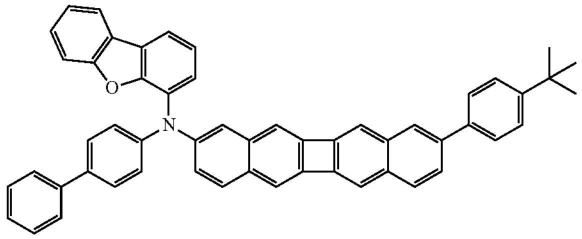
-continued
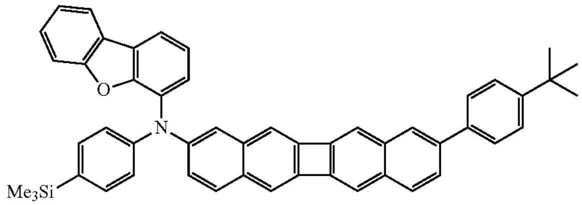
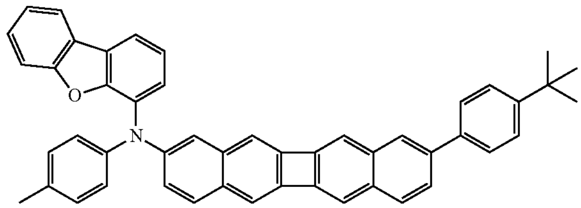
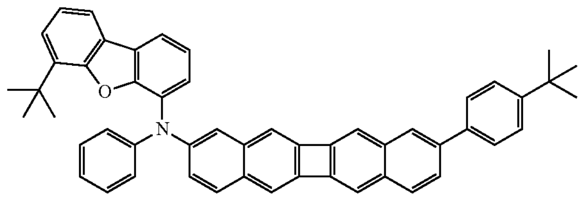
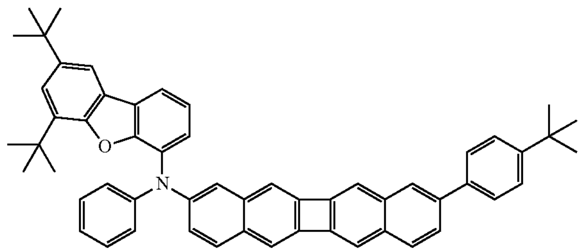
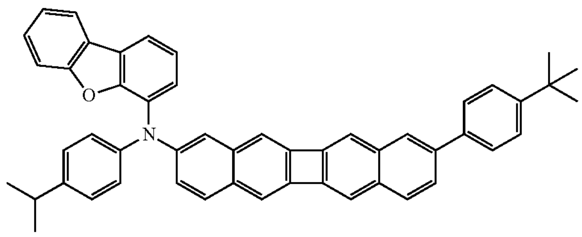
[Formula 125]
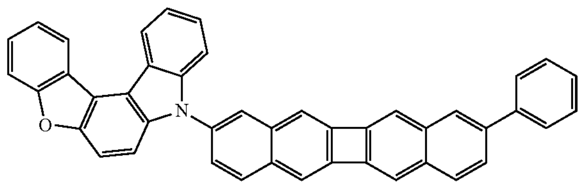
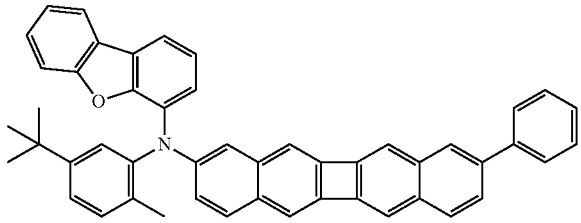

-continued
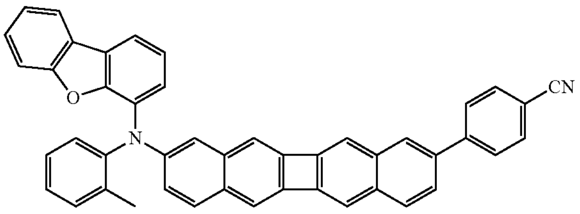
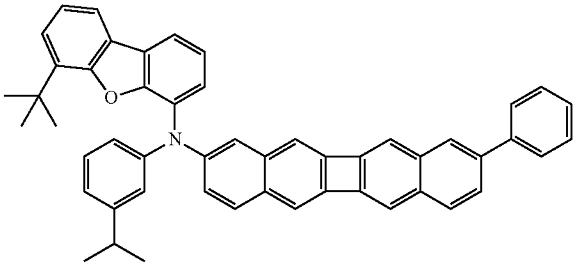
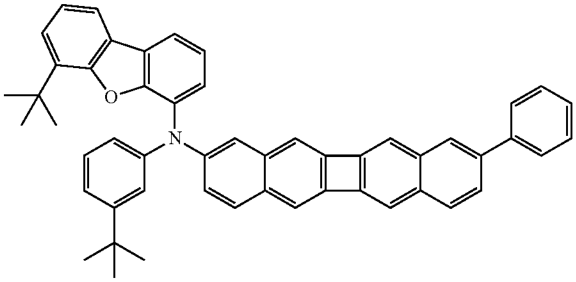
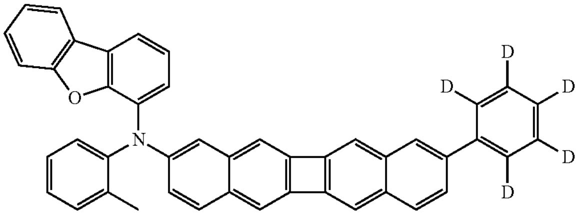
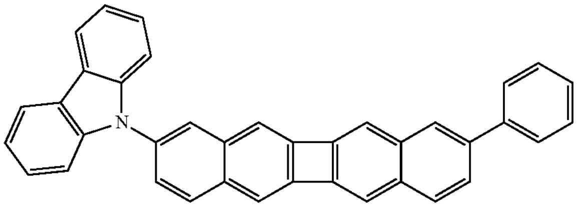
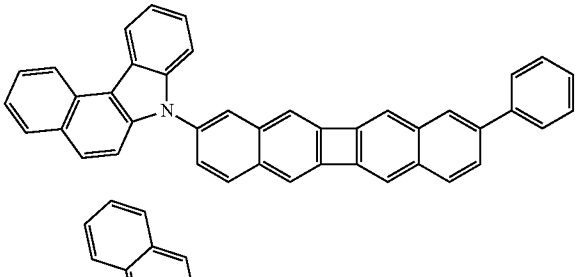
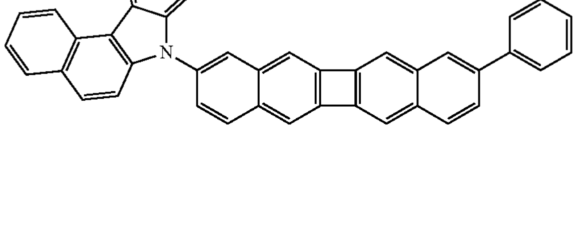
-continued
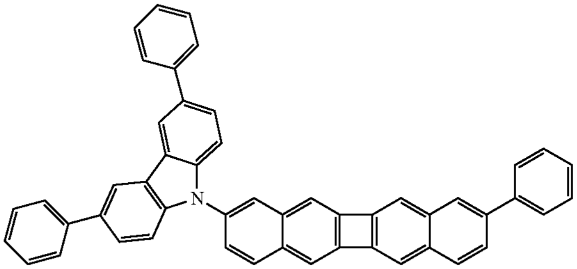
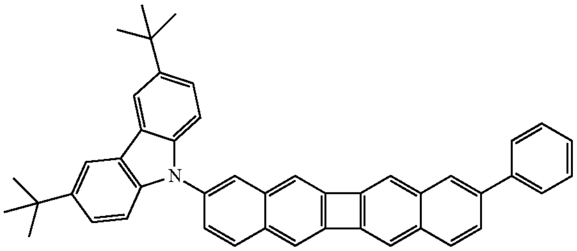
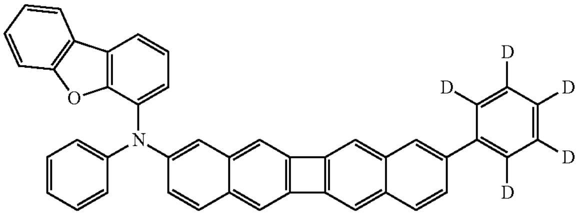
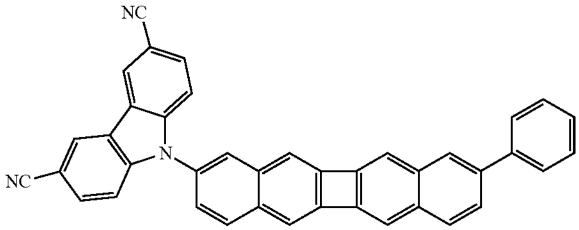
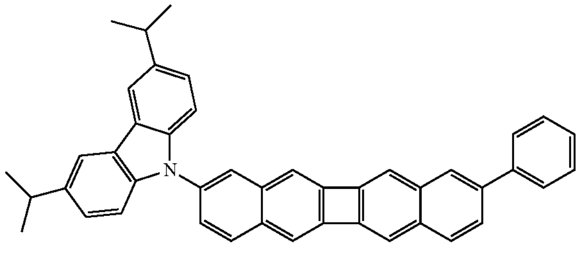
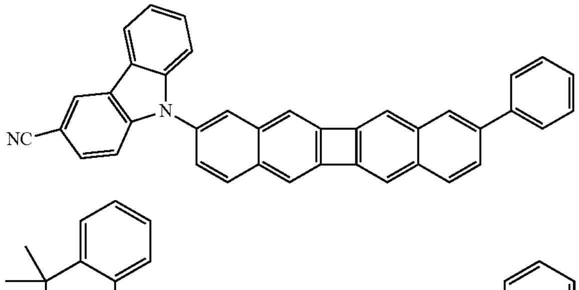
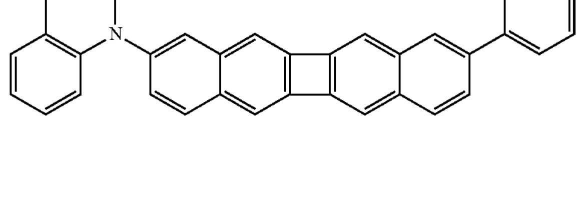

-continued
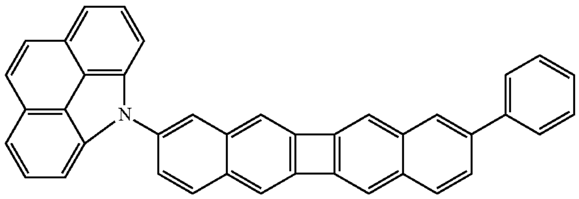
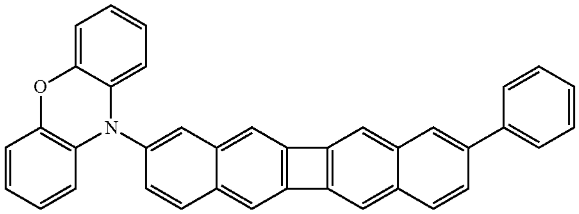
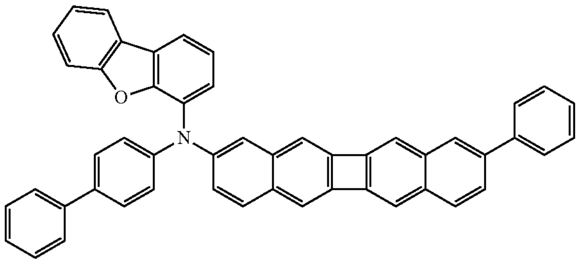
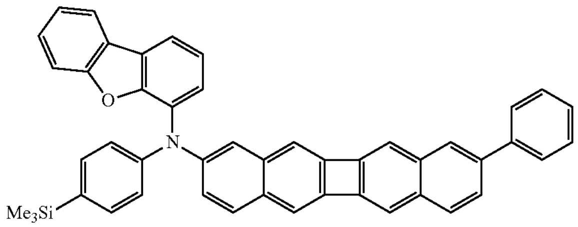
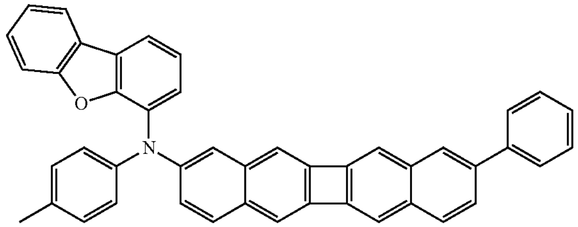
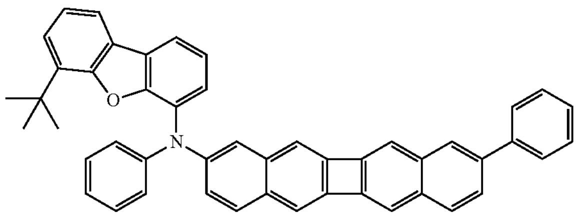
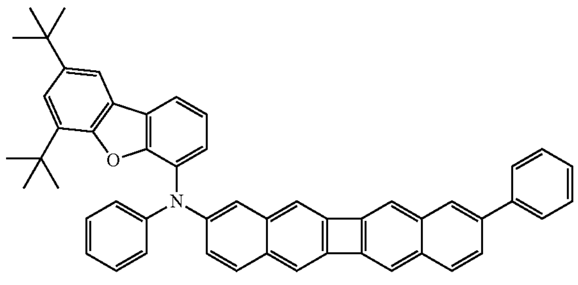
-continued
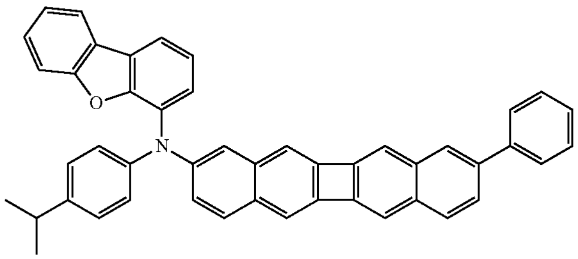
[Formula 126]
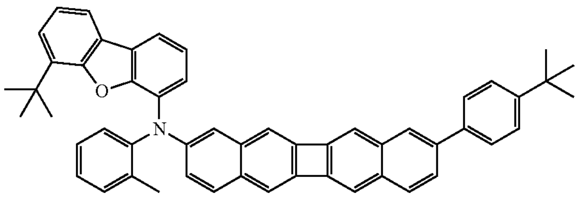
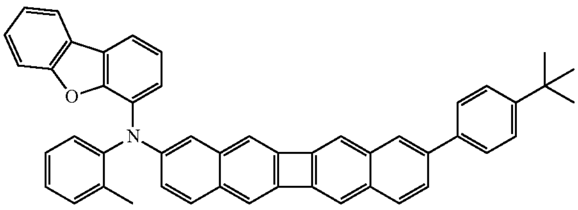
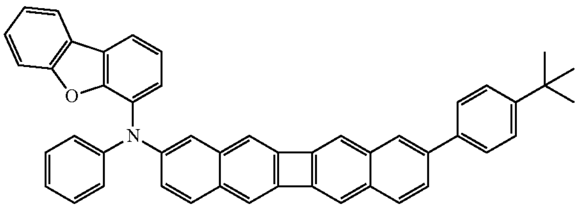
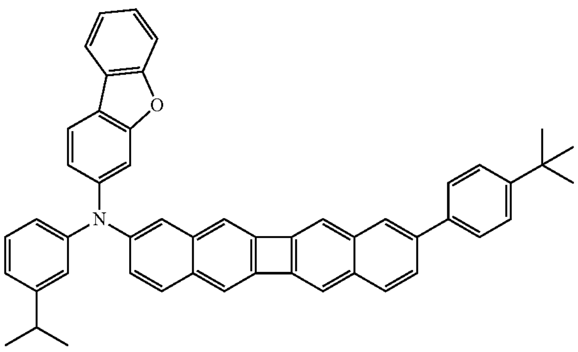
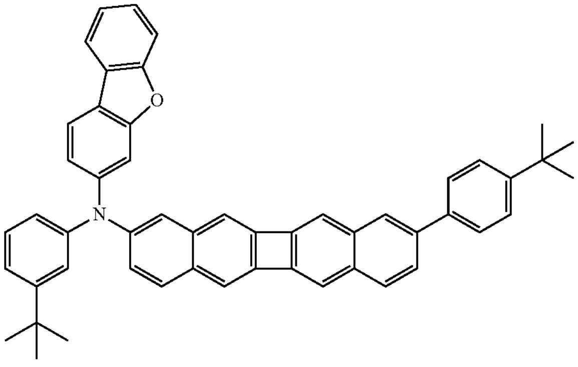

-continued
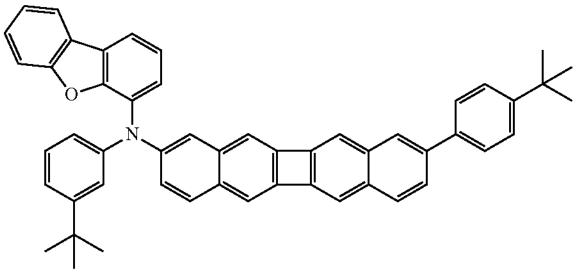
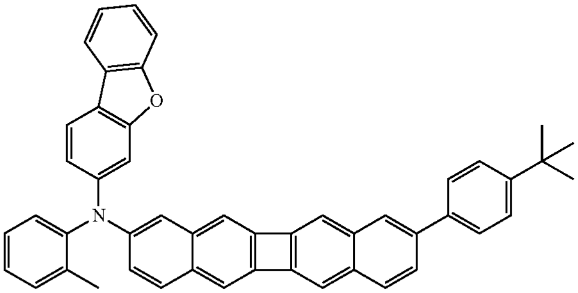
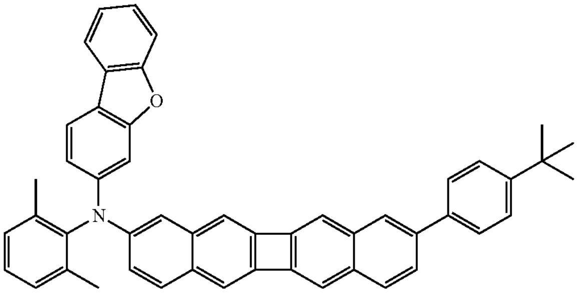
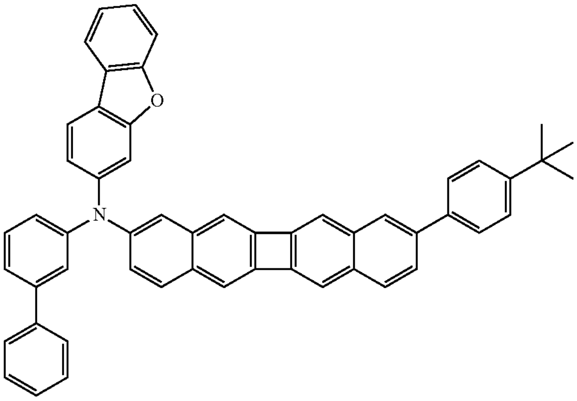
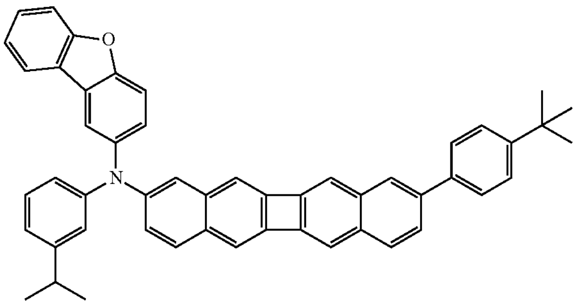
-continued
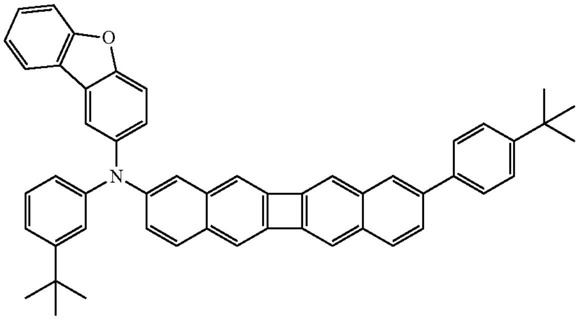
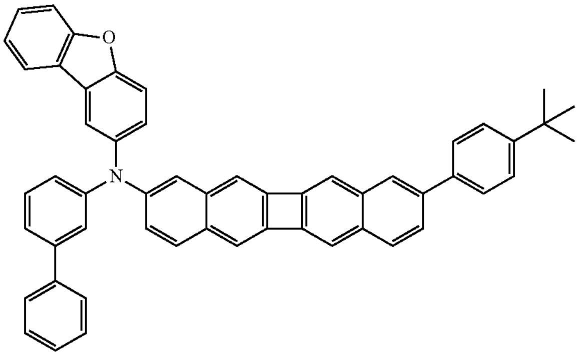
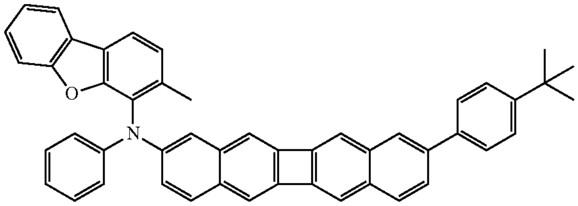
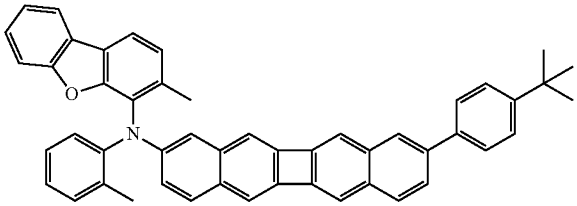
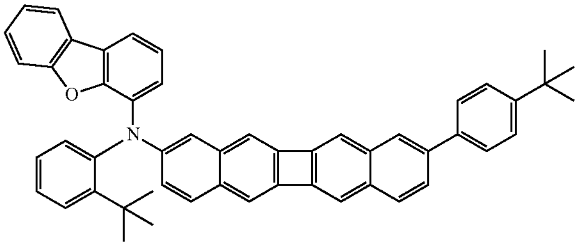
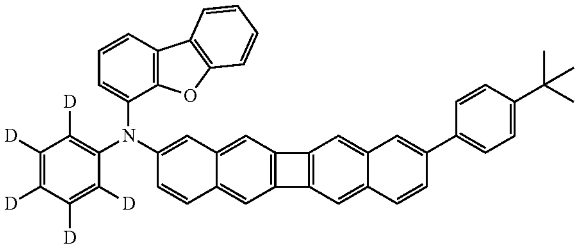

-continued
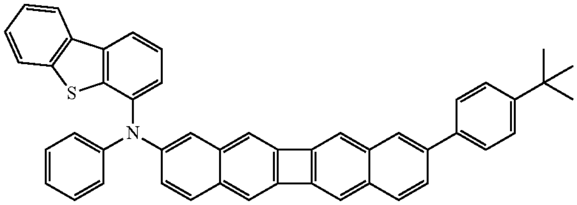
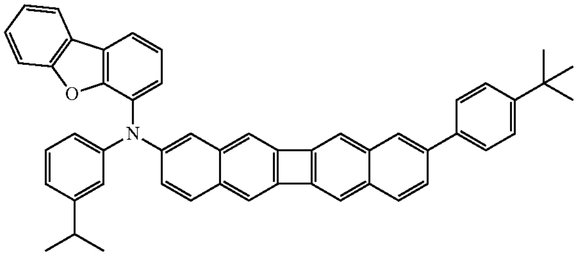
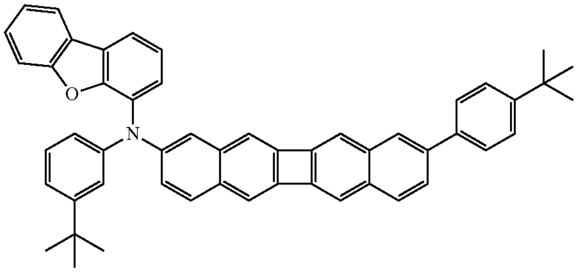
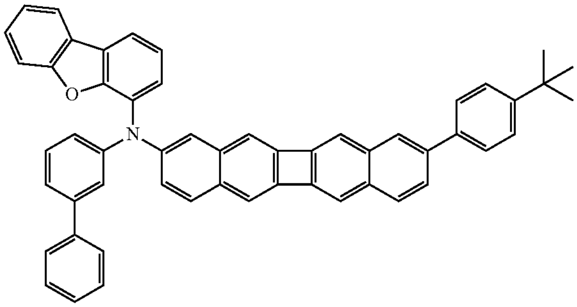
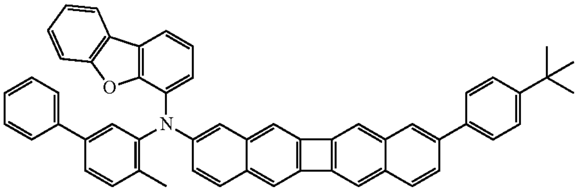
[Formula 127]
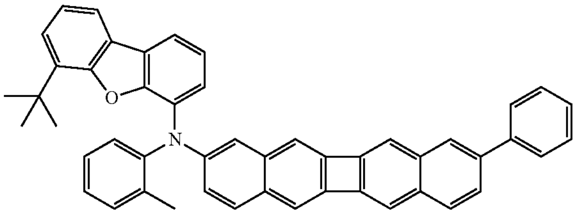
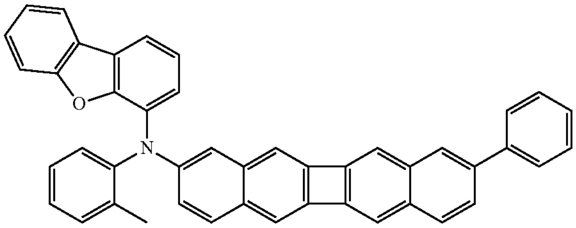
-continued
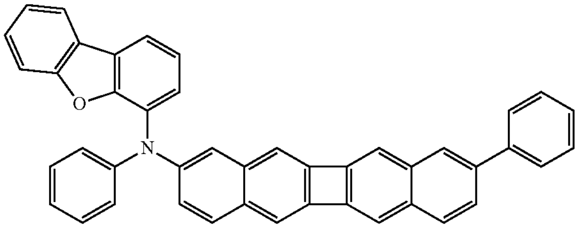
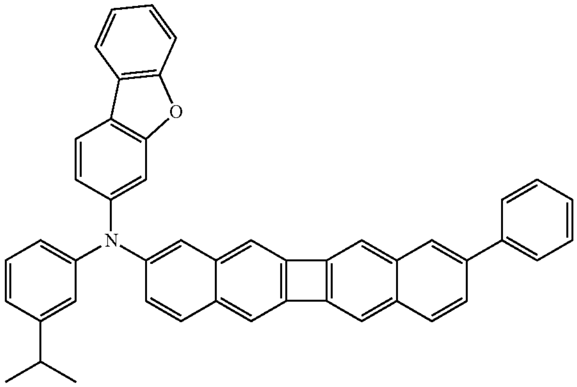
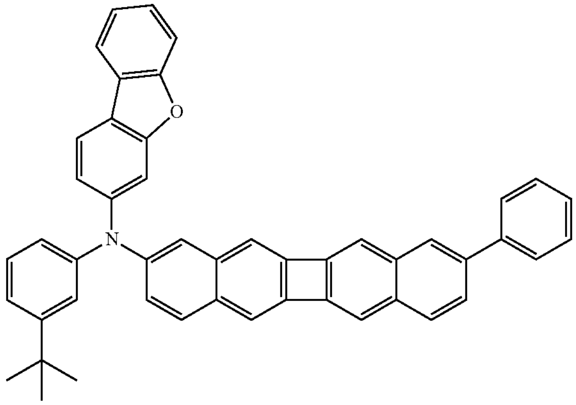
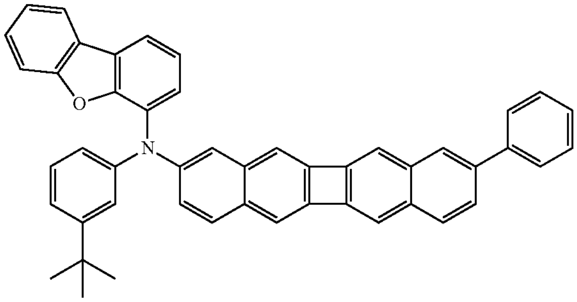
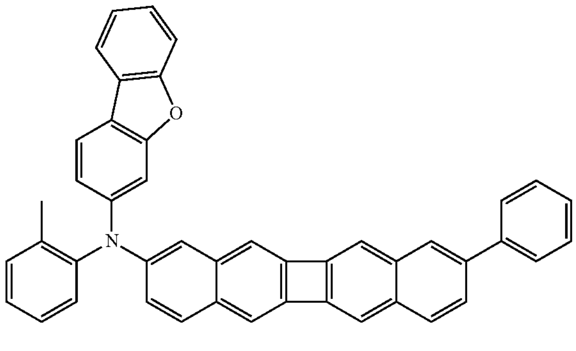

-continued
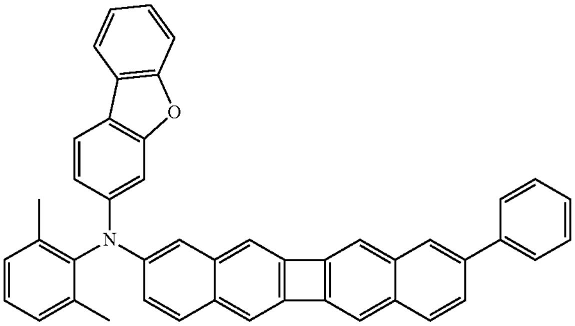
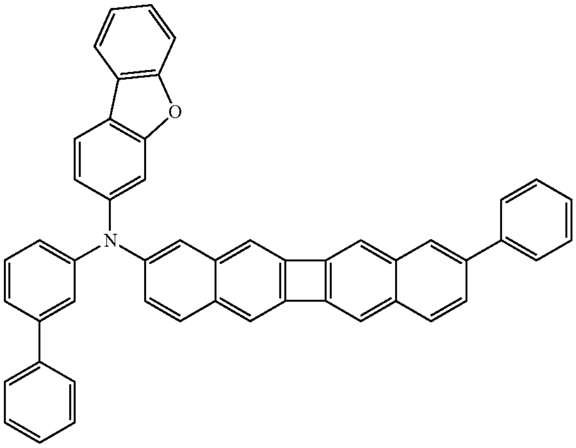
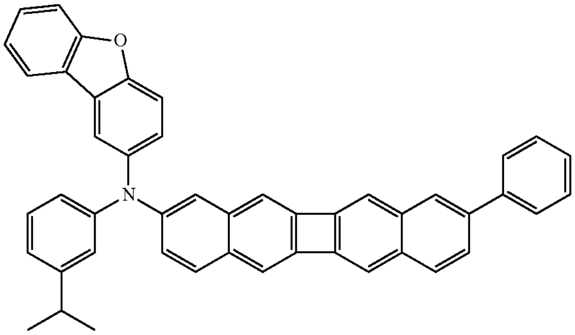
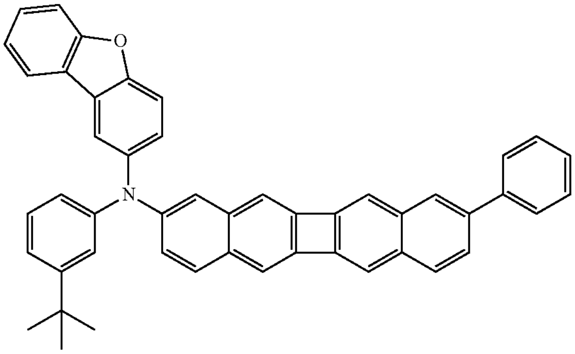
-continued
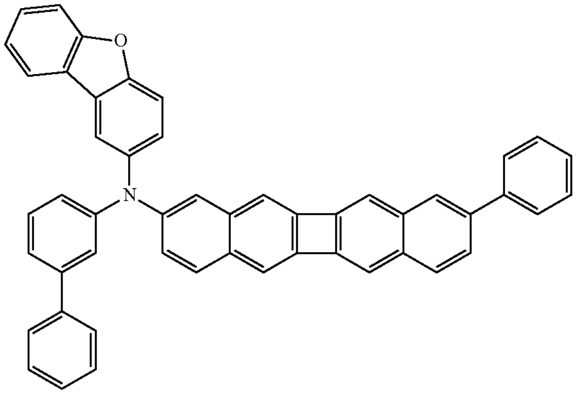
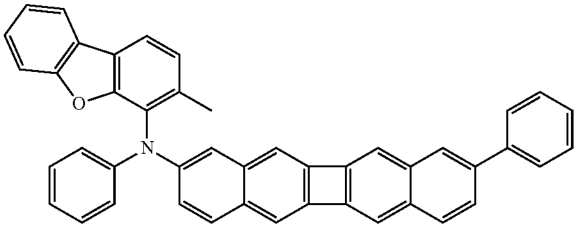
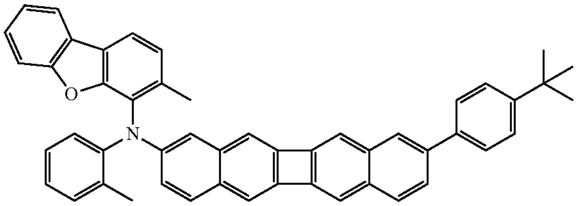
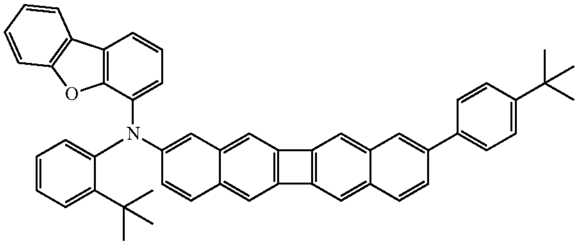
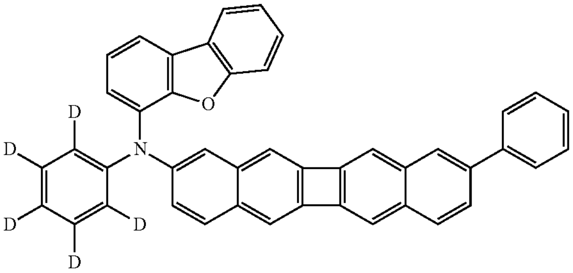
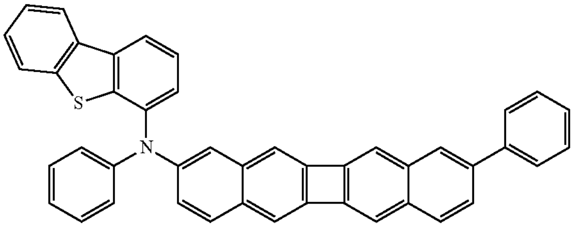

-continued
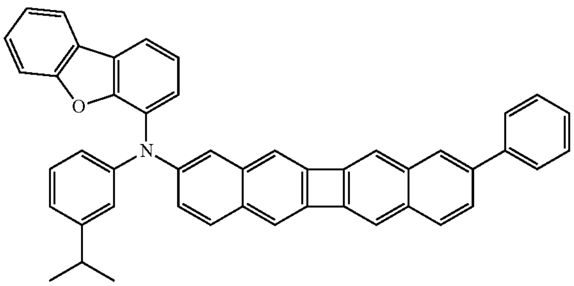
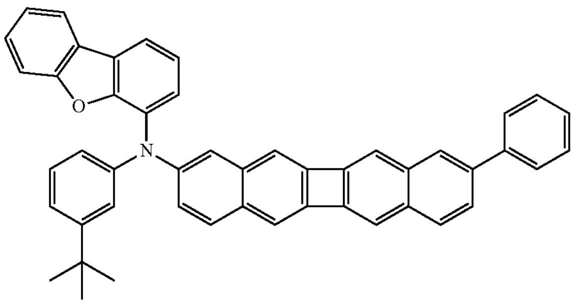
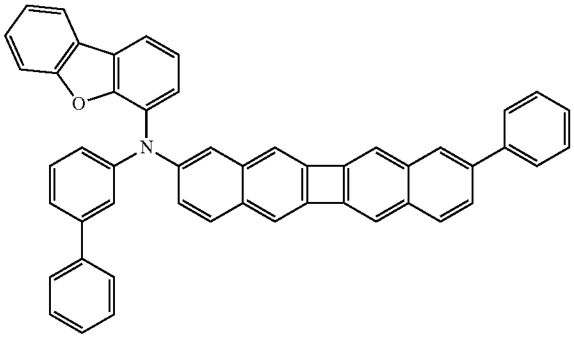
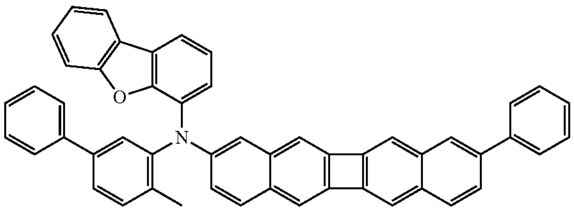
[Formula 128]
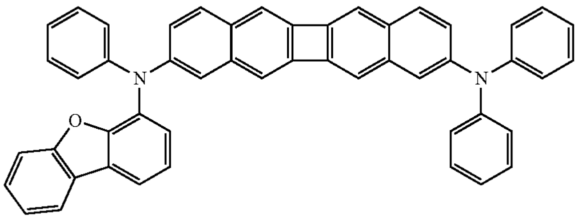
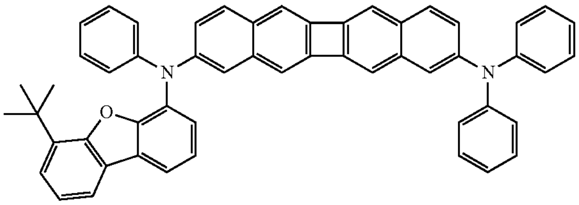
-continued
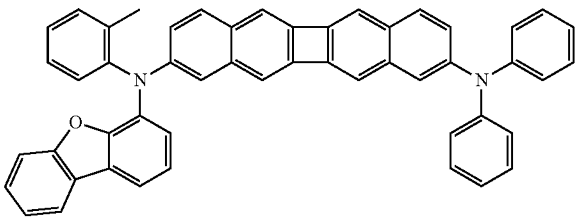
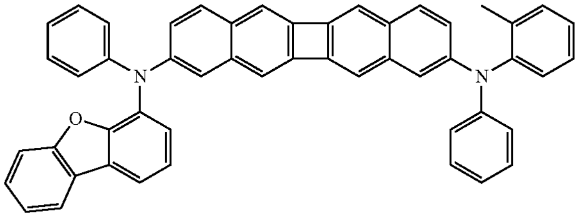
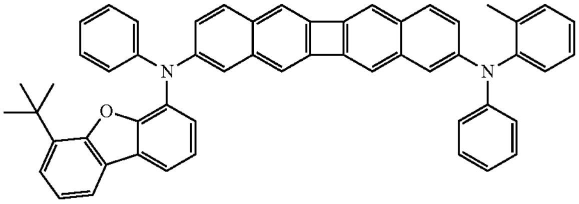
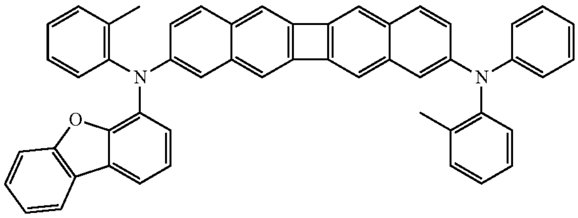
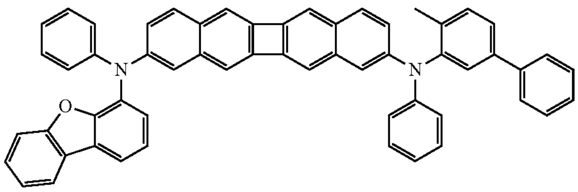
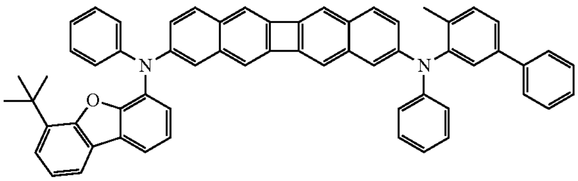
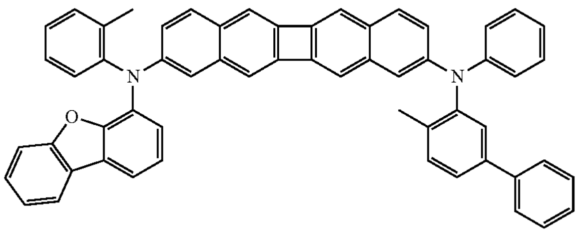
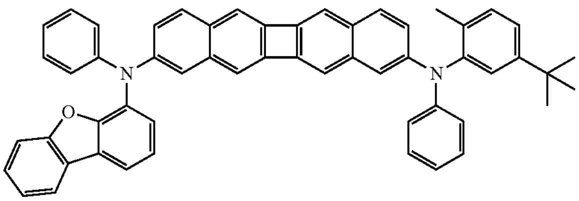

-continued
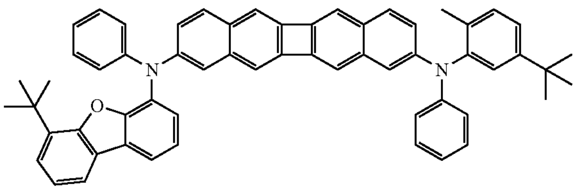
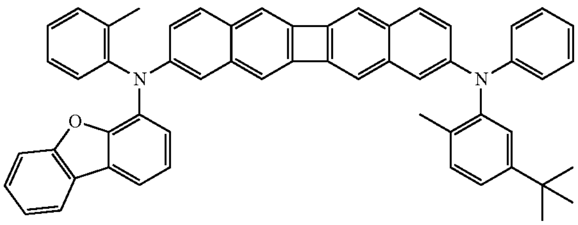
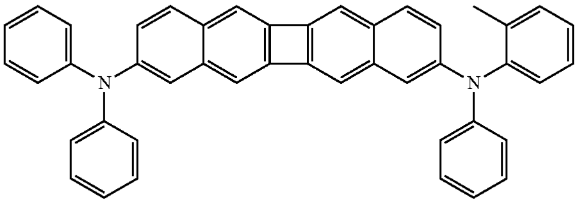
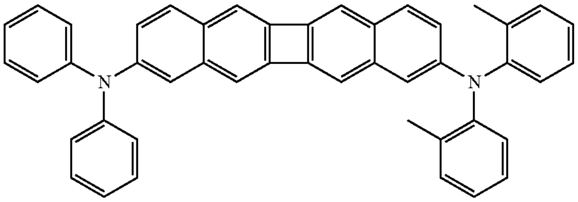
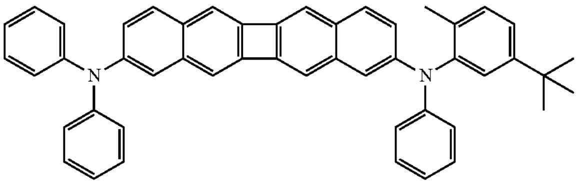
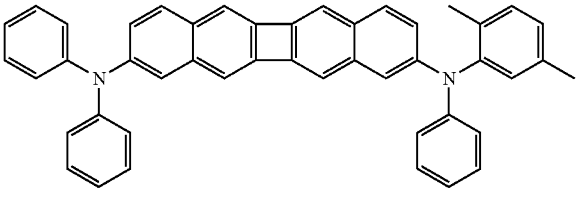
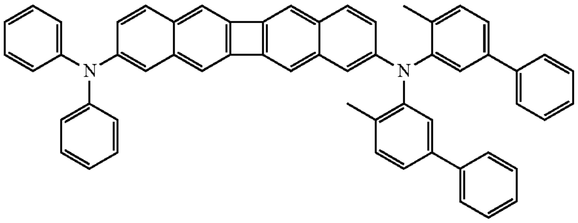
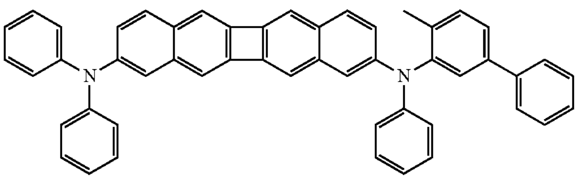
-continued
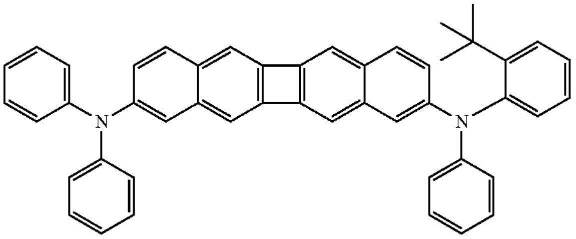
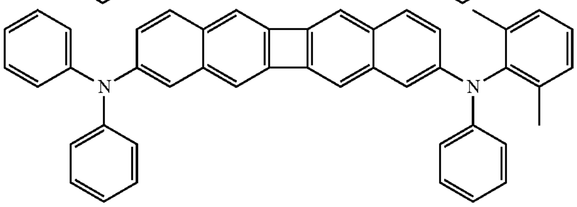
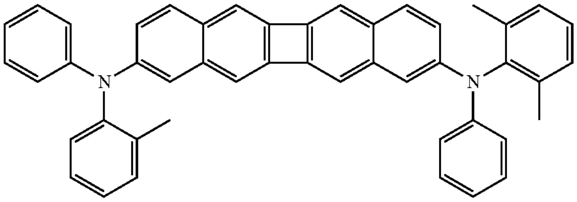
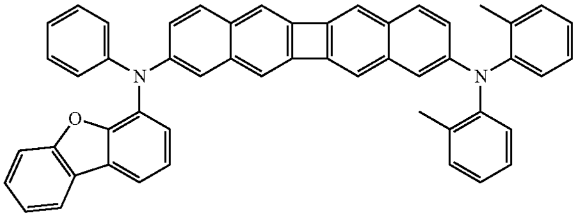
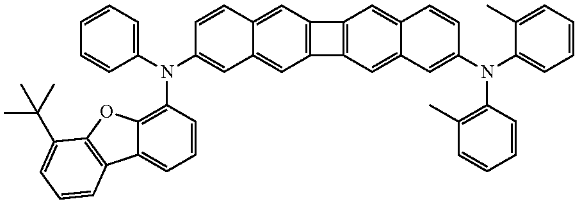
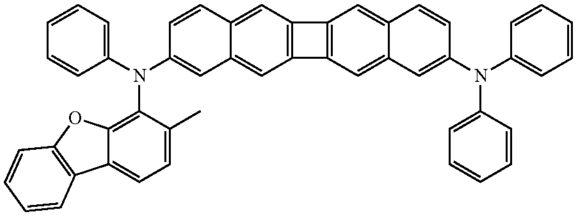
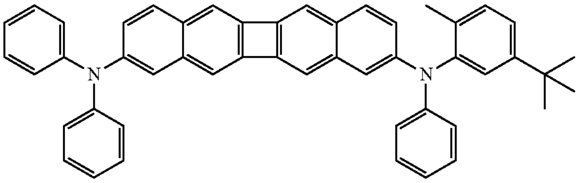
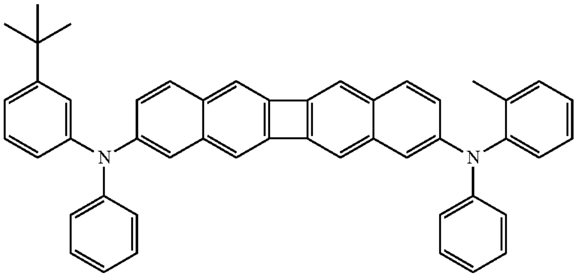

-continued
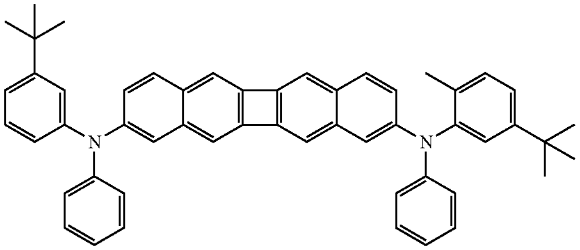
[Formula 129]
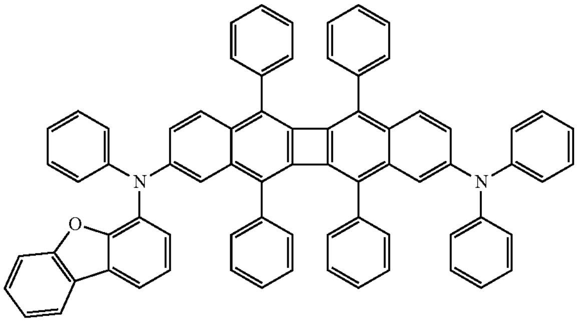
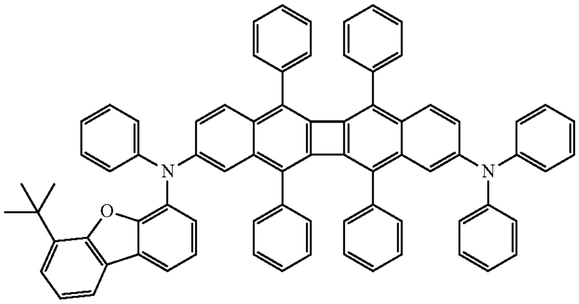
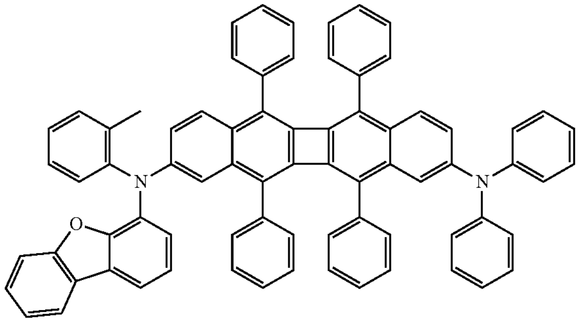
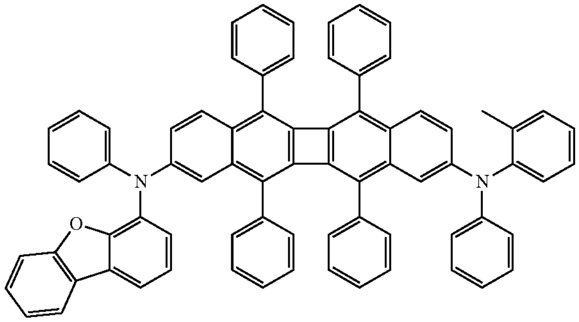
-continued
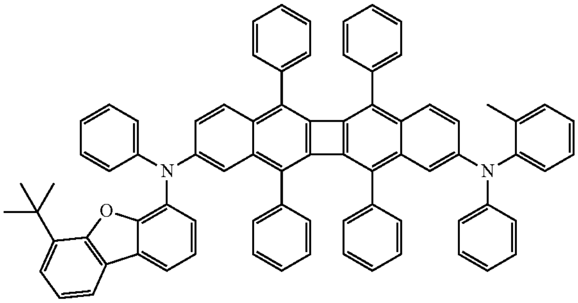
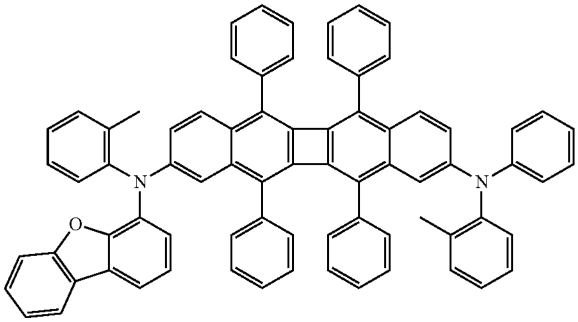
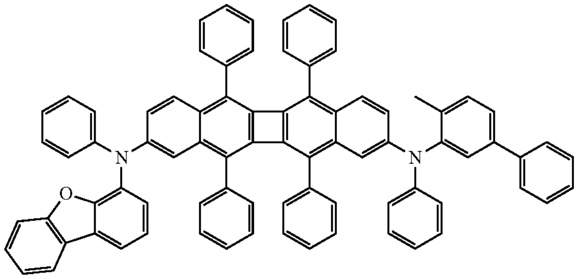
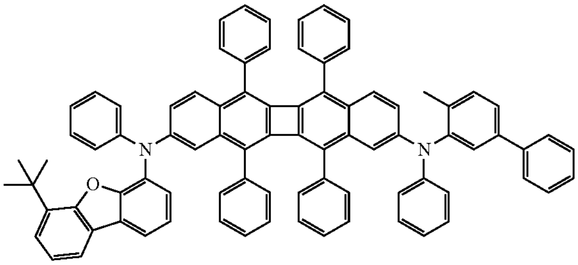
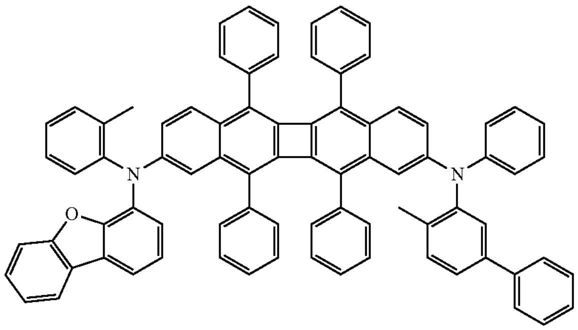

-continued
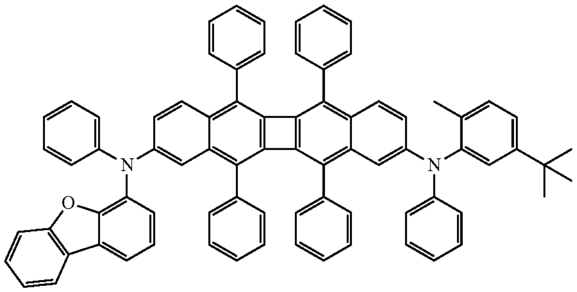
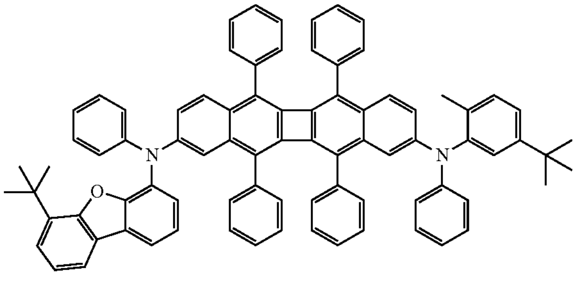
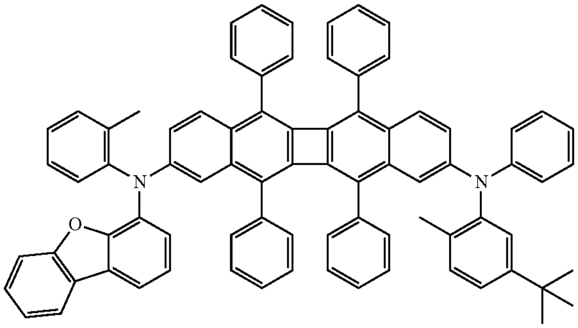
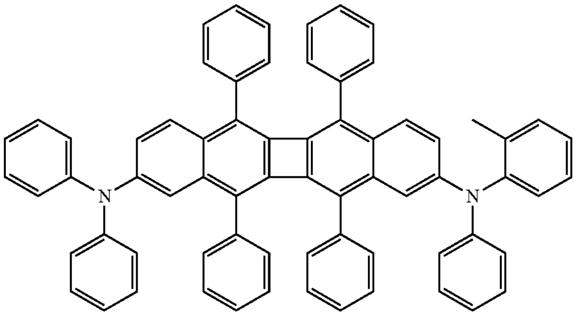
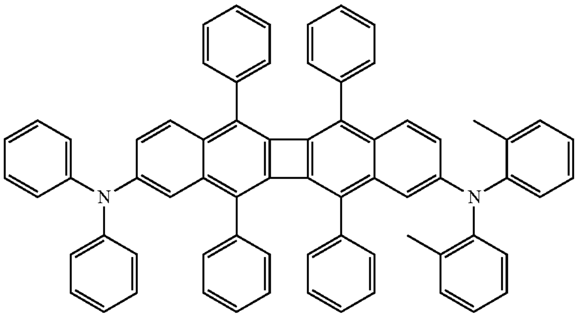
-continued
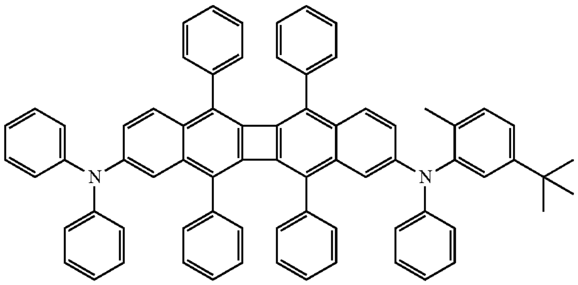
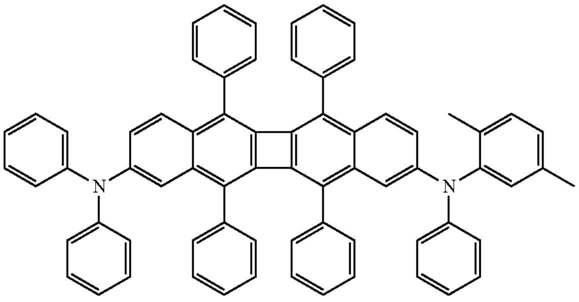
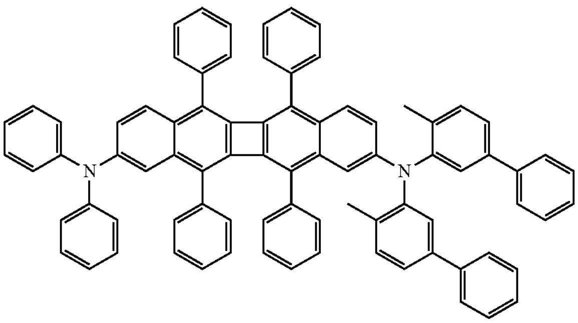
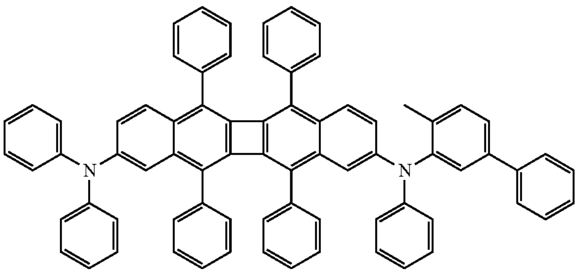
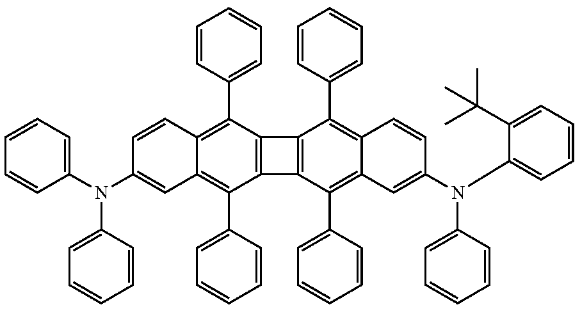

-continued
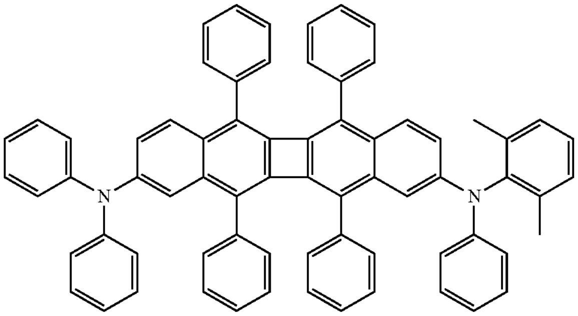
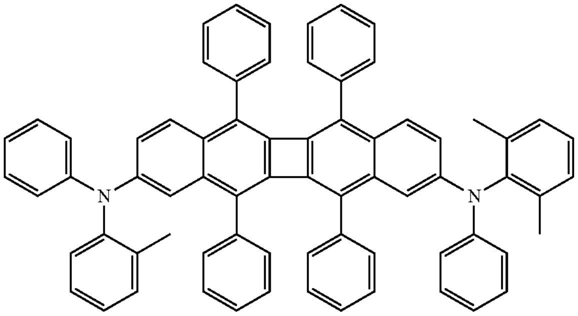
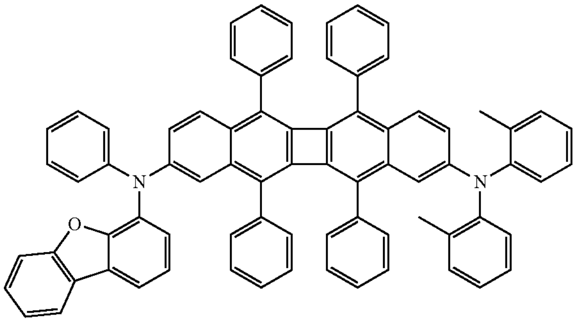
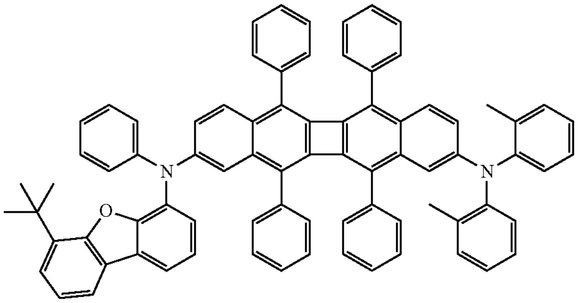
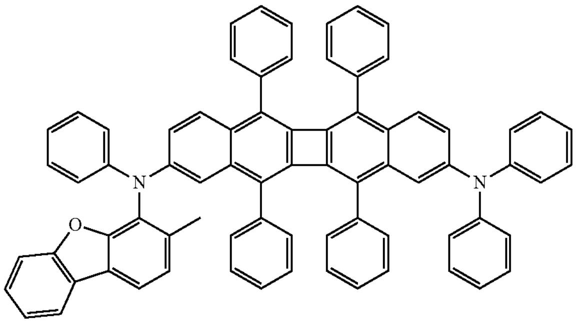
-continued
[Formula 130]
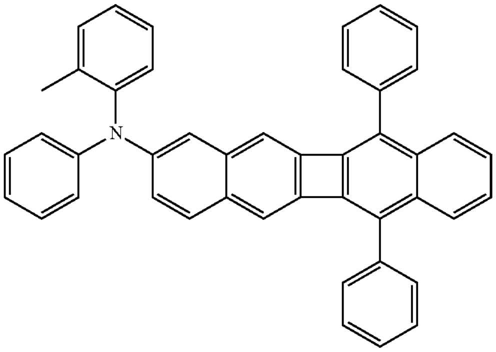
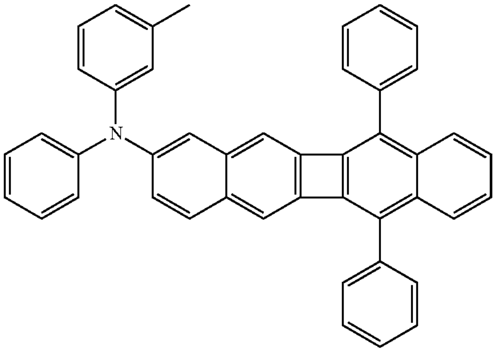
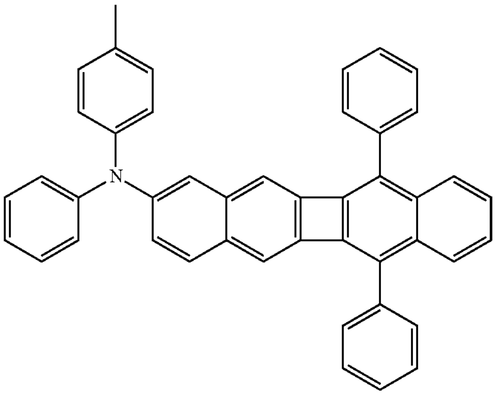
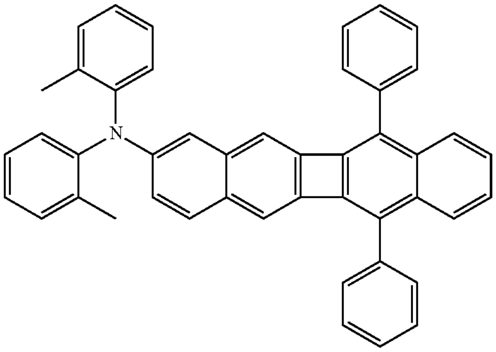

-continued
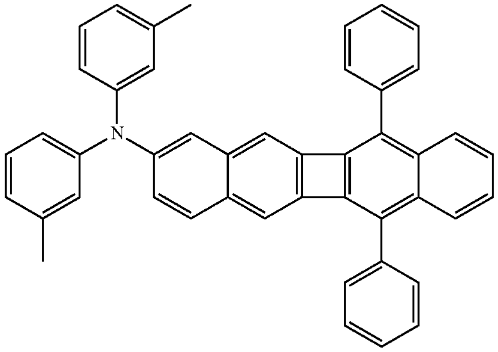
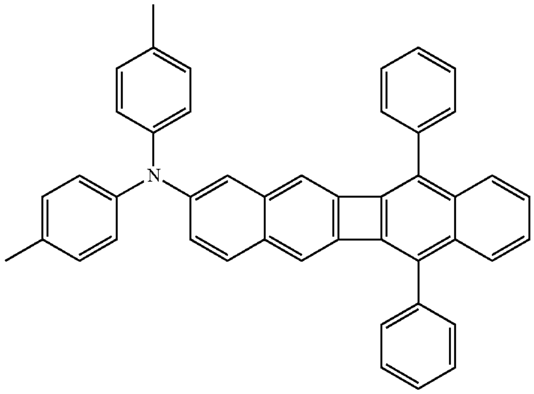
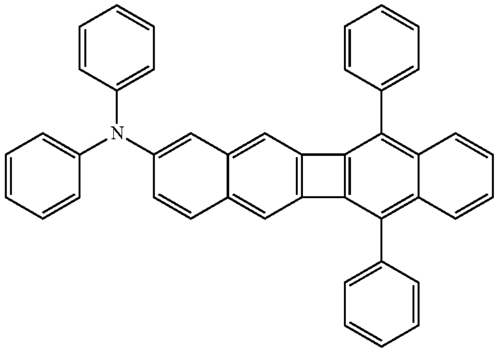
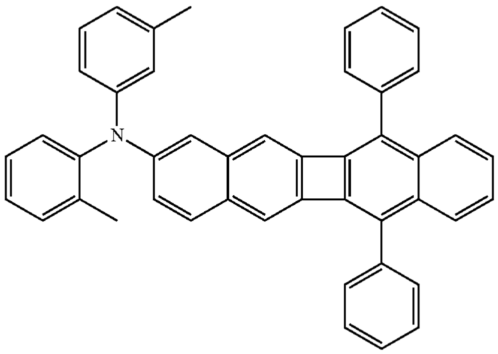
-continued
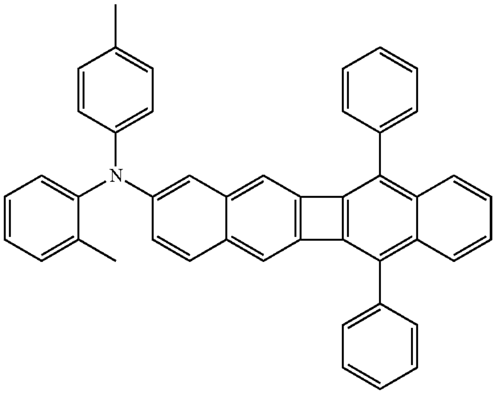
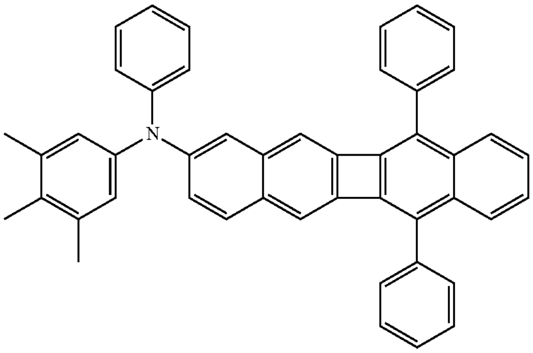
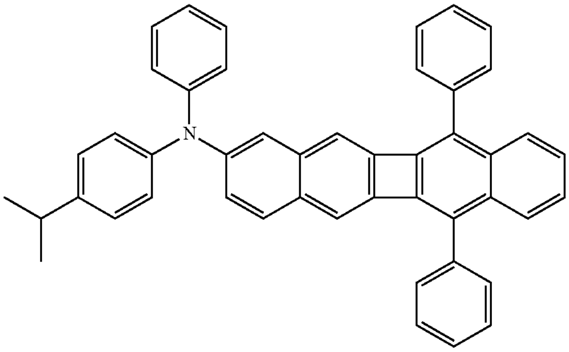
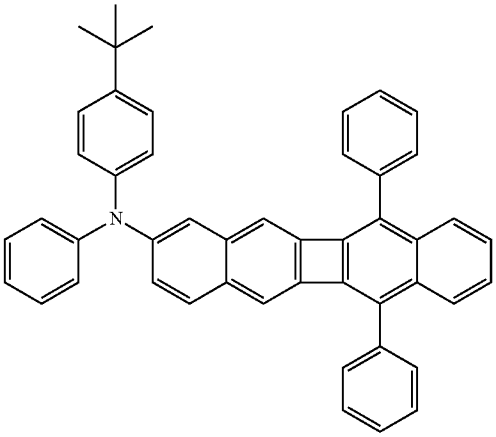

-continued
[Formula 131]
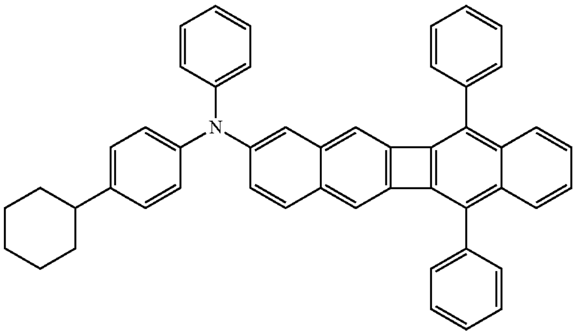
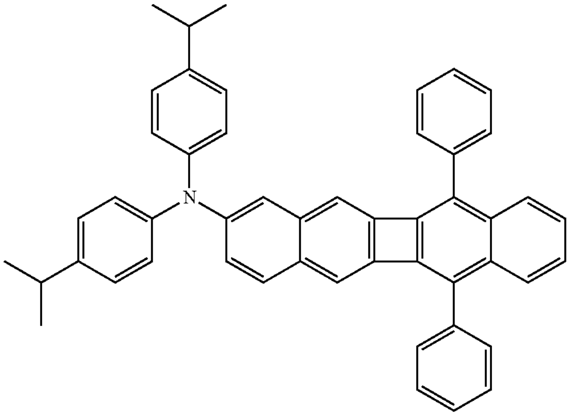
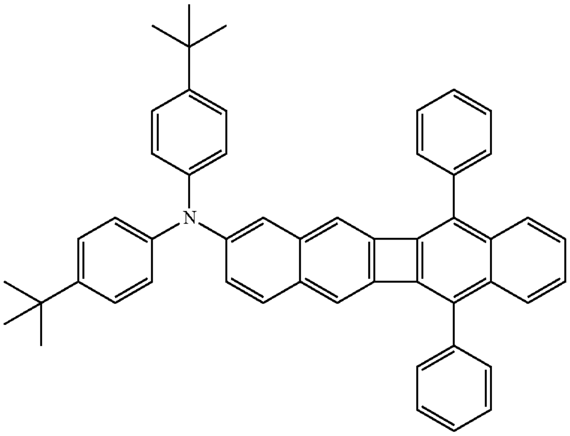
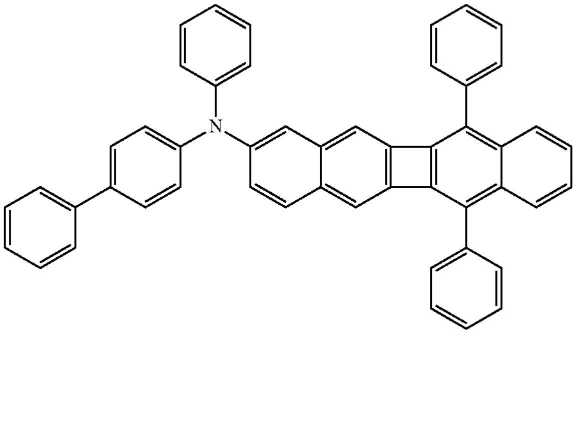
-continued
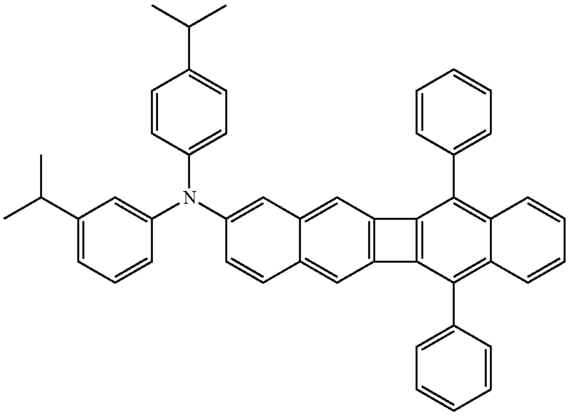
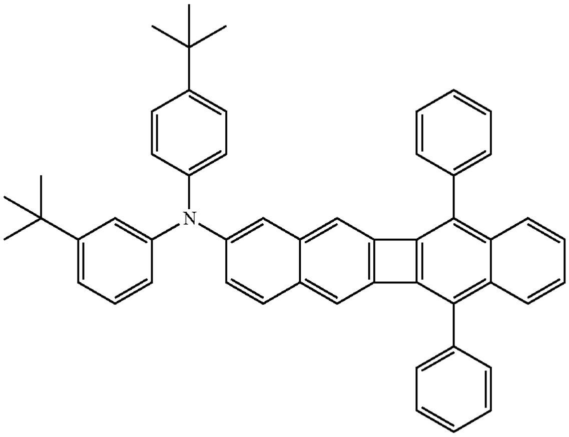
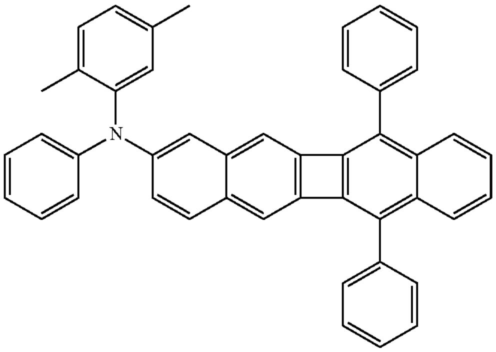
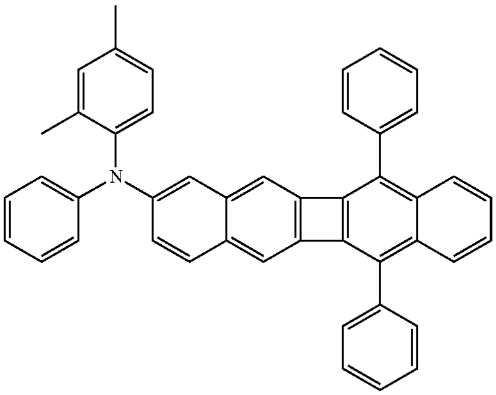

-continued
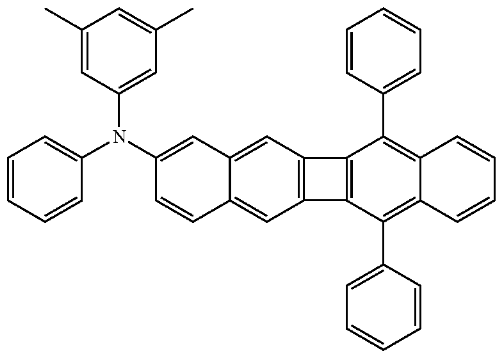
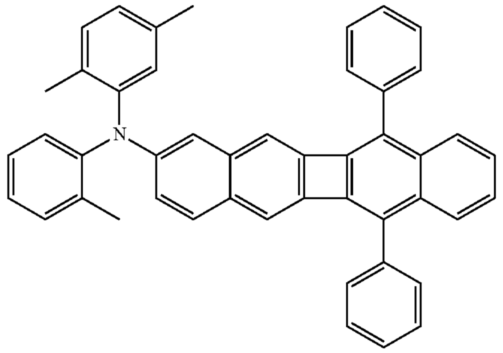
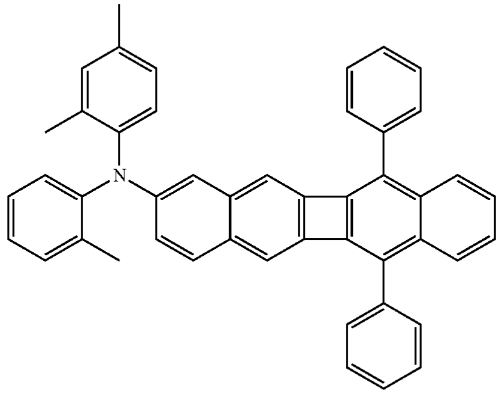
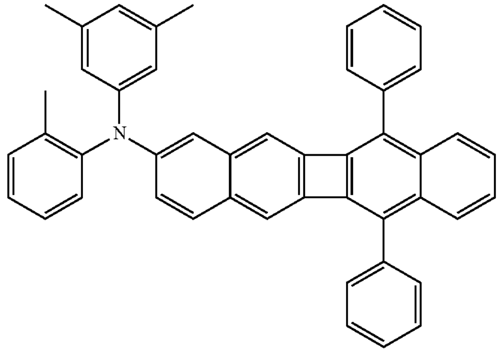
-continued
[Formula 132]
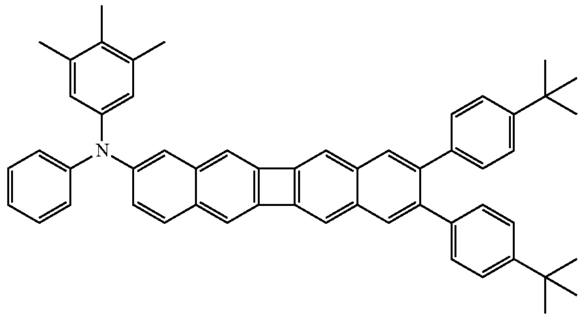
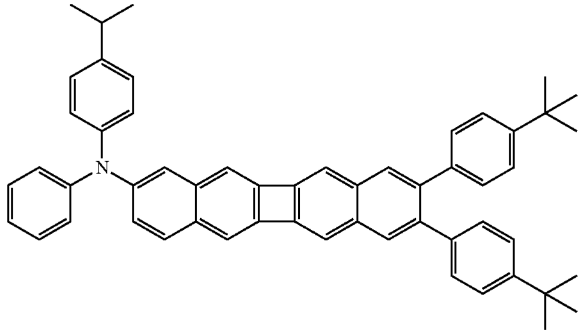
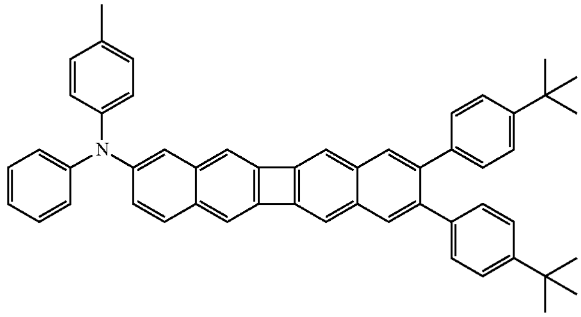
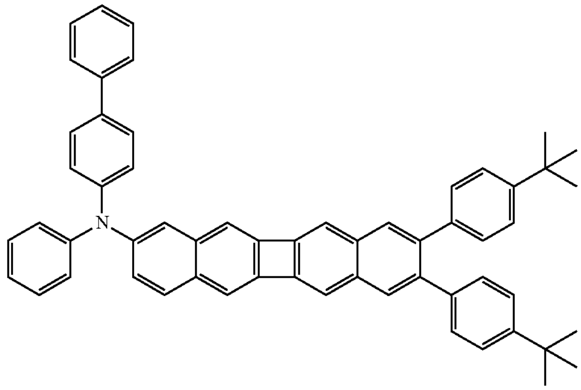

-continued
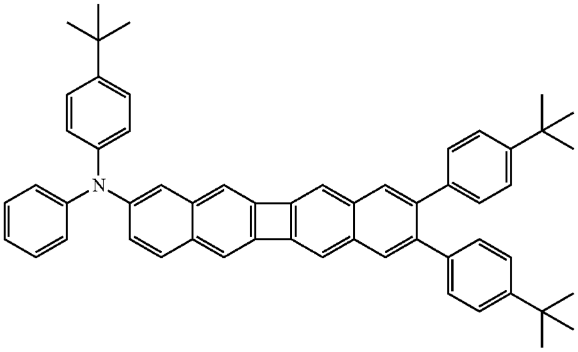
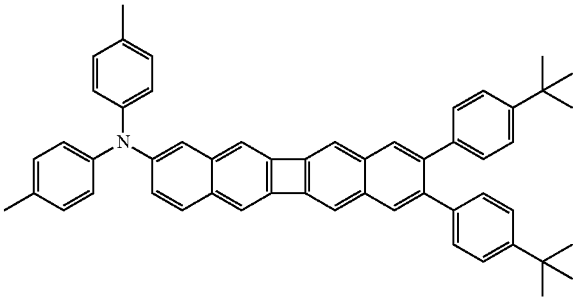
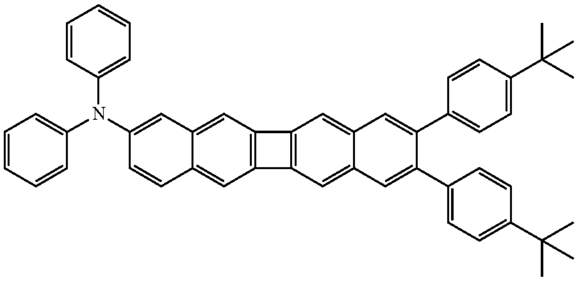
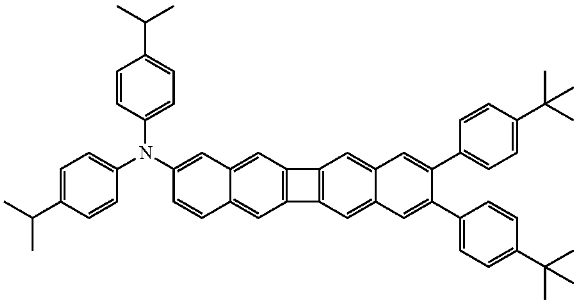
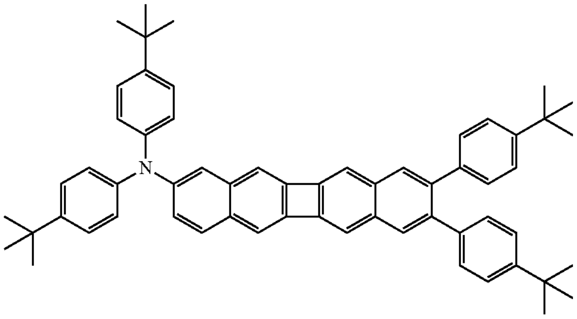
-continued
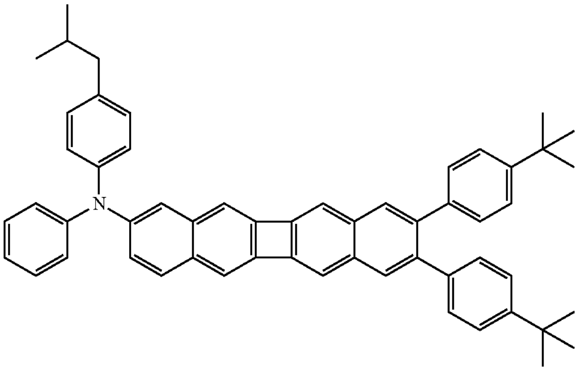
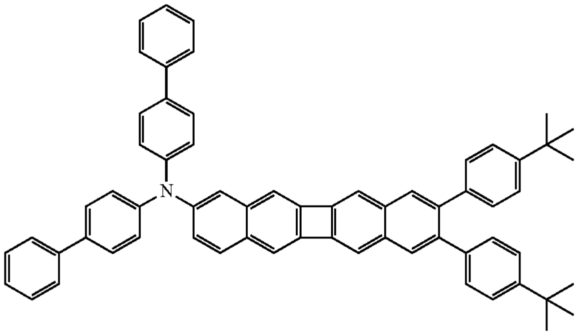
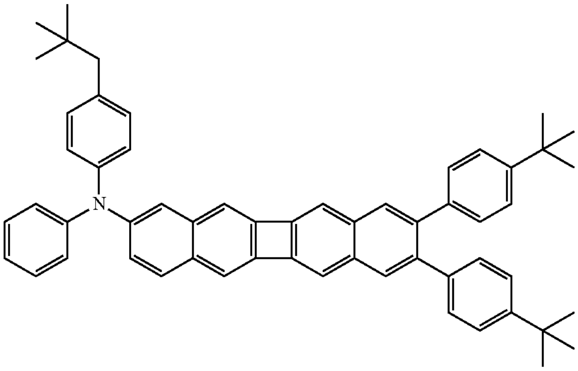
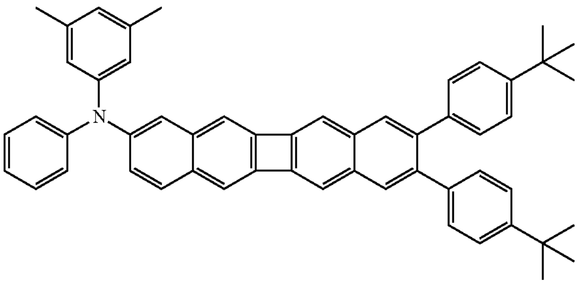
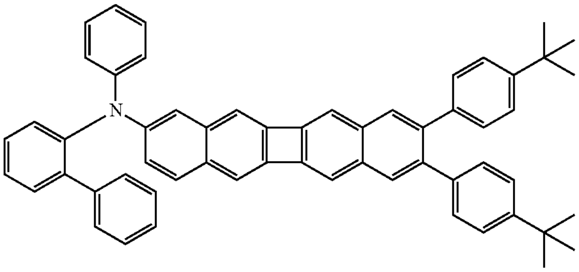

-continued
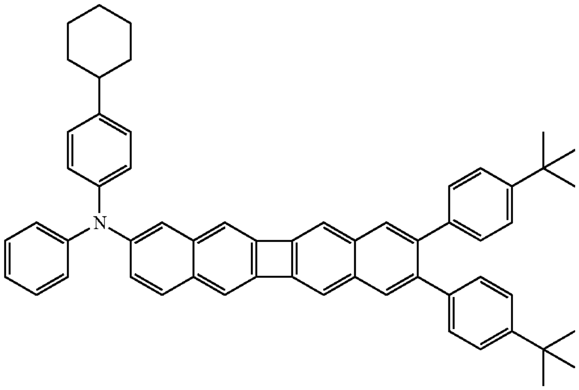
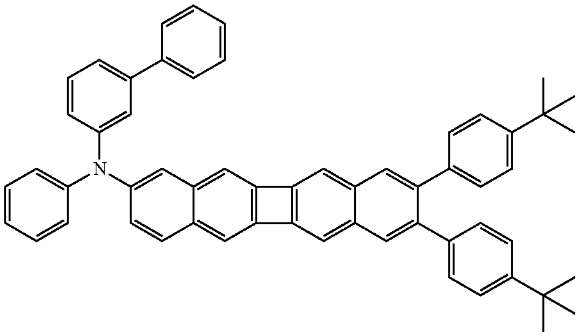
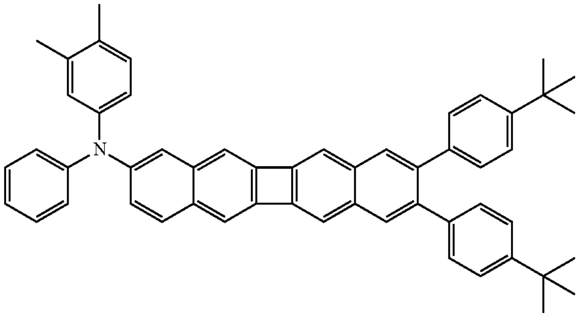
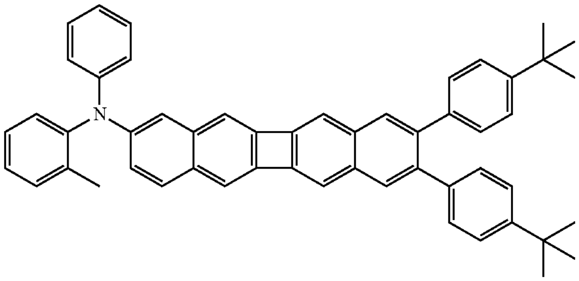
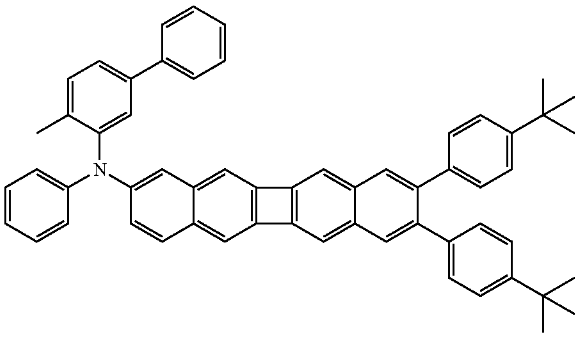
-continued
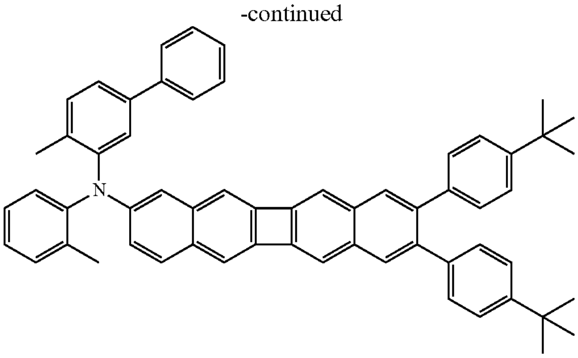
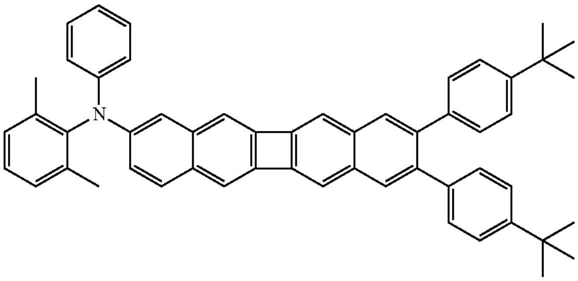
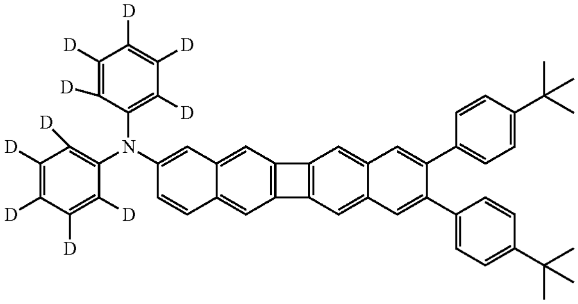
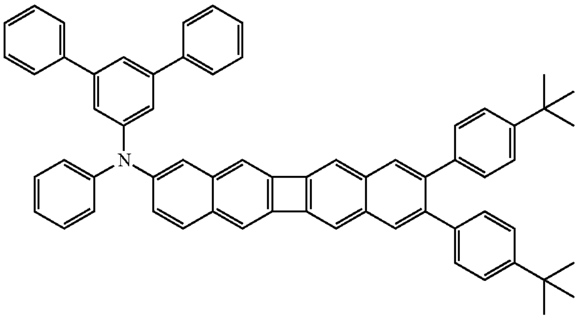
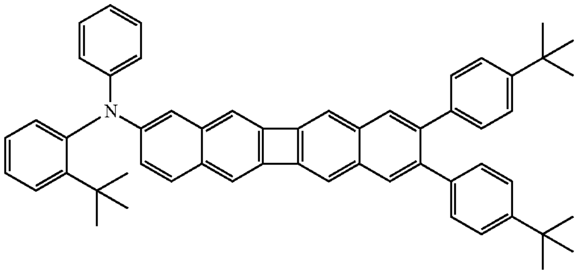

-continued
[Formula 133]
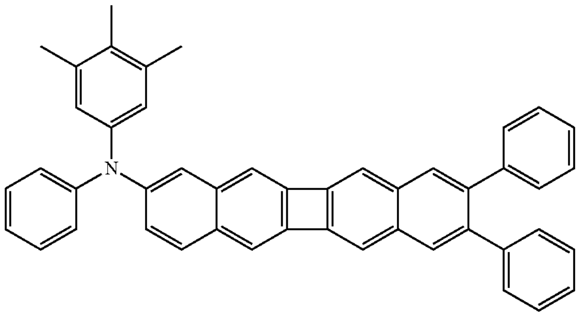
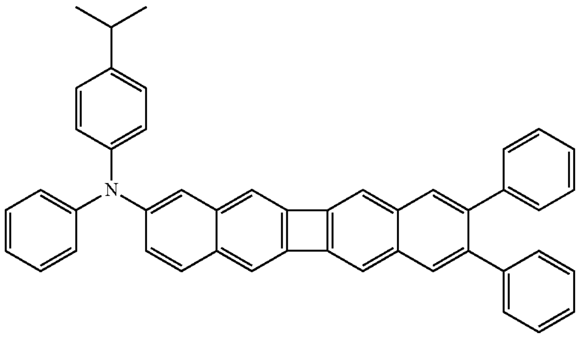
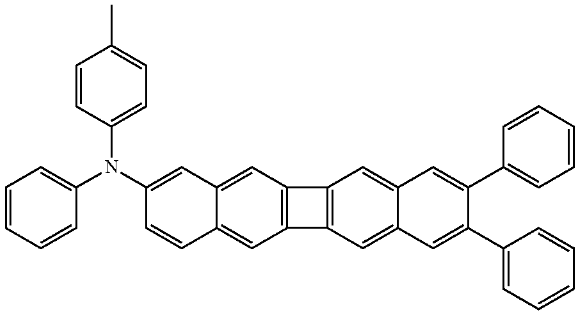
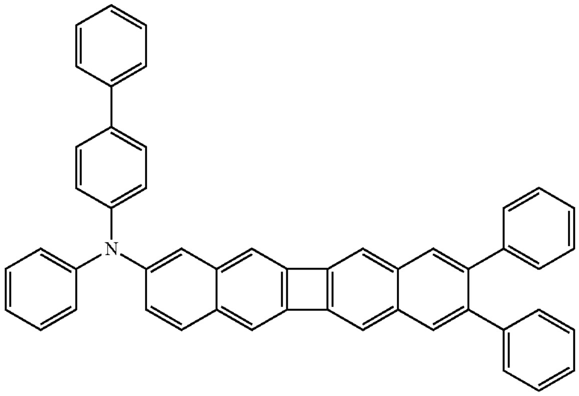
-continued
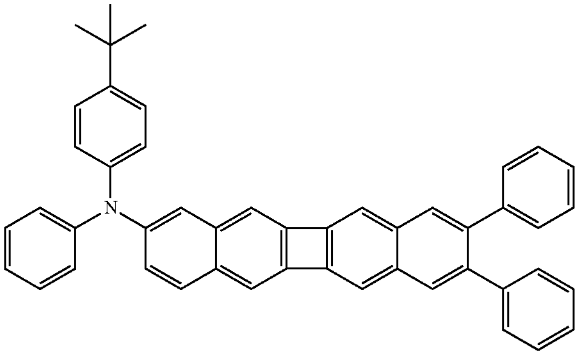
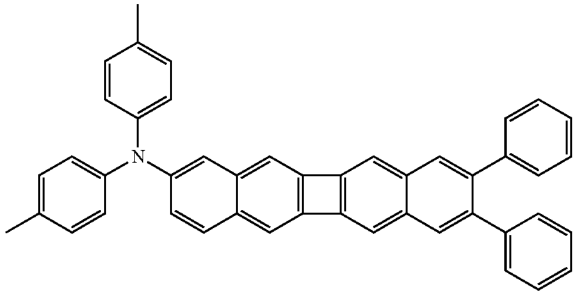
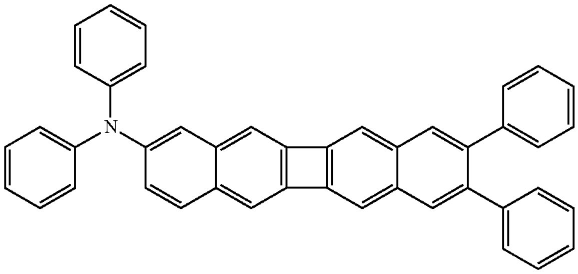
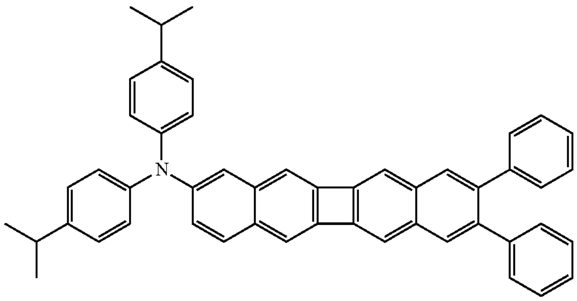

-continued
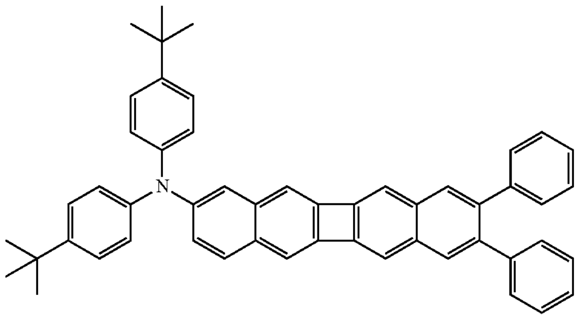
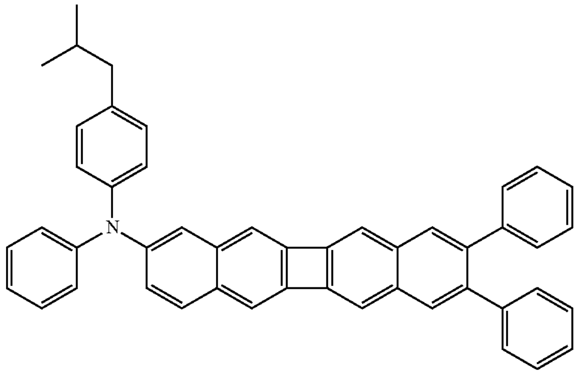
-continued
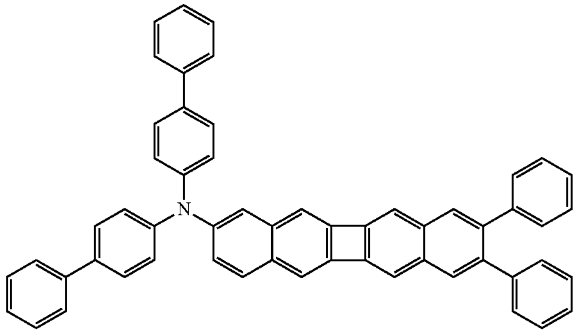
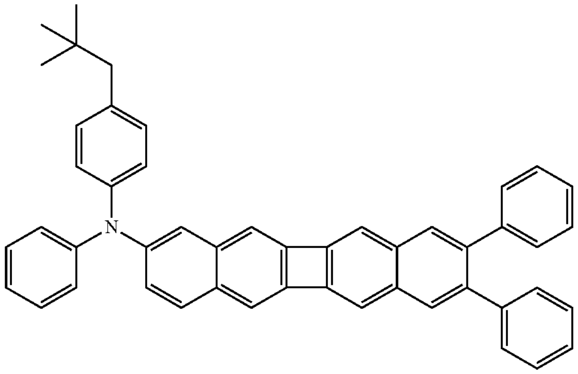
[Formula 134]
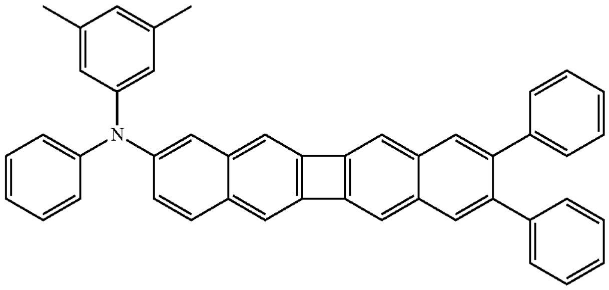
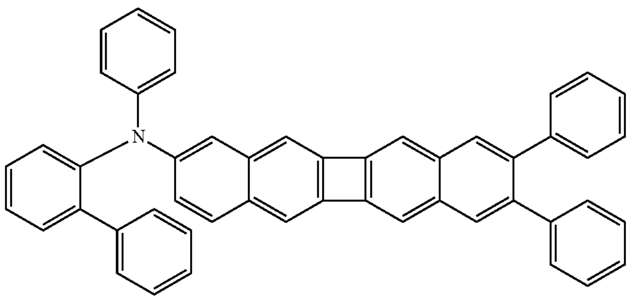

-continued
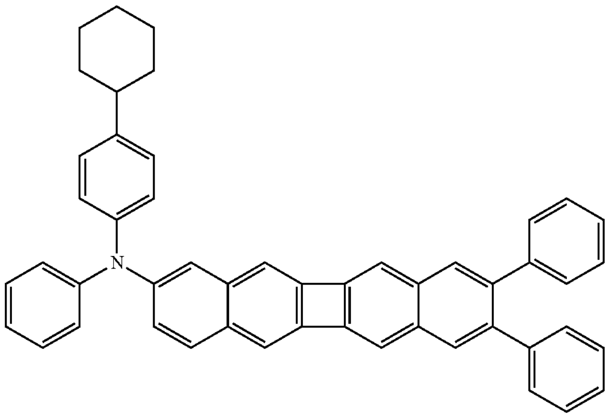
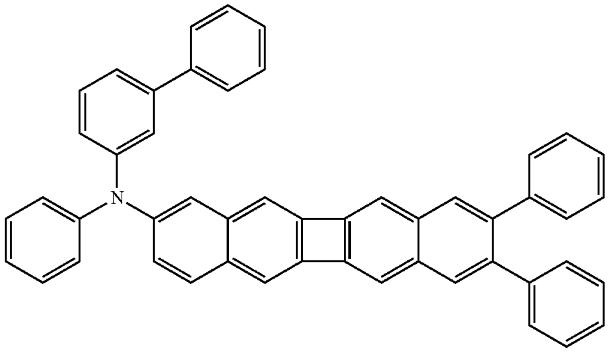
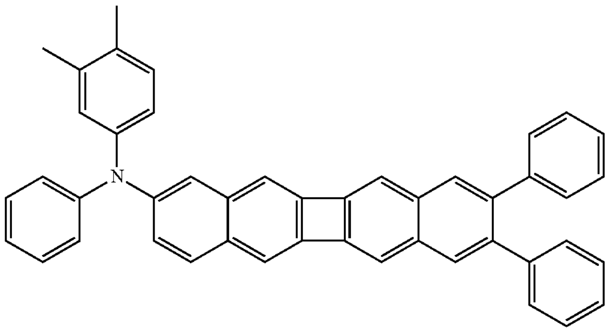
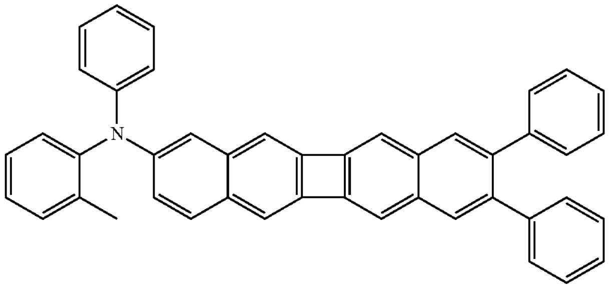

-continued
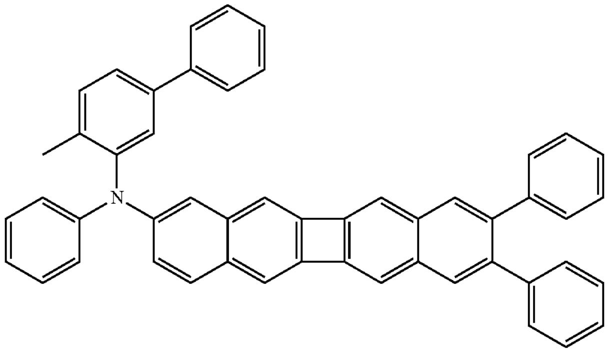
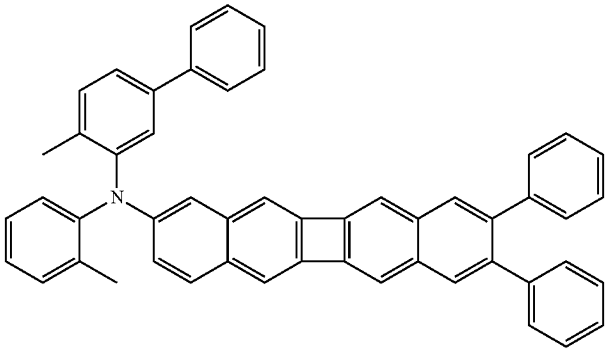
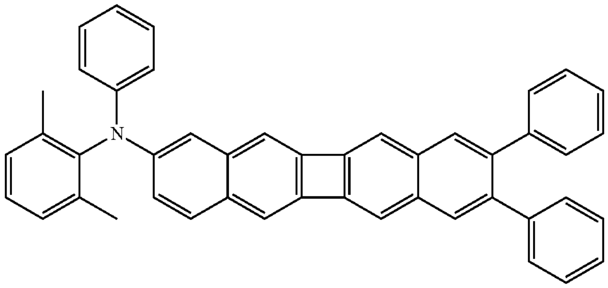
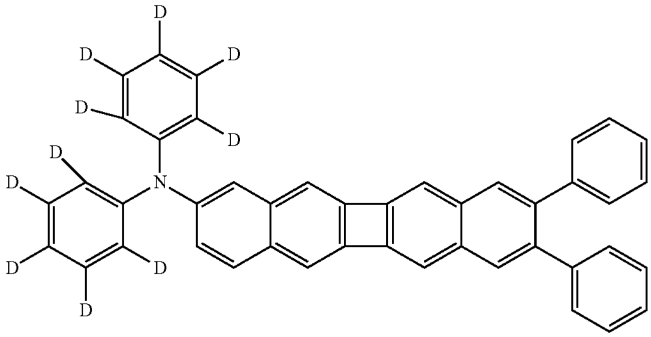
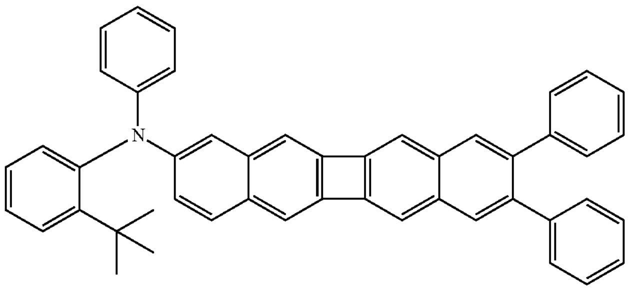

-continued
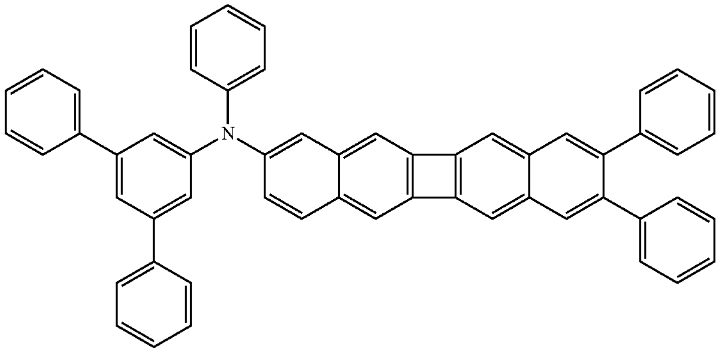
[Formula 135]
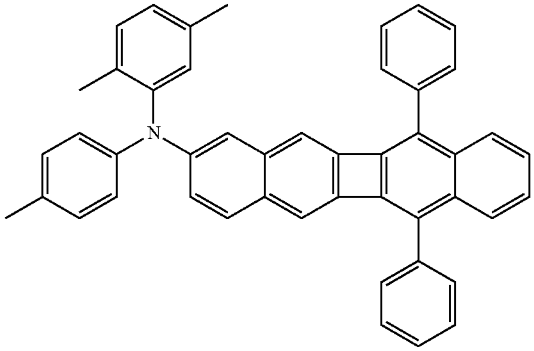
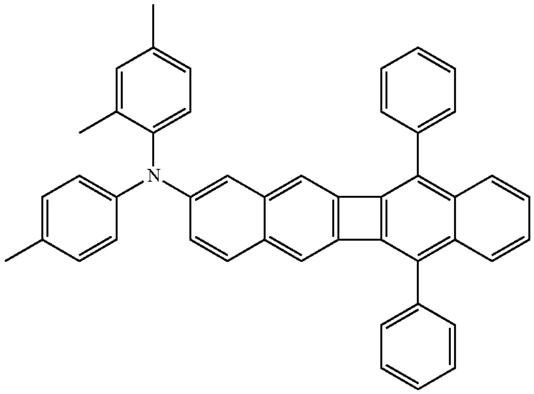
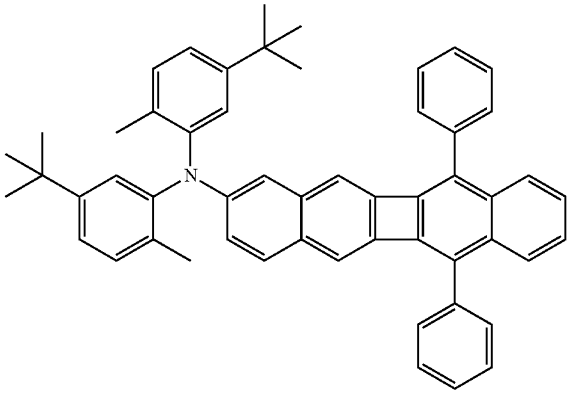
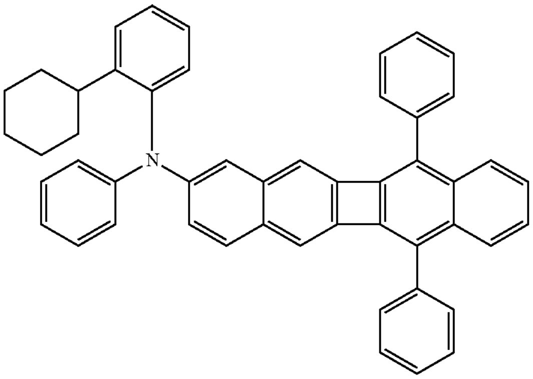
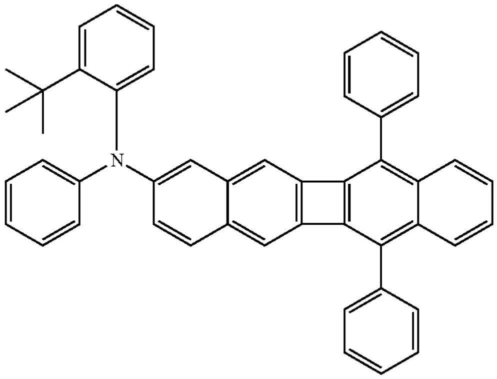
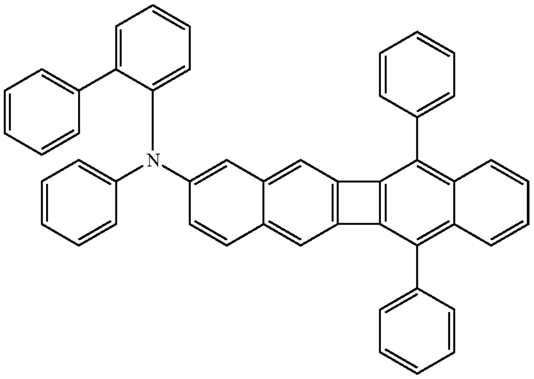

-continued
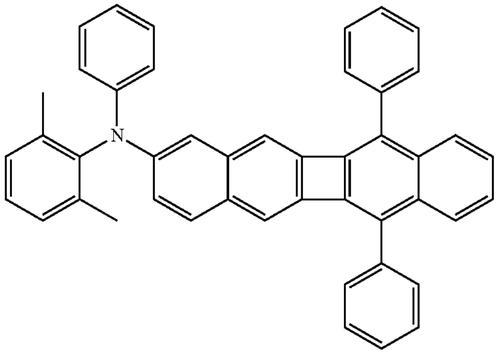
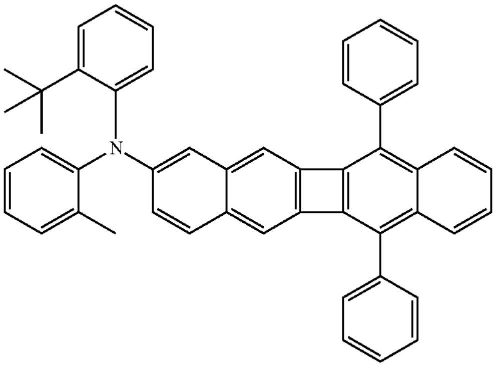
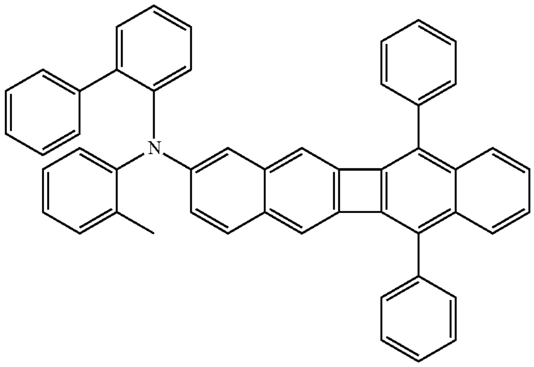
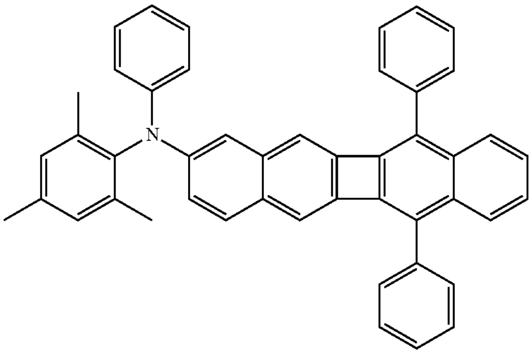
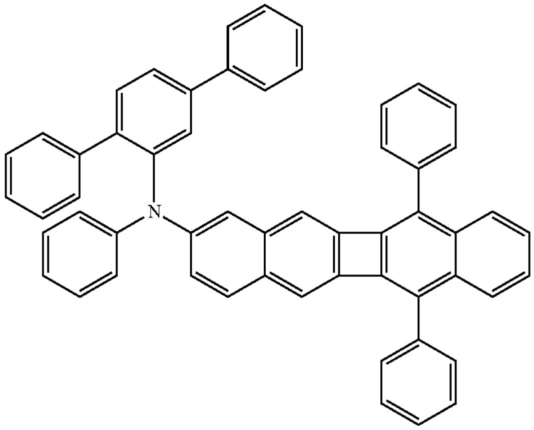
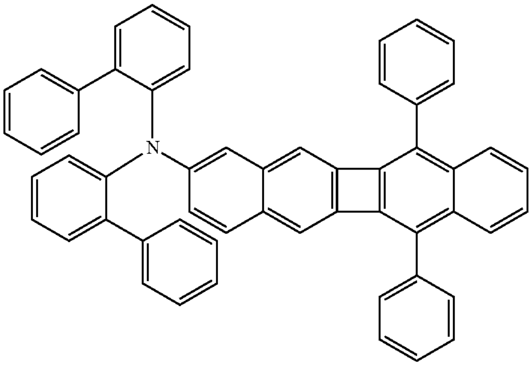
[Formula 136]
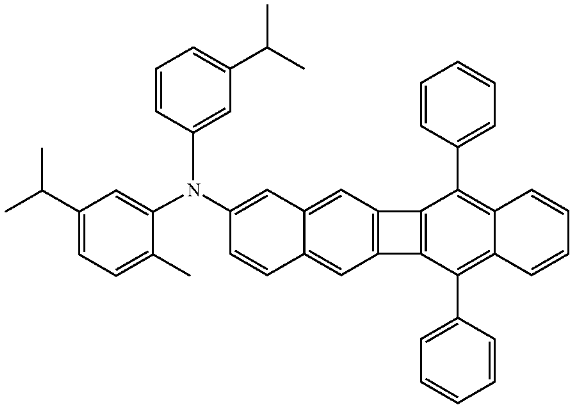

-continued
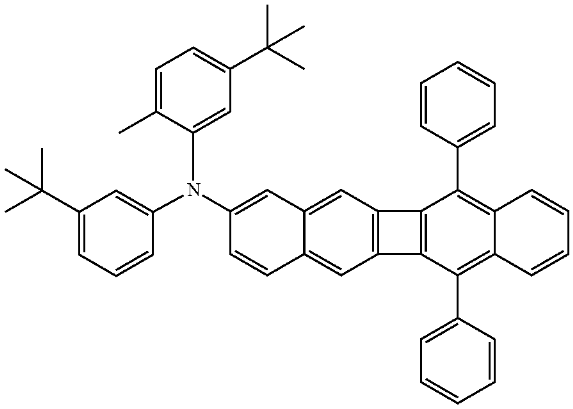
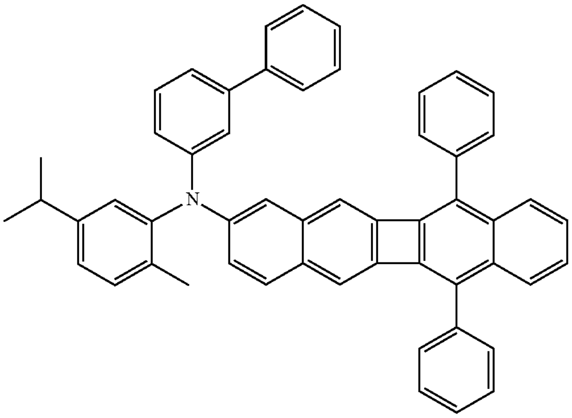
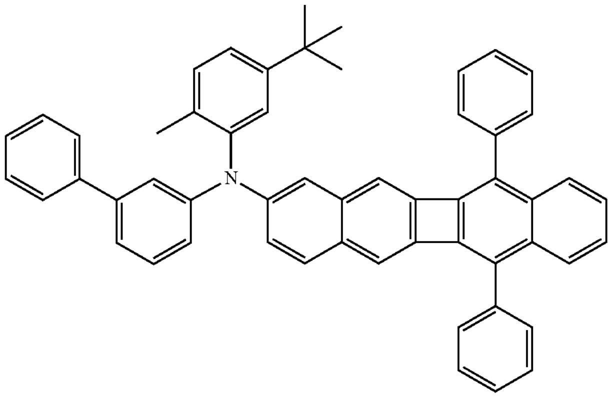
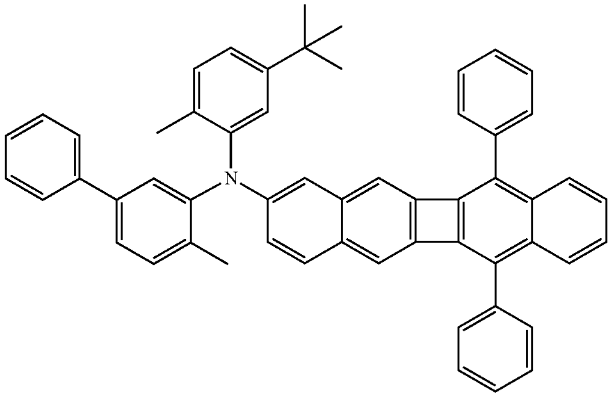
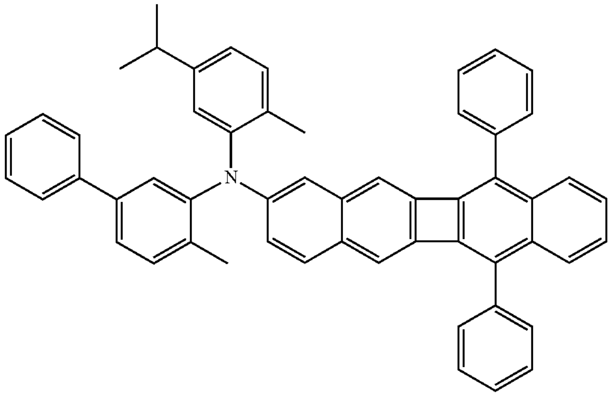

-continued
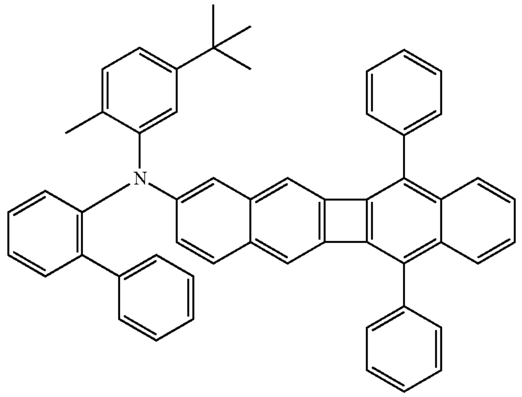
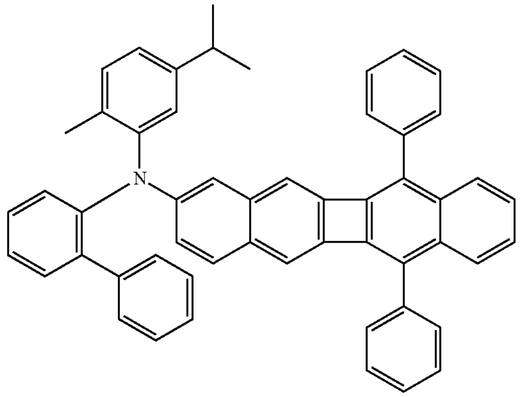
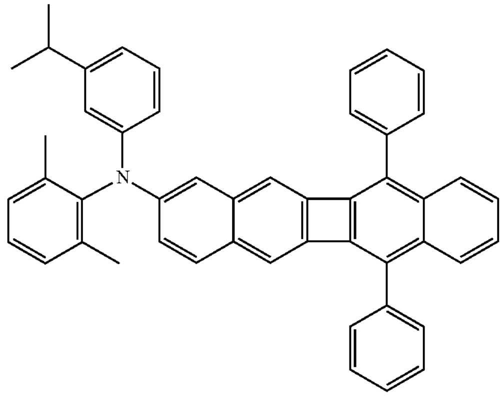
[Formula 137]
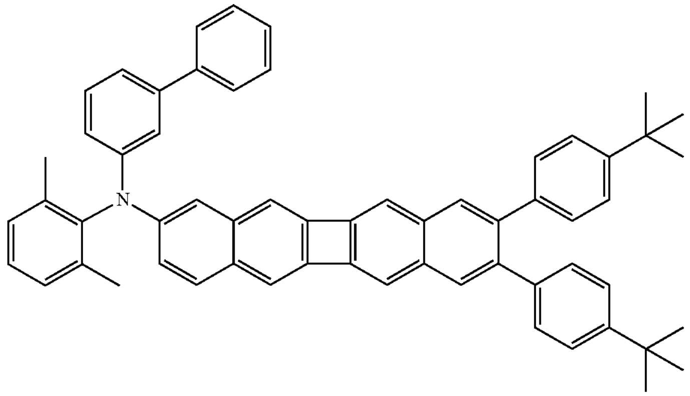
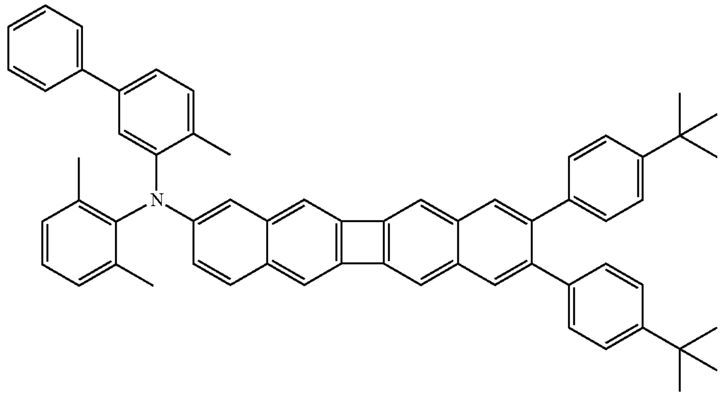

-continued
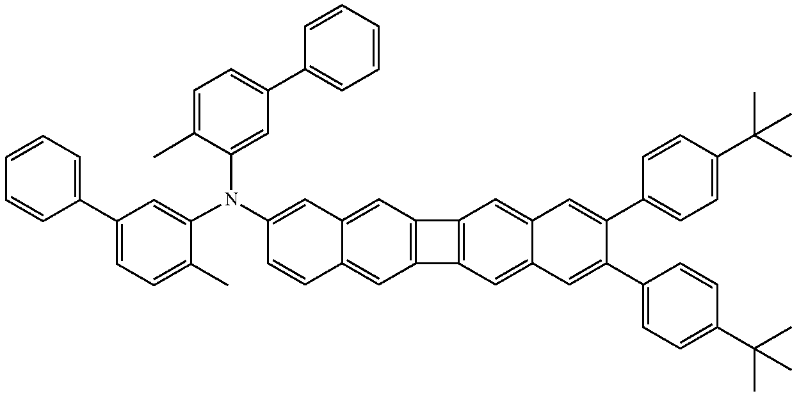
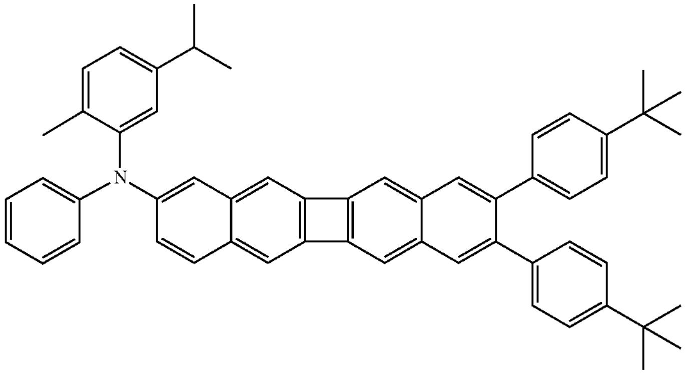
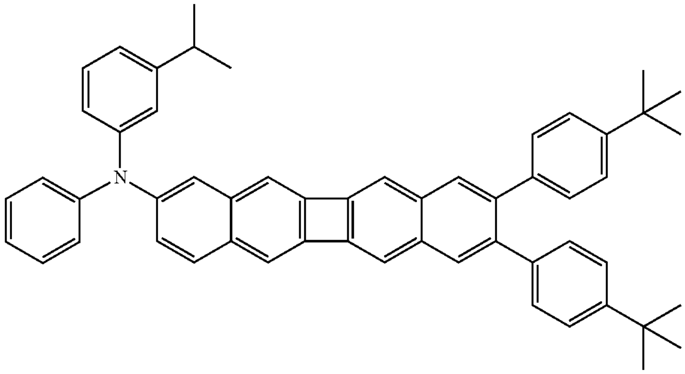
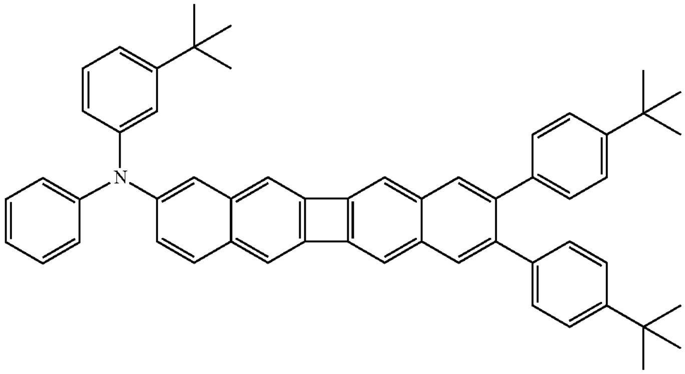

-continued
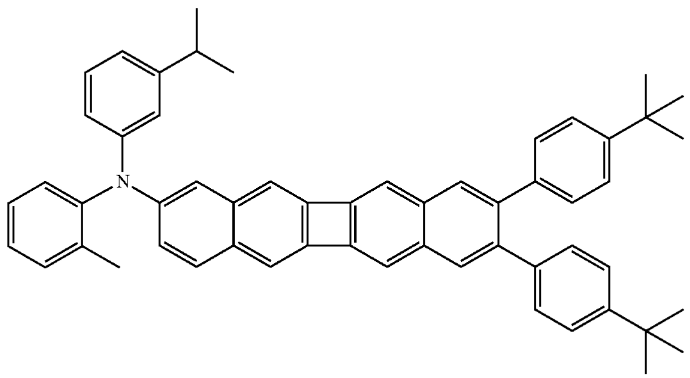
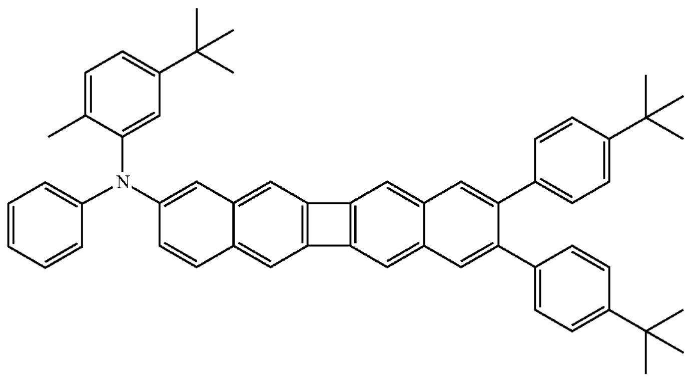
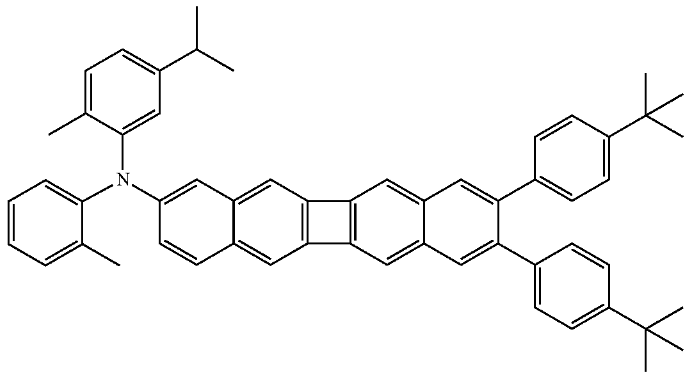
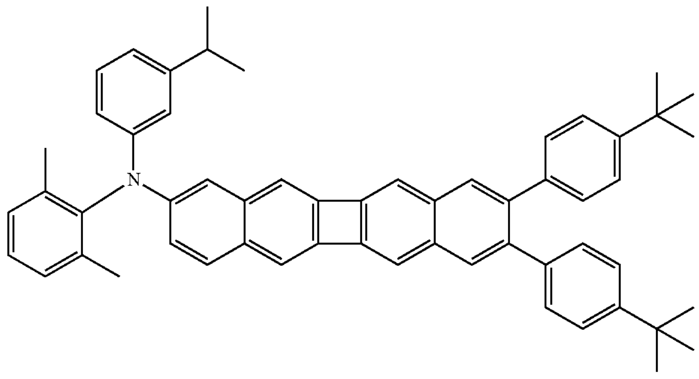

-continued
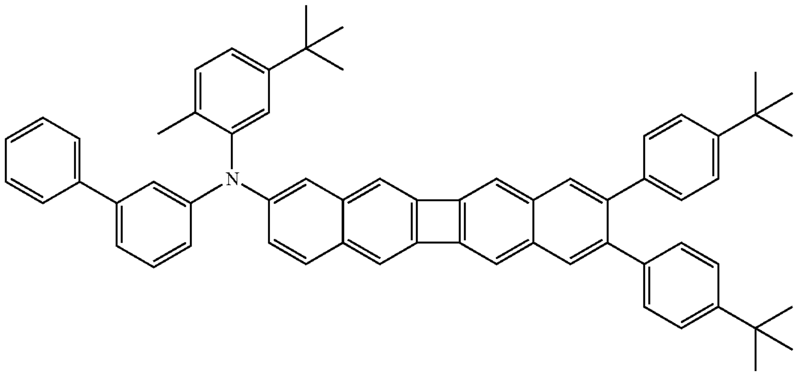
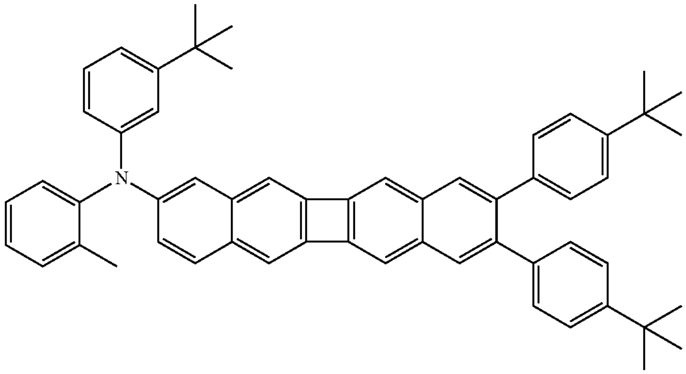
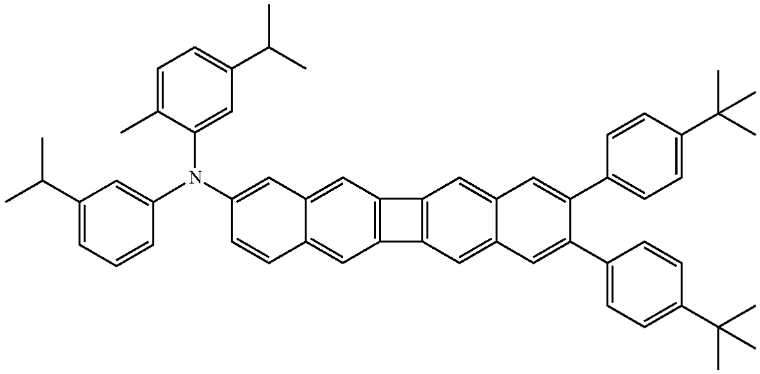
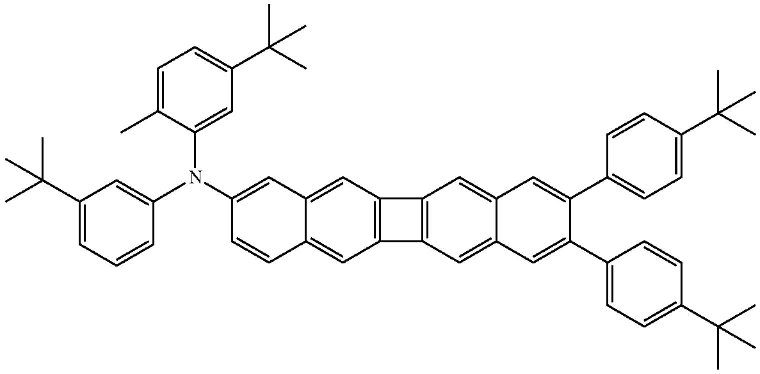

-continued
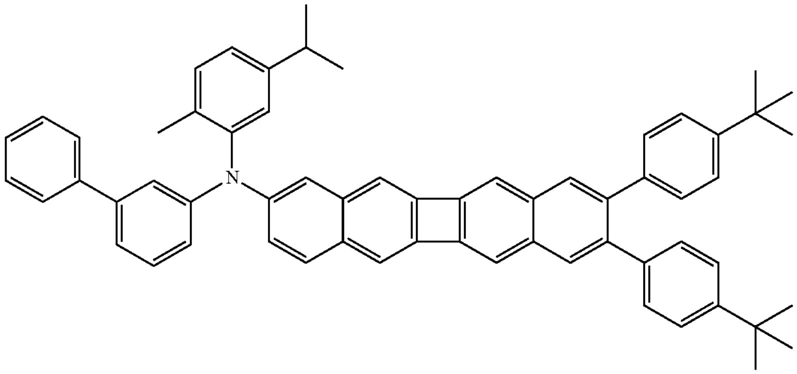
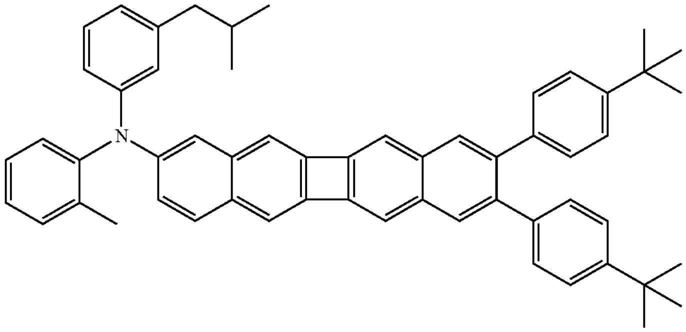
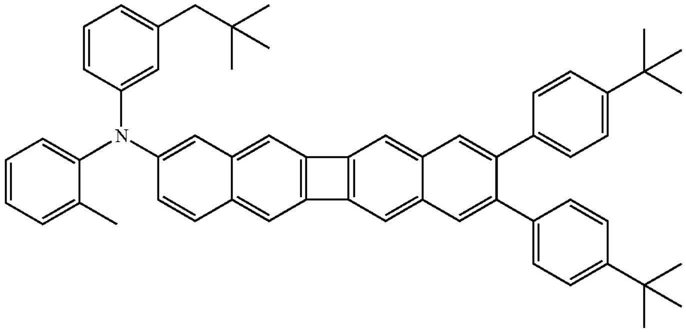
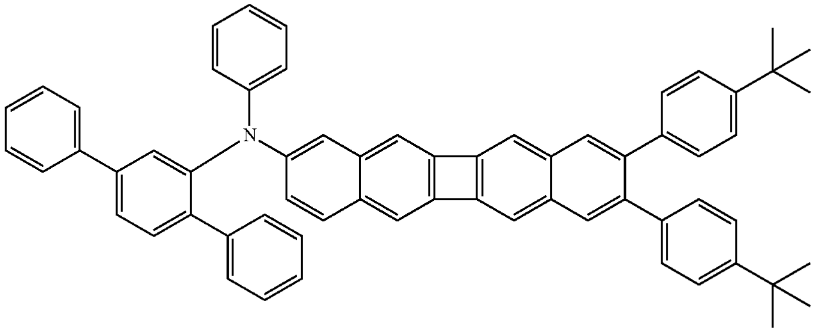
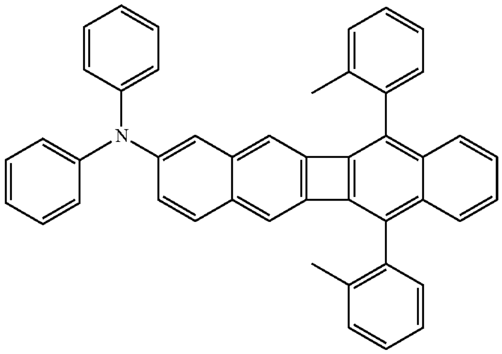
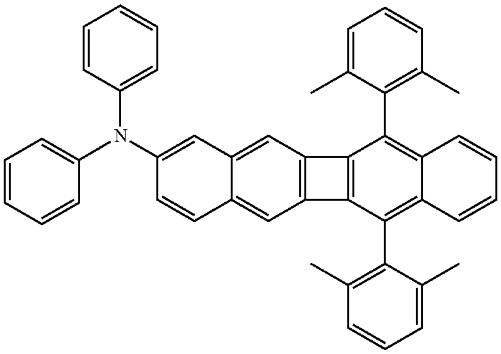

-continued
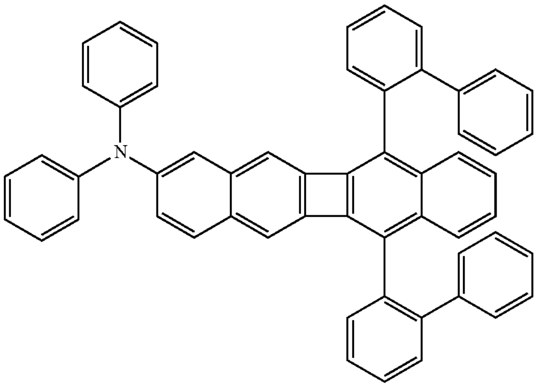
[Formula 138]
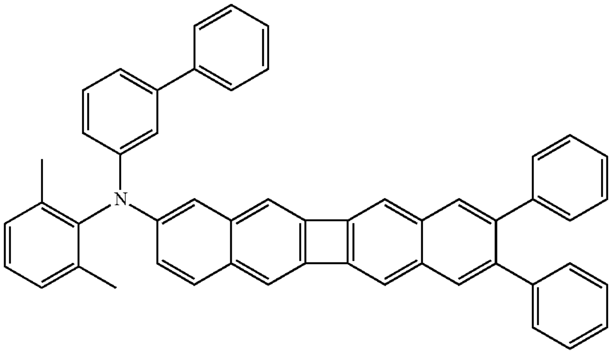
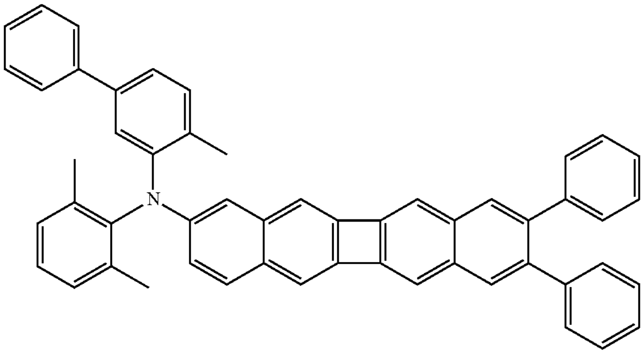
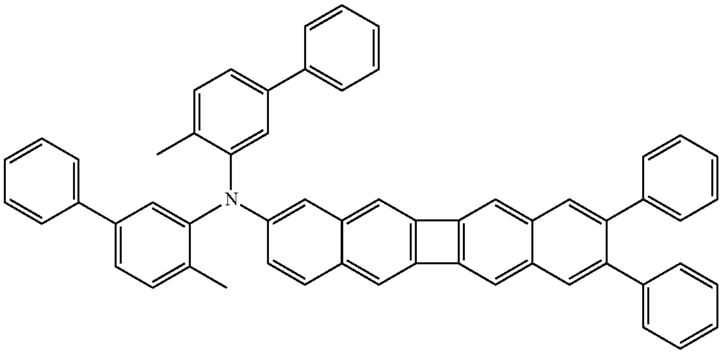

-continued
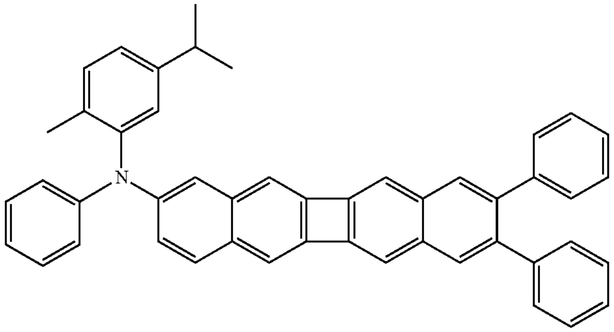
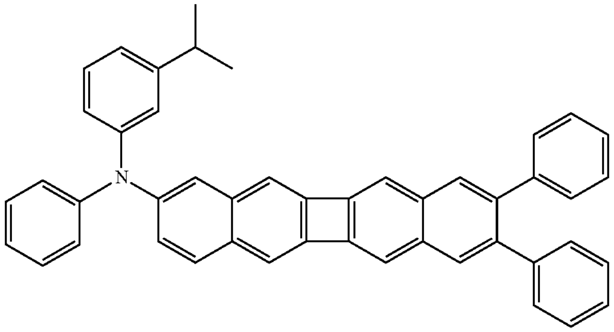
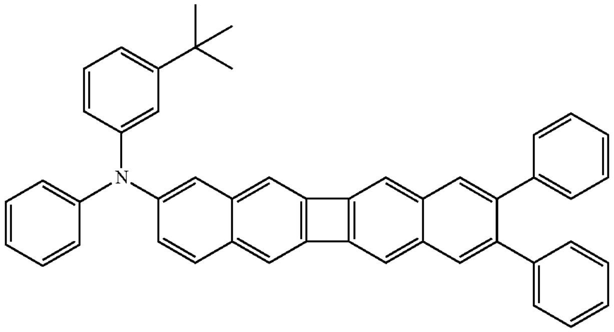
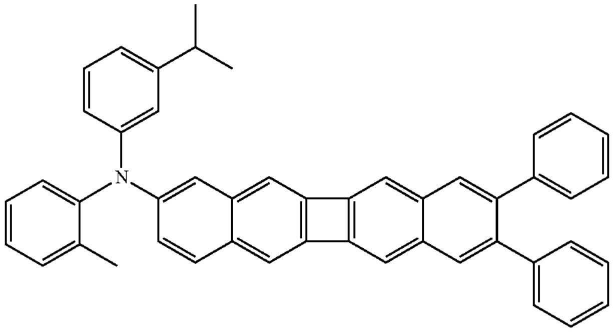
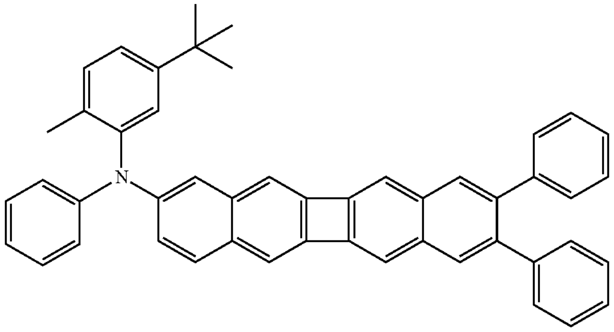

-continued
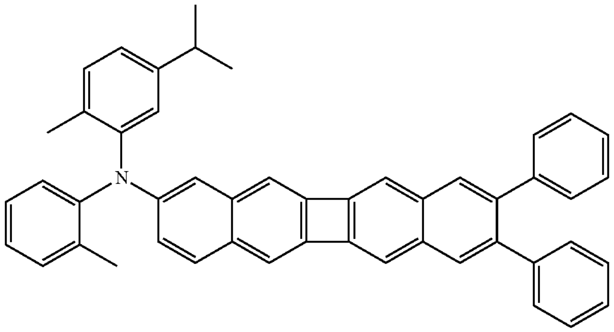
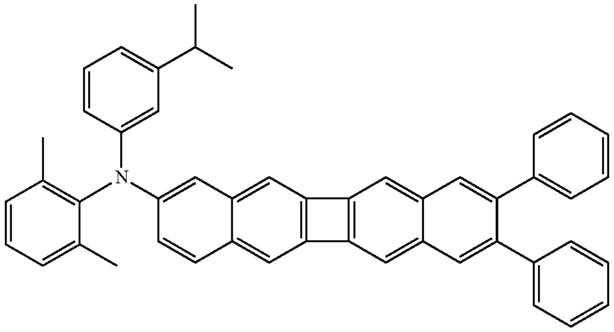
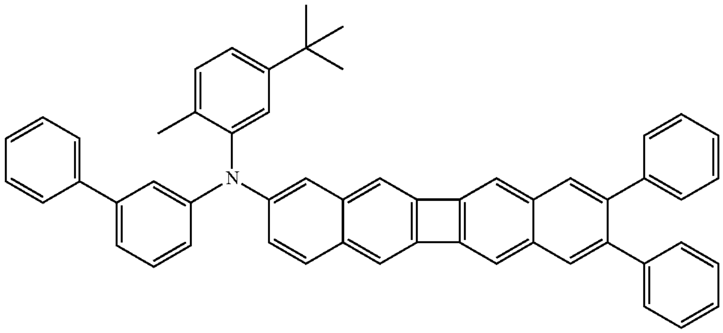
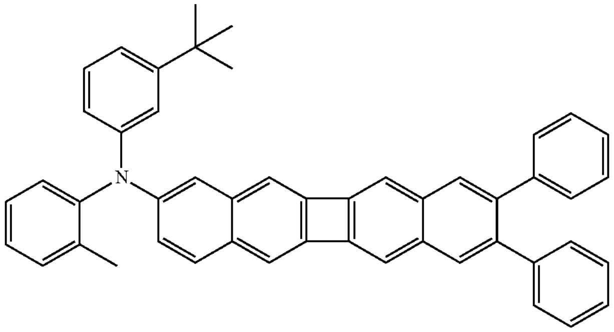
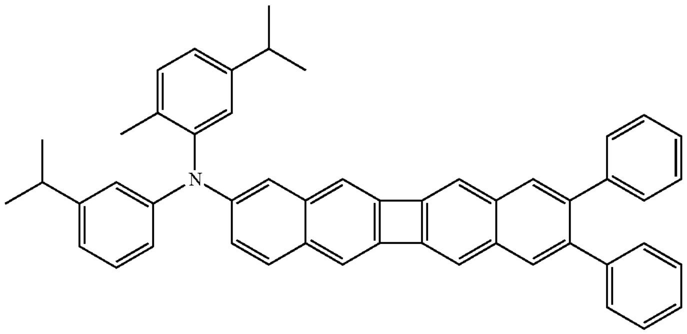

-continued
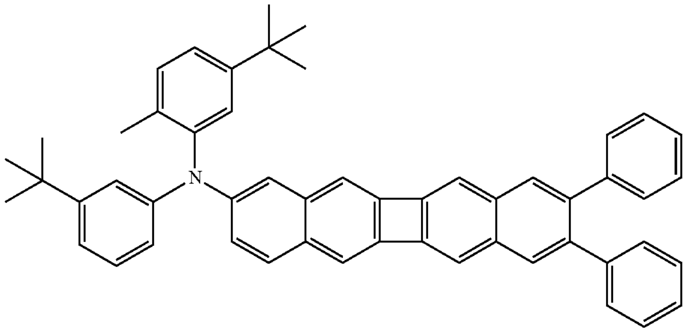
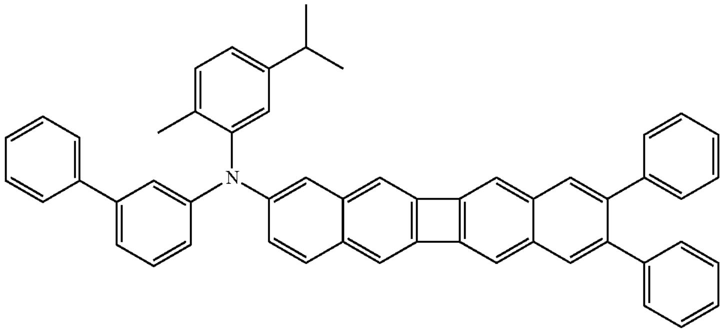
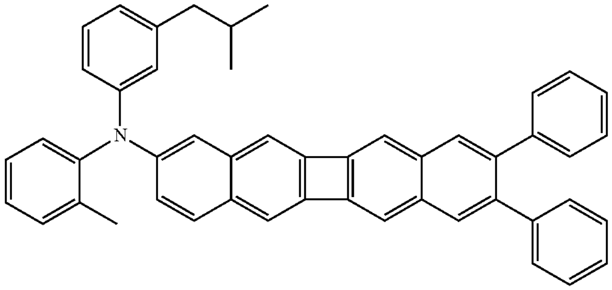
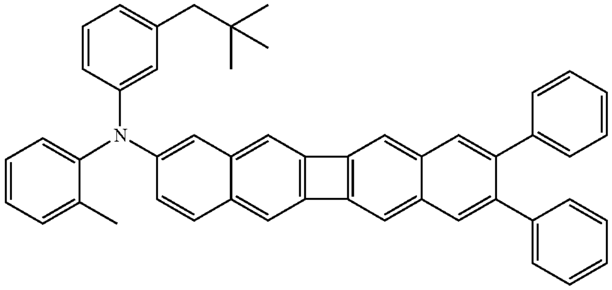
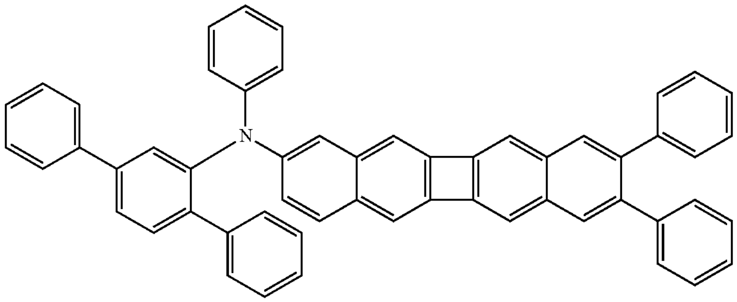

-continued
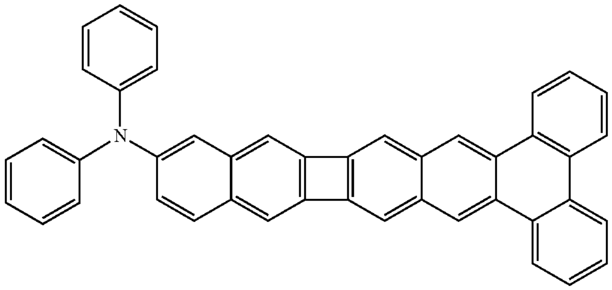
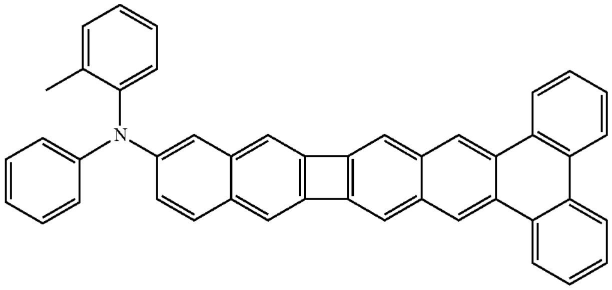
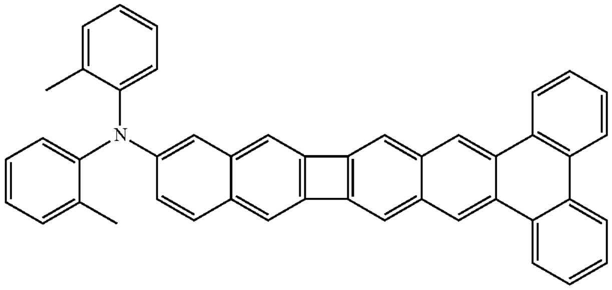
[Formula 139]
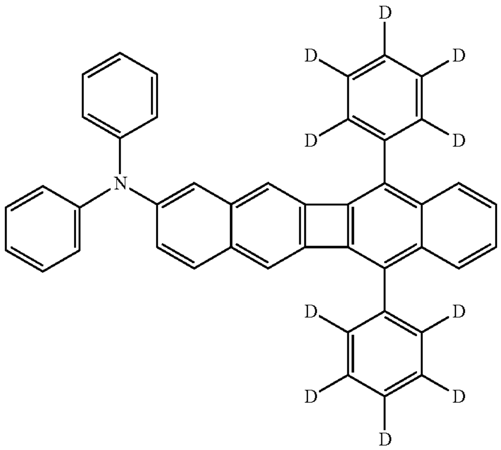
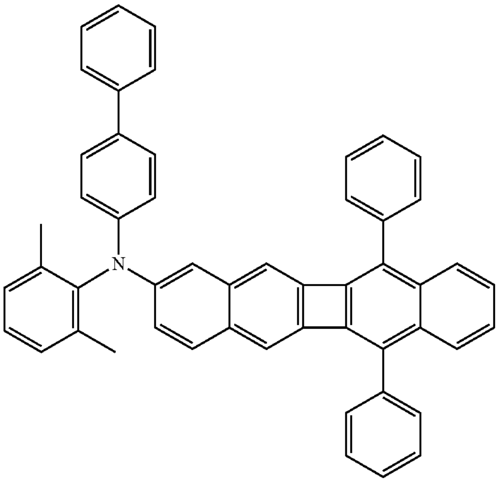

-continued
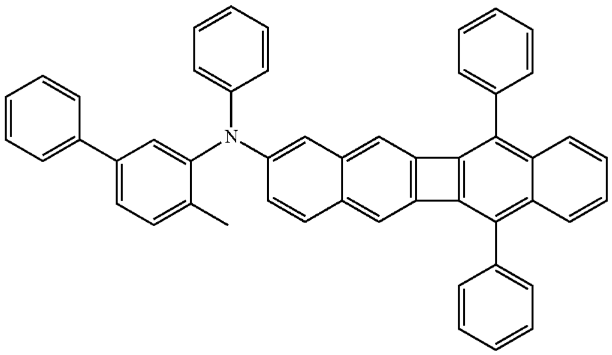
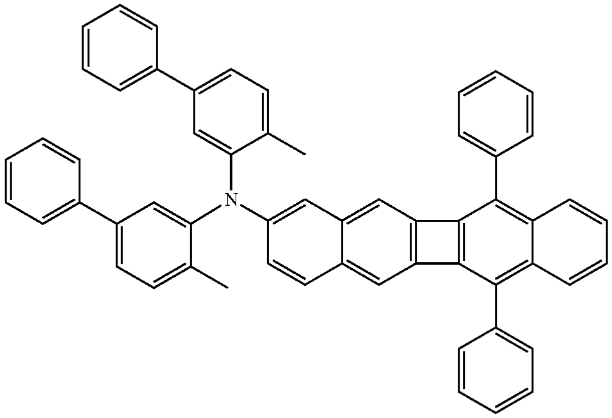
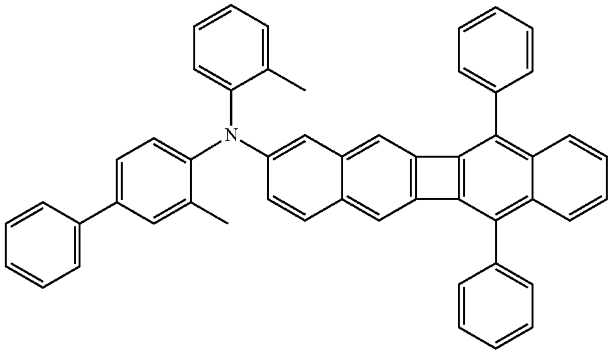
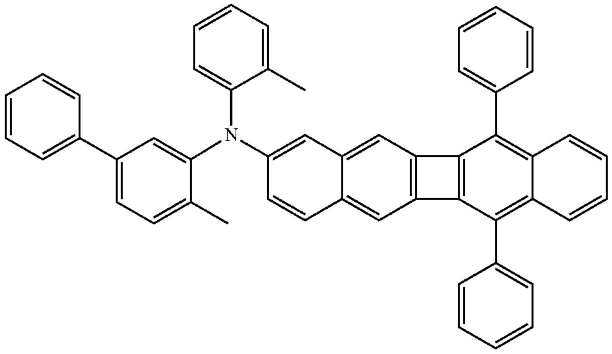

-continued
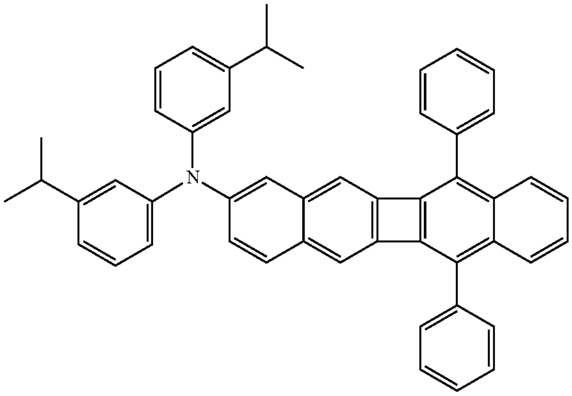
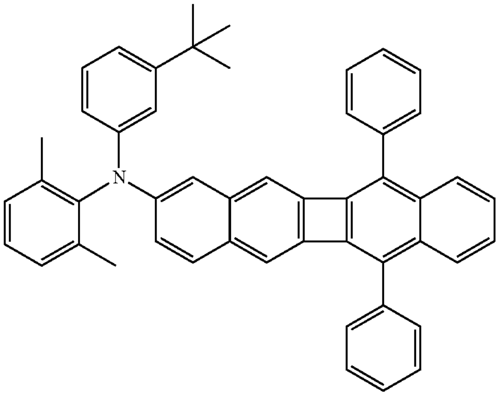
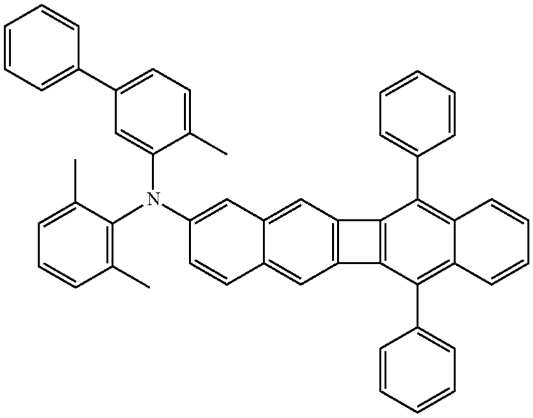
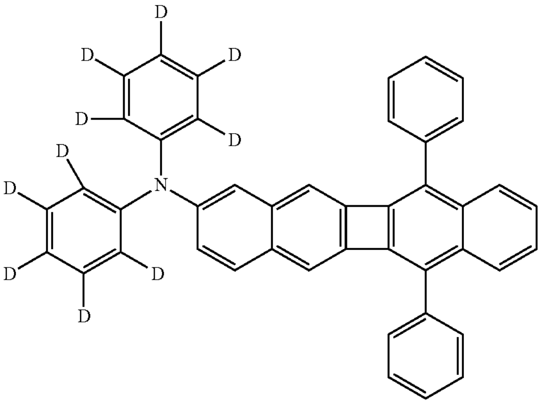
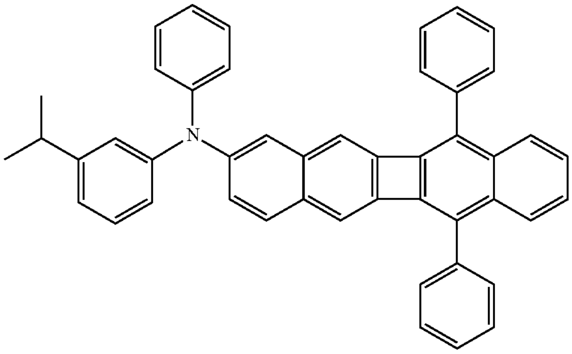
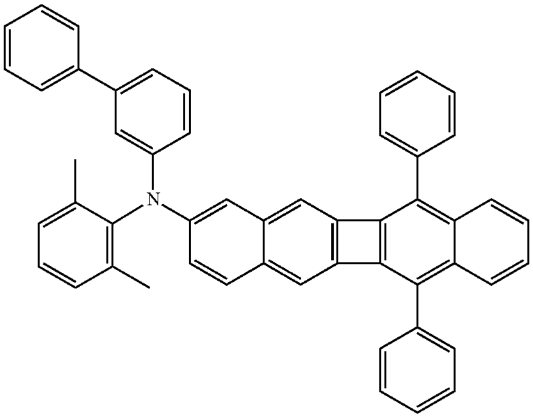
[Formula 140]
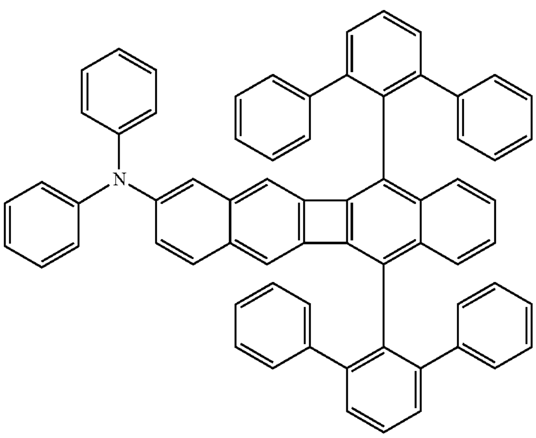
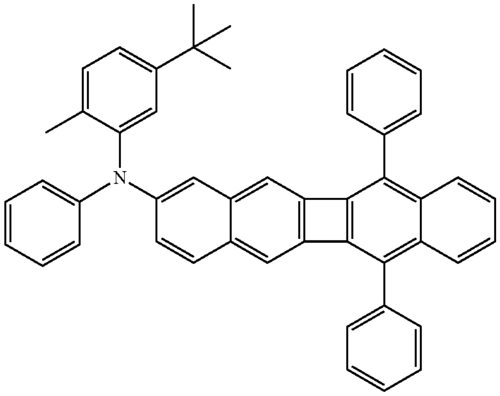

-continued
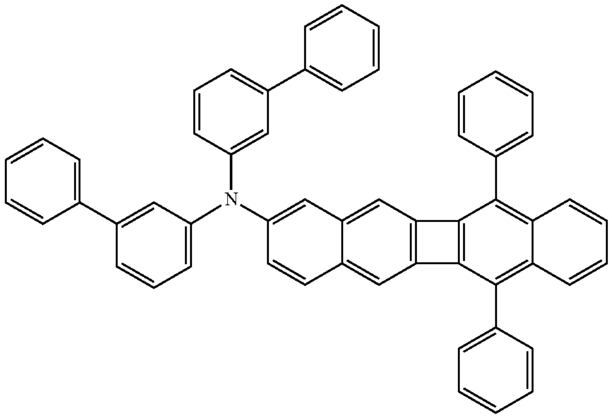
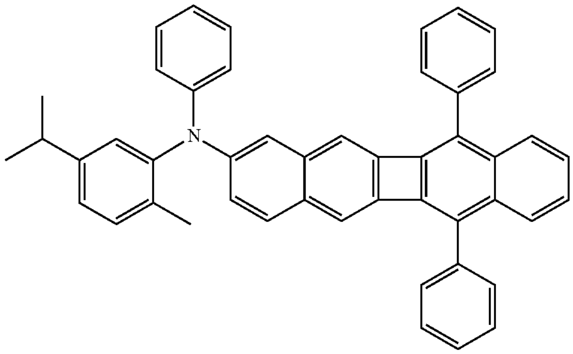
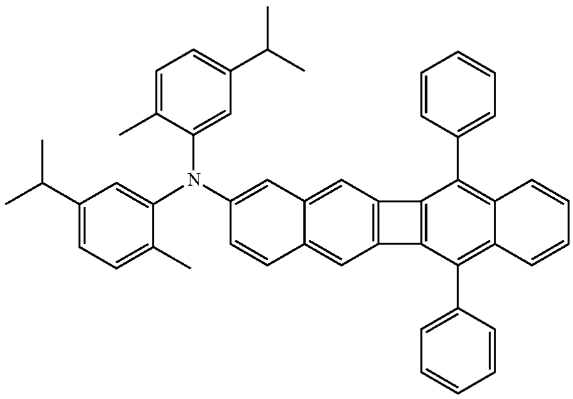
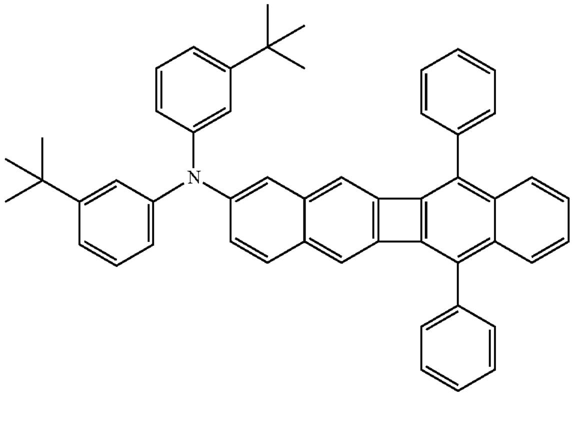

-continued
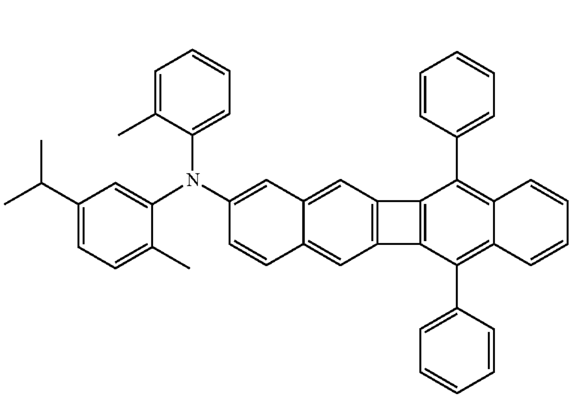
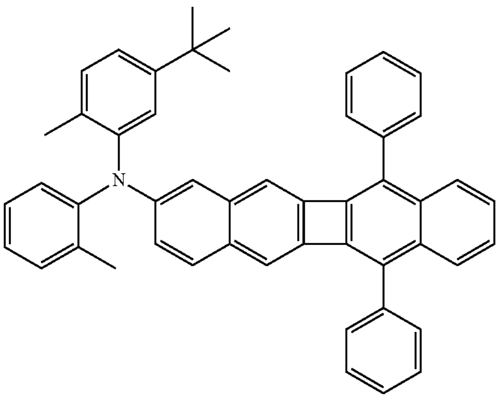
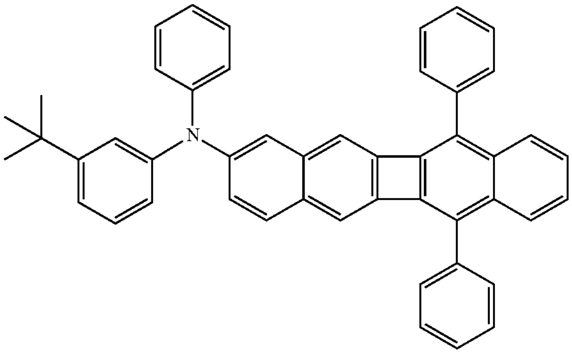
[Formula 141]
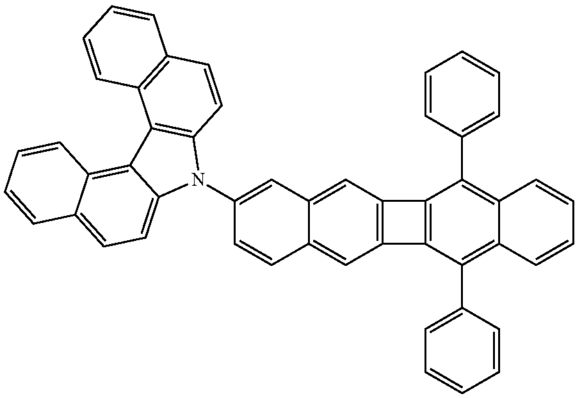
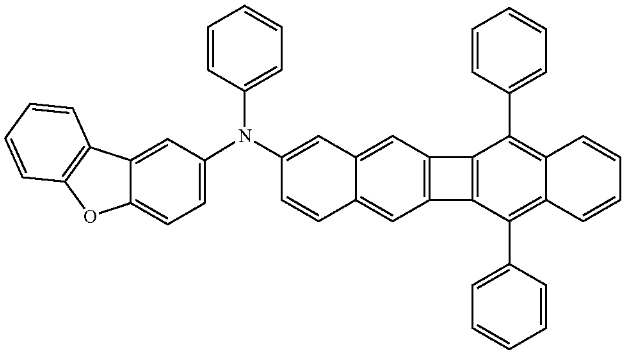

-continued
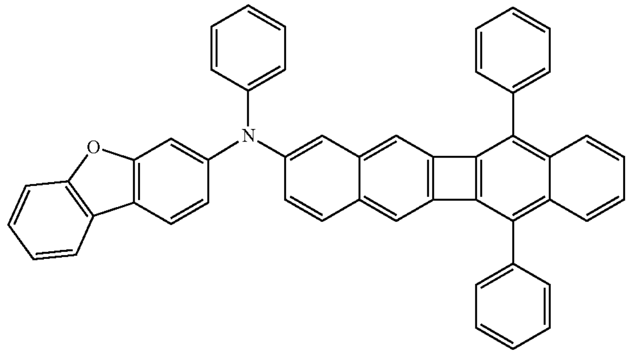
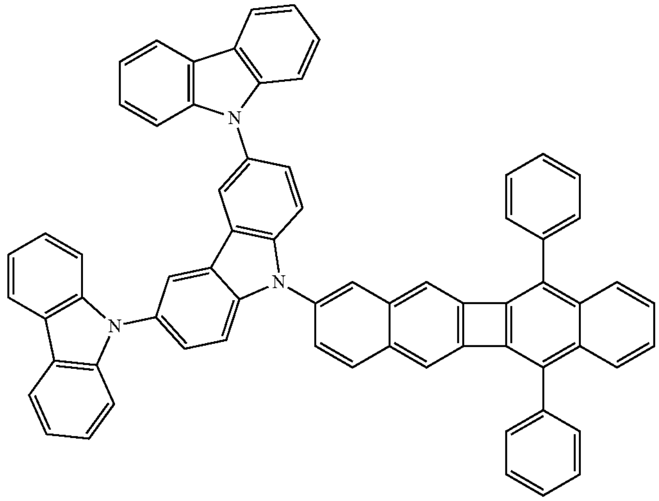
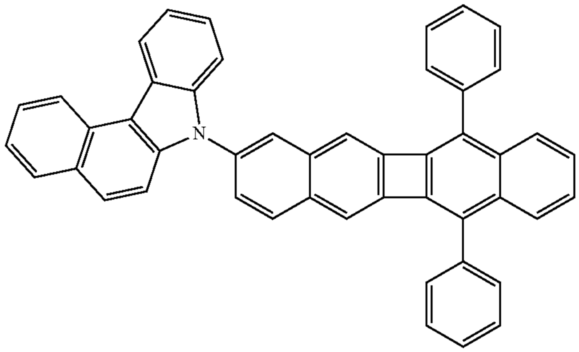
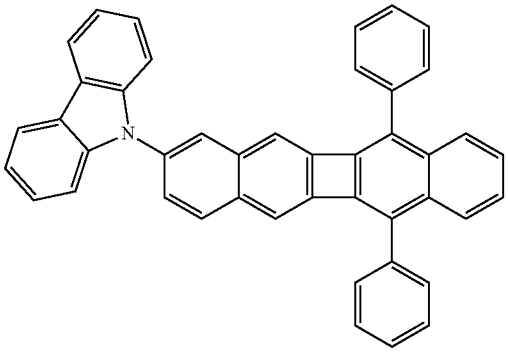
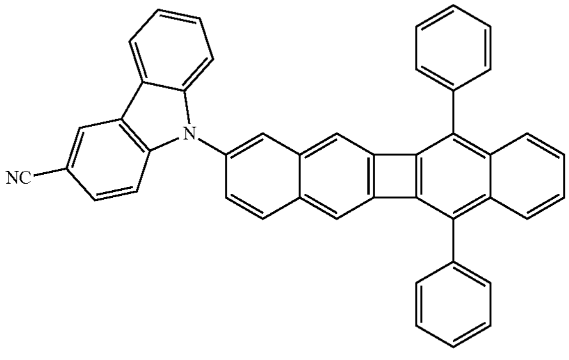

-continued
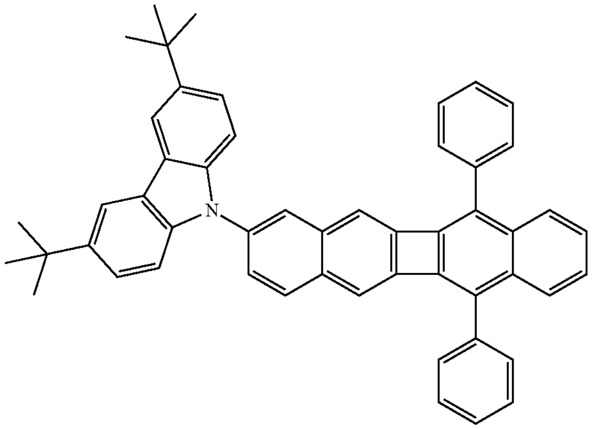
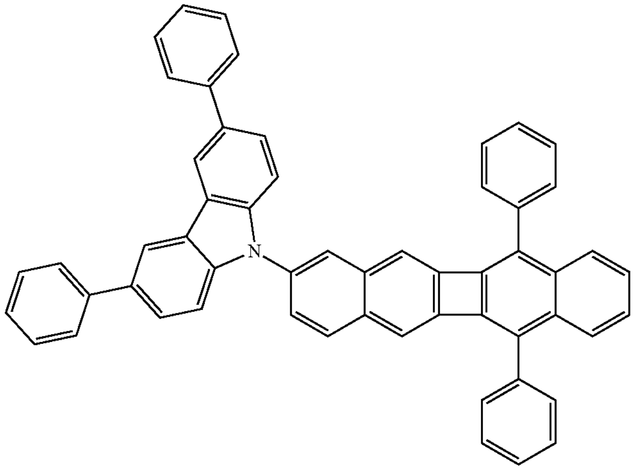
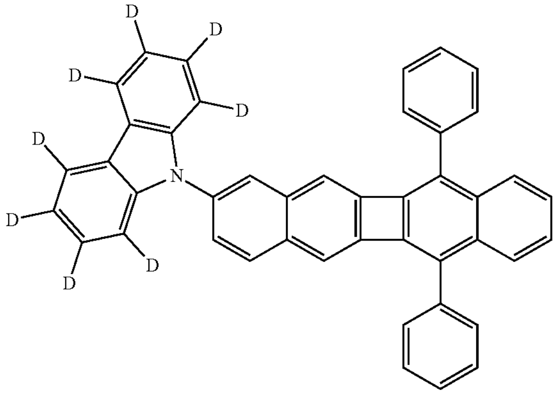
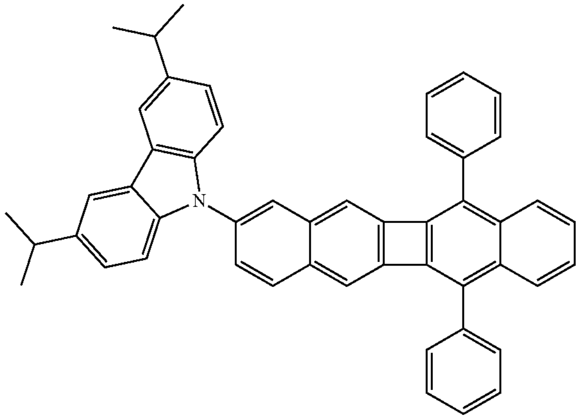
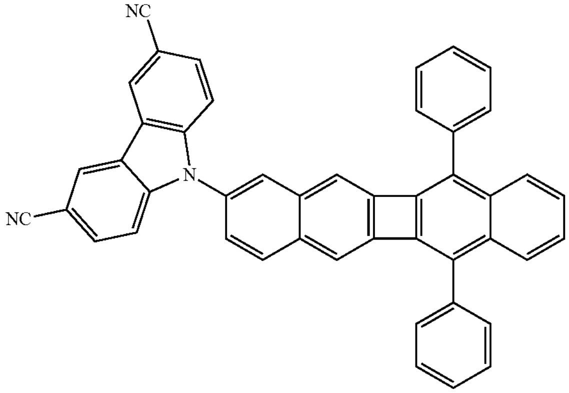

-continued
[Formula 142]
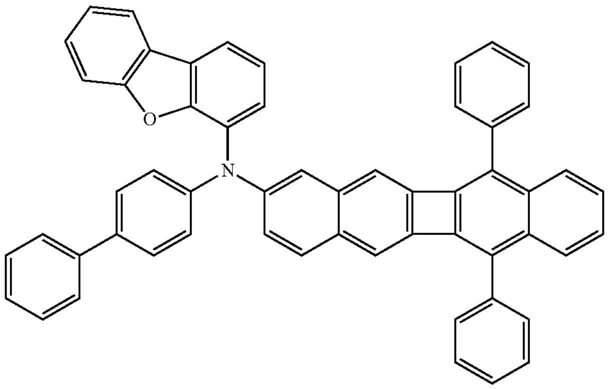
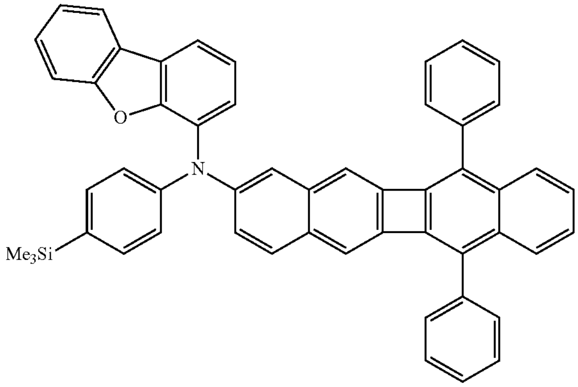
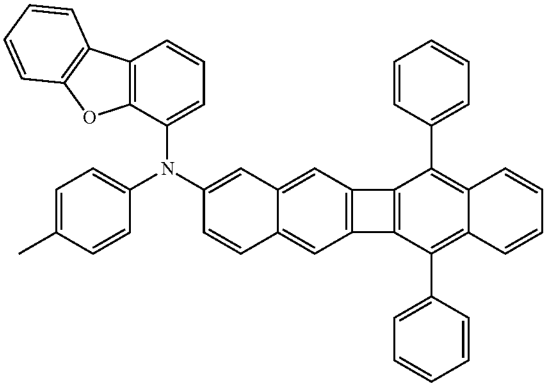
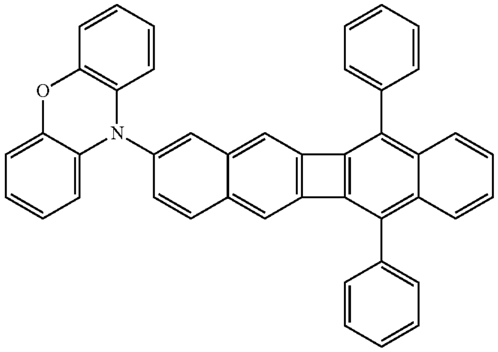
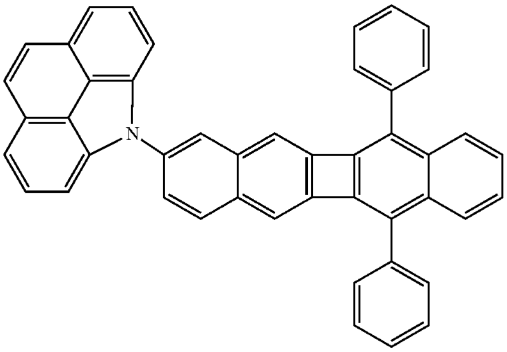
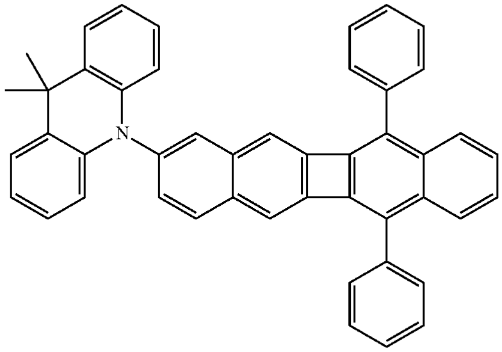
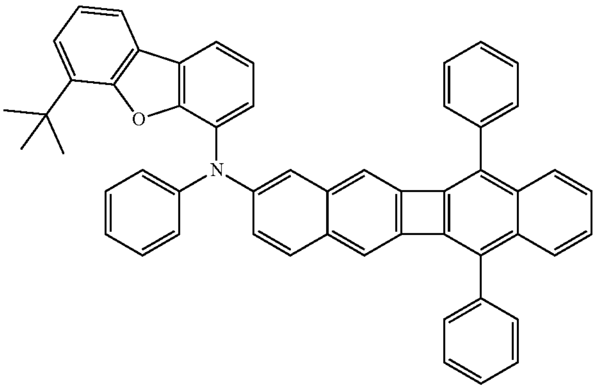

-continued
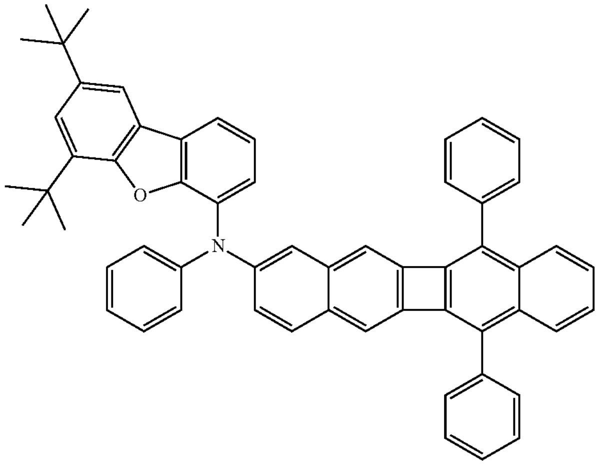
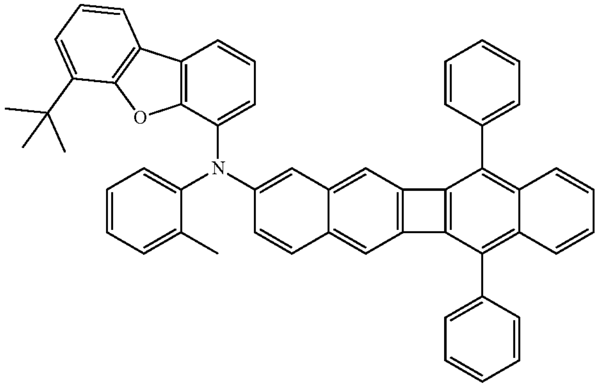
[Formula 143]
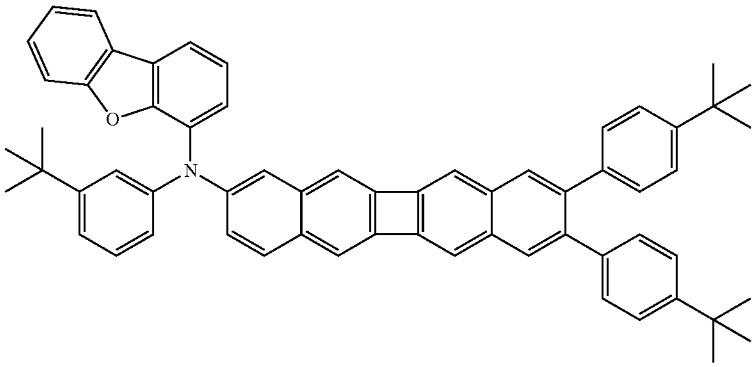
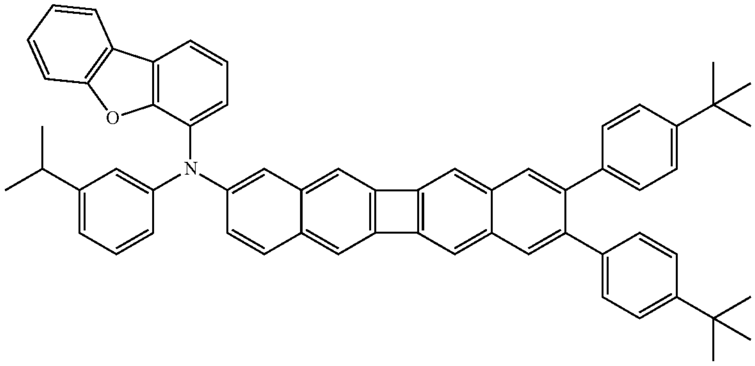

-continued
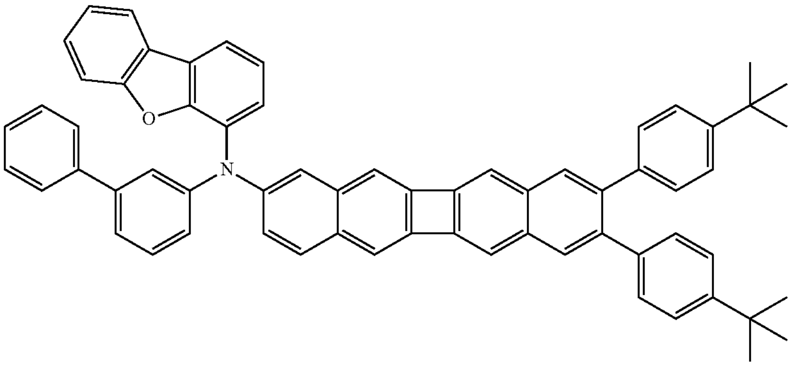
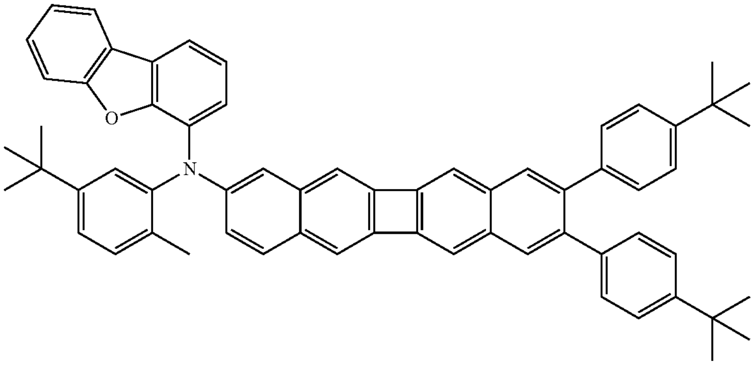
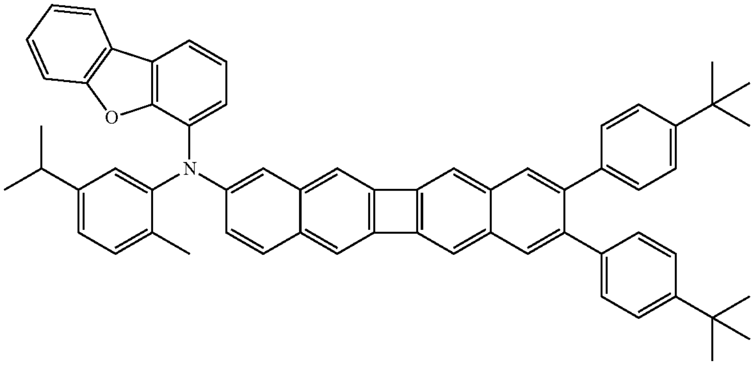
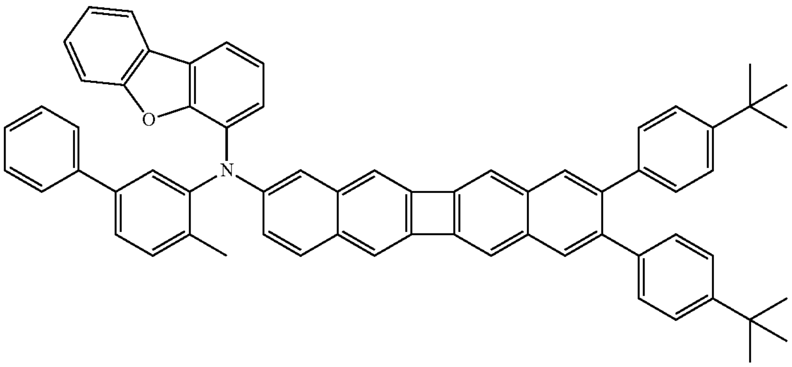

-continued
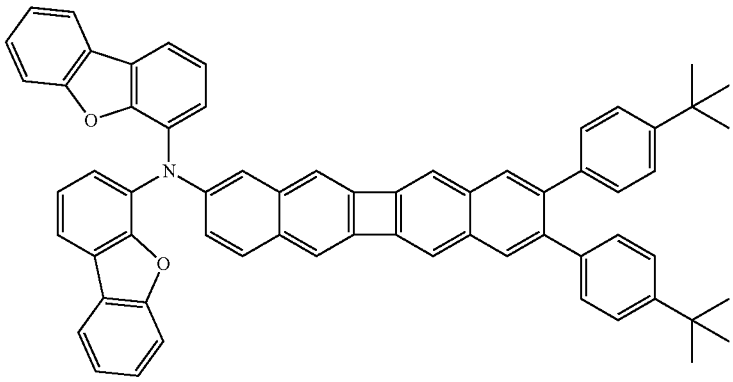
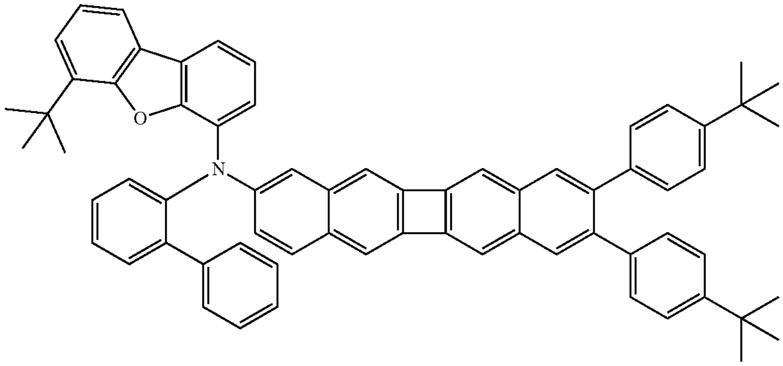
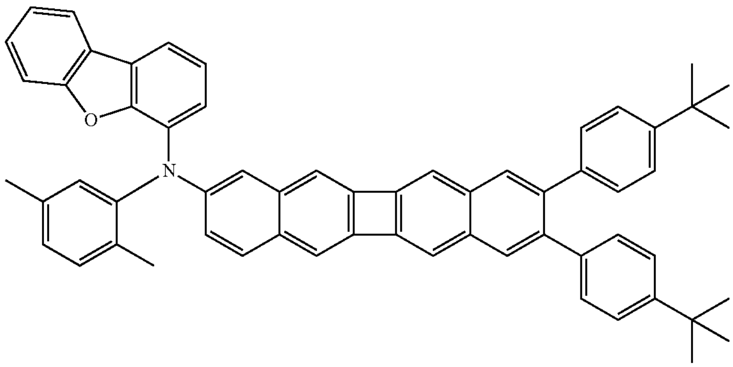
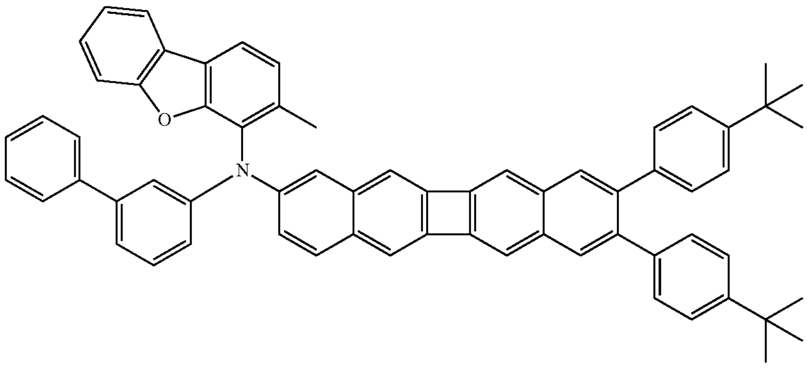

-continued
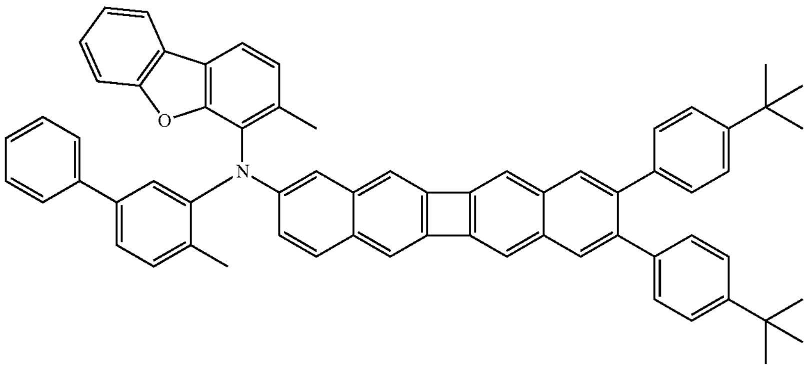
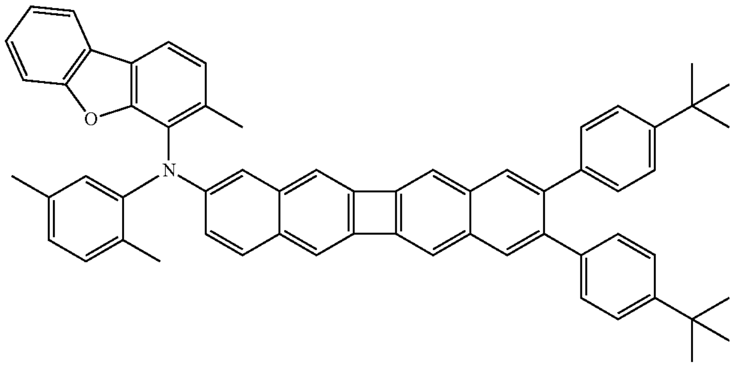
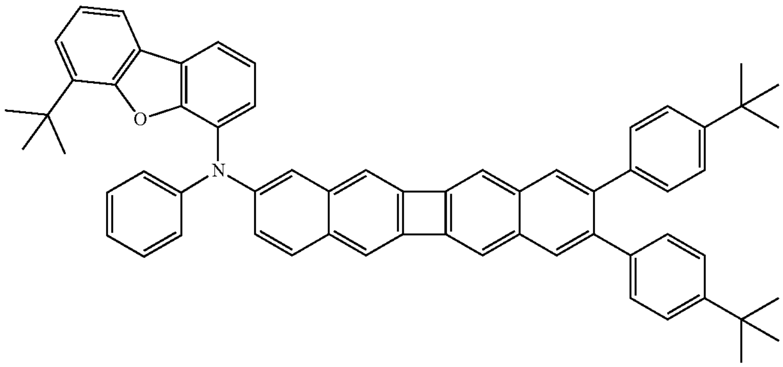
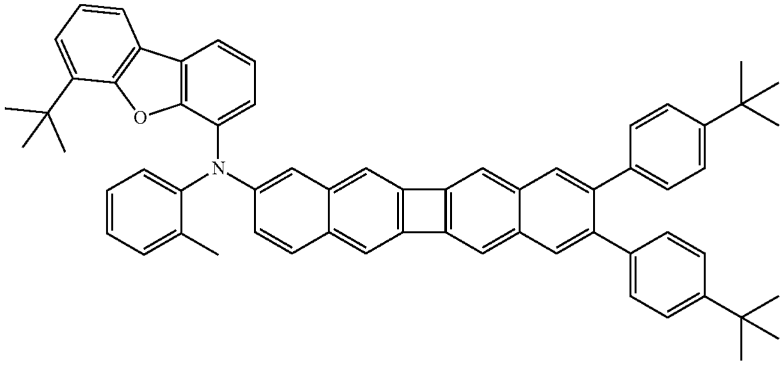

-continued
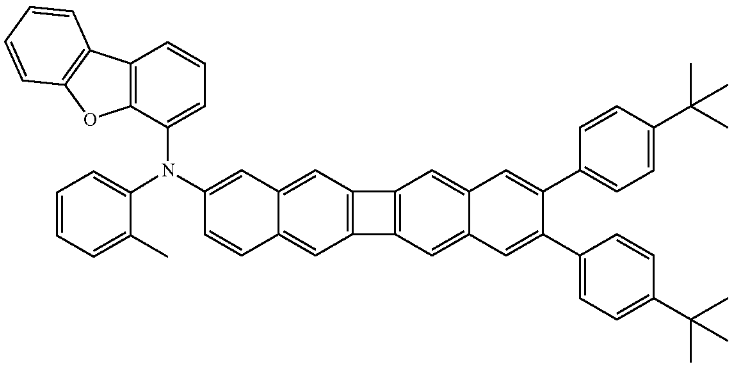
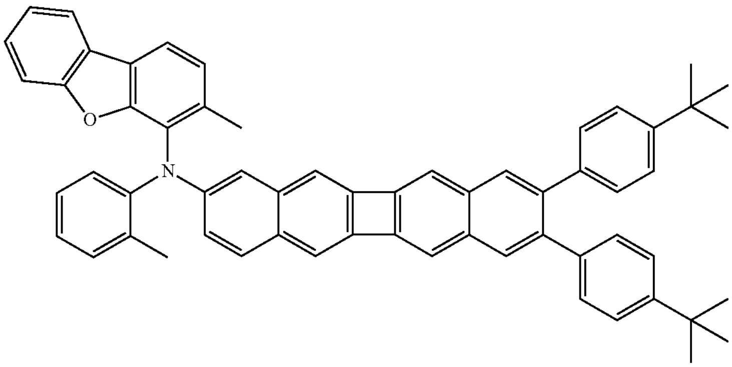
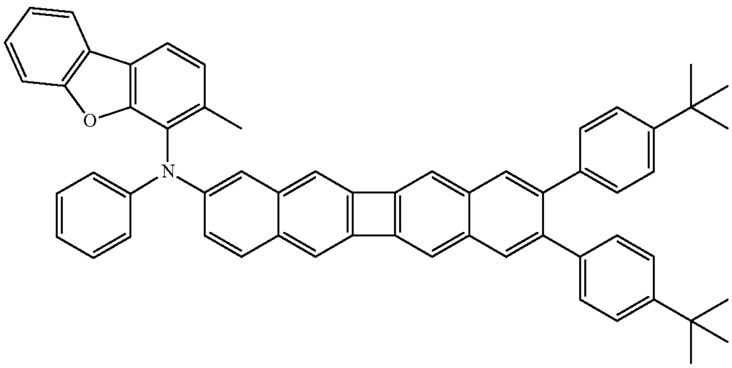
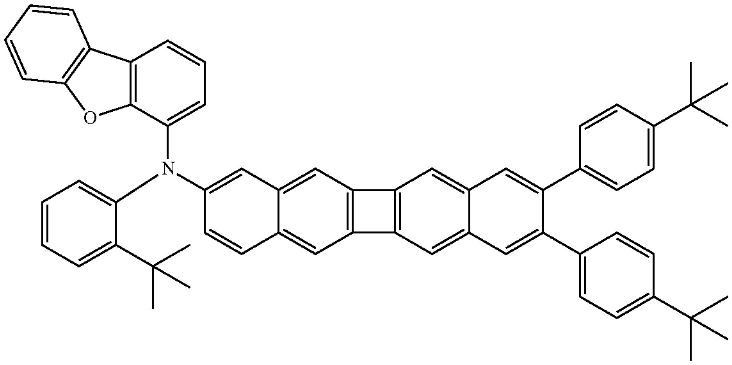

-continued
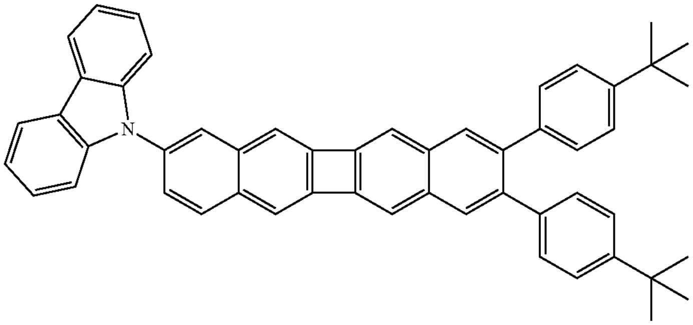
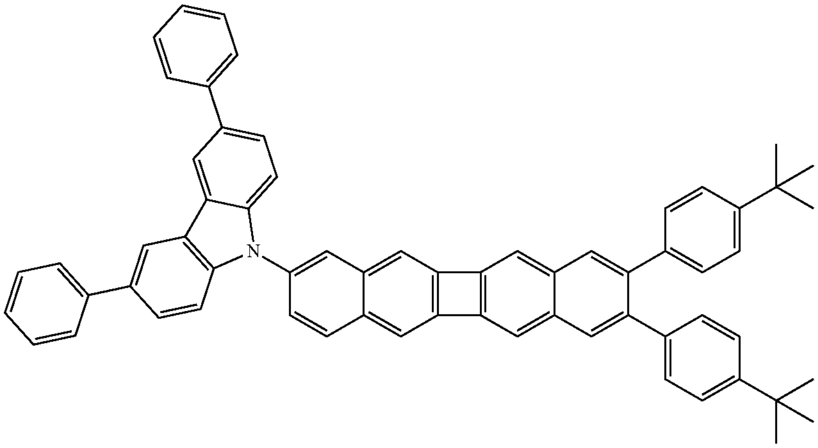
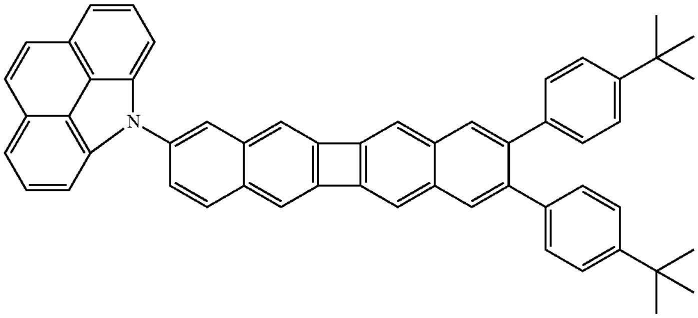
[Formula 144]
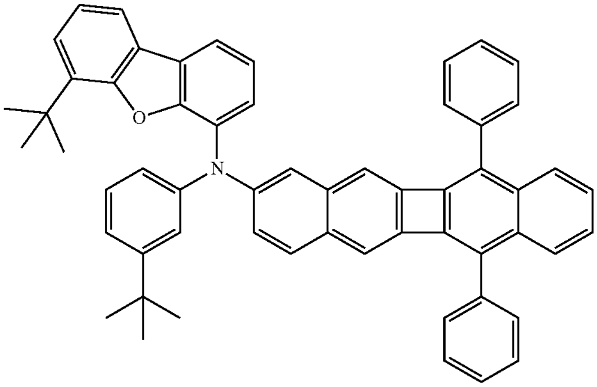

-continued
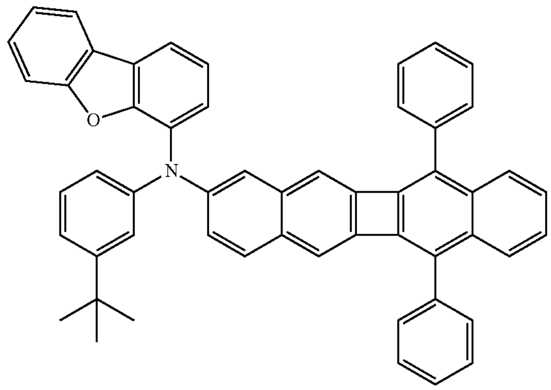
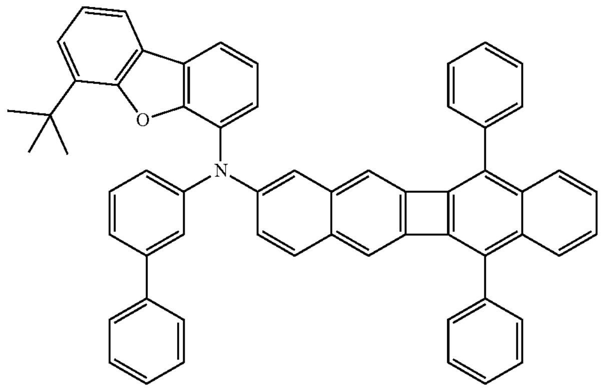
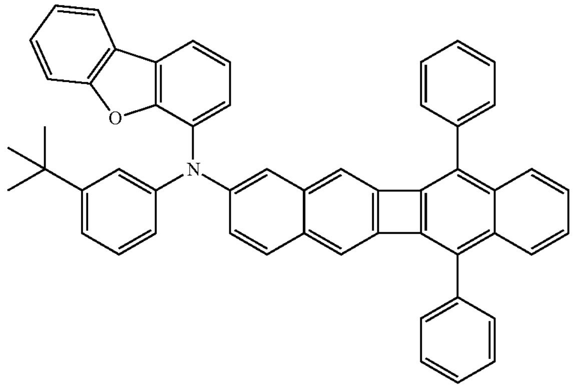
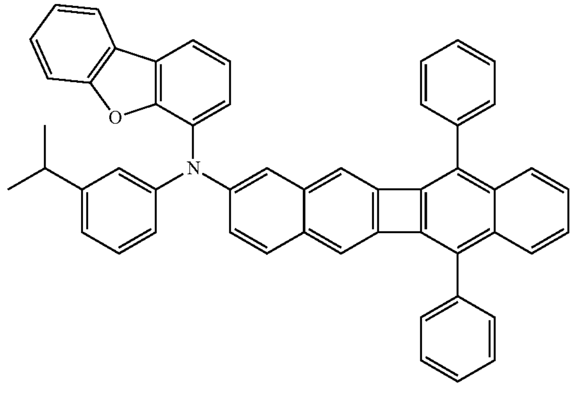

-continued
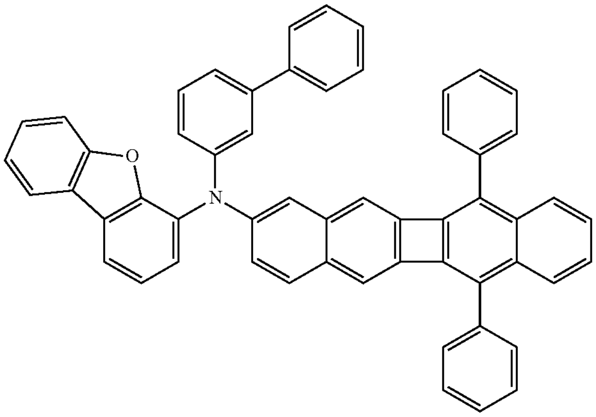
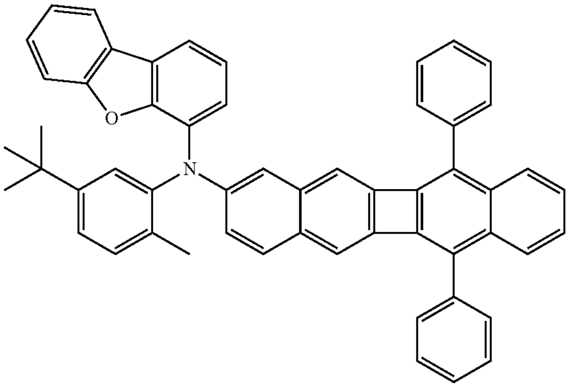
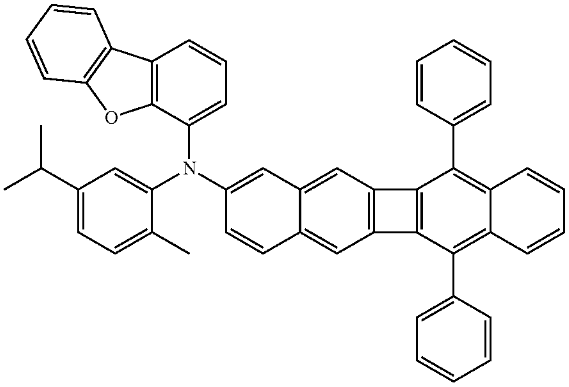
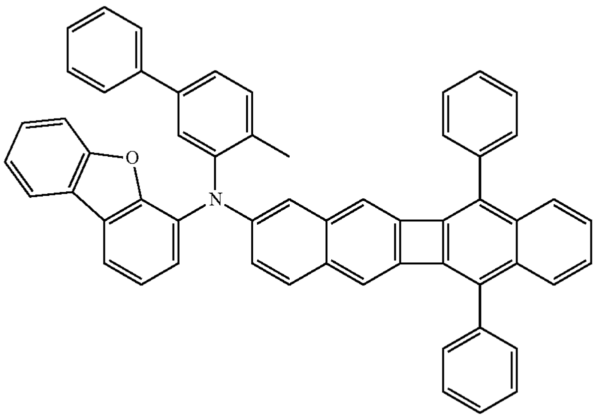

-continued
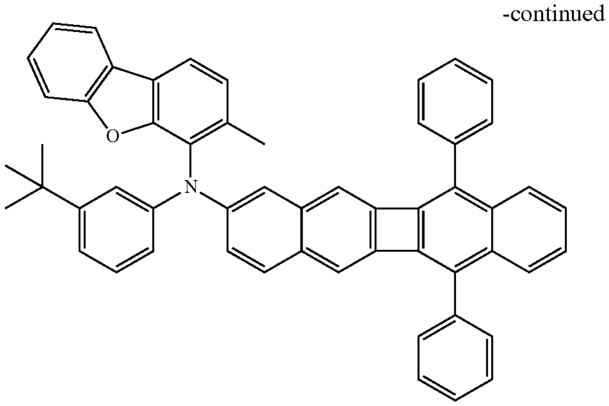
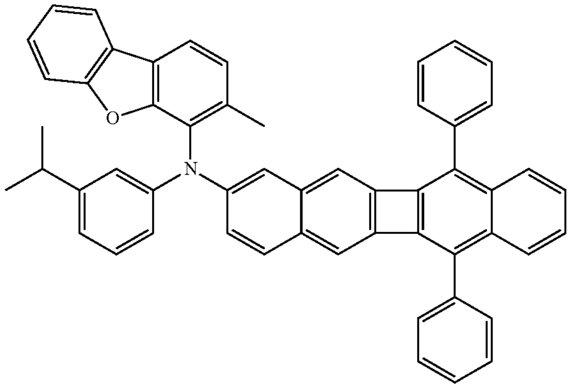
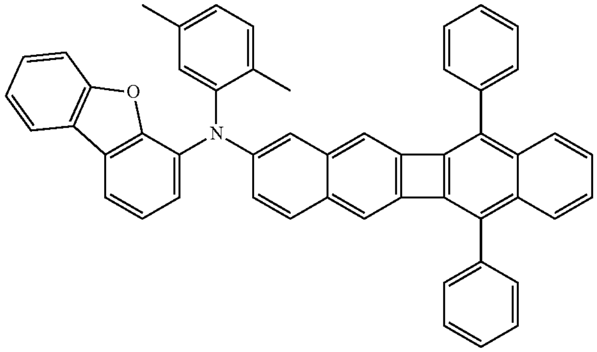
[Formula 145]
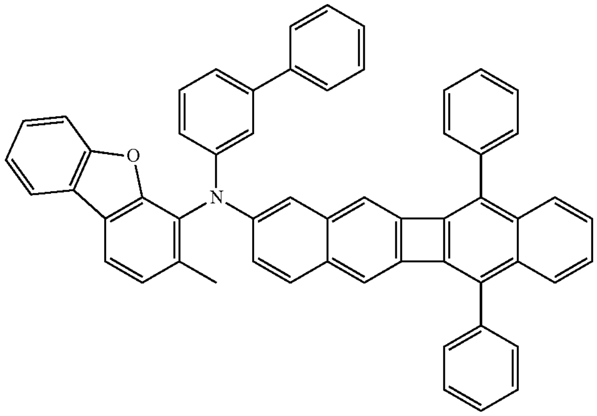

-continued
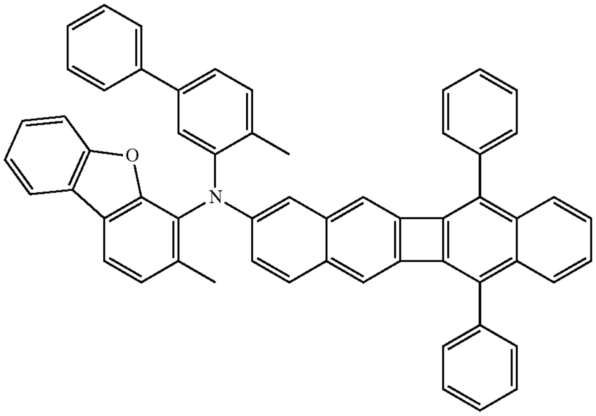
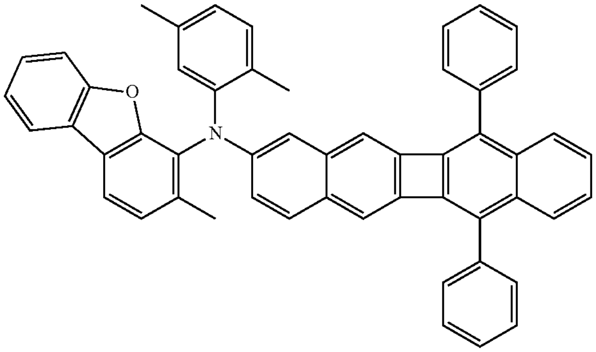
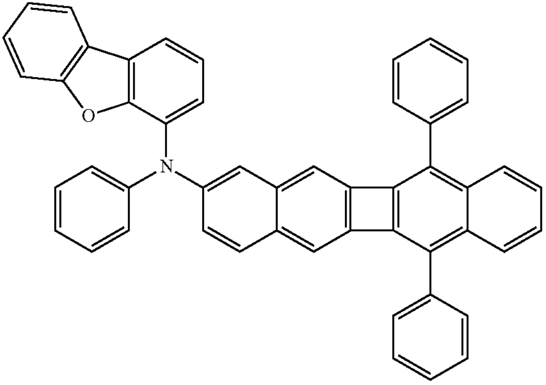
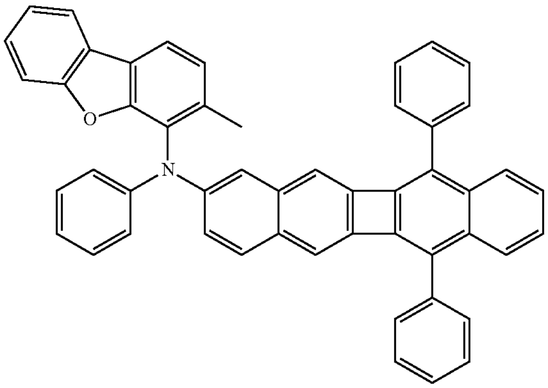
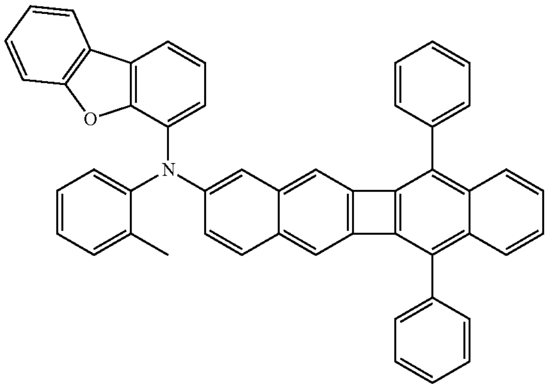
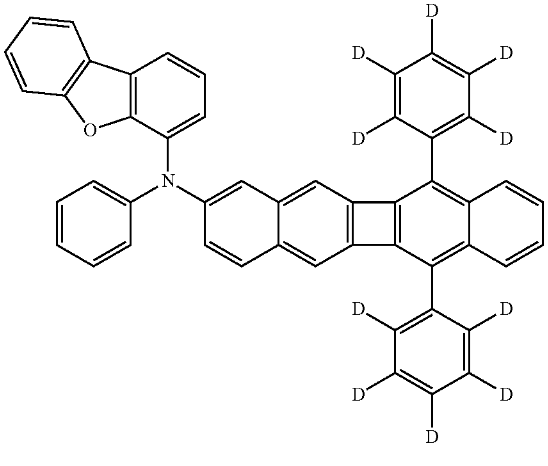
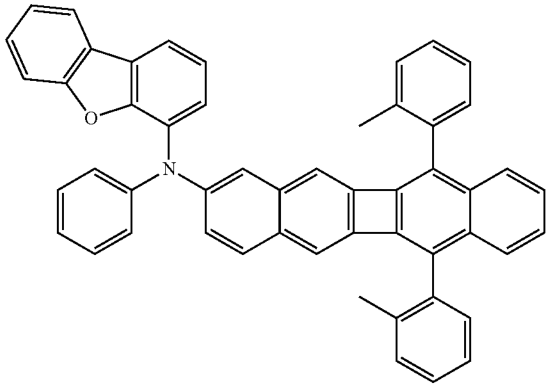

-continued
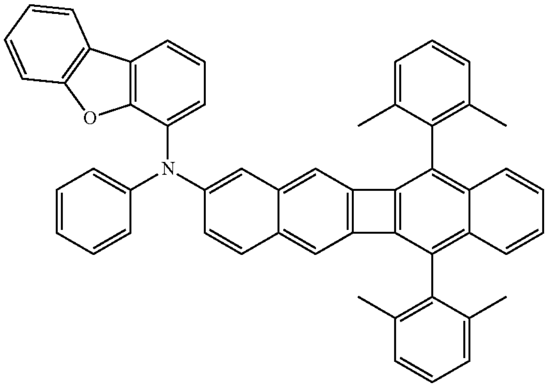
[Formula 146]
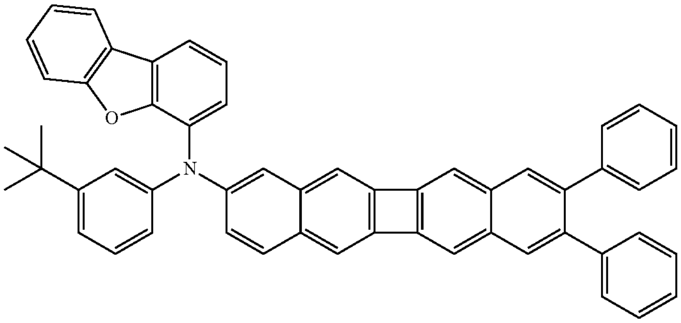
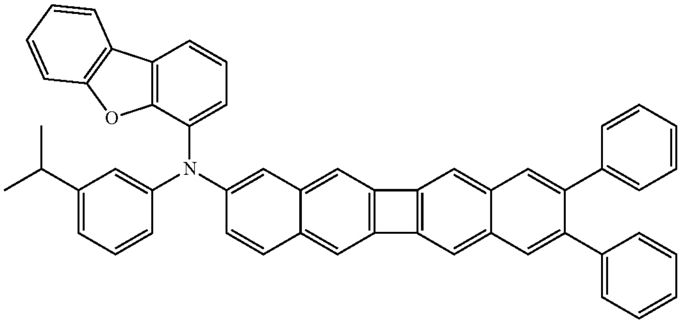
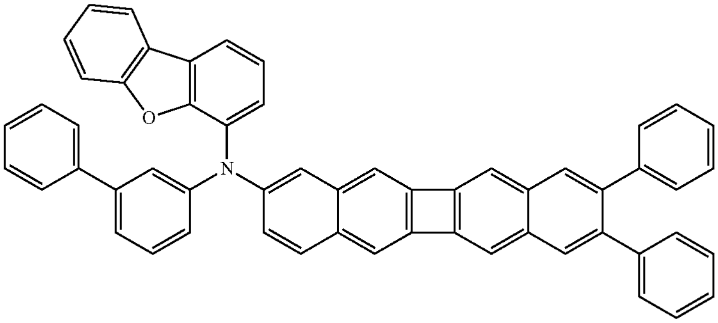
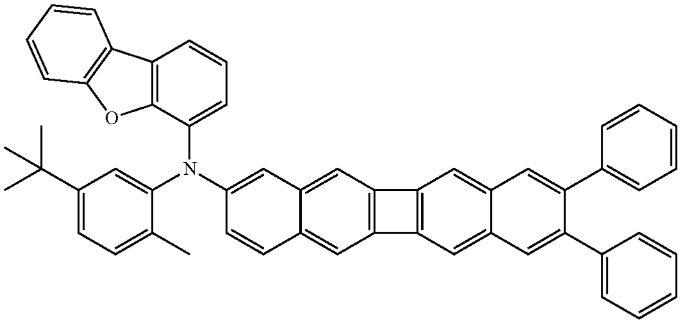

-continued
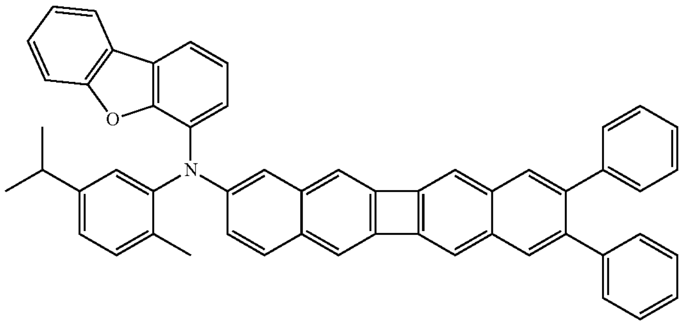
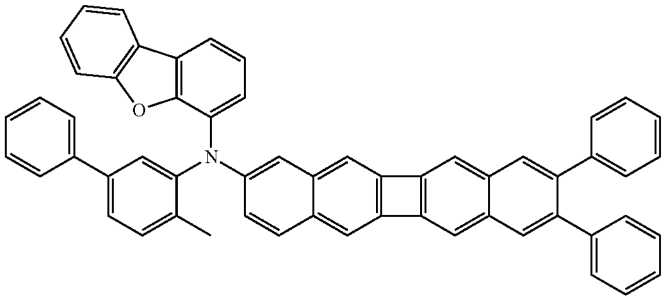
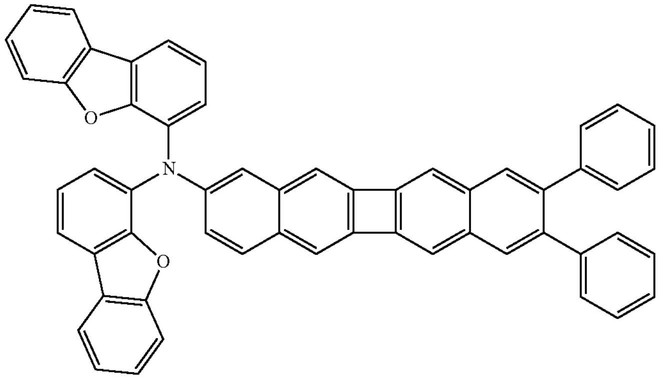
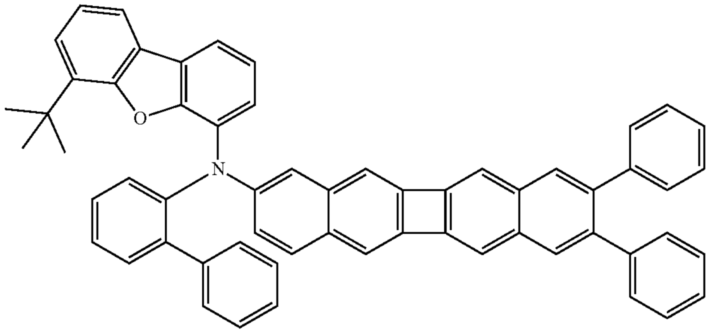
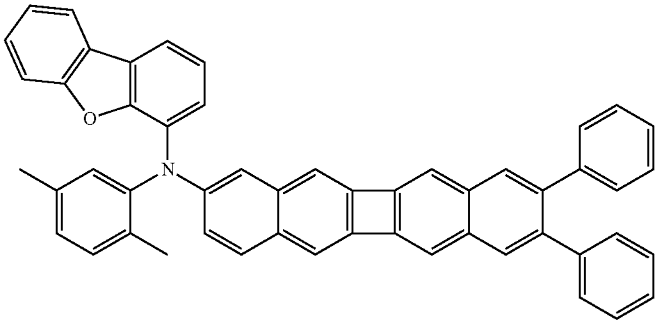

-continued
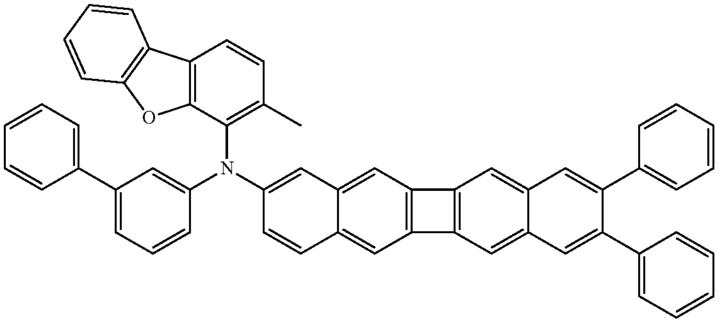
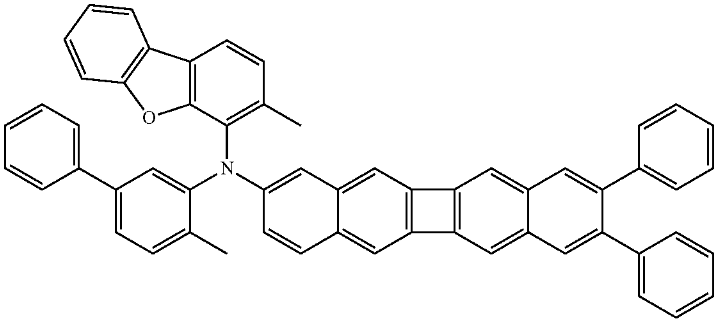
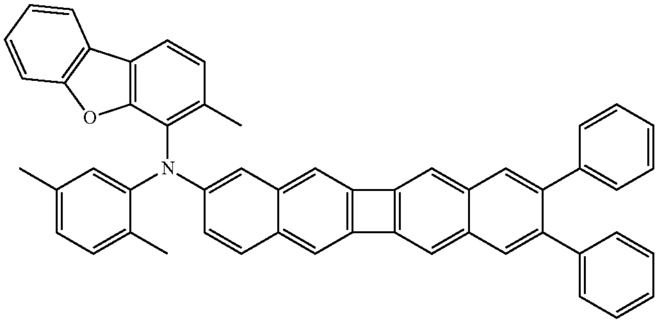
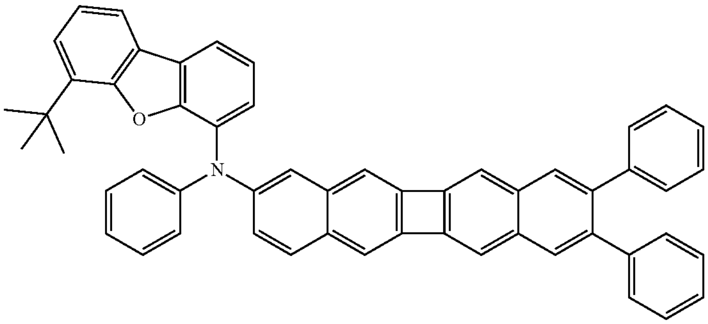
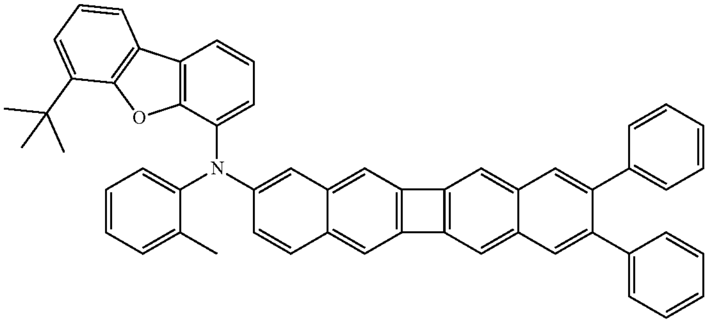

-continued
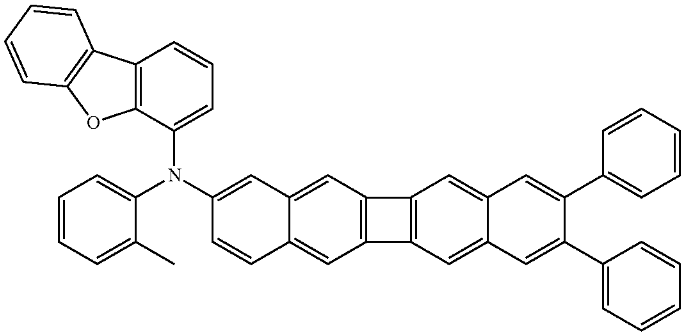
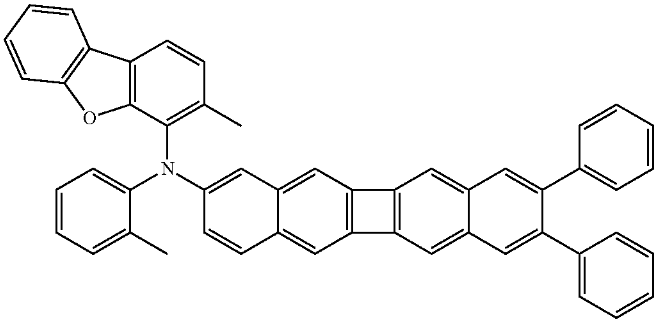
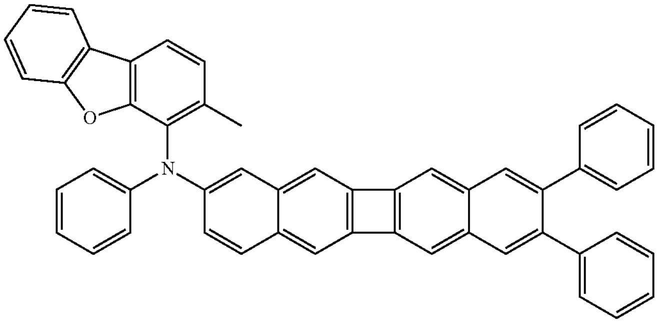
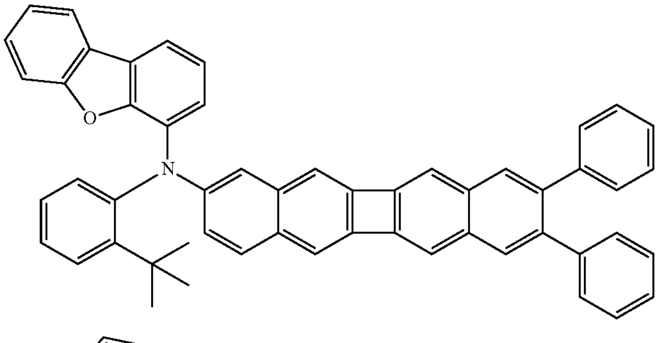
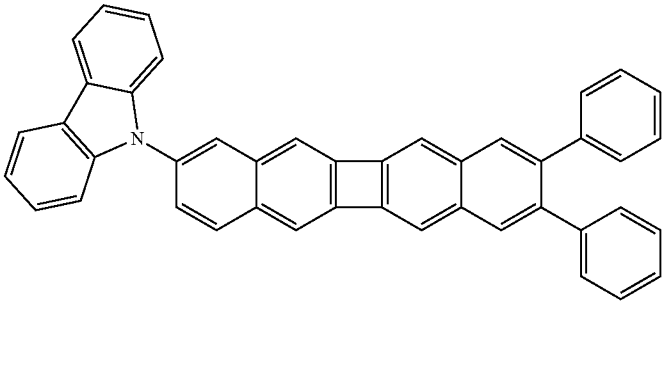

-continued
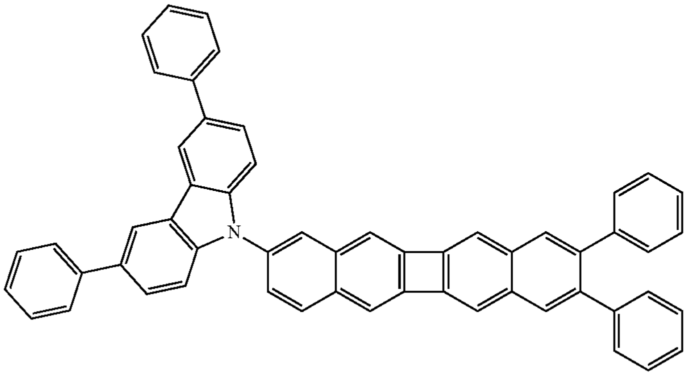
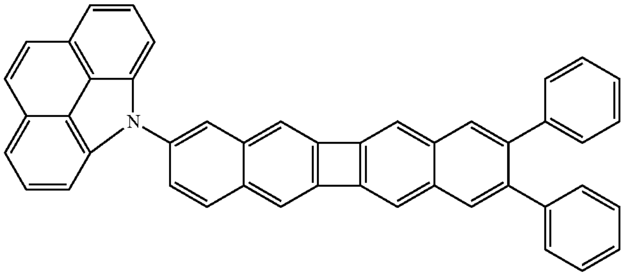
[Formula 147]
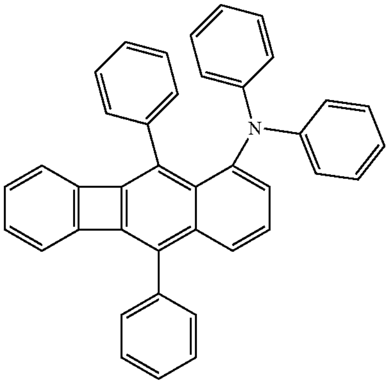
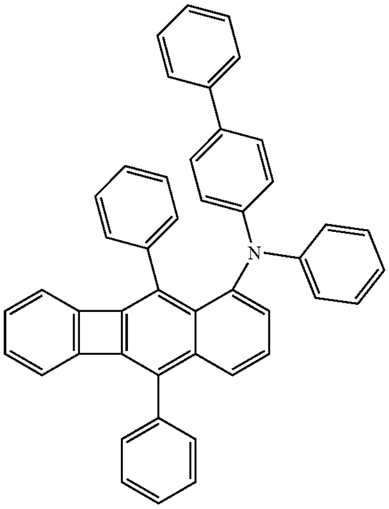
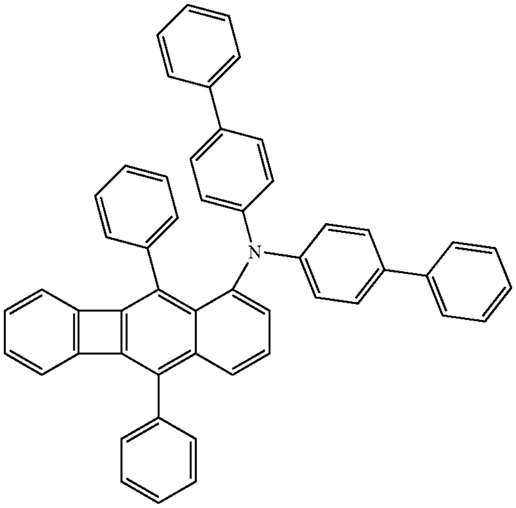
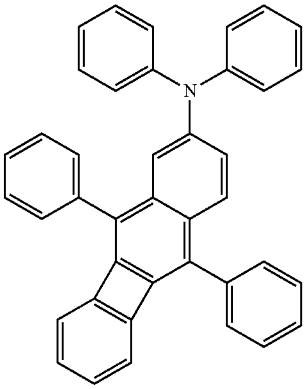

-continued
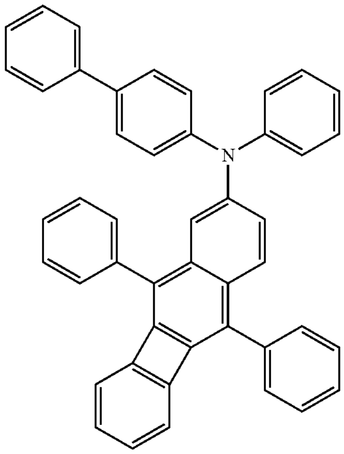
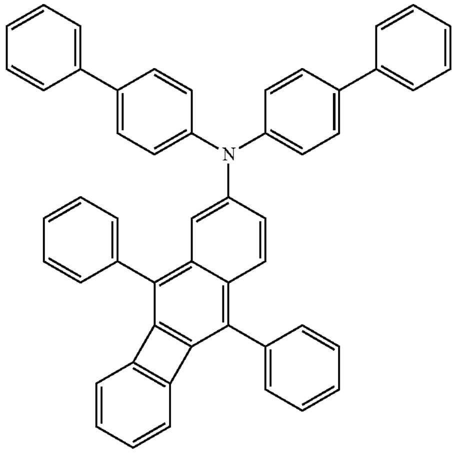
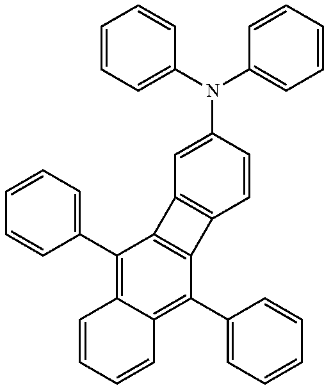
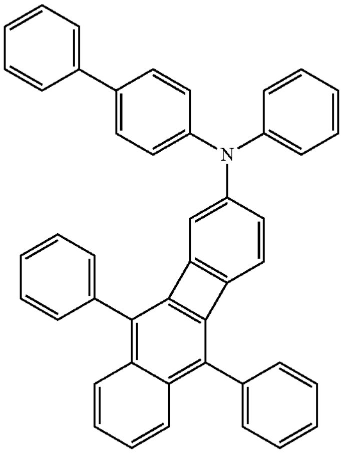
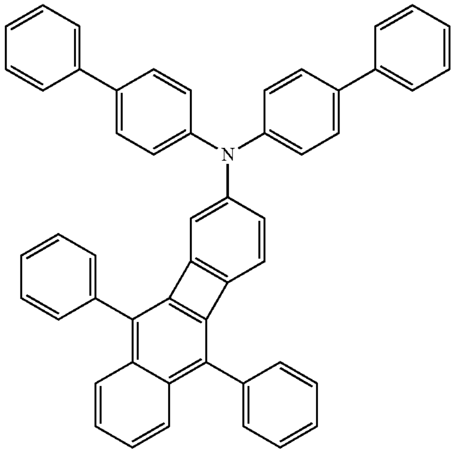
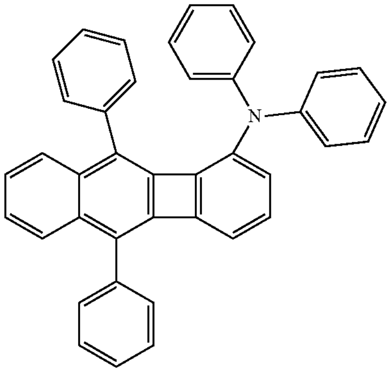

-continued
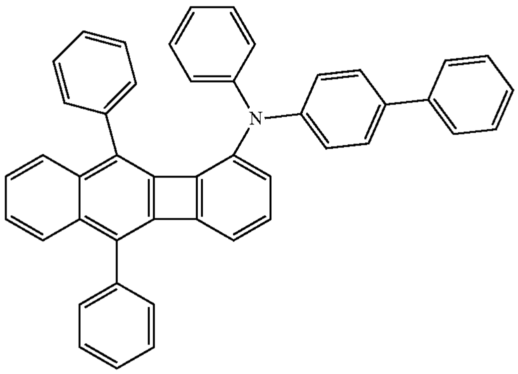
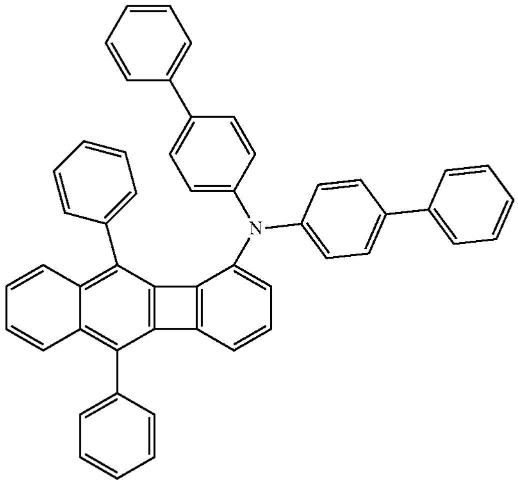
[Formula 148]
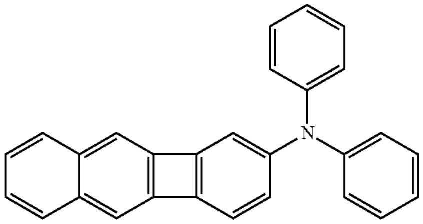
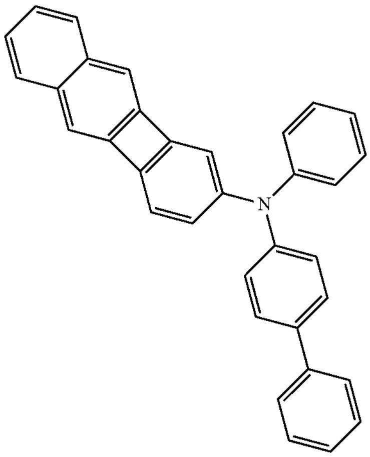
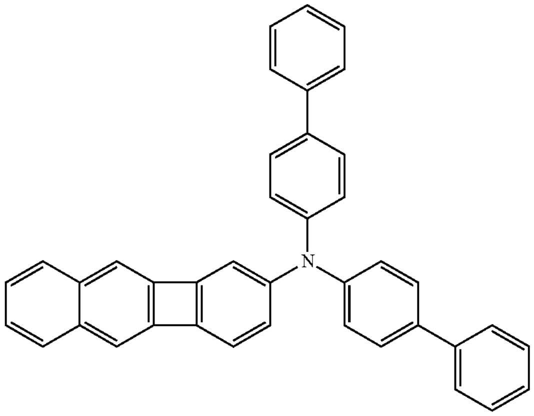
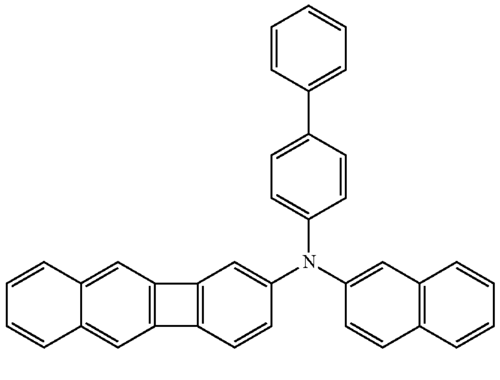

-continued
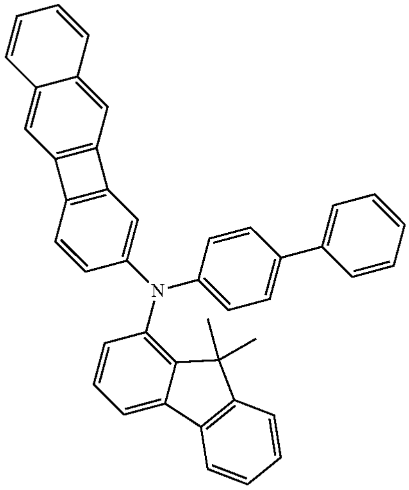
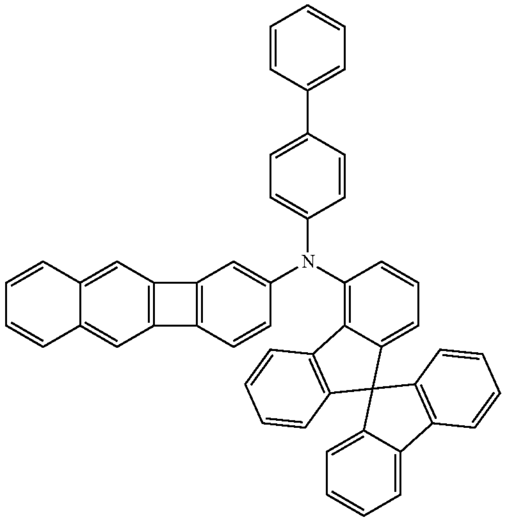
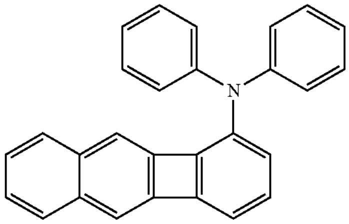
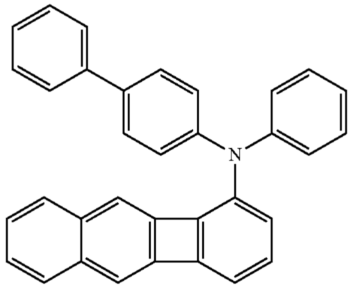
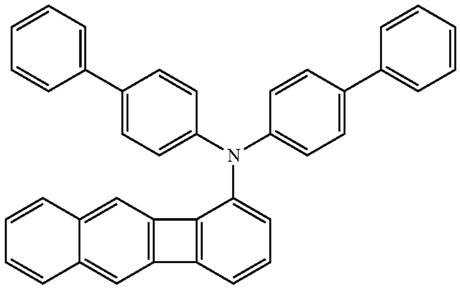
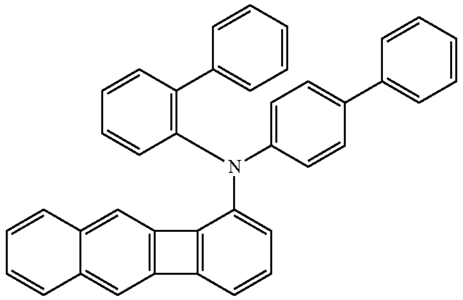
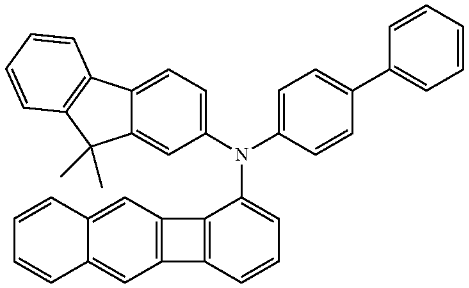
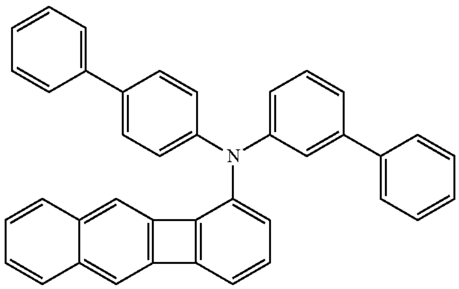
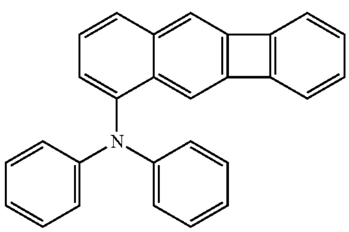
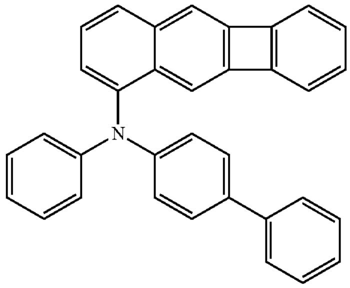

-continued
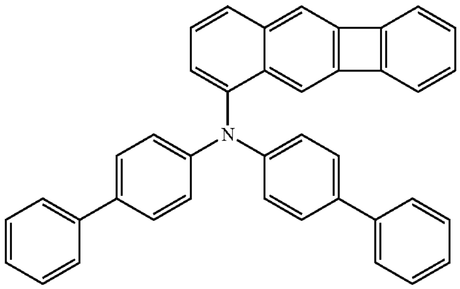
[Formula 149]
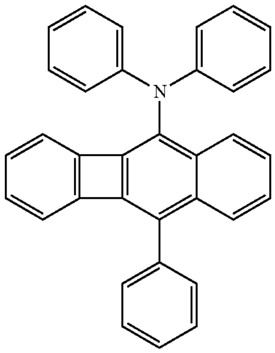
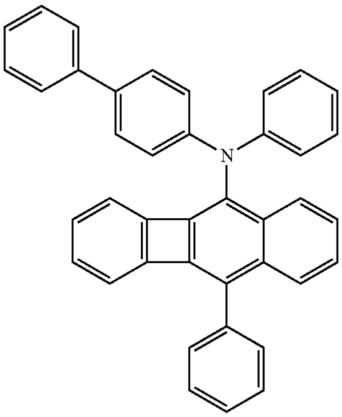
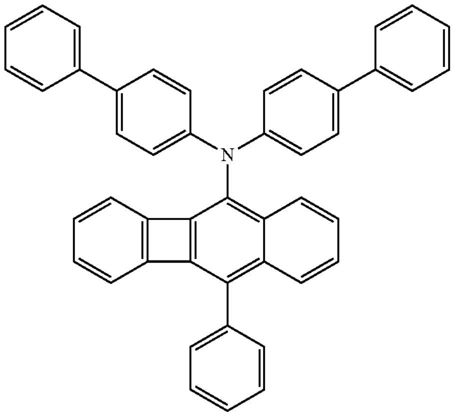
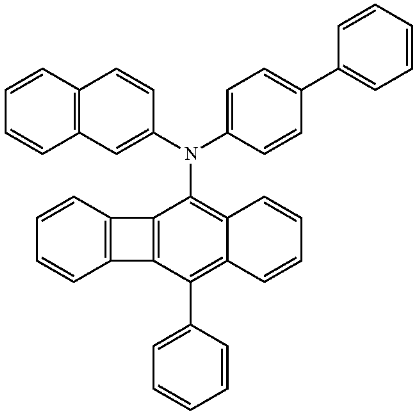
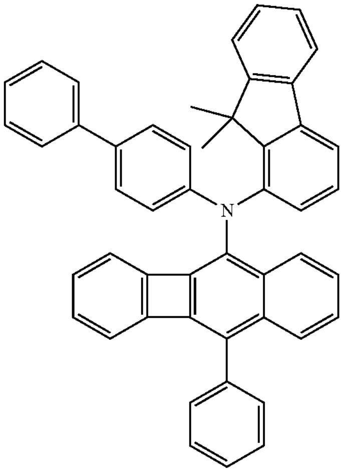

-continued
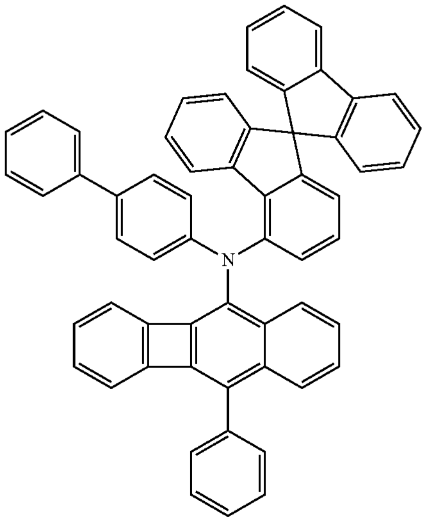
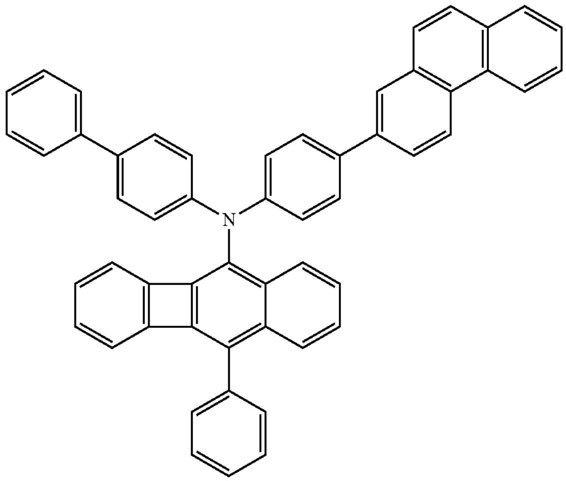
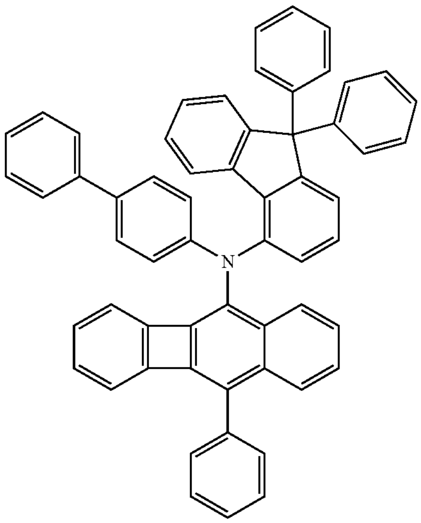

-continued
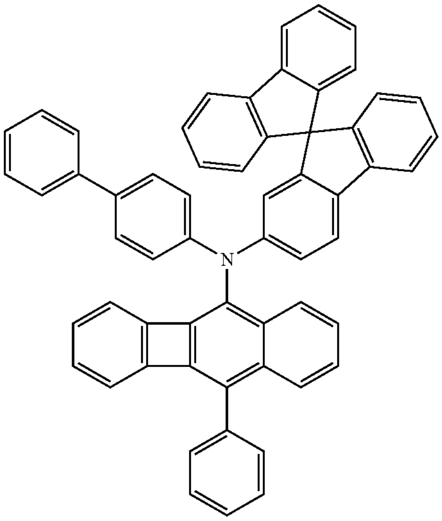
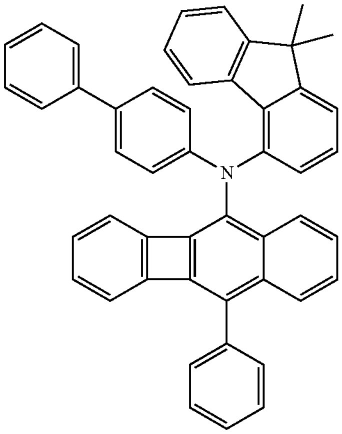
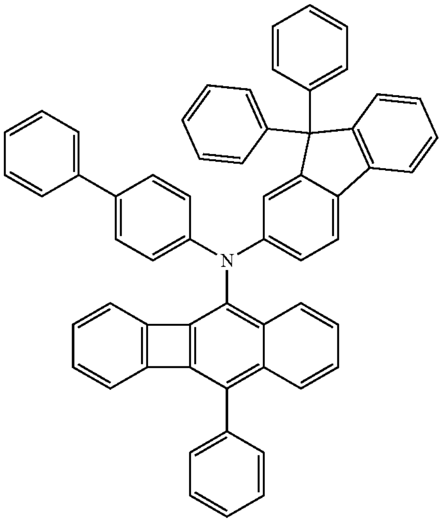
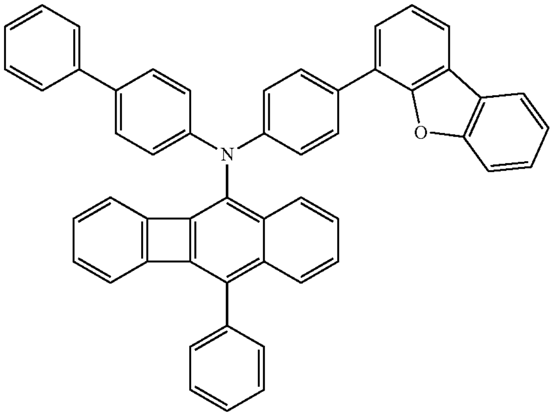
[Formula 150]
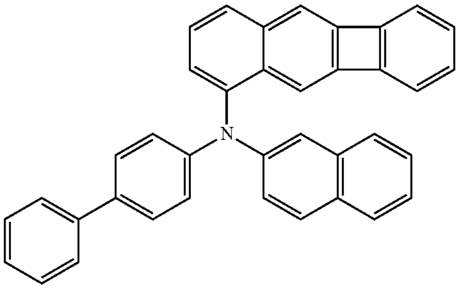
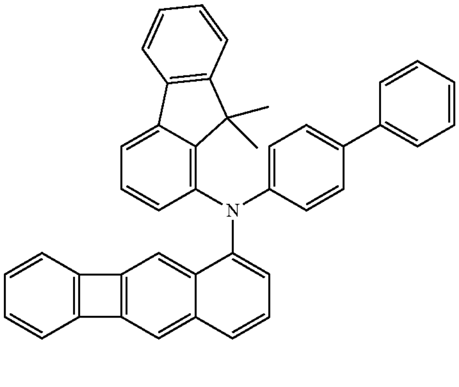

-continued
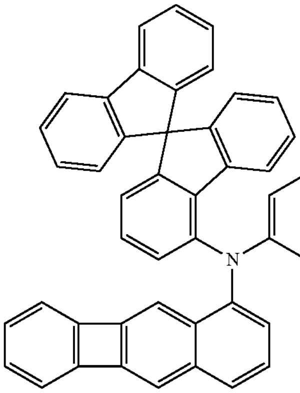
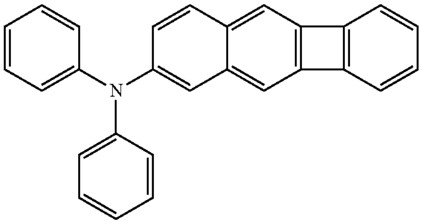
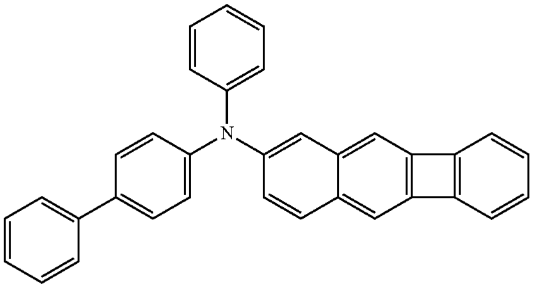
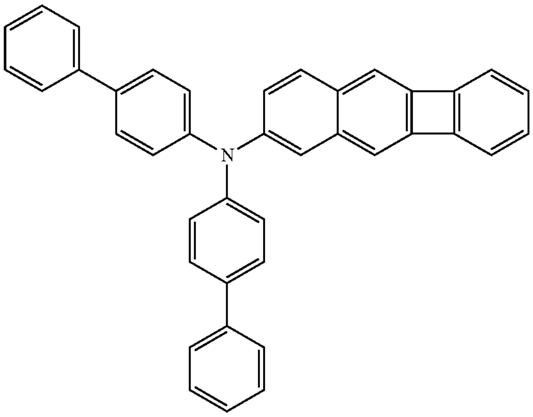
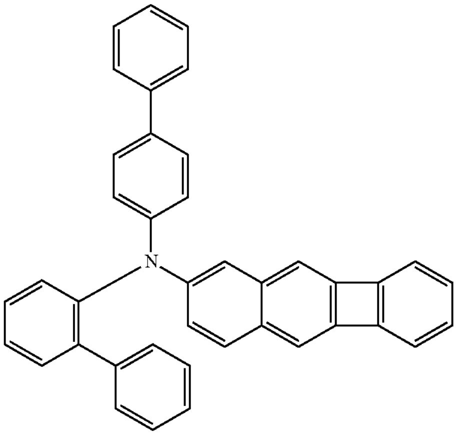
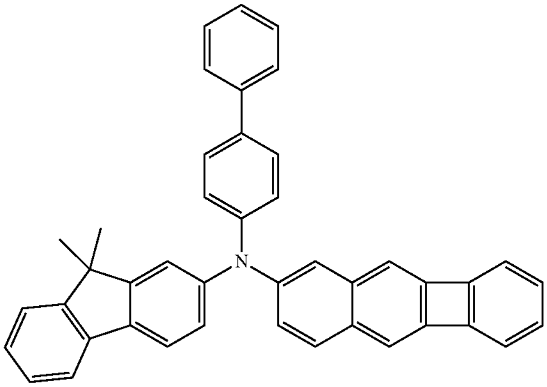
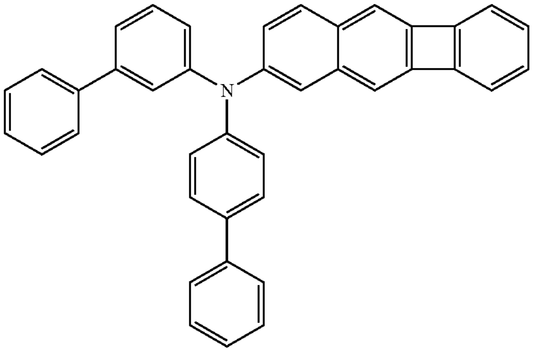
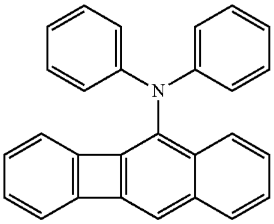

-continued
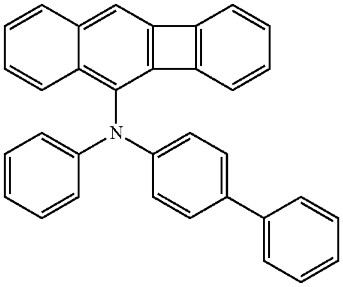
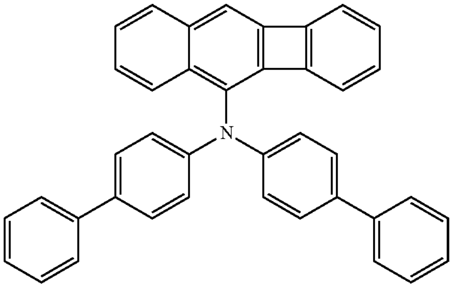
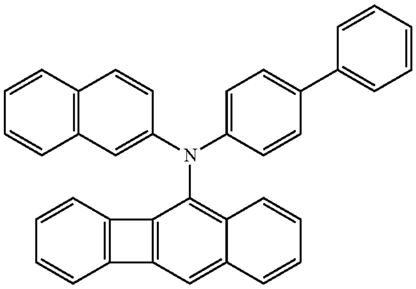
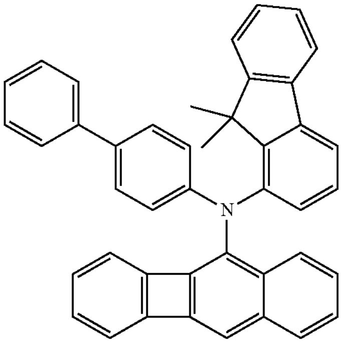
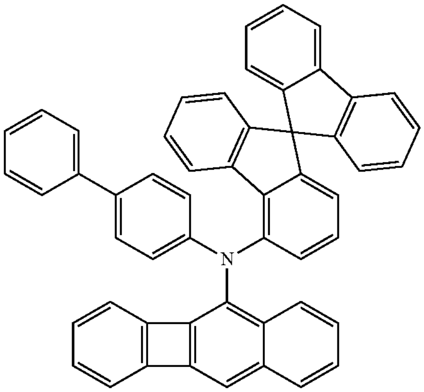
[Formula 151]
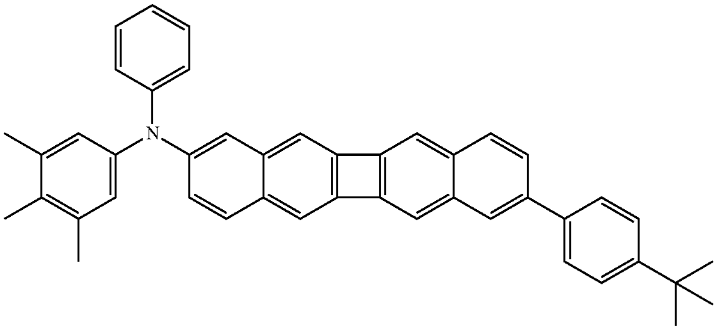
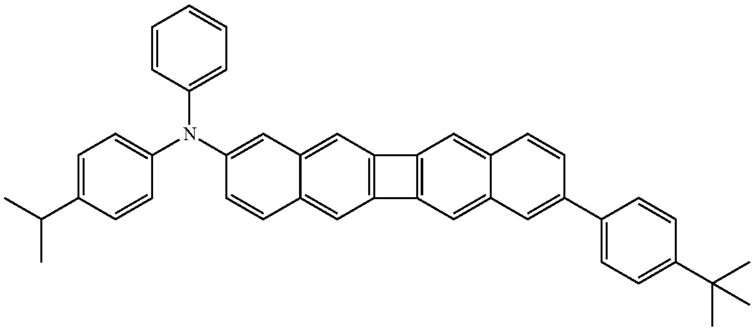

-continued
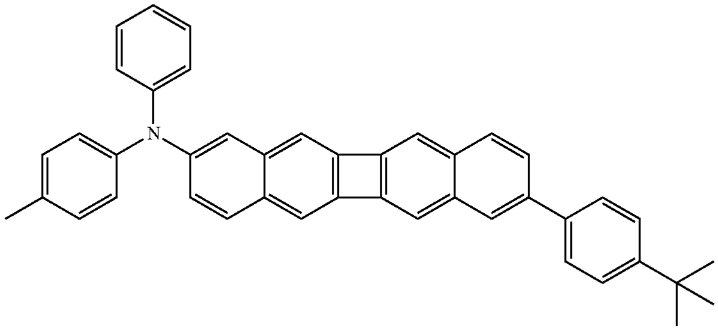
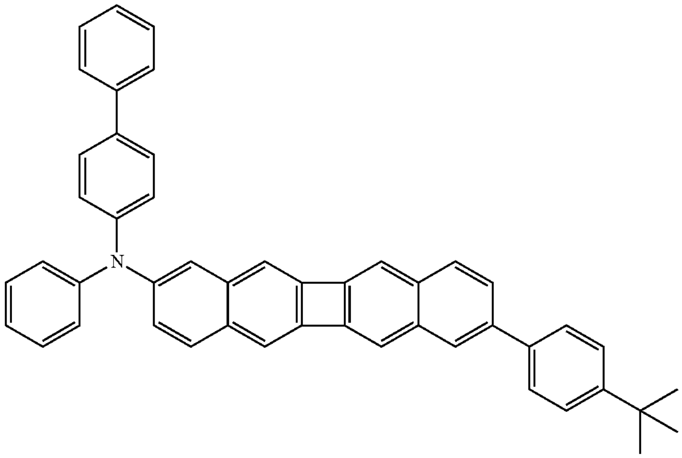
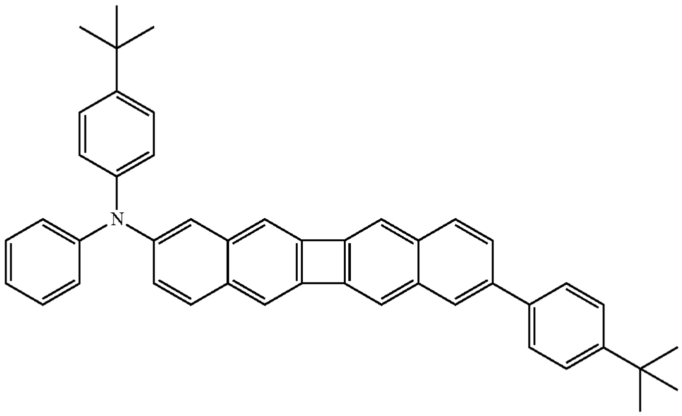
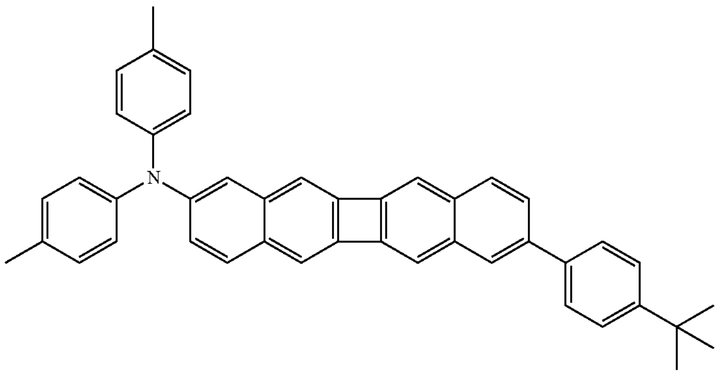

-continued
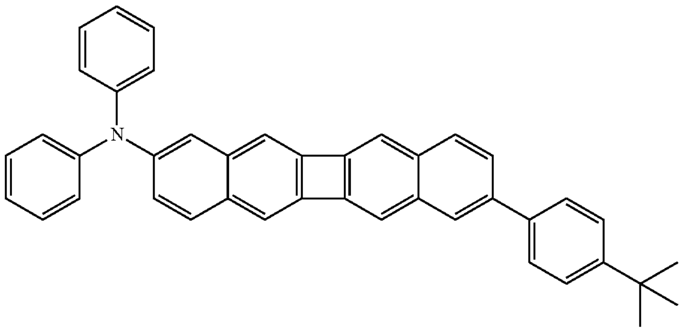
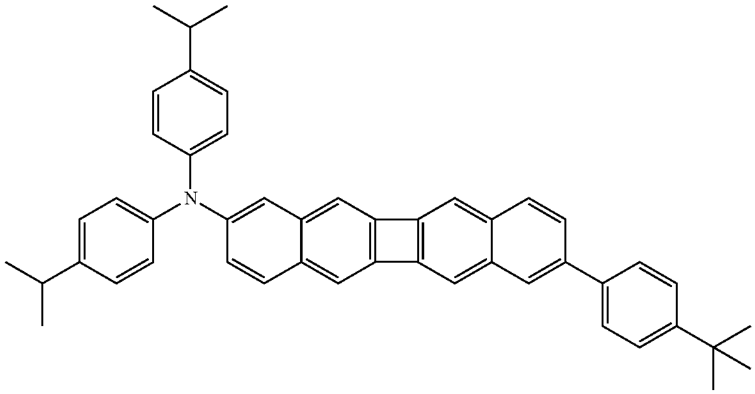
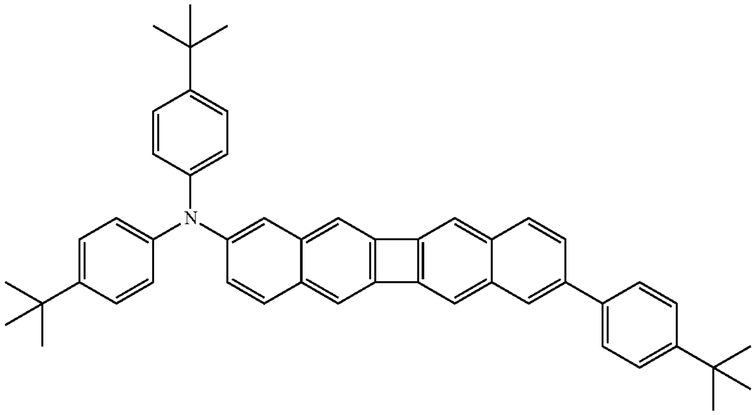
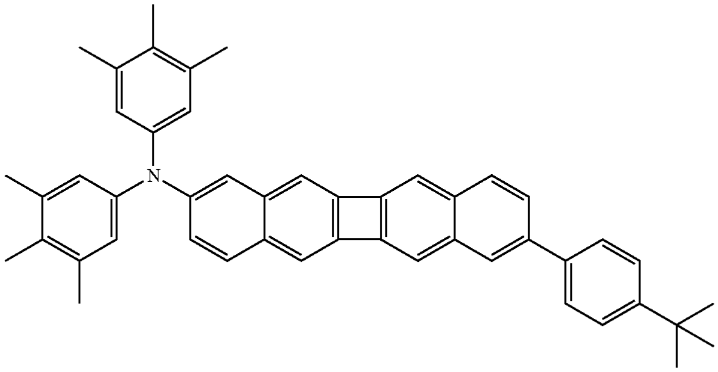

-continued
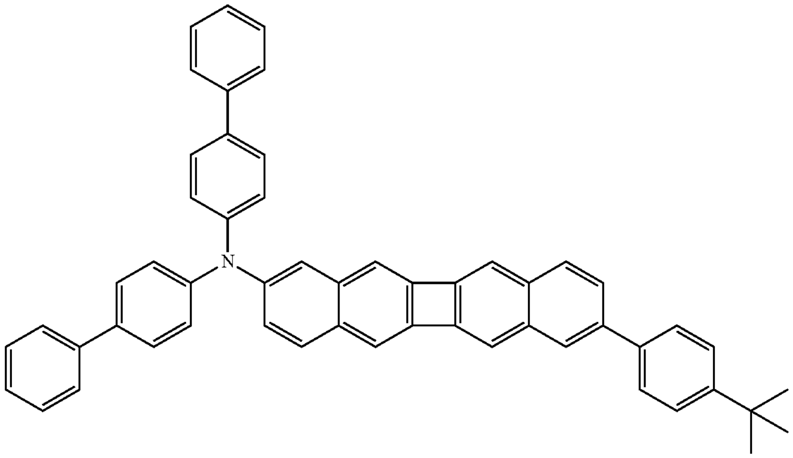
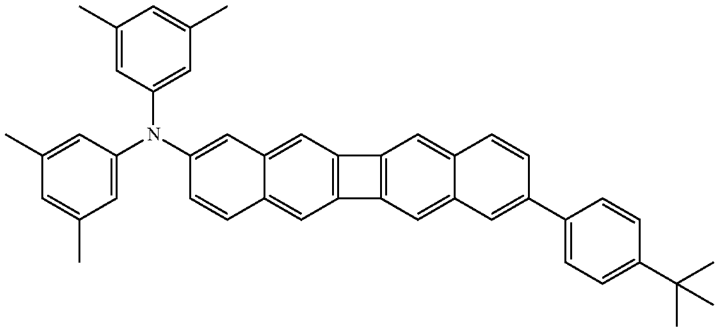
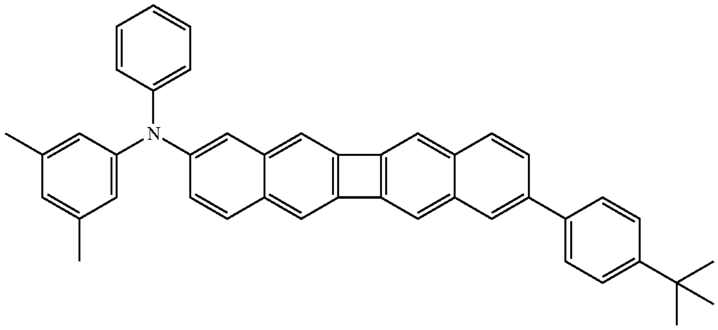
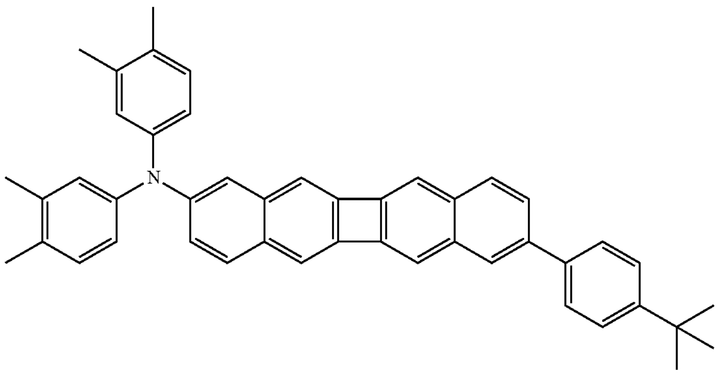

-continued
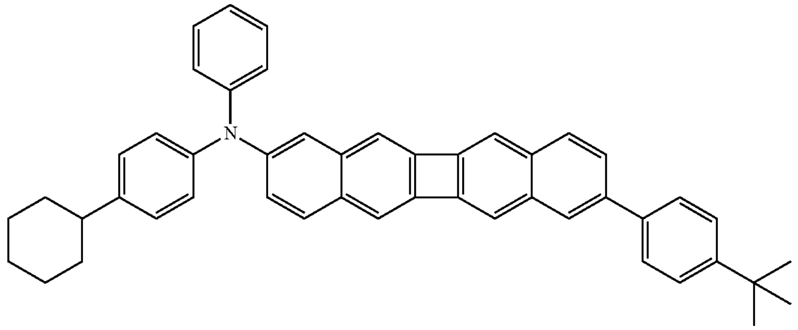
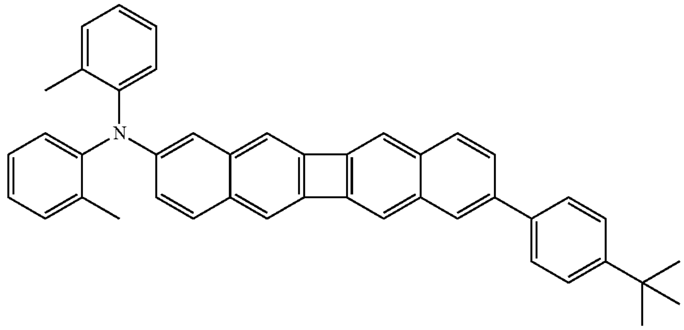
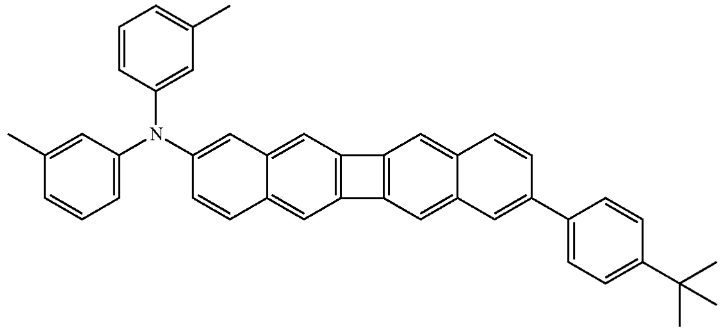
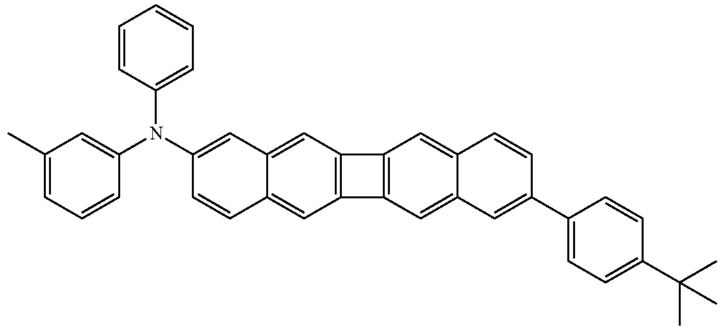
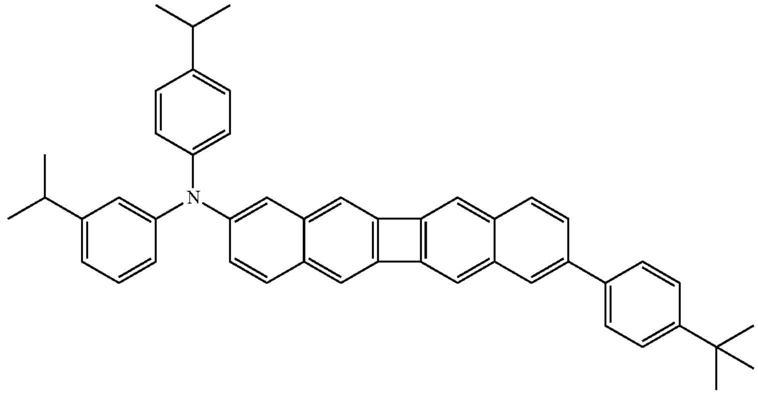

-continued
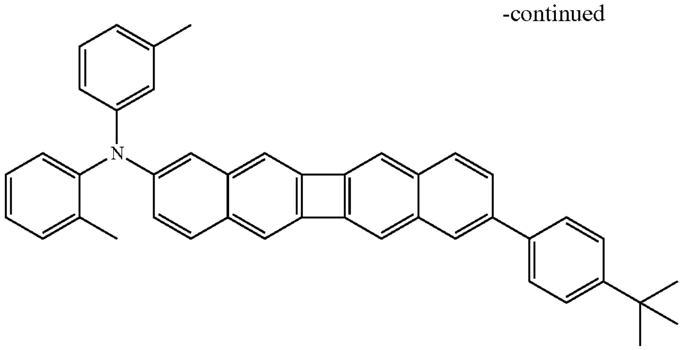
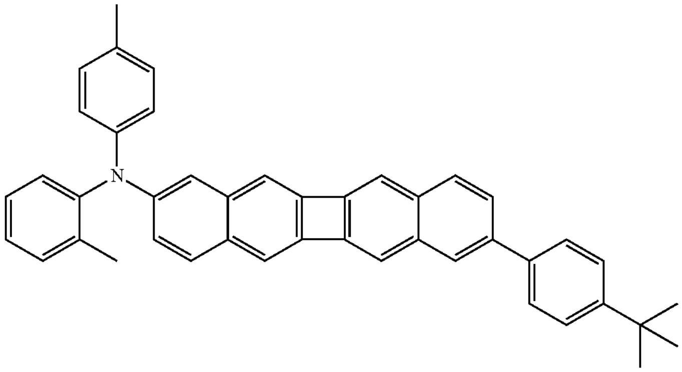
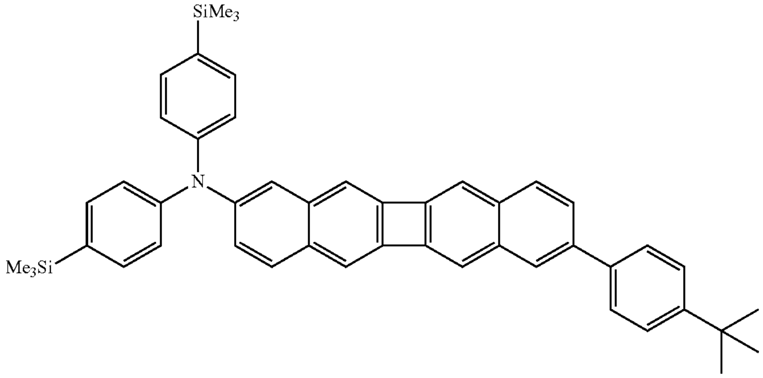
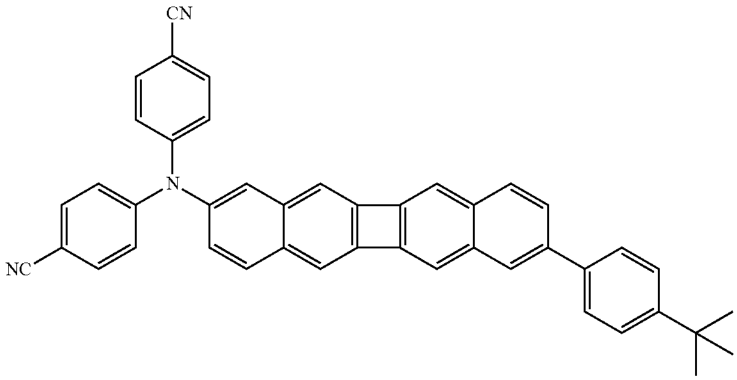

-continued
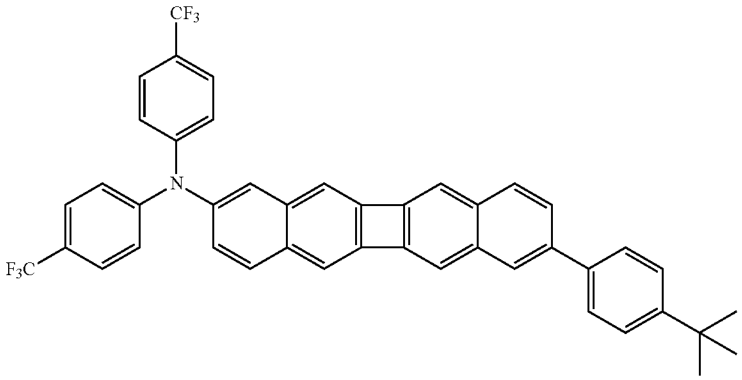
[Formula 152]
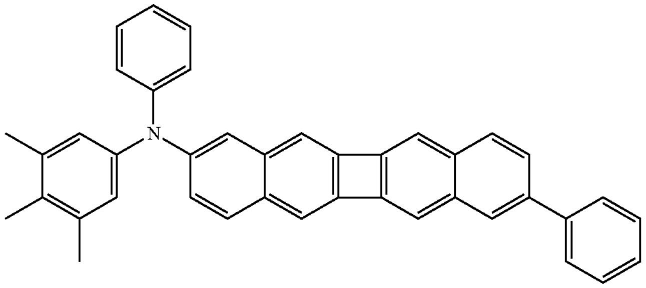
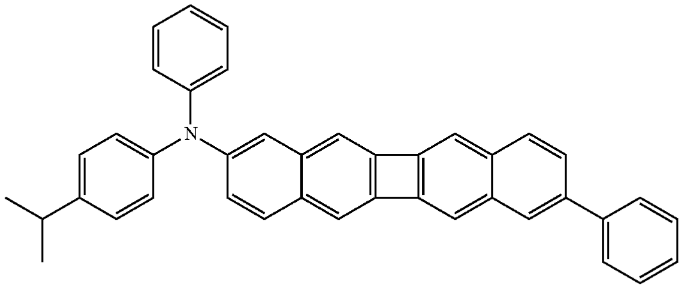
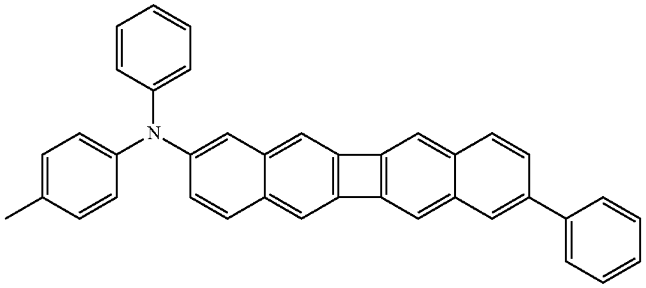
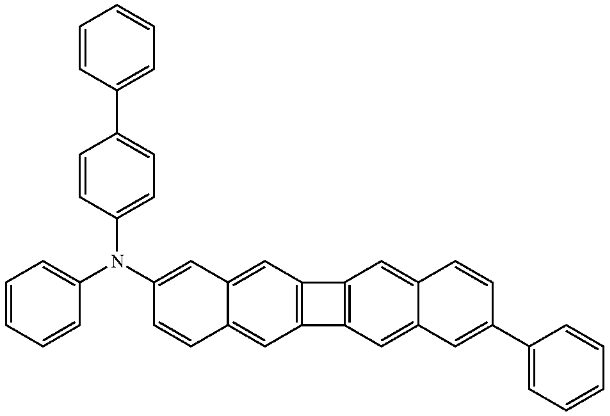

-continued
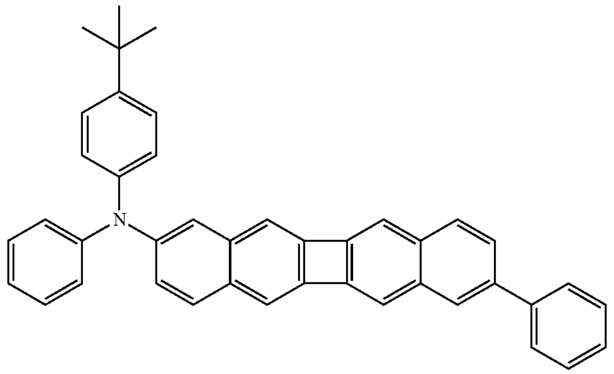
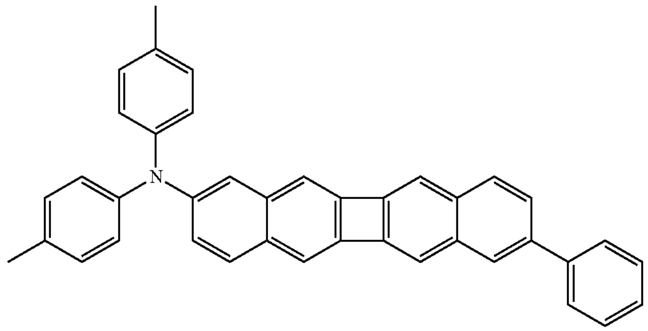
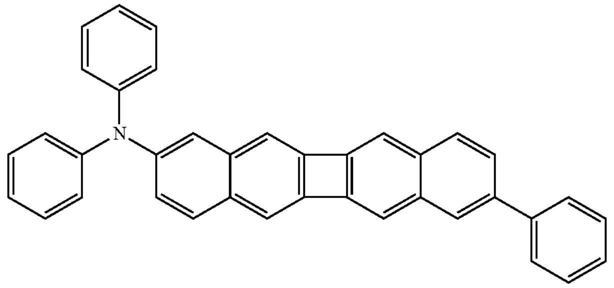
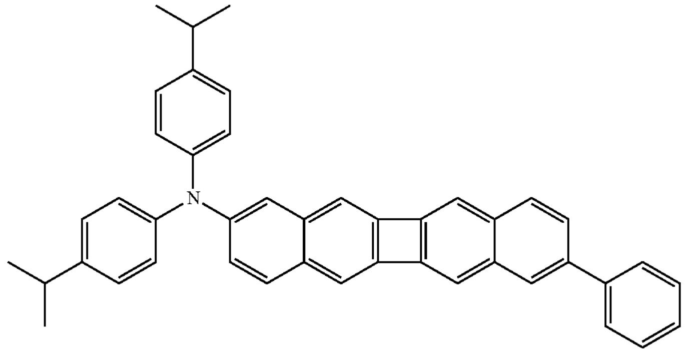
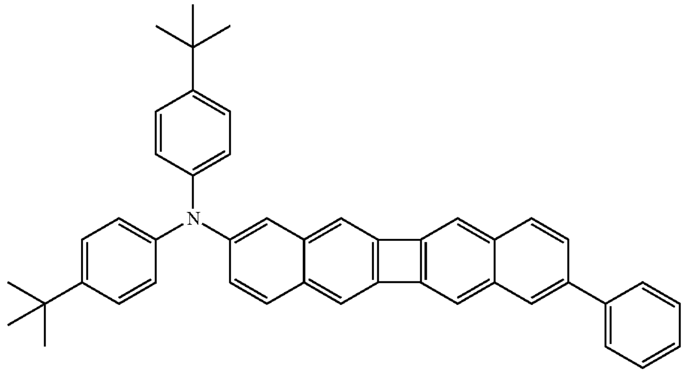

-continued
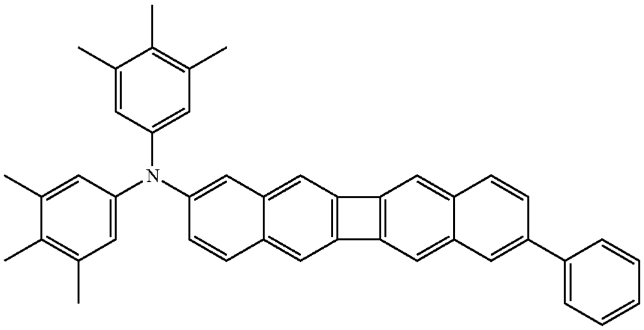
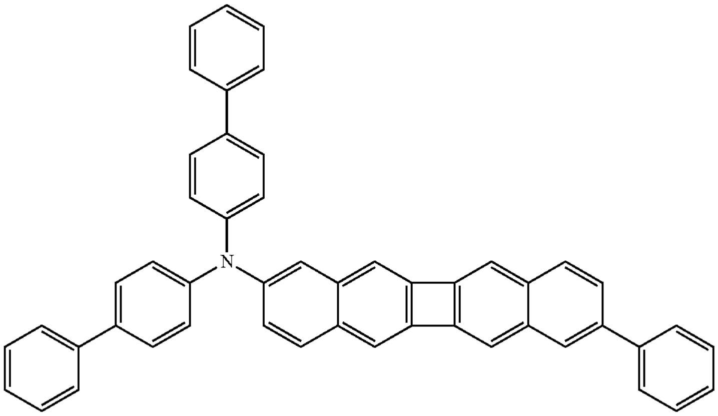
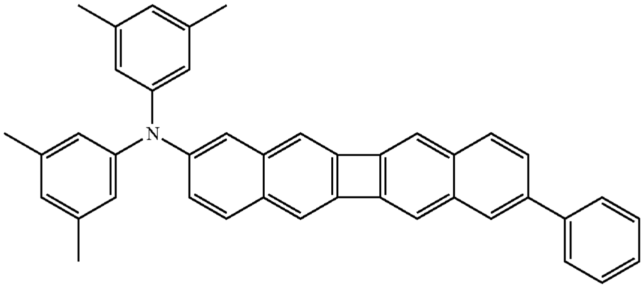
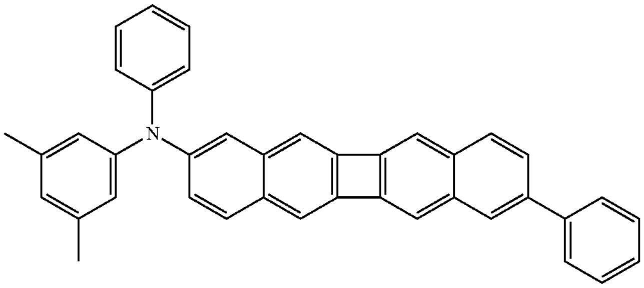
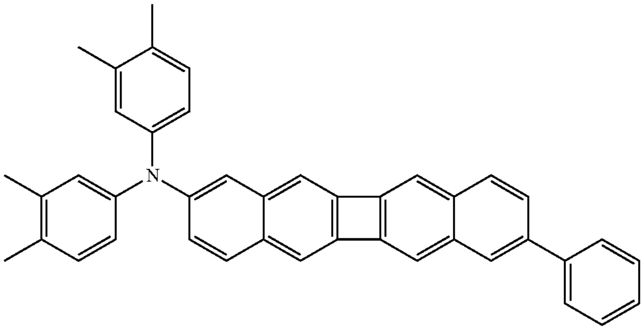

-continued
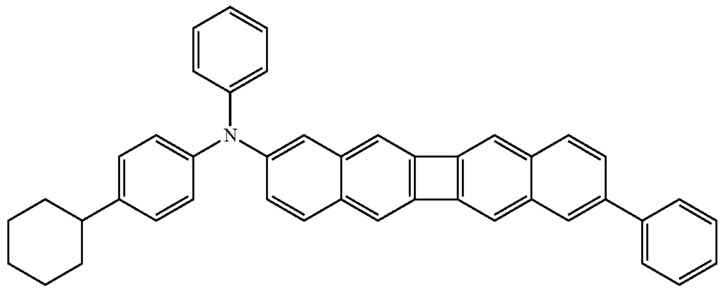
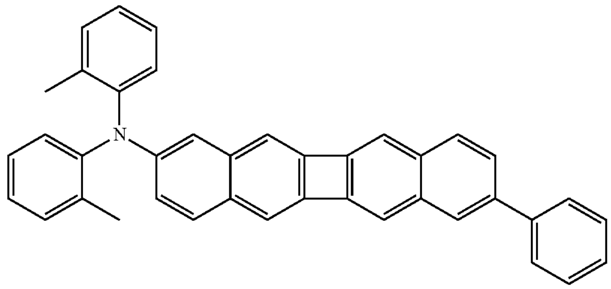
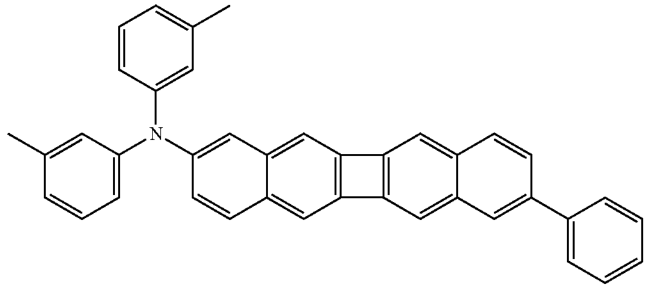
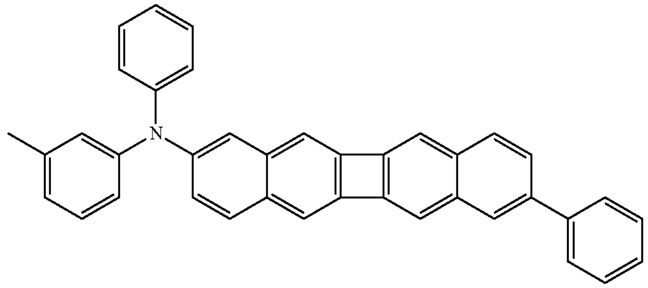
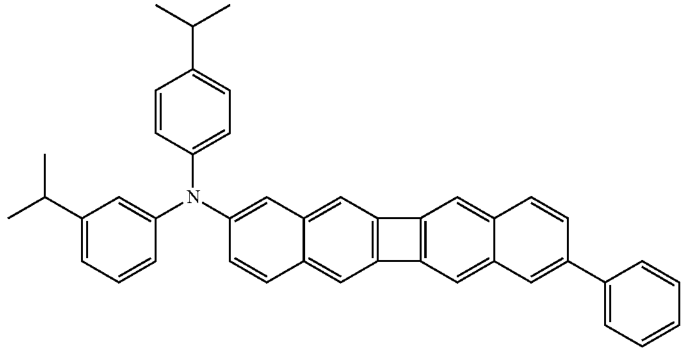

-continued
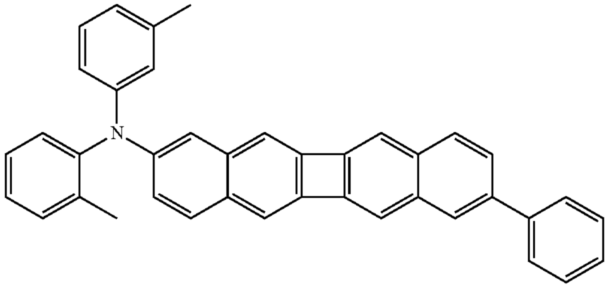
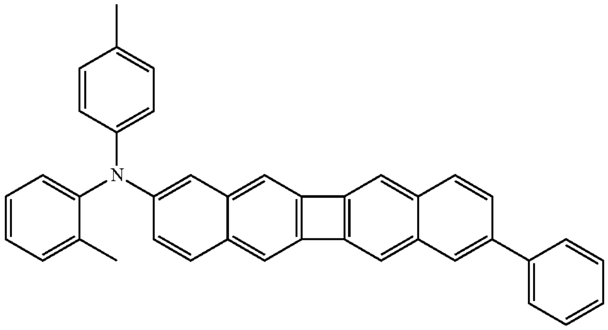
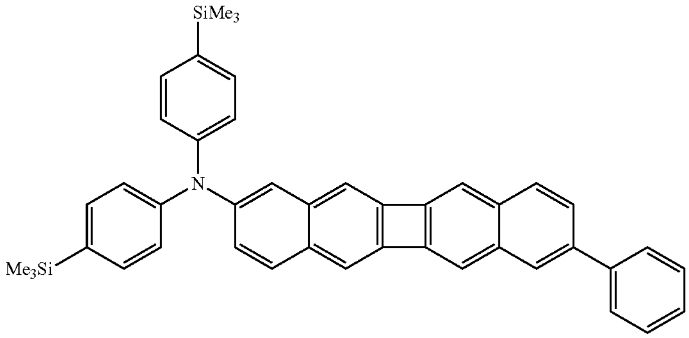
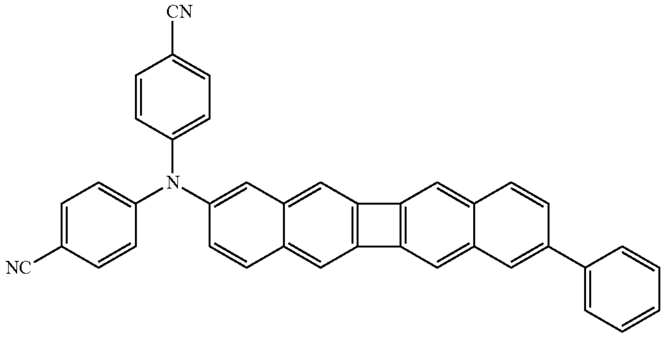
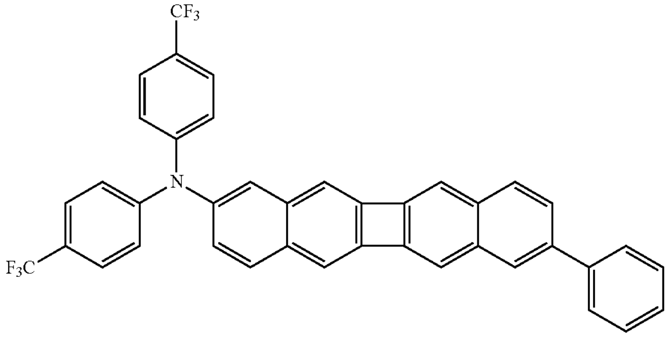

-continued
[Formula 153]
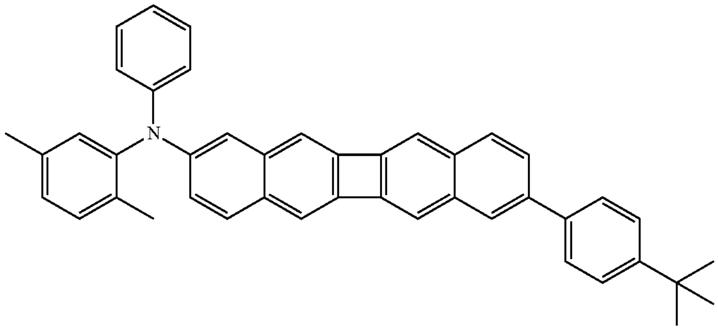
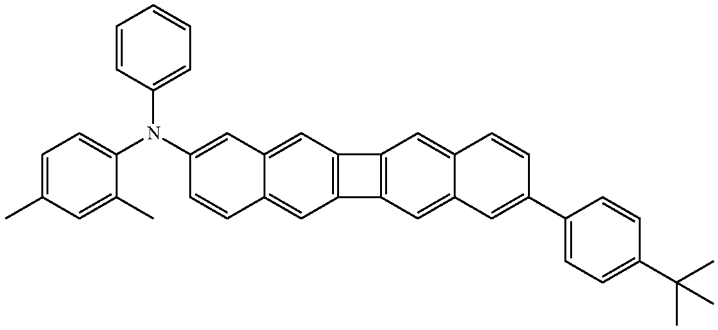
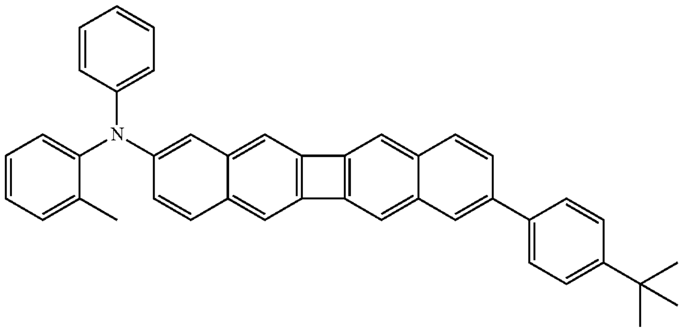
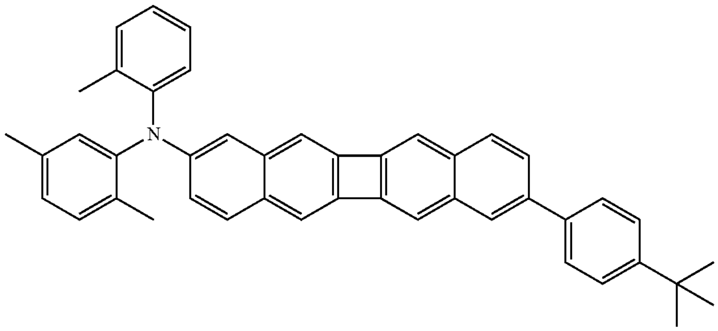
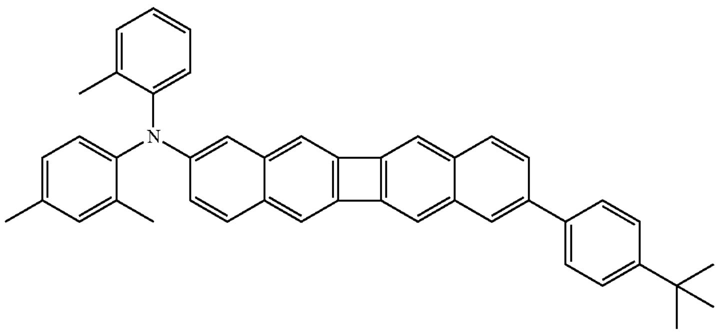

-continued
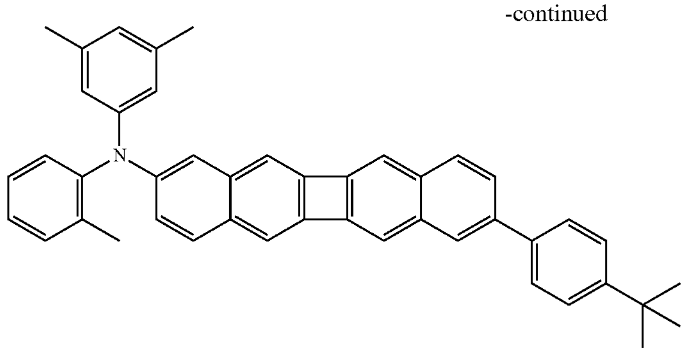
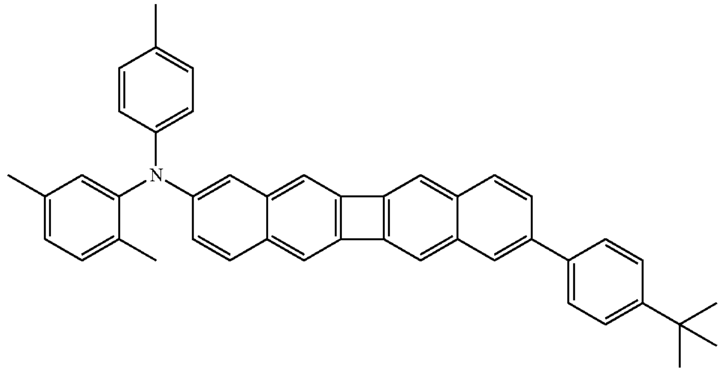
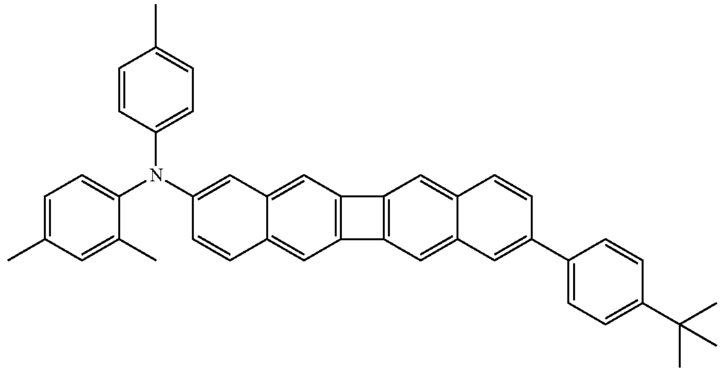
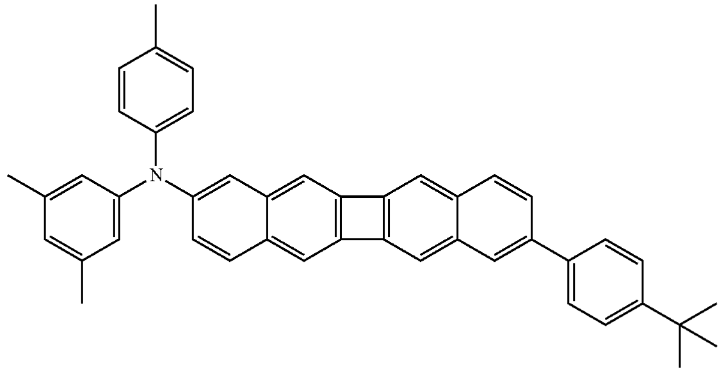

-continued
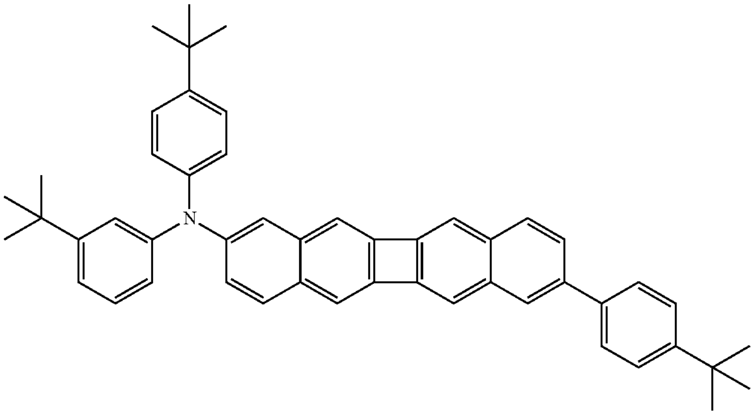
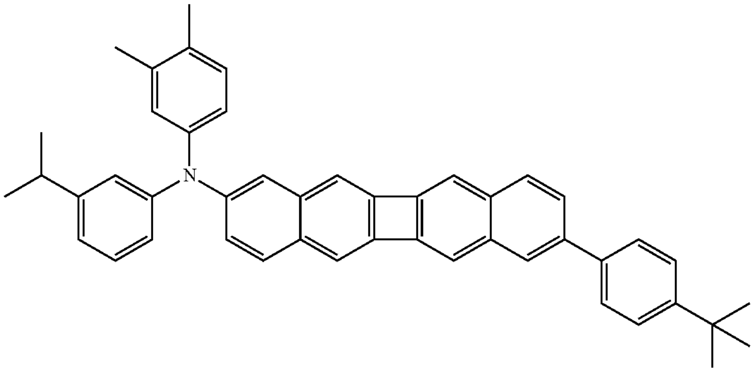
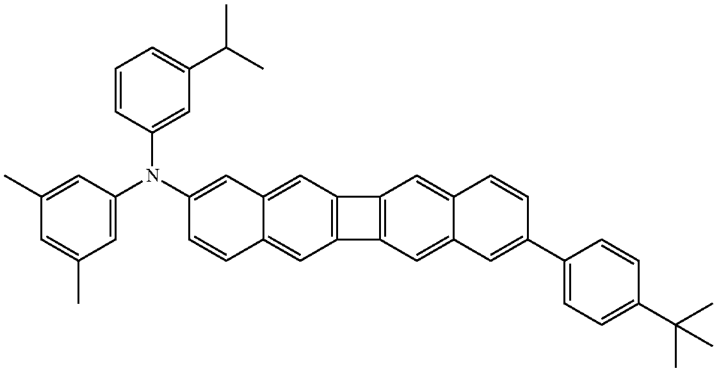
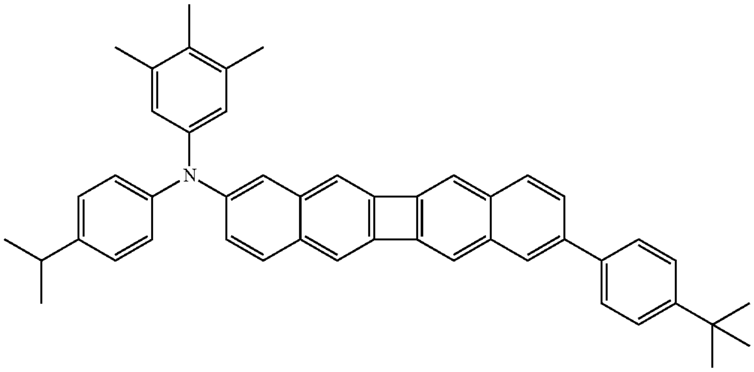

-continued
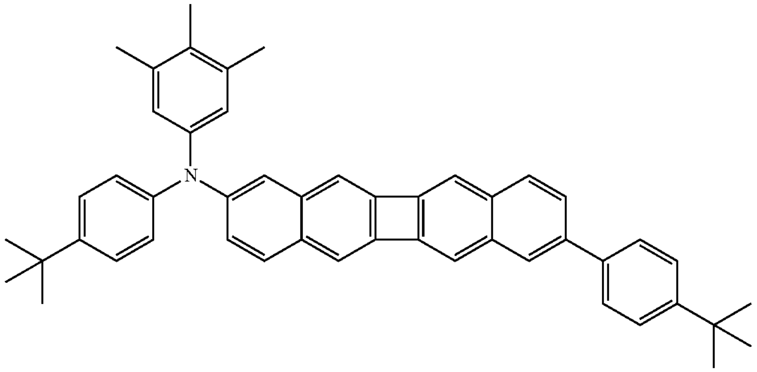
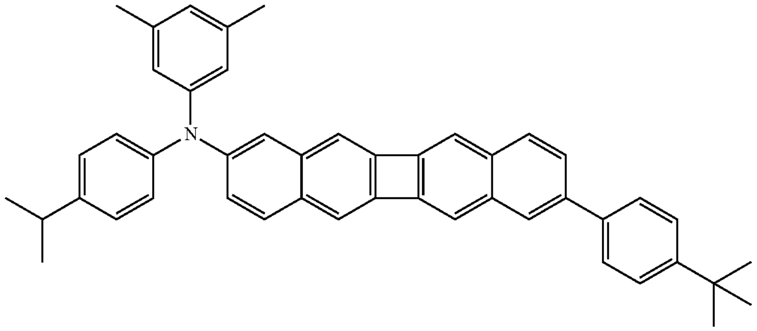
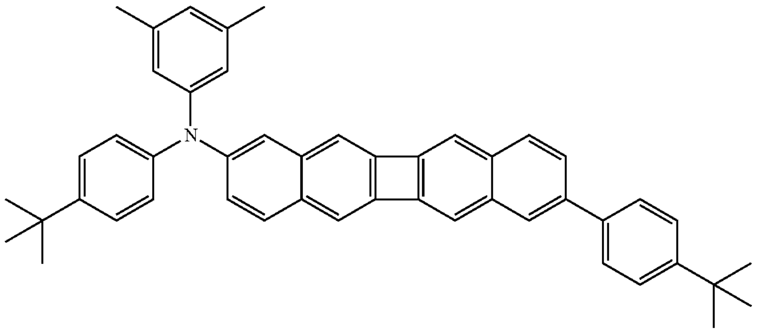
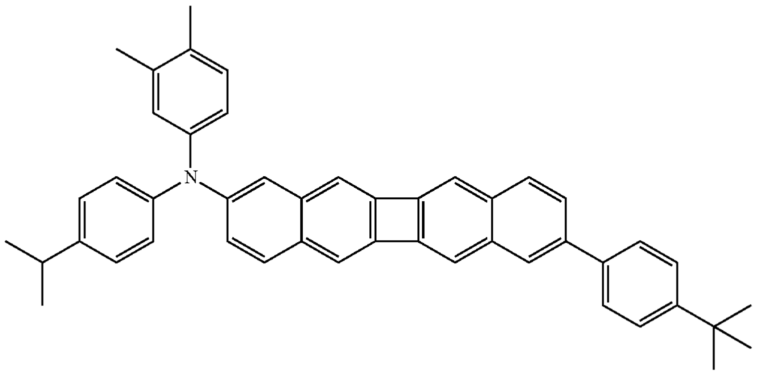

-continued
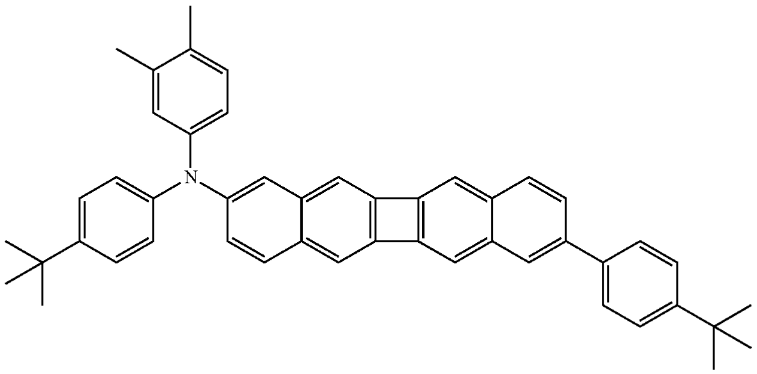
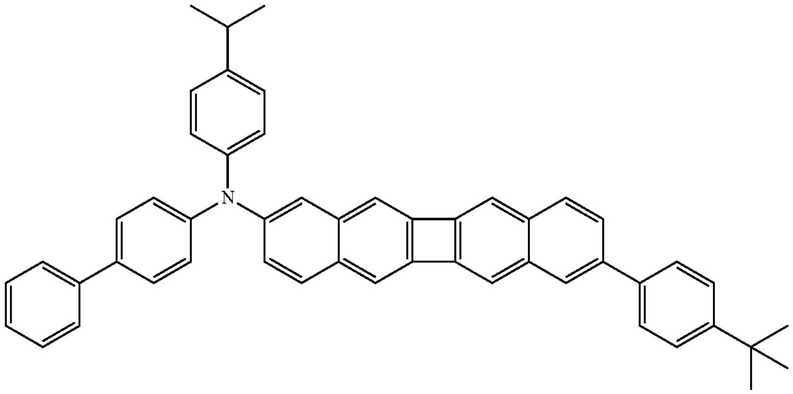
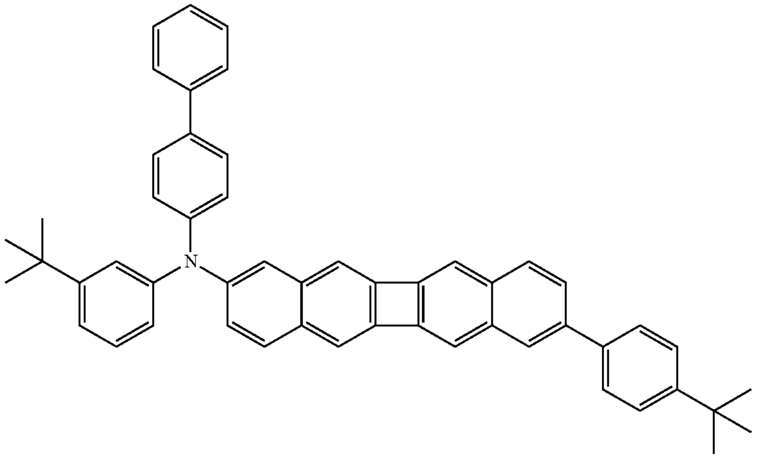
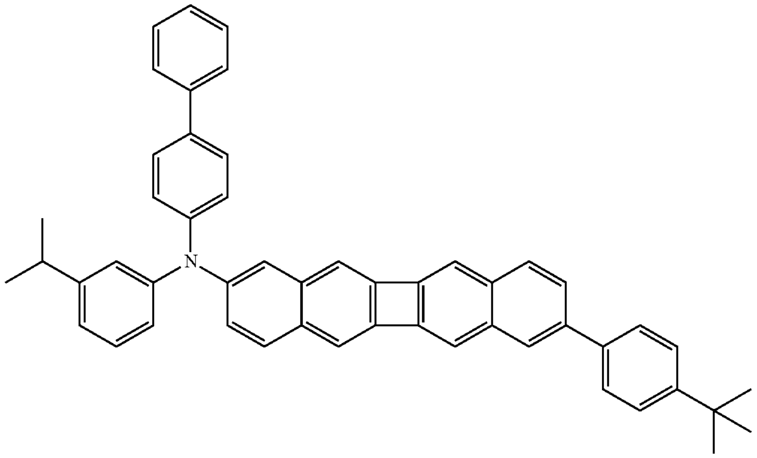

-continued
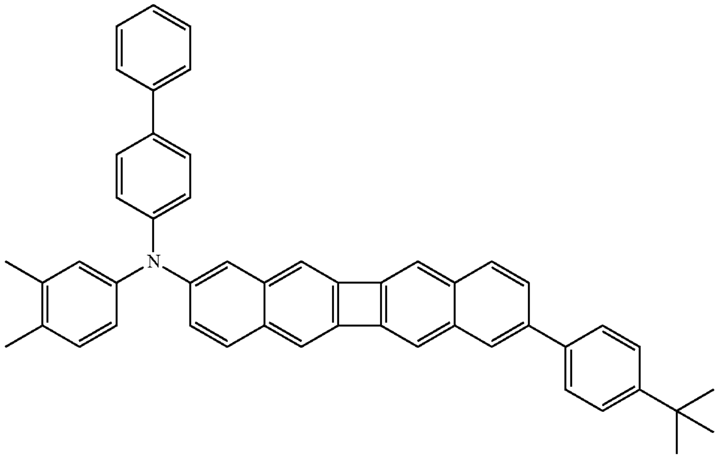
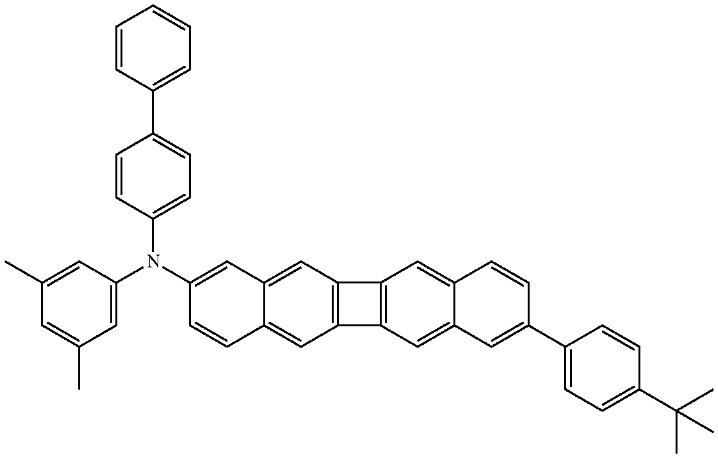
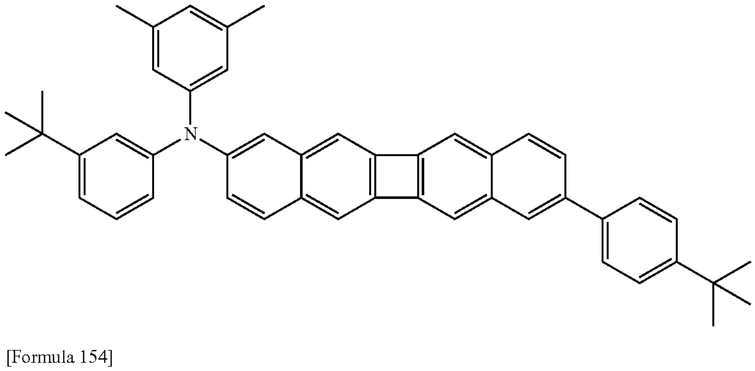
[Formula 154]
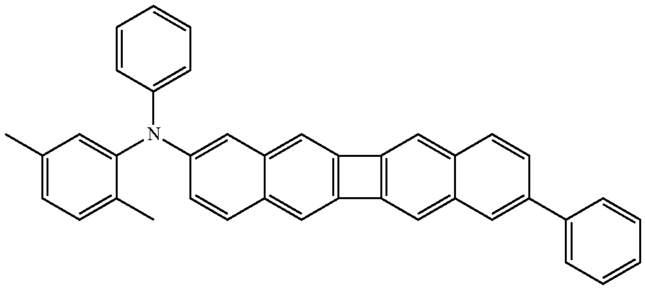

-continued
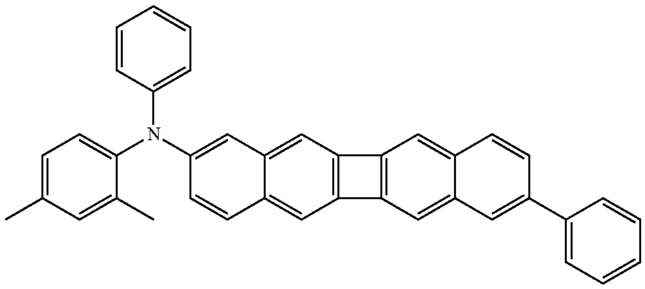
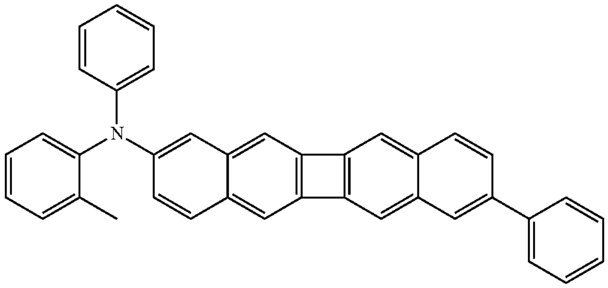
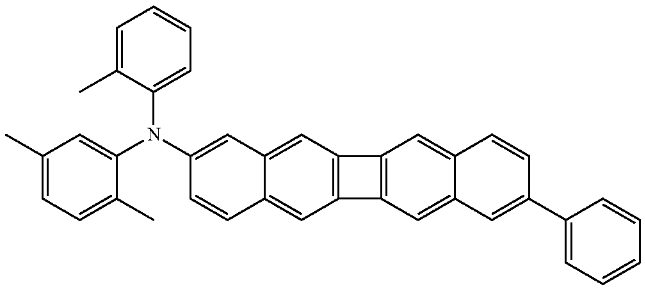
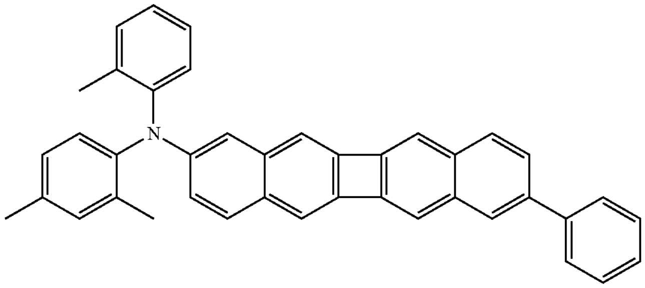
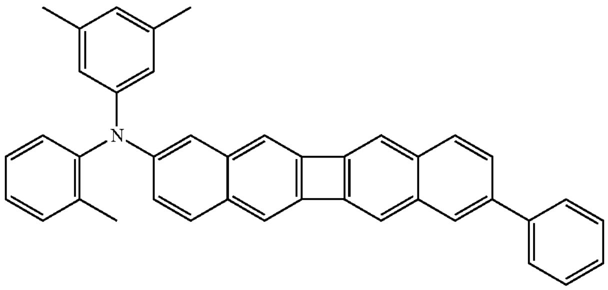

-continued
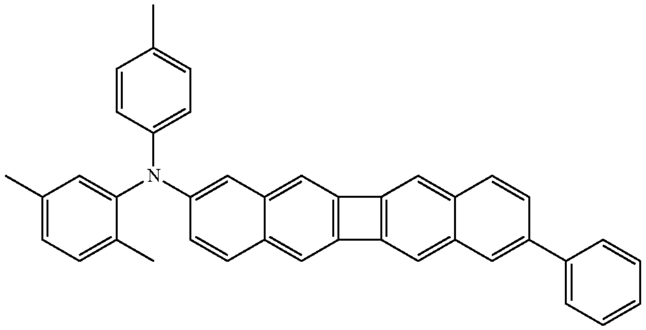
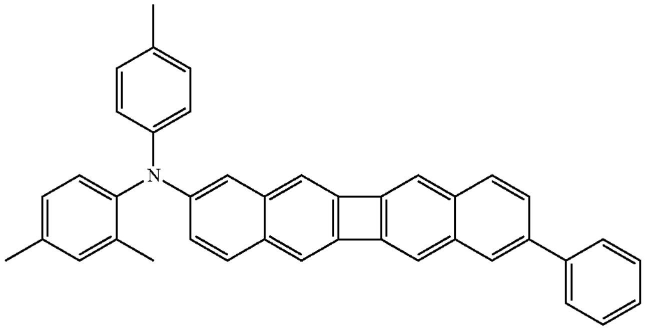
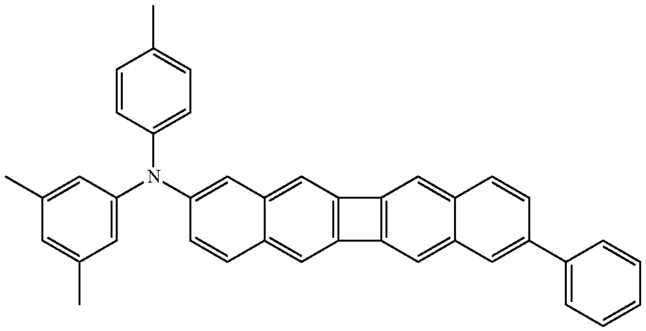
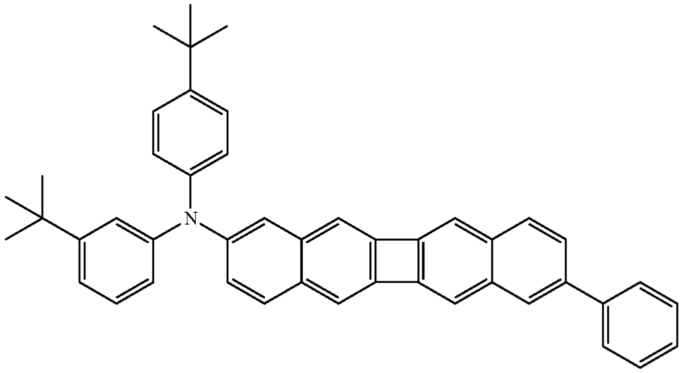
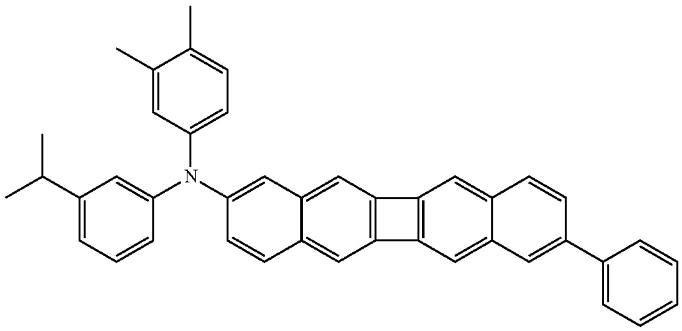

-continued
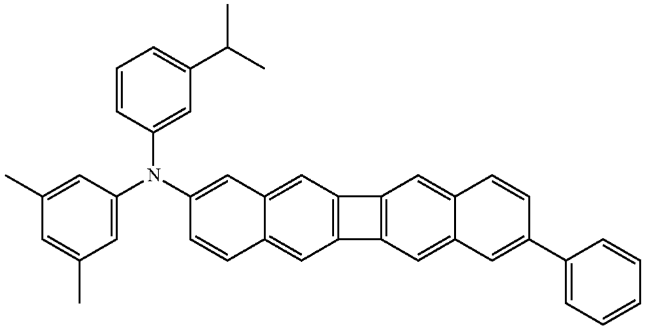
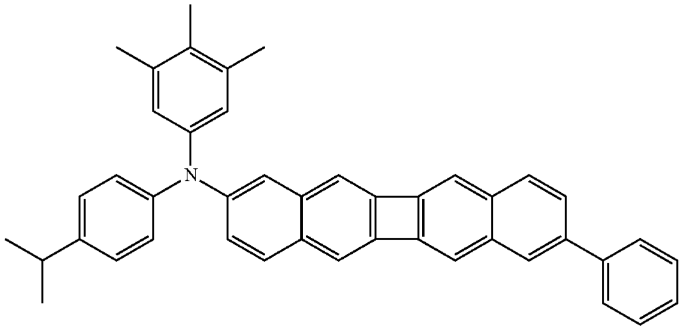
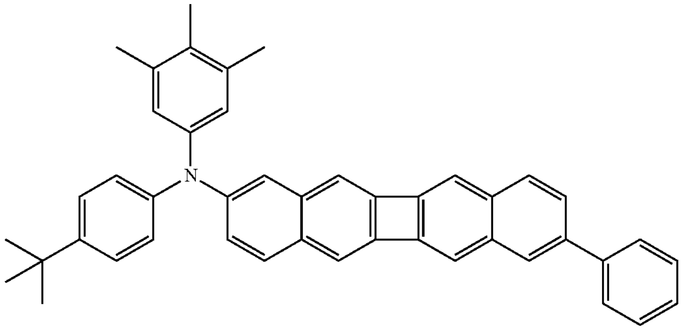
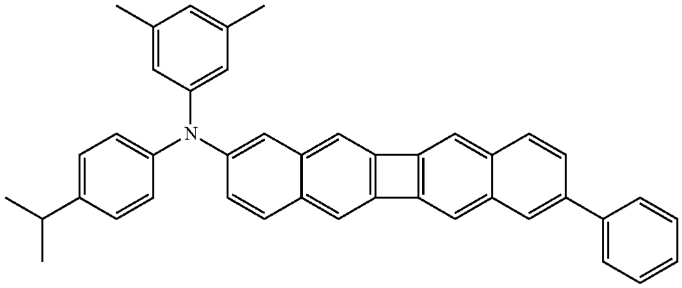
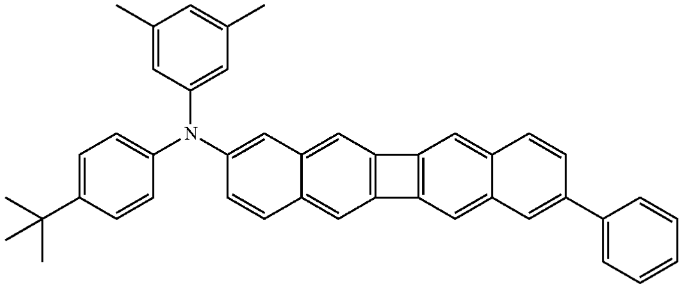

-continued
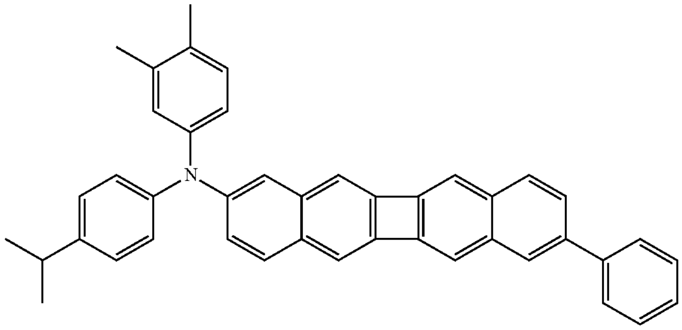
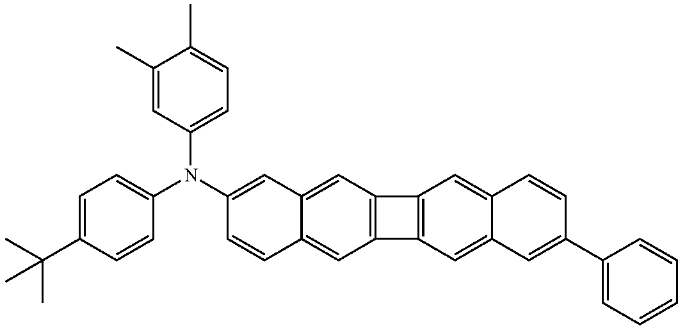
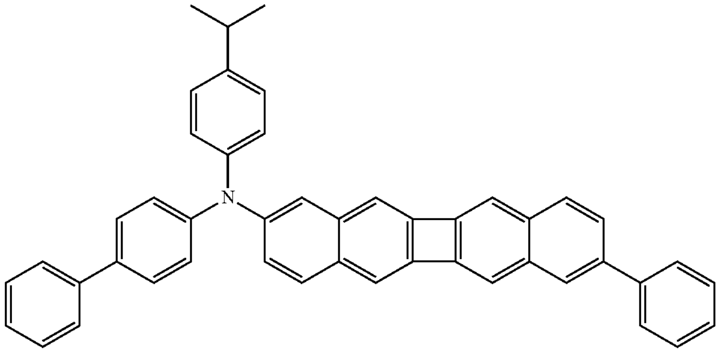
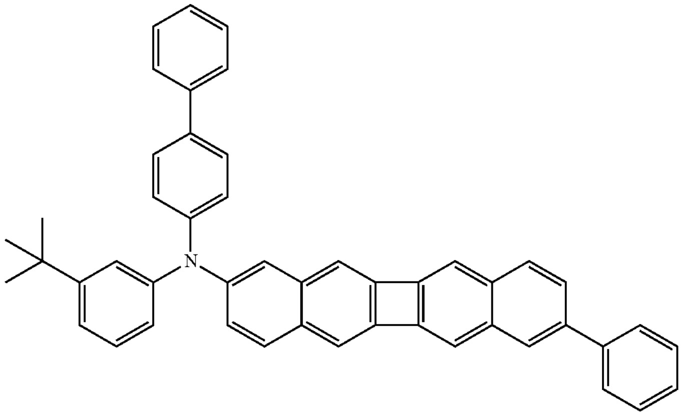

-continued
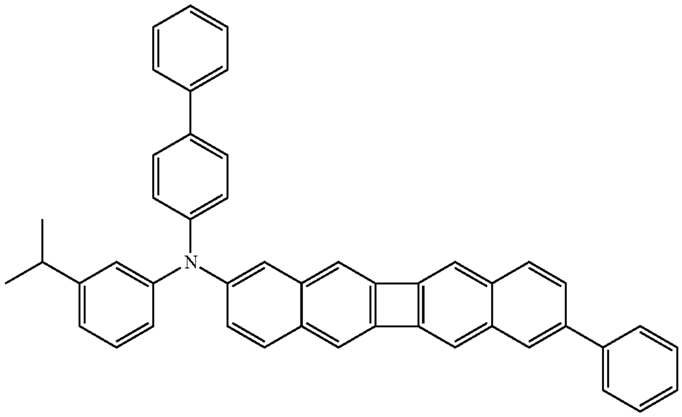
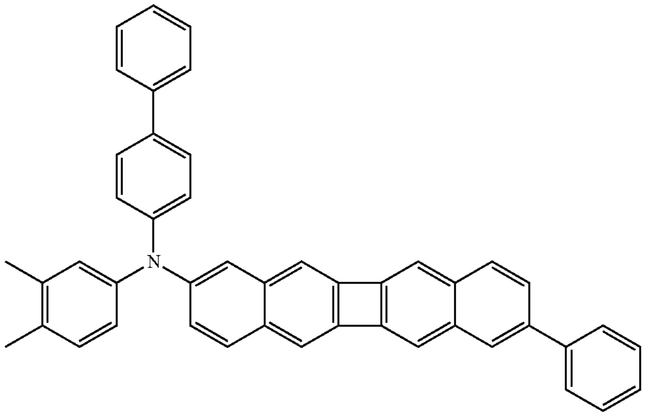
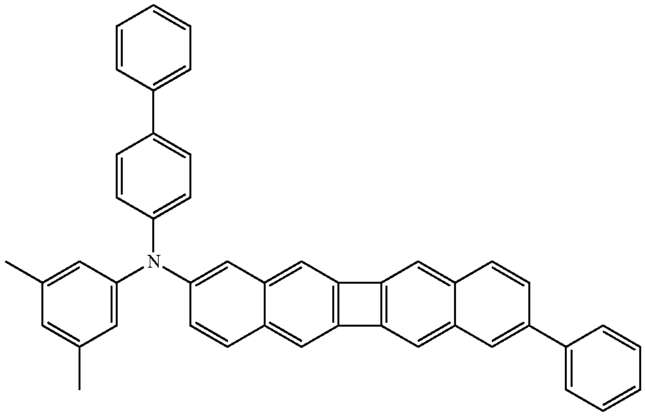
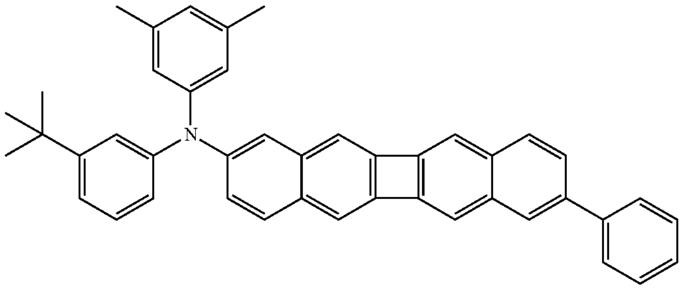

-continued
[Formula 155]
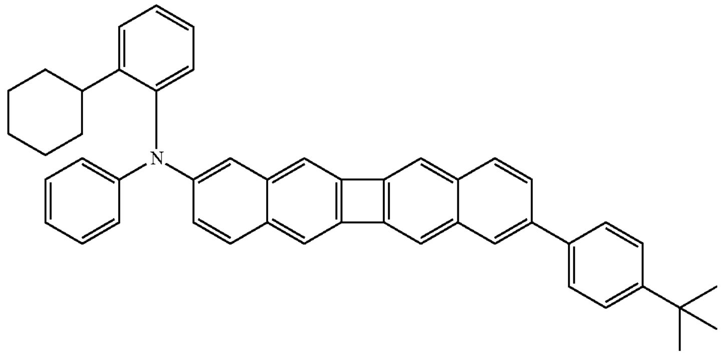
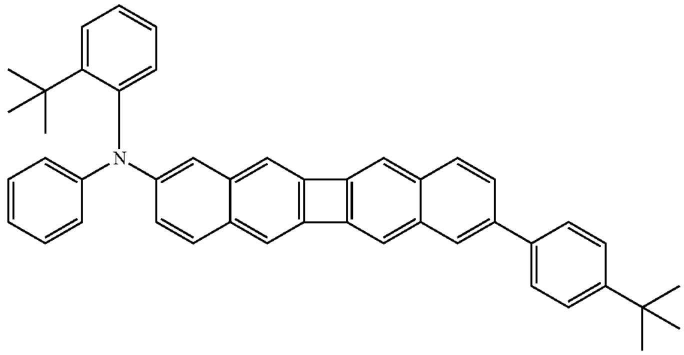
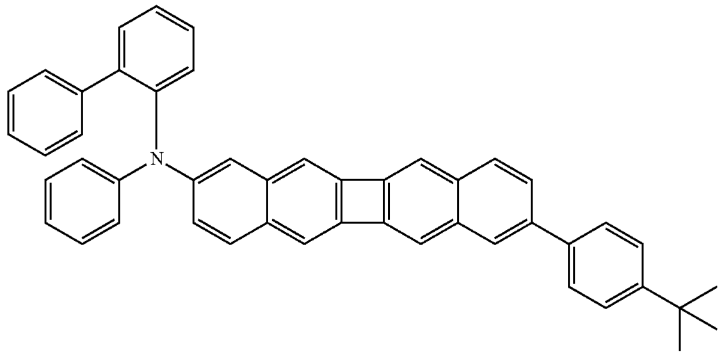
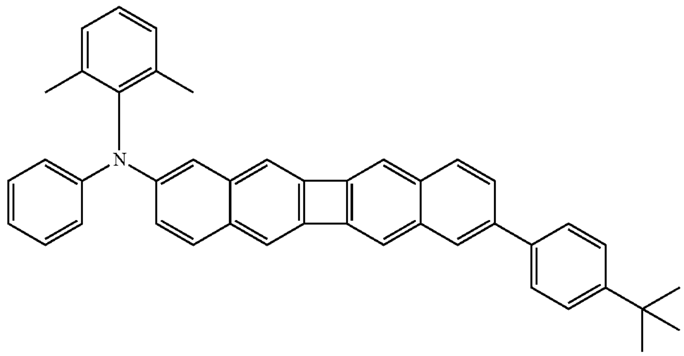

-continued
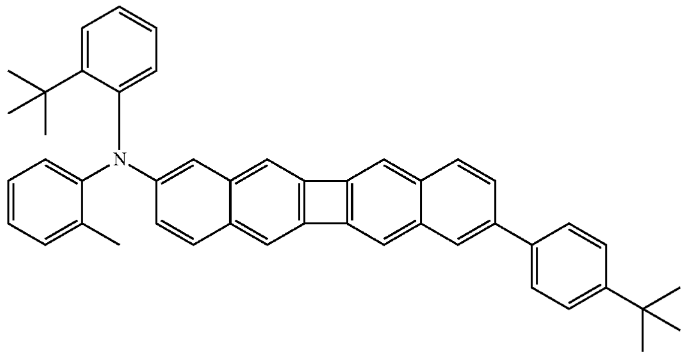
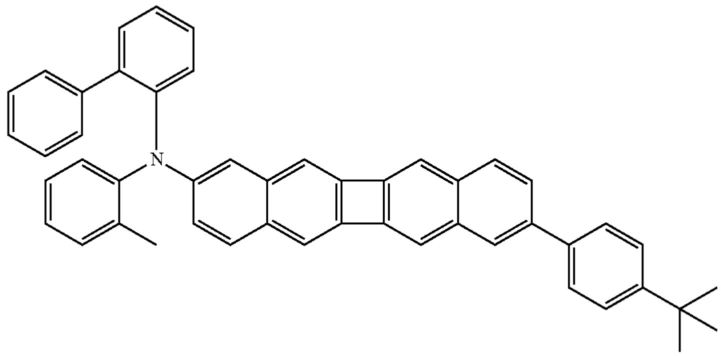
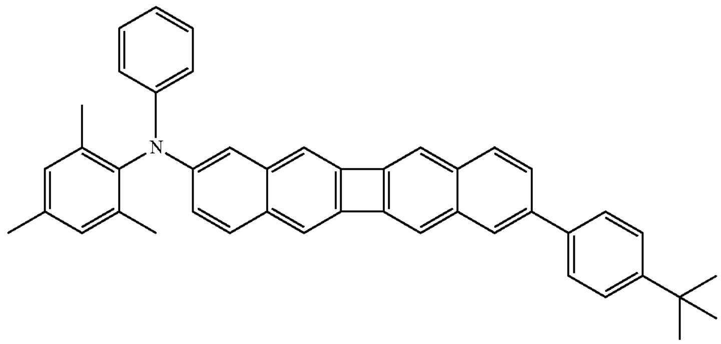
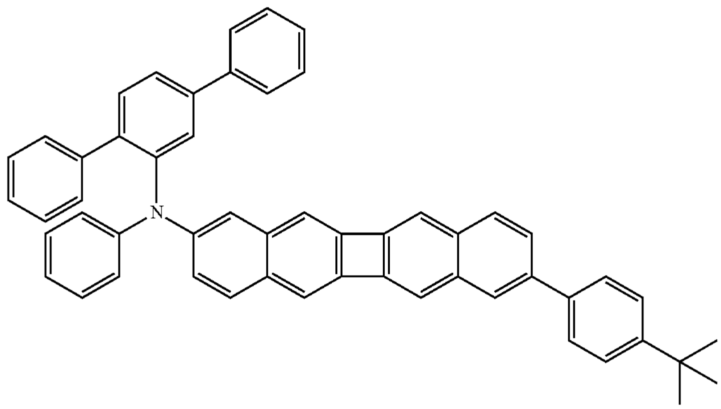

-continued
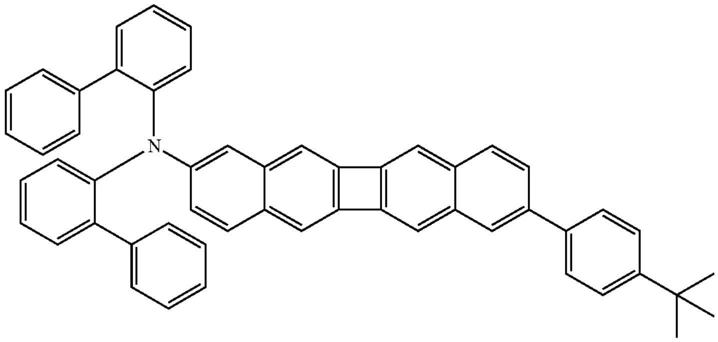
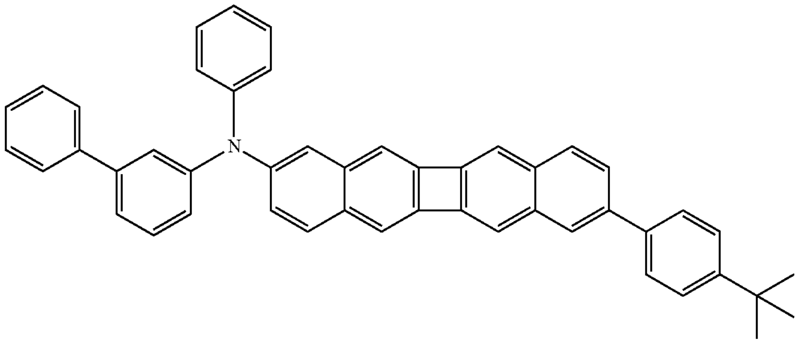
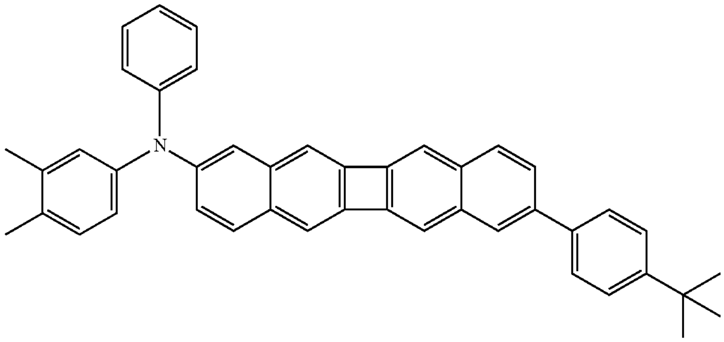
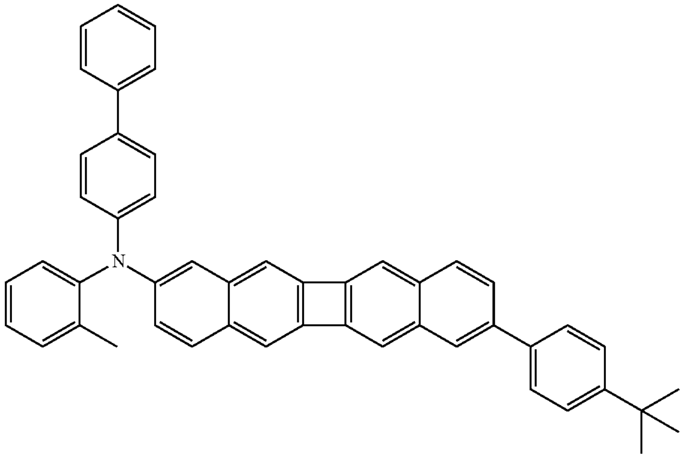

-continued
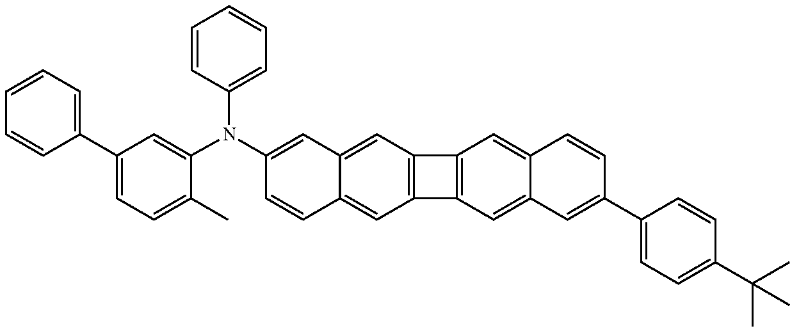
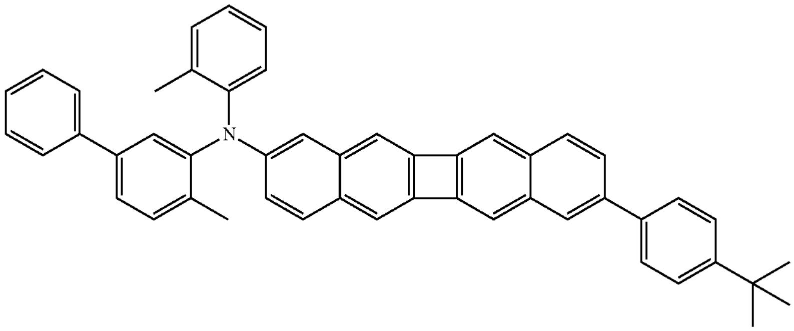
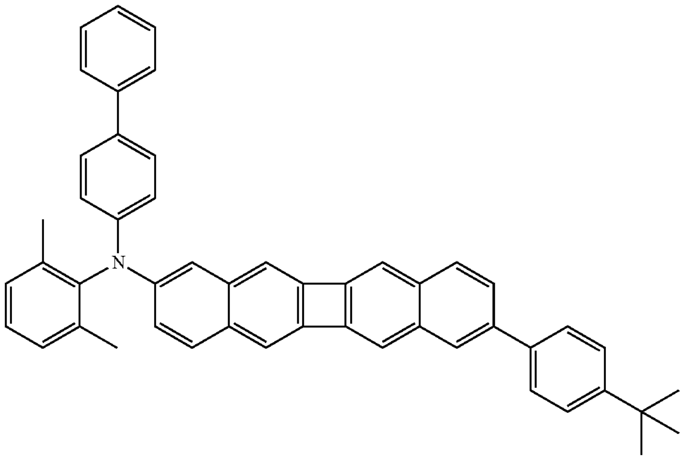
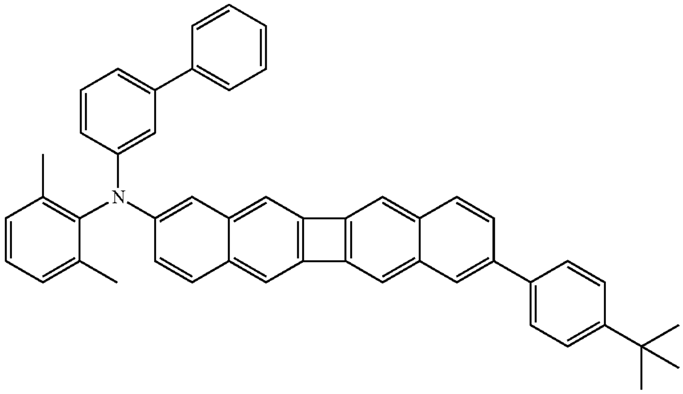

-continued
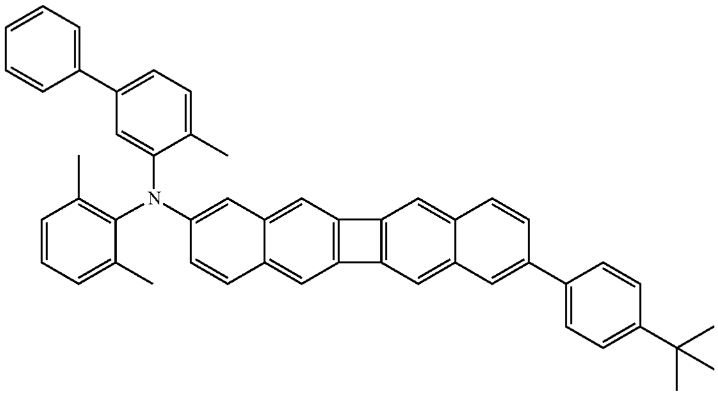
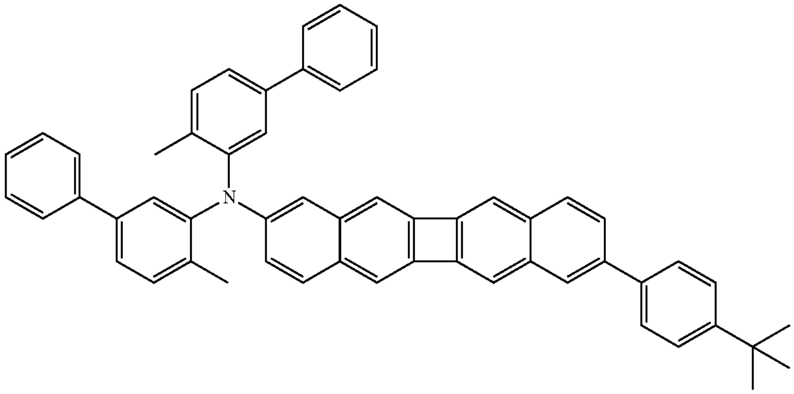
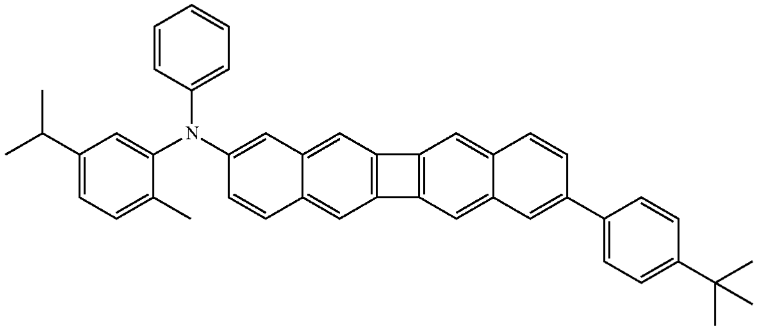
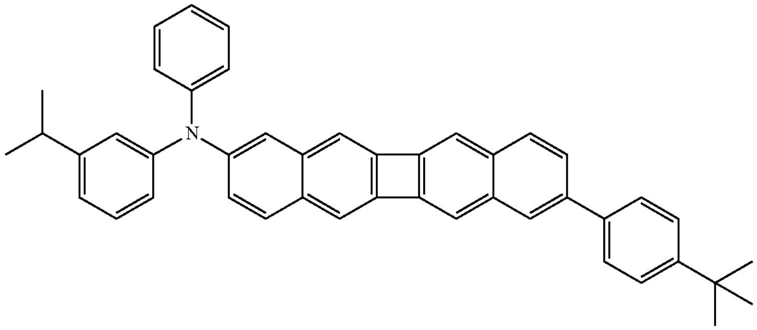

-continued
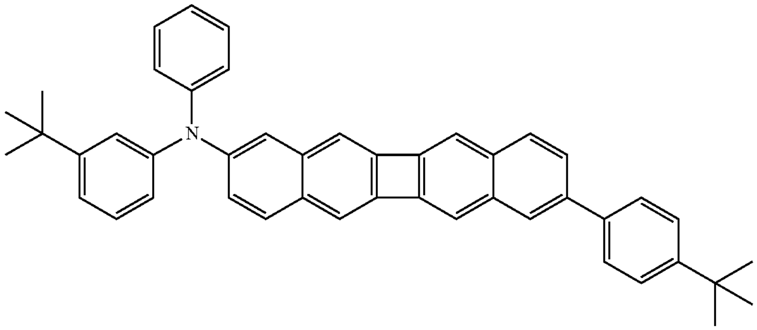
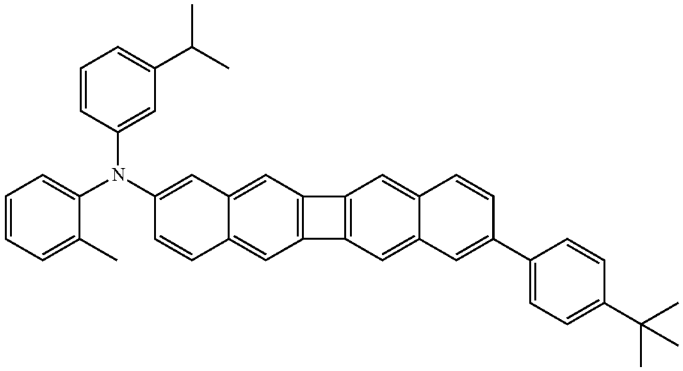
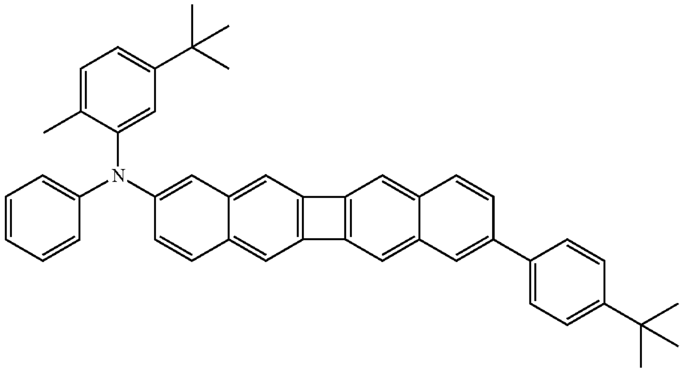
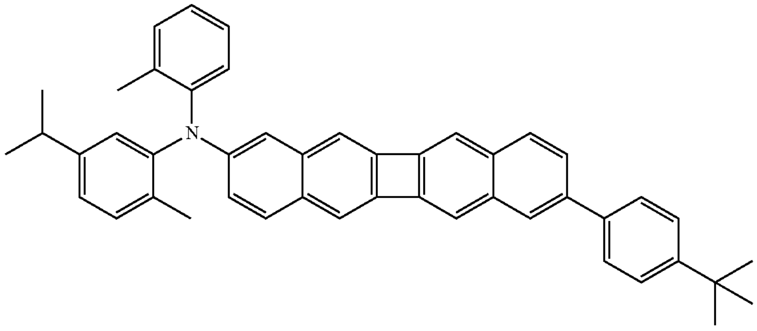 [SMILES: Cc1ccccc1N(c1ccc2cc3c(cc2c1)-c1cc2ccc(-c4ccc(C(C)(C)C)cc4)cc2cc1-3)c1cc(C(C)C)ccc1C]

[Formula 156]
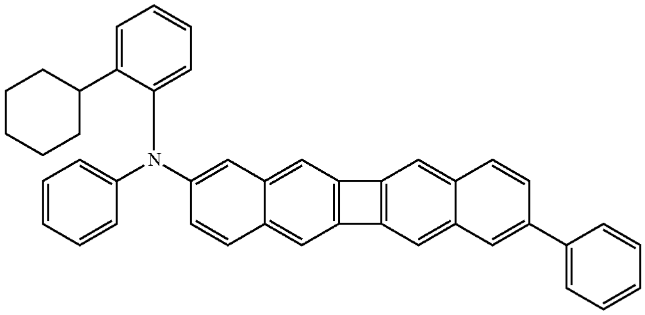
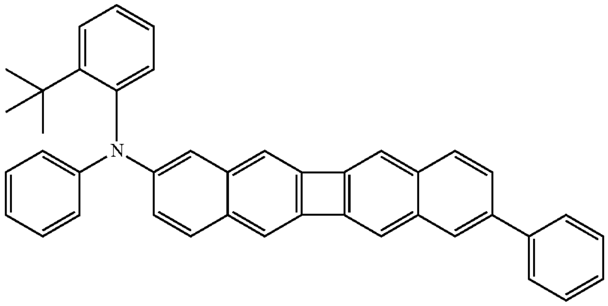
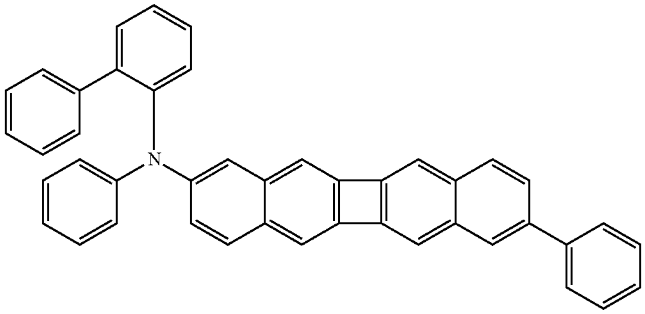
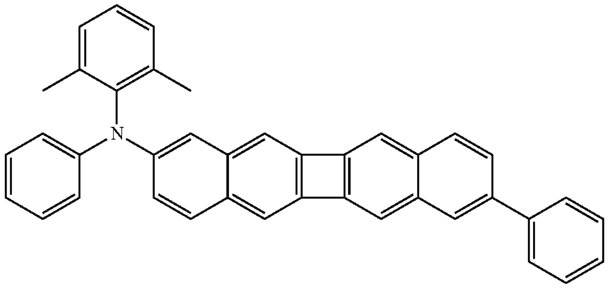
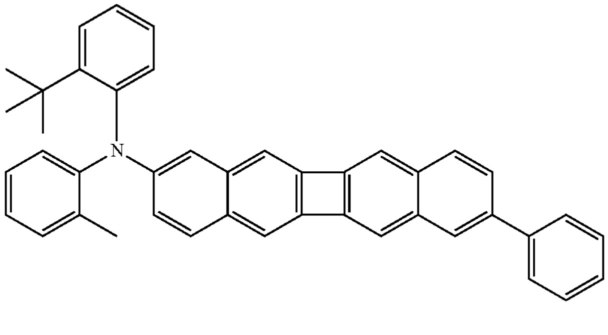

-continued
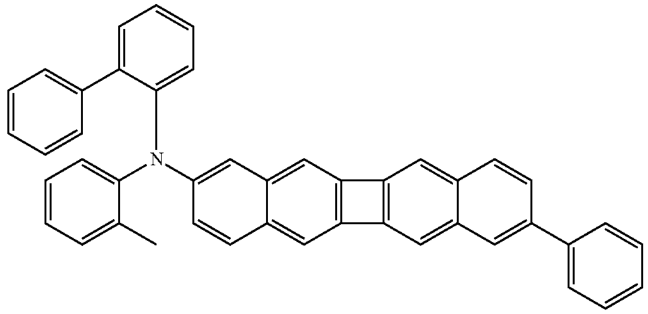
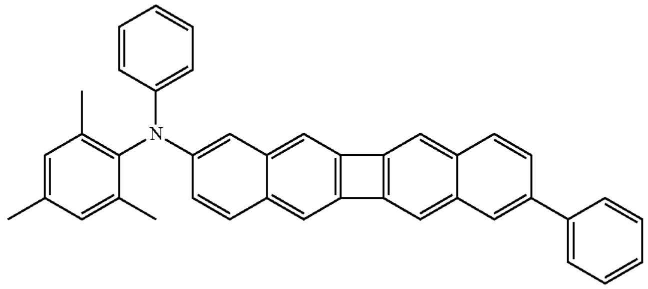
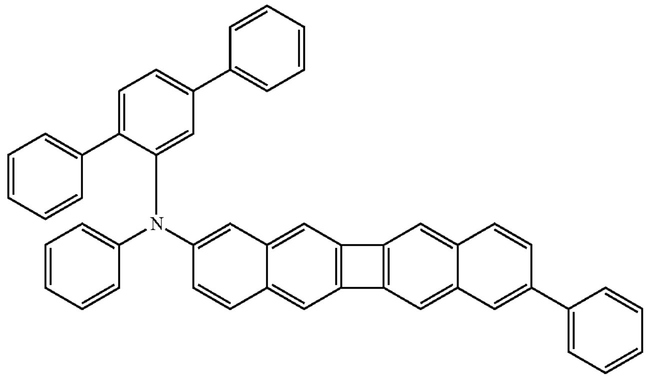
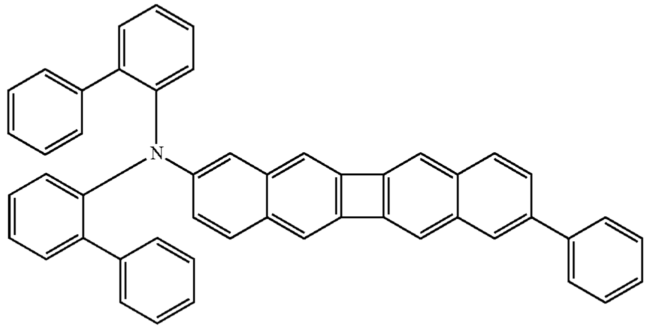
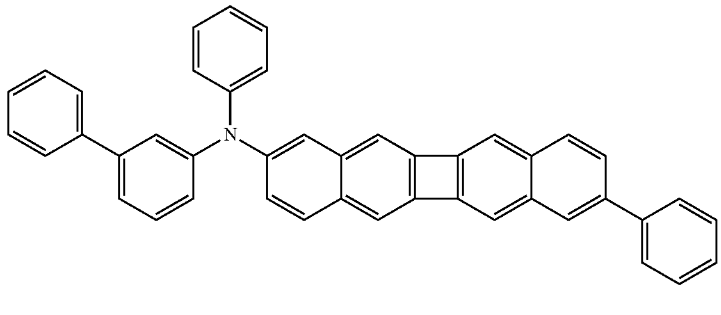

-continued
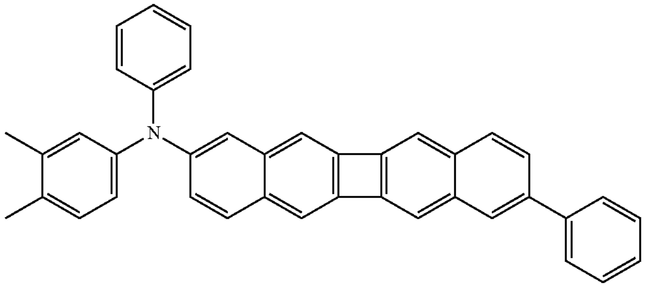
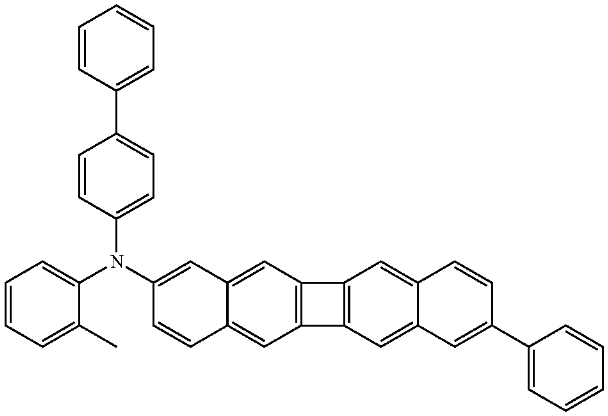
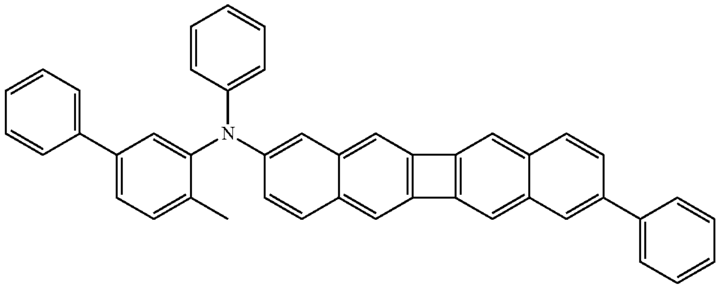
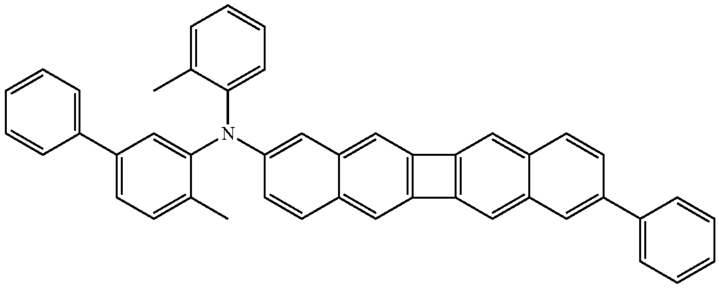
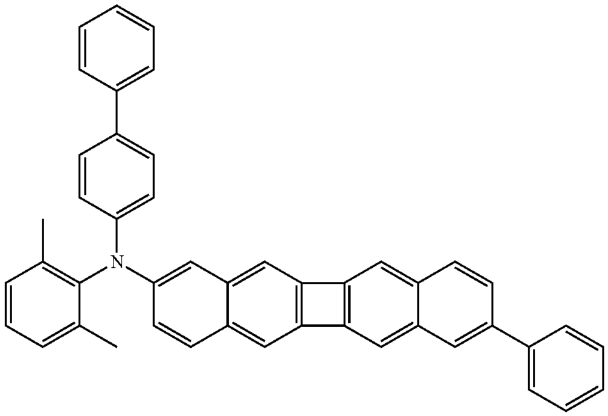

-continued
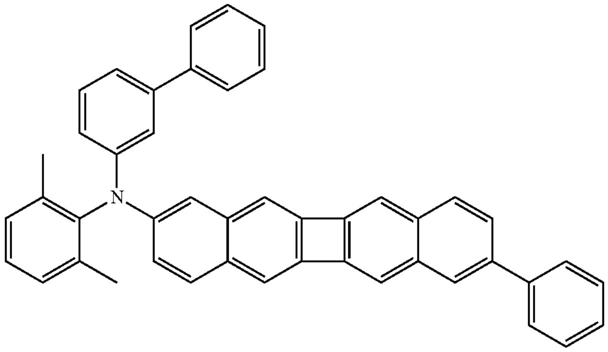 [SMILES: Cc1cccc(C)c1N(c1cccc(-c2ccccc2)c1)c1ccc2cc3c(cc2c1)-c1cc2ccc(-c4ccccc4)cc2cc1-3]
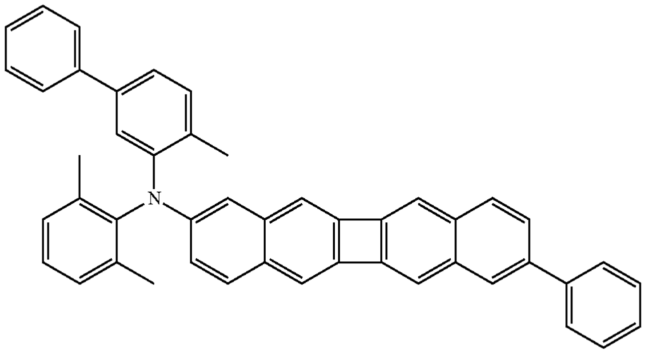
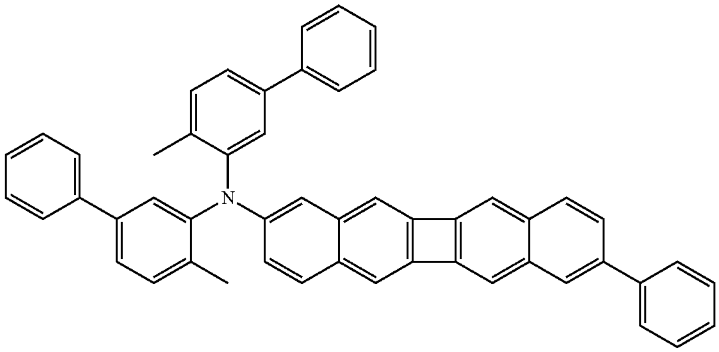
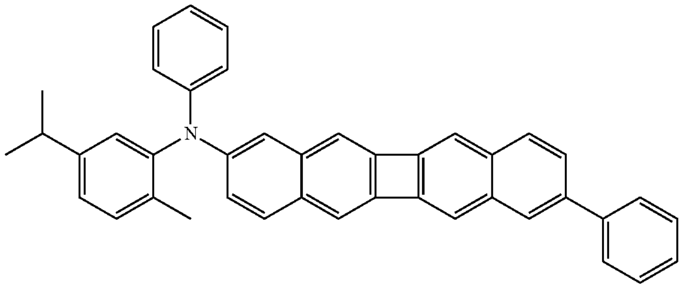
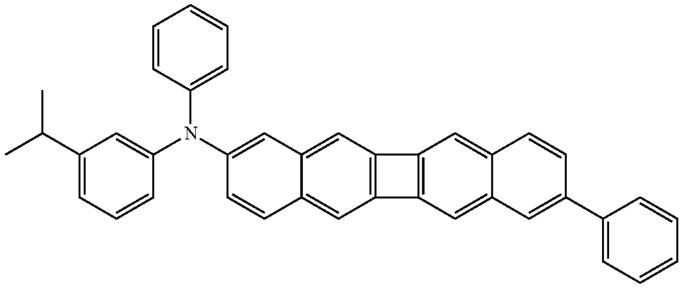

-continued
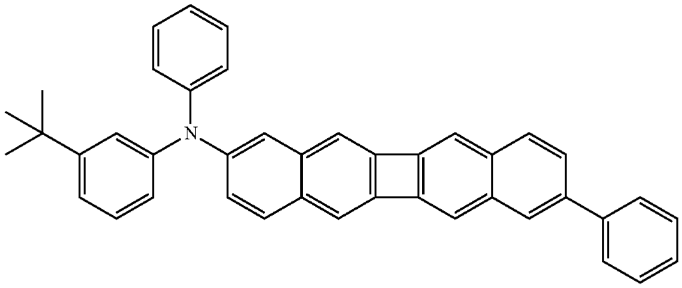
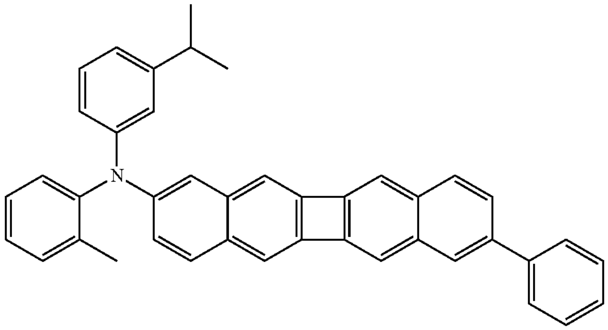
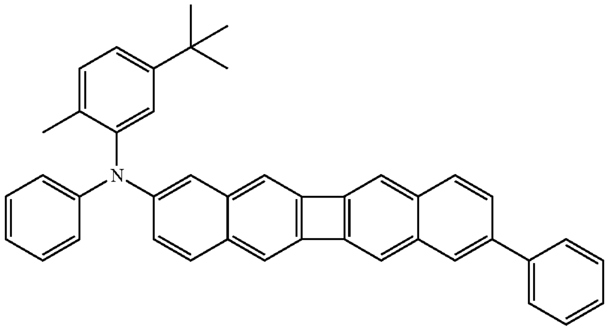
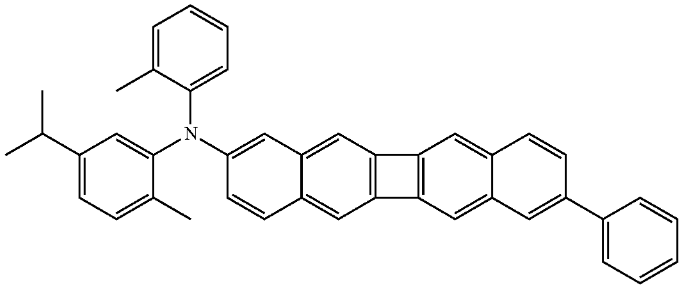
[Formula 157]
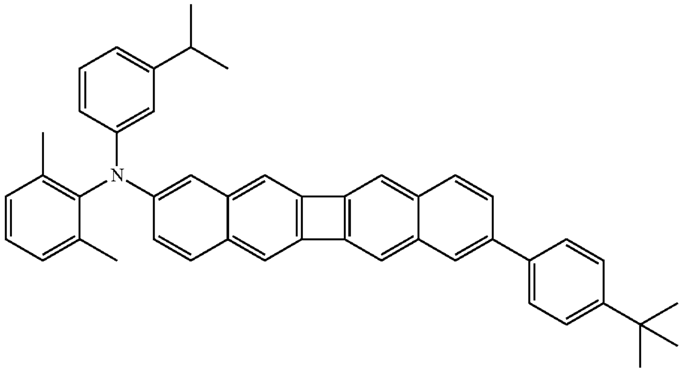

-continued
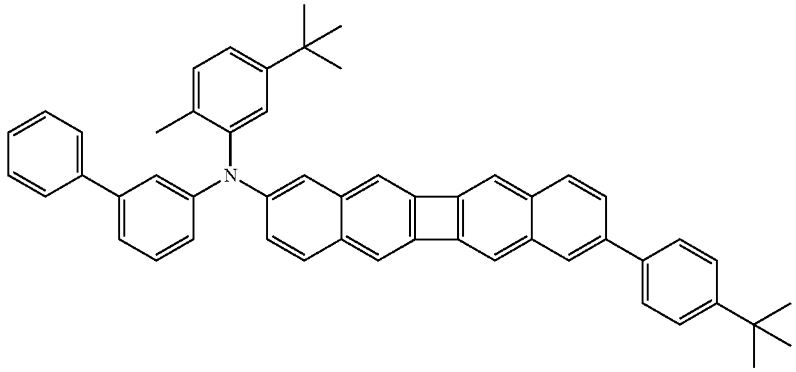
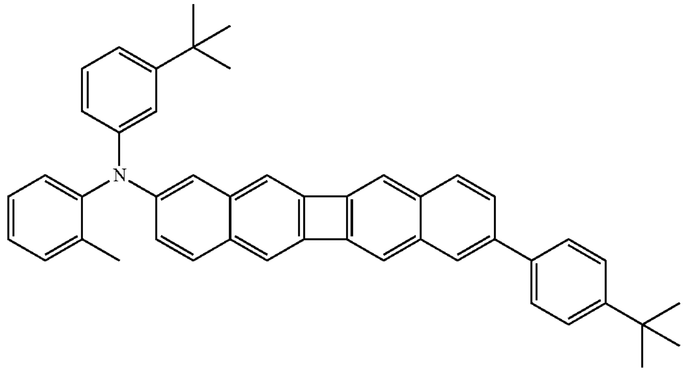
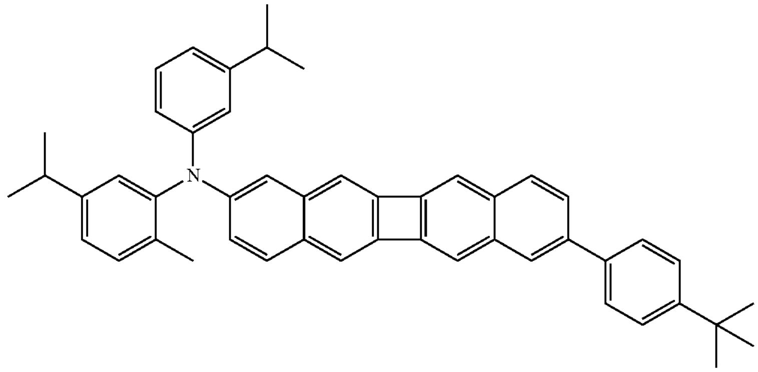
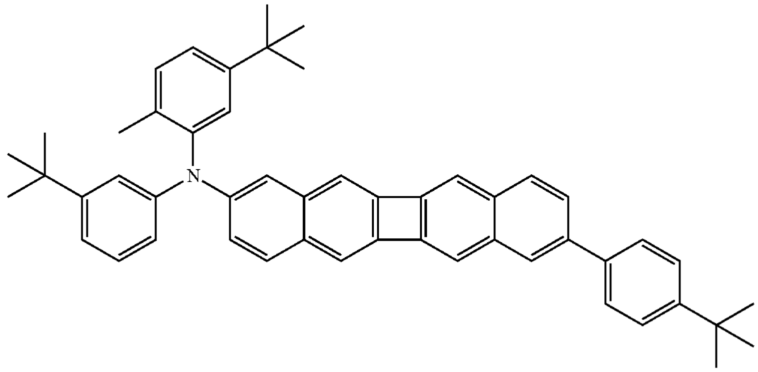

-continued
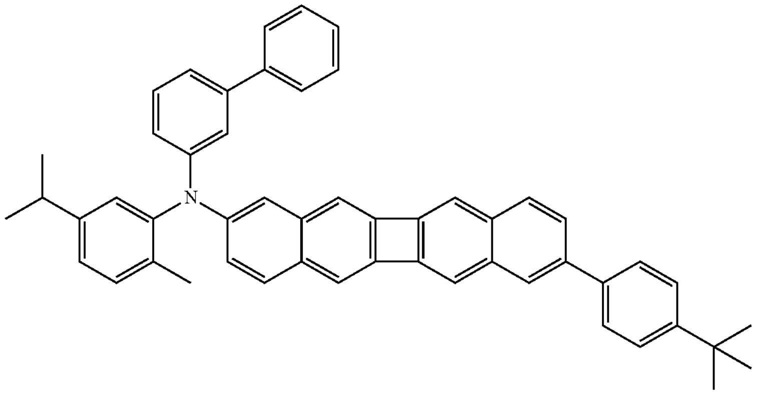
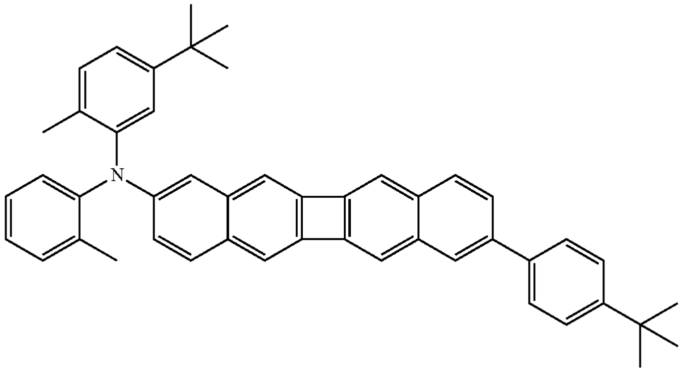
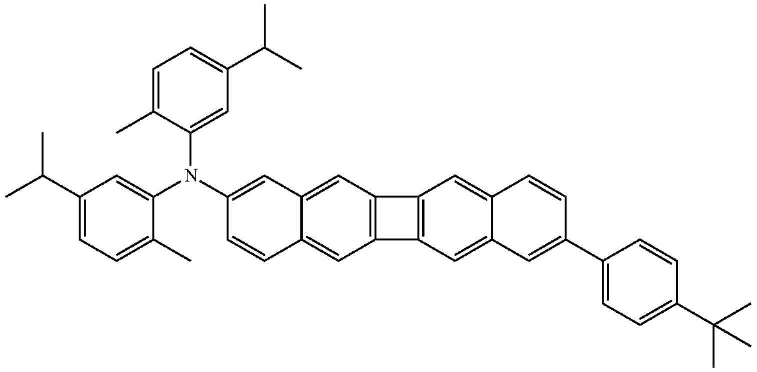
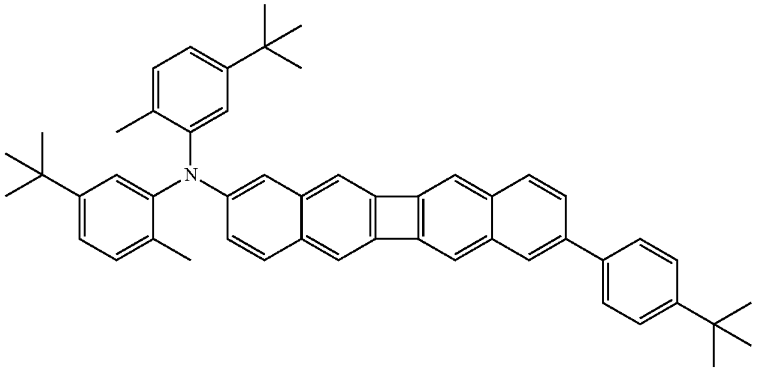

-continued
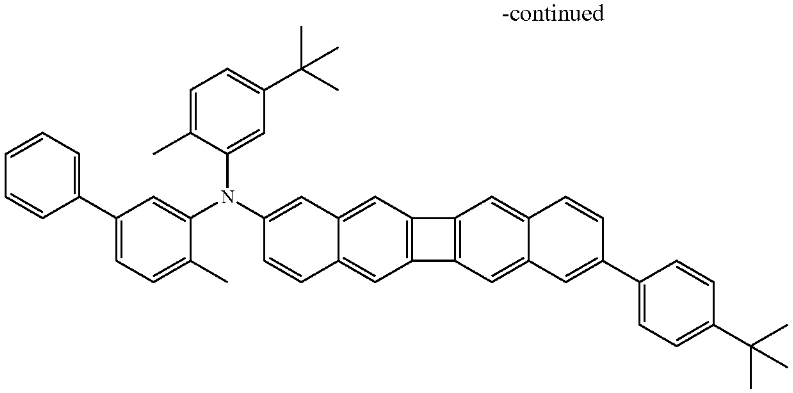
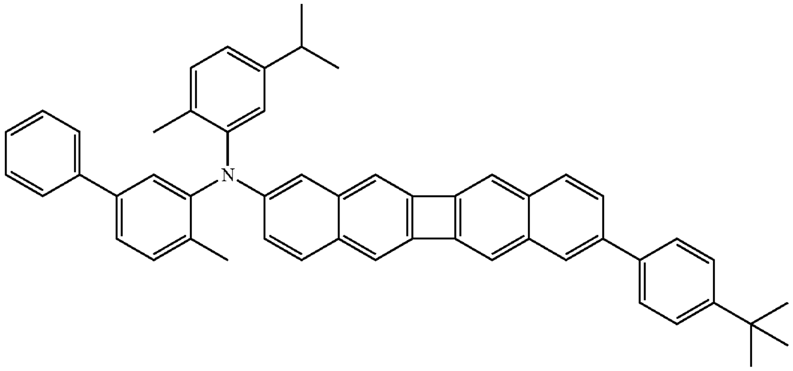
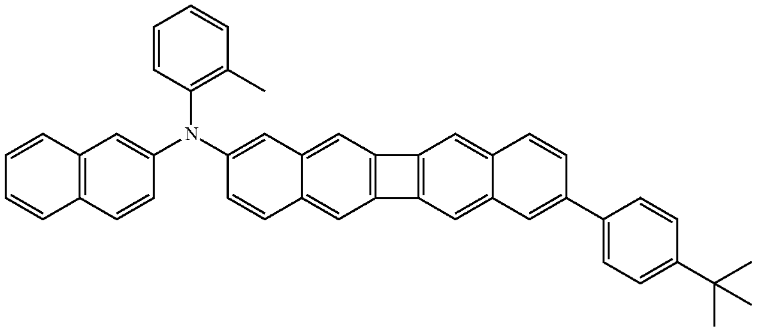
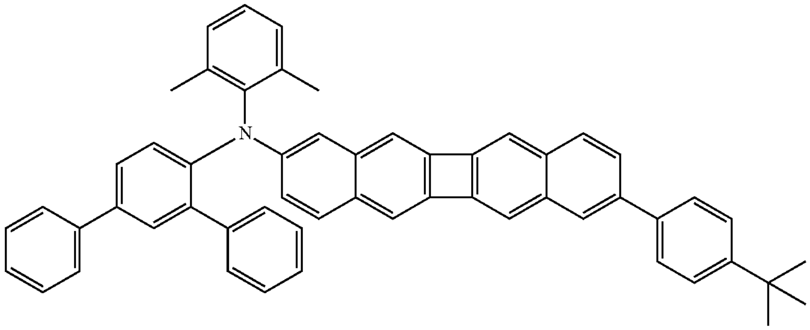
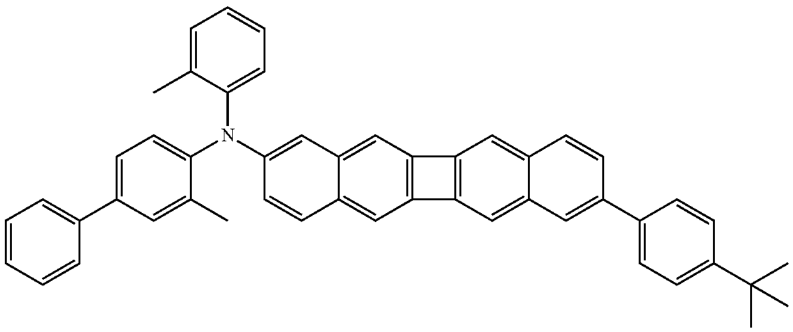

-continued
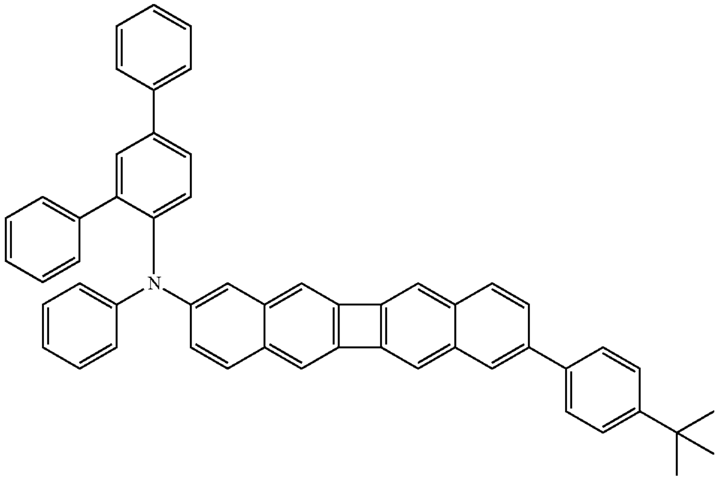
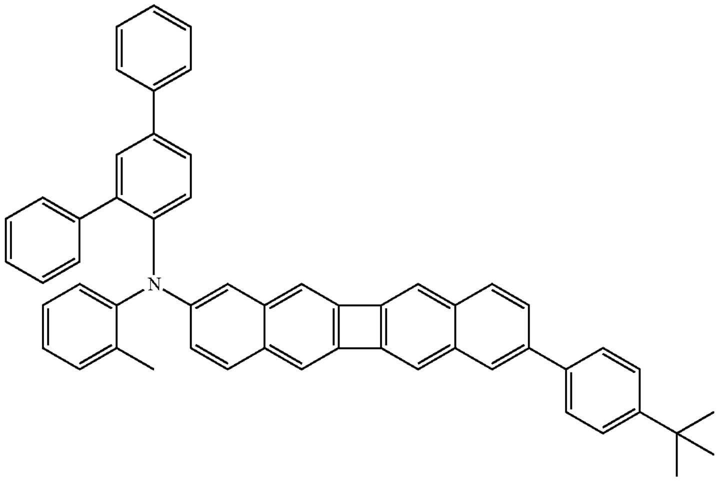
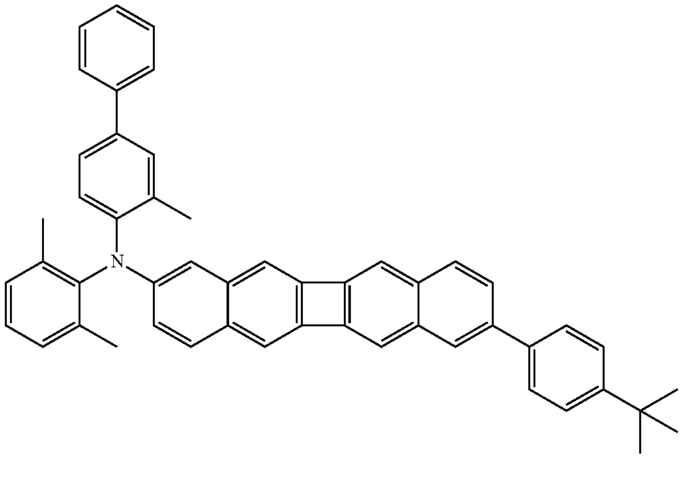

-continued
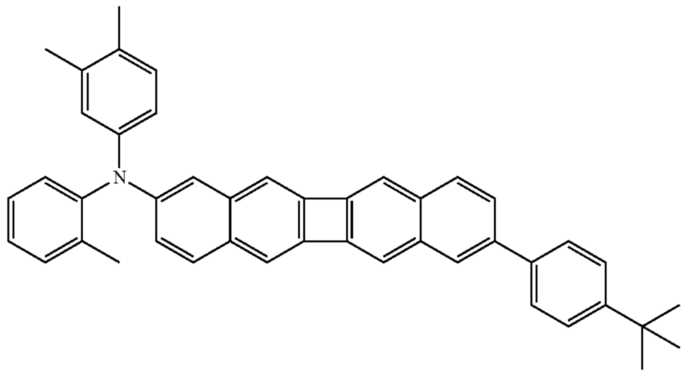
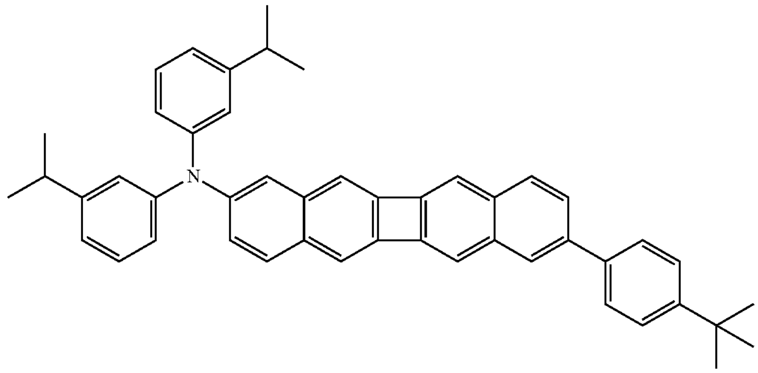
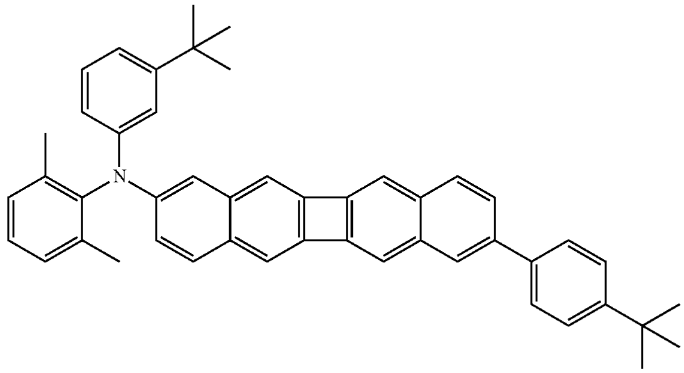
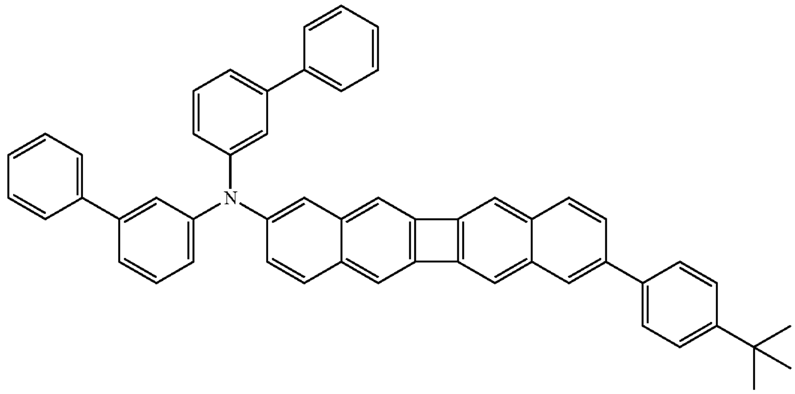

-continued
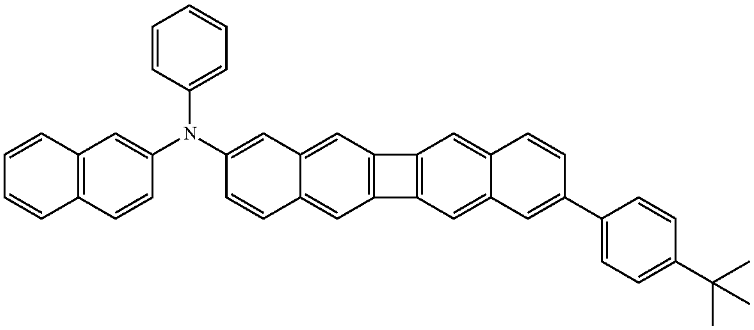
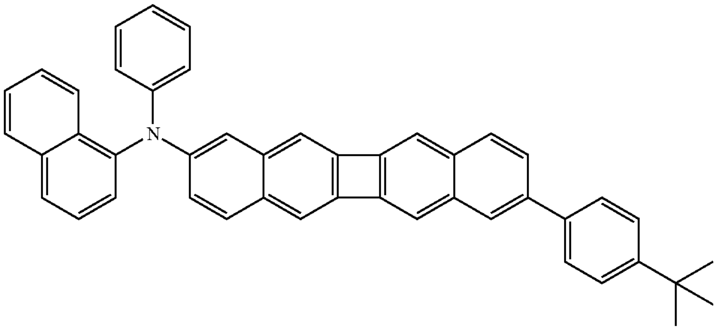
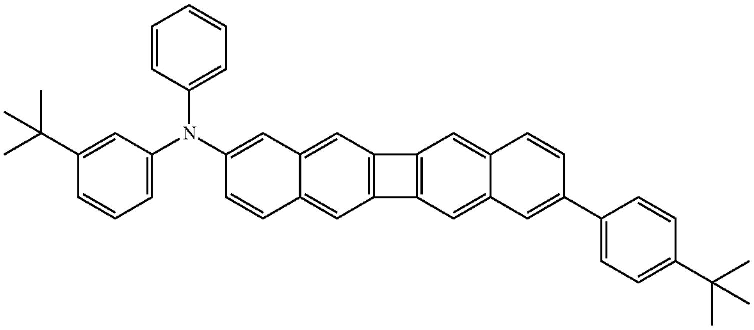
[Formula 158]
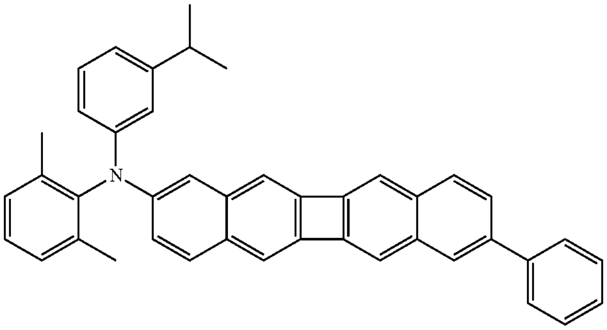
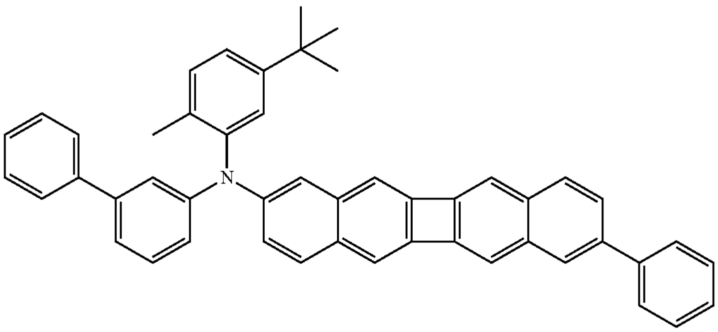

-continued
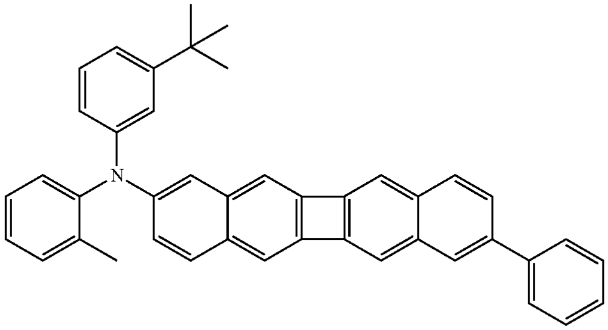
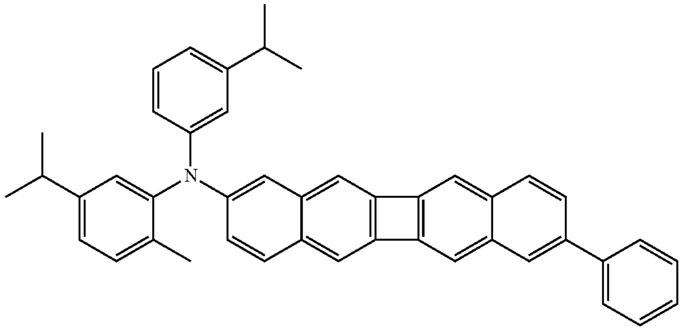
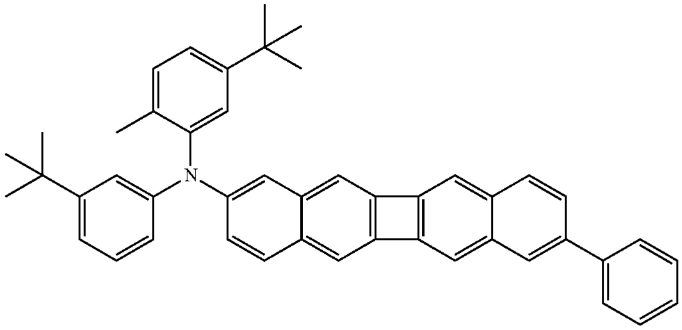
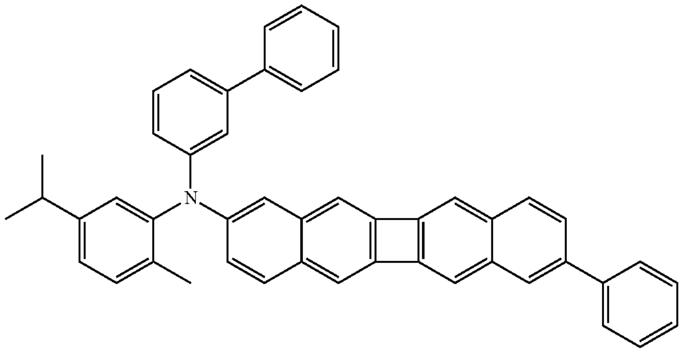
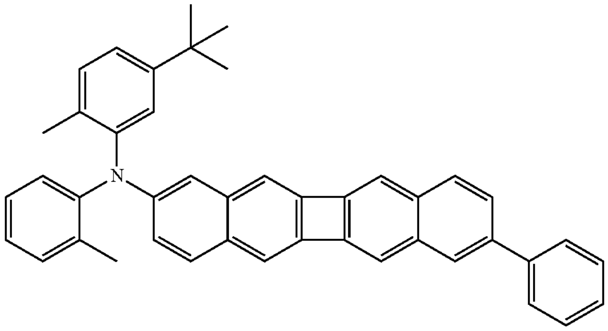

-continued
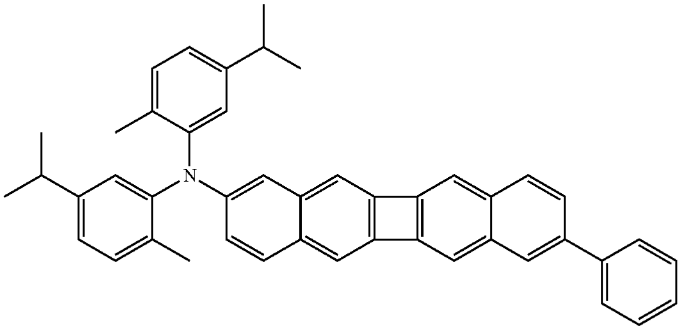
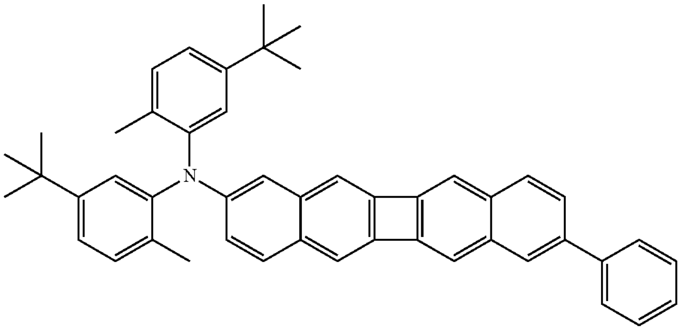
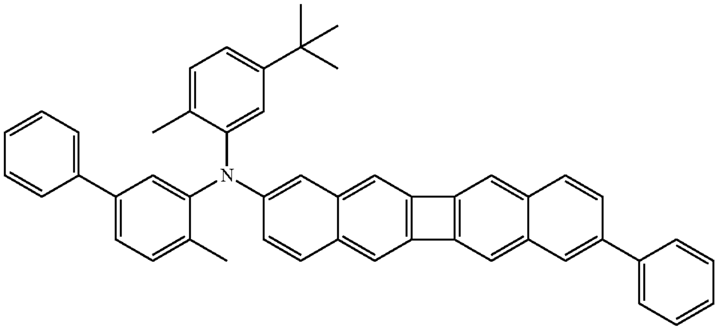
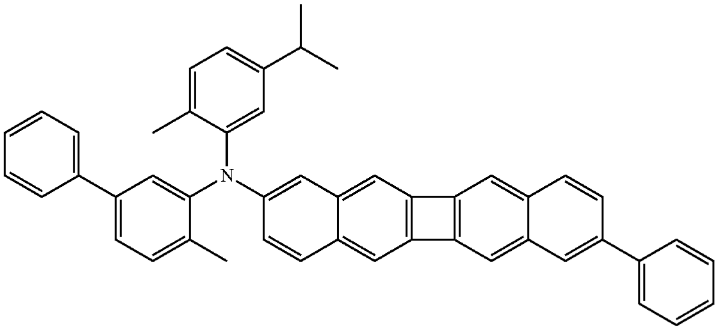
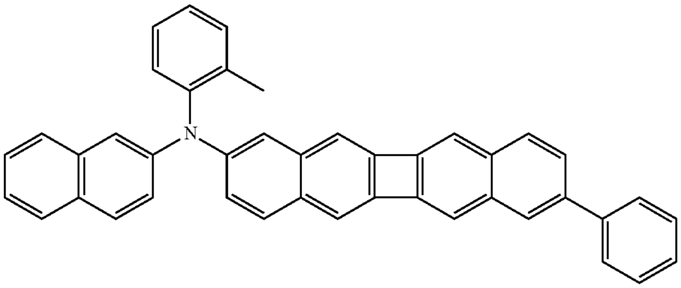

-continued
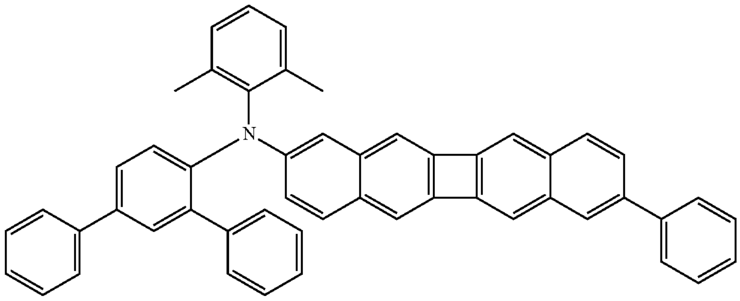
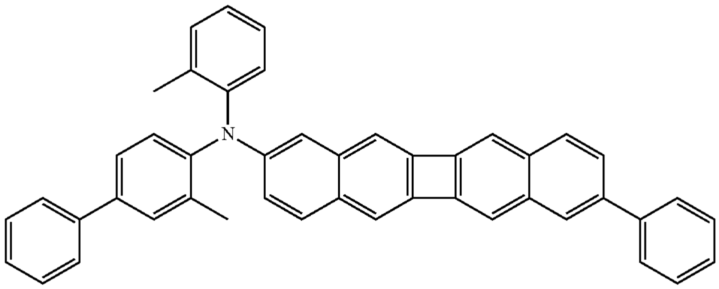
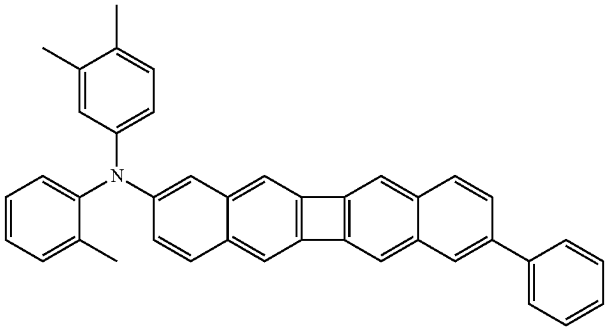
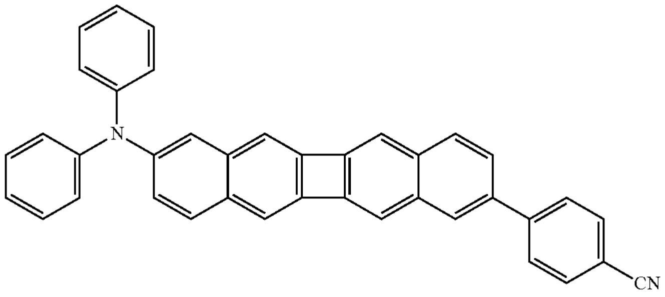
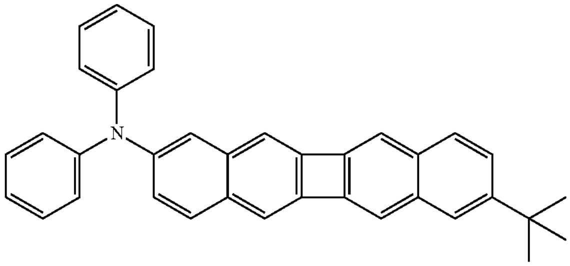
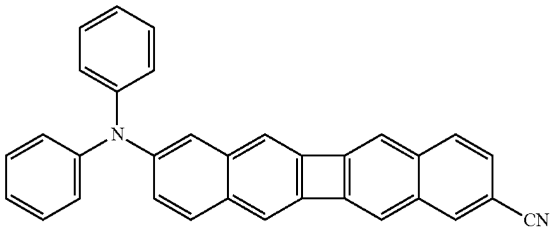

-continued
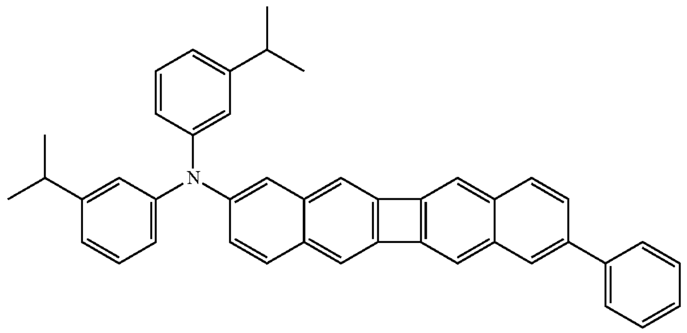
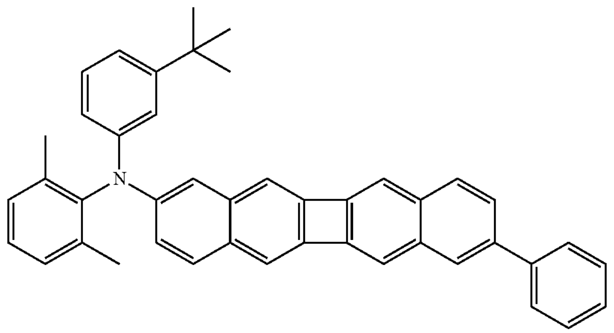
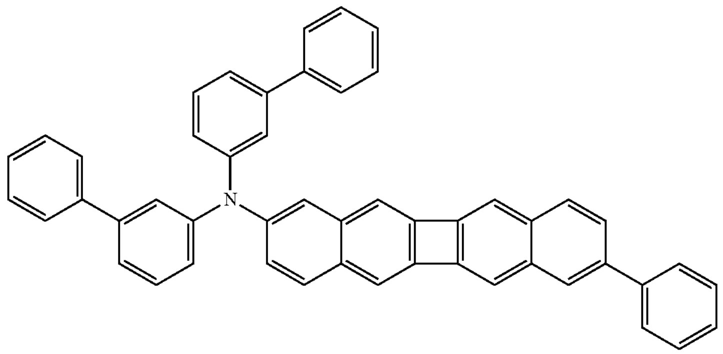
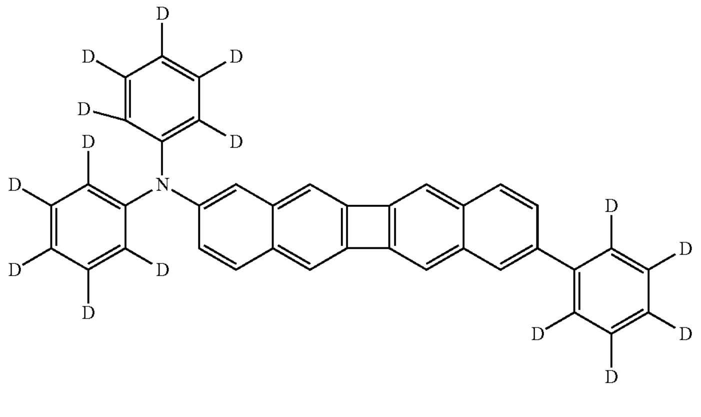

-continued
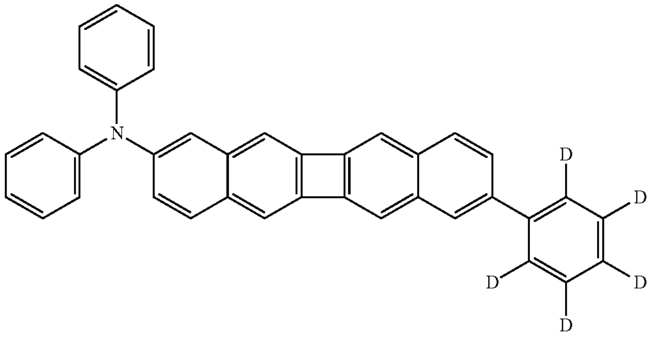
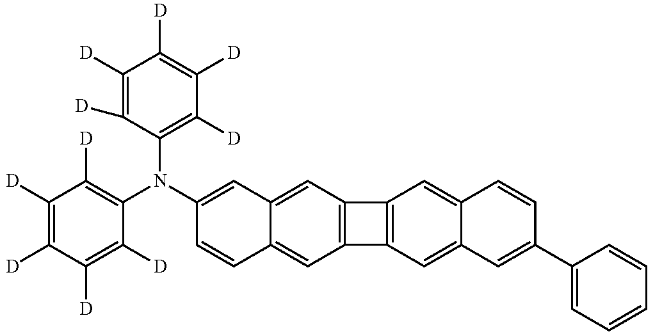
[Formula 159]
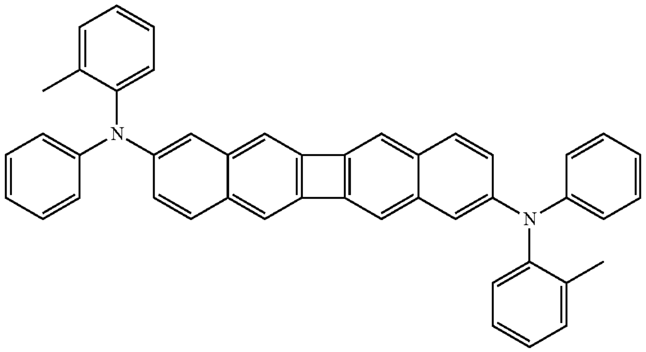
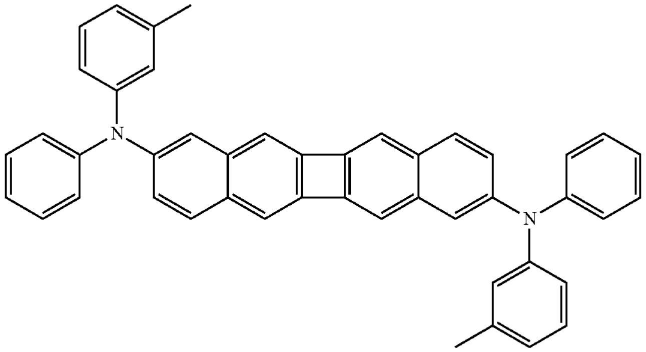

-continued
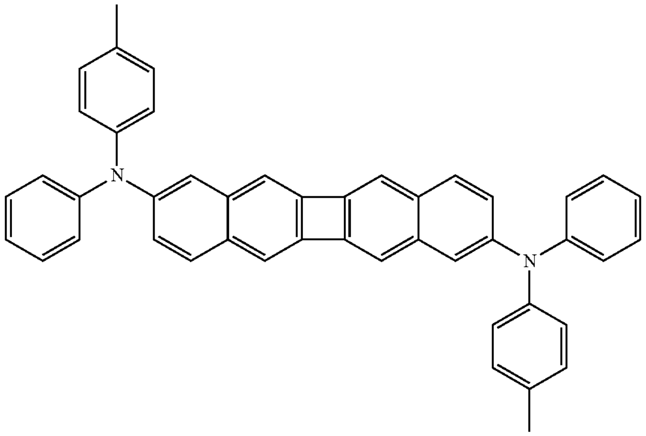
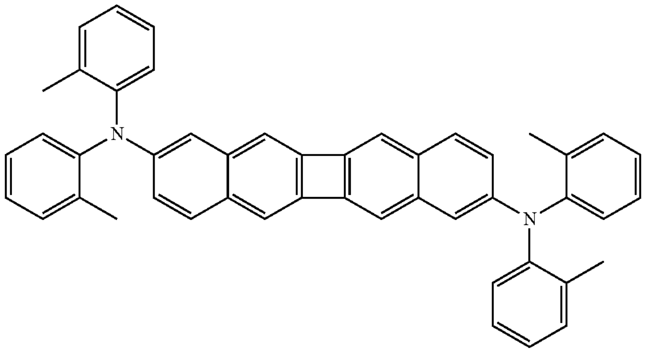
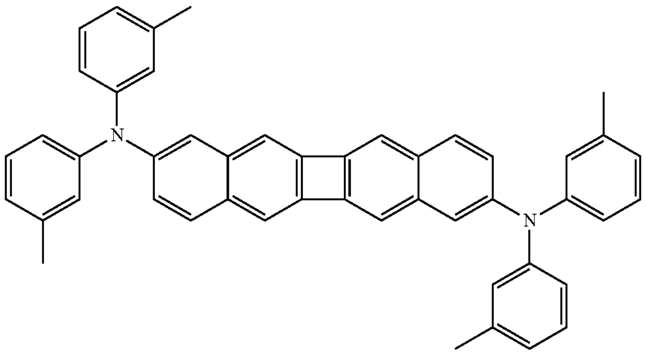
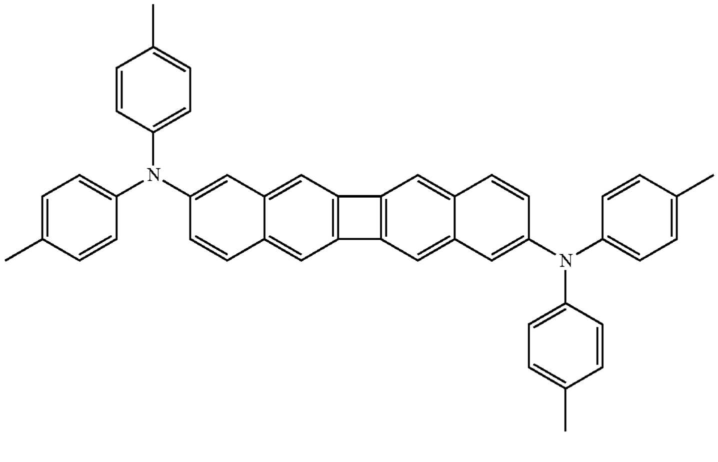

-continued
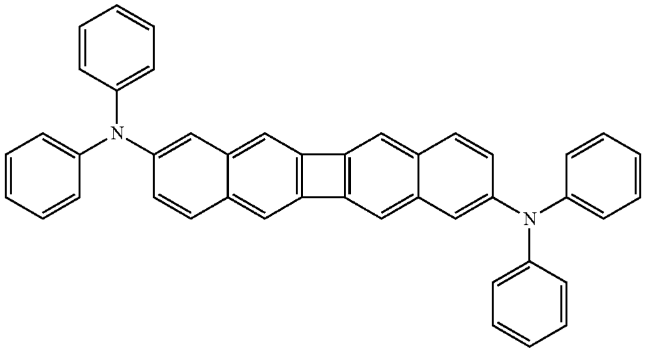
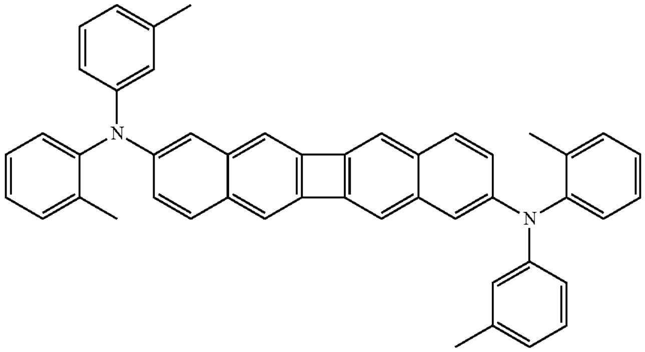
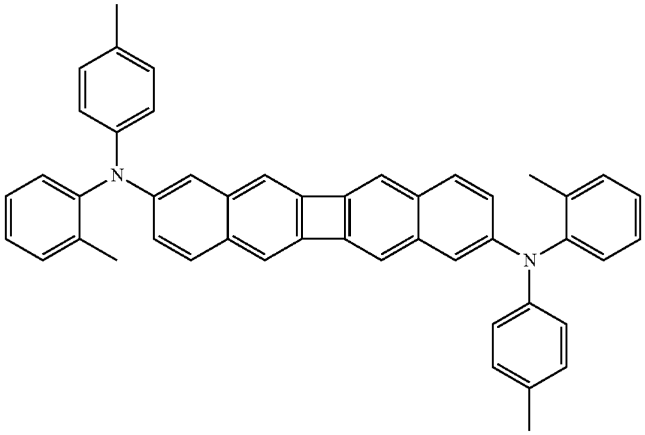
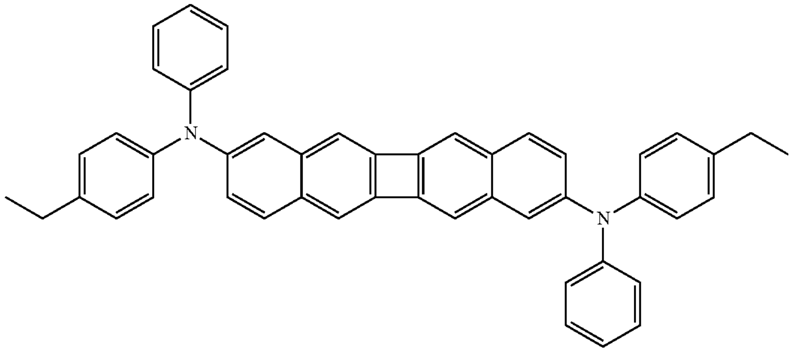

-continued
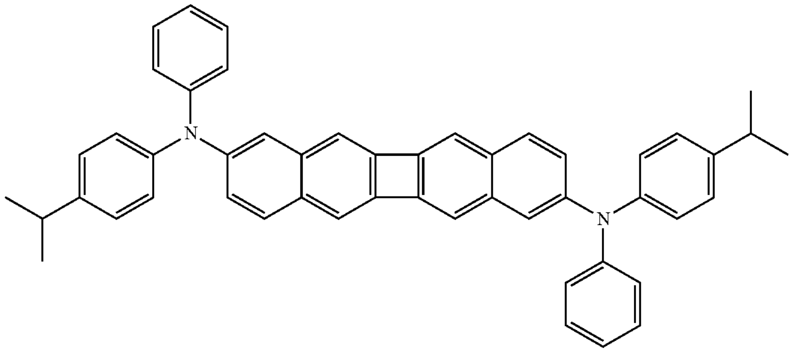
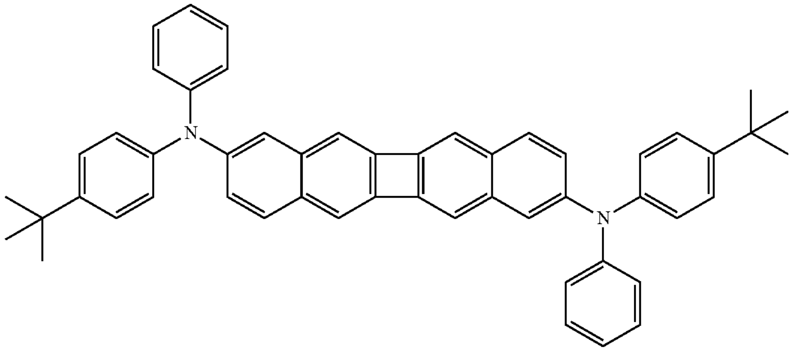
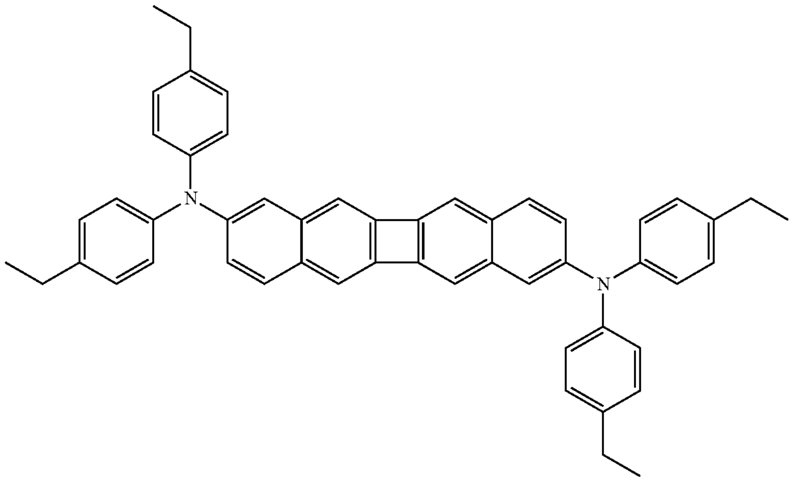
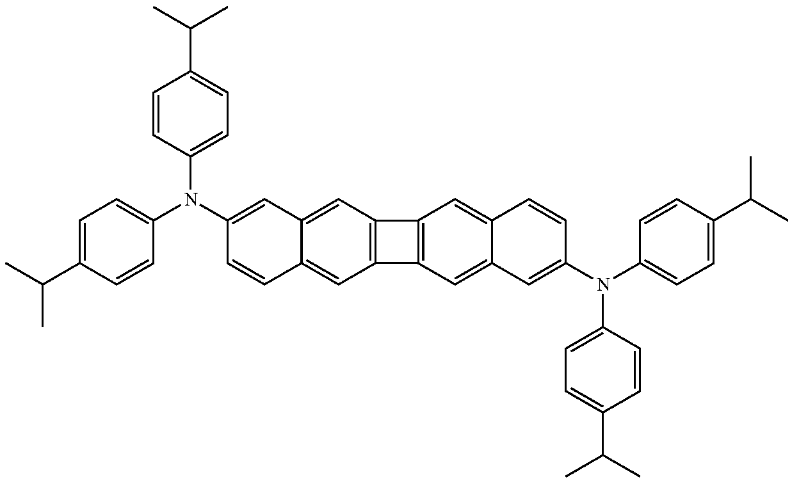

-continued
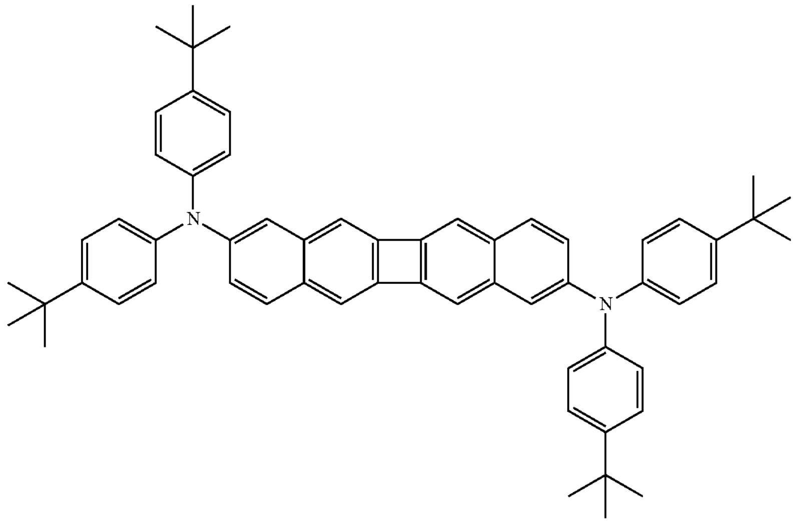
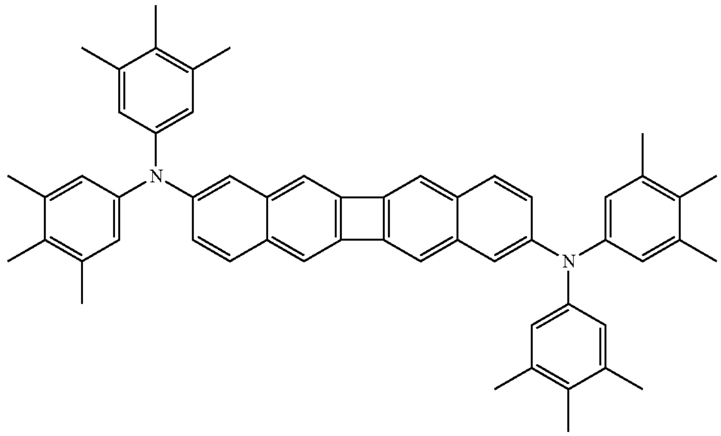
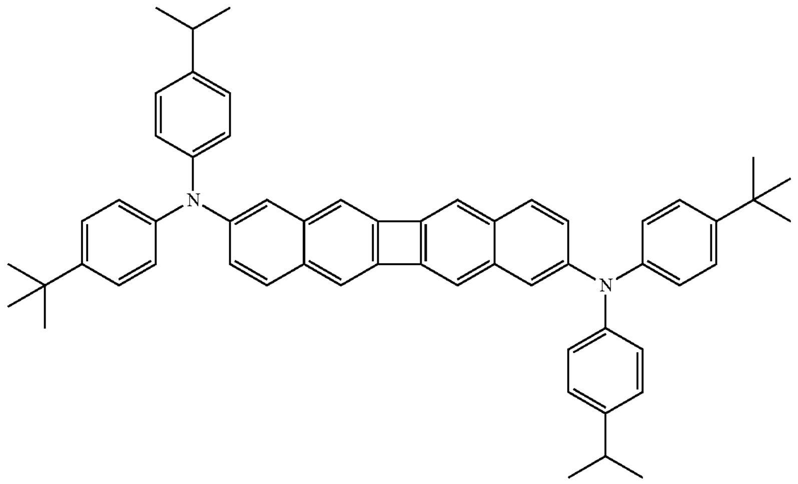

-continued
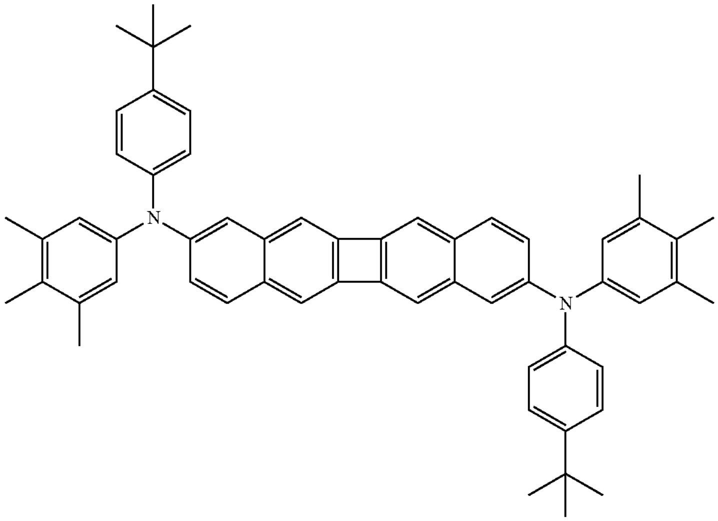
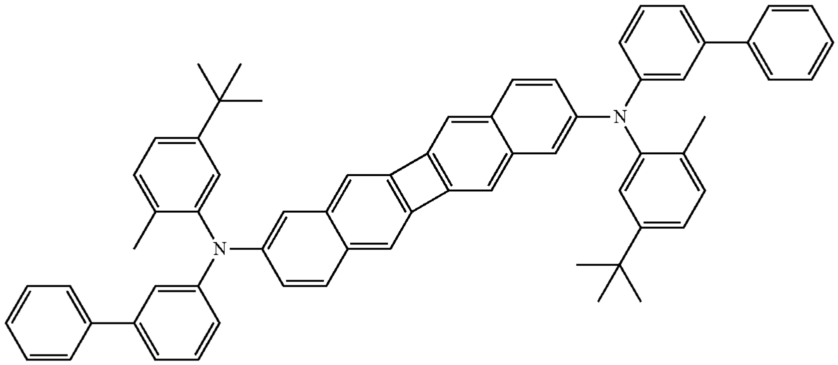
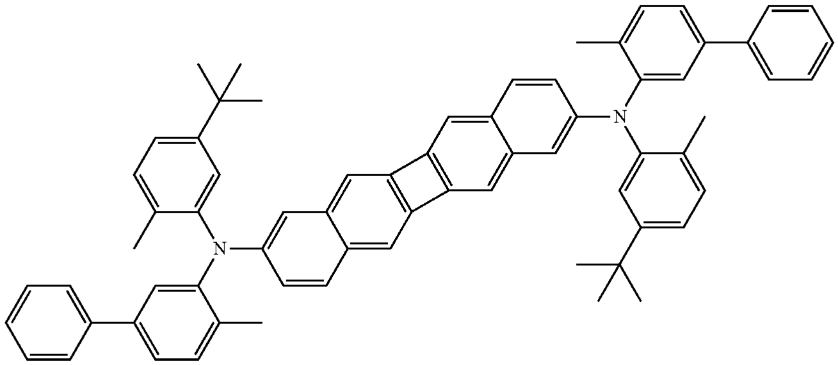
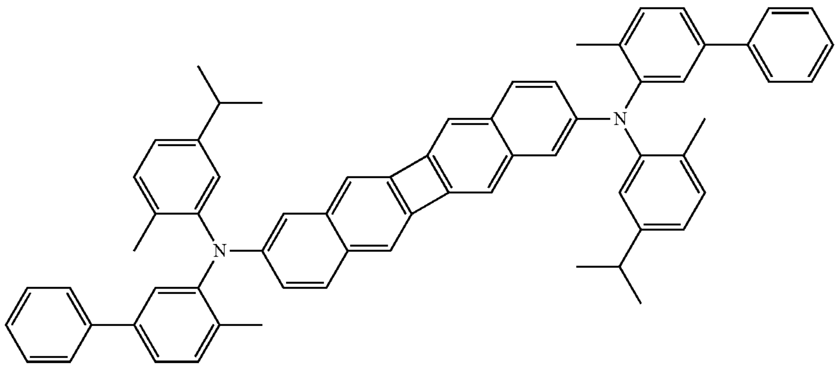

-continued
[Formula 160]
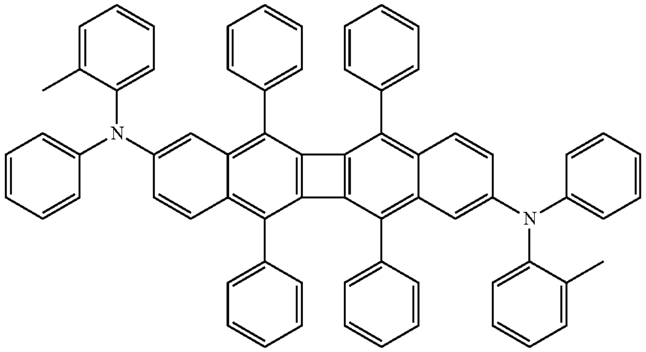
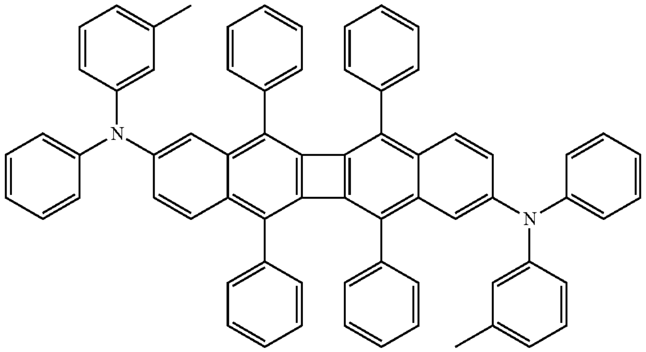
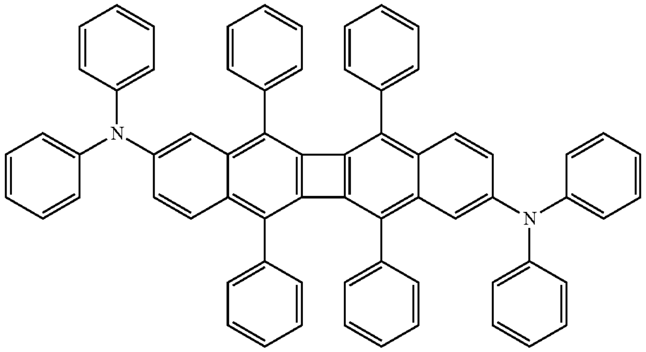
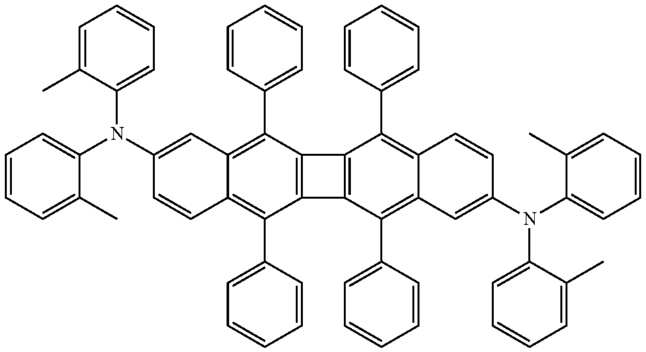

-continued
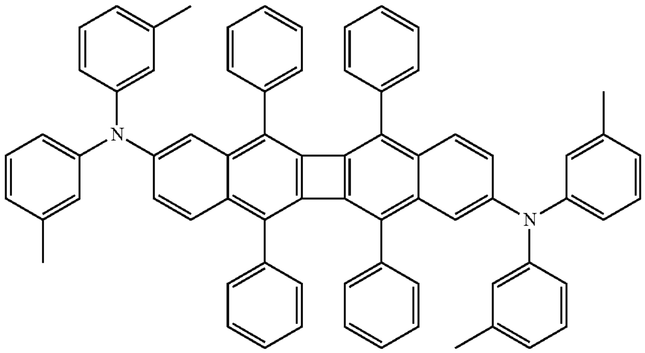 [SMILES: Cc1cccc(N(c2cccc(C)c2)c2ccc3c(-c4ccccc4)c4c(c(-c5ccccc5)c3c2)-c2c-4c(-c3ccccc3)c3cc(N(c4cccc(C)c4)c4cccc(C)c4)ccc3c2-c2ccccc2)c1]
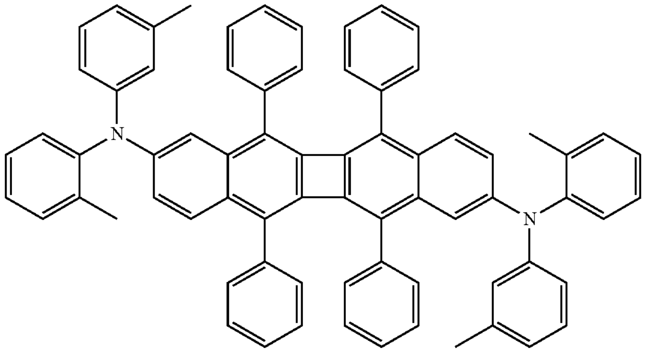
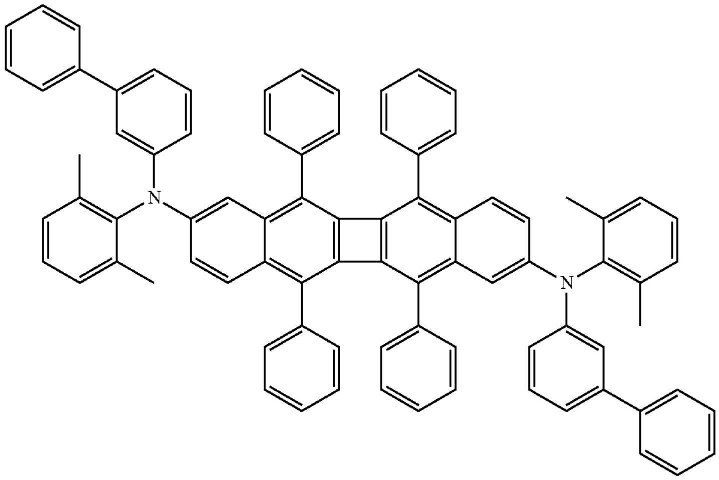
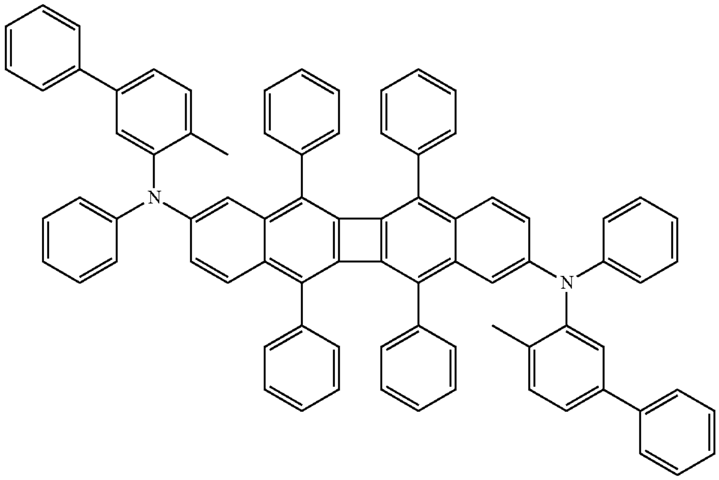

-continued
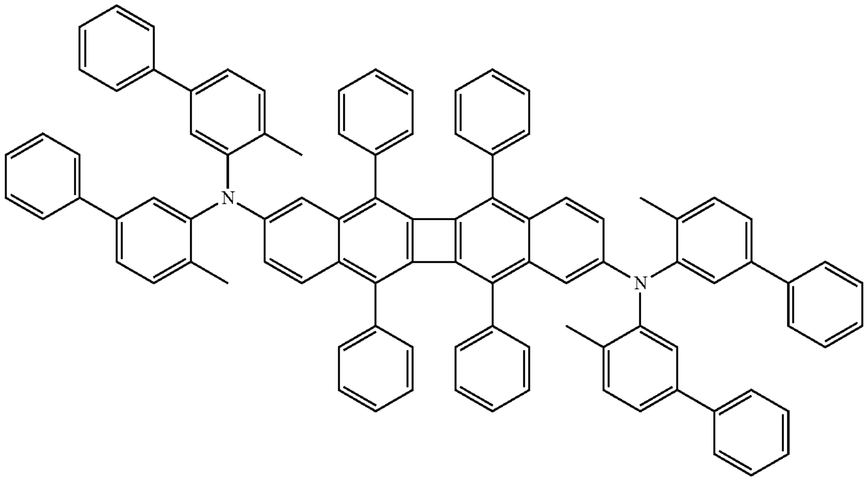
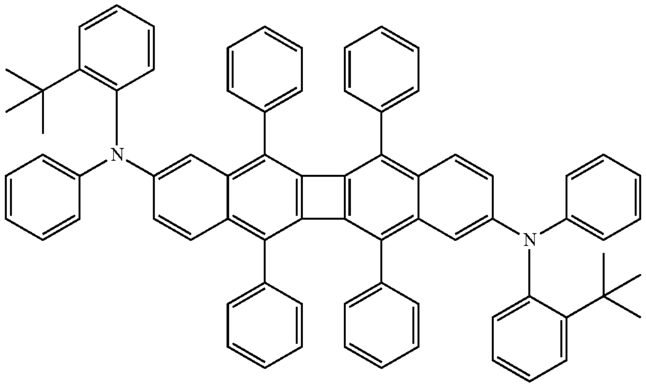
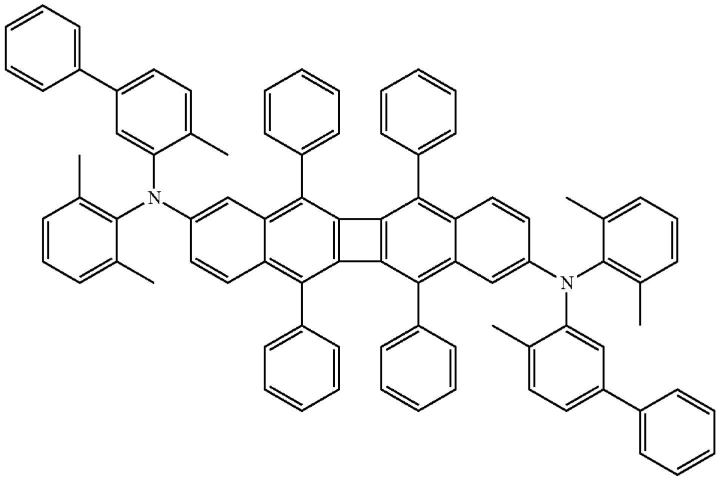

-continued
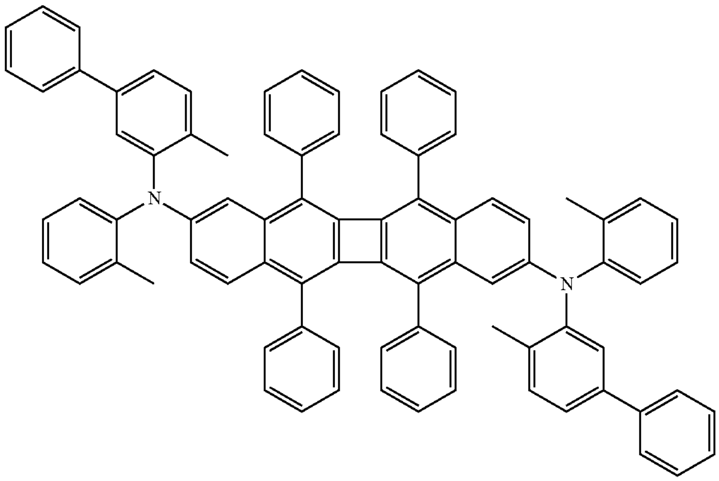
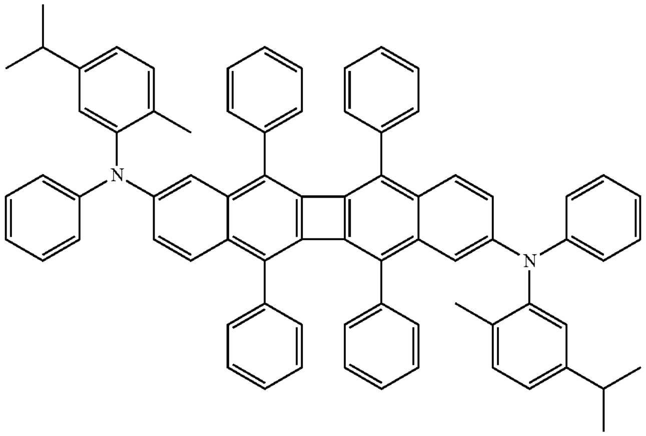
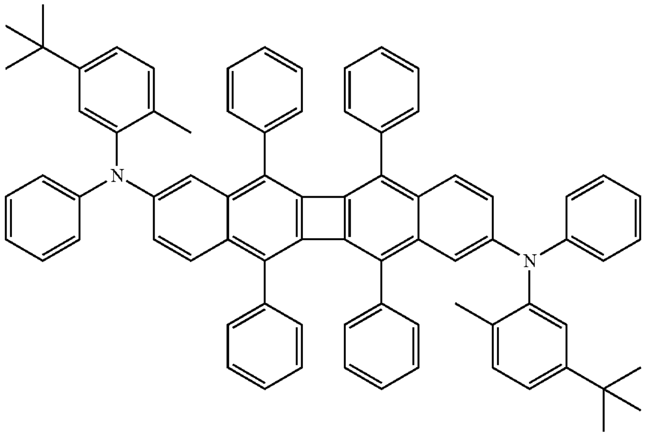

-continued
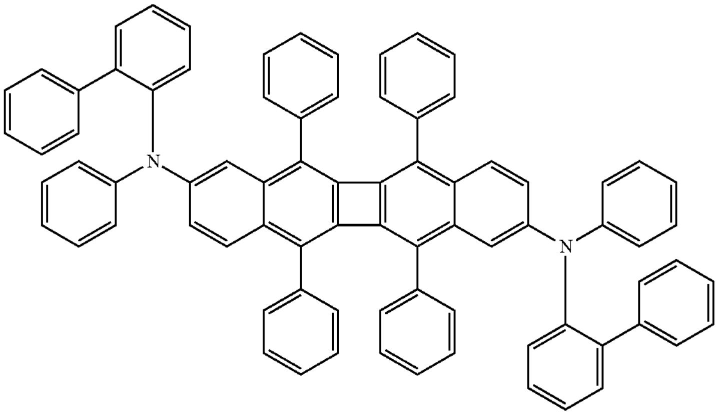
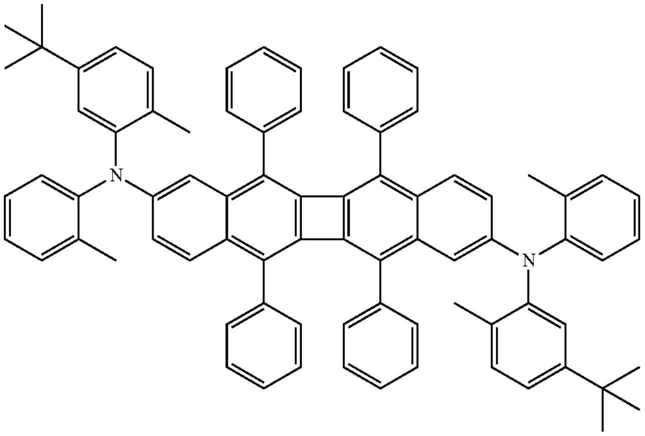
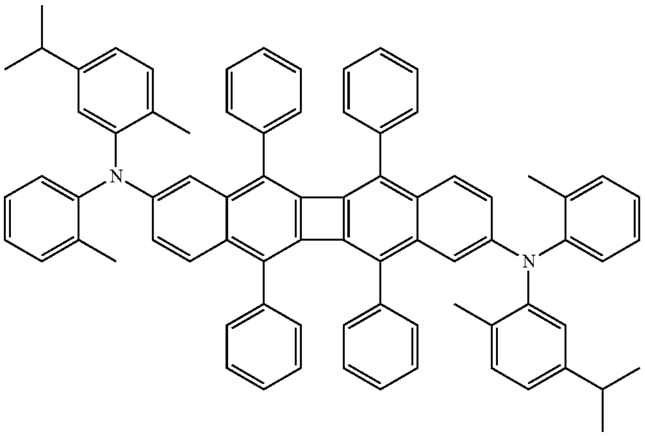

-continued
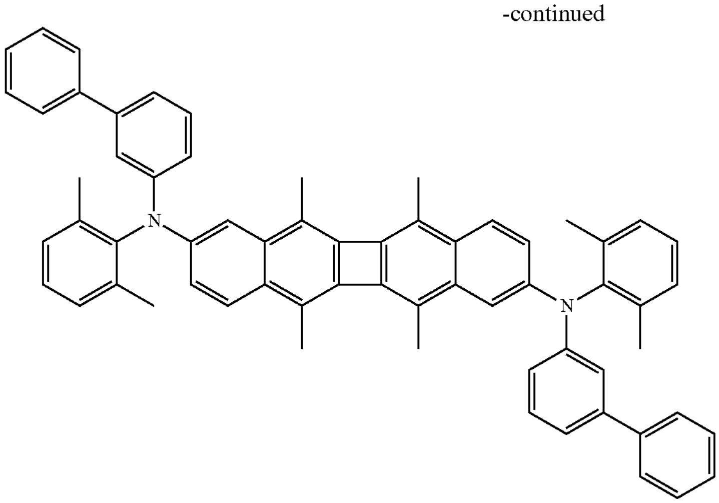
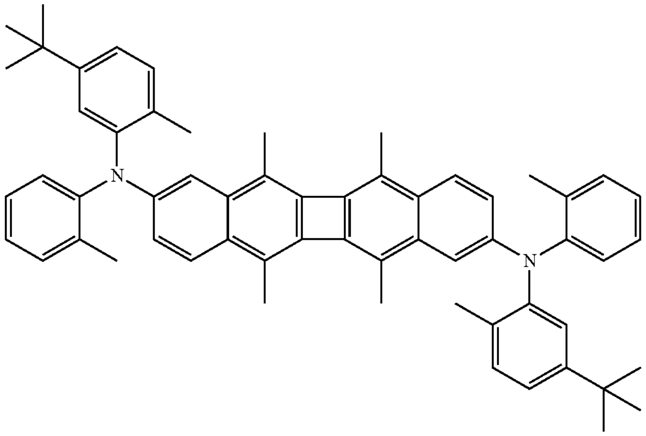
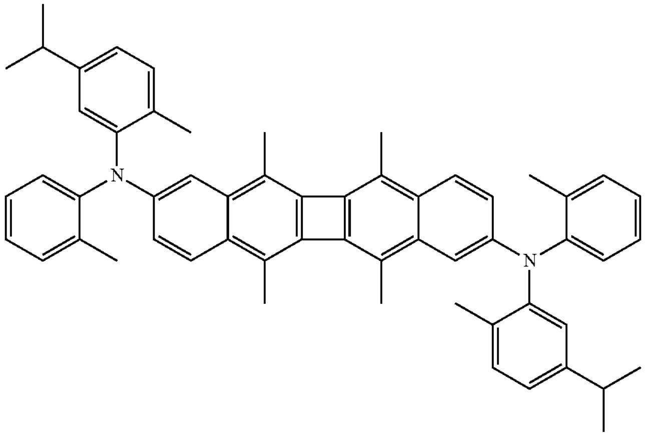

-continued
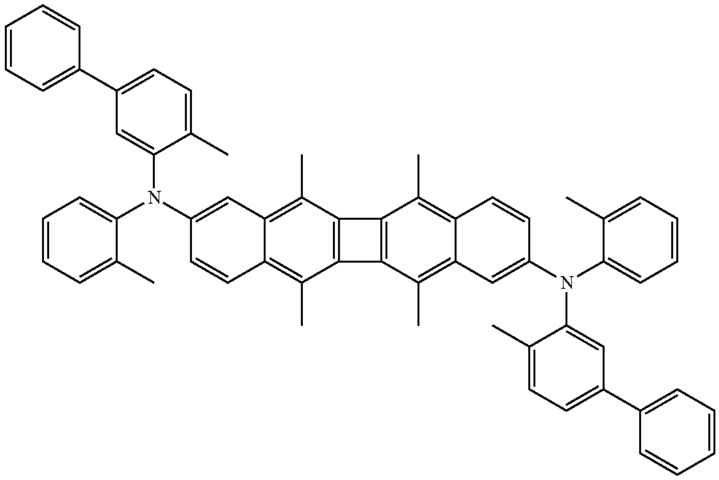
[Formula 161]
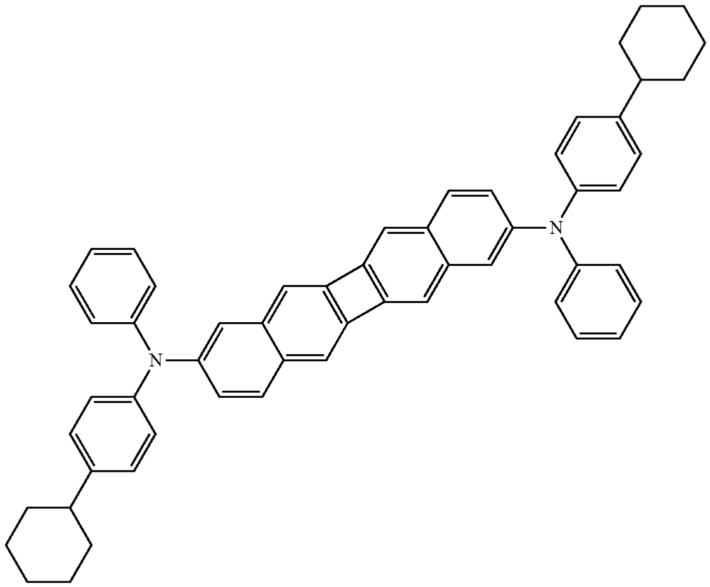
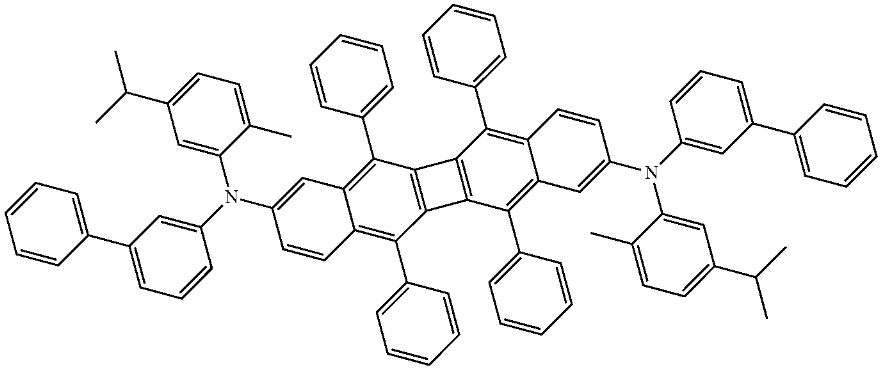

-continued
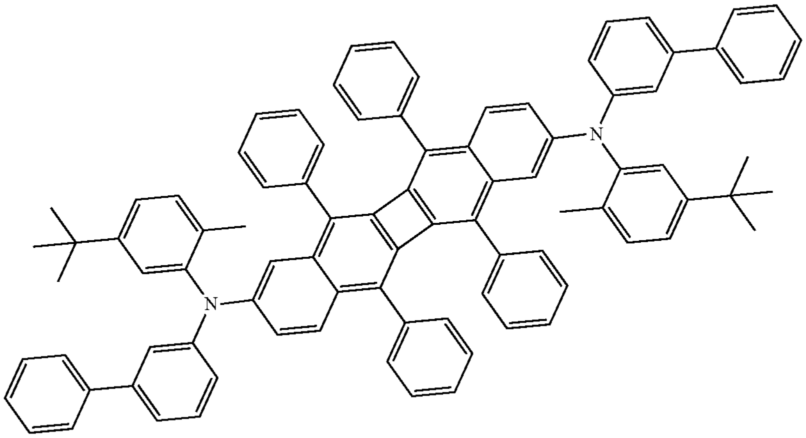
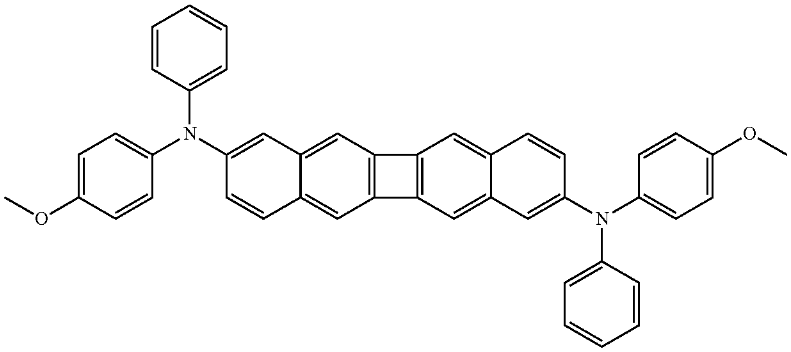
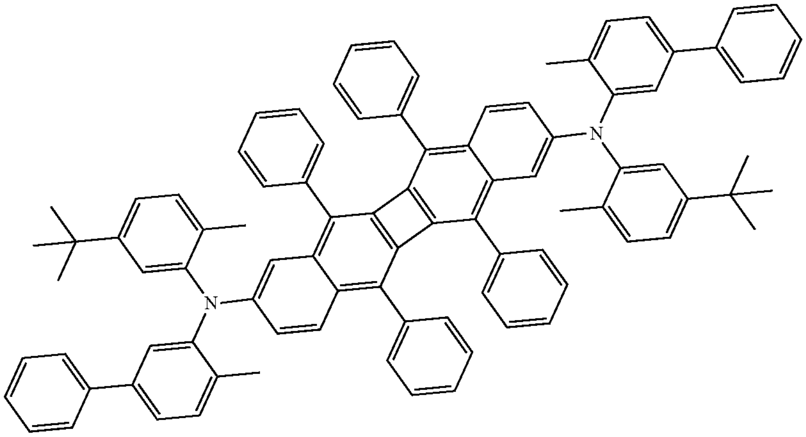
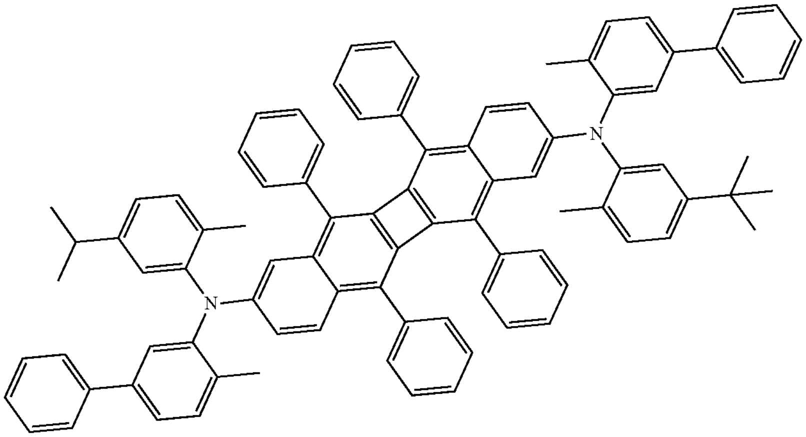

-continued
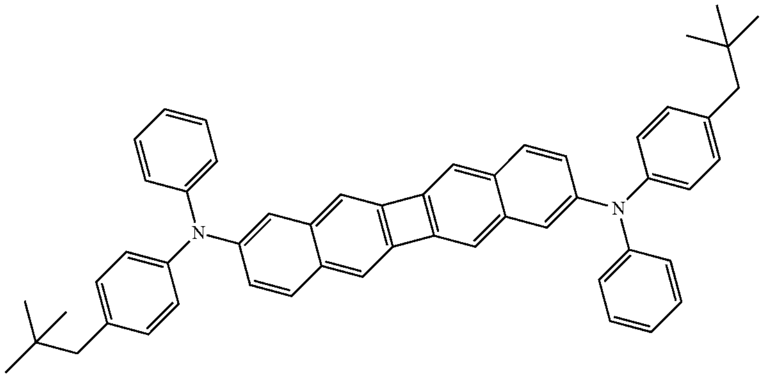
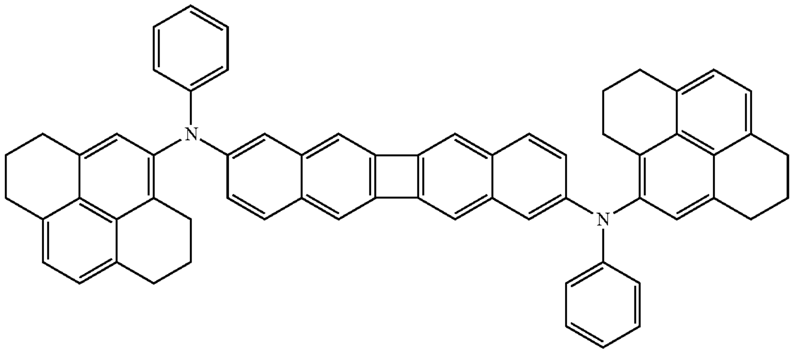
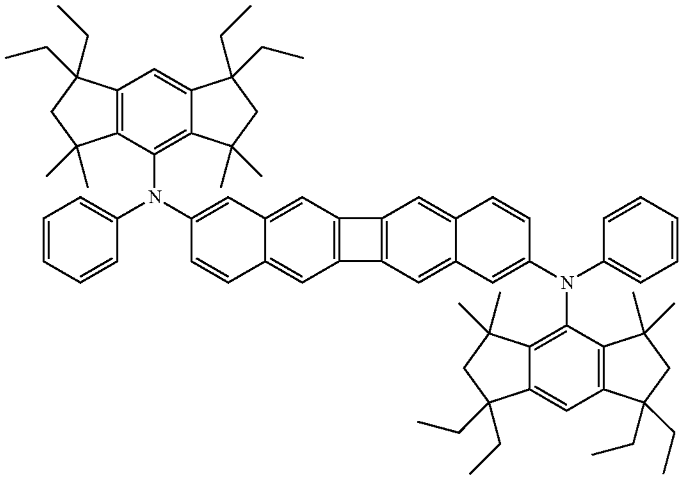
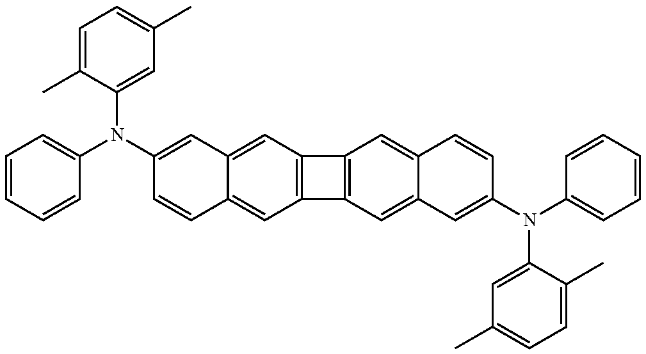

-continued
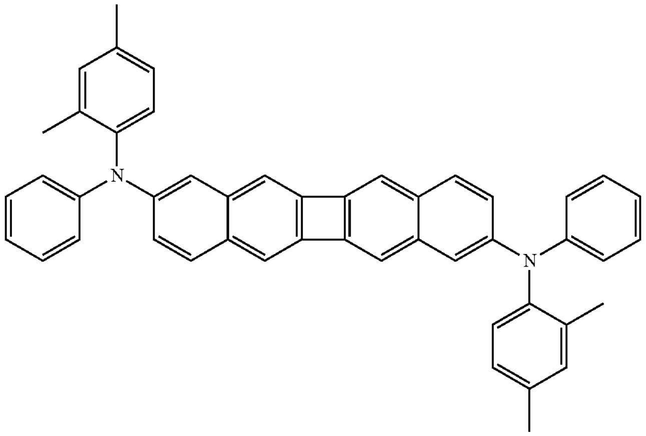
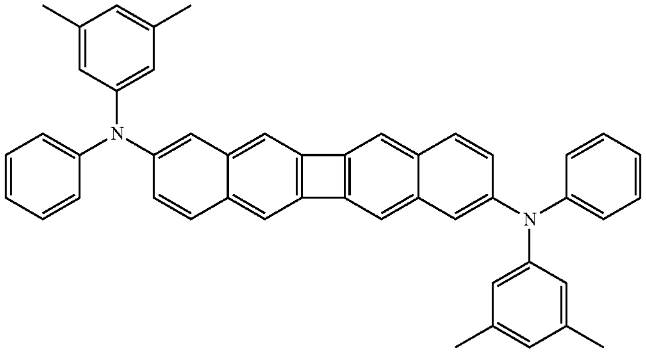
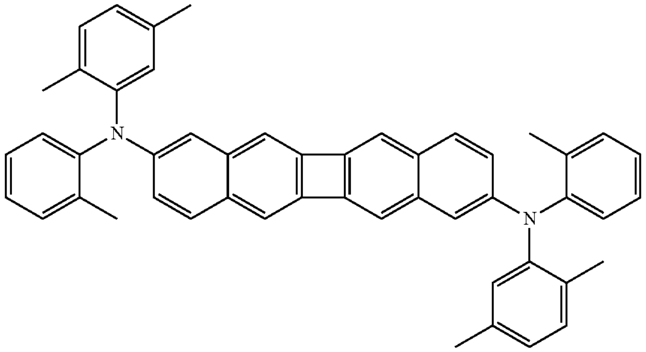
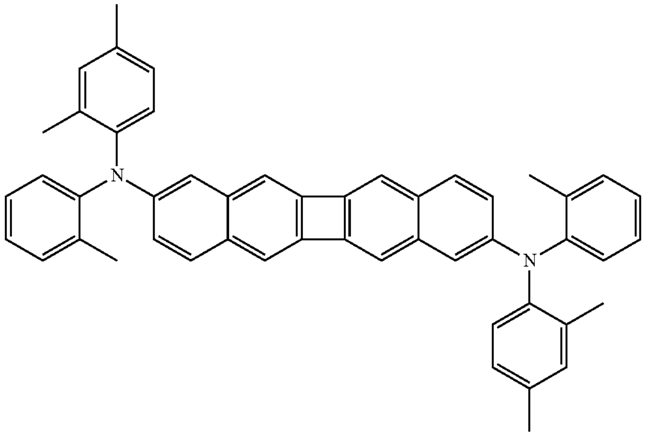

-continued
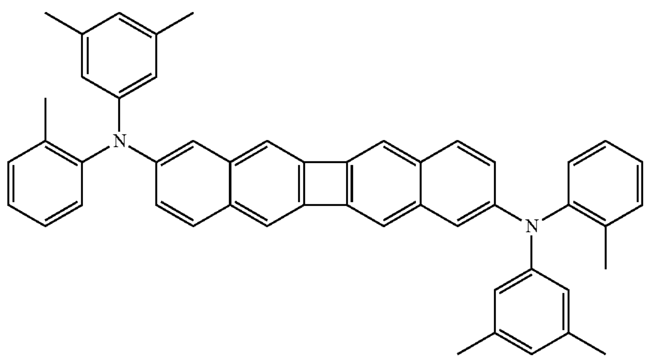
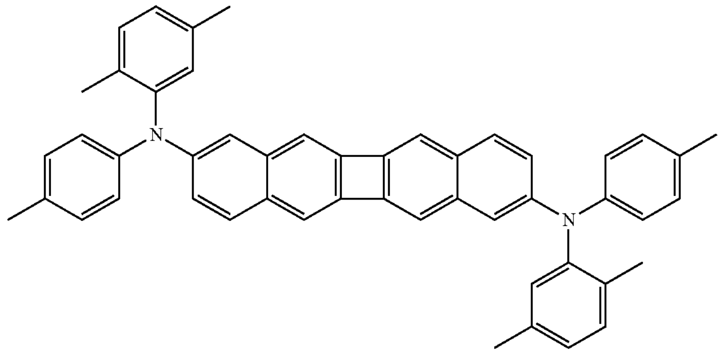
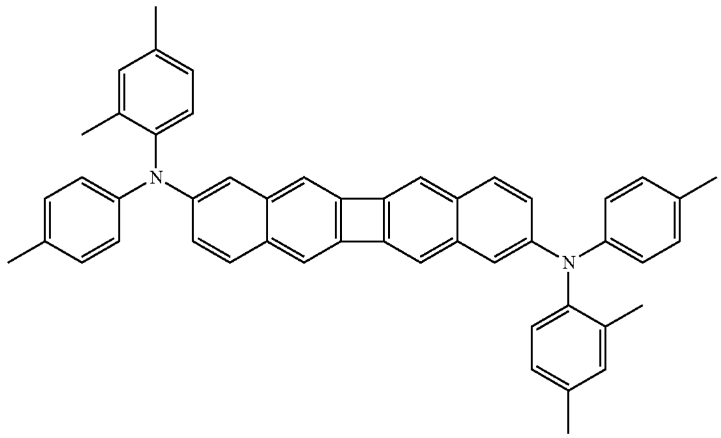
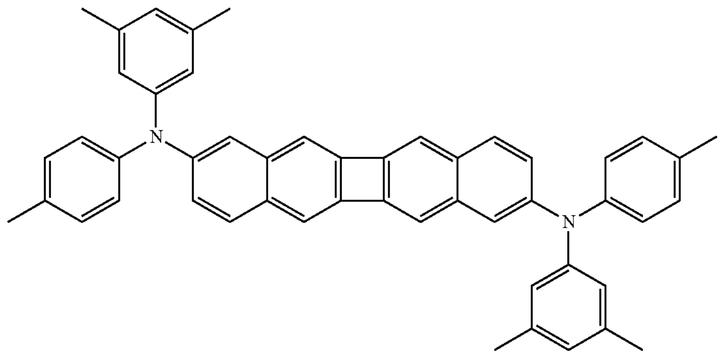

-continued
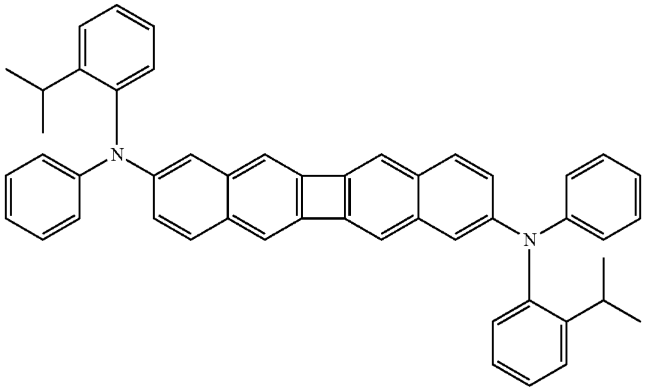
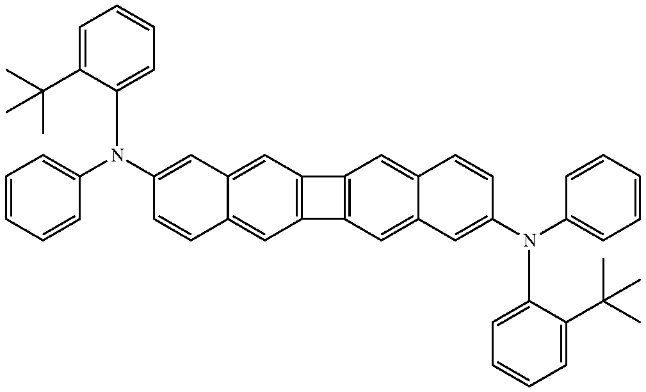
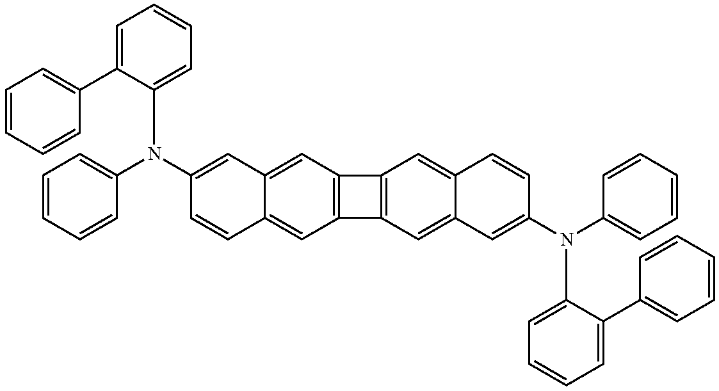
[Formula 162]
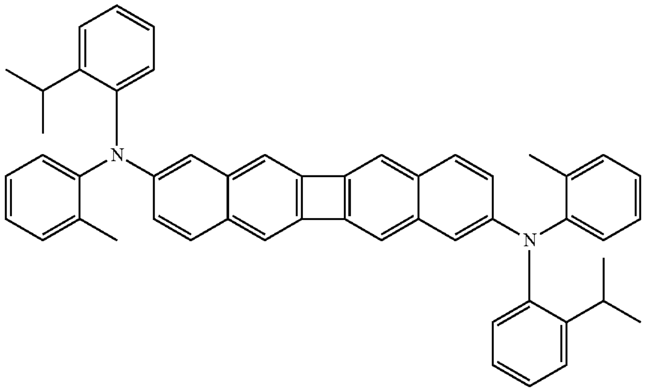

-continued
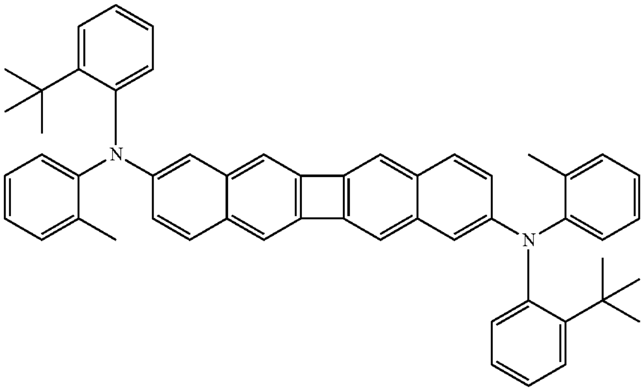
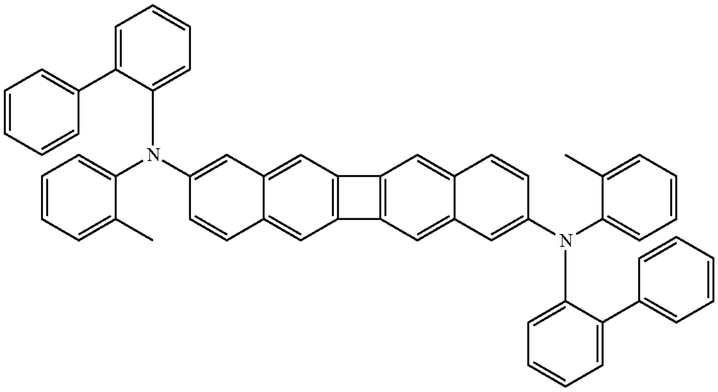
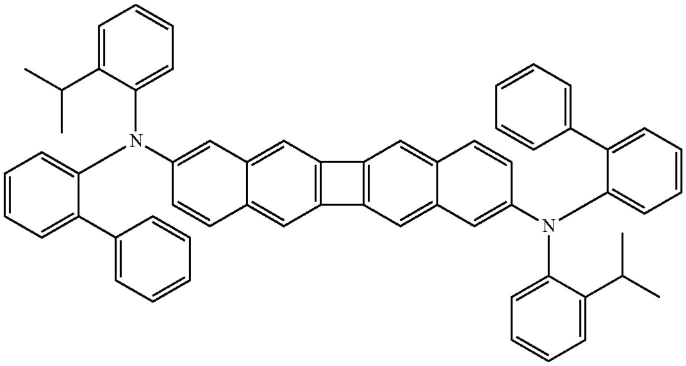
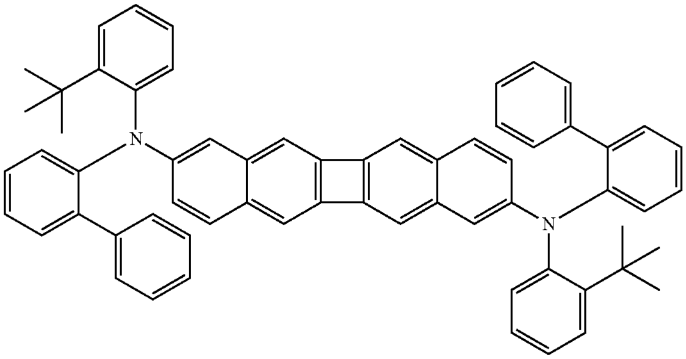

-continued
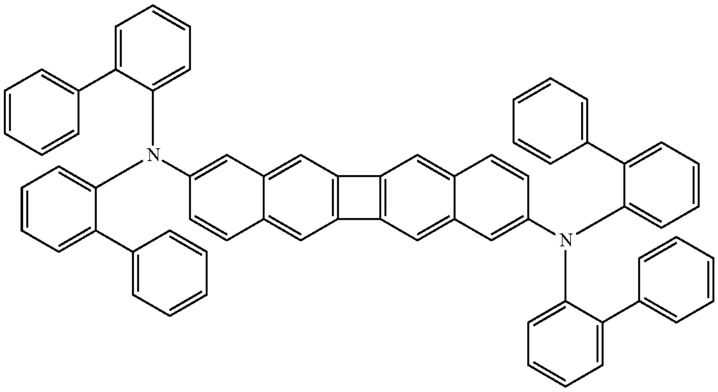
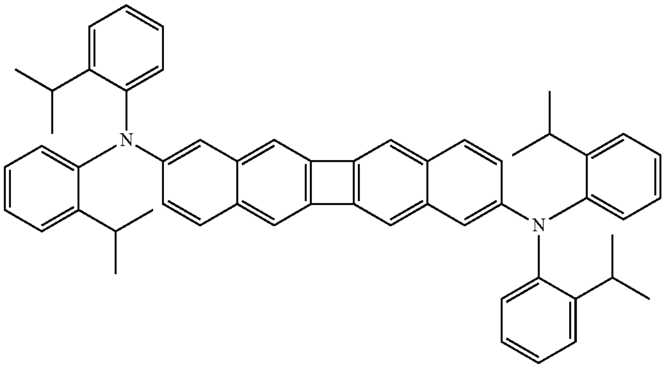
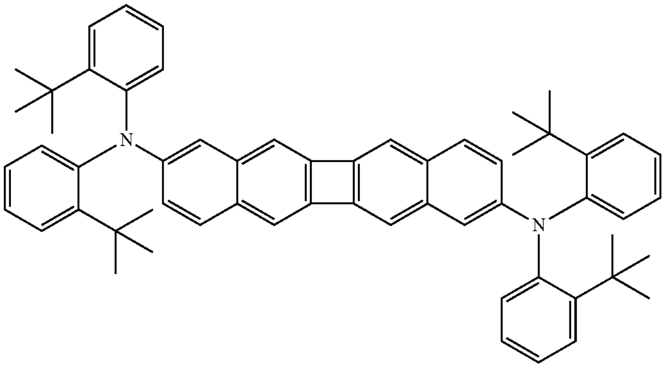
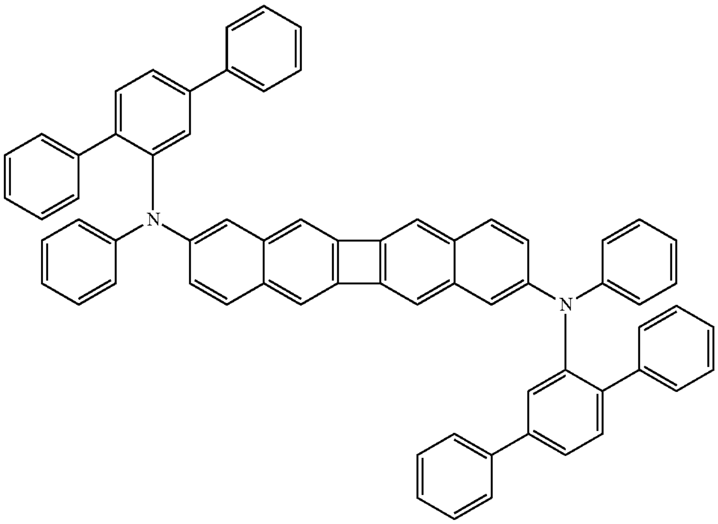

-continued
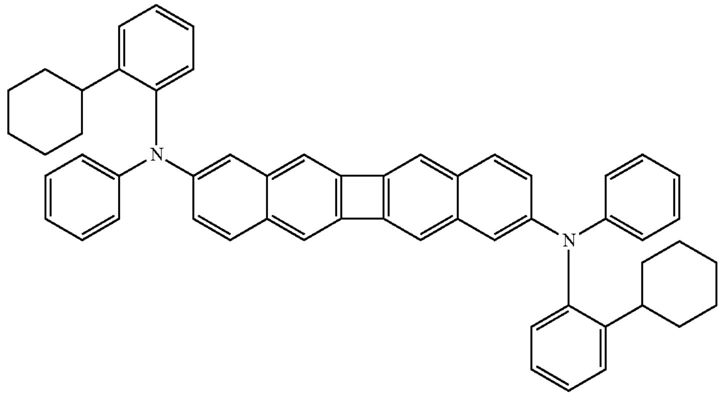
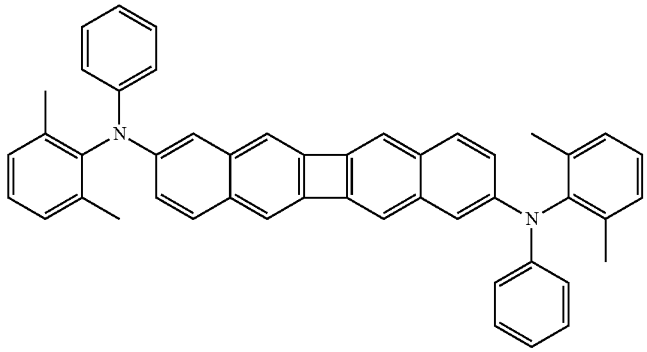
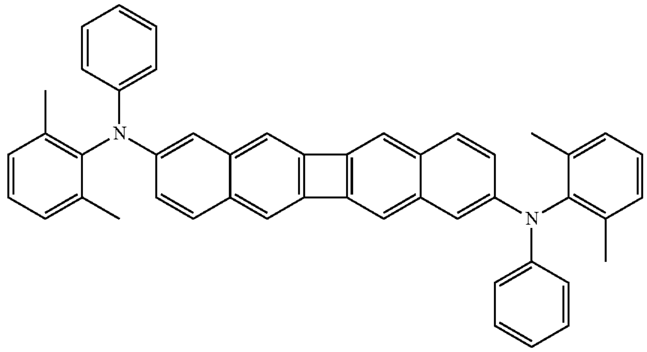
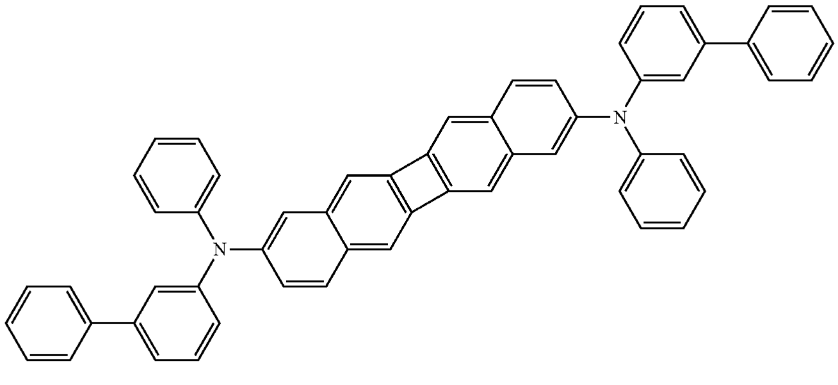

-continued
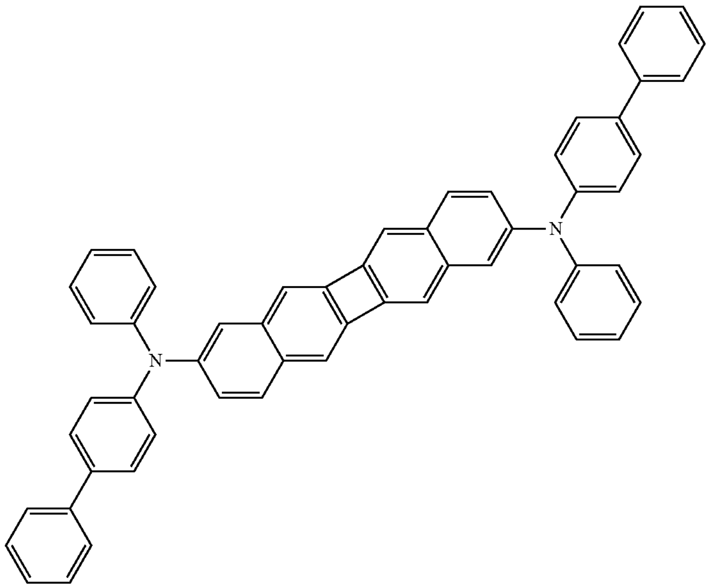
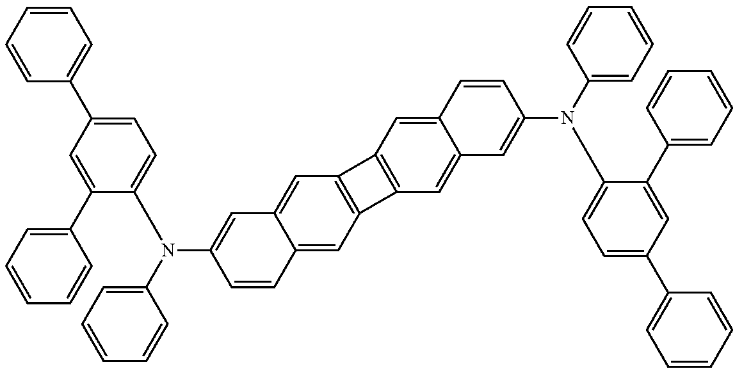
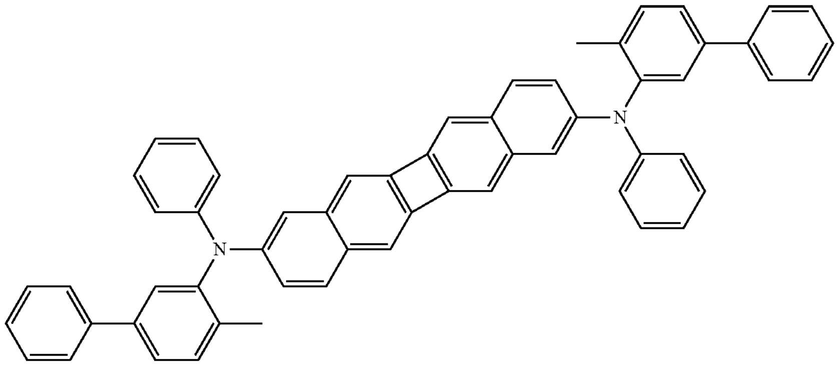

-continued
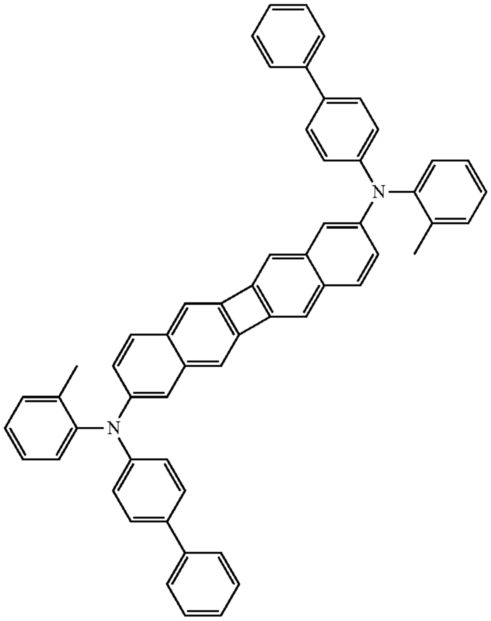
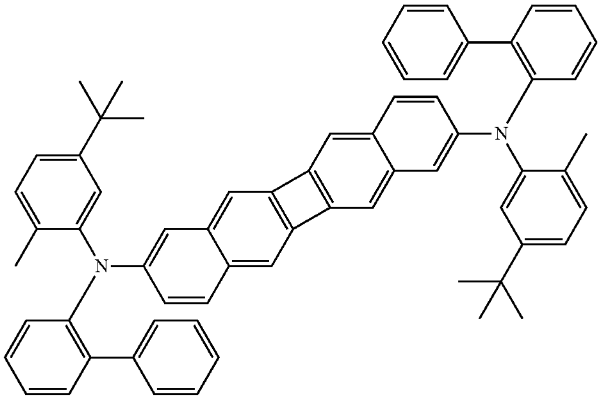
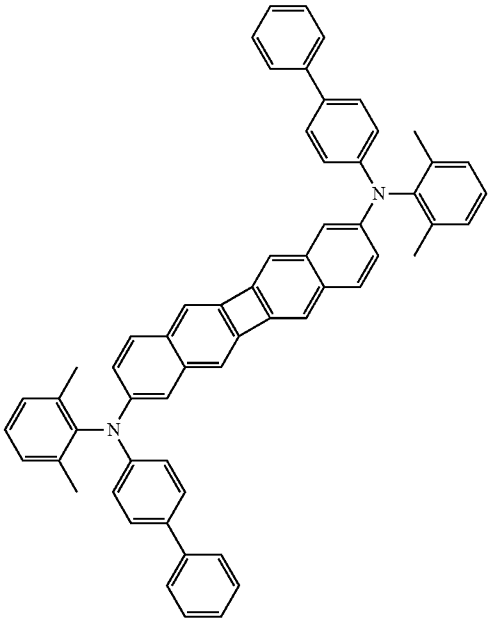

-continued
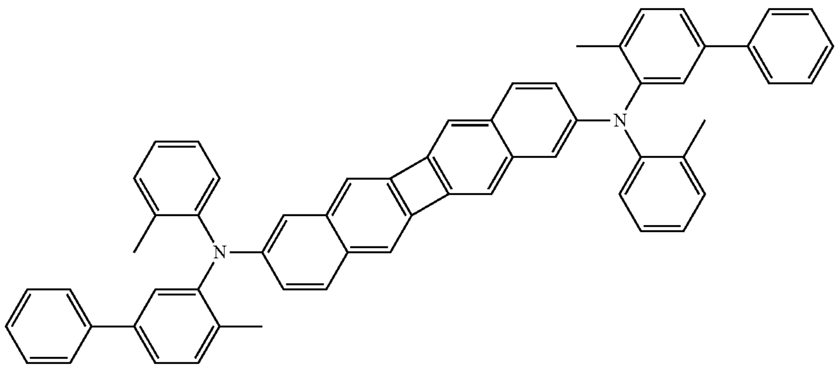
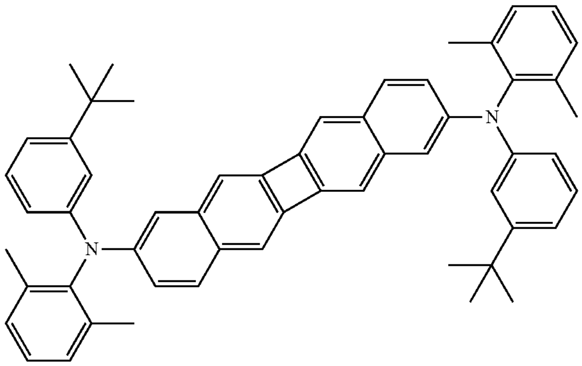
[Formula 163]
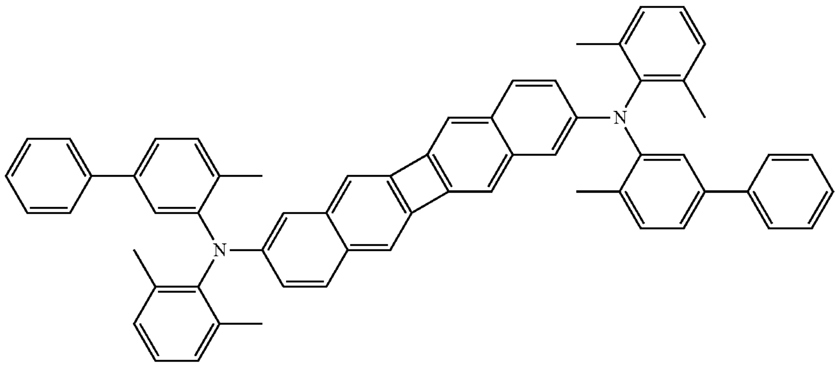
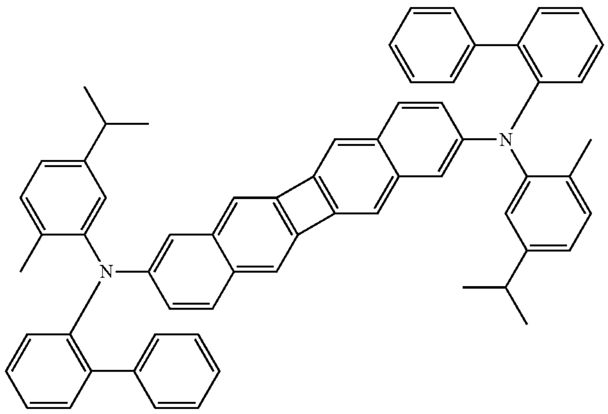

-continued
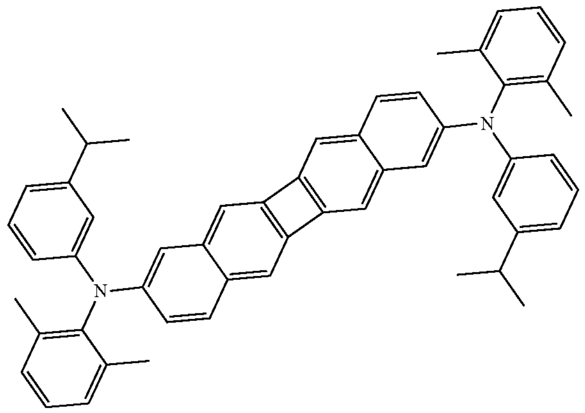
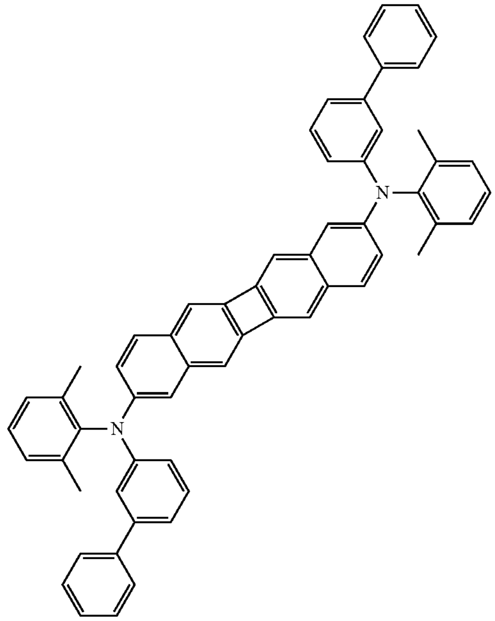
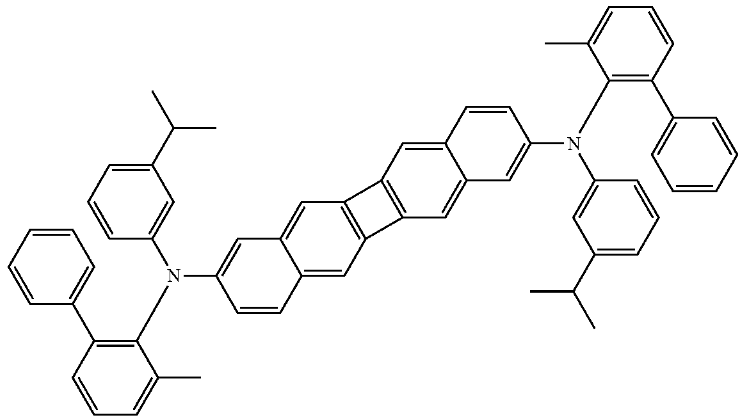

-continued
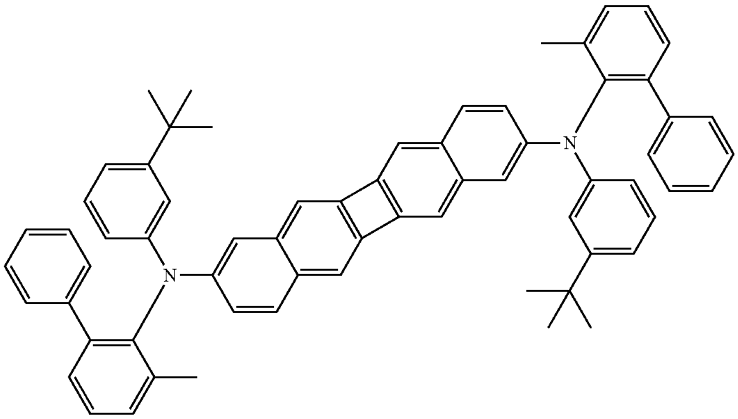
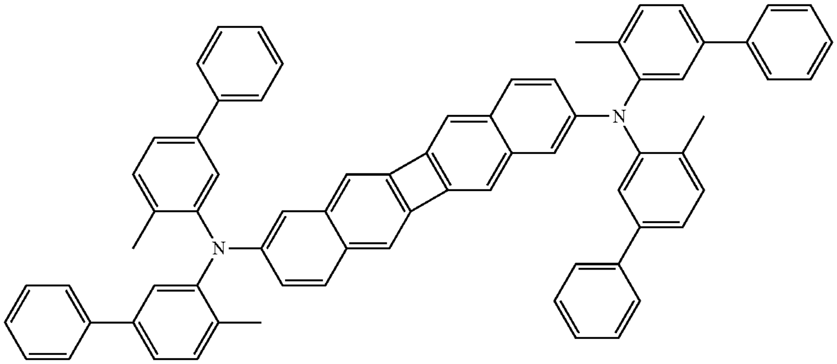
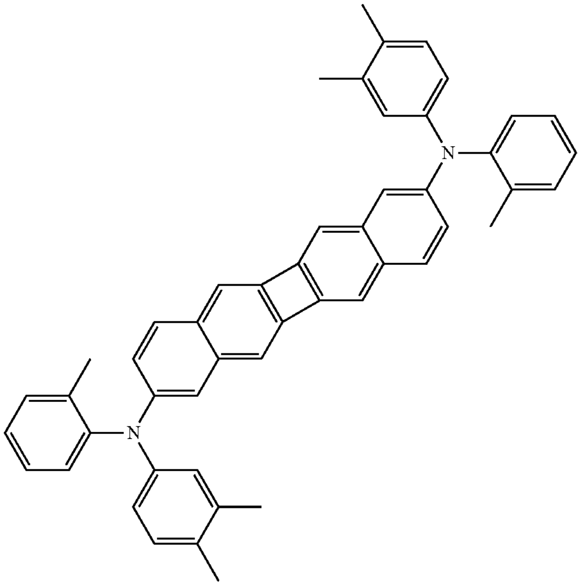

-continued
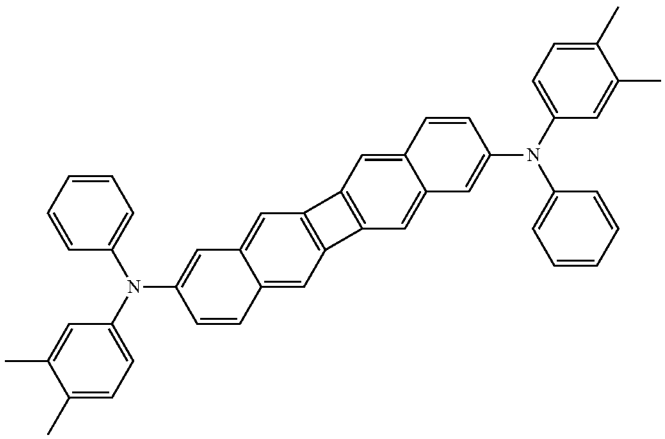
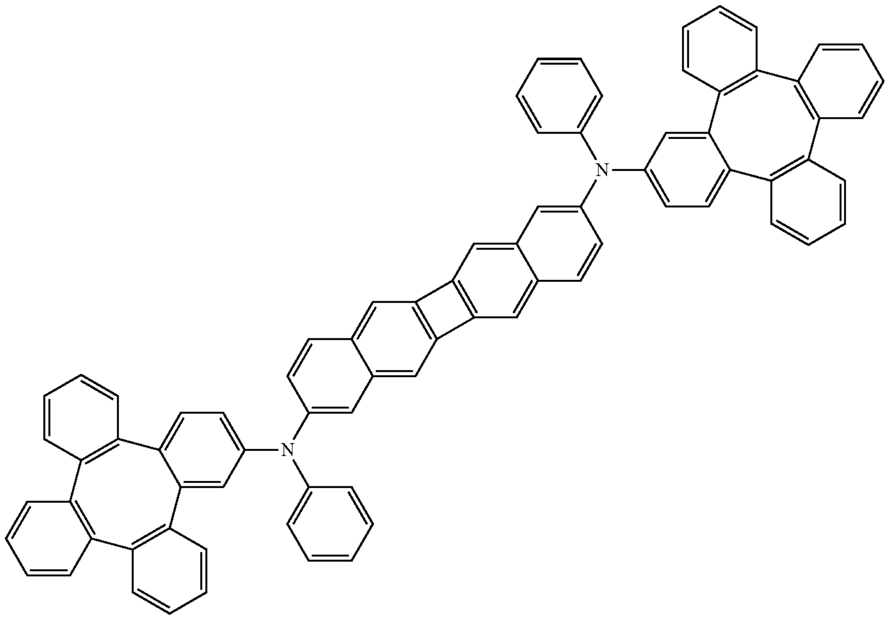
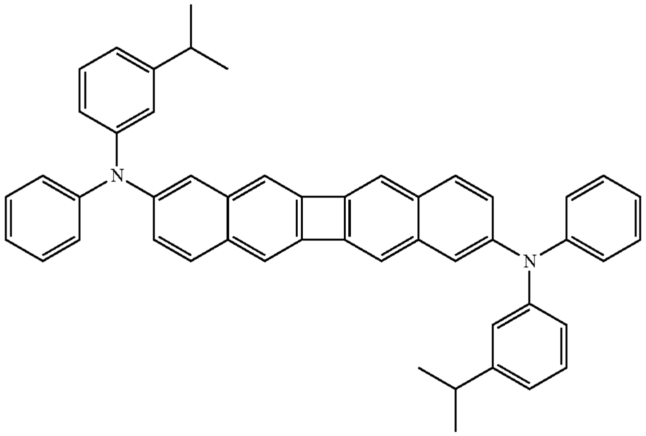

-continued
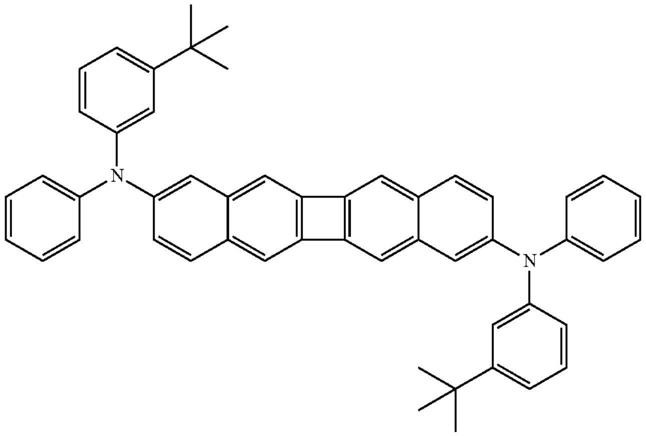
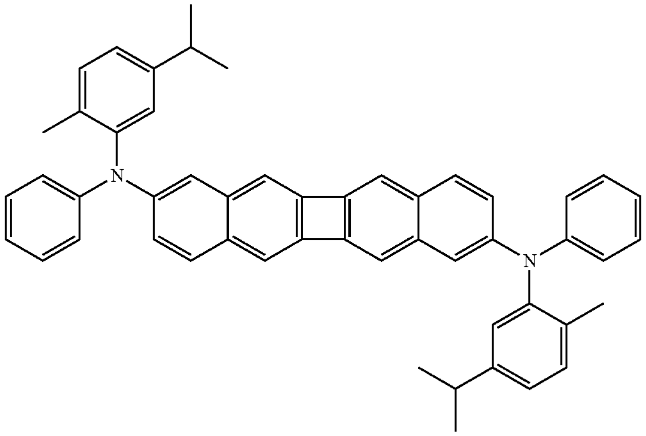
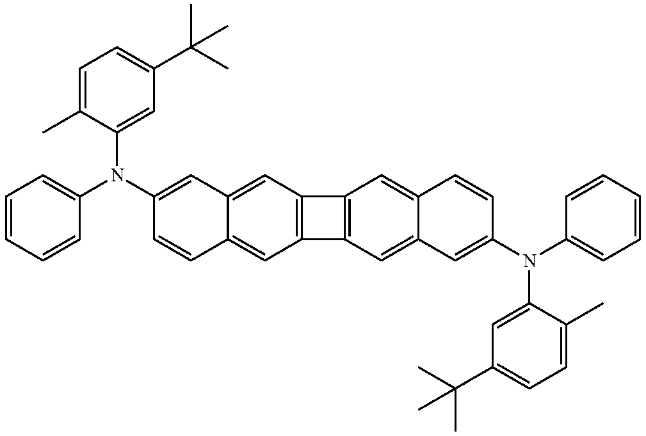

-continued
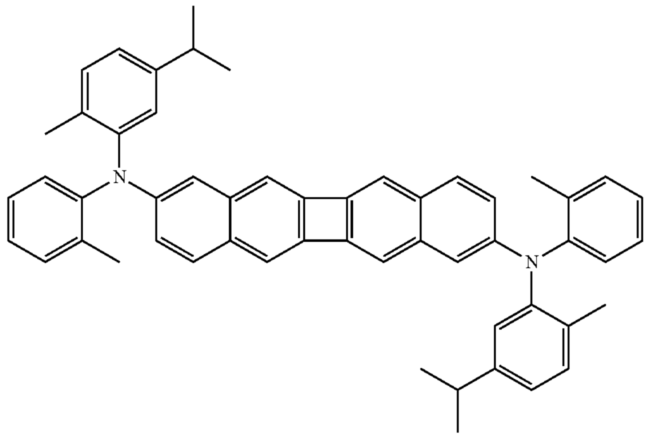
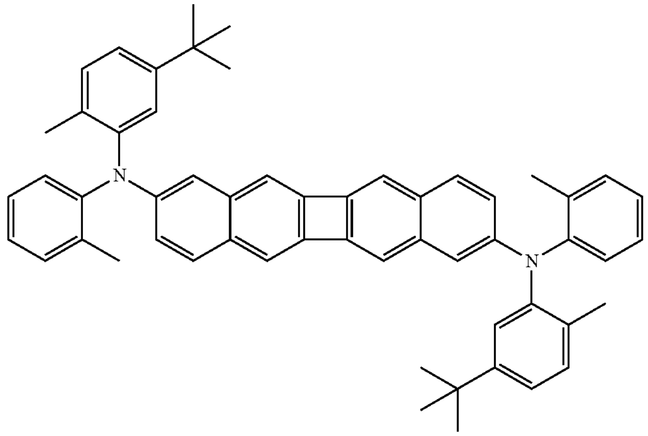
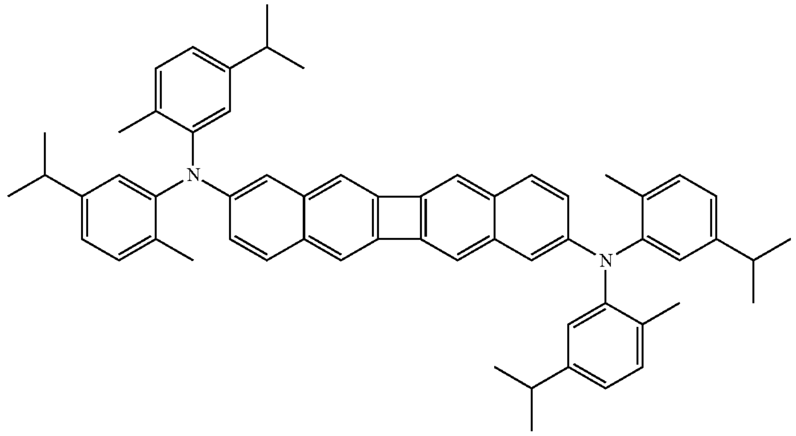

-continued
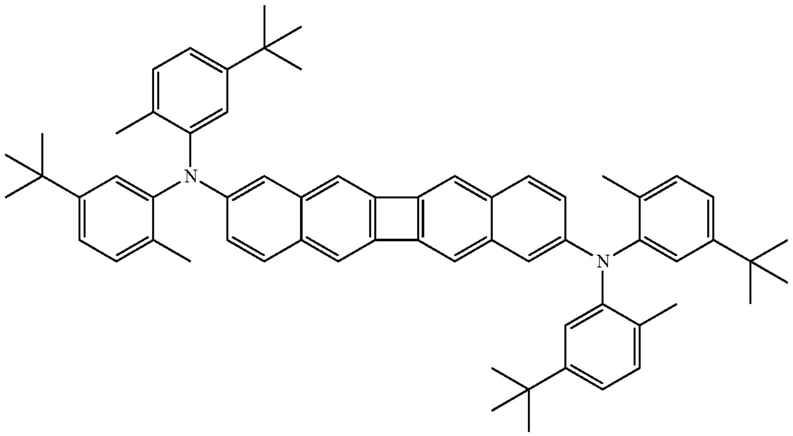
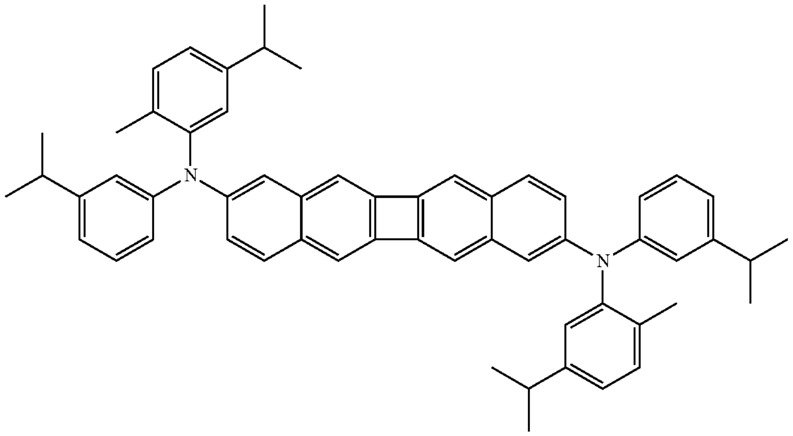
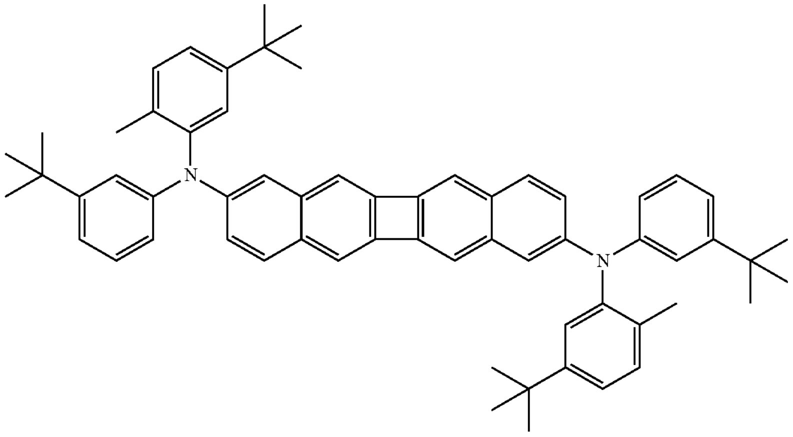

-continued
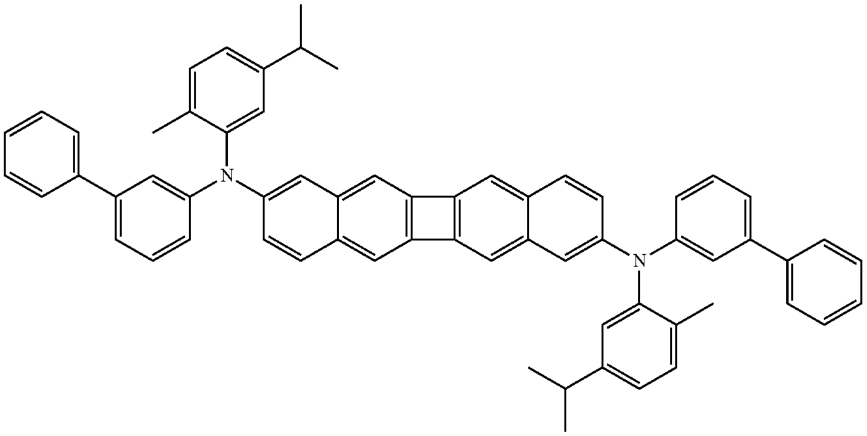
[Formula 164]
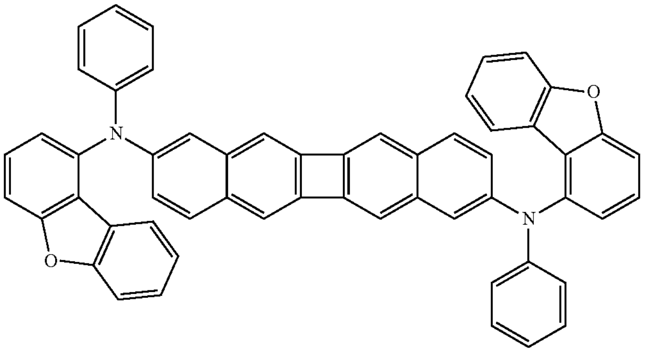
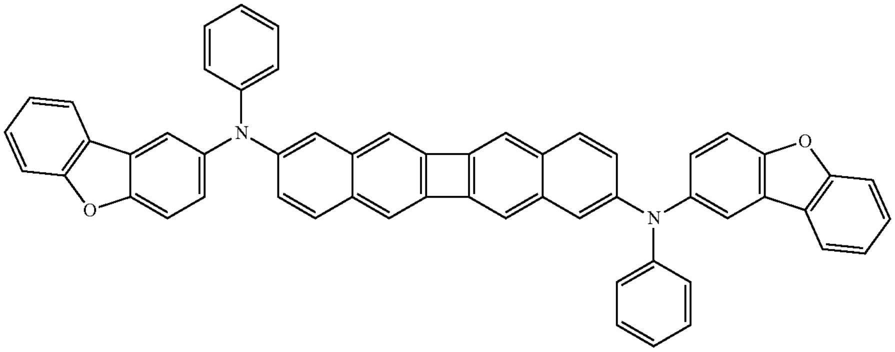
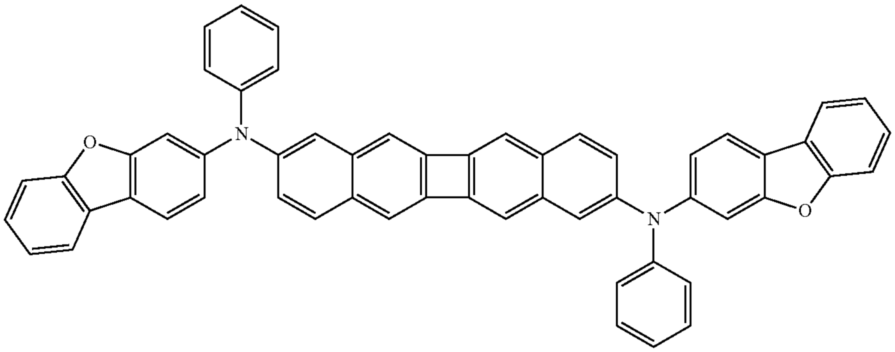

-continued
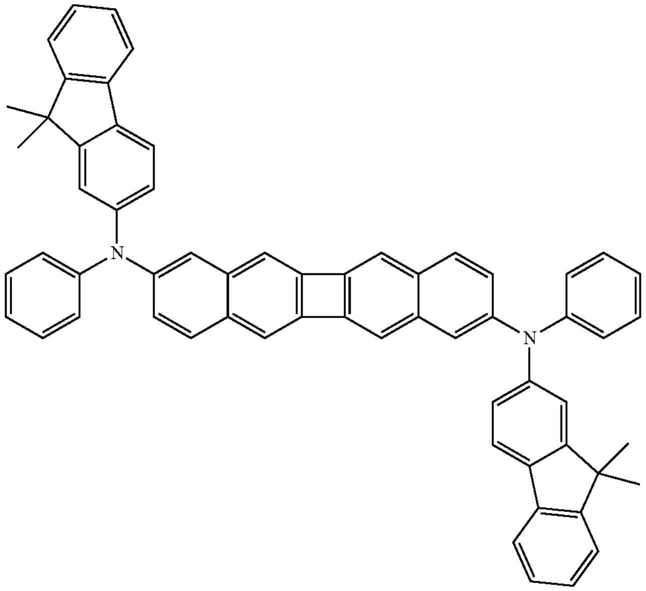
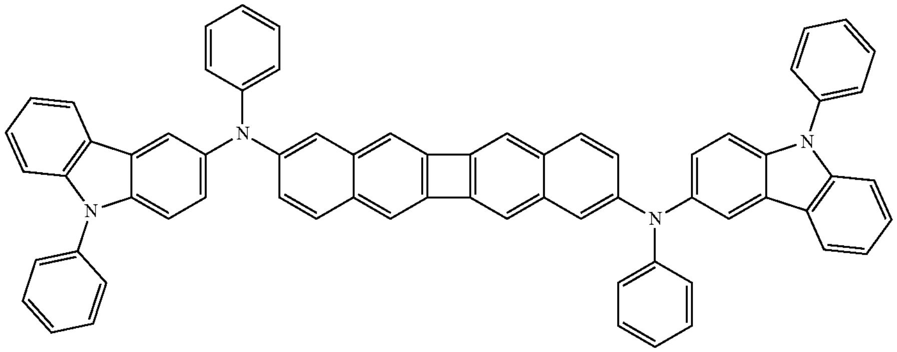
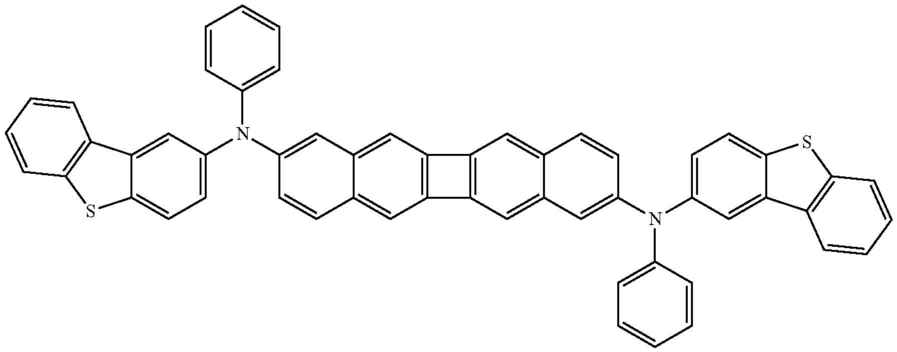

-continued
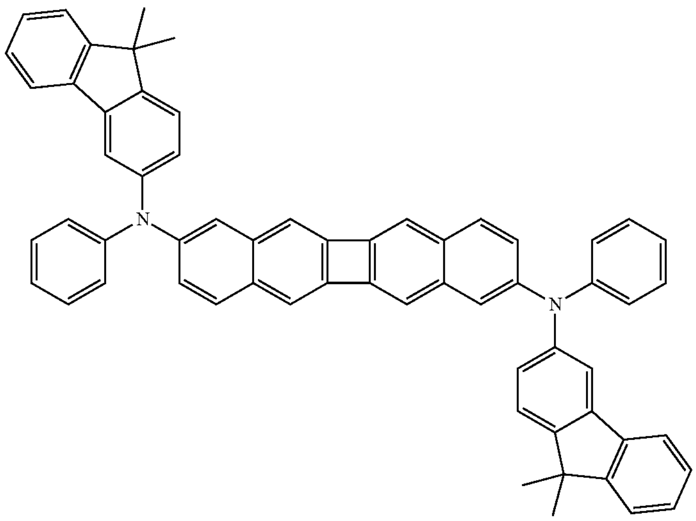
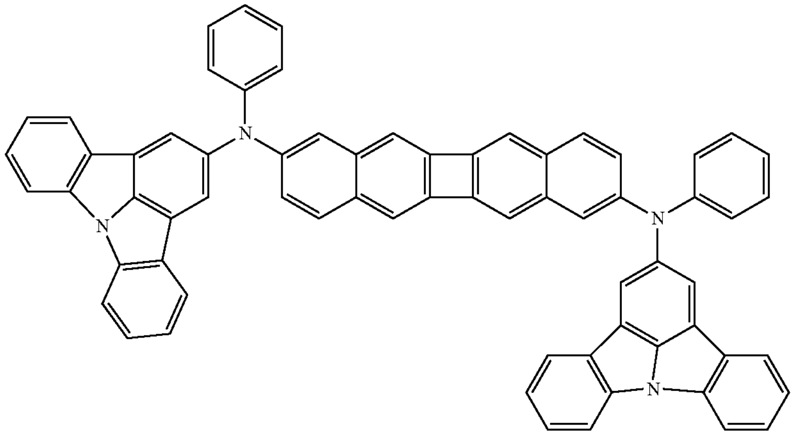
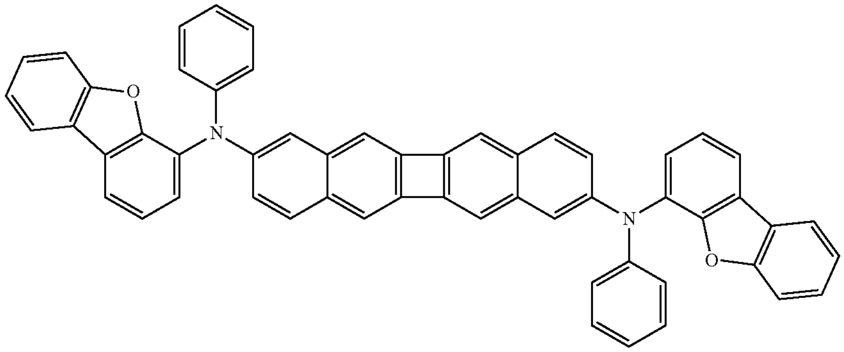
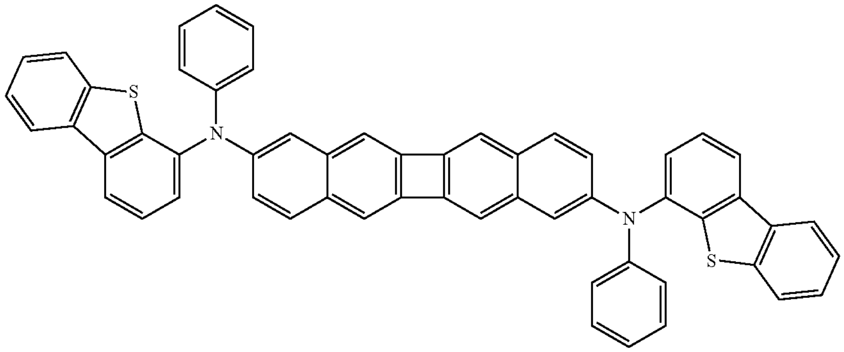

-continued
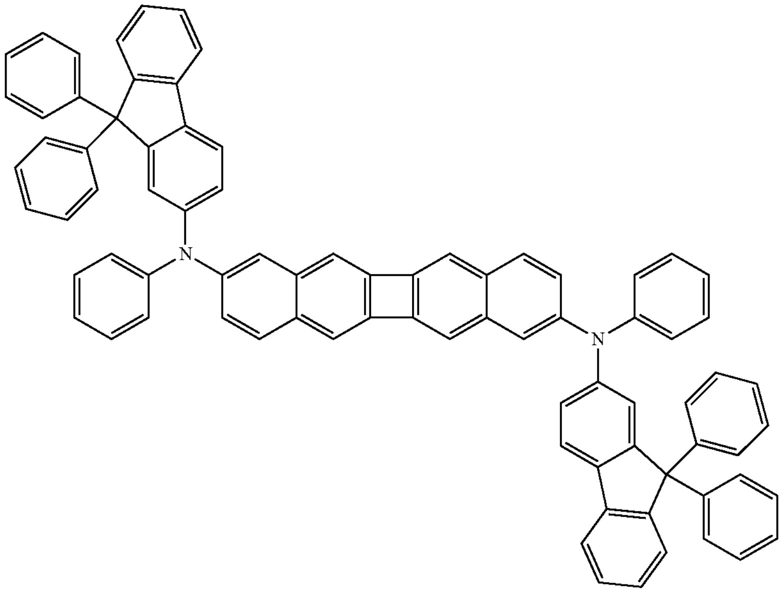
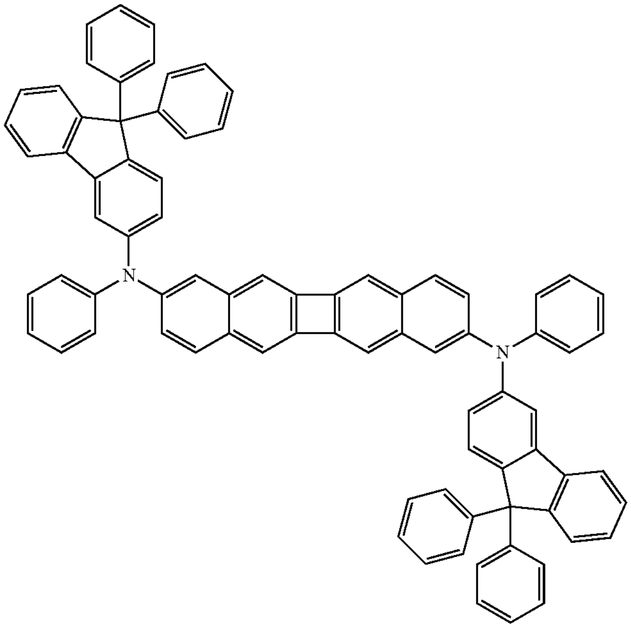

-continued
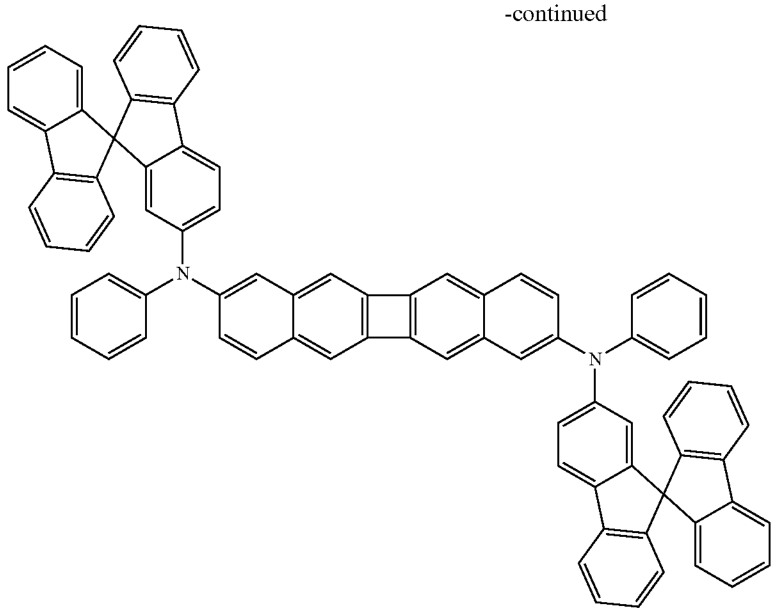
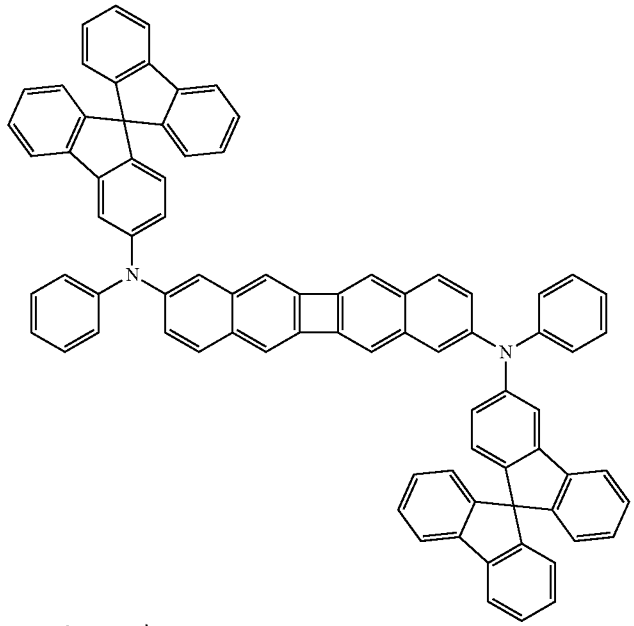
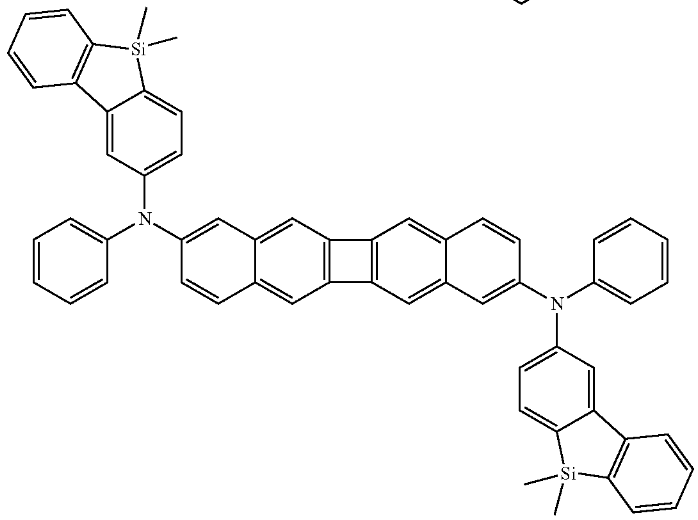

-continued
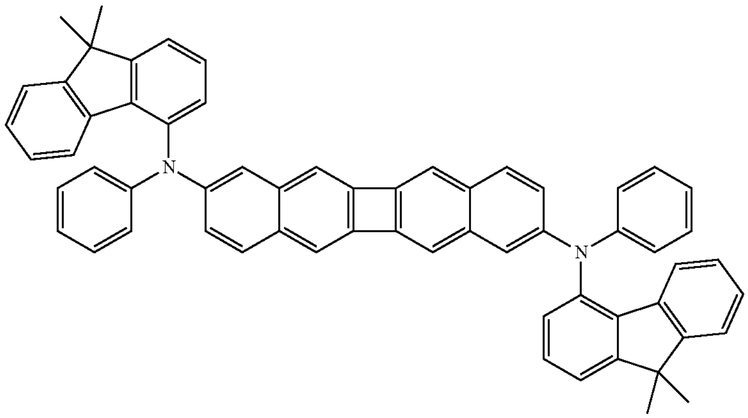
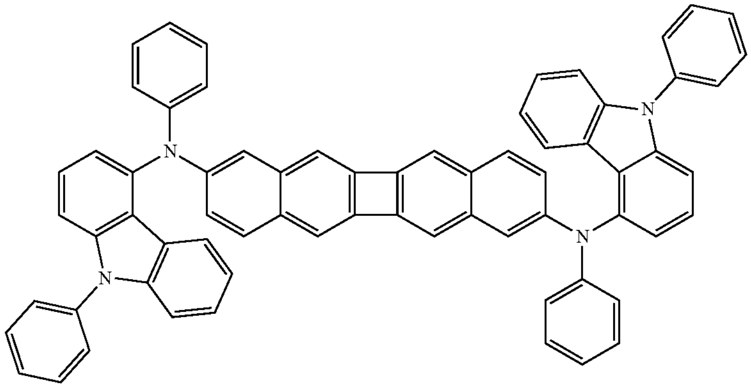
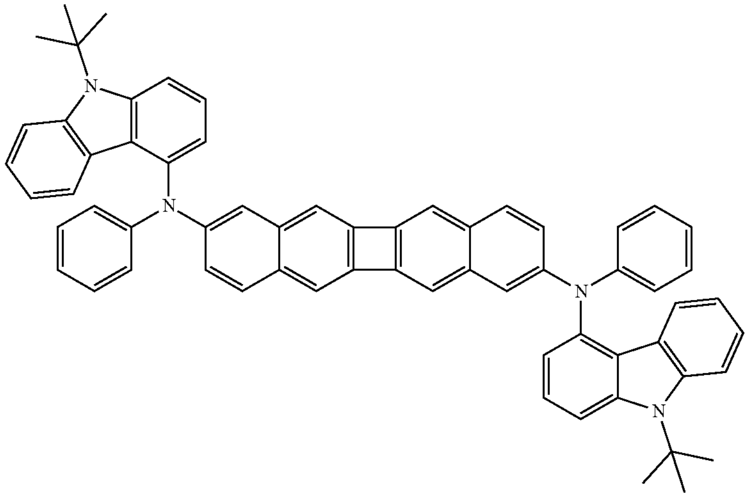

-continued
[Formula 165]
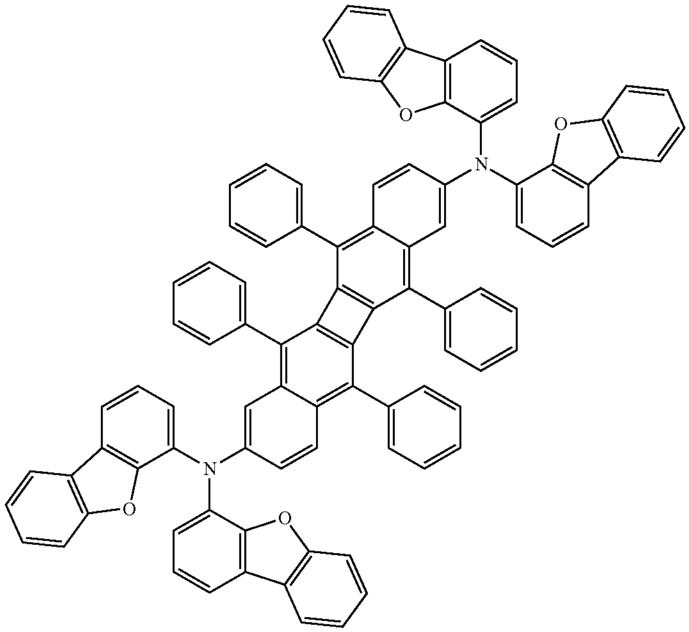
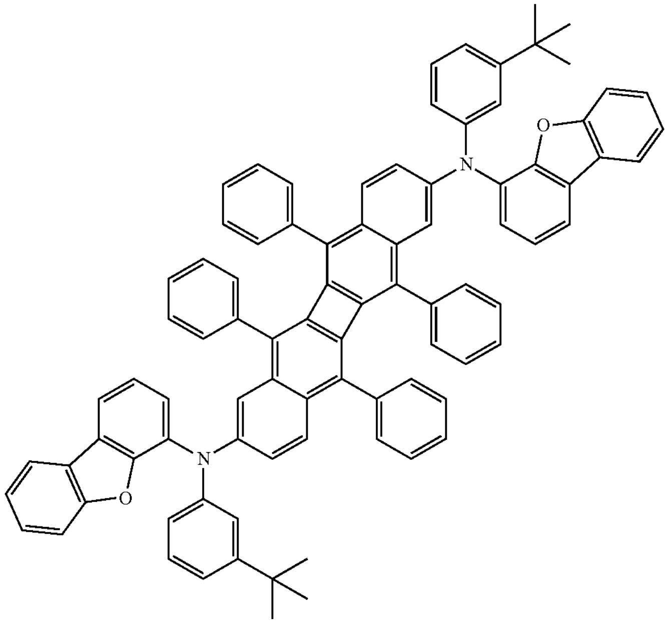

-continued
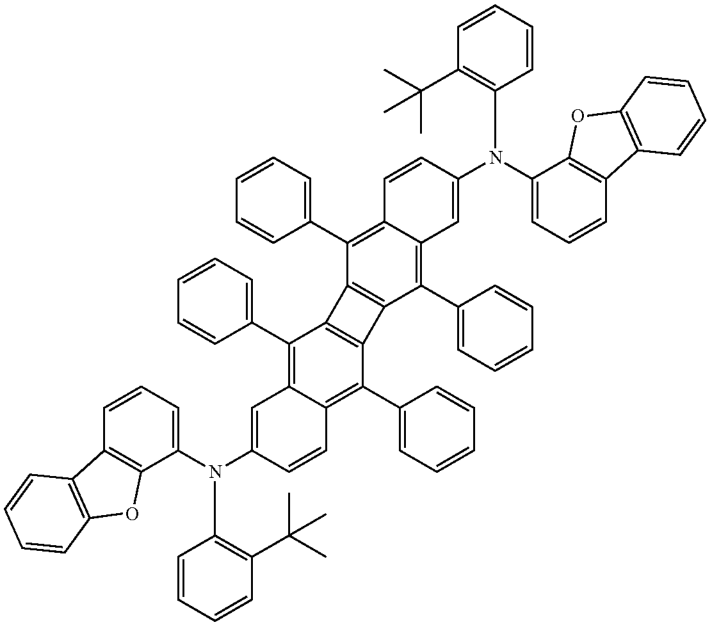
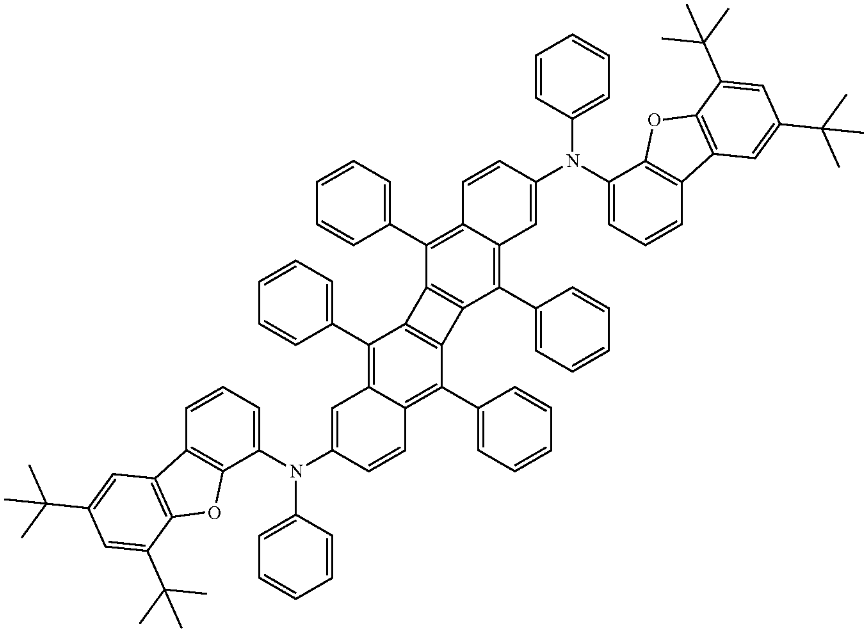

-continued
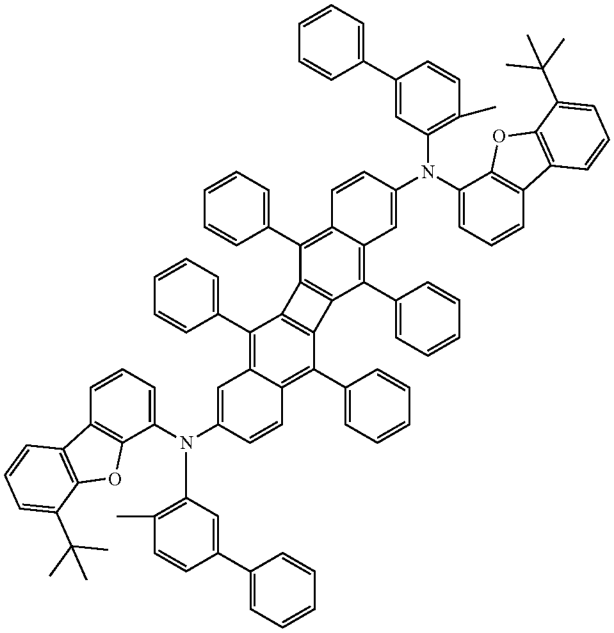
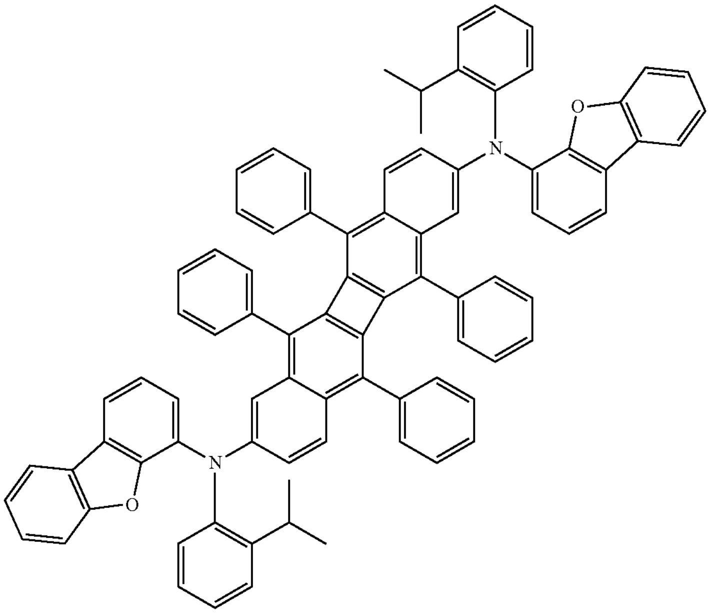

-continued
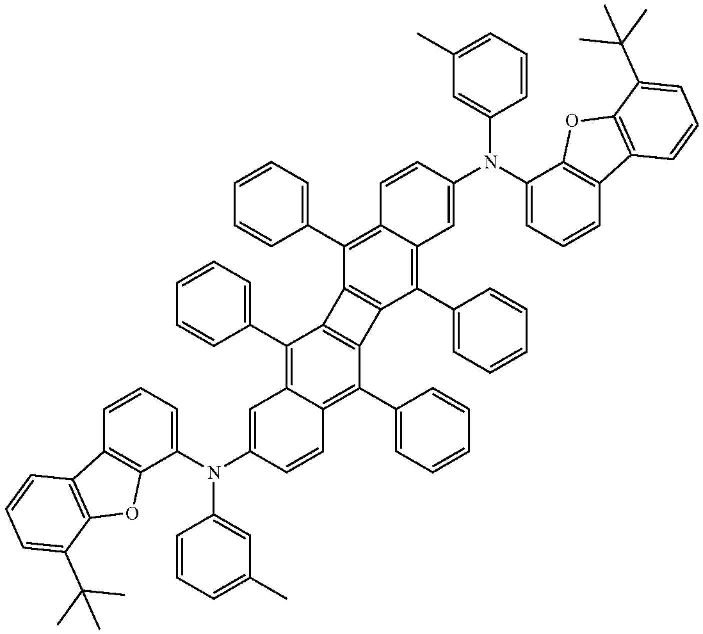
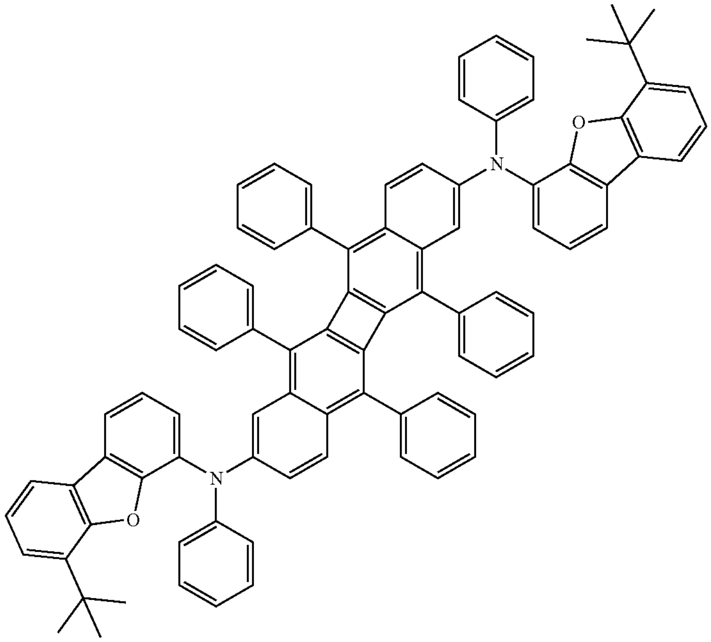

-continued
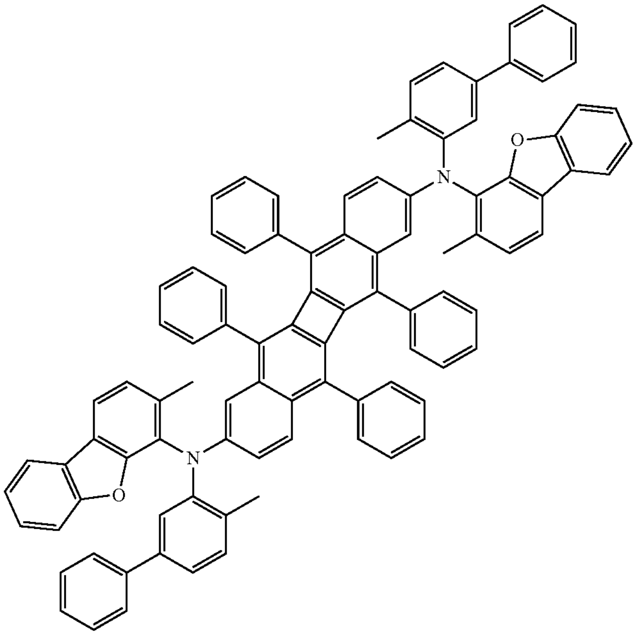
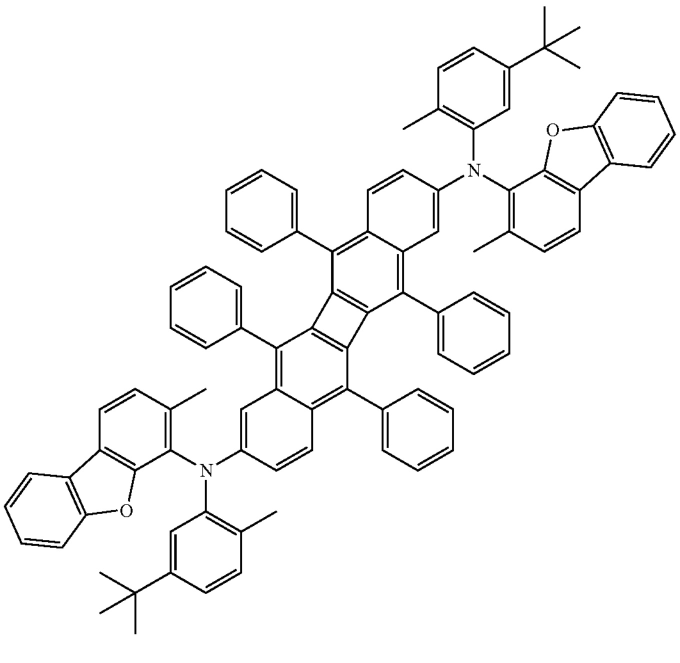

-continued
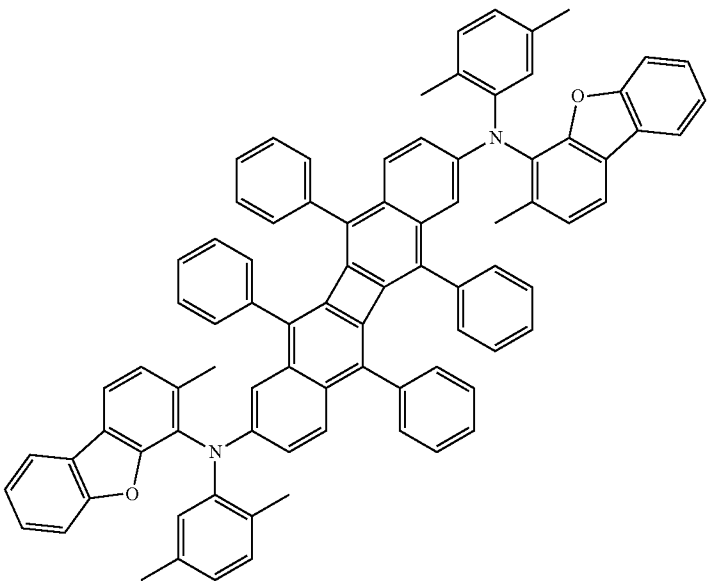
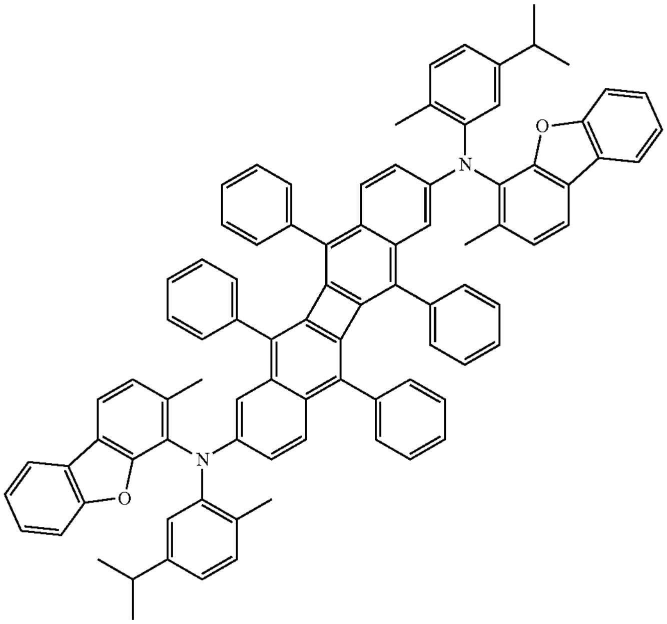

-continued
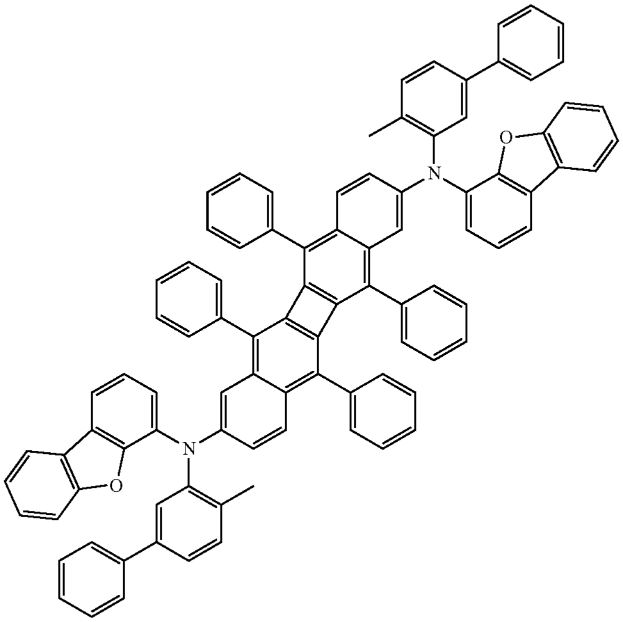
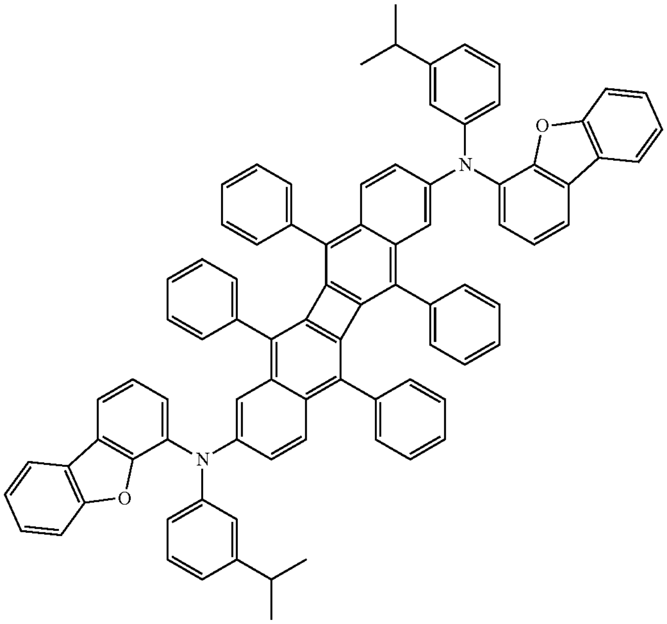

-continued
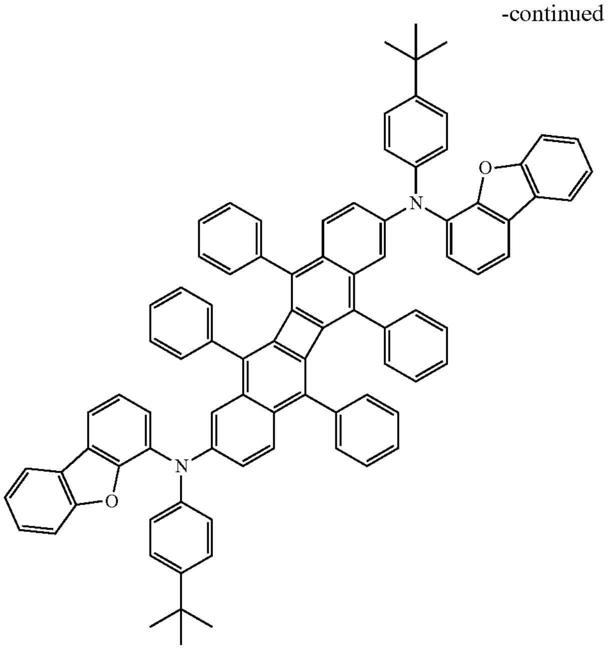
[Formula 166]
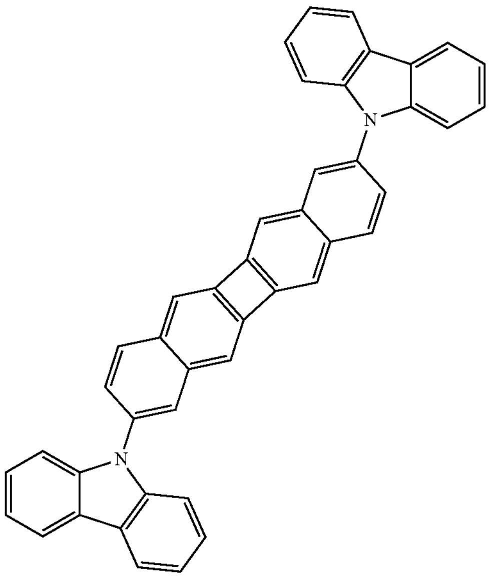
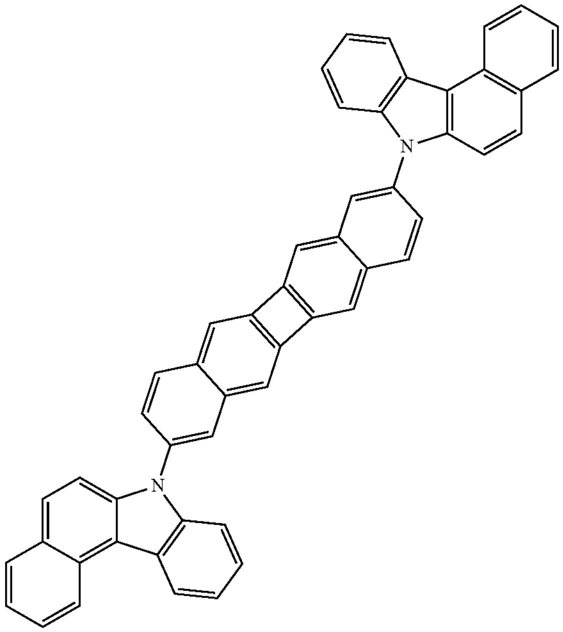

-continued
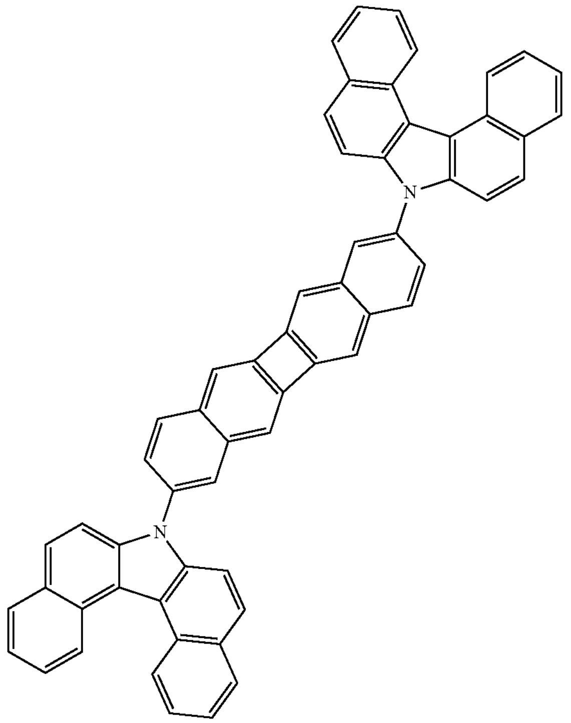
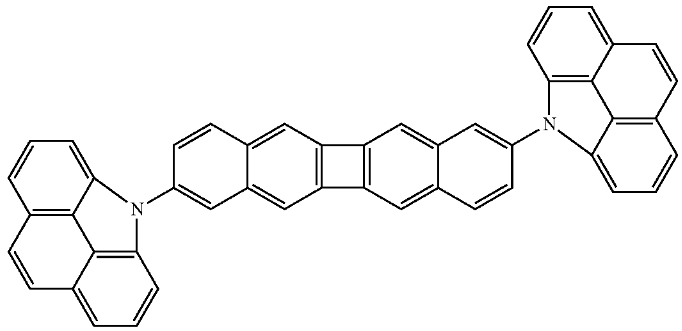
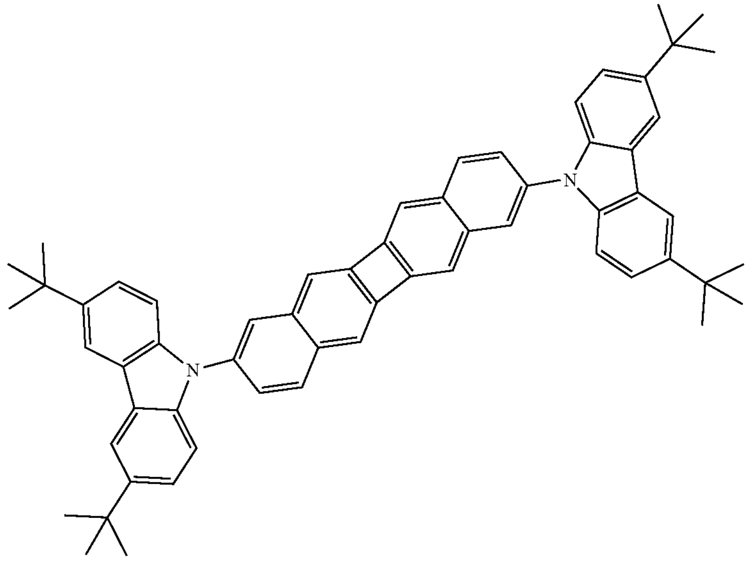

-continued
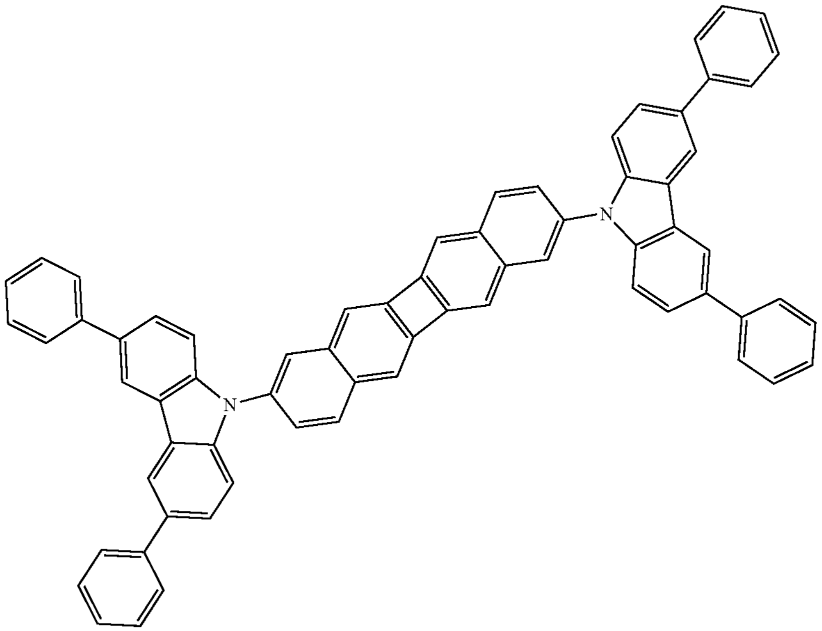
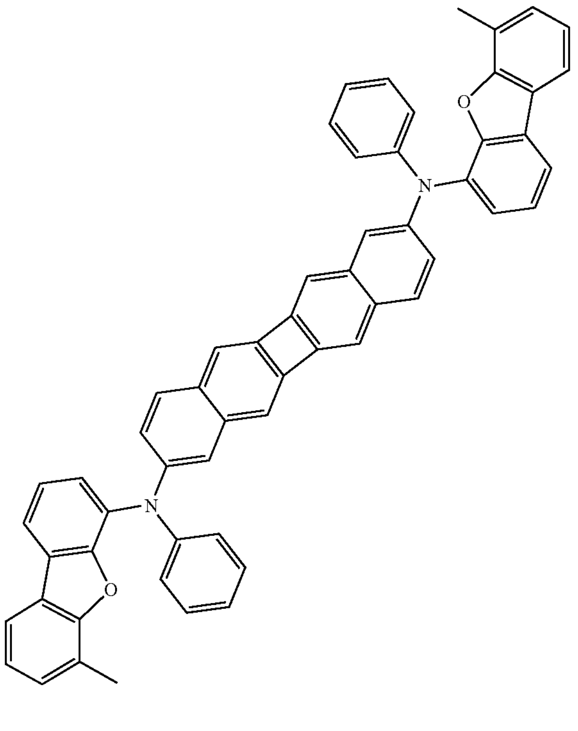
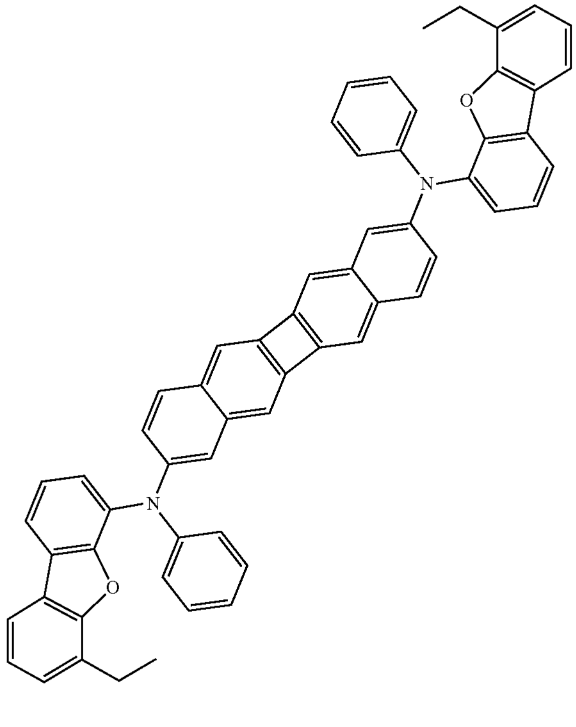

-continued
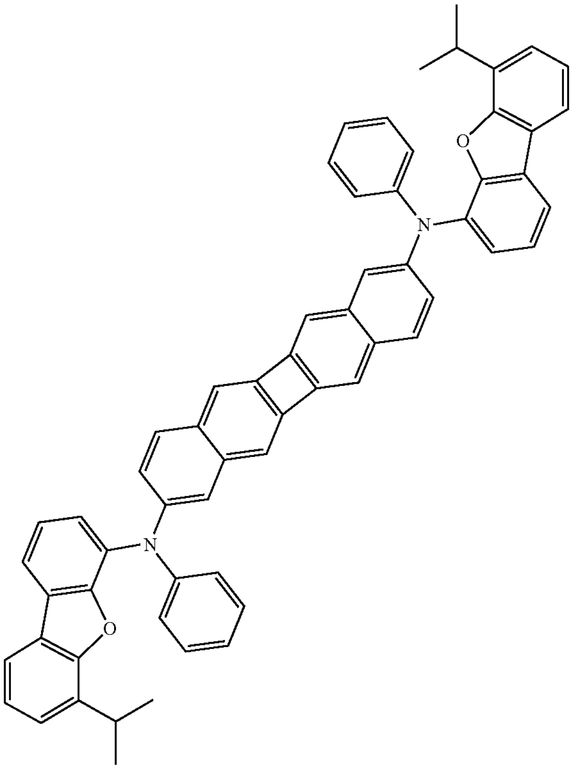
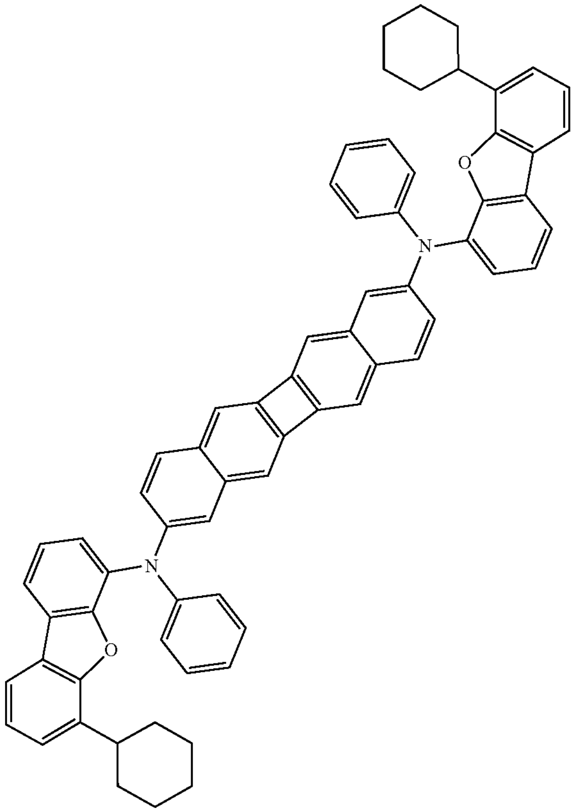
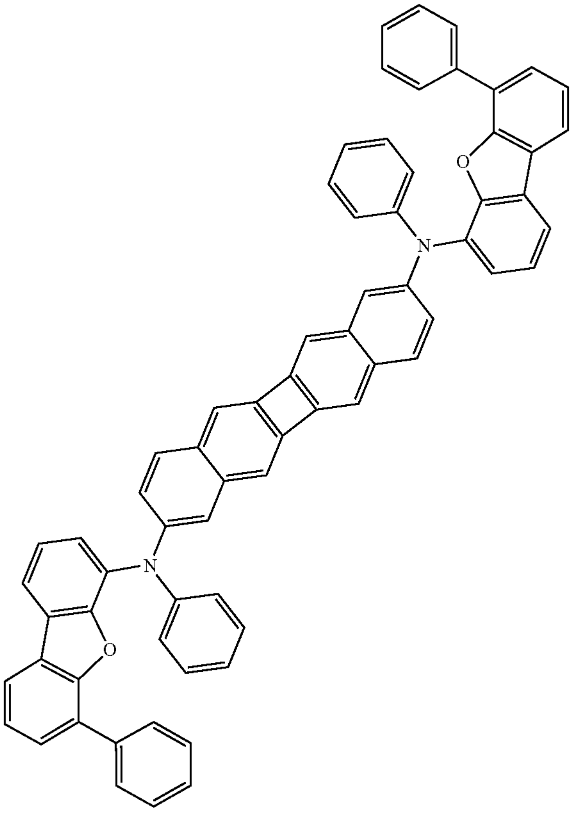
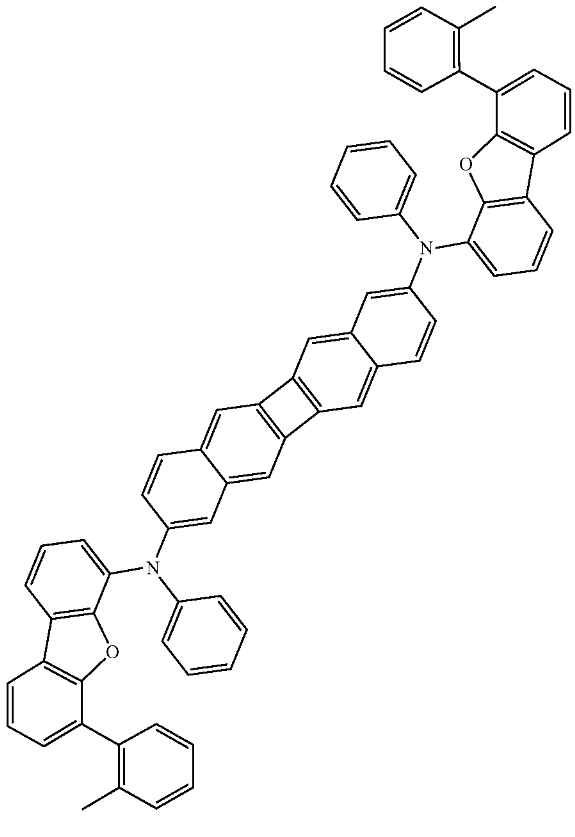

-continued
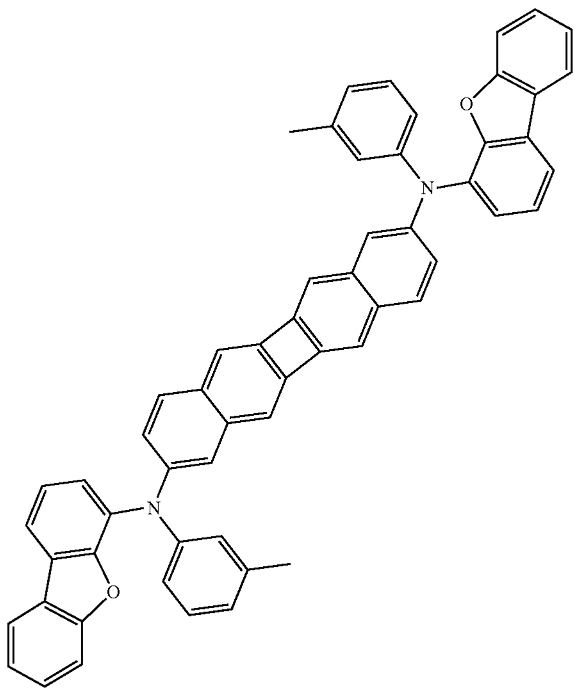
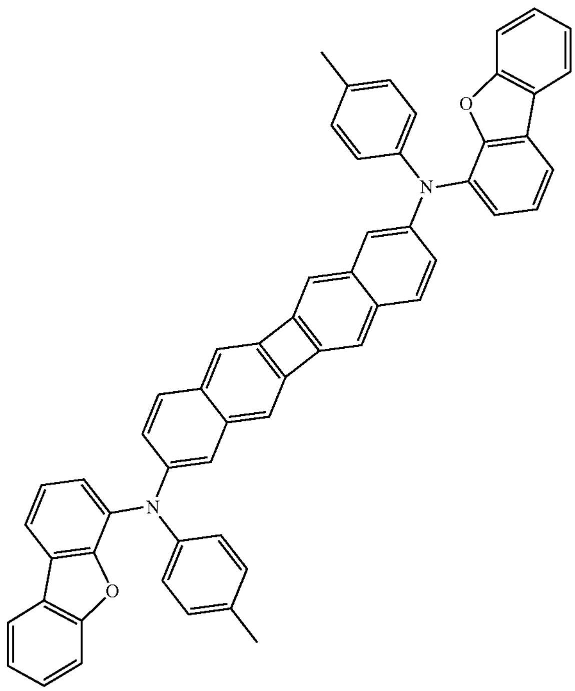
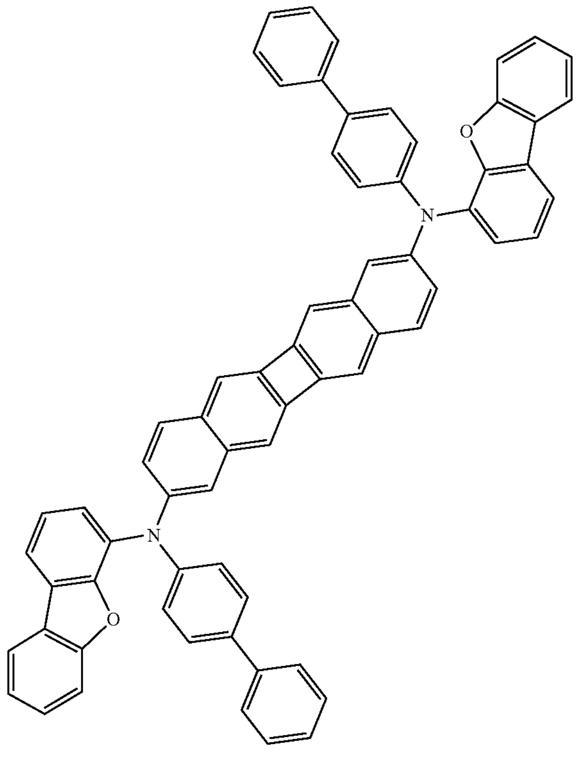

-continued
[Formula 167]
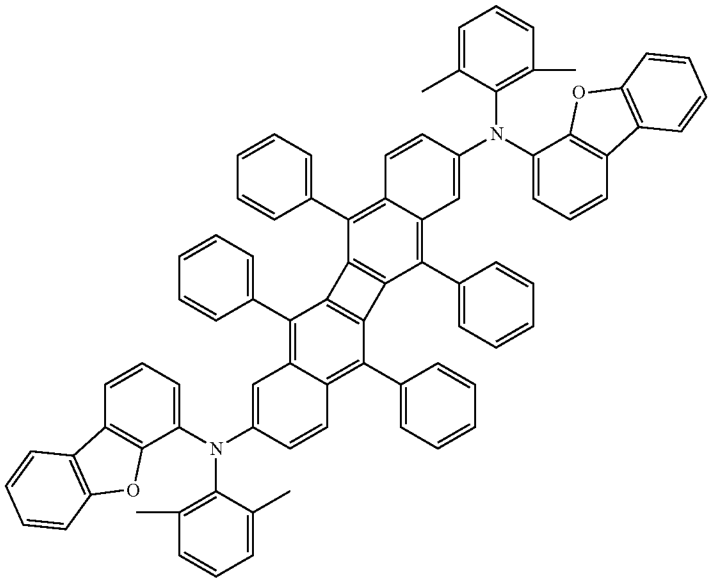
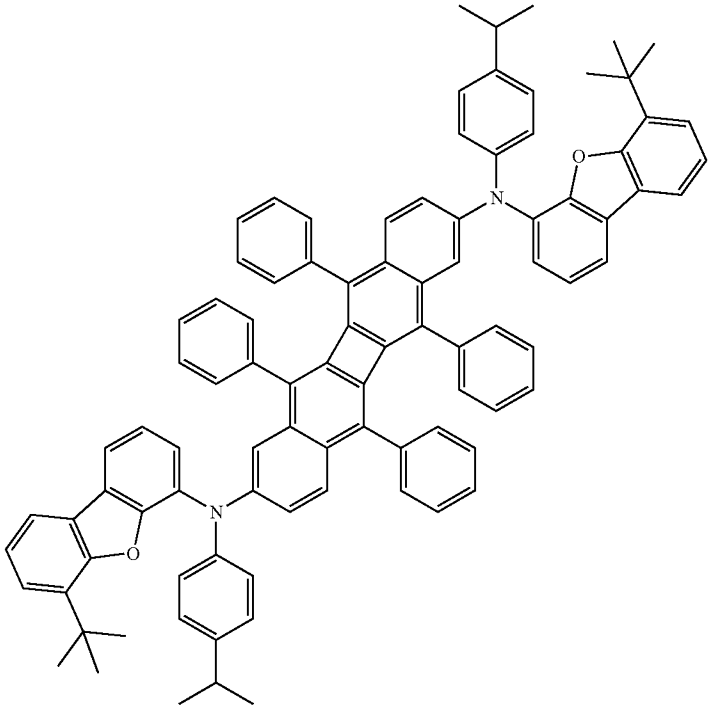

-continued
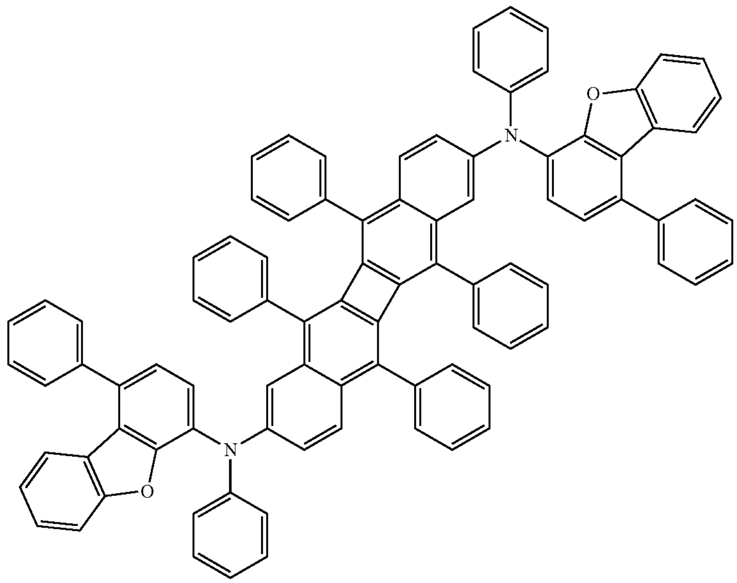
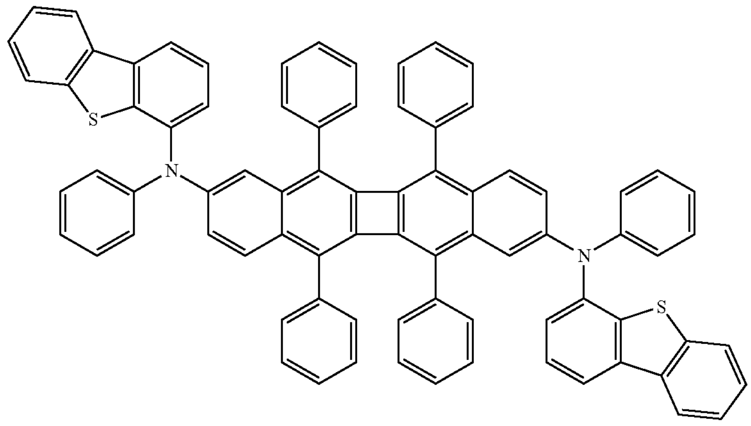
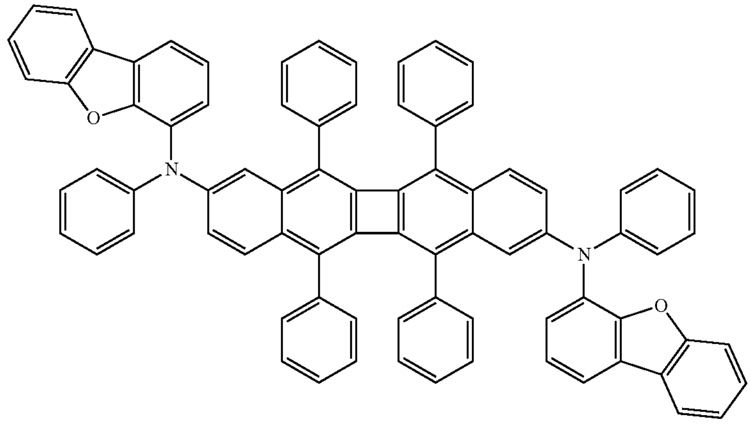

-continued
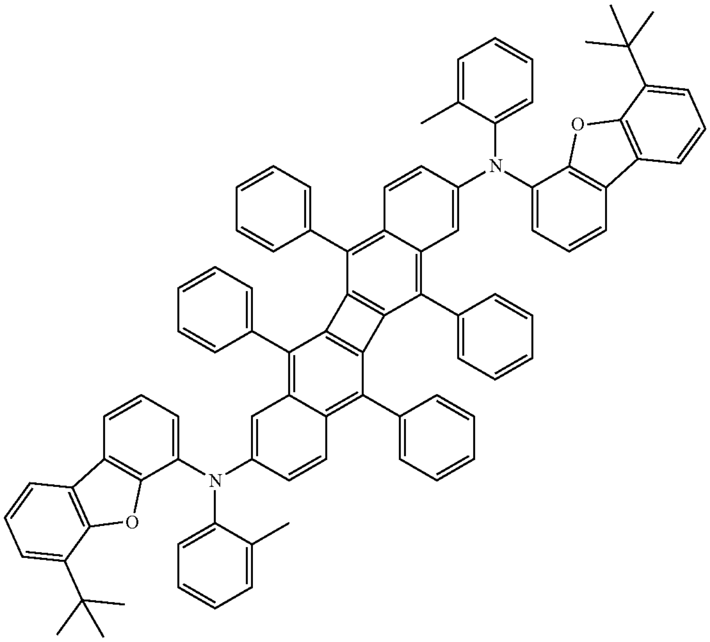
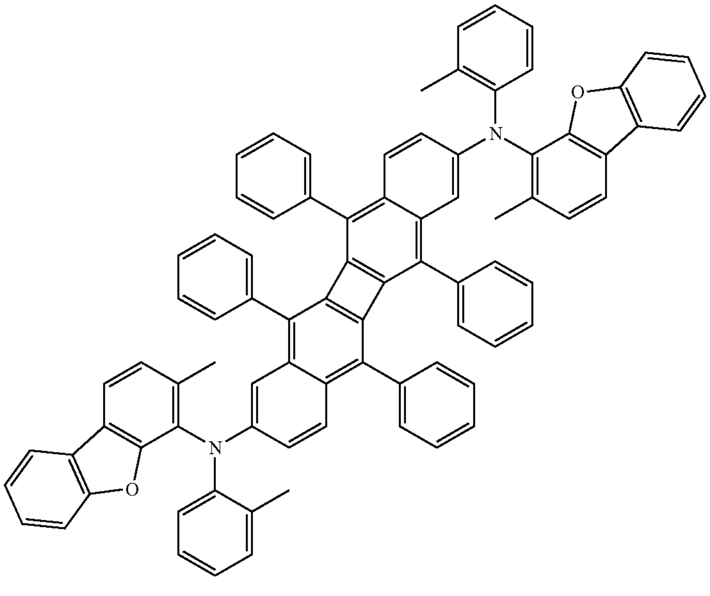

-continued
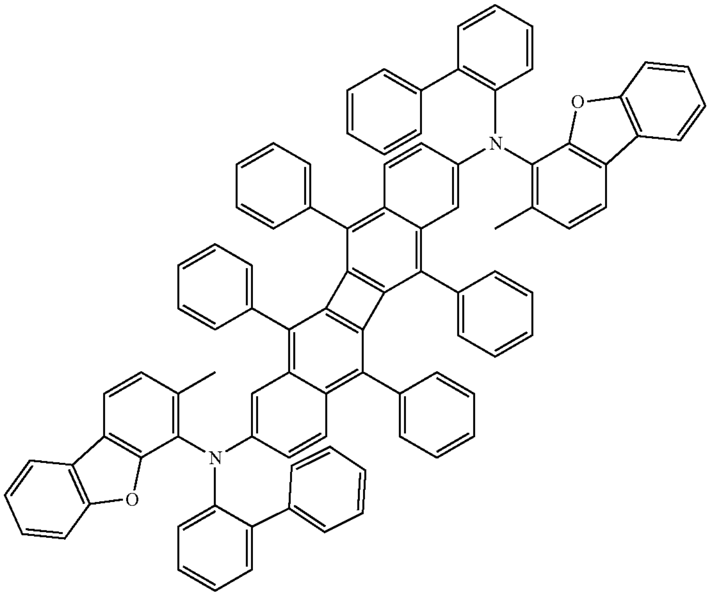
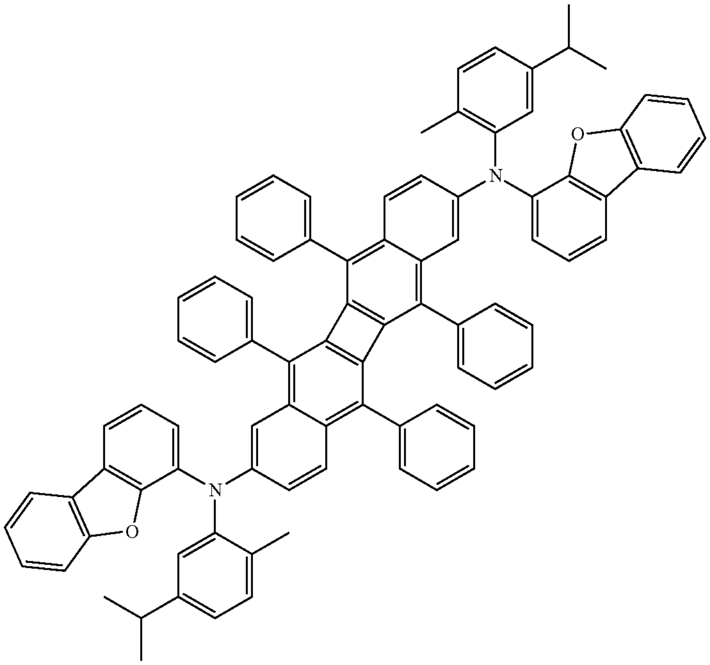
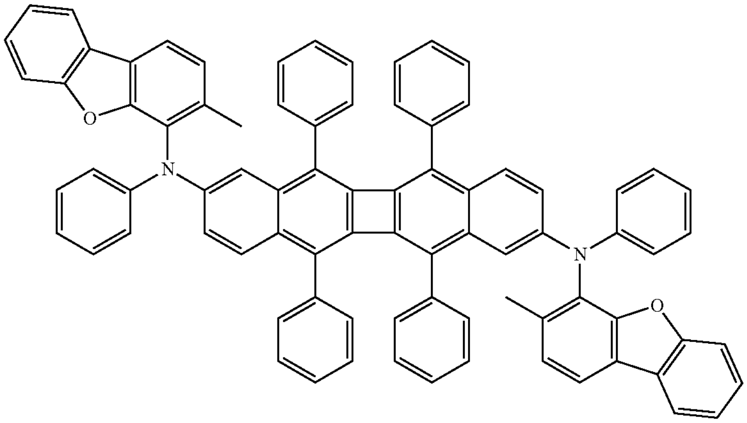

-continued
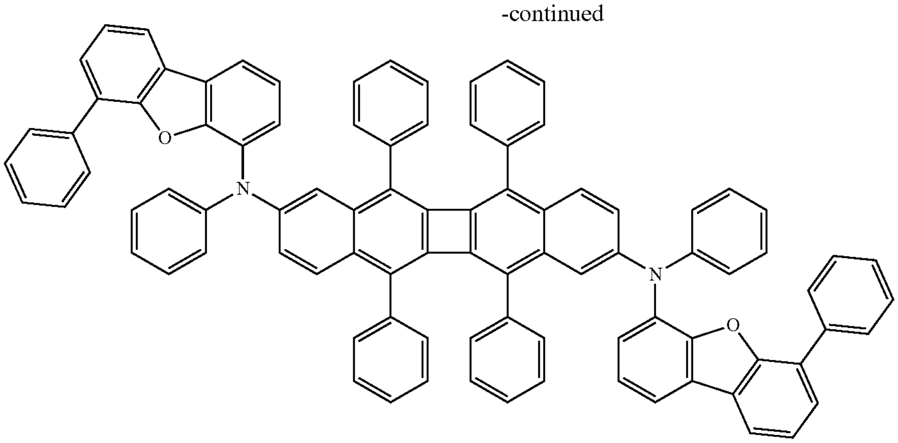
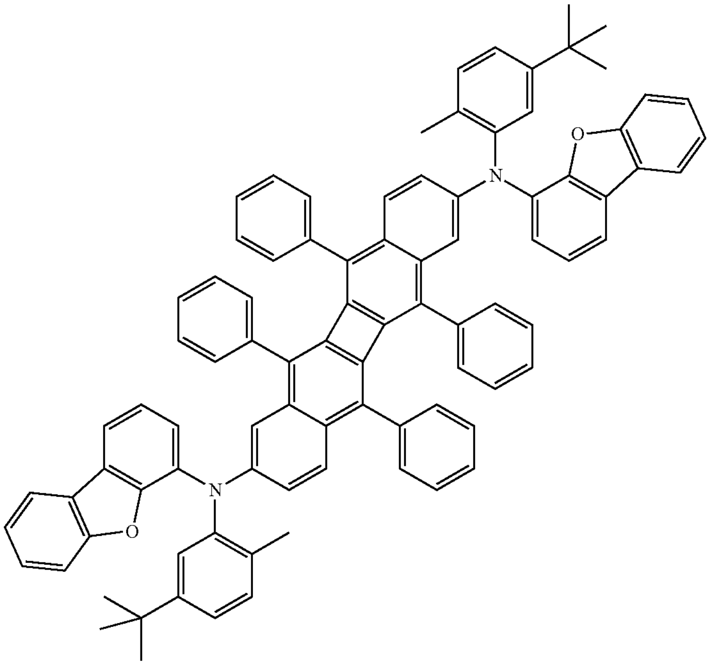
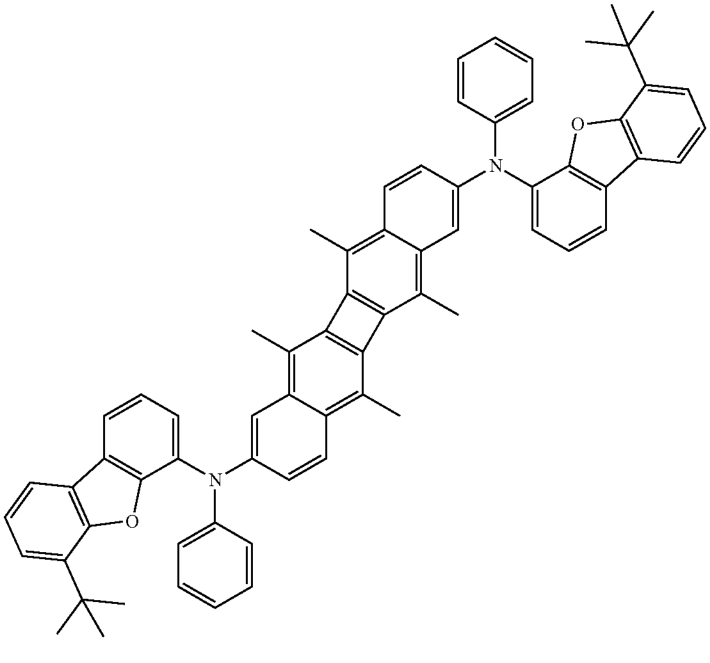

-continued
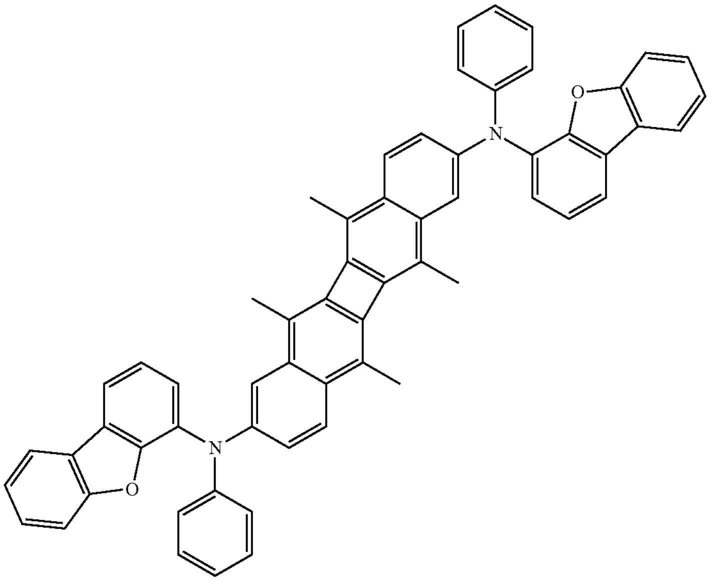
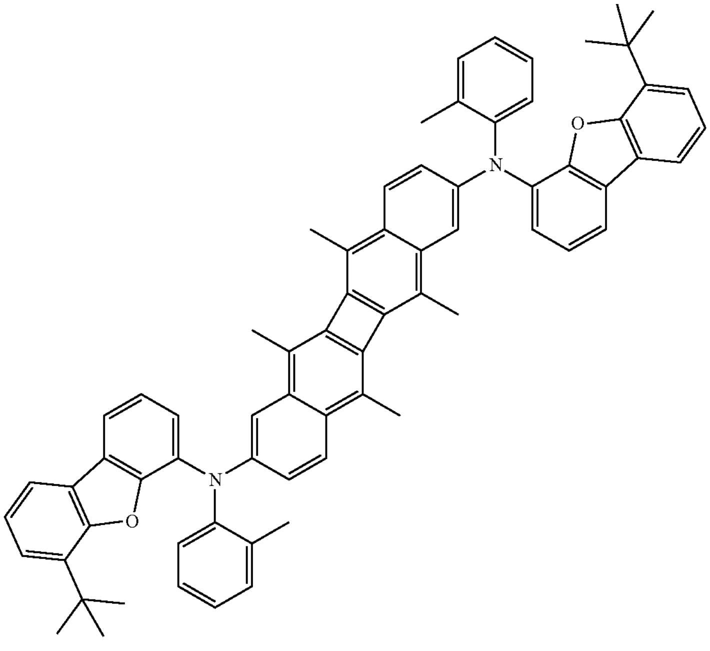

-continued
[Formula 168]
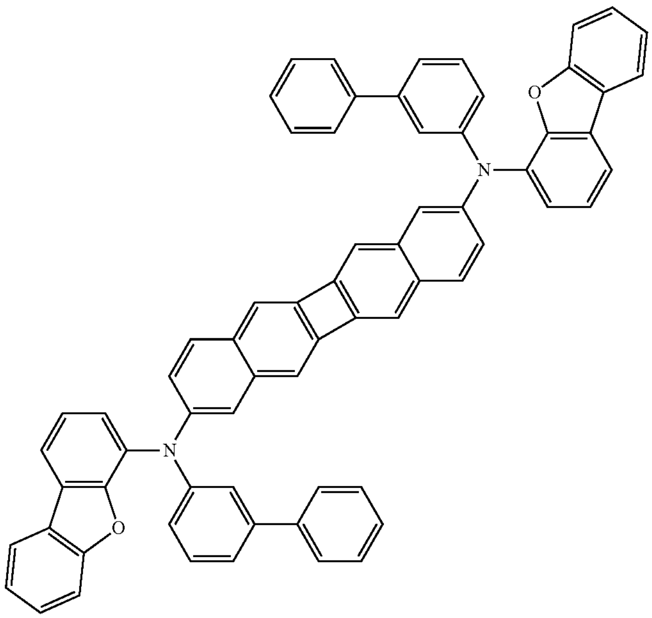
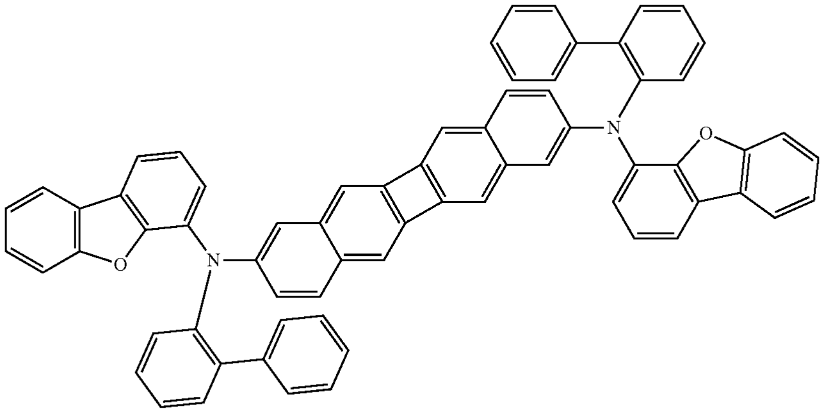
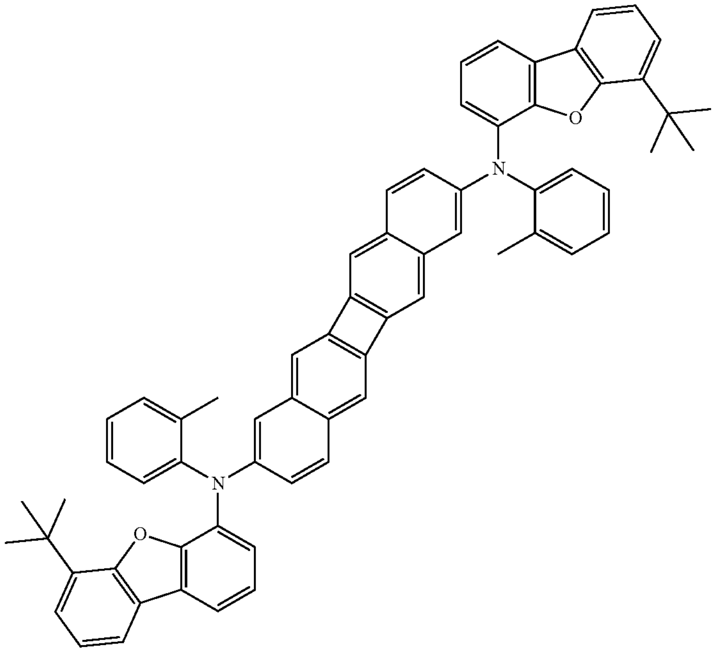

-continued
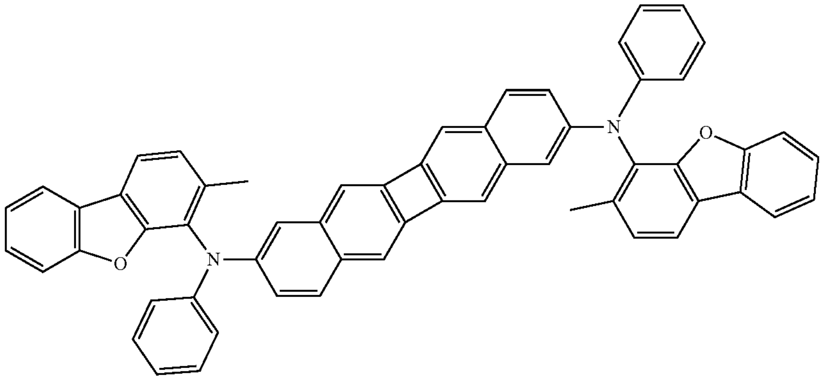
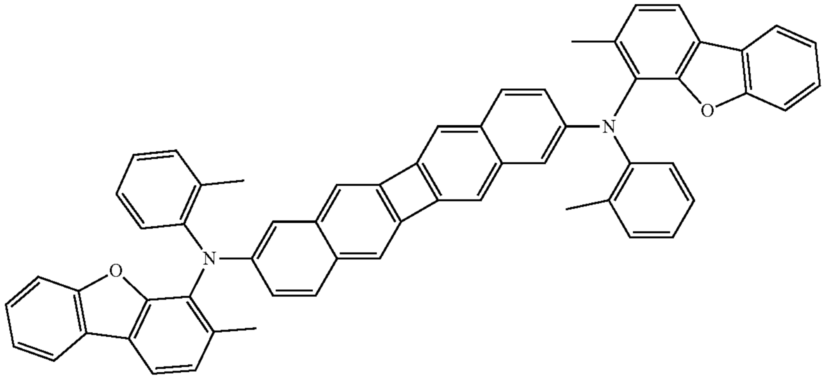
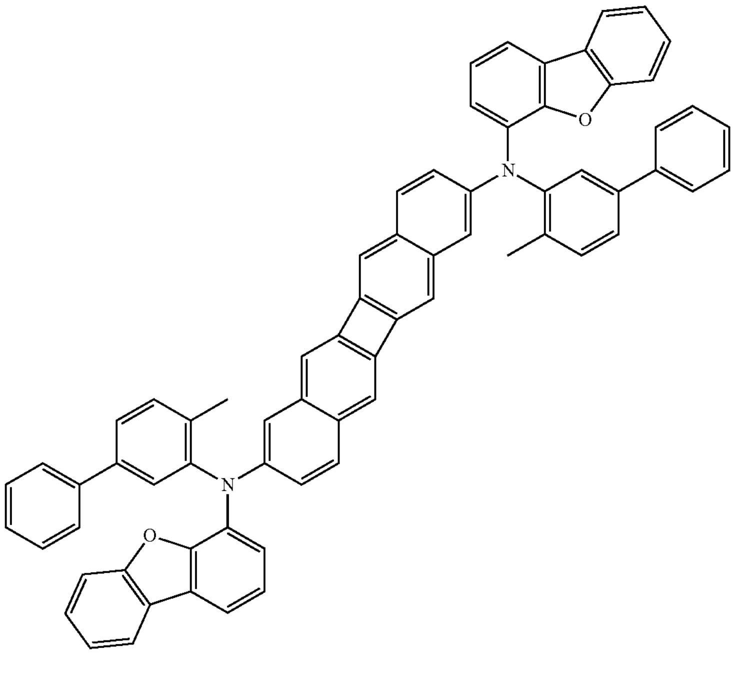

-continued
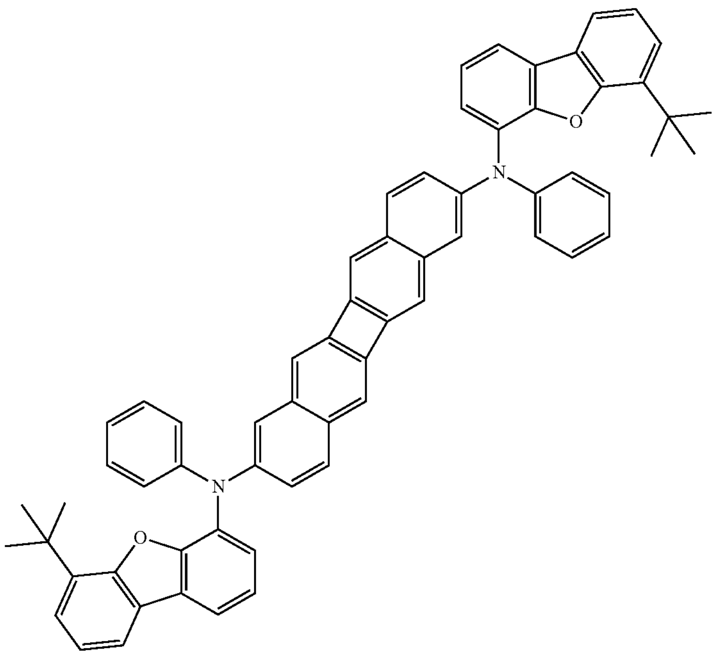
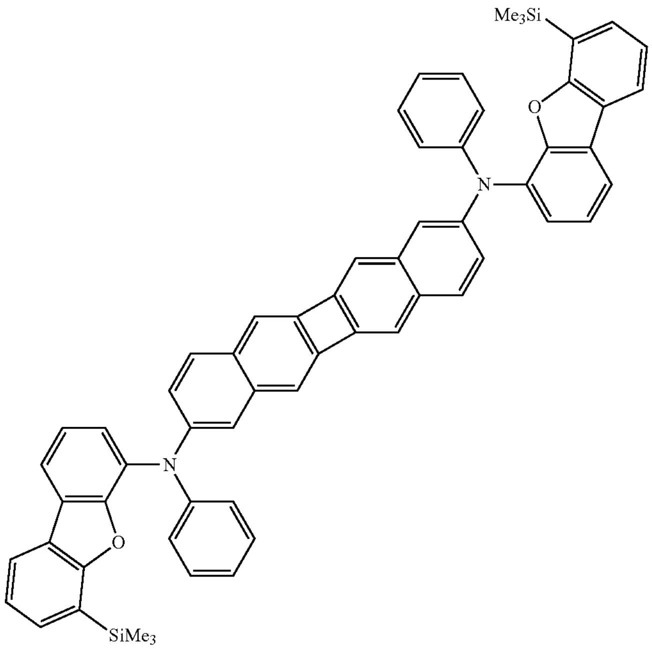

-continued
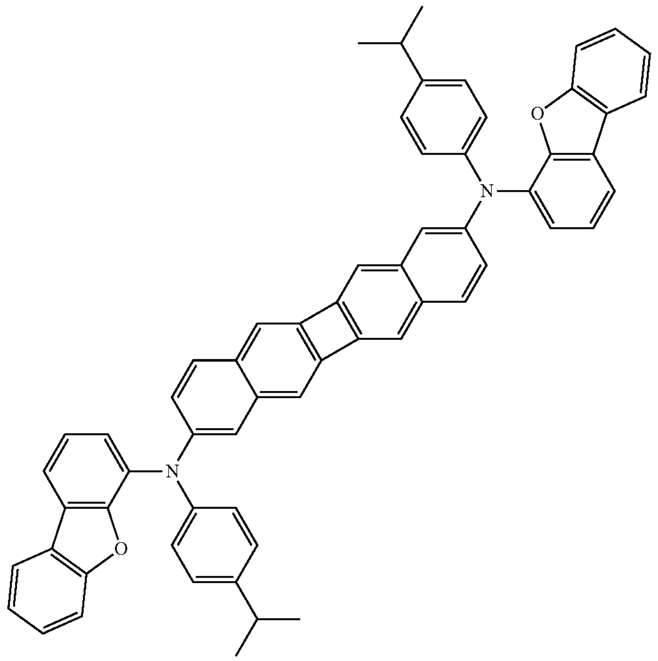
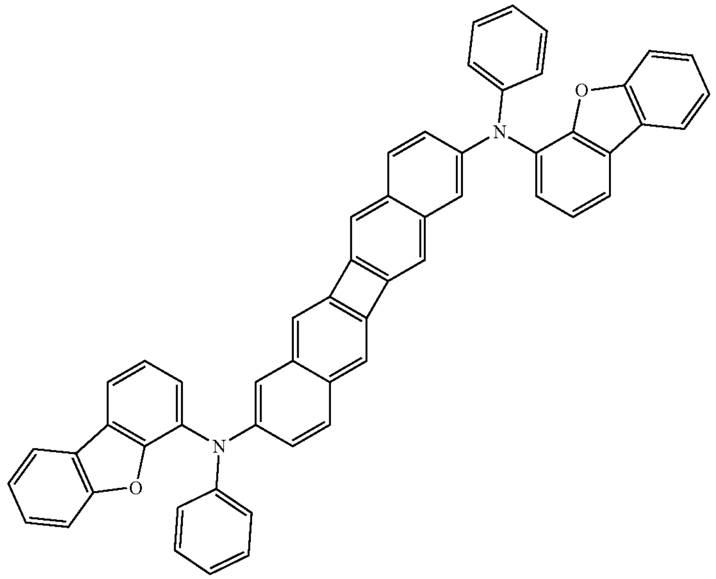
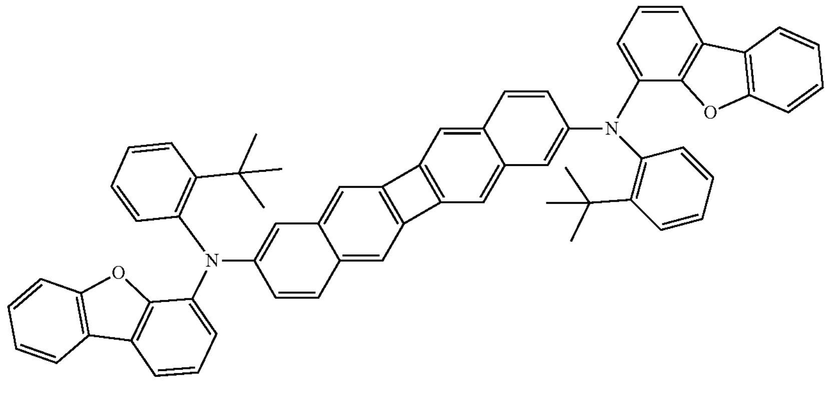

-continued
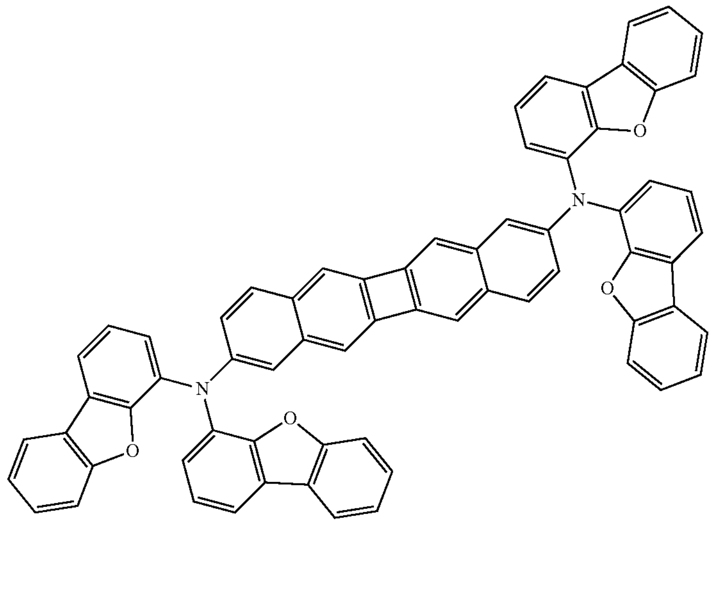
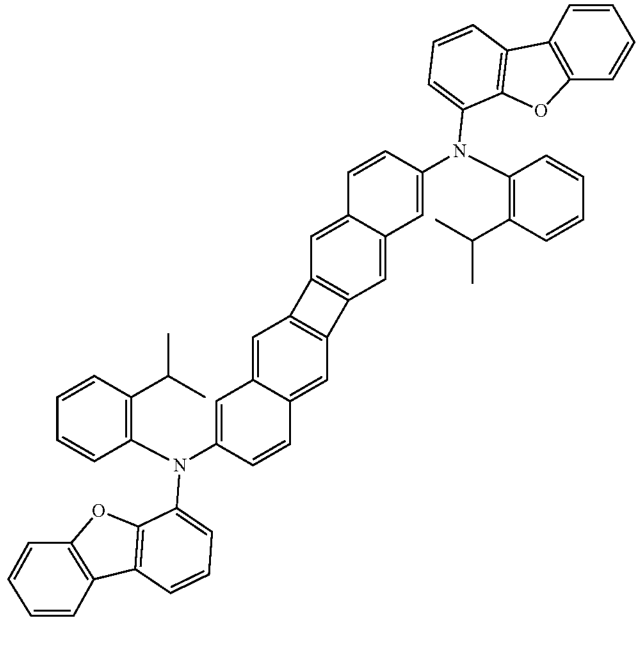

-continued
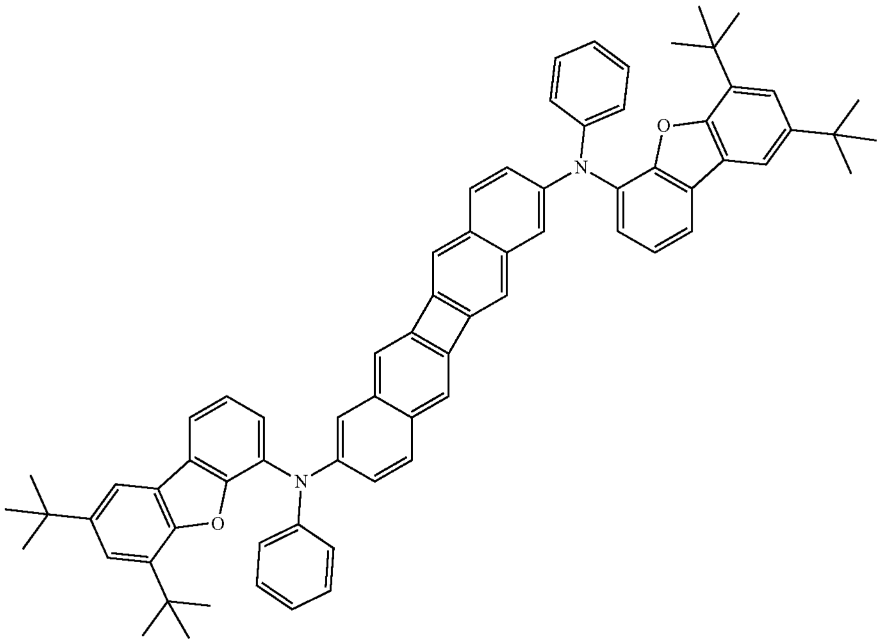
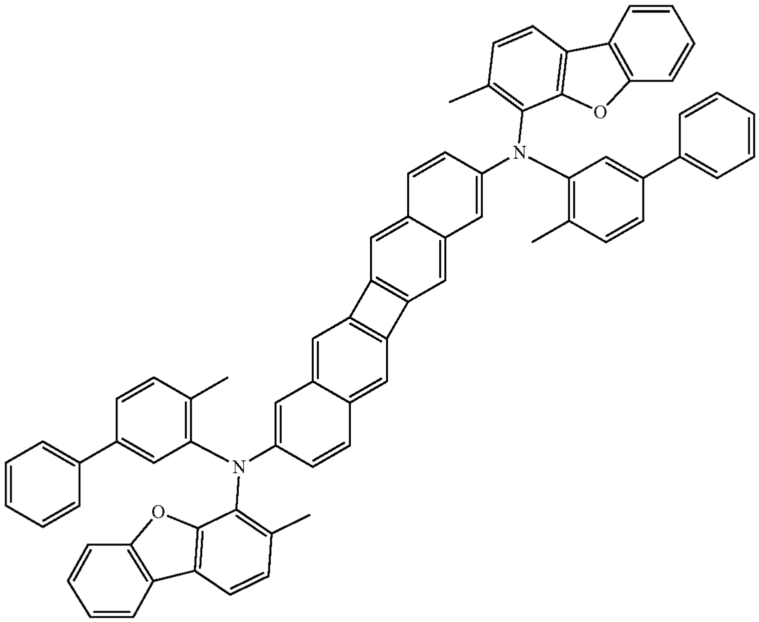
[Formula 169]
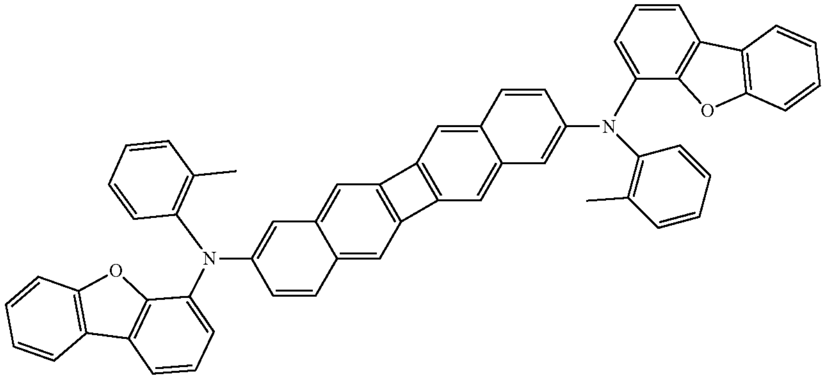

-continued
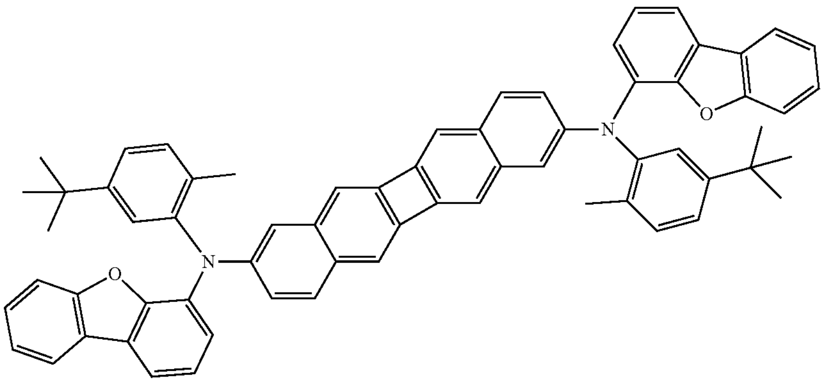
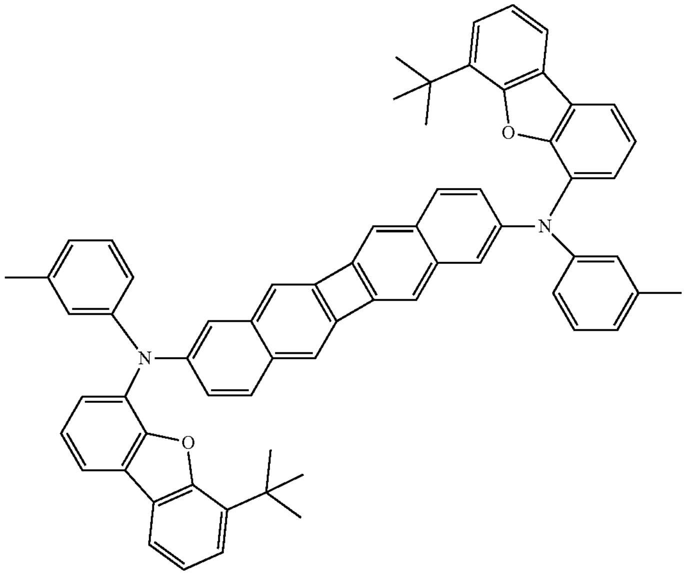
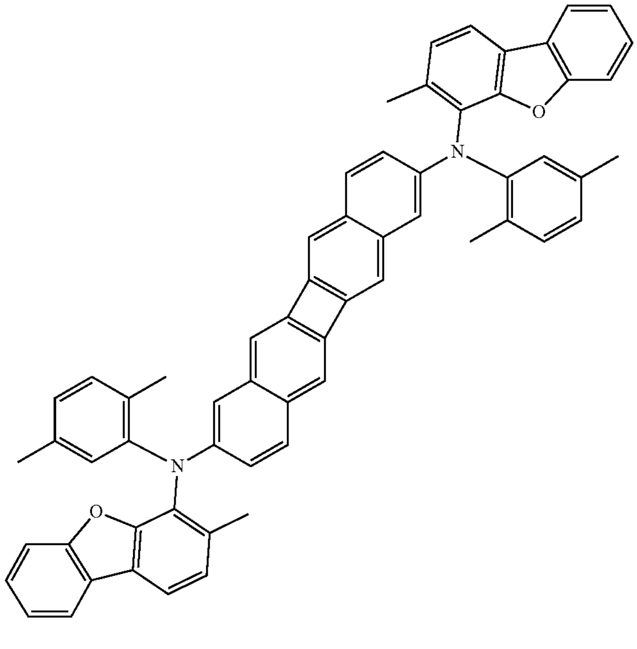

-continued
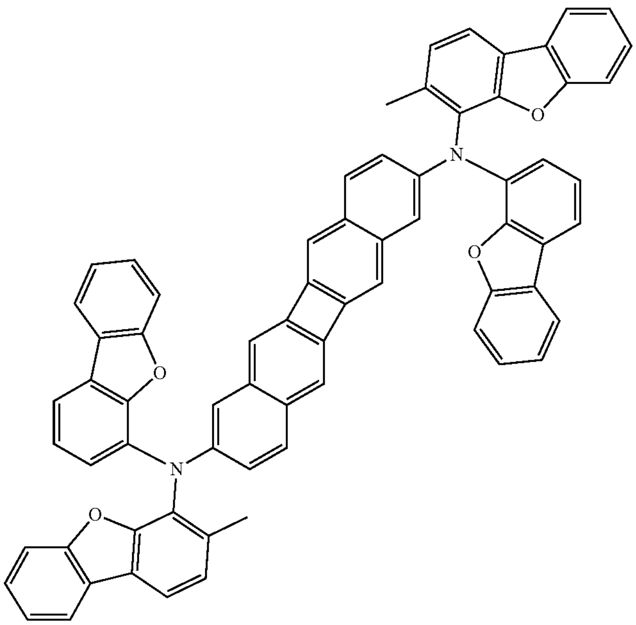
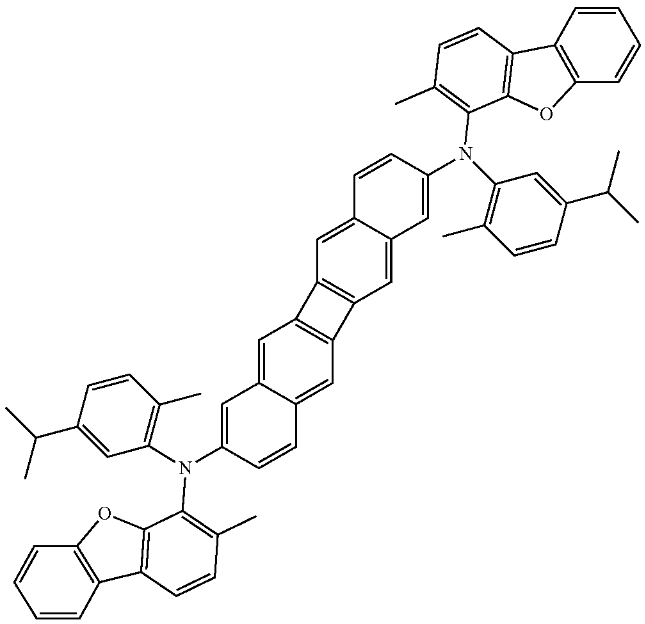

-continued
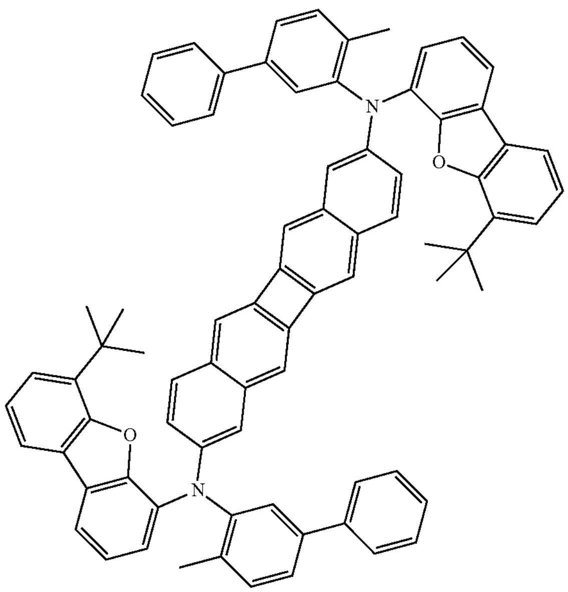
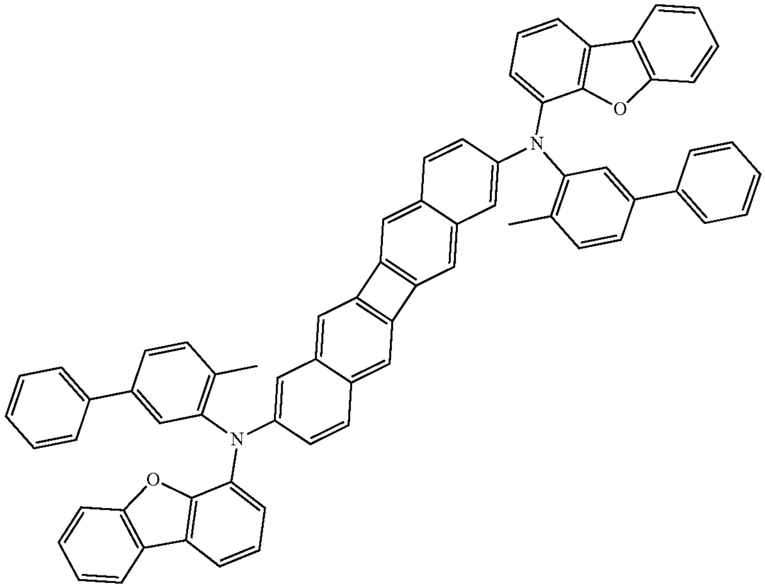

-continued
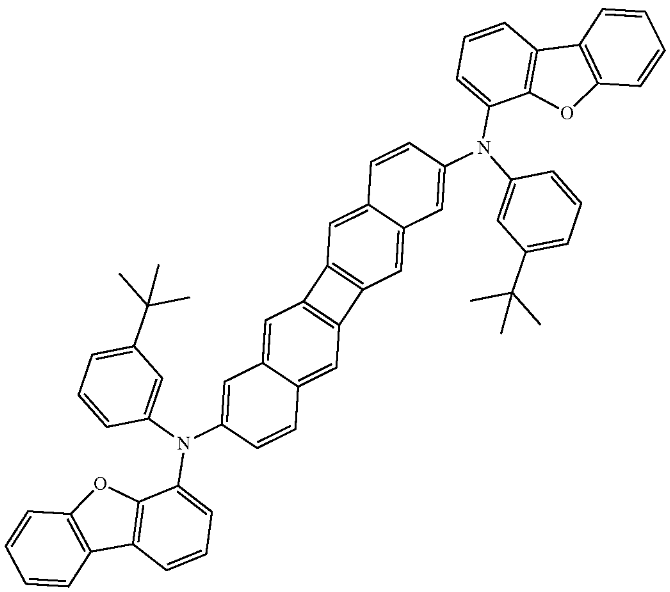
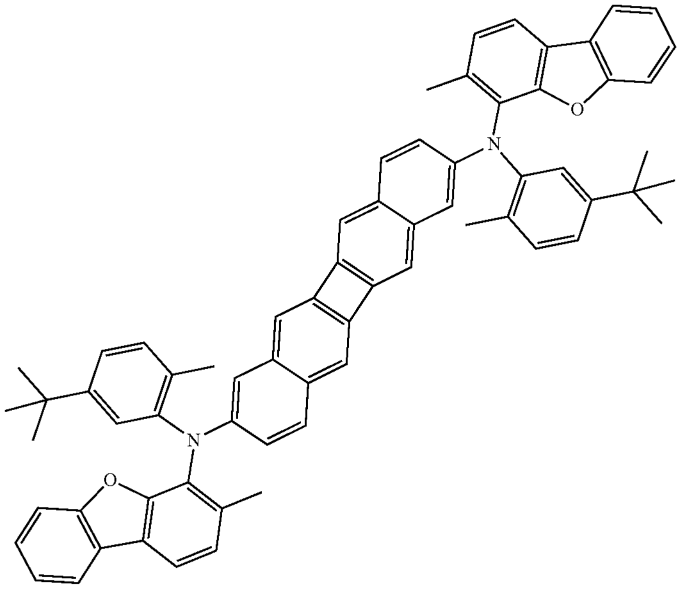

-continued
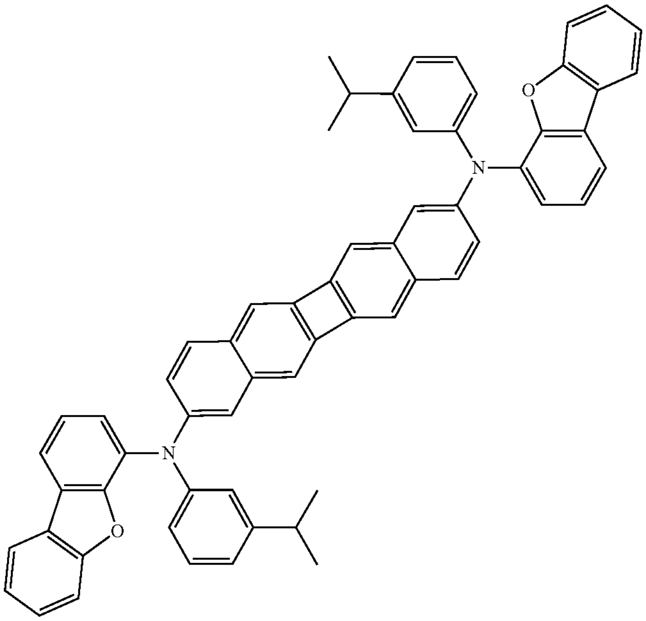
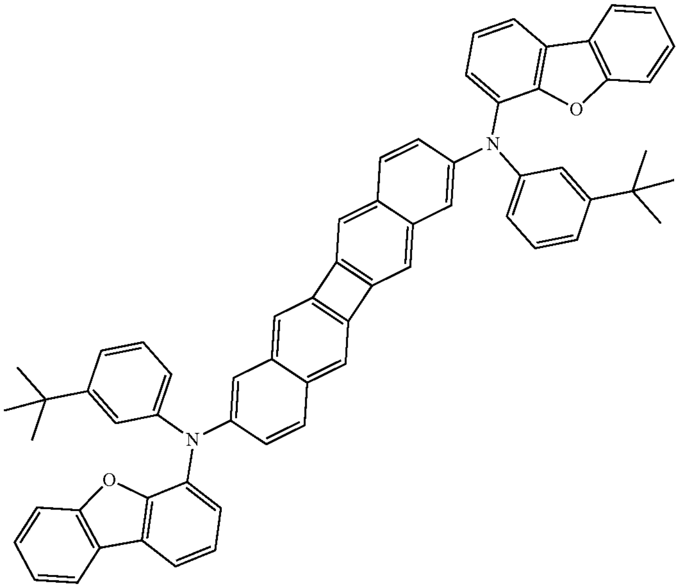

-continued
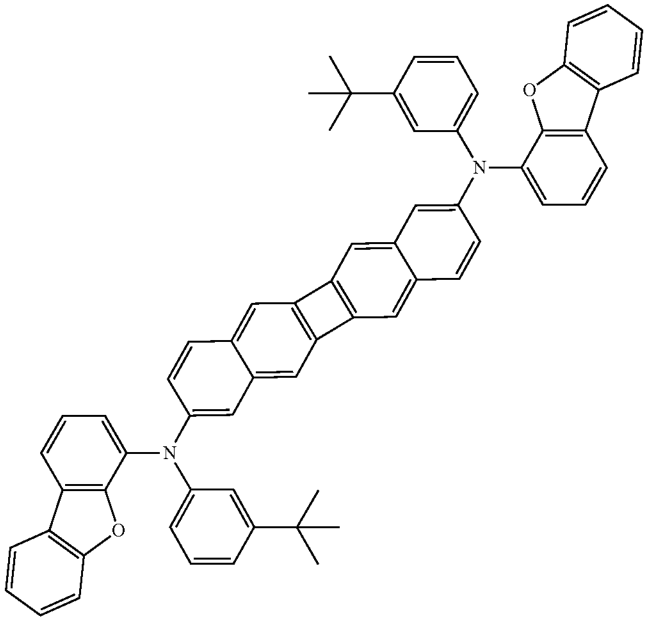
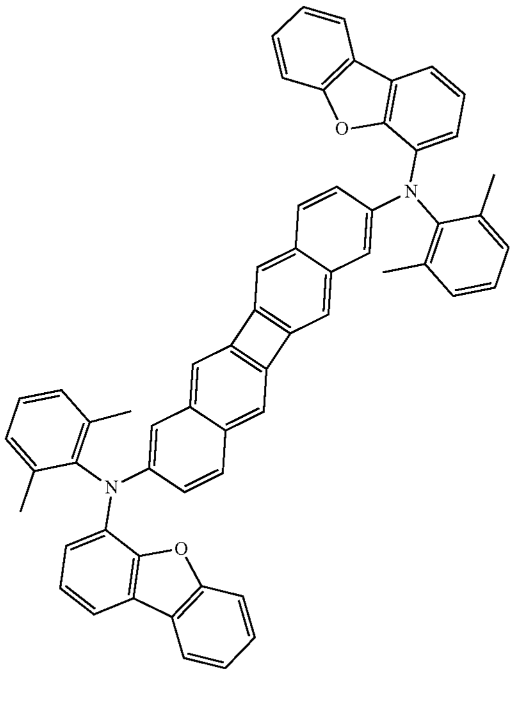
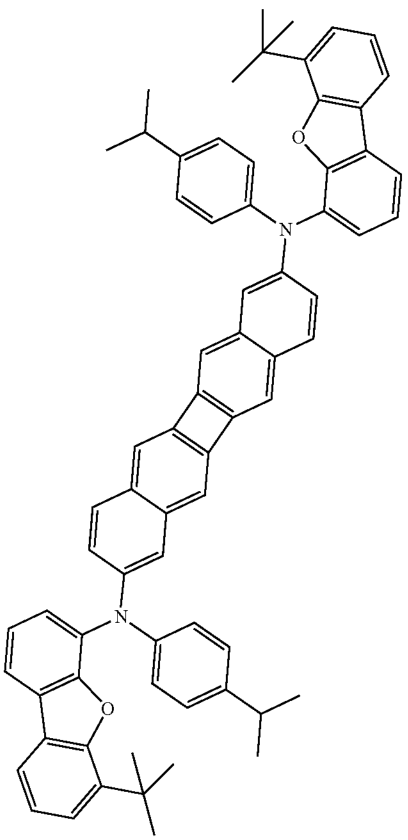

-continued
[Formula 170]
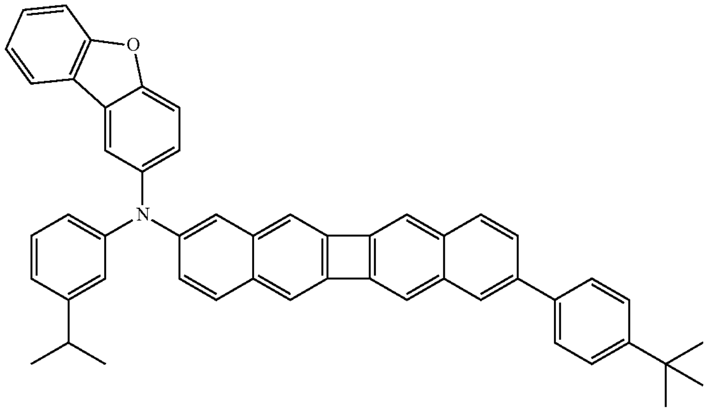
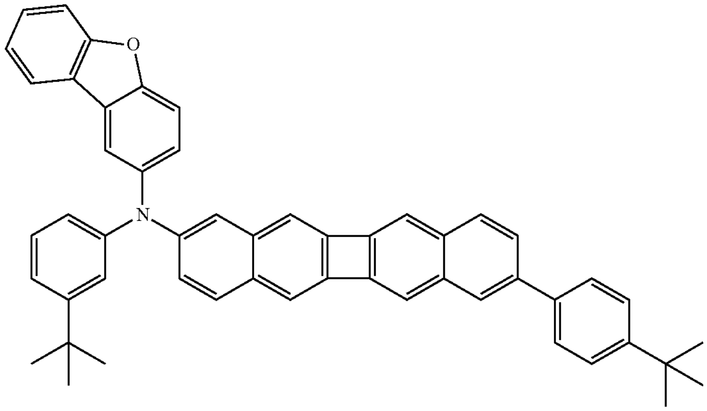
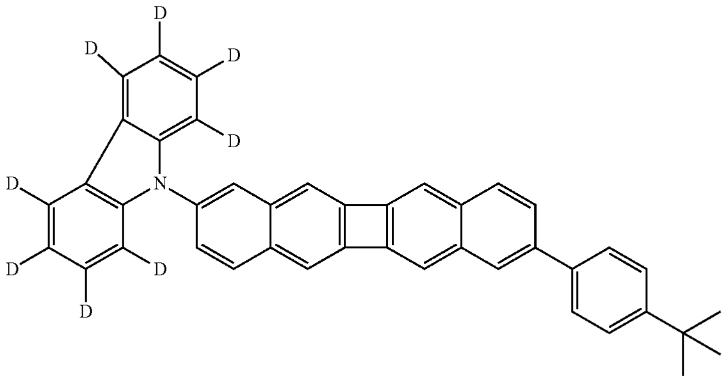
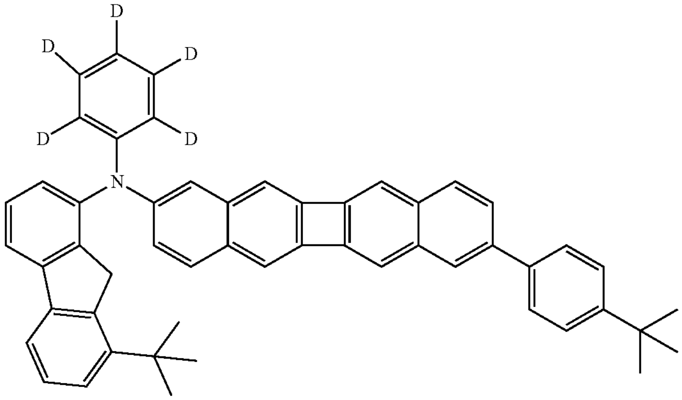

-continued
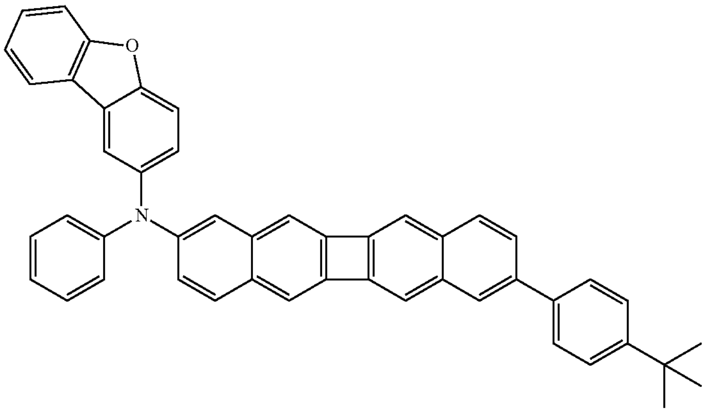
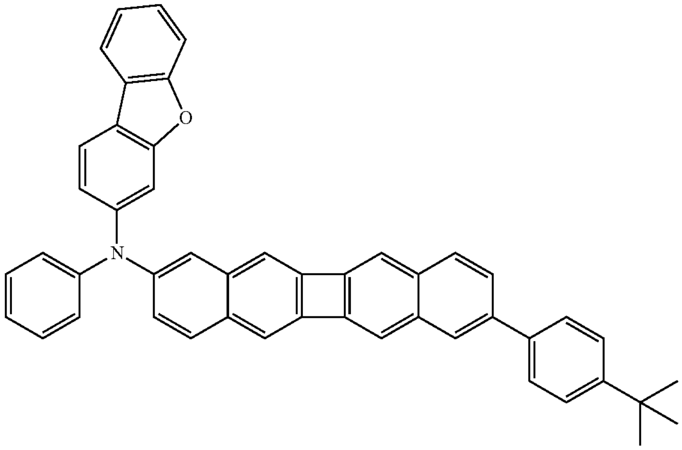
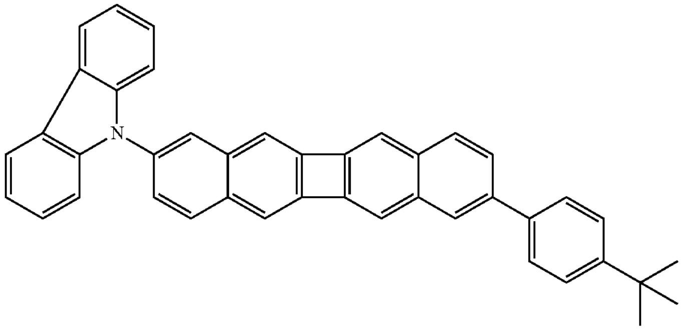
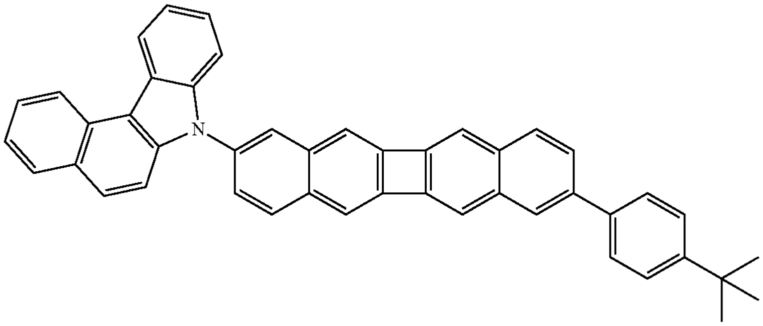

-continued
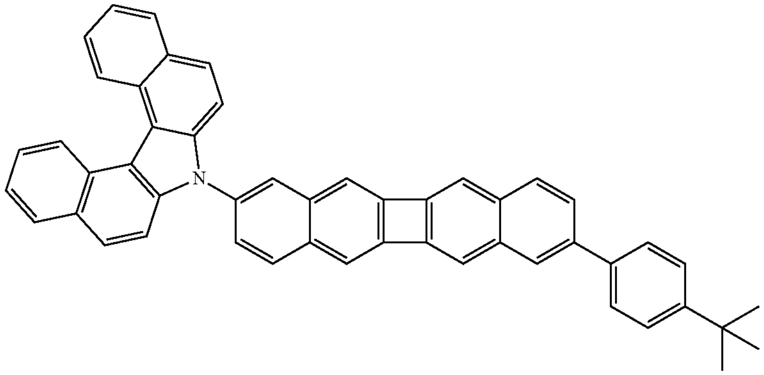
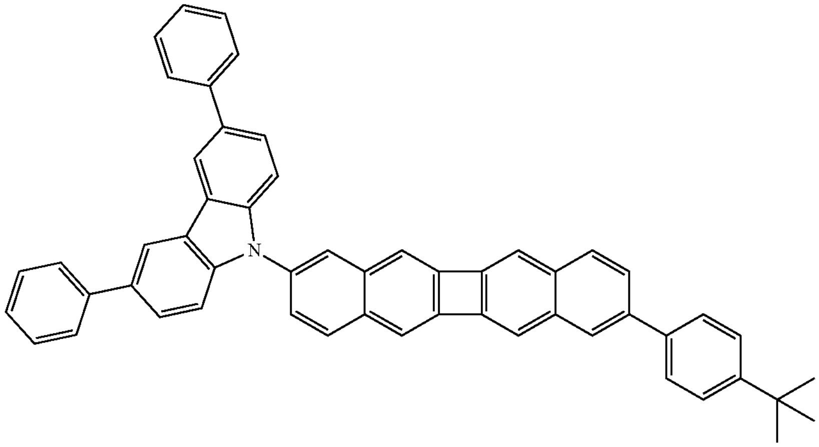
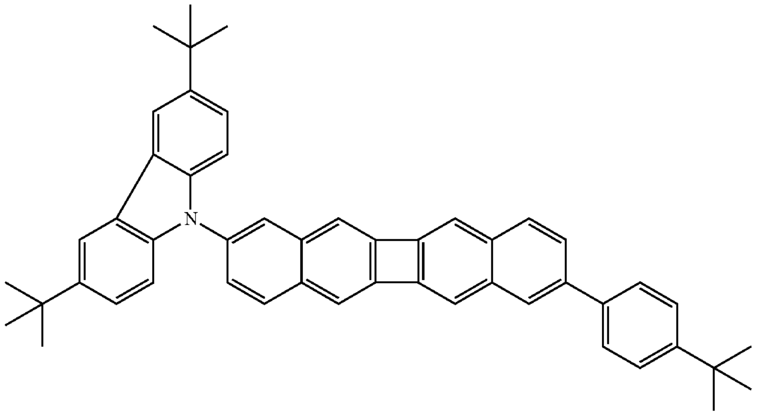
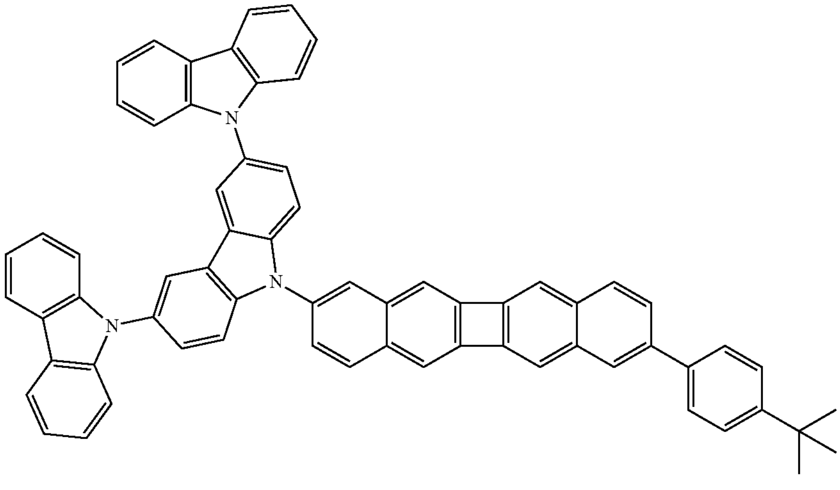

-continued
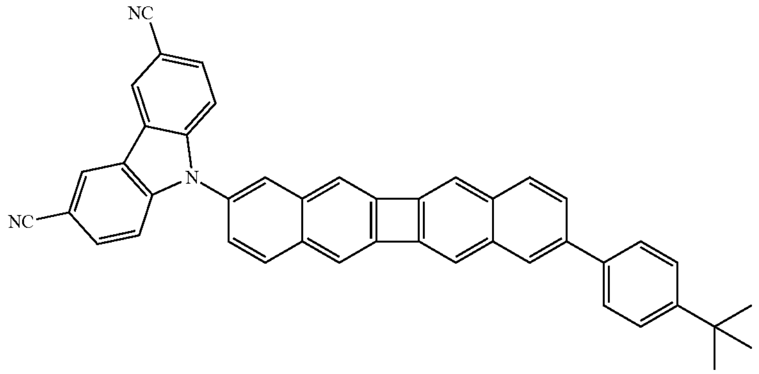
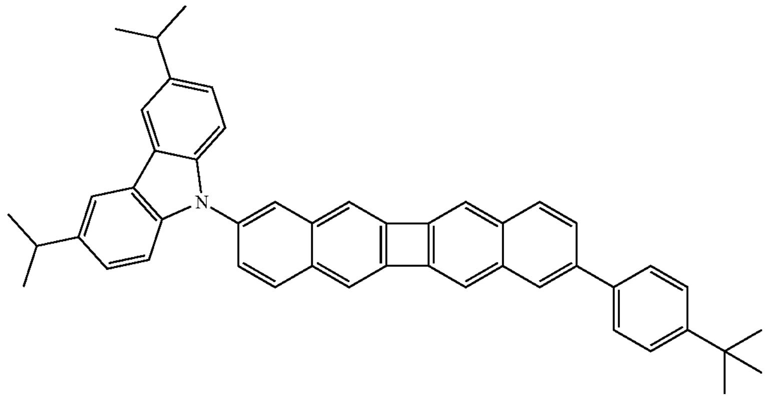
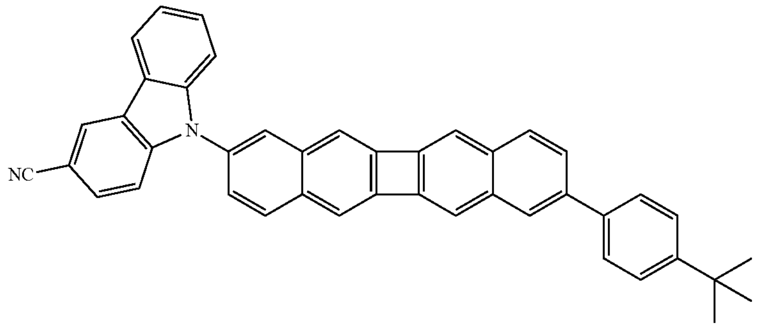
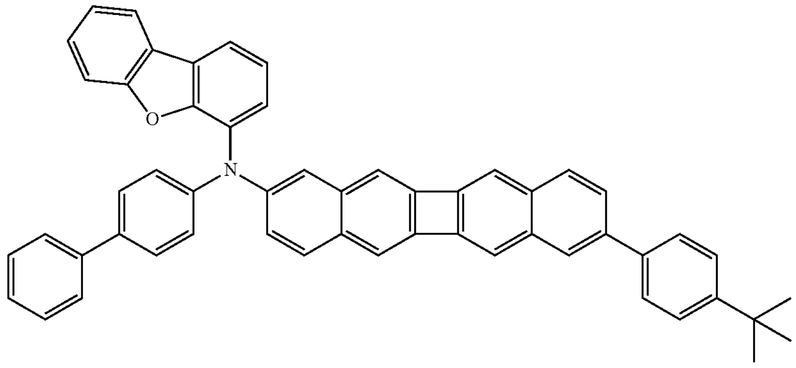

-continued
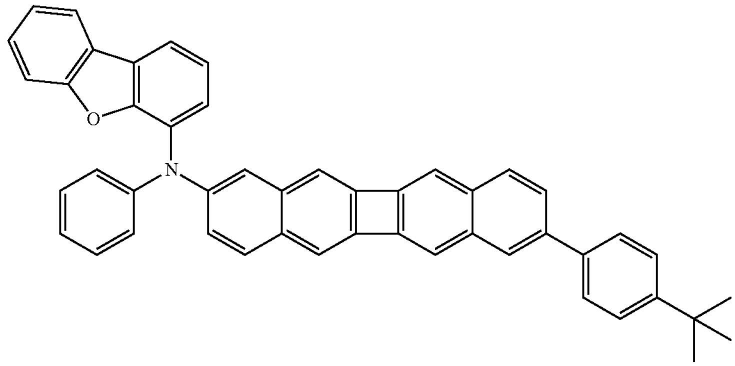
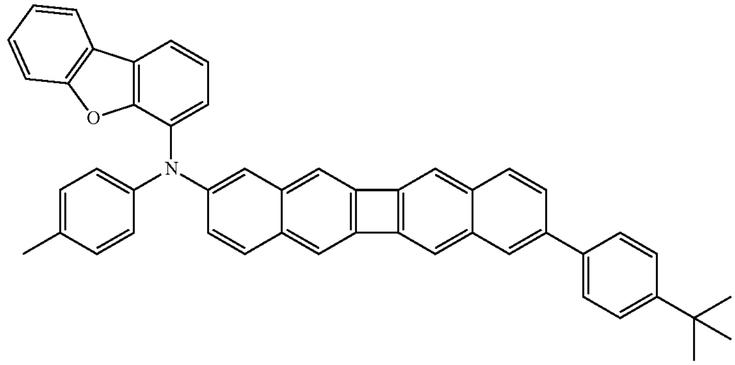
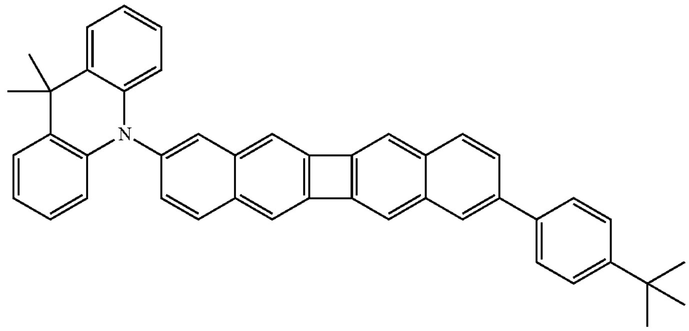
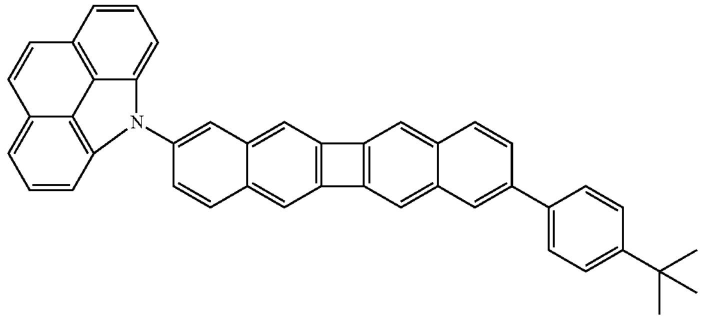
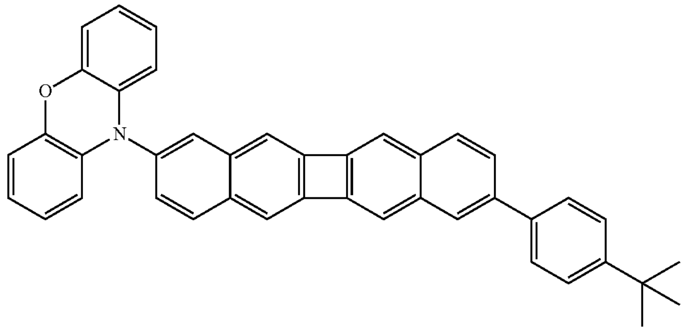

-continued
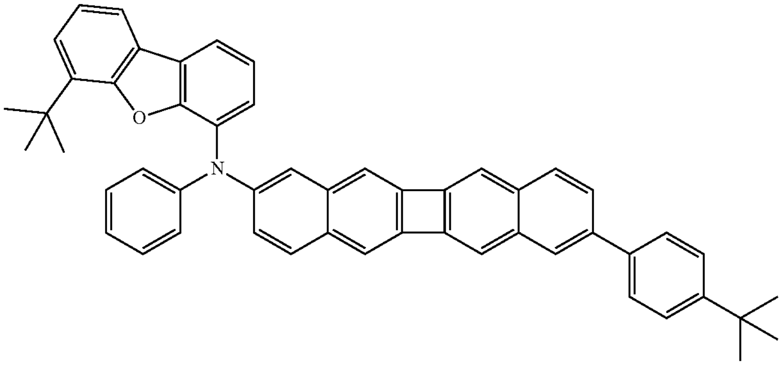
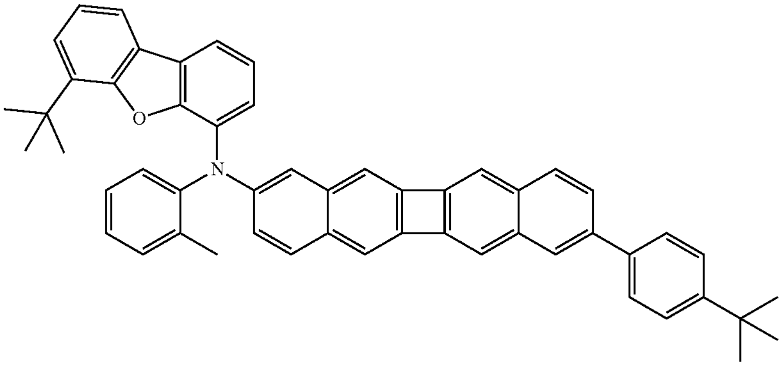
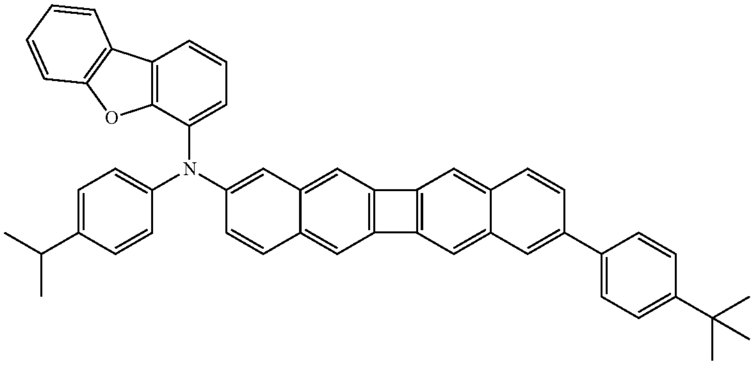
[Formula 171]
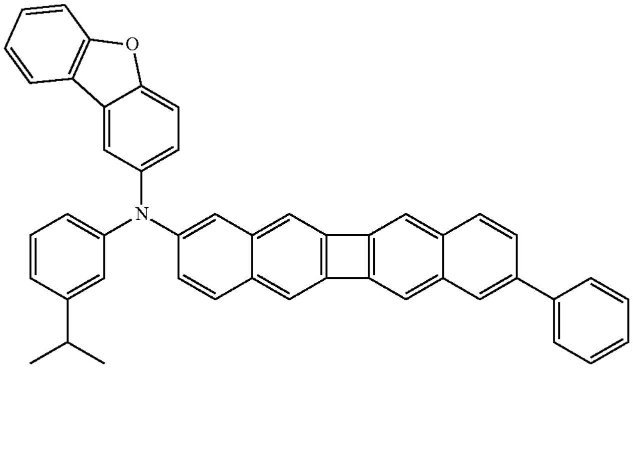

-continued
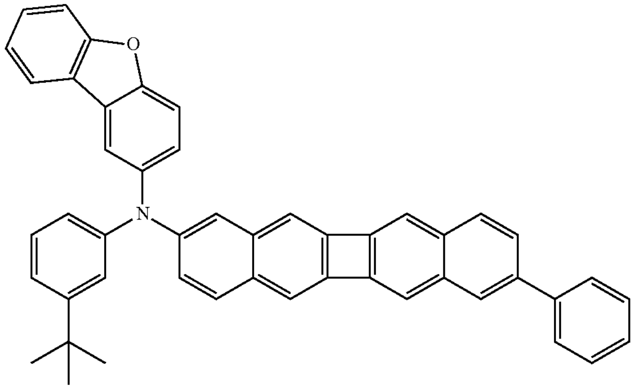
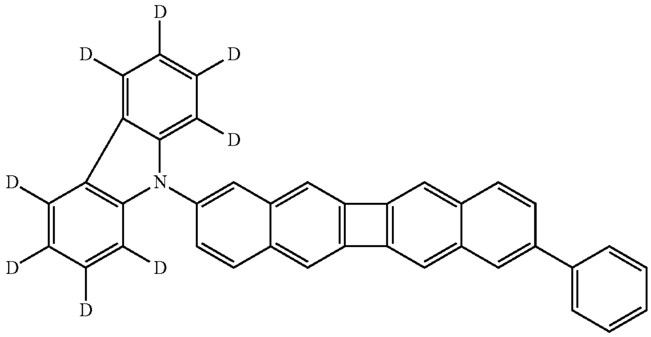
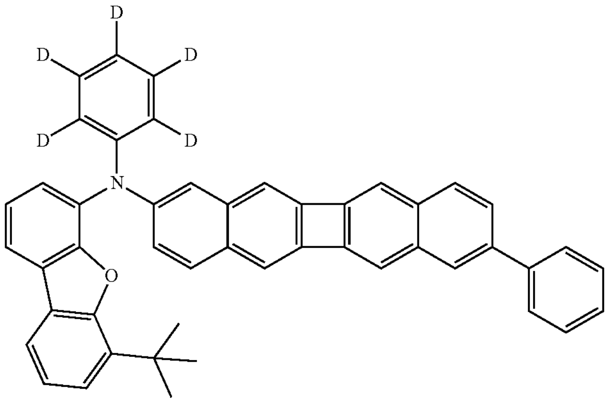
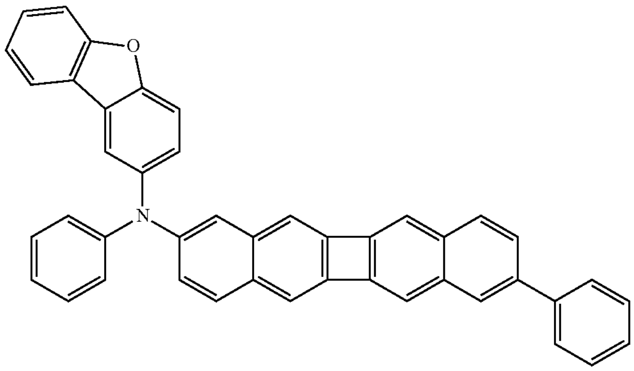

-continued
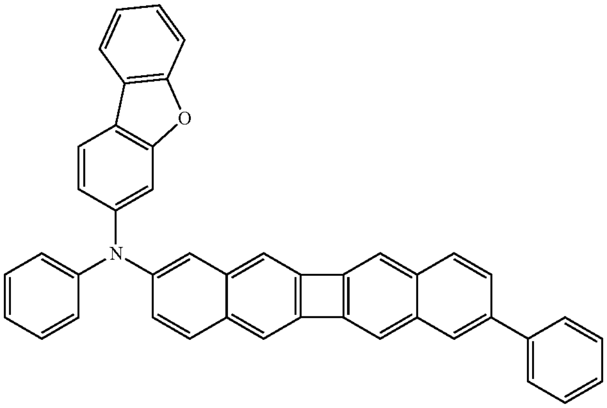
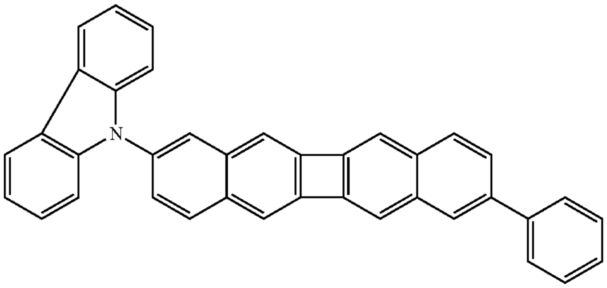
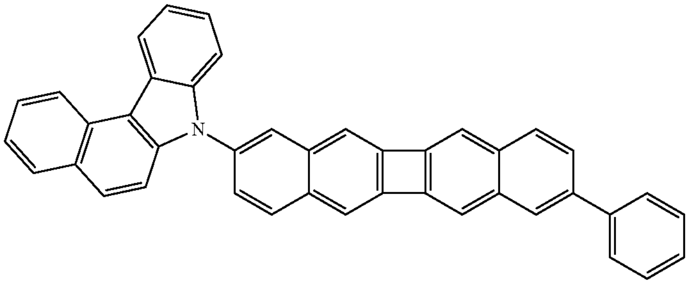
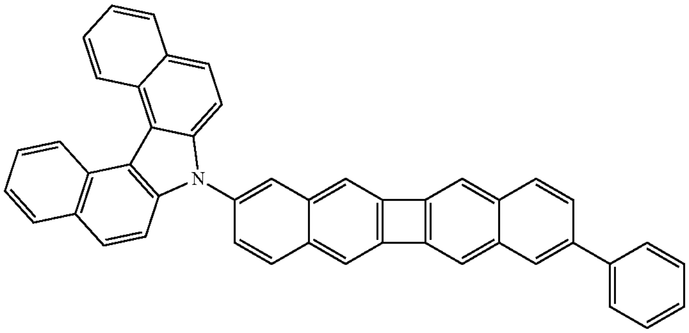
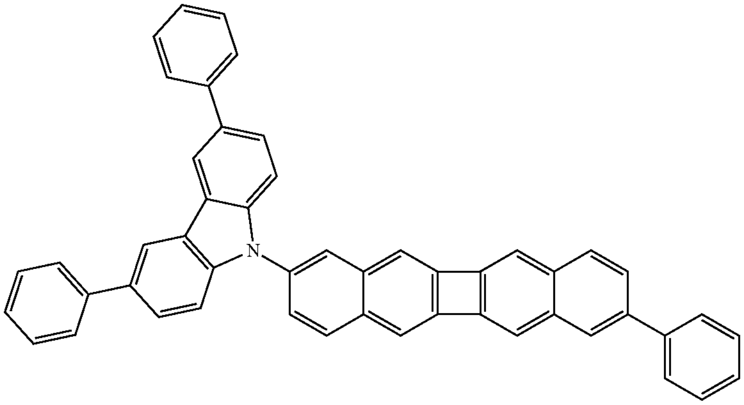

-continued
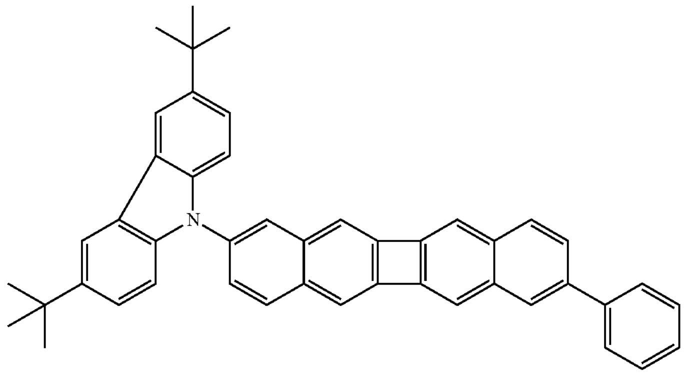
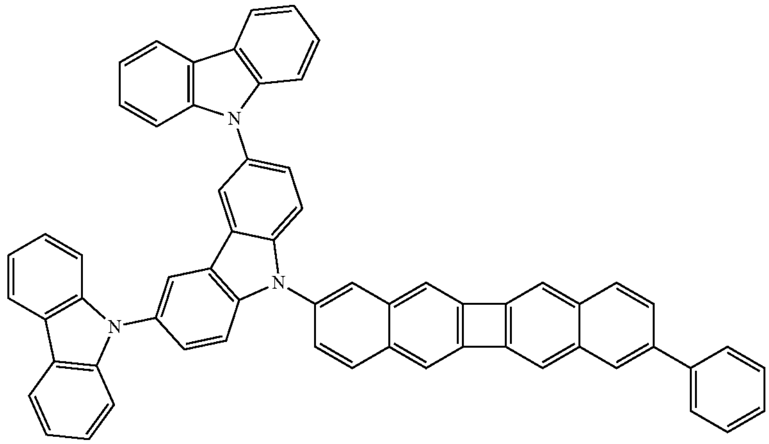
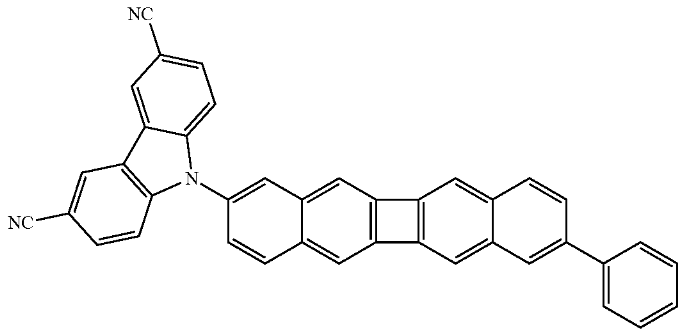
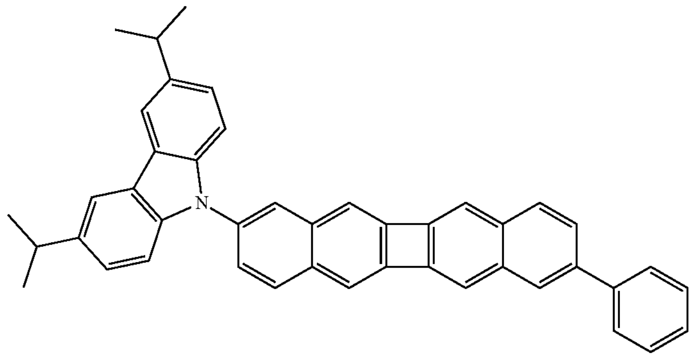

-continued
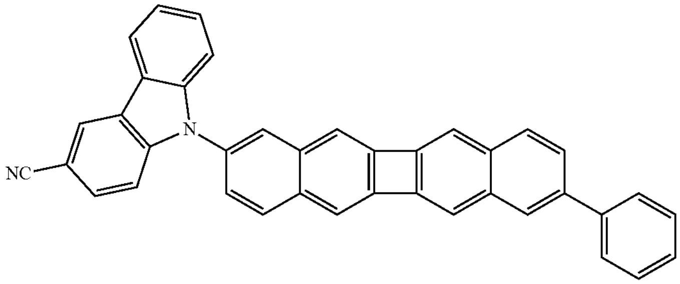
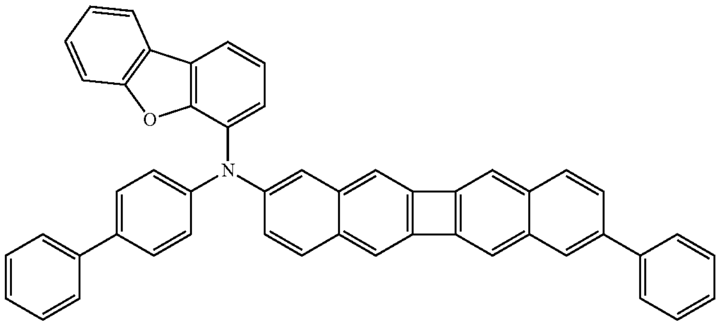
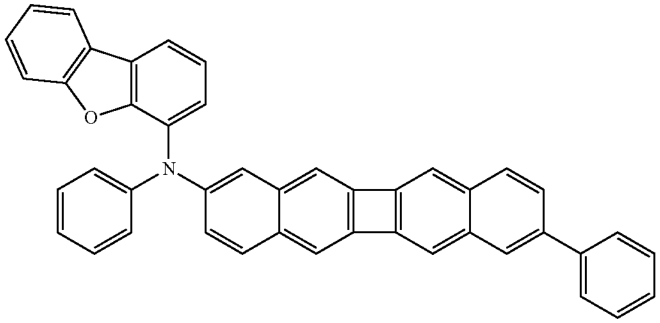
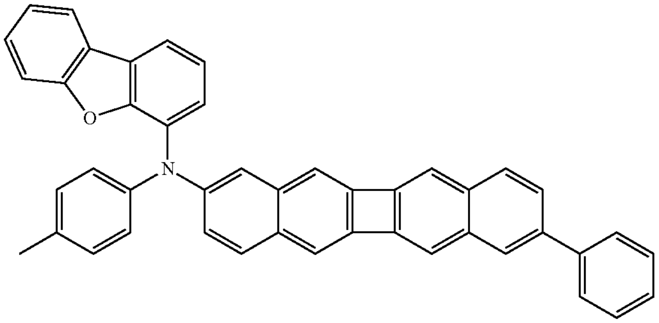
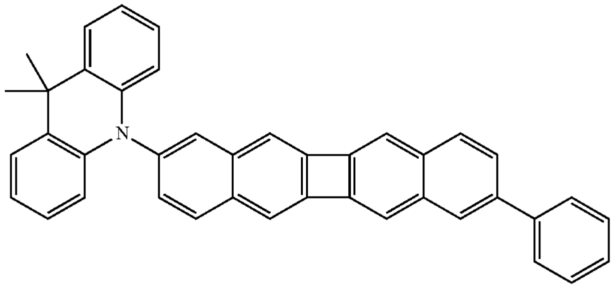

-continued
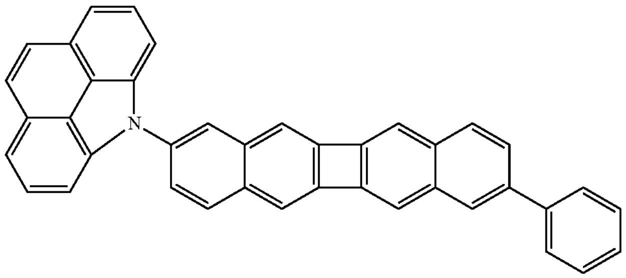
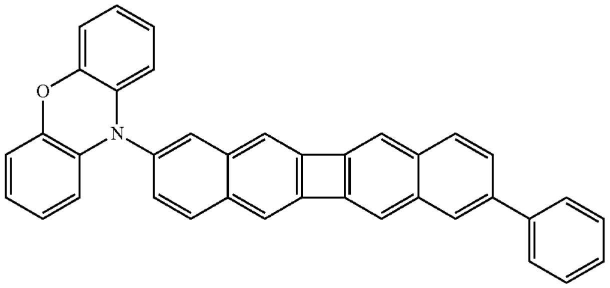
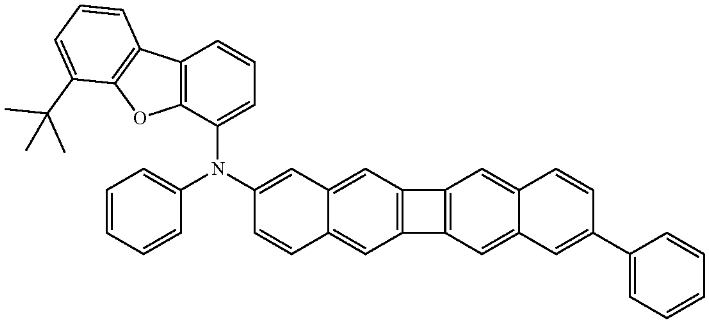
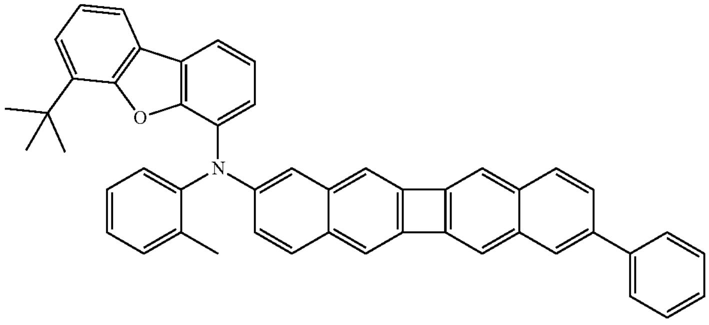
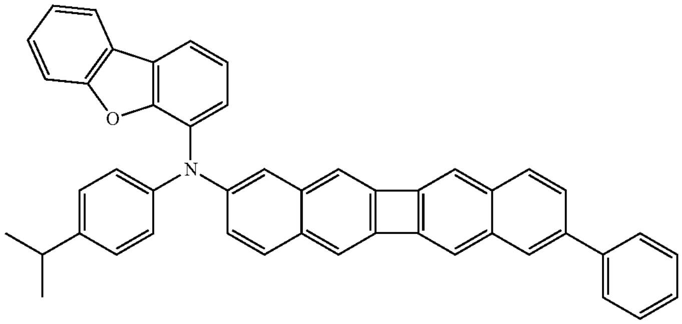

-continued
[Formula 172]
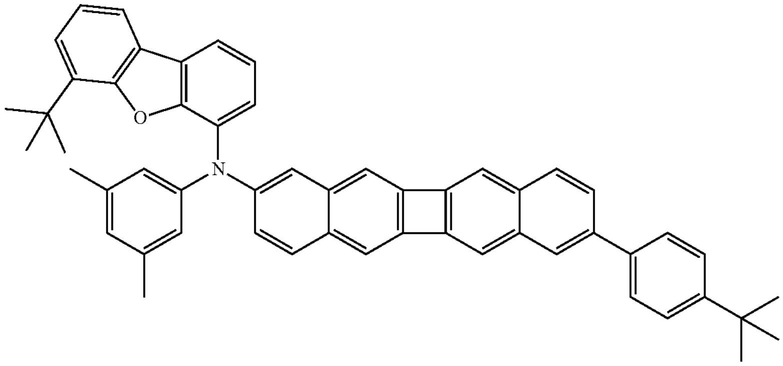
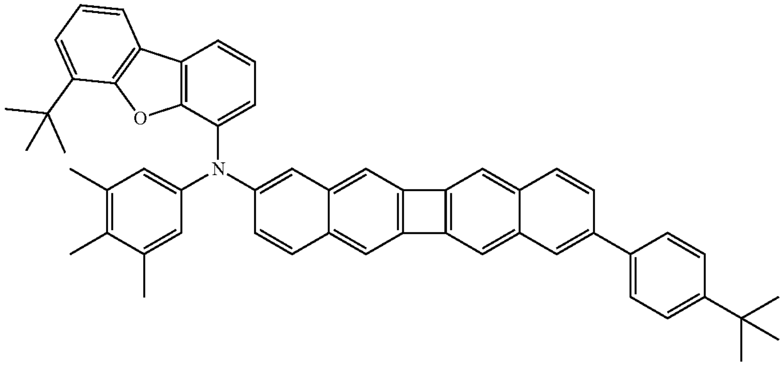
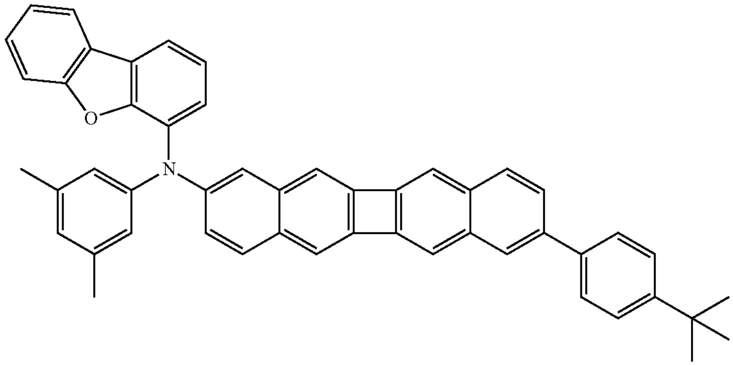
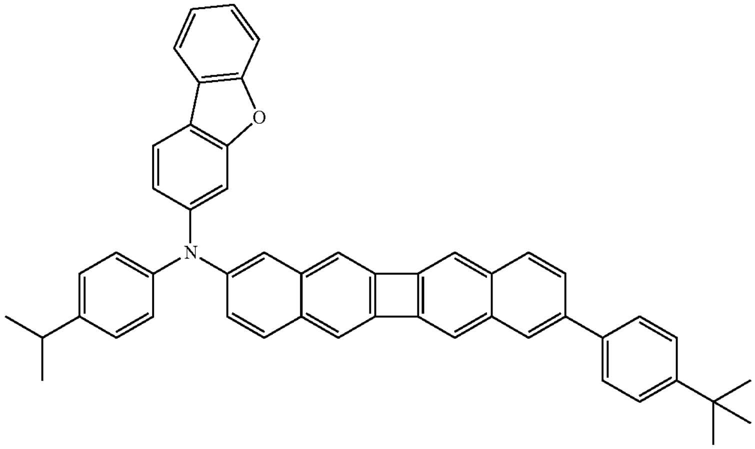

-continued
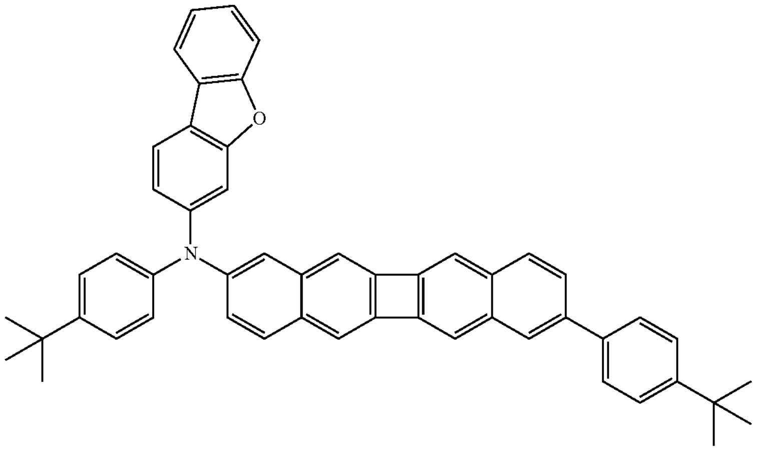
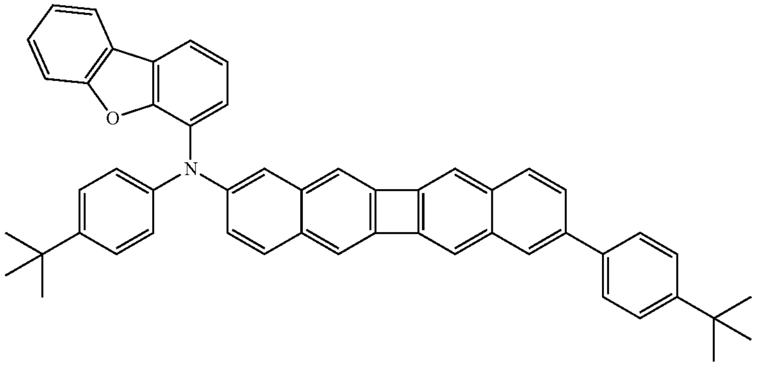
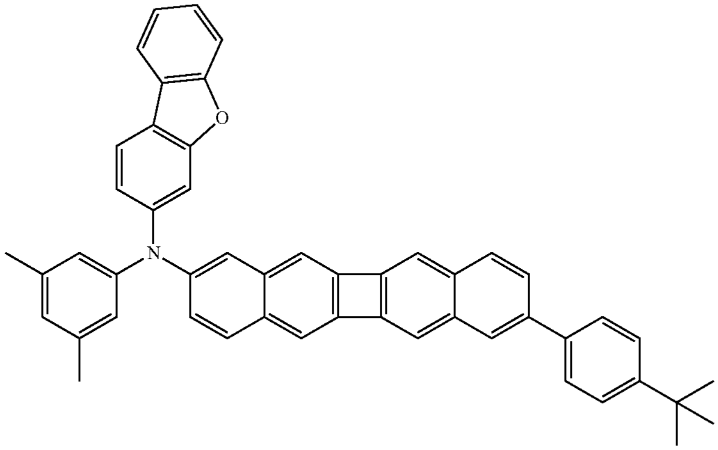
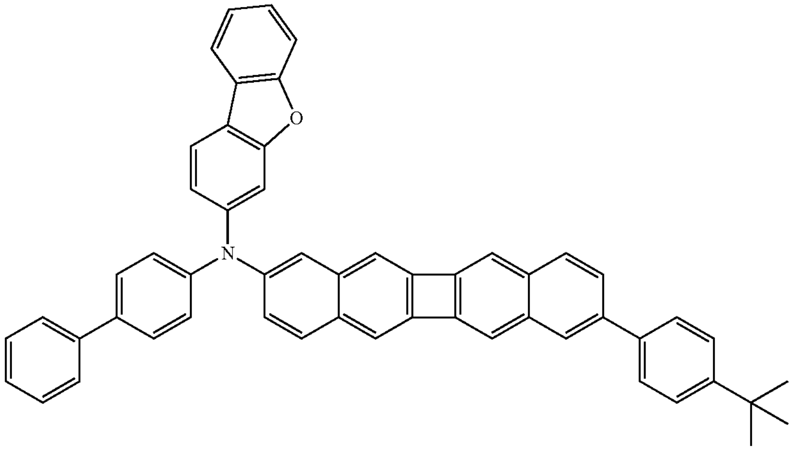

-continued
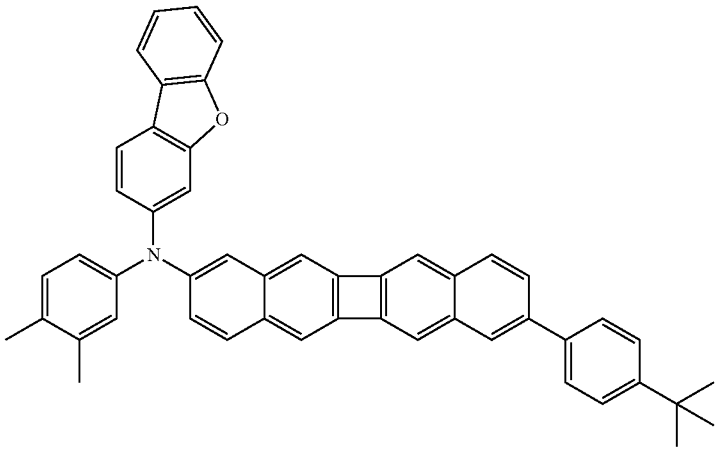
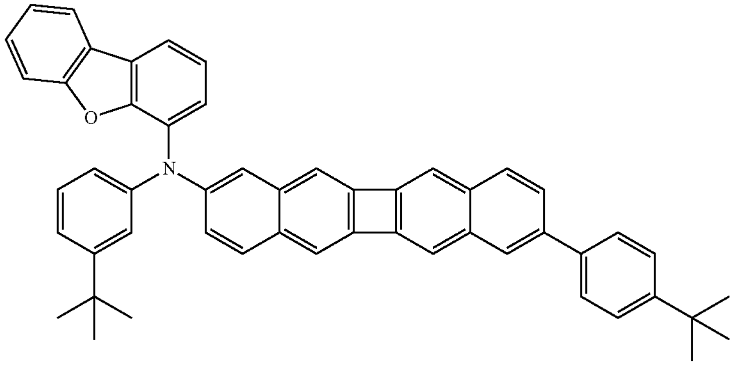
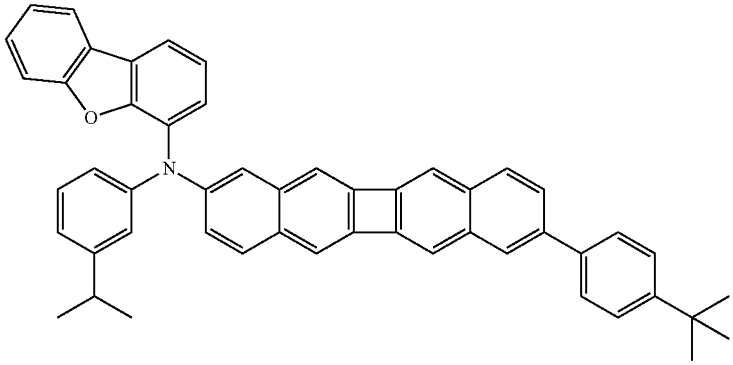
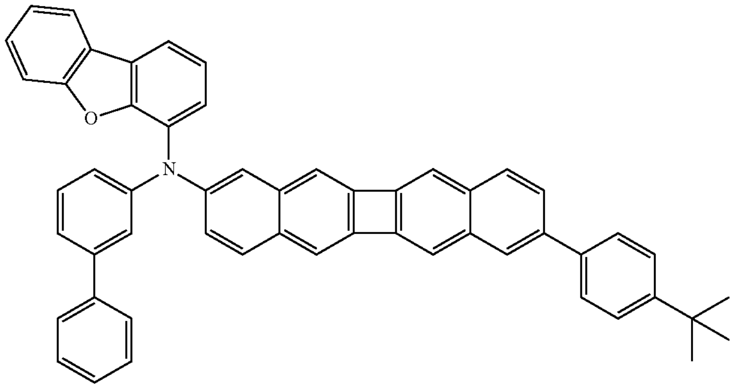

-continued
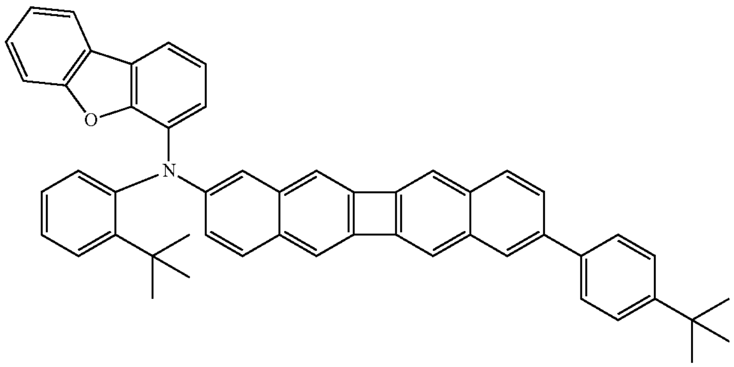
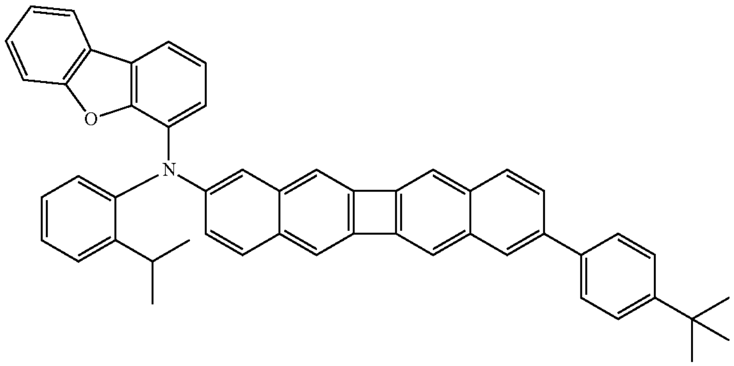
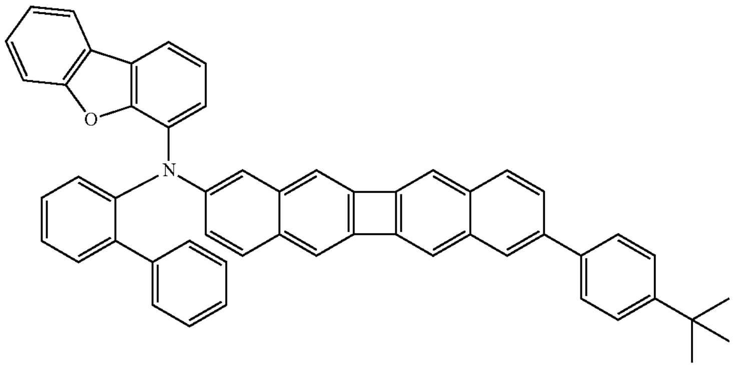
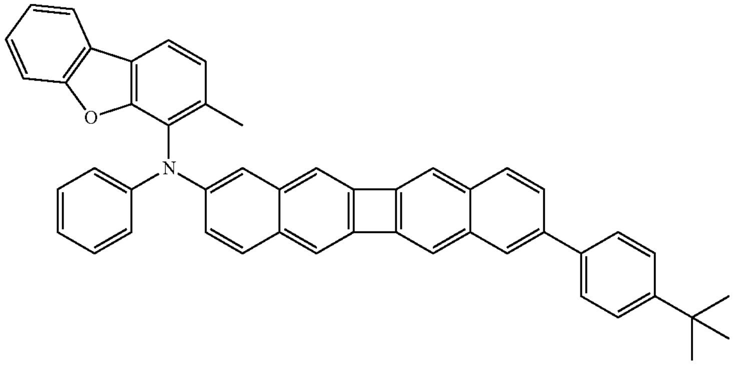

-continued
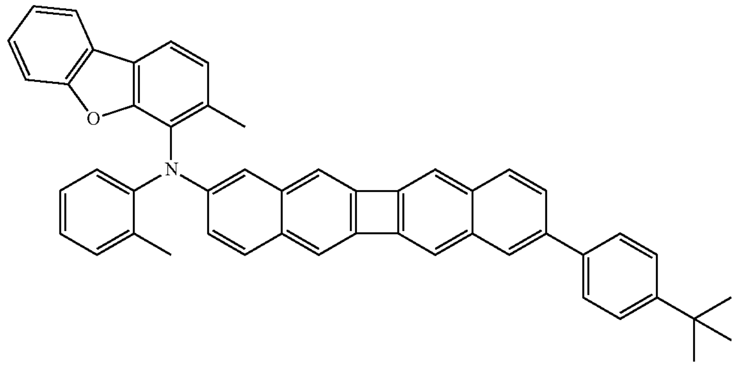
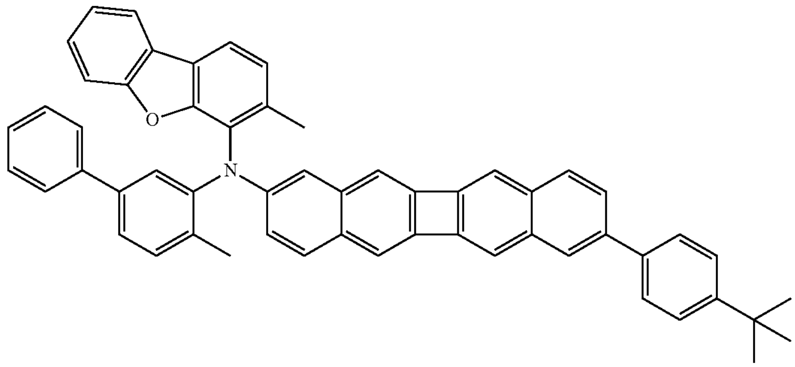
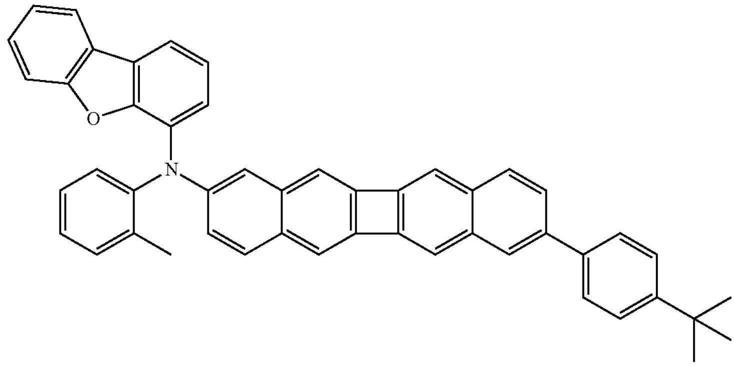
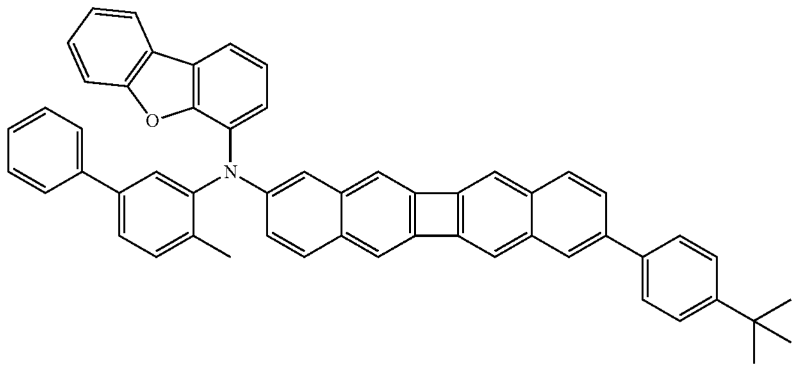

-continued
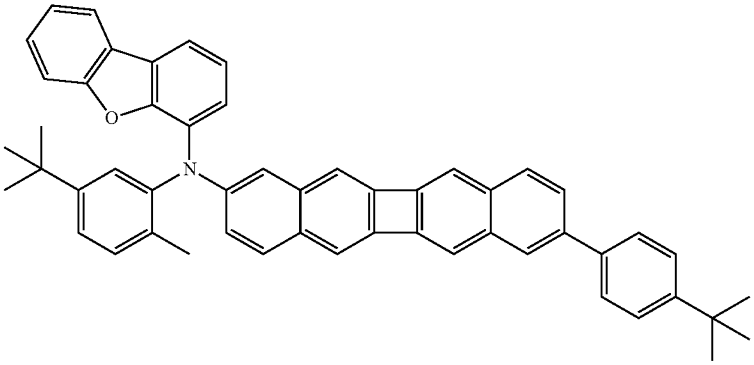
[Formula 173]
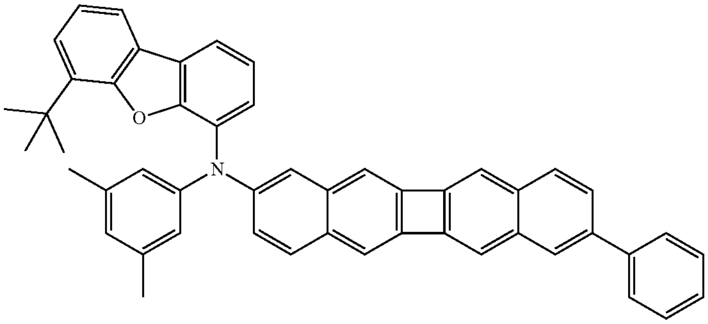
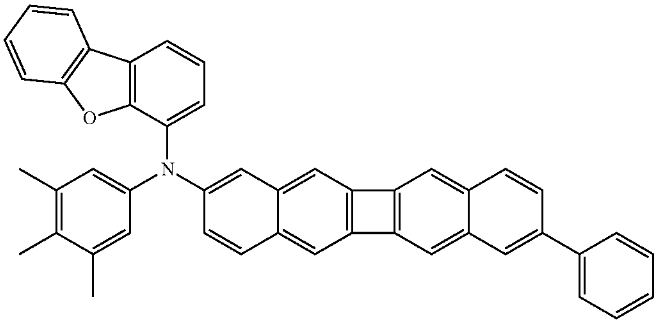
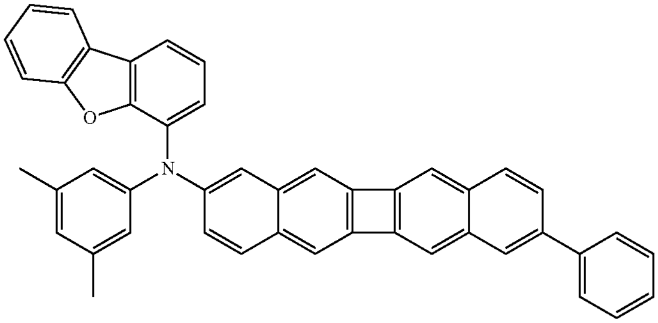

-continued
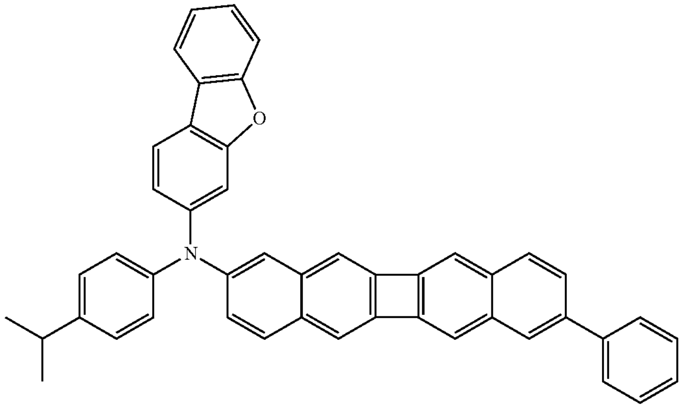
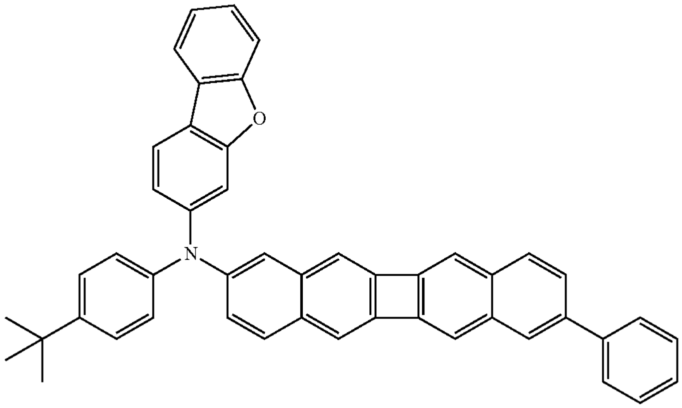
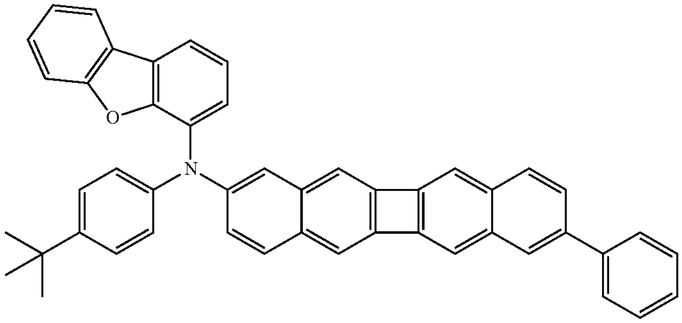
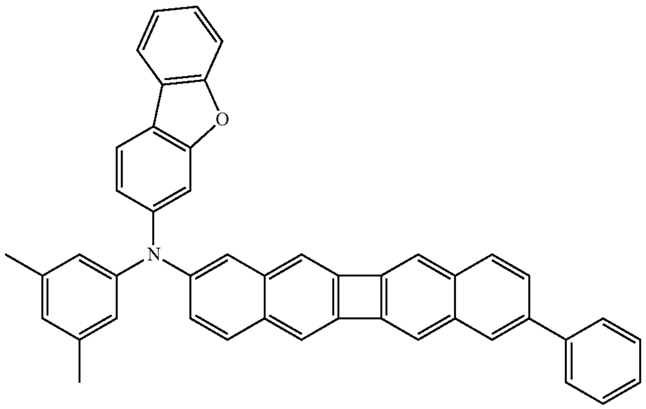

-continued
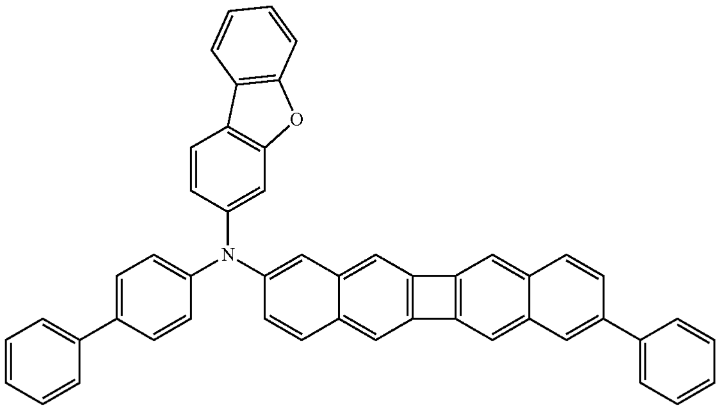
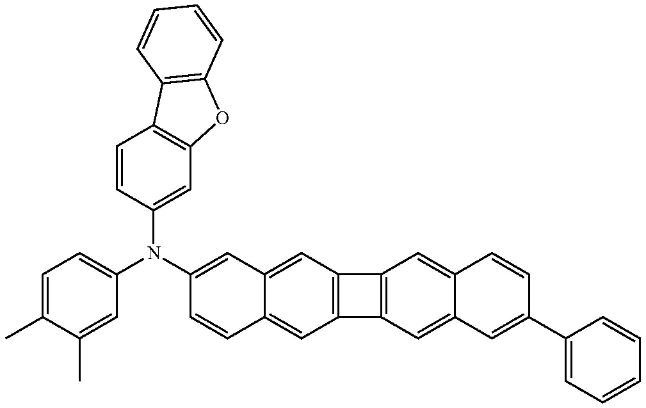
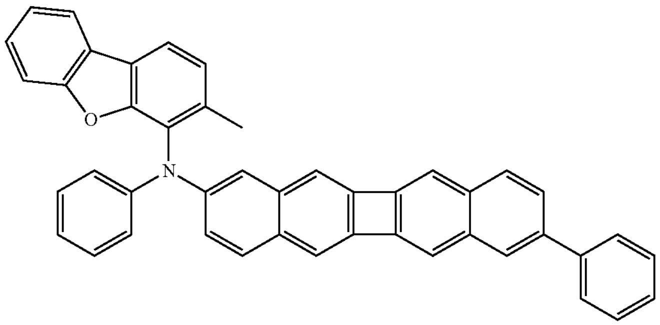
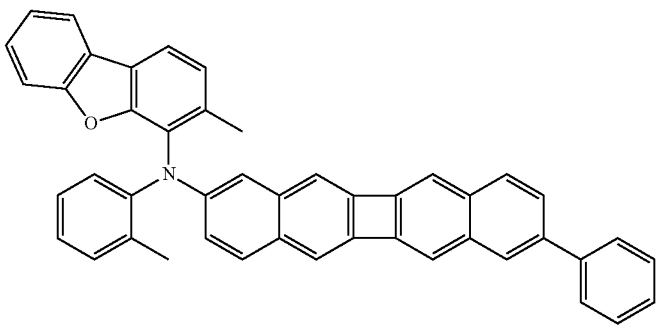

-continued
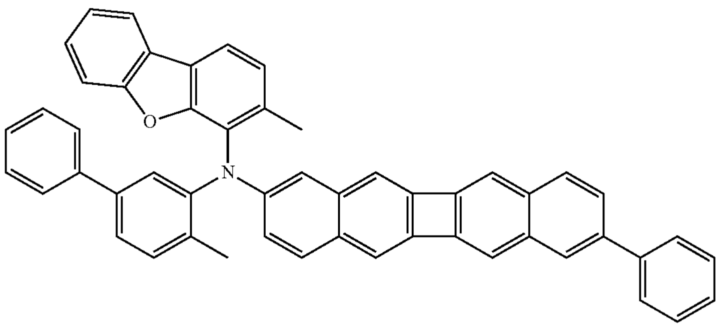
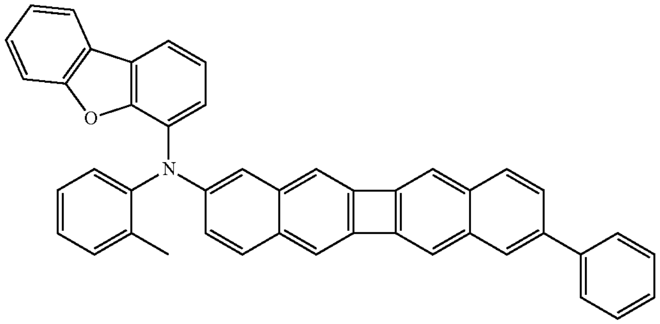
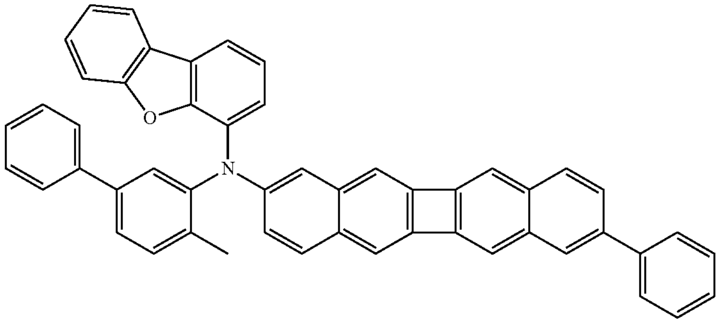
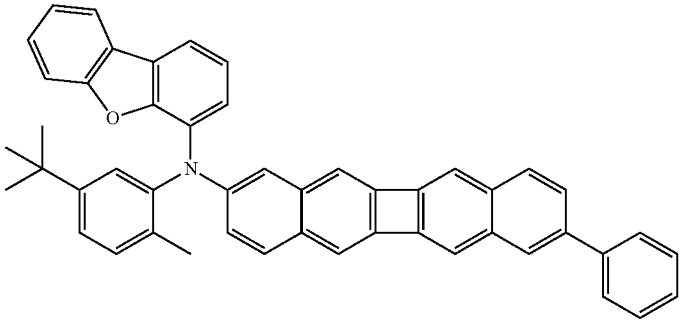
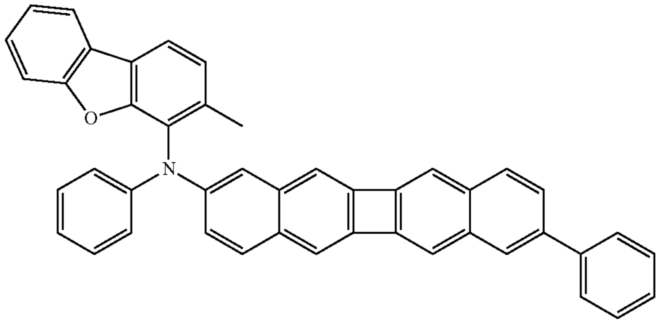

-continued
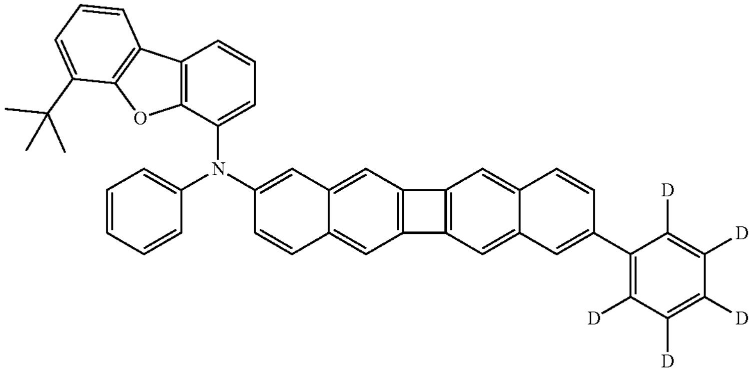
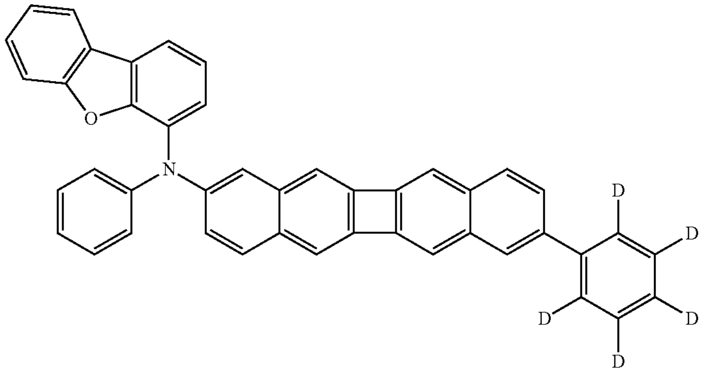
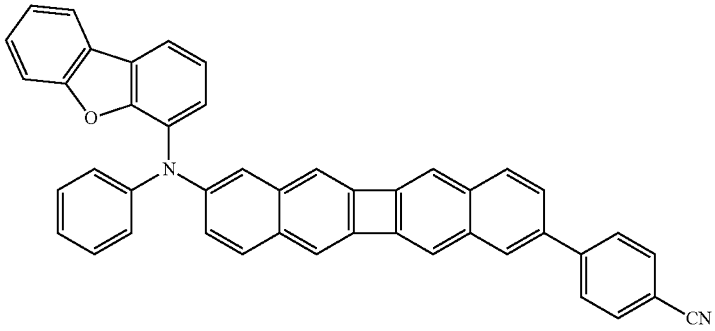
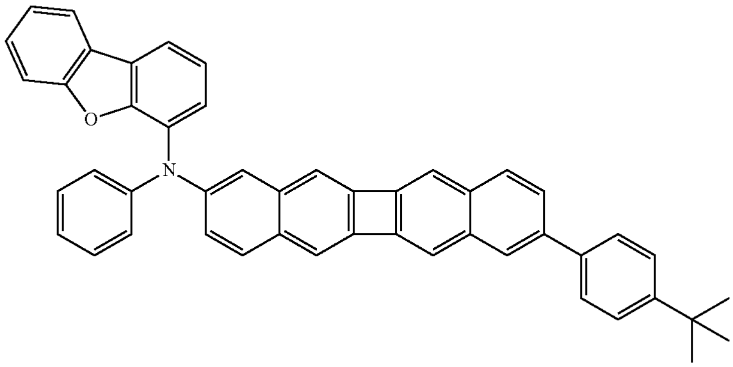
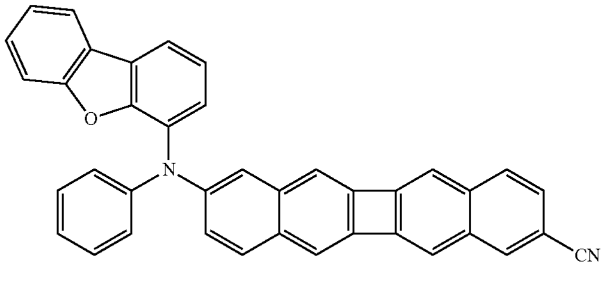

-continued
[Formula 174]
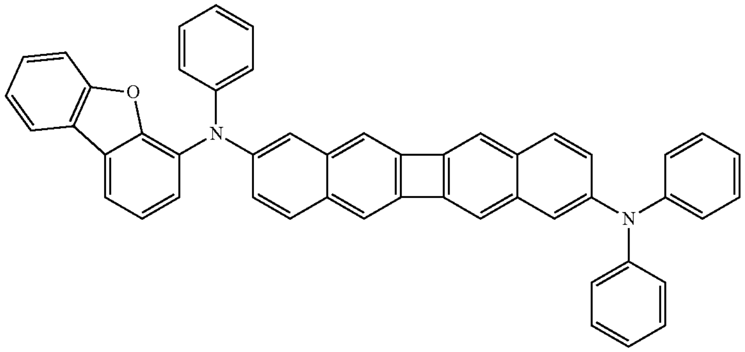
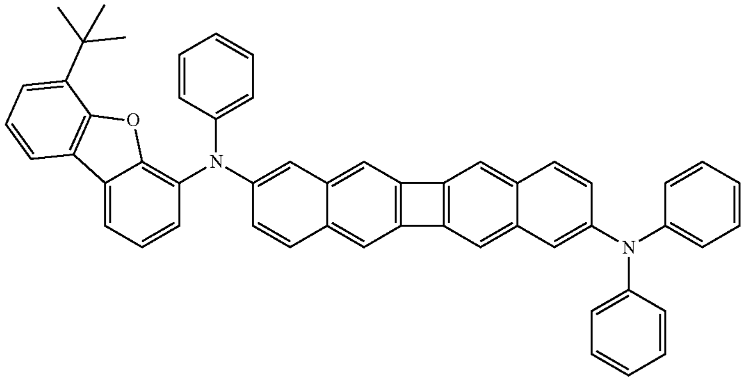
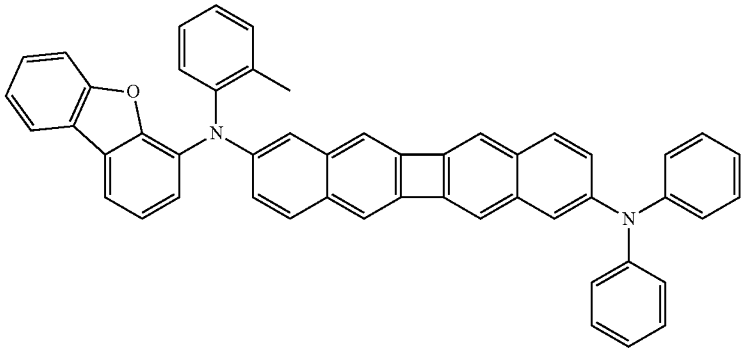
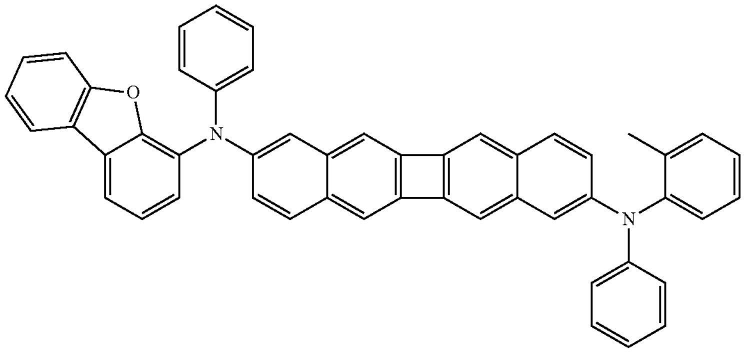

-continued
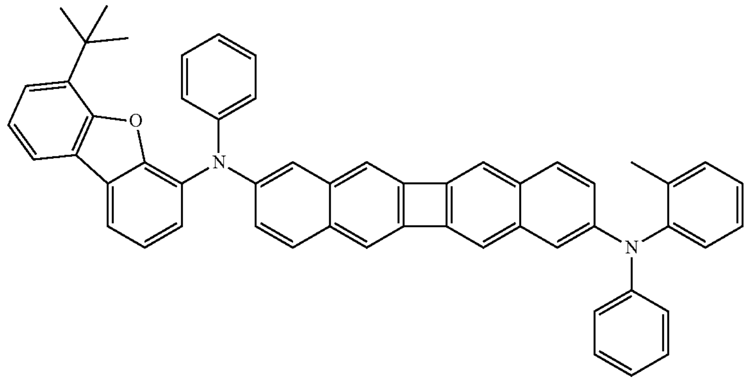
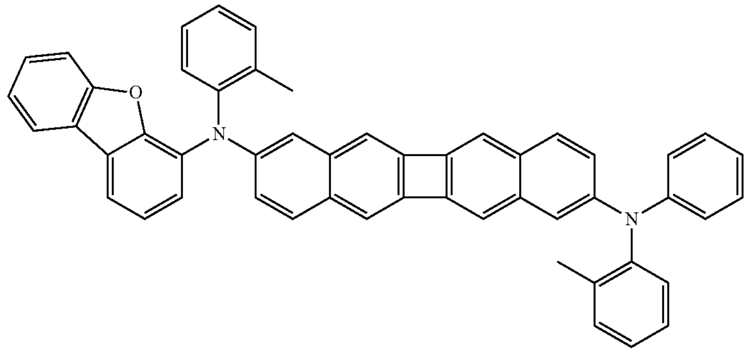
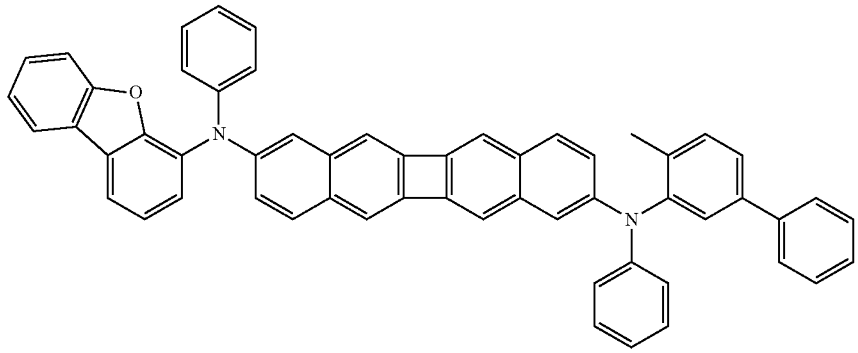
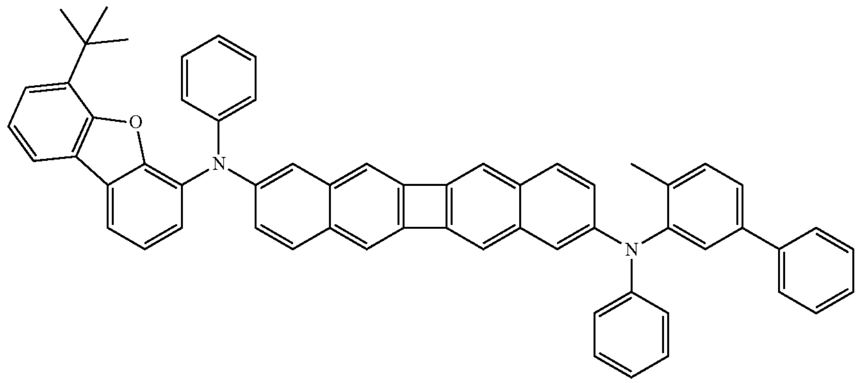

-continued
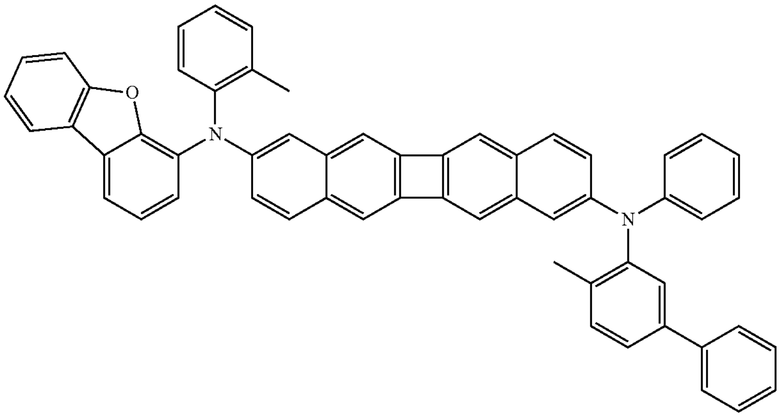
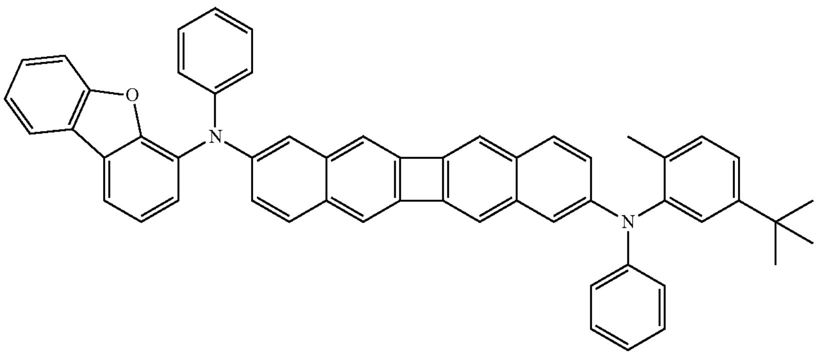
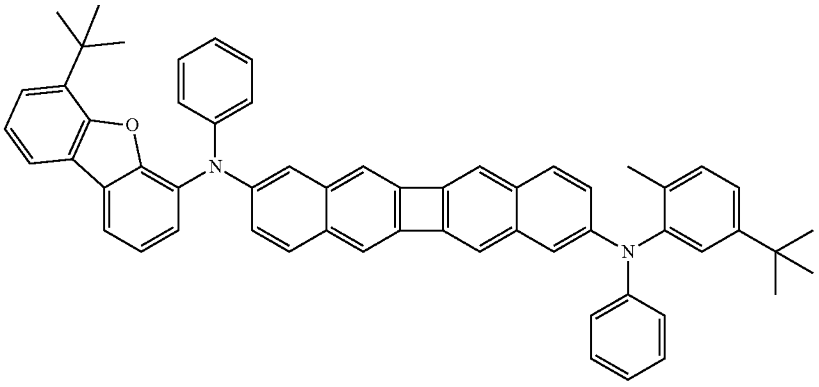
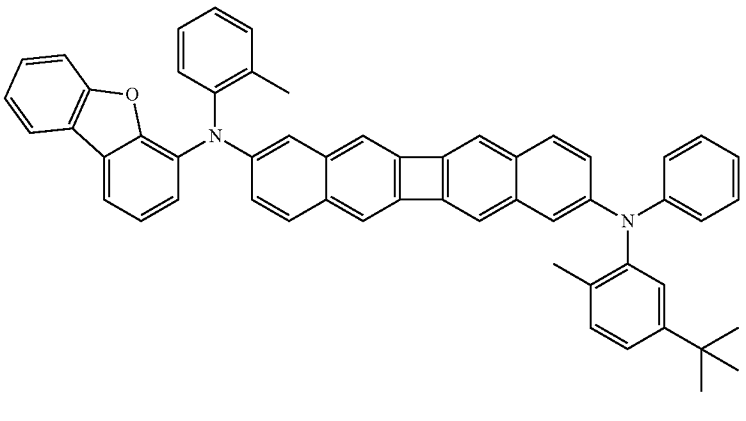

-continued
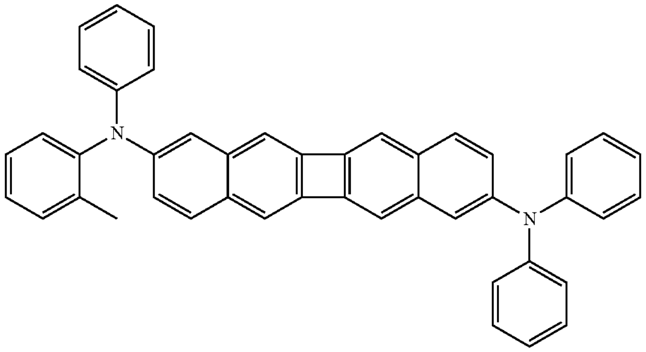
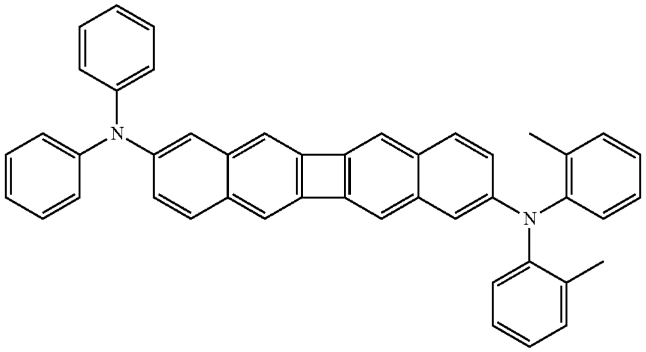
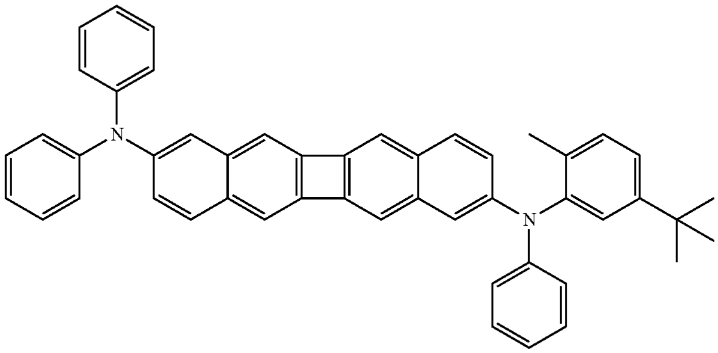
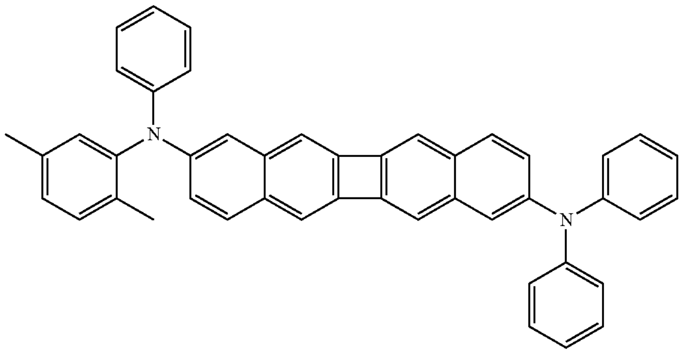

-continued
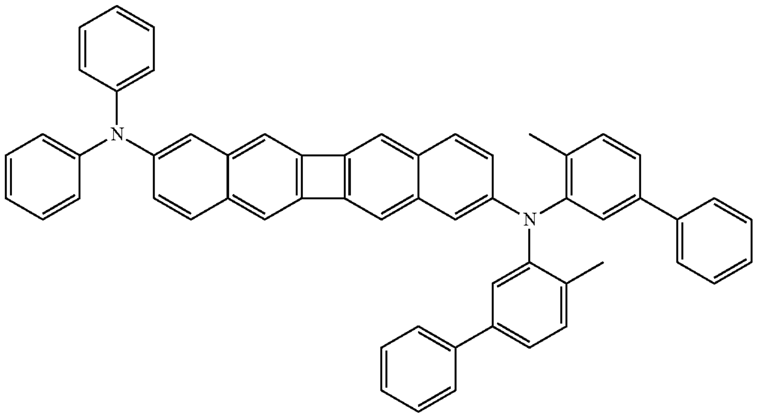
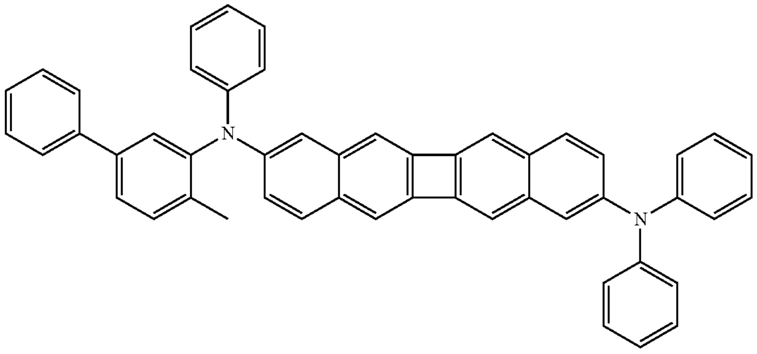
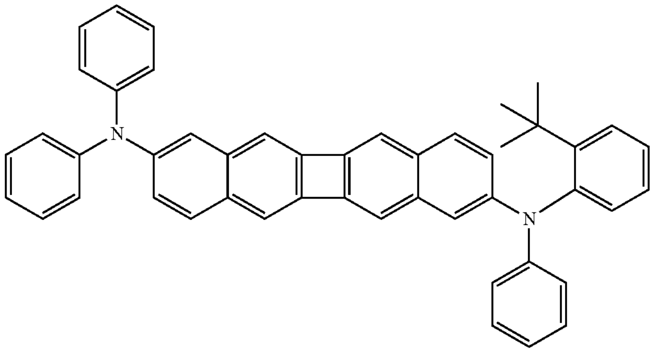
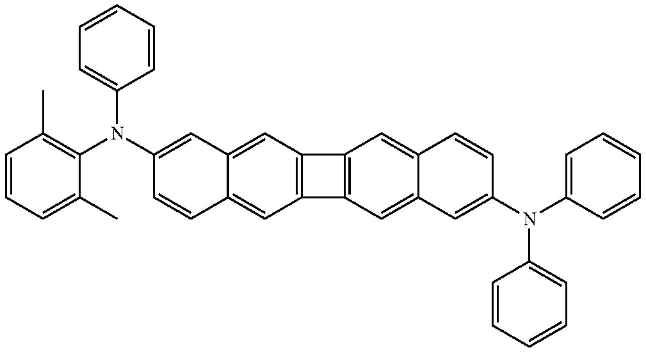

-continued
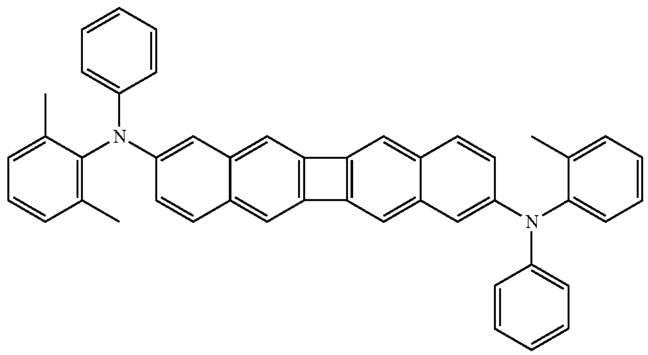
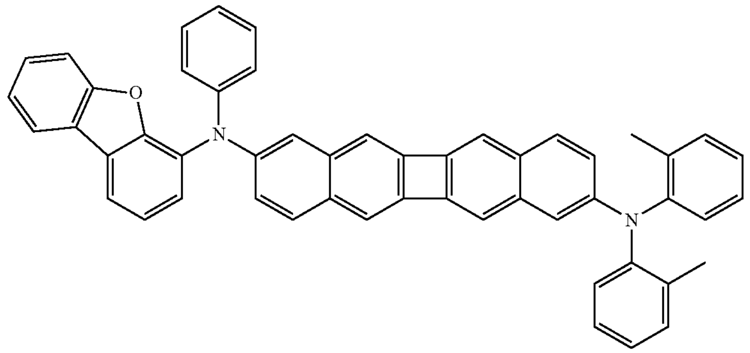
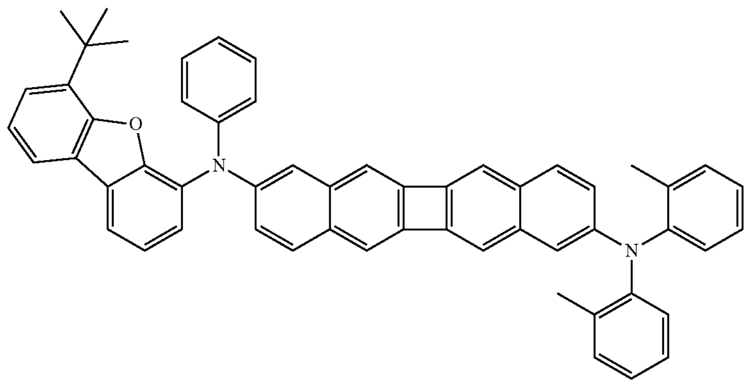
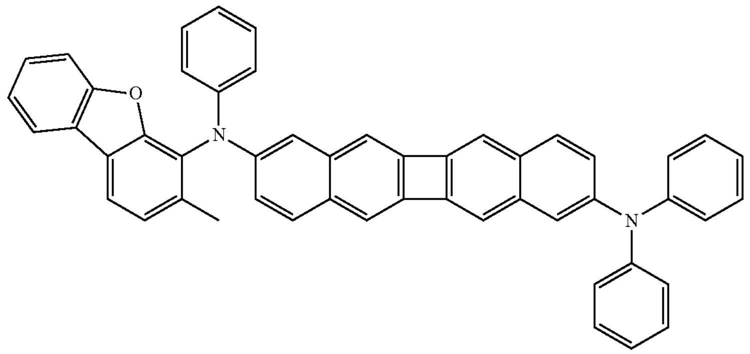

-continued
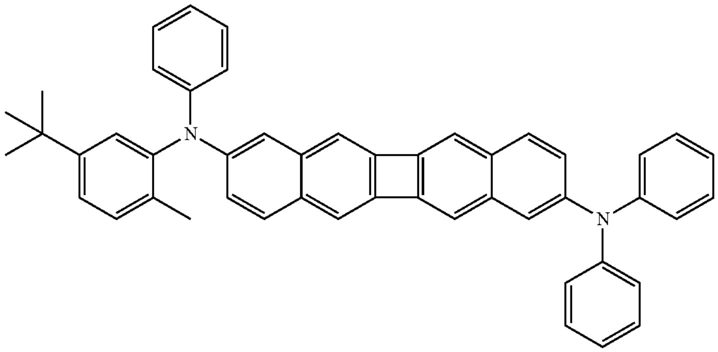
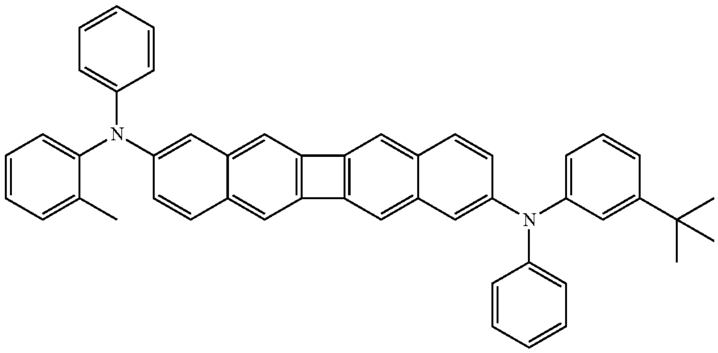
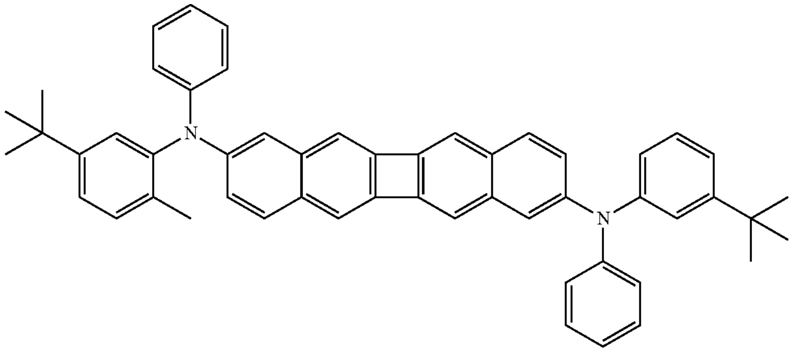
[Formula 175]
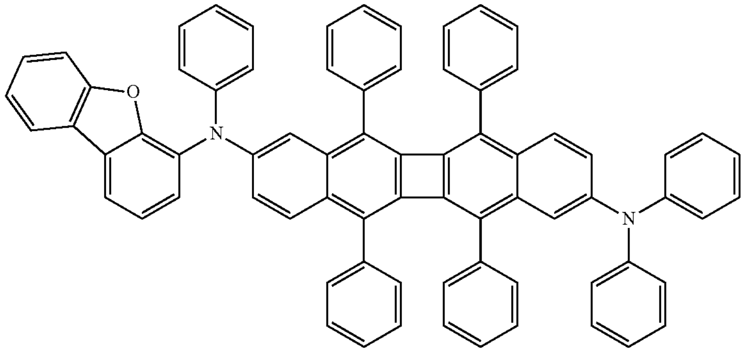

-continued
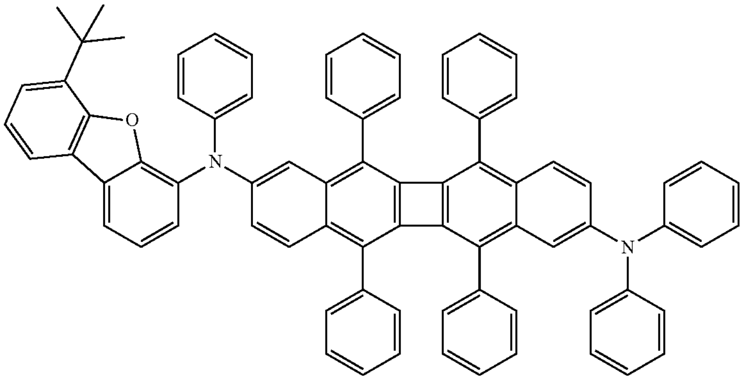
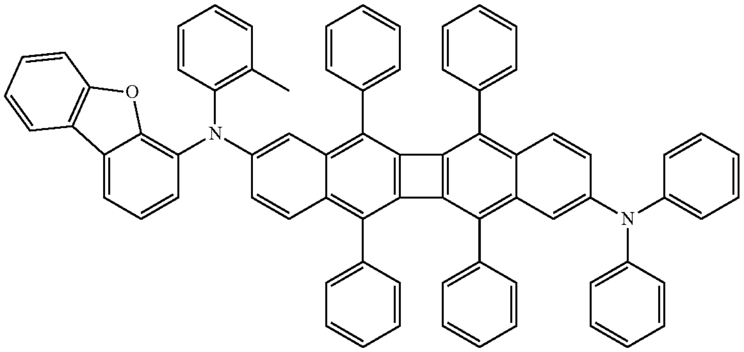
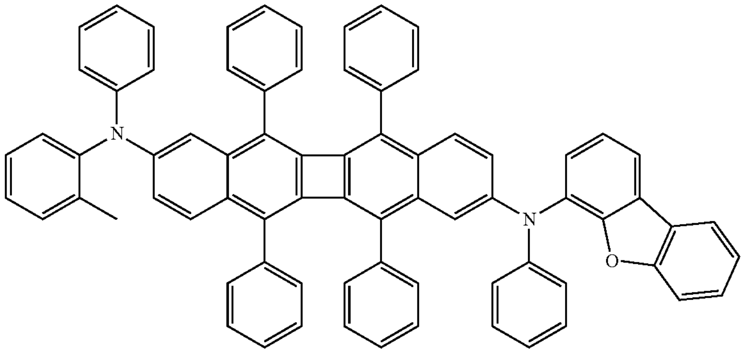
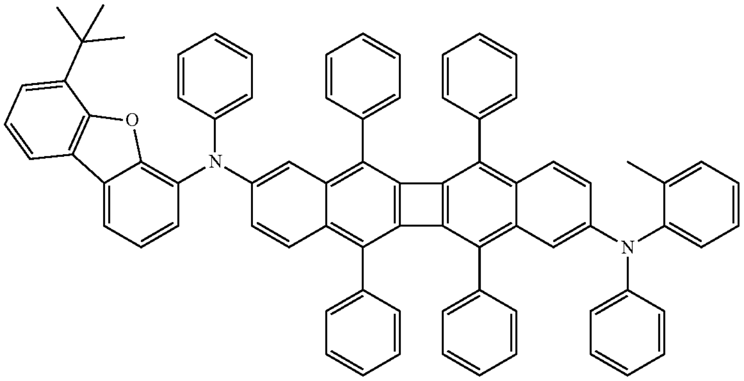

-continued
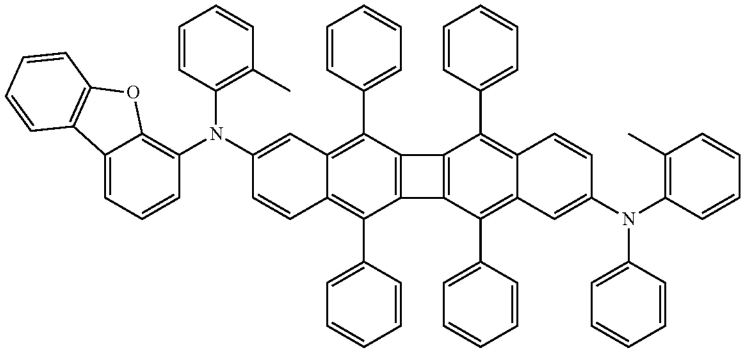
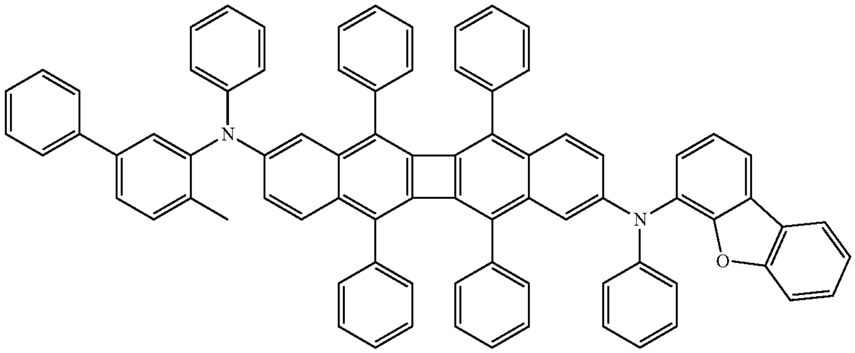
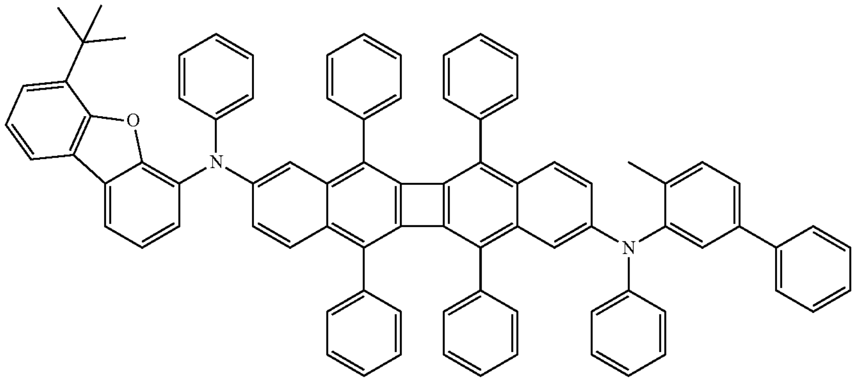
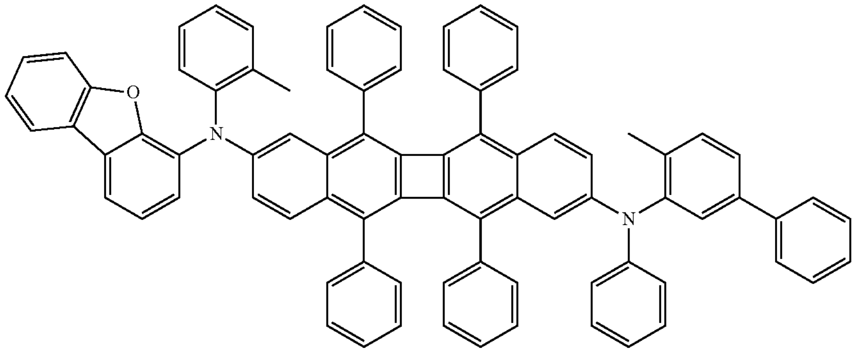

-continued
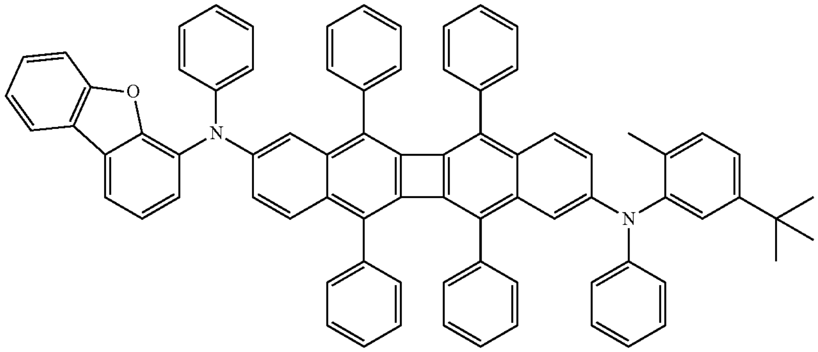
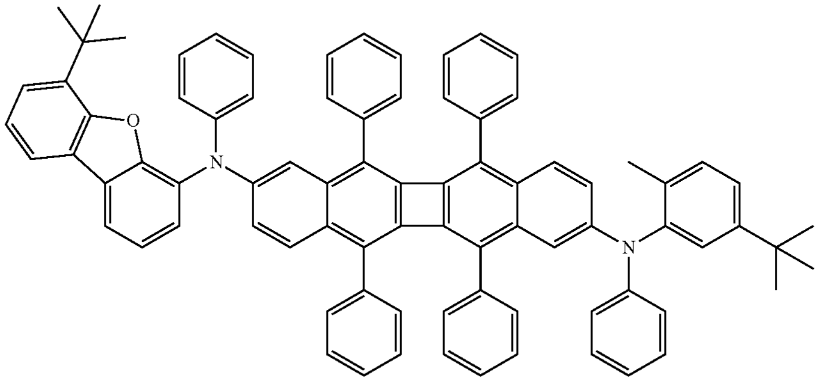
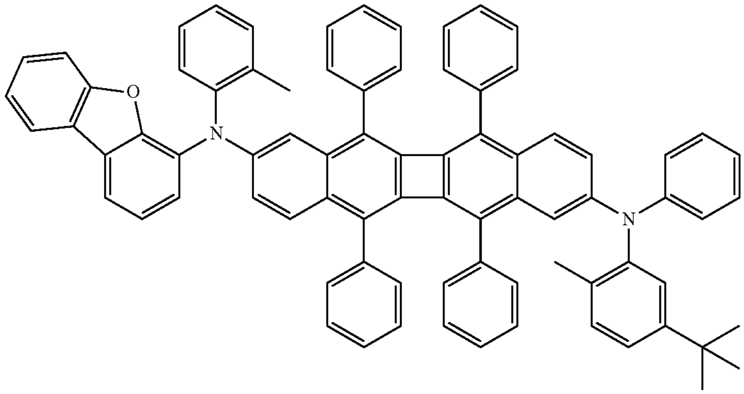
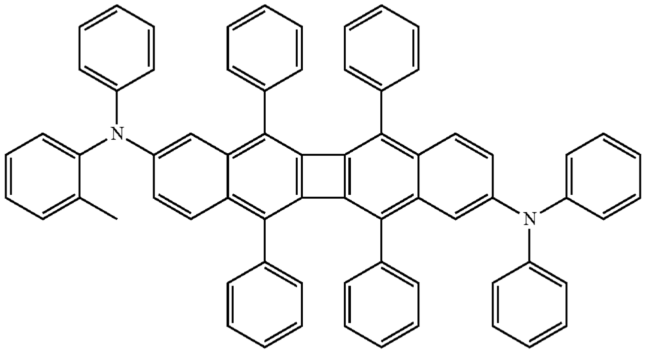

-continued
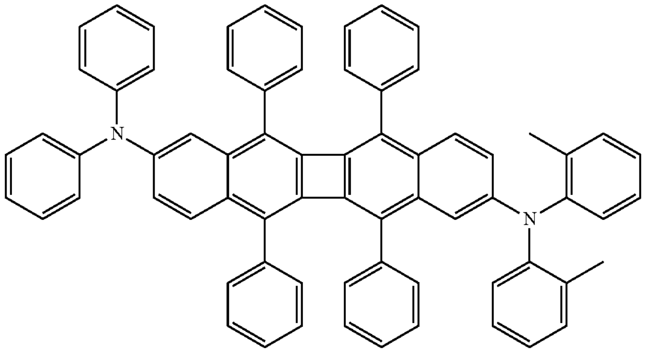
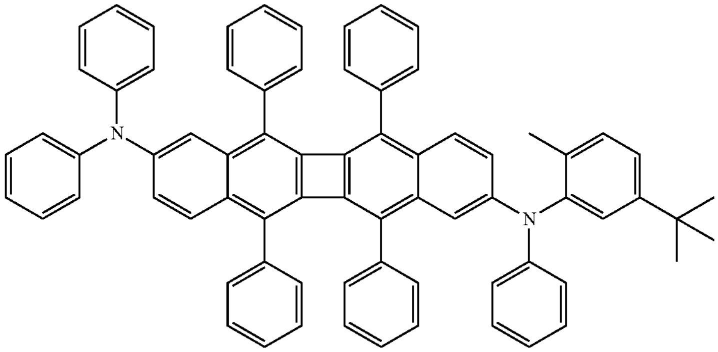
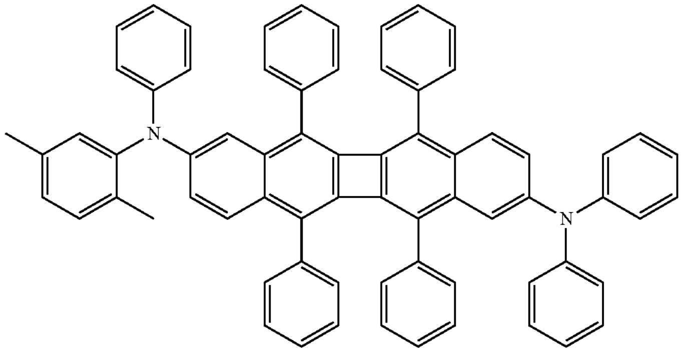
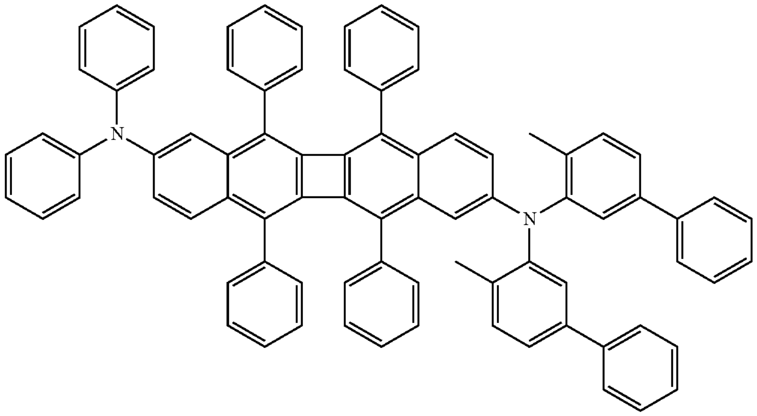

-continued
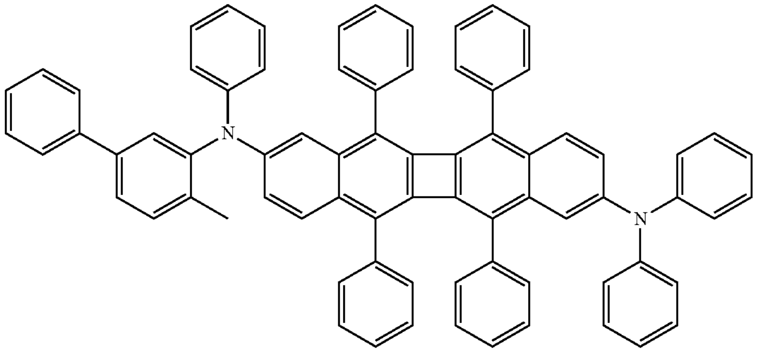
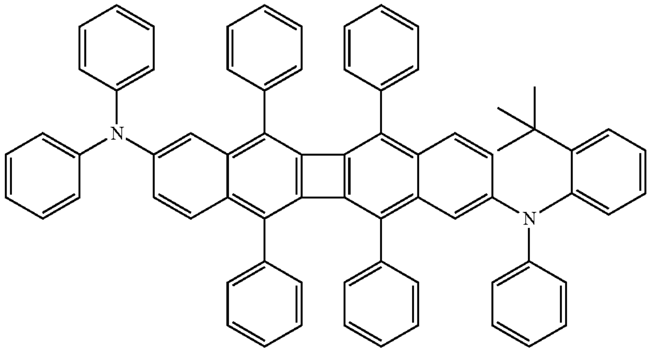
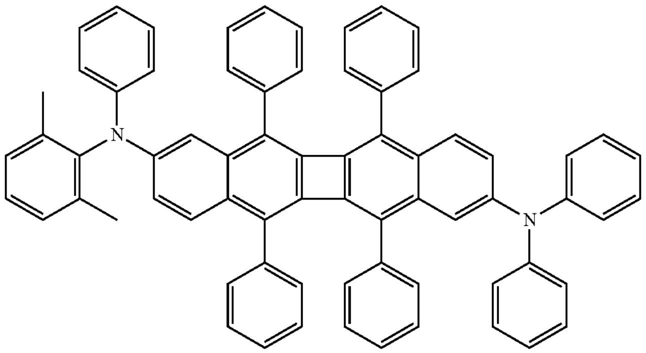
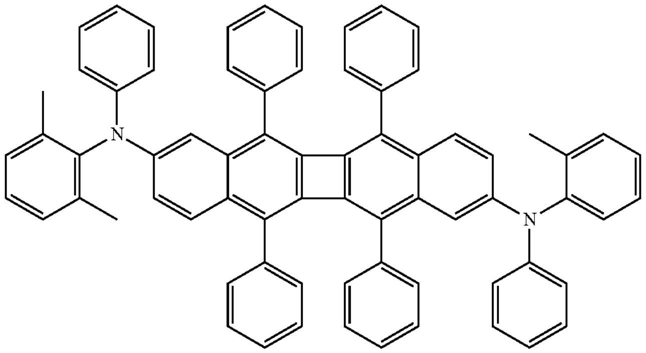

-continued
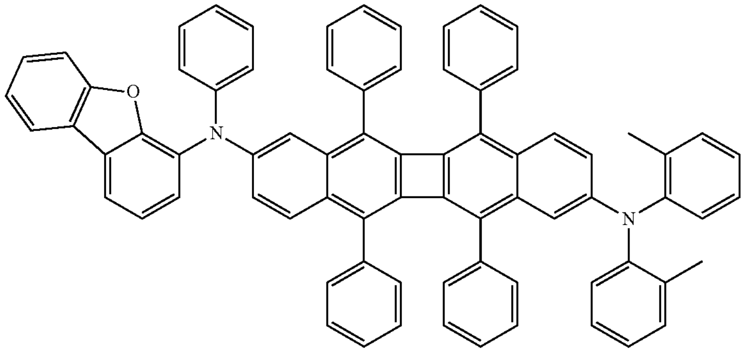
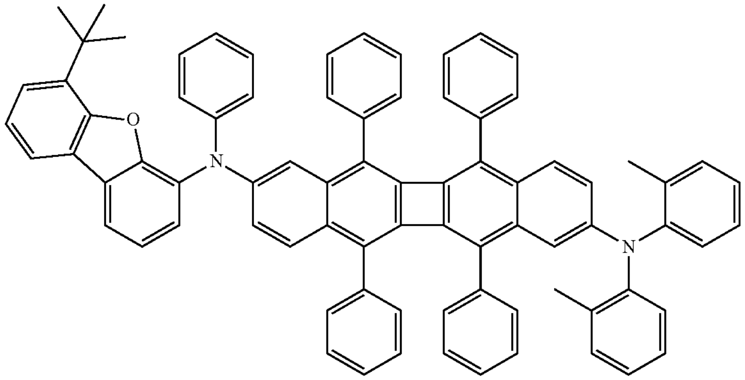
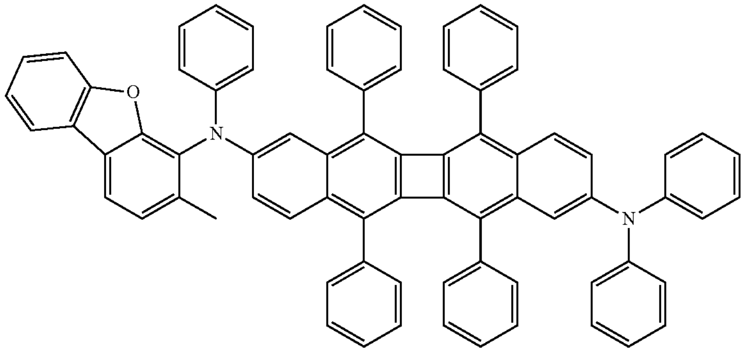
[Formula 176]
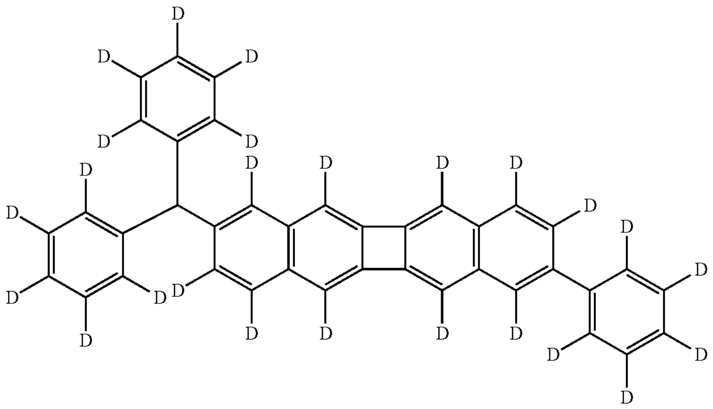

-continued
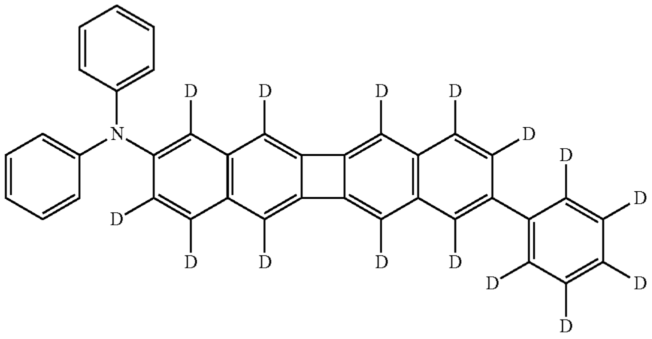
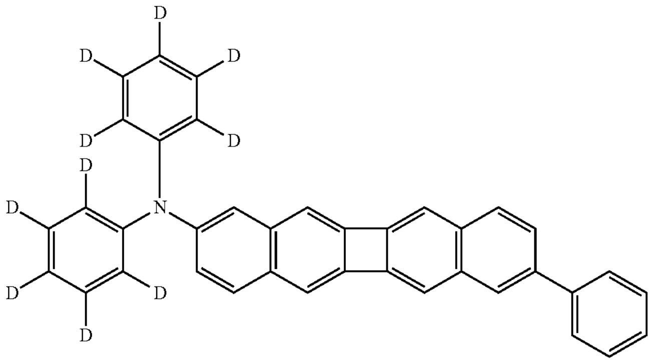
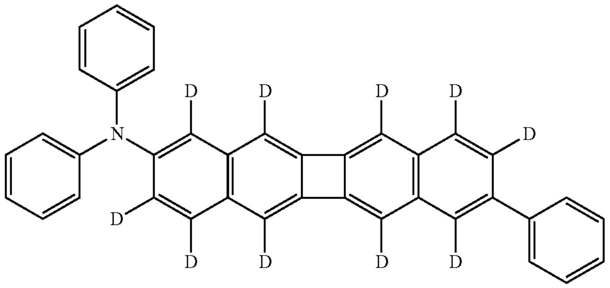
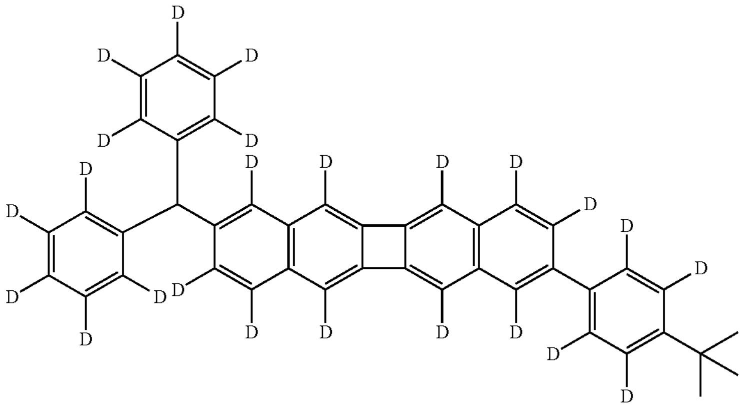

-continued
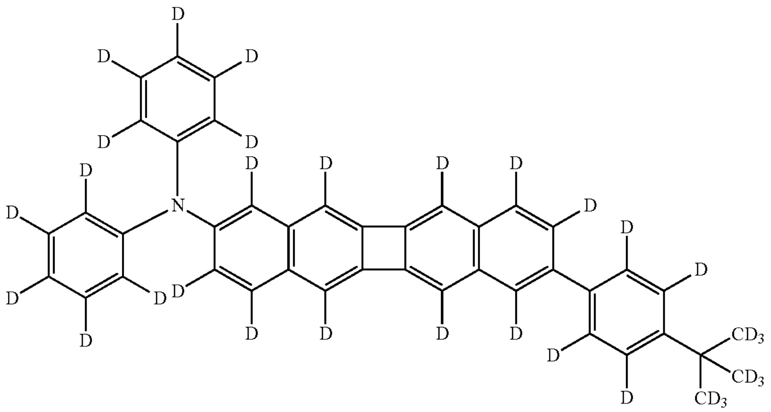
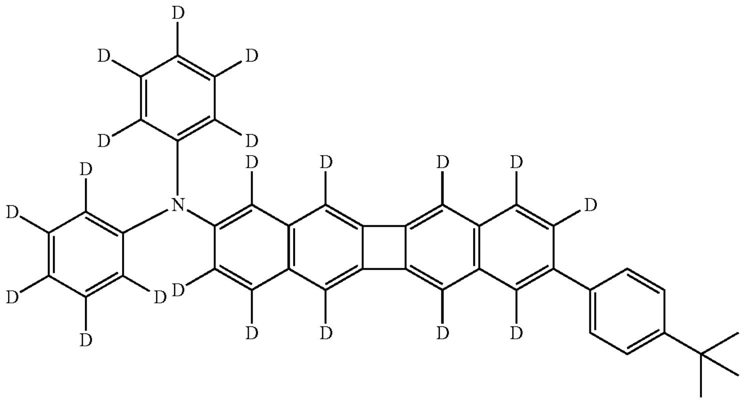
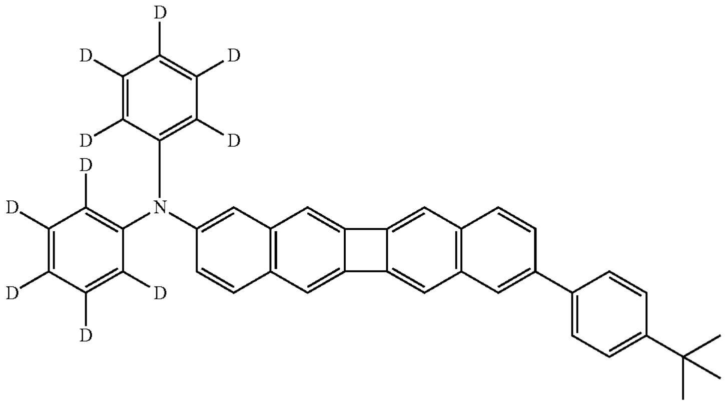
[Formula 177]
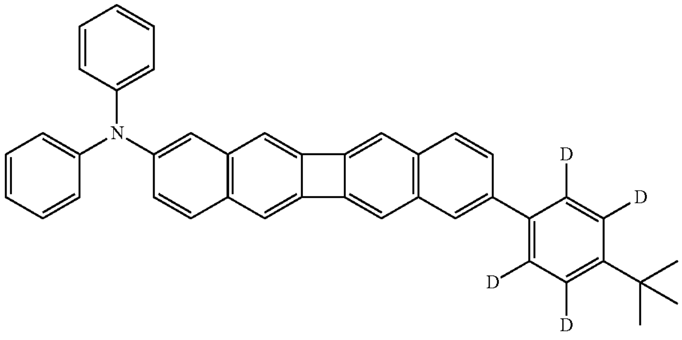

-continued
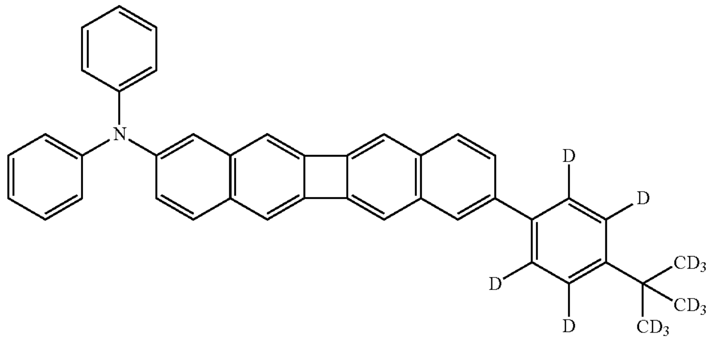
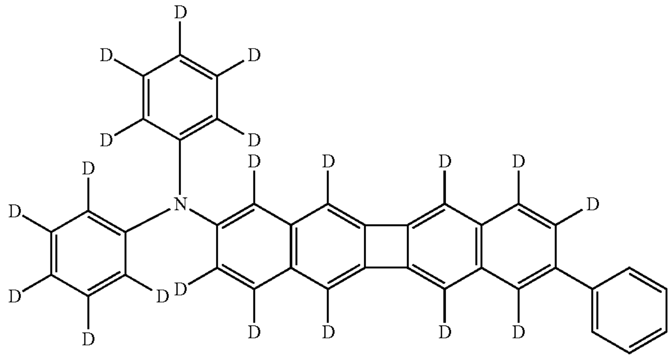
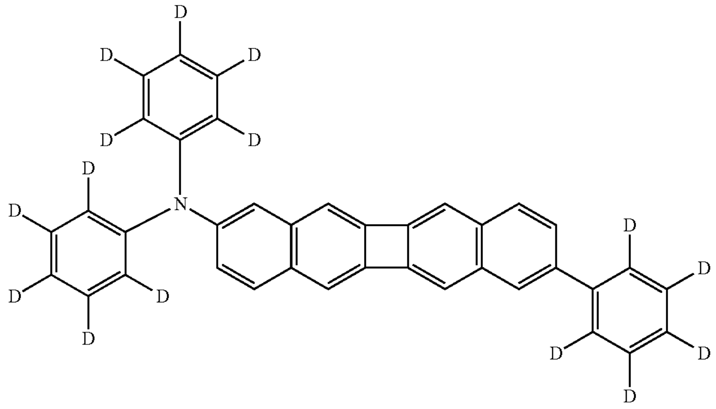
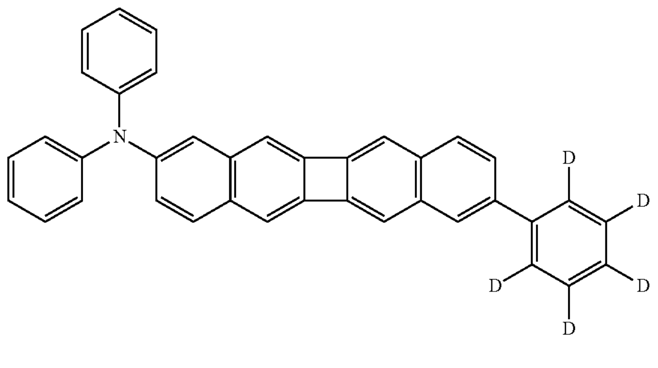

-continued
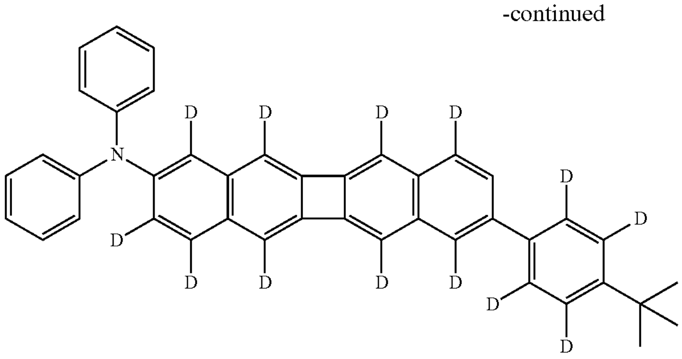
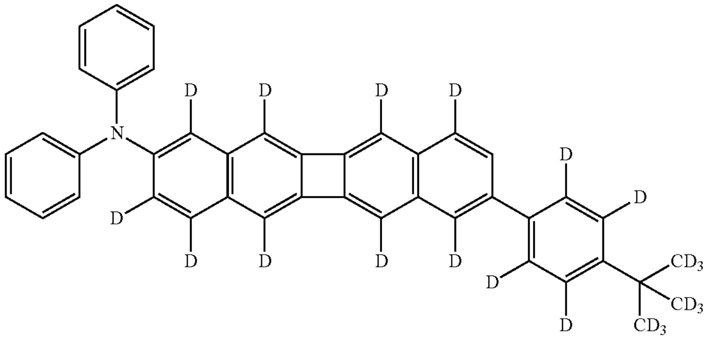
[Formula 178]
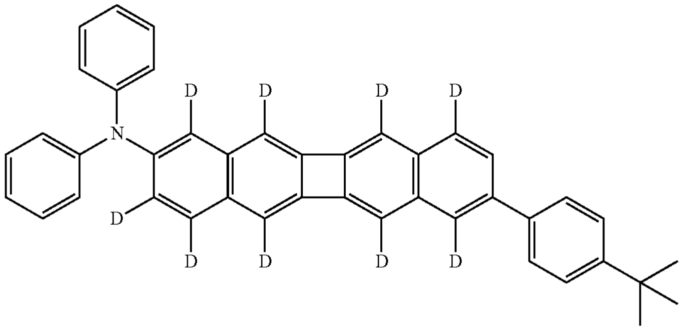
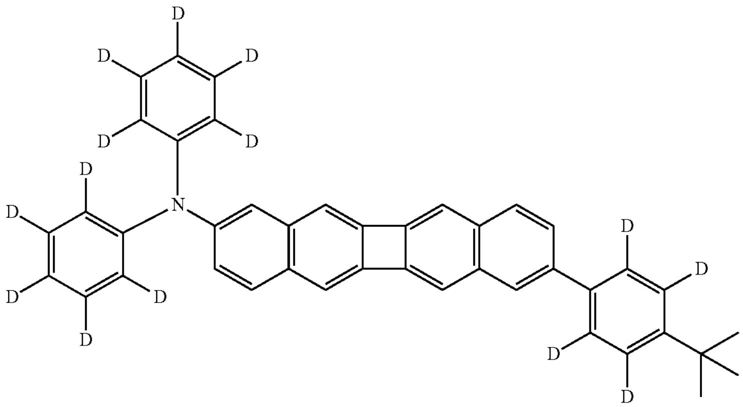

-continued

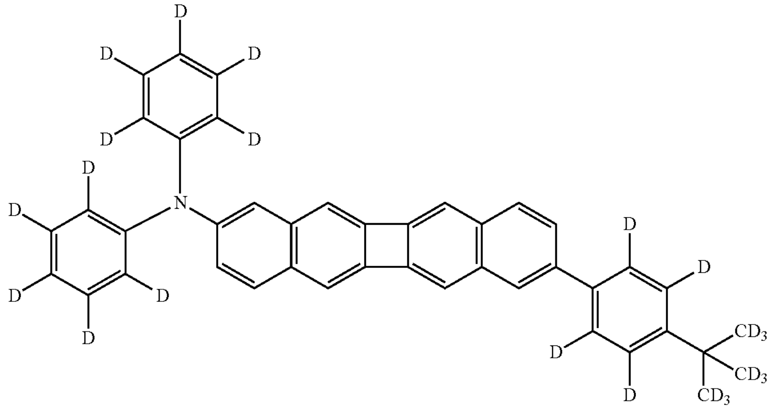 [SMILES: [2H]c1c([2H])c([2H])c(N(c2ccc3cc4c(cc3c2)-c2cc3ccc(-c5c([2H])c([2H])c(C(C([2H])([2H])[2H])(C([2H])([2H])[2H])C([2H])([2H])[2H])c([2H])c5[2H])cc3cc2-4)c2c([2H])c([2H])c([2H])c([2H])c2[2H])c([2H])c1[2H]]

According to the exemplary embodiment, a compound having a high photoluminescence quantum yield (PLQY) and exhibiting a fluorescence spectrum having a high blue color purity can be provided. Moreover, according to an example of the exemplary embodiment, a compound capable of improving a luminous efficiency can be provided.

Second Exemplary Embodiment

Organic-Electroluminescence-Device Material

An organic-electroluminescence-device material according to a second exemplary embodiment contains the compound according to the first exemplary embodiment. An example of the organic-electroluminescence-device material contains only the compound according to the first exemplary embodiment. Another example of the organic-electroluminescence-device material contains the compound according to the first exemplary embodiment and another compound different from the compound according to the first exemplary embodiment.

In the organic-electroluminescence-device material according to the exemplary embodiment, the compound according to the first exemplary embodiment is preferably a dopant material. In this case, the organic-electroluminescence-device material may contain the compound according to the first exemplary embodiment as the dopant material and another compound such as a host material.

Third Exemplary Embodiment

Organic Electroluminescence Device

An organic EL device according to a third exemplary embodiment will be described.

The organic EL device according to the exemplary embodiment includes an anode, a cathode, and at least one organic layer between the anode and the cathod. The organic layer includes at least one layer formed of an organic compound. Alternatively, the organic layer is provided by laminating a plurality of layers each formed of an organic compound. The organic layer may further contain an inorganic compound.

The organic EL device according to the exemplary embodiment includes one or more organic layers, in which at least one layer of the one or more organic layers contains the compound according to the first exemplary embodiment.

The organic EL device according to the exemplary embodiment includes a first organic layer as the organic layer.

In the organic EL device according to the exemplary embodiment, at least one layer of the one or more organic layers is preferably an emitting layer. In the exemplary embodiment, the emitting layer preferably contains the compound according to the first exemplary embodiment.

For instance, the organic layer may be a single emitting layer or may further include at least one layer usable for the organic EL device. The layer usable fo the organic EL device is not particularly limited, but, for instance, is at least one layer selected from the group consisting of a hole injecting layer, hole transporting layer, electron injecting layer, electron transporting layer, electron blocking layer, and hole blocking layer.

The organic layer other than the emitting layer may contain the compound according to the first exemplary embodiment.

In the organic EL device according to the exemplary embodiment, the organic layer may consist of the emitting layer as the first organic layer, but, for instance, may further include at least one layer selected from the group consisting of a hole injecting layer, hole transporting layer, electron injecting layer, electron transporting layer, hole blocking layer, and electron blocking layer.

Hole Transporting Layer

The organic EL device according to the exemplary embodiment preferably further contains a second organic layer between the anode and the first organic layer, in which the second organic layer is preferably a hole transporting layer.

Electron Transporting Layer

The organic EL device according to the exemplary embodiment preferably further contains a third organic layer between the cathode and the first organic layer, in which the third organic layer is preferably an electron transporting layer.

In an exemplary embodiment, the first organic layer as the emitting layer may contain a metal complex.

Alternatively, in an exemplary embodiment, the first organic layer as the emitting layer preferably does not contain a metal complex.

Alternatively, in an exemplary embodiment, the emitting layer preferably does not contain a phosphorescent material (dopant material).

Alternatively, in an exemplary embodiment, the emitting layer preferably does not contain a heavy metal complex and phosphorescent rare earth metal complex. Examples of the heavy metal complex includes an iridium complex, osmium complex, and platinum complex.

The FIGURE schematically shows an exemplary structure of the organic EL device of the exemplary embodiment.

An organic EL device 1 includes a light-transmissive substrate 2, an anode 3, a cathode 4, and an organic layer 10 provided between the anode 3 and the cathode 4. The organic layer 10 includes a hole injecting layer 6, a hole transporting layer 7, an emitting layer 5 as the first organic layer, an electron transporting layer 8, and an electron injecting layer 9 which are sequentially laminated on the anode 3.

The invention is by no means limited to a structure of the organic EL device shown in the FIGURE.

Emitting Layer

In the exemplary embodiment, the first organic layer is the emitting layer. The first organic layer as the emitting layer contains a first compound and a second compound. The second compound in the first organic layer is preferably the compound according to the first exemplary embodiment.

In this example, the first compound is preferably a host material (sometimes referred to as a matrix material), and the second compound is preferably a dopant material (sometimes referred to as a guest material, emitter or luminescent material).

Example of the host material includes a heterocyclic compound and a fused aromatic compound. Preferable examples of the fused aromatic compound include an anthracene derivative, pyrene derivative, chrysene derivative, and naphthacene derivative.

Moreover, a delayed fluorescent (thermally activated delayed fluorescent) compound is usable as the host material. It is also preferable that the emitting layer contains the compound according to the first exemplary embodiment and a delayed fluorescent host compound.

In the exemplary embodiment, when the emitting layer contains the compound according to the first exemplary embodiment, the emitting layer preferably does not contain a phosphorescent metal complex and preferably does not further contain a metal complex other than the phosphorescent metal complex.

In the organic EL device according to the exemplary embodiment, when the first organic layer as the emitting layer contains the first compound and the second compound, singlet energy $S_1(H)$ of the first compound and singlet energy $S_1(D)$ of the second compound preferably satisfy a relationship of the following numerical formula (Numerical Formula 1).

$$S_1(H)>S_1(D) \quad \text{(Numerical Formula 1)}$$

Singlet Energy $S_1$

A method of measuring the singlet energy $S_1$ with use of a solution (occasionally referred to as a solution method) is exemplified by a method below.

A toluene solution of a measurement target compound at a concentration of 10 μmol/L is prepared and put in a quartz cell. An absorption spectrum (ordinate axis: absorption intensity, abscissa axis: wavelength) of the thus-obtained sample is measured at a normal temperature (300K). A tangent was drawn to the fall of the absorption spectrum close to the long-wavelength region, and a wavelength value λedge (nm) at an intersection of the tangent and the abscissa axis assigned to a conversion equation (F2) below to calculate the singlet energy.

$$\text{Conversion Equation}(F2)\text{: } S_1[\text{eV}]=1239.85/\lambda\text{edge}$$

Any device for measuring absorption spectrum is usable. For instance, a spectrophotometer (U3310 manufactured by Hitachi, Ltd.) is usable.

The tangent to the fall of the absorption spectrum close to the long-wavelength region is drawn as follows. While moving on a curve of the absorption spectrum from the local maximum value closest to the long-wavelength region, among the local maximum values of the absorption spectrum, in a long-wavelength direction, a tangent at each point on the curve is checked. An inclination of the tangent is decreased and increased in a repeated manner as the curve falls (i.e., a value of the ordinate axis decreased). A tangent drawn at a point where the inclination of the curve is the local minimum closest to the long-wavelength region (except when absorbance is 0.1 or less) is defined as the tangent to the fall of the absorption spectrum close to the long-wavelength region.

The local maximum absorbance of 0.2 or less is not counted as the above-mentioned local maximum absorbance closest to the long-wavelength region.

Emission Wavelength of Organic EL Device

When the organic EL device according to the exemplary embodiment is driven, a main peak wavelength of light radiated from the organic EL device is preferably in a range from 380 nm to 500 nm, more preferably in a range from 430 nm to 470 nm.

The main peak wavelength of light radiated from the organic EL device is measured as follows. Voltage is applied on the organic EL devices such that a current density becomes 10 mA/cm$^2$, where spectral radiance spectrum is measured by a spectroradiometer CS-2000 (manufactured by Konica Minolta, Inc.). A peak wavelength of an emission spectrum, at which the luminous intensity of the resultant spectral radiance spectrum is at the maximum, is measured and defined as the main peak wavelength (unit: nm).

Film Thickness of Emitting Layer

A film thickness of the emitting layer of the organic EL device according to the exemplary embodiment is preferably in a range from 5 nm to 50 nm, more preferably in a range from 7 nm to 50 nm, further preferably in a range from 10 nm to 50 nm. When the film thickness of the emitting layer is 5 nm or more, it is easy to form the emitting layer and adjust chromaticity. When the film thickness of the emitting layer is 50 nm or less, it is easy to suppress an increase in the drive voltage.

Content Ratios of Compounds in Emitting Layer

When the emitting layer contains the first compound and the second compound, content ratios of the first compound and the second compound in the emitting layer preferably fall, for instance, the respective ranges below.

The content ratio of the first compound is preferably in a range from 80 mass % to 99 mass %, more preferably in a range from 90 mass % to 99 mass %, further preferably in a range from 95 mass % to 99 mass %.

The content ratio of the second compound is preferably in a range from 1 mass % to 10 mass %, more preferably in a range from 1 mass % to 7 mass %, further preferably in a range from 1 mass % to 5 mass %.

It should be noted that the upper limit of the total of the content ratios of the first compound and the second compound in the emitting layer is 100 mass %.

In the exemplary embodiment, it is not excluded that a material other than the first compound and the second compound is contained in the emitting layer.

The emitting layer may contain only one type of the first compound or contain two or more types thereof. The emitting layer may contain only one type of the second compound or contain two or more types thereof.

Second Compound

In the organic EL device according to the exemplary embodiment, the compound represented by the formula (2) or the like described in the first exemplary embodiment is usable as the second compound.

First Compound

In the organic EL device according to the exemplary embodiment, the first compound is preferably a compound represented by a formula (10) below.

In the organic EL device according to the exemplary embodiment, it is also preferable that at least one layer of the organic layer contains the compound according to the first exemplary embodiment and the compound represented by the formula (10) below.

Compound Represented by Formula (10)

The compound represented by the formula (10) will be described below.

[Formula 179]

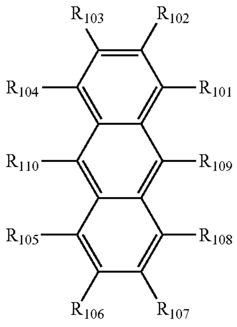

(10)

In the formula (10):

at least one combination of adjacent two or more of $R_{101}$ to $R_{110}$ are mutually bonded to form a substituted or unsubstituted monocyclic ring, mutually bonded to form a substituted or unsubstituted fused ring, or not mutually bonded, $R_{101}$ to $R_{110}$ not forming the monocyclic ring and not forming the fused ring are each independently a hydrogen atom, a substituent R, or a group represented by a formula (11) below.

$$-L_{101}-Ar_{101} \quad (11)$$

In the formula (11):

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

the substituent R is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms;

when two or more substituents R are present, the two or more substituents R are mutually the same or different;

$R_{901}$ to $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when two or more $R_{901}$ are present, the two or more $R_{901}$ are mutually the same or different;

when two or more $R_{902}$ are present, the two or more $R_{902}$ are mutually the same or different;

when two or more $R_{903}$ are present, the two or more $R_{903}$ are mutually the same or different;

when two or more $R_{904}$ are present, the two or more $R_{904}$ are mutually the same or different;

when two or more $R_{905}$ are present, the two or more $R_{905}$ are mutually the same or different;

when two or more $R_{906}$ are present, the two or more $R_{906}$ are mutually the same or different;

when two or more $R_{907}$ are present, the two or more $R_{907}$ are mutually the same or different;

at least one of $R_{101}$ to $R_{110}$ not forming the substituted or unsubstituted monocyclic ring and not forming the substituted or unsubstituted fused ring is the group represented by the formula (11);

when two or more groups represented by the formula (11) are present, the two or more groups represented by the formula (11) are mutually the same or different;

when two or more $L_{101}$ are present, the two or more $L_{101}$ are mutually the same or different; and when two or more $Ar_{101}$ are present, the two or more $Ar_{101}$ are mutually the same or different.

In an exemplary embodiment, the compound represented by the formula (10) contains at least one group represented by the formula (11) in a molecule.

The compound represented by the formula (10) may contain a deutrium atom as a hydrogen atom.

In an exemplary embodiment, at least one of $Ar_{101}$ in the formula (10) is a substituted or unsubstituted aryl group having 6 to 50 ring carbon atoms.

In an exemplary embodiment, at least one of $Ar_{101}$ in the formula (10) is a substituted or unsubstituted heterocyclic group having 5 to 50 ring atoms.

In an exemplary embodiment, all of $Ar_{101}$ in the formula (10) are each a substituted or unsubstituted aryl group having 6 to 50 ring carbon atoms. A plurality of $Ar_{101}$ are mutually the same or different.

In an exemplary embodiment, one of $Ar_{101}$ in the formula (10) is a substituted or unsubstituted heterocyclic group having 5 to 50 ring atoms and the rest of $Ar_{101}$ are each a substituted or unsubstituted aryl group having 6 to 50 ring carbon atoms. A plurality of $Ar_{101}$ are mutually the same or different.

In an exemplary embodiment, at least one of $L_{101}$ in the formula (10) is a single bond.

In an exemplary embodiment, all of $L_{101}$ in the formula (10) are each a single bond.

In an exemplary embodiment, at least one of $L_{101}$ in the formula (10) is a substituted or unsubstituted arylene group having 6 to 50 ring carbon atoms.

In an exemplary embodiment, at least one of $L_{101}$ in the formula (10) is a substituted or unsubstituted phenylene group or a substituted or unsubstituted naphthylene group.

In an exemplary embodiment, a group represented by $-L_{101}-Ar_{101}$ in the formula (10) is selected from the group consisting of a substituted or unsubstituted phenyl group, a substituted or unsubstituted naphthyl group, a substituted or unsubstituted biphenyl group, a substituted or unsubstituted phenanthrenyl group, a substituted or unsubstituted benzophenanthrenyl group, a substituted or unsubstituted fluorenyl group, a substituted or unsubstituted benzofluorenyl group, a substituted or unsubstituted dibenzofuranyl group, a substituted or unsubstituted naphthobenzofuranyl group, a substituted or unsubstituted dibenzothiophenyl group, and a substituted or unsubstituted carbazolyl group.

In an exemplary embodiment, a substituent R in the formula (10) is each independently a substituted or unsubstituted alkyl group having 1 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a halogen atom, a cyano group, a nitro group, or a substituted or unsubstituted aryl group having 6 to 50 ring carbon atoms; and $R_{901}$ to $R_{907}$ are the same as defined in the formula (10).

In an exemplary embodiment, a substituent for a "substituted or unsubstituted" group is each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms; and $R_{901}$ to $R_{907}$ are the same as defined in the formula (10).

In an exemplary embodiment, a substituent for a "substituted or unsubstituted" group is each independently a substituted or unsubstituted alkyl group having 1 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a halogen atom, a cyano group, a nitro group, or a substituted or unsubstituted aryl group having 6 to 50 ring carbon atoms; and $R_{901}$ to $R_{907}$ are the same as defined in the formula (10).

In an exemplary embodiment, a substituent for a "substituted or unsubstituted" group is selected from the group consisting of an alkyl group having 1 to 18 carbon atoms, an aryl group having 6 to 18 ring carbon atoms, and a heterocyclic group having 5 to 18 ring atoms.

In an exemplary embodiment, a substituent for a "substituted or unsubstituted" group in the formula (10) is an alkyl group having 1 to 5 carbon atoms.

In an exemplary embodiment, the compound represented by the formula (10) is a compound represented by a formula (120) below.

[Formula 180]

(120)

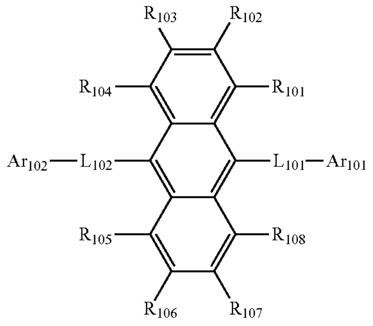

$R_{101}$ to $R_{108}$, $L_{101}$ and $Ar_{101}$ in the formula (120) are the same as defined in the formula (10).

The compound represented by the formula (120) may contain a deutrium atom as a hydrogen atom.

In an exemplary embodiment, the compound represented by the formula (10) or (120) contains at least two groups each represented by the formula (11).

In an exemplary embodiment, the compound represented by the formula (10) or (120) contains two or three groups each represented by the formula (11).

In an exemplary embodiment, $R_{101}$ to $R_{110}$ in the formulae (10) and (120) do not form a substituted or unsubstituted monocyclic ring and do not form a substituted or unsubstituted fused ring.

In an exemplary embodiment, $R_{101}$ to $R_{110}$ in the formulae (10) and (120) are each a hydrogen atom.

In an exemplary embodiment, the compound represented by the formula (120) is a compound represented by a formula (30) below.

[Formula 181]

(30)

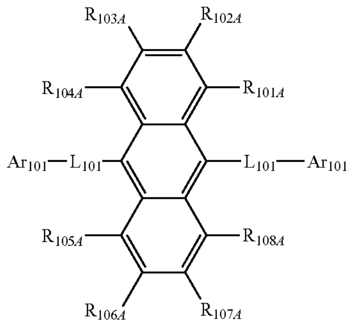

In the formula (30): $L_{101}$ and $Ar_{101}$ are the same as defined in the formula (10);

All combinations of adjacent two or more of $R_{101A}$ to $R_{108A}$ do not form a substituted or unsubstituted monocyclic ring and a substituted or unsubstituted fused ring;

$R_{101A}$ to $R_{108A}$ are each independently a hydrogen atom, or a substituent R; and the substituent R is the same as defined in the formula (10).

In other words, the compound represented by the formula (30) is a compound having two groups each represented by the formula (11).

The compound represented by the formula (30) has substantially only a protium atom as a hydrogen atom.

To "have substantially only a protium atom" means that a ratio of protium isotope to a total of the protium isotope and a deuterium isotope is 90 mol % or more, 95 mol % or more, or 99 mol % or more, the protium isotope meaning a compound having only a protium atom as a hydrogen atom, the deuterium isotope meaning a compound having a deuterium atom as a hydrogen atom, the protium isotope and the deuterium isotope having the same structure.

In an exemplary embodiment, the compound represented by the formula (30) is a compound represented by a formula (31) below.

[Formula 182]

(31)

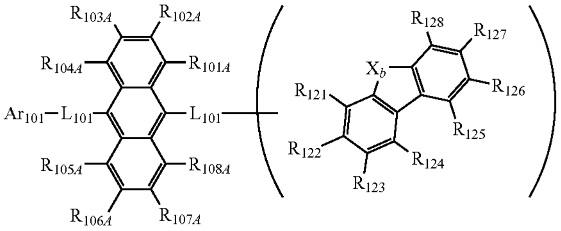

In the formula (31): $L_{101}$ and $Ar_{101}$ are the same as defined in the formula (10);

$R_{101A}$ to $R_{10A}$ are the same as defined in the formula (30);

$X_b$ is an oxygen atom, a sulfur atom, $N(R_{131})$, or $C(R_{132})(R_{133})$;

one of $R_{121}$ to $R_{128}$, and $R_{131}$ to $R_{133}$ is a single bond bonded to $L_{101}$;

at least one combination of adjacent two or more of $R_{121}$ to $R_{128}$ that are not a single bond bonded to $L_{101}$ are mutually bonded to form a substituted or unsubstituted monocyclic ring, mutually bonded to form a substituted or unsubstituted fused ring, or not mutually bonded;

$R_{121}$ to $R_{128}$ that are not a single bond bonded to $L_{101}$ and do not form the substituted or unsubstituted monocyclic ring and do not form the substituted or unsubstituted fused ring are each independently a hydrogen atom, or a substituent R; and the substituent R is the same as defined in the formula (10);

$R_{131}$ to $R_{133}$ that are not a single bond bonded to $L_{101}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when two or more $R_{131}$ are present, the two or more $R_{131}$ are mutually the same or different;

when two or more $R_{132}$ are present, the two or more $R_{132}$ are mutually the same or different; and when two or more $R_{133}$ are present, the two or more $R_{133}$ are mutually the same or different.

In an exemplary embodiment, the compound represented by the formula (31) is a compound represented by a formula (32) below.

[Formula 183]

(32)

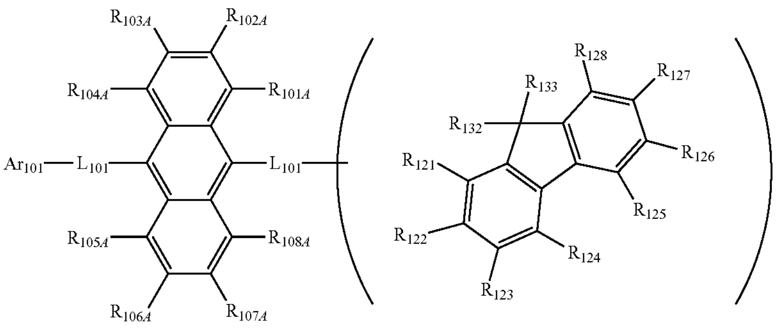

In the formula (32), $R_{101A}$ to $R_{108A}$, $L_{101}$, $Ar_{101}$, $R_{121}$ to $R_{128}$, $R_{132}$, and $R_{133}$ are the same as defined in the formula (31).

In an exemplary embodiment, the compound represented by the formula (31) is a compound represented by a formula (33) below.

[Formula 184]

(33)

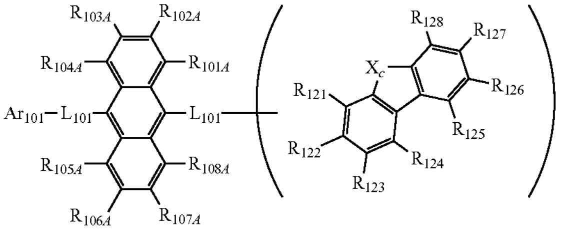

In the formula (33), $R_{101A}$ to $R_{108A}$, $L_{101}$, $Ar_{101}$, and $R_{121}$ to $R_{128}$ are the same as defined in the formula (31); $X_c$ is an oxygen atom, a sulfur atom, or $N(R_{131})$; and $R_{131}$ is the same as defined in the formula (31).

In an exemplary embodiment, the compound represented by the formula (31) is a compound represented by a formula (34) below.

[Formula 185]

(34)

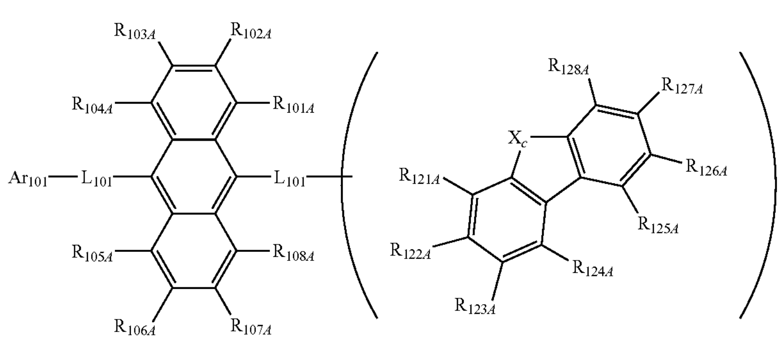

In the formula (34): $R_{101A}$ to $R_{108A}$, $L_{101}$ and $Ar_{101}$ are the same as defined in the formula (31);

$X_c$ is an oxygen atom, a sulfur atom, or $N(R_{131})$;

$R_{131}$ is the same as defined in the formula (31);

one of $R_{121A}$ to $R_{128A}$ is a single bond bonded to $L_{101}$;

at least one combination of adjacent two or more of $R_{121A}$ to $R_{128A}$ that each are not a single bond bonded to $L_{101}$ do not form a substituted or unsubstituted monocyclic ring and do not form a substituted or unsubstituted fused ring;

$R_{121A}$ to $R_{128A}$ that are not a single bond bonded to $L_{101}$ are each independently a hydrogen atom, or a substituent R; and the substituent R is the same as defined in the formula (10).

In an exemplary embodiment, the compound represented by the formula (31) is a compound represented by a formula (35) below.

[Formula 186]

(35)

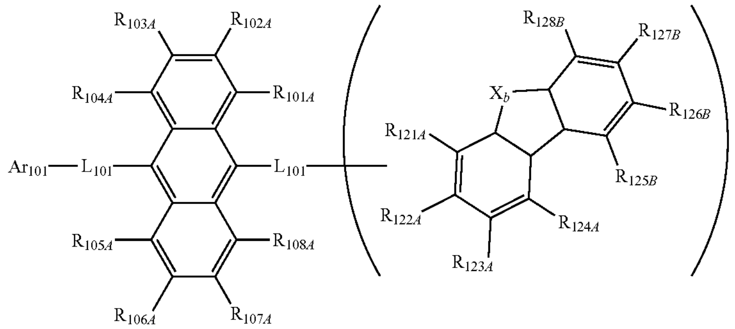

In the formula (35): $R_{11A}$ to $R_{108A}$, $L_{101}$, $Ar_{101}$, and $X_b$ are the same as defined in the formula (31);

at least one combination of adjacent two or more of $R_{121A}$ to $R_{124A}$ do not form a substituted or unsubstituted monocyclic ring and do not form a substituted or unsubstituted fused ring; and one combination of a combination of $R_{125B}$ and $R_{126B}$, a combination of $R_{126B}$ and $R_{127B}$, and a combination of $R_{127B}$ and $R_{128B}$ are bonded to each other to form a ring represented by a formula (35a) or a formula (35b).

[Formula 187]

(35a)

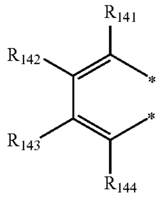

-continued (35b)

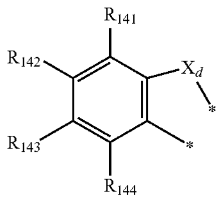

In the formulae (35a) and (35b):

two * are each bonded to one combination of the combination of $R_{125B}$ and $R_{126B}$, the combination of $R_{126B}$ and $R_{127B}$, and the combination of $R_{127B}$ and $R_{128B}$;

$R_{141}$ to $R_{144}$ are each independently a hydrogen atom, or a substituent R; the substituent R is the same as defined in the formula (10);

$X_d$ is an oxygen atom or a sulfur atom;

one selected from $R_{121A}$ to $R_{124A}$, $R_{125B}$ to $R_{128B}$ that do not form the ring represented by the formula (35a) or (35b), and $R_{141}$ to $R_{144}$ is a single bond bonded to $L_{101}$; and $R_{121A}$ to $R_{124A}$ that are not a single bond bonded to $L_{101}$ and $R_{125B}$ to $R_{128B}$ that are not a single bond bonded to $L_{101}$ and do not form the ring represented by the formula (35a) or (35b) are each independently a hydrogen atom, or a substituent R; and the substituent R is the same as defined in the formula (10).

In an exemplary embodiment, the compound represented by the formula (35) is a compound represented by a formula (36) below.

[Formula 188]

(36)

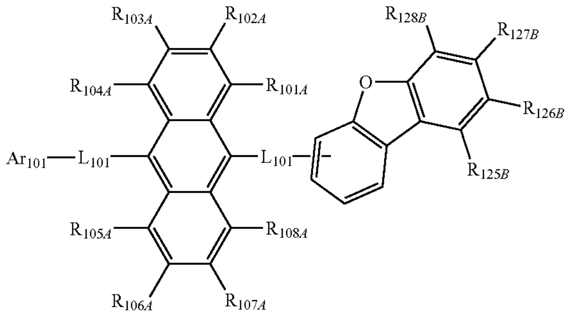

In the formula (36), $R_{101A}$ to $R_{108A}$, $L_{101}$, $Ar_{101}$, and $R_{125B}$ to $R_{128B}$ are the same as defined in the formula (35).

In an exemplary embodiment, the compound represented by the formula (34) is a compound represented by a formula (37) below.

(37)

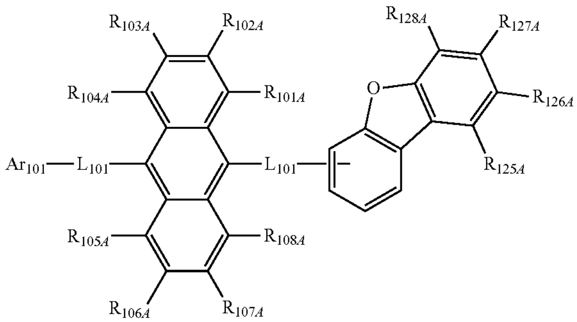

In the formula (37): $R_{101A}$ to $R_{108A}$, $R_{125A}$ to $R_{128A}$, $L_{101}$ and $Ar_{101}$ are the same as defined in the formula (34).

In an exemplary embodiment, $R_{101A}$ to $R_{108A}$ in the formulae (30) to (37) are each a hydrogen atom.

In an exemplary embodiment, the compound represented by the formula (10) is a compound represented by a formula (40) below.

[Formula 190]

(40)

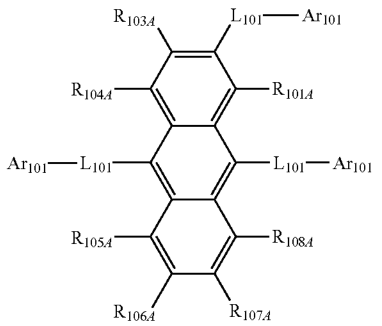

In the formula (40):

$L_{101}$ and $Ar_{101}$ are the same as defined in the formula (10);

at least one combination of adjacent two or more of $R_{101A}$ and $R_{103A}$ to $R_{108A}$ are mutually bonded to form a substituted or unsubstituted monocyclic ring, mutually bonded to form a substituted or unsubstituted fused ring, or not mutually bonded; and $R_{101A}$ and $R_{103A}$ to $R_{108A}$ not forming the substituted or unsubstituted monocyclic ring and not forming the substituted or unsubstituted fused ring are each independently a hydrogen atom, or a substituent R; and the substituent R is the same as defined in the formula (10).

In other words, the compound represented by the formula (40) is a compound having three groups represented by the formula (11). The compound represented by the formula (40) have substantially only a protium atom as a hydrogen atom.

In an exemplary embodiment, the compound represented by the formula (40) is represented by a formula (41).

[Formula 191]

(41)

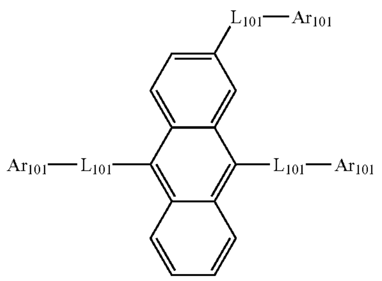

In the formula (41), $L_{101}$ and $Ar_{101}$ are the same as defined in the formula (40).

In an exemplary embodiment, the compound represented by the formula (40) is a compound represented by any one of formulae (42-1) to (42-3) below.

[Formula 192]

(42-1)

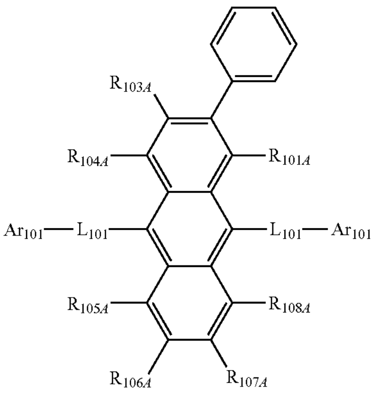

(42-2)

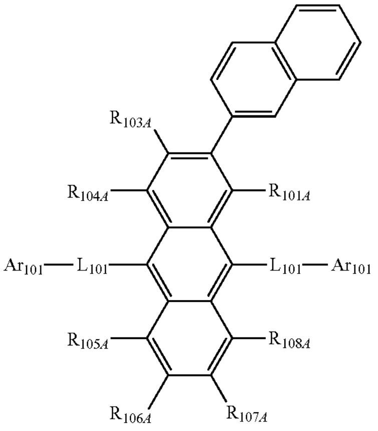

(42-3)

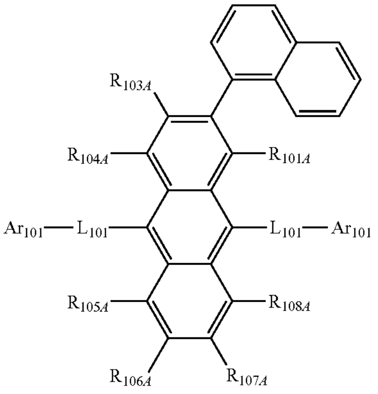

In the formulae (42-1) to (42-3), $R_{101A}$ to $R_{108A}$, $L_{101}$ and $Ar_{101}$ are the same as defined in the formula (40).

In an exemplary embodiment, the compounds represented by the formulae (42-1) to (42-3) are each a compound represented by any one of formulae (43-1) to (43-3) below.

[Formula 193]

(43-1)

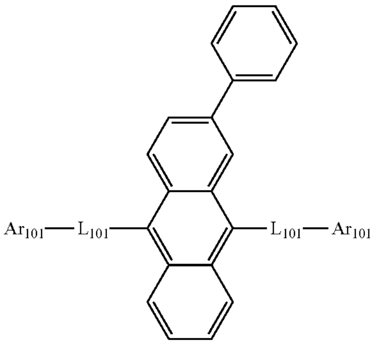

(43-2)

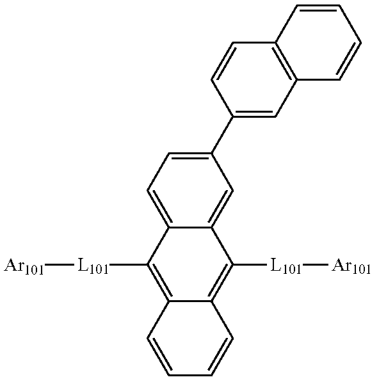

(43-3)

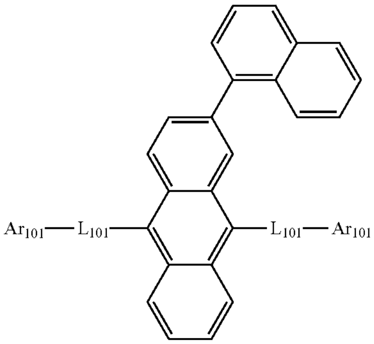

In the formulae (43-1) to (43-3), $L_{101}$ and $Ar_{101}$ are the same as defined in the formula (40).

In an exemplary embodiment, a group represented by $-L_{101}-Ar_{101}$ in the formulae (40), (41), (42-1) to (42-3), and (43-1) to (43-3) is selected from the group consisting of a substituted or unsubstituted phenyl group, a substituted or unsubstituted naphthyl group, a substituted or unsubstituted biphenyl group, a substituted or unsubstituted phenanthrenyl group, a substituted or unsubstituted benzophenanthrenyl group, a substituted or unsubstituted fluorenyl group, a substituted or unsubstituted benzofluorenyl group, a substituted or unsubstituted dibenzofuranyl group, a substituted or unsubstituted naphthobenzofuranyl group, a substituted or unsubstituted dibenzothiophenyl group, and a substituted or unsubstituted carbazolyl group.

In an exemplary embodiment, the compound represented by the formula (10) or (120) is exemplified by the compound represented by the formula (10) or (120) in which at least one of hydrogen atoms contained therein is a deutrium atom.

In an exemplary embodiment, in the formula (120), at least one of hydrogen atoms as $R_{101}$ to $R_{108}$, hydrogen atoms contained in $R_{101}$ to $R_{108}$ being the substituent R, a hydrogen atom contained in $L_{101}$, a hydrogen atom contained in a substituent for $L_{101}$, a hydrogen atom contained in $Ar_{101}$, and a hydrogen atom contained in a substituent for $Ar_{101}$ is a deutrium atom.

The compounds represented by the formulae (30) to (37) are exemplified by the compounds represented by the formulae (30) to (37) in which at least one of hydrogen atoms contained therein is a deutrium atom.

In an exemplary embodiment, at least one of hydrogen atoms bonded to carbon atoms of anthracene skeletons in the respective compounds represented by the formulae (30) to (37) is a deutrium atom.

In an exemplary embodiment, the compound represented by the formula (30) is a compound represented by a formula (30D) below.

[Formula 194]

(30D)

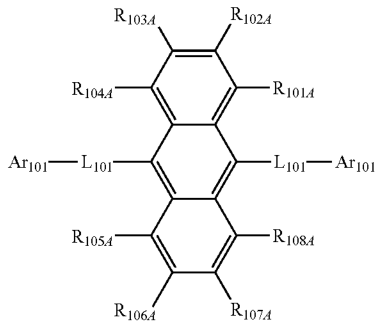

In the formula (30D): $R_{101A}$ to $R_{108A}$, $L_{101}$ and $Ar_{101}$ are the same as defined in the formula (30).

However, at least one of hydrogen atoms as $R_{101A}$ to $R_{110A}$, hydrogen atoms contained in $R_{101A}$ to $R_{110A}$ being the substituent R, a hydrogen atom contained in $L_{101}$, a hydrogen atom contained in a substituent for $L_{101}$, a hydrogen atom contained in $Ar_{101}$, and a hydrogen atom contained in a substituent for $Ar_{101}$ is a deutrium atom.

In other words, the compound represented by the formula (30D) is exemplified by the compound represented by the formula (30) in which at least one of hydrogen atoms contained therein is a deutrium atom.

In an exemplary embodiment, at least one of $R_{101A}$ to $R_{108A}$ being hydrogen atoms in the formula (30D) is a deutrium atom.

In an exemplary embodiment, the compound represented by the formula (30D) is a compound represented by a formula (31 D) below.

[Formula 195]

(31D)

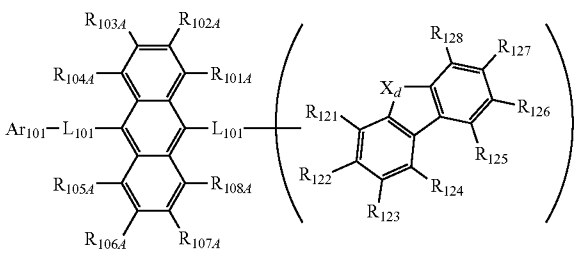

In the formula (31 D): $R_{101A}$ to $R_{10A}$, $L_{101}$ and $Ar_{101}$ are the same as defined in the formula (30D);

$X_d$ is an oxygen atom or a sulfur atom;

one of $R_{121}$ to $R_{128}$ is a single bond bonded to $L_{101}$;

at least one combination of adjacent two or more of $R_{121}$ to $R_{128}$ that are not a single bond bonded to $L_{101}$ are mutually bonded to form a substituted or unsubstituted monocyclic ring, mutually bonded to form a substituted or unsubstituted fused ring, or not mutually bonded;

$R_{121}$ to $R_{128}$ that are not a single bond bonded to $L_{101}$ and do not form the substituted or unsubstituted monocyclic ring and do not form the substituted or unsubstituted fused ring are each independently a hydrogen atom, or a substituent R; and the substituent R is the same as defined in the formula (10); and at least one of hydrogen atoms as $R_{101A}$ to $R_{110A}$, hydrogen atoms contained in $R_{101A}$ to $R_{110A}$ being the substituent R, a hydrogen atom contained in $L_{101}$, a hydrogen atom contained in a substituent for $L_{101}$, a hydrogen atom contained in $Ar_{101}$, a hydrogen atom contained in a substituent for $Ar_{101}$ hydrogen atoms as $R_{121}$ to $R_{128}$, and hydrogen atoms contained in $R_{121}$ to $R_{128}$ as the substituent R is a deutrium atom.

In an exemplary embodiment, the compound represented by the formula (31 D) is a compound represented by a formula (32D) below.

[Formula 196]

(32D)

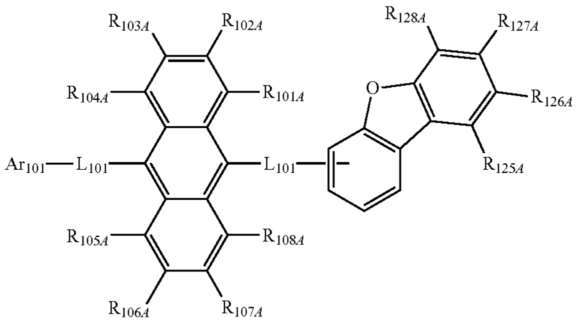

In the formula (32D): $R_{101A}$ to $R_{108A}$, $R_{125A}$ to $R_{128A}$, $L_{101}$ and $Ar_{101}$ are the same as defined in the formula (35).

However, at least one of hydrogen atoms as $R_{101A}$ to $R_{108A}$, hydrogen atoms contained in $R_{101A}$ to $R_{108A}$ being the substituent R, hydrogen atoms as $R_{125A}$ to $R_{128A}$, hydrogen atoms contained in $R_{125A}$ to $R_{128A}$ being the substituent R, a hydrogen atom bonded to a carbon atom in a dibenzofuran skeleton in the formula (32D), a hydrogen atom contained in $L_{101}$, a hydrogen atom contained in a substituent for $L_{101}$, a hydrogen atom contained in $Ar_{101}$, and a hydrogen atom contained in a substituent for $Ar_{101}$ is a deutrium atom.

In an exemplary embodiment, the compound represented by the formula (32D) is a compound represented by a formula (32D-1) or (32D-2) below.

[Formula 197]

(32D-1)

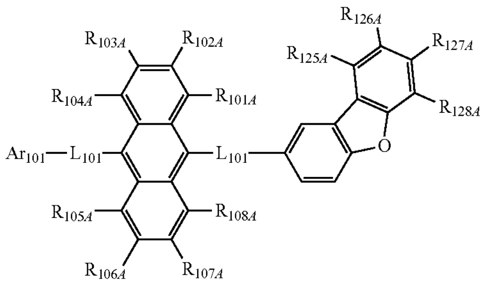

(32D-2)

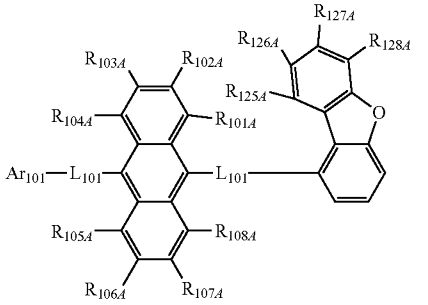

In the formulae (32D-1) and (32D-2): $R_{101A}$ to $R_{108A}$, $R_{125A}$ to $R_{128A}$, $L_{101}$ and $Ar_{101}$ are the same as defined in the formula (32D).

However, at least one of hydrogen atoms as $R_{101A}$ to $R_{108A}$, hydrogen atoms contained in $R_{101A}$ to $R_{108A}$ being the substituent R, hydrogen atoms as $R_{125A}$ to $R_{128A}$, hydrogen atoms contained in $R_{125A}$ to $R_{128A}$ being the substituent R, a hydrogen atom bonded to a carbon atom in a dibenzofuran skeleton in the formulae (32D-1) and (32D-2), a hydrogen atom contained in $L_{101}$, a hydrogen atom contained in a substituent for $L_{101}$, a hydrogen atom contained in $Ar_{101}$, and a hydrogen atom contained in a substituent for $Ar_{101}$ is a deutrium atom.

In an exemplary embodiment, at least one of hydrogen atoms contained in the compound represented by the formula (40), (41), (42-1) to (42-3), or (43-1) to (43-3) is a deutrium atom.

In an exemplary embodiment, at least one of hydrogen atoms (i.e., $R_{101A}$ to $R_{108A}$ being hydrogen atoms) bonded to carbon atoms of an anthracene skeleton in the compound represented by the formula (41) is a deutrium atom.

In an exemplary embodiment, the compound represented by the formula (40) is a compound represented by a formula (40D) below.

[Formula 198]

(40D)

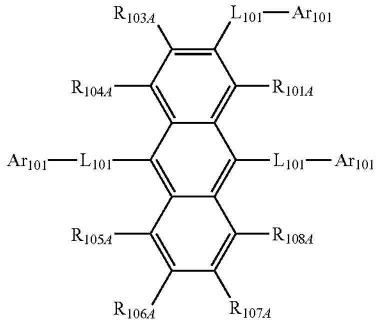

In the formula (40D):

$L_{101}$ and $Ar_{101}$ are the same as defined in the formula (10); at least one combination of adjacent two or more of $R_{101A}$ and $R_{103A}$ to $R_{108A}$ do not form a substituted or unsubstituted monocyclic ring and do not form a substituted or unsubstituted fused ring; and $R_{101A}$ and $R_{103A}$ to $R_{108A}$ are each independently a hydrogen atom, or a substituent R; and the substituent R is the same as defined in the formula (10).

However, at least one of hydrogen atoms as $R_{101A}$ and $R_{103A}$ to $R_{108A}$, hydrogen atoms contained in $R_{101A}$ and $R_{103A}$ to $R_{108A}$ being the substituent R, a hydrogen atom contained in $L_{101}$, a hydrogen atom contained in a substituent for $L_{101}$, a hydrogen atom contained in $Ar_{101}$, and a hydrogen atom contained in a substituent for $Ar_{101}$ is a deutrium atom.

In an exemplary embodiment, at least one of $R_{101A}$ or $R_{103A}$ to $R_{108A}$ in the formula (40D) is a deutrium atom.

In an exemplary embodiment, the compound represented by the formula (40D) is a compound represented by a formula (41 D) below.

[Formula 199]

(41D)

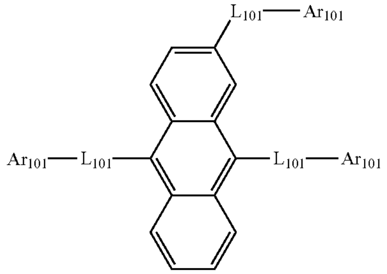

In the formula (41 D), $L_{101}$ and $Ar_{101}$ are the same as defined in the formula (40D).

In the formula (41 D), at least one of hydrogen atoms bonded to carbon atoms in an anthracene skeleton, a hydrogen atom contained in $L_{101}$, a hydrogen atom contained in a substituent for $L_{101}$, a hydrogen atom contained in $Ar_{101}$, and a hydrogen atom contained in a substituent for $Ar_{101}$ is a deutrium atom.

In an exemplary embodiment, the compound represented by the formula (40D) is a compound represented by any one of formulae (42D-1) to (42D-3) below.

[Formula 200]

(42D-1)

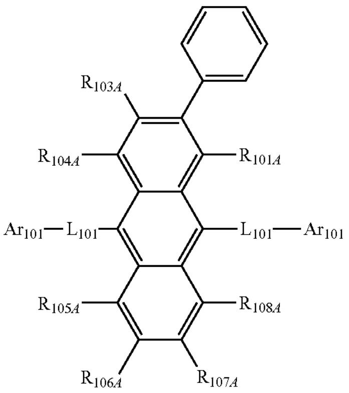

(42D-2)

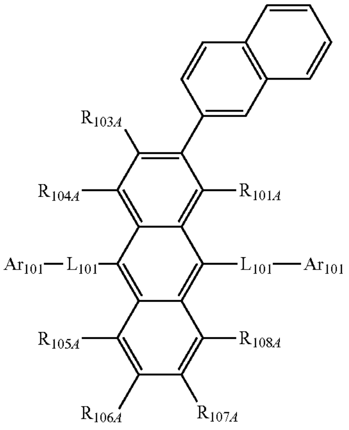

(42D-3)

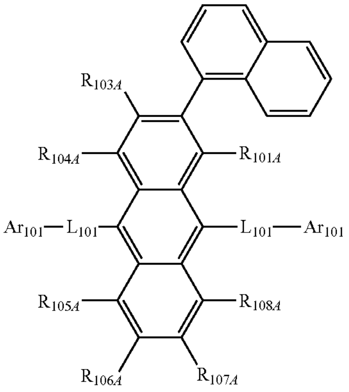

In the formulae (42D-1) to (42D-3): $R_{101A}$ to $R_{108A}$, $L_{101}$ and $Ar_{101}$ are the same as defined in the formula (40D).

In the formula (42D-1), at least one of hydrogen atoms as $R_{101A}$ and $R_{103A}$ to $R_{108A}$, hydrogen atoms contained in $R_{101A}$ and $R_{103A}$ to $R_{108A}$ being the substituent R, a hydrogen atom contained in $L_{101}$, a hydrogen atom contained in a substituent for $L_{101}$, a hydrogen atom contained in $Ar_{101}$, a hydrogen atom contained in a substituent for $Ar_{101}$, and hydrogen atoms bonded to carbon atoms of a phenyl group in the formula (42D-1) is a deutrium atom.

In the formula (42D-2), at least one of hydrogen atoms as $R_{101A}$ and $R_{103A}$ to $R_{108A}$, hydrogen atoms contained in $R_{101A}$ and $R_{103A}$ to $R_{108A}$ being the substituent R, a hydrogen atom contained in $L_{101}$, a hydrogen atom contained in a substituent for $L_{101}$, a hydrogen atom contained in $Ar_{101}$, a hydrogen atom contained in a substituent for $Ar_{101}$, and hydrogen atoms bonded to carbon atoms of a naphthyl group in the formula (42D-2) is a deutrium atom.

In the formula (42D-3), at least one of hydrogen atoms as $R_{101A}$ and $R_{103A}$ to $R_{108A}$, hydrogen atoms contained in $R_{101A}$ and $R_{103A}$ to $R_{108A}$ being the substituent R, a hydrogen atom contained in $L_{101}$, a hydrogen atom contained in a substituent for $L_{101}$, a hydrogen atom contained in $Ar_{101}$, a hydrogen atom contained in a substituent for $Ar_{101}$, and hydrogen atoms bonded to carbon atoms of a naphthyl group in the formula (42D-3) is a deutrium atom.

In an exemplary embodiment, the compounds represented by the formulae (42D-1) to (42D-3) are each a compound represented by any one of formulae (43D-1) to (43D-3) below.

[Formula 201]

(43D-1)

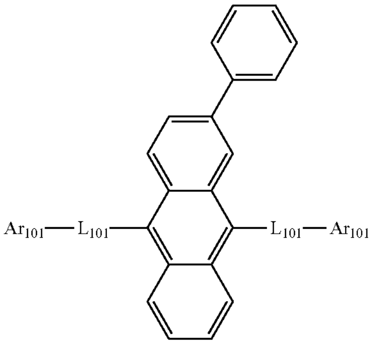

(43D-2)

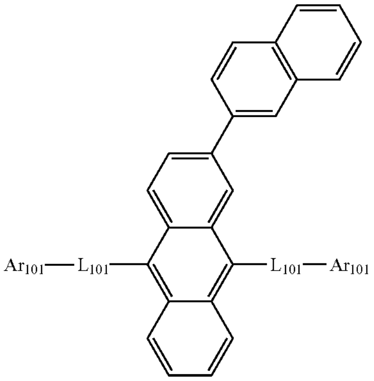

(43D-3)

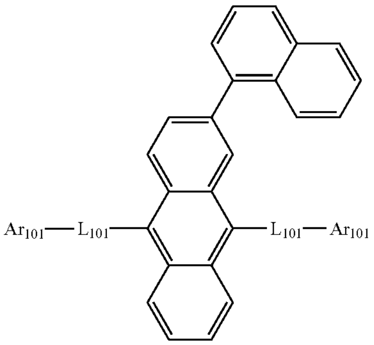

In the formulae (43D-1) to (43D-3), $L_{101}$ and $Ar_{101}$ are the same as defined in the formula (40D).

In the formula (43D-1), at least one of hydrogen atoms bonded to carbon atoms in an anthracene skeleton, a hydrogen atom contained in $L_{101}$, a hydrogen atom contained in a substituent for $L_{101}$, a hydrogen atom contained in $Ar_{101}$, a hydrogen atom contained in a substituent for $Ar_{101}$, and hydrogen atoms bonded to carbon atoms of a phenyl group in the formula (43D-1) is a deutrium atom.

In the formula (43D-2), at least one of hydrogen atoms bonded to carbon atoms in an anthracene skeleton, a hydrogen atom contained in $L_{101}$, a hydrogen atom contained in a substituent for $L_{101}$, a hydrogen atom contained in $Ar_{101}$, a hydrogen atom contained in a substituent for $Ar_{101}$, and hydrogen atoms bonded to carbon atoms of a naphthyl group in the formula (43D-2) is a deutrium atom.

In the formula (43D-3), at least one of hydrogen atoms bonded to carbon atoms in an anthracene skeleton, a hydrogen atom contained in $L_{101}$, a hydrogen atom contained in a substituent for $L_{101}$, a hydrogen atom contained in $Ar_{101}$, a hydrogen atom contained in a substituent for $Ar_{101}$, and hydrogen atoms bonded to carbon atoms of a naphthyl group in the formula (43D-3) is a deutrium atom.

In the description of the first compound, details of a substituent for "substituted or unsubstituted" group are the same as defined in the section of "Definitions" herein.

Specific Examples of Compound Represented by Formula (10)

Specific examples of the compound represented by the formula (10) include compounds shown below. The compound represented by the formula (10) is by no means limited to these specific examples. In the specific examples, Me represents a methyl group and D represents a deutrium atom.

[Formula 202]

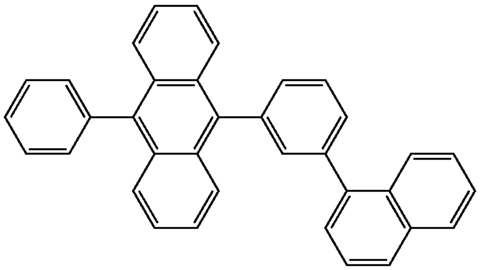

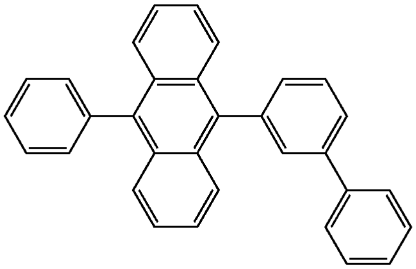

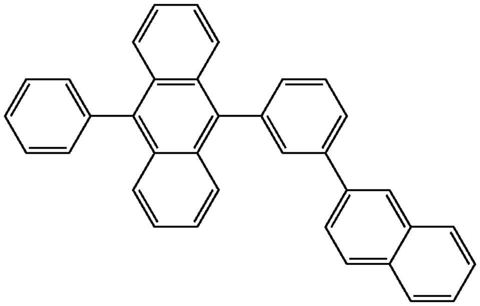

-continued

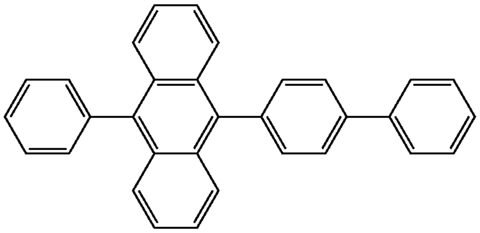

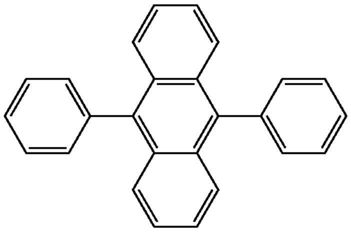

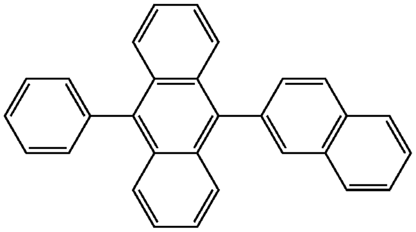

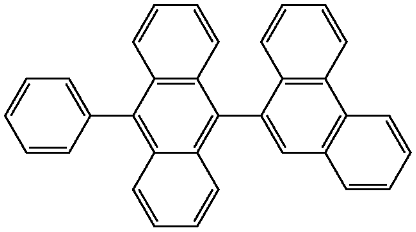

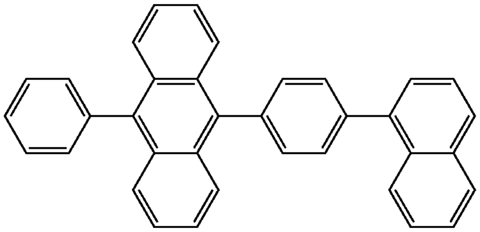

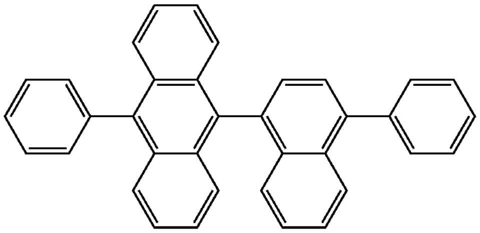

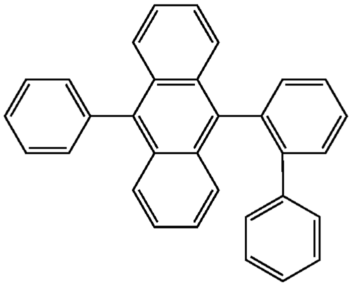

-continued
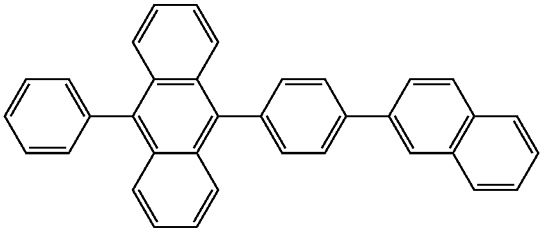
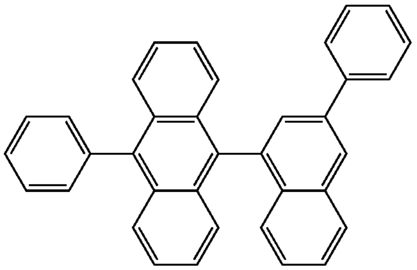
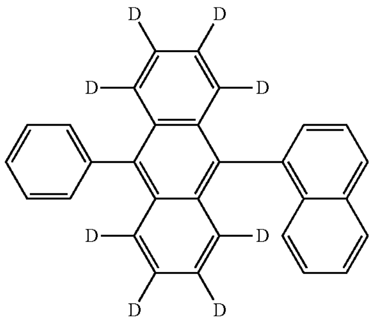
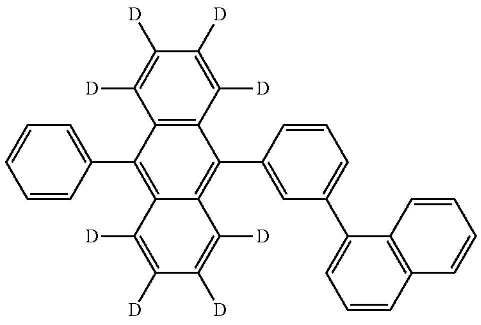
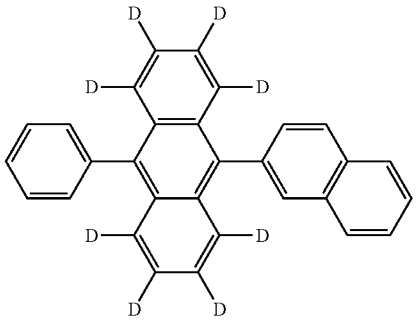
-continued
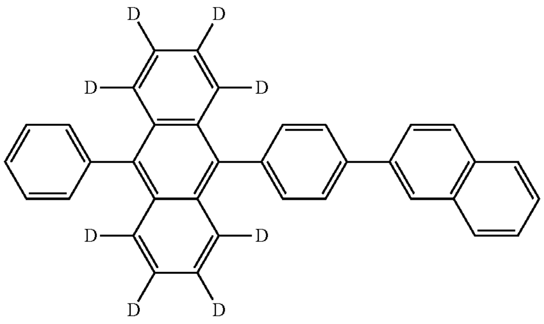
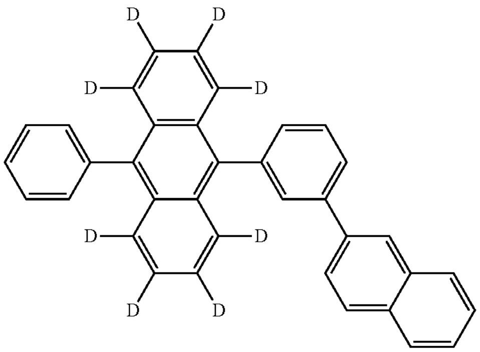
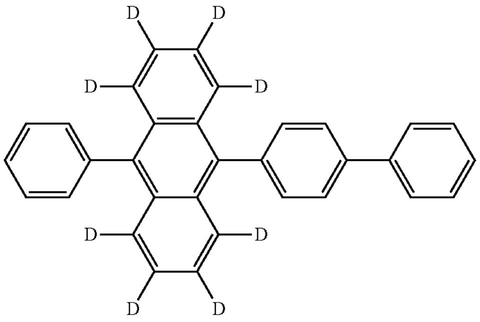
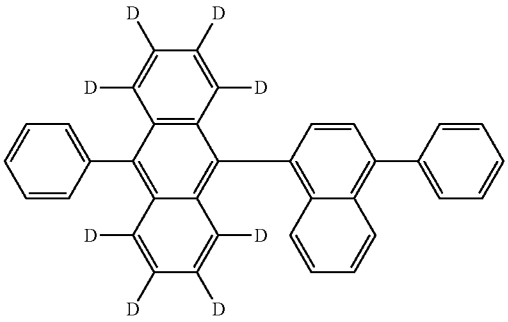
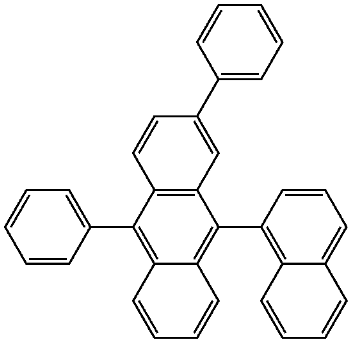

-continued
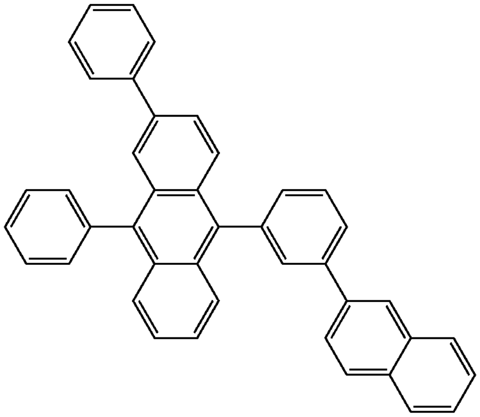
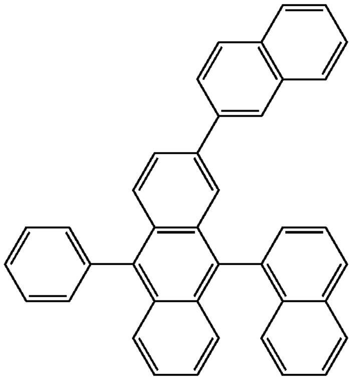
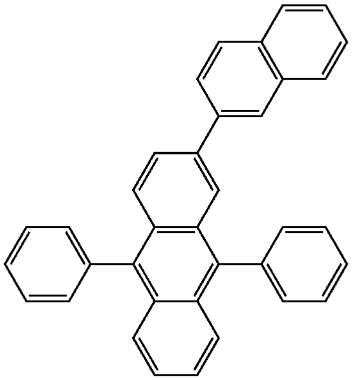
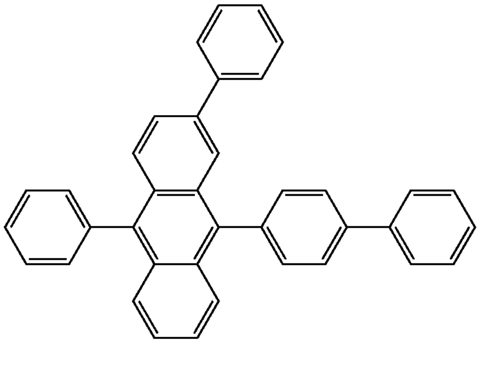
-continued
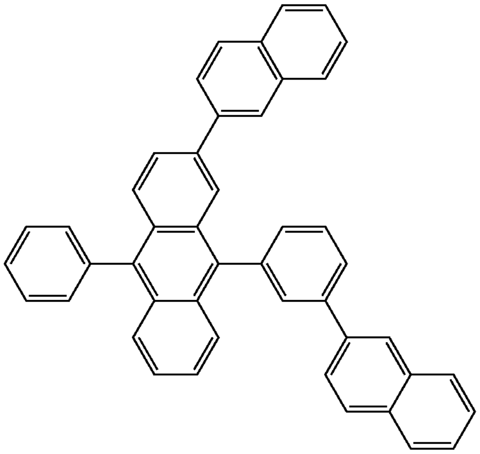
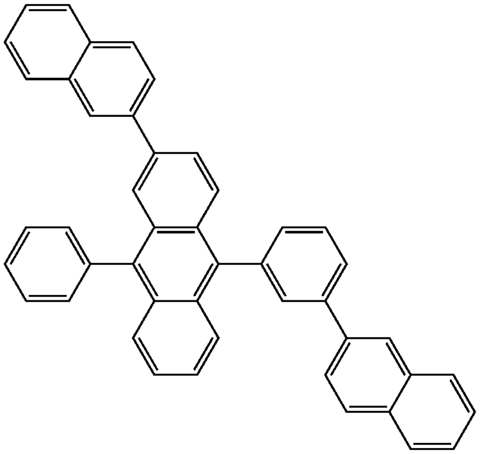
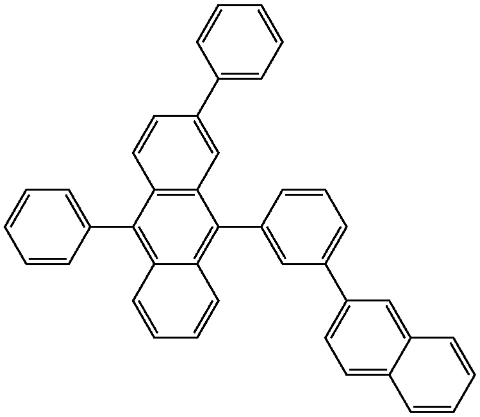
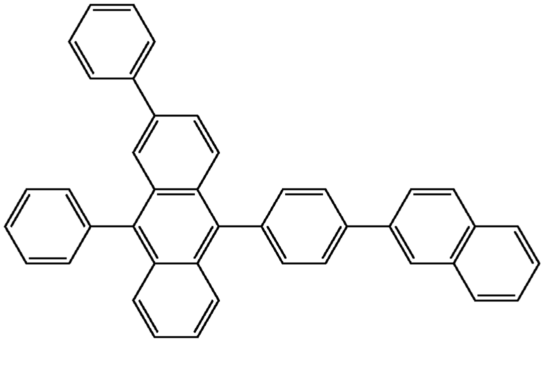

-continued
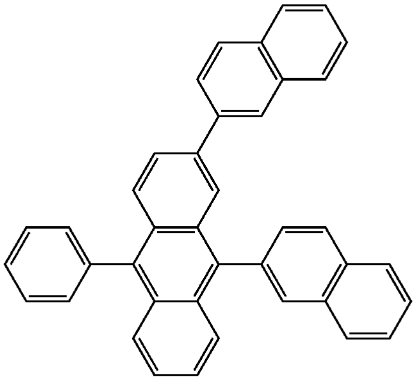
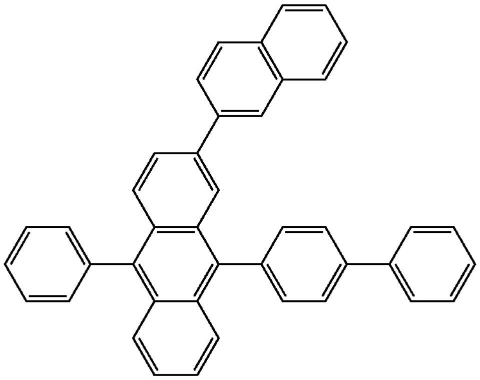
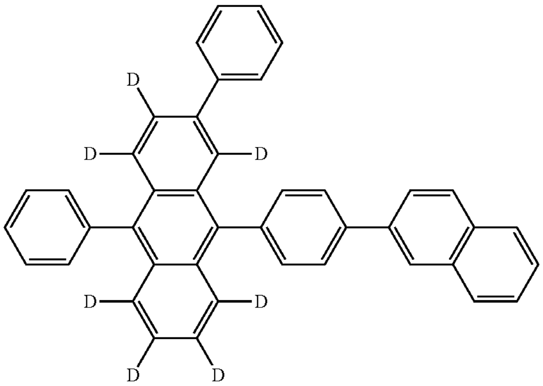
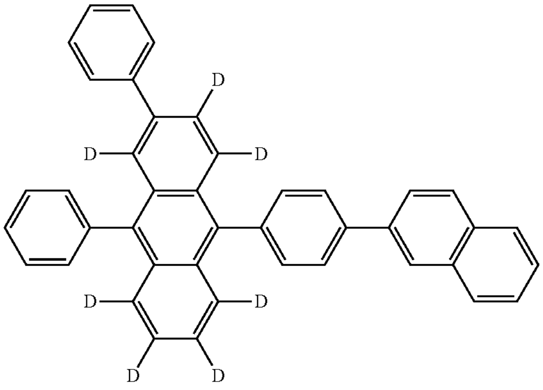
-continued
[Formula 203]
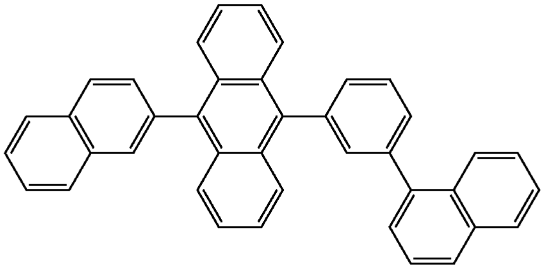
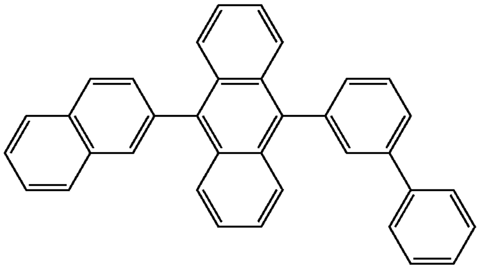
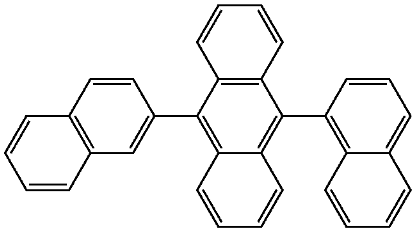
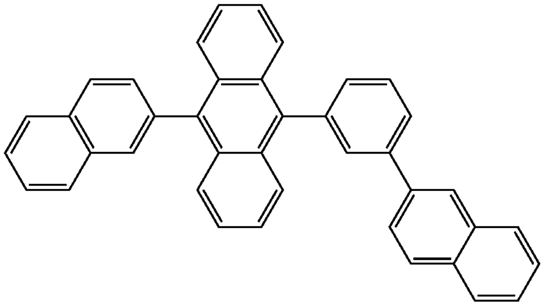
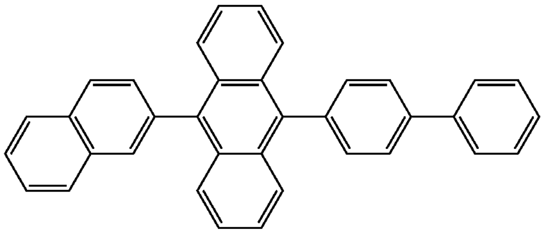
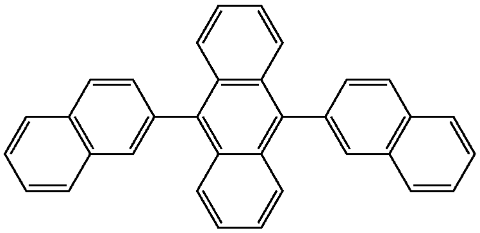

-continued
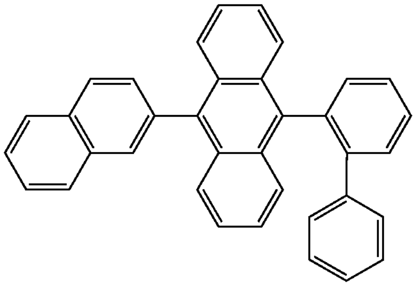
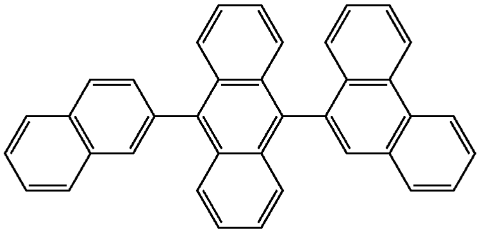
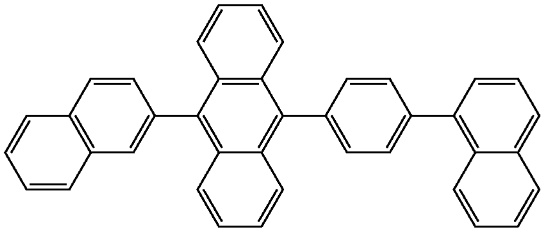
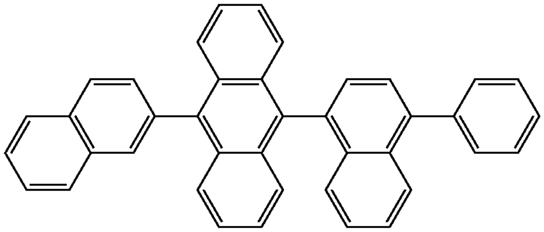
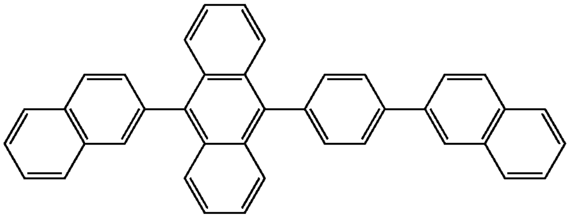
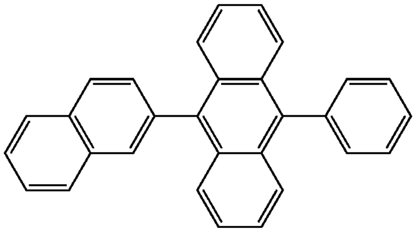
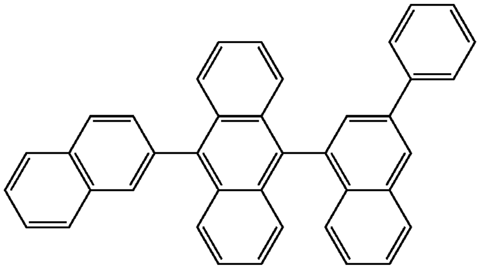
-continued
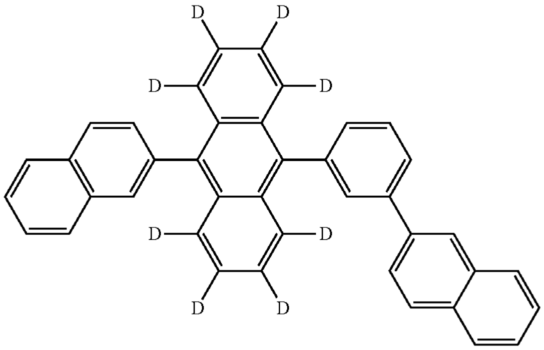
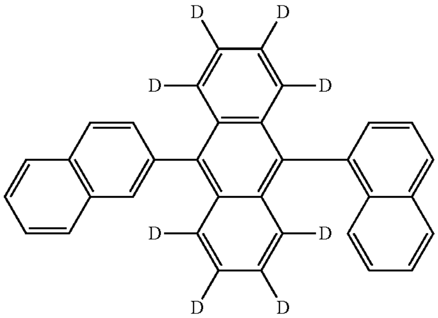
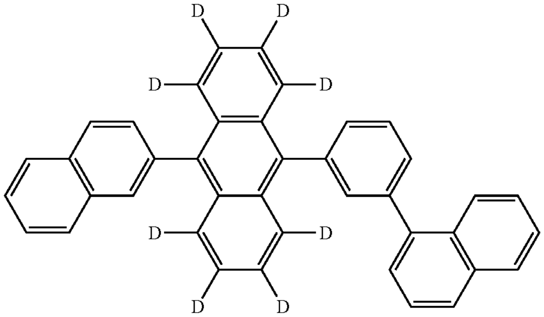
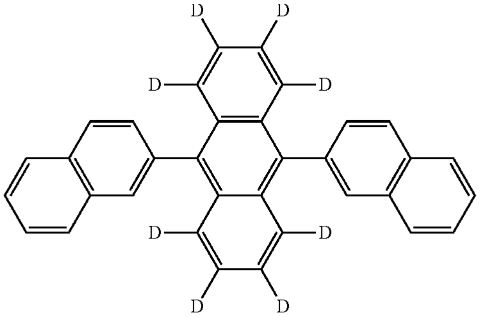
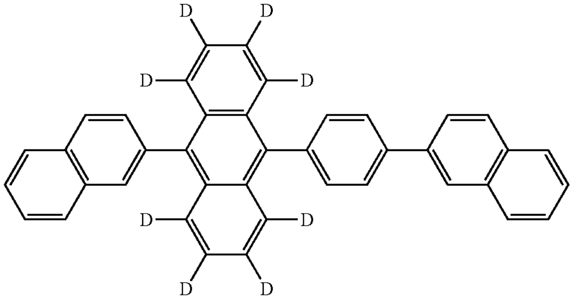

-continued
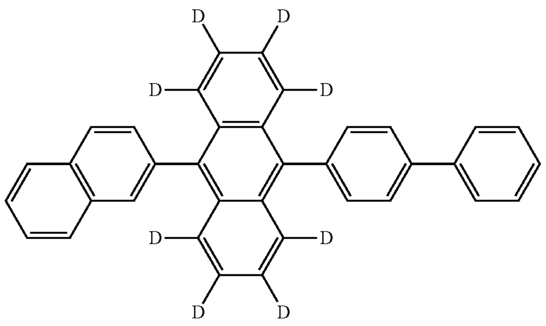
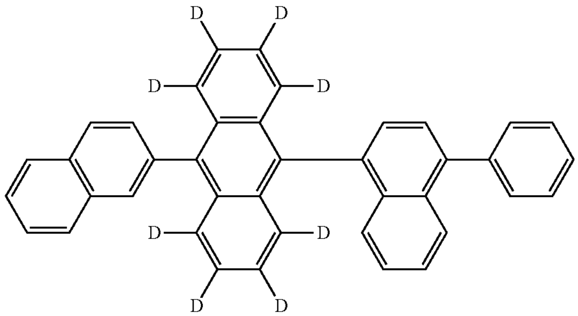
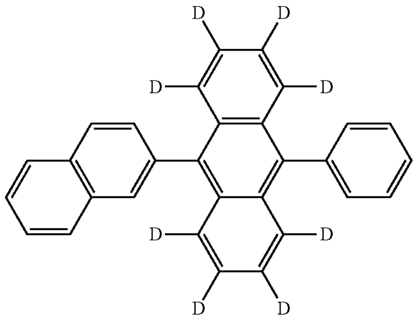
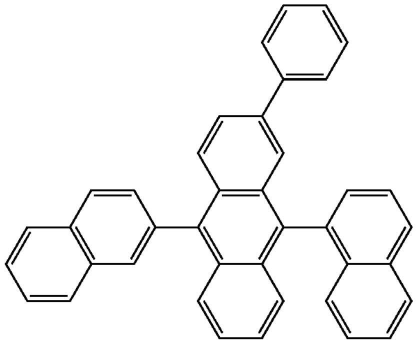
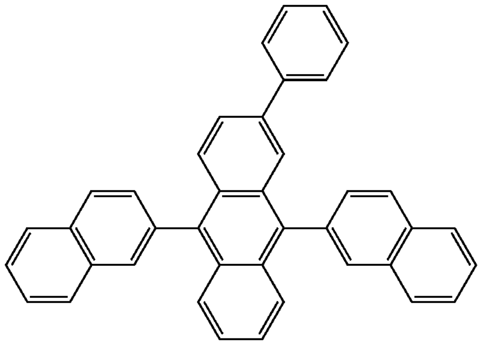
-continued
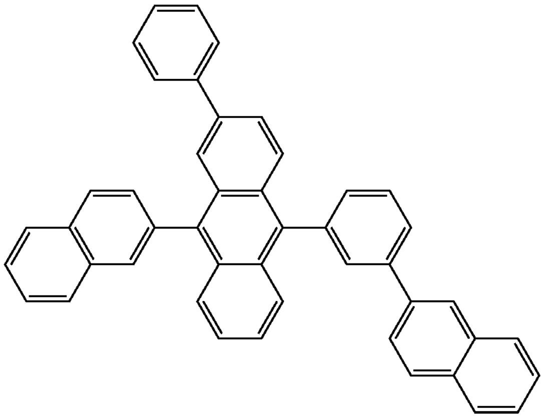
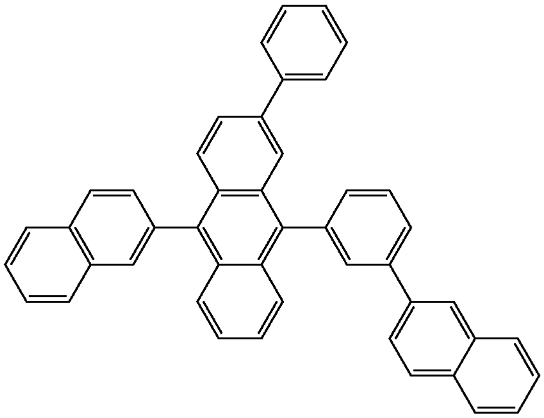
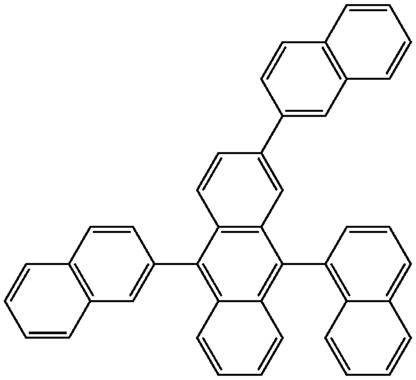
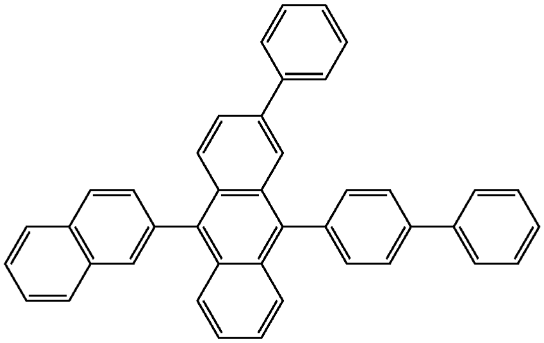

-continued
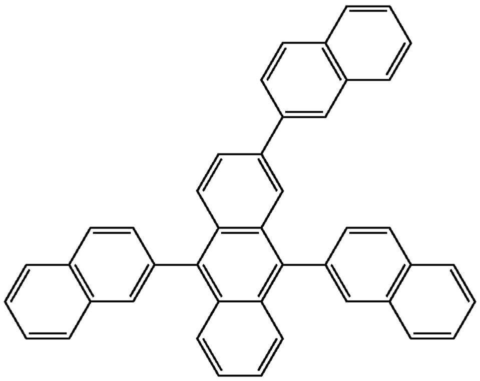
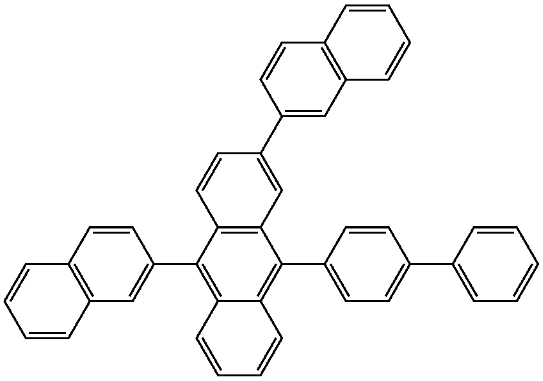
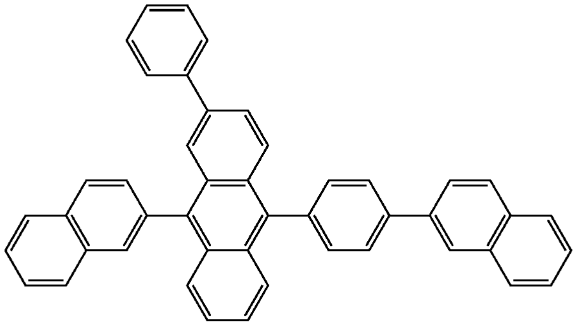
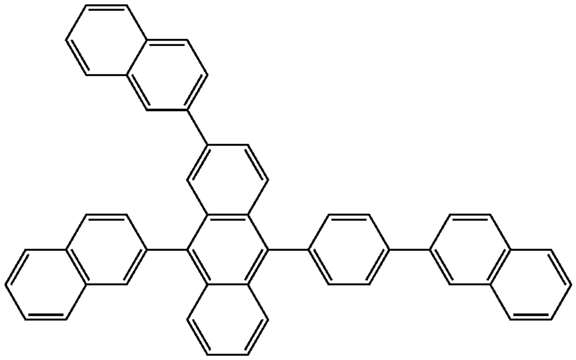
-continued
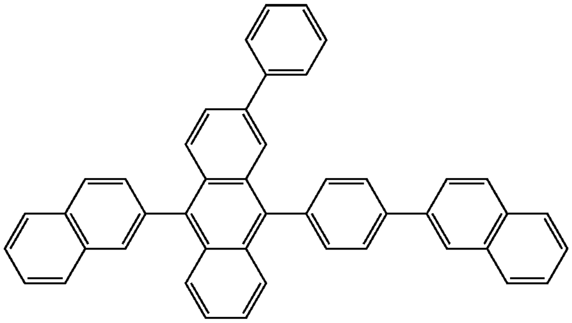
[Formula 204]
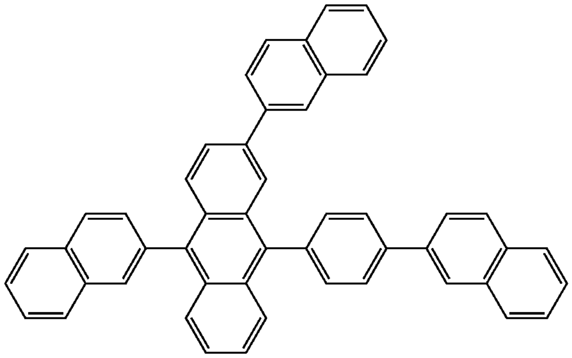
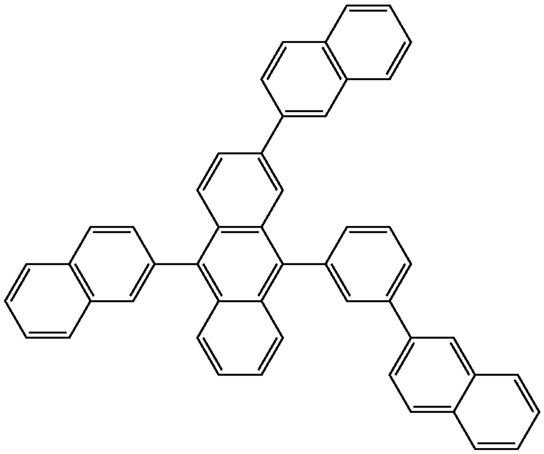
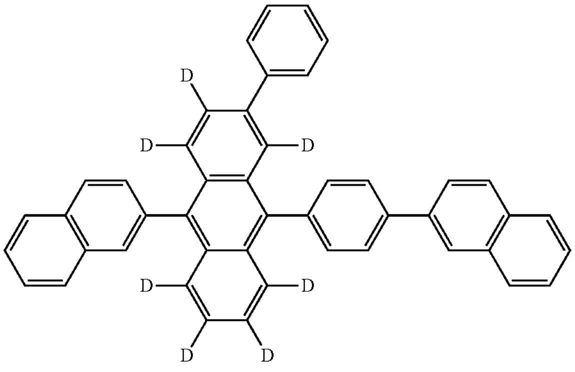

-continued
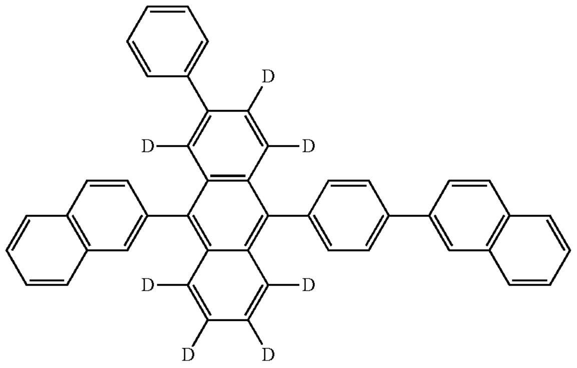
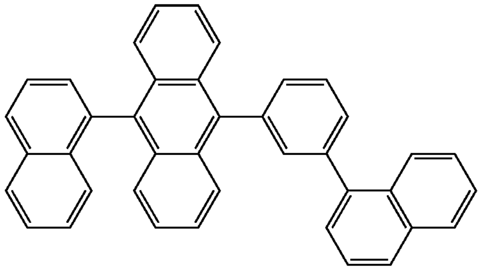
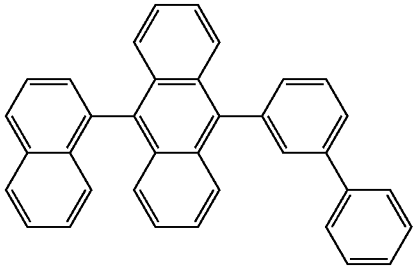
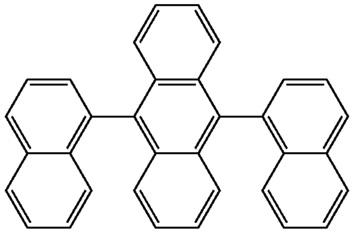
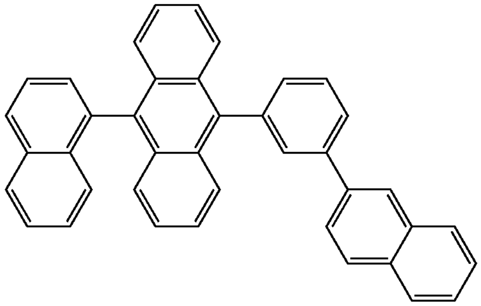
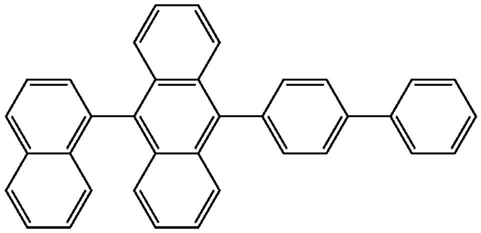
-continued
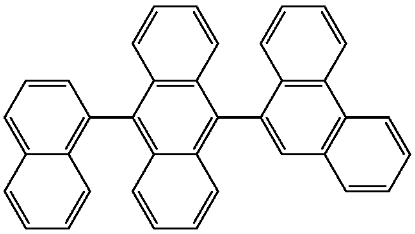
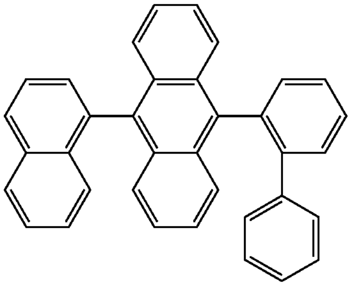
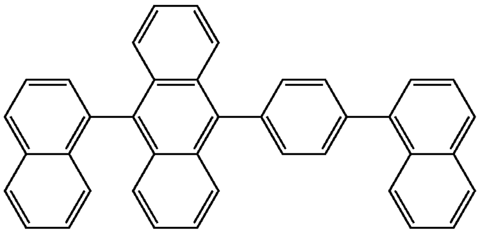
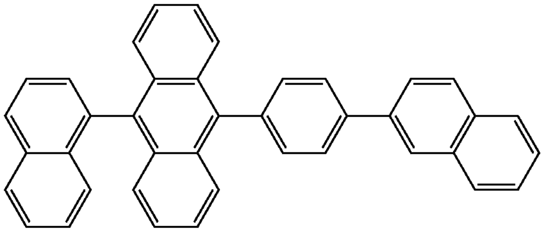
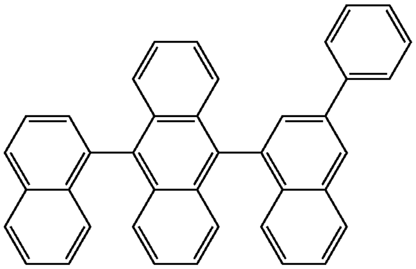
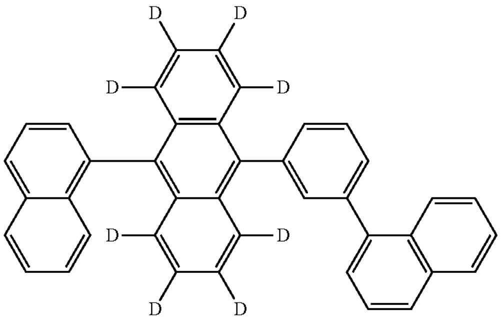

-continued
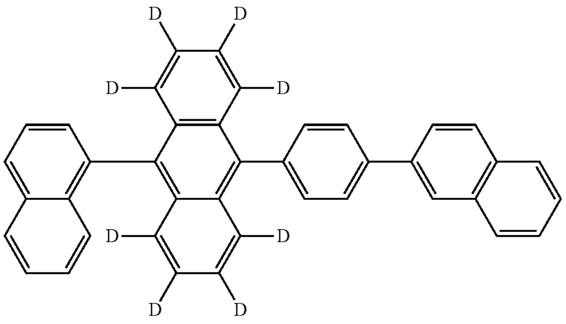
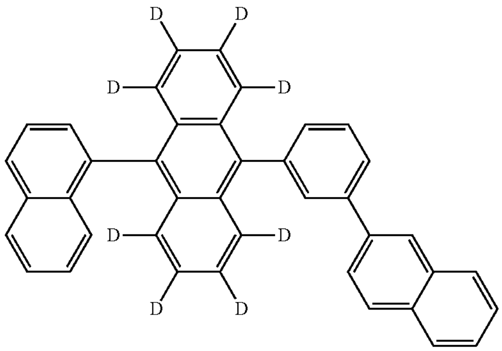
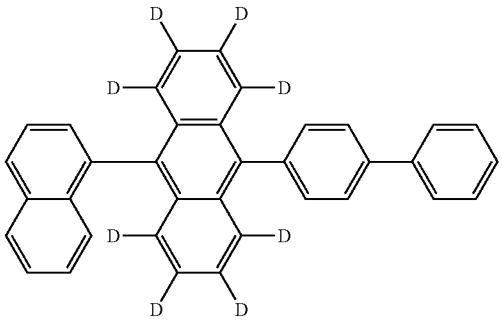
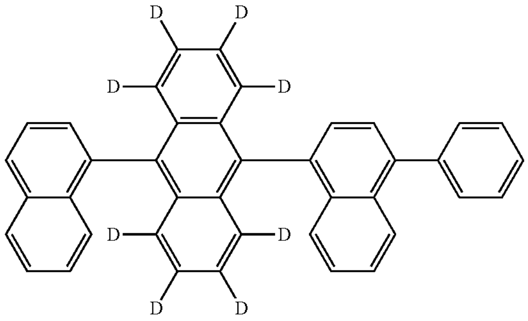
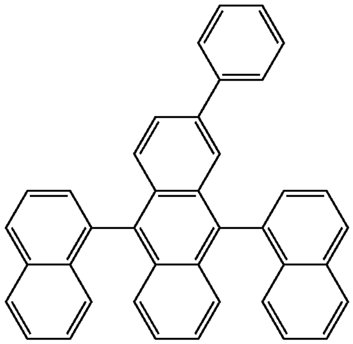
-continued
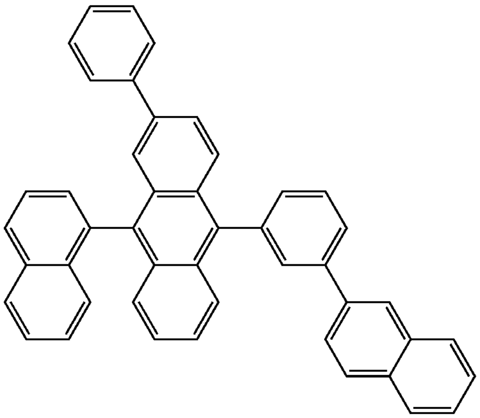
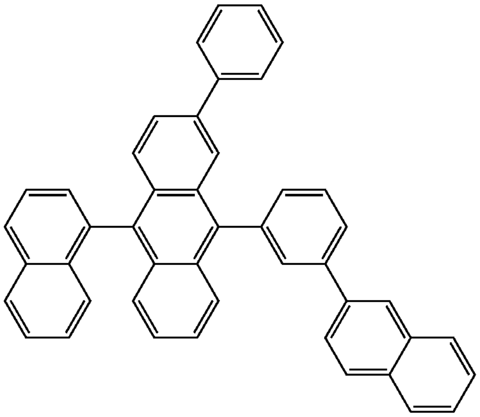
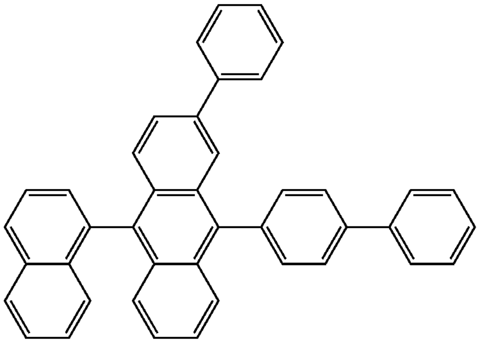
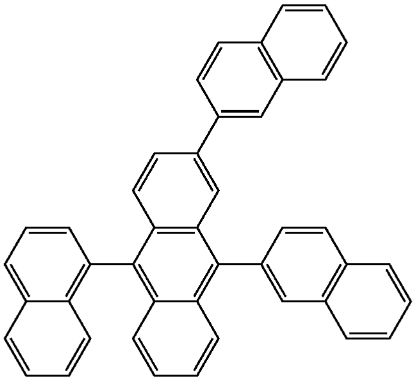

-continued
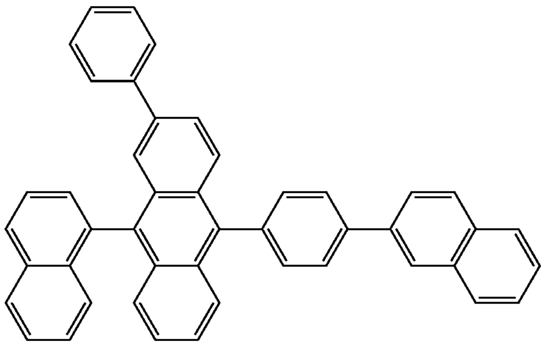
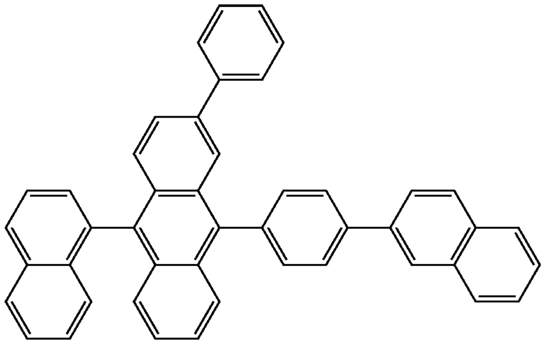
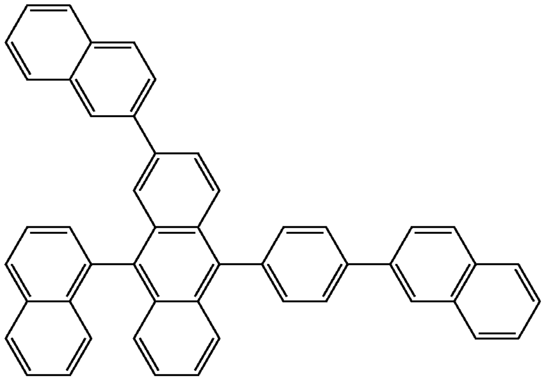
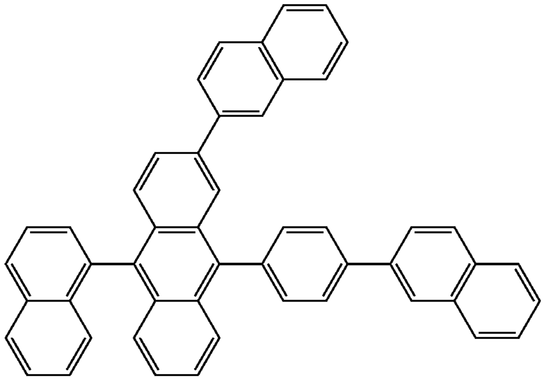
-continued
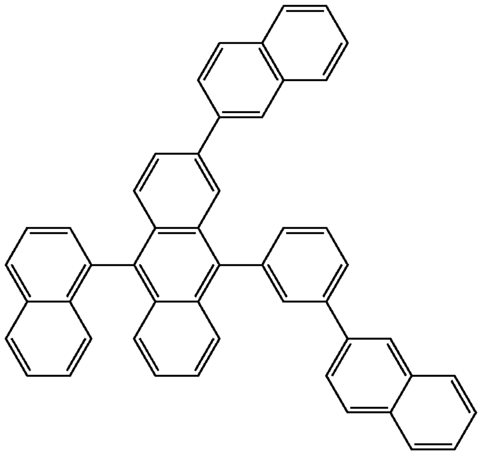
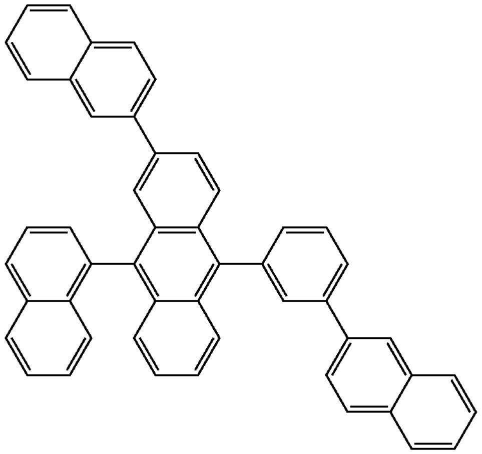
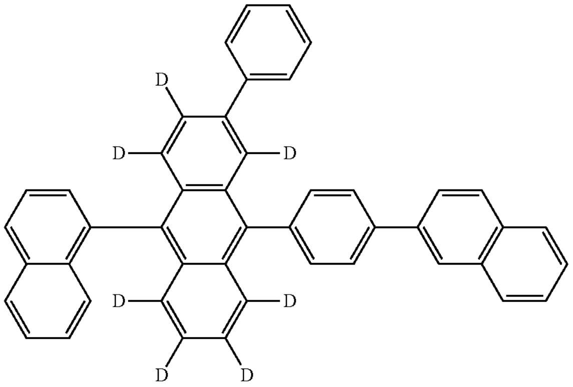
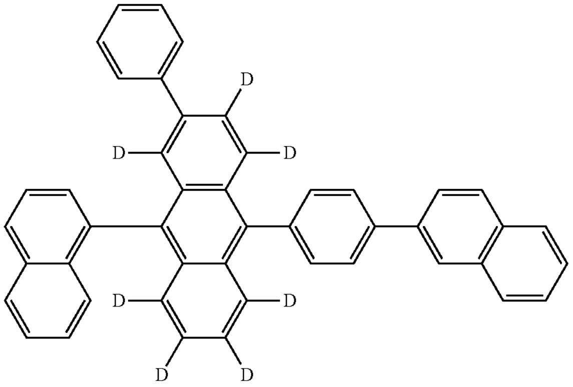

-continued
[Formula 205]
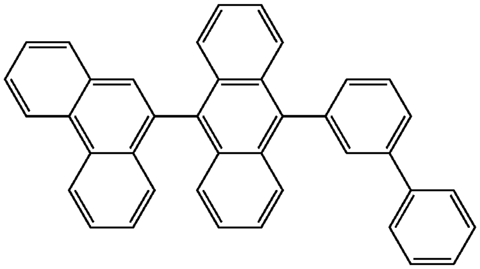
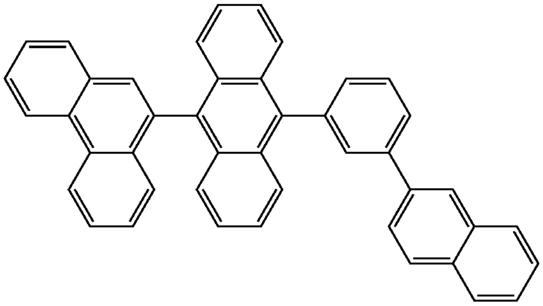
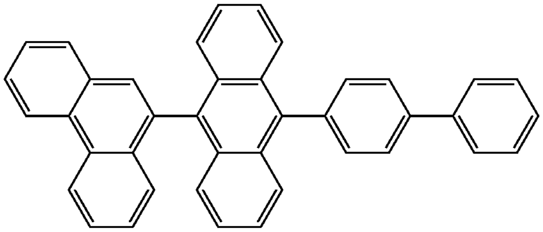
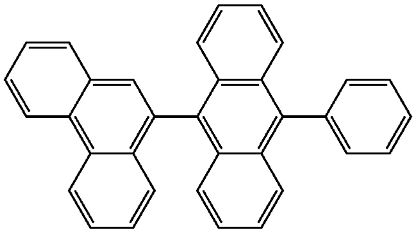
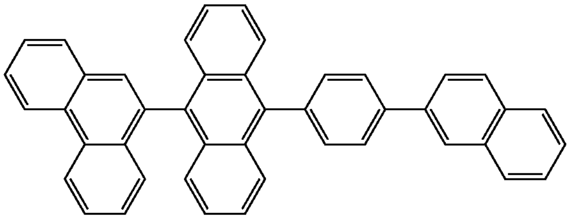
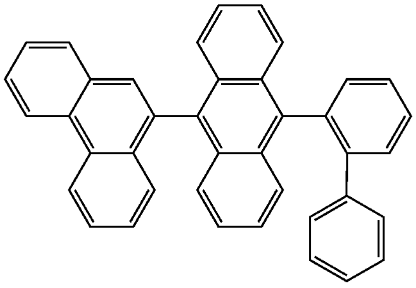
-continued
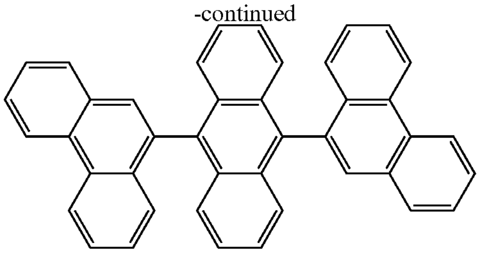
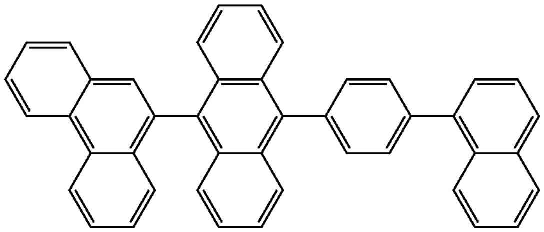
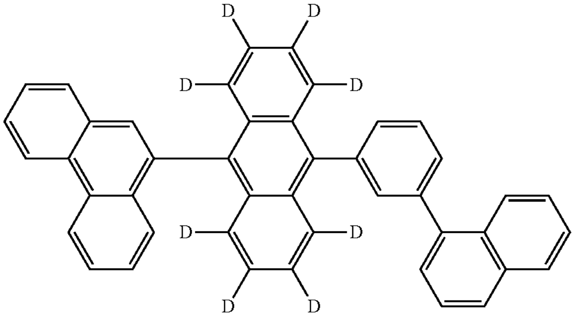
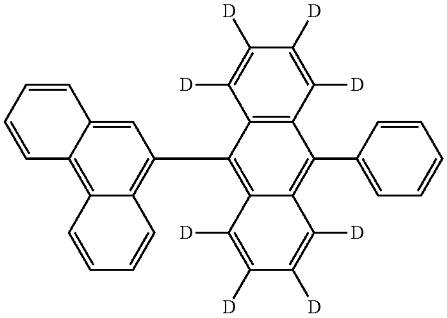
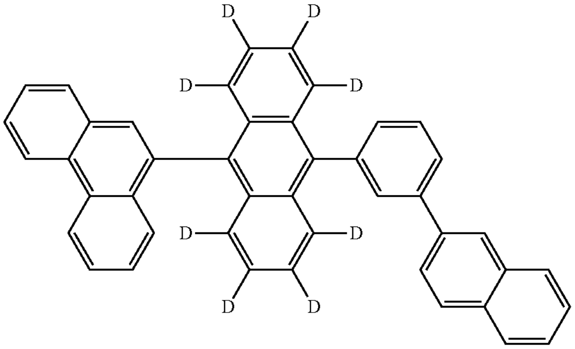
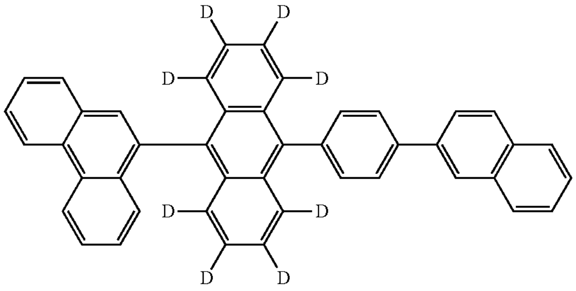

-continued
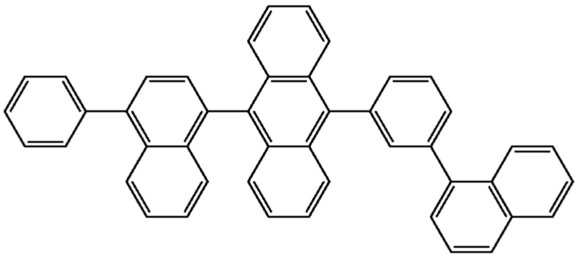
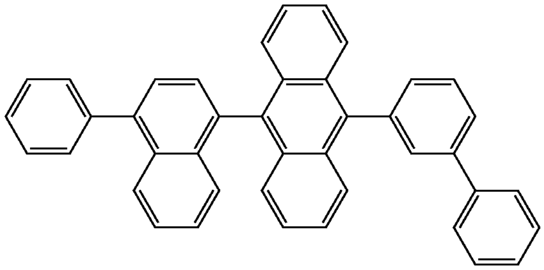
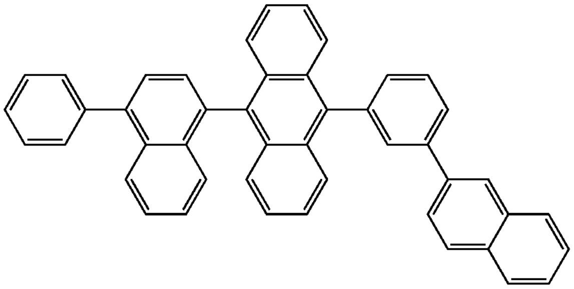
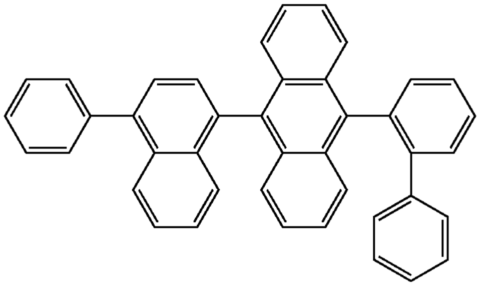
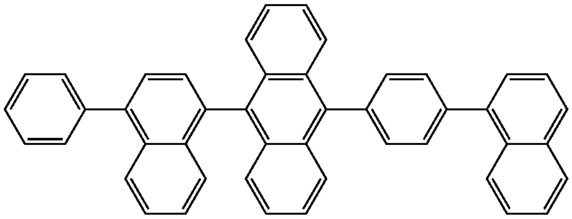
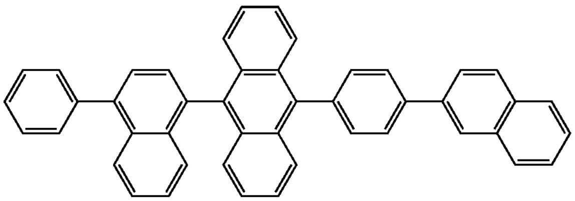
-continued
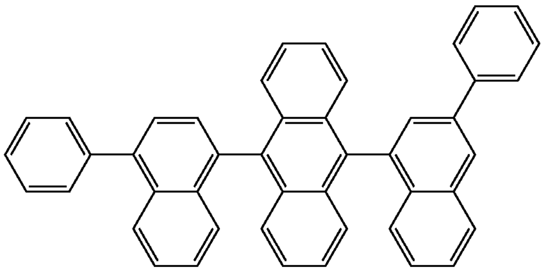
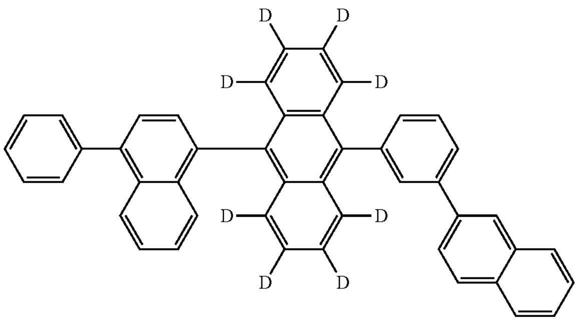
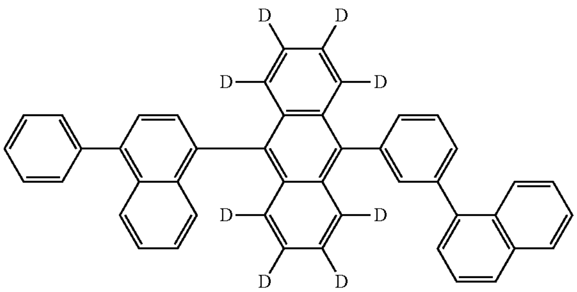
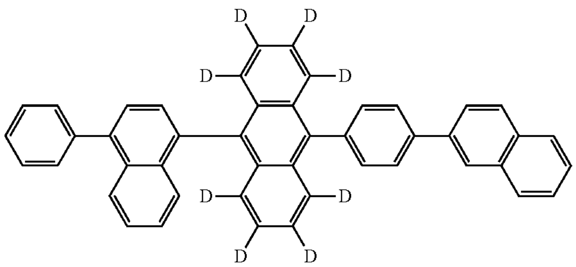
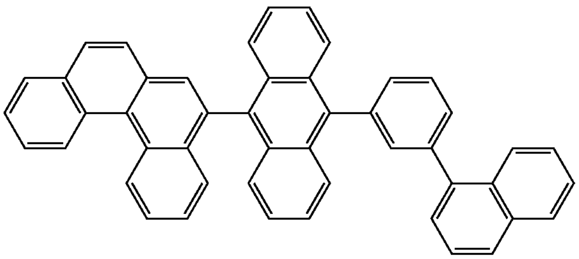

-continued
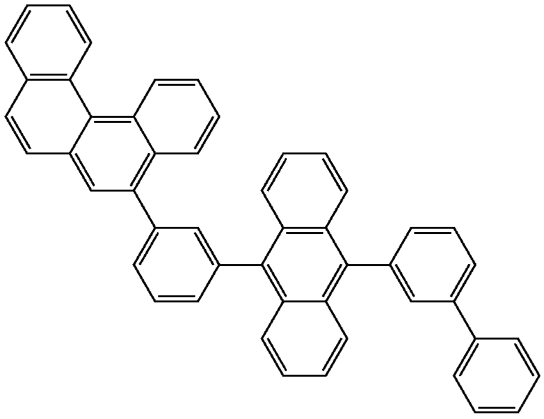
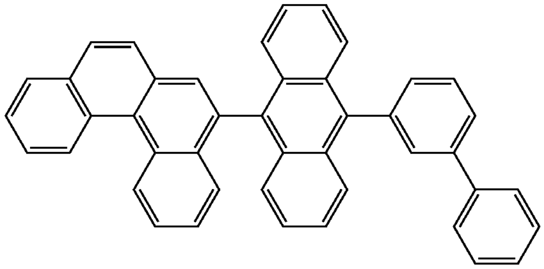
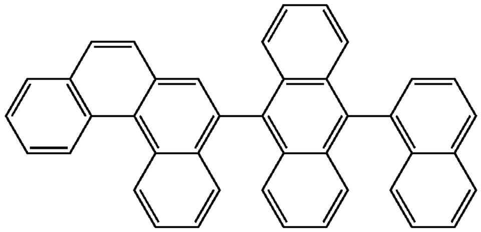
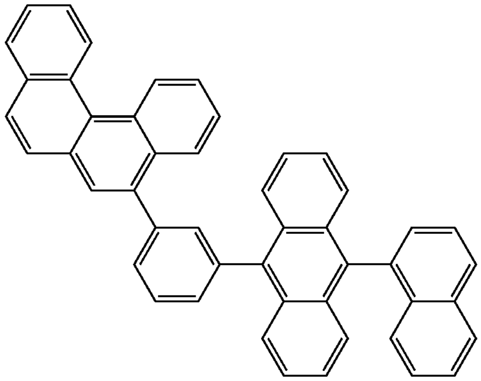
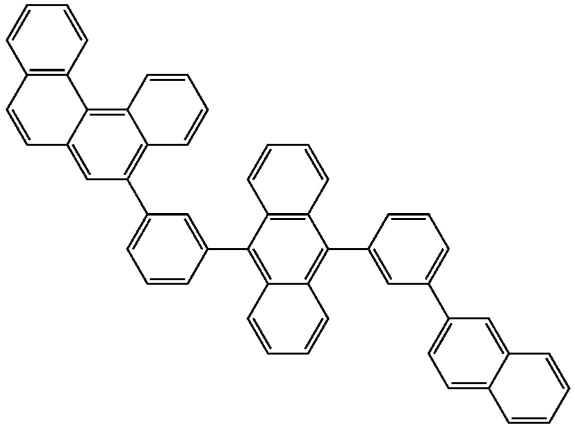
-continued
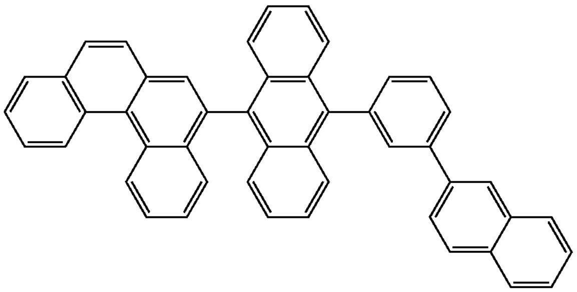
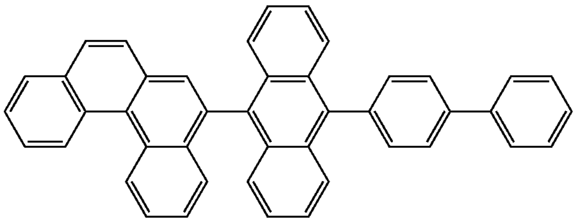
[Formula 206]
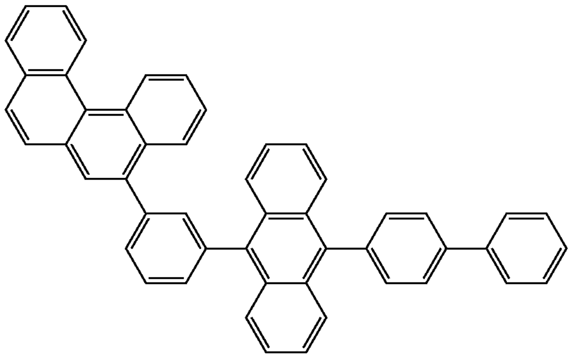
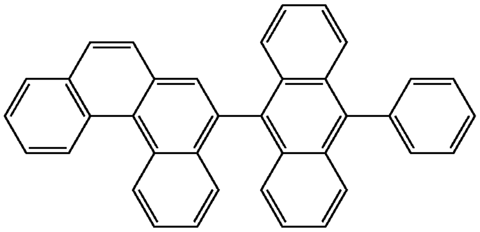
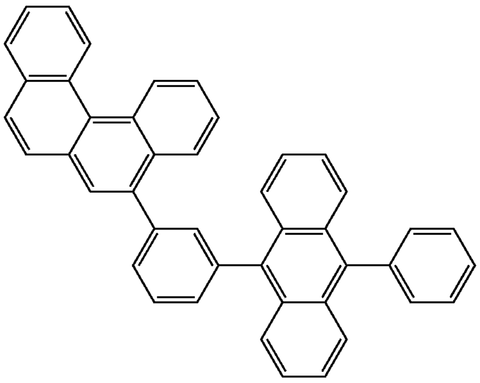

-continued
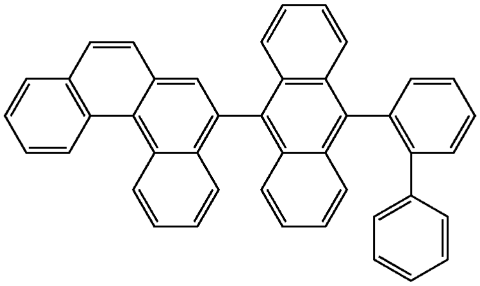
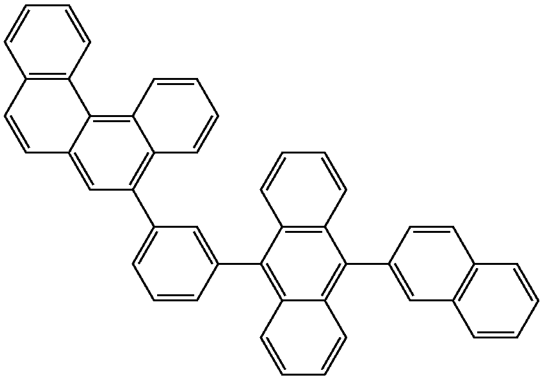
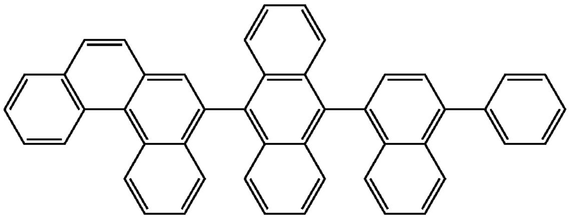
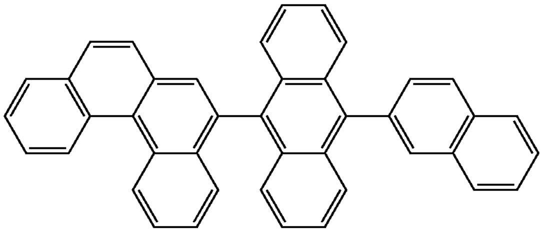
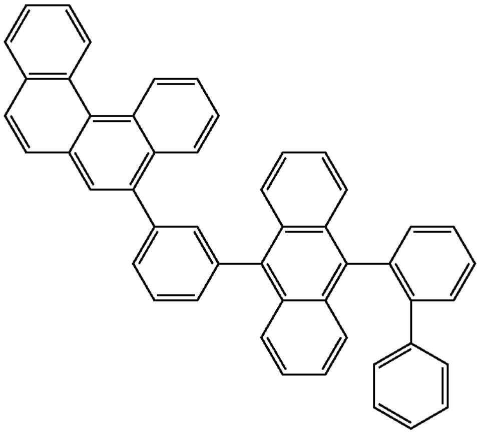
-continued
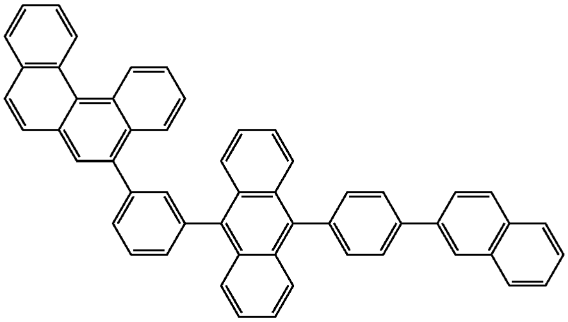
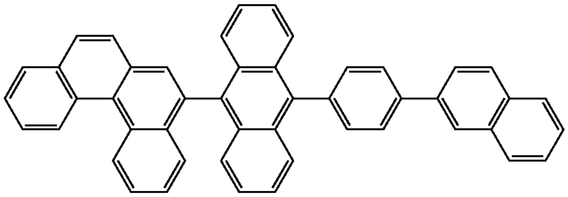
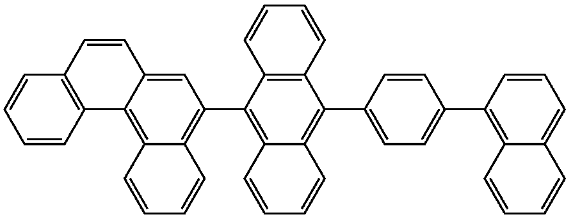
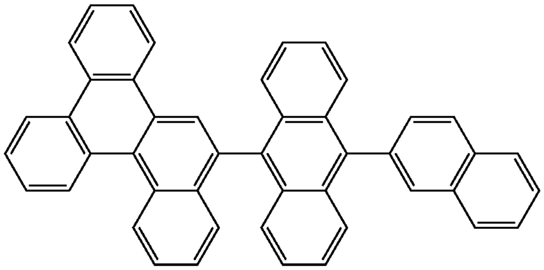
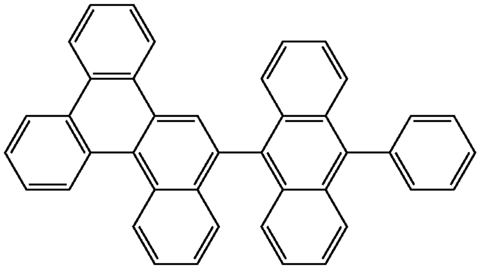
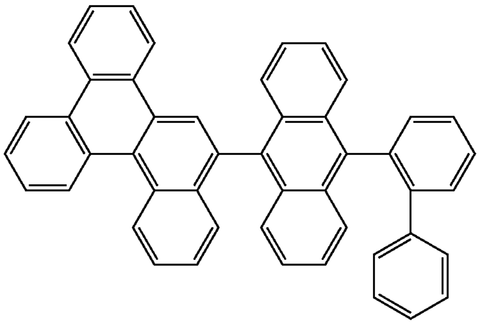

-continued
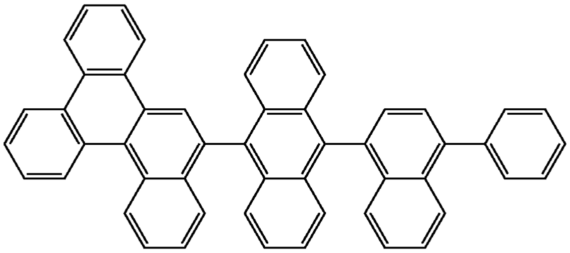
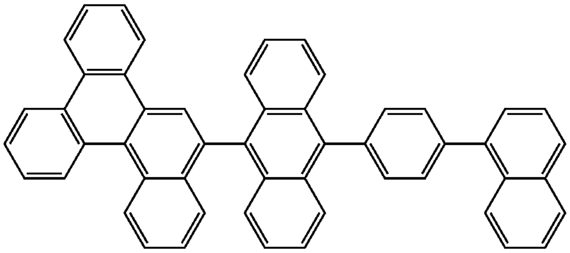
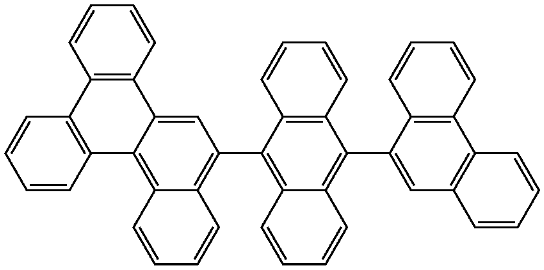
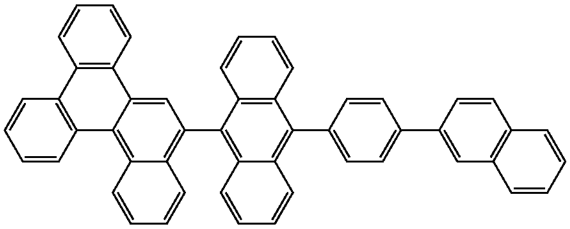
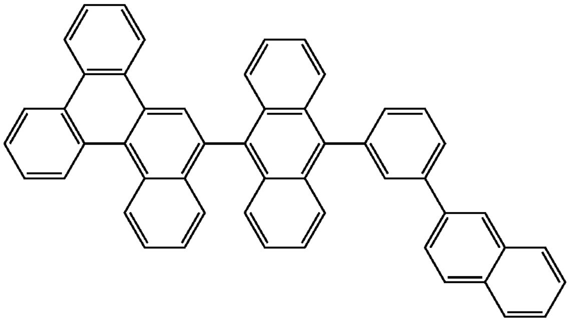
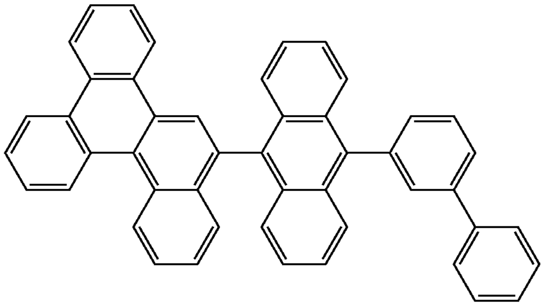
-continued
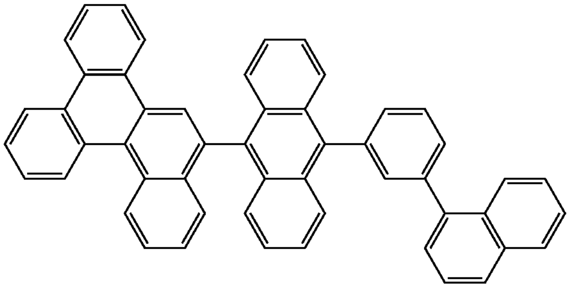
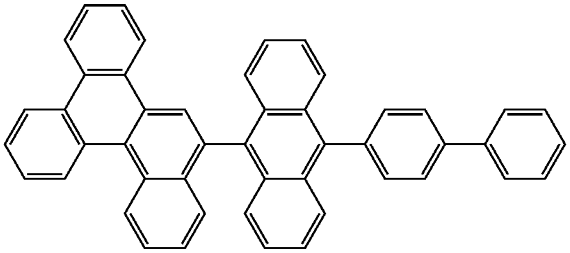
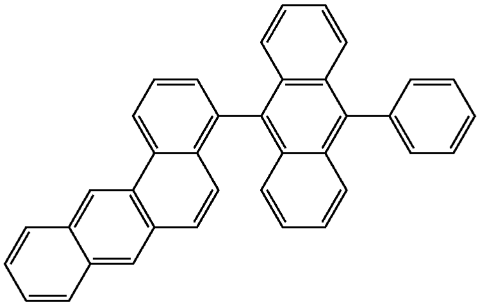
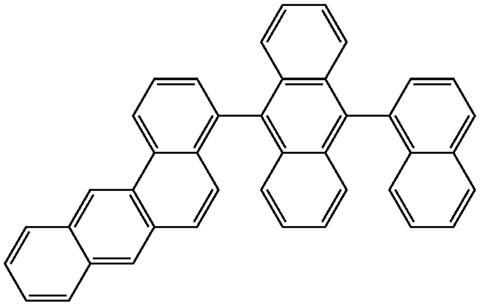
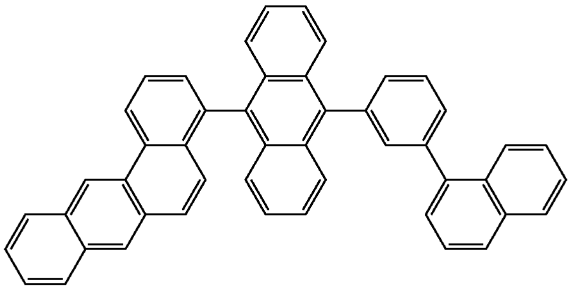

-continued
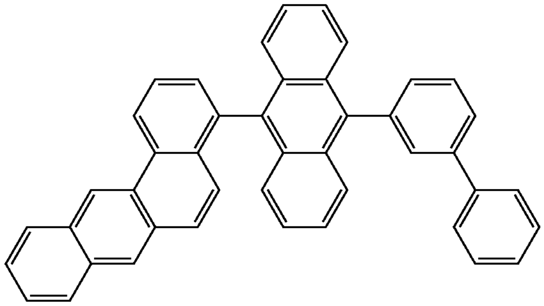
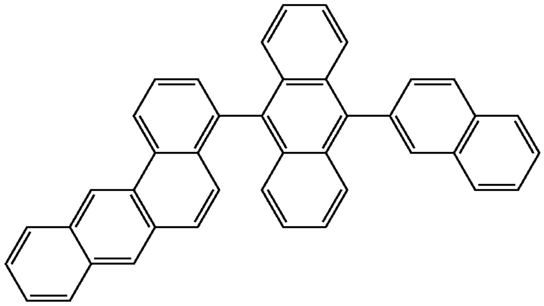
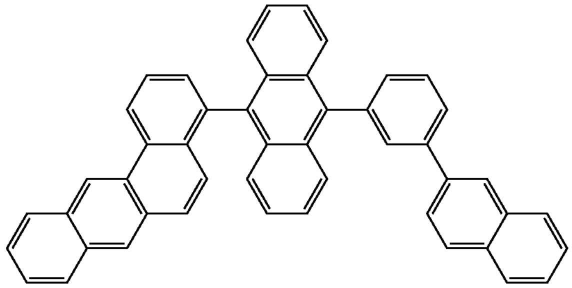
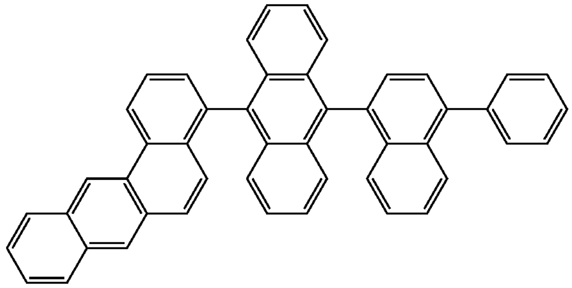
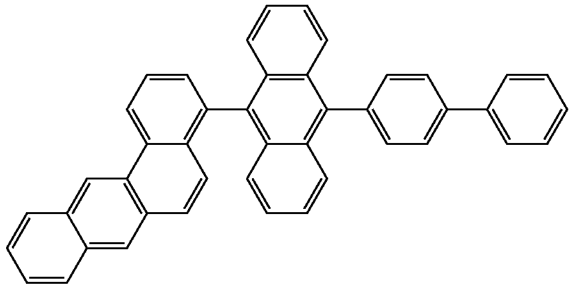
-continued
[Formula 207]
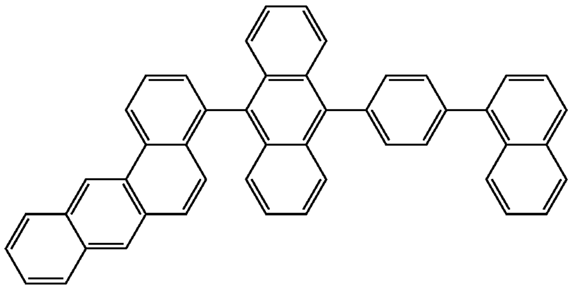
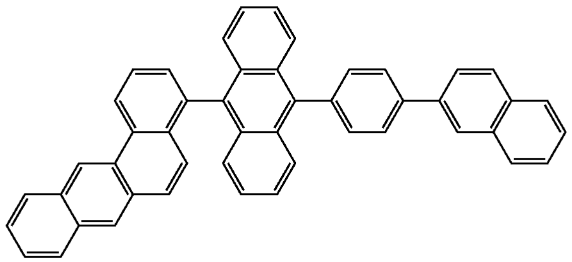
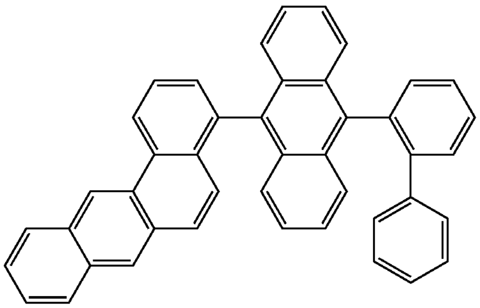
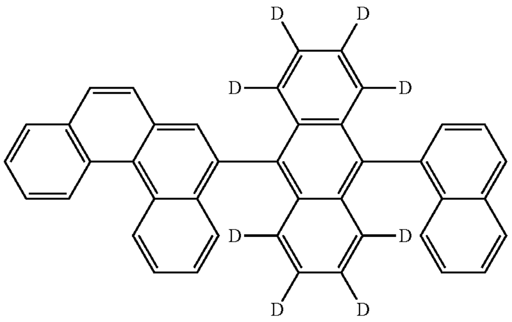
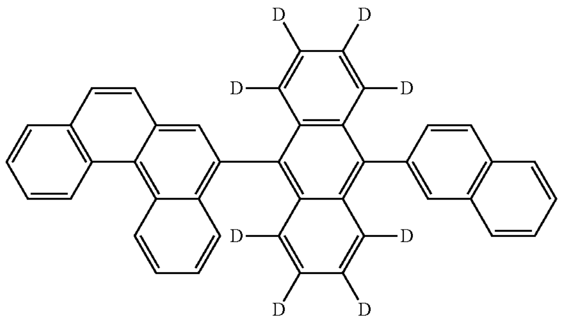

-continued
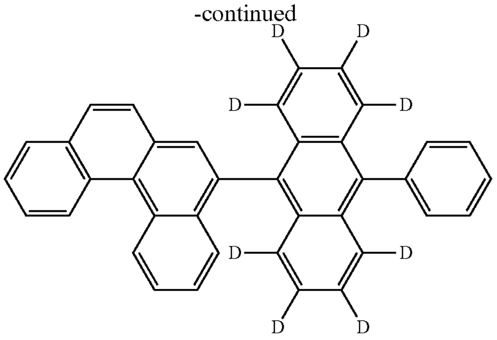
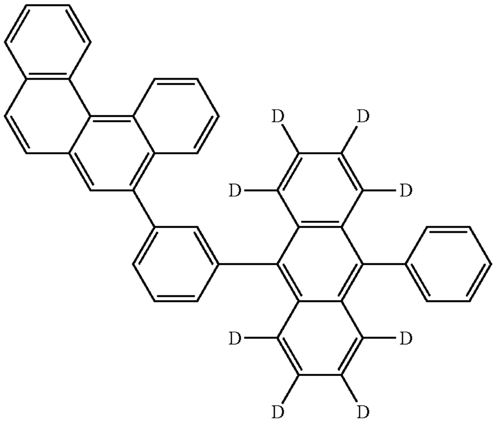
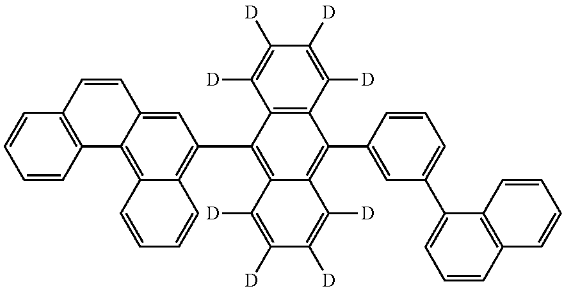
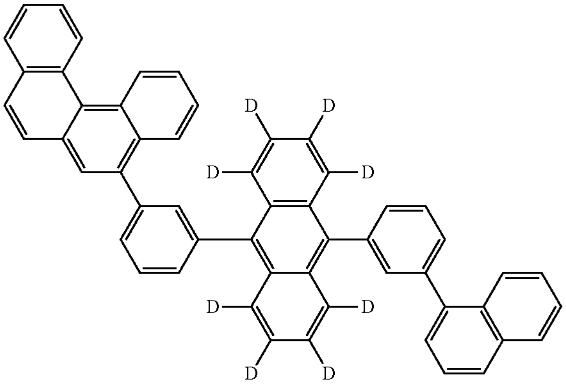
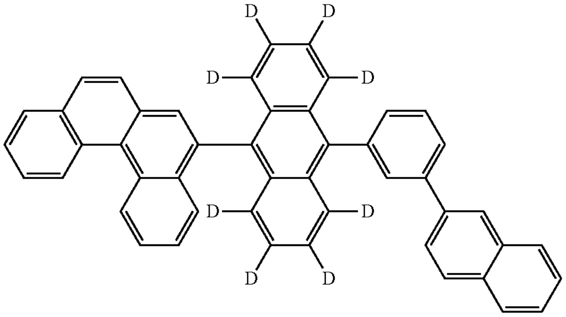
-continued
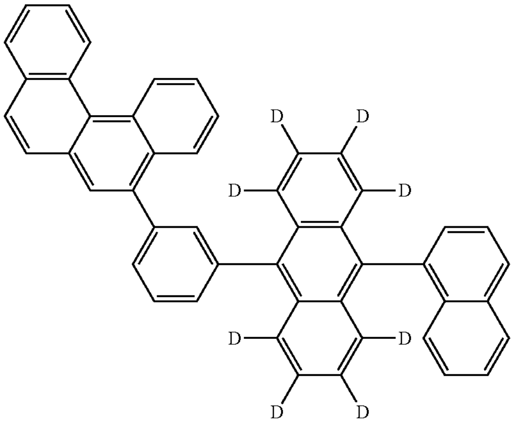
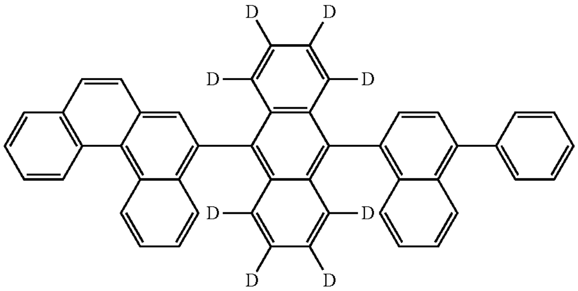
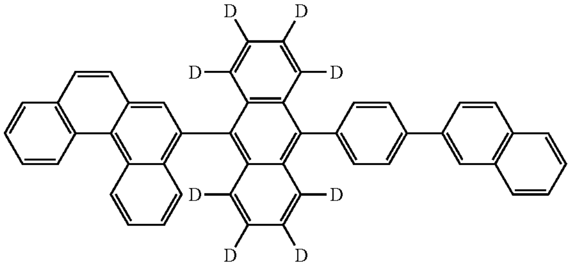
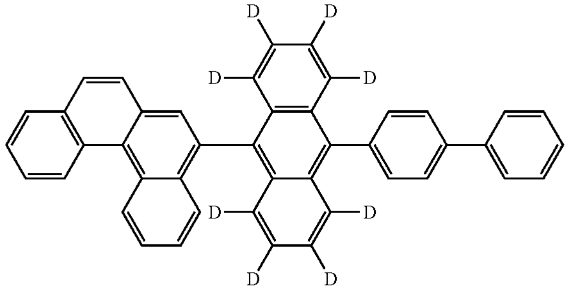
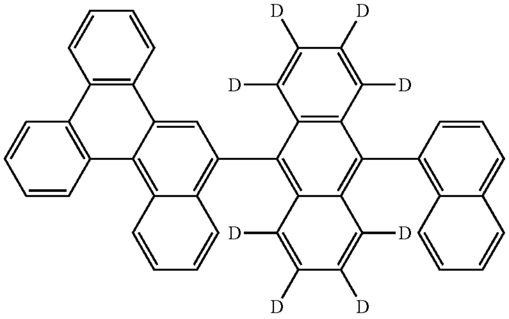

-continued
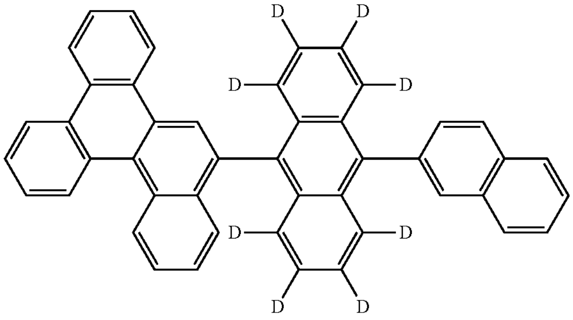
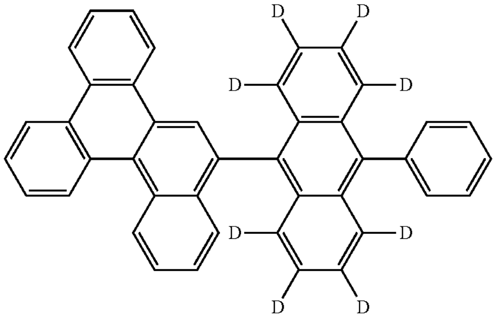
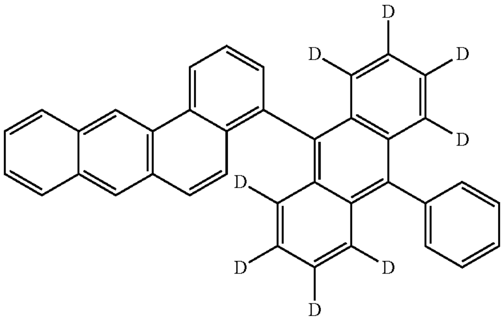
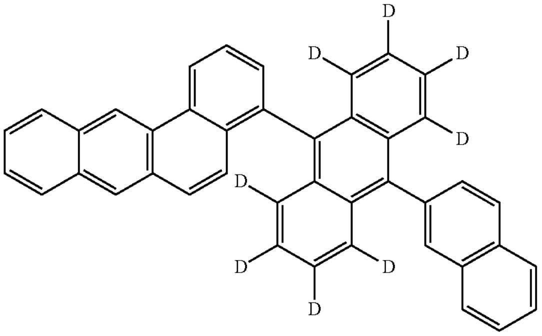
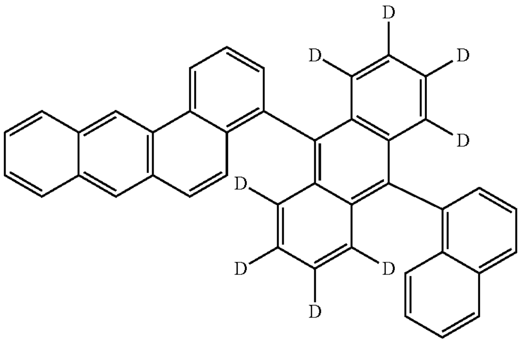
-continued
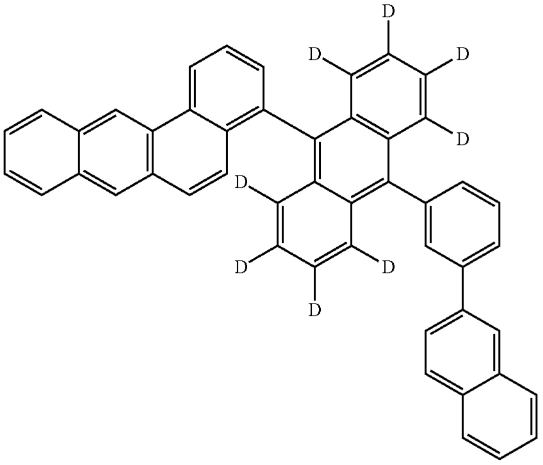
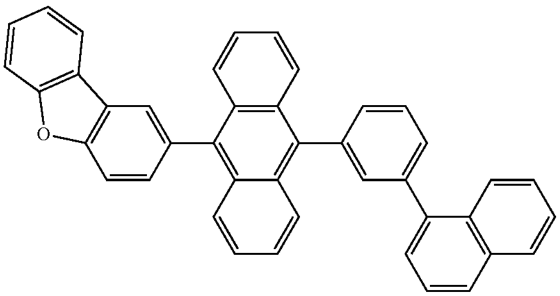
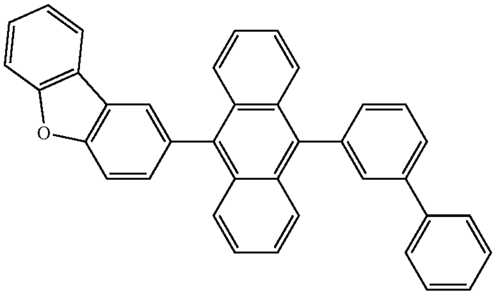
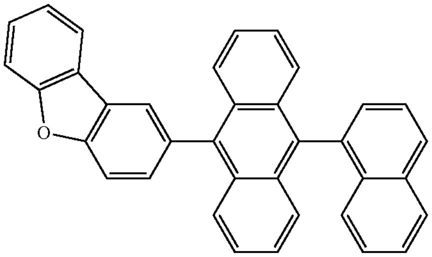
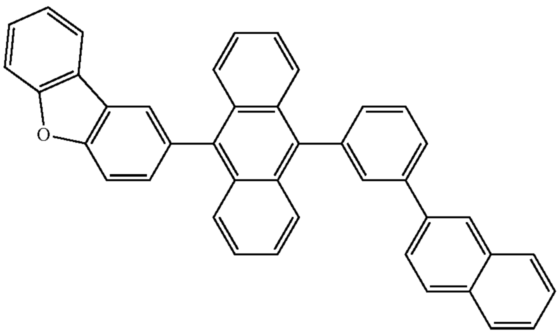

-continued
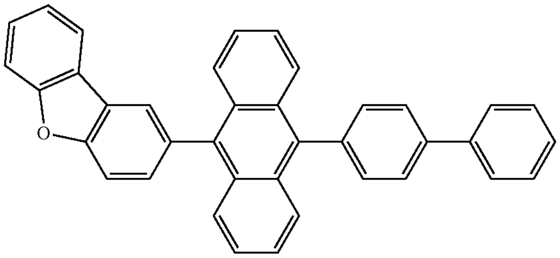
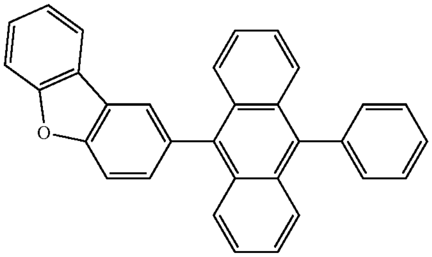
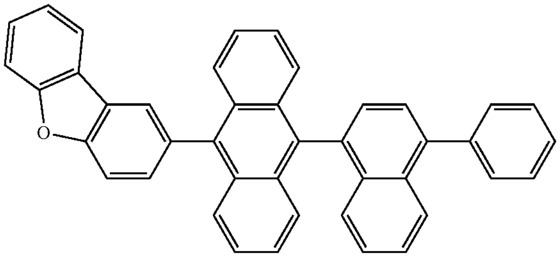
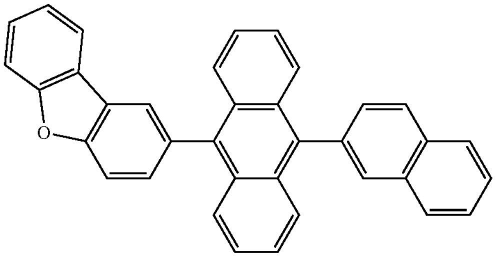
[Formula 208]
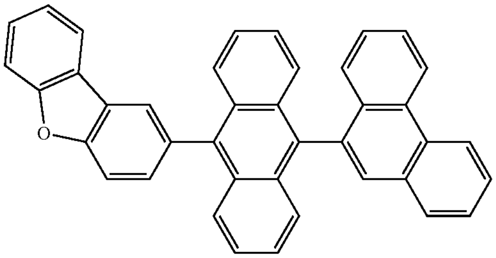
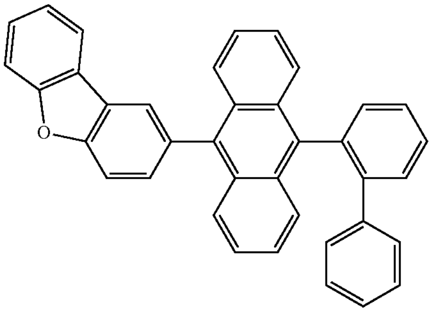
-continued
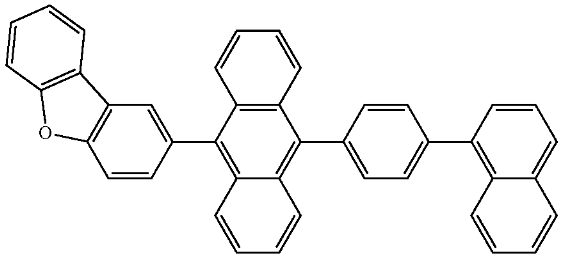
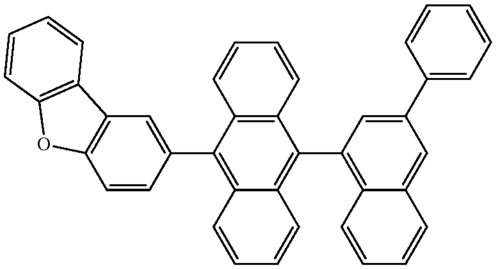
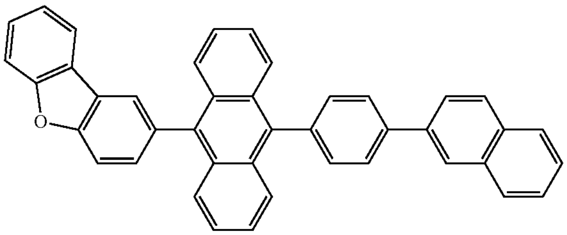
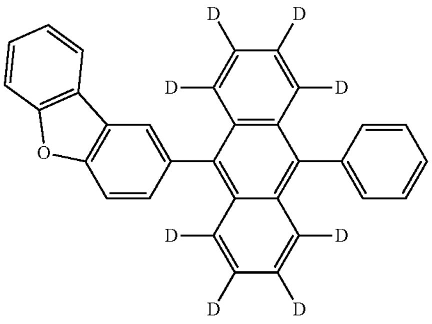
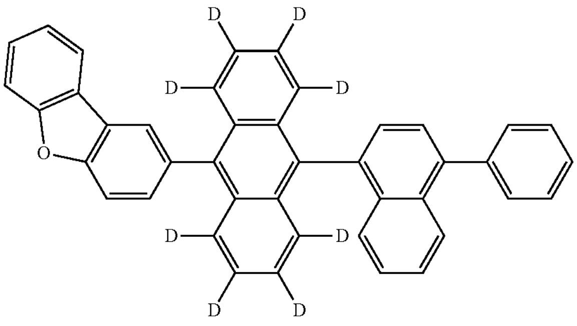
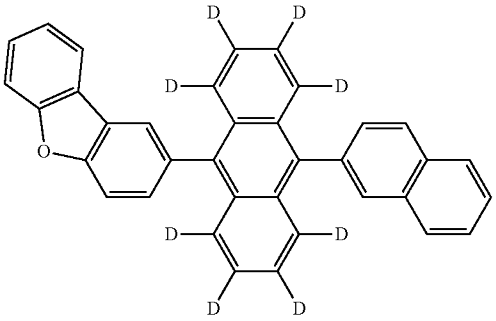

-continued
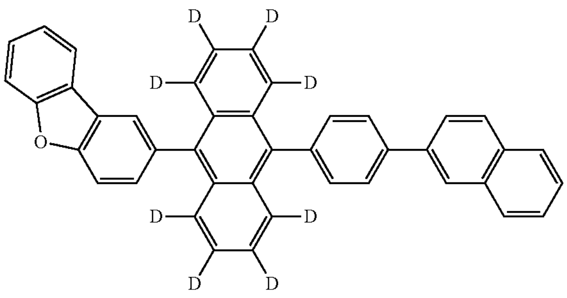
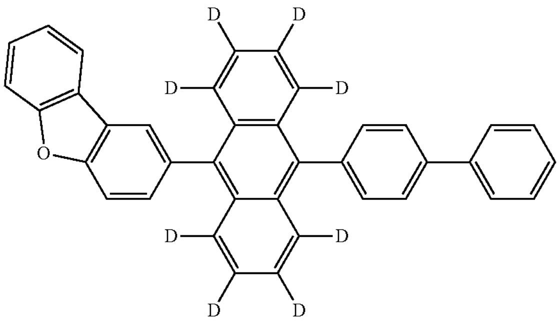
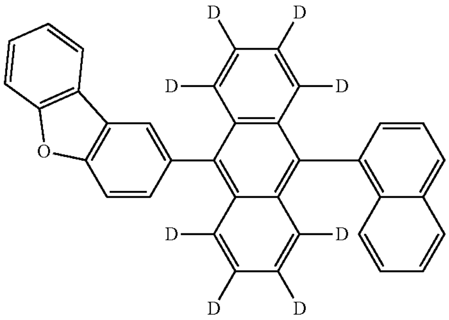
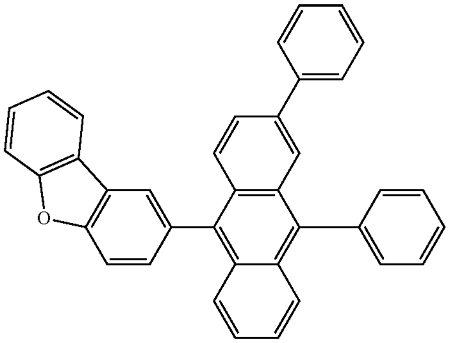
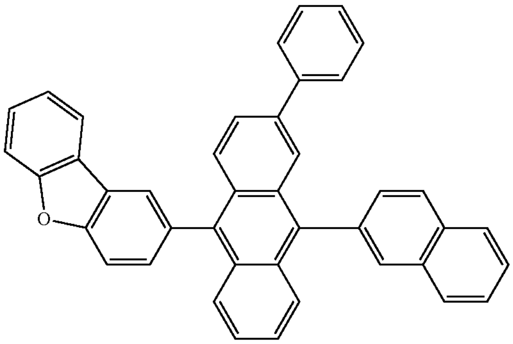
-continued
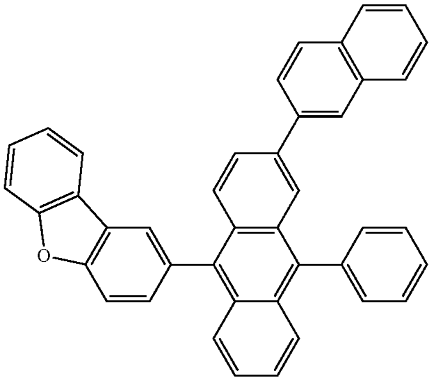
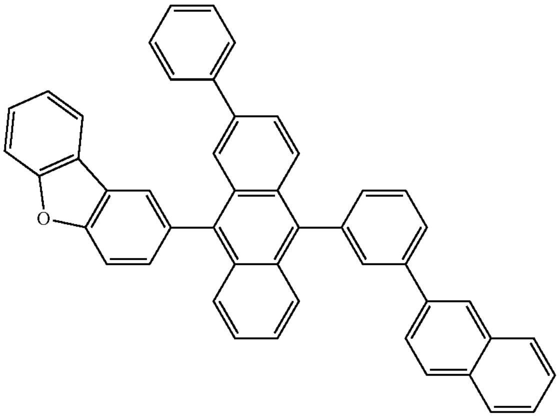
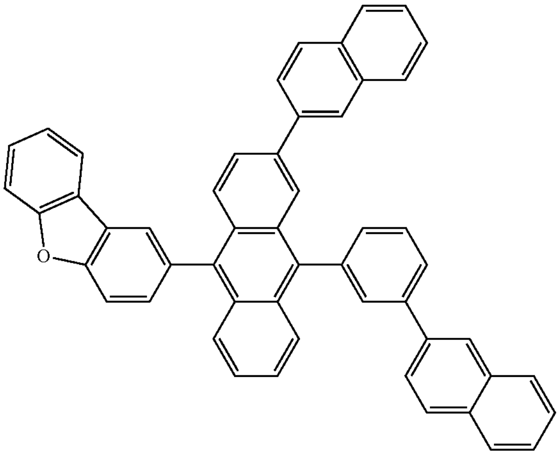
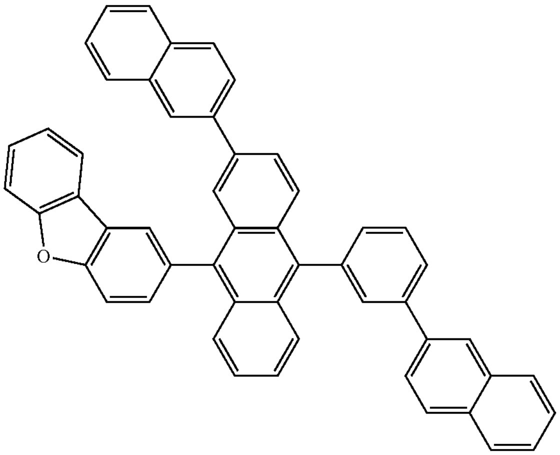

-continued
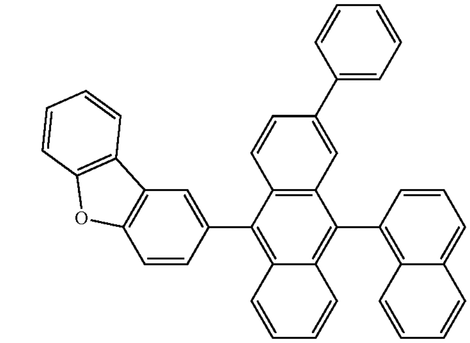
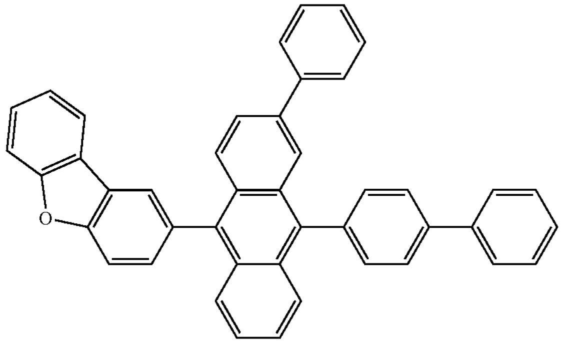
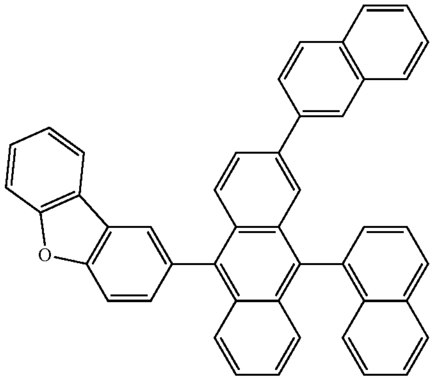
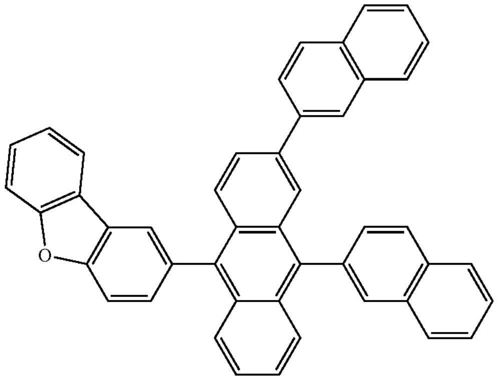
-continued
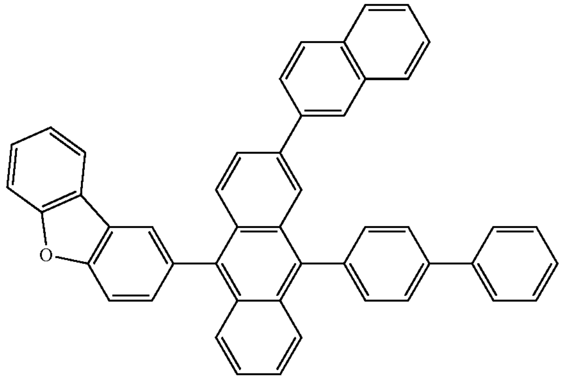
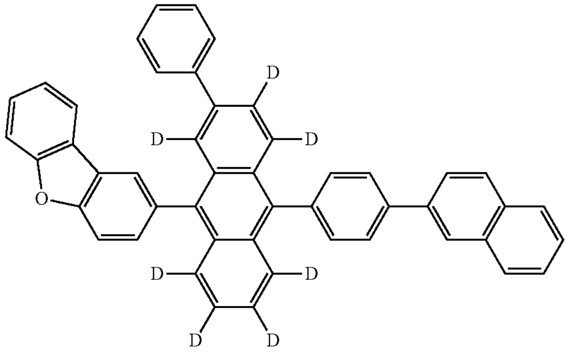
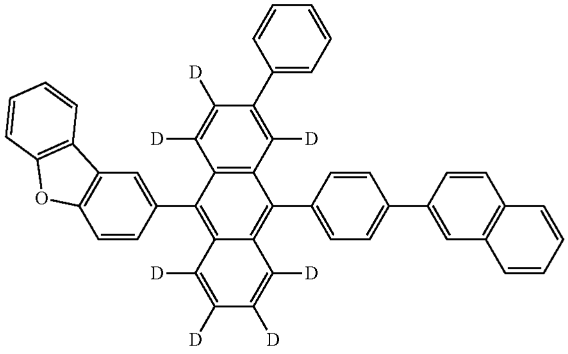
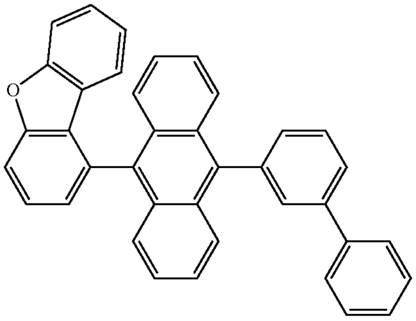
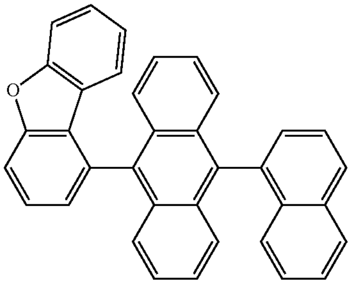

-continued
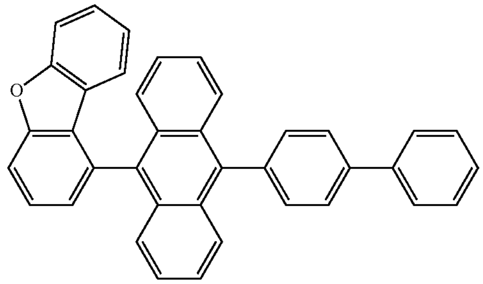
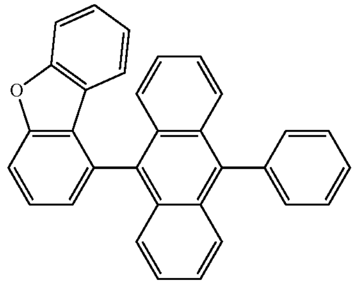
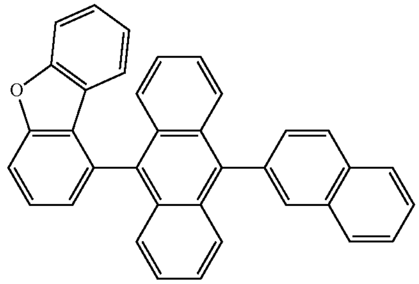
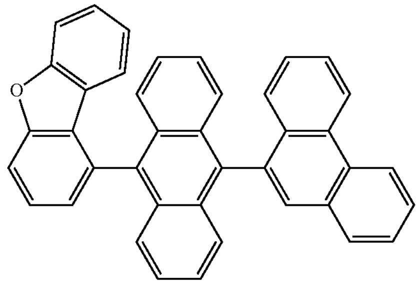
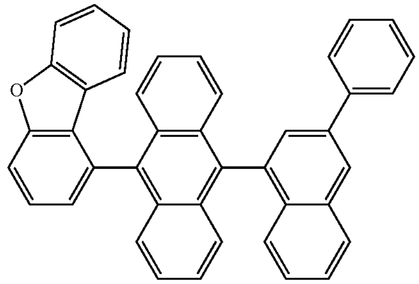
-continued
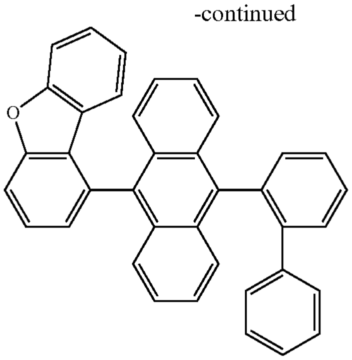
[Formula 209]
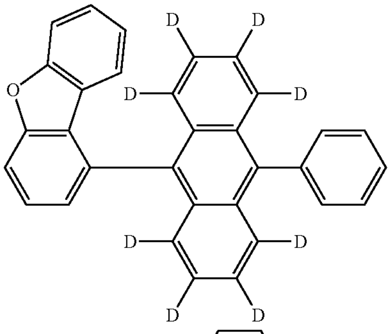
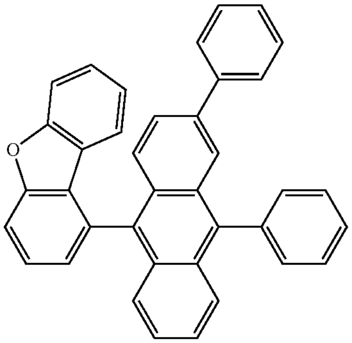
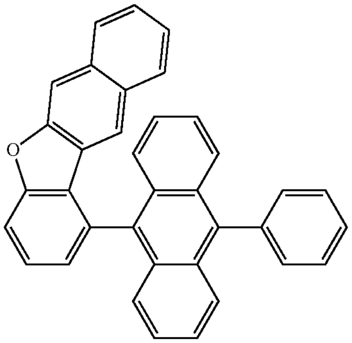
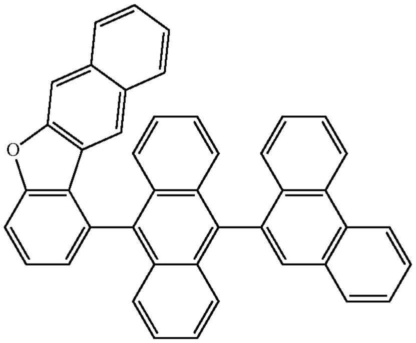

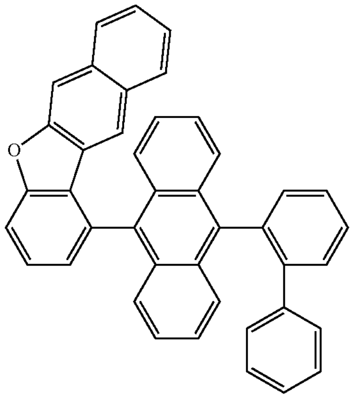
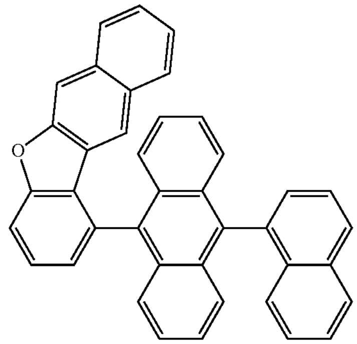
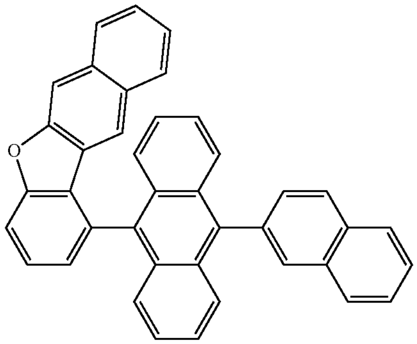
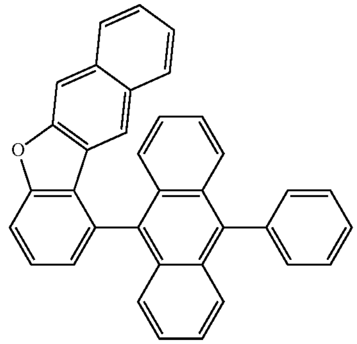
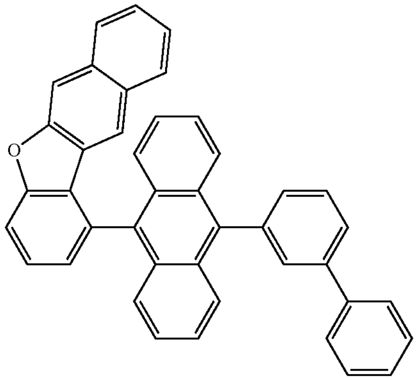
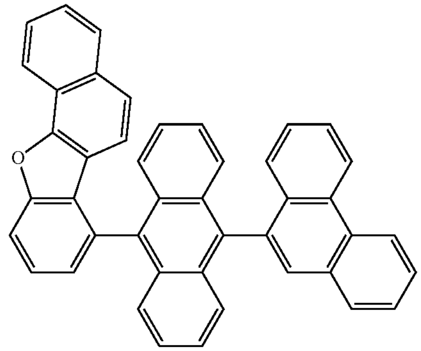
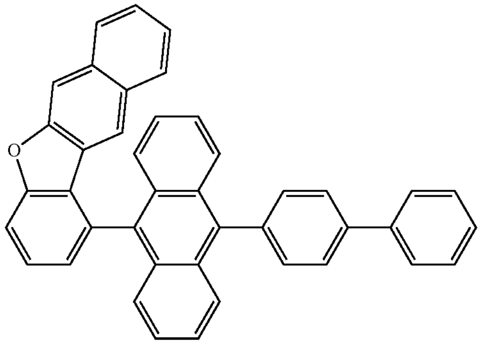
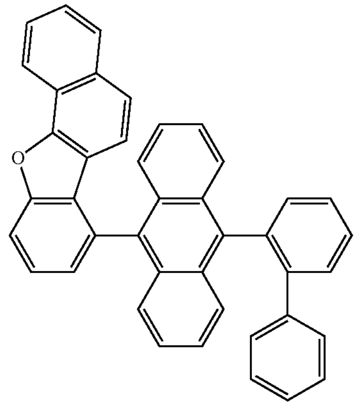

-continued
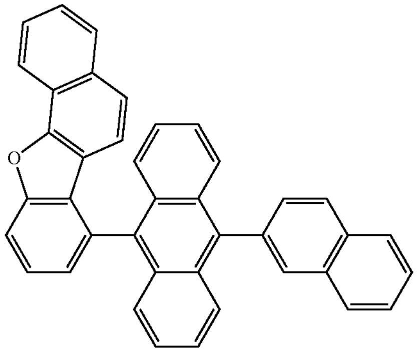
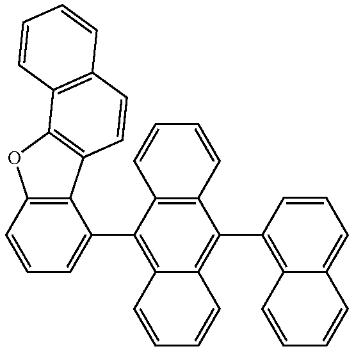
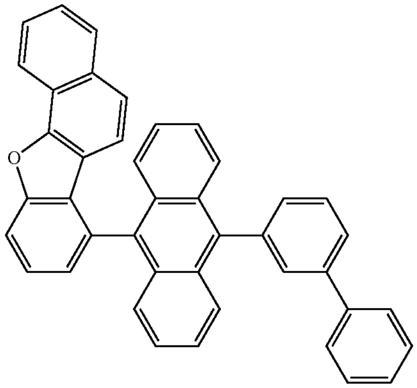
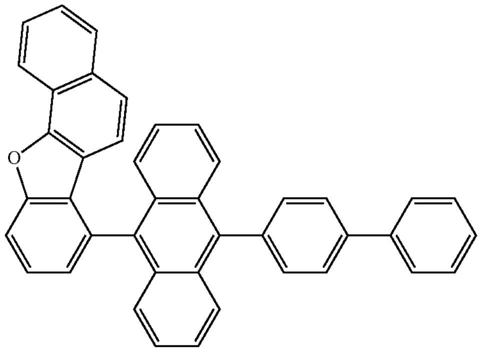
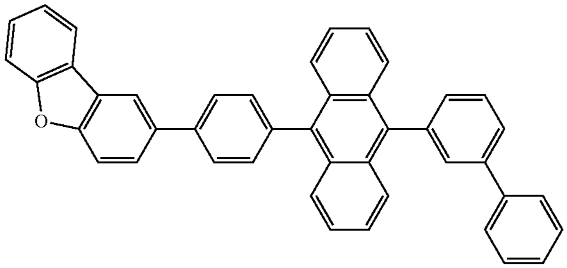
-continued
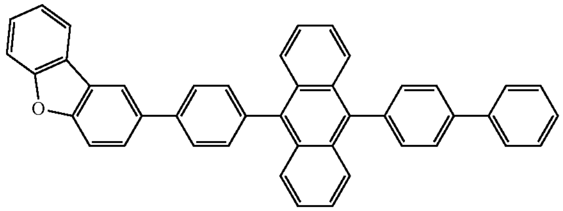
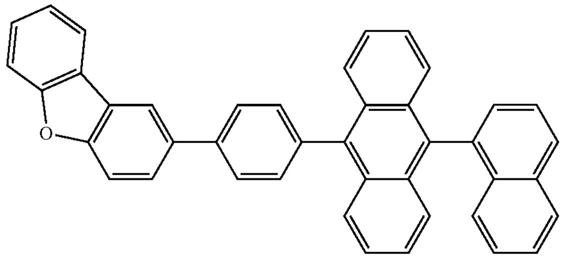
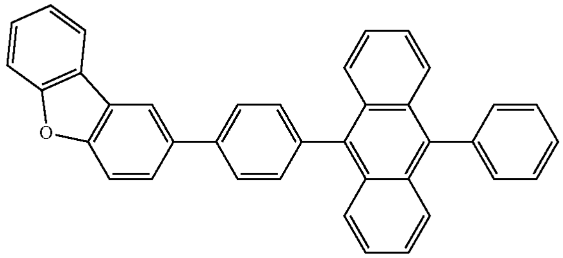
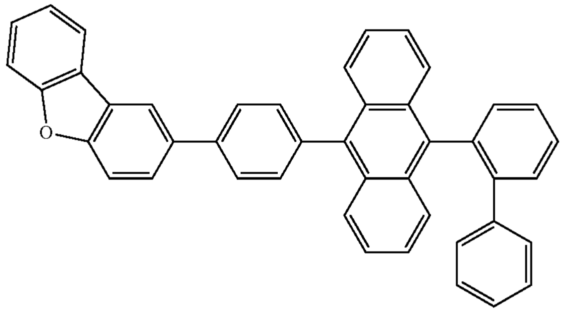
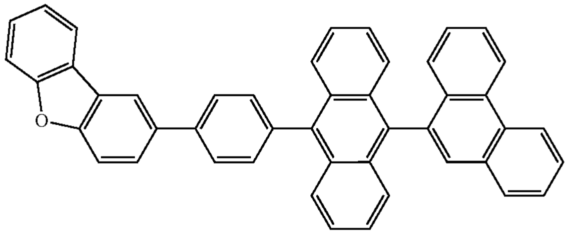
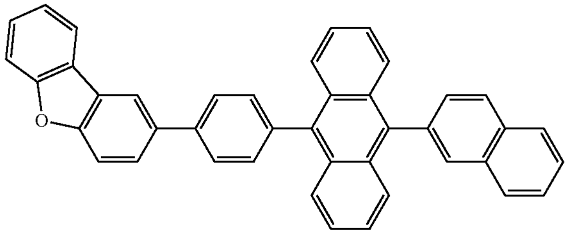

-continued
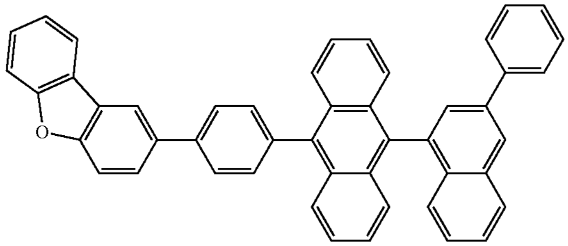
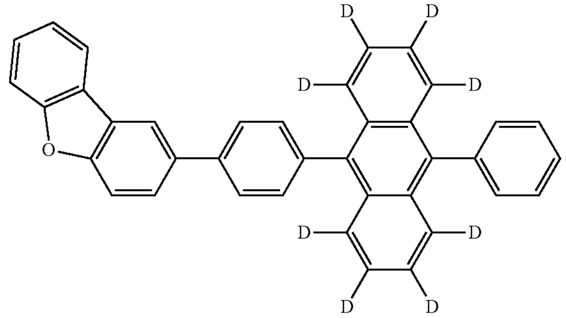
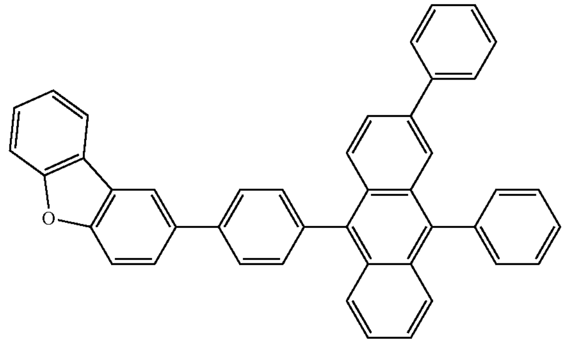
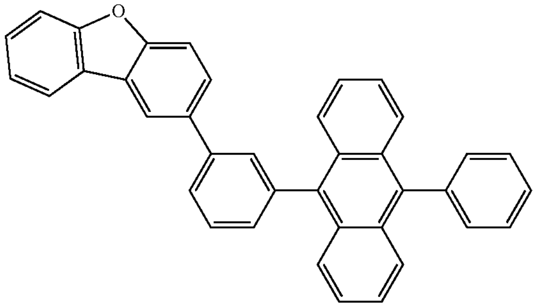
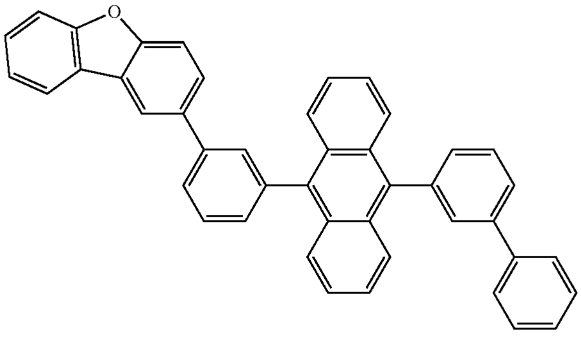
[Formula 210]
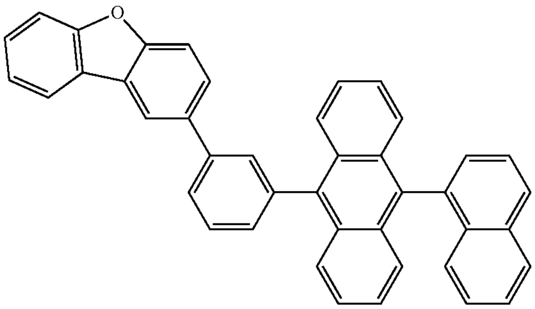
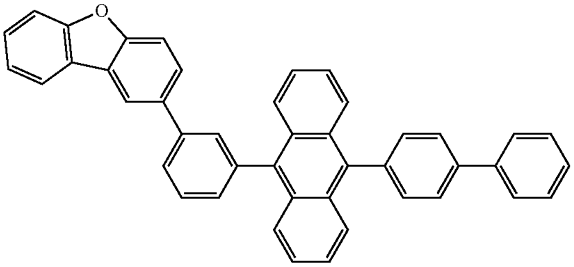
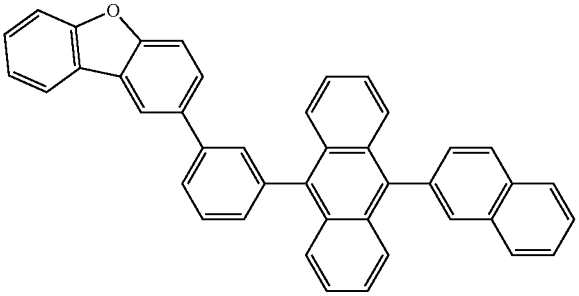
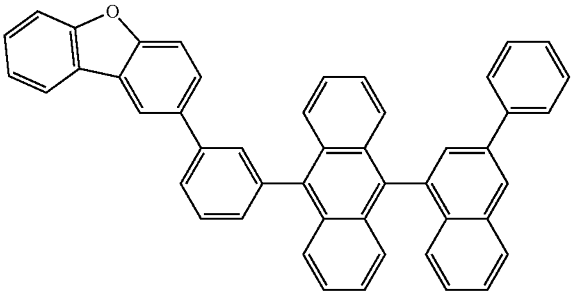
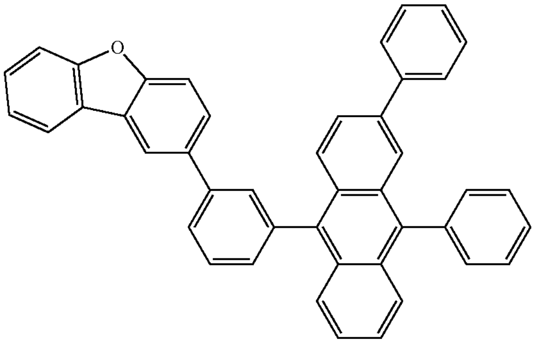

-continued
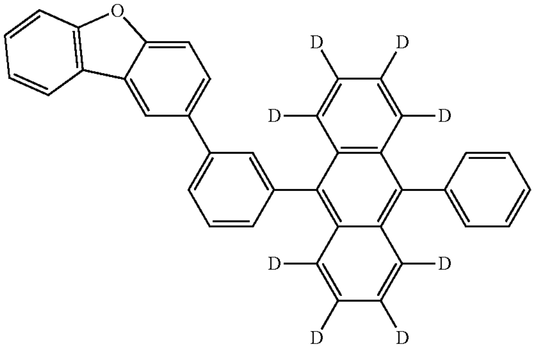
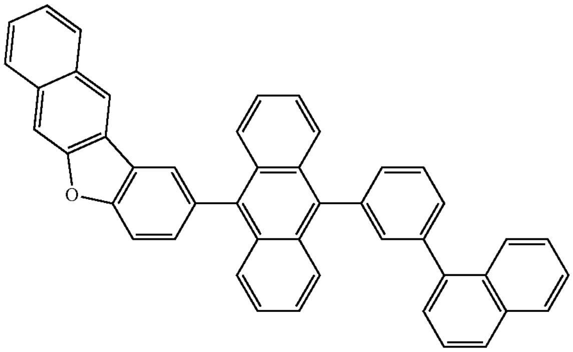
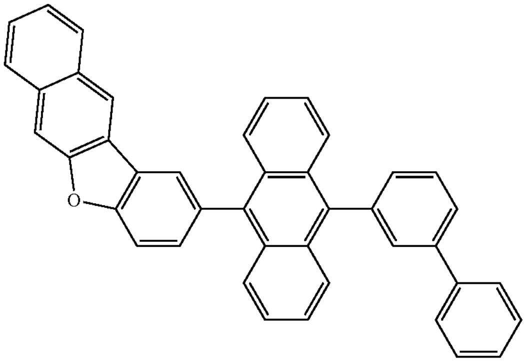
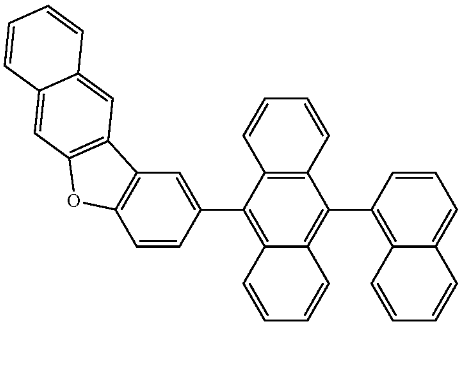
-continued
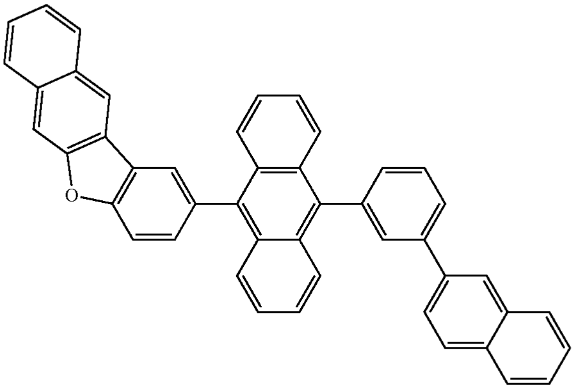
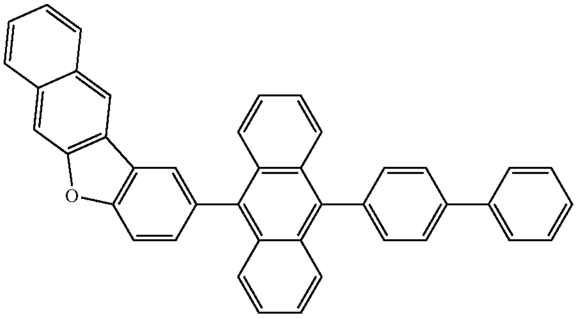
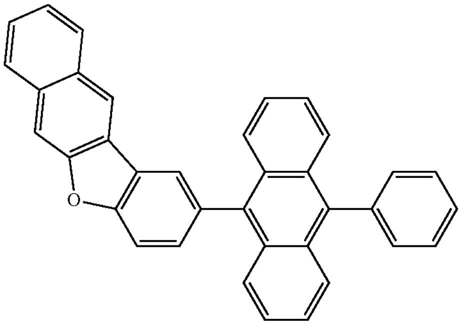
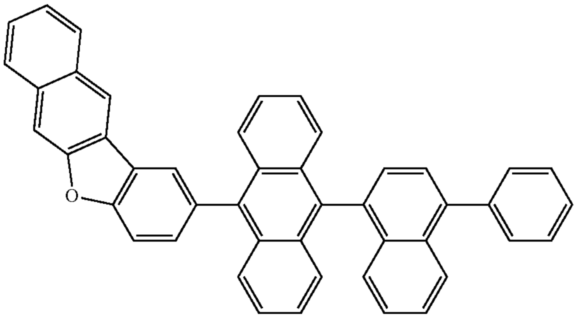
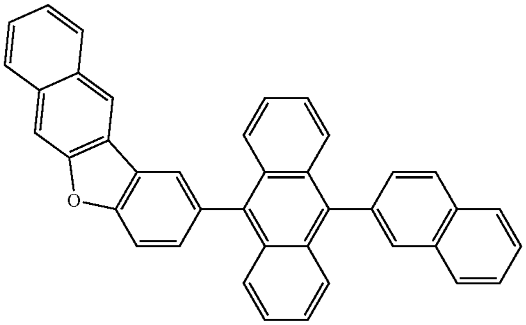

-continued
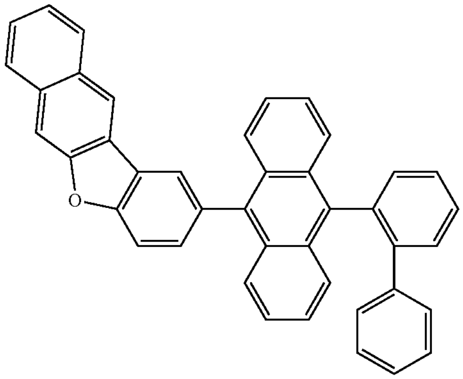
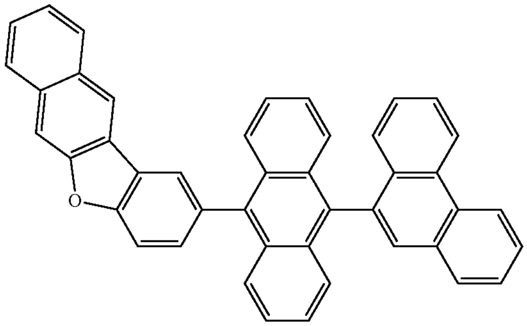
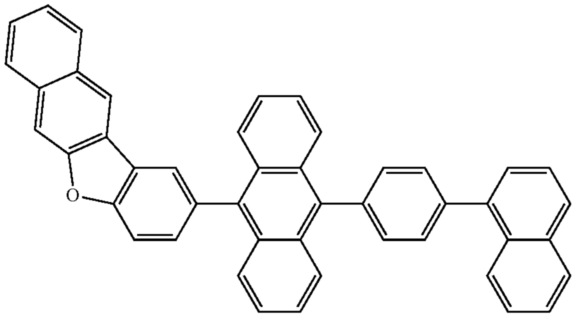
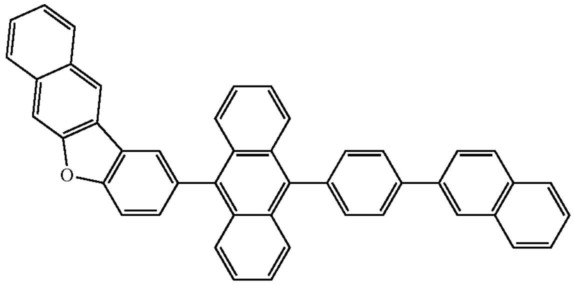
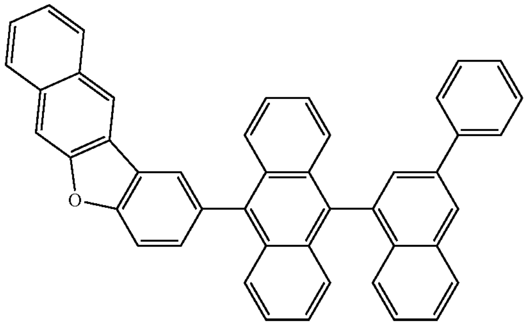
-continued
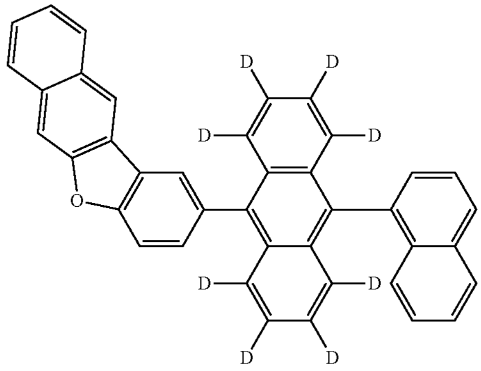
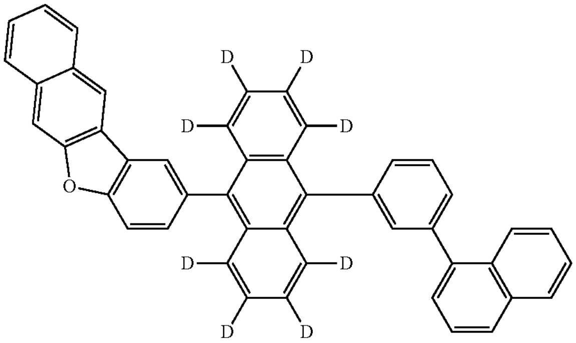
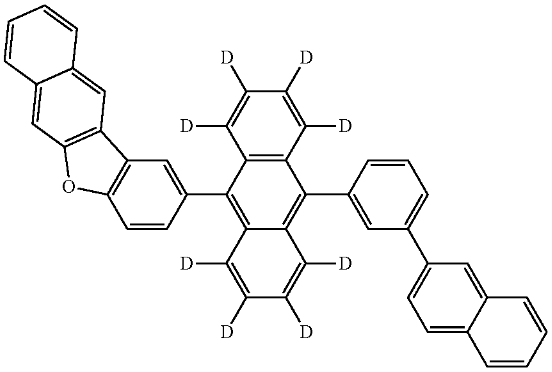
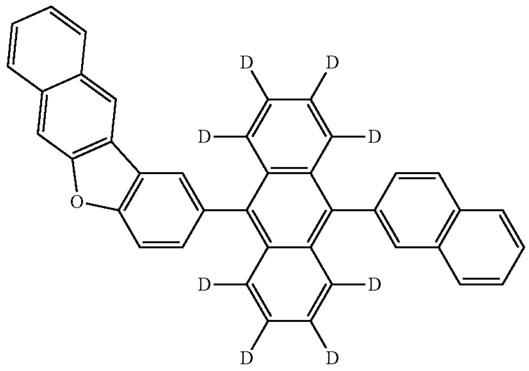

-continued
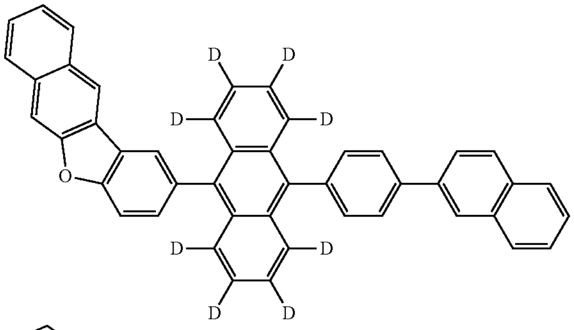
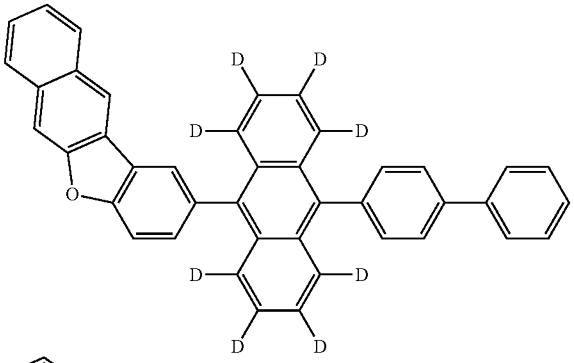
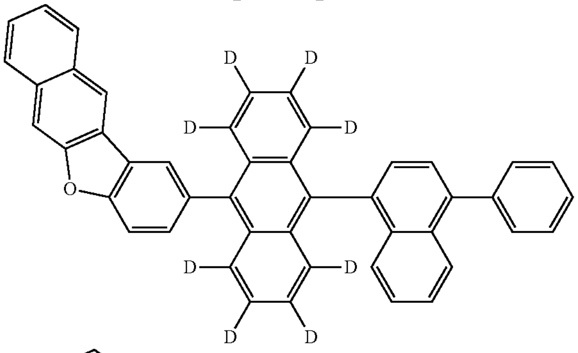
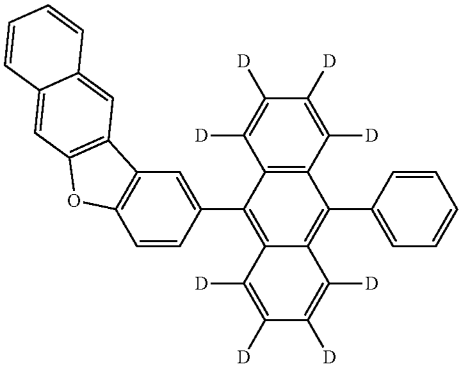
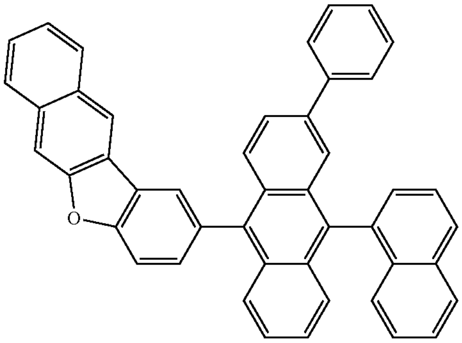
-continued
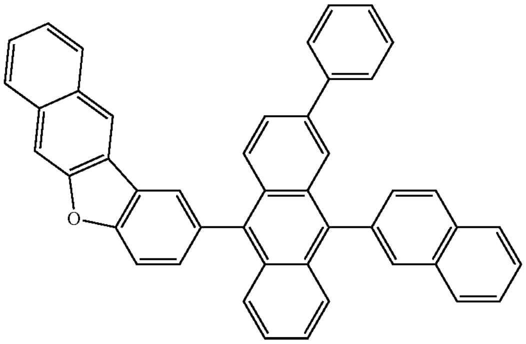
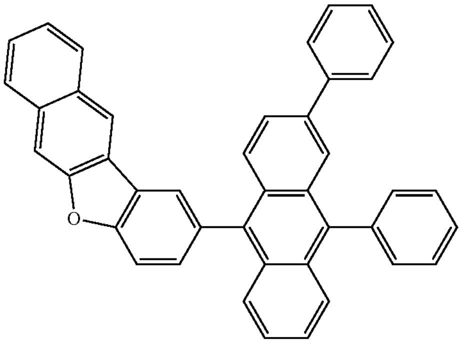
[Formula 211]
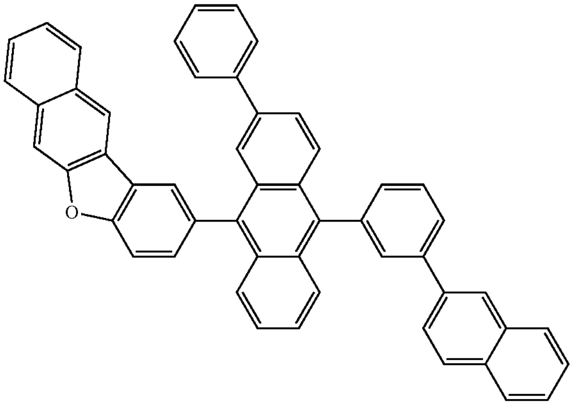
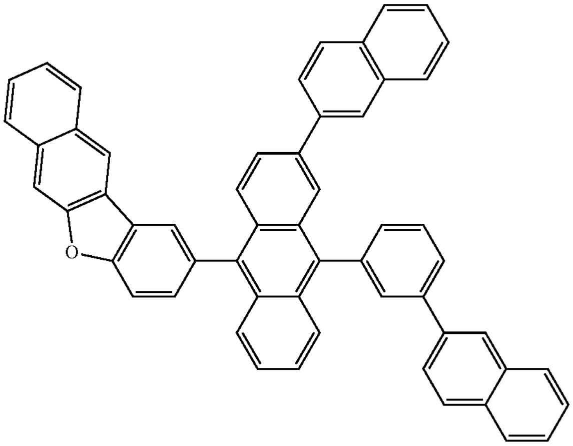

-continued
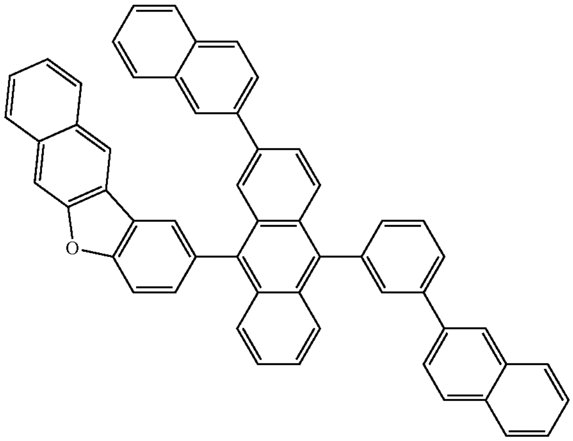
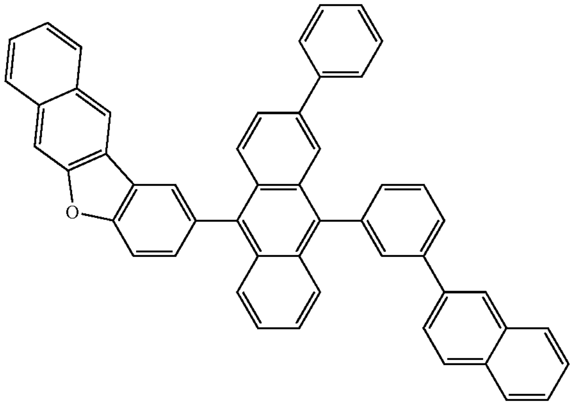
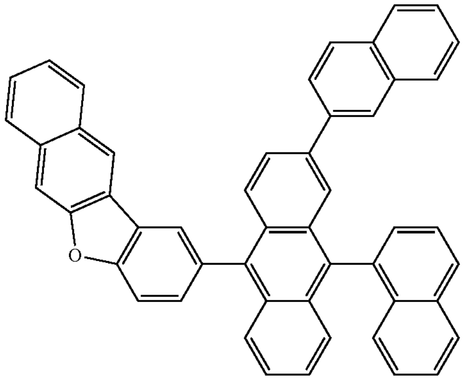
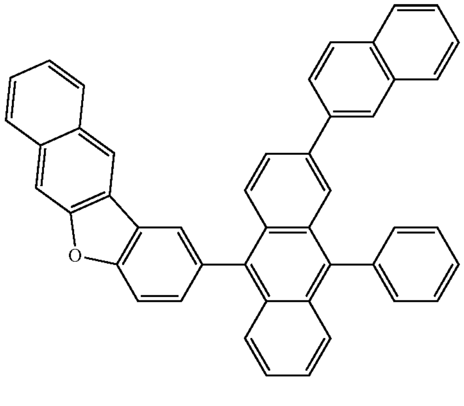
-continued
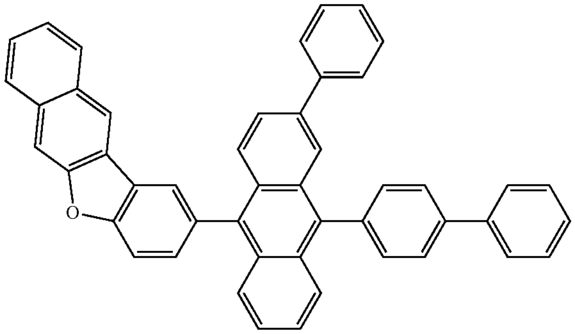
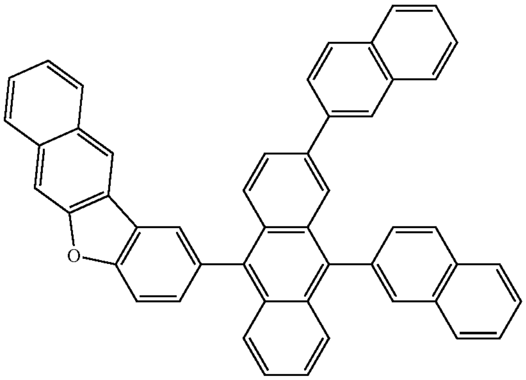
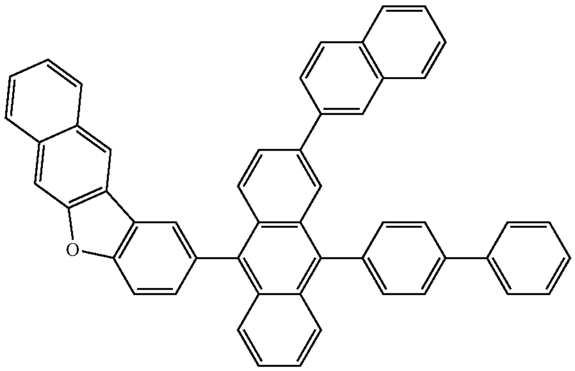
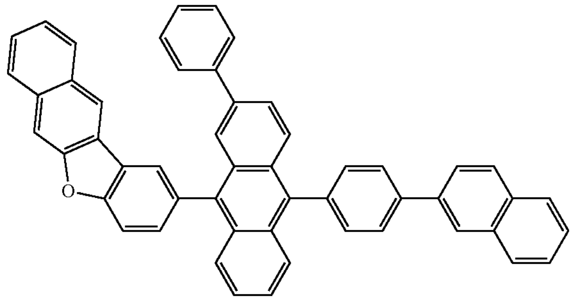
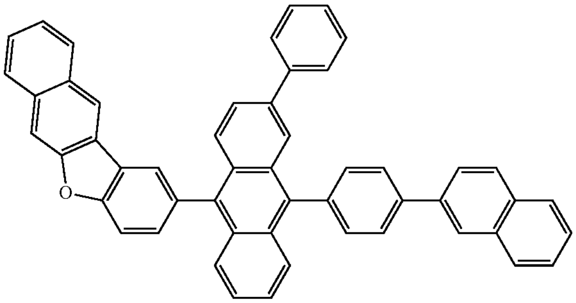

-continued
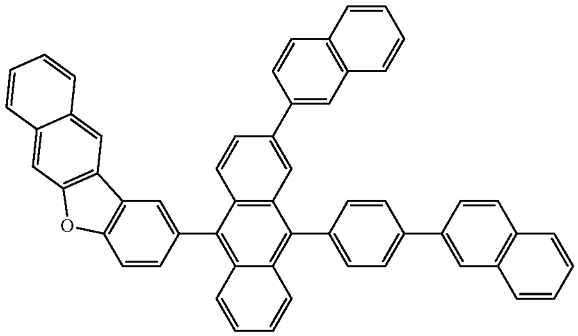
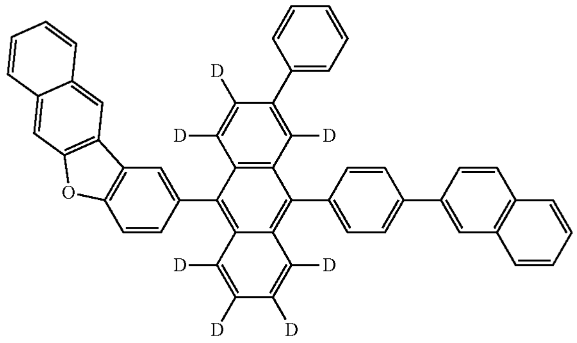
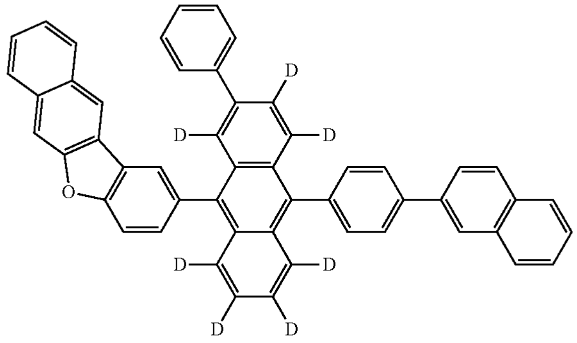
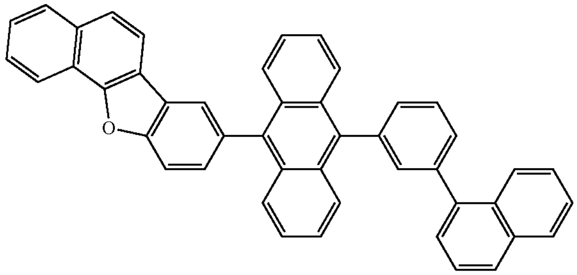
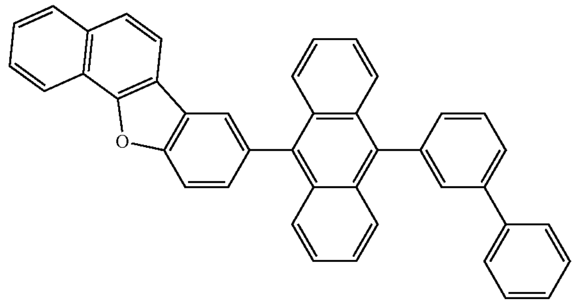
-continued
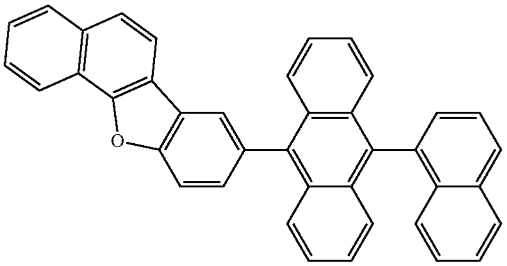
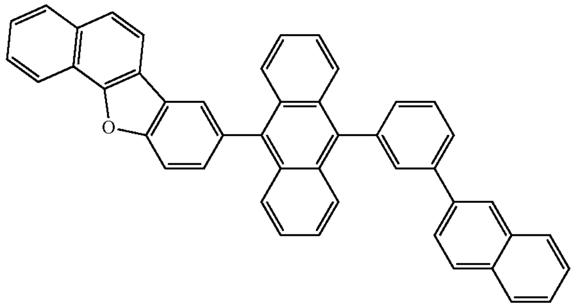
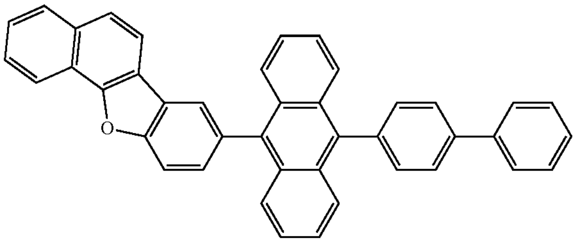
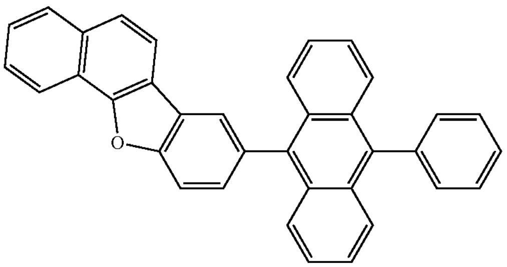
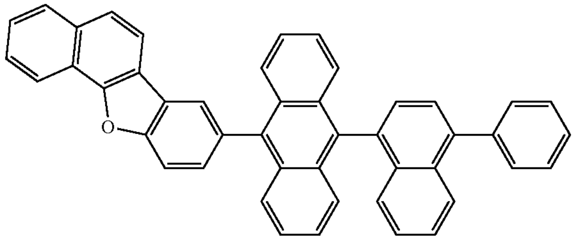
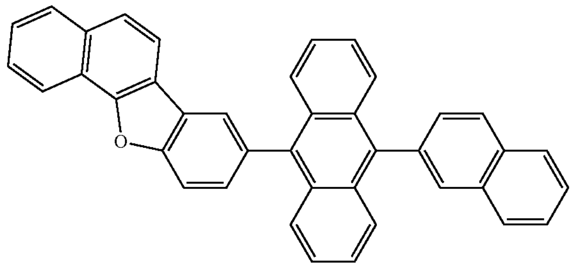

-continued
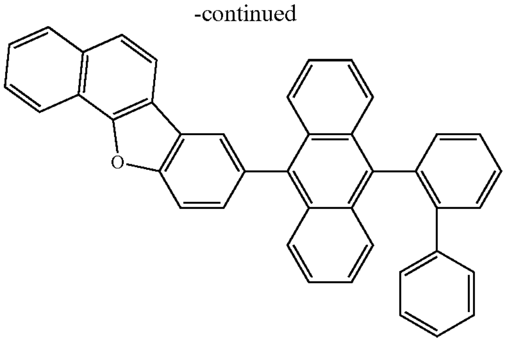
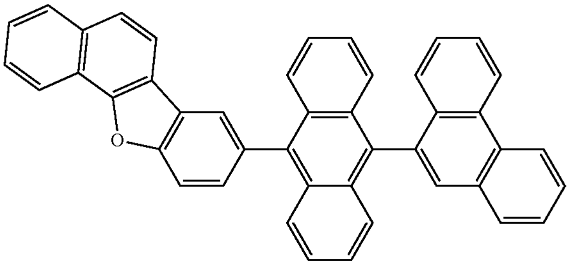
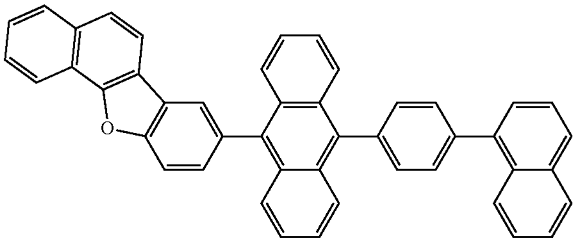
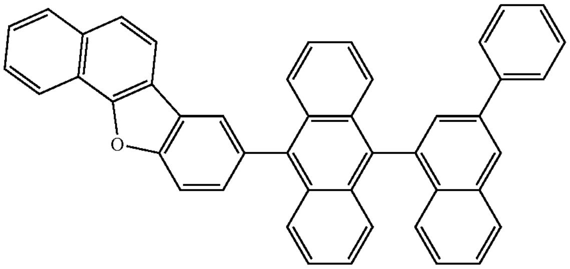
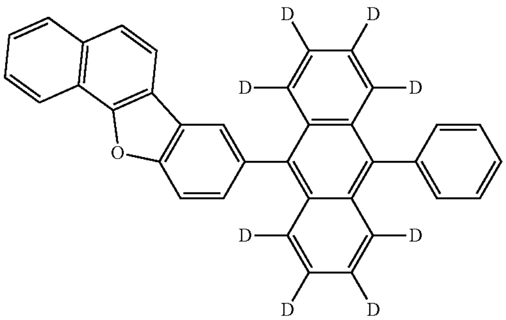
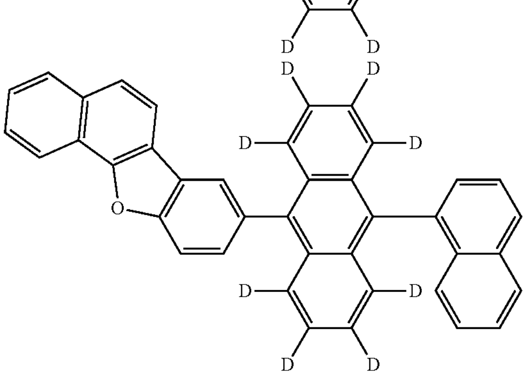
-continued
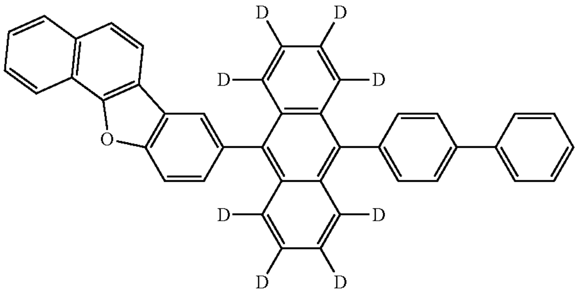
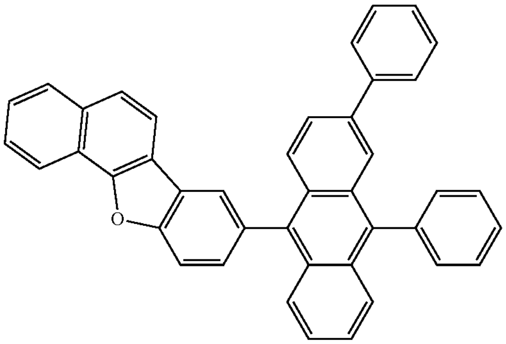
[Formula 212]
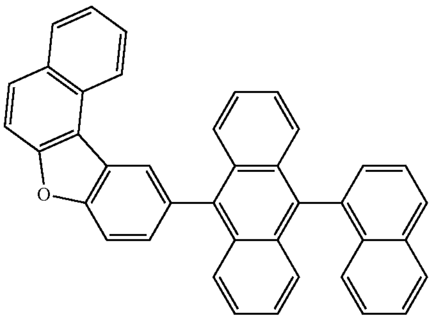
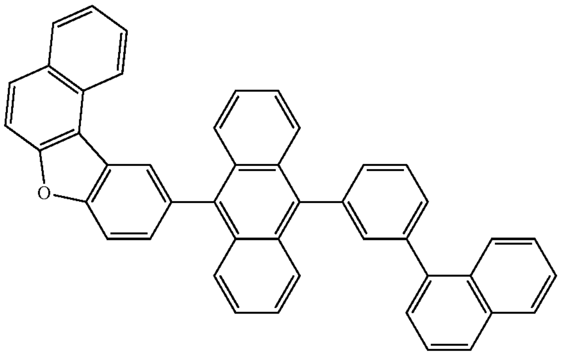
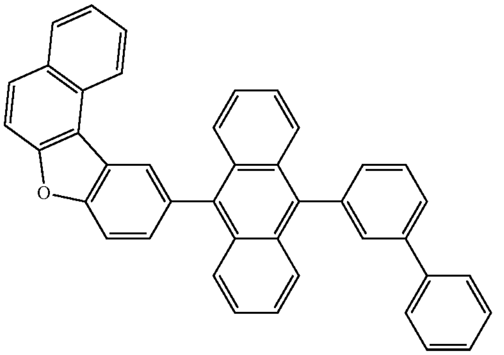

-continued
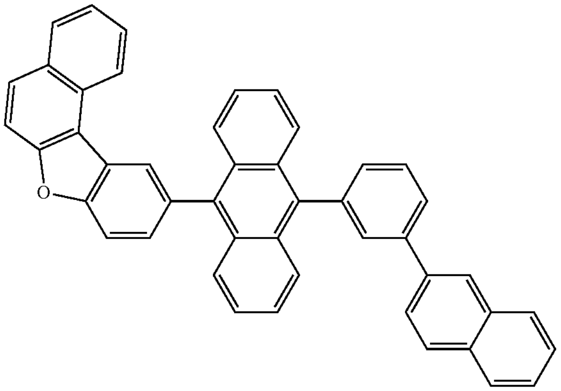
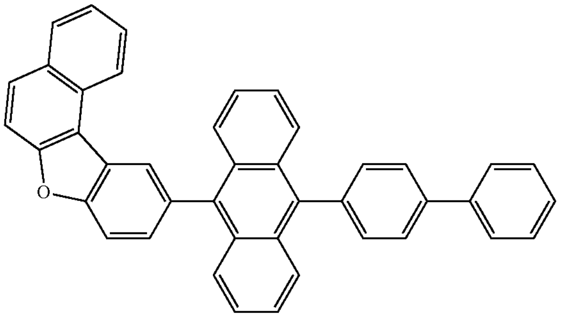
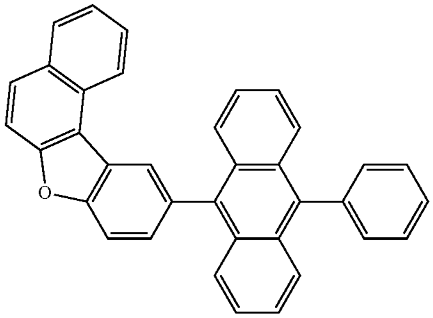
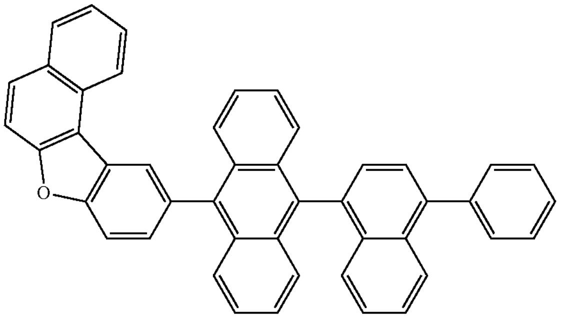
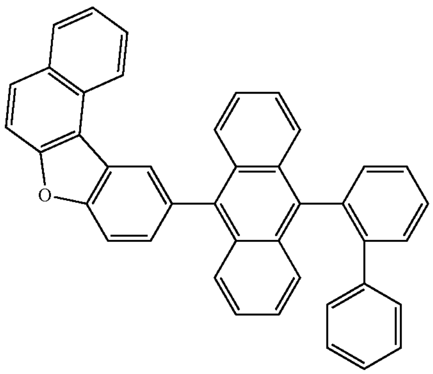
-continued
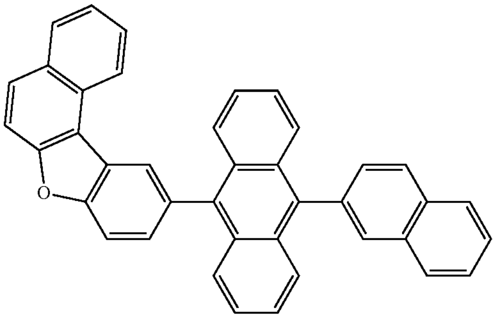
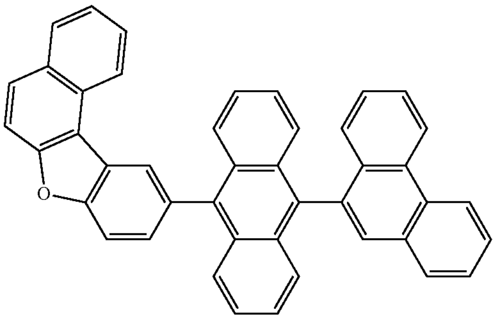
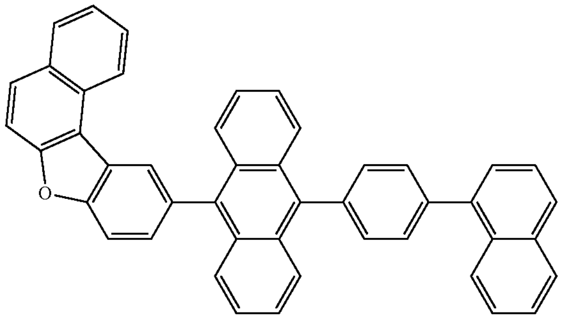
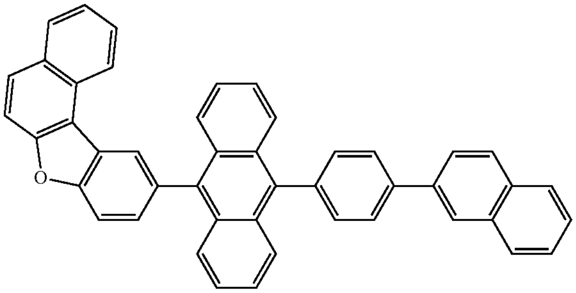
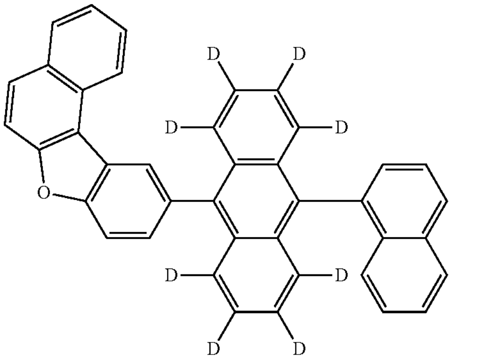

-continued
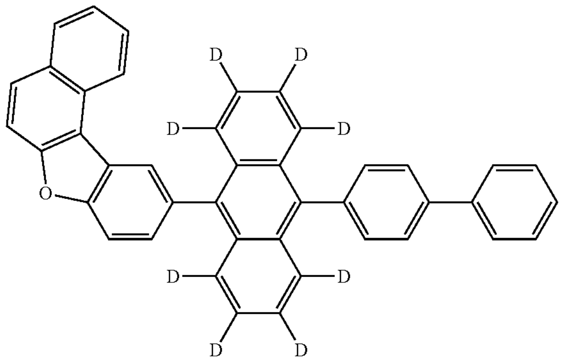
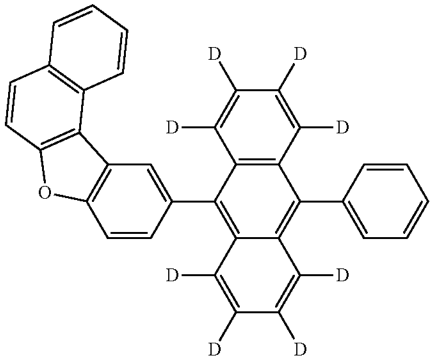
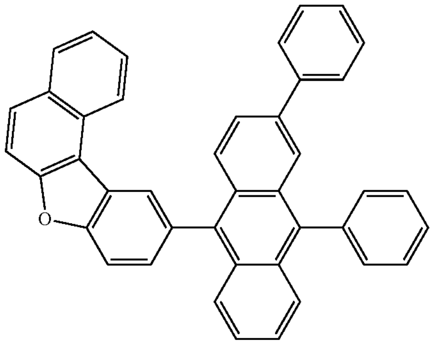
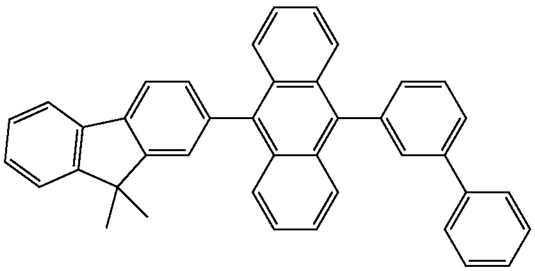
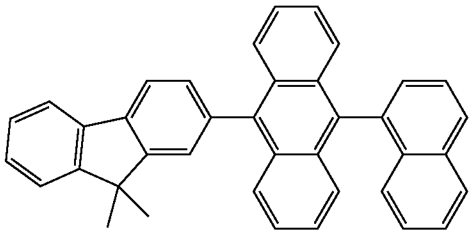
-continued
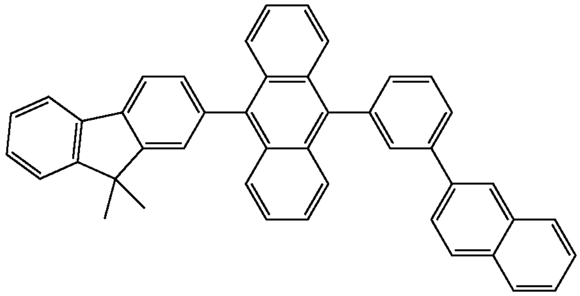
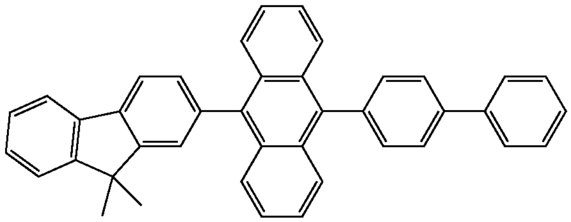
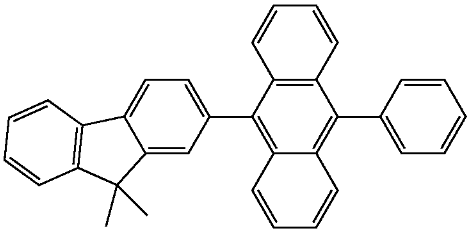
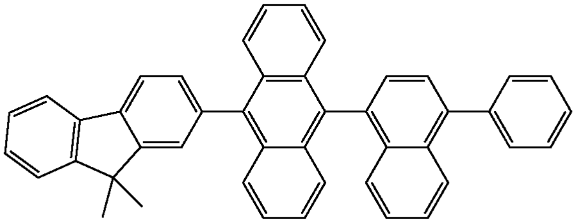
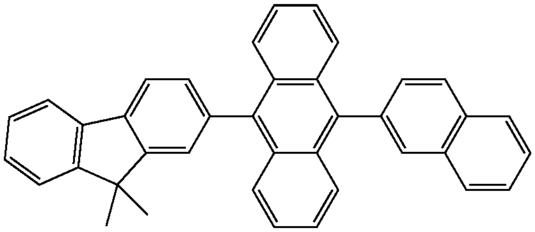
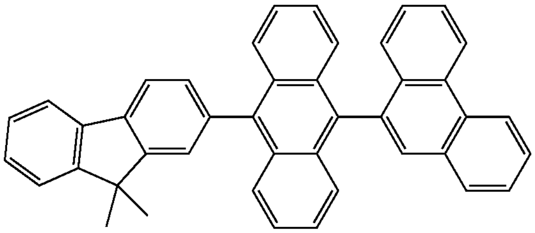
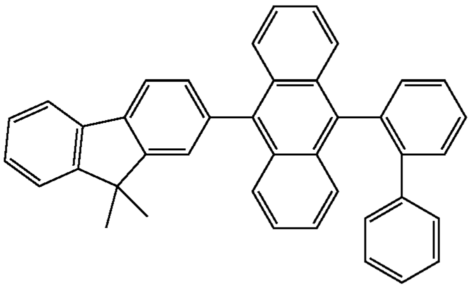

-continued
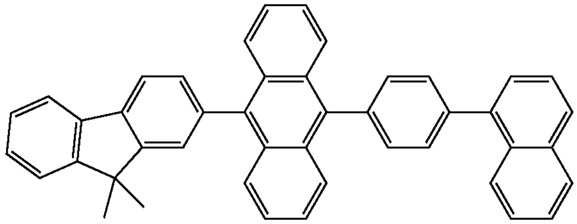
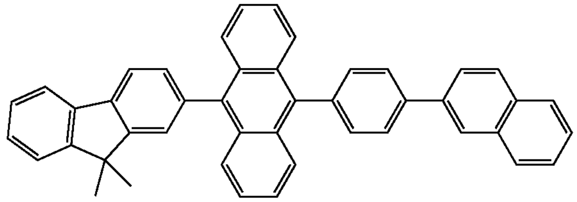
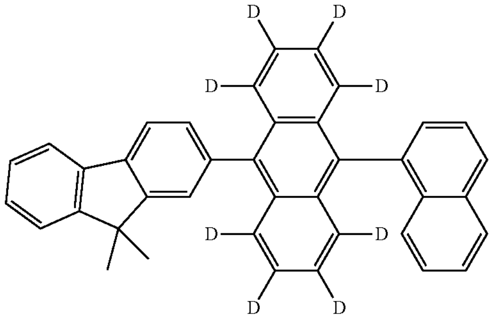
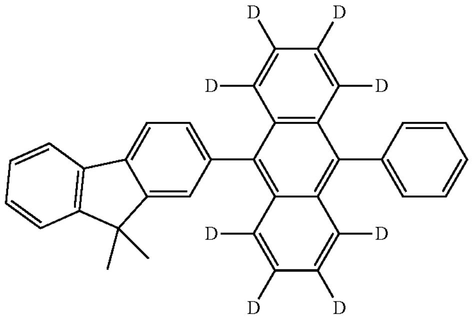
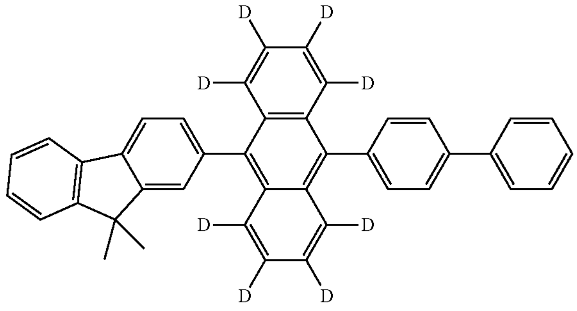
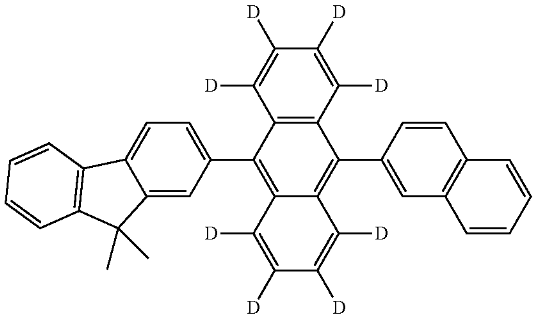
-continued
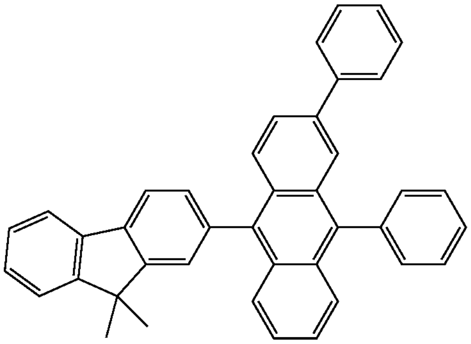
[Formula 213]
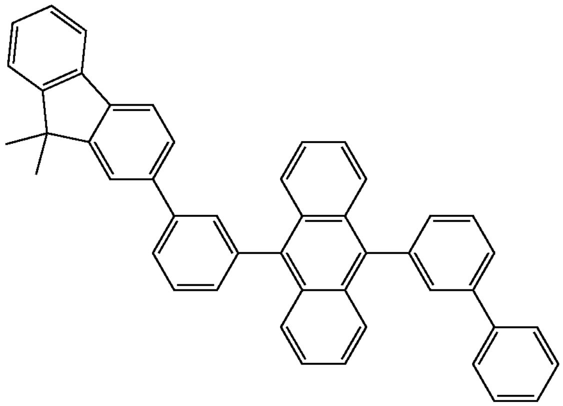
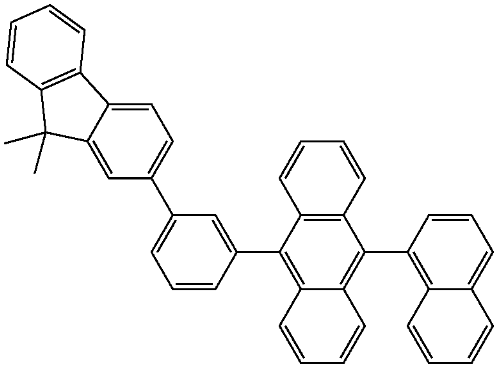
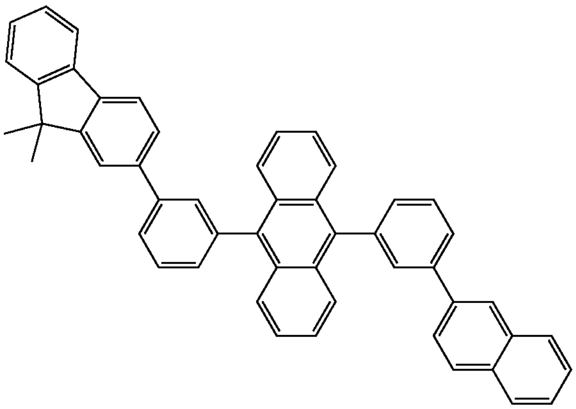

-continued
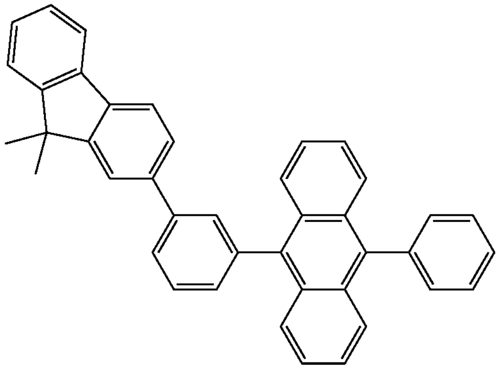
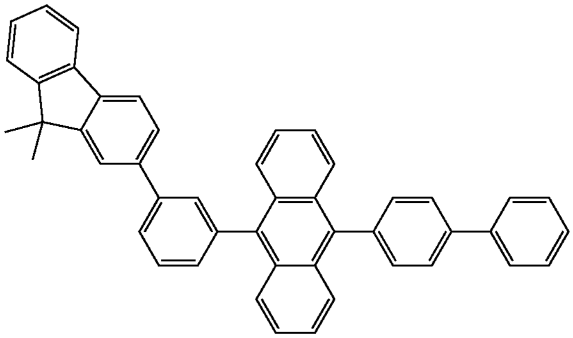
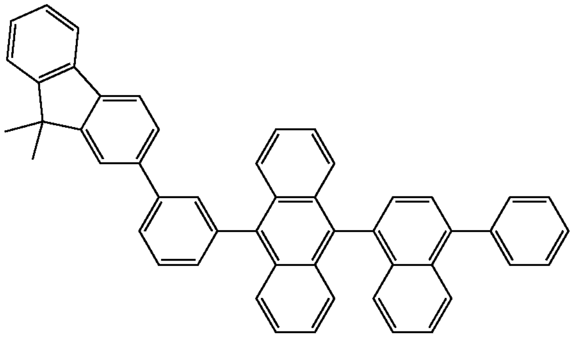
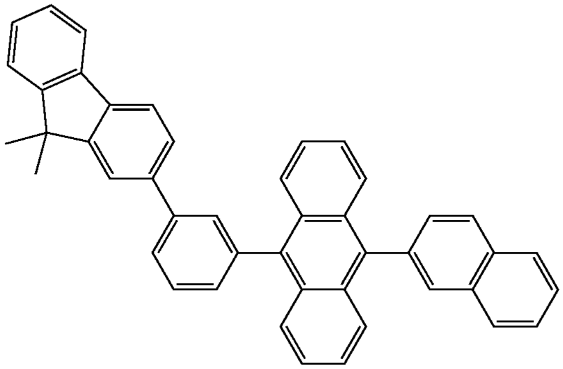
-continued
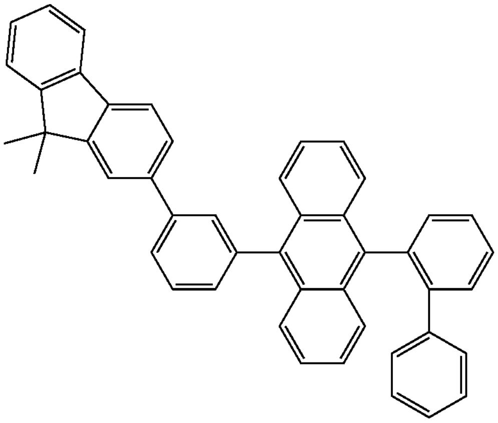
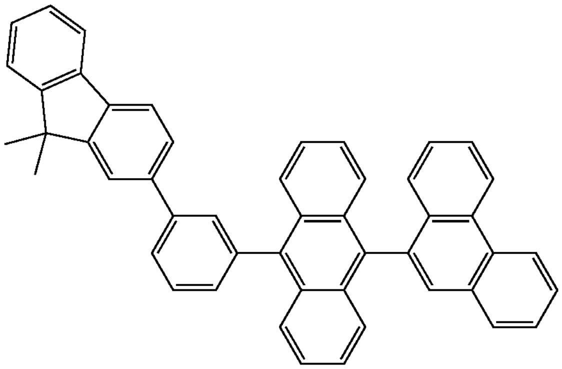
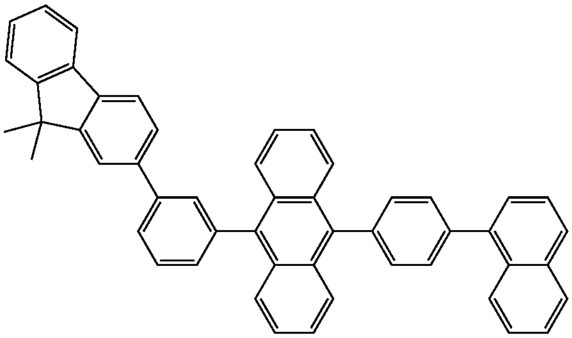
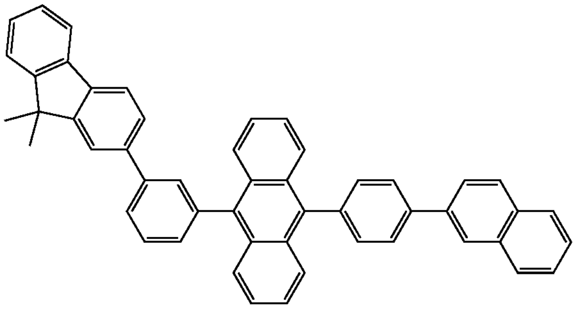

-continued
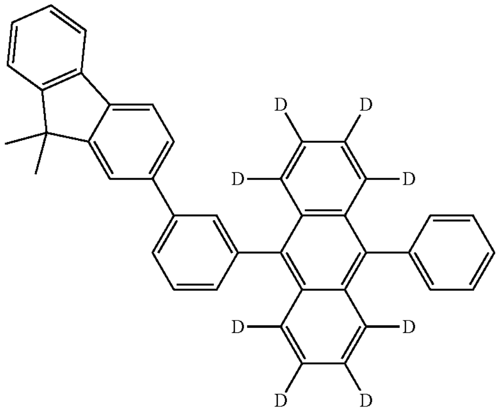
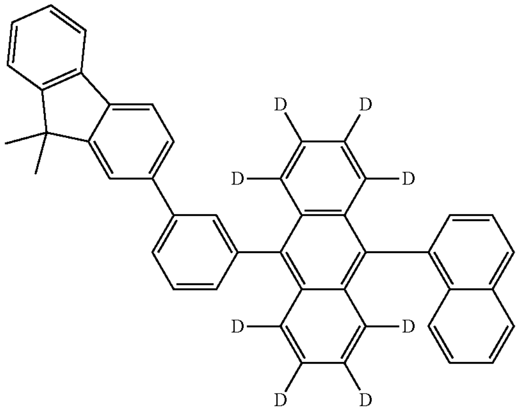
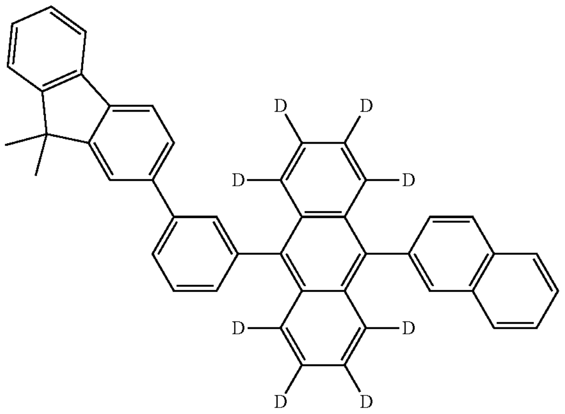
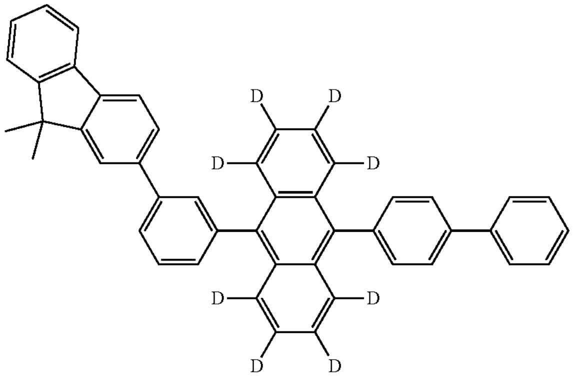
-continued
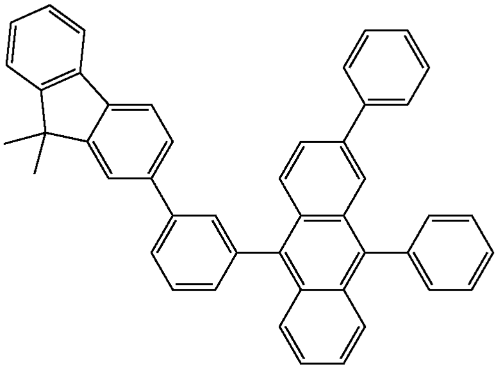
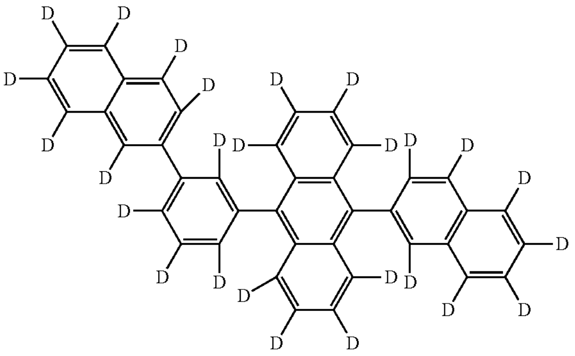
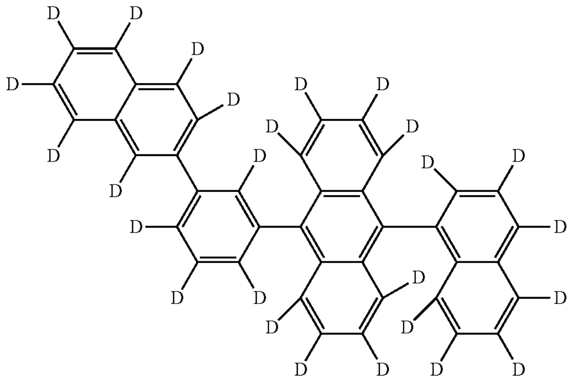
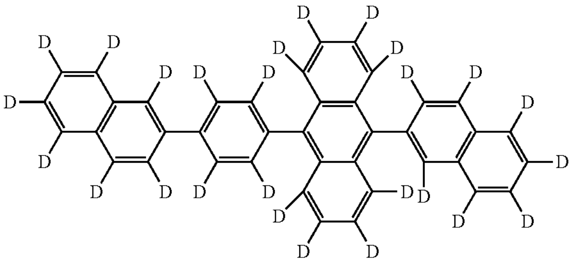
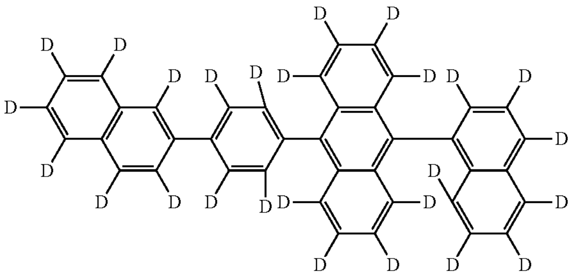

-continued

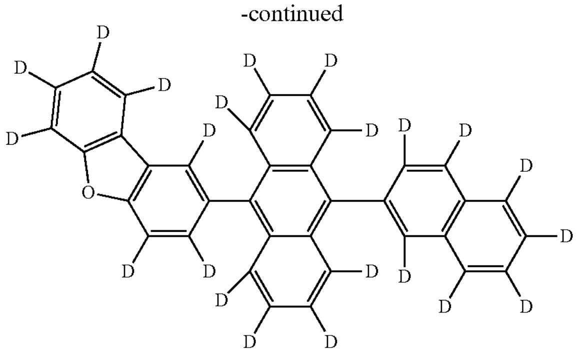

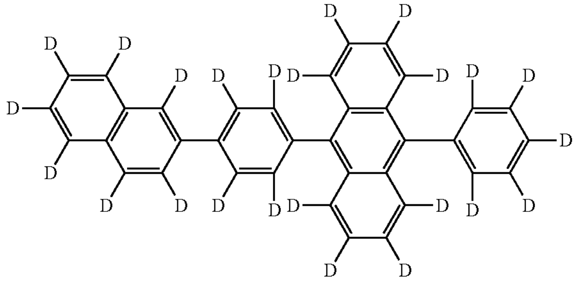

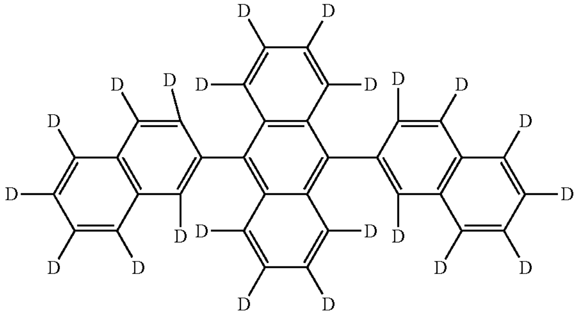

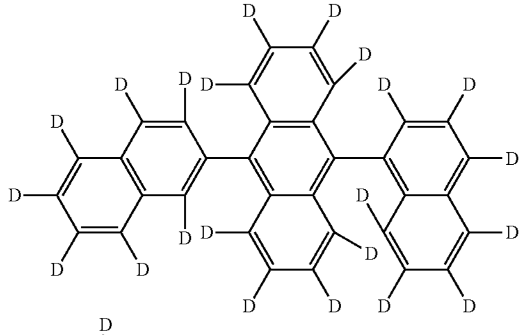

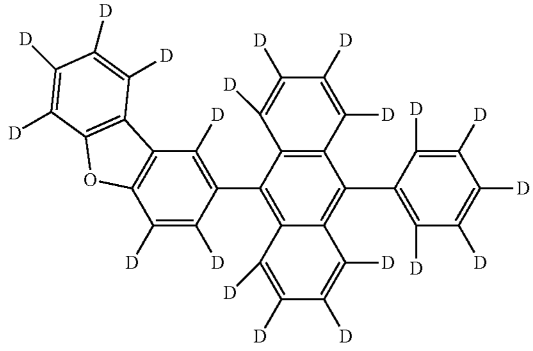

A structure of the organic EL device according to the exemplary embodiment is further described below.

A substrate is used as a support for a light emission device. For instance, glass, quartz, plastics and the like are usable as the substrate. A flexible substrate is also usable. The flexible substrate is a bendable substrate, which is exemplified by a plastic substrate formed from polycarbonate, polyvinyl chloride, or the like.

Metal, an alloy, an electrically conductive compound, a mixture thereof, and the like having a large work function (specifically, 4.0 eV or more) is preferably used for the anode formed on the substrate. Specific examples of the material include ITO (Indium Tin Oxide), indium oxide-tin oxide containing silicon or silicon oxide, indium oxide-zinc oxide, indium oxide containing tungsten oxide and zinc oxide, and graphene. In addition, gold (Au), platinum (Pt), nitrides of a metal material (e.g., titanium nitride) and the like are usable.

The hole injecting layer is a layer containing a substance exhibiting a high hole injectability. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, manganese oxide, aromatic amine compound, ladder compound such as a fluorene derivative, and high polymer compound (e.g., oligomer, dendrimer and polymer).

The hole transporting layer is a layer containing a substance exhibiting a high hole transportability. An aromatic amine compound, carbazole derivative, anthracene derivative and the like are usable for the hole transporting layer. A high polymer compound such as poly(N-vinylcarbazole) (abbreviation: PVK) and poly(4-vinyltriphenylamine) (abbreviation: PVTPA) is also usable. However, in addition to the above substances, any substance exhibiting a higher hole transportability than an electron transportability may be used. It should be noted that the layer containing the substance exhibiting a high hole transportability may be not only a single layer but also a laminate of two or more layers formed of the above substance(s).

The electron transporting layer is a layer containing a highly electron-transporting substance. For the electron transporting layer are usable (1) metal complexes such as a lithium complex, aluminum complex, beryllium complex, and zinc complex; (2) heteroaromatic compounds such as an imidazole derivative, benzimidazole derivative, azine derivative, carbazole derivative, and phenanthroline derivative; and (3) a high polymer compound.

The electron injecting layer is a layer containing a highly electron-injectable substance. For the electron injecting layer, an alkali metal, alkaline earth metal, or compounds thereof are usable. For instance, lithium (Li), lithium complex, lithium fluoride (LiF), cesium fluoride (CsF), calcium fluoride ($CaF_2$), and lithium oxide (LiOx) are usable.

Metal, an alloy, an electrically conductive compound, a mixture thereof, and the like having a small work function (specifically, 3.8 eV or less) is preferably used for the cathode. Specific examples of a material of the cathode includes elements belonging to Groups 1 and 2 in the periodic table of the elements, specifically, alkali metal such as lithium (Li) and cesium (Cs), alkaline earth metal such as magnesium (Mg), and alloys (e.g., MgAg and AlLi) including the alkali metal or the alkaline earth metal.

In an example of the organic EL device according to the exemplary embodiment, a method of forming each layer is not particularly limited. As the method of forming each layer, conventionally-known methods such as vacuum deposition and spin coating are usable. Each layer such as the emitting layer can be formed by known coating methods such as vacuum deposition, molecular beam epitaxy (MBE method) and coating methods using a solution, such as a dipping, spin coating, casting, bar coating, and roll coating.

In an example of the organic EL device according to the exemplary embodiment, a film thickness of each layer is not particularly limited. The film thickness of each layer is typically preferably in a range from several nm to 1 μm, in general, in order to inhibit defects such as pin holes and make an applied voltage low to improve the luminous efficiency.

According to the exemplary embodiment, the organic electroluminescence device containing the compound having a high PLQY and exhibiting a fluorescence spectrum having a high blue color purity can be provided. Moreover, according to an example of the exemplary embodiment, the organic EL device having an improved luminous efficiency can be provided.

Fourth Exemplary Embodiment

Electronic Device

An electronic device according to a fourth exemplary embodiment is installed with any one of the organic EL devices according to the above exemplary embodiment. Examples of the electronic device include a display device and a light-emitting device. Examples of the display device include a display component (e.g., an organic EL panel module), TV, mobile phone, tablet and personal computer. Examples of the light-emitting unit include an illuminator and a vehicle light.

According to the exemplary embodiment, the electronic device including the organic electroluminescence device containing the compound having a high PLQY can be provided. Moreover, according to an example of the exemplary embodiment, the electronic device including the organic EL device having an improved luminous efficiency can be provided.

Modification of Exemplary Embodiment(s)

The scope of the invention is not limited by the above-described exemplary embodiments but includes any modification and improvement as long as such modification and improvement are compatible with the invention.

For instance, the emitting layer is not limited to a single layer, but may be provided by laminating a plurality of emitting layers. When the organic EL device has the plurality of emitting layers, it is only required that at least one of the emitting layers satisfies the conditions described in the above exemplary embodiment. For instance, in some embodiments, the rest of the emitting layers is a fluorescent emitting layer or a phosphorescent emitting layer with use of emission caused by electron transfer from the triplet excited state directly to the ground state.

When the organic EL device includes a plurality of emitting layers, these emitting layers may be mutually adjacently provided, or may form a so-called tandem organic EL device, in which a plurality of emitting units are layered via an intermediate layer.

For instance, a blocking layer may be provided adjacent to at least one of a side of the emitting layer close to the anode or a side of the emitting layer close to the cathode. The blocking layer is preferably provided in contact with the emitting layer to block at least any of holes, electrons, excitons or combinations thereof.

For instance, when the blocking layer is provided in contact with the side of the emitting layer close to the cathode, the blocking layer permits transport of electrons and blocks holes from reaching a layer provided close to the cathode (e.g., the electron transporting layer) beyond the blocking layer. When the organic EL device includes the electron transporting layer, the blocking layer is preferably interposed between the emitting layer and the electron transporting layer.

When the blocking layer is provided in contact with the side of the emitting layer close to the anode, the blocking layer permits transport of holes and blocks electrons from reaching a layer provided closer to the anode (e.g., the hole transporting layer) beyond the blocking layer. When the organic EL device includes the hole transporting layer, the blocking layer is preferably interposed between the emitting layer and the hole transporting layer.

Alternatively, the blocking layer may be provided adjacent to the emitting layer so that excitation energy does not leak out from the emitting layer toward neighboring layer(s). The blocking layer blocks excitons generated in the emitting layer from being transferred to a layer(s) (e.g., the electron transporting layer and the hole transporting layer) closer to the electrode(s) beyond the blocking layer.

The emitting layer is preferably bonded with the blocking layer.

Specific structure, shape and the like of the components in the invention may be designed in any manner as long as an object of the invention can be achieved.

EXAMPLES

Example(s) of the invention will be described below. However, the invention is not limited to Example(s).

Compounds

The compounds each represented by the formula (2) which were used in Examples 1 to 4 are shown below.

[Formula 214]

BD1

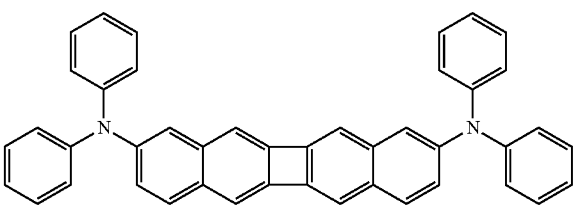

BD2

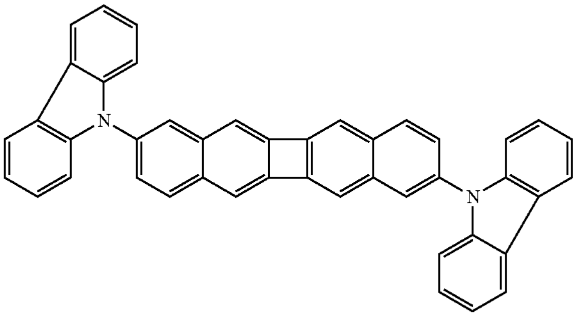

-continued
BD3
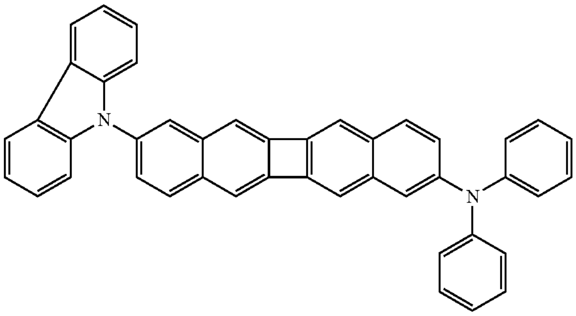
[Formula 215]
BD4
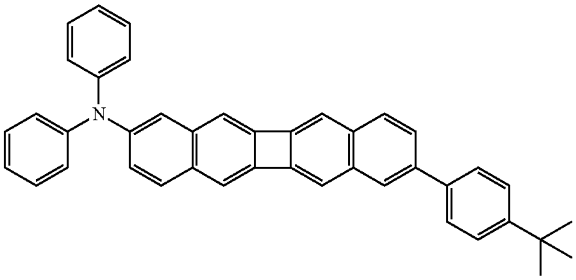
Comparative compounds that were used in Comparatives 1 and 2 are shown below.
[Formula 216]
Ref-1
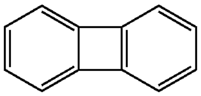
Ref-2
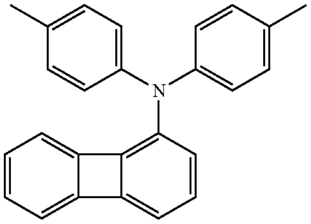
Structures of other compounds that were used for manufacturing the organic EL device in Example 4 and Comparative 2 are shown below.
[Formula 217]
HI1
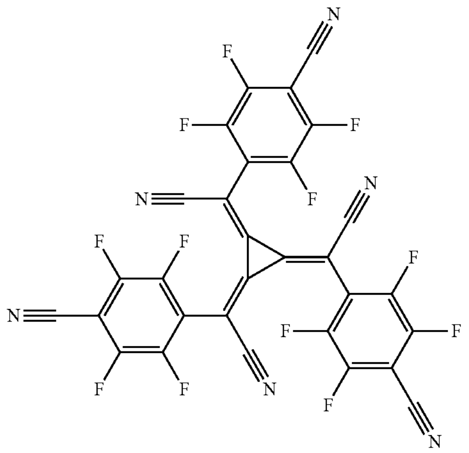
HT1
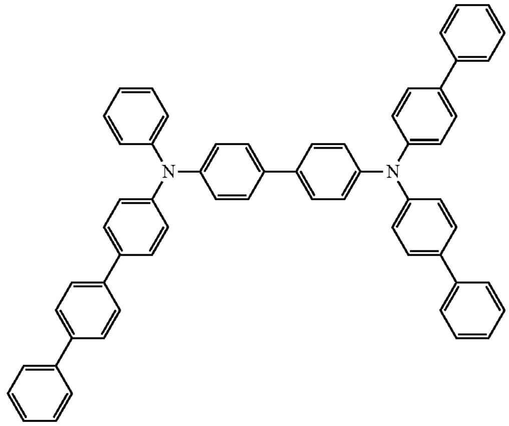
[Formula 218]
HT2
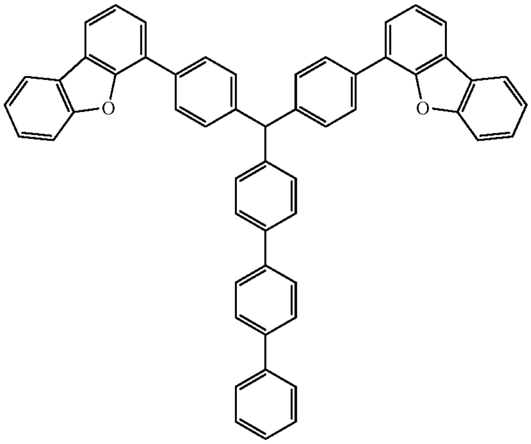

-continued

BH1

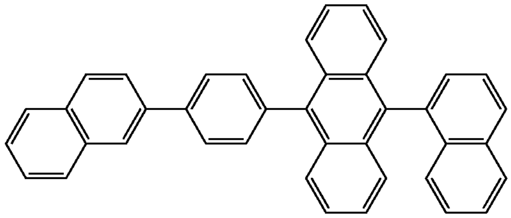

[Formula 219]

ET1

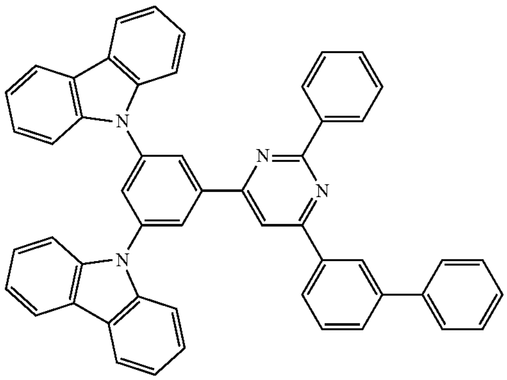

ET2

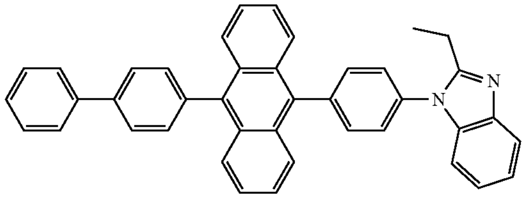

Evaluation of Compounds

Preparation of Toluene Solution

A compound BD1 was dissolved in toluene so as to have a concentration of 5 μmol/L, thereby preparing a toluene solution of the compound BD1.

A toluene solution of each of compounds BD2, BD3, and Ref-1 was prepared in the same manner as that of the compound BD1.

Measurement of Photoluminescence Quantum Yield (PLQY)

PLQY of each of the toluene solutions of the respective compounds BD1, BD2, BD3, and Ref-1 was measured using an absolute PL (Photoluminescence) quantum yield measurement device Quantaurus-QY (manufactured by HAMAMATSU PHOTONICS K.K.).

Measurement results of values of PLQY of the compounds BD1, BD2, BD3, and Ref-1 are shown in Table 1.

Fluorescence Main Peak Wavelength of Compounds

A toluene solutions of each of measurement target compounds at a concentration of 5 μmol/L was prepared and put in a quartz cell. A fluorescence spectrum (ordinate axis: fluorescence intensity, abscissa axis: wavelength) of each sample was measured at a normal temperature (300K). In Examples, the fluorescence spectrum was measured using a spectrophotometer (device name: F-7000) manufactured by Hitachi, Ltd. It should be noted that a measurement device of the fluorescence spectrum is not limited to the device used herein. A peak wavelength of the fluorescence spectrum exhibiting the maximum luminous intensity was defined as a fluorescence main peak wavelength.

Measurement results of the main peak wavelengths of the fluorescence spectra of the compounds BD1, BD2, BD3, and Ref-1 are shown in Table 1.

TABLE 1

| | | Main Peak Wavelength [nm] | PLQY [%] |
|---|---|---|---|
| Example 1 | Compound BD1 | 468 | 67 |
| Example 1 | Compound BD2 | 428 | 82 |
| Example 1 | Compound BD3 | 457 | 74 |
| Comparative 1 | Comparative Compound Ref-1 | 395 | <0.01 |

As shown in Table 1, the compound represented by the formula (2) improved PLQY more than the comparative compound Ref-1. PLQY of the comparative compound Ref-1 was less than 0.01%. Moreover, as shown in Table 1, the compound represented by the formula (2) exhibited a fluorescence spectrum having a high blue color purity.

Preparation of Organic EL Device

The organic EL devices were prepared and evaluated as follows.

Example 4

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

After the glass substrate having the transparent electrode line was cleaned, the glass substrate was mounted on a substrate holder of a vacuum deposition apparatus. First, compounds HT1 and HI1 were co-deposited on a surface of the glass substrate where the transparent electrode line was provided in a manner to cover the transparent electrode, thereby forming a 10-nm-thick hole injecting layer (HI). The ratios of the compound HT1 and the compound HI1 in the hole injecting layer were 97 mass % and 3 mass %, respectively.

After the formation of the hole injecting layer, the compound HT1 was vapor-deposited to form an 80-nm-thick first hole transporting layer (HT).

After the formation of the first hole transporting layer, a compound HT2 was vapor-deposited to form a 10-nm-thick second hole transporting layer (also referred to as an electron blocking layer (EBL)).

A compound BH1 and a compound BD4 were co-deposited on the second hole transporting layer to form a 25-nm-thick emitting layer. The ratios of the compound BH1 and the compound BD4 in the emitting layer were 99 mass % and 1 mass %, respectively.

A compound ET1 was vapor-deposited on the emitting layer to form a 10-nm-thick first electron transporting layer (also referred to as a hole blocking layer (HBL)).

The compound ET2 was vapor-deposited on the first electron transporting layer (HBL) to form a 15-nm-thick second electron transporting layer (ET).

LiF was vapor-deposited on the second electron transporting layer to form a 0.5-nm-thick electron injecting layer.

Metal aluminum (Al) was vapor-deposited on the electron injecting layer to form an 80-nm-thick cathode.

A device arrangement of the organic EL device in Example 4 is roughly shown as follows.

ITO(130)/HT1: HI1(10,97%:3%)/HT1(80)/HT2(10)/BH1:BD4(25,99%:1%)/ET1(10)/ET2(15)/LiF(0.5)/Al (80)

Numerals in parentheses represent a film thickness (unit: nm).

The numerals (97%:3%) represented by percentage in the same parentheses indicate a ratio (mass %) between the compound HT1 and the compound HI1 in the hole injecting layer, and the numerals (99%:1%) represented by percentage in the same parentheses indicate a ratio (mass %) between the compound BH1 and the compound BD4 in the emitting layer. Similar notations apply to the description below.

Comparative 2

An organic EL device in Comparative 2 was manufactured in the same manner as in Example 4 except that a compound Ref-2 described in Table 2 was used in place of the compound BD4 in the emitting layer.

Evaluation of Organic EL Devices

The organic EL devices manufactured in Example 4 and Comparative 2 were evaluated as follows. Evaluation results are shown in Table 2.

External Quantum Efficiency EQE

Voltage was applied on each of the organic EL devices such that a current density was 10 mA/cm$^2$, where spectral radiance spectra were measured by a spectroradiometer CS-2000 (manufactured by Konica Minolta, Inc.). The external quantum efficiency EQE (unit: %) was calculated based on the obtained spectral-radiance spectra, assuming that the spectra was provided under a Lambertian radiation.

Table 2 shows relative values (unit: %) of EQE of the organic EL device in Example 4 or Comparative 2 relative to the EQE of the organic EL device in Comparative 2.

EQE (relative value)=[EQE of the organic EL device in Example 4 or Comparative 2]/[EQE of the organic EL device in Comparative 2]×100

TABLE 2

| | Compound in Emitting Layer | | EQE (Relative Value) [%] |
|---|---|---|---|
| Example 4 | BH1 | BD4 | 180 |
| Comparative 2 | BH1 | Ref-2 | 100 |

As shown in Table 2, the organic EL device in Example 4 in which the compound BD4 was used significantly improved the external quantum efficiency EQE of the organic EL device as compared with the organic EL device in Comparative 2 in which the comparative compound Ref-2 was used.

Synthesis of Compounds

Synthesis Example 1 (Synthesis of Compound BD1)

[Formula 220]

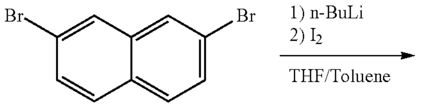

-continued

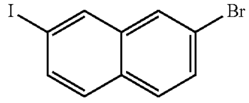

1a

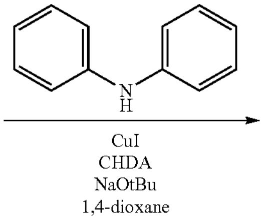

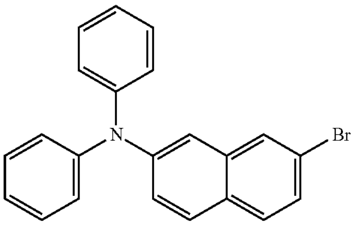

1b

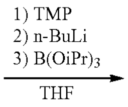

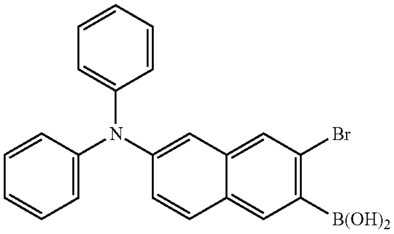

1c

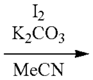

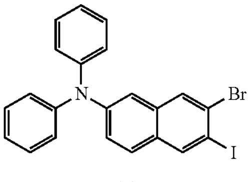

1d

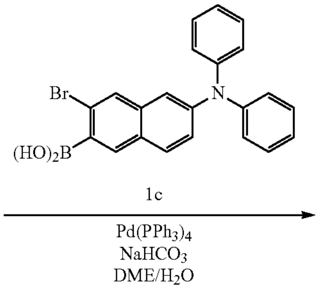

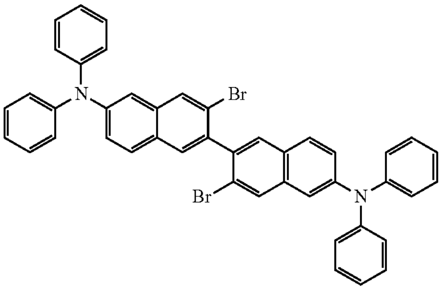

1e

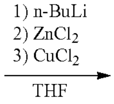

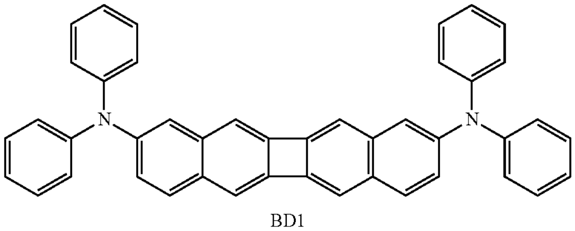

BD1

(1-1) Synthesis of Intermediate 1a

Under argon atmosphere, a mixed solution of 2,7-dibromonaphthalene (16.0 g, 55.9 mmol) in tetrahydrofuran (THF, 200 mL) and toluene (200 mL) was cooled to −30 degrees C., into which a hexane solution of 1.55M n-butyl lithium (n-BuLi, 36 mL, 55.8 mmol) was dropped. The obtained solution was stirred at −30 degrees C. for 15 minutes. Subsequently, the solution was cooled to −70 degrees C. and stirred for 45 minutes. Next, THF solution (40 mL) of iodine ($I_2$, 15.6 g, 61.4 mmol) was dropped into the above solution. The obtained solution was stirred at −70 degrees C. for one hour. The solution was stirred for two hours while being returned to the room temperature. Subsequently, the solution was quenched with a 10% aqueous solution of sodium thiosulfate. An organic phase was separated, washed with saturated saline water, then dried with anhydrous magnesium sulfate, and a solvent was distilled under reduced pressure, so that an intermediate 1a was obtained (18.2 g, a yield of 98%). A molecular weight of the intermediate 1a was 332.966. A result of mass spectroscopy analysis of the obtained compound was m/z (a ratio of mass to charge)=332, so that the obtained compound was identified as the target substance.

(1-2) Synthesis of Intermediate 1b

Under argon atmosphere, trans-1,2-cyclohexanediamine (CHDA, 0.38 mL, 3.2 mmol) was added into a mixed solution of the intermediate 1a (10.61 g, 31.9 mmol), diphenylamine (5.38 g, 31.8 mmol), copper iodide(I) (CuI, 0.06 g, 0.32 mmol), sodium tert-butoxide (NaOtBu, 4.3 g, 44.8 mmol), and 1,4-dioxane (40 mL), and was stirred at 110 degrees C. for 11 hours. The obtained reaction solution was returned to the room temperature, diluted with toluene, and then filtered by passing through Celite No. 545. A solid obtained by distilling the solvent under reduced pressure was purified by silica-gel column chromatography to obtain an intermediate 1b (8.92 g, a yield of 75%). A molecular weight of the intermediate 1b was 374.281. A result of mass spectroscopy analysis of the obtained compound was m/z (a ratio of mass to charge)=374, so that the obtained compound was identified as the target substance.

(1-3) Synthesis of Intermediate 1c

Under argon atmosphere, 2,2,6,6-tetramethylpiperidine (TMP, 6.7 g, 47.5 mmol) was dissolved in THF (70 mL) and cooled to −45 degrees C. 1.55M n-BuLi hexane solution (31 mL, 48.1 mmol) was added to the above solution, stirred at −40 degrees C. for 20 minutes, and cooled to −70 degrees C. Boric acid triisopropyl ester ($B(OiPr)_3$, 15 mL, 65.0 mmol) was dropped into the solution and, after five minutes, into which THF (40 mL) solution of the intermediate 1b (8.92 g, 23.9 mmol) was slowly dropped. The obtained solution was stirred in a cooling bath for nine hours. Then, this reaction solution was returned to the room temperature, added with 10% hydrochloric acid, and stirred for 30 minutes. The solution was extracted with ethyl acetate. The obtained organic phase was washed with saturated saline water and then dried with anhydrous magnesium sulfate, and a solvent was distilled under reduced pressure, so that a yellow amorphous solid was obtained. The yellow amorphous solid was purified by silica-gel column chromatography to obtain an intermediate 1c (7.09 g, a yield of 71%). A molecular weight of the intermediate 1c was 418.097. A result of mass spectroscopy analysis of the obtained compound was m/z (a ratio of mass to charge)=418, so that the obtained compound was identified as the target substance.

(1-4) Synthesis of Intermediate 1d

Under argon atmosphere, $I_2$ (0.72 g, 2.83 mmol) was added into a mixed solution of the intermediate 1c (0.79 g, 1.89 mmol), potassium carbonate ($K_2CO_3$, 0.52 g, 3.77 mmol), and acetonitrile (MeCN, 10 mL), and stirred at 80 degrees C. for 11 hours. The reaction solution was returned to the room temperature, then diluted with toluene, washed with 5% aqueous solution of sodium thiosulfate and saturated saline water, and dried with anhydrous magnesium sulfate, and a solvent was distilled under reduced pressure, so that a light brown solid was obtained. This light brown solid was purified by silica-gel column chromatography to obtain an intermediate 1d (0.76 g, a yield of 80%). A molecular weight of the intermediate 1d was 500.177. A result of mass spectroscopy analysis of the obtained compound was m/z (a ratio of mass to charge)=500, so that the obtained compound was identified as the target substance.

(1-5) Synthesis of Intermediate 1e

Under argon atmosphere, a mixed solution of the intermediate 1c (0.40 g, 0.96 mmol), the intermediate 1d (0.44 g, 0.88 mmol), tetrakis (triphenylphosphine)palladium(0) ($Pd(PPh_3)_4$, 0.05 g, 0.043 mmol), sodium hydrogen carbonate ($NaHCO_3$, 0.3 g, 3.6 mmol), 1,2-dimethoxyethane (DME, 10 mL), and water ($H_2O$, 5 mL) was stirred in a reflux state for 11 hours. The obtained reaction solution was returned to the room temperature, then extracted with dichloromethane, and dried with anhydrous magnesium sulfate, and then a solvent was distilled under reduced pressure, so that a light yellow solid was obtained. This light yellow solid was purified by silica-gel column chromatography to obtain an intermediate 1e (0.48 g, a yield of 73%). A molecular weight of the intermediate 1e was 746.546. A result of mass spectroscopy analysis of the obtained compound was m/z (a ratio of mass to charge)=746, so that the obtained compound was identified as the target substance.

(1-6) Synthesis of Compound BD1

Under argon atmosphere, the intermediate 1e (0.073 g, 0.098 mmol) was dissolved in THF (4 mL) and cooled to −78 degrees C. 1.6M n-BuLi hexane solution (0.113 mL, 0.180 mmol) was added to the obtained solution and stirred at −70 degrees C. for 30 minutes, and then heated to −50 degrees C. Zinc chloride ($ZnCl_2$, 0.013 g, 0.094 mmol) was added to the reaction solution and stirred for 20 minutes. The reaction solution was again cooled to −78 degrees C., added with copper chloride(II) ($CuCl_2$, 0.035 g, 0.257 mmol), and stirred at −70 degrees C. for three hours. The obtained reaction solution was returned to the room temperature, and then added with water for quenching. Toluene was added to the reaction solution for extraction. The obtained organic phase was washed with saturated saline water, then dried with anhydrous magnesium sulfate, and then a solvent was distilled under reduced pressure. The obtained solid was purified by silica-gel column chromatography and preparative liquid chromatography (prominence preparative system manufactured by SHIMADZU CORPORATION), so that the compound BD1 was obtained (0.015 g, a yield of 30%). A molecular weight of the compound BD1 was 586.738. A result of mass spectroscopy analysis of the obtained compound was m/z (a ratio of mass to charge)=586, so that the obtained compound was identified as the target substance.

Synthesis Example 2 (Synthesis of Compound BD2)

[Formula 221

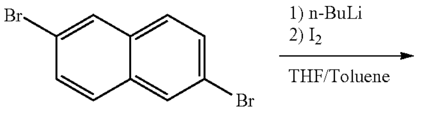

-continued

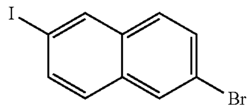

2a

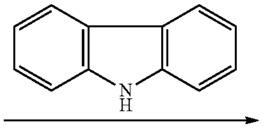

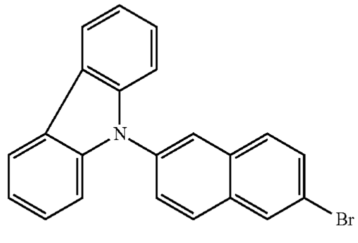

2b

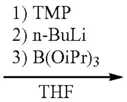

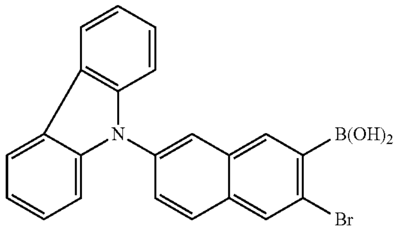

2c

[Formula 222]

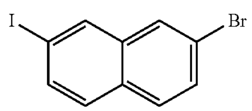

1a

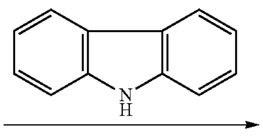

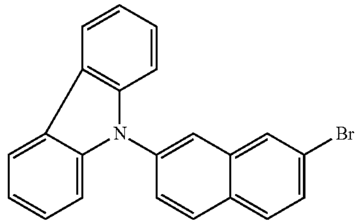

2d

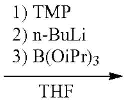

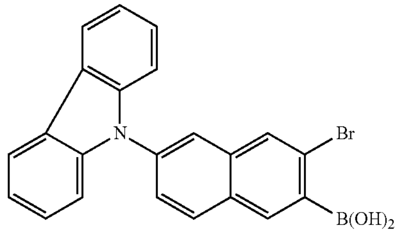

2e

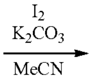

-continued

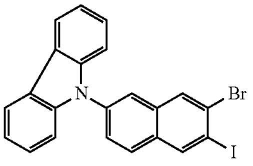

2f

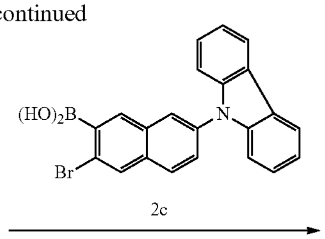

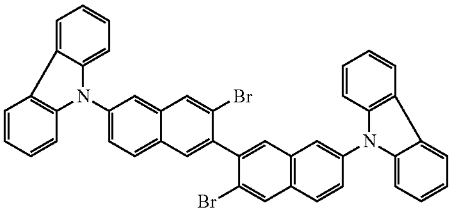

2g

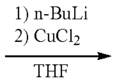

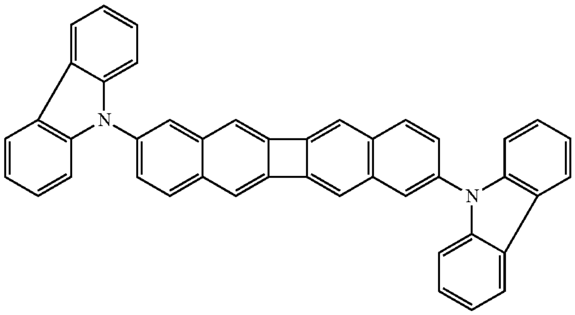

BD2

(2-1) Synthesis of Intermediate 2a

Under argon atmosphere, a mixed solution of 2,6-dibromonaphthalene (14.44 g, 50.5 mmol) in THF (173 mL) and toluene (173 mL) was cooled to −30 degrees C., into which 1.57M n-BuLi hexane solution (32 mL, 50.5 mmol) was dropped for 10 minutes. The obtained solution was stirred at −30 degrees C. for 20 minutes. Next, the reaction solution was cooled to −78 degrees C. Subsequently, THF solution (30 mL) of iodine ($I_2$, 14.15 g, 55.7 mmol) was dropped into the reaction solution. The obtained solution was stirred at −70 degrees C. for one hour. The solution was stirred for four hours while being returned to the room temperature. Subsequently, the solution was quenched with a 10% aqueous solution of sodium thiosulfate. Toluene was added to the reaction solution for dilution. The obtained solution was washed with saturated saline water, and then dried with anhydrous magnesium sulfate. A solid obtained by distilling the solvent under reduced pressure was suspended in and washed with methanol for purification, so that an intermediate 2a was obtained (13.5 g, a yield of 80%). A molecular weight of the intermediate 2a was 332.966. A result of mass spectroscopy analysis of the obtained compound was m/z (a ratio of mass to charge)=332, so that the obtained compound was identified as the target substance.

(2-2) Synthesis of Intermediate 2b

Under argon atmosphere, CHDA (4.40 mL, 36.6 mmol) was added into a mixed solution of the intermediate 2a (13.4 g, 40.2 mmol), carbazole (6.12 g, 36.6 mmol), CuI (0.697 g, 3.66 mmol), tripotassium phosphate ($K_3PO_4$, 23.31 g, 110 mmol), and 1,4-dioxane (47 mL), and was stirred at 110 degrees C. for four hours. The obtained reaction solution was returned to the room temperature, diluted with toluene, and then filtered by passing through Celite No. 545. A solid obtained by distilling the solvent under reduced pressure was purified by silica-gel column chromatography to obtain an intermediate 2b (10.33 g, a yield of 76%). A molecular weight of the intermediate 2b was 372.265. A result of mass spectroscopy analysis of the obtained compound was m/z (a ratio of mass to charge)=372, so that the obtained compound was identified as the target substance.

(2-3) Synthesis of Intermediate 2c

Under argon atmosphere, TMP (1.39 mL, 8.17 mmol) was dissolved in THF (12 mL) and cooled to −45 degrees C. 1.6M n-BuLi hexane solution (5.15 mL, 8.25 mmol) was added to the above solution, stirred at −35 degrees C. for 20 minutes, and cooled to −78 degrees C. $B(OiPr)_3$ (2.81 mL, 12.25 mmol) was dropped into the solution and, after 10 minutes, into which THF (8 mL) solution of the intermediate 2b (1.52 g, 4.08 mmol) was slowly dropped. The obtained solution was stirred in a cooling bath for six hours. Then, this reaction solution was returned to the room temperature, added with 10% hydrochloric acid, and stirred for 30 minutes. Ethyl acetate was used for extraction. The obtained organic phase was washed with saturated saline water, then dried with anhydrous magnesium sulfate, and then a solvent was distilled under reduced pressure. The obtained solid was purified by silica-gel column chromatography to obtain an intermediate 2c (1.13 g, a yield of 67%). A molecular weight of the intermediate 2c was 416.081. A result of mass spectroscopy analysis of the obtained compound was m/z (a ratio of mass to charge)=416, so that the obtained compound was identified as the target substance.

(2-4) Synthesis of Intermediate 2d

Under argon atmosphere, CHDA (0.19 mL, 1.58 mmol) was added into a mixed solution of the intermediate 1a (5.7 g, 17.12 mmol), carbazole (2.55 g, 15.25 mmol), CuI (0.03 g, 0.16 mmol), $K_3PO_4$ (7.5 g, 35.4 mmol)), and 1,4-dioxane (20 mL), and was stirred at 110 degrees C. for 10 hours. The obtained reaction solution was returned to the room temperature, diluted with toluene, and then filtered by passing through Celite No. 545. A solid obtained by distilling the solvent under reduced pressure was purified by silica-gel column chromatography to obtain an intermediate 2d (3.8 g, a yield of 68%). A molecular weight of the intermediate 2d was 372.265. A result of mass spectroscopy analysis of the obtained compound was m/z (a ratio of mass to charge) =372, so that the obtained compound was identified as the target substance.

(2-5) Synthesis of Intermediate 2e

Under argon atmosphere, TMP (2.9 mL, 20.6 mmol) was dissolved in THF (30 mL) and cooled to −43 degrees C. 1.64M n-BuLi hexane solution (12.5 mL, 20.5 mmol) was added to the above solution, stirred at −36 degrees C. for 20 minutes, and cooled to −70 degrees C. $B(OiPr)_3$ (7.0 mL, 30.3 mmol) was dropped into the solution and, after five minutes, into which THF (20 mL) solution of the intermediate 2d (3.8 g, 10.2 mmol) was slowly dropped. The obtained solution was stirred in a cooling bath for nine hours. Then, this reaction solution was returned to the room temperature, added with 5% hydrochloric acid, and stirred for 30 minutes. Ethyl acetate was used for extraction. The obtained organic phase was washed with saturated saline water, then dried with anhydrous magnesium sulfate, and then a solvent was distilled under reduced pressure. The obtained solid was purified by silica-gel column chromatography to obtain an intermediate 2e (2.9 g, a yield of 68%). A molecular weight of the intermediate 2e was 416.081. A result of mass spectroscopy analysis of the obtained compound was m/z (a ratio of mass to charge)=416, so that the obtained compound was identified as the target substance.

(2-6) Synthesis of Intermediate 2f

Under argon atmosphere, $I_2$ (0.76 g, 3.0 mmol) was added into a mixed solution of the intermediate 2e (0.83 g, 2.0 mmol), $K_2CO_3$ (0.55 g, 4.0 mmol), and MeCN (10 mL), and stirred at 80 degrees C. for 8 hours. The reaction solution was returned to the room temperature, then diluted with toluene, washed with 5% aqueous solution of sodium hydrogen sulfite and saturated saline water, and dried with anhydrous magnesium sulfate, and a solvent was distilled under reduced pressure. The obtained solid was purified by silica-gel column chromatography to obtain an intermediate 2f (0.50 g, a yield of 50%). A molecular weight of the intermediate 2f was 498.161. A result of mass spectroscopy analysis of the obtained compound was m/z (a ratio of mass to charge)=498, so that the obtained compound was identified as the target substance.

(2-7) Synthesis of Intermediate 2g

Under argon atmosphere, a mixed solution of the intermediate 2f (0.46 g, 0.94 mmol), the intermediate 2c (0.43 g, 1.03 mmol), $Pd(PPh_3)_4$ (0.054 g, 0.047 mmol), $NaHCO_3$ (0.32 g, 3.75 mmol), DME (10 mL), and $H_2O$ (5 mL) was stirred in a reflux state for 23 hours. The obtained reaction solution was returned to the room temperature, then extracted with dichloromethane, and dried with anhydrous magnesium sulfate, and then a solvent was distilled under reduced pressure. The obtained solid was purified by silica-gel column chromatography to obtain an intermediate 2g (0.31 g, a yield of 45%). A molecular weight of the intermediate 2g was 742.514. A result of mass spectroscopy analysis of the obtained compound was m/z (a ratio of mass to charge)=742, so that the obtained compound was identified as the target substance.

(2-8) Synthesis of Compound BD2

Under argon atmosphere, the intermediate 2g (0.3 g, 0.40 mmol) was dissolved in THF (18 mL) and cooled to −78 degrees C. 1.6M n-BuLi hexane solution (1.2 mL, 2.02 mmol) was added to the obtained solution and stirred at −70 degrees C. for two hours, next, to which $CuCl_2$ (0.33 g, 2.50 mmol) was added and stirred at −65 degrees C. for two hours. The obtained reaction solution was returned to the room temperature, added with a saturated aqueous solution of ammonium chloride for quenching. Toluene was added for extraction. The obtained organic phase was washed with saturated saline water, then dried with anhydrous magnesium sulfate, and then a solvent was distilled under reduced pressure. The obtained solid was purified by recrystallization using toluene and xylene, so that the compound BD2 was obtained (0.034 g, a yield of 14%). A molecular weight of the compound BD2 was 582.706. A result of mass spectroscopy analysis of the obtained compound was m/z (a ratio of mass to charge)=582, so that the obtained compound was identified as the target substance.

Synthesis Example 3 (Synthesis of Compound BD3)

[Formula 223]

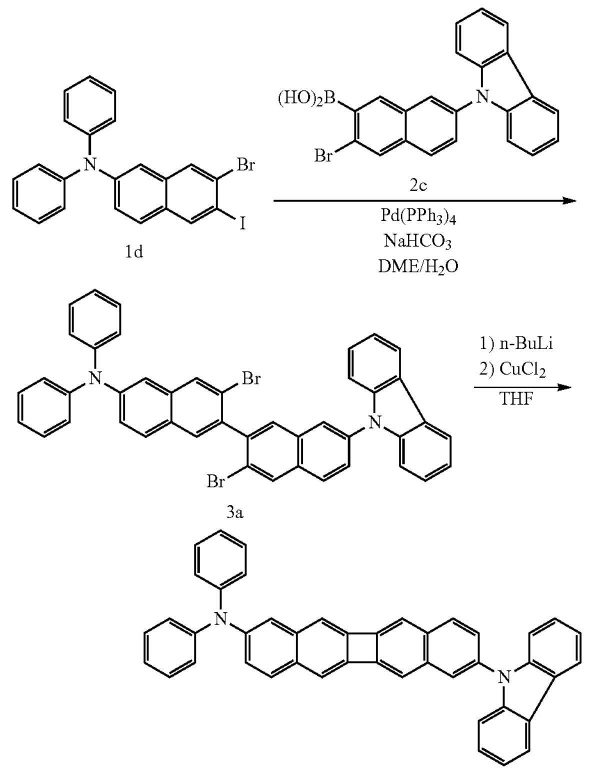

BD3

(3-1) Synthesis of Intermediate 3a

Under argon atmosphere, a mixed solution of the intermediate 1d (0.45 g, 0.90 mmol), the intermediate 2c (0.41 g, 0.99 mmol), $Pd(PPh_3)_4$ (0.052 g, 0.045 mmol), $NaHCO_3$ (0.30 g, 3.61 mmol), DME (10 mL), and $H_2O$ (5 mL) was stirred in a reflux state for 24 hours. The obtained reaction solution was returned to the room temperature, then extracted with dichloromethane, and dried with anhydrous magnesium sulfate, and then a solvent was distilled under reduced pressure. The obtained solid was purified by silica-gel column chromatography to obtain an intermediate 3a (0.42 g, a yield of 63%). A molecular weight of the intermediate 3a was 744.530. A result of mass spectroscopy analysis of the obtained compound was m/z (a ratio of mass to charge)=744, so that the obtained compound was identified as the target substance.

(3-2) Synthesis of Compound BD3

Under argon atmosphere, the intermediate 3a (0.42 g, 0.57 mmol) was dissolved in THF (26 mL) and cooled to −78 degrees C. 1.6M n-BuLi hexane solution (1.8 mL, 2.87 mmol) was added to the obtained solution and stirred at −70 degrees C. for two hours, next, to which $CuCl_2$ (0.47 g, 3.56 mmol) was added and stirred at −65 degrees C. for two hours. The obtained reaction solution was returned to the room temperature and then added with 3N hydrochloric acid for quenching. Toluene was added for extraction. The obtained organic phase was washed with saturated saline water, then dried with anhydrous magnesium sulfate, and then a solvent was distilled under reduced pressure. The obtained solid was purified by silica-gel column chromatography and recrystallization using toluene, so that the compound BD3 was obtained (0.096 g, a yield of 29%). A molecular weight of the compound BD3 was 584.722. A result of mass spectroscopy analysis of the obtained compound was m/z (a ratio of mass to charge)=584, so that the obtained compound was identified as the target substance.

Synthesis Example 4 (Synthesis of Compound BD4)

[Formula 224]

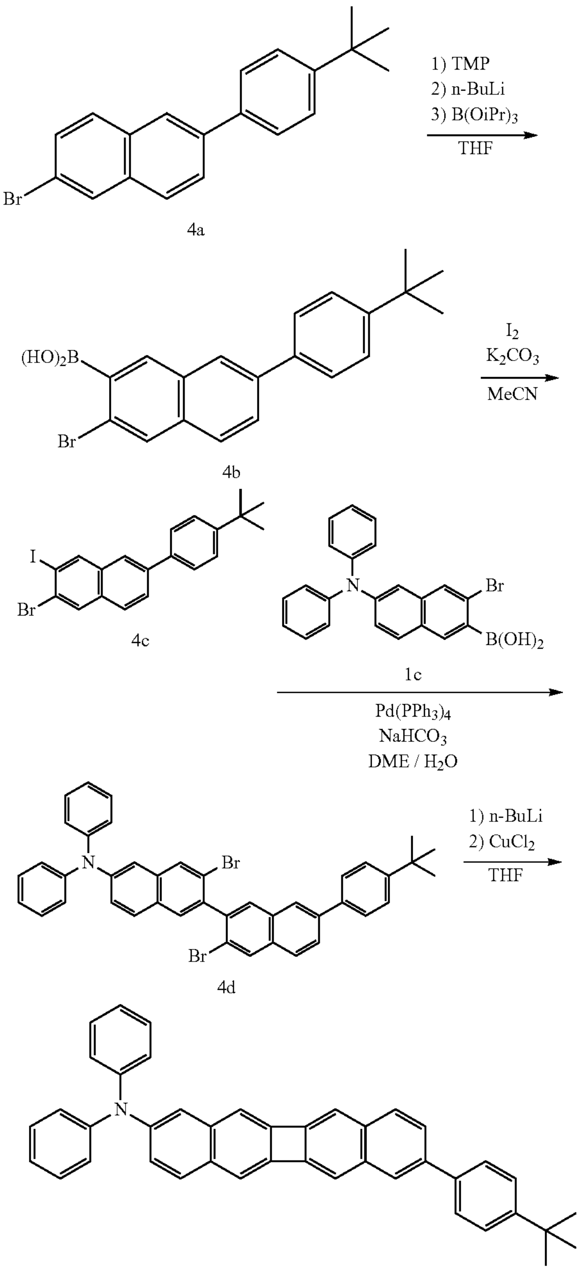

BD4

(4-1) Synthesis of Intermediate 4b

An intermediate 4b was synthesized by the same method as in synthesis of the intermediate 1c except using an intermediate 4a in place of the intermediate 1b as the reaction material. A molecular weight of the intermediate 4b was 383.092. A result of mass spectroscopy analysis of the obtained compound was m/z (a ratio of mass to charge) =383, so that the obtained compound was identified as the target substance.

(4-2) Synthesis of Intermediate 4c

An intermediate 4c was synthesized by the same method as in synthesis of the intermediate 1d except using the intermediate 4b in place of the intermediate 1c as the reaction material. A molecular weight of the intermediate 4c was 465.172. A result of mass spectroscopy analysis of the obtained compound was m/z (a ratio of mass to charge) =465, so that the obtained compound was identified as the target substance.

(4-3) Synthesis of Intermediate 4d

The intermediate 4d was synthesized by the same method as in synthesis of the intermediate 1e except using the intermediate 4c in place of the intermediate 1d as the reaction material. A molecular weight of the intermediate 4d was 711.541. A result of mass spectroscopy analysis of the obtained compound was m/z (a ratio of mass to charge)=711, so that the obtained compound was identified as the target substance.

(4-4) Synthesis of Compound BD4

The compound BD4 was synthesized by the same method as in synthesis of the compound BD2 except using the intermediate 4d in place of the intermediate 2g as the reaction material. A molecular weight of the compound BD4 was 551.733. A result of mass spectroscopy analysis of the obtained compound was m/z (a ratio of mass to charge)= 551, so that the obtained compound was identified as the target substance.

Synthesis Example 5 (Synthesis of Compound BD5)

[Formula 225]

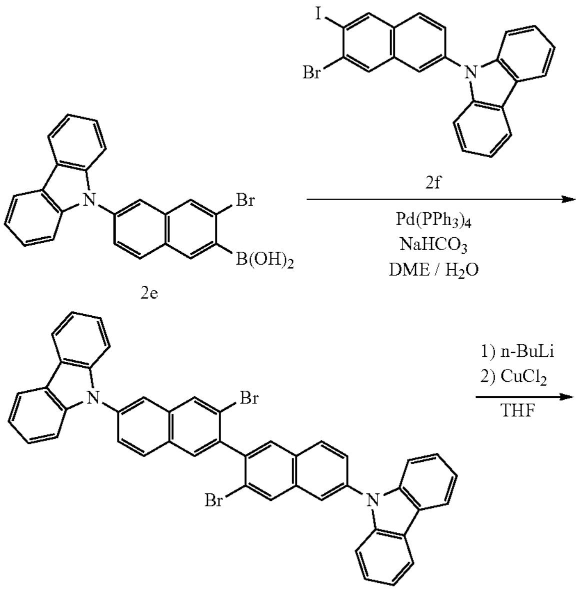

2e

5a

-continued

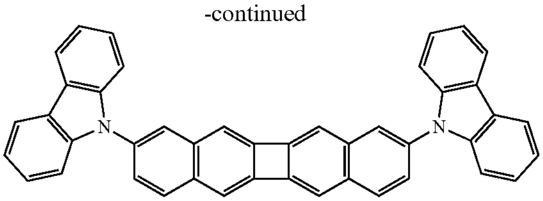

BD5

(5-1) Synthesis of Intermediate 5a

An intermediate 5a was synthesized by the same method as in synthesis of the intermediate 2g except using the intermediate 2e in place of the intermediate 2c as the reaction material. A molecular weight of the intermediate 5a was 742.514. A result of mass spectroscopy analysis of the obtained compound was m/z (a ratio of mass to charge)= 742, so that the obtained compound was identified as the target substance.

(5-2) Synthesis of Compound BD5

The compound BD5 was synthesized by the same method as in synthesis of the compound BD2 except using the intermediate 5a in place of the intermediate 2g as the reaction material. A molecular weight of the compound BD5 was 582.706. A result of mass spectroscopy analysis of the obtained compound was m/z (a ratio of mass to charge) =582, so that the obtained compound was identified as the target substance.

Synthesis Example 6 (Synthesis of Compound BD6)

[Formula 226]

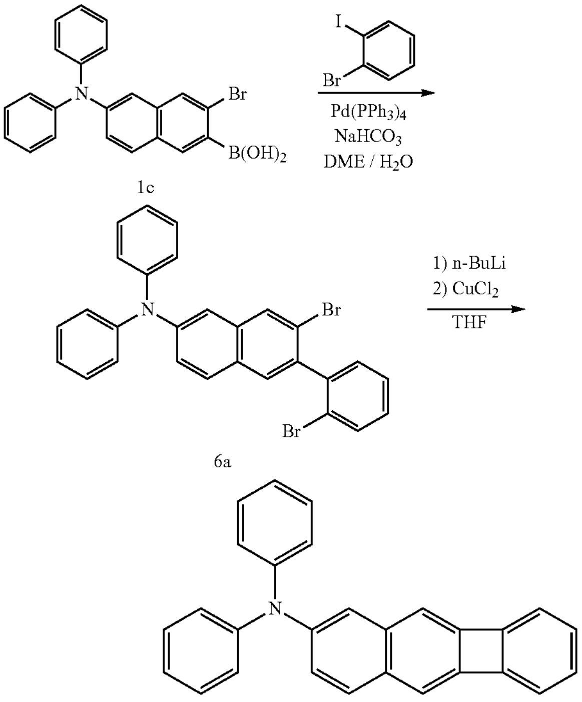

1c

6a

BD6

(6-1) Synthesis of Intermediate 6a

The intermediate 6a was synthesized by the same method as in synthesis of the intermediate 1e except using 1-bromo- 2-iodobenzene in place of the intermediate 1d as the reaction material. A molecular weight of the intermediate 6a was 529.275. A result of mass spectroscopy analysis of the obtained compound was m/z (a ratio of mass to charge) =529, so that the obtained compound was identified as the target substance.

(6-2) Synthesis of Compound BD6

The compound BD6 was synthesized by the same method as in synthesis of the compound BD2 except using the intermediate 6a in place of the intermediate 2g as the reaction material. A molecular weight of the compound BD6 was 369.467. A result of mass spectroscopy analysis of the obtained compound was m/z (a ratio of mass to charge) =369, so that the obtained compound was identified as the target substance.

The invention claimed is:

1. A compound represented by a formula (2) below and comprising at least one group represented by a formula (20) below, (2)

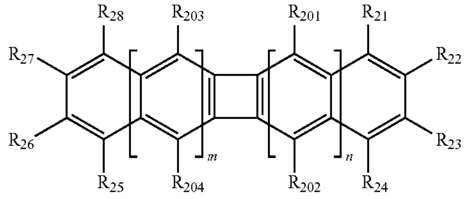

(20)

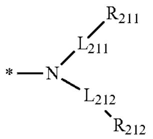

where: in the formula (2):

m is 0, 1, 2 or 3;

n is 0, 1, 2 or 3;

m+n is an integer of 1 or more;

at least one combination of adjacent two or more of $R_{21}$ to $R_{28}$ and $R_{201}$ to $R_{204}$ are mutually bonded to form a substituted or unsubstituted monocyclic ring, mutually bonded to form a substituted or unsubstituted fused ring, or not mutually bonded;

neither a combination of a combination of $R_{22}$ and $R_{23}$, nor a combination of $R_{26}$ and $R_{27}$ are mutually bonded to form a substituted or unsubstituted fused ring;

$R_{21}$ to $R_{28}$ and $R_{201}$ to $R_{204}$ not forming the monocyclic ring and not forming the fused ring are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, a substituted or unsubstituted heterocyclic group having 5 to 50 ring atoms, or the group represented by the formula (20);

when n is 2 or 3, at least two $R_{201}$ are the same or different, and at least two $R_{202}$ are the same or different;

when m is 2 or 3, at least two $R_{203}$ are the same or different, and at least two $R_{204}$ are the same or different;

at least one of $R_{21}$ to $R_{28}$ or $R_{201}$ to $R_{204}$ is the group represented by the formula (20);

in the group represented by the formula (20), a combination of $R_{211}$ and $R_{212}$ are mutually bonded to form a substituted or unsubstituted monocyclic ring, mutually bonded to form a substituted or unsubstituted fused ring, or not mutually bonded;

$R_{211}$ and $R_{212}$ not forming the monocyclic ring and not forming the fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{211}$ and $L_{212}$ are each independently a single bond, a substituted or unsubstituted arylene group having 6 to 50 ring carbon atoms, or a substituted or unsubstituted divalent heterocyclic group having 5 to 50 ring atoms;

* in the formula (20) represents a bonding position to a structure of the compound represented by the formula (2);

in the compound represented by the formula (2), $R_{901}$ to $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when two or more $R_{901}$ are present, the two or more $R_{901}$ are mutually the same or different;

when two or more $R_{902}$ are present, the two or more $R_{902}$ are mutually the same or different;

when two or more $R_{903}$ are present, the two or more $R_{903}$ are mutually the same or different;

when two or more $R_{904}$ are present, the two or more $R_{904}$ are mutually the same or different;

when two or more $R_{905}$ are present, the two or more $R_{905}$ are mutually the same or different;

when two or more $R_{906}$ are present, the two or more $R_{906}$ are mutually the same or different; and when two or more $R_{907}$ are present, the two or more $R_{907}$ are mutually the same or different.

2. The compound according to claim 1, wherein the compound represented by the formula (2) is a compound represented by a formula (22) below, (22)

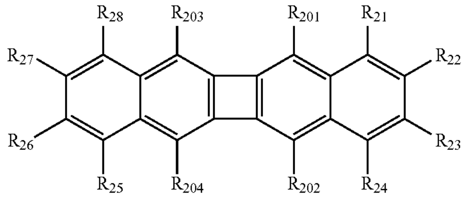

where:

$R_{21}$ to $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a substituted or unsubstituted aryl group having 6 to 50 ring carbon atoms, a substituted or unsubstituted heterocyclic group having 5 to 50 ring atoms, or the group represented by the formula (20);

at least one of $R_{21}$ to $R_{28}$ or $R_{201}$ to $R_{204}$ is the group represented by the formula (20); and in the compound represented by the formula (22), $R_{901}$ to $R_{907}$ are each independently the same as defined in the formula (2).

3. The compound according to claim 1, wherein the compound represented by the formula (2) comprises at least one group selected from the group consisting of a group represented by a formula (20a) and a group represented by a formula (20b) below, (20a)

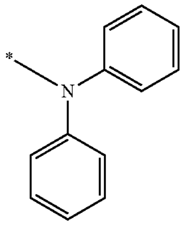

(20b)

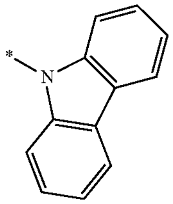

where: * each independently represents a bonding position to a structure of the compound represented by the formula (2).

4. The compound according to claim 1, wherein the compound represented by the formula (2) is a compound represented by a formula (23) below, (23)

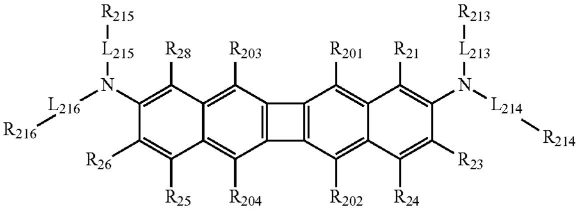

where:

$R_{21}$, $R_{23}$, $R_{24}$ to $R_{26}$, $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a substituted or unsubstituted aryl group having 6 to 50 ring carbon atoms, a substituted or unsubstituted heterocyclic group having 5 to 50 ring atoms, or the group represented by the formula (20);

a combination of $R_{213}$ and $R_{214}$ are mutually bonded to form a substituted or unsubstituted monocyclic ring, mutually bonded to form a substituted or unsubstituted fused ring, or not mutually bonded;

a combination of $R_{215}$ and $R_{216}$ are mutually bonded to form a substituted or unsubstituted monocyclic ring, mutually bonded to form a substituted or unsubstituted fused ring, or not mutually bonded;

$R_{213}$ to $R_{216}$ not forming the monocyclic ring and not forming the fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{213}$ to $L_{216}$ are each independently a single bond, a substituted or unsubstituted arylene group having 6 to 50 ring carbon atoms, or a substituted or unsubstituted divalent heterocyclic group having 5 to 50 ring atoms; and in the compound represented by the formula (23), $R_{901}$ to $R_{907}$ are each independently the same as defined in the formula (2).

5. The compound according to claim 4, wherein $R_{213}$ to $R_{216}$ are each a substituted or unsubstituted phenyl group.

6. The compound according to claim 1, wherein the compound represented by the formula (2) is a compound represented by a formula (24) below, (24)

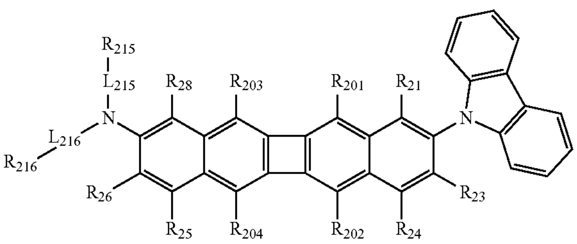

where:

$R_{21}$, $R_{23}$, $R_{24}$ to $R_{26}$, $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, a substituted or unsubstituted heterocyclic group having 5 to 50 ring atoms, or the group represented by the formula (20);

a combination of $R_{215}$ and $R_{216}$ are mutually bonded to form a substituted or unsubstituted monocyclic ring, mutually bonded to form a substituted or unsubstituted fused ring, or not mutually bonded;

$R_{215}$ and $R_{216}$ not forming the monocyclic ring and not forming the fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{215}$ and $L_{216}$ are each independently a single bond, a substituted or unsubstituted arylene group having 6 to 50 ring carbon atoms, or a substituted or unsubstituted divalent heterocyclic group having 5 to 50 ring atoms; and in the compound represented by the formula (24), $R_{901}$ to $R_{907}$ are each independently the same as defined in the formula (2).

7. The compound according to claim 6, wherein $R_{215}$ and $R_{216}$ are each a substituted or unsubstituted phenyl group.

8. The compound according to claim 1, wherein the compound represented by the formula (2) is a compound represented by a formula (25) below, (25)

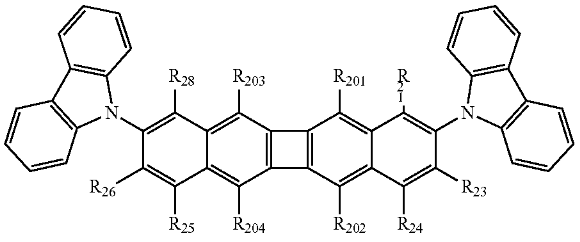

where:

$R_{21}$, $R_{23}$, $R_{24}$ to $R_{26}$, $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, a substituted or unsubstituted heterocyclic group having 5 to 50 ring atoms, or the group represented by the formula (20); and in the compound represented by the formula (25), $R_{901}$ to $R_{907}$ are each independently the same as defined in the formula (2).

9. The compound according to claim 1, wherein $R_{21}$, $R_{23}$, $R_{24}$ to $R_{26}$, $R_{28}$ and $R_{201}$ to $R_{204}$ are each independently a hydrogen atom, a halogen atom, a substituted or unsubstituted alkyl group having 1 to 50 carbon atoms, a substituted or unsubstituted cycloalkyl group having 3 to 50 ring carbon atoms, or a group represented by —Si($R_{901}$)($R_{902}$)($R_{903}$).

10. The compound according to claim 1, wherein the compound represented by the formula (2) is a compound represented by a formula (26) below, (26)

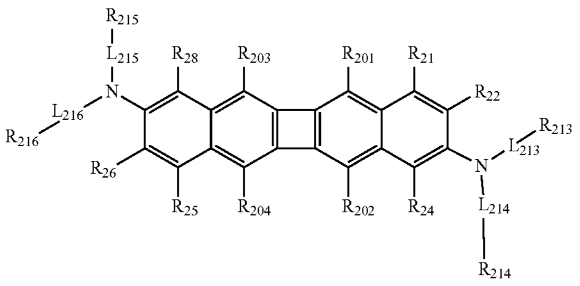

where:

$R_{21}$, $R_{22}$, $R_{24}$ to $R_{26}$, $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, a substituted or unsubstituted heterocyclic group having 5 to 50 ring atoms, or the group represented by the formula (20);

a combination of $R_{213}$ and $R_{214}$ are mutually bonded to form a substituted or unsubstituted monocyclic ring, mutually bonded to form a substituted or unsubstituted fused ring, or not mutually bonded;

a combination of $R_{215}$ and $R_{216}$ are mutually bonded to form a substituted or unsubstituted monocyclic ring, mutually bonded to form a substituted or unsubstituted fused ring, or not mutually bonded;

$R_{213}$ to $R_{216}$ not forming the monocyclic ring and not forming the fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{213}$ to $L_{216}$ are each independently a single bond, a substituted or unsubstituted arylene group having 6 to 50 ring carbon atoms, or a substituted or unsubstituted divalent heterocyclic group having 5 to 50 ring atoms; and $R_{901}$ to $R_{907}$ in the compound represented by the formula (26) are each independently the same as defined in the formula (2).

11. The compound according to claim 10, wherein $R_{213}$ to $R_{216}$ are each a substituted or unsubstituted phenyl group.

12. The compound according to claim 1, wherein the compound represented by the formula (2) is a compound represented by a formula (27) below, (27)

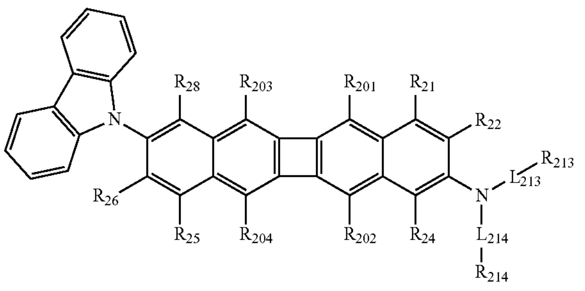

where:

$R_{21}$, $R_{22}$, $R_{24}$ to $R_{26}$, $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, a substituted or unsubstituted heterocyclic group having 5 to 50 ring atoms, or the group represented by the formula (20);

a combination of $R_{213}$ and $R_{214}$ are mutually bonded to form a substituted or unsubstituted monocyclic ring, mutually bonded to form a substituted or unsubstituted fused ring, or not mutually bonded;

$R_{213}$ and $R_{214}$ not forming the monocyclic ring and not forming the fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{213}$ and $L_{214}$ are each independently a single bond, a substituted or unsubstituted arylene group having 6 to 50 ring carbon atoms, or a substituted or unsubstituted divalent heterocyclic group having 5 to 50 ring atoms; and $R_{901}$ to $R_{907}$ in the compound represented by the formula (27) are each independently the same as defined in the formula (2).

13. The compound according to claim 12, wherein $R_{213}$ and $R_{214}$ are each a substituted or unsubstituted phenyl group.

14. The compound according to claim 1, wherein the compound represented by the formula (2) is a compound represented by a formula (28) below, (28)

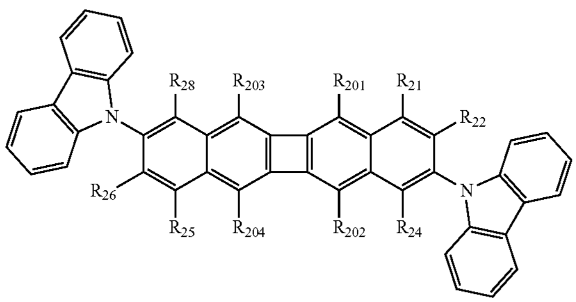

where:

$R_{21}$, $R_{22}$, $R_{24}$ to $R_{26}$, $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, a substituted or unsubstituted heterocyclic group having 5 to 50 ring atoms, or the group represented by the formula (20); and $R_{901}$ to $R_{907}$ in the compound represented by the formula (28) are each independently the same as defined in the formula (2).

15. The compound according to claim 10, wherein $R_{21}$, $R_{22}$, $R_{24}$ to $R_{26}$, $R_{28}$ and $R_{201}$ to $R_{204}$ are each independently a hydrogen atom, a halogen atom, a substituted or unsubstituted alkyl group having 1 to 50 carbon atoms, a substituted or unsubstituted cycloalkyl group having 3 to 50 ring carbon atoms, or a group represented by —Si($R_{901}$)($R_{902}$)($R_{903}$).

16. The compound according to claim 1, wherein the compound represented by the formula (2) is a compound represented by a formula (29) below, (29)

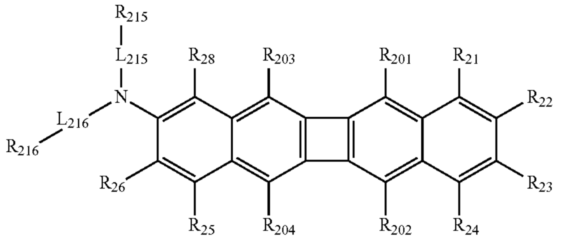

where:

$R_{21}$ to $R_{26}$, $R_{28}$ and $R_{201}$ to $R_{204}$ are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aryl group having 6 to 50 ring carbon atoms, or a substituted or unsubstituted heterocyclic group having 5 to 50 ring atoms;

a combination of $R_{215}$ and $R_{216}$ are mutually bonded to form a substituted or unsubstituted monocyclic ring, mutually bonded to form a substituted or unsubstituted fused ring, or not mutually bonded;

$R_{215}$ and $R_{216}$ not forming the monocyclic ring and not forming the fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{215}$ and $L_{216}$ are each independently a single bond, a substituted or unsubstituted arylene group having 6 to 50 ring carbon atoms, or a substituted or unsubstituted divalent heterocyclic group having 5 to 50 ring atoms; and $R_{901}$ to $R_{905}$ in the compound represented by the formula (29) are each independently the same as defined in the formula (2).

17. The compound according to claim 16, wherein $R_{215}$ and $R_{216}$ are each a substituted or unsubstituted phenyl group.

18. The compound according to claim 16, wherein $R_{21}$ to $R_{26}$, $R_{28}$ and $R_{201}$ to $R_{204}$ are each independently a hydrogen atom, a halogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a group represented by —Si($R_{901}$)($R_{902}$)($R_{903}$).

19. An organic-electroluminescence-device material comprising the compound according to claim 1.

20. An organic electroluminescence device comprising:

a cathode;

an anode; and one or more organic layers provided between the cathode and the anode, wherein at least one layer of the one or more organic layers comprises the compound defined in the formula (2) according to claim 1.

21. An organic electroluminescence device comprising:

a cathode;

an anode; and one or more organic layers provided between the cathode and the anode, wherein at least one layer of the one or more organic layers comprises the compound defined in the formula (2) according to claim 1 and a compound represented by a formula (10) below,

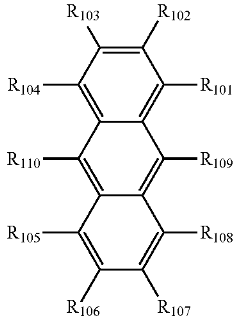

(10)

where:

at least one combination of adjacent two or more of $R_{101}$ to $R_{110}$ are mutually bonded to form a substituted or unsubstituted monocyclic ring, mutually bonded to form a substituted or unsubstituted fused ring, or not mutually bonded; and $R_{101}$ to $R_{110}$ not forming the monocyclic ring and not forming the fused ring are each independently a hydrogen atom, a substituent R, or a group represented by a formula (11) below, $$-L_{101}-Ar_{101} \quad (11)$$

in the formula (11):

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

the substituent R is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms;

when two or more substituents R are present, the two or more substituents R are mutually the same or different, and $R_{901}$ to $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when two or more $R_{901}$ are present, the two or more $R_{901}$ are mutually the same or different;

when two or more $R_{902}$ are present, the two or more $R_{902}$ are mutually the same or different;

when two or more $R_{903}$ are present, the two or more $R_{903}$ are mutually the same or different;

when two or more $R_{904}$ are present, the two or more $R_{904}$ are mutually the same or different;

when two or more $R_{905}$ are present, the two or more $R_{905}$ are mutually the same or different;

when two or more $R_{906}$ are present, the two or more $R_{906}$ are mutually the same or different;

when two or more $R_{907}$ are present, the two or more $R_{907}$ are mutually the same or different;

at least one of $R_{101}$ to $R_{110}$ not forming the monocyclic ring and not forming the fused ring is the group represented by the formula (11);

when two or more groups represented by the formula (11) are present, the two or more groups represented by the formula (11) are mutually the same or different;

when two or more $L_{101}$ are present, the two or more $L_{101}$ are mutually the same or different; and when two or more $Ar_{101}$ are present, the two or more $Ar_{101}$ are mutually the same or different.

22. The organic electroluminescence device according to claim 20, wherein the at least one layer comprising the compound defined in the formula (2) is an emitting layer, and the organic electroluminescence device comprises a hole transporting layer between the anode and the emitting layer.

23. The organic electroluminescence device according to claim 20, wherein the at least one layer comprising the compound defined in the formula (2) is an emitting layer, and the organic electroluminescence device comprises an electron transporting layer between the cathode and the emitting layer.

24. The organic electroluminescence device according to claim 20, wherein the at least one layer comprising the compound defined in the formula (2) is an emitting layer, and the emitting layer further comprises a delayed fluorescent host compound.

25. An electronic device comprising the organic electroluminescence device according to claim 20.

* * * * *